(12) United States Patent
Eriksen et al.

(10) Patent No.: US 10,774,064 B2
(45) Date of Patent: *Sep. 15, 2020

(54) POTASSIUM CHANNEL MODULATORS

(71) Applicant: Cadent Therapeutics, Inc., Cambridge, MA (US)

(72) Inventors: Birgitte Langer Eriksen, Farum (DK); Magnus Gustafsson, Frederiksberg (DK); Charlotte Hougaard, Ballerup (DK); Thomas Amos Jacobsen, Oested (DK); Martin R. Jefson, Stonington, CT (US); Gregg F. Keaney, Lexington, MA (US); Jessica Klein, Copenhagen (DK); Janus Schreiber Larsen, Holbæk (DK); John A. Lowe, III, Stonington, CT (US); John M. McCall, Boca Grande, FL (US); Dorte Strøbæk, Farum (DK); Nadia Lybøl von Schoubye, Copenhagen (DK)

(73) Assignee: Cadent Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/749,325

(22) PCT Filed: Jun. 2, 2017

(86) PCT No.: PCT/US2017/035662
§ 371 (c)(1),
(2) Date: Jan. 31, 2018

(87) PCT Pub. No.: WO2017/210545
PCT Pub. Date: Dec. 7, 2017

(65) Prior Publication Data
US 2019/0218200 A1    Jul. 18, 2019

Related U.S. Application Data

(60) Provisional application No. 62/449,309, filed on Jan. 23, 2017, provisional application No. 62/344,513, filed on Jun. 2, 2016.

(51) Int. Cl.
| | |
|---|---|
| *C07D 401/04* | (2006.01) |
| *C07D 413/14* | (2006.01) |
| *C07D 403/04* | (2006.01) |
| *C07D 409/14* | (2006.01) |
| *C07D 417/04* | (2006.01) |
| *C07D 491/10* | (2006.01) |
| *C07D 498/08* | (2006.01) |
| *C07D 403/14* | (2006.01) |
| *C07D 405/14* | (2006.01) |
| *C07D 487/04* | (2006.01) |

(Continued)

(52) U.S. Cl.
CPC ........ *C07D 401/04* (2013.01); *C07D 401/14* (2013.01); *C07D 403/04* (2013.01); *C07D 403/14* (2013.01); *C07D 405/14* (2013.01); *C07D 409/14* (2013.01); *C07D 413/14* (2013.01); *C07D 417/04* (2013.01); *C07D 417/14* (2013.01); *C07D 471/04* (2013.01); *C07D 487/04* (2013.01); *C07D 487/08* (2013.01); *C07D 491/10* (2013.01); *C07D 498/08* (2013.01)

(58) Field of Classification Search
CPC .................................................. C07D 401/04
USPC ........................................................ 544/316
See application file for complete search history.

(56) References Cited

U.S. PATENT DOCUMENTS

| 4,992,150 A | 2/1991 | Igarashi et al. |
| 5,250,530 A | 10/1993 | Giencke et al. |

(Continued)

FOREIGN PATENT DOCUMENTS

| CN | 101684098 A | 3/2010 |
| CN | 102731492 A | 10/2012 |

(Continued)

OTHER PUBLICATIONS

Venkatesh et al., J. Pharm. Sci. 89, 145-54 (2000).*

(Continued)

*Primary Examiner* — Nizal S Chandrakumar
(74) *Attorney, Agent, or Firm* — McCarter & English, LLP; Steven G. Davis; Michael J. DeGrazia

(57) ABSTRACT

Provided are novel compounds of Formula (I): and pharmaceutically acceptable salts thereof, which are useful for treating a variety of diseases, disorders or conditions which can be affected by potassium channel modulation. Also provided are pharmaceutical compositions comprising the novel compounds of Formula (I), pharmaceutically acceptable salts thereof, and methods for their use in treating one or more diseases, disorders or conditions, associated with potassium channels.

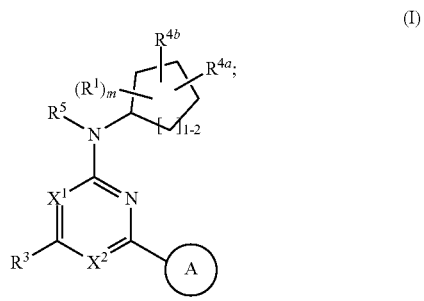

17 Claims, 2 Drawing Sheets

(51) Int. Cl.
*C07D 417/14* (2006.01)
*C07D 487/08* (2006.01)
*C07D 401/14* (2006.01)
*C07D 471/04* (2006.01)

(56) References Cited

U.S. PATENT DOCUMENTS

| | | | |
|---|---|---|---|
| 6,225,052 B1 | 5/2001 | Batz et al. | |
| 7,767,777 B2 | 8/2010 | Buesing et al. | |
| 7,919,046 B2 | 4/2011 | Delapierre et al. | |
| 8,106,217 B2 | 1/2012 | Ignatyev et al. | |
| 8,222,262 B2 | 7/2012 | Eriksen et al. | |
| 8,252,806 B2 | 8/2012 | Eriksen et al. | |
| 8,362,024 B2 | 1/2013 | Eriksen et al. | |
| 8,563,552 B2 | 10/2013 | Hanyu et al. | |
| 8,586,573 B2 | 11/2013 | Dubois et al. | |
| 9,050,266 B2 | 6/2015 | Poinsard et al. | |
| 9,321,727 B2 | 4/2016 | Bissantz et al. | |
| 9,340,544 B2 | 5/2016 | Eriksen et al. | |
| 9,505,720 B2 | 11/2016 | Poinsard et al. | |
| 9,579,324 B2 * | 2/2017 | Konteatis | C07D 417/04 |
| 9,975,886 B1 * | 5/2018 | Amrutkar | C07D 413/14 |
| 10,351,553 B2 | 7/2019 | Amrutkar et al. | |
| 2002/0137747 A1 | 9/2002 | Moriarty et al. | |
| 2004/0229864 A1 | 11/2004 | Bourrain et al. | |
| 2005/0113382 A1 | 5/2005 | Jahangir et al. | |
| 2005/0277640 A1 | 12/2005 | Dixon et al. | |
| 2006/0069066 A1 | 3/2006 | Eldar-Finkelman et al. | |
| 2006/0156481 A1 | 7/2006 | Lim | |
| 2006/0281712 A1 | 12/2006 | Yen et al. | |
| 2007/0135437 A1 | 6/2007 | Benjamin et al. | |
| 2008/0221103 A1 | 9/2008 | Sharma et al. | |
| 2008/0249097 A1 | 10/2008 | Daifuku et al. | |
| 2008/0255183 A1 | 10/2008 | Arnould et al. | |
| 2009/0036475 A1 | 2/2009 | Eriksen et al. | |
| 2009/0068634 A1 | 3/2009 | Cerda | |
| 2009/0143302 A1 | 6/2009 | Yen et al. | |
| 2009/0253717 A1 | 10/2009 | Brown et al. | |
| 2009/0306102 A1 | 12/2009 | Eriksen et al. | |
| 2010/0324273 A1 | 12/2010 | Singer et al. | |
| 2011/0144140 A1 | 6/2011 | Eriksen et al. | |
| 2011/0152292 A1 | 6/2011 | Rayner-Branes et al. | |
| 2011/0224155 A1 | 9/2011 | Tachdjian et al. | |
| 2011/0230484 A1 | 9/2011 | Eriksen et al. | |
| 2011/0257196 A1 | 10/2011 | Lu et al. | |
| 2012/0004246 A1 | 1/2012 | Eriksen et al. | |
| 2012/0046301 A1 | 2/2012 | Frank et al. | |
| 2012/0071524 A1 | 3/2012 | Lu et al. | |
| 2012/0202806 A1 | 8/2012 | Durrenberger et al. | |
| 2013/0197049 A1 | 8/2013 | Li et al. | |
| 2014/0275024 A1 | 9/2014 | Maxwell et al. | |
| 2015/0291515 A1 | 10/2015 | Uerdingen et al. | |
| 2016/0155959 A1 | 6/2016 | Kaiser et al. | |
| 2016/0237069 A1 | 8/2016 | Beaton et al. | |
| 2017/0015871 A1 | 1/2017 | Wutti et al. | |
| 2017/0299609 A1 | 10/2017 | Elbasiouny | |
| 2017/0355708 A1 | 12/2017 | Jefson et al. | |
| 2018/0207138 A1 | 7/2018 | Amrutkar et al. | |

FOREIGN PATENT DOCUMENTS

| | | |
|---|---|---|
| CN | 103626741 A | 3/2014 |
| CN | 106349156 A | 1/2017 |
| DE | 3634341 A1 | 5/1987 |
| DE | 4034762 A1 | 5/1992 |
| DE | 102012006896 A1 | 10/2013 |
| EP | 353123 A1 | 1/1990 |
| EP | 407899 A2 | 1/1991 |
| EP | 646648 A1 | 4/1995 |
| EP | 1270551 A1 | 1/2003 |
| EP | 1506967 A1 | 2/2005 |
| EP | 2042570 A1 | 4/2009 |
| EP | 2746373 A2 | 6/2014 |
| EP | 2746374 A2 | 6/2014 |
| ES | 2469290 A1 | 6/2014 |
| FR | 2904316 A1 | 2/2008 |
| GB | 2263639 A | 8/1993 |
| JP | 54-147921 A | 11/1979 |
| JP | H02282251 A | 11/1990 |
| JP | H11158073 A | 6/1999 |
| JP | H11282132 A | 10/1999 |
| JP | 2000-072695 A | 3/2000 |
| JP | 2000-075449 A | 3/2000 |
| JP | 2007-091649 A | 4/2007 |
| JP | 2013-020223 A | 1/2013 |
| JP | 2013-061465 A | 4/2013 |
| JP | 2013-125180 A | 6/2013 |
| KR | 20120018236 A | 3/2012 |
| WO | 1989/11279 A1 | 11/1989 |
| WO | 1993/25550 A1 | 12/1993 |
| WO | 1995/00478 A1 | 1/1995 |
| WO | 1998/06709 A1 | 2/1998 |
| WO | 1998/17630 A1 | 4/1998 |
| WO | 2001/017942 A1 | 3/2001 |
| WO | 2001/32170 A1 | 5/2001 |
| WO | 2002/000217 A1 | 1/2002 |
| WO | 2002/030358 A2 | 4/2002 |
| WO | 2002/046172 A2 | 6/2002 |
| WO | 2002/055012 A2 | 7/2002 |
| WO | 2002/055013 A2 | 7/2002 |
| WO | 2002/055014 A2 | 7/2002 |
| WO | 2002/064096 A2 | 8/2002 |
| WO | 2003/053933 A1 | 7/2003 |
| WO | 2003/075828 A2 | 9/2003 |
| WO | 2004/000820 A2 | 12/2003 |
| WO | 2004/000833 A1 | 12/2003 |
| WO | 2004/017920 A2 | 3/2004 |
| WO | 2004/018452 A1 | 3/2004 |
| WO | 2005/035507 A2 | 4/2005 |
| WO | 2005/037826 A1 | 4/2005 |
| WO | 2005/075461 A1 | 8/2005 |
| WO | 2005/095357 A2 | 10/2005 |
| WO | 2005/112938 A2 | 12/2005 |
| WO | 2006/014136 A1 | 2/2006 |
| WO | 2006/034473 A2 | 3/2006 |
| WO | 2006/040113 A2 | 4/2006 |
| WO | 2006/048330 A1 | 5/2006 |
| WO | 2006/053109 A1 | 5/2006 |
| WO | 2006/065590 A2 | 6/2006 |
| WO | 2006/074057 A2 | 7/2006 |
| WO | 2006/077364 A1 | 7/2006 |
| WO | 2006/077365 A1 | 7/2006 |
| WO | 2006/077366 A1 | 7/2006 |
| WO | 2006/077367 A1 | 7/2006 |
| WO | 2006/077412 A1 | 7/2006 |
| WO | 2006/100212 A1 | 9/2006 |
| WO | 2006/128563 A1 | 12/2006 |
| WO | 2006/138266 A2 | 12/2006 |
| WO | 2007/015064 A1 | 2/2007 |
| WO | 2007/031185 A1 | 3/2007 |
| WO | 2007/042810 A1 | 4/2007 |
| WO | 2007/048924 A1 | 5/2007 |
| WO | 2007/062222 A2 | 5/2007 |
| WO | 2007/070556 A2 | 6/2007 |
| WO | 2007/070600 A2 | 6/2007 |
| WO | 2007/128462 A1 | 11/2007 |
| WO | 2008/005538 A2 | 1/2008 |
| WO | 2008/016300 A2 | 2/2008 |
| WO | 2008/052861 A2 | 5/2008 |
| WO | 2008/064218 A2 | 5/2008 |
| WO | 2008/070661 A1 | 6/2008 |
| WO | 2008/090382 A1 | 7/2008 |
| WO | 2008/098058 A1 | 8/2008 |
| WO | 2008/104994 A2 | 9/2008 |
| WO | 2008/116909 A1 | 10/2008 |
| WO | 2008/116910 A1 | 10/2008 |
| WO | 2008/116911 A1 | 10/2008 |
| WO | 2008/116912 A2 | 10/2008 |
| WO | 2008/116914 A1 | 10/2008 |
| WO | 2008/154221 A2 | 12/2008 |
| WO | 2009/017838 A2 | 2/2009 |
| WO | 2009/099193 A1 | 8/2009 |
| WO | 2009/105881 A1 | 9/2009 |
| WO | 2009/120094 A2 | 10/2009 |

(56) References Cited

FOREIGN PATENT DOCUMENTS

| WO | 2009/125870 A1 | 10/2009 |
|----|----------------|---------|
| WO | 2009/150462 A1 | 12/2009 |
| WO | 2009/152902 A2 | 12/2009 |
| WO | 2010/000396 A1 | 1/2010 |
| WO | 2010/020432 A2 | 2/2010 |
| WO | 2010/026087 A1 | 3/2010 |
| WO | 2010/034707 A1 | 4/2010 |
| WO | 2010/048149 A2 | 4/2010 |
| WO | 2010/052569 A2 | 5/2010 |
| WO | 2010/068863 A2 | 6/2010 |
| WO | 2010/072823 A1 | 7/2010 |
| WO | 2010/120994 A2 | 10/2010 |
| WO | 2010/129053 A2 | 11/2010 |
| WO | 2010/151711 A1 | 12/2010 |
| WO | 2010/151797 A2 | 12/2010 |
| WO | 2011/004162 A2 | 1/2011 |
| WO | 2011/008931 A2 | 1/2011 |
| WO | 2011/026579 A1 | 3/2011 |
| WO | 2011/026835 A1 | 3/2011 |
| WO | 2011/029832 A1 | 3/2011 |
| WO | 2011/060304 A2 | 5/2011 |
| WO | 2011/077043 A2 | 6/2011 |
| WO | 2011/079343 A2 | 7/2011 |
| WO | 2011/109059 A1 | 9/2011 |
| WO | 2011/143365 A1 | 11/2011 |
| WO | 2012/009258 A2 | 1/2012 |
| WO | 2012/016133 A2 | 2/2012 |
| WO | 2012/022487 A1 | 2/2012 |
| WO | 2012/042005 A1 | 4/2012 |
| WO | 2012/052540 A1 | 4/2012 |
| WO | 2012/080729 A2 | 6/2012 |
| WO | 2012/088438 A1 | 6/2012 |
| WO | 2012/109343 A2 | 8/2012 |
| WO | 2012/129562 A2 | 9/2012 |
| WO | 2012/154880 A1 | 11/2012 |
| WO | 2012/154967 A1 | 11/2012 |
| WO | 2012/163489 A1 | 12/2012 |
| WO | 2012/167171 A2 | 12/2012 |
| WO | 2013/033240 A1 | 3/2013 |
| WO | 2013/120040 A1 | 8/2013 |
| WO | 2013/178816 A1 | 12/2013 |
| WO | 2013/190212 A1 | 12/2013 |
| WO | 2014/017938 A2 | 1/2014 |
| WO | 2014/031681 A1 | 2/2014 |
| WO | 2014/031872 A2 | 2/2014 |
| WO | 2014/045031 A1 | 3/2014 |
| WO | 2014/067603 A1 | 5/2014 |
| WO | 2014/078733 A1 | 5/2014 |
| WO | 2014/107622 A1 | 7/2014 |
| WO | 2014/108487 A1 | 7/2014 |
| WO | 2014/134141 A1 | 9/2014 |
| WO | 2014/165827 A1 | 10/2014 |
| WO | 2015/000548 A1 | 1/2015 |
| WO | 2015/003640 A1 | 1/2015 |
| WO | 2015/011284 A2 | 1/2015 |
| WO | 2015/013715 A2 | 1/2015 |
| WO | 2015/031725 A1 | 3/2015 |
| WO | 2015/049034 A1 | 4/2015 |
| WO | 2015/061247 A2 | 4/2015 |
| WO | 2015/069752 A1 | 5/2015 |
| WO | 2015/079028 A1 | 6/2015 |
| WO | 2015/084936 A1 | 6/2015 |
| WO | 2015/154039 A2 | 10/2015 |
| WO | 2016/058544 A1 | 4/2016 |
| WO | 2016/128772 A1 | 8/2016 |
| WO | 2017/044889 A1 | 3/2017 |
| WO | 2017/210545 A1 | 12/2017 |

OTHER PUBLICATIONS

Dorwald F. A. Side Reactions in Organic Synthesis, 2005, Wiley: VCH, Weinheim p. IX of Preface p. 1-15.*

Addolorato et al., Novel therapeutic strategies for alcohol and drug addiction: focus on GABA, ion channels and transcranial magnetic stimulation. Neuropsychopharmacology. Jan. 2012;37(1):163-77.

Boucherat et al., Potassium channels in pulmonary arterial hypertension. Eur Respir J. Oct. 2015;46(4):1167-77.

Cueni et al., T-type Ca2+ channels, SK2 channels and SERCAs gate sleep-related oscillations in thalamic dendrites. Nat Neurosci. Jun. 2008;11(6):683-92.

Kanai et al., Altered axonal excitability properties in amyotrophic lateral sclerosis: impaired potassium channel function related to disease stage. Brain. Apr. 2006;129(Pt 4):953-62.

Kobayashi et al., Effects of nicorandil, a potassium channel opener, on idiopathic ventricular tachycardia. J Am Coll Cardiol. Nov. 1998;32(5):1377-83.

Lei et al., Alterations of A-type potassium channels in hippocampal neurons after traumatic brain injury. J Neurotrauma. Jan. 20, 2012;29(2):235-45.

Liu et al., Modulation of the activity of dopaminergic neurons by SK channels: a potential target for the treatment of Parkinson's disease? Neurosci Bull. Jun. 2010;26(3):265-71.

Tano et al., Calcium-activated potassium channels in ischemia reperfusion: a brief update. Front Physiol. Oct. 6, 2014;5:381. 5 pages.

Waszkielewicz et al., Ion channels as drug targets in central nervous system disorders. Curr Med Chem. 2013;20(10):1241-85.

Windler et al., The Ca21-dependent K1-channel KCa3.1 as a therapeutic target in cardiovascular disease. European Heart Journal Supplements. 2014;16(Suppl A):A30-A32.

Yi et al., Down-regulation of the Small-Conductance Calcium-Activated Potassium Channels in Diabetic Mouse Atria. JBC Papers in Press, published on Jan. 20, 2015 as Manuscript M114.607952, retrieved online at: http://www.jbc.org/cgi/doi/10.1074/jbc.M114.607952. 21 pages, (2015)

Zaki et al., Nicorandil—A Potassium Channel Opener—Ameliorates Overactive Bladder Induced by Type-1 Diabetes in the Male Albino Rats. Med J Cairo Univ. Dec. 2015;83(2):325-332.

Copending U.S. Appl. No. 16/431,212, filed Jun. 4, 2019.

U.S. Appl. No. 15/617,091, filed Jun. 8, 2017, 2017-0355708, Published.

U.S. Appl. No. 15/877,910, filed Jan. 23, 2018, U.S. Pat. No. 9,975,886, Granted.

U.S. Appl. No. 15/938,292, filed Mar. 28, 2018, Pending.

U.S. Appl. No. 15/877,918, filed Jan. 23, 2018, Pending.

U.S. Appl. No. 15/617,091, filed Jun. 8, 2017, US 2017-0355708 A1, Abandoned.

U.S. Appl. No. 15/877,910, filed Jan. 23, 2018, U.S. Pat. No. 9,975,886, Issued.

U.S. Appl. No. 15/938,292, filed Mar. 28, 2018, U.S. Pat. No. 10,351,553, Issued.

U.S. Appl. No. 16/431,212, filed Jun. 4, 2019, Pending.

U.S. Appl. No. 15/877,918, filed Jan. 23, 2018, US 2018-0207138 A1, Abandoned.

Bagal et al., Ion channels as therapeutic targets: a drug discovery perspective. J Med Chem. Feb. 14, 2013;56(3):593-624.

Cao et al., Modulation of recombinant and native neuronal SK channels by the neuroprotective drug riluzole. Eur J Pharmacol. Aug. 2, 2002;449(1-2):47-54.

Kasumu et al., Novel Selective positive modulator of calcium-activated potassium channels exerts beneficial effects in a mouse model of spinocerebellar ataxia type 2. Chem Biol. Oct. 26, 2012;19(10):1340-53.

Nilsson et al., Structural basis for the inhibition of *Mycobacterium tuberculosis* glutamine synthetase by novel ATP-competitive inhibitors. J Mol Biol. Oct. 23, 2009;393(2):504-13.

Rahimi Shourmasti et al., Effects of riluzole on harmaline induced tremor and ataxia in rats: biochemical, histological and behavioral studies. Eur J Pharmacol. Nov. 15, 2012;695(1-3):40-7.

Copending U.S. Appl. No. 15/617,091, filed Jun. 8, 2017.

Copending U.S. Appl. No. 15/938,292, filed Mar. 28, 2018.

Copending U.S. Appl. No. 15/877,918, filed Jan. 23, 2018.

* cited by examiner

POTASSIUM CHANNEL MODULATORS

RELATED APPLICATIONS

This application is a 35 U.S.C. § 371 national stage filing of International Application No. PCT/US2017/035662, filed Jun. 2, 2017, which claims priority to U.S. Provisional Application No. 62/344,513, filed Jun. 2, 2016, and U.S. Provisional Application No. 62/449,309, filed Jan. 23, 2017, the entire contents of each of which are incorporated herein by reference.

BACKGROUND

Among the ion channels, potassium channels are the largest and most diverse, being found in a variety of animal cells such as nervous, muscular, glandular, immune, reproductive, and epithelial tissue. These channels allow the flow of potassium in and/or out of the cell under certain conditions. These channels are regulated, e.g., by calcium sensitivity, voltage-gating, second messengers, extracellular ligands, and ATP-sensitivity.

Dysfunction of potassium channels, as well as other ion channels, generates loss of cellular control and results in altered physiological functioning and disease conditions. Because of their ability to modulate ion channel function and/or regain ion channel activity in acquired or inherited channelopathies, potassium channel modulators are being used in the pharmacological treatment of a wide range of pathological diseases and have the potential to address an even wider variety of therapeutic indications.

The small conductance calcium-activated potassium channels (SK channel) are a subfamily of $Ca^{2+}$-activated $K^+$ channels and the SK channel family contains 4 members—SK1, SK2, SK3, and SK4 (often referred to as intermediate conductance). The physiological roles of the SK channels have been especially studied in the nervous system, where for example they are key regulators of neuronal excitability and of neurotransmitter release, and in smooth muscle, where they are crucial in modulating the tone of vascular, broncho-tracheal, urethral, uterine or gastro-intestinal musculature.

Given these implications, small molecule modulators of potassium ion channels could have potentially powerful influence in the modulation and control of numerous consequences of a variety of conditions.

SUMMARY

Disclosed are compounds and pharmaceutically acceptable salts thereof, and pharmaceutical compositions thereof, which are useful in the treatment of diseases associated with the modulation of ion channels, such as potassium ion channels. (See e.g., Table 2). Such compounds include those of structural Formula I:

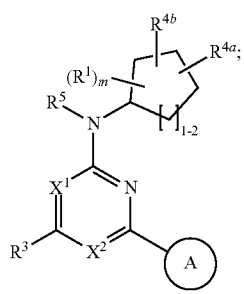

or a pharmaceutically acceptable salt thereof, wherein each of $R^1$, $R^3$, $R^5$, $R^{4a}$, $R^{4b}$, $X^1$, $X^2$, and A are defined and described herein.

Compounds described herein, and pharmaceutically acceptable compositions thereof, are useful for treating a variety of diseases, disorders or conditions, associated with the modulation of potassium channels. Such diseases, disorders, or conditions include those described herein.

DETAILED DESCRIPTION

Figure 1:
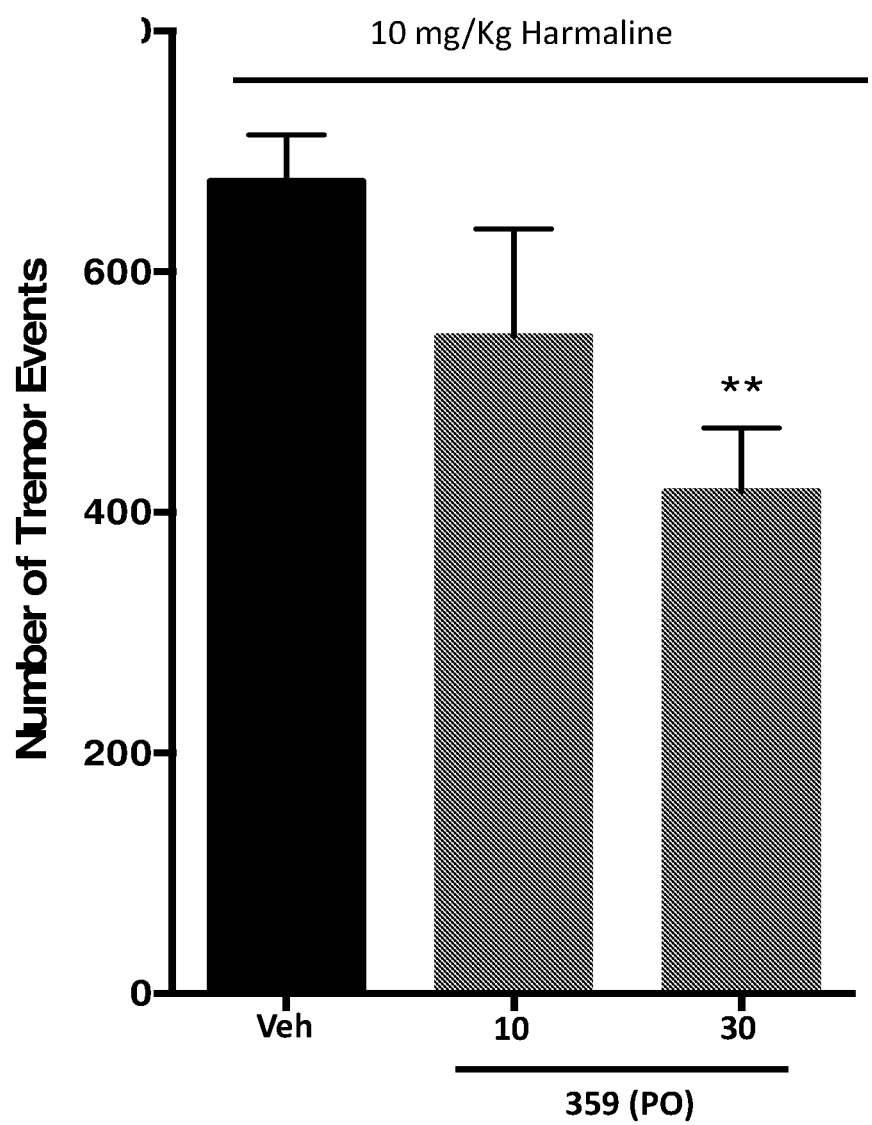
FIG. 1 is a diagram illustrating the effect of Compound 359 following oral (PO) dosing on harmaline induced tremor.

I. General Description of Compounds of the Invention

In certain embodiments, provided herein is a compound of Formula I:

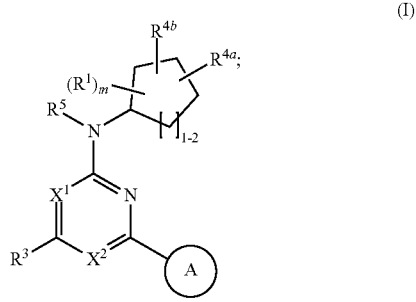

or a pharmaceutically acceptable salt thereof, wherein:
  ring A is selected from

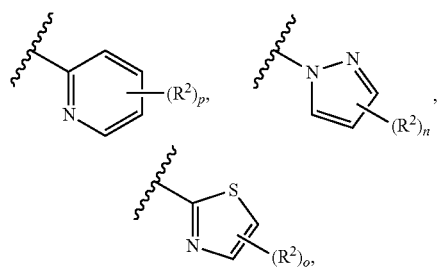

and

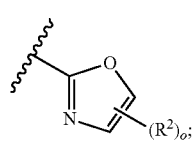

$X^1$ is selected from $C(R^a)$ and N;
$X^2$ is selected from $C(R^b)$ and N, wherein $X^1$ and $X^2$ are not simultaneously nitrogen;

each of $R^a$ and $R^b$ is independently selected from hydrogen, halo, —CN, optionally substituted $C_1$-$C_4$ alkyl, optionally substituted —O—($C_1$-$C_4$ alkyl), —OH, —NH$_2$, optionally substituted —NH($C_1$-$C_4$ alkyl), optionally substituted —N($C_1$-$C_4$ alkyl)$_2$, optionally substituted —S—($C_1$-$C_4$ alkyl), and optionally substituted —S(O)$_2$—$C_1$-$C_4$ alkyl;

each $R^1$, if present, is independently selected from halo, —CN, optionally substituted —$C_1$-$C_6$ alkyl, optionally substituted —O—($C_1$-$C_4$ alkyl), optionally substituted —NH($C_1$-$C_4$ alkyl), optionally substituted —N($C_1$-$C_4$ alkyl)$_2$, optionally substituted —S—($C_1$-$C_4$ alkyl), optionally substituted —S(O)—($C_1$-$C_4$ alkyl), and optionally substituted —S(O)$_2$—$C_1$-$C_4$ alkyl;

each $R^2$ is independently selected from halo, —CN, optionally substituted $C_3$-$C_6$ cycloalkyl, optionally substituted —$C_1$-$C_6$ alkyl, optionally substituted —O—($C_1$-$C_4$ alkyl), optionally substituted —NH($C_1$-$C_4$ alkyl), optionally substituted —S—($C_1$-$C_4$ alkyl), optionally substituted —S(O)—($C_1$-$C_4$ alkyl), and optionally substituted —S(O)$_2$—$C_1$-$C_4$ alkyl;

$R^3$ is selected from halo, —C(=O)NH$_2$, —OH, —CN, —($C_0$-$C_4$ alkylene)-carbocyclyl, —($C_0$-$C_4$ alkylene)-heteroaryl, —($C_0$-$C_4$ alkylene)-heterocyclyl, —($C_0$-$C_4$ alkylene)-aryl, —N($R^6$)-carbocyclyl, —N($R^6$)-heterocyclyl, —N($R^6$)-heteroaryl, —N($R^6$)-aryl, —O($C_0$-$C_4$ alkyl)carbocyclyl, —O($C_0$-$C_4$ alkylene)heterocyclyl, —O($C_0$-$C_4$ alkylene)heteroaryl, —O($C_0$-$C_4$ alkylene)aryl, —S($C_0$-$C_4$ alkylene)carbocyclyl, —S($C_0$-$C_4$ alkylene)heterocyclyl, —S($C_0$-$C_4$ alkylene)heteroaryl, —S($C_0$-$C_4$ alkylene)aryl, —S(O)($C_0$-$C_4$ alkylene)carbocyclyl, —S(O)($C_0$-$C_4$ alkylene)heterocyclyl, —S(O)($C_0$-$C_4$ alkylene)heteroaryl, —S(O)($C_0$-$C_4$ alkylene)aryl, —S(O)$_2$($C_0$-$C_4$ alkylene)carbocyclyl, —S(O)$_2$($C_0$-$C_4$ alkylene)heterocyclyl, —S(O)$_2$($C_0$-$C_4$ alkylene)heteroaryl, —S(O)$_2$($C_0$-$C_4$ alkylene)aryl, —O—($C_1$-$C_4$ alkyl), —NH($C_1$-$C_4$ alkyl), —S—($C_1$-$C_4$ alkyl), —S(O)—($C_1$-$C_4$ alkyl), —S(O)$_2$—($C_1$-$C_4$ alkyl), and —$C_1$-$C_6$ alkyl, wherein each instance of said heterocyclyl, carbocyclyl, heteroaryl, aryl, alkylene, and alkyl are optionally substituted; or $R^3$ and $R^a$ or $R^3$ and $R^b$ taken together with the atoms they are attached form an optionally substituted 5-6 membered heterocyclyl or carbocyclyl;

$R^{4a}$ is selected from fluoro and —CF$_3$;

$R^{4b}$ is selected from hydrogen and fluoro;

$R^5$ is selected from hydrogen and optionally substituted $C_1$-$C_4$ alkyl;

each $R^6$ is independently selected from hydrogen and optionally substituted $C_1$-$C_4$ alkyl;

m is 0, 1, 2, 3, 4, 5, 6, 7, 8, or 9;

n is 1, 2 or 3;

o is 1 or 2; and p is 1, 2, 3 or 4, provided the compound of Formula I is not

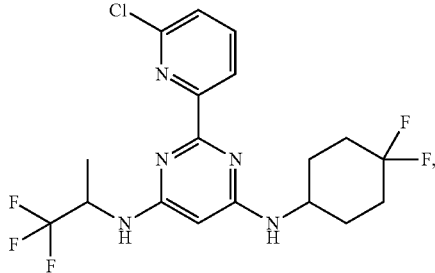 [SMILES: CC(Nc1cc(NC2CCC(F)(F)CC2)nc(-c2cccc(Cl)n2)n1)C(F)(F)F]

or a pharmaceutically acceptable salt thereof.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl" used alone or as part of a larger moiety, such as "alkoxy", "haloalkyl", "aralkyl", "heteroaralkyl" and the like, means saturated straight-chain or branched monovalent hydrocarbon radical. Unless otherwise specified, an alkyl group typically has 1-6 carbon atoms, i.e., ($C_1$-$C_6$)alkyl. As used herein, a "($C_1$-$C_6$)alkyl" group is means a radical having from 1 to 6 carbon atoms in a linear or branched arrangement.

The term "haloalkyl" includes mono, poly, and perhaloalkyl groups where the halogens are independently selected from fluorine, chlorine, bromine, and iodine.

"Alkoxy" means an alkyl radical attached through an oxygen linking atom, represented by —O-alkyl. For example, "($C_1$-$C_4$)alkoxy" includes methoxy, ethoxy, proproxy, and butoxy.

The term "aryl" used alone or as part of a larger moiety as in "aralkyl", "aralkoxy", or "aryloxyalkyl", refers to an aromatic monocyclic or bicyclic carbon ring system having, unless otherwise specified, a total of 6 to 14 ring members. The term "aryl" may be used interchangeably with the term "aryl ring", "aryl group", "aryl moiety," or "aryl radical". Also included within the scope of the term "aryl", as it is used herein, is a group in which an aromatic carbon ring is fused to one or more carbocyclyl rings, e.g., tetrahydronaphthalenyl. In certain embodiments of the present disclosure, "aryl" refers to an aromatic ring system which includes, but is not limited to, phenyl (abbreviated as "Ph"), naphthyl and the like. It will be understood that when specified, optional substituents on an aryl group (e.g., in the case of an optionally substituted aryl or aryl which is optionally substituted) may be present on any substitutable position, i.e., any ring carbon substituted with hydrogen.

The term "carbocyclyl" (also referred to herein as "carbocycle" or "cycloaliphatic", as used herein, means a monocyclic, bicyclic (e.g., a bridged or spiro bicyclic ring), polycyclic (e.g., tricyclic), or fused hydrocarbon ring system that is completely saturated or that contains one or more units of partial unsaturation, but where there is no aromatic ring. Cycloalkyl is a completely saturated carbocycle. Monocyclic carbocyclyl groups include, without limitation, cyclopropyl, cyclobutyl, cyclopentyl, cyclopentenyl, cyclohexyl, cyclohexenyl, cycloheptyl, cycloheptenyl, and cyclooctyl. Bridged bicyclic carbocyclyl groups include, without limitation, bicyclo[3.2.1]octane, bicyclo[2.2.1]heptane, bicyclo[3.1.0]hexane, and the like. Spiro bicyclic carbocyclyl groups include, e.g., spiro[3.6]decane, spiro[4.5]decane, and the like. Fused carbocyclyl rings include, e.g., decahydronaphthalene, octahydropentalene, and the like. It will be understood that when specified, optional substituents on a carbocyclyl (e.g., in the case of an optionally substituted carbocyclyl or carbocyclyl which is optionally substituted) may be present on any substitutable position and, include, e.g., the position at which the carbocyclyl group is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, quaternary ammonium cation, O, and S, and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". Nonlimiting examples include indolyl, indazolyl, benzimidazolyl, benzthiazolyl, pyrrolopyridinyl, quinolyl, quinazolinyl, and quinoxalinyl. It will be understood that when specified, optional substituents on a heteroaryl group may be present on any substitutable position (carbon and nitrogen).

The term "heterocyclyl" means a 3-12 membered (e.g., a 4-, 5-, 6- and 7-membered) saturated or partially unsaturated heterocyclic ring containing 1 to 4 heteroatoms independently selected from N, O, and S. It can be monocyclic, bicyclic (e.g., a bridged, fused, or spiro bicyclic ring), or tricyclic. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, 3-azabicyclo[3.1.0]hexanyl, 2-oxa-6-azaspiro[3.3]heptanyl, 1-azaspiro[4.5]decane, and tetrahydropyrimidinyl. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached (e.g., in the case of an optionally substituted heterocyclyl or heterocyclyl which is optionally substituted).

The term "spiro" refers to two rings that share one ring atom (e.g., carbon).

The term "fused" refers to two rings that share two adjacent ring ring atoms.

The term "bridged" refers to two rings that share at least three ring atoms.

As described herein, compounds herein may contain "optionally substituted" moieties. Unless otherwise indicated, an "optionally substituted" group may have a suitable substituent that results in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In one embodiment, suitable substituents for an optionally substituted alkyl, carbocyclyl, heterocyclyl, aryl group and heteroaryl group are those which do not substantially diminish the potassium ion channel activity of the compound. Examples include halogen, CN, —OR$^c$, —NR$^d$R$^e$, —S(O)$_j$R$^c$, —NR$^c$S(O)$_2$R$^c$, —S(O)$_2$NR$^d$R$^e$, —C(=O)OR$^c$, —OC(=O)OR$^c$, —OC(=O)R$^c$, —OC(=S)OR$^c$, —C(=S)OR$^c$, —O(C=S)R$^c$, —C(=O)NR$^d$R$^e$, —NR$^c$C(=O)R$^c$, —C(=S)NR$^d$R$^e$, —NR$^c$C(=S)R$^c$, —NR$^c$(C=O)OR$^c$, —O(C=O)NR$^d$R$^e$, —NR$^c$(C=S)OR$^c$, —O(C=S)NR$^d$R$^e$, —NR$^c$(C=O)NR$^d$R$^e$, —NR$^c$(C=S)NR$^d$R$^e$, —C(=S)R$^c$, —C(=O)R$^c$, (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —NHC(=O)-heterocyclyl, —NHC(=O)-cycloalkyl, —(CH$_2$)$_{1-4}$-aryl, heteroaryl or —(CH$_2$)$_{1-4}$-heteroaryl, wherein each of said (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl are optionally substituted with halogen, OR$^c$, —NO$_2$, —CN, —NR$^c$C(=O)R$^c$, —NR$^d$R$^e$, —S(O)$_k$R$^c$, —C(=O)OR$^c$, —C(=O)NR$^d$R$^e$, —C(=O)R$^c$, (C$_1$-C$_3$)alkyl, halo(C$_1$-C$_3$) alkyl, (C$_1$-C$_3$)alkoxy(C$_1$-C$_3$)alkyl, (C$_1$-C$_3$)alkoxy, and halo (C$_1$-C$_3$)alkoxy, wherein R$^c$ is hydrogen or (C$_1$-C$_6$)alkyl optionally substituted with 1 to 3 halogen; R$^d$ and R$^e$ are each independently selected from hydrogen and (C$_1$-C$_6$) alkyl; and k is 0, 1 or 2. Suitable substituents for optionally substituted alkyl, carbocyclyl, and heterocyclyl also include =O.

In another embodiment, suitables substituents are selected from halo, —NHC(=O)O(C$_1$-C$_4$ alkyl), —NHC(=O)—C$_1$-C$_4$ alkyl, —CN, —NHC(=O)-cyclobutyl, —NHC(=O)-oxetanyl, C=O, —C(=O)NR$^d$R$^e$, —C(=O)R$^c$, OR$^c$, —C(=O)OR$^c$, —NR$^d$R$^e$, or (C$_1$-C$_4$)alkyl optionally substituted with —C(=O)OR$^c$ or OR$^c$, wherein R$^c$ is hydrogen or (C$_1$-C$_4$)alkyl optionally substituted with 1 to 3 halogen; and R$^d$ and R$^e$ are each independently selected from hydrogen and (C$_1$-C$_4$)alkyl.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" or "therapeutically effective amount" includes an amount of a compound described herein that will elicit a biological or medical response of a subject.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. "Geometric isomer" are stereoisomers that differ in the orientation of substituent atoms in relationship to a carbon-carbon double bond, to a carbocyclyl ring, or to a bridged bicyclic system.

"Racemate" or "racemic mixture" means a compound of equimolar quantities of two enantiomers, wherein such mixtures exhibit no optical activity, i.e., they do not rotate the plane of polarized light.

The compounds of the invention may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisiomer over the weight of the the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical and geometric isomer, a racemic mixture of the compound, and mixtures enriched in one enantiomer relative to its corresponding optical isomer.

When a disclosed compound is named or depicted by structure without indicating the stereochemistry and e.g, the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

With respect to the generic Formula I, Ia, II, III, IV, V, VI, and VII, unless otherwise specified, one or more hydrogens can be replaced by deuterium. Isotopic enrichments include e.g., at least 10%, 25%, 50%, 75%, 80%, 85%, 90&, 95%, 87%, 98%, 99.0%, 99.5% and 99.8%". In one embodiment, all hydrogen atoms represented in Formula I, Ia, II, III, IV, V, VI, and VII are present in natural abundance. With respect to specific compounds disclosed herein, such as those in Table 1 and in the Exemplification section, all hydrogen atoms are present in natural abundance unless otherwise specified.

The compounds described herein may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

3. Description of Exemplary Compounds

In a first embodiment, the present disclosure provides a compound of Formula I:

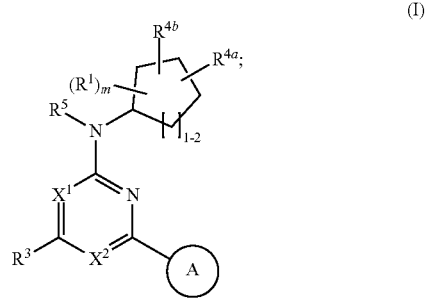

or a pharmaceutically acceptable salt thereof, wherein the variables are as described above.

In a second embodiment, the compound of Formula I is of the Formula Ia:

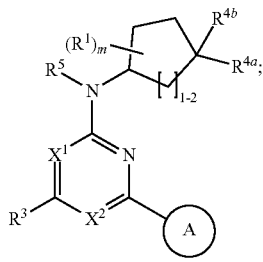

or a pharmaceutically acceptable salt thereof, wherein the variables in Formula Ia are as described in Formula I.

In a third embodiment, the compound of Formula I or Formula Ia is of the Formula II or III:

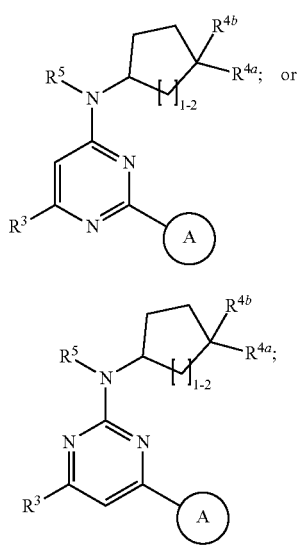

or a pharmaceutically acceptable salt thereof, wherein the variables in Formula II and III are as described in Formula I. In one alternative to the second embodiment, the optional substituents for each occurrence of an optionally group for the compounds of Formulas I, Ia, II, or III are 1 to 3 groups independently selected from $R^7$ as defined in the sixth embodiment.

In a fourth embodiment, $R^3$ in Formulas I, Ia, II, or III is selected from —C(=O)NH$_2$, —(C$_0$-C$_4$ alkylene)-heteroaryl, —(C$_0$-C$_4$ alkylene)-aryl, —N(R$^6$)-carbocyclyl, —N(R$^6$)-heterocyclyl, —N(R$^6$)-heteroaryl, —N(R$^6$)-aryl, —O(C$_0$-C$_4$ alkylene)carbocyclyl, —O(C$_0$-C$_4$ alkylene)heterocyclyl, —O(C$_0$-C$_4$ alkylene)heteroaryl, —O(C$_0$-C$_4$ alkylene)aryl, —S(C$_0$-C$_4$ alkylene)carbocyclyl, —S(C$_0$-C$_4$ alkylene)heterocyclyl, —S(C$_0$-C$_4$ alkylene)heteroaryl, —S(C$_0$-C$_4$ alkylene)aryl, —S(O)(C$_0$-C$_4$ alkylene)carbocyclyl, —S(O)(C$_0$-C$_4$ alkylene)heterocyclyl, —S(O)(C$_0$-C$_4$ alkylene)heteroaryl, —S(O)(C$_0$-C$_4$ alkylene)aryl, —S(O)$_2$(C$_0$-C$_4$ alkylene)carbocyclyl, —S(O)$_2$(C$_0$-C$_4$ alkylene)heterocyclyl, —S(O)$_2$(C$_0$-C$_4$ alkylene)heteroaryl, —S(O)$_2$(C$_0$-C$_4$ alkylene)aryl, —NH(C$_1$-C$_4$ alkyl), —S—(C$_1$-C$_4$ alkyl), —S(O)—(C$_1$-C$_4$ alkyl), —S(O)$_2$—(C$_1$-C$_4$ alkyl), and —C$_1$-C$_6$ alkyl, wherein each instance of said heterocyclyl, carbocyclyl, heteroaryl, aryl, C$_1$-C$_4$ alkylene, and C$_1$-C$_4$ alkyl are optionally substituted, and wherein said (C$_1$-C$_6$)alkyl is substituted with —NH$_2$, —N(C$_1$-C$_4$ alkyl)$_2$, —NHC(=O)—O—(C$_1$-C$_4$ alkyl), —NHC(=O)—(C$_1$-C$_4$ alkyl), —CN, —NHC(=O)-cycloalkyl, —NHC(=O)-heterocyclyl, —OH, or —O(C$_1$-C$_4$ alkyl); or $R^3$ and $R^a$ or $R^3$ and $R^b$ taken together with the atoms they are attached form an optionally substituted 5-6 membered heterocyclyl or carbocyclyl, wherein the remaining variables are as described in Formula I or the second or third embodiment.

In a fifth embodiment, $R^3$ in Formulas I, Ia, II, or III is selected from —C(=O)NH$_2$, —(C$_0$-C$_4$ alkylene)-heteroaryl, —(C$_0$-C$_4$ alkylene)-aryl, —O(C$_0$-C$_4$ alkylene)carbocyclyl, —O(C$_0$-C$_4$ alkylene)heterocyclyl, —O(C$_0$-C$_4$ alkylene)heteroaryl, —O(C$_0$-C$_4$ alkylene)aryl, —S(C$_0$-C$_4$ alkylene)carbocyclyl, —S(C$_0$-C$_4$ alkylene)heterocyclyl, —S(C$_0$-C$_4$ alkylene)heteroaryl, —S(C$_0$-C$_4$ alkylene)aryl, —S(O)(C$_0$-C$_4$ alkylene)carbocyclyl, —S(O)(C$_0$-C$_4$ alkylene)heterocyclyl, —S(O)(C$_0$-C$_4$ alkylene)heteroaryl, —S(O)(C$_0$-C$_4$ alkylene)aryl, —S(O)$_2$(C$_0$-C$_4$ alkylene)carbocyclyl, —S(O)$_2$(C$_0$-C$_4$ alkylene)heterocyclyl, —S(O)$_2$(C$_0$-C$_4$ alkylene)heteroaryl, —S(O)$_2$(C$_0$-C$_4$ alkylene)aryl, —S—(C$_1$-C$_4$ alkyl), —S(O)—(C$_1$-C$_4$ alkyl), —S(O)$_2$—(C$_1$-C$_4$ alkyl), and —C$_1$-C$_6$ alkyl, wherein each of said heterocyclyl, carbocyclyl, heteroaryl, aryl, C$_1$-C$_4$ alkylene, and C$_1$-C$_4$ alkyl are optionally substituted, and wherein said (C$_1$-C$_6$)alkyl is substituted with —NH$_2$, —N(C$_1$-C$_4$ alkyl)$_2$, —NHC(=O)—O—(C$_1$-C$_4$ alkyl), NHC(=O)—(C$_1$-C$_4$ alkyl), —CN, —NHC(=O)-cycloalkyl, —NHC(=O)-heterocyclyl, —OH, or —O(C$_1$-C$_4$ alkyl); or $R^3$ and $R^a$ or $R^3$ and $R^b$ taken together with the atoms they are attached form an optionally substituted 5-6 membered heterocyclyl or carbocyclyl, wherein the remaining variables are as described in Formula I or the second, third or fourth embodiment.

In a sixth embodiment, each of said heterocyclyl, heteroaryl, carbocyclyl, aryl, C$_1$-C$_4$ alkylene, and C$_1$-C$_4$ alkyl for $R^3$ in the first, second, third, or fourth embodiment are optionally substituted with 1 to 3 groups independently selected from $R^7$, where $R^7$ is halogen, CN, —OR$^c$, —NR$^d$R$^e$, —S(O)$_k$R$^c$, —NR$^c$S(O)$_2$R$^c$, —S(O)$_2$NR$^d$R$^e$, —C(=O)OR$^c$, —OC(=O)OR$^c$, —OC(=O)R$^c$, —OC(=S)OR$^c$, —C(=S)OR$^c$, —OC(=S)R$^c$, —C(=O)NR$^d$R$^e$, —NR$^c$C(=O)R$^c$, —C(=S)NR$^d$R$^e$, —NR$^c$C(=S)R$^c$, —NR$^c$C(=O)OR$^c$, —O(C=O)NR$^d$R$^e$, —NR$^c$C(=S)OR$^c$, —O(C=S)NR$^d$R$^e$, —NR$^c$C(=O)NR$^d$R$^e$, —NR$^c$C(=S)NR$^d$R$^e$, —C(=S)R$^c$, —C(=O)R$^c$, (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl or —(CH$_2$)$_{1-4}$-heteroaryl, wherein each of said (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl for $R^7$ are optionally substituted with halogen, OR$^c$, —NO$_2$, —CN, —NR$^c$C(=O)R$^c$, —NR$^d$R$^e$, —S(O)$_k$R$^c$, —C(=O)OR$^c$, —C(=O)NR$^d$R$^e$, —C(=O)R$^c$, (C$_1$-C$_3$)alkyl, halo(C$_1$-C$_3$)alkyl, (C$_1$-C$_3$)alkoxy(C$_1$-C$_3$)alkyl, (C$_1$-C$_3$)alkoxy, and halo(C$_1$-C$_3$)alkoxy; or two instances of $R^7$ are taken together on the same atom to form =O; $R^c$ is hydrogen or (C$_1$-C$_6$)alkyl optionally substituted with 1 to 3 halogen; $R^d$ and $R^e$ are each independently selected from hydrogen and (C$_1$-C$_6$)alkyl; and k is 0, 1 or 2, wherein the remaining variables are as described in Formula I or the second, third, fourth, or fifth embodiment.

In a seventh embodiment, $R^3$ in Formulas I, Ia, II, or III is selected from 1) piperizinyl, 2-oxa-6-azaspiro[3.3]heptan-6-yl, morpholinyl, azetidinyl, pyrazolyl, 4,5-dihydro-1,2,4-oxadiazolyl, 1,2,4-oxadiazolyl, tetrahydropyranyl, 2,5-diazabicyclo[2.2.1]heptanyl, and 3-azabicyclo[3.1.0]hexanyl, each of which is optionally substituted with 1 to 3 groups selected from $R^7$; 2) —S—(C$_1$-C$_2$ alkyl), —O—(C$_1$-C$_2$ haloalkyl), —C(=O)NH$_2$, —(C$_1$-C$_2$ alkylene)-morpholinyl, —(C$_1$-C$_2$ alkylene)-piperazinyl, —O(C$_1$-C$_2$ alkylene)azetidinyl, —O(C$_1$-C$_2$ alkylene)triazolyl, —O(C$_1$-C$_2$ alkylene)pyrrolidinyl, —O(C$_1$-C$_2$ alkylene)oxadiazole, —O(C$_1$-C$_2$ alkylene)thiomorpholinyl, —O(C$_1$-C$_2$ alkylene)thiomorpholinyl-1,1-dioxide, —O(C$_1$-C$_2$ alkylene)oxazolyl, —O(C$_1$-C$_2$ hydroxyalkylene)oxazolyl, —O(C$_1$-C$_2$ alkylene)phenyl, and —O(C$_1$-C$_2$ alkylene)cyclobutyl each of said morpholinyl, piperazinyl, azetidinyl, triazolyl, pyrrolidinyl, oxadiazole, thiomorpholinyl, thiomorpholinyl-1,1-dioxide, oxazolyl, phenyl, and cyclobutyl being optionally substituted with 1 to 3 groups selected from $R^7$; and 3) (C$_1$-C$_4$) alkyl substituted with —NH$_2$, —N(C$_1$-C$_4$ alkyl)$_2$, —NHC(=O)O(C$_1$-C$_4$ alkyl), —NHC(=O)—C$_1$-C$_4$ alkyl, —CN, —NHC(=O)-cyclobutyl, —NHC(=O)-oxetanyl, —OH, or —O(C$_1$-C$_4$ alkyl); $R^7$ is halo, —C(=O)NR$^d$R$^e$, —C(=O)R$^c$, OR$^c$, —C(=O)OR$^c$, —NR$^d$R$^e$, or (C$_1$-C$_4$)alkyl optionally substituted with —C(=O)OR$^c$ or OR$^c$; or two instances of R$^7$ are taken together on the same atom to form =O; R$^c$ is hydrogen or (C$_1$-C$_4$)alkyl optionally substituted with 1 to 3 halogen; R$^d$ and R$^e$ are each independently selected from hydrogen and (C$_1$-C$_4$)alkyl, wherein the remaining variables are as described in Formula I or the second, third, fourth, fifth, or sixth embodiment.

In an eighth embodiment, R$^3$ in Formulas I, Ia, II, or III is selected from 1) piperizinyl, 2-oxa-6-azaspiro[3.3]heptan-6-yl, morpholinyl, azetidinyl, pyrazolyl, 4,5-dihydro-1,2,4-oxadiazolyl, 1,2,4-oxadiazolyl, tetrahydropyranyl, 2,5-diazabicyclo[2.2.1]heptanyl, and 3-azabicyclo[3.1.0]hexanyl, each of which is optionally substituted with 1 to 2 groups selected from R$^7$; 2) —S—(C$_1$-C$_2$ alkyl), —O—(C$_1$-C$_2$ haloalkyl), —C(=O)NH$_2$, —(C$_1$-C$_2$ alkylene)-morpholinyl, —(C$_1$-C$_2$ alkylene)-piperazinyl, —O(C$_1$-C$_2$ alkylene) azetidinyl, —O(C$_1$-C$_2$ alkylene)triazolyl, —O(C$_1$-C$_2$ alkylene)pyrrolidinyl, —O(C$_1$-C$_2$ alkylene)oxadiazole, —O(C$_1$-C$_2$ alkylene)thiomorpholinyl, —O(C$_1$-C$_2$ alkylene) thiomorpholinyl-1,1-dioxide, —O(C$_1$-C$_2$ alkylene)oxazolyl, —O(C$_1$-C$_2$ hydroxyalkylene)oxazolyl, —O(C$_1$-C$_2$ alkylene) phenyl, and —O(C$_1$-C$_2$ alkylene)cyclobutyl, each of said azetidinyl, triazolyl, pyrrolidinyl, oxadiazole, phenyl, and cyclobutyl being optionally substituted with 1 to 2 groups selected from R$^7$; and 3) (C$_1$-C$_4$)alkyl substituted with —NH$_2$, —N(C$_1$-C$_4$ alkyl)$_2$, —NHC(=O)O—C$_1$-C$_4$ alkyl, —NHC(=O)—C$_1$-C$_4$ alkyl, —CN, —NHC(=O)-cyclobutyl, —NHC(=O)-oxetanyl, —OH, or —O(C$_1$-C$_4$ alkyl), wherein the remaining variables are as described in Formula I or the second, third, fourth, fifth, sixth, or seventh embodiment.

In a ninth embodiment, R$^2$ in Formulas I, Ia, II, or III is independently selected from halo, —CN, —O(C$_1$-C$_4$ alkyl), C$_1$-C$_4$ alkyl, C$_3$-C$_4$ cycloalkyl, cyanoC$_1$-C$_4$ alkyl, haloC$_1$-C$_4$ alkyl, and hydroxyC$_1$-C$_4$ alkyl, wherein the remaining variables are as described in Formula I or Formula Ia, or the second, third, fourth, fifth, sixth, seventh, or eighth embodiment. Alternatively, R$^2$ in Formulas I, Ia, II, or III is independently selected from chloro, bromo, fluoro, —CN, —CH$_3$, —CH$_2$F, —CHF$_2$, —CF$_3$, —CH$_2$OH, —CH$_2$CH$_3$, —CH$_2$CN, —CH(CH$_3$)CH$_3$, —CH(CH$_3$)OH, —C((CH$_3$)$_2$) OH, —OCH$_3$, and cyclopropyl, wherein the remaining variables are as described in Formula I or the second, third, fourth, fifth, sixth, seventh, or eighth embodiment.

In a tenth embodiment, each of n, o, and p in Formulas I, Ia, II, or III is 1 or 2, wherein the remaining variables are as described in Formula I or the second, third, fourth, fifth, sixth, seventh, eighth, or ninth embodiment.

In an eleventh embodiment, each of R$^a$ and R$^b$ in Formula I or Formula Ia is independently selected from hydrogen and C$_1$-C$_4$ alkyl, or wherein R$^3$ and R$^a$ or R$^3$ and R$^b$ taken together with the atoms they are attached form an optionally substituted 5-6 membered, nitrogen-containing heterocyclyl, wherein the remaining variables are as described in Formula I or the fourth, fifth, sixth, seventh, eighth, ninth, or tenth embodiment.

In a twelfth embodiment, R$^a$ in Formula I or Formula Ia is selected from hydrogen, methyl, and ethyl; or R$^a$ and R$^3$ are taken together with the atoms they are attached form an optionally substituted piperidinyl or an optionally substituted 1H-imidazolyl, wherein the remaining variables are as described in Formula I or Formula Ia, or the fourth, fifth, sixth, seventh, eighth, ninth, tenth, or eleventh embodiment. In one alternative, the piperidinyl or 1H-imidazolyl in the eleventh embodiment is optionally substituted at a ring nitrogen, wherein the remaining variables are as described in Formula I or Formula Ia, or the fourth, fifth, sixth, seventh, eighth, ninth, tenth, or eleventh embodiment.

In a thirteenth embodiment, R$^3$ in Formulas I, Ia, II, or III is selected from halo, —CN, alkyl, —NH—(C$_1$-C$_6$ alkyl), alkyl-NH(R$^7$), —C(O)NH(R$^7$), carbocyclyl, heterocyclyl, —O-heterocyclyl, —NH-heterocyclyl, —O-alkylene-heterocyclyl, —O-alkylene-carbocyclyl, —NH-alkylene-carbocyclyl, and —NH-alkylene-heterocyclyl, or R$^3$ is taken together with R$^a$ to form an optionally substituted heterocyclyl, wherein R$^7$ is selected from hydrogen and C$_1$-C$_4$ alkyl; and any alkyl, alkylene, carbocyclyl, or heterocyclyl portion of R$^3$ is optionally substituted, wherein the remaining variables are as described in Formula I or the second, third, ninth, tenth, eleventh, or twelfth embodiment. Alternatively, R$^3$ in Formulas I, Ia, II, or III is selected from:

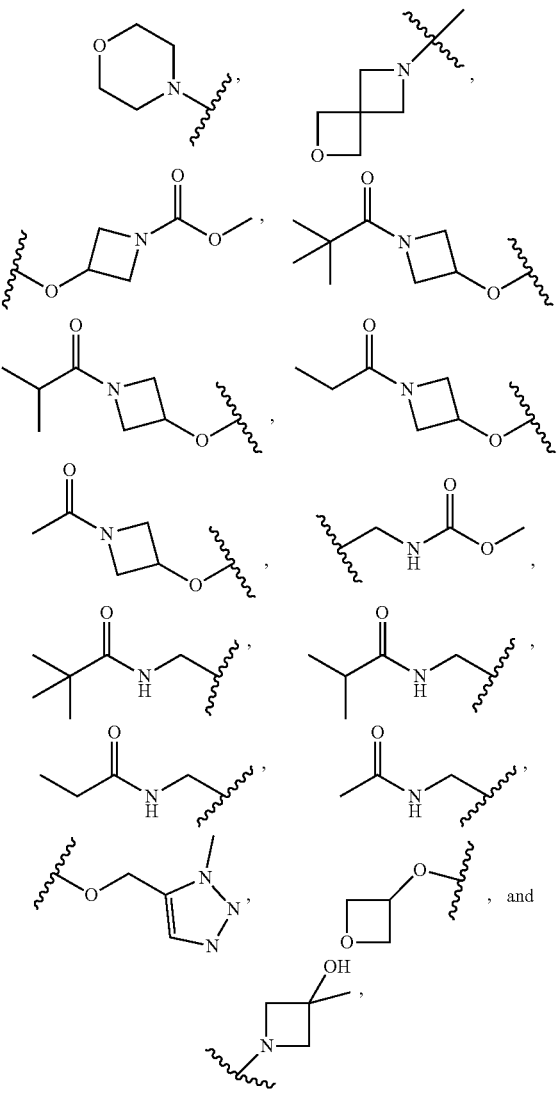

wherein the remaining variables are as described in Formula I or the second, third, fourth, fifth, sixth, seventh, eighth, ninth, tenth, eleventh, or twelfth embodiment.

In a fourteenth embodiment, R$^5$ in Formulas I, Ia, II, or III is selected from hydrogen, methyl and ethyl, wherein the remaining variables are as described in Formula I or the second, third, fourth, fifth, sixth, seventh, eighth, ninth, tenth, eleventh, twelfth, or thirteenth embodiment.

In a fifteenth embodiment, $R^{4a}$ and $R^{4b}$ in Formulas I, Ia, II, or III are simultaneously fluoro, wherein the remaining variables are as described in Formula I or the second, third, fourth, fifth, sixth, seventh, eighth, ninth, tenth, eleventh, twelfth, thirteenth, or fourteenth embodiment. Alternatively, $R^{4a}$ is —$CF_3$ and $R^{4b}$ hydrogen in Formulas I, Ia, II, or III are simultaneously fluoro, wherein the remaining variables are as described in Formula I or the second, third, fourth, fifth, sixth, seventh, eighth, ninth, tenth, eleventh, twelfth, thirteenth, or fourteenth embodiment.

In a sixteenth embodiment, m in Formulas I, Ia, II, or III is 0, wherein the remaining variables are as described in Formula I or the second, third, fourth, fifth, sixth, seventh, eighth, ninth, tenth, eleventh, twelfth, thirteenth, fourteenth, or fifteenth embodiment.

In a seventeenth embodiment, $R^3$ in Formulas I, Ia, II, or III is selected from:

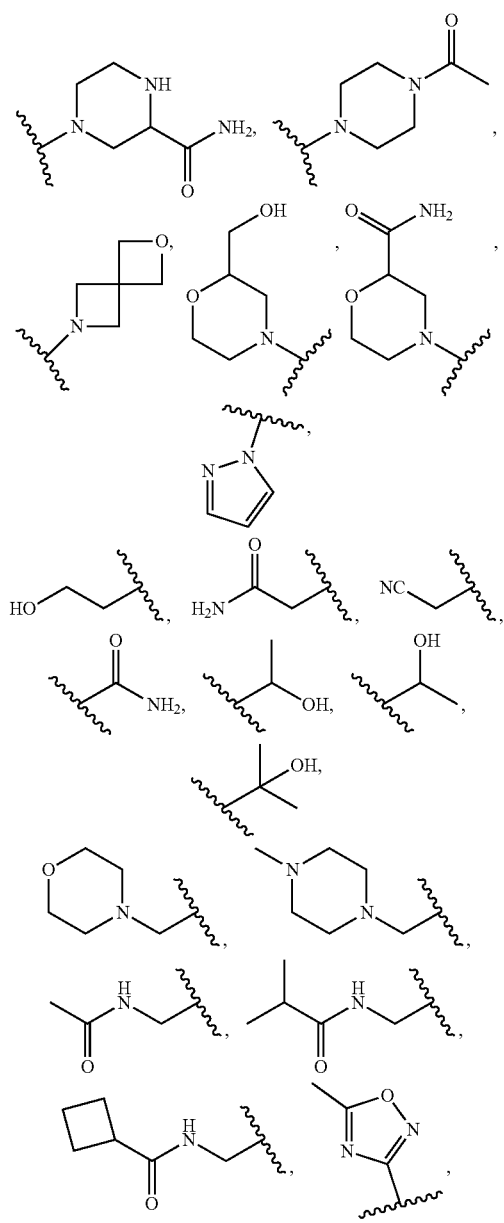

-continued

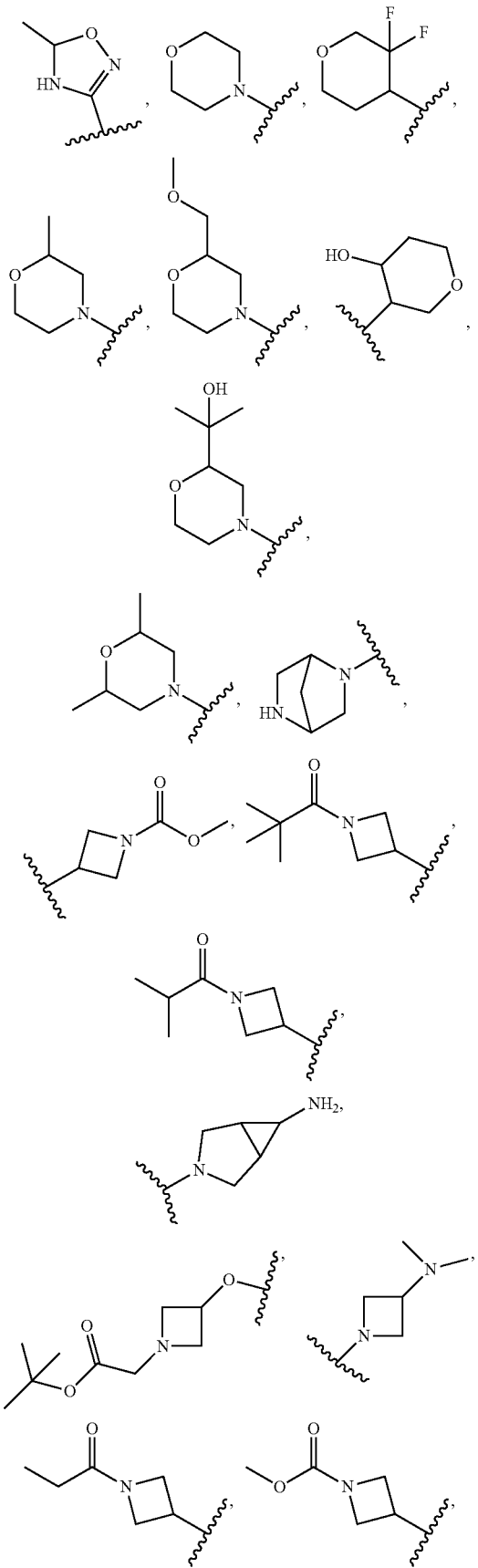

-continued
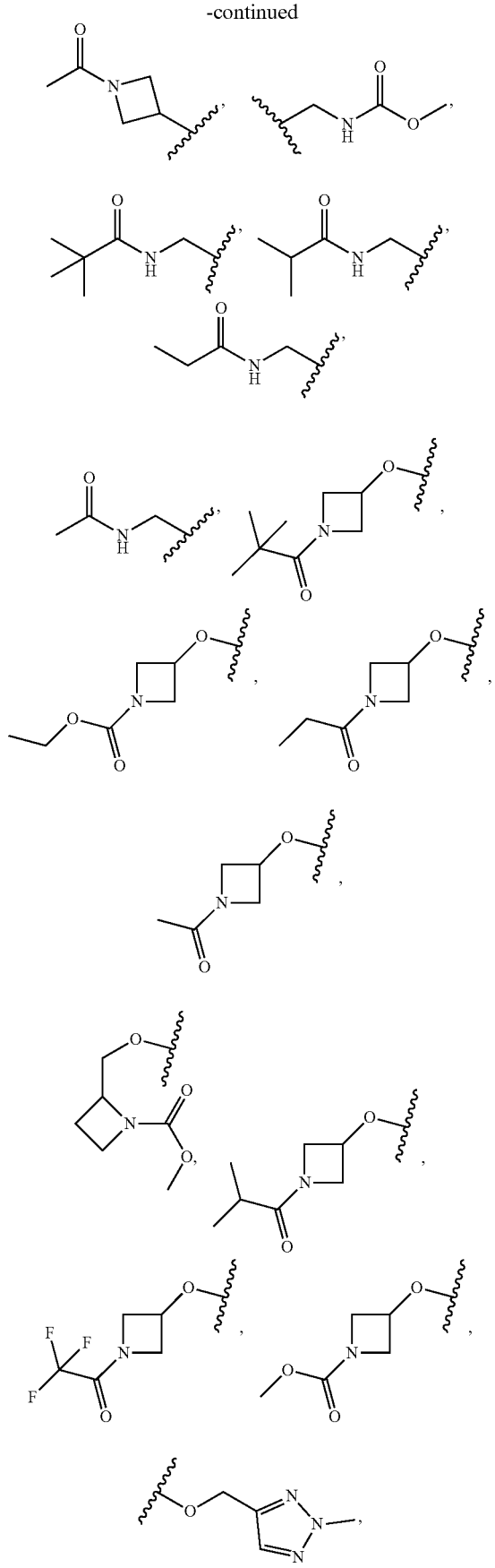
-continued
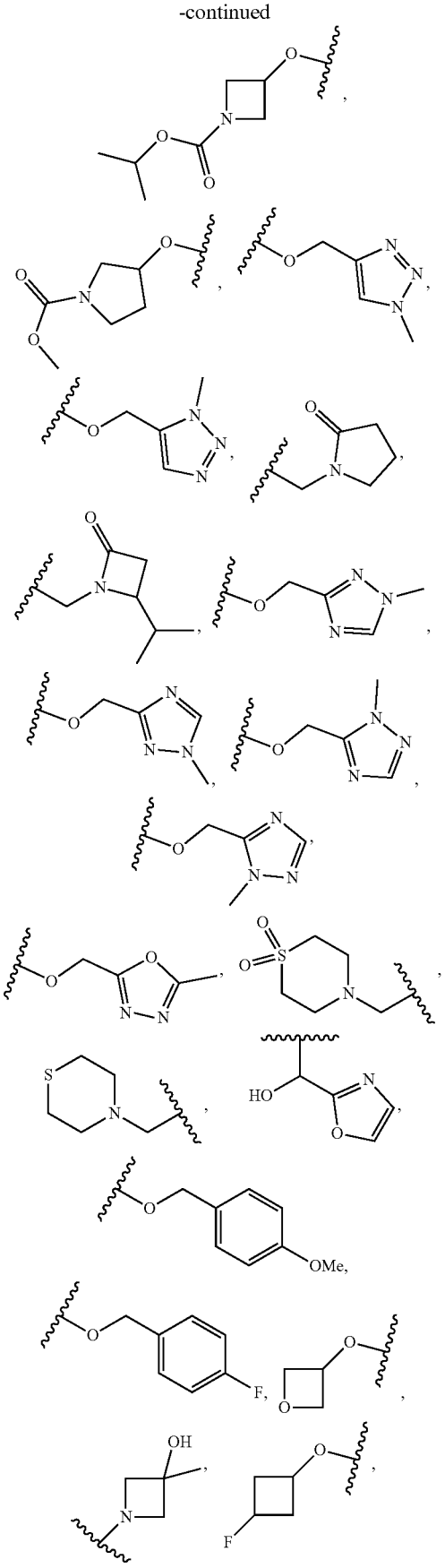

-continued

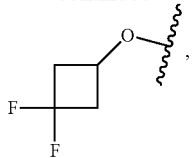

—CH$_2$OH, OCHF$_2$, —SO$_2$Me, CH$_2$NH$_2$, and —CH$_2$NMe$_2$, wherein the remaining variables are as described in Formula I or the second, third, fourth, fifth, sixth, seventh, or eighth embodiment. Alternatively, R$^3$ in Formulas I, Ia, II, or III is selected from:

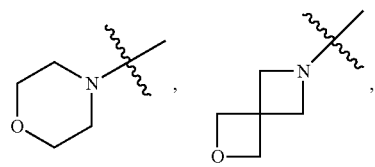 [SMILES: *N1CCOCC1 ; *N1CC2(COC2)C1]

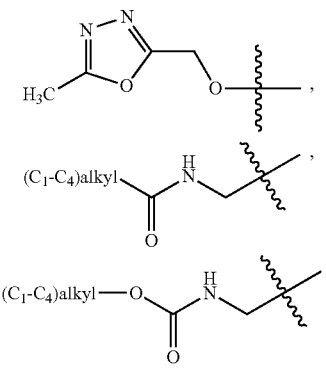

and

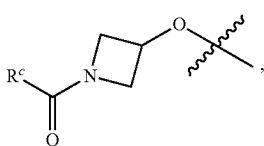

wherein the remaining variables are as described in Formula I or the second, third, fourth, fifth, sixth, seventh, or eighth embodiment. In another alternative, R$^3$ in Formulas I, Ia, II, or III is selected from:

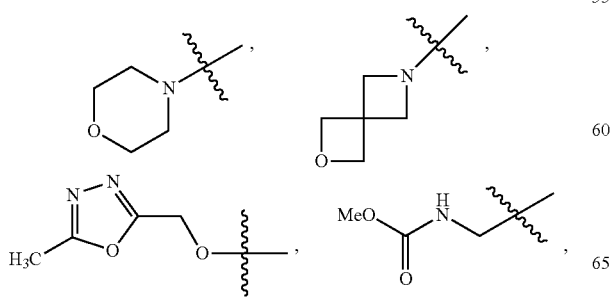

-continued

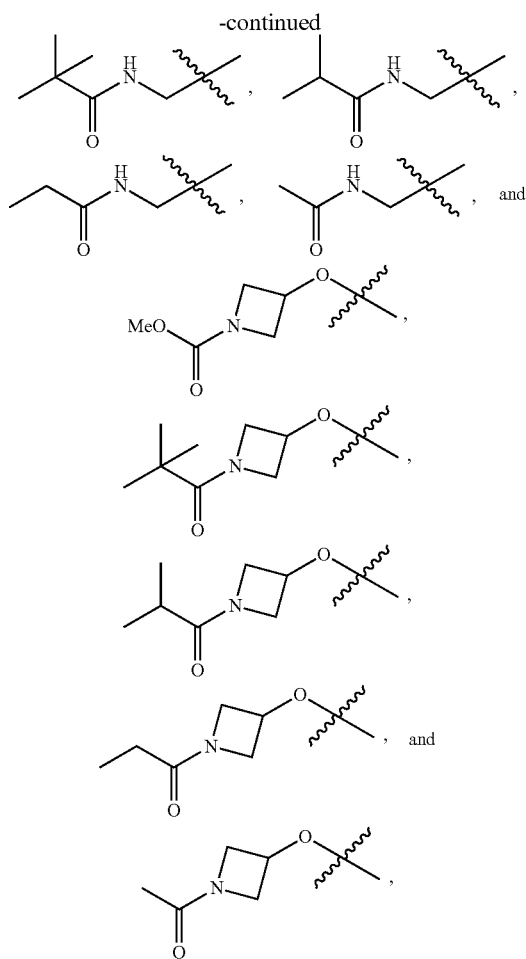

wherein the remaining variables are as described in Formula I or the second, third, fourth, fifth, sixth, seventh, or eighth embodiment. In yet another alternative, R$^3$ in Formulas I, Ia, II, or III is

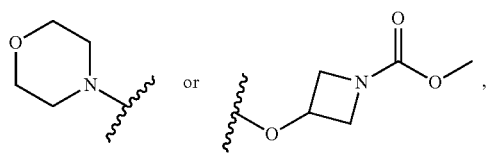

wherein the remaining variables are as described in Formula I or the second, third, fourth, fifth, sixth, seventh, or eighth embodiment.

In an eighteenth embodiment, the compound of Formula I, Ia, II, or III, is of the Formula IV or V:

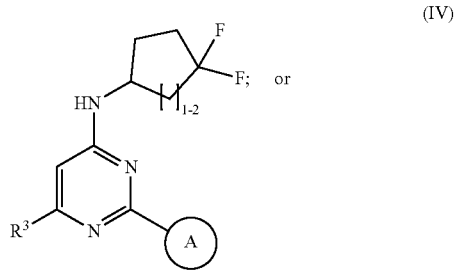

(IV)

-continued

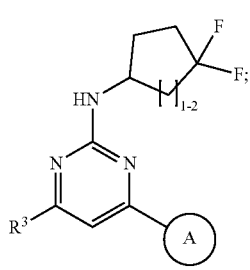
(V)

or a pharmaceutically acceptable salt thereof, wherein the remaining variables are as described in Formula I or the second, third, fourth, fifth, sixth, seventh, eighth, or seventeenth embodiment.

In a ninteenth embodiment, the compound of Formula I, Ia, II, or III, is of the Formula VI or VII:

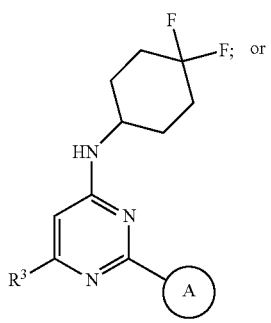
(VI)

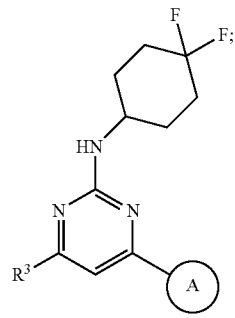
(VII)

or a pharmaceutically acceptable salt thereof, wherein the remaining variables are as described in Formula I or the second, third, fourth, fifth, sixth, seventh, eighth, or sixteenth embodiment.

In a twentieth embodiment, ring A in Formulas I, Ia, II, III, IV, V, VI, or VII is

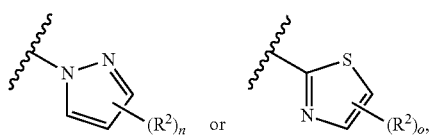

wherein the remaining variables are as described in Formula I or the second, third, fourth, fifth, sixth, seventh, eighth, seventeenth, eighteenth, or nineteenth embodiment. Alternatively, ring A in Formulas I, Ia, II, III, IV, V, VI, or VII is

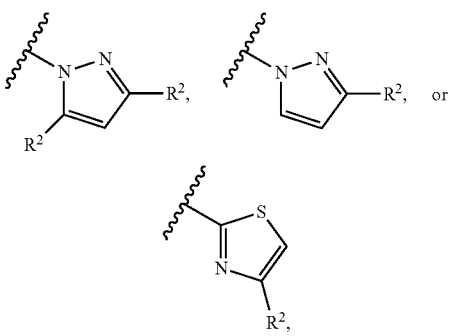

wherein the remaining variables are as described in Formula I or the second, third, fourth, fifth, sixth, seventh, eighth, seventeenth, eighteenth, or nineteenth embodiment.

In a twenty-first embodiment, $R^2$ in Formulas I, Ia, II, III, IV, V, VI, or VII is independently selected from $C_1$-$C_4$ alkyl, halo$C_1$-$C_4$ alkyl, and hydroxy$C_1$-$C_4$ alkyl, wherein the remaining variables are as described in Formula I or the second, third, fourth, fifth, sixth, seventh, eighth, seventeenth, eighteenth, nineteenth, or twentieth embodiment. Alternatively, $R^2$ in Formulas I, Ia, II, III, IV, V, VI, or VII is independently selected from $CH_3$, $CHF_2$, $CH_2F$, —CH($CH_3$)OH, and —$CH_2OH$, wherein the remaining variables are as described in Formula I or the second, third, fourth, fifth, sixth, seventh, eighth, seventeenth, eighteenth, nineteenth, or twentieth embodiment.

In a twenty-second embodiment, $R^5$ in Formulas I, Ia, II, III, IV, V, VI, or VII is hydrogen or $C_1$-$C_4$ alkyl, wherein the remaining variables are as described in Formula I or or the second, third, fourth, fifth, sixth, seventh, eighth, seventeenth, eighteenth, nineteenth, twentieth, or twenty-first embodiment. Alternatively, $R^5$ in Formulas I, Ia, II, III, IV, V, VI, or VII is hydrogen, wherein the remaining variables are as described in Formula I or the second, third, fourth, fifth, sixth, seventh, eighth, seventeenth, eighteenth, nineteenth, twentieth, or twenty-first embodiment.

Specific examples of compounds are provided in Table 1 and Table 2 as well as the EXEMPLIFICATION section and are included as part of a twenty-third embodiment herein. Pharmaceutically acceptable salts as well as the neutral forms of the compounds in Table 1 and the EXEMPLIFICATION are also included.

TABLE 1

| Compound # | Structure |
|---|---|
| 100 | 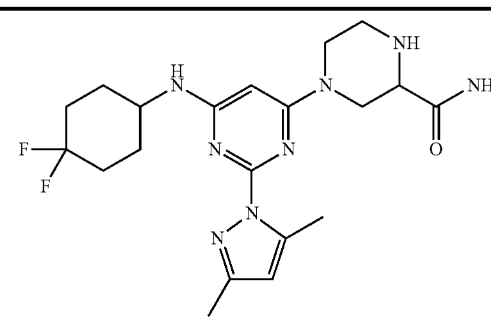 |

TABLE 1-continued

| Compound # | Structure |
|---|---|
| 101 | |
| 102 | |
| 103 | |
| 104 | |
| 105 | 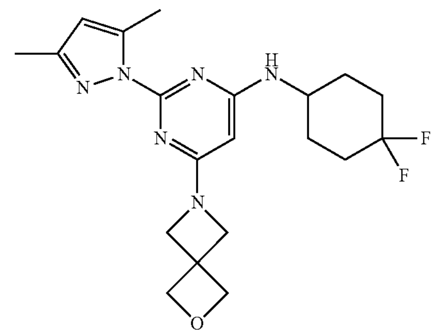 [SMILES: Cc1cc(C)n(-c2nc(NC3CCC(F)(F)CC3)cc(N3CC4(COC4)C3)n2)n1] |
| 106 | 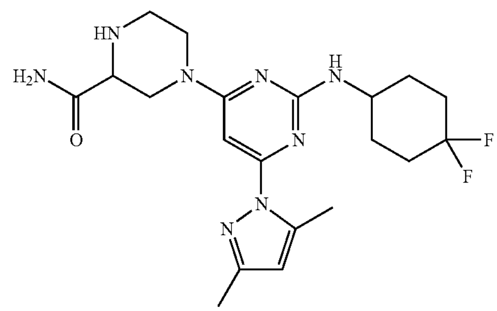 [SMILES: Cc1cc(C)n(-c2cc(N3CCNC(C(N)=O)C3)nc(NC3CCC(F)(F)CC3)n2)n1] |
| 107 | 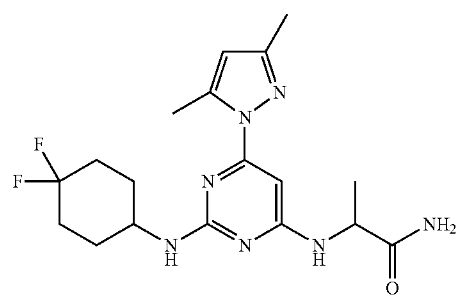 [SMILES: Cc1cc(C)n(-c2cc(NC(C)C(N)=O)nc(NC3CCC(F)(F)CC3)n2)n1] |
| 108 | 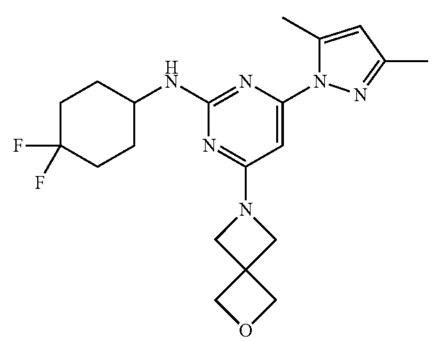 [SMILES: Cc1cc(C)n(-c2cc(N3CC4(COC4)C3)nc(NC3CCC(F)(F)CC3)n2)n1] |
| 109 | 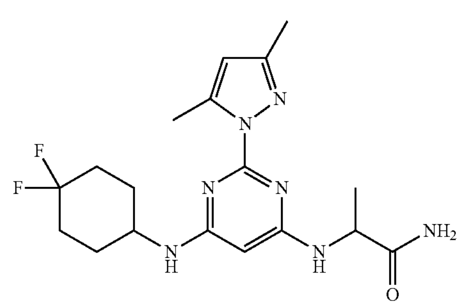 [SMILES: Cc1cc(C)n(-c2nc(NC3CCC(F)(F)CC3)cc(NC(C)C(N)=O)n2)n1] |

TABLE 1-continued

| Compound # | Structure |
|---|---|
| 110 | 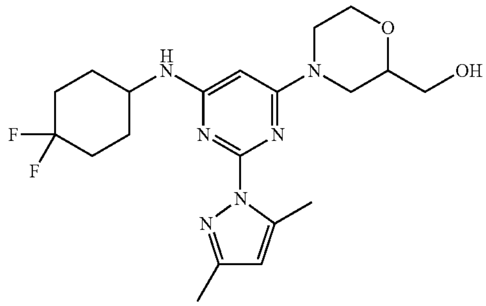 [SMILES: Cc1cc(C)n(-c2nc(NC3CCC(F)(F)CC3)cc(N3CCOC(CO)C3)n2)n1] |
| 111 | 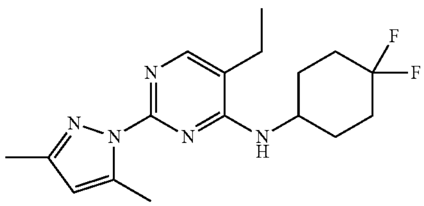 [SMILES: CCc1cnc(-n2nc(C)cc2C)nc1NC1CCC(F)(F)CC1] |
| 112 | 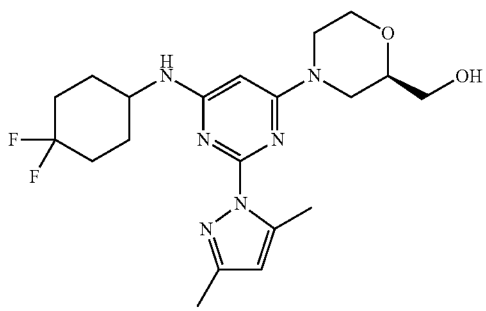 [SMILES: Cc1cc(C)n(-c2nc(NC3CCC(F)(F)CC3)cc(N3CCO[C@@H](CO)C3)n2)n1] |
| 113 | 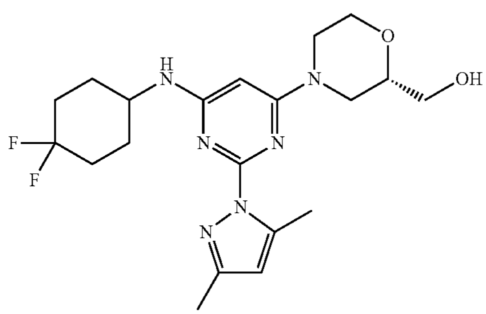 [SMILES: Cc1cc(C)n(-c2nc(NC3CCC(F)(F)CC3)cc(N3CCO[C@H](CO)C3)n2)n1] |
| 114 | 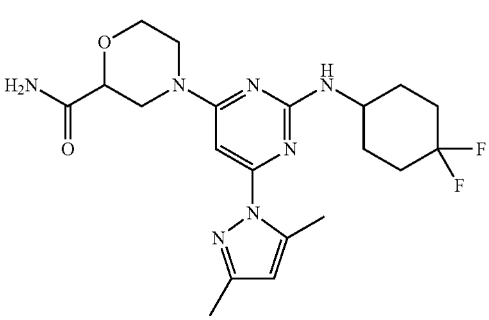 [SMILES: Cc1cc(C)n(-c2cc(N3CCOC(C(N)=O)C3)nc(NC3CCC(F)(F)CC3)n2)n1] |
| 115 | |
| 116 | |
| 117 | |
| 118 | |
| 119 | |

TABLE 1-continued

| Compound # | Structure |
|---|---|
| 120 | 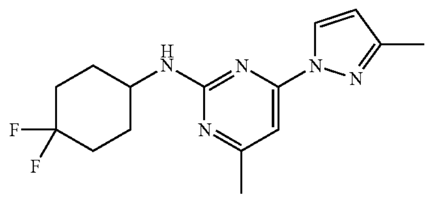 [SMILES: Cc1cc(-n2ccc(C)n2)nc(NC2CCC(F)(F)CC2)n1] |
| 121 | 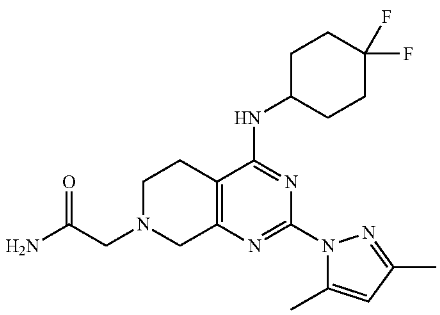 [SMILES: Cc1cc(C)n(-c2nc3c(c(NC4CCC(F)(F)CC4)n2)CCN(CC(N)=O)C3)n1] |
| 122 | 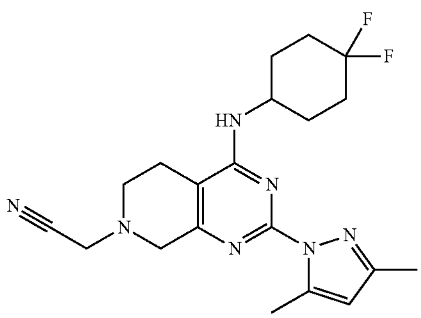 [SMILES: Cc1cc(C)n(-c2nc3c(c(NC4CCC(F)(F)CC4)n2)CCN(CC#N)C3)n1] |
| 123 | 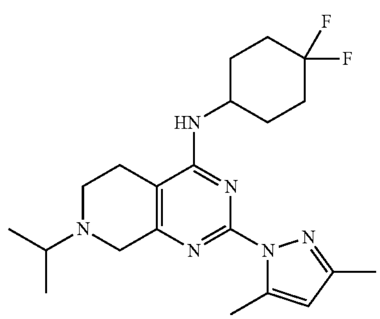 [SMILES: Cc1cc(C)n(-c2nc3c(c(NC4CCC(F)(F)CC4)n2)CCN(C(C)C)C3)n1] |
| 124 | 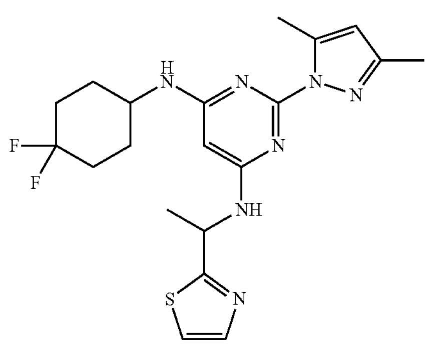 [SMILES: Cc1cc(C)n(-c2nc(NC3CCC(F)(F)CC3)cc(NC(C)c3nccs3)n2)n1] |
| 125 | |
| 126 | |
| 127 | |
| 128 | |
| 129 | |

TABLE 1-continued

| Compound # | Structure |
|---|---|
| 130 | (structure) |
| 131 | (structure) |
| 132 | (structure) |
| 133 | (structure) |
| 134 | (structure) |
| 135 | (structure) |
| 136 | (structure) |
| 137 | (structure) |
| 138 | (structure) |

TABLE 1-continued

| Compound # | Structure |
|---|---|
| 139 | 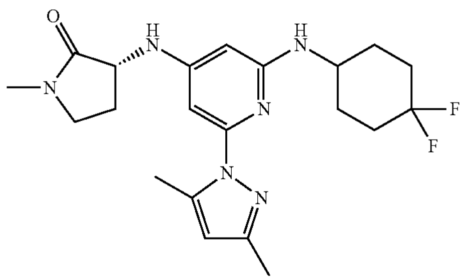 [SMILES: Cc1cc(C)n(-c2cc(N[C@@H]3CCN(C)C3=O)cc(NC3CCC(F)(F)CC3)n2)n1] |
| 140 | 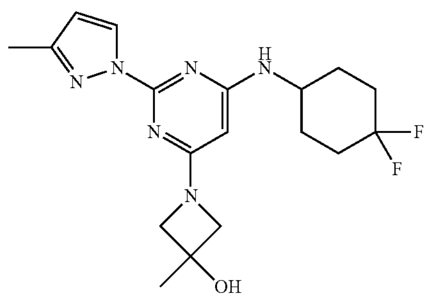 [SMILES: Cc1ccn(-c2nc(NC3CCC(F)(F)CC3)cc(N3CC(C)(O)C3)n2)n1] |
| 141 | 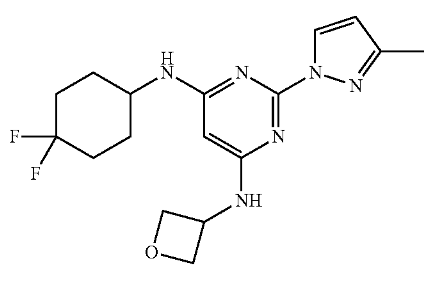 [SMILES: Cc1ccn(-c2nc(NC3CCC(F)(F)CC3)cc(NC3COC3)n2)n1] |
| 142 | 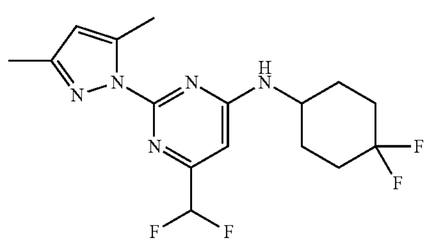 [SMILES: Cc1cc(C)n(-c2nc(NC3CCC(F)(F)CC3)cc(C(F)F)n2)n1] |
| 143 | 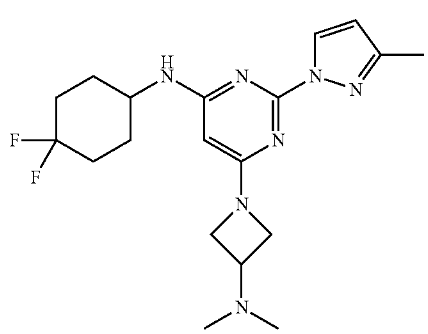 [SMILES: Cc1ccn(-c2nc(NC3CCC(F)(F)CC3)cc(N3CC(N(C)C)C3)n2)n1] |
| 144 | |
| 145 | |
| 146 | |
| 147 | |
| 148 | |

US 10,774,064 B2
TABLE 1-continued
| Compound # | Structure |
|---|---|
| 149 | 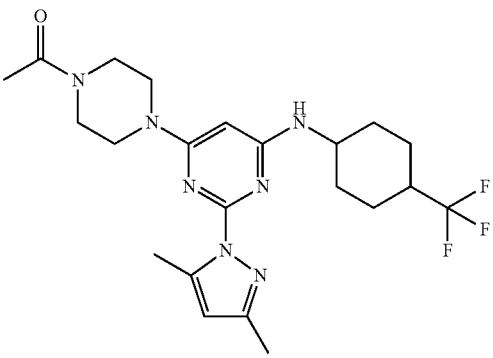 [SMILES: CC(=O)N1CCN(c2cc(NC3CCC(C(F)(F)F)CC3)nc(-n3nc(C)cc3C)n2)CC1] |
| 150 | 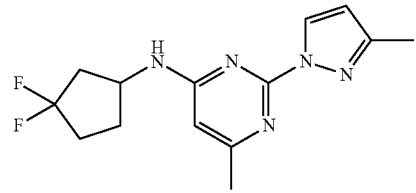 [SMILES: Cc1cc(NC2CCC(F)(F)C2)nc(-n2ccc(C)n2)n1] |
| 151 | 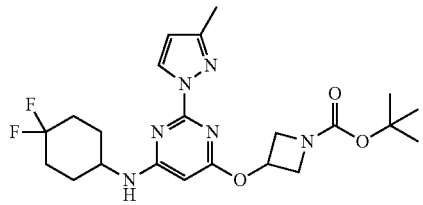 [SMILES: Cc1ccn(-c2nc(NC3CCC(F)(F)CC3)cc(OC3CN(C(=O)OC(C)(C)C)C3)n2)n1] |
| 152 | 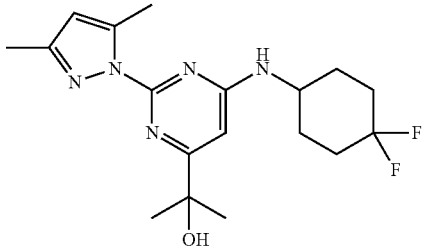 [SMILES: Cc1cc(C)n(-c2nc(NC3CCC(F)(F)CC3)cc(C(C)(C)O)n2)n1] |
| 153 | 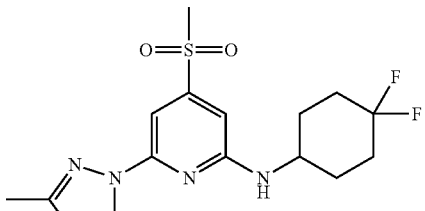 |
| 154 | 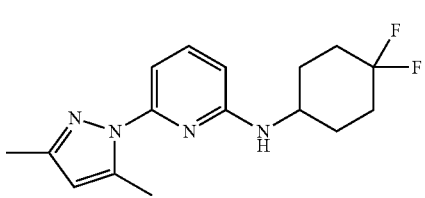 [SMILES: Cc1cc(C)n(-c2cccc(NC3CCC(F)(F)CC3)n2)n1] |
TABLE 1-continued
| Compound # | Structure |
|---|---|
| 155 | 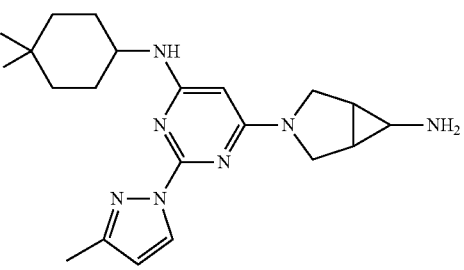 |
| 156 | 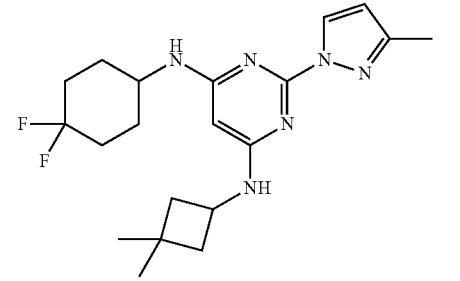 [SMILES: Cc1ccn(-c2nc(NC3CCC(F)(F)CC3)cc(NC3CC(C)(C)C3)n2)n1] |
| 157 | 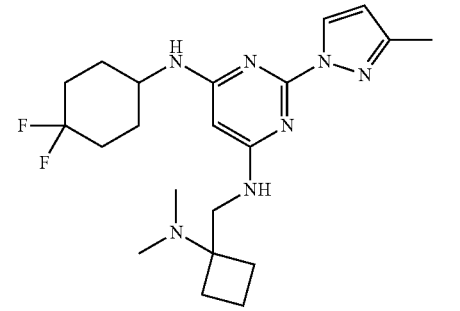 [SMILES: Cc1ccn(-c2nc(NCC3(N(C)C)CCC3)cc(NC3CCC(F)(F)CC3)n2)n1] |
| 158 | 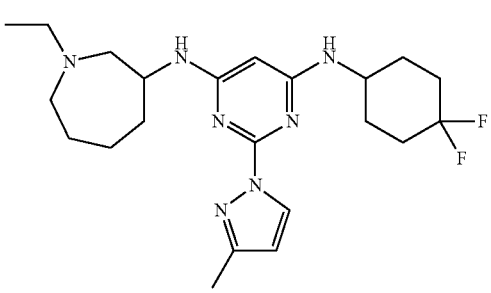 [SMILES: CCN1CCCCC(Nc2cc(NC3CCC(F)(F)CC3)nc(-n3ccc(C)n3)n2)C1] |
| 159 | 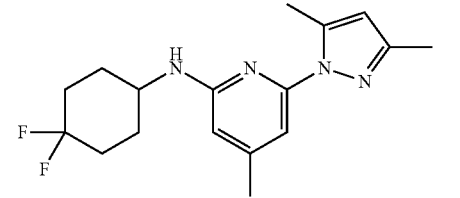 [SMILES: Cc1cc(NC2CCC(F)(F)CC2)nc(-n2nc(C)cc2C)c1] |

TABLE 1-continued

| Compound # | Structure |
|---|---|
| 160 | (structure) |
| 161 | (structure) |
| 162 | (structure) |
| 163 | (structure) |
| 164 | (structure) |
| 165 | (structure) |
| 166 | (structure) |
| 167 | (structure) |
| 168 | (structure) |
| 169 | (structure) |
| 170 | (structure) |

TABLE 1-continued
| Compound # | Structure |
|---|---|
| 171 | 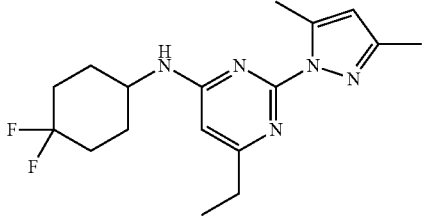 [SMILES: CCc1cc(NC2CCC(F)(F)CC2)nc(-n2nc(C)cc2C)n1] |
| 172 | 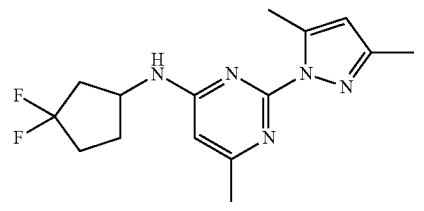 [SMILES: Cc1cc(NC2CCC(F)(F)C2)nc(-n2nc(C)cc2C)n1] |
| 173 | 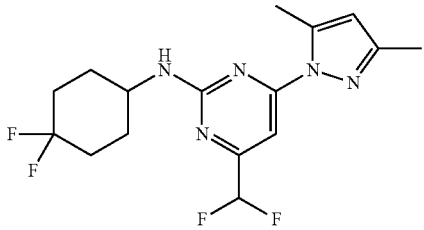 [SMILES: Cc1cc(C)n(-c2cc(C(F)F)nc(NC3CCC(F)(F)CC3)n2)n1] |
| 174 | 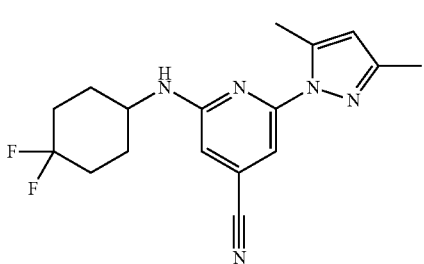 [SMILES: Cc1cc(C)n(-c2cc(C#N)cc(NC3CCC(F)(F)CC3)n2)n1] |
| 175 | 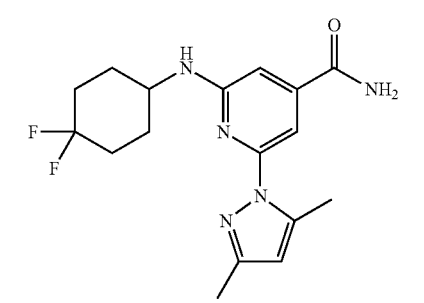 [SMILES: Cc1cc(C)n(-c2cc(C(N)=O)cc(NC3CCC(F)(F)CC3)n2)n1] |
| 176 | 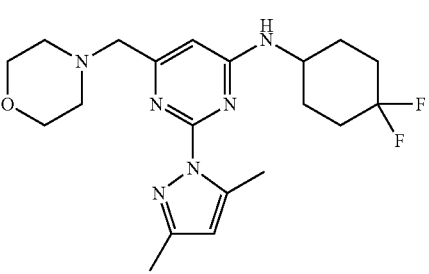 [SMILES: Cc1cc(C)n(-c2nc(CN3CCOCC3)cc(NC3CCC(F)(F)CC3)n2)n1] |
| 177 | 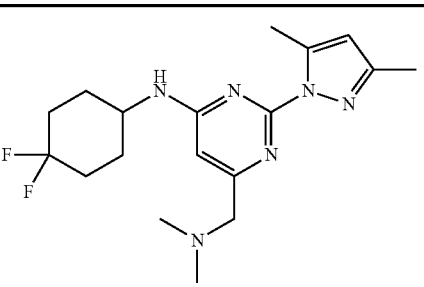 |
| 178 | 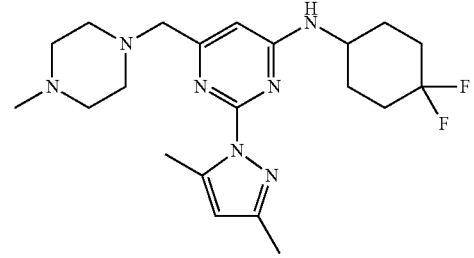 [SMILES: Cc1cc(C)n(-c2nc(CN3CCN(C)CC3)cc(NC3CCC(F)(F)CC3)n2)n1] |
| 179 | 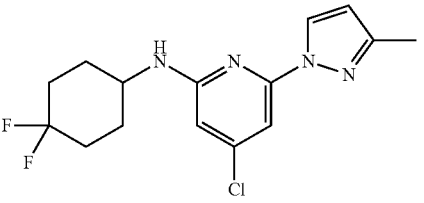 [SMILES: Cc1ccn(-c2cc(Cl)cc(NC3CCC(F)(F)CC3)n2)n1] |
| 180 | 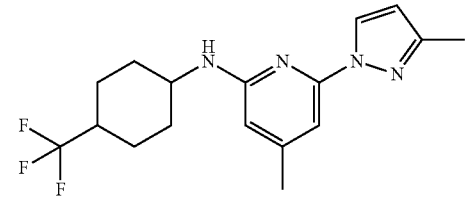 [SMILES: Cc1cc(NC2CCC(C(F)(F)F)CC2)nc(-n2ccc(C)n2)c1] |
| 181 | 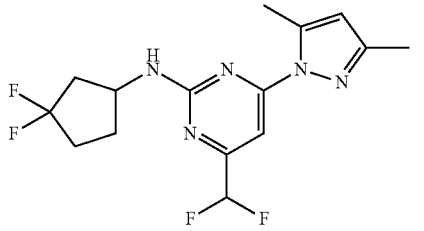 [SMILES: Cc1cc(C)n(-c2cc(C(F)F)nc(NC3CCC(F)(F)C3)n2)n1] |
| 182 | 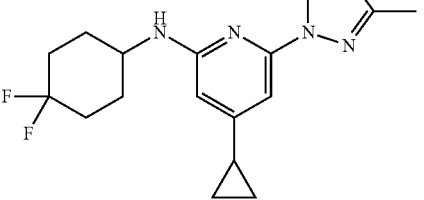 |

TABLE 1-continued

| Compound # | Structure |
|---|---|
| 183 | (structure) |
| 184 | (structure) |
| 185 | (structure) |
| 186 | (structure) |
| 187 | (structure) |
| 188 | (structure) |
| 189 | (structure) |
| 190 | (structure) |
| 191 | (structure) |

TABLE 1-continued

| Compound # | Structure |
|---|---|
| 192 | |
| 193 | |
| 194 | |
| 195 | |
| 196 | |
| 197 | |
| 198 | 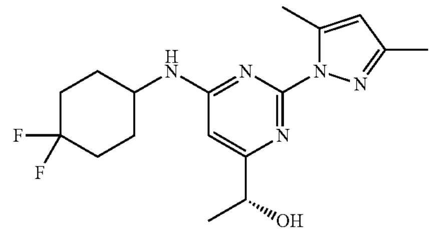 |
| 199 | 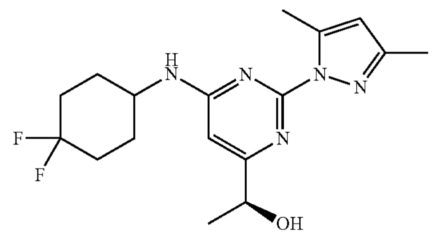 [SMILES: Cc1cc(C)n(-c2nc(NC3CCC(F)(F)CC3)cc([C@H](C)O)n2)n1] |
| 200 | 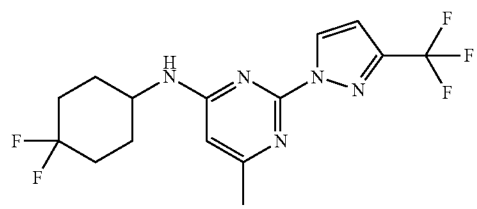 [SMILES: Cc1cc(NC2CCC(F)(F)CC2)nc(-n2ccc(C(F)(F)F)n2)n1] |
| 201 | 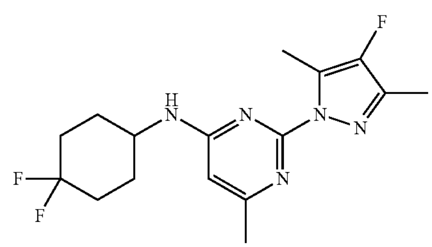 [SMILES: Cc1cc(NC2CCC(F)(F)CC2)nc(-n2nc(C)c(F)c2C)n1] |
| 202 | 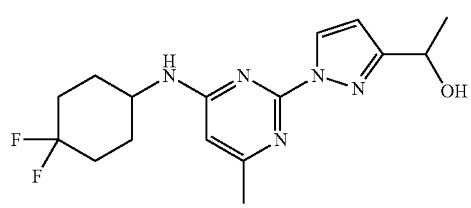 [SMILES: Cc1cc(NC2CCC(F)(F)CC2)nc(-n2ccc(C(C)O)n2)n1] |
| 203 | 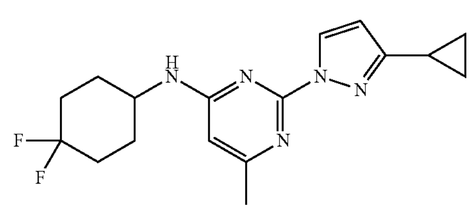 [SMILES: Cc1cc(NC2CCC(F)(F)CC2)nc(-n2ccc(C3CC3)n2)n1] |
| 204 | 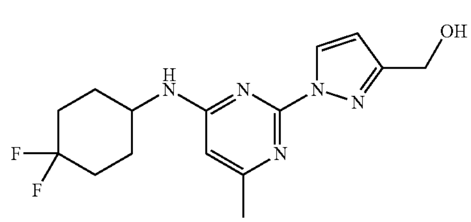 [SMILES: Cc1cc(NC2CCC(F)(F)CC2)nc(-n2ccc(CO)n2)n1] |

TABLE 1-continued

| Compound # | Structure |
|---|---|
| 205 | |
| 206 | |
| 207 | |
| 208 | |
| 209 | |
| 210 | 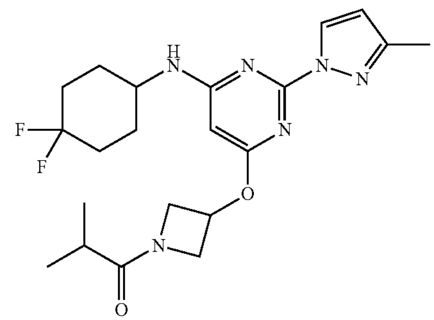 [SMILES: COC(=O)N1CC(Oc2cc(NC3CCC(F)(F)CC3)nc(-n3ccc(C)n3)n2)C1] |
| 211 | 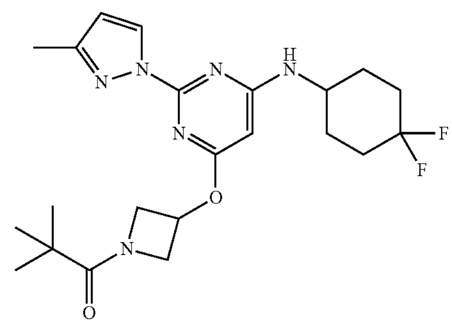 [SMILES: Cc1ccn(-c2nc(NC3CCC(F)(F)CC3)cc(OC3CN(C(=O)C(C)(C)C)C3)n2)n1] |
| 212 | 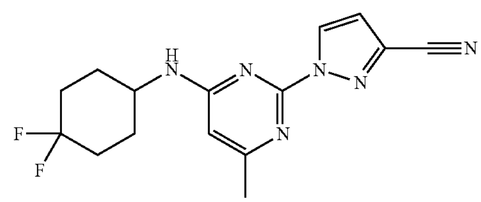 [SMILES: Cc1cc(NC2CCC(F)(F)CC2)nc(-n2ccc(C#N)n2)n1] |
| 213 | 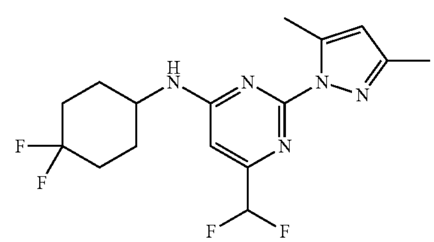 [SMILES: Cc1cc(C)n(-c2nc(NC3CCC(F)(F)CC3)cc(C(F)F)n2)n1] |
| 214 | 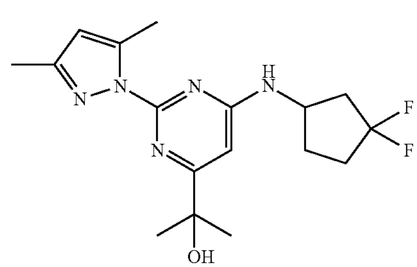 [SMILES: Cc1cc(C)n(-c2nc(NC3CCC(F)(F)C3)cc(C(C)(C)O)n2)n1] |
| 215 | 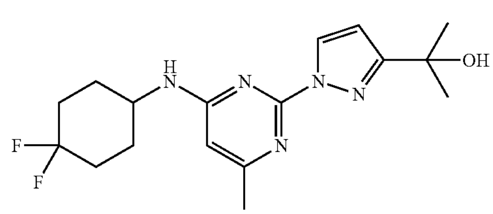 [SMILES: Cc1cc(NC2CCC(F)(F)CC2)nc(-n2ccc(C(C)(C)O)n2)n1] |

TABLE 1-continued

| Compound # | Structure |
|---|---|
| 216 | 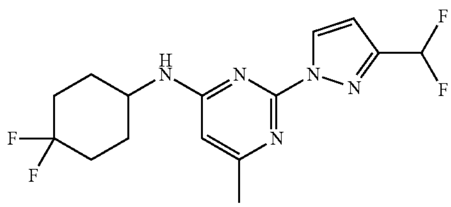 [SMILES: Cc1cc(NC2CCC(F)(F)CC2)nc(-n2ccc(C(F)F)n2)n1] |
| 217 | 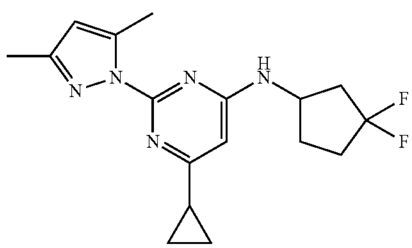 [SMILES: Cc1cc(C)n(-c2nc(NC3CCC(F)(F)C3)cc(C3CC3)n2)n1] |
| 218 | 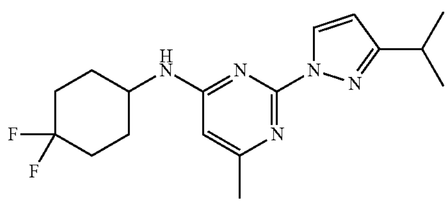 [SMILES: Cc1cc(NC2CCC(F)(F)CC2)nc(-n2ccc(C(C)C)n2)n1] |
| 219 | 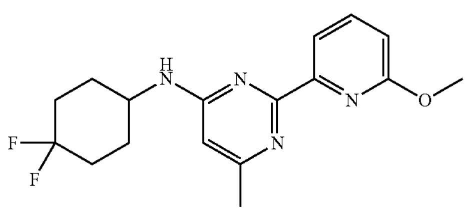 [SMILES: COc1cccc(-c2nc(C)cc(NC3CCC(F)(F)CC3)n2)n1] |
| 220 | 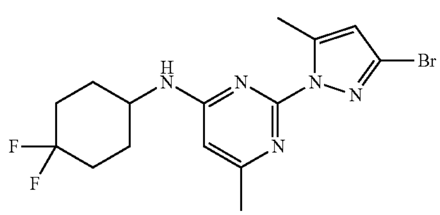 [SMILES: Cc1cc(NC2CCC(F)(F)CC2)nc(-n2nc(Br)cc2C)n1] |
| 221 | 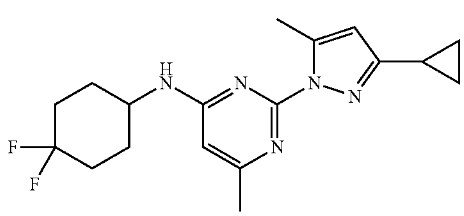 [SMILES: Cc1cc(NC2CCC(F)(F)CC2)nc(-n2nc(C3CC3)cc2C)n1] |
| 222 | 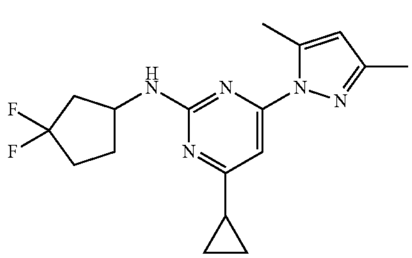 [SMILES: Cc1cc(C)n(-c2cc(C3CC3)nc(NC3CCC(F)(F)C3)n2)n1] |
| 223 | |
| 224 | |
| 225 | |
| 226 | |
| 227 | |
| 228 | |

TABLE 1-continued

| Compound # | Structure |
|---|---|
| 229 | 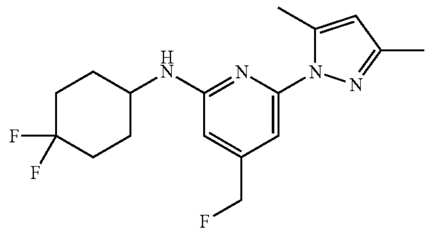 [SMILES: Cc1cc(C)n(-c2cc(CF)cc(NC3CCC(F)(F)CC3)n2)n1] |
| 230 | 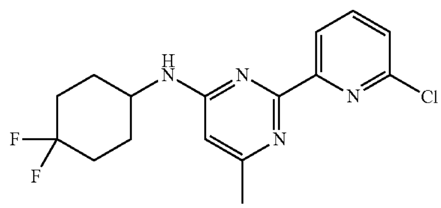 [SMILES: Cc1cc(NC2CCC(F)(F)CC2)nc(-c2cccc(Cl)n2)n1] |
| 231 | 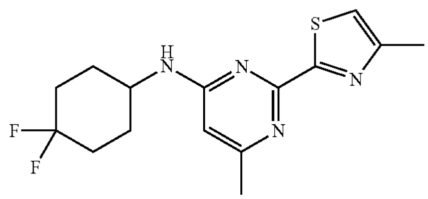 [SMILES: Cc1cc(NC2CCC(F)(F)CC2)nc(-c2nc(C)cs2)n1] |
| 232 | 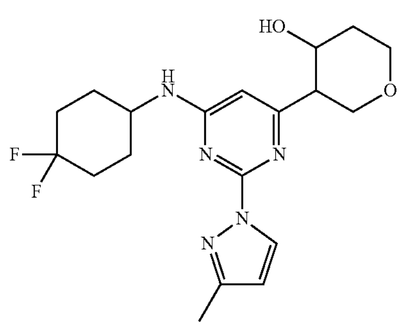 [SMILES: Cc1ccn(-c2nc(NC3CCC(F)(F)CC3)cc(C3COCCC3O)n2)n1] |
| 233 | 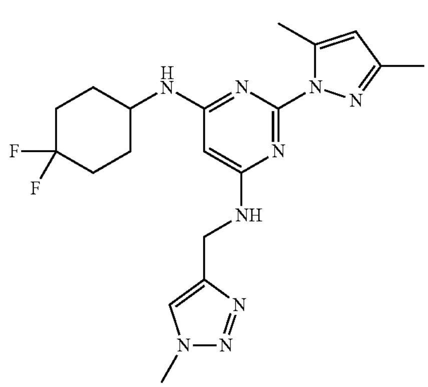 [SMILES: Cc1cc(C)n(-c2nc(NCc3cn(C)nn3)cc(NC3CCC(F)(F)CC3)n2)n1] |
| 234 | 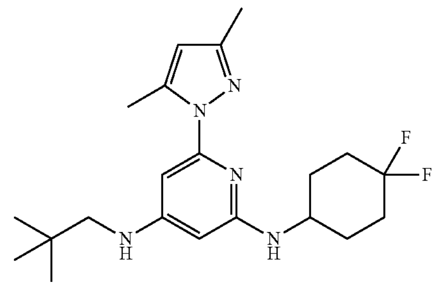 [SMILES: Cc1cc(C)n(-c2cc(NCC(C)(C)C)cc(NC3CCC(F)(F)CC3)n2)n1] |
| 235 | 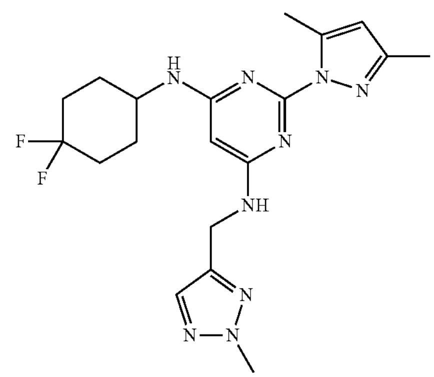 [SMILES: Cc1cc(C)n(-c2nc(NCc3cnn(C)n3)cc(NC3CCC(F)(F)CC3)n2)n1] |
| 236 | 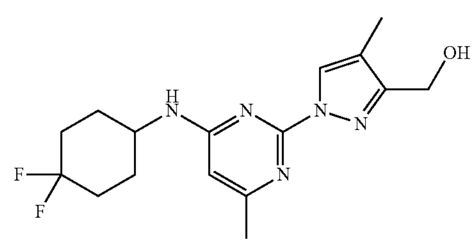 [SMILES: Cc1cc(NC2CCC(F)(F)CC2)nc(-n2cc(C)c(CO)n2)n1] |
| 237 | 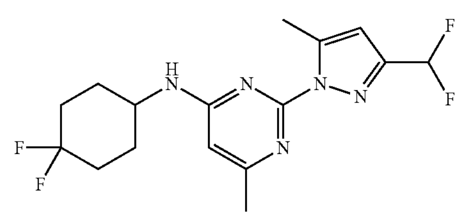 [SMILES: Cc1cc(NC2CCC(F)(F)CC2)nc(-n2nc(C(F)F)cc2C)n1] |
| 238 | 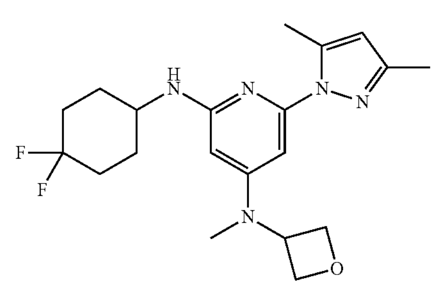 [SMILES: Cc1cc(C)n(-c2cc(N(C)C3COC3)cc(NC3CCC(F)(F)CC3)n2)n1] |

TABLE 1-continued
| Compound # | Structure |
|---|---|
| 239 | 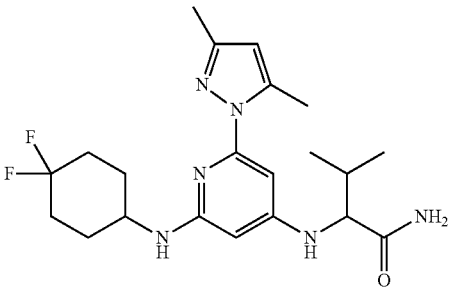 [SMILES: Cc1cc(C)n(-c2cc(NC(C(N)=O)C(C)C)cc(NC3CCC(F)(F)CC3)n2)n1] |
| 240 | 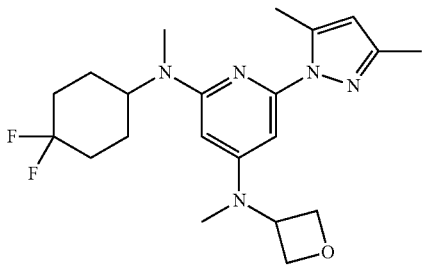 |
| 241 | 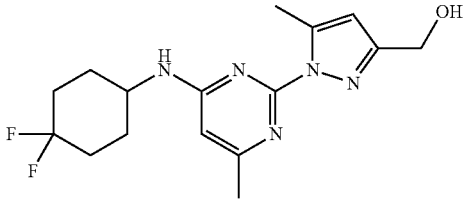 [SMILES: Cc1cc(NC2CCC(F)(F)CC2)nc(-n2nc(CO)cc2C)n1] |
| 242 | 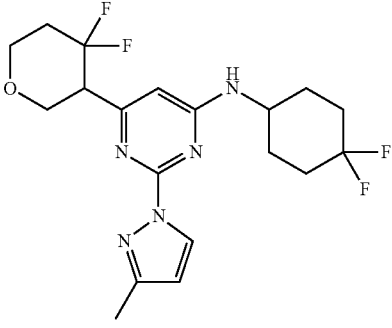 [SMILES: Cc1ccn(-c2nc(NC3CCC(F)(F)CC3)cc(C3COCCC3(F)F)n2)n1] |
| 243 | 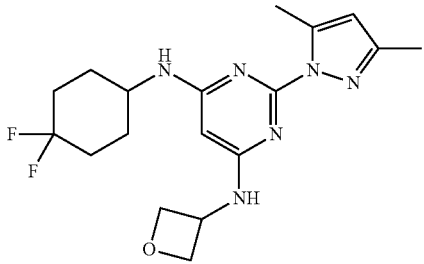 [SMILES: Cc1cc(C)n(-c2nc(NC3CCC(F)(F)CC3)cc(NC3COC3)n2)n1] |
| 244 | 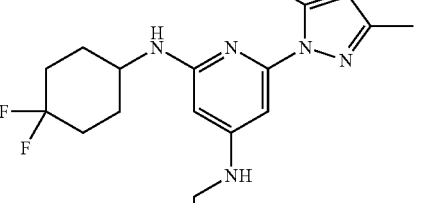 |
| 245 | 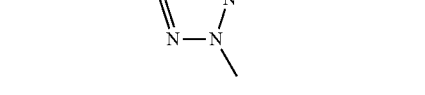 |
| 246 | 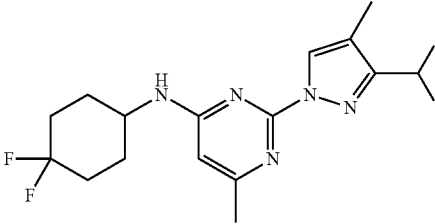 |
| 247 | 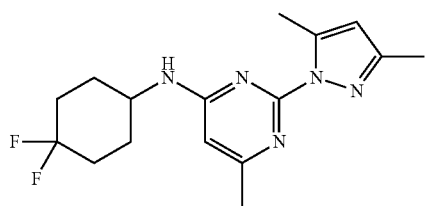 |
| 248 | 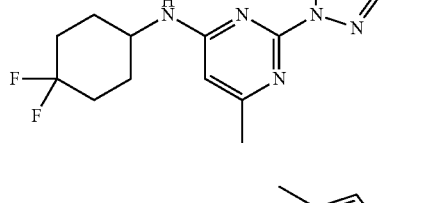 |

TABLE 1-continued
| Compound # | Structure |
|---|---|
| 249 | 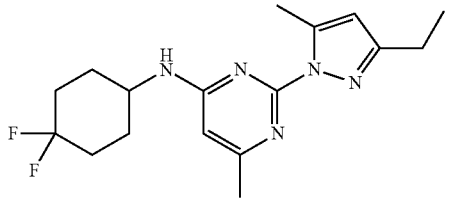 |
| 250 | 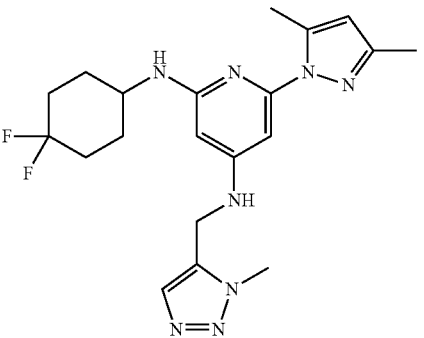 [SMILES: Cc1cc(C)n(-c2cc(NCc3cnnn3C)cc(NC3CCC(F)(F)CC3)n2)n1] |
| 251 | 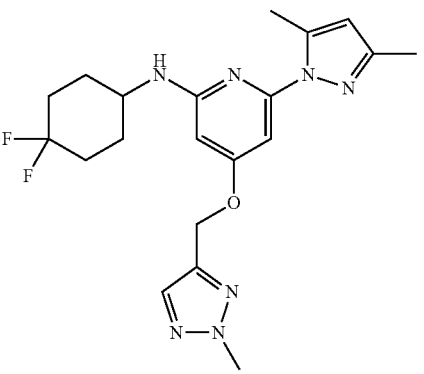 [SMILES: Cc1cc(C)n(-c2cc(OCc3cnn(C)n3)cc(NC3CCC(F)(F)CC3)n2)n1] |
| 252 | 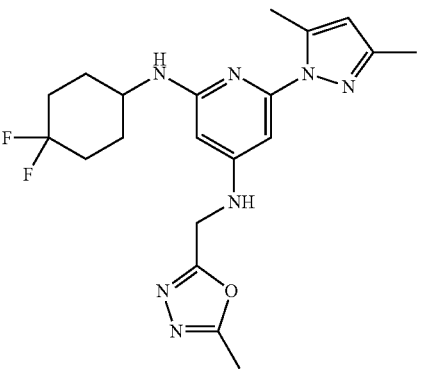 [SMILES: Cc1cc(C)n(-c2cc(NCc3nnc(C)o3)cc(NC3CCC(F)(F)CC3)n2)n1] |
| 253 | 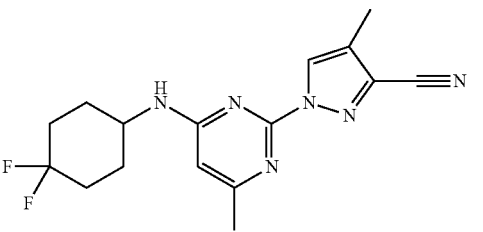 [SMILES: Cc1cc(NC2CCC(F)(F)CC2)nc(-n2cc(C)c(C#N)n2)n1] |
| 254 | 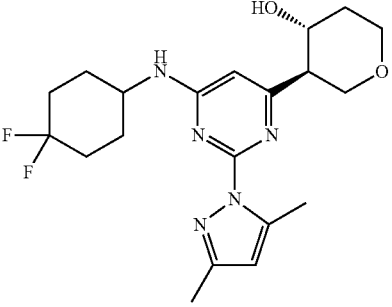 [SMILES: Cc1cc(C)n(-c2nc(NC3CCC(F)(F)CC3)cc([C@@H]3COCC[C@H]3O)n2)n1] |
| 255 | 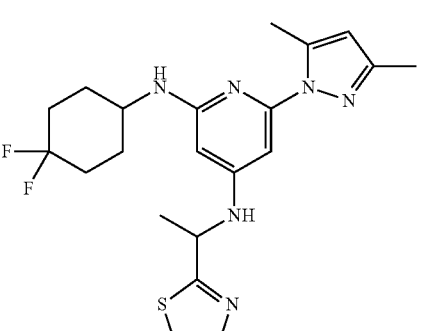 |
| 256 | 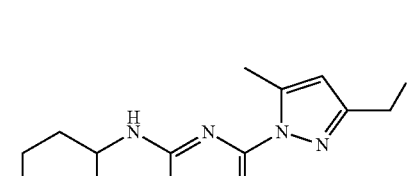 |
| 257 | 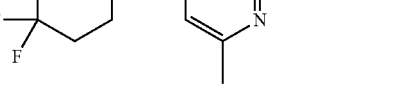 |
| 258 | 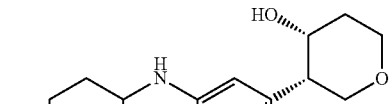 |

TABLE 1-continued

| Compound # | Structure |
|---|---|
| 259 | (structure) |
| 260 | (structure) |
| 261 | (structure) |
| 262 | (structure) |
| 263 | (structure) |
| 264 | (structure) |
| 265 | (structure) |
| 266 | (structure) |
| 267 | (structure) |

TABLE 1-continued
| Compound # | Structure |
|---|---|
| 268 | 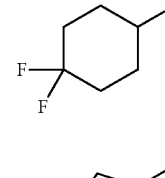 |
| 269 | |
| 270 | |
| 271 | |
| 272 | |
| 273 | 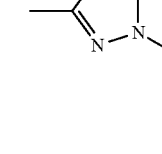 |
| 274 | 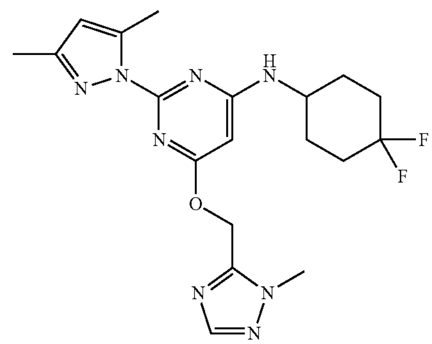 |
| 275 | 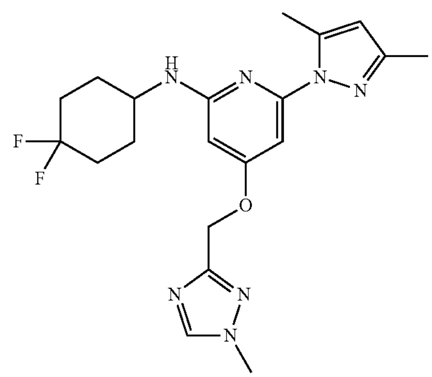 [SMILES: Cc1cc(C)n(-c2cc(OCc3ncn(C)n3)cc(NC3CCC(F)(F)CC3)n2)n1] |
| 276 | 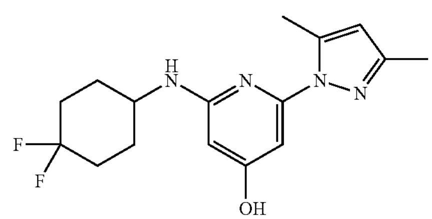 [SMILES: Cc1cc(C)n(-c2cc(O)cc(NC3CCC(F)(F)CC3)n2)n1] |
| 277 | 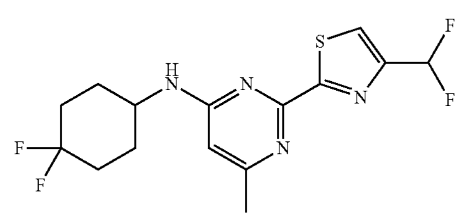 [SMILES: Cc1cc(NC2CCC(F)(F)CC2)nc(-c2nc(C(F)F)cs2)n1] |
| 278 | 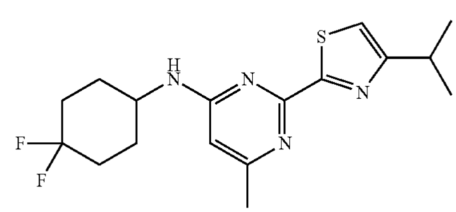 [SMILES: Cc1cc(NC2CCC(F)(F)CC2)nc(-c2nc(C(C)C)cs2)n1] |

TABLE 1-continued

| Compound # | Structure |
|---|---|
| 279 | (structure) |
| 280 | (structure) |
| 281 | (structure) |
| 282 | (structure) |
| 283 | (structure) |
| 284 | (structure) |
| 285 | (structure) |
| 286 | (structure) |
| 287 | (structure) |
| 288 | (structure) |

TABLE 1-continued
| Compound # | Structure |
|---|---|
| 289 | 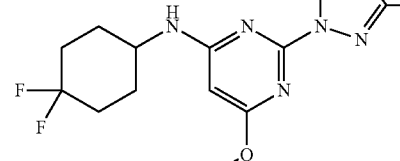 |
| 290 | 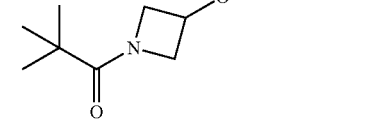 |
| 291 | 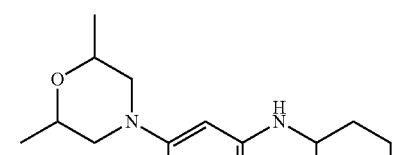 |
| 292 | 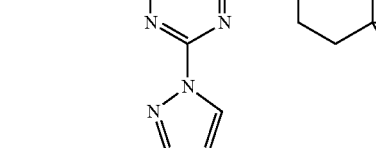 |
| 293 | 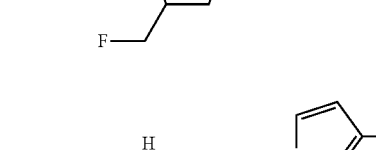 |
| 294 | 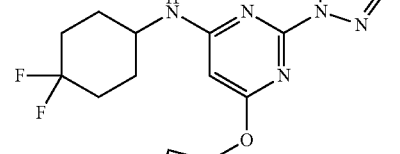 |
| 295 | 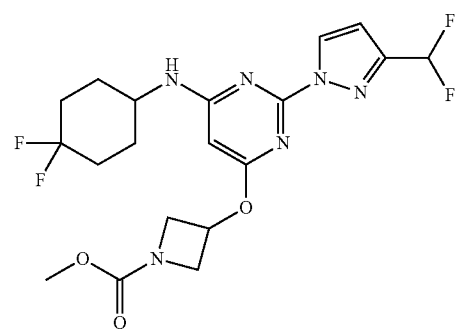 [SMILES: COC(=O)N1CC(Oc2cc(NC3CCC(F)(F)CC3)nc(-n3ccc(C(F)F)n3)n2)C1] |
| 296 | 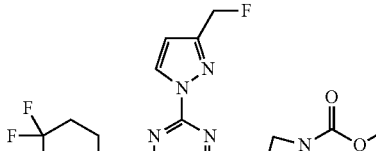 |
| 297 | 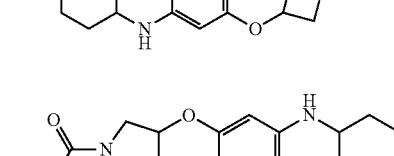 |

TABLE 1-continued

| Compound # | Structure |
|---|---|
| 298 | 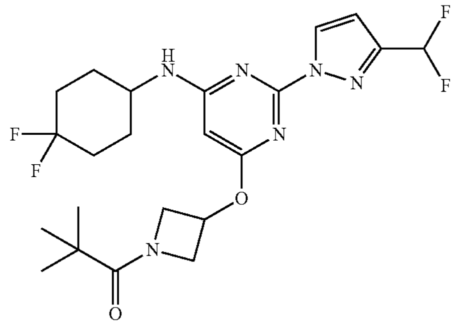 [SMILES: CC(C)(C)C(=O)N1CC(Oc2cc(NC3CCC(F)(F)CC3)nc(-n3ccc(C(F)F)n3)n2)C1] |
| 299 | 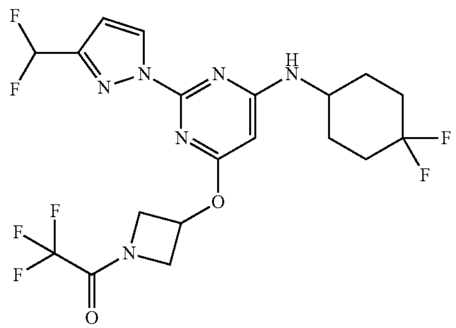 [SMILES: O=C(N1CC(Oc2cc(NC3CCC(F)(F)CC3)nc(-n3ccc(C(F)F)n3)n2)C1)C(F)(F)F] |
| 300 | 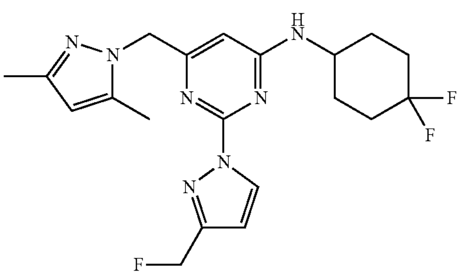 [SMILES: Cc1cc(C)n(Cc2cc(NC3CCC(F)(F)CC3)nc(-n3ccc(CF)n3)n2)n1] |
| 301 | 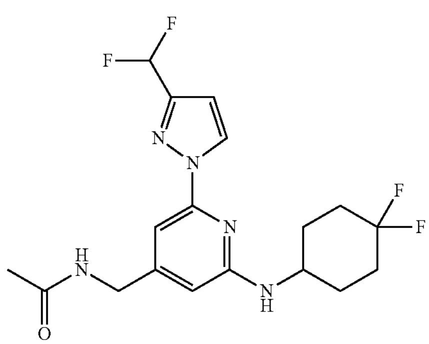 [SMILES: CC(=O)NCc1cc(NC2CCC(F)(F)CC2)nc(-n2ccc(C(F)F)n2)c1] |
| 302 | 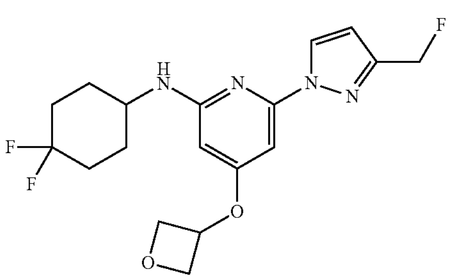 [SMILES: FCc1ccn(-c2cc(OC3COC3)cc(NC3CCC(F)(F)CC3)n2)n1] |
| 303 | |
| 304 | |
| 305 | |
| 306 | |
| 307 | |

TABLE 1-continued

| Compound # | Structure |
|---|---|
| 308 | (structure) |
| 309 | (structure) |
| 310 | (structure) |
| 311 | (structure) |
| 312 | (structure) |
| 313 | (structure) |
| 314 | (structure) |
| 315 | (structure) |

TABLE 1-continued
| Compound # | Structure |
|---|---|
| 316 | 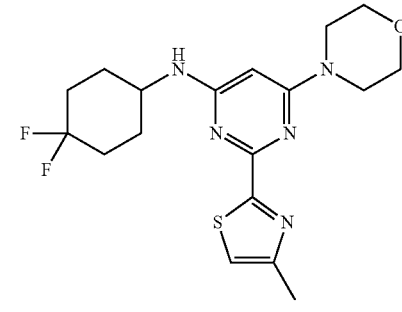 |
| 317 | 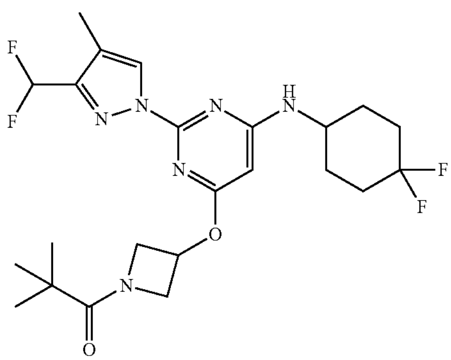 [SMILES: Cc1cn(-c2nc(NC3CCC(F)(F)CC3)cc(OC3CN(C(=O)C(C)(C)C)C3)n2)nc1C(F)F] |
| 318 | 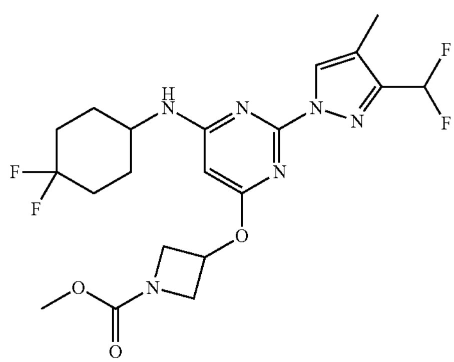 [SMILES: COC(=O)N1CC(Oc2cc(NC3CCC(F)(F)CC3)nc(-n3cc(C)c(C(F)F)n3)n2)C1] |
| 319 | 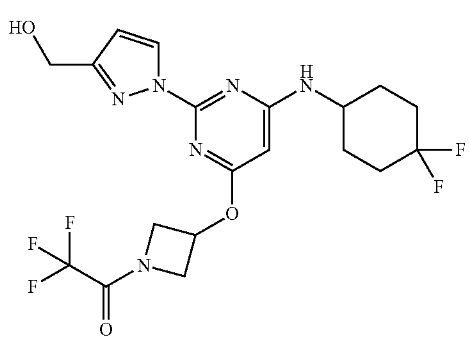 [SMILES: O=C(N1CC(Oc2cc(NC3CCC(F)(F)CC3)nc(-n3ccc(CO)n3)n2)C1)C(F)(F)F] |
| 320 | 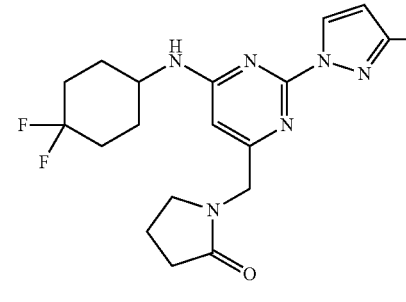 |
| 321 | |
| 322 | |
| 323 | |

TABLE 1-continued
| Compound # | Structure |
|---|---|
| 324 | 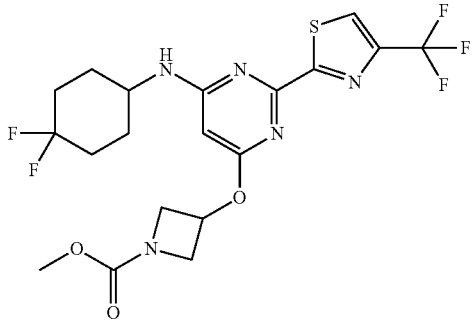 [SMILES: COC(=O)N1CC(Oc2cc(NC3CCC(F)(F)CC3)nc(-c3nc(C(F)(F)F)cs3)n2)C1] |
| 325 | 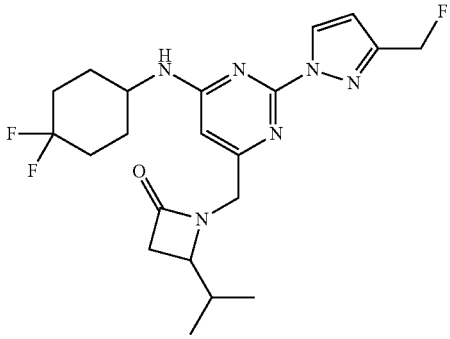 [SMILES: CC(C)C1CC(=O)N1Cc1cc(NC2CCC(F)(F)CC2)nc(-n2ccc(CF)n2)n1] |
| 326 | 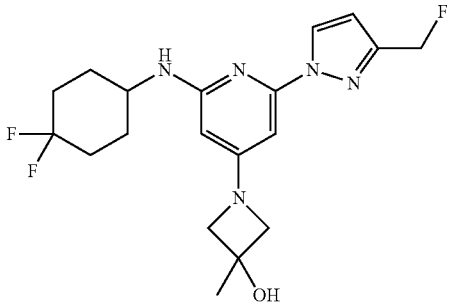 [SMILES: CC1(O)CN(c2cc(NC3CCC(F)(F)CC3)nc(-n3ccc(CF)n3)c2)C1] |
| 327 | 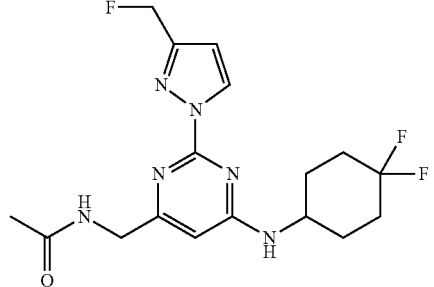 [SMILES: CC(=O)NCc1cc(NC2CCC(F)(F)CC2)nc(-n2ccc(CF)n2)n1] |
| 328 | 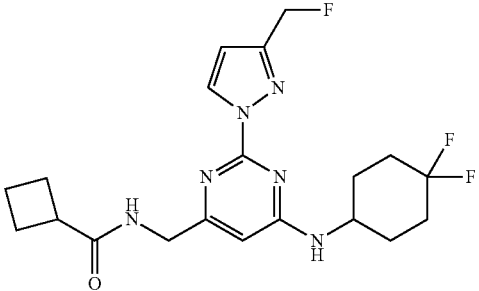 [SMILES: O=C(NCc1cc(NC2CCC(F)(F)CC2)nc(-n2ccc(CF)n2)n1)C1CCC1] |
| 329 | 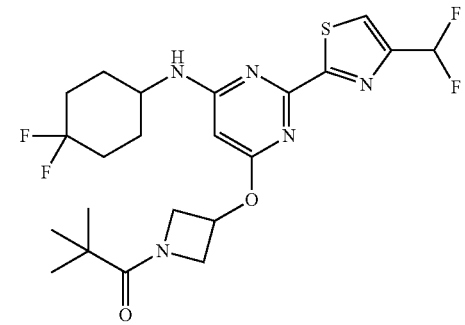 [SMILES: CC(C)(C)C(=O)N1CC(Oc2cc(NC3CCC(F)(F)CC3)nc(-c3nc(C(F)F)cs3)n2)C1] |
| 330 | 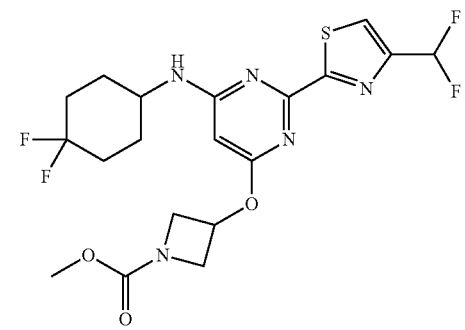 [SMILES: COC(=O)N1CC(Oc2cc(NC3CCC(F)(F)CC3)nc(-c3nc(C(F)F)cs3)n2)C1] |
| 331 | 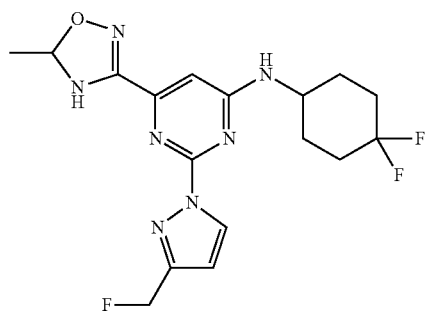 [SMILES: CC1NC(c2cc(NC3CCC(F)(F)CC3)nc(-n3ccc(CF)n3)n2)=NO1] |

TABLE 1-continued
| Compound # | Structure |
|---|---|
| 332 | 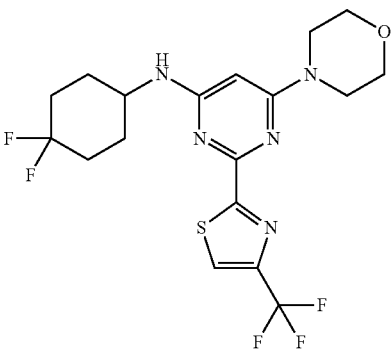 [SMILES: FC1(F)CCC(Nc2cc(N3CCOCC3)nc(-c3nc(C(F)(F)F)cs3)n2)CC1] |
| 333 | 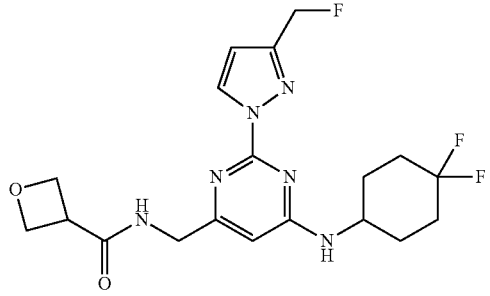 [SMILES: O=C(NCc1cc(NC2CCC(F)(F)CC2)nc(-n2ccc(CF)n2)n1)C1COC1] |
| 334 | 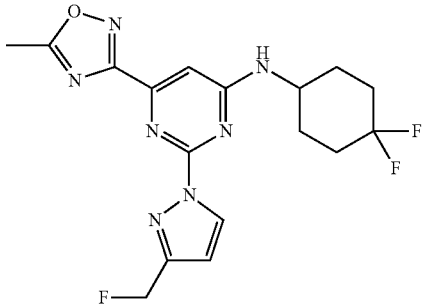 [SMILES: Cc1nc(-c2cc(NC3CCC(F)(F)CC3)nc(-n3ccc(CF)n3)n2)no1] |
| 335 | 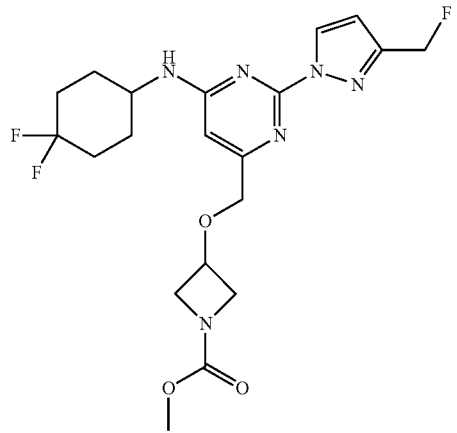 [SMILES: COC(=O)N1CC(OCc2cc(NC3CCC(F)(F)CC3)nc(-n3ccc(CF)n3)n2)C1] |
| 336 | 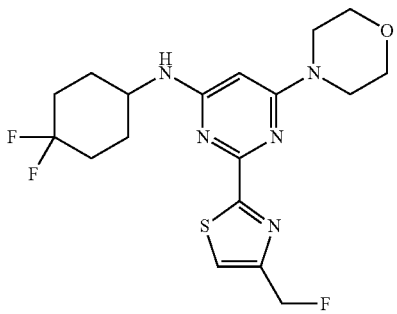 [SMILES: FCc1csc(-c2nc(NC3CCC(F)(F)CC3)cc(N3CCOCC3)n2)n1] |
| 337 | 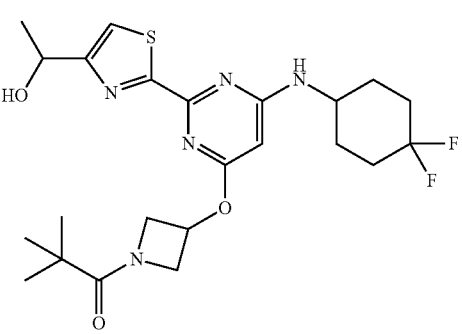 [SMILES: CC(O)c1csc(-c2nc(NC3CCC(F)(F)CC3)cc(OC3CN(C(=O)C(C)(C)C)C3)n2)n1] |
| 338 | 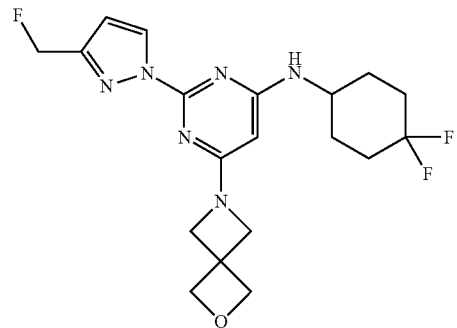 [SMILES: FCc1ccn(-c2nc(NC3CCC(F)(F)CC3)cc(N3CC4(COC4)C3)n2)n1] |
| 339 | 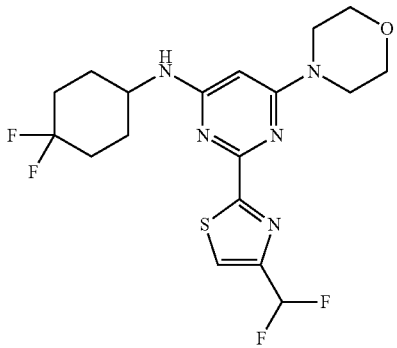 [SMILES: FC(F)c1csc(-c2nc(NC3CCC(F)(F)CC3)cc(N3CCOCC3)n2)n1] |

TABLE 1-continued

| Compound # | Structure |
|---|---|
| 340 | 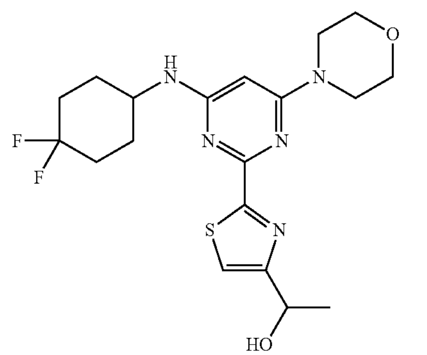 [SMILES: CC(O)c1csc(-c2nc(NC3CCC(F)(F)CC3)cc(N3CCOCC3)n2)n1] |
| 341 | 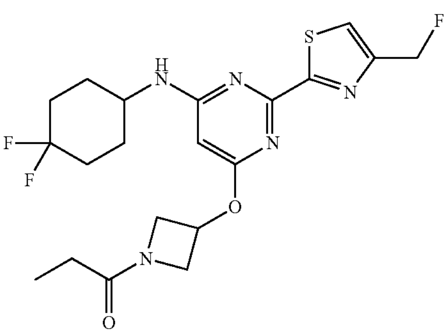 [SMILES: CCC(=O)N1CC(Oc2cc(NC3CCC(F)(F)CC3)nc(-c3nc(CF)cs3)n2)C1] |
| 342 | 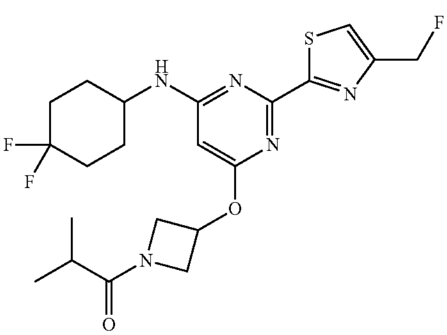 |
| 343 | 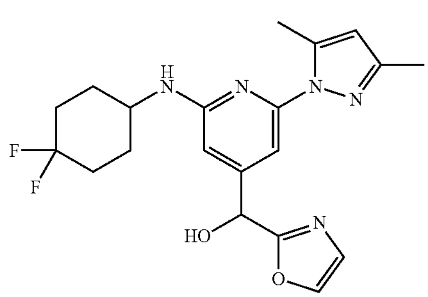 [SMILES: Cc1cc(C)n(-c2cc(C(O)c3ncco3)cc(NC3CCC(F)(F)CC3)n2)n1] |
| 344 | |
| 345 | |
| 346 | |
| 347 | |

TABLE 1-continued

| Compound # | Structure |
|---|---|
| 348 | 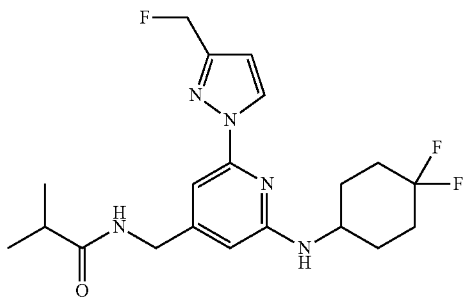 [SMILES: CC(C)C(=O)NCc1cc(NC2CCC(F)(F)CC2)nc(-n2ccc(CF)n2)c1] |
| 349 | 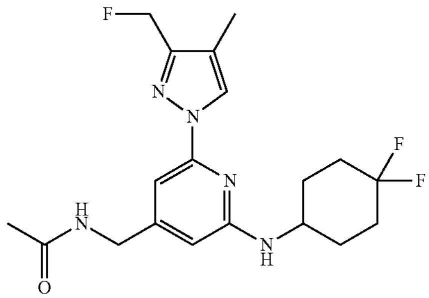 [SMILES: CC(=O)NCc1cc(NC2CCC(F)(F)CC2)nc(-n2cc(C)c(CF)n2)c1] |
| 350 | 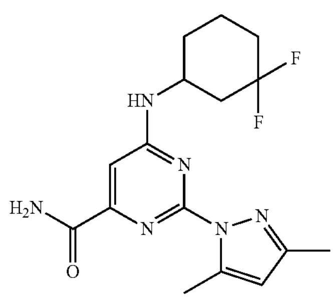 [SMILES: Cc1cc(C)n(-c2nc(NC3CCCC(F)(F)C3)cc(C(N)=O)n2)n1] |
| 351 | 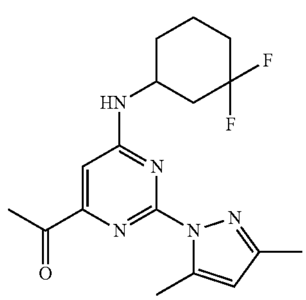 [SMILES: CC(=O)c1cc(NC2CCCC(F)(F)C2)nc(-n2nc(C)cc2C)n1] |
| 352 | 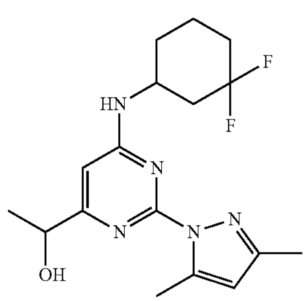 [SMILES: Cc1cc(C)n(-c2nc(NC3CCCC(F)(F)C3)cc(C(C)O)n2)n1] |
| 353 | |
| 354 | |
| 355 | |
| 356 | |
| 357 | |

TABLE 1-continued
| Compound # | Structure |
|---|---|
| 358 | 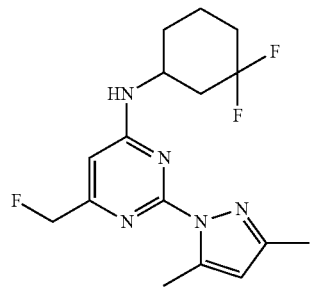 [SMILES: Cc1cc(C)n(-c2nc(CF)cc(NC3CCCC(F)(F)C3)n2)n1] |
| 359 | 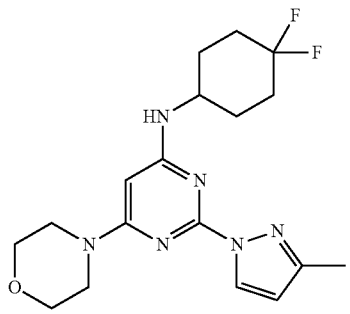 [SMILES: Cc1ccn(-c2nc(NC3CCC(F)(F)CC3)cc(N3CCOCC3)n2)n1] |
| 360 | 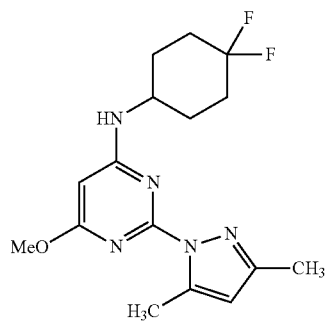 [SMILES: COc1cc(NC2CCC(F)(F)CC2)nc(-n2nc(C)cc2C)n1] |
| 361 | 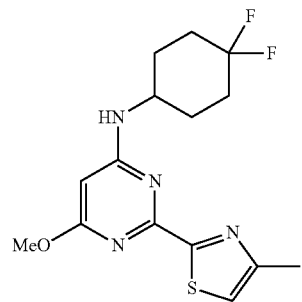 [SMILES: COc1cc(NC2CCC(F)(F)CC2)nc(-c2nc(C)cs2)n1] |
| 362 | 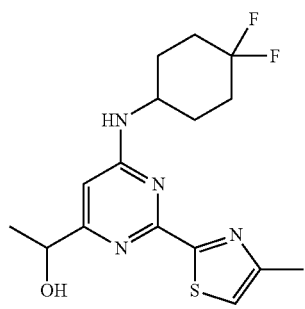 [SMILES: Cc1csc(-c2nc(NC3CCC(F)(F)CC3)cc(C(C)O)n2)n1] |
| 363 | 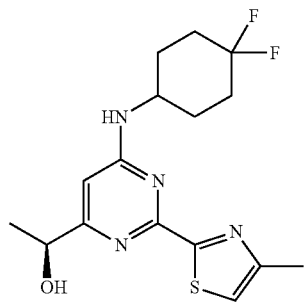 [SMILES: Cc1csc(-c2nc(NC3CCC(F)(F)CC3)cc([C@H](C)O)n2)n1] |
| 364 | 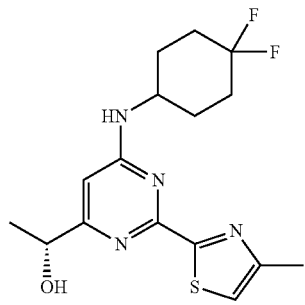 [SMILES: Cc1csc(-c2nc(NC3CCC(F)(F)CC3)cc([C@@H](C)O)n2)n1] |
| 365 | 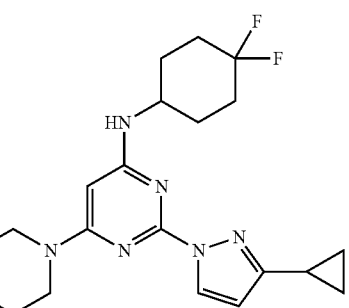 |

TABLE 2

| Compound Ref | Structure | m/z data |
|---|---|---|
| NSSy6909 | 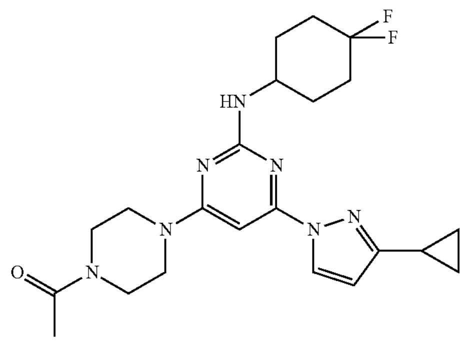 [SMILES: CC(=O)N1CCN(c2cc(-n3ccc(C4CC4)n3)nc(NC3CCC(F)(F)CC3)n2)CC1] | 445.5151 |
| NSSy6957 | 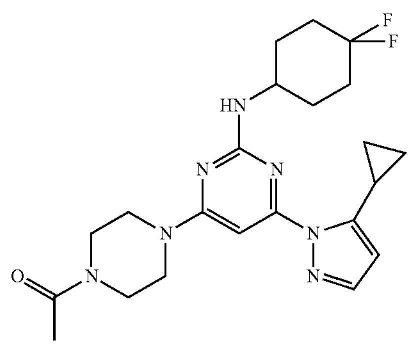 [SMILES: CC(=O)N1CCN(c2cc(-n3nccc3C3CC3)nc(NC3CCC(F)(F)CC3)n2)CC1] | 445.5151 |
| NSSy6629 | 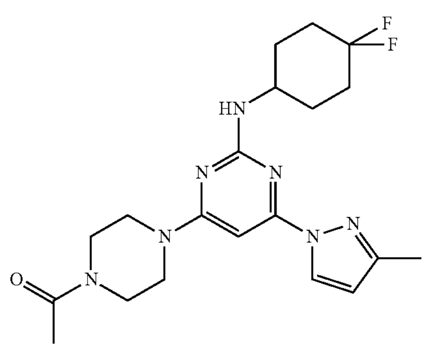 [SMILES: CC(=O)N1CCN(c2cc(-n3ccc(C)n3)nc(NC3CCC(F)(F)CC3)n2)CC1] | 419.4773 |
| NSSy6607 | 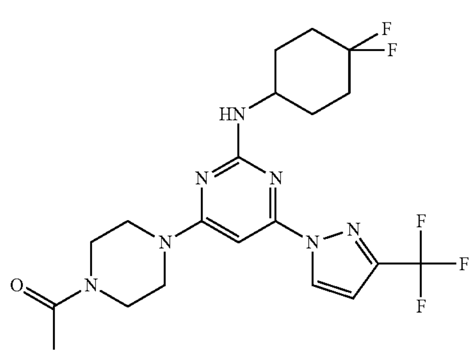 [SMILES: CC(=O)N1CCN(c2cc(-n3ccc(C(F)(F)F)n3)nc(NC3CCC(F)(F)CC3)n2)CC1] | 473.4476 |

TABLE 2-continued
| Compound Ref | Structure | m/z data |
|---|---|---|
| NSSy6598 | 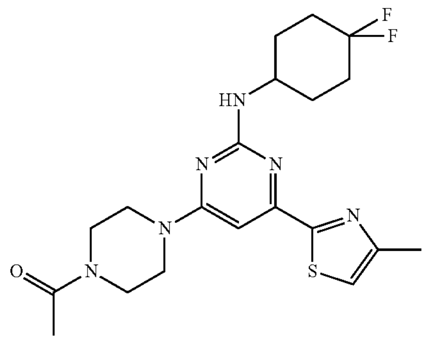 [SMILES: CC(=O)N1CCN(c2cc(-c3nc(C)cs3)nc(NC3CCC(F)(F)CC3)n2)CC1] | 436.5284 |
| NSSy6989 | 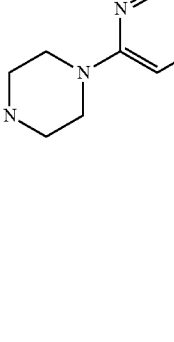 | 430.5002 |
| NSSy6886 | 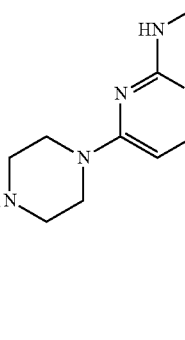 | 423.4406 |
| NSSy6919 | 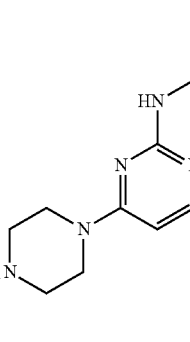 | 484.3466 |

TABLE 2-continued
| Compound Ref | Structure | m/z data |
|---|---|---|
| NSSy6936 | 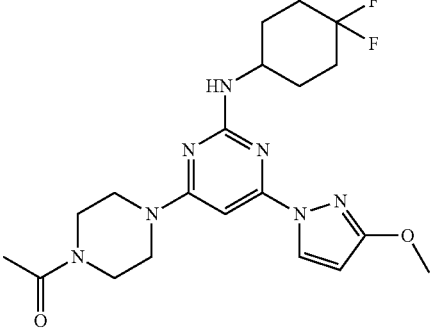 | 435.4763 |
| NSSy6972 | 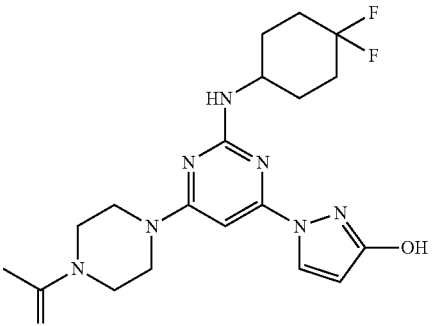 | 421.4495 |
| NSSy6389 | 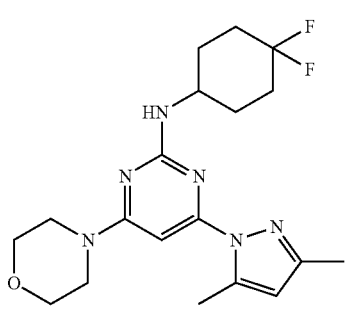 [SMILES: Cc1cc(C)n(-c2cc(N3CCOCC3)nc(NC3CCC(F)(F)CC3)n2)n1] | 392.4514 |
| NSSy6564 | 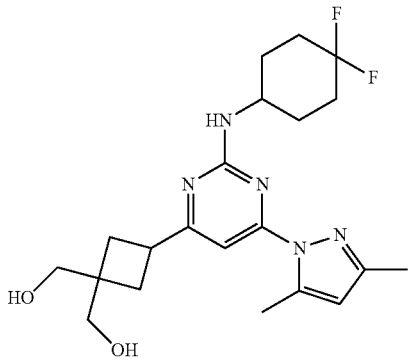 [SMILES: Cc1cc(C)n(-c2cc(C3CC(CO)(CO)C3)nc(NC3CCC(F)(F)CC3)n2)n1] | 422.4772 |

TABLE 2-continued

| Compound Ref | Structure | m/z data |
|---|---|---|
| NSSy6519 | 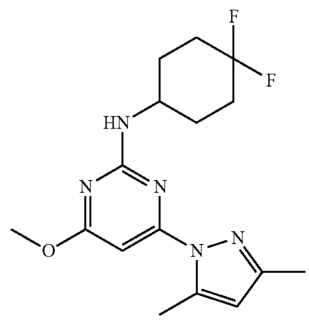 | 337.3719 |
| NSSy6638 | Chiral | 404.4624 |
| NSSy6639 | Chiral | 404.4624 |
| NSSy6644 | 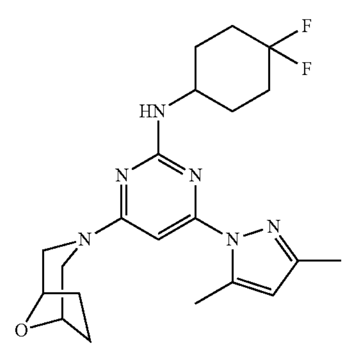 [SMILES: Cc1cc(C)n(-c2cc(N3CC4CCC(C3)O4)nc(NC3CCC(F)(F)CC3)n2)n1] | 418.4892 |

TABLE 2-continued

| Compound Ref | Structure | m/z data |
|---|---|---|
| NSSy6654 | 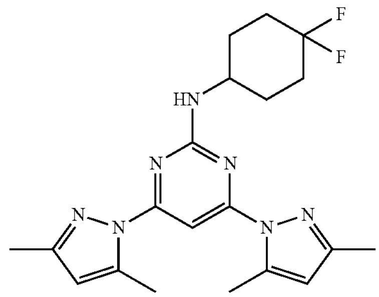 | 401.4625 |
| NSSy6391 | 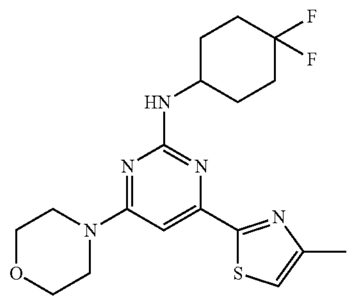 [SMILES: Cc1csc(-c2cc(N3CCOCC3)nc(NC3CCC(F)(F)CC3)n2)n1] | 395.4757 |
| NSSy6558 | 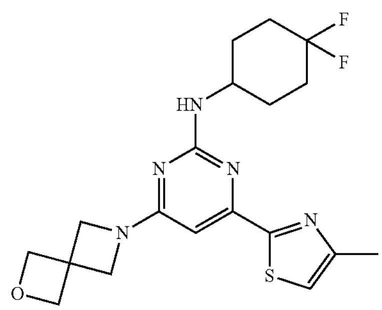 [SMILES: Cc1csc(-c2cc(N3CC4(COC4)C3)nc(NC3CCC(F)(F)CC3)n2)n1] | 407.4867 |
| NSSy6710 | 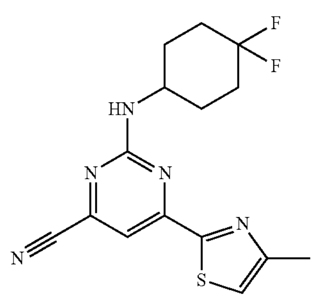 [SMILES: Cc1csc(-c2cc(C#N)nc(NC3CCC(F)(F)CC3)n2)n1] | 335.3805 |
| NSSy6711 | 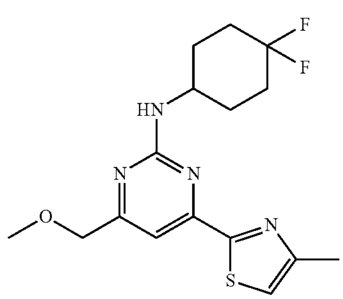 | 354.423 |

TABLE 2-continued

| Compound Ref | Structure | m/z data |
|---|---|---|
| NSSy6499 NSSy6524 | 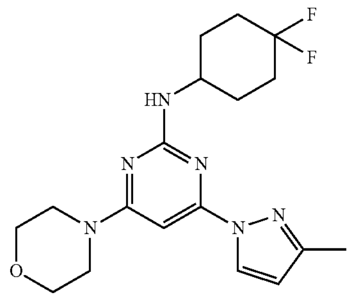 [SMILES: Cc1ccn(-c2cc(N3CCOCC3)nc(NC3CCC(F)(F)CC3)n2)n1] | 378.4246 |
| NSSy6522 NSSy6498 | 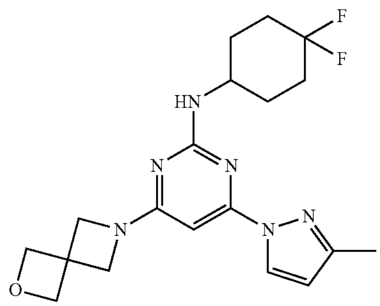 [SMILES: Cc1ccn(-c2cc(N3CC4(COC4)C3)nc(NC3CCC(F)(F)CC3)n2)n1] | 390.4356 |
| NSSy6585 NSSy6608 | 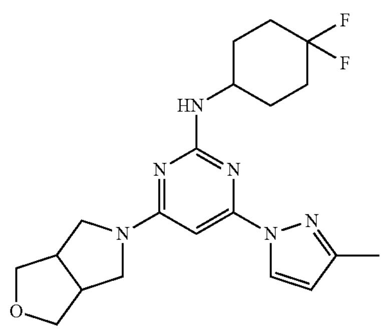 [SMILES: Cc1ccn(-c2cc(N3CC4COCC4C3)nc(NC3CCC(F)(F)CC3)n2)n1] | 404.4624 |
| NSSy6958 | 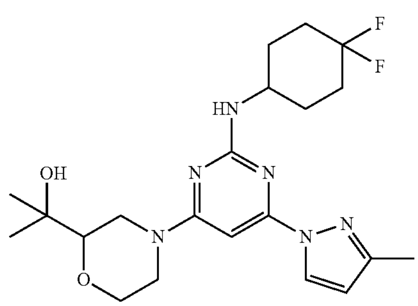 [SMILES: Cc1ccn(-c2cc(N3CCOC(C(C)(C)O)C3)nc(NC3CCC(F)(F)CC3)n2)n1] | 436.504 |
| NSSy6677 | 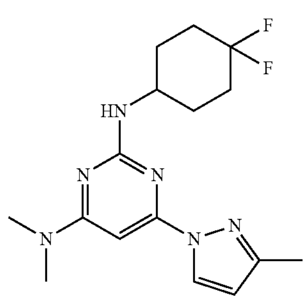 | 336.3878 |

TABLE 2-continued

| Compound Ref | Structure | m/z data |
|---|---|---|
| NSSy6679 | 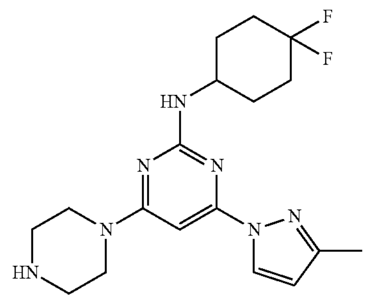 [SMILES: Cc1ccn(-c2cc(N3CCNCC3)nc(NC3CCC(F)(F)CC3)n2)n1] | 377.4405 |
| NSSy6688 | 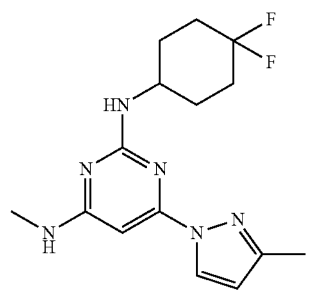 | 322.361 |
| NSSy6698 | 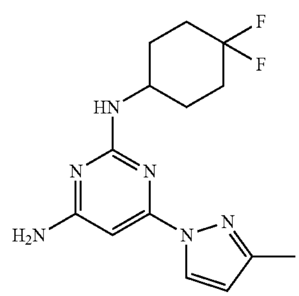 [SMILES: Cc1ccn(-c2cc(N)nc(NC3CCC(F)(F)CC3)n2)n1] | 308.3342 |
| NSSy6574 | 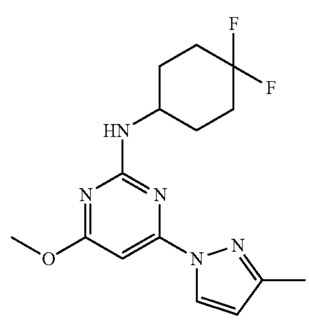 | 323.3451 |
| NSSy6580 | 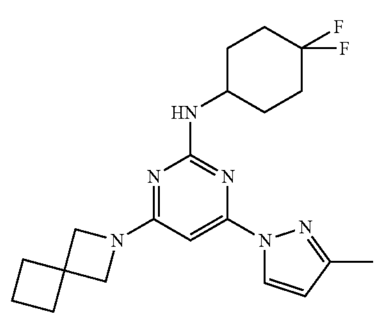 [SMILES: Cc1ccn(-c2cc(N3CC4(CCC4)C3)nc(NC3CCC(F)(F)CC3)n2)n1] | 388.4634 |

TABLE 2-continued
| Compound Ref | Structure | m/z data |
|---|---|---|
| NSSy6581 | 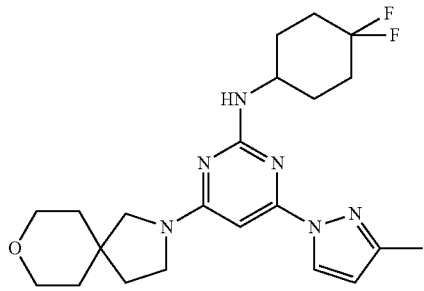 [SMILES: Cc1ccn(-c2cc(N3CCC4(CCOCC4)C3)nc(NC3CCC(F)(F)CC3)n2)n1] | 432.516 |
| NSSy6584 | 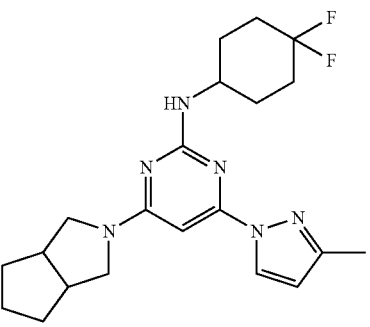 [SMILES: Cc1ccn(-c2cc(N3CC4CCCC4C3)nc(NC3CCC(F)(F)CC3)n2)n1] | 402.4902 |
| NSSy6700 | 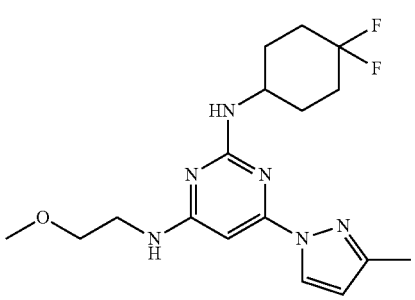 | 366.4136 |
| NSSy6913 | 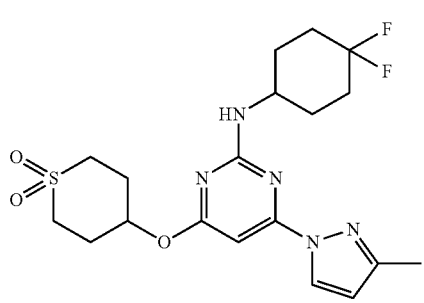 [SMILES: Cc1ccn(-c2cc(OC3CCS(=O)(=O)CC3)nc(NC3CCC(F)(F)CC3)n2)n1] | 441.5005 |
| NSSy6914 | 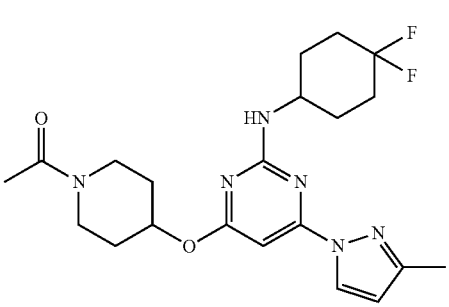 [SMILES: CC(=O)N1CCC(Oc2cc(-n3ccc(C)n3)nc(NC3CCC(F)(F)CC3)n2)CC1] | 434.4882 |

TABLE 2-continued
| Compound Ref | Structure | m/z data |
|---|---|---|
| NSSy6675 | 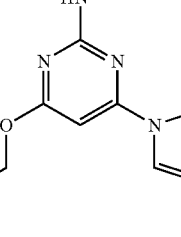 | 367.3977 |
| NSSy6686 | 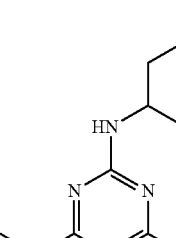 | 380.4404 |
| NSSy6625 | 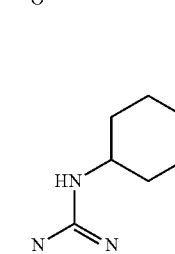 | 337.3719 |
| NSSy6525 | 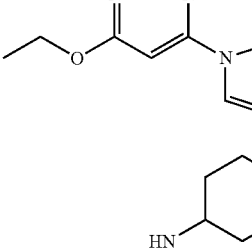 | 378.4246 |
| NSSy6523 | 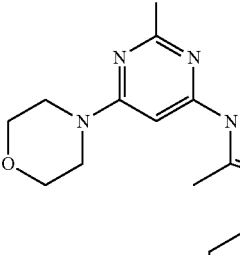 | 390.4356 |

TABLE 2-continued

| Compound Ref | Structure | m/z data |
|---|---|---|
| NSSy6924 | 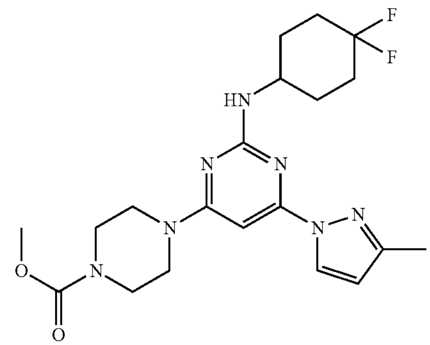 [SMILES: COC(=O)N1CCN(c2cc(-n3ccc(C)n3)nc(NC3CCC(F)(F)CC3)n2)CC1] | 435.4763 |
| NSSy6995 | 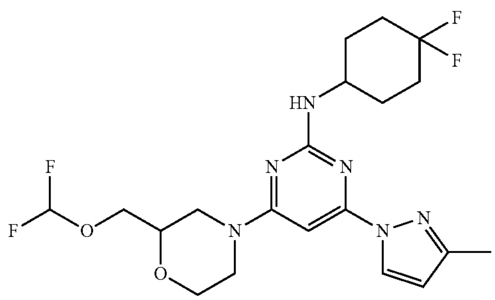 [SMILES: Cc1ccn(-c2cc(N3CCOC(COC(F)F)C3)nc(NC3CCC(F)(F)CC3)n2)n1] | 458.4574 |
| NSSy6986 | 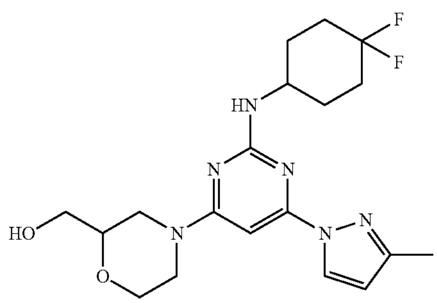 [SMILES: Cc1ccn(-c2cc(N3CCOC(CO)C3)nc(NC3CCC(F)(F)CC3)n2)n1] | 408.4504 |
| NSSy6722 | 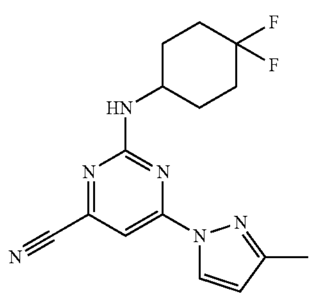 [SMILES: Cc1ccn(-c2cc(C#N)nc(NC3CCC(F)(F)CC3)n2)n1] | 318.3294 |
| NSSy6684 | 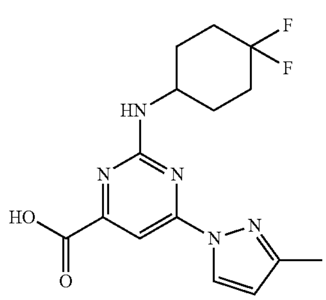 [SMILES: Cc1ccn(-c2cc(C(=O)O)nc(NC3CCC(F)(F)CC3)n2)n1] | 337.3283 |

TABLE 2-continued

| Compound Ref | Structure | m/z data |
|---|---|---|
| NSSy6704 | 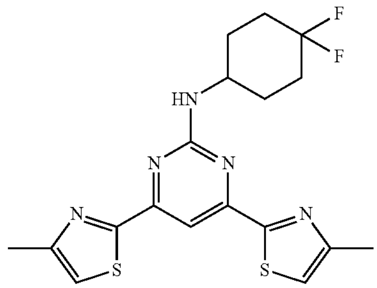 | 407.5111 |
| NSSy6800 | 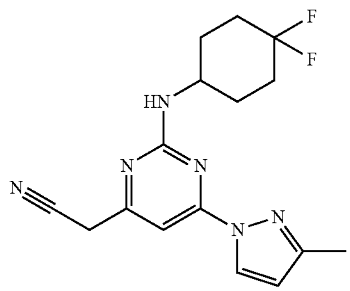 [SMILES: Cc1ccn(-c2cc(CC#N)nc(NC3CCC(F)(F)CC3)n2)n1] | 332.3562 |
| NSSy6744 | 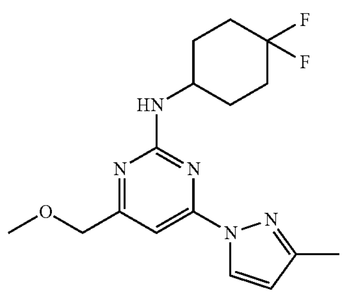 | 337.3719 |
| NSSy6783 | 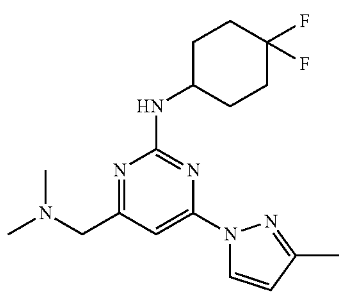 | 350.4146 |
| NSSy6468 | 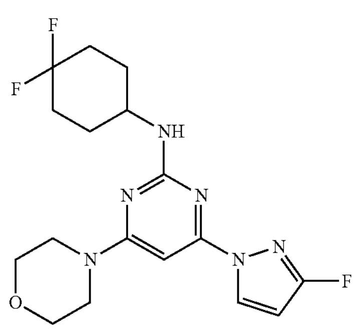 [SMILES: Fc1ccn(-c2cc(N3CCOCC3)nc(NC3CCC(F)(F)CC3)n2)n1] | 382.3879 |

TABLE 2-continued

| Compound Ref | Structure | m/z data |
|---|---|---|
| NSSy6467 | 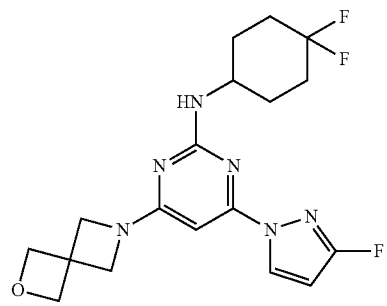 [SMILES: Fc1ccn(-c2cc(N3CC4(COC4)C3)nc(NC3CCC(F)(F)CC3)n2)n1] | 394.3989 |
| NSSy6471 | 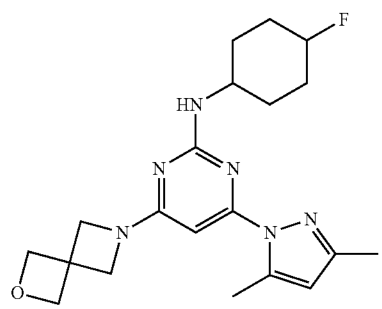 [SMILES: Cc1cc(C)n(-c2cc(N3CC4(COC4)C3)nc(NC3CCC(F)CC3)n2)n1] | 386.4723 |
| NSSy6931 | 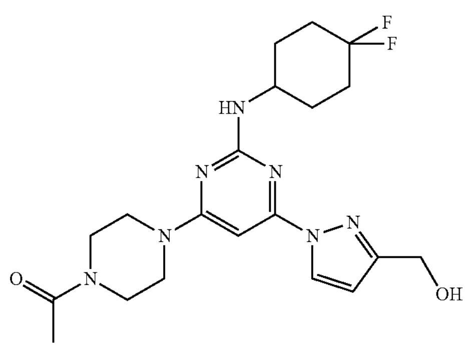 [SMILES: CC(=O)N1CCN(c2cc(-n3ccc(CO)n3)nc(NC3CCC(F)(F)CC3)n2)CC1] | 435.4763 |
| NSSy6917 | 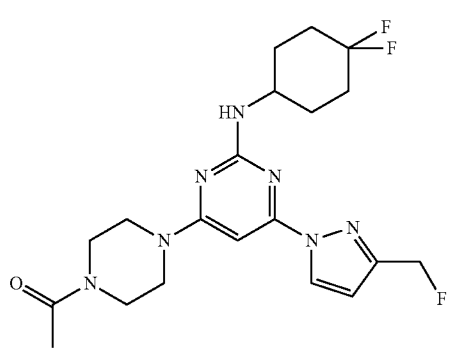 [SMILES: CC(=O)N1CCN(c2cc(-n3ccc(CF)n3)nc(NC3CCC(F)(F)CC3)n2)CC1] | 437.4674 |

TABLE 2-continued

| Compound Ref | Structure | m/z data |
|---|---|---|
| NSSy6930 | 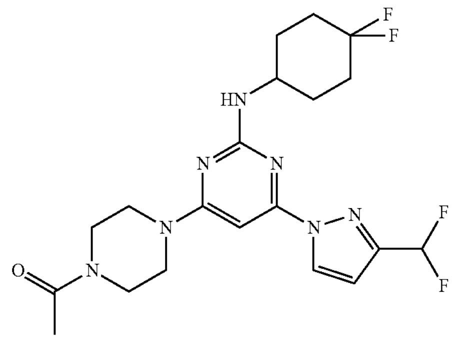 [SMILES: CC(=O)N1CCN(c2cc(-n3ccc(C(F)F)n3)nc(NC3CCC(F)(F)CC3)n2)CC1] | 455.4575 |
| NSSy6721 | 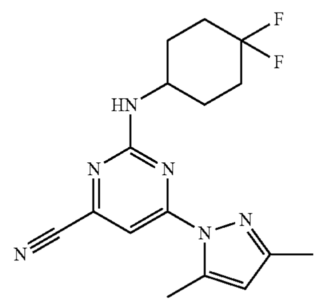 [SMILES: Cc1cc(C)n(-c2cc(C#N)nc(NC3CCC(F)(F)CC3)n2)n1] | 332.3562 |
| NSSy6724 | 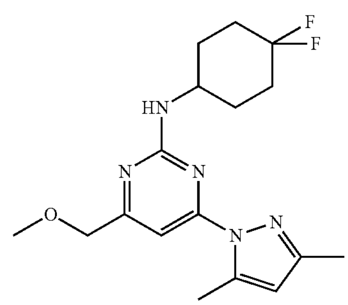 | 351.3987 |
| NSSy6464 | 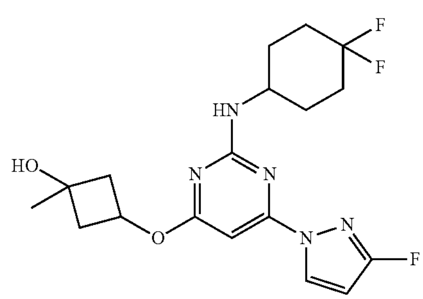 [SMILES: CC1(O)CC(Oc2cc(-n3ccc(F)n3)nc(NC3CCC(F)(F)CC3)n2)C1] | 397.3988 |
| NSSy6590 | 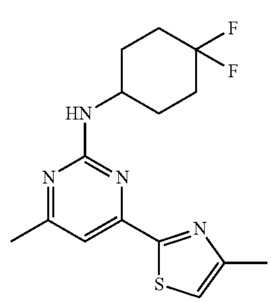 | 324.3972 |

TABLE 2-continued

| Compound Ref | Structure | m/z data |
|---|---|---|
| NSSy6591 | 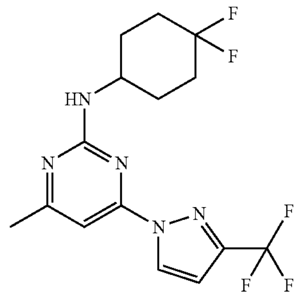 [SMILES: Cc1cc(-n2ccc(C(F)(F)F)n2)nc(NC2CCC(F)(F)CC2)n1] | 361.3164 |
| NSSy6593 | 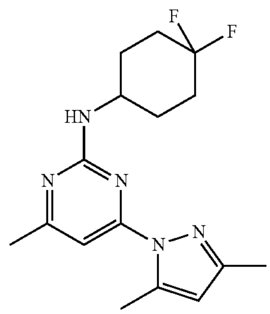 | 321.3729 |
| NSSy6736 | 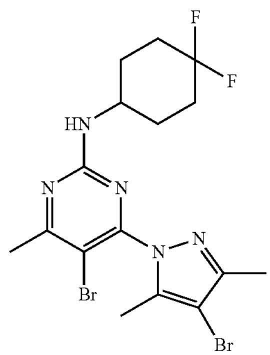 | 479.1651 |
| NSSy6678 | 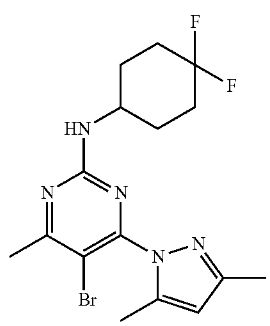 | 400.269 |
| NSSy6604 | 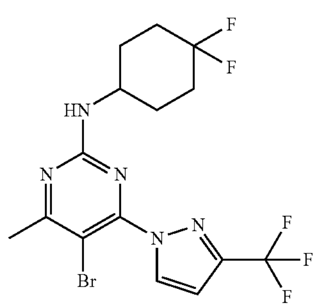 [SMILES: Cc1nc(NC2CCC(F)(F)CC2)nc(-n2ccc(C(F)(F)F)n2)c1Br] | 440.2125 |

TABLE 2-continued

| Compound Ref | Structure | m/z data |
|---|---|---|
| NSSy6697 | 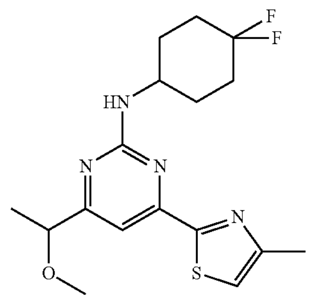 [SMILES: COC(C)c1cc(-c2nc(C)cs2)nc(NC2CCC(F)(F)CC2)n1] | 368.4498 |
| NSSy6729 | Chiral | 368.4498 |
| NSSy6612 | 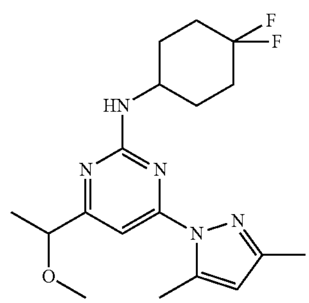 [SMILES: COC(C)c1cc(-n2nc(C)cc2C)nc(NC2CCC(F)(F)CC2)n1] | 365.4255 |
| NSSy6613 | 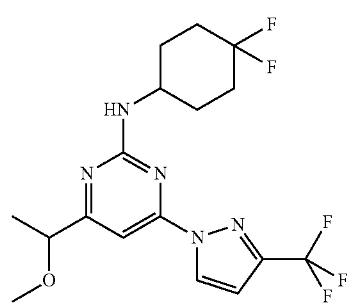 [SMILES: COC(C)c1cc(-n2ccc(C(F)(F)F)n2)nc(NC2CCC(F)(F)CC2)n1] | 405.369 |
| NSSy6651 | 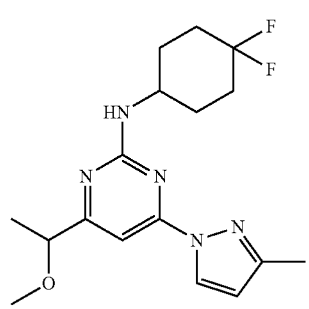 | 351.3987 |

TABLE 2-continued

| Compound Ref | Structure | m/z data |
|---|---|---|
| NSSy6614 | 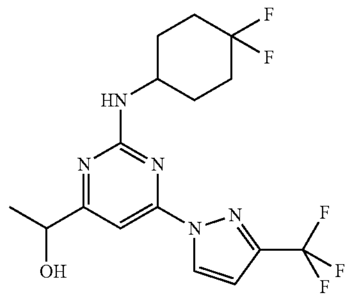 [SMILES: CC(O)c1cc(-n2ccc(C(F)(F)F)n2)nc(NC2CCC(F)(F)CC2)n1] | 391.3422 |
| NSSy6650 | 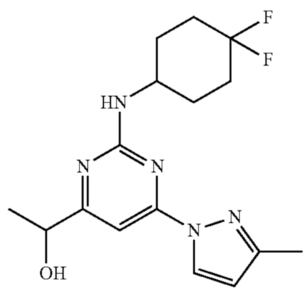 [SMILES: Cc1ccn(-c2cc(C(C)O)nc(NC3CCC(F)(F)CC3)n2)n1] | 337.3719 |
| NSSy6674 | 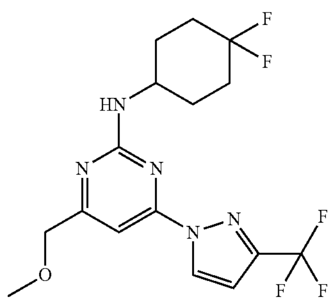 [SMILES: COCc1cc(-n2ccc(C(F)(F)F)n2)nc(NC2CCC(F)(F)CC2)n1] | 391.3422 |
| NSSy6941 | 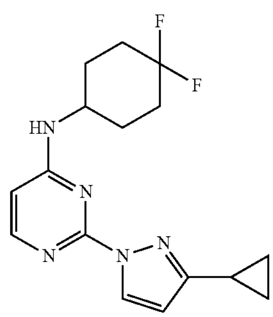 [SMILES: FC1(F)CCC(Nc2ccnc(-n3ccc(C4CC4)n3)n2)CC1] | 319.3571 |
| NSSy6945 | 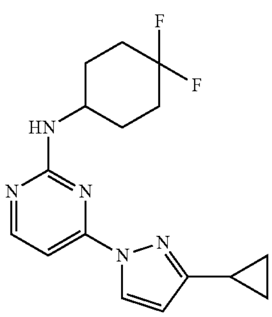 [SMILES: FC1(F)CCC(Nc2nccc(-n3ccc(C4CC4)n3)n2)CC1] | 319.3571 |

TABLE 2-continued

| Compound Ref | Structure | m/z data |
|---|---|---|
| NSSy7043 | 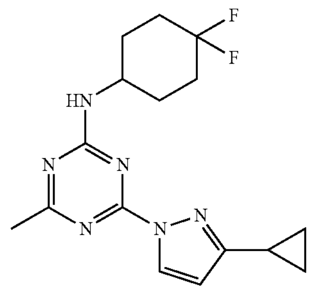 [SMILES: Cc1nc(NC2CCC(F)(F)CC2)nc(-n2ccc(C3CC3)n2)n1] | 334.372 |
| NSSy6061 | 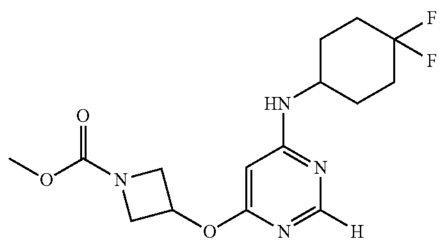 [SMILES: COC(=O)N1CC(Oc2cc(NC3CCC(F)(F)CC3)ncn2)C1] | 342.344 |
| NSSy6128 | 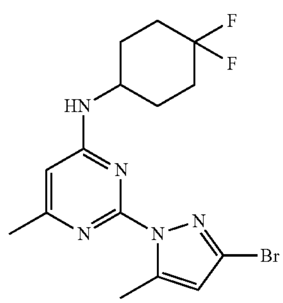 [SMILES: Cc1cc(NC2CCC(F)(F)CC2)nc(-n2nc(Br)cc2C)n1] | 386.2422 |
| NSSy6935 NSSy5161 | | 333.3839 |
| NSSy7028 | 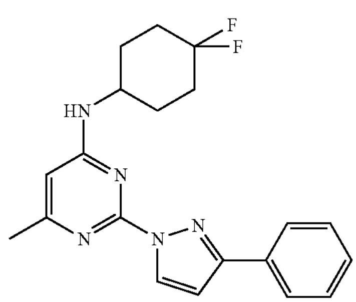 [SMILES: Cc1cc(NC2CCC(F)(F)CC2)nc(-n2ccc(-c3ccccc3)n2)n1] | 369.4169 |

TABLE 2-continued

| Compound Ref | Structure | m/z data |
|---|---|---|
| NSSy7012 | 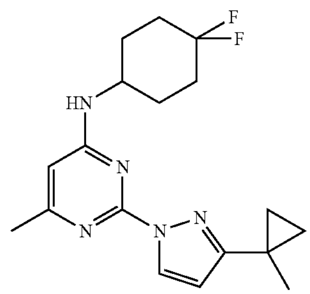 [SMILES: Cc1cc(NC2CCC(F)(F)CC2)nc(-n2ccc(C3(C)CC3)n2)n1] | 347.4107 |
| NSSy6994 | 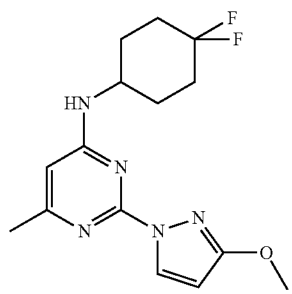 | 323.3451 |
| NSSy7027 | 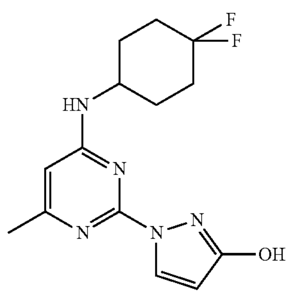 [SMILES: Cc1cc(NC2CCC(F)(F)CC2)nc(-n2ccc(O)n2)n1] | 309.3183 |
| NSSy7059 | 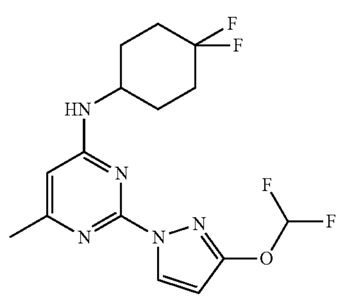 [SMILES: Cc1cc(NC2CCC(F)(F)CC2)nc(-n2ccc(OC(F)F)n2)n1] | 359.3253 |
| NSSy7062 | 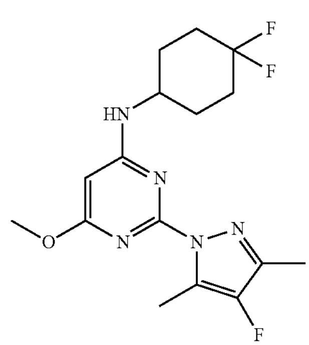 | 355.362 |

TABLE 2-continued

| Compound Ref | Structure | m/z data |
| --- | --- | --- |
| NSSy6850 | 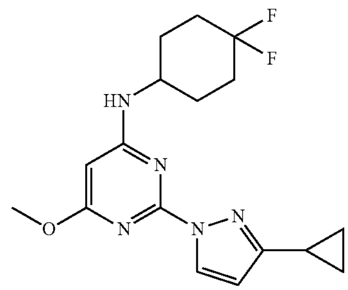 [SMILES: COc1cc(NC2CCC(F)(F)CC2)nc(-n2ccc(C3CC3)n2)n1] | 349.3829 |
| NSSy6889 | 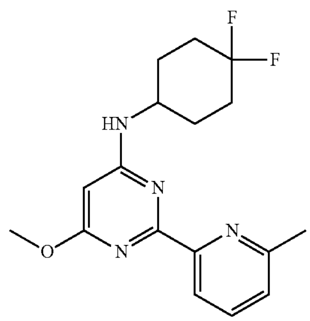 | 334.368 |
| NSSy6067 | 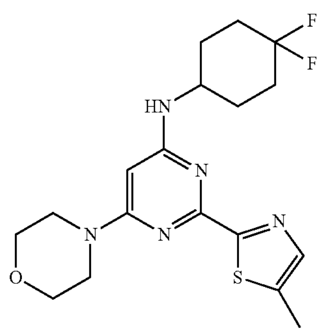 [SMILES: Cc1cnc(-c2nc(NC3CCC(F)(F)CC3)cc(N3CCOCC3)n2)s1] | 395.4757 |
| NSSy6134 | 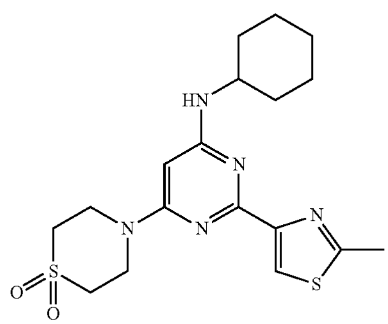 [SMILES: Cc1nc(-c2nc(NC3CCCCC3)cc(N3CCS(=O)(=O)CC3)n2)cs1] | 407.5605 |
| NSSy6140 | 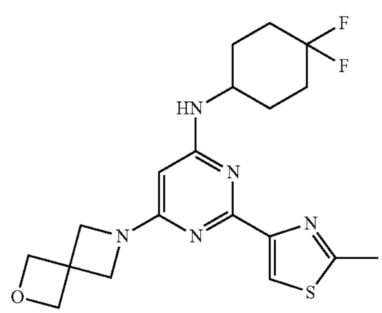 [SMILES: Cc1nc(-c2nc(NC3CCC(F)(F)CC3)cc(N3CC4(COC4)C3)n2)cs1] | 407.4867 |

TABLE 2-continued
| Compound Ref | Structure | m/z data |
|---|---|---|
| NSSy6133 | 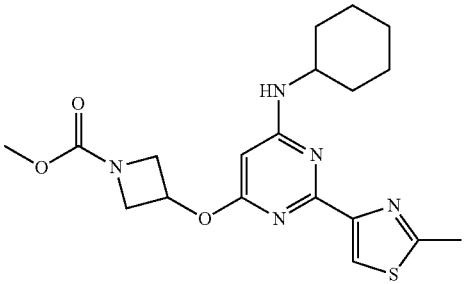 | 403.5045 |
| NSSy6165 | 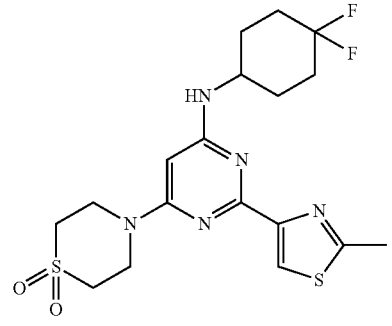 [SMILES: Cc1nc(-c2nc(NC3CCC(F)(F)CC3)cc(N3CCS(=O)(=O)CC3)n2)cs1] | 443.5407 |
| NSSy6132 | 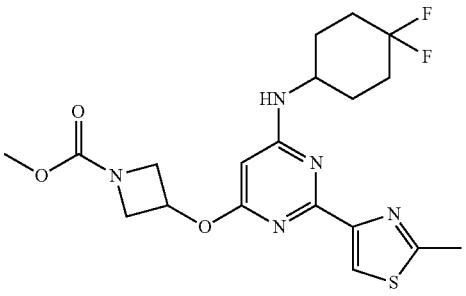 | 439.4847 |
| NSSy5662, NSSy6408 | 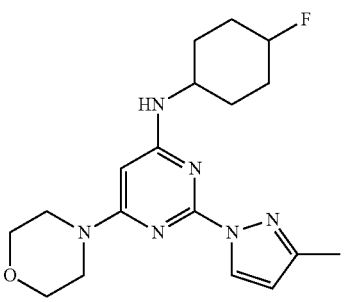 [SMILES: Cc1ccn(-c2nc(NC3CCC(F)CC3)cc(N3CCOCC3)n2)n1] | 360.4345 |
| NSSy5691 NSSy6407 | 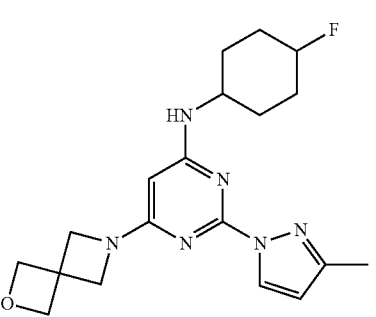 [SMILES: Cc1ccn(-c2nc(NC3CCC(F)CC3)cc(N3CC4(COC4)C3)n2)n1] | 372.4455 |

TABLE 2-continued

| Compound Ref | Structure | m/z data |
|---|---|---|
| NSSy5663 | 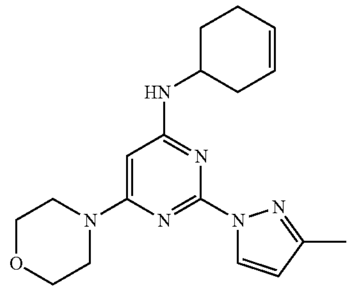 [SMILES: Cc1ccn(-c2nc(NC3CC=CCC3)cc(N3CCOCC3)n2)n1] | 340.4286 |
| NSSy5670, NSSy6341 | 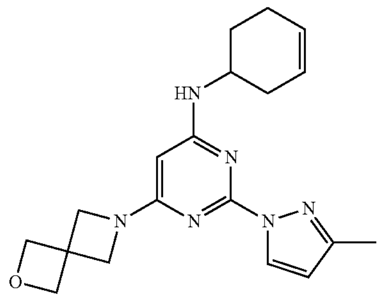 [SMILES: Cc1ccn(-c2nc(NC3CC=CCC3)cc(N3CC4(COC4)C3)n2)n1] | 352.4396 |
| NSSy6097 | 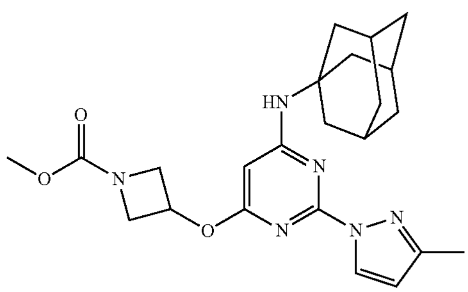 | 438.529 |
| NSSy6091 | 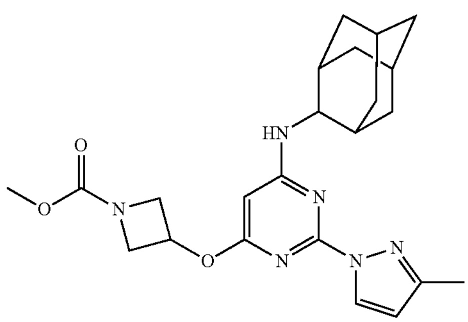 | 438.529 |
| NSSy6127 | 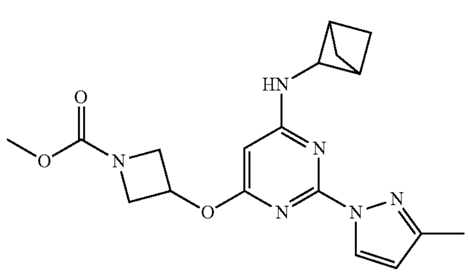 | 370.4108 |

TABLE 2-continued
| Compound Ref | Structure | m/z data |
|---|---|---|
| NSSy5741 | 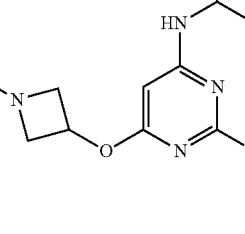 | 404.4435 |
| NSSy5765 | 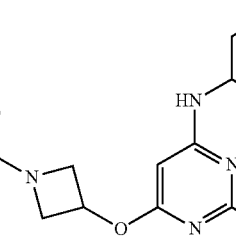 | 416.4981 |
| NSSy5762 | 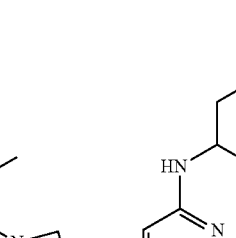 | 396.4922 |
| NSSy5786 | 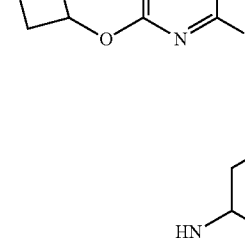 | 384.4376 |
| NSSy5684 | 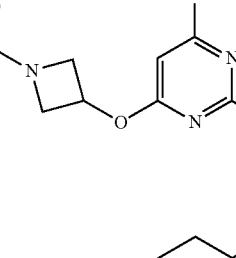 | 378.4246 |

TABLE 2-continued
| Compound Ref | Structure | m/z data |
|---|---|---|
| NSSy5683 | 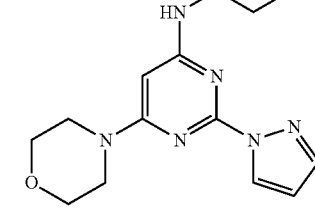 | 358.4187 |
| NSSy6125 | 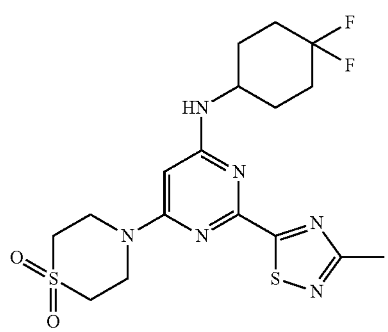 [SMILES: Cc1nsc(-c2nc(NC3CCC(F)(F)CC3)cc(N3CCS(=O)(=O)CC3)n2)n1] | 444.5288 |
| NSSy6145 | 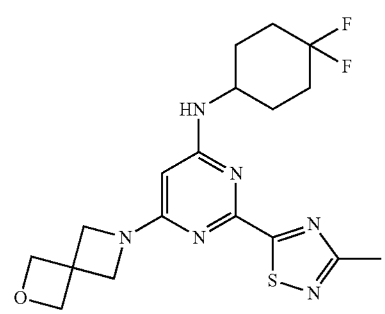 [SMILES: Cc1nsc(-c2nc(NC3CCC(F)(F)CC3)cc(N3CC4(COC4)C3)n2)n1] | 408.4748 |
| NSSy6178 | 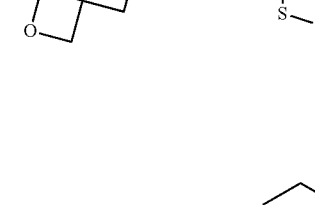 | 451.4997 |

TABLE 2-continued

| Compound Ref | Structure | m/z data |
|---|---|---|
| NSSy6251 | Chiral | 451.4997 |
| NSSy6252 | Chiral | 451.4997 |
| NSSy6201 | 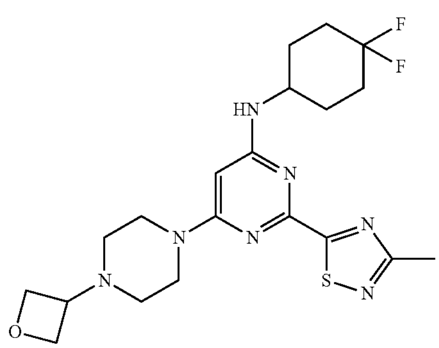 [SMILES: Cc1nsc(-c2nc(NC3CCC(F)(F)CC3)cc(N3CCN(C4COC4)CC3)n2)n1] | 451.5433 |
| NSSy5832 | 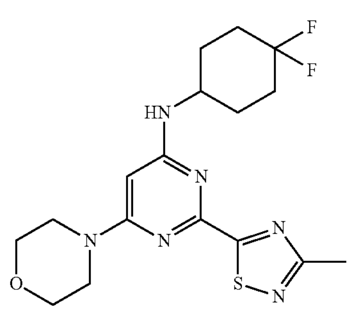 [SMILES: Cc1nsc(-c2nc(NC3CCC(F)(F)CC3)cc(N3CCOCC3)n2)n1] | 396.4638 |

TABLE 2-continued
| Compound Ref | Structure | m/z data |
|---|---|---|
| NSSy5857 NSSy6368 | 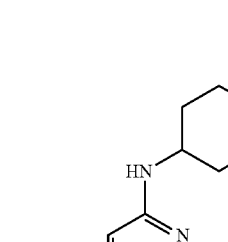 | 440.4728 |
| NSSy6202 | 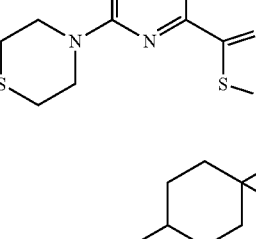 | 408.5486 |
| NSSy5835 | 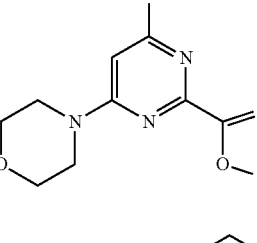 | 380.3968 |
| NSSy5830 | 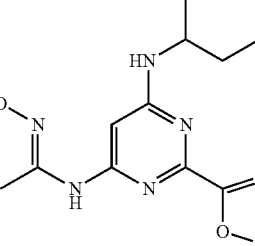 | 367.3581 |
| NSSy5887 | 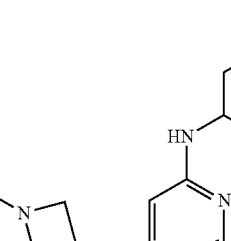 | 424.4058 |

TABLE 2-continued

| Compound Ref | Structure | m/z data |
|---|---|---|
| NSSy5779 | 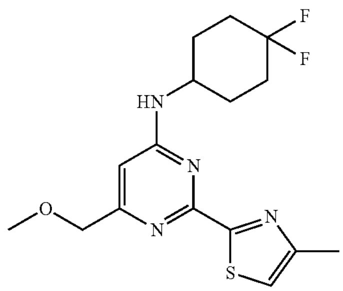 | 354.423 |
| NSSy5818 | 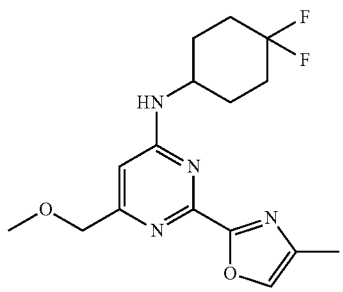 | 338.356 |
| NSSy6880 NSSy7001 | | 363.4097 |
| NSSy6881 | 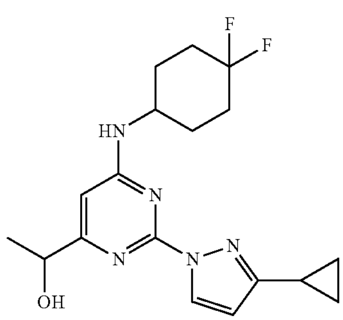 [SMILES: CC(O)c1cc(NC2CCC(F)(F)CC2)nc(-n2ccc(C3CC3)n2)n1] | 363.4097 |
| NSSy6167 | 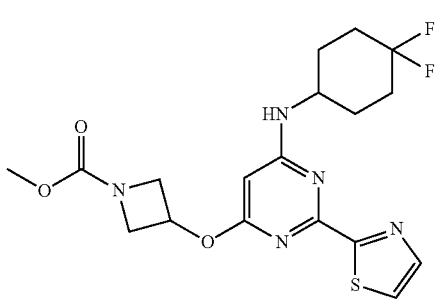 [SMILES: COC(=O)N1CC(Oc2cc(NC3CCC(F)(F)CC3)nc(-c3nccs3)n2)C1] | 425.4579 |

TABLE 2-continued
| Compound Ref | Structure | m/z data |
|---|---|---|
| NSSy6152 | 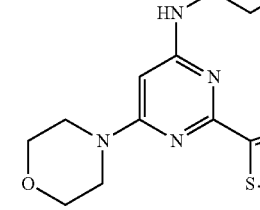 | 381.4489 |
| NSSy6166 | 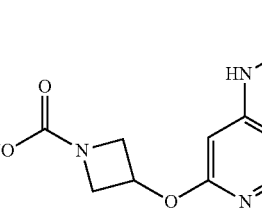 | 389.4777 |
| NSSy6170 | 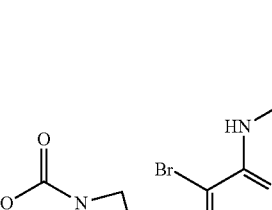 | 468.3738 |
| NSSy6263 | 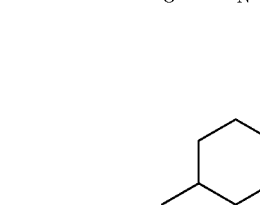 | 394.4876 |
| NSSy5774 | 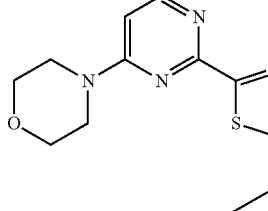 | 450.5116 |

TABLE 2-continued
| Compound Ref | Structure | m/z data |
|---|---|---|
| NSSy5787 | 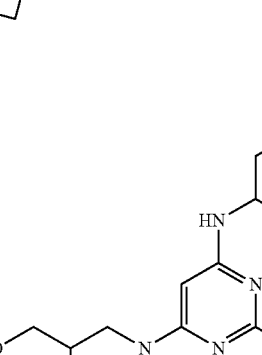 | 449.5671 |
| NSSy5789 | 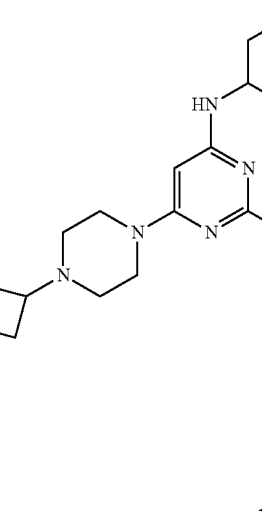 | 439.5283 |
| NSSy5792 | 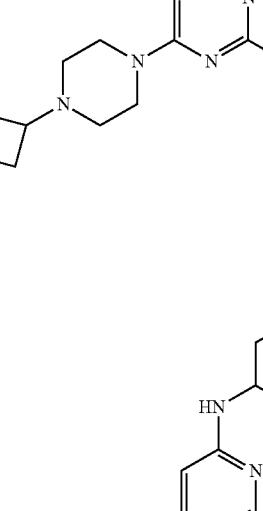 | 450.5552 |
| NSSy5795 | 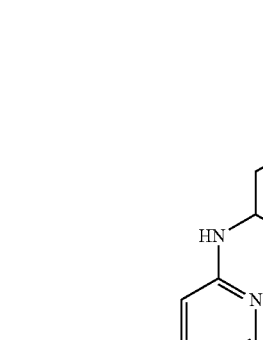 Chiral | 439.5283 |

TABLE 2-continued

| Compound Ref | Structure | m/z data |
|---|---|---|
| NSSy6055 | 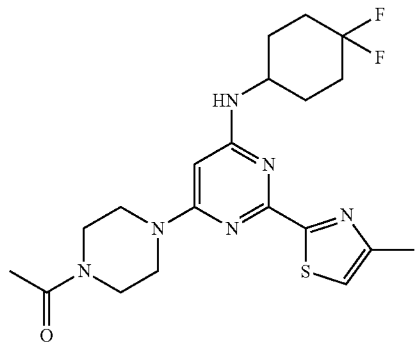 [SMILES: CC(=O)N1CCN(c2cc(NC3CCC(F)(F)CC3)nc(-c3nc(C)cs3)n2)CC1] | 436.5284 |
| NSSy6062 | 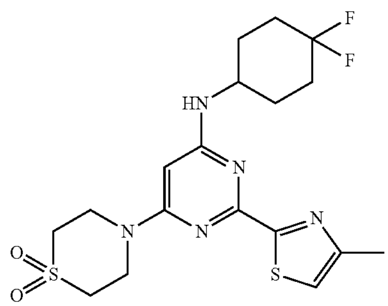 [SMILES: Cc1csc(-c2nc(NC3CCC(F)(F)CC3)cc(N3CCS(=O)(=O)CC3)n2)n1] | 443.5407 |
| NSSy6093 | 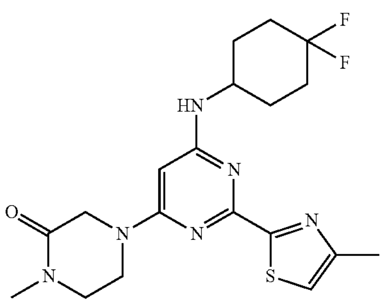 [SMILES: Cc1csc(-c2nc(NC3CCC(F)(F)CC3)cc(N3CCN(C)C(=O)C3)n2)n1] | 422.5016 |
| NSSy6116 | 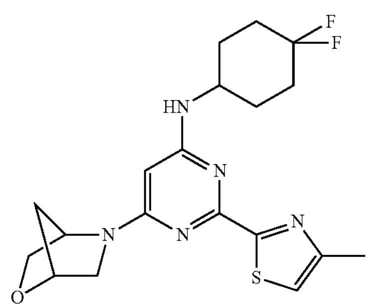 [SMILES: Cc1csc(-c2nc(NC3CCC(F)(F)CC3)cc(N3CC4CC3CO4)n2)n1] | 407.4867 |
| NSSy6129 | 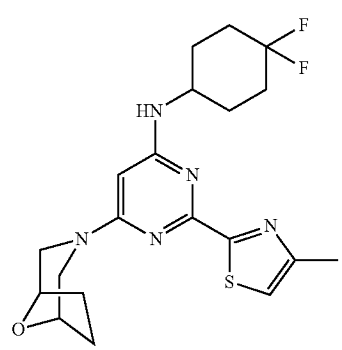 [SMILES: Cc1csc(-c2nc(NC3CCC(F)(F)CC3)cc(N3CC4CCC(C3)O4)n2)n1] | 421.5135 |

TABLE 2-continued

| Compound Ref | Structure | m/z data |
|---|---|---|
| NSSy5796 | Chiral | 439.5283 |
| NSSy6171 | 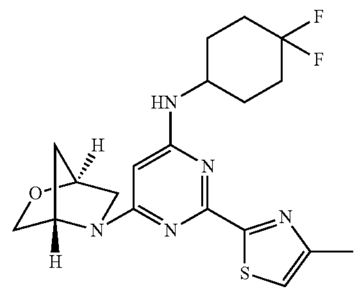 [SMILES: Cc1csc(-c2nc(NC3CCC(F)(F)CC3)cc(N3C[C@@H]4C[C@H]3CO4)n2)n1] | 407.4867 |
| NSSy6111 | 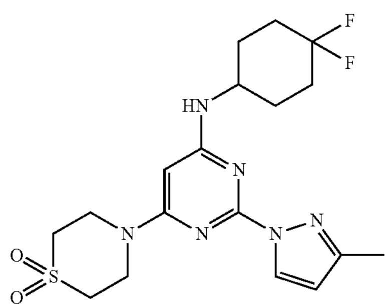 [SMILES: Cc1ccn(-c2nc(NC3CCC(F)(F)CC3)cc(N3CCS(=O)(=O)CC3)n2)n1] | 426.4896 |
| NSSy5740 | 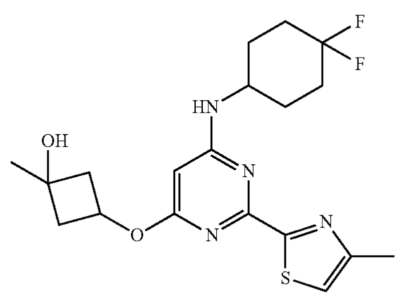 | 410.4866 |
| NSSy6253 | 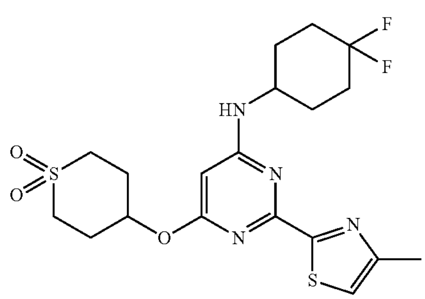 [SMILES: Cc1csc(-c2nc(NC3CCC(F)(F)CC3)cc(OC3CCS(=O)(=O)CC3)n2)n1] | 458.5516 |

TABLE 2-continued

| Compound Ref | Structure | m/z data |
|---|---|---|
| NSSy5730 | 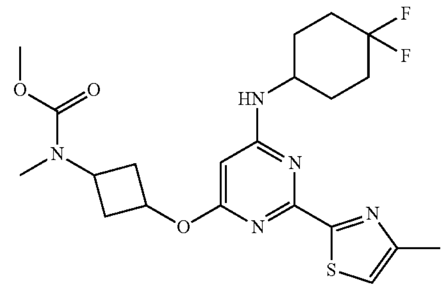 | 467.5383 |
| NSSy6007 | 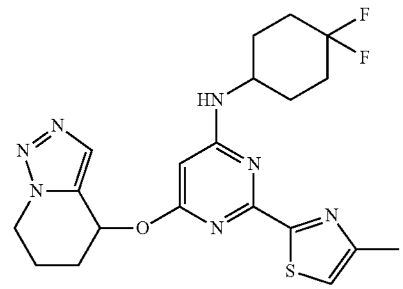 [SMILES: Cc1csc(-c2nc(NC3CCC(F)(F)CC3)cc(OC3CCCn4nncc43)n2)n1] | 447.5117 |
| NSSy6258 | 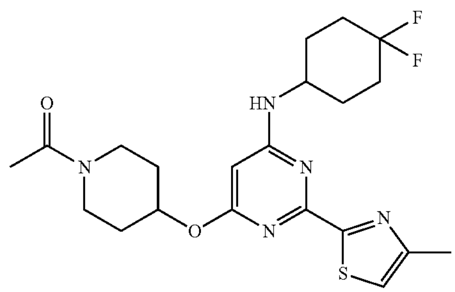 [SMILES: CC(=O)N1CCC(Oc2cc(NC3CCC(F)(F)CC3)nc(-c3nc(C)cs3)n2)CC1] | 451.5393 |
| NSSy6056 | 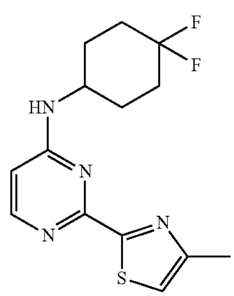 [SMILES: Cc1csc(-c2nccc(NC3CCC(F)(F)CC3)n2)n1] | 310.3704 |
| NSSy6106 | 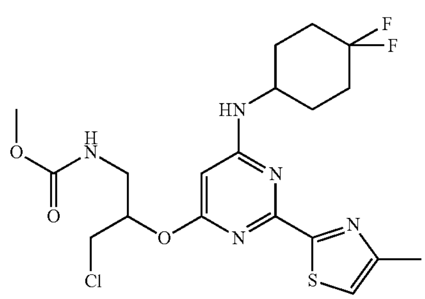 [SMILES: COC(=O)NCC(CCl)Oc1cc(NC2CCC(F)(F)CC2)nc(-c2nc(C)cs2)n1] | 475.9456 |

TABLE 2-continued

| Compound Ref | Structure | m/z data |
|---|---|---|
| NSSy5868 NSSy5943 | | 518.3808 |
| NSSy6045 | 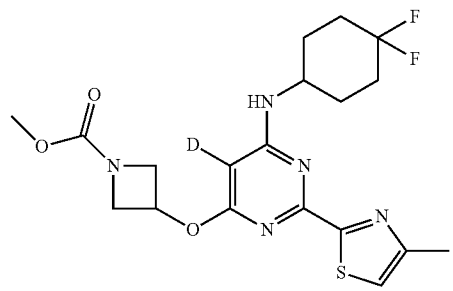 | 440.4908 |
| NSSy6078 | 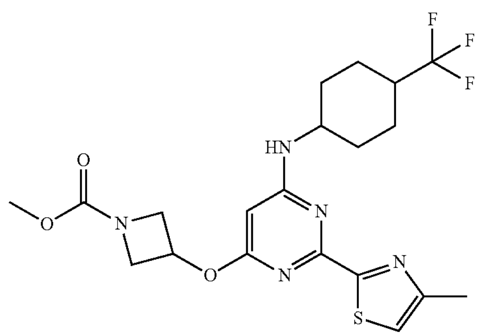 [SMILES: COC(=O)N1CC(Oc2cc(NC3CCC(C(F)(F)F)CC3)nc(-c3nc(C)cs3)n2)C1] | 471.5016 |
| NSSy6082 | 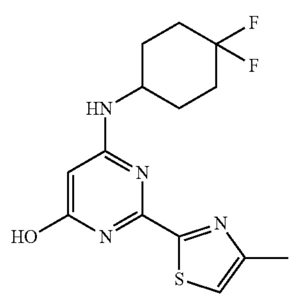 [SMILES: Cc1csc(-c2nc(O)cc(NC3CCC(F)(F)CC3)n2)n1] | 326.3694 |
| NSSy6131 | 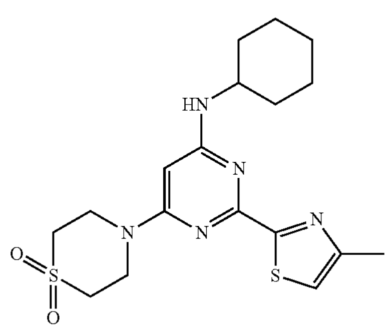 [SMILES: Cc1csc(-c2nc(NC3CCCCC3)cc(N3CCS(=O)(=O)CC3)n2)n1] | 407.5605 |

TABLE 2-continued

| Compound Ref | Structure | m/z data |
|---|---|---|
| NSSy6100 | 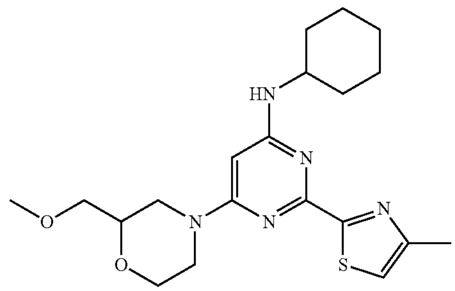 | 403.5481 |
| NSSy6124 | Chiral | 403.5481 |
| NSSy6115 | Chiral | 403.5481 |
| NSSy6149 | 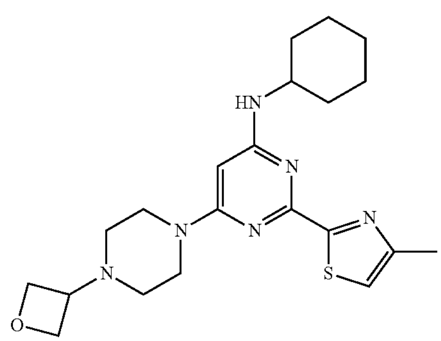 [SMILES: Cc1csc(-c2nc(NC3CCCCC3)cc(N3CCN(C4COC4)CC3)n2)n1] | 414.575 |
| NSSy6099 | 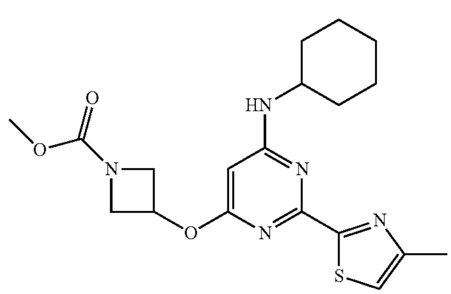 | 403.5045 |

TABLE 2-continued

| Compound Ref | Structure | m/z data |
|---|---|---|
| NSSy6105 | 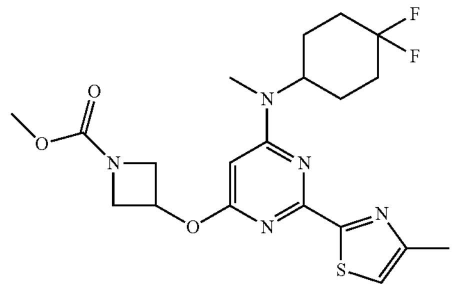 | 453.5115 |
| NSSy5854 | 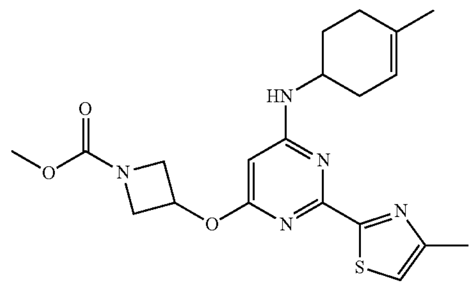 | 415.5155 |
| NSSy6126 | 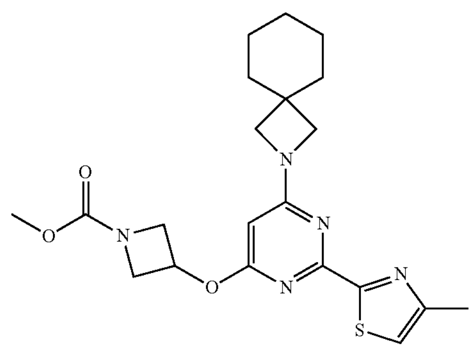 | 429.5423 |
| NSSy6057 | 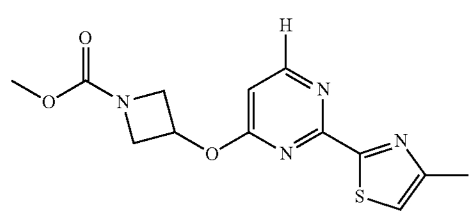 | 306.3446 |
| NSSy5699 | 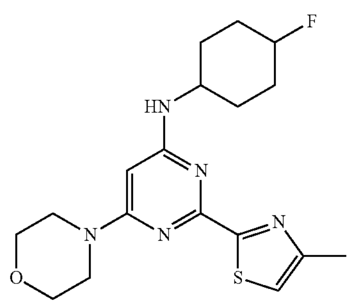 [SMILES: Cc1csc(-c2nc(NC3CCC(F)CC3)cc(N3CCOCC3)n2)n1] | 377.4856 |

TABLE 2-continued

| Compound Ref | m/z data |
|---|---|
| NSSy5703 | 357.4797 |
| NSSy5709 | 433.5492 |
| NSSy5710 | 421.4946 |
| NSSy5715 | 425.4768 |
| NSSy6348 | 371.5065 |

TABLE 2-continued
| Compound Ref | Structure | m/z data |
|---|---|---|
| NSSy6265 | 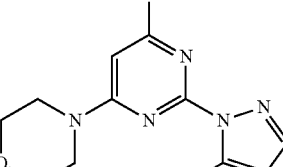 | 392.4514 |
| NSSy6386 | 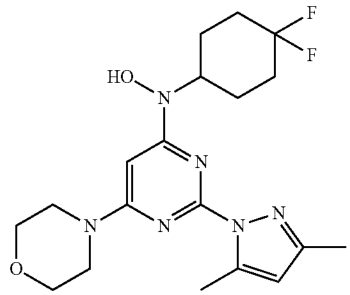 [SMILES: Cc1cc(C)n(-c2nc(N3CCOCC3)cc(N(O)C3CCC(F)(F)CC3)n2)n1] | 408.4504 |
| NSSy6420 | 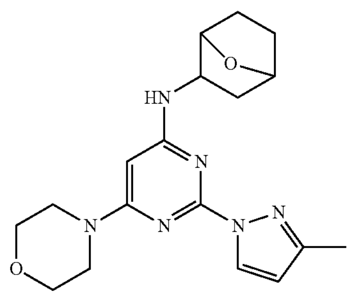 [SMILES: Cc1ccn(-c2nc(NC3CC4CCC3O4)cc(N3CCOCC3)n2)n1] | 356.4276 |
| NSSy6445 | Chiral  | 356.4276 |
| NSSy6446 | Chiral  | 356.4276 |

TABLE 2-continued
| Compound Ref | Structure | m/z data |
|---|---|---|
| NSSy6511 | 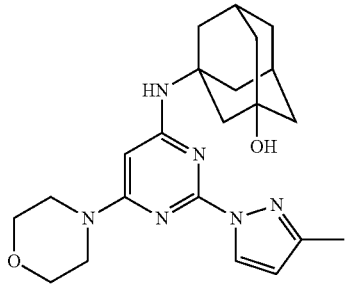 [SMILES: Cc1ccn(-c2nc(NC34CC5CC(CC(O)(C5)C3)C4)cc(N3CCOCC3)n2)n1] | 410.519 |
| NSSy6486 | 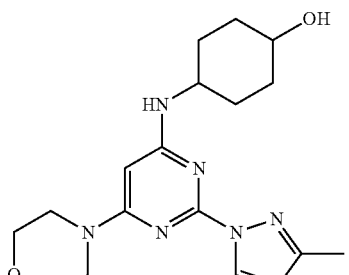 | 358.4434 |
| NSSy6526 | 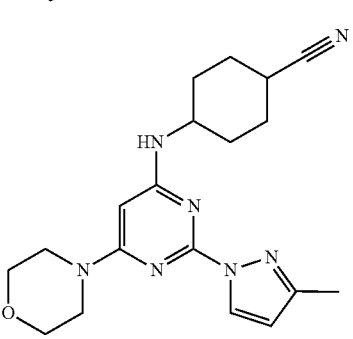 | 367.4545 |
| NSSy6540 | 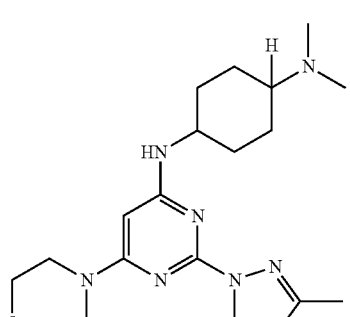 | 385.5129 |
| NSSy6541 | 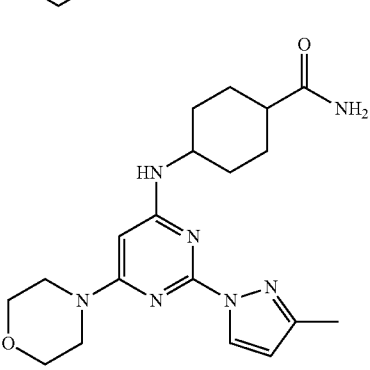 | 385.4693 |

TABLE 2-continued

| Compound Ref | Structure | m/z data |
| --- | --- | --- |
| NSSy6539 | 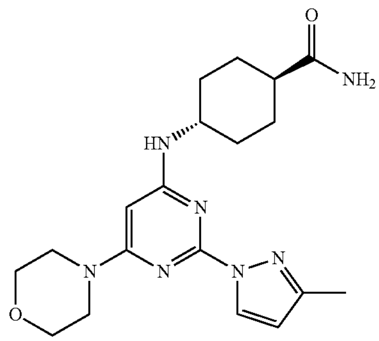 [SMILES: Cc1ccn(-c2nc(N[C@H]3CC[C@H](C(N)=O)CC3)cc(N3CCOCC3)n2)n1] | 385.4693 |
| NSSy6550 | 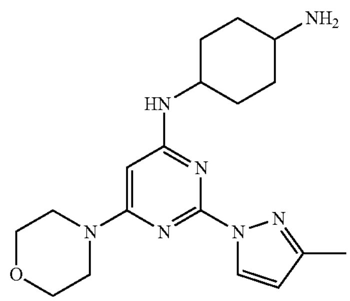 [SMILES: Cc1ccn(-c2nc(NC3CCC(N)CC3)cc(N3CCOCC3)n2)n1] | 357.4593 |
| NSSy6394 | 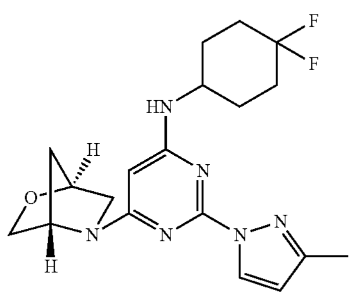 [SMILES: Cc1ccn(-c2nc(NC3CCC(F)(F)CC3)cc(N3C[C@@H]4C[C@H]3CO4)n2)n1] | 390.4356 |
| NSSy6272 | 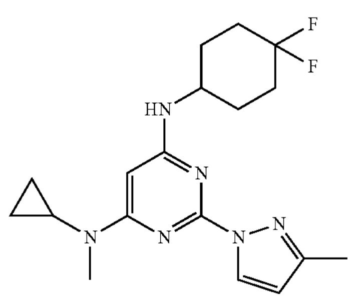 [SMILES: Cc1ccn(-c2nc(NC3CCC(F)(F)CC3)cc(N(C)C3CC3)n2)n1] | 362.4256 |
| NSSy6529 | 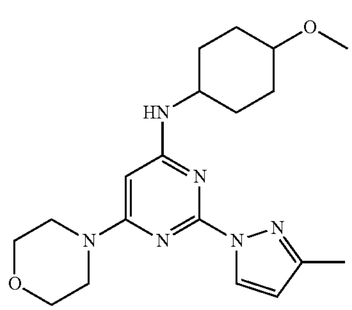 [SMILES: COC1CCC(Nc2cc(N3CCOCC3)nc(-n3ccc(C)n3)n2)CC1] | 372.4702 |

TABLE 2-continued

| Compound Ref | Structure | m/z data |
|---|---|---|
| NSSy6993 | 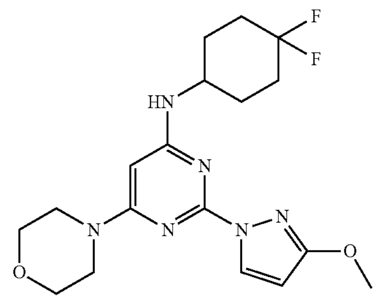 [SMILES: COc1ccn(-c2nc(NC3CCC(F)(F)CC3)cc(N3CCOCC3)n2)n1] | 394.4236 |
| NSSy7011 | 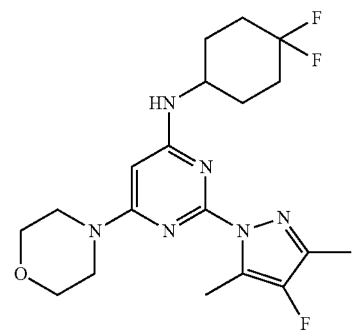 [SMILES: Cc1nn(-c2nc(NC3CCC(F)(F)CC3)cc(N3CCOCC3)n2)c(C)c1F] | 410.4415 |
| NSSy7021 | 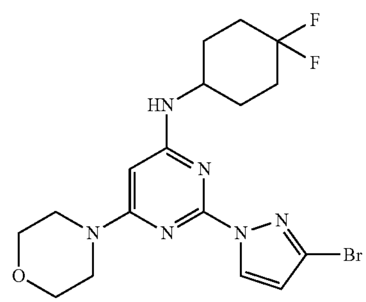 [SMILES: FC1(F)CCC(Nc2cc(N3CCOCC3)nc(-n3ccc(Br)n3)n2)CC1] | 443.2939 |
| NSSy7034 | 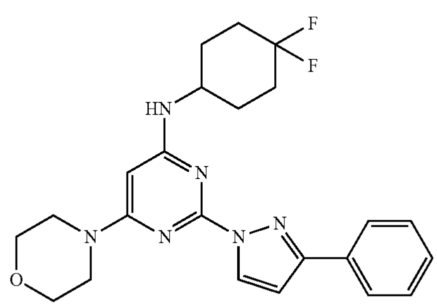 [SMILES: FC1(F)CCC(Nc2cc(N3CCOCC3)nc(-n3ccc(-c4ccccc4)n3)n2)CC1] | 440.4954 |
| NSSy6343 | 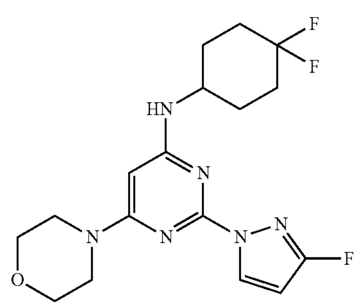 [SMILES: Fc1ccn(-c2nc(NC3CCC(F)(F)CC3)cc(N3CCOCC3)n2)n1] | 382.3879 |

TABLE 2-continued

| Compound Ref | Structure | m/z data |
|---|---|---|
| NSSy7087 | 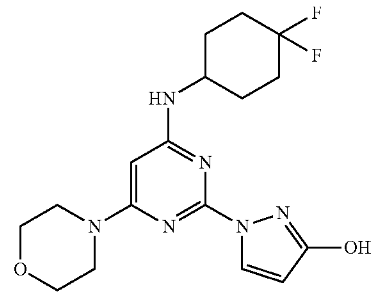 [SMILES: Oc1ccn(-c2nc(NC3CCC(F)(F)CC3)cc(N3CCOCC3)n2)n1] | 380.3968 |
| NSSy5618 | 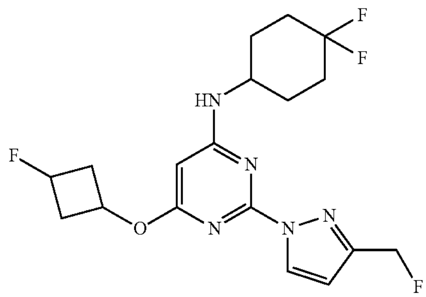 [SMILES: FCc1ccn(-c2nc(NC3CCC(F)(F)CC3)cc(OC3CC(F)C3)n2)n1] | 399.3899 |
| NSSy5619 | 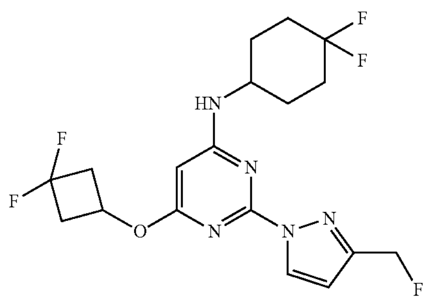 [SMILES: FCc1ccn(-c2nc(NC3CCC(F)(F)CC3)cc(OC3CC(F)(F)C3)n2)n1] | 417.38 |
| NSSy5624 | 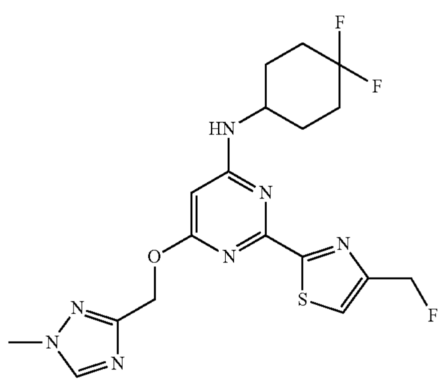 [SMILES: Cn1cnc(COc2cc(NC3CCC(F)(F)CC3)nc(-c3nc(CF)cs3)n2)n1] | 439.464 |
| NSSy5625 | 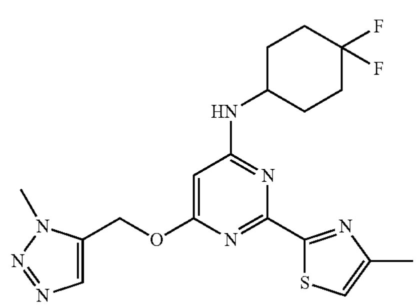 [SMILES: Cc1csc(-c2nc(NC3CCC(F)(F)CC3)cc(OCc3cnnn3C)n2)n1] | 421.4739 |

TABLE 2-continued

| Compound Ref | Structure | m/z data |
|---|---|---|
| NSSy5651 | 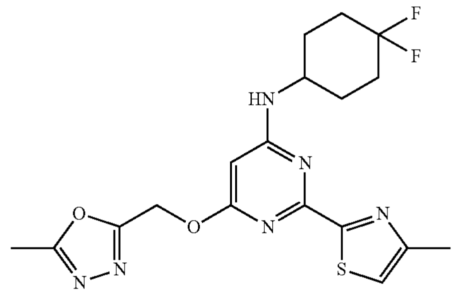 | 422.458 |
| NSSy5689 | 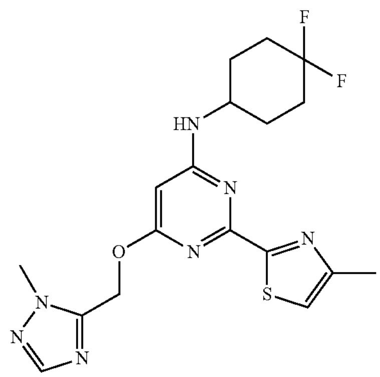 [SMILES: Cc1csc(-c2nc(NC3CCC(F)(F)CC3)cc(OCc3ncnn3C)n2)n1] | 421.4739 |
| NSSy5690 | 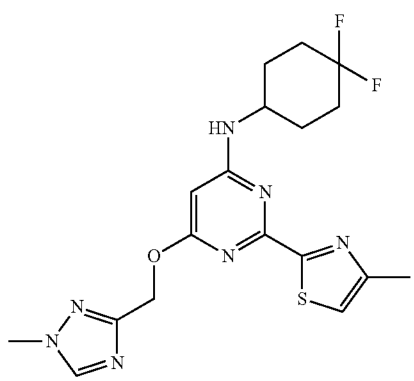 | 421.4739 |
| NSSy6049 | 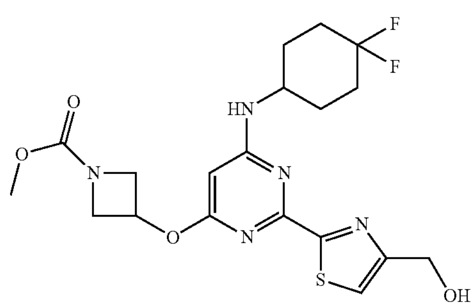 [SMILES: COC(=O)N1CC(Oc2cc(NC3CCC(F)(F)CC3)nc(-c3nc(CO)cs3)n2)C1] | 455.4837 |

TABLE 2-continued

| Compound Ref | Structure | m/z data |
|---|---|---|
| NSSy6050 | 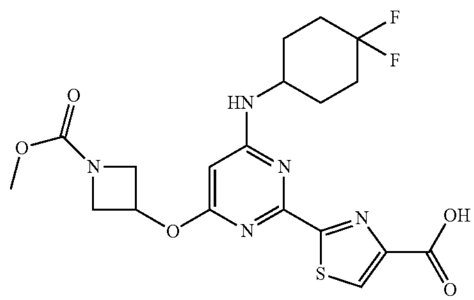 [SMILES: COC(=O)N1CC(Oc2cc(NC3CCC(F)(F)CC3)nc(-c3nc(C(=O)O)cs3)n2)C1] | 469.4669 |
| NSSy5648 | 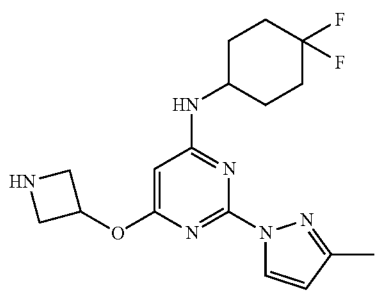 [SMILES: Cc1ccn(-c2nc(NC3CCC(F)(F)CC3)cc(OC3CNC3)n2)n1] | 364.3978 |
| NSSy5629 | 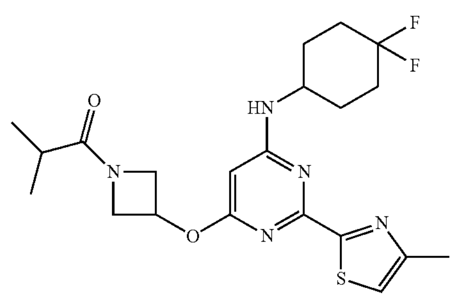 [SMILES: Cc1csc(-c2nc(NC3CCC(F)(F)CC3)cc(OC3CN(C(=O)C(C)C)C3)n2)n1] | 451.5393 |
| NSSy5726 NSSy5630 | | 437.5125 |
| NSSy5879 | 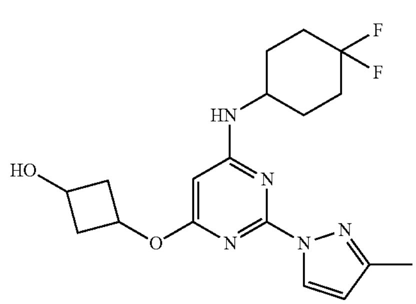 [SMILES: Cc1ccn(-c2nc(NC3CCC(F)(F)CC3)cc(OC3CC(O)C3)n2)n1] | 379.4087 |

TABLE 2-continued
| Compound Ref | Structure | m/z data |
|---|---|---|
| NSSy5647 | 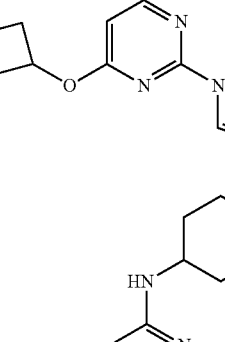 | 381.3998 |
| NSSy5893 | 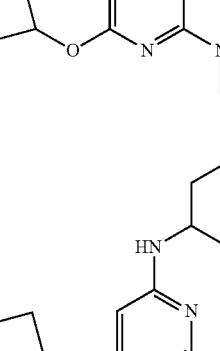 | 399.3899 |
| NSSy5902 | 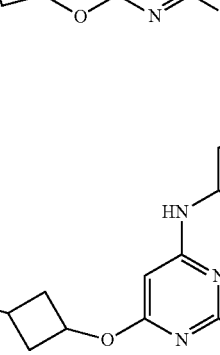 | 393.4355 |
| NSSy5672 | 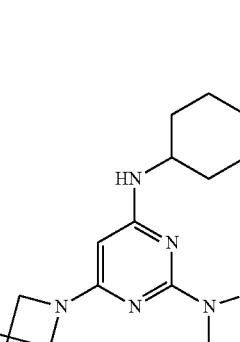 | 450.4872 |
| NSSy5631 | 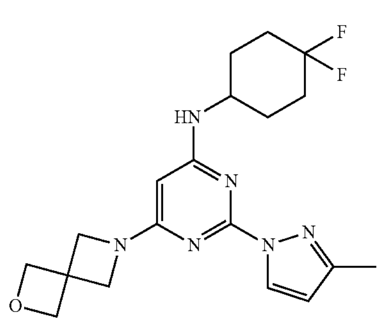 [SMILES: Cc1ccn(-c2nc(NC3CCC(F)(F)CC3)cc(N3CC4(COC4)C3)n2)n1] | 390.4356 |

| Compound Ref | Structure | m/z data |
|---|---|---|
| NSSy5664 | 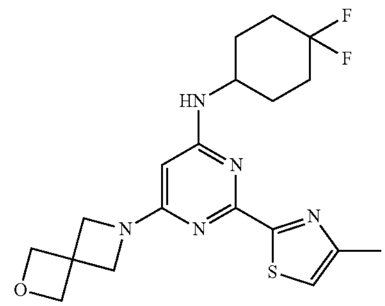 [SMILES: Cc1csc(-c2nc(NC3CCC(F)(F)CC3)cc(N3CC4(COC4)C3)n2)n1] | 407.4867 |
| NSSy5847 | 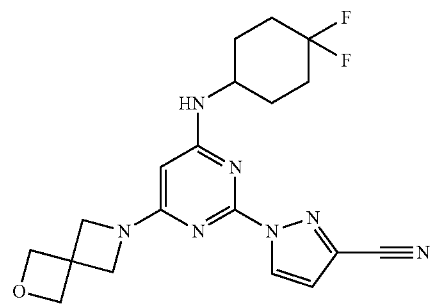 [SMILES: N#Cc1ccn(-c2nc(NC3CCC(F)(F)CC3)cc(N3CC4(COC4)C3)n2)n1] | 401.4189 |
| NSSy5848 | 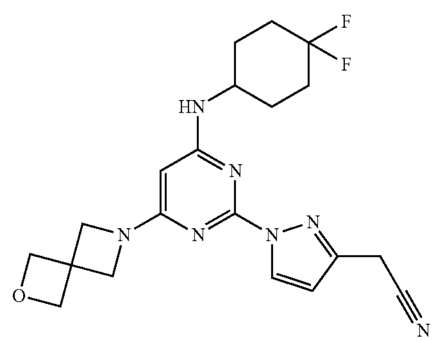 [SMILES: N#CCc1ccn(-c2nc(NC3CCC(F)(F)CC3)cc(N3CC4(COC4)C3)n2)n1] | 415.4457 |
| NSSy6054 | 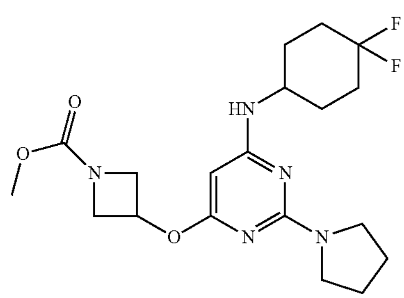 [SMILES: COC(=O)N1CC(Oc2cc(NC3CCC(F)(F)CC3)nc(N3CCCC3)n2)C1] | 411.4503 |
| NSSy6101 | 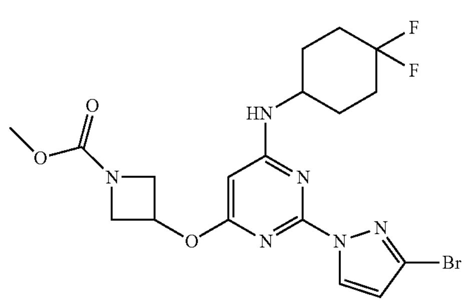 [SMILES: COC(=O)N1CC(Oc2cc(NC3CCC(F)(F)CC3)nc(-n3ccc(Br)n3)n2)C1] | 487.3029 |

TABLE 2-continued

| Compound Ref | Structure | m/z data |
| --- | --- | --- |
| NSSy6113 | 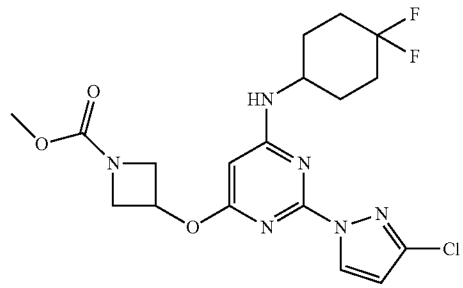 [SMILES: COC(=O)N1CC(Oc2cc(NC3CCC(F)(F)CC3)nc(-n3ccc(Cl)n3)n2)C1] | 442.8519 |
| NSSy6162<br>NSSy6347 | 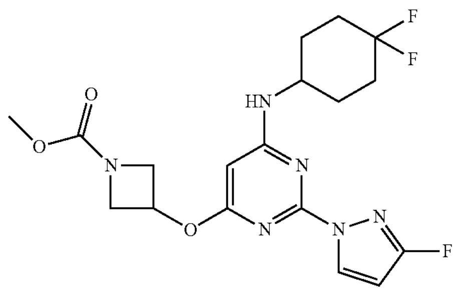 [SMILES: COC(=O)N1CC(Oc2cc(NC3CCC(F)(F)CC3)nc(-n3ccc(F)n3)n2)C1] | 426.3969 |
| NSSy6072 | 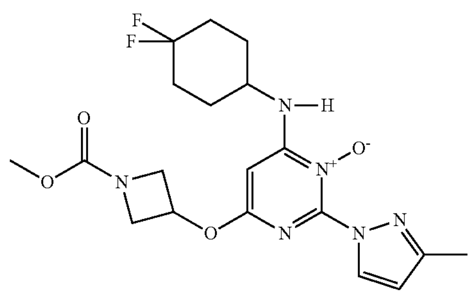 | 438.4326 |
| NSSy6982 | 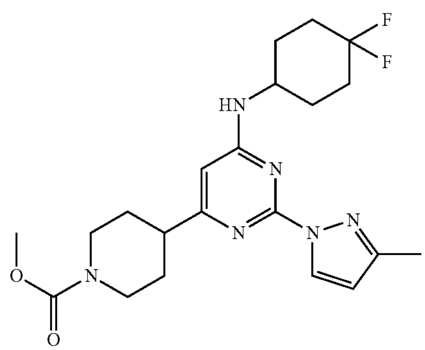 [SMILES: COC(=O)N1CCC(c2cc(NC3CCC(F)(F)CC3)nc(-n3ccc(C)n3)n2)CC1] | 434.4882 |
| NSSy6981 | 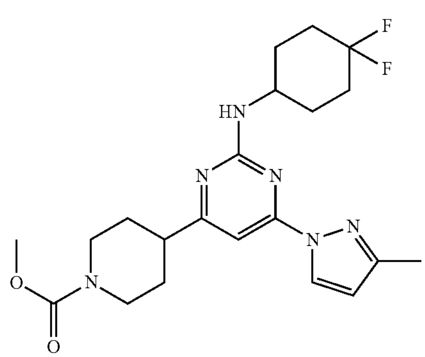 [SMILES: COC(=O)N1CCC(c2cc(-n3ccc(C)n3)nc(NC3CCC(F)(F)CC3)n2)CC1] | 434.4882 |

TABLE 2-continued

| Compound Ref | Structure | m/z data |
|---|---|---|
| NSSy6369 | 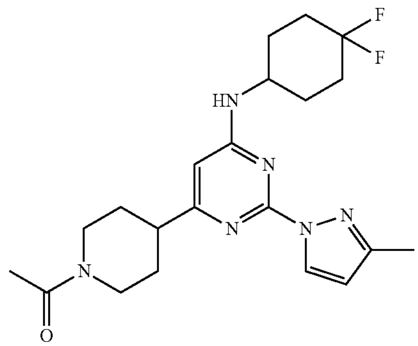 [SMILES: CC(=O)N1CCC(c2cc(NC3CCC(F)(F)CC3)nc(-n3ccc(C)n3)n2)CC1] | 418.4892 |
| NSSy7063 | 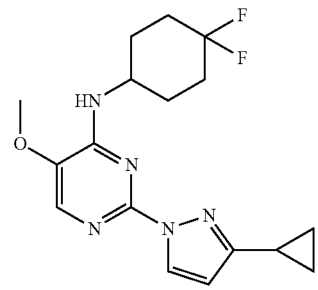 [SMILES: COc1cnc(-n2ccc(C3CC3)n2)nc1NC1CCC(F)(F)CC1] | 349.3829 |
| NSSy7042 | 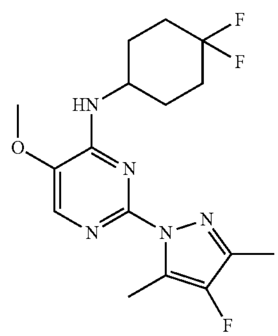 [SMILES: COc1cnc(-n2nc(C)c(F)c2C)nc1NC1CCC(F)(F)CC1] | 355.362 |
| NSSy7031 | 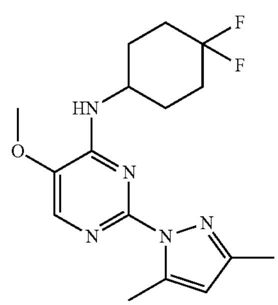 [SMILES: COc1cnc(-n2nc(C)cc2C)nc1NC1CCC(F)(F)CC1] | 337.3719 |
| NSSy7055 | 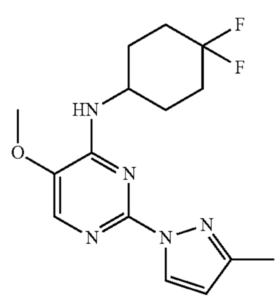 [SMILES: COc1cnc(-n2ccc(C)n2)nc1NC1CCC(F)(F)CC1] | 323.3451 |

TABLE 2-continued

| Compound Ref | Structure | m/z data |
|---|---|---|
| NSSy5620 | 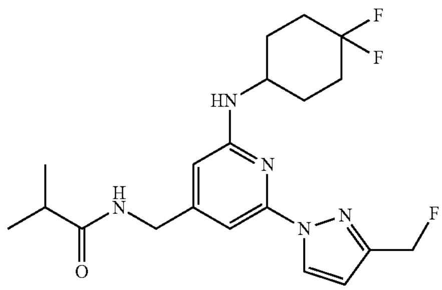 [SMILES: CC(C)C(=O)NCc1cc(NC2CCC(F)(F)CC2)nc(-n2ccc(CF)n2)c1] | 409.4534 |
| NSSy5653 | 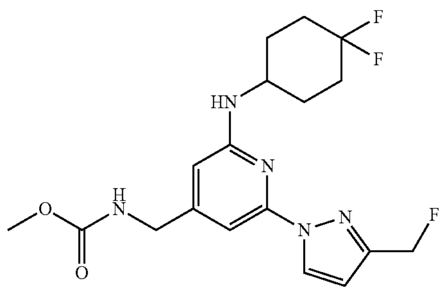 [SMILES: COC(=O)NCc1cc(NC2CCC(F)(F)CC2)nc(-n2ccc(CF)n2)c1] | 397.3988 |
| NSSy5622 | 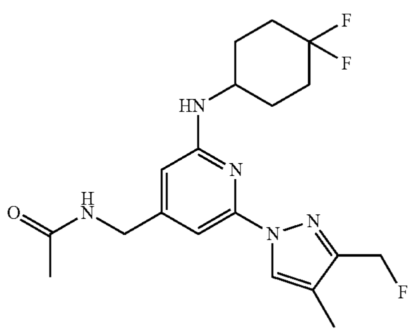 [SMILES: CC(=O)NCc1cc(NC2CCC(F)(F)CC2)nc(-n2cc(C)c(CF)n2)c1] | 395.4266 |
| NSSy5826 | 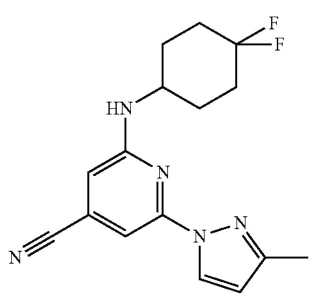 [SMILES: Cc1ccn(-c2cc(C#N)cc(NC3CCC(F)(F)CC3)n2)n1] | 317.3413 |
| NSSy5635 | 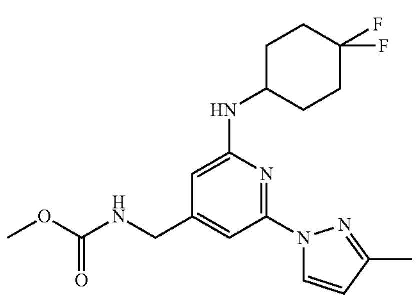 | 379.4087 |

TABLE 2-continued

| Compound Ref | Structure | m/z data |
|---|---|---|
| NSSy5637 | 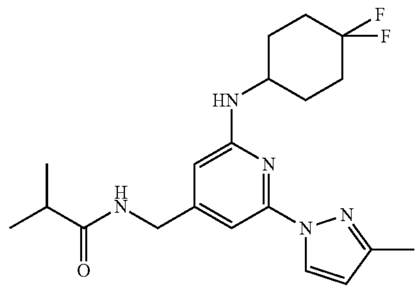 [SMILES: Cc1ccn(-c2cc(CNC(=O)C(C)C)cc(NC3CCC(F)(F)CC3)n2)n1] | 391.4633 |
| NSSy5827, NSSy6791 | 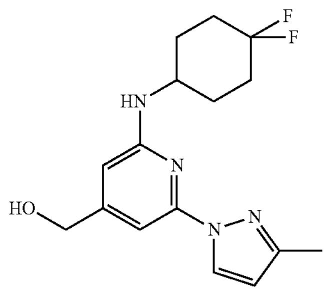 [SMILES: Cc1ccn(-c2cc(CO)cc(NC3CCC(F)(F)CC3)n2)n1] | 322.357 |
| NSSy5828 | 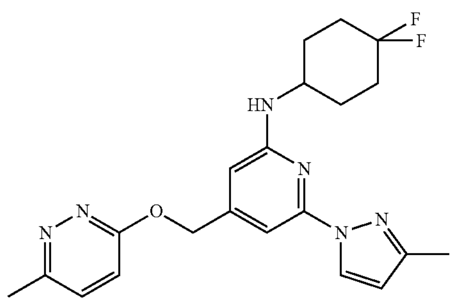 | 414.4576 |
| NSSy5860 | 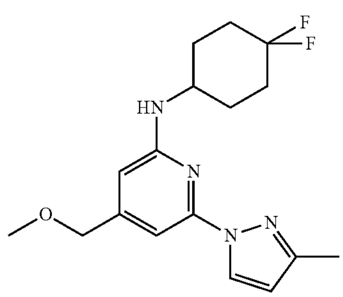 | 336.3838 |
| NSSy5861 | 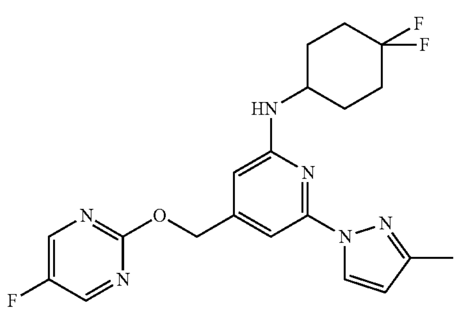 | 418.4209 |

TABLE 2-continued

| Compound Ref | Structure | m/z data |
|---|---|---|
| NSSy5869 | 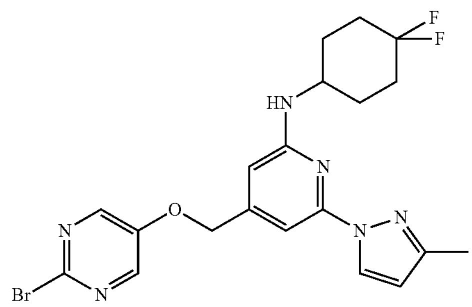 [SMILES: Cc1ccn(-c2cc(COc3cnc(Br)nc3)cc(NC3CCC(F)(F)CC3)n2)n1] | 479.3269 |
| NSSy5996 | 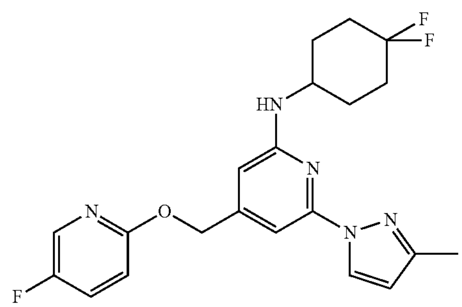 [SMILES: Cc1ccn(-c2cc(COc3ccc(F)cn3)cc(NC3CCC(F)(F)CC3)n2)n1] | 417.4328 |
| NSSy6371 | 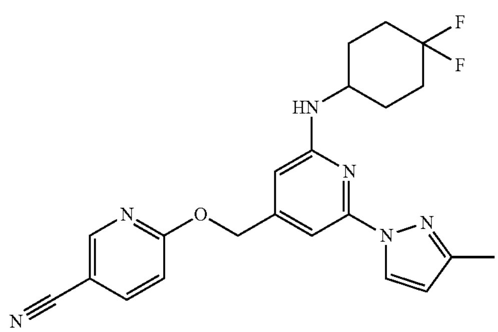 [SMILES: Cc1ccn(-c2cc(COc3ccc(C#N)cn3)cc(NC3CCC(F)(F)CC3)n2)n1] | 424.4528 |
| NSSy6417 | 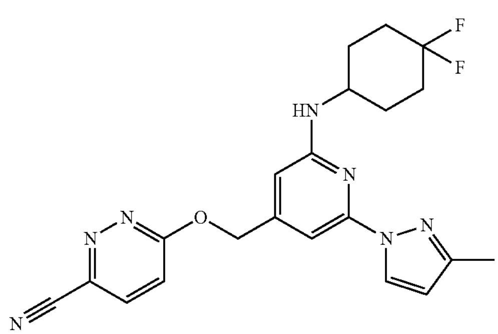 [SMILES: Cc1ccn(-c2cc(COc3ccc(C#N)nn3)cc(NC3CCC(F)(F)CC3)n2)n1] | 425.4409 |

TABLE 2-continued

| Compound Ref | Structure | m/z data |
|---|---|---|
| NSSy6451 | 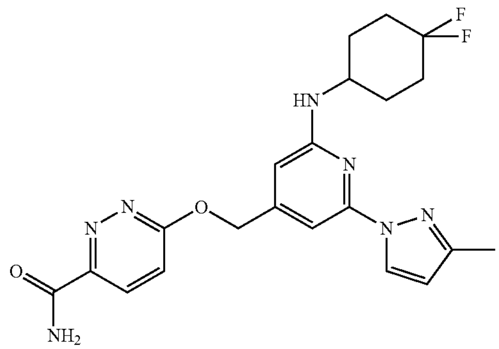 [SMILES: Cc1ccn(-c2cc(COc3ccc(C(N)=O)nn3)cc(NC3CCC(F)(F)CC3)n2)n1] | 443.4557 |
| NSSy5846 | 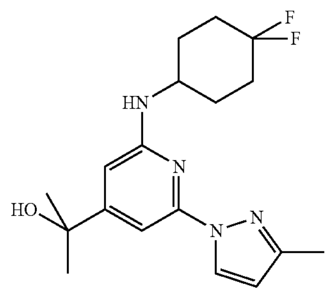 [SMILES: Cc1ccn(-c2cc(C(C)(C)O)cc(NC3CCC(F)(F)CC3)n2)n1] | 350.4106 |
| NSSy6019 | 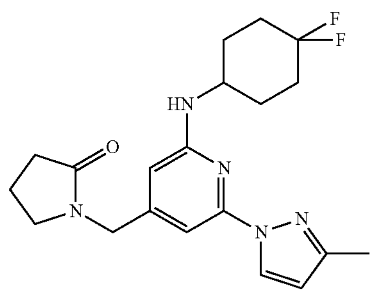 [SMILES: Cc1ccn(-c2cc(CN3CCCC3=O)cc(NC3CCC(F)(F)CC3)n2)n1] | 389.4475 |
| NSSy5829 | 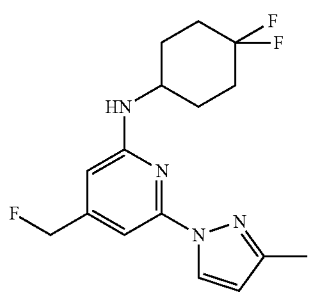 [SMILES: Cc1ccn(-c2cc(CF)cc(NC3CCC(F)(F)CC3)n2)n1] | 324.3481 |
| NSSy5839 | 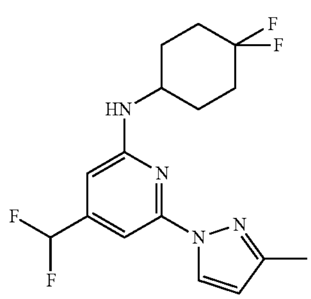 [SMILES: Cc1ccn(-c2cc(C(F)F)cc(NC3CCC(F)(F)CC3)n2)n1] | 342.3382 |

TABLE 2-continued
| Compound Ref | Structure | m/z data |
|---|---|---|
| NSSy6395 NSSy6685 | 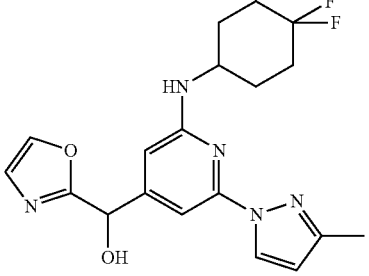 | 389.4039 |
| NSSy6846 | 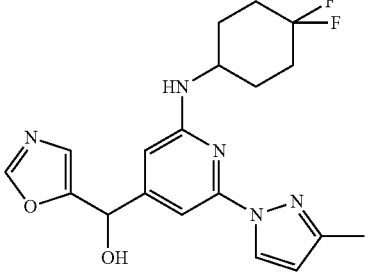 | 389.4039 |
| NSSy6415 | Chiral<br />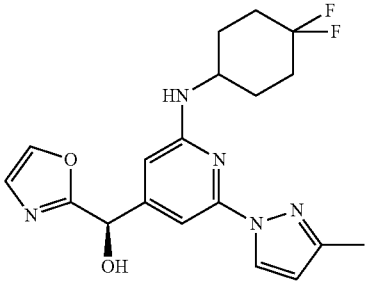 [SMILES: Cc1ccn(-c2cc(C(O)c3ncco3)cc(NC3CCC(F)(F)CC3)n2)n1] | 389.4039 |
| NSSy6416 | Chiral<br />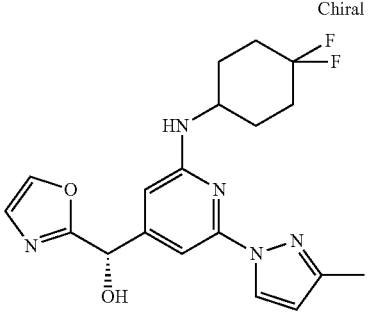 [SMILES: Cc1ccn(-c2cc([C@H](O)c3ncco3)cc(NC3CCC(F)(F)CC3)n2)n1] | 389.4039 |
| NSSy6576 | 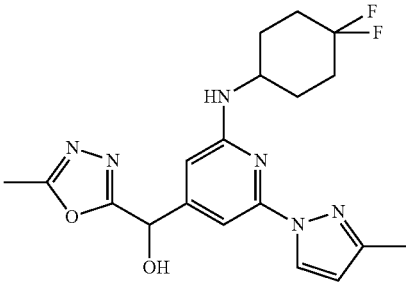 | 404.4188 |

TABLE 2-continued

| Compound Ref | Structure | m/z data |
| --- | --- | --- |
| NSSy6469 | 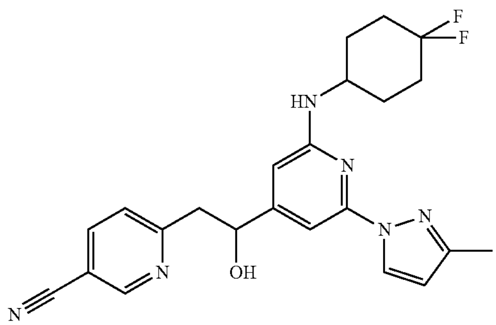 [SMILES: Cc1ccn(-c2cc(C(O)Cc3ccc(C#N)cn3)cc(NC3CCC(F)(F)CC3)n2)n1] | 438.4796 |
| NSSy6891 | 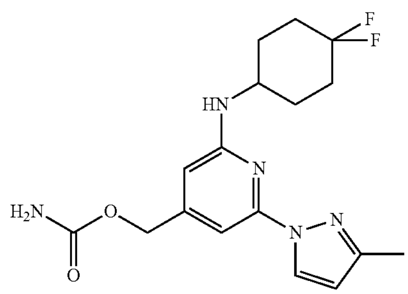 [SMILES: Cc1ccn(-c2cc(COC(N)=O)cc(NC3CCC(F)(F)CC3)n2)n1] | 365.3819 |
| NSSy6812 | 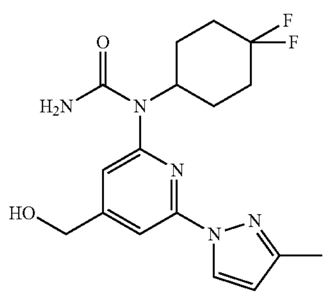 [SMILES: Cc1ccn(-c2cc(CO)cc(N(C(N)=O)C3CCC(F)(F)CC3)n2)n1] | 365.3819 |
| NSSy5933 | 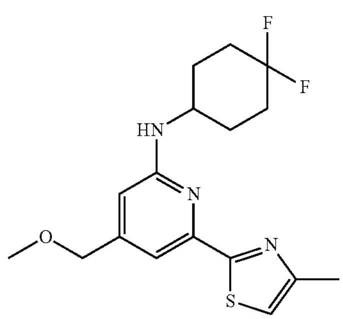 | 353.4349 |
| NSSy5640 | 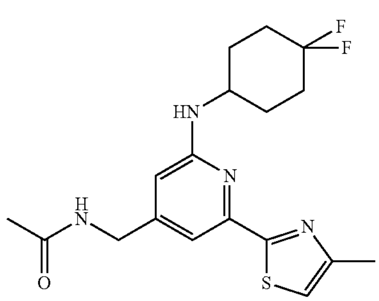 [SMILES: CC(=O)NCc1cc(NC2CCC(F)(F)CC2)nc(-c2nc(C)cs2)c1] | 380.4608 |

TABLE 2-continued

| Compound Ref | Structure | m/z data |
|---|---|---|
| NSSy5644 | 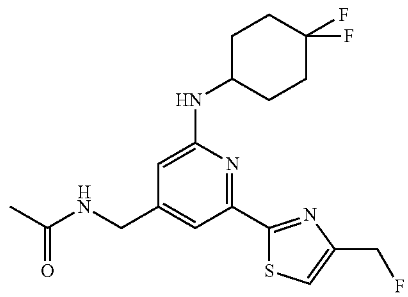 [SMILES: CC(=O)NCc1cc(NC2CCC(F)(F)CC2)nc(-c2nc(CF)cs2)c1] | 398.4509 |
| NSSy5645 | 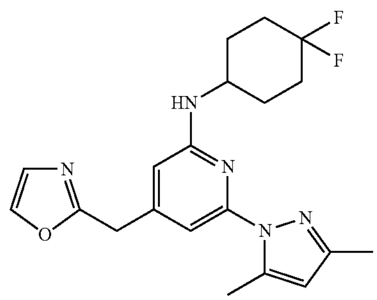 [SMILES: Cc1cc(C)n(-c2cc(Cc3ncco3)cc(NC3CCC(F)(F)CC3)n2)n1] | 387.4317 |
| NSSy5676 | 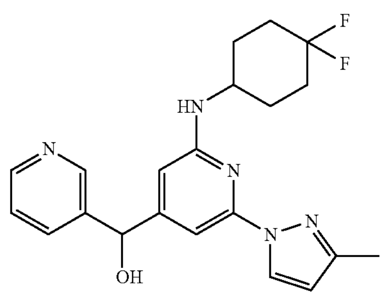 [SMILES: Cc1ccn(-c2cc(C(O)c3cccnc3)cc(NC3CCC(F)(F)CC3)n2)n1] | 399.4427 |
| NSSy6355<br>NSSy6740<br>Nssy 6851<br>Nssy 5129 | 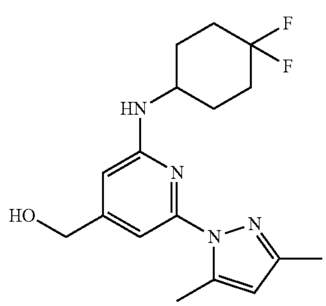 [SMILES: Cc1cc(C)n(-c2cc(CO)cc(NC3CCC(F)(F)CC3)n2)n1] | 336.3838 |
| NSSy6861 | 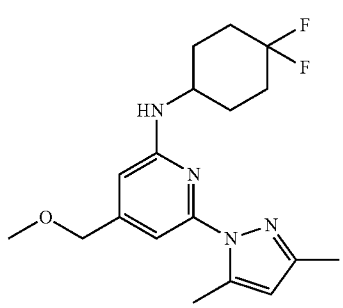 | 350.4106 |

TABLE 2-continued

| Compound Ref | Structure | m/z data |
| --- | --- | --- |
| NSSy7053 | 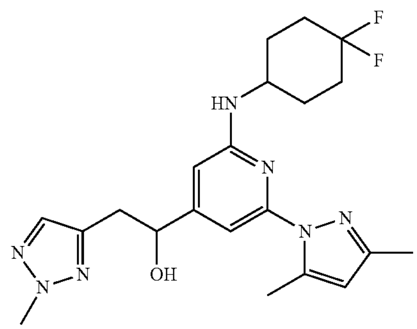 [SMILES: Cc1cc(C)n(-c2cc(C(O)Cc3cnn(C)n3)cc(NC3CCC(F)(F)CC3)n2)n1] | 431.4883 |
| NSSy7079 | 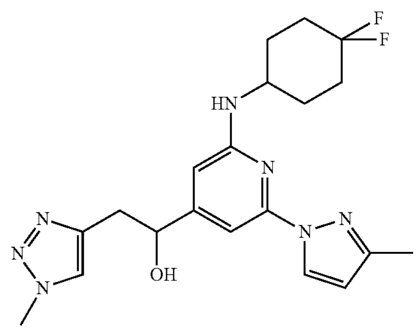 [SMILES: Cc1ccn(-c2cc(C(O)Cc3cn(C)nn3)cc(NC3CCC(F)(F)CC3)n2)n1] | 417.4615 |
| NSSy7064 | 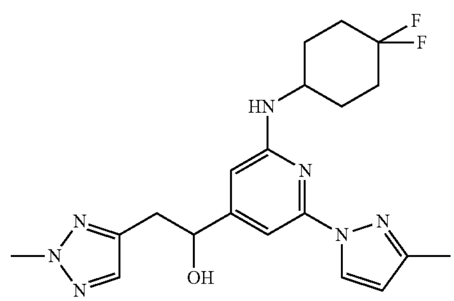 | 417.4615 |
| NSSy7065 | 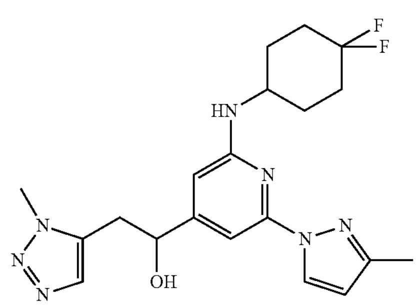 [SMILES: Cc1ccn(-c2cc(C(O)Cc3cnnn3C)cc(NC3CCC(F)(F)CC3)n2)n1] | 417.4615 |
| NSSy6470 | 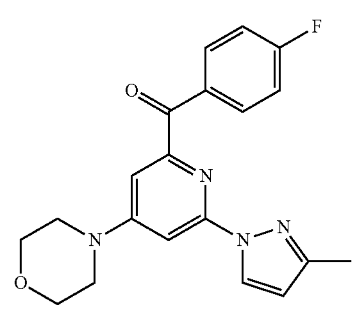 [SMILES: Cc1ccn(-c2cc(N3CCOCC3)cc(C(=O)c3ccc(F)cc3)n2)n1] | 366.3941 |

TABLE 2-continued

| Compound Ref | Structure | m/z data |
|---|---|---|
| NSSy6472 | 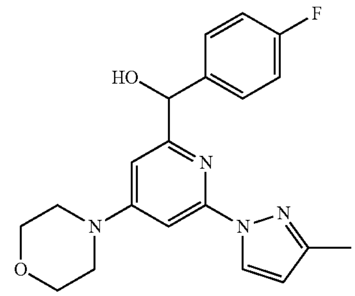 [SMILES: Cc1ccn(-c2cc(N3CCOCC3)cc(C(O)c3ccc(F)cc3)n2)n1] | 368.4099 |
| NSSy6513 | Chiral | 368.4099 |
| NSSy6514 | Chiral | 368.4099 |
| NSSy6473 | 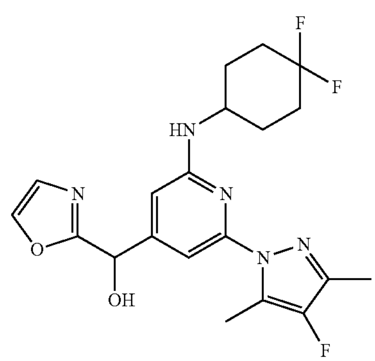 [SMILES: Cc1nn(-c2cc(C(O)c3ncco3)cc(NC3CCC(F)(F)CC3)n2)c(C)c1F] | 421.4208 |

TABLE 2-continued

| Compound Ref | Structure | m/z data |
|---|---|---|
| NSSy6563 | 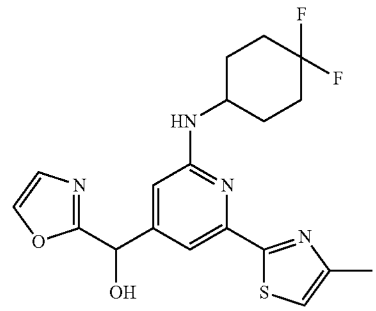 [SMILES: Cc1csc(-c2cc(C(O)c3ncco3)cc(NC3CCC(F)(F)CC3)n2)n1] | 406.455 |
| NSSy6435 | 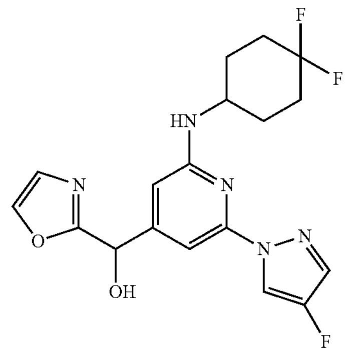 [SMILES: OC(c1cc(NC2CCC(F)(F)CC2)nc(-n2cc(F)cn2)c1)c1ncco1] | 393.3672 |
| NSSy6730 | 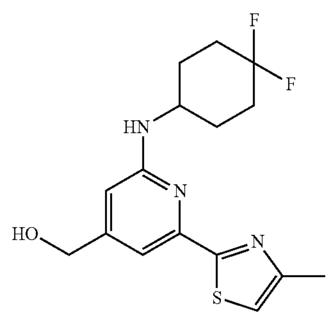 [SMILES: Cc1csc(-c2cc(CO)cc(NC3CCC(F)(F)CC3)n2)n1] | 339.4081 |
| NSSy6750 | 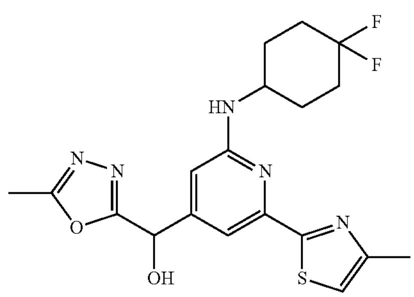 | 421.4699 |
| NSSy6782 | 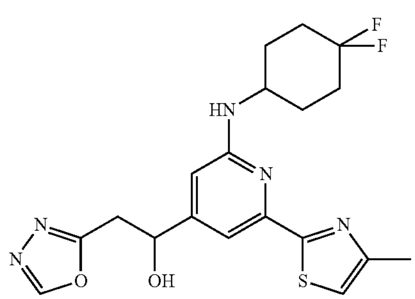 [SMILES: Cc1csc(-c2cc(C(O)Cc3nnco3)cc(NC3CCC(F)(F)CC3)n2)n1] | 421.4699 |

TABLE 2-continued

| Compound Ref | Structure | m/z data |
|---|---|---|
| NSSy5615 | 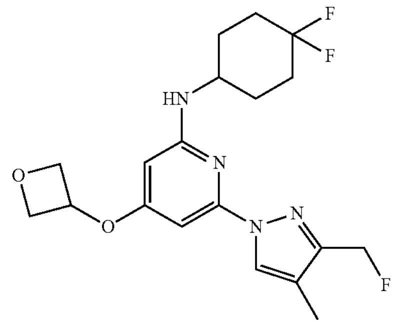 [SMILES: Cc1cn(-c2cc(OC3COC3)cc(NC3CCC(F)(F)CC3)n2)nc1CF] | 396.4107 |
| NSSy5641 NSSy5722 | | 403.4347 |
| NSSy5638 | 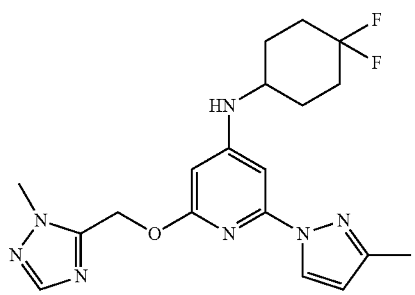 [SMILES: Cc1ccn(-c2cc(NC3CCC(F)(F)CC3)cc(OCc3ncnn3C)n2)n1] | 403.4347 |
| NSSy5737 | 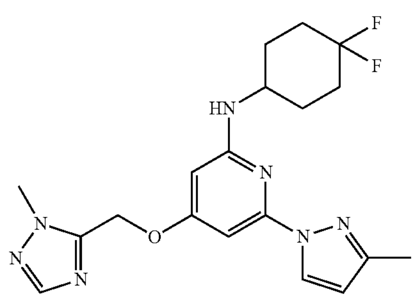 [SMILES: Cc1ccn(-c2cc(OCc3ncnn3C)cc(NC3CCC(F)(F)CC3)n2)n1] | 403.4347 |
| NSSy5643, NSSy5756 | | 403.4347 |

TABLE 2-continued

| Compound Ref | Structure | m/z data |
|---|---|---|
| NSSy5681 NSSy5753 | 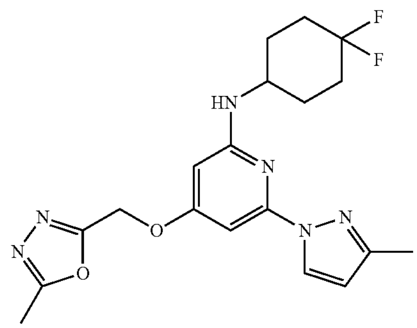 [SMILES: Cc1ccn(-c2cc(OCc3nnc(C)o3)cc(NC3CCC(F)(F)CC3)n2)n1] | 404.4188 |
| NSSy6849 | 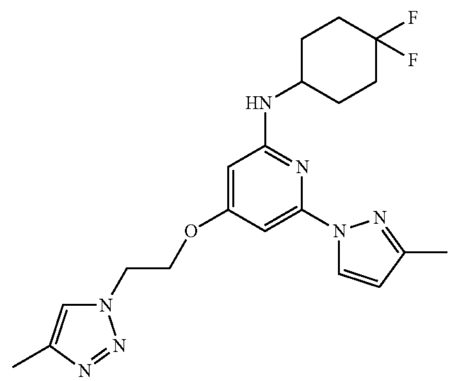 | 417.4615 |
| NSSy6719 | 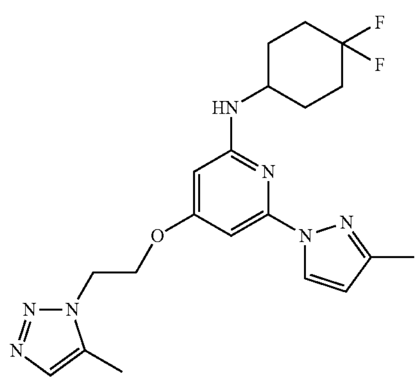 [SMILES: Cc1ccn(-c2cc(OCCn3nncc3C)cc(NC3CCC(F)(F)CC3)n2)n1] | 417.4615 |
| NSSy5759 | 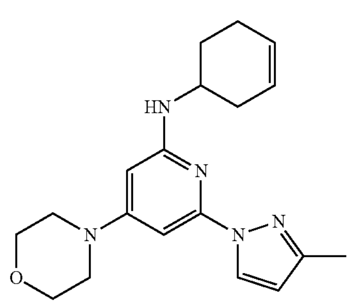 [SMILES: Cc1ccn(-c2cc(N3CCOCC3)cc(NC3CC=CCC3)n2)n1] | 339.4405 |

TABLE 2-continued

| Compound Ref | Structure | m/z data |
|---|---|---|
| NSSy5763 | 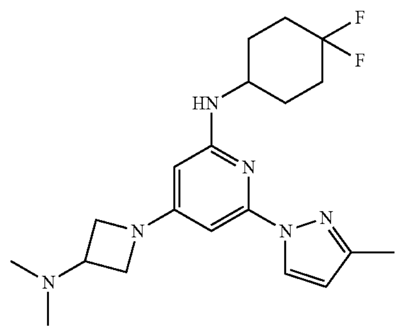 | 390.4792 |
| NSSy6573 | 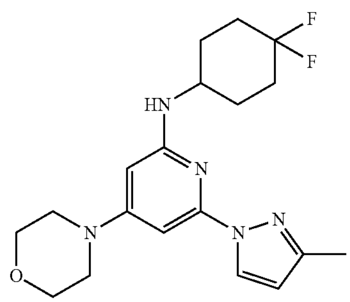 [SMILES: Cc1ccn(-c2cc(N3CCOCC3)cc(NC3CCC(F)(F)CC3)n2)n1] | 377.4365 |
| NSSy5721 | 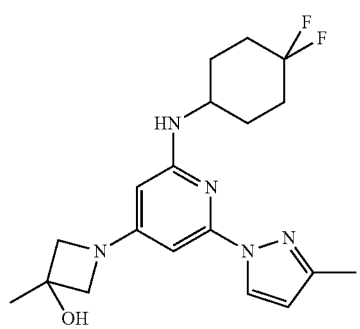 | 377.4365 |
| NSSy5824 | 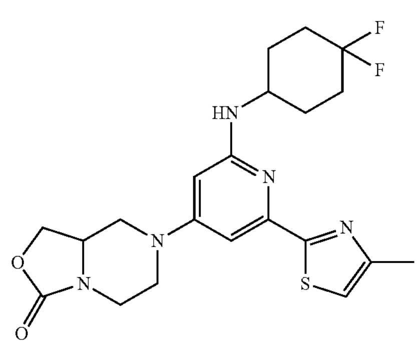 [SMILES: Cc1csc(-c2cc(N3CCN4C(=O)OCC4C3)cc(NC3CCC(F)(F)CC3)n2)n1] | 449.5235 |

TABLE 2-continued

| Compound Ref | Structure | m/z data |
|---|---|---|
| NSSy5838 | Chiral | 449.5235 |
| NSSy5837 | Chiral | 449.5235 |
| NSSy5819 | 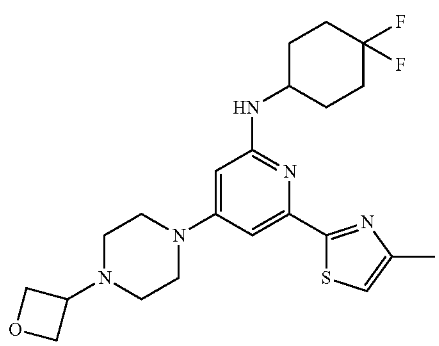 | 449.5671 |
| NSSy5815 | 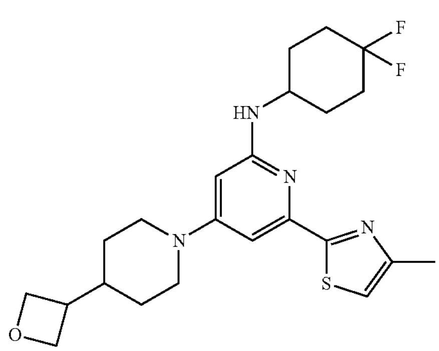 [SMILES: Cc1csc(-c2cc(N3CCC(C4COC4)CC3)cc(NC3CCC(F)(F)CC3)n2)n1] | 448.579 |

TABLE 2-continued
| Compound Ref | Structure | m/z data |
|---|---|---|
| NSSy6288 | 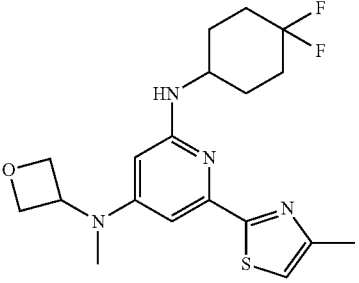 [SMILES: Cc1csc(-c2cc(N(C)C3COC3)cc(NC3CCC(F)(F)CC3)n2)n1] | 394.4876 |
| NSSy5646 | 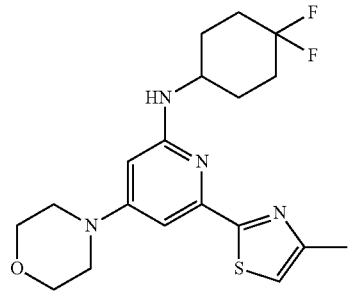 [SMILES: Cc1csc(-c2cc(N3CCOCC3)cc(NC3CCC(F)(F)CC3)n2)n1] | 394.4876 |
| NSSy5675 | 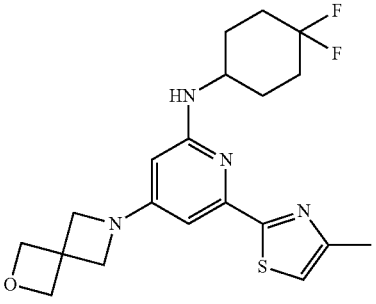 [SMILES: Cc1csc(-c2cc(N3CC4(COC4)C3)cc(NC3CCC(F)(F)CC3)n2)n1] | 406.4986 |
| NSSy5807 | 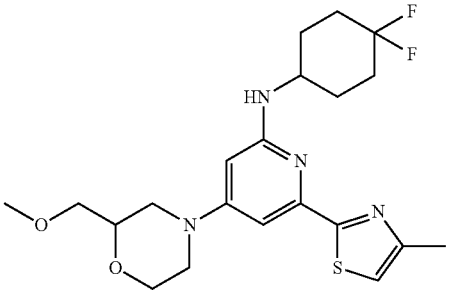 | 438.5402 |
| NSSy5695 | 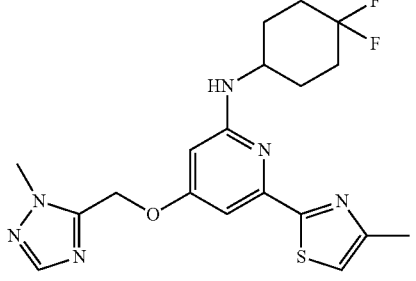 | 420.4858 |

TABLE 2-continued

| Compound Ref | Structure | m/z data |
|---|---|---|
| NSSy5686 | 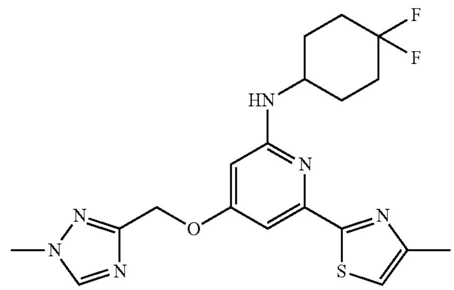 | 420.4858 |
| NSSy5717 | 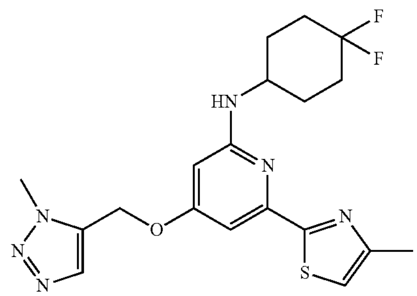 [SMILES: Cc1csc(-c2cc(OCc3cnnn3C)cc(NC3CCC(F)(F)CC3)n2)n1] | 420.4858 |
| NSSy5680 | 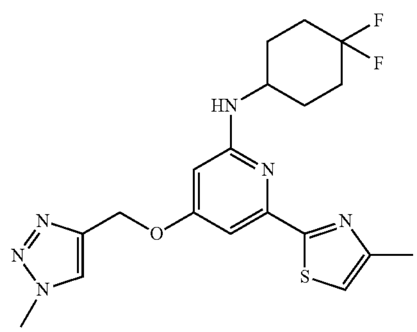 [SMILES: Cc1csc(-c2cc(OCc3cn(C)nn3)cc(NC3CCC(F)(F)CC3)n2)n1] | 420.4858 |
| NSSy5694 | 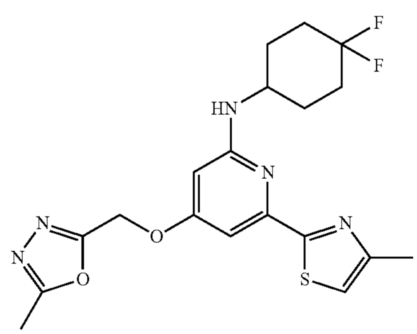 [SMILES: Cc1csc(-c2cc(OCc3nnc(C)o3)cc(NC3CCC(F)(F)CC3)n2)n1] | 421.4699 |
| NSSy5677 | 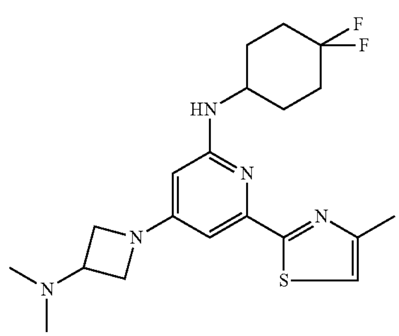 | 407.5303 |

TABLE 2-continued

| Compound Ref | Structure | m/z data |
|---|---|---|
| NSSy5687 | 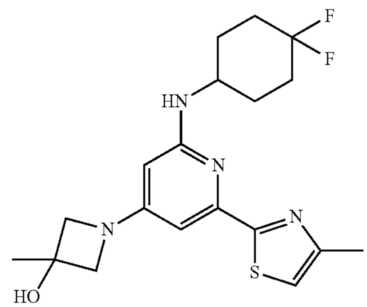 | 394.4876 |
| NSSy5980 | 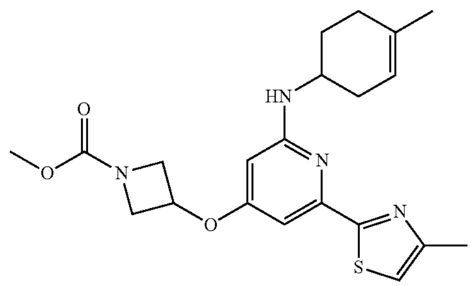 | 414.5274 |
| NSSy5655 | 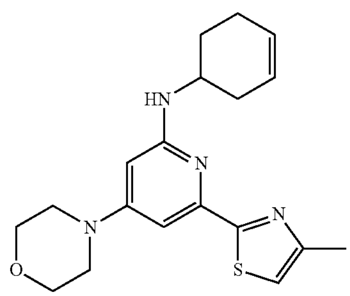 [SMILES: Cc1csc(-c2cc(N3CCOCC3)cc(NC3CC=CCC3)n2)n1] | 356.4916 |
| NSSy5688 | 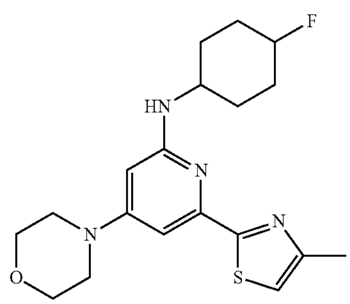 [SMILES: Cc1csc(-c2cc(N3CCOCC3)cc(NC3CCC(F)CC3)n2)n1] | 376.4975 |
| NSSy6285 | 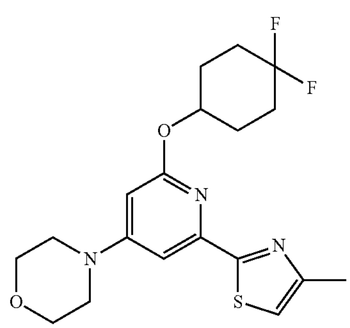 [SMILES: Cc1csc(-c2cc(N3CCOCC3)cc(OC3CCC(F)(F)CC3)n2)n1] | 395.4717 |

TABLE 2-continued

| Compound Ref | Structure | m/z data |
|---|---|---|
| NSSy5674 | 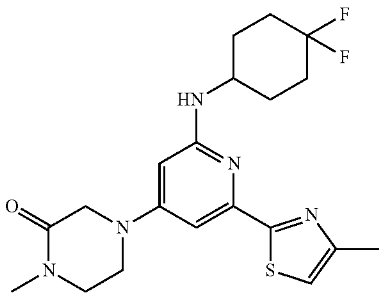 [SMILES: Cc1csc(-c2cc(N3CCN(C)C(=O)C3)cc(NC3CCC(F)(F)CC3)n2)n1] | 421.5135 |
| NSSy6374 | 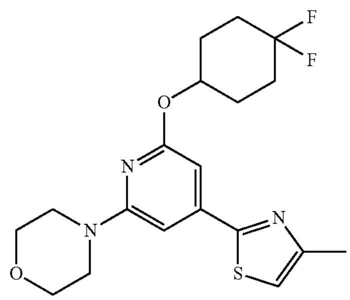 [SMILES: Cc1csc(-c2cc(OC3CCC(F)(F)CC3)nc(N3CCOCC3)c2)n1] | 395.4717 |
| NSSy5959 | 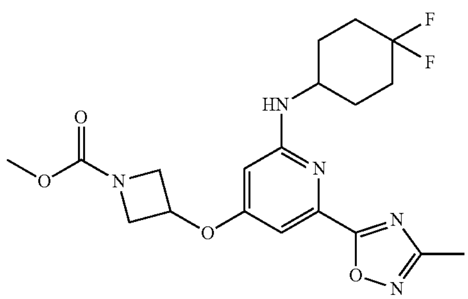 | 423.4177 |
| NSSy5957 | 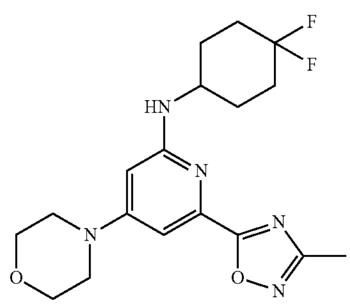 [SMILES: Cc1noc(-c2cc(N3CCOCC3)cc(NC3CCC(F)(F)CC3)n2)n1] | 379.4087 |
| NSSy6044 | 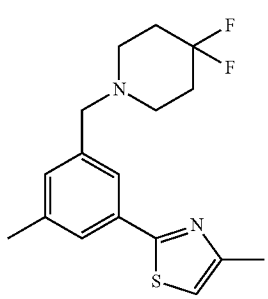 | 322.421 |

TABLE 2-continued
| Compound Ref | Structure | m/z data |
|---|---|---|
| NSSy5808 | 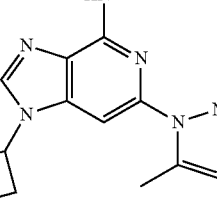 | 402.4466 |
| NSSy5934 | 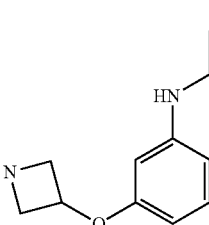 | 420.4574 |
| NSSy5972 | 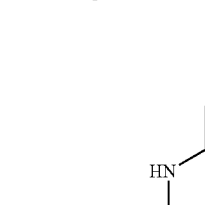 | 437.5085 |
| NSSy6342 | 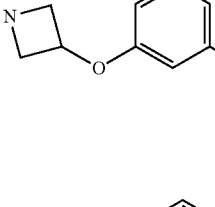 | 403.5045 |
| NSSy6910 NSSy6370 | 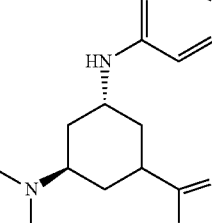 | 417.5011 |

TABLE 2-continued
| Compound Ref | Structure | m/z data |
|---|---|---|
| NSSy6885 | 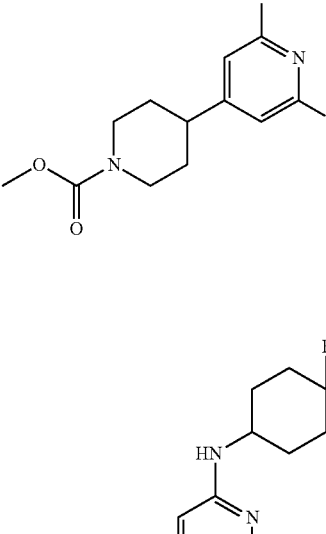 | 433.5001 |
| NSSy6897 | 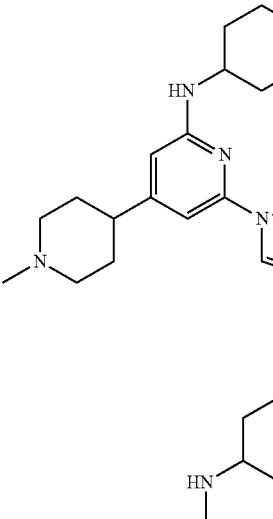 | 375.4643 |
| NSSy6888 | 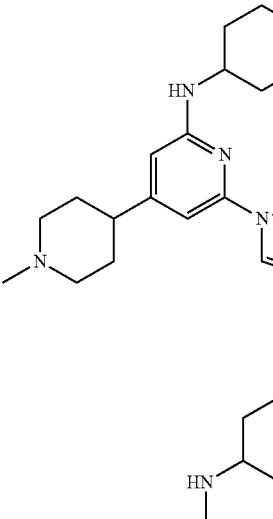 | 389.4911 |
| NSSy6436 | 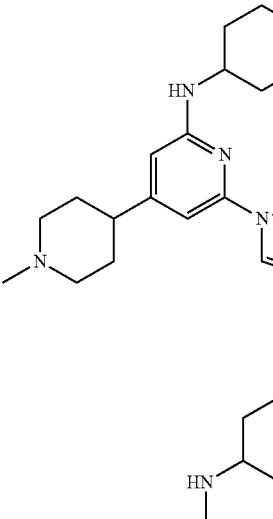 | 450.5512 |

TABLE 2-continued

| Compound Ref | Structure | m/z data |
|---|---|---|
| NSSy6489 | 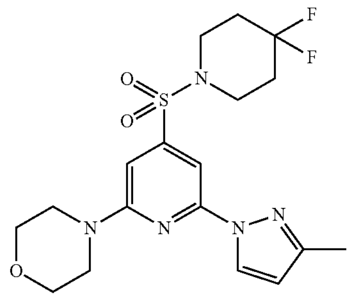 [SMILES: Cc1ccn(-c2cc(S(=O)(=O)N3CCC(F)(F)CC3)cc(N3CCOCC3)n2)n1] | 427.4737 |
| IN11251-020-P1 | 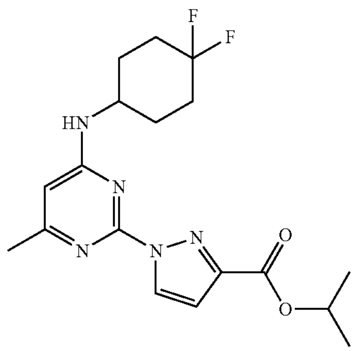 [SMILES: Cc1cc(NC2CCC(F)(F)CC2)nc(-n2ccc(C(=O)OC(C)C)n2)n1] | 379.404 |
| IN11218-030-P1 | 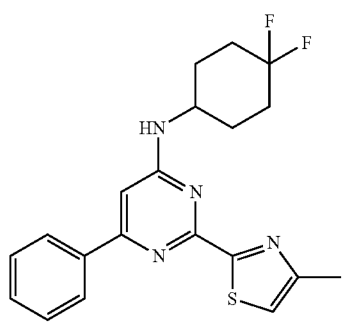 [SMILES: Cc1csc(-c2nc(NC3CCC(F)(F)CC3)cc(-c3ccccc3)n2)n1] | 386.461 |
| IN11147-096-P1 | 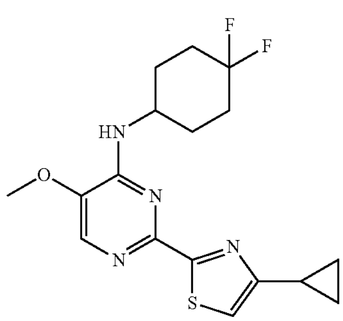 [SMILES: COc1cnc(-c2nc(C3CC3)cs2)nc1NC1CCC(F)(F)CC1] | 366.429 |

TABLE 2-continued

| Compound Ref | Structure | m/z data |
|---|---|---|
| IN11251-011-P2 | 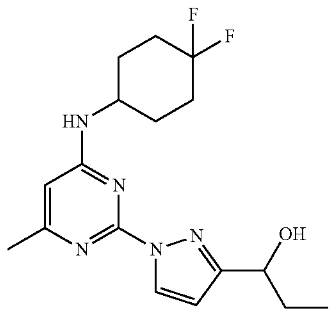 [SMILES: CCC(O)c1ccn(-c2nc(C)cc(NC3CCC(F)(F)CC3)n2)n1] | 351.394 |
| IN11250-007-P1 | 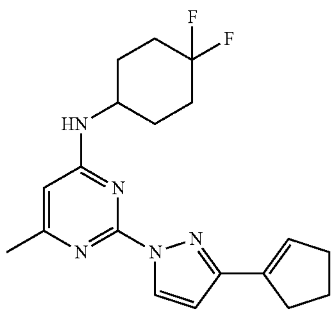 [SMILES: Cc1cc(NC2CCC(F)(F)CC2)nc(-n2ccc(C3=CCCC3)n2)n1] | 359.416 |
| IN11147-082-P1 | 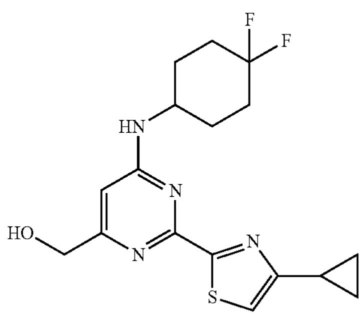 [SMILES: OCc1cc(NC2CCC(F)(F)CC2)nc(-c2nc(C3CC3)cs2)n1] | 366.429 |
| IN11196-080-P1 | 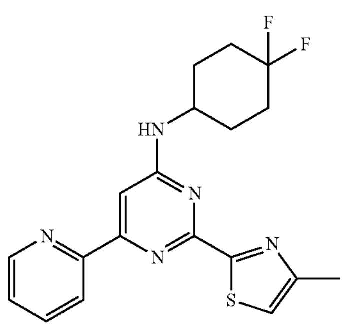 [SMILES: Cc1csc(-c2nc(NC3CCC(F)(F)CC3)cc(-c3ccccn3)n2)n1] | 387.449 |
| IN11177-064-P1 | 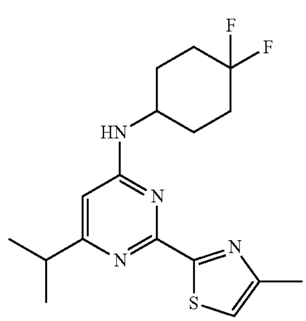 [SMILES: Cc1csc(-c2nc(NC3CCC(F)(F)CC3)cc(C(C)C)n2)n1] | 352.445 |

TABLE 2-continued

| Compound Ref | Structure | m/z data |
|---|---|---|
| IN11177-049-P1 | 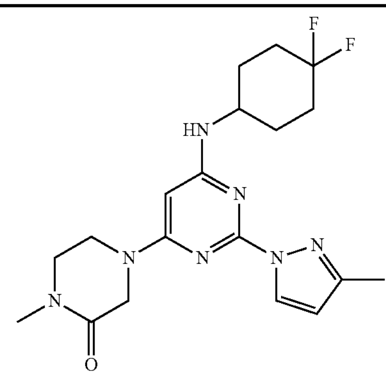 | 405.445 |
| IN11239-029-P1 | 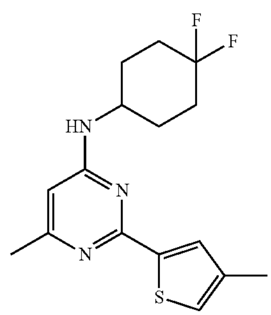 | 323.404 |
| IN11218-026-P1 | 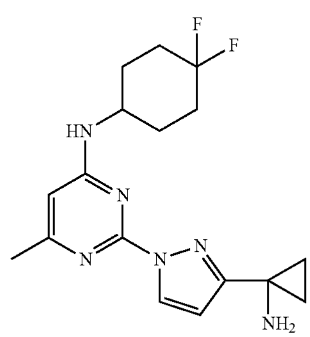 [SMILES: Cc1cc(NC2CCC(F)(F)CC2)nc(-n2ccc(C3(N)CC3)n2)n1] | 348.394 |
| IN11251-011-P1 | 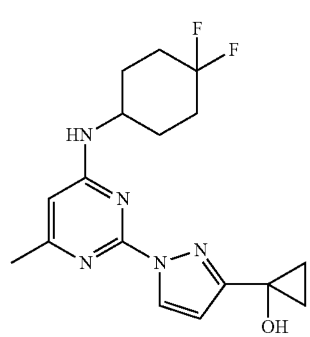 [SMILES: Cc1cc(NC2CCC(F)(F)CC2)nc(-n2ccc(C3(O)CC3)n2)n1] | 349.378 |

TABLE 2-continued

| Compound Ref | Structure | m/z data |
|---|---|---|
| IN11250-017-P1 | 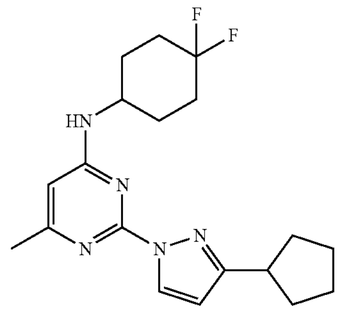 [SMILES: Cc1cc(NC2CCC(F)(F)CC2)nc(-n2ccc(C3CCCC3)n2)n1] | 361.432 |
| IN11218-025-P1 | 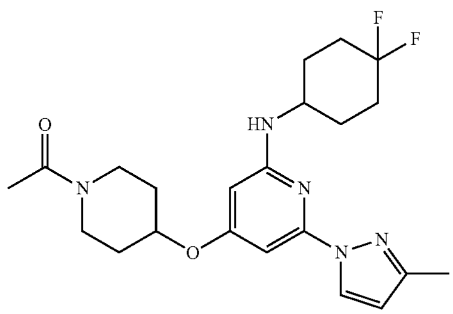 [SMILES: CC(=O)N1CCC(Oc2cc(NC3CCC(F)(F)CC3)nc(-n3ccc(C)n3)c2)CC1] | 433.495 |
| IN11177-056-P1 | 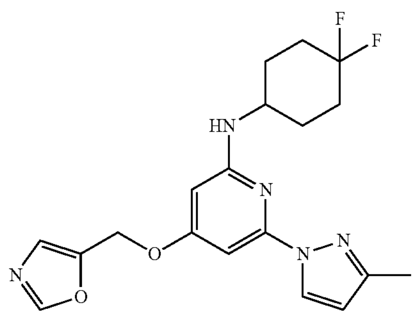 [SMILES: Cc1ccn(-c2cc(OCc3cnco3)cc(NC3CCC(F)(F)CC3)n2)n1] | 389.399 |
| IN11196-081-P1 | 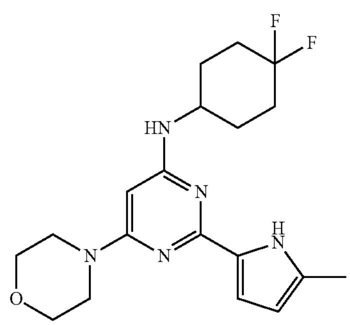 [SMILES: Cc1ccc(-c2nc(NC3CCC(F)(F)CC3)cc(N3CCOCC3)n2)[nH]1] | 377.432 |
| IN11196-041-P1 | 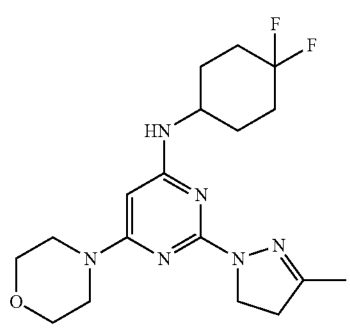 [SMILES: CC1=NN(c2nc(NC3CCC(F)(F)CC3)cc(N3CCOCC3)n2)CC1] | 380.435 |

TABLE 2-continued

| Compound Ref | Structure | m/z data |
|---|---|---|
| IN11196-039-P1 | 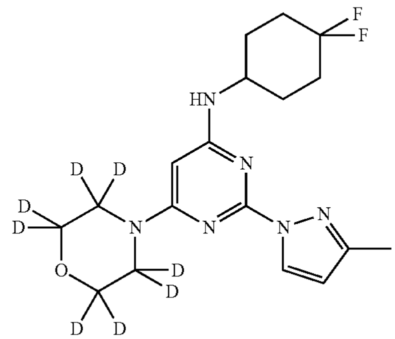 [SMILES: [2H]C1([2H])OC([2H])([2H])C([2H])([2H])N(c2cc(NC3CCC(F)(F)CC3)nc(-n3ccc(C)n3)n2)C1([2H])[2H]] | 386.469 |
| IN11239-001-P1 | 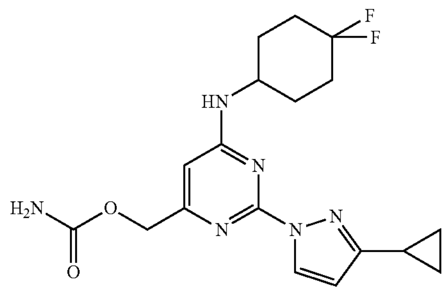 [SMILES: NC(=O)OCc1cc(NC2CCC(F)(F)CC2)nc(-n2ccc(C3CC3)n2)n1] | 392.403 |
| IN11147-077-P1 | 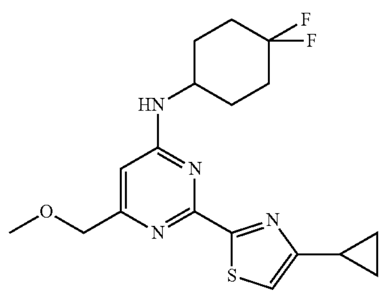 [SMILES: COCc1cc(NC2CCC(F)(F)CC2)nc(-c2nc(C3CC3)cs2)n1] | 380.455 |
| IN11146-089-P1 | 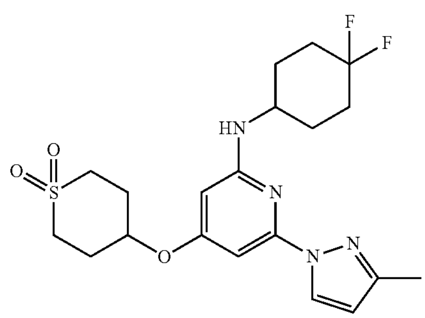 [SMILES: Cc1ccn(-c2cc(OC3CCS(=O)(=O)CC3)cc(NC3CCC(F)(F)CC3)n2)n1] | 440.507 |
| IN11217-003-P1 | 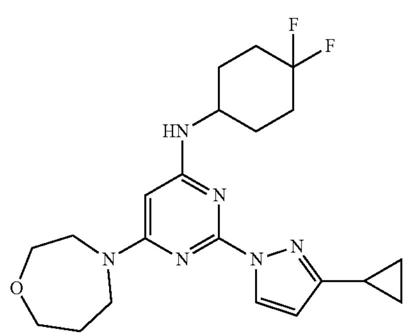 [SMILES: FC1(F)CCC(Nc2cc(N3CCCOCC3)nc(-n3ccc(C4CC4)n3)n2)CC1] | 418.483 |

TABLE 2-continued

| Compound Ref | Structure | m/z data |
|---|---|---|
| IN11147-066-P1 | 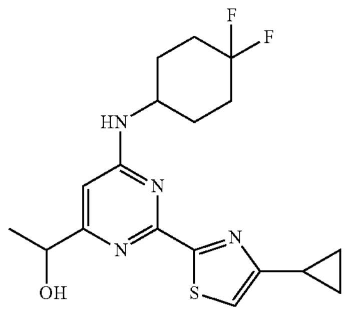 [SMILES: CC(O)c1cc(NC2CCC(F)(F)CC2)nc(-c2nc(C3CC3)cs2)n1] | 380.455 |
| IN11177-043-P1 | 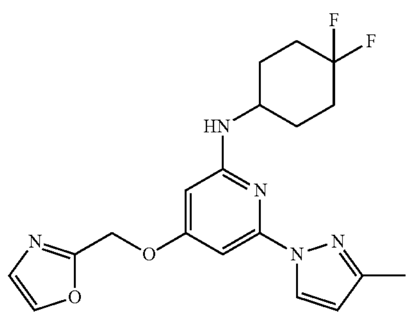 [SMILES: Cc1ccn(-c2cc(OCc3ncco3)cc(NC3CCC(F)(F)CC3)n2)n1] | 389.399 |
| IN11111-097-P1 | 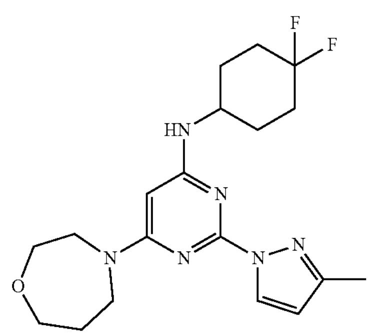 [SMILES: Cc1ccn(-c2nc(NC3CCC(F)(F)CC3)cc(N3CCCOCC3)n2)n1] | 392.446 |
| IN11106-091-P1 | 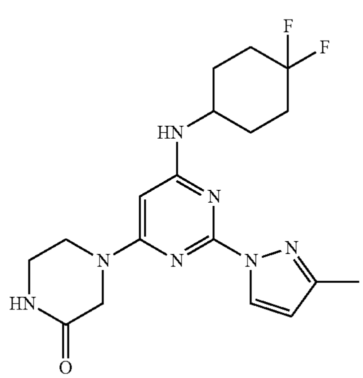 [SMILES: Cc1ccn(-c2nc(NC3CCC(F)(F)CC3)cc(N3CCNC(=O)C3)n2)n1] | 391.418 |

TABLE 2-continued
| Compound Ref | Structure | m/z data |
|---|---|---|
| IN11125-095-P1 | 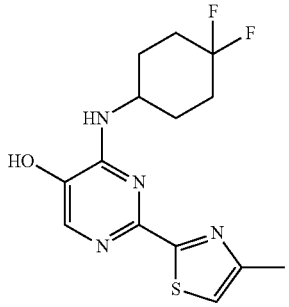 [SMILES: Cc1csc(-c2ncc(O)c(NC3CCC(F)(F)CC3)n2)n1] | 326.365 |
| IN11133-094-P1 | 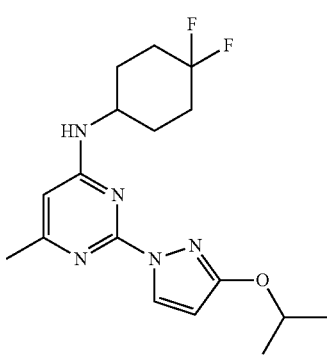 [SMILES: Cc1cc(NC2CCC(F)(F)CC2)nc(-n2ccc(OC(C)C)n2)n1] | 351.394 |
| IN11216-001-P1 | 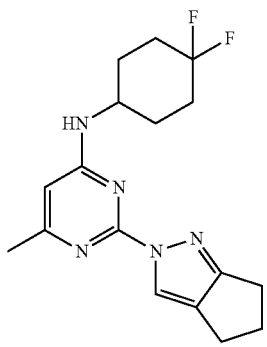 [SMILES: Cc1cc(NC2CCC(F)(F)CC2)nc(-n2cc3c(n2)CCC3)n1] | 333.379 |
| IN11111-100-P1 | 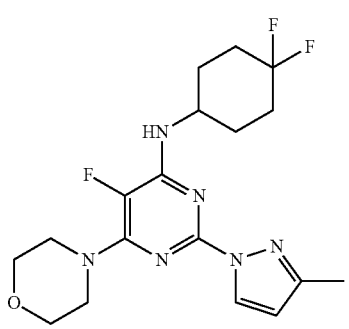 [SMILES: Cc1ccn(-c2nc(NC3CCC(F)(F)CC3)c(F)c(N3CCOCC3)n2)n1] | 396.41 |

TABLE 2-continued

| Compound Ref | Structure | m/z data |
|---|---|---|
| IN11177-029-P1 | 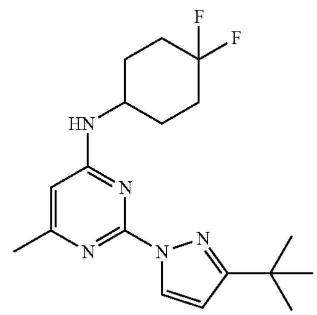 [SMILES: Cc1cc(NC2CCC(F)(F)CC2)nc(-n2ccc(C(C)(C)C)n2)n1] | 349.421 |
| IN11196-026-P1 | 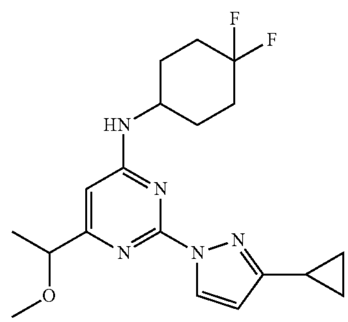 [SMILES: COC(C)c1cc(NC2CCC(F)(F)CC2)nc(-n2ccc(C3CC3)n2)n1] | 377.432 |
| IN11133-097-P1 | 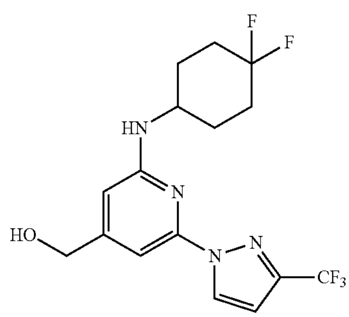 [SMILES: OCc1cc(NC2CCC(F)(F)CC2)nc(-n2ccc(C(F)(F)F)n2)c1] | 376.324 |
| IN11140-089-P1 | 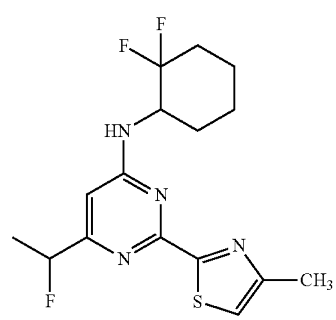 [SMILES: Cc1csc(-c2nc(NC3CCCCC3(F)F)cc(C(C)F)n2)n1] | 356.409 |
| IN11140-096-P1 | 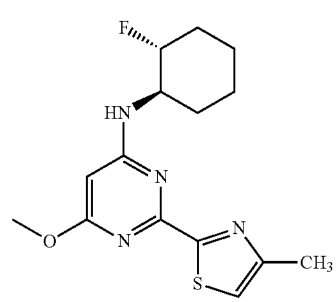 | 322.401 |

TABLE 2-continued

| Compound Ref | Structure | m/z data |
|---|---|---|
| IN11137-079-P1 | 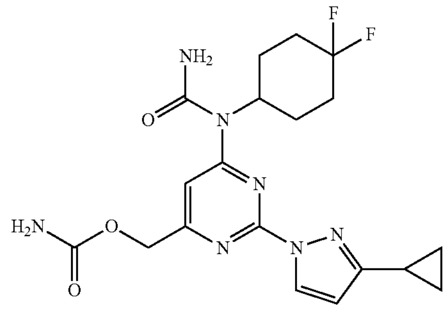 [SMILES: NC(=O)OCc1cc(N(C(N)=O)C2CCC(F)(F)CC2)nc(-n2ccc(C3CC3)n2)n1] | 435.428 |
| IN11130-077-P1 | 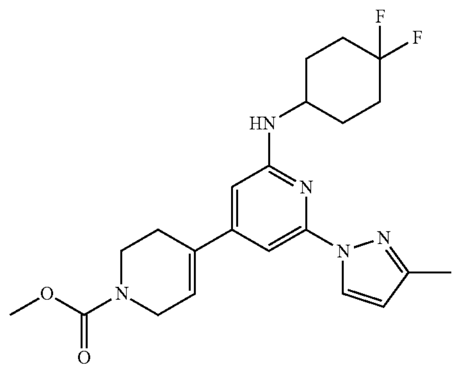 | 431.479 |
| IN11166-042-P1 | 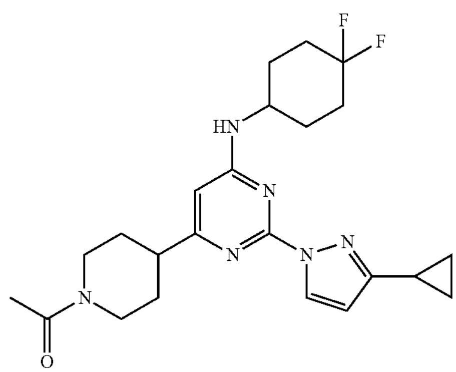 [SMILES: CC(=O)N1CCC(c2cc(NC3CCC(F)(F)CC3)nc(-n3ccc(C4CC4)n3)n2)CC1] | 444.521 |
| IN11147-054-P1 | 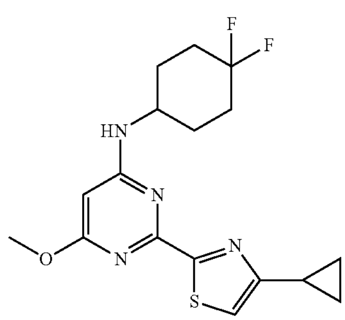 [SMILES: COc1cc(NC2CCC(F)(F)CC2)nc(-c2nc(C3CC3)cs2)n1] | 366.429 |

TABLE 2-continued

| Compound Ref | Structure | m/z data |
|---|---|---|
| IN11125-091-P1 | 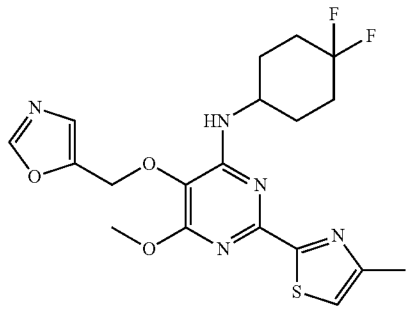 [SMILES: COc1nc(-c2nc(C)cs2)nc(NC2CCC(F)(F)CC2)c1OCc1cnco1] | 437.464 |
| IN11140-086-P1 | 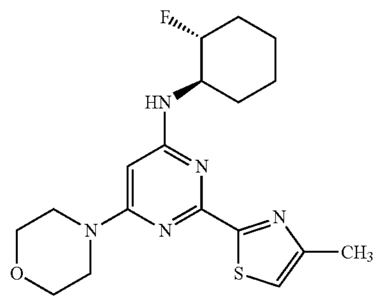 [SMILES: Cc1csc(-c2nc(N[C@@H]3CCCC[C@H]3F)cc(N3CCOCC3)n2)n1] | 377.479 |
| IN11140-081-P1 | 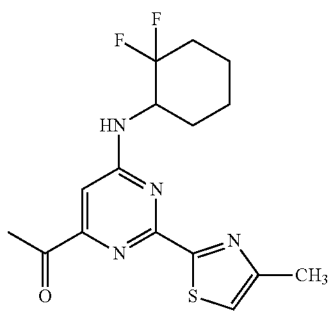 [SMILES: CC(=O)c1cc(NC2CCCCC2(F)F)nc(-c2nc(C)cs2)n1] | 352.402 |
| IN11196-007-P2 | 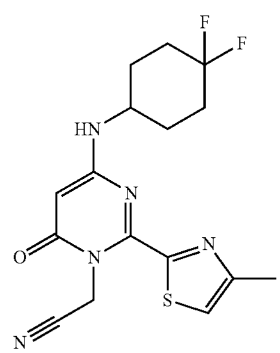 [SMILES: Cc1csc(-c2nc(NC3CCC(F)(F)CC3)cc(=O)n2CC#N)n1] | 365.401 |
| IN11196-007-P1 | 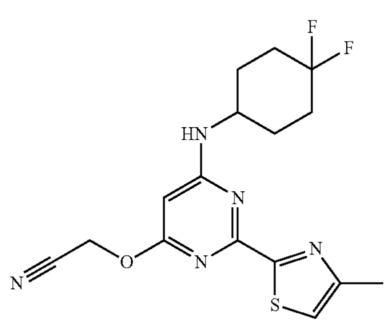 [SMILES: Cc1csc(-c2nc(NC3CCC(F)(F)CC3)cc(OCC#N)n2)n1] | 365.401 |

TABLE 2-continued

| Compound Ref | Structure | m/z data |
|---|---|---|
| IN11130-076-P1 | 4-((4,4-difluorocyclohexyl)amino)-5-methyl-2-(4-methylthiazol-2-yl)pyrimidine | 324.392 |
| IN11177-025-P1 | 2-(3-tert-butyl-1H-pyrazol-1-yl)-N-(4,4-difluorocyclohexyl)-6-morpholinopyrimidin-4-amine | 420.499 |
| IN11111-092-P1 | (2-(3-cyclopropyl-1H-pyrazol-1-yl)-6-((4,4-difluorocyclohexyl)amino)pyridin-4-yl)methanol | 348.39 |
| IN11140-083-P1 | 1-(6-((2,2-difluorocyclohexyl)amino)-2-(4-methylthiazol-2-yl)pyrimidin-4-yl)ethanol | 354.418 |
| IN11147-036-P1 | N-(4,4-difluorocyclohexyl)-4-(methylsulfonyl)-6-(4-methylthiazol-2-yl)pyridin-2-amine | 387.468 |

TABLE 2-continued

| Compound Ref | Structure | m/z data |
|---|---|---|
| IN11133-062-P1 | 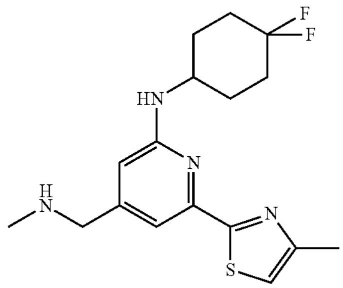 | 352.445 |
| IN11137-074-P1 | 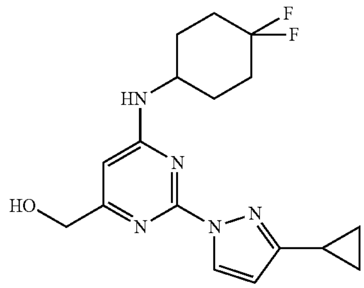 [SMILES: OCc1cc(NC2CCC(F)(F)CC2)nc(-n2ccc(C3CC3)n2)n1] | 349.378 |
| IN11106-077-P1 | 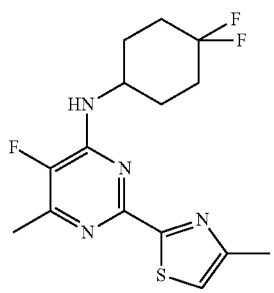 | 342.382 |
| IN11166-036-P1 | 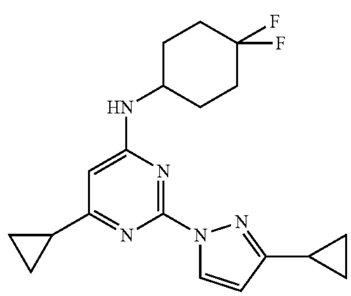 [SMILES: FC1(F)CCC(Nc2cc(C3CC3)nc(-n3ccc(C4CC4)n3)n2)CC1] | 359.416 |
| IN11133-061-P1 | 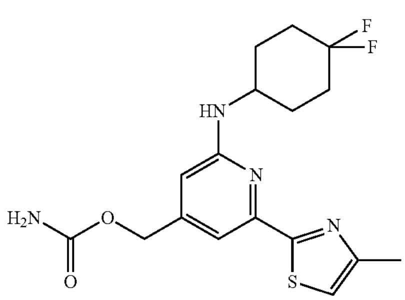 [SMILES: Cc1csc(-c2cc(COC(N)=O)cc(NC3CCC(F)(F)CC3)n2)n1] | 382.428 |

TABLE 2-continued

| Compound Ref | Structure | m/z data |
|---|---|---|
| IN11133-069-P1 | 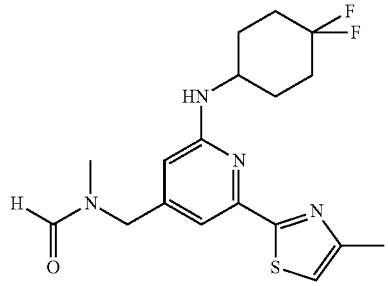 [SMILES: Cc1csc(-c2cc(CN(C)C=O)cc(NC3CCC(F)(F)CC3)n2)n1] | 380.455 |
| IN11133-068-P1 | 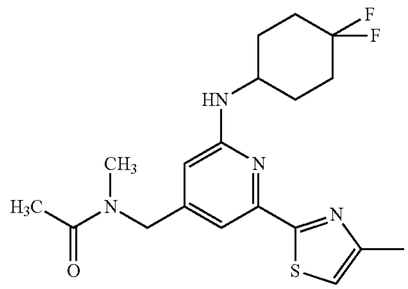 [SMILES: CC(=O)N(C)Cc1cc(NC2CCC(F)(F)CC2)nc(-c2nc(C)cs2)c1] | 394.482 |
| IN11140-065-P1 | 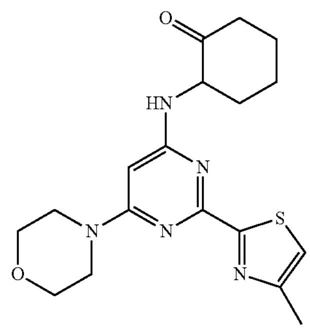 [SMILES: Cc1csc(-c2nc(NC3CCCCC3=O)cc(N3CCOCC3)n2)n1] | 373.473 |
| IN11104-059-P1 | 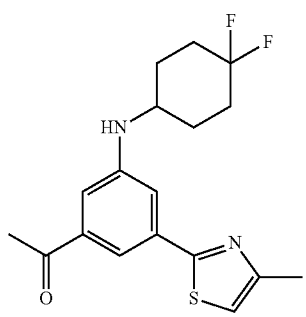 [SMILES: CC(=O)c1cc(NC2CCC(F)(F)CC2)cc(-c2nc(C)cs2)c1] | 350.426 |
| IN11130-053-P1 | 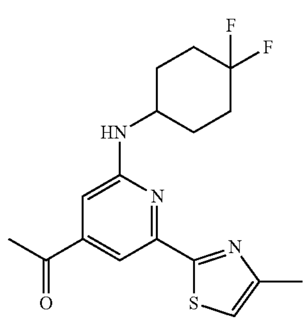 [SMILES: CC(=O)c1cc(NC2CCC(F)(F)CC2)nc(-c2nc(C)cs2)c1] | 351.414 |

TABLE 2-continued

| Compound Ref | Structure | m/z data |
|---|---|---|
| IN11166-038-P1 | 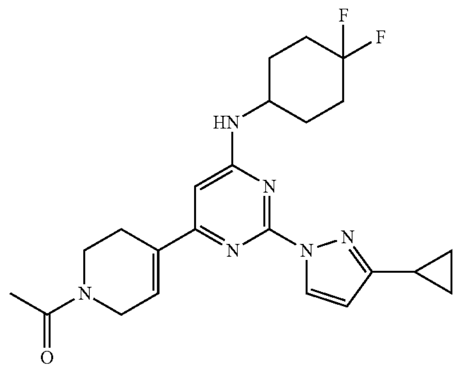 [SMILES: CC(=O)N1CC=C(c2cc(NC3CCC(F)(F)CC3)nc(-n3ccc(C4CC4)n3)n2)CC1] | 442.505 |
| IN11104-100-P1 | 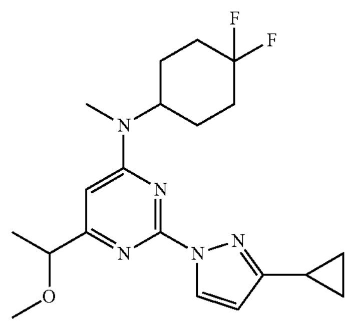 [SMILES: COC(C)c1cc(N(C)C2CCC(F)(F)CC2)nc(-n2ccc(C3CC3)n2)n1] | 391.458 |
| IN11140-066-P1 | 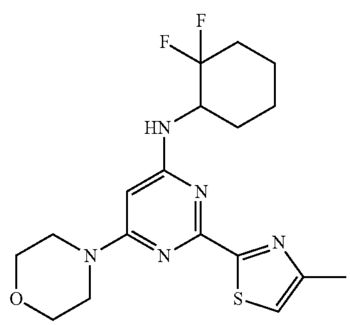 [SMILES: Cc1csc(-c2nc(NC3CCCCC3(F)F)cc(N3CCOCC3)n2)n1] | 395.47 |
| IN11133-049-P1 | 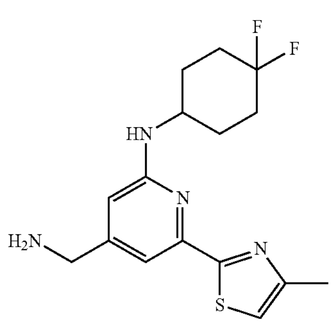 [SMILES: Cc1csc(-c2cc(CN)cc(NC3CCC(F)(F)CC3)n2)n1] | 338.419 |

TABLE 2-continued

| Compound Ref | Structure | m/z data |
|---|---|---|
| IN11137-072-P1 | 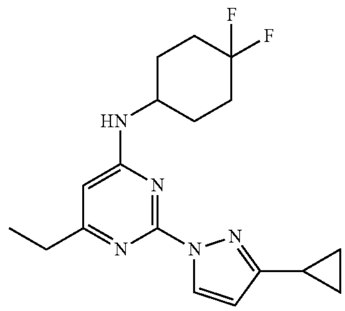 [SMILES: CCc1cc(NC2CCC(F)(F)CC2)nc(-n2ccc(C3CC3)n2)n1] | 347.406 |
| IN11106-066-P1 | 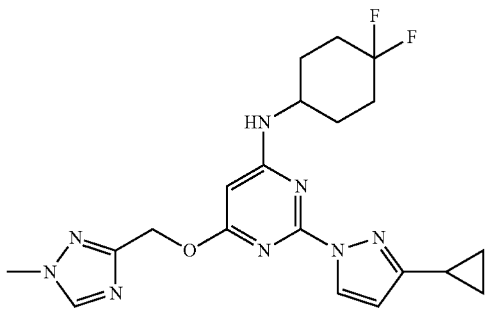 [SMILES: Cn1cnc(COc2cc(NC3CCC(F)(F)CC3)nc(-n3ccc(C4CC4)n3)n2)n1] | 430.454 |
| IN11140-063-P1 | 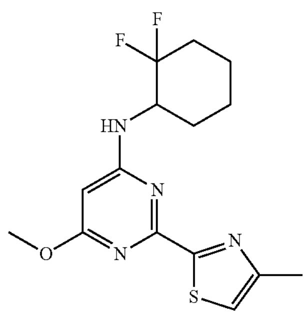 | 340.391 |
| IN11106-065-P1 | 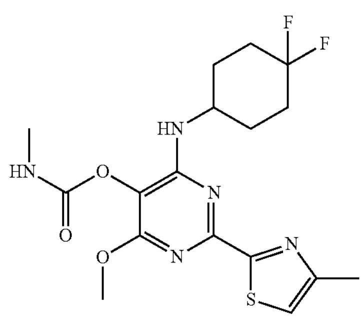 [SMILES: CNC(=O)Oc1c(NC2CCC(F)(F)CC2)nc(-c2nc(C)cs2)nc1OC] | 413.442 |
| IN11147-031-P1 | 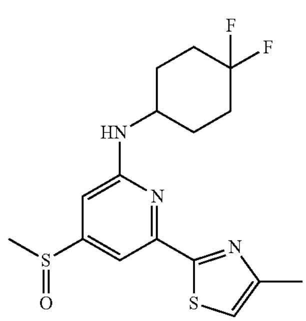 | 371.468 |

TABLE 2-continued

| Compound Ref | Structure | m/z data |
| --- | --- | --- |
| IN11146-039-P1 | 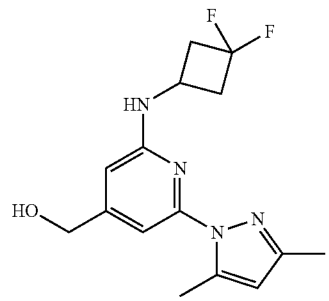 [SMILES: Cc1cc(C)n(-c2cc(CO)cc(NC3CC(F)(F)C3)n2)n1] | 308.326 |
| IN11104-094-P1 | 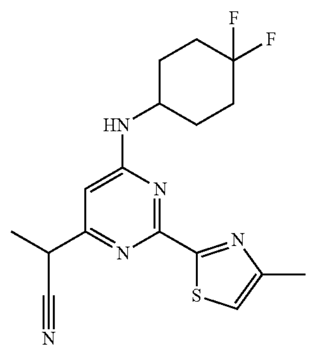 [SMILES: Cc1csc(-c2nc(NC3CCC(F)(F)CC3)cc(C(C)C#N)n2)n1] | 363.428 |
| IN11147-026-P1 | 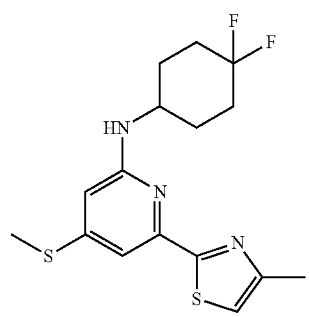 | 355.469 |
| IN11140-058-P1 | 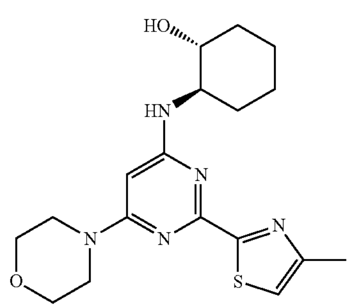 [SMILES: Cc1csc(-c2nc(N[C@@H]3CCCC[C@H]3O)cc(N3CCOCC3)n2)n1] | 375.488 |

TABLE 2-continued

| Compound Ref | Structure | m/z data |
|---|---|---|
| IN11140-052-P1 | 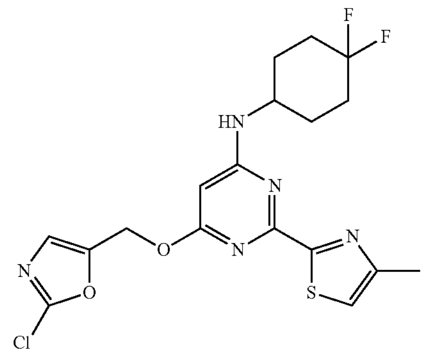 [SMILES: Cc1csc(-c2nc(NC3CCC(F)(F)CC3)cc(OCc3cnc(Cl)o3)n2)n1] | 441.883 |
| IN11121-042-P1 | 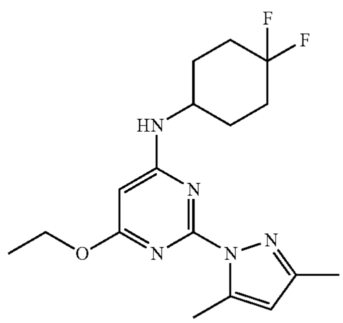 [SMILES: CCOc1cc(NC2CCC(F)(F)CC2)nc(-n2nc(C)cc2C)n1] | 351.394 |
| IN11166-020-P1 | 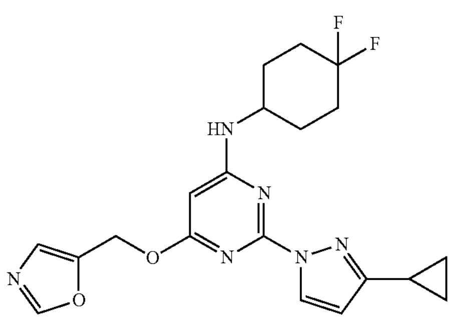 [SMILES: FC1(F)CCC(Nc2cc(OCc3cnco3)nc(-n3ccc(C4CC4)n3)n2)CC1] | 416.424 |
| IN11106-062-P1 | 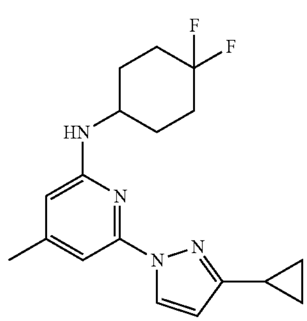 [SMILES: Cc1cc(NC2CCC(F)(F)CC2)nc(-n2ccc(C3CC3)n2)c1] | 332.391 |

TABLE 2-continued

| Compound Ref | Structure | m/z data |
|---|---|---|
| IN11111-063-P1 | 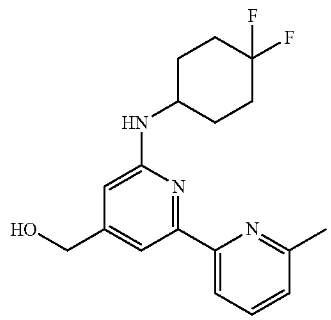 [SMILES: Cc1cccc(-c2cc(CO)cc(NC3CCC(F)(F)CC3)n2)n1] | 333.376 |
| IN11140-062-P1 | 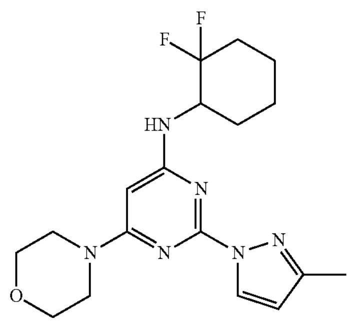 [SMILES: Cc1ccn(-c2nc(NC3CCCCC3(F)F)cc(N3CCOCC3)n2)n1] | 378.42 |
| IN11125-065-P1 | 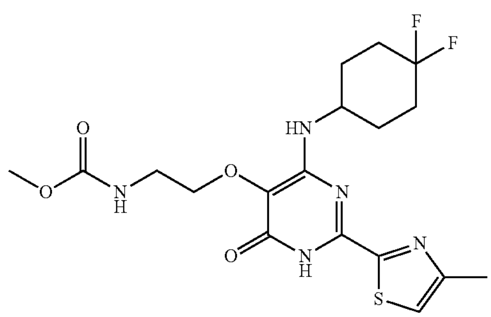 | 443.468 |
| IN11108-038-P1 | 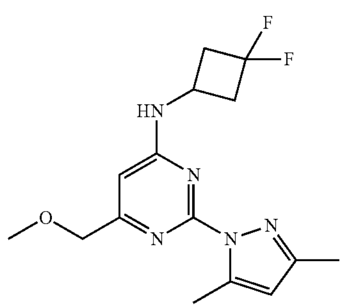 | 323.341 |
| IN11104-084-P2 | 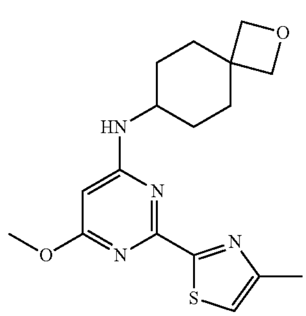 | 346.447 |

TABLE 2-continued

| Compound Ref | Structure | m/z data |
|---|---|---|
| IN11146-033-P1 | 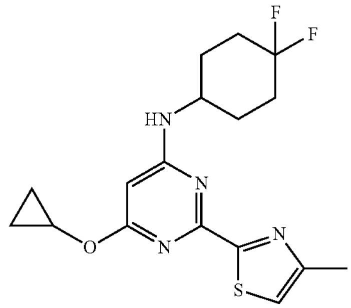 [SMILES: Cc1csc(-c2nc(NC3CCC(F)(F)CC3)cc(OC3CC3)n2)n1] | 366.429 |
| IN11104-095-P1 | 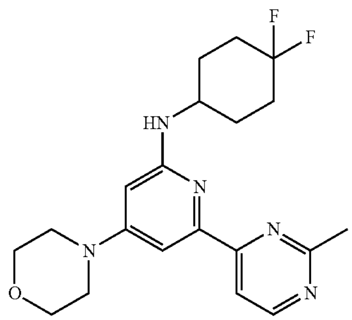 [SMILES: Cc1nccc(-c2cc(N3CCOCC3)cc(NC3CCC(F)(F)CC3)n2)n1] | 389.442 |
| IN11130-047-P1 | 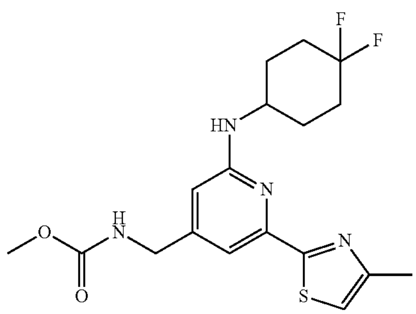 | 396.455 |
| IN11130-051-P1 | 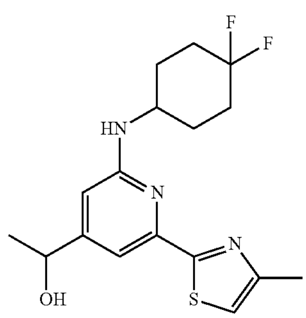 [SMILES: Cc1csc(-c2cc(C(C)O)cc(NC3CCC(F)(F)CC3)n2)n1] | 353.43 |
| IN11146-016-P1 | 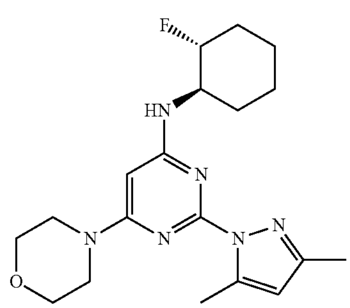 [SMILES: Cc1cc(C)n(-c2nc(N[C@@H]3CCCC[C@H]3F)cc(N3CCOCC3)n2)n1] | 374.456 |

TABLE 2-continued

| Compound Ref | Structure | m/z data |
|---|---|---|
| IN11133-031-P1 | 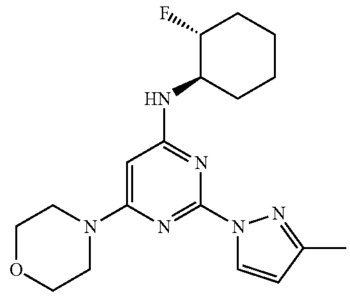 [SMILES: Cc1ccn(-c2nc(N[C@@H]3CCCC[C@H]3F)cc(N3CCOCC3)n2)n1] | 360.429 |
| IN11137-041-P1 | 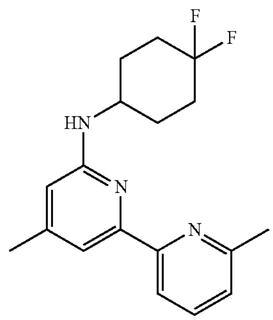 | 317.376 |
| IN11125-052-P1 | 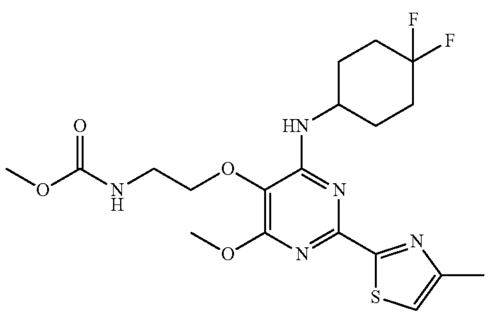 | 457.495 |
| IN11133-037-P1 | 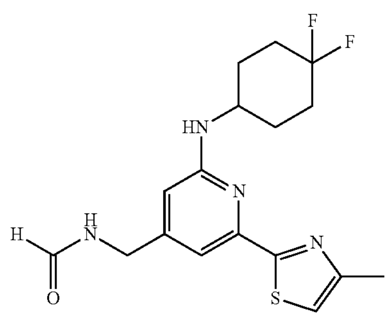 [SMILES: Cc1csc(-c2cc(CNC=O)cc(NC3CCC(F)(F)CC3)n2)n1] | 366.429 |
| IN11104-077-P1 | 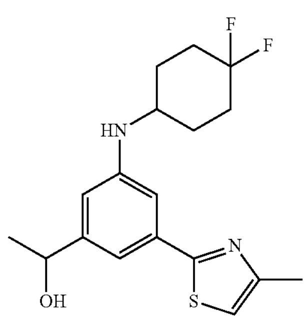 [SMILES: Cc1csc(-c2cc(NC3CCC(F)(F)CC3)cc(C(C)O)c2)n1] | 352.442 |

TABLE 2-continued

| Compound Ref | Structure | m/z data |
| --- | --- | --- |
| IN11130-031-P2 | 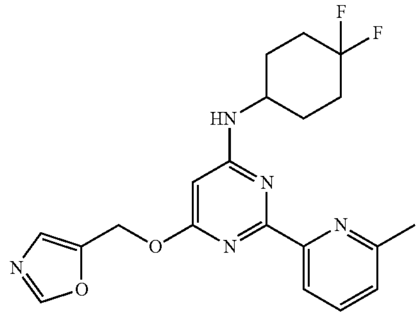 [SMILES: Cc1cccc(-c2nc(NC3CCC(F)(F)CC3)cc(OCc3cnco3)n2)n1] | 401.41 |
| IN11130-030-P1 | 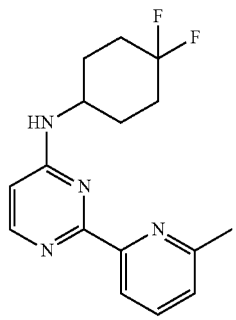 [SMILES: Cc1cccc(-c2nccc(NC3CCC(F)(F)CC3)n2)n1] | 304.338 |
| IN11146-013-P1 | 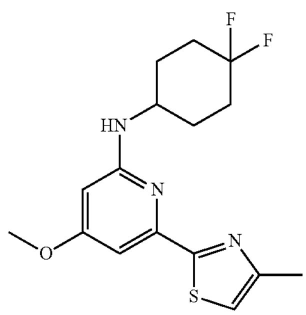 | 339.403 |
| IN11108-019-P1 | 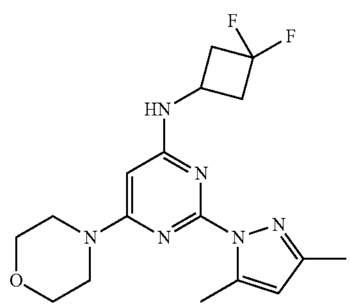 [SMILES: Cc1cc(C)n(-c2nc(NC3CC(F)(F)C3)cc(N3CCOCC3)n2)n1] | 364.393 |
| IN11108-018-P1 | 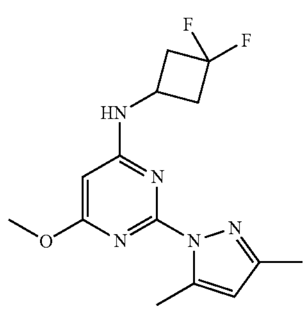 | 309.314 |

TABLE 2-continued

| Compound Ref | Structure | m/z data |
|---|---|---|
| IN11059-090-P1 | 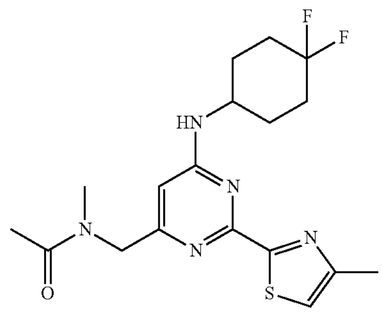 [SMILES: CC(=O)N(C)Cc1cc(NC2CCC(F)(F)CC2)nc(-c2nc(C)cs2)n1] | 395.47 |
| IN11059-095-P1 | 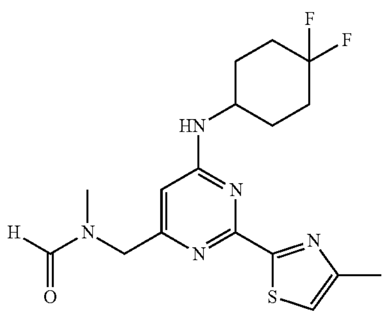 [SMILES: Cc1csc(-c2nc(CN(C)C=O)cc(NC3CCC(F)(F)CC3)n2)n1] | 381.443 |
| IN11107-023-P1 | 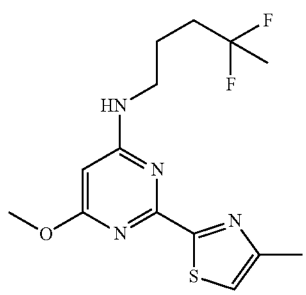 | 328.381 |
| IN11107-021-P1 | 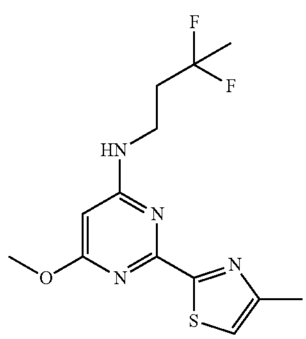 | 314.354 |
| IN11133-020-P1 | 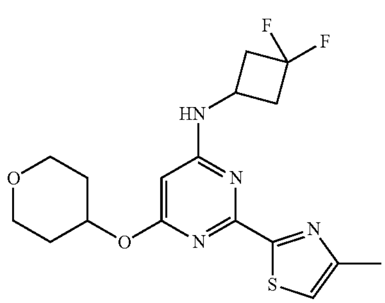 [SMILES: Cc1csc(-c2nc(NC3CC(F)(F)C3)cc(OC3CCOCC3)n2)n1] | 382.428 |

TABLE 2-continued

| Compound Ref | Structure | m/z data |
|---|---|---|
| IN11125-028-P1 | 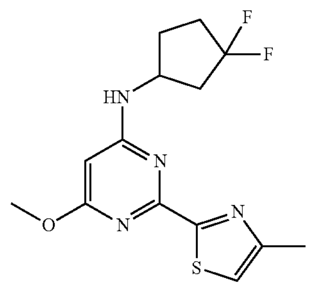 | 326.365 |
| IN11137-018-P1 | 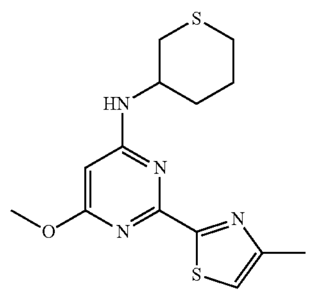 | 322.449 |
| IN11106-027-P1 | 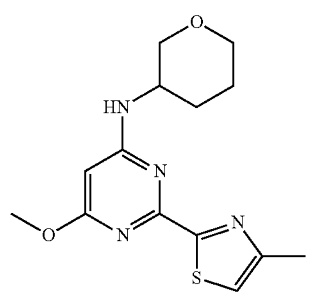 | 306.383 |
| IN11106-033-P1 | 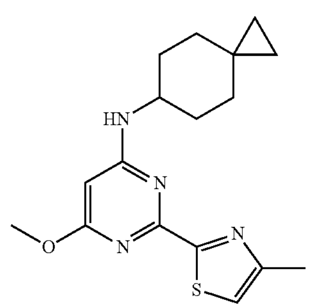 | 330.448 |
| IN11140-007-P1 | 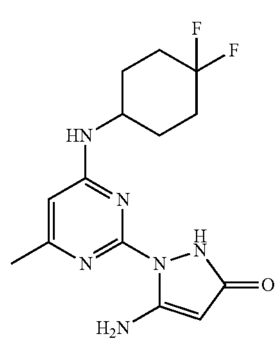 [SMILES: Cc1cc(NC2CCC(F)(F)CC2)nc(-n2[nH]c(=O)cc2N)n1] | 324.329 |

TABLE 2-continued

| Compound Ref | Structure | m/z data |
| --- | --- | --- |
| IN11104-099-P1 | 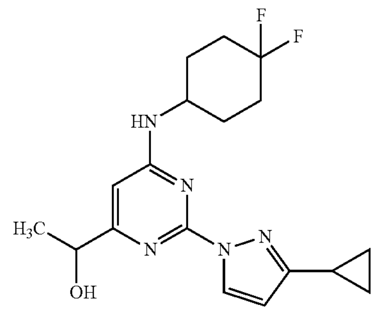 [SMILES: CC(O)c1cc(NC2CCC(F)(F)CC2)nc(-n2ccc(C3CC3)n2)n1] | 363.405 |
| IN11079-066-P1 | 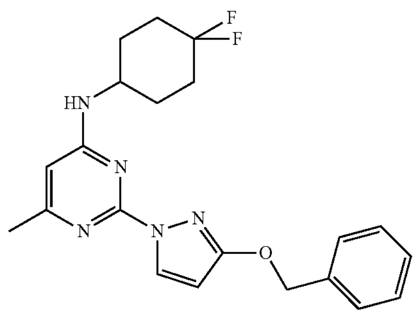 [SMILES: Cc1cc(NC2CCC(F)(F)CC2)nc(-n2ccc(OCc3ccccc3)n2)n1] | 399.437 |
| IN11059-096-P1 | 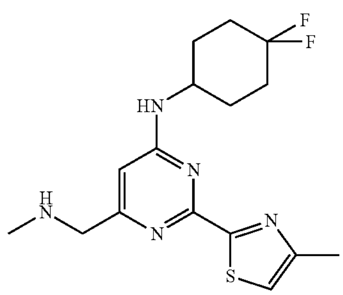 | 353.433 |
| IN11111-024-P1 | 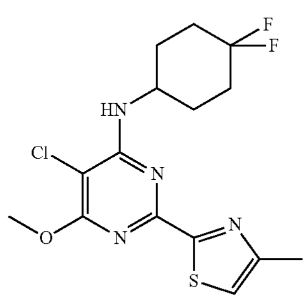 | 374.836 |
| IN11125-014-P1 | 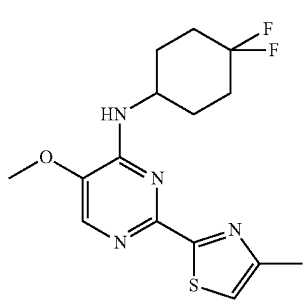 | 340.391 |

TABLE 2-continued

| Compound Ref | Structure | m/z data |
| --- | --- | --- |
| IN11104-041-P1 | 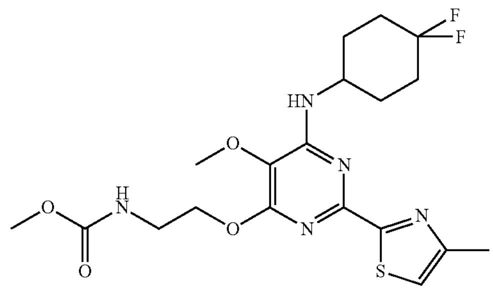 | 340.391 |
| IN11111-023-P1 | 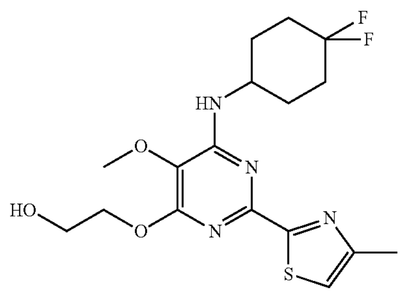 [SMILES: COc1c(NC2CCC(F)(F)CC2)nc(-c2nc(C)cs2)nc1OCCO] | 400.443 |
| IN11107-020-P1 | 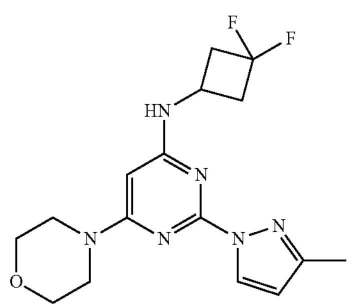 [SMILES: Cc1ccn(-c2nc(NC3CC(F)(F)C3)cc(N3CCOCC3)n2)n1] | 350.366 |
| IN11133-014-P1 | 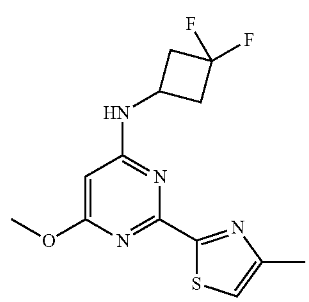 | 312.338 |
| IN11079-072-P1 | 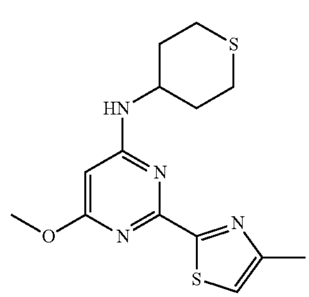 | 322.449 |

TABLE 2-continued

| Compound Ref | Structure | m/z data |
|---|---|---|
| IN11079-067-P1 | 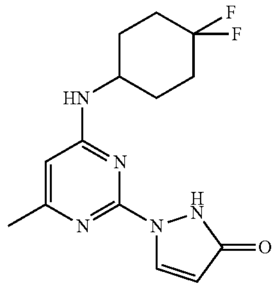 [SMILES: Cc1cc(NC2CCC(F)(F)CC2)nc(-n2ccc(=O)[nH]2)n1] | 309.314 |
| IN11054-100-P1 | 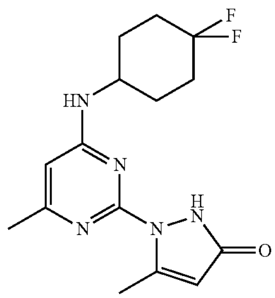 [SMILES: Cc1cc(NC2CCC(F)(F)CC2)nc(-n2[nH]c(=O)cc2C)n1] | 323.341 |
| IN11130-005-P1 | 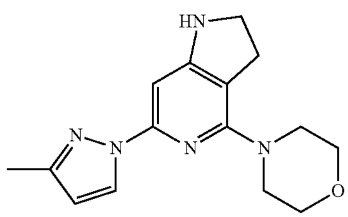 [SMILES: Cc1ccn(-c2cc3c(c(N4CCOCC4)n2)CCN3)n1] | 285.344 |
| IN11039-094-P1 | 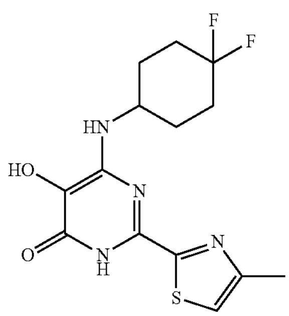 [SMILES: Cc1csc(-c2nc(NC3CCC(F)(F)CC3)c(O)c(=O)[nH]2)n1] | 342.364 |
| IN11125-012-P1 | 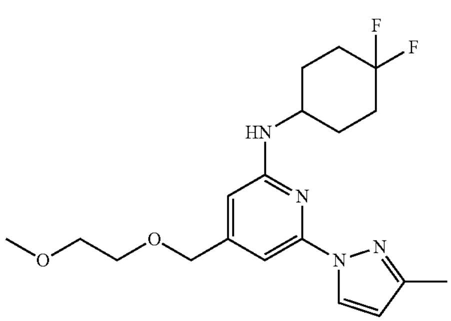 | 380.432 |

TABLE 2-continued

| Compound Ref | Structure | m/z data |
|---|---|---|
| IN11125-006-P1 | 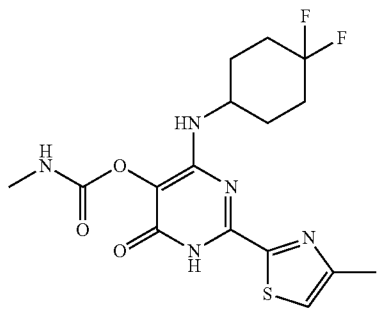 | 399.416 |
| IN11125-001-P1 | 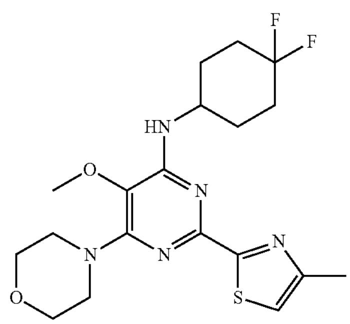 [SMILES: COc1c(NC2CCC(F)(F)CC2)nc(-c2nc(C)cs2)nc1N1CCOCC1] | 425.496 |
| IN11104-039-P1 | 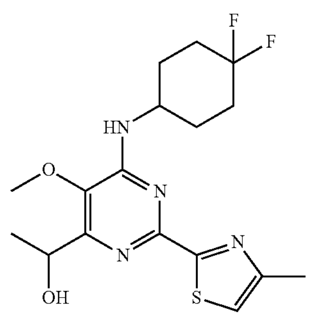 [SMILES: COc1c(NC2CCC(F)(F)CC2)nc(-c2nc(C)cs2)nc1C(C)O] | 384.444 |
| IN11111-021-P1 | 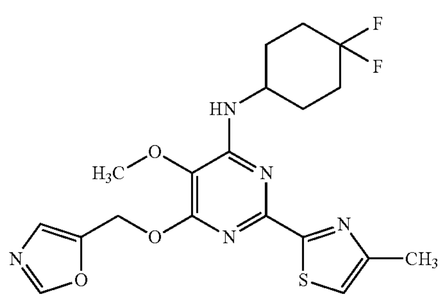 [SMILES: COc1c(NC2CCC(F)(F)CC2)nc(-c2nc(C)cs2)nc1OCc1cnco1] | 437.464 |
| IN11125-013-P1 | 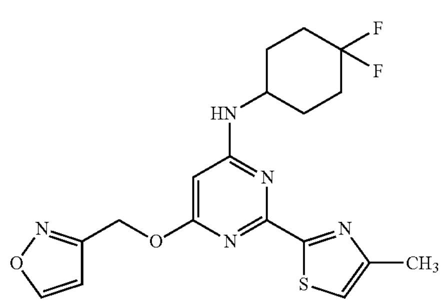 [SMILES: Cc1csc(-c2nc(NC3CCC(F)(F)CC3)cc(OCc3ccon3)n2)n1] | 407.438 |

TABLE 2-continued
| Compound Ref | Structure | m/z data |
|---|---|---|
| IN11055-087-P1 | 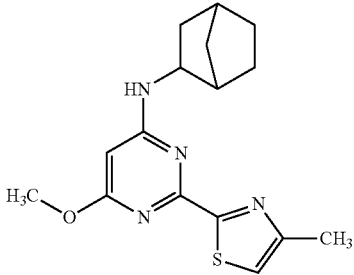 | 316.421 |
| IN11133-002-P1 | 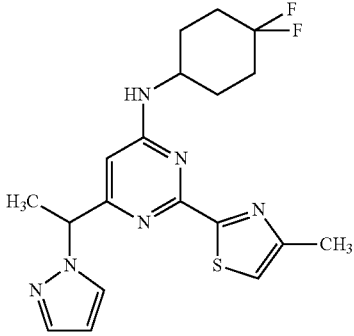 [SMILES: Cc1csc(-c2nc(NC3CCC(F)(F)CC3)cc(C(C)n3cccn3)n2)n1] | 404.48 |
| IN11130-007-P1 | 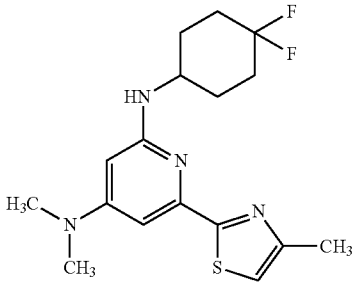 | 352.445 |
| IN11063-096-P1 | 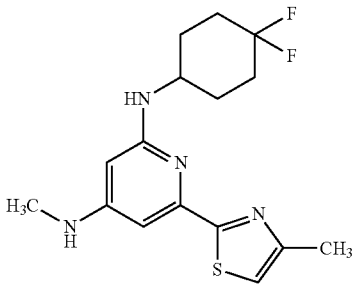 | 338.419 |
| IN11063-092-P1 | 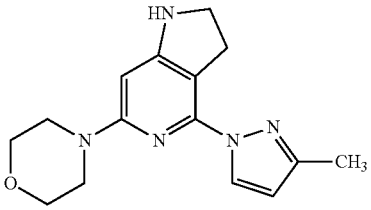 [SMILES: Cc1ccn(-c2nc(N3CCOCC3)cc3c2CCN3)n1] | 285.344 |

TABLE 2-continued

| Compound Ref | Structure | m/z data |
|---|---|---|
| IN11125-008-P1 | 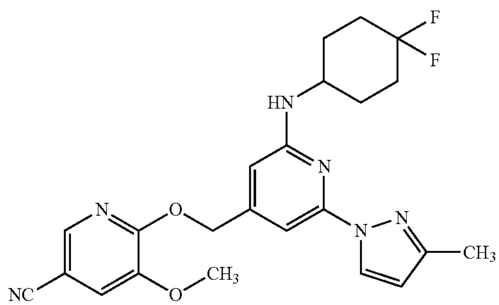 [SMILES: COc1cc(C#N)cnc1OCc1cc(NC2CCC(F)(F)CC2)nc(-n2ccc(C)n2)c1] | 454.472 |
| IN11039-092-P1 | 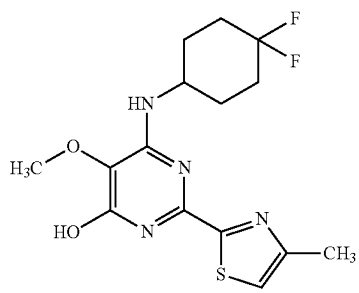 | 356.391 |
| IN11079-040-P1 | 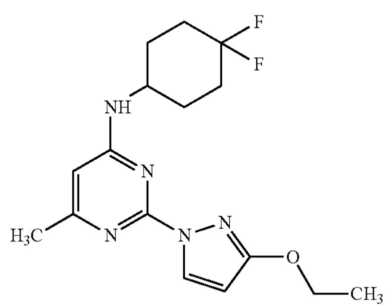 [SMILES: CCOc1ccn(-c2nc(C)cc(NC3CCC(F)(F)CC3)n2)n1] | 337.368 |
| IN11059-071-P1 | 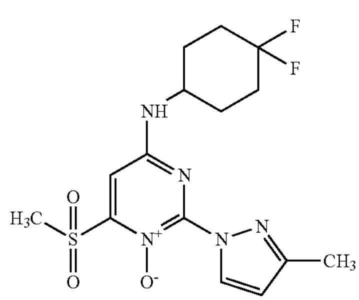 | 387.405 |
| IN11059-070-P1 | 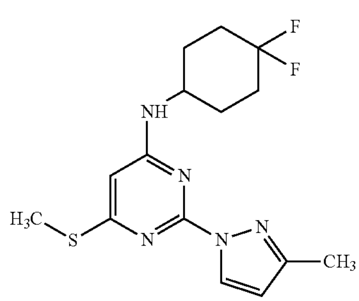 | 339.407 |

TABLE 2-continued

| Compound Ref | Structure | m/z data |
|---|---|---|
| IN11067-061-P1 | 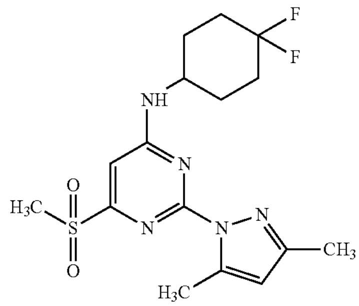 | 385.432 |
| IN11067-060-P1 | 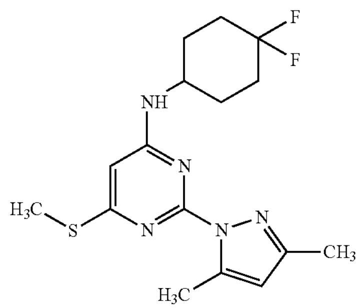 | 353.433 |
| IN11067-062-P1 | 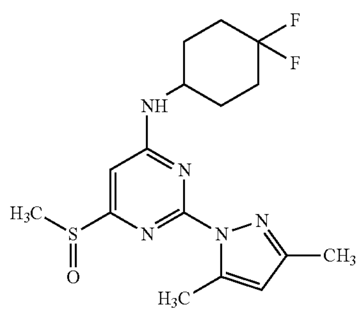 | 369.433 |
| IN11059-069-P1 | 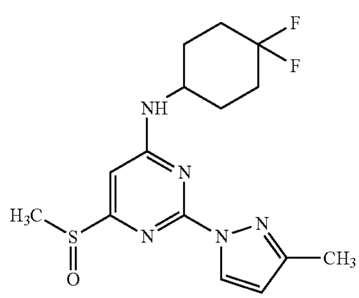 | 355.406 |
| IN11111-003-P1 | 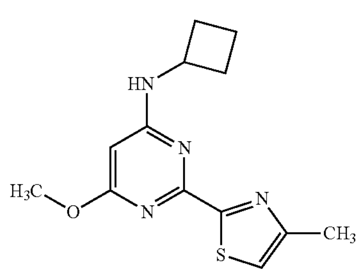 | 276.357 |

TABLE 2-continued

| Compound Ref | Structure | m/z data |
|---|---|---|
| IN11106-004-P1 | 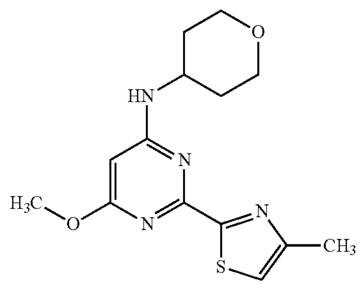 | 306.383 |
| IN11063-087-P1 | 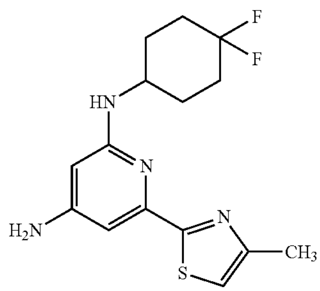 | 324.392 |
| IN11063-086-P2 | 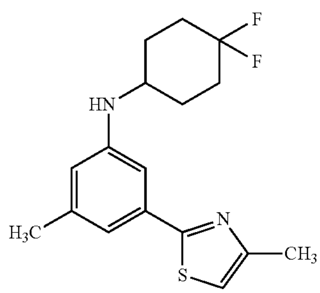 | 322.416 |
| IN11054-081-P1 | 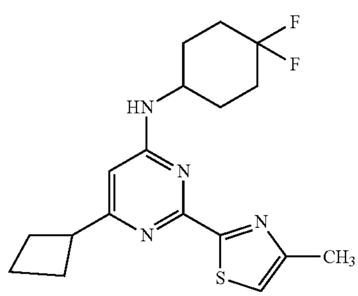 [SMILES: Cc1csc(-c2nc(NC3CCC(F)(F)CC3)cc(C3CCC3)n2)n1] | 364.456 |
| IN11055-079-P1 | 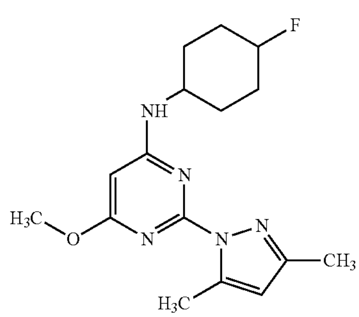 | 319.377 |

TABLE 2-continued
| Compound Ref | Structure | m/z data |
|---|---|---|
| IN11067-072-P1 | 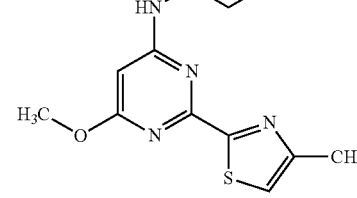 | 322.401 |
| IN11079-047-P1 | 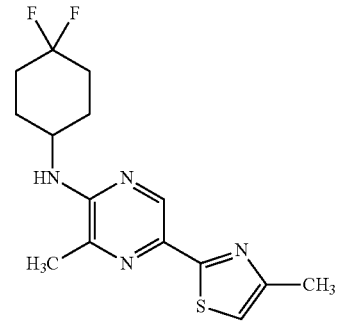 [SMILES: Cc1csc(-c2cnc(NC3CCC(F)(F)CC3)c(C)n2)n1] | 324.392 |
| IN11055-069-P1 | 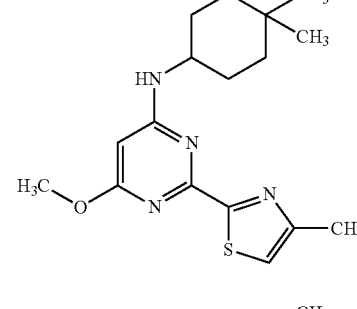 | 332.464 |
| IN11055-078-P1 | 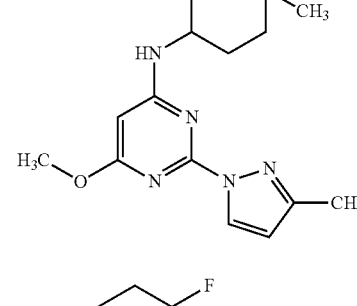 | 315.413 |
| IN11054-078-P1 | 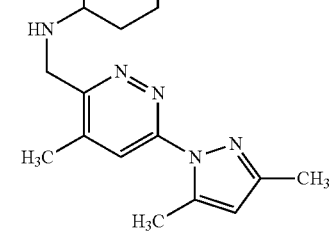 | 335.395 |

TABLE 2-continued

| Compound Ref | Structure | m/z data |
|---|---|---|
| IN11083-048-P1 | 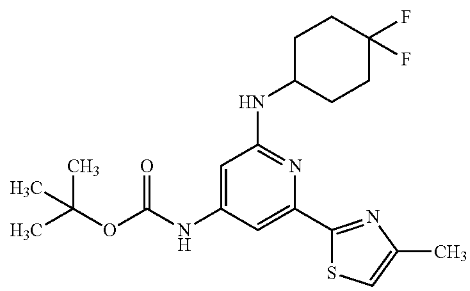 [SMILES: Cc1csc(-c2cc(NC(=O)OC(C)(C)C)cc(NC3CCC(F)(F)CC3)n2)n1] | 424.508 |
| IN11079-033-P1 | 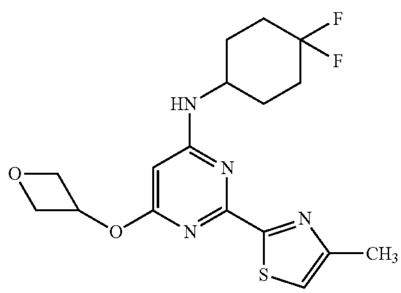 [SMILES: Cc1csc(-c2nc(NC3CCC(F)(F)CC3)cc(OC3COC3)n2)n1] | 382.428 |
| IN11055-066-P1 | 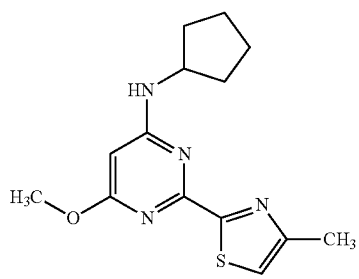 | 290.384 |
| IN11039-069-P1 | 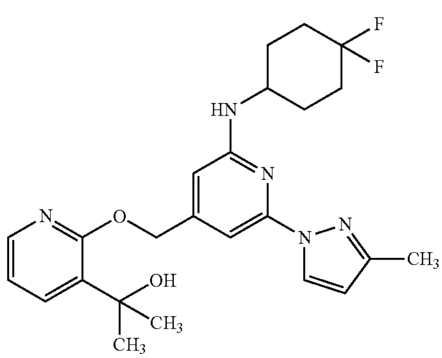 [SMILES: Cc1ccn(-c2cc(COc3ncccc3C(C)(C)O)cc(NC3CCC(F)(F)CC3)n2)n1] | 457.516 |
| IN11055-068-P1 | 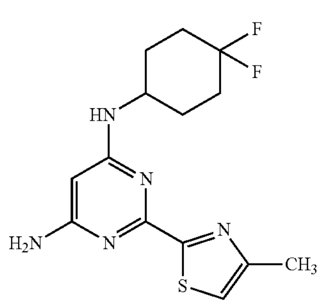 [SMILES: Cc1csc(-c2nc(N)cc(NC3CCC(F)(F)CC3)n2)n1] | 325.38 |

TABLE 2-continued

| Compound Ref | Structure | m/z data |
|---|---|---|
| IN11053-076-P1 | 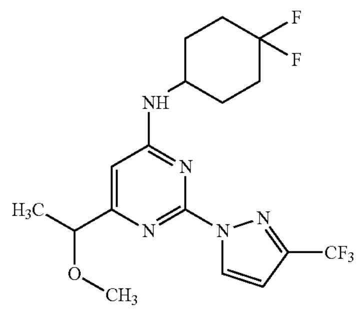 [SMILES: COC(C)c1cc(NC2CCC(F)(F)CC2)nc(-n2ccc(C(F)(F)F)n2)n1] | 405.366 |
| IN11053-073-P1 | 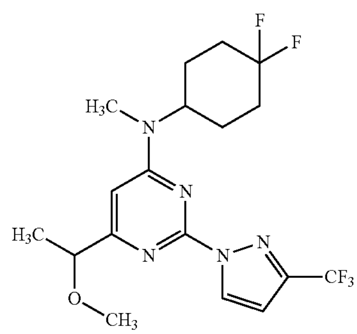 [SMILES: COC(C)c1cc(N(C)C2CCC(F)(F)CC2)nc(-n2ccc(C(F)(F)F)n2)n1] | 419.392 |
| IN11053-062-P1 | 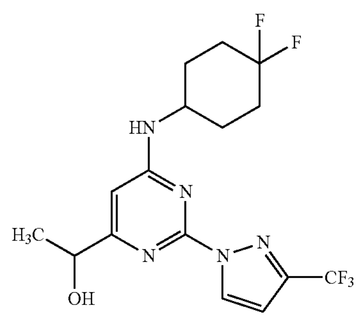 [SMILES: CC(O)c1cc(NC2CCC(F)(F)CC2)nc(-n2ccc(C(F)(F)F)n2)n1] | 391.339 |
| IN11053-059-P1 | 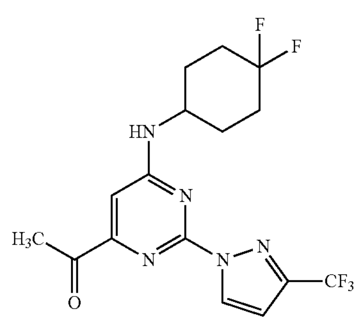 [SMILES: CC(=O)c1cc(NC2CCC(F)(F)CC2)nc(-n2ccc(C(F)(F)F)n2)n1] | 389.323 |
| IN11053-060-P1 | 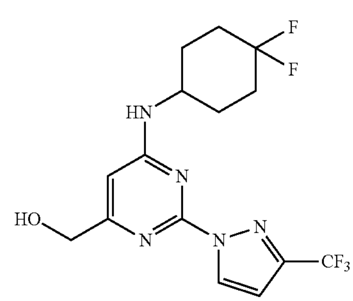 [SMILES: OCc1cc(NC2CCC(F)(F)CC2)nc(-n2ccc(C(F)(F)F)n2)n1] | 377.312 |

TABLE 2-continued

| Compound Ref | Structure | m/z data |
|---|---|---|
| IN11055-049-P1 | 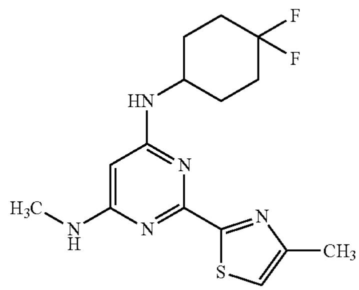 | 339.407 |
| IN11125-010-P1 | 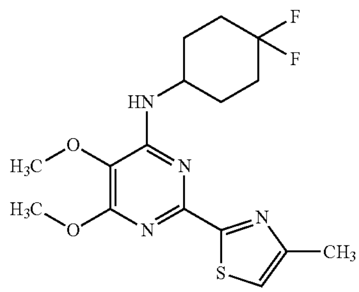 | 370.417 |
| IN11059-052-P1 | 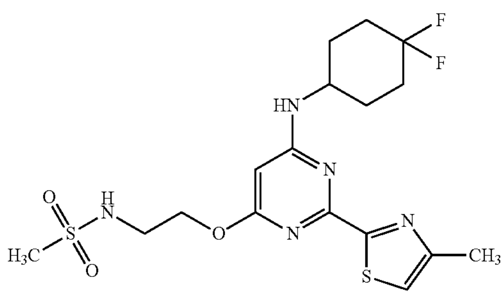 | 447.523 |
| IN11053-071-P1 | 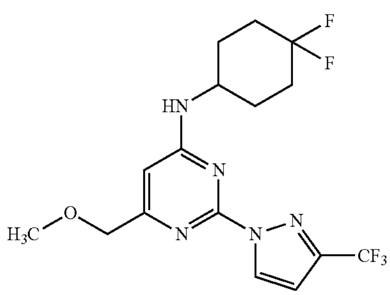 [SMILES: COCc1cc(NC2CCC(F)(F)CC2)nc(-n2ccc(C(F)(F)F)n2)n1] | 391.339 |
| IN11039-066-P1 | 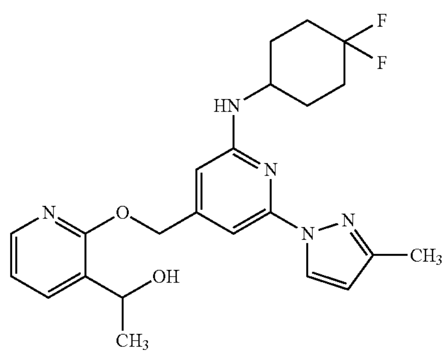 [SMILES: Cc1ccn(-c2cc(COc3ncccc3C(C)O)cc(NC3CCC(F)(F)CC3)n2)n1] | 443.49 |

TABLE 2-continued

| Compound Ref | Structure | m/z data |
|---|---|---|
| IN11054-054-P1 | 4,4-difluorocyclohexyl-NH-pyrimidine(OMe)-(3-methylpyrazol-1-yl) | 322.353 |
| IN11030-095-P1 | 4,4-difluorocyclohexyl-NH-pyrimidine-O-CH2CH2CN, 2-(3-methylpyrazol-1-yl) | 362.377 |
| IN11054-046-P1 | 4,4-difluorocyclohexyl-NH-pyrimidine(SO2CH3)-(4-methylthiazol-2-yl) | 388.456 |
| IN11030-081-P1 | 4,4-difluorocyclohexyl-NH-quinazoline(8-OMe)-2-(4-methylthiazol-2-yl) | 390.45 |
| IN11059-047-P1 | 4,4-difluorocyclohexyl-NH-pyrimidine-O-CH2-(oxazol-5-yl), 2-(4-methylthiazol-2-yl) | 407.438 |

TABLE 2-continued

| Compound Ref | Structure | m/z data |
|---|---|---|
| IN11055-046-P1 | 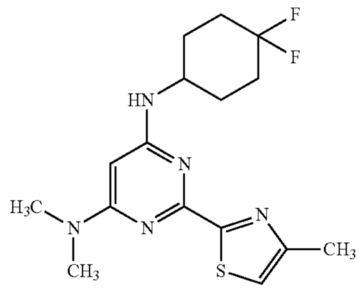 | 353.433 |
| IN11055-044-P1 | 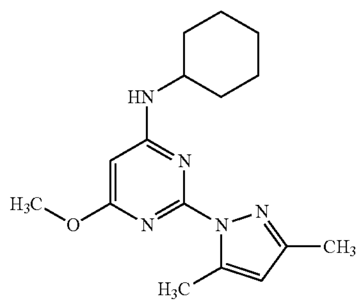 | 301.387 |
| IN11039-058-P1 | 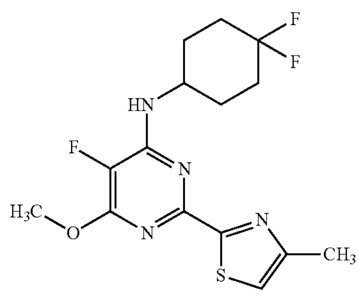 | 358.382 |
| IN11053-052-P1 | 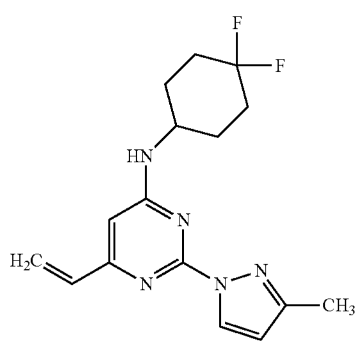 [SMILES: C=Cc1cc(NC2CCC(F)(F)CC2)nc(-n2ccc(C)n2)n1] | 319.352 |
| IN11054-030-P1 | 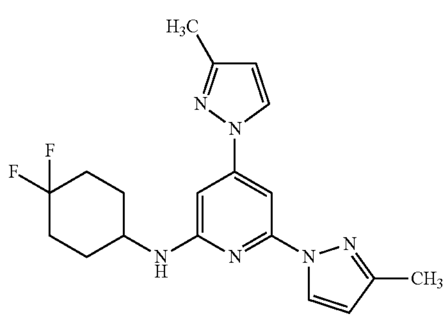 [SMILES: Cc1ccn(-c2cc(NC3CCC(F)(F)CC3)nc(-n3ccc(C)n3)c2)n1] | 372.415 |

TABLE 2-continued

| Compound Ref | Structure | m/z data |
|---|---|---|
| IN11067-035-P1 | 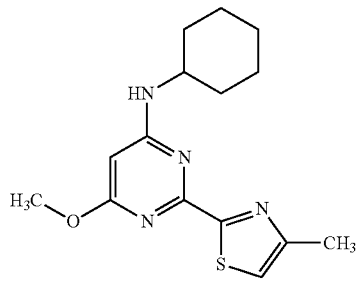 | 304.41 |
| IN11054-046-P2 | 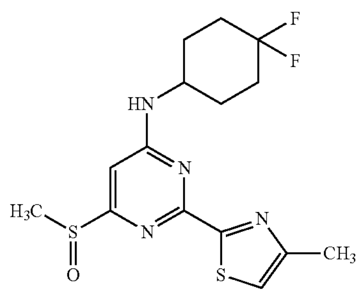 | 372.456 |
| IN11030-083-P1 | 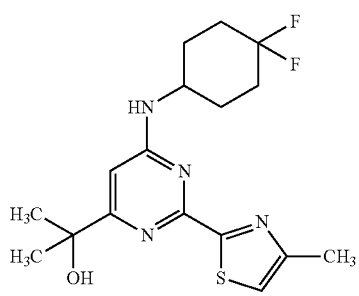 [SMILES: Cc1csc(-c2nc(NC3CCC(F)(F)CC3)cc(C(C)(C)O)n2)n1] | 368.445 |
| IN11054-039-P1 | 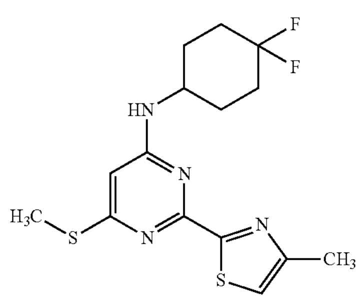 | 356.457 |
| IN11079-014-P1 | 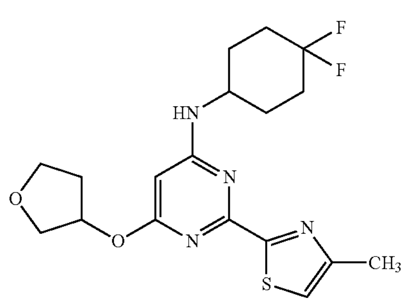 [SMILES: Cc1csc(-c2nc(NC3CCC(F)(F)CC3)cc(OC3CCOC3)n2)n1] | 396.455 |

TABLE 2-continued

| Compound Ref | Structure | m/z data |
|---|---|---|
| IN11053-046-P1 | 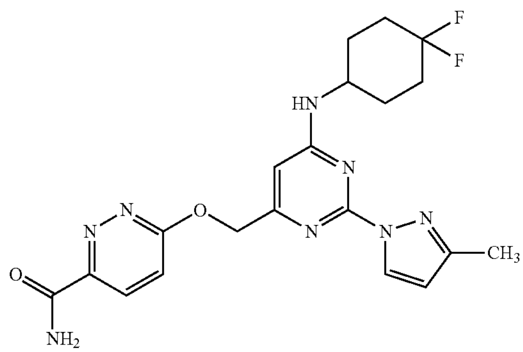 [SMILES: Cc1ccn(-c2nc(COc3ccc(C(N)=O)nn3)cc(NC3CCC(F)(F)CC3)n2)n1] | 444.438 |
| IN11054-038-P1 | 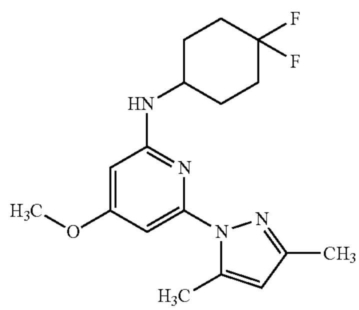 | 336.38 |
| IN11030-054-P1 | 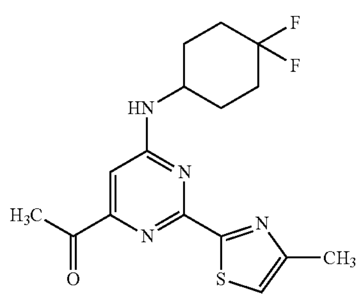 [SMILES: CC(=O)c1cc(NC2CCC(F)(F)CC2)nc(-c2nc(C)cs2)n1] | 352.402 |
| IN11039-036-P1 | 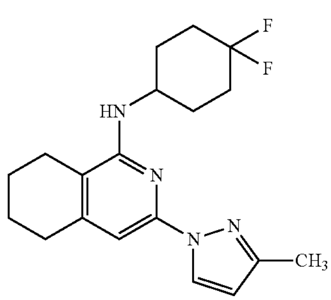 [SMILES: Cc1ccn(-c2cc3c(c(NC4CCC(F)(F)CC4)n2)CCCC3)n1] | 346.418 |
| IN11079-007-P1 | 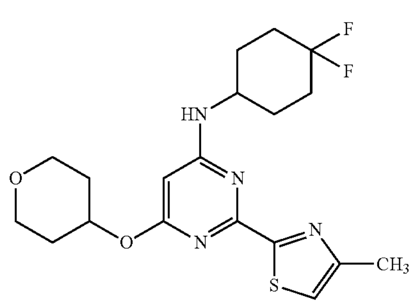 [SMILES: Cc1csc(-c2nc(NC3CCC(F)(F)CC3)cc(OC3CCOCC3)n2)n1] | 410.481 |

TABLE 2-continued

| Compound Ref | Structure | m/z data |
|---|---|---|
| IN11079-009-P1 | 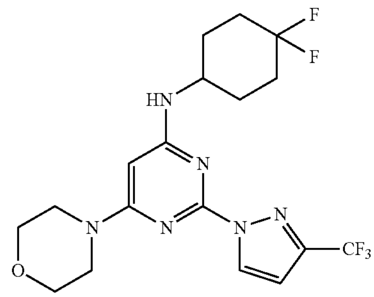 [SMILES: FC1(F)CCC(Nc2cc(N3CCOCC3)nc(-n3ccc(C(F)(F)F)n3)n2)CC1] | 432.391 |
| IN11067-023-P1 | 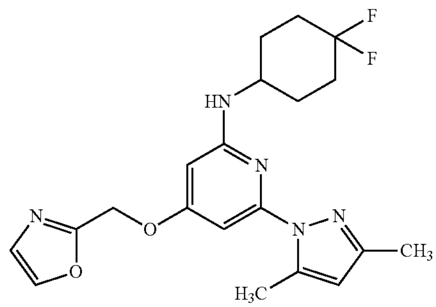 [SMILES: Cc1cc(C)n(-c2cc(OCc3ncco3)cc(NC3CCC(F)(F)CC3)n2)n1] | 403.426 |
| IN11063-030-P1 | 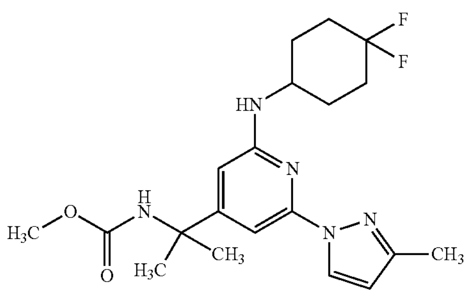 | 407.458 |
| IN11053-033-P1 | 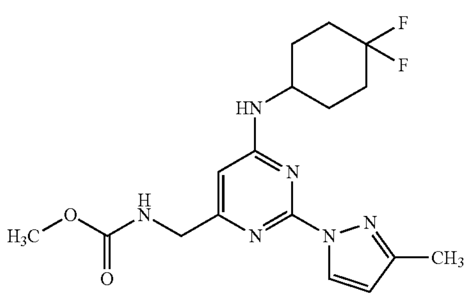 | 380.392 |
| IN11083-014-P1 | 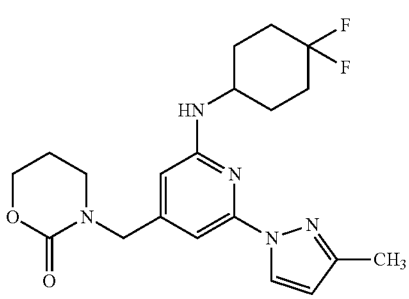 [SMILES: Cc1ccn(-c2cc(CN3CCCOC3=O)cc(NC3CCC(F)(F)CC3)n2)n1] | 405.442 |

TABLE 2-continued

| Compound Ref | Structure | m/z data |
|---|---|---|
| IN11030-044-P1 | 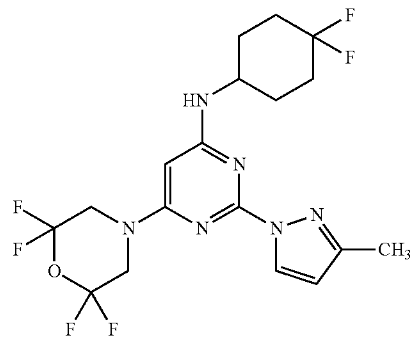 [SMILES: Cc1ccn(-c2nc(NC3CCC(F)(F)CC3)cc(N3CC(F)(F)OC(F)(F)C3)n2)n1] | 450.381 |
| IN11039-026-P1 | 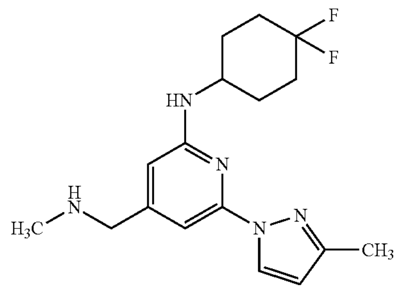 | 335.395 |
| IN10966-095-P1 | 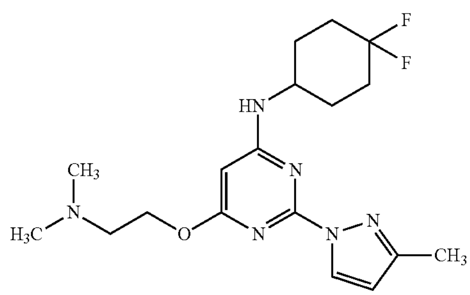 | 380.435 |
| IN11053-021-P1 | 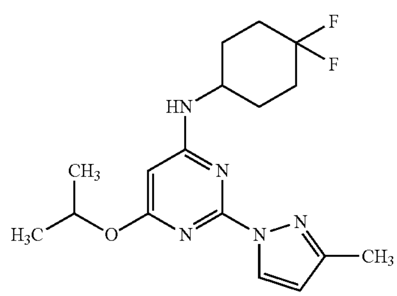 [SMILES: Cc1ccn(-c2nc(NC3CCC(F)(F)CC3)cc(OC(C)C)n2)n1] | 351.394 |
| IN11054-012-P1 | 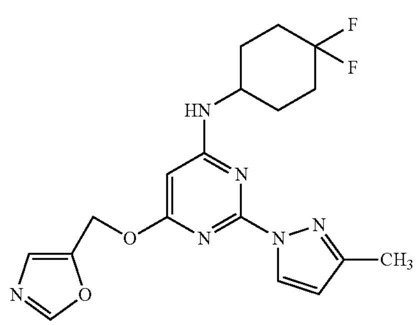 [SMILES: Cc1ccn(-c2nc(NC3CCC(F)(F)CC3)cc(OCc3cnco3)n2)n1] | 390.387 |

TABLE 2-continued
| Compound Ref | Structure | m/z data |
|---|---|---|
| IN11053-024-P1 | 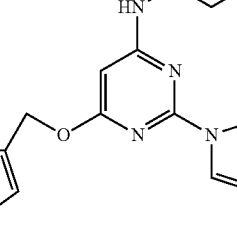 | 390.387 |
| IN11053-022-P1 | 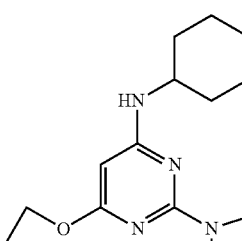 | 390.387 |
| IN11067-004-P1 | 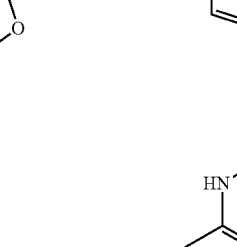 | 463.521 |
| IN10966-093-P1 | 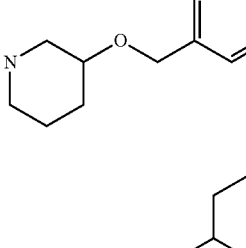 | 367.394 |
| IN11063-005-P1 | 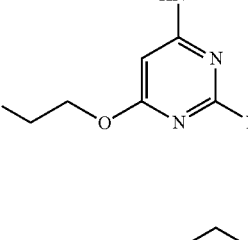 | 337.368 |

TABLE 2-continued

| Compound Ref | Structure | m/z data |
|---|---|---|
| IN11063-006-P1 | 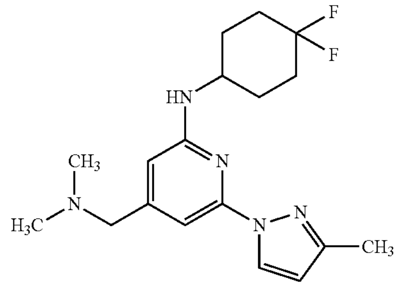 | 349.421 |
| IN11030-035-P1 | 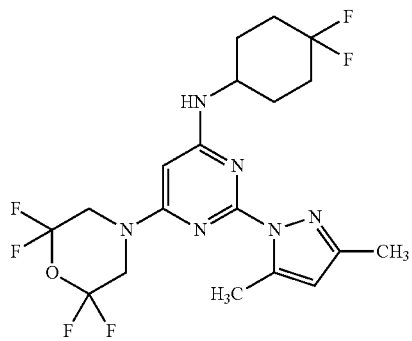 [SMILES: Cc1cc(C)n(-c2nc(NC3CCC(F)(F)CC3)cc(N3CC(F)(F)OC(F)(F)C3)n2)n1] | 464.408 |
| IN11055-016-P1 | 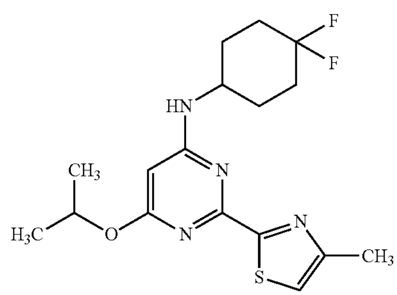 [SMILES: Cc1csc(-c2nc(NC3CCC(F)(F)CC3)cc(OC(C)C)n2)n1] | 368.445 |
| IN11055-015-P1 | 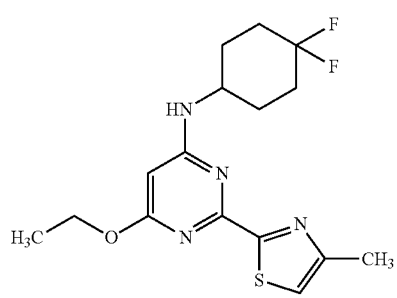 [SMILES: CCOc1cc(NC2CCC(F)(F)CC2)nc(-c2nc(C)cs2)n1] | 354.418 |
| IN10991-091-P1 | 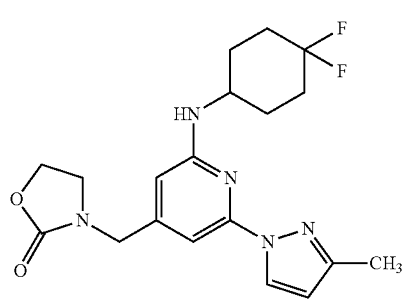 [SMILES: Cc1ccn(-c2cc(CN3CCOC3=O)cc(NC3CCC(F)(F)CC3)n2)n1] | 391.415 |

TABLE 2-continued

| Compound Ref | Structure | m/z data |
|---|---|---|
| IN11039-023-P1 | 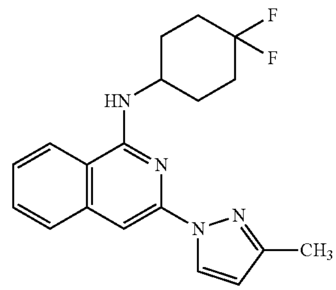 [SMILES: Cc1ccn(-c2cc3ccccc3c(NC3CCC(F)(F)CC3)n2)n1] | 342.386 |
| IN11054-011-P1 | 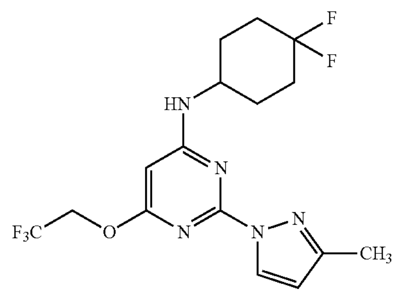 [SMILES: Cc1ccn(-c2nc(NC3CCC(F)(F)CC3)cc(OCC(F)(F)F)n2)n1] | 391.339 |
| IN11053-013-P1 | 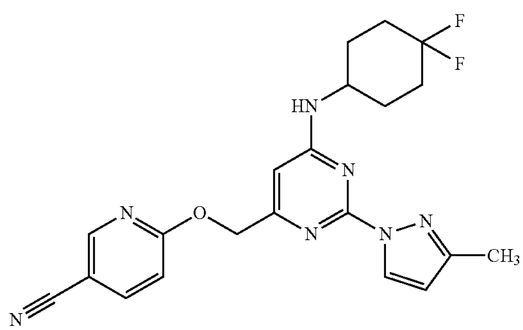 [SMILES: Cc1ccn(-c2nc(COc3ccc(C#N)cn3)cc(NC3CCC(F)(F)CC3)n2)n1] | 425.434 |
| IN11053-005-P1 | 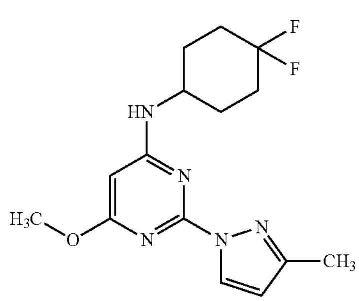 | 323.341 |
| IN11067-003-P1 | 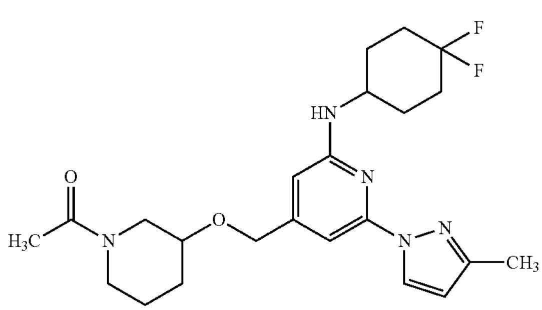 [SMILES: CC(=O)N1CCCC(OCc2cc(NC3CCC(F)(F)CC3)nc(-n3ccc(C)n3)c2)C1] | 447.521 |

TABLE 2-continued

| Compound Ref | Structure | m/z data |
|---|---|---|
| IN11053-007-P1 | 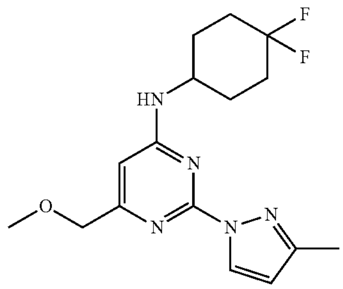 | 337.368 |
| IN10966-083-P1 | 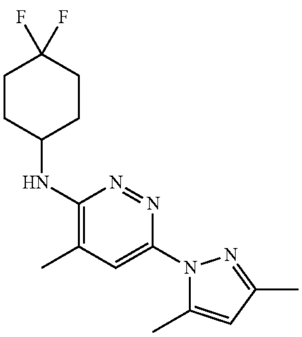 [SMILES: Cc1cc(C)n(-c2cc(C)c(NC3CCC(F)(F)CC3)nn2)n1] | 321.368 |
| IN11039-019-P1 | 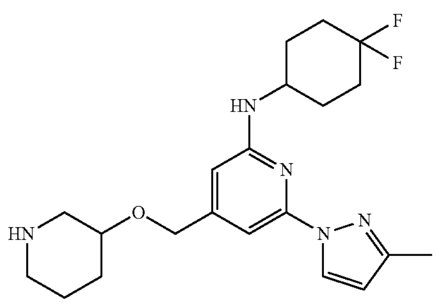 [SMILES: Cc1ccn(-c2cc(COC3CCCNC3)cc(NC3CCC(F)(F)CC3)n2)n1] | 405.485 |
| IN11039-017-P1 | 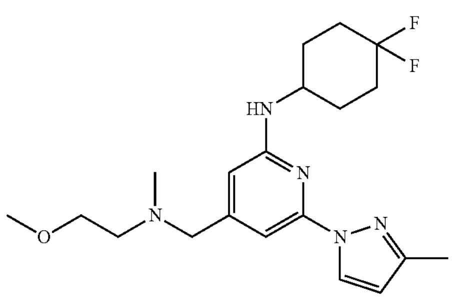 | 393.474 |
| IN11030-032-P1 | 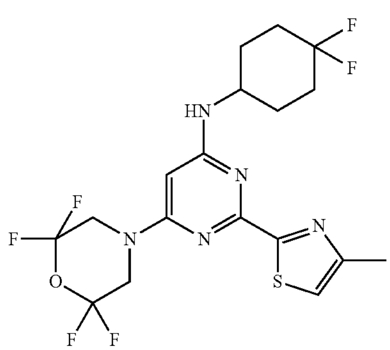 [SMILES: Cc1csc(-c2nc(NC3CCC(F)(F)CC3)cc(N3CC(F)(F)OC(F)(F)C3)n2)n1] | 467.432 |

TABLE 2-continued

| Compound Ref | Structure | m/z data |
|---|---|---|
| IN11039-009-P1 | 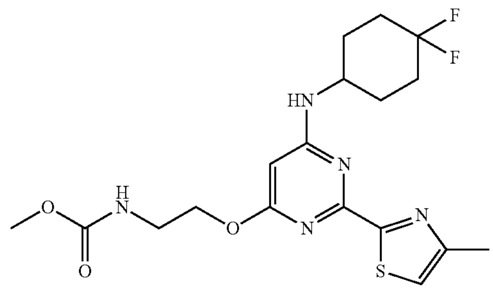 | 427.469 |
| IN10965-091-P1 | 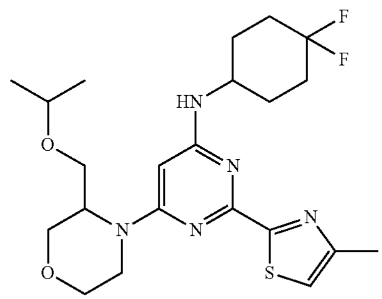 [SMILES: Cc1csc(-c2nc(NC3CCC(F)(F)CC3)cc(N3CCOCC3COC(C)C)n2)n1] | 467.576 |
| IN11054-005-P1 | 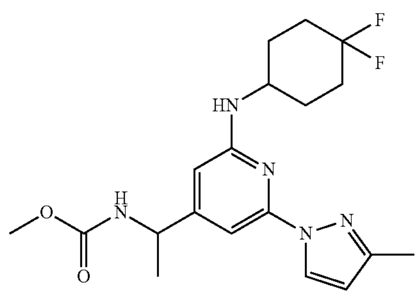 | 393.431 |
| IN11054-003-P1 | 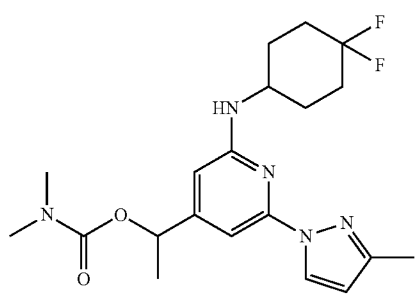 | 407.458 |
| IN10984-079-P1 | 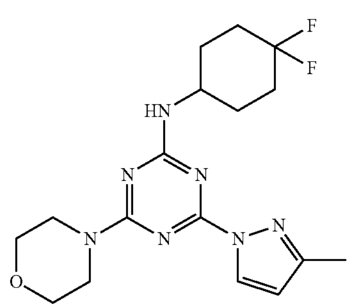 [SMILES: Cc1ccn(-c2nc(NC3CCC(F)(F)CC3)nc(N3CCOCC3)n2)n1] | 379.408 |

TABLE 2-continued

| Compound Ref | Structure | m/z data |
|---|---|---|
| IN11030-023-P1 | 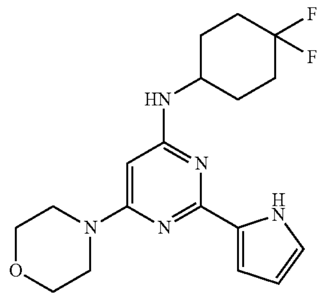 [SMILES: FC1(F)CCC(Nc2cc(N3CCOCC3)nc(-c3ccc[nH]3)n2)CC1] | 363.405 |
| IN11039-006-P1 | 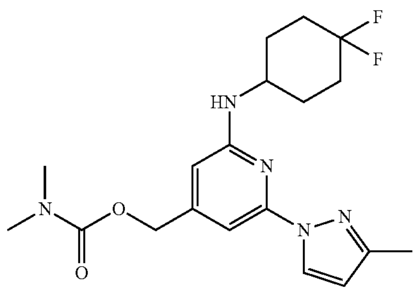 | 393.431 |
| IN10965-089-P1 | 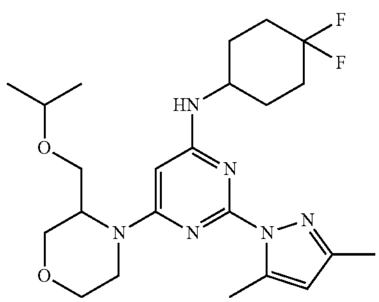 [SMILES: Cc1cc(C)n(-c2nc(NC3CCC(F)(F)CC3)cc(N3CCOCC3COC(C)C)n2)n1] | 464.552 |
| IN10963-077-P1 | 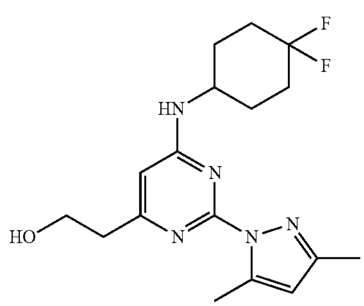 [SMILES: Cc1cc(C)n(-c2nc(CCO)cc(NC3CCC(F)(F)CC3)n2)n1] | 351.394 |
| IN10971-088-P1 | 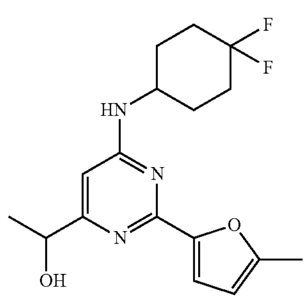 [SMILES: Cc1ccc(-c2nc(NC3CCC(F)(F)CC3)cc(C(C)O)n2)o1] | 337.364 |

TABLE 2-continued

| Compound Ref | Structure | m/z data |
|---|---|---|
| IN10991-065-P1 | 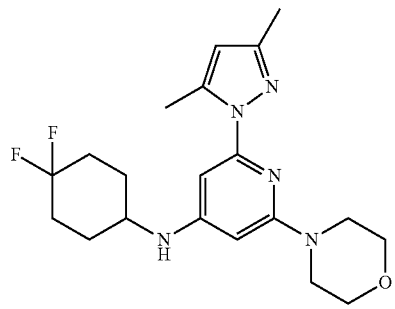 [SMILES: Cc1cc(C)n(-c2cc(NC3CCC(F)(F)CC3)cc(N3CCOCC3)n2)n1] | 391.458 |
| IN10991-067-P1 | 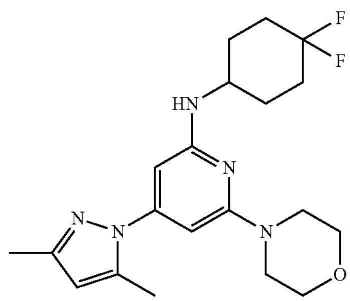 [SMILES: Cc1cc(C)n(-c2cc(NC3CCC(F)(F)CC3)nc(N3CCOCC3)c2)n1] | 391.458 |
| IN11030-013-P1 | 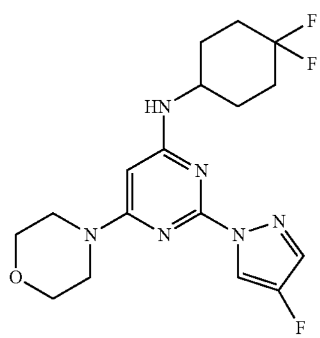 [SMILES: Fc1cnn(-c2nc(NC3CCC(F)(F)CC3)cc(N3CCOCC3)n2)c1] | 382.383 |
| IN10967-061-P1 | 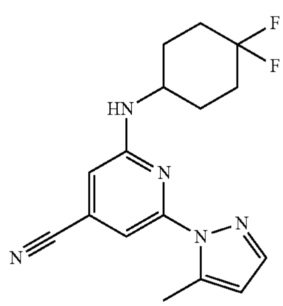 [SMILES: Cc1ccnn1-c1cc(C#N)cc(NC2CCC(F)(F)CC2)n1] | 317.336 |
| IN10966-057-P2 | 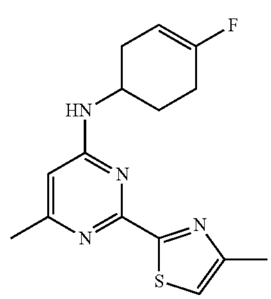 | 304.386 |

TABLE 2-continued

| Compound Ref | Structure | m/z data |
|---|---|---|
| IN10967-063-P1 | 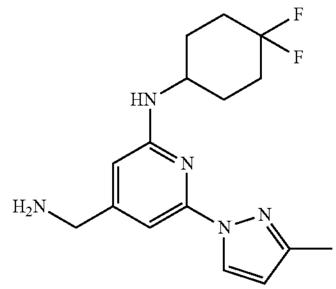 [SMILES: Cc1ccn(-c2cc(CN)cc(NC3CCC(F)(F)CC3)n2)n1] | 321.368 |
| IN10963-068-P1 | 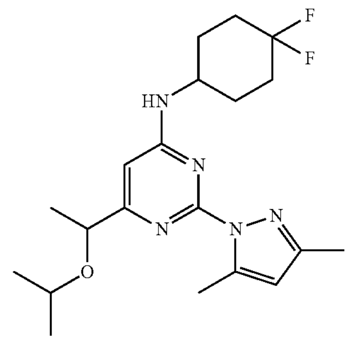 [SMILES: Cc1cc(C)n(-c2nc(NC3CCC(F)(F)CC3)cc(C(C)OC(C)C)n2)n1] | 393.474 |
| IN10973-099-P1 | 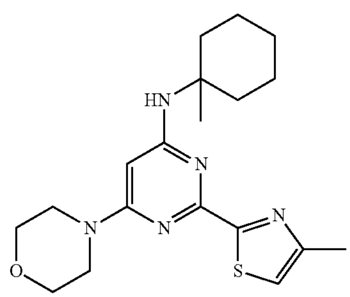 [SMILES: Cc1csc(-c2nc(NC3(C)CCCCC3)cc(N3CCOCC3)n2)n1] | 373.516 |
| IN10973-098-P1 | 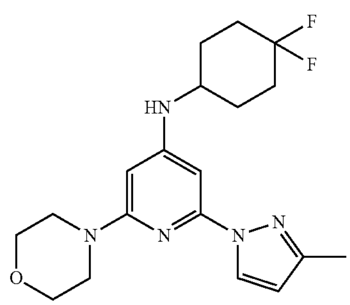 [SMILES: Cc1ccn(-c2cc(NC3CCC(F)(F)CC3)cc(N3CCOCC3)n2)n1] | 377.432 |
| IN10971-081-P1 | 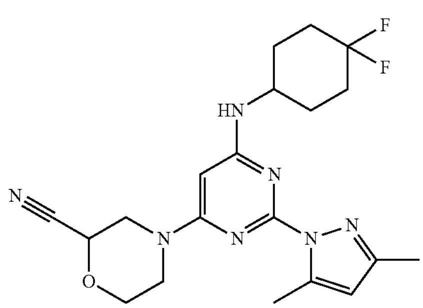 [SMILES: Cc1cc(C)n(-c2nc(NC3CCC(F)(F)CC3)cc(N3CCOC(C#N)C3)n2)n1] | 417.456 |

TABLE 2-continued

| Compound Ref | Structure | m/z data |
|---|---|---|
| IN10971-077-P1 | 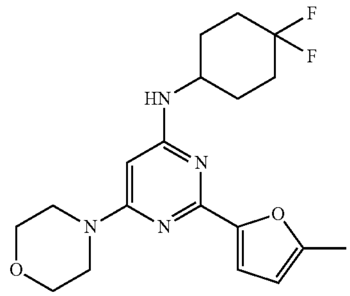 [SMILES: Cc1ccc(-c2nc(NC3CCC(F)(F)CC3)cc(N3CCOCC3)n2)o1] | 378.416 |
| IN10987-055-P1 | 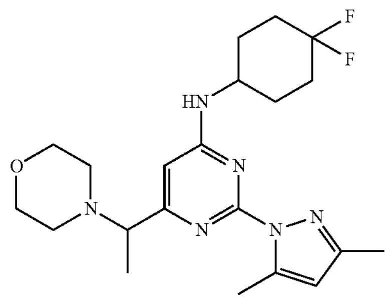 [SMILES: Cc1cc(C)n(-c2nc(NC3CCC(F)(F)CC3)cc(C(C)N3CCOCC3)n2)n1] | 420.499 |
| IN10987-056-P1 | 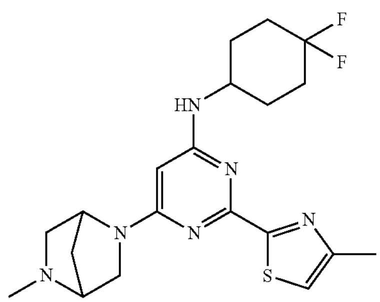 | 420.522 |
| IN10964-046-P1 | 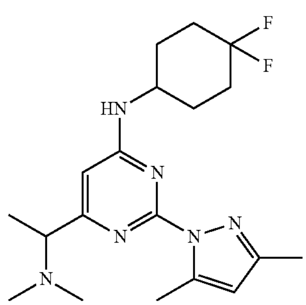 [SMILES: Cc1cc(C)n(-c2nc(NC3CCC(F)(F)CC3)cc(C(C)N(C)C)n2)n1] | 378.463 |
| IN10991-044-P1 | 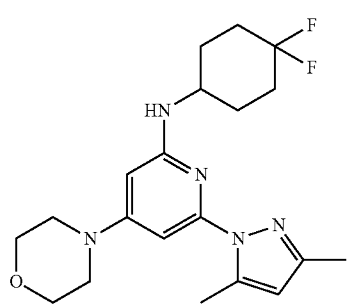 [SMILES: Cc1cc(C)n(-c2cc(N3CCOCC3)cc(NC3CCC(F)(F)CC3)n2)n1] | 391.458 |

TABLE 2-continued

| Compound Ref | Structure | m/z data |
|---|---|---|
| IN10973-069-P1 | 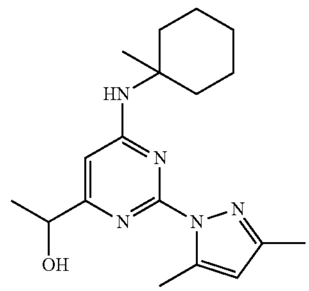 [SMILES: Cc1cc(C)n(-c2nc(NC3(C)CCCCC3)cc(C(C)O)n2)n1] | 315.413 |
| IN10973-083-P1 | 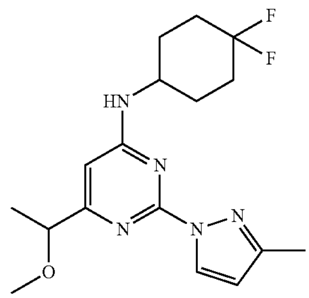 [SMILES: COC(C)c1cc(NC2CCC(F)(F)CC2)nc(-n2ccc(C)n2)n1] | 351.394 |
| IN10987-050-P1 | 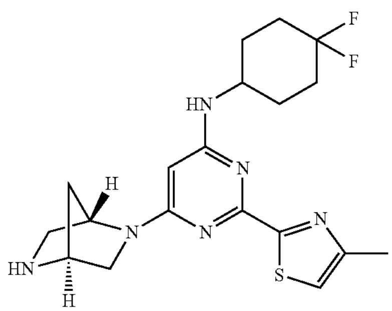 [SMILES: Cc1csc(-c2nc(NC3CCC(F)(F)CC3)cc(N3C[C@@H]4C[C@H]3CN4)n2)n1] | 406.496 |
| IN10973-060-P1 | 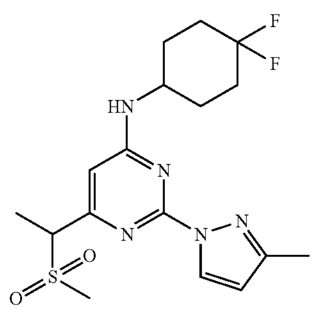 [SMILES: Cc1ccn(-c2nc(NC3CCC(F)(F)CC3)cc(C(C)S(C)(=O)=O)n2)n1] | 399.459 |
| IN10971-060-P1 | 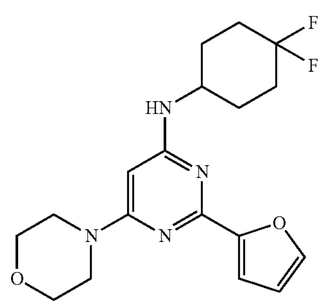 [SMILES: FC1(F)CCC(Nc2cc(N3CCOCC3)nc(-c3ccco3)n2)CC1] | 364.39 |

TABLE 2-continued

| Compound Ref | Structure | m/z data |
|---|---|---|
| IN10971-059-P1 | 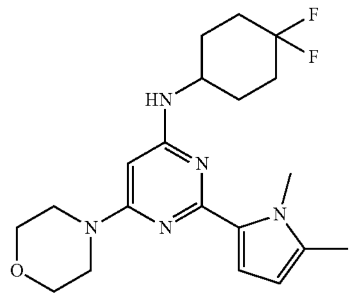 | 391.458 |
| IN10987-039-P1 | 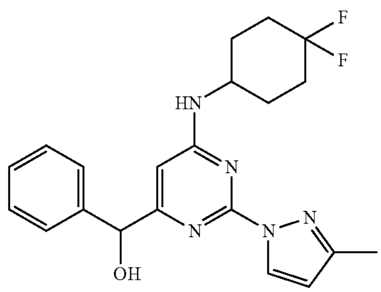 [SMILES: Cc1ccn(-c2nc(NC3CCC(F)(F)CC3)cc(C(O)c3ccccc3)n2)n1] | 399.437 |
| IN10984-043-P1 | 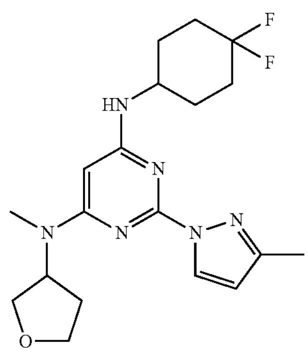 | 392.446 |
| IN10963-049-P1 | 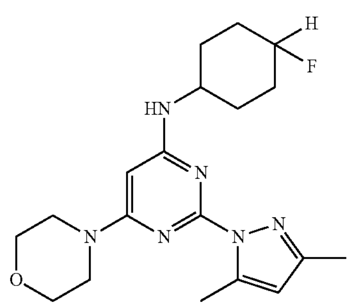 [SMILES: Cc1cc(C)n(-c2nc(NC3CCC(F)CC3)cc(N3CCOCC3)n2)n1] | 374.456 |
| IN10964-041-P1 | 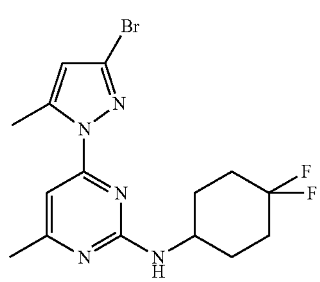 [SMILES: Cc1cc(-n2nc(Br)cc2C)nc(NC2CCC(F)(F)CC2)n1] | 386.238 |

TABLE 2-continued

| Compound Ref | Structure | m/z data |
|---|---|---|
| IN10973-053-P1 | 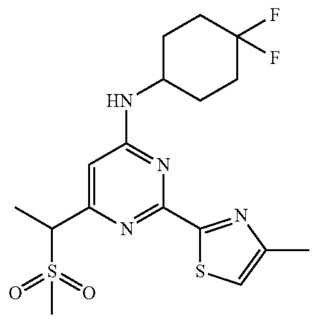 [SMILES: Cc1csc(-c2nc(NC3CCC(F)(F)CC3)cc(C(C)S(C)(=O)=O)n2)n1] | 416.509 |
| IN10966-028-P1 | 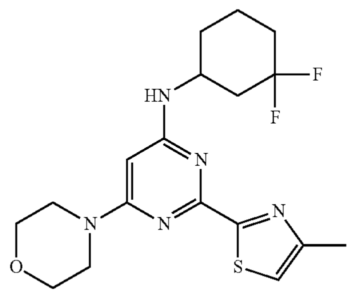 [SMILES: Cc1csc(-c2nc(NC3CCCC(F)(F)C3)cc(N3CCOCC3)n2)n1] | 395.47 |
| IN10987-030-P1 | 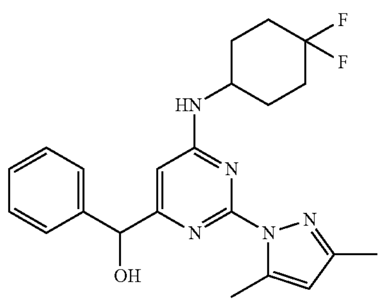 [SMILES: Cc1cc(C)n(-c2nc(NC3CCC(F)(F)CC3)cc(C(O)c3ccccc3)n2)n1] | 413.464 |
| IN10973-028-P1 | 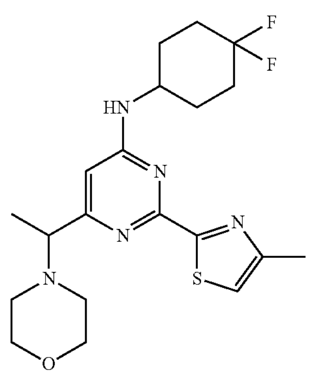 [SMILES: Cc1csc(-c2nc(NC3CCC(F)(F)CC3)cc(C(C)N3CCOCC3)n2)n1] | 423.523 |
| IN10973-041-P1 | 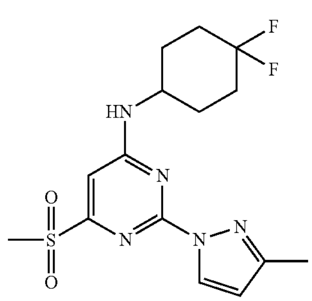 | 371.405 |

TABLE 2-continued

| Compound Ref | Structure | m/z data |
|---|---|---|
| IN10973-038-P1 | 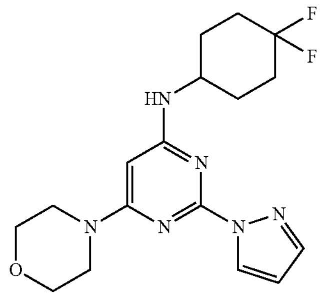 [SMILES: FC1(F)CCC(Nc2cc(N3CCOCC3)nc(-n3cccn3)n2)CC1] | 364.393 |
| IN10991-021-P1 | 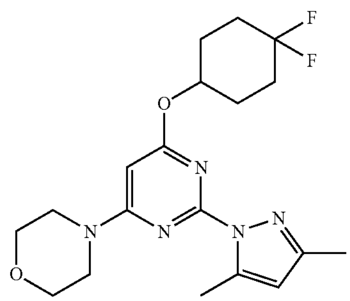 [SMILES: Cc1cc(C)n(-c2nc(OC3CCC(F)(F)CC3)cc(N3CCOCC3)n2)n1] | 393.431 |
| IN10984-022-P1 | 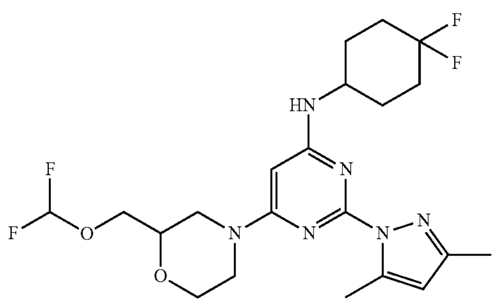 [SMILES: Cc1cc(C)n(-c2nc(NC3CCC(F)(F)CC3)cc(N3CCOC(COC(F)F)C3)n2)n1] | 472.48 |
| IN10963-024-P1 | 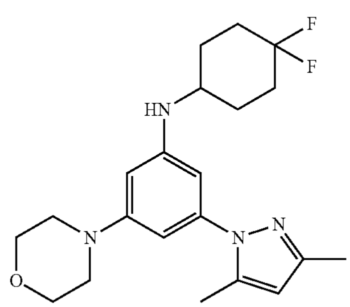 [SMILES: Cc1cc(C)n(-c2cc(NC3CCC(F)(F)CC3)cc(N3CCOCC3)c2)n1] | 390.47 |
| IN10971-033-P1 | 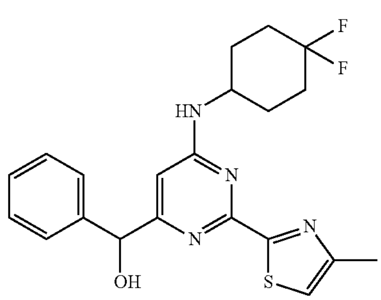 [SMILES: Cc1csc(-c2nc(NC3CCC(F)(F)CC3)cc(C(O)c3ccccc3)n2)n1] | 416.487 |

TABLE 2-continued

| Compound Ref | Structure | m/z data |
|---|---|---|
| IN10973-025-P1 | 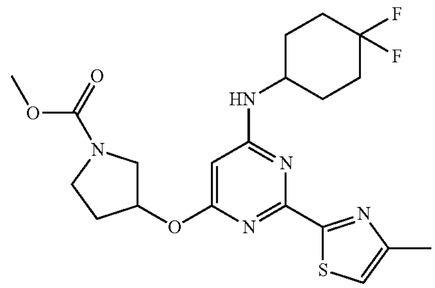 | 453.506 |
| IN10966-011-P1 | 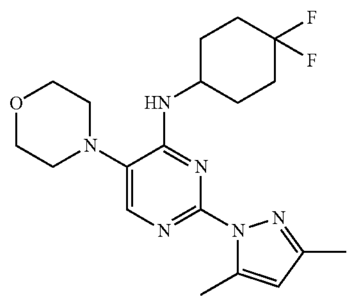 [SMILES: Cc1cc(C)n(-c2ncc(N3CCOCC3)c(NC3CCC(F)(F)CC3)n2)n1] | 392.446 |
| IN10964-008-P1 | 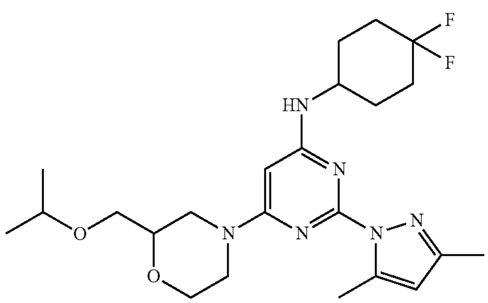 [SMILES: Cc1cc(C)n(-c2nc(NC3CCC(F)(F)CC3)cc(N3CCOC(COC(C)C)C3)n2)n1] | 464.552 |
| IN10964-007-P1 | 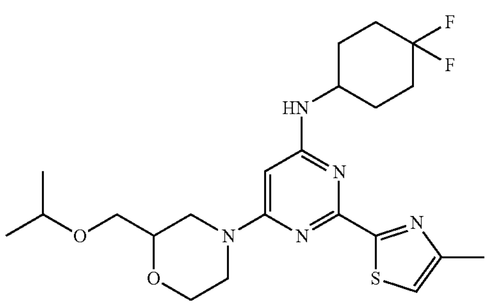 [SMILES: Cc1csc(-c2nc(NC3CCC(F)(F)CC3)cc(N3CCOC(COC(C)C)C3)n2)n1] | 467.576 |
| IN10876-092-P1 | 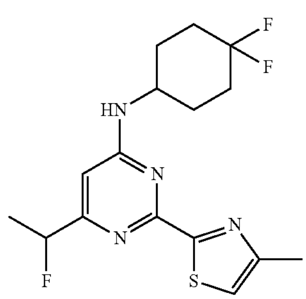 [SMILES: Cc1csc(-c2nc(NC3CCC(F)(F)CC3)cc(C(C)F)n2)n1] | 356.409 |

TABLE 2-continued

| Compound Ref | Structure | m/z data |
|---|---|---|
| IN10881-099-P1 | 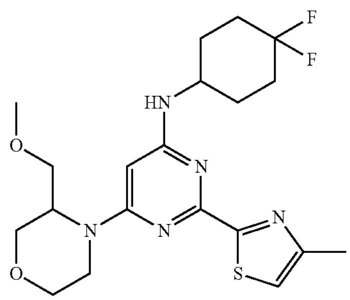 [SMILES: COCC1COCCN1c1cc(NC2CCC(F)(F)CC2)nc(-c2nc(C)cs2)n1] | 439.522 |
| IN10881-098-P1 | 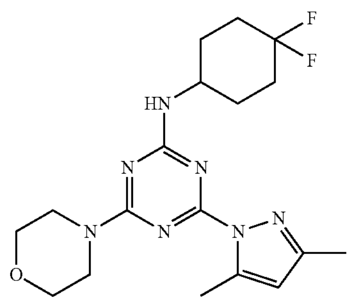 [SMILES: Cc1cc(C)n(-c2nc(NC3CCC(F)(F)CC3)nc(N3CCOCC3)n2)n1] | 393.434 |
| IN10881-092-P1 | 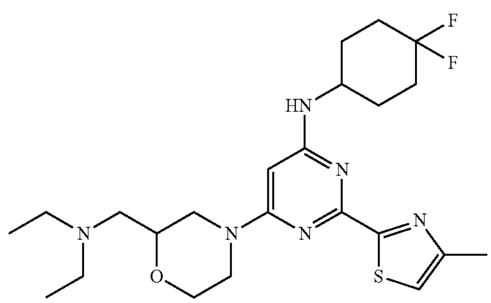 [SMILES: CCN(CC)CC1CN(c2cc(NC3CCC(F)(F)CC3)nc(-c3nc(C)cs3)n2)CCO1] | 480.617 |
| IN10876-082-P1 | 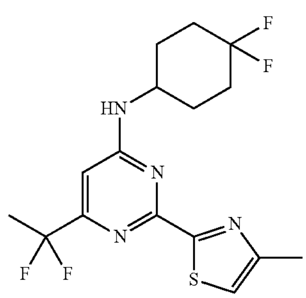 [SMILES: Cc1csc(-c2nc(NC3CCC(F)(F)CC3)cc(C(C)(F)F)n2)n1] | 374.4 |
| IN10876-080-P1 | 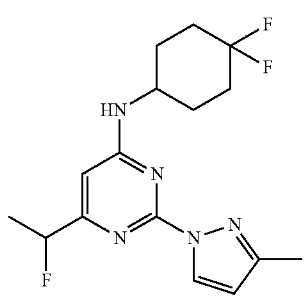 [SMILES: Cc1ccn(-c2nc(NC3CCC(F)(F)CC3)cc(C(C)F)n2)n1] | 339.359 |

TABLE 2-continued
| Compound Ref | Structure | m/z data |
|---|---|---|
| IN10973-008-P1 | 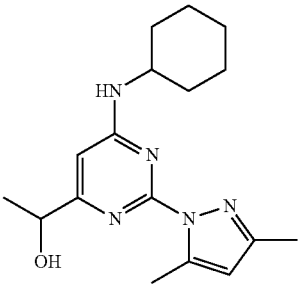 [SMILES: Cc1cc(C)n(-c2nc(NC3CCCCC3)cc(C(C)O)n2)n1] | 315.413 |
| IN10973-004-P1 | 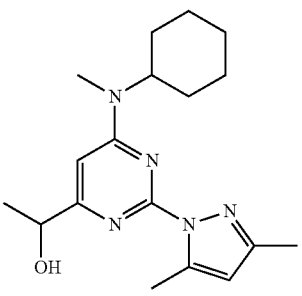 [SMILES: Cc1cc(C)n(-c2nc(C(C)O)cc(N(C)C3CCCCC3)n2)n1] | 329.44 |
| IN10973-005-P1 | 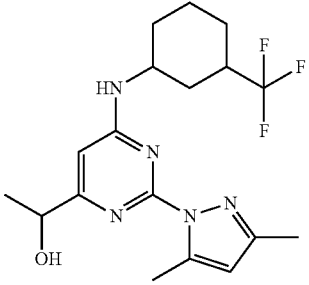 [SMILES: Cc1cc(C)n(-c2nc(NC3CCCC(C(F)(F)F)C3)cc(C(C)O)n2)n1] | 383.411 |
| IN10880-093-P1 | 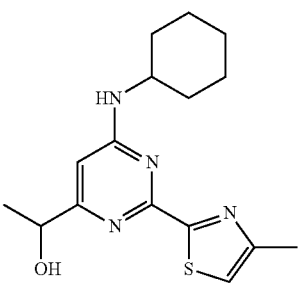 [SMILES: Cc1csc(-c2nc(NC3CCCCC3)cc(C(C)O)n2)n1] | 318.437 |
| IN10881-090-P1 | 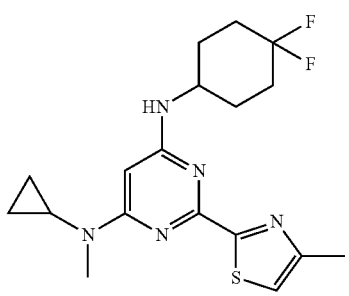 [SMILES: Cc1csc(-c2nc(NC3CCC(F)(F)CC3)cc(N(C)C3CC3)n2)n1] | 379.471 |

TABLE 2-continued

| Compound Ref | Structure | m/z data |
| --- | --- | --- |
| IN10882-083-P1 | 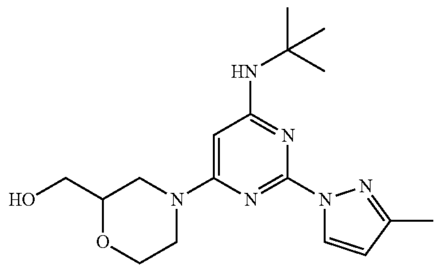 | 346.427 |
| IN10876-069-P1 | 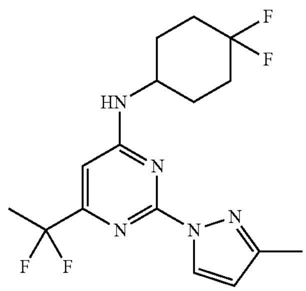 [SMILES: Cc1ccn(-c2nc(NC3CCC(F)(F)CC3)cc(C(C)(F)F)n2)n1] | 357.349 |
| IN10882-072-P1 | 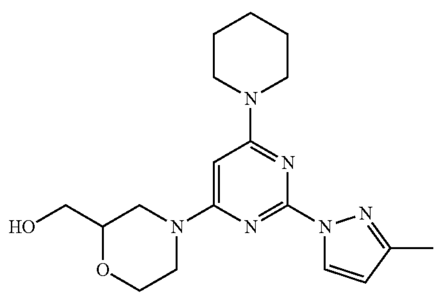 [SMILES: Cc1ccn(-c2nc(N3CCCCC3)cc(N3CCOC(CO)C3)n2)n1] | 358.438 |
| IN10880-085-P1 | 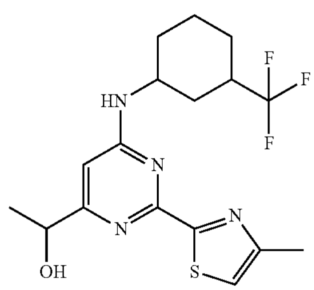 [SMILES: Cc1csc(-c2nc(NC3CCCC(C(F)(F)F)C3)cc(C(C)O)n2)n1] | 386.435 |
| IN10880-084-P1 | 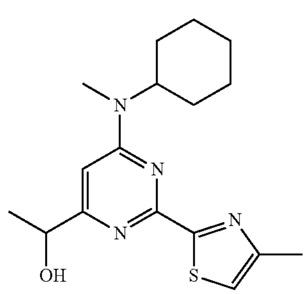 [SMILES: Cc1csc(-c2nc(C(C)O)cc(N(C)C3CCCCC3)n2)n1] | 332.464 |

TABLE 2-continued
| Compound Ref | Structure | m/z data |
|---|---|---|
| IN10882-068-P1 | 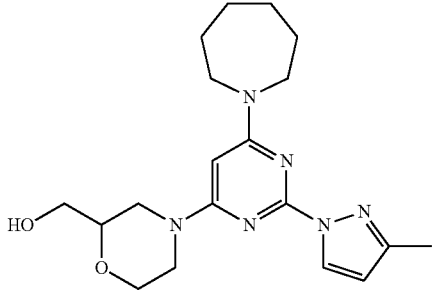 [SMILES: Cc1ccn(-c2nc(N3CCCCCC3)cc(N3CCOC(CO)C3)n2)n1] | 372.465 |
| IN10880-065-P1 | 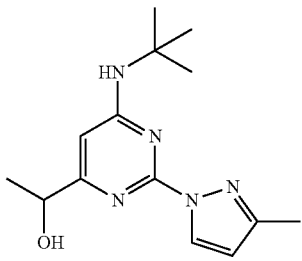 [SMILES: Cc1ccn(-c2nc(NC(C)(C)C)cc(C(C)O)n2)n1] | 275.349 |
| IN10880-062-P1 | 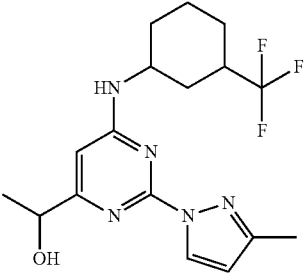 [SMILES: Cc1ccn(-c2nc(NC3CCCC(C(F)(F)F)C3)cc(C(C)O)n2)n1] | 369.385 |
| IN10876-061-P1 | 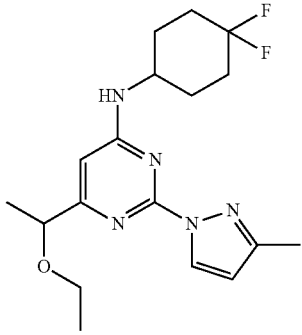 [SMILES: CCOC(C)c1cc(NC2CCC(F)(F)CC2)nc(-n2ccc(C)n2)n1] | 365.421 |
| IN10881-060-P1 | 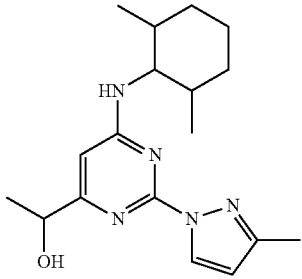 [SMILES: Cc1ccn(-c2nc(NC3C(C)CCCC3C)cc(C(C)O)n2)n1] | 329.44 |

TABLE 2-continued

| Compound Ref | Structure | m/z data |
|---|---|---|
| IN10881-059-P1 | 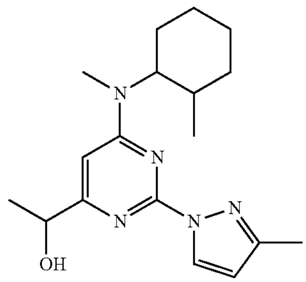 [SMILES: Cc1ccn(-c2nc(C(C)O)cc(N(C)C3CCCCC3C)n2)n1] | 329.44 |
| IN10881-058-P1 | 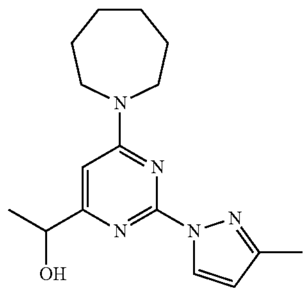 [SMILES: Cc1ccn(-c2nc(C(C)O)cc(N3CCCCCC3)n2)n1] | 301.387 |
| IN10881-054-P1 | 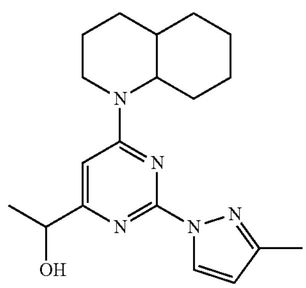 [SMILES: Cc1ccn(-c2nc(C(C)O)cc(N3CCCC4CCCCC43)n2)n1] | 341.451 |
| IN10880-059-P1 | 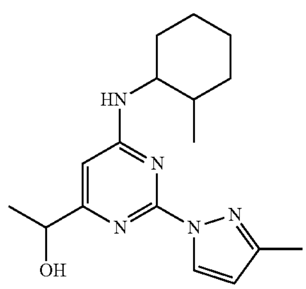 [SMILES: Cc1ccn(-c2nc(NC3CCCCC3C)cc(C(C)O)n2)n1] | 315.413 |
| IN10880-058-P1 | 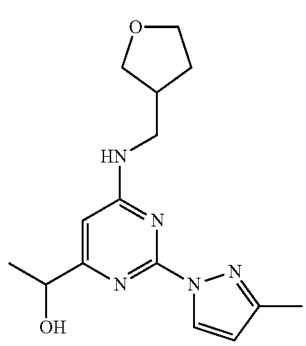 [SMILES: Cc1ccn(-c2nc(NCC3CCOC3)cc(C(C)O)n2)n1] | 303.36 |

TABLE 2-continued

| Compound Ref | Structure | m/z data |
|---|---|---|
| IN10880-064-P1 | 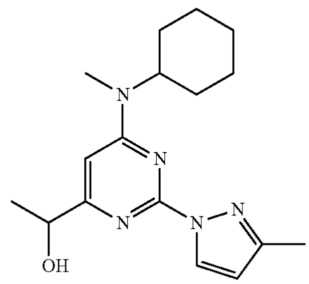 [SMILES: Cc1ccn(-c2nc(C(C)O)cc(N(C)C3CCCCC3)n2)n1] | 315.413 |
| IN10864-066-P1 | 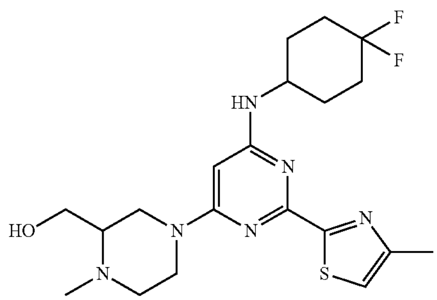 [SMILES: Cc1csc(-c2nc(NC3CCC(F)(F)CC3)cc(N3CCN(C)C(CO)C3)n2)n1] | 438.538 |
| IN10882-055-P1 | 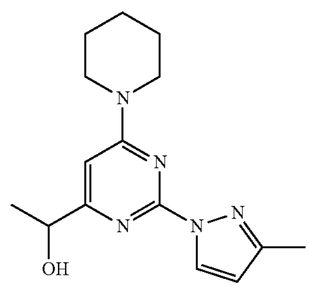 [SMILES: Cc1ccn(-c2nc(C(C)O)cc(N3CCCCC3)n2)n1] | 287.36 |
| IN10882-057-P1 | 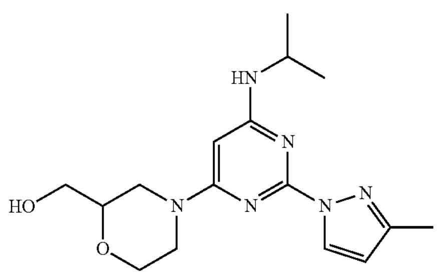 [SMILES: Cc1ccn(-c2nc(NC(C)C)cc(N3CCOC(CO)C3)n2)n1] | 332.401 |
| IN10864-060-P1 | 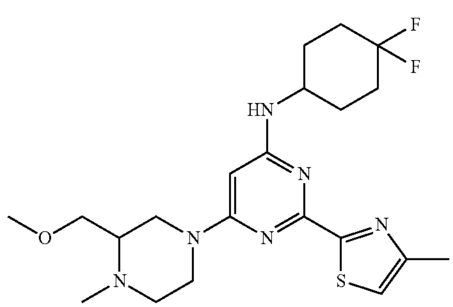 | 452.564 |

TABLE 2-continued

| Compound Ref | Structure | m/z data |
|---|---|---|
| IN10880-056-P1 | 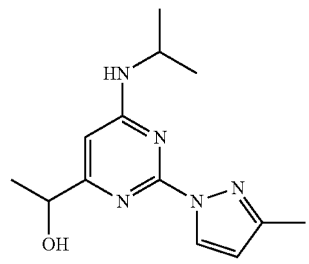 [SMILES: Cc1ccn(-c2nc(NC(C)C)cc(C(C)O)n2)n1] | 261.323 |
| IN10876-041-P2 | 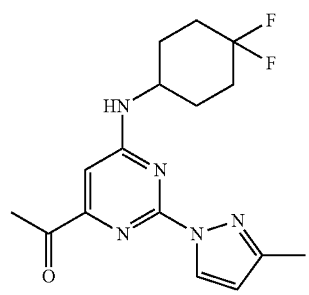 [SMILES: CC(=O)c1cc(NC2CCC(F)(F)CC2)nc(-n2ccc(C)n2)n1] | 335.352 |
| IN10880-055-P1 | 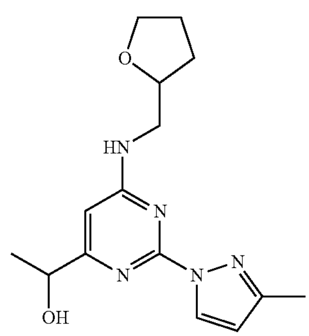 [SMILES: Cc1ccn(-c2nc(NCC3CCCO3)cc(C(C)O)n2)n1] | 303.36 |
| IN10882-040-P1 | 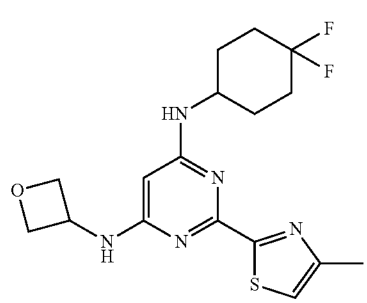 [SMILES: Cc1csc(-c2nc(NC3CCC(F)(F)CC3)cc(NC3COC3)n2)n1] | 381.443 |
| IN10882-043-P1 | 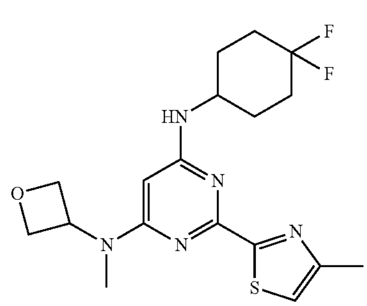 [SMILES: Cc1csc(-c2nc(NC3CCC(F)(F)CC3)cc(N(C)C3COC3)n2)n1] | 395.47 |

TABLE 2-continued

| Compound Ref | Structure | m/z data |
|---|---|---|
| IN10876-051-P1 | 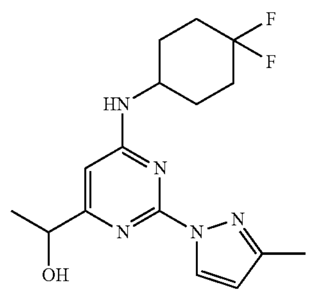 [SMILES: Cc1ccn(-c2nc(NC3CCC(F)(F)CC3)cc(C(C)O)n2)n1] | 337.368 |
| IN10881-040-P1 | 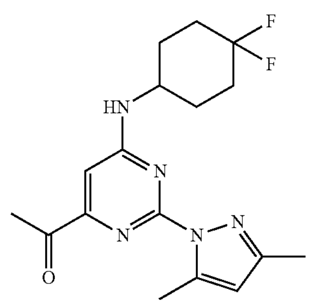 [SMILES: CC(=O)c1cc(NC2CCC(F)(F)CC2)nc(-n2nc(C)cc2C)n1] | 349.378 |
| IN10880-029-P1 | 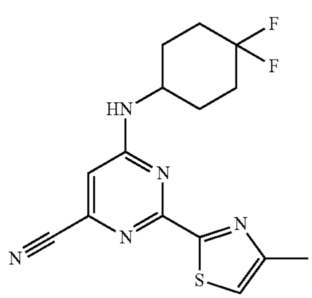 [SMILES: Cc1csc(-c2nc(C#N)cc(NC3CCC(F)(F)CC3)n2)n1] | 335.375 |
| IN10864-043-P1 | 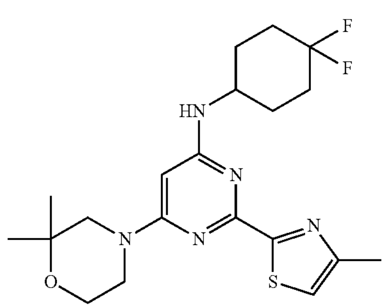 | 423.523 |
| IN10881-027-P1 | 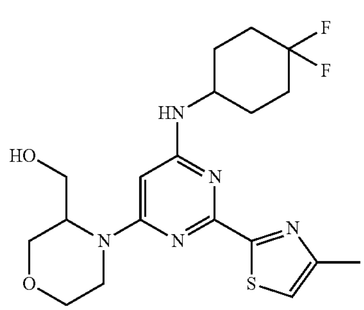 [SMILES: Cc1csc(-c2nc(NC3CCC(F)(F)CC3)cc(N3CCOCC3CO)n2)n1] | 425.496 |

TABLE 2-continued

| Compound Ref | Structure | m/z data |
|---|---|---|
| IN10880-033-P1 | 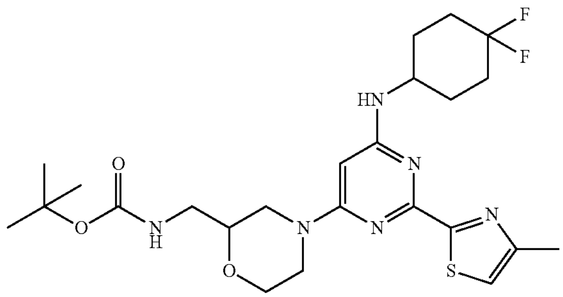 [SMILES: Cc1csc(-c2nc(NC3CCC(F)(F)CC3)cc(N3CCOC(CNC(=O)OC(C)(C)C)C3)n2)n1] | 524.627 |
| IN10880-035-P1 | 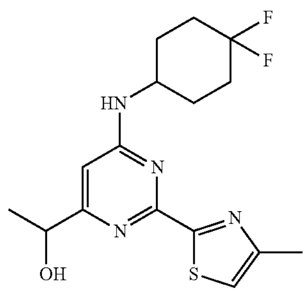 [SMILES: Cc1csc(-c2nc(NC3CCC(F)(F)CC3)cc(C(C)O)n2)n1] | 354.418 |
| IN10881-025-P1 | 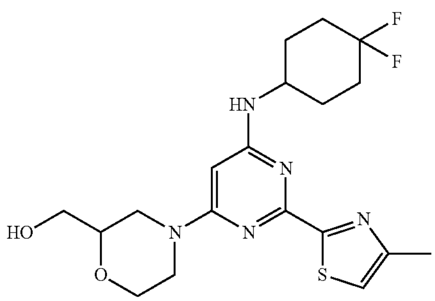 [SMILES: Cc1csc(-c2nc(NC3CCC(F)(F)CC3)cc(N3CCOC(CO)C3)n2)n1] | 425.496 |
| IN10880-032-P1 | 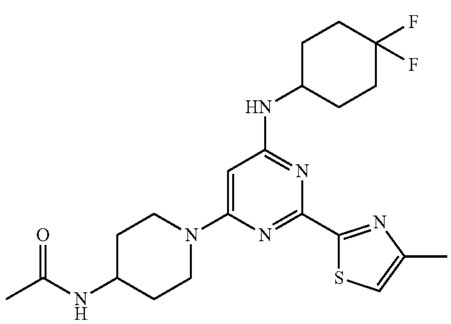 [SMILES: CC(=O)NC1CCN(c2cc(NC3CCC(F)(F)CC3)nc(-c3nc(C)cs3)n2)CC1] | 450.548 |
| IN10864-034.P1 | 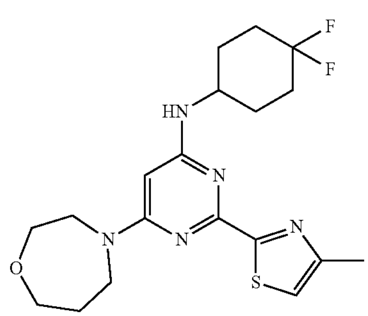 [SMILES: Cc1csc(-c2nc(NC3CCC(F)(F)CC3)cc(N3CCCOCC3)n2)n1] | 409.497 |

TABLE 2-continued
| Compound Ref | Structure | m/z data |
|---|---|---|
| IN10882-020-P1 | 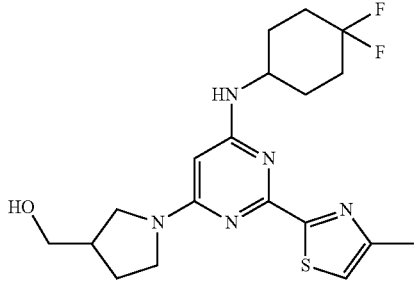 [SMILES: Cc1csc(-c2nc(NC3CCC(F)(F)CC3)cc(N3CCC(CO)C3)n2)n1] | 409.497 |
| IN10881-023-P2 | 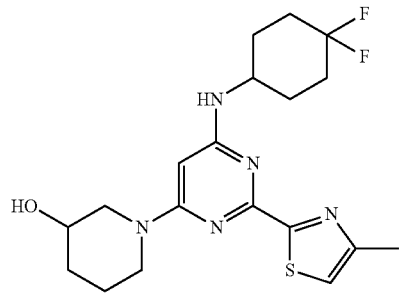 [SMILES: Cc1csc(-c2nc(NC3CCC(F)(F)CC3)cc(N3CCCC(O)C3)n2)n1] | 409.497 |
| IN10864-33.P1 | 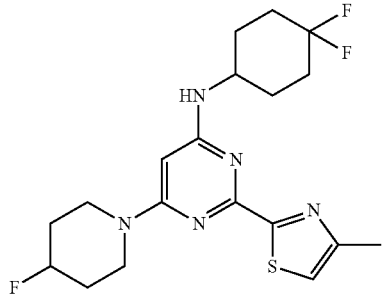 [SMILES: Cc1csc(-c2nc(NC3CCC(F)(F)CC3)cc(N3CCC(F)CC3)n2)n1] | 411.488 |
| IN10880-018-P1 | 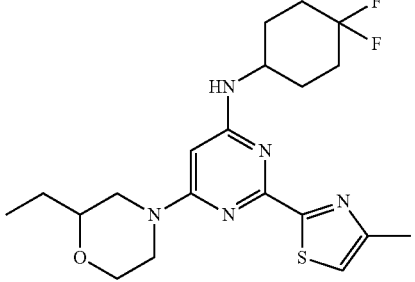 | 423.523 |
| IN10882-014-P1 | 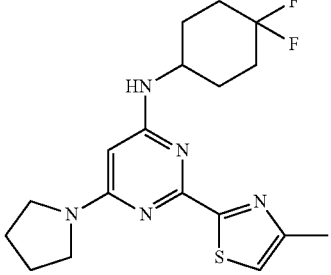 | 379.471 |

TABLE 2-continued

| Compound Ref | Structure | m/z data |
|---|---|---|
| IN10876-013-P1 | 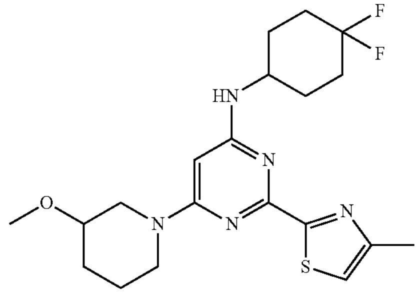 [SMILES: CCC1CN(c2cc(NC3CCC(F)(F)CC3)nc(-c3nc(C)cs3)n2)CCO1] | 423.523 |
| IN10881-020.P1 | 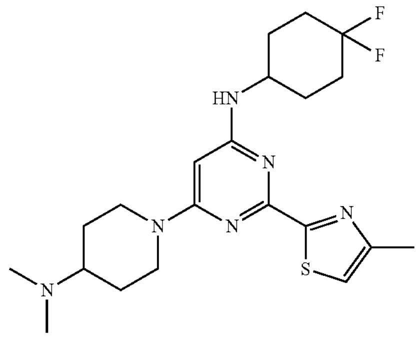 | 436.565 |
| IN10881-021.P1 | 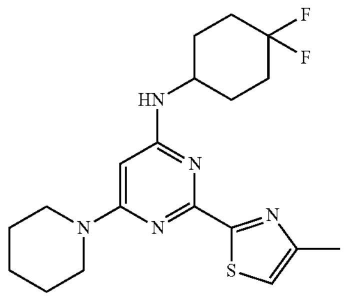 [SMILES: Cc1csc(-c2nc(NC3CCC(F)(F)CC3)cc(N3CCCCC3)n2)n1] | 393.497 |
| IN10864-031-P1 | 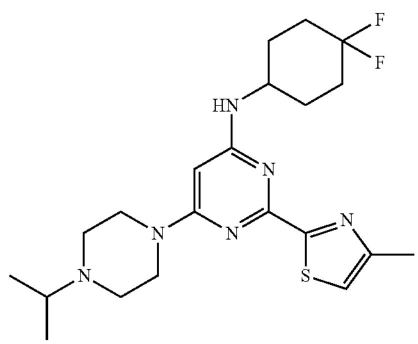 [SMILES: Cc1csc(-c2nc(NC3CCC(F)(F)CC3)cc(N3CCN(C(C)C)CC3)n2)n1] | 436.565 |
| IN10880-014-P1 | 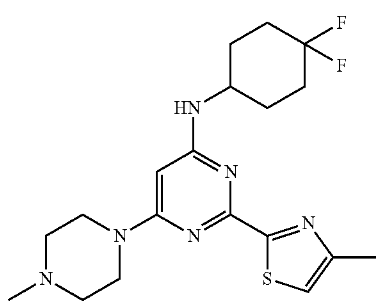 | 408.512 |

TABLE 2-continued

| Compound Ref | Structure | m/z data |
|---|---|---|
| IN11147-062-P1 | 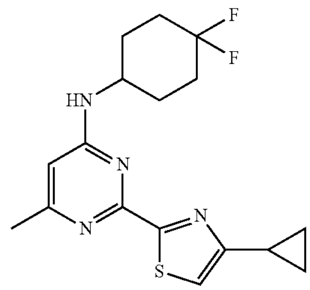 [SMILES: Cc1cc(NC2CCC(F)(F)CC2)nc(-c2nc(C3CC3)cs2)n1] | 350.429 |
| IN11218-034-P1 | 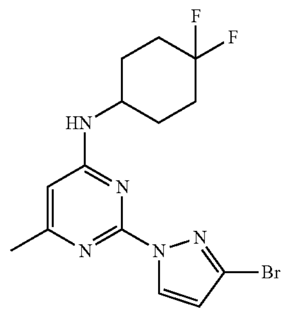 [SMILES: Cc1cc(NC2CCC(F)(F)CC2)nc(-n2ccc(Br)n2)n1] | 372.211 |
| IN11104-090-P1 | 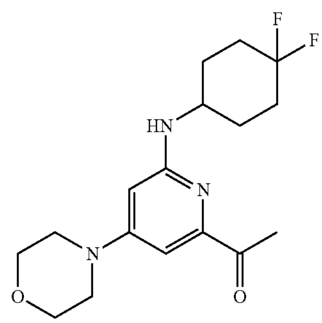 [SMILES: CC(=O)c1cc(N2CCOCC2)cc(NC2CCC(F)(F)CC2)n1] | 339.38 |
| IN11288-025-P1 | 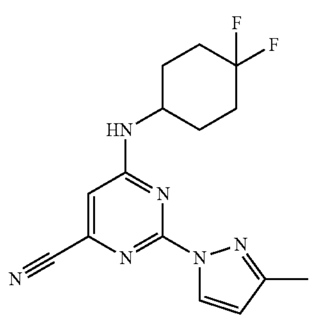 [SMILES: Cc1ccn(-c2nc(C#N)cc(NC3CCC(F)(F)CC3)n2)n1] | 318.324 |
| IN11196-065-P1 | 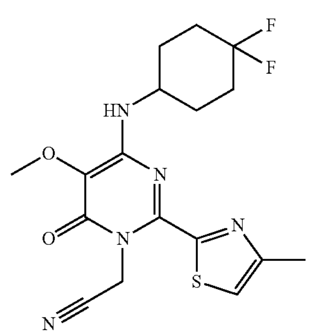 | 395.427 |

TABLE 2-continued

| Compound Ref | Structure | m/z data |
|---|---|---|
| IN11216-072-P1 | 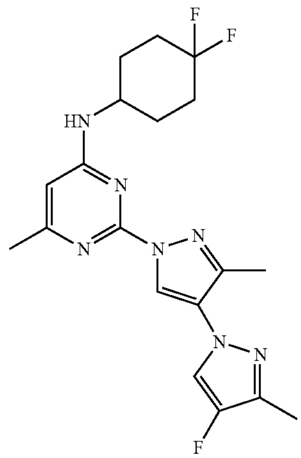 | 405.42 |
| IN11273-018-P1 | 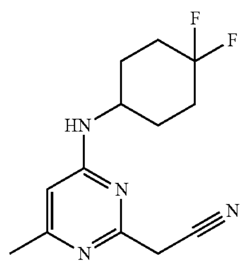 [SMILES: Cc1cc(NC2CCC(F)(F)CC2)nc(CC#N)n1] | 266.29 |
| IN11250-031-P1 | 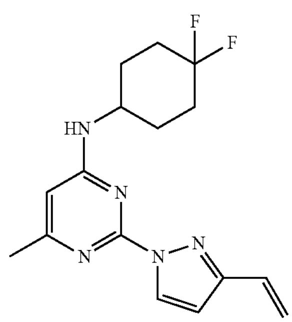 [SMILES: C=Cc1ccn(-c2nc(C)cc(NC3CCC(F)(F)CC3)n2)n1] | 319.352 |
| IN11243-031-P1 | 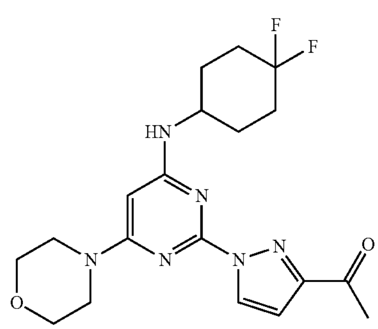 [SMILES: CC(=O)c1ccn(-c2nc(NC3CCC(F)(F)CC3)cc(N3CCOCC3)n2)n1] | 406.43 |

TABLE 2-continued

| Compound Ref | Structure | m/z data |
|---|---|---|
| IN11216-043-P1 | 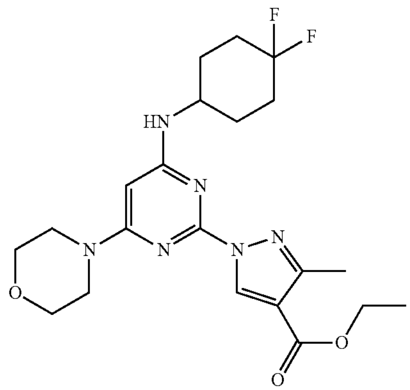 [SMILES: CCOC(=O)c1cn(-c2nc(NC3CCC(F)(F)CC3)cc(N3CCOCC3)n2)nc1C] | 450.482 |
| IN11177-068-P1 | 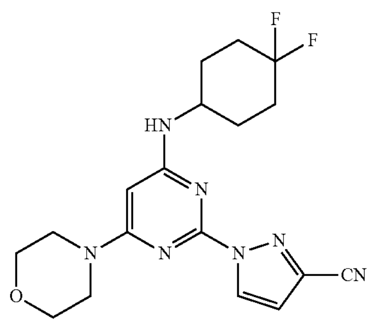 [SMILES: N#Cc1ccn(-c2nc(NC3CCC(F)(F)CC3)cc(N3CCOCC3)n2)n1] | 389.402 |
| IN11147-071-P1 | 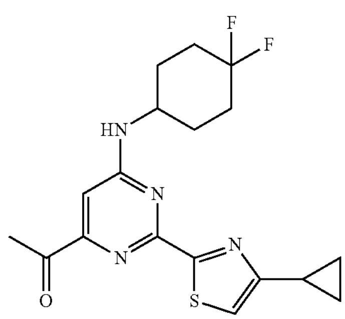 [SMILES: CC(=O)c1cc(NC2CCC(F)(F)CC2)nc(-c2nc(C3CC3)cs2)n1] | 378.439 |
| IN11140-099-P1 | 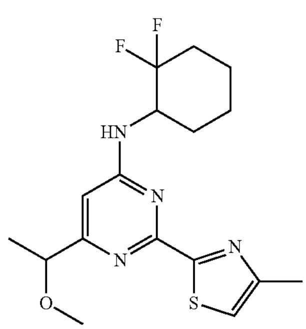 [SMILES: COC(C)c1cc(NC2CCCCC2(F)F)nc(-c2nc(C)cs2)n1] | 368.445 |

TABLE 2-continued
| Compound Ref | Structure | m/z data |
|---|---|---|
| IN11140-090-P1 | 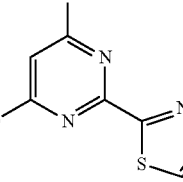 | 334.436 |
| IN11216-073-P1 | 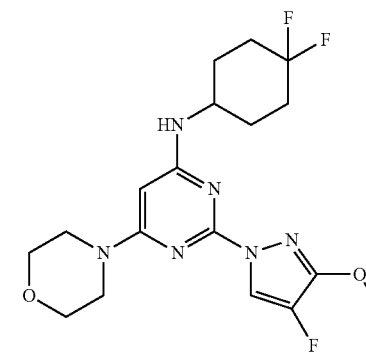 | 412.409 |
| IN11217-088-P1 | 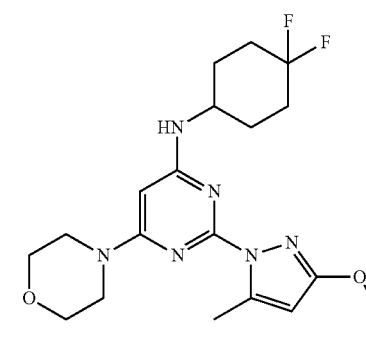 | 408.446 |
| IN11273-015-P2 | 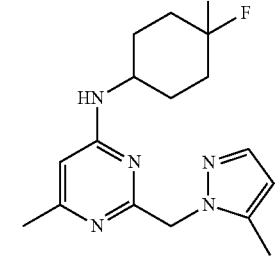 | 321.368 |
| IN11243-050-P2 | 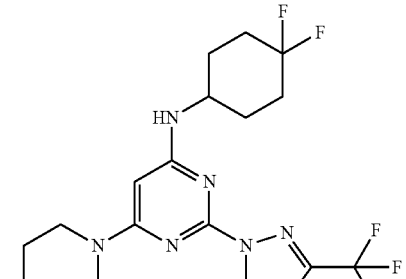 | 428.427 |

TABLE 2-continued

| Compound Ref | Structure | m/z data |
|---|---|---|
| IN11273-015-P1 | 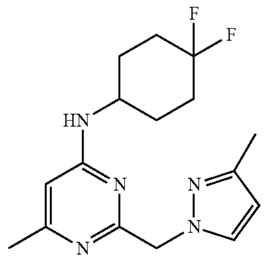 [SMILES: Cc1cc(NC2CCC(F)(F)CC2)nc(Cn2ccc(C)n2)n1] | 321.368 |
| IN11217-069-P1 | 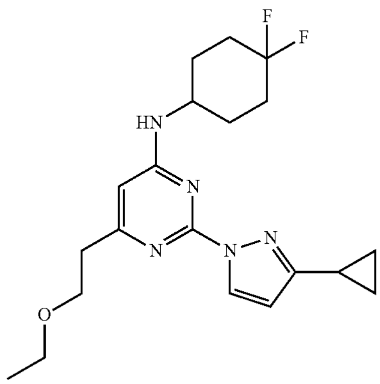 [SMILES: CCOCCc1cc(NC2CCC(F)(F)CC2)nc(-n2ccc(C3CC3)n2)n1] | 391.458 |
| IN11217-068-P1 | 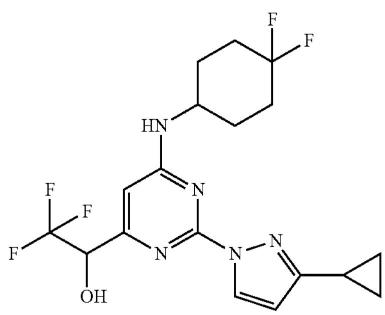 [SMILES: OC(c1cc(NC2CCC(F)(F)CC2)nc(-n2ccc(C3CC3)n2)n1)C(F)(F)F] | 417.376 |
| IN11273-006-P1 | 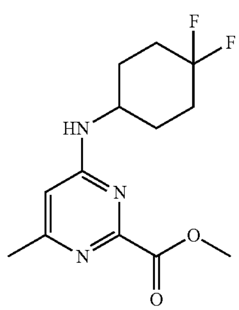 | 285.29 |
| IN11251-043-P1 | 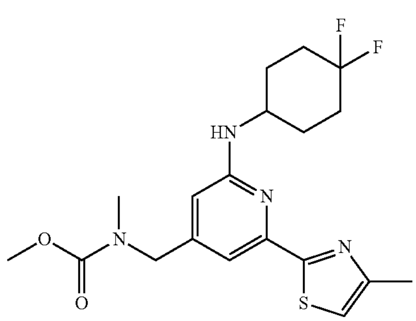 | 410.481 |

TABLE 2-continued

| Compound Ref | Structure | m/z data |
|---|---|---|
| IN11216-050-P1 | 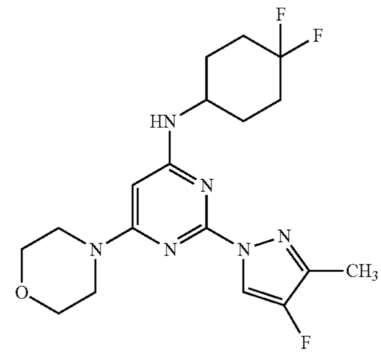 [SMILES: Cc1nn(-c2nc(NC3CCC(F)(F)CC3)cc(N3CCOCC3)n2)cc1F] | 396.41 |
| IN11288-005-P1 | 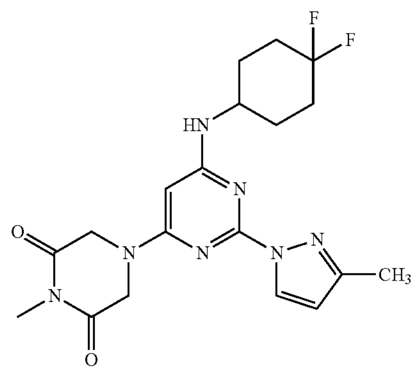 [SMILES: Cc1ccn(-c2nc(NC3CCC(F)(F)CC3)cc(N3CC(=O)N(C)C(=O)C3)n2)n1] | 419.428 |
| IN11243-042-P1 | 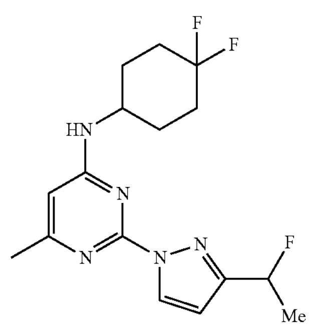 [SMILES: Cc1cc(NC2CCC(F)(F)CC2)nc(-n2ccc(C(C)F)n2)n1] | 339.359 |
| IN11243-041-P1 | 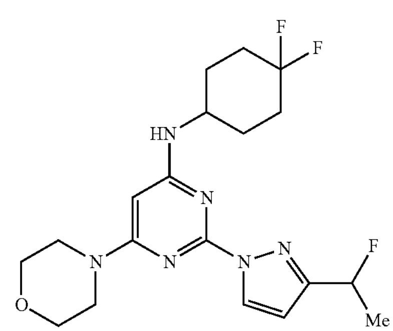 [SMILES: CC(F)c1ccn(-c2nc(NC3CCC(F)(F)CC3)cc(N3CCOCC3)n2)n1] | 410.437 |

TABLE 2-continued

| Compound Ref | Structure | m/z data |
|---|---|---|
| IN11250-032-P1 | 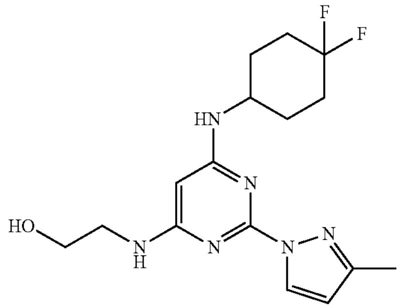 [SMILES: Cc1ccn(-c2nc(NCCO)cc(NC3CCC(F)(F)CC3)n2)n1] | 352.382 |
| IN11273-001-P1 | 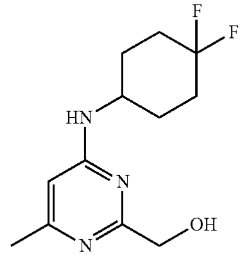 [SMILES: Cc1cc(NC2CCC(F)(F)CC2)nc(CO)n1] | 257.28 |
| IN11238-035-P1 | 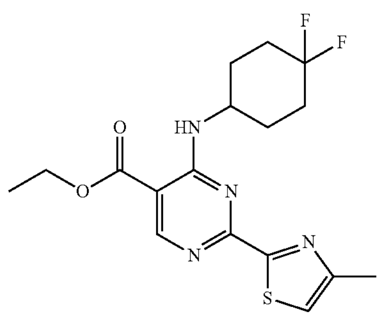 [SMILES: CCOC(=O)c1cnc(-c2nc(C)cs2)nc1NC1CCC(F)(F)CC1] | 382.428 |
| IN11238-046-P1 | 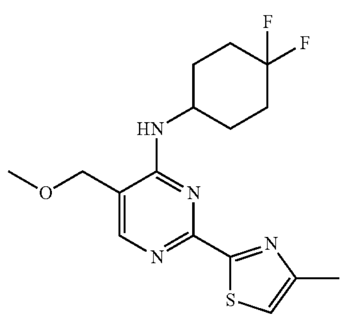 | 354.418 |
| IN11238-040-P1 | 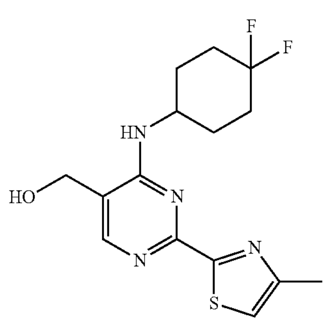 [SMILES: Cc1csc(-c2ncc(CO)c(NC3CCC(F)(F)CC3)n2)n1] | 340.391 |

TABLE 2-continued

| Compound Ref | Structure | m/z data |
|---|---|---|
| IN11251-035-P1 | 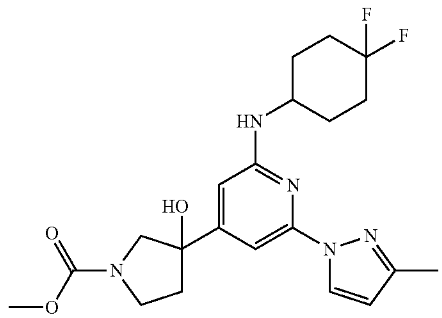 | 435.468 |
| IN11251-024-P1 | 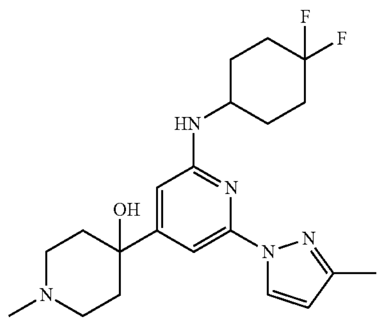 | 405.485 |
| IN11217-056-P1 | 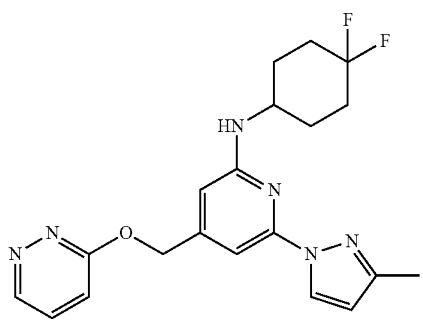 [SMILES: Cc1ccn(-c2cc(COc3cccnn3)cc(NC3CCC(F)(F)CC3)n2)n1] | 400.425 |
| IN11220-039-P1 | 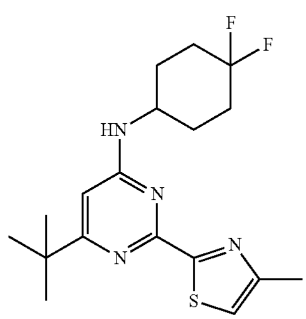 [SMILES: Cc1csc(-c2nc(NC3CCC(F)(F)CC3)cc(C(C)(C)C)n2)n1] | 366.472 |
| IN11238-088-P1 | 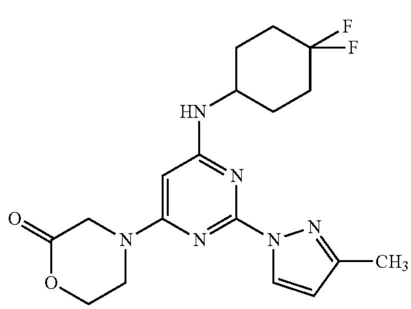 [SMILES: Cc1ccn(-c2nc(NC3CCC(F)(F)CC3)cc(N3CCOC(=O)C3)n2)n1] | 393.2 |

TABLE 2-continued

| Compound Ref | Structure | m/z data |
| --- | --- | --- |
| IN11288-060-P1 | 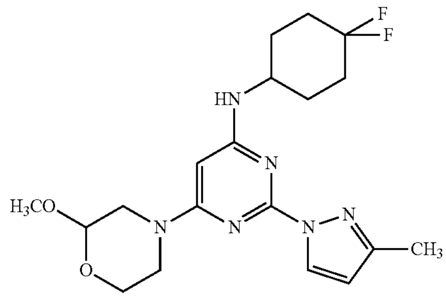 [SMILES: COC1CN(c2cc(NC3CCC(F)(F)CC3)nc(-n3ccc(C)n3)n2)CCO1] | 408.7 |
| IN11237-056-P1 | 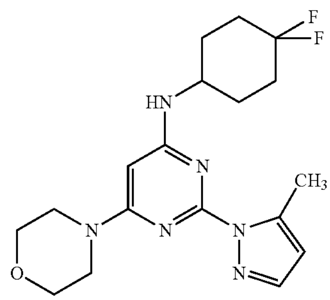 [SMILES: Cc1ccnn1-c1nc(NC2CCC(F)(F)CC2)cc(N2CCOCC2)n1] | 379.420 |
| IN11251-091-P1 | 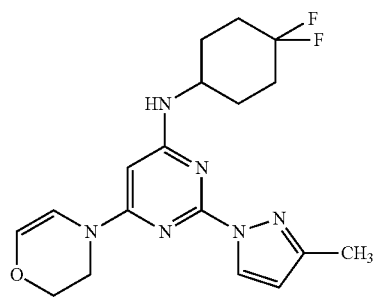 [SMILES: Cc1ccn(-c2nc(NC3CCC(F)(F)CC3)cc(N3C=COCC3)n2)n1] | 376.7 |
| IN11251-092-P1 | 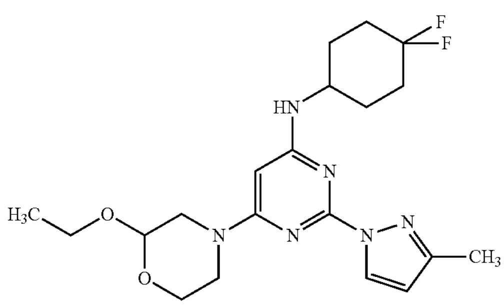 [SMILES: CCOC1CN(c2cc(NC3CCC(F)(F)CC3)nc(-n3ccc(C)n3)n2)CCO1] | 422.3 |
| IN11337-019-P1 | 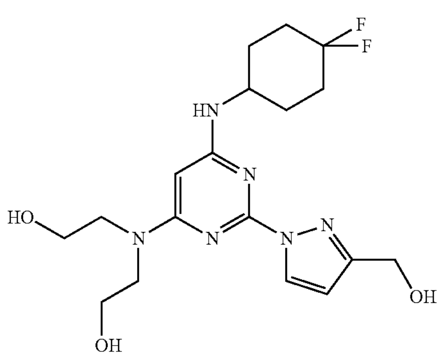 [SMILES: OCCN(CCO)c1cc(NC2CCC(F)(F)CC2)nc(-n2ccc(CO)n2)n1] | 412.7 |

TABLE 2-continued

| Compound Ref | Structure | m/z data |
|---|---|---|
| IN11216-078-P1 | *[structure]* | 397.2 |
| IN11251-099-P1 | *[structure]* | 394.9 |

4. Uses, Formulation and Administration

Pharmaceutically Acceptable Compositions

According to another embodiment, this disclosure provides a composition comprising a compound described herein or a pharmaceutically acceptable derivative thereof and a pharmaceutically acceptable carrier, adjuvant, or vehicle. The amount of compound in compositions is such that is effective to measurably modulate potassium channels in a biological sample or in a patient.

In certain embodiments, a composition described herein is formulated for administration to a patient in need of such composition. In some embodiments, a composition described herein is formulated for oral administration to a patient.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable compositions described herein may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Pharmaceutically acceptable compositions described herein may also be prepared in injectable form. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Pharmaceutically acceptable compositions described herein may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

The amount of compounds described herein that may be combined with the carrier materials to produce a composition in a single dosage form will vary depending upon the host treated and the particular mode of administration. In some embodiments, provided compositions should be formulated so that a dosage of between 0.01-100 mg/kg body weight/day of the inhibitor, such as e.g., 0.1-100 mg/kg body weight/day, can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

Uses of Compounds and Pharmaceutically Acceptable Compositions

In some embodiments, compounds and compositions described herein are useful in treating diseases and/or disorders associated with the activity of potassium channels. Such diseases and/or disorders include e.g., neurodegenerative and neurological conditions (e.g., Parkinson's disease, tremors, Alzheimer's disease, dementia, amyotrophic lateral sclerosis (ALS) ataxia, anxiety, depression, mood disorders, memory and attention deficits, bipolar disorder, psychosis, schizophrenia, traumatic brain injury, and narcolepsy), heart disease and realted conditions (e.g., ischaemic heart disease, coronary heart disease, angina pectoris, and coronary artery spasms), metabolic disease and bladder diseases (e.g., bladder spasms, urinary incontinence, bladder outflow obstruction, gastrointestinal dysfunction, irritable bowel syndrome, and diabetes), withdrawal symptoms associated with termination of addiction, and other conditions associated with the modulation of potassium channels such as e.g., respiratory diseases, epilepsy, convulsions, seizures, absence seizures, vascular spasms, renal disorders (e.g., polycystic kidney disease), erectile dysfunction, secretory diarrhoea, ischaemia, cerebral ischaemia, dysmenorrhea, Reynaud's disease, intermittent claudication, Sjorgren's syndrome, arrhythmia, hypertension, myotonic muscle dystrophia, spasticity, xerostomi, hyperinsulinemia, premature labour, baldness, cancer, immune suppression, migraine and pain.

In one, the present disclosure provides a method of modulating the activity of a potassium channel in a subject comprising the step of administering a compound of Formula I, or a composition comprising any of the compounds herein. In another embodiment, the present disclosure provides a method of positively modulating a SK2 channel in a cell comprising the step of contacting the cell with a compound of Formula I, or a composition comprising any of the compounds herein.

The present disclosure further provides a method of treating essential tremor in a subject comprising the step of administering a compound or pharmaceutically acceptable salt or composition described herein.

In some embodiments, the present disclosure provides a method of treating a disease or condition selected from a neurodegenerative disease, dementia, heart disease, withdrawal symptoms associated with termination of addiction, metabolic disease, and bladder disease. In other embodiments, the present disclosure provides a method of treating a disease or condition selected from ataxia, dystonia, Parkinson's disease, ischemia, traumatic brain injury, amyotrophic lateral sclerosis, hypertension, atherosclerosis, diabetes, arrhythmia, over-active bladder, and withdrawal symptoms caused by the termination of abuse of alcohol and other drugs of abuse.

Certain exemplary provided compounds, e.g., having structural formula I are set forth in the EXEMPLIFICATION section below. In some embodiments, a provided compound is one or more compounds selected from those exemplified in the EXEMPLIFICATION section below, or a pharmaceutically acceptable salt thereof.

EXEMPLIFICATION

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

General Synthetic Scheme:

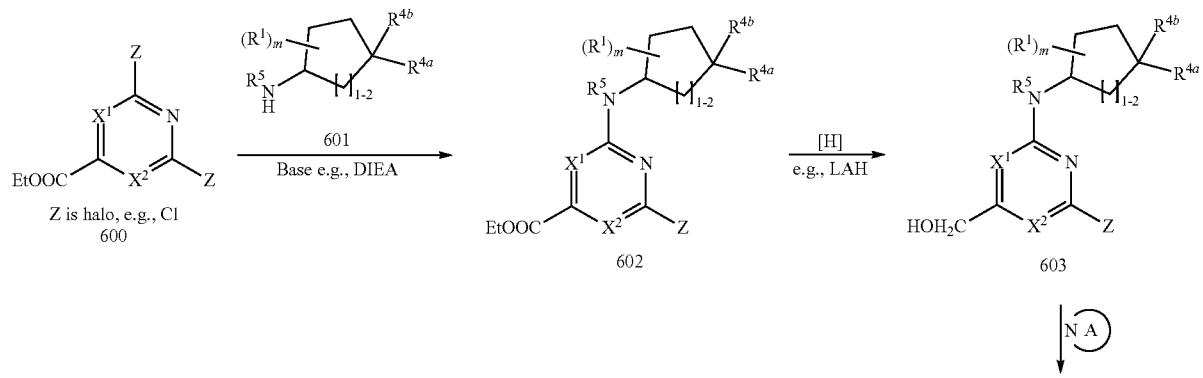

Scheme 1.

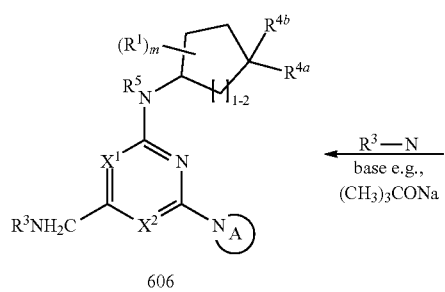

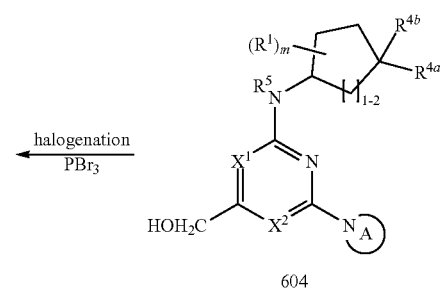

In one aspect, compounds of Formula I can be prepared according to Scheme 1, where the variables $R^1$, $R^3$, $R^5$, $R^{4a}$, $R^{4b}$, $X^1$, $X^2$, and A are defined for Formula I. For example, compounds of Formula I can be prepared by reacting a compound of Formula 600 with a compound of Formula 601 in the presence of base, such as, e.g., diisopropylethylamine to form intermediate 602. Reduction with e.g., a reducing agent such as lithium aluminum hydride forms a compound of Formula 603. Reaction with a nitrogen atom on ring A affords 604 followed by halogenation with e.g., phosphorous tribromide gives 605. Treatment with amine reagent having the formula $R^3$—N in the presence of base, such as e.g., sodium t-butoxide gives 606. Scheme 1 is in no way limiting and represents only one method by which certain compounds described herein can be made. Other methods of making compounds of Formula I would be apparent to one of skill in the art.

Preparation of Compounds of Formula I

Compounds of Formula I were prepared according to the general procedures outlined below.

Example 1

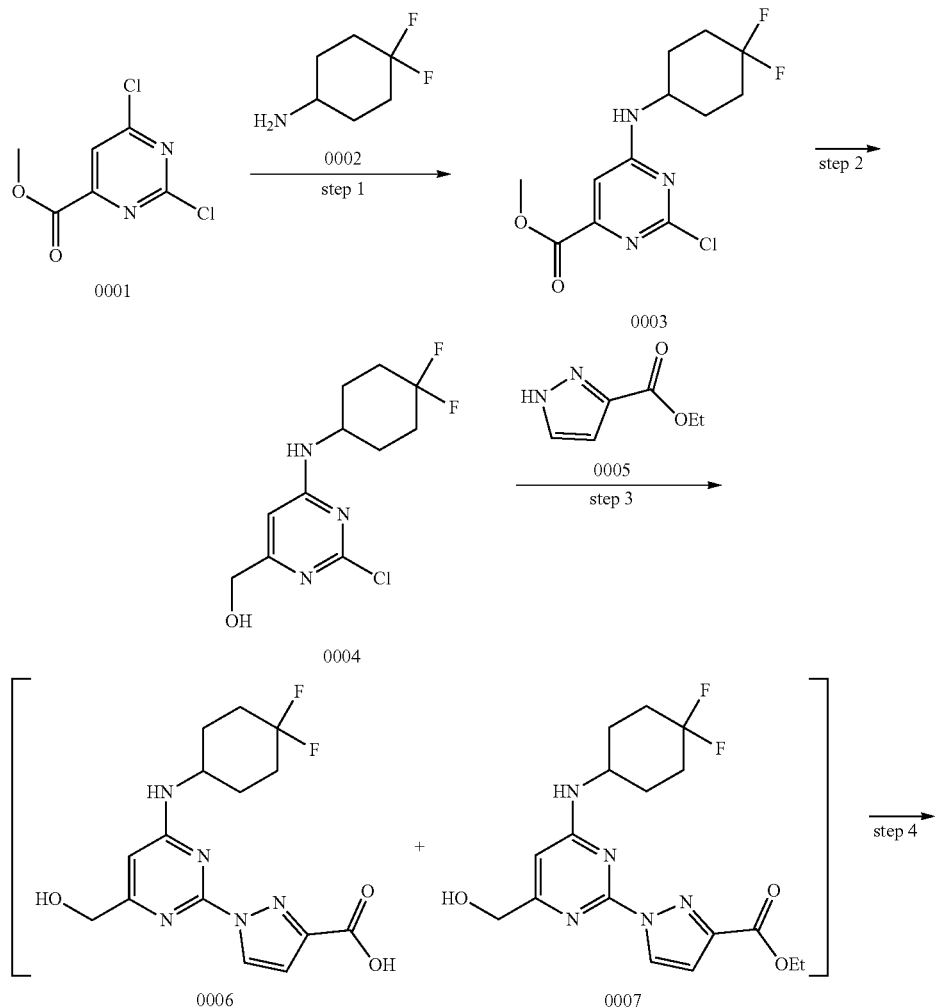

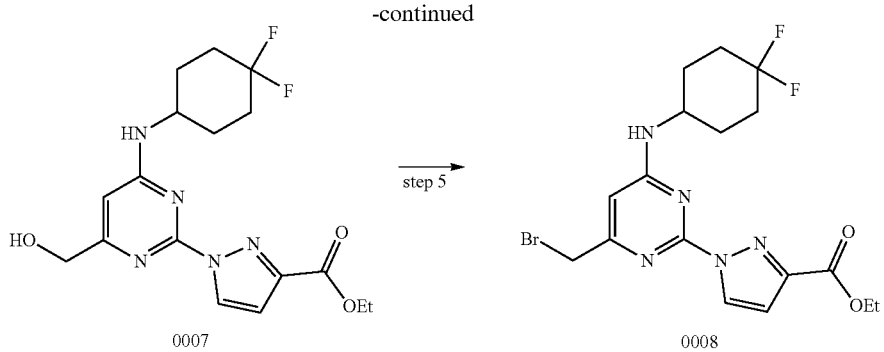

Step 1 [0003]: To a stirred solution of methyl 2,4-dichloropyrimidine-6-carboxylate [0001] (5 g, 24.16 mmol) in acetonitrile (50 mL) was added 4,4-difluorocyclohexylamine hydrochloride [0002] (4.1 g, 24.158 mmol) and N,N-diisopropyl ethylamine (8.8 mL, 50.72 mmol) at rt and the mixture was stirred for 2 h. The reaction mixture was concentrated under reduced pressure. To the residue water (25 mL) was added, the solid thus formed was filtered and dried by suction to afford 4 g of crude which was purified by column chromatography using 15% ethyl acetate in pet ether as eluent to afford 2.8 g of methyl 2-chloro-6-((4,4-difluorocyclohexyl)amino)pyrimidine-4-carboxylate [0003] as a white solid. MS(M+1)$^+$=306.0.

Step 2[0004]: To a stirred solution of methyl 2-chloro-6-((4,4-difluorocyclohexyl)amino)pyrimidine-4-carboxylate [0003] (0.5 g, 1.635 mmol) in tetrahydrofuran (10 mL) was added a solution of lithium aluminum hydride in tetrahydrofuran (2 M, 1.63 mL, 3.27 mmol) at 0° C. The reaction mixture was stirred at rt for 2 h. The reaction mixture was cooled to 0° C., quenched with saturated ammonium chloride solution (2 mL) and extracted with ethyl acetate (2×25 mL). The combined organic layer was dried over anhydrous sodium sulfate, filtered and concentrated under reduced pressure to afford 0.4 g of crude (2-chloro-6-((4,4-difluorocyclohexyl)amino)pyrimidin-4-yl)methanol [0004] as a brown gum. MS(M+1/M+3)$^+$=278.2/280.2.

Step 3[0006 and 0007]: To a stirred solution of (2-chloro-6-((4,4-difluorocyclohexyl)amino)pyrimidin-4-yl)methanol [0004] (1.7 g, 6.12 mmol) in acetonitrile (20 mL) were added ethyl-1H-pyrazole-3-carboxylate [0005] (0.87 g, 6.12 mmol) and cesium carbonate (2.99 g, 9.18 mmol). The reaction mixture was irradiated in microwave at 100° C. for 2 h. The reaction mixture was concentrated under reduced pressure. The residue was quenched with water (15 mL), acidified with 4 N HCl solutions (25 mL) and extracted with ethyl acetate (2×25 mL). The combined organic layer was dried over anhydrous sodium sulfate, filtered and concentrated under reduced pressure to afford 1.5 g as a mixture of 1-(4-((4,4-difluorocyclohexyl)amino)-6-(hydroxymethyl)pyrimidin-2-yl)-1H-pyrazole-3-carboxylic acid [0006] MS(M+1)$^+$=354.1 and its ethyl ester [0007] MS(M+1)$^+$=382.2.

Step 4[0007]: To a stirred solution of a mixture of 1-(4-((4,4-difluorocyclohexyl)amino)-6-(hydroxymethyl)pyrimidin-2-yl)-1H-pyrazole-3-carboxylic acid [0006] and its ester [0007] (3 g, 8.4 mmol) in ethanol (30 mL) was added conc. sulfuric acid (0.923 mL, 16.98 mmol). The reaction mixture was refluxed at 85° C. for 5 h and concentrated under reduced pressure. The residue was quenched with water (15 mL), neutralized with saturated aqueous sodium bicarbonate solution (20 mL), extracted with ethyl acetate (2×100 mL). The combined organic layer was dried over anhydrous sodium sulfate, filtered and concentrated under reduced pressure to afford 3.3 g of crude which was purified by column chromatography using 65% ethyl acetate in pet ether as eluent to afford 2 g of ethyl 1-(4-((4,4-difluorocyclohexyl)amino)-6-(hydroxymethyl)pyrimidin-2-yl)-1H-pyrazole-3-carboxylate [0007] as an off-white solid. MS(M+1)$^+$=381.8.

Step 5[0008]: To a stirred solution of ethyl 1-(4-((4,4-difluorocyclohexyl)amino)-6-(hydroxymethyl)pyrimidin-2-yl)-1H-pyrazole-3-carboxylate [0007] (2 g, 5.24 mmol) in dichloromethane (10 mL) was added phosphorus tribromide (1.41 g, 5.24 mmol) at 0° C. The reaction mixture was stirred at rt for 1 h. The reaction mixture was quenched with ice cold water (50 mL) and extracted with dichloromethane (2×50 mL). The combined organic extracts was dried over anhydrous sodium sulfate, filtered and concentrated under reduced pressure. The residue was purified by column chromatography using 35% ethyl acetate in pet ether as eluent to afford 0.7 g of ethyl 1-(4-(bromomethyl)-6-((4,4-difluorocyclohexyl)amino)pyrimidin-2-yl)-1H-pyrazole-3-carboxylate [0008] as a white solid. MS(M+1/M+3)$^+$=444.2/446.1.

Example 2

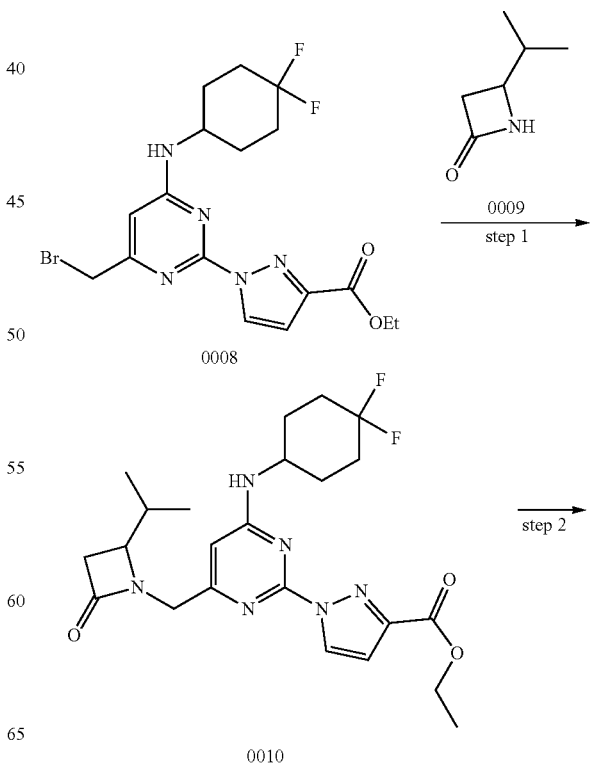

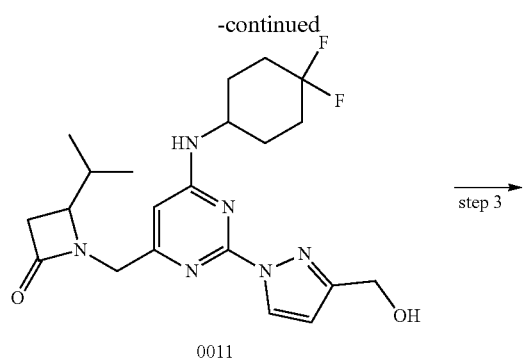

0011

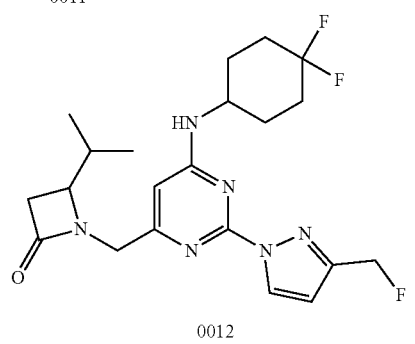

0012

Step 1[0010]: To a stirred solution of ethyl 1-(4-(bromomethyl)-6-((4,4-difluorocyclohexyl)amino)pyrimidin-2-yl)-1H-pyrazole-3-carboxylate [0008] (0.45 g, 1.01 mmol) in tetrahydrofuran (10 mL) were added 4-isopropyl-2-azetidinone [0009] (0.126 g) and sodium tert-butoxide (0.146 g, 1.52 mmol) at 0° C. The reaction mixture was stirred at same temperature for 30 min. The reaction mixture was quenched with water (15 mL) and extracted with ethyl acetate (2×50 mL). The organic layer was dried over anhydrous sodium sulfate, filtered and concentrated under reduced pressure. The residue was purified by column chromatography using 28% ethyl acetate in pet ether as eluent to afford ethyl 1-(4-((4,4-difluorocyclohexyl)amino)-6-((2-isopropyl-4-oxoazetidin-1-yl)methyl)pyrimidin-2-yl)-1H-pyrazole-3-carboxylate [0010] as an off-white solid (0.28 g). MS(M+1)$^+$=476.8.

Step 2[0011]: To a stirred solution of ethyl 1-(4-((4,4-difluorocyclohexyl)amino)-6-((2-isopropyl-4-oxoazetidin-1-yl)methyl)pyrimidin-2-yl)-1H-pyrazole-3-carboxylate [0010] (0.28 g, 0.58 mmol) in tetrahydrofuran (5 mL) was added lithium borohydride (0.038 g, 1.76 mmol) at 0° C. The reaction mixture was stirred at rt for 1.5 h, quenched with ice and extracted with ethyl acetate (2×15 mL). The combined organic layer was washed with brine (10 mL), dried over anhydrous sodium sulfate, filtered and concentrated under reduced pressure to afford 1-((6-((4,4-difluorocyclohexyl)amino)-2-(3-(hydroxymethyl)-1H-pyrazol-1-yl)pyrimidin-4-yl)methyl)-4-isopropylazetidin-2-one [0011] as a white solid (0.220 g). MS(M+1)$^+$=434.9.

Step 3[0012]: To a stirred solution of 1-((6-((4,4-difluorocyclohexyl)amino)-2-(3-(hydroxymethyl)-1H-pyrazol-1-yl)pyrimidin-4-yl)methyl)-4-isopropylazetidin-2-one [0011] (0.22 g, 0.506 mmol) in dichloromethane (5 mL) was added diethylaminosulfur trifluoride (0.133 mL, 1.01 mmol) at 0° C. The reaction mixture was stirred at rt for 15 min, quenched with 10% sodium bicarbonate solution (10 mL) and extracted with dichloromethane (2×20 mL). The combined organic layer was dried over anhydrous sodium sulfate, filtered and concentrated under reduced pressure to afford crude which was purified by column chromatography using 32% ethyl acetate in pet ether as eluent to obtain 1-((6-((4,4-difluorocyclohexyl)amino)-2-(3-(fluoromethyl)-1H-pyrazol-1-yl)pyrimidin-4-yl)methyl)-4-isopropylazetidin-2-one [0012], Compound 325 as a white solid (0.037 g).

MS(M+1)$^+$=437.2, $^1$H NMR (400 MHz, DMSO-d$_6$) δ 8.52 (d, J=2.4 Hz, 1H), 7.63 (d, J=6.4 Hz, 1H), 6.60 (s, 1H), 6.40 (s, 1H), 5.45 (d, JF=48 Hz, 2H), 4.35 (d, J=16.8 Hz, 1H), 4.11 (d, J=16.1 Hz, 2H), 3.59 (s, 1H), 3.55 (m, 1H), 2.92 (dd, J=14.8, 5.2 Hz, 1H), 2.65 (m, 1H), 2.18-1.90 (m, 6H), 1.70-1.60 (m, 2H), 0.88 (dd, J=24 Hz, 6.8 Hz, 6H).

Example 3

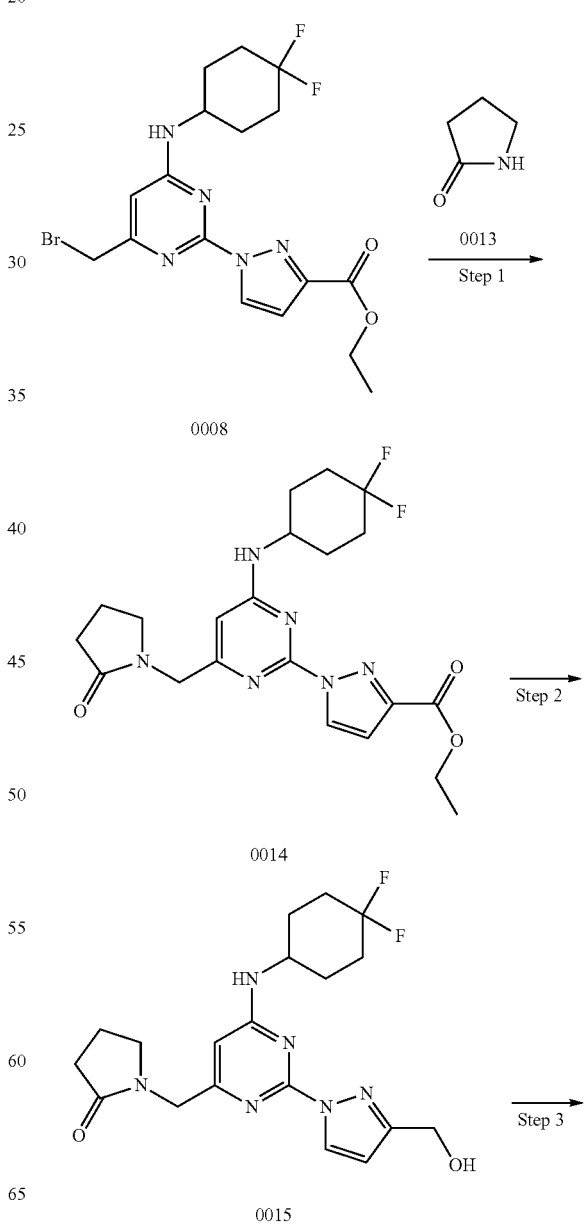

-continued

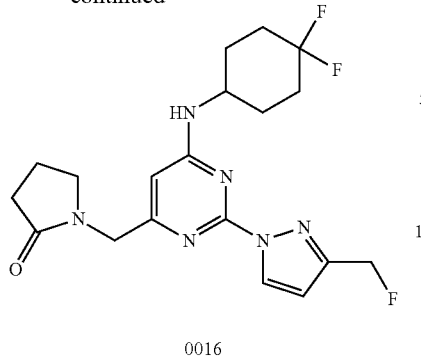

0016

Step 1[0014]: To a stirred solution of ethyl 1-(4-(bromomethyl)-6-((4,4-difluorocyclohexyl)amino)pyrimidin-2-yl)-1H-pyrazole-3-carboxylate [0008] (0.5 g, 1.012 mmol) in tetrahydrofuran (5 mL) was added 2-pyrrolidone [0013] (0.478 g, 5.63 mmol) and potassium tert-butoxide (0.151 g, 1.351 mmol) at 0° C. The reaction mixture was stirred at same temperature for 15 min. The reaction mixture was quenched with water (10 mL) and extracted with ethyl acetate (2×25 mL). The combined organic extract was dried over anhydrous sodium sulfate, filtered and concentrated under reduced pressure. The residue of was purified by column chromatography using 65% ethyl acetate in pet ether as eluent to afford ethyl 1-(4-((4,4-difluorocyclohexyl)amino)-6-((2-oxopyrrolidin-1-yl)methyl)pyrimidin-2-yl)-1H-pyrazole-3-carboxylate [0014] as a white solid (0.25 g). MS(M+1)$^+$=449.3.

Step 2[0015]: The procedure is similar to step 2[0011] in example 2. 0.25 g of ethyl 1-(4-((4,4-difluorocyclohexyl)amino)-6-((2-oxopyrrolidin-1-yl)methyl)pyrimidin-2-yl)-1H-pyrazole-3-carboxylate [0014] gave 0.2 g of 1-((6-((4,4-difluorocyclohexyl)amino)-2-(3-(hydroxymethyl)-1H-pyrazol-1-yl)pyrimidin-4-yl)methyl) pyrrolidin-2-one [0015] as a brown solid. MS(M+1)$^+$=407.4.

Step 3[0016]: The procedure is similar to step 3[0012] in example 2. 0.2 g of 1-((6-((4,4-difluorocyclohexyl)amino)-2-(3-(hydroxymethyl)-1H-pyrazol-1-yl)pyrimidin-4-yl) methyl) pyrrolidin-2-one [0015] gave 0.035 g of 1-((6-((4,4-difluorocyclohexyl)amino)-2-(3-(fluoromethyl)-1H-pyrazol-1-yl)pyrimidin-4-yl)methyl)pyrrolidin-2-one [0016], Compound 321 as a white solid. MS(M+1)$^+$=409.2, $^1$H NMR (400 MHz, DMSO-d6) δ 8.62 (s, 1H), 7.78 (d, J=7.2 Hz, 1H), 6.66 (dd, J=2.6, 1.3 Hz, 1H), 6.20 (s, 1H), 5.45 (d, JF=48.0 Hz, 2H), 4.27 (s, 2H), 4.18 (bs, 1H), 3.42 (t, J=6.84 Hz, 2H), 2.33 (t, J=8.0 Hz, 2H), 2.15-1.90 (m, 8H), 1.65-1.5 (m, 2H).

Example 4

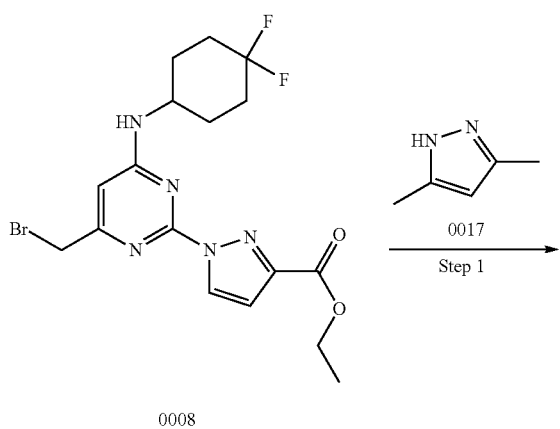

0008

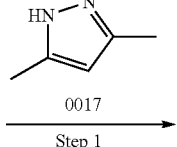

0017
Step 1

-continued

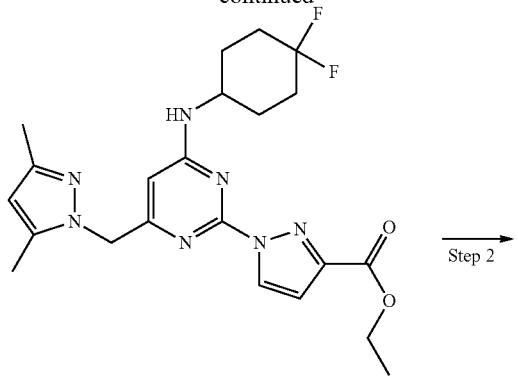

0018

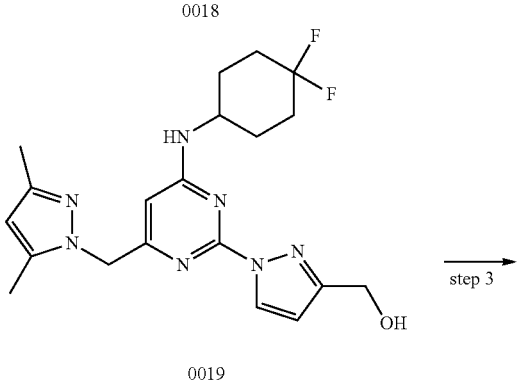

0019

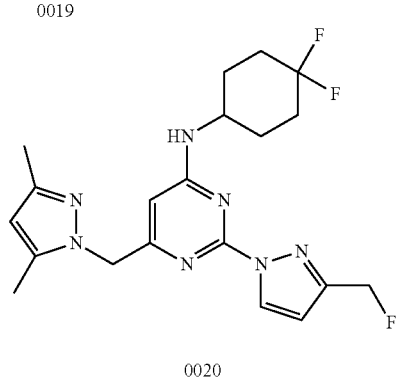

0020

Step 1[0018]: To a stirred solution of ethyl 1-(4-(bromomethyl)-6-((4,4-difluorocyclohexyl)amino)pyrimidin-2-yl)-1H-pyrazole-3-carboxylate [0008] (0.5 g, 1.126 mmol) in acetonitrile (10 mL) were added 3,5-dimethyl pyrazole [0017] (0.119 g, 1.23 mmol) and cesium carbonate (0.550 g, 1.69 mmol). The reaction mixture was irradiated in microwave at 100° C. for 1 h, added water (10 mL) and extracted with ethyl acetate (2×15 mL). The organic layer was dried over anhydrous sodium sulfate, filtered and concentrated under reduced pressure. The residue was purified by column chromatography using 55% ethyl acetate in pet ether as eluent to afford 0.23 g of ethyl 1-(4-((4,4-difluorocyclohexyl)amino)-6-((3,5-dimethyl-1H-pyrazol-1-yl)methyl)pyrimidin-2-yl)-1H-pyrazole-3-carboxylate [0018] as an off-white solid. MS(M+1)$^+$=460.2.

Step 2[0019]: To a stirred solution of ethyl 1-(4-((4,4-difluorocyclohexyl)amino)-6-((3,5-dimethyl-1H-pyrazol-1-yl)methyl)pyrimidin-2-yl)-1H-pyrazole-3-carboxylate [0018] (0.220 g, 0.478 mmol) in tetrahydrofuran (5 mL) was added a solution of lithium aluminium hydride in tetrahydrofuran (478 mL, 2 M, 0.957 mmol) at 0° C. The reaction mixture was stirred at rt for 1 h. The reaction mixture was quenched with saturated aqueous ammonium chloride solution (3 mL) and extracted with ethyl acetate (2×25 mL). The combined organic layer was dried over anhydrous sodium sulfate, filtered and concentrated to afford N-(4,4-difluoro-cyclohexyl)-6-((3,5-dimethyl-1H-pyrazol-1-yl)methyl)-2-(3-(fluoromethyl)-1H-pyrazol-1-yl)pyrimidin-4-amine [0019] as an off-white solid (0.2 g). MS(M+1)⁺=418.2.

Step 3[0020]: The procedure is similar to step 3[0012] in example 2. 0.2 g of N-(4,4-difluorocyclohexyl)-6-((3,5-dimethyl-1H-pyrazol-1-yl)methyl)-2-(3-(fluoromethyl)-1H-pyrazol-1-yl)pyrimidin-4-amine [0019] gave 0.036 g of N-(4,4-difluorocyclohexyl)-6-((3,5-dimethyl-1H-pyrazol-1-yl)methyl)-2-(3-(fluoromethyl)-1H-pyrazol-1-yl)pyrimidin-4-amine [0020], Compound 300 as an off-white solid. MS(M+1)⁺=420.2/421.2, ¹H NMR (400 MHz, DMSO-d6) δ 8.62 (s, 1H), 7.82 (d, J=7.4 Hz, 1H), 6.67 (d, J=2.6 Hz, 1H), 5.93 (s, 1H), 5.66 (s, 1H), 5.52-5.40 (d, JF=49.96 Hz, 2H), 5.09 (s, 2H), 4.16 (s, 1H), 2.21 (s, 3H), 2.13 (s, 3H), 2.04-1.92 (m, 6H), 1.54-1.51 (m, 2H).

Example 5

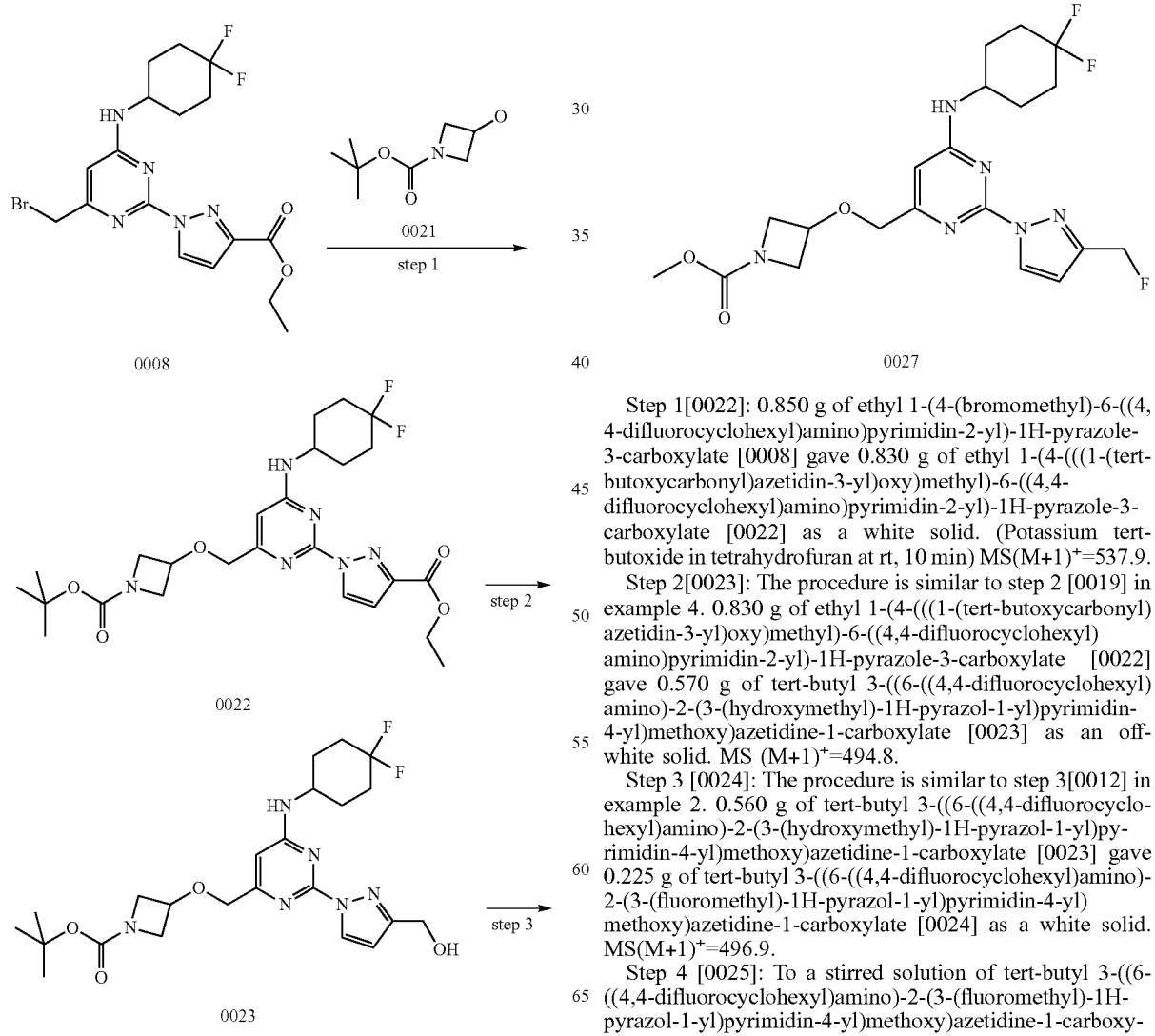

Step 1[0022]: 0.850 g of ethyl 1-(4-(bromomethyl)-6-((4,4-difluorocyclohexyl)amino)pyrimidin-2-yl)-1H-pyrazole-3-carboxylate [0008] gave 0.830 g of ethyl 1-(4-(((1-(tert-butoxycarbonyl)azetidin-3-yl)oxy)methyl)-6-((4,4-difluorocyclohexyl)amino)pyrimidin-2-yl)-1H-pyrazole-3-carboxylate [0022] as a white solid. (Potassium tert-butoxide in tetrahydrofuran at rt, 10 min) MS(M+1)⁺=537.9.

Step 2[0023]: The procedure is similar to step 2 [0019] in example 4. 0.830 g of ethyl 1-(4-(((1-(tert-butoxycarbonyl)azetidin-3-yl)oxy)methyl)-6-((4,4-difluorocyclohexyl)amino)pyrimidin-2-yl)-1H-pyrazole-3-carboxylate [0022] gave 0.570 g of tert-butyl 3-((6-((4,4-difluorocyclohexyl)amino)-2-(3-(hydroxymethyl)-1H-pyrazol-1-yl)pyrimidin-4-yl)methoxy)azetidine-1-carboxylate [0023] as an off-white solid. MS (M+1)⁺=494.8.

Step 3 [0024]: The procedure is similar to step 3[0012] in example 2. 0.560 g of tert-butyl 3-((6-((4,4-difluorocyclohexyl)amino)-2-(3-(hydroxymethyl)-1H-pyrazol-1-yl)pyrimidin-4-yl)methoxy)azetidine-1-carboxylate [0023] gave 0.225 g of tert-butyl 3-((6-((4,4-difluorocyclohexyl)amino)-2-(3-(fluoromethyl)-1H-pyrazol-1-yl)pyrimidin-4-yl)methoxy)azetidine-1-carboxylate [0024] as a white solid. MS(M+1)⁺=496.9.

Step 4 [0025]: To a stirred solution of tert-butyl 3-((6-((4,4-difluorocyclohexyl)amino)-2-(3-(fluoromethyl)-1H-pyrazol-1-yl)pyrimidin-4-yl)methoxy)azetidine-1-carboxylate [0024] (0.2 g, 0.402 mmol) in dichloromethane (5 mL)

was added trifluoroacetic acid (0.468 mL, 6.042 mmol) at 0° C. and the mixture was stirred at rt for 2 h. The reaction mixture was concentrated under reduced pressure to afford 0.180 g of 6-((azetidin-3-yloxy)methyl)-N-(4,4-difluorocyclohexyl)-2-(3-(fluoromethyl)-1H-pyrazol-1-yl)pyrimidin-4-amine [0025] as an off-white solid. MS(M+1)$^+$=397.3

Step 5 [0027]: To a stirred solution of 6-((azetidin-3-yloxy)methyl)-N-(4,4-difluorocyclohexyl)-2-(3-(fluoromethyl)-1H-pyrazol-1-yl)pyrimidin-4-amine [0025] (0.180 g, 0.454 mmol) in dichloromethane (5 mL) were added triethylamine (0.17 mL, 1.20 mmol) and methyl chloroformate (0.180 g, 0.81 mmol) at 0° C. The reaction mixture was stirred at same temperature for 10 min., partitioned between dichloromethane (10 mL) and water (3 mL). The organic layer was dried over anhydrous sodium sulfate, filtered and concentrated under reduced pressure. The crude was purified by column chromatography using 75% ethyl acetate in pet ether as eluent to afford 0.125 g of methyl 3-((6-((4,4-difluorocyclohexyl)amino)-2-(3-(fluoromethyl)-1H-pyrazol-1-yl)pyrimidin-4-yl)methoxy)azetidine-1-carboxylate [0027], Compound 335 as a white solid.

MS(M+1)$^+$=455.2, 1H-NMR (400 MHz, DMSO-d6): δ 8.61 (s, 1H), 7.85 (d, J=6.84 Hz, 1H), 6.64 (s, 1H), 6.52 (s, 1H), 5.45 (d, JF=48.0 Hz, 2H), 4.46 (s, 1H), 4.39 (s, 2H), 4.16-4.14 (m, 3H), 3.82 (s, 2H), 3.56 (s, 3H) 2.15-1.88 (m, 6H), 1.65-1.5 (m, 2H).

Example 6

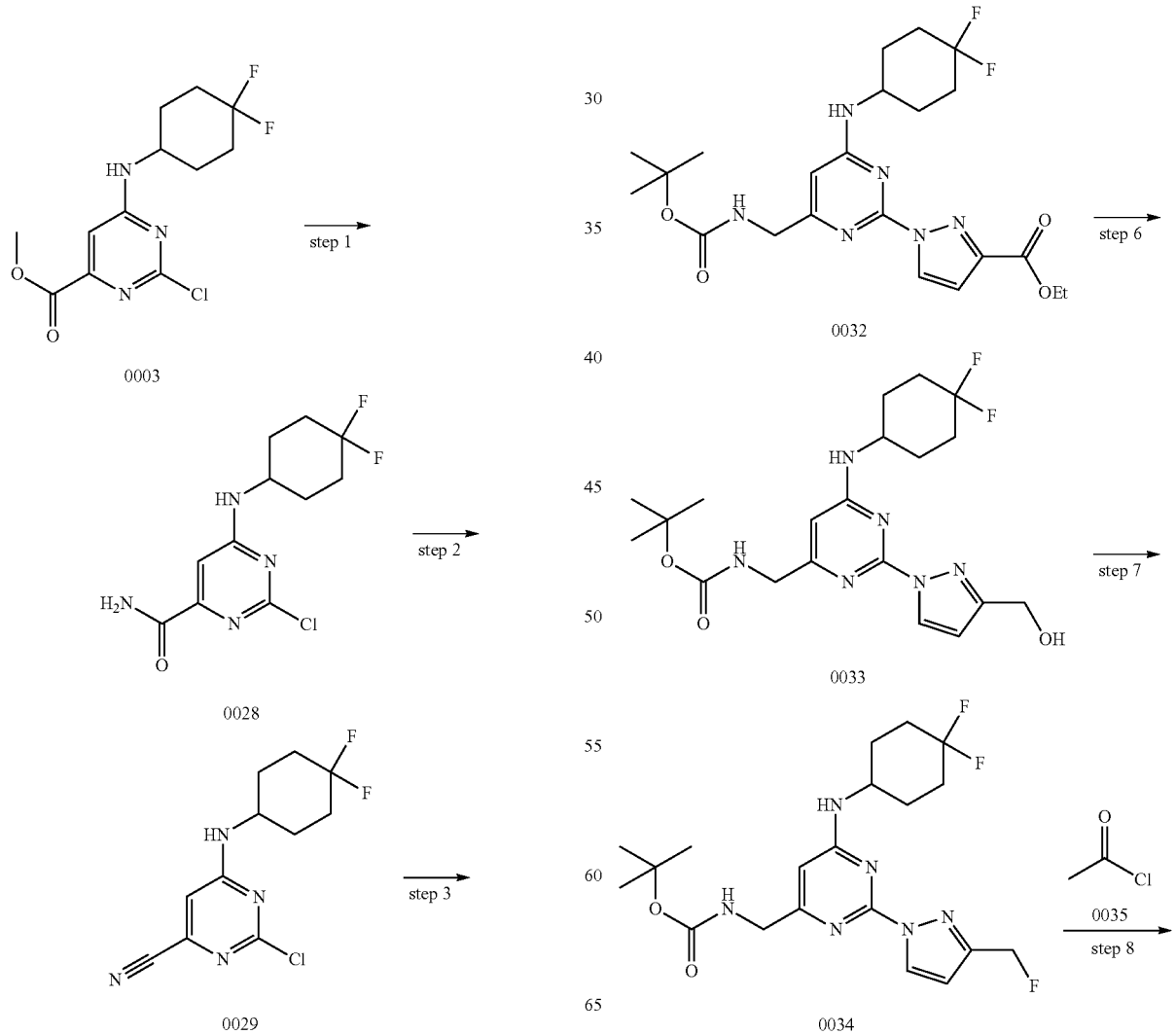

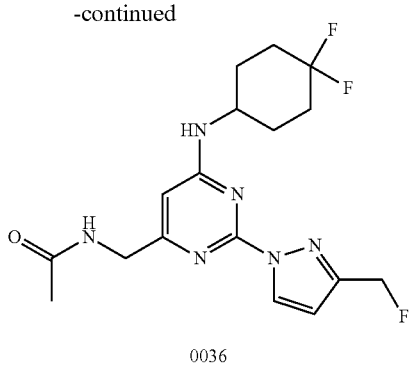

Step 1[0028]: To a stirred solution of methyl-2-chloro-6-((4,4-difluorocyclohexyl)amino)pyrimidine-4-carboxylate [0003] (6.6 g, 21.589 mmol) in methanol was added methanolic ammonia (60 mL) at rt. After 2 h the reaction mixture was purged with nitrogen to remove excess ammonia and then concentrated under reduced pressure. The residue was diluted with water (100 mL) and stirred for 10 min. The solid formed was filtered, washed with water (25 mL) and dried under vacuum to afford 2-chloro-6-((4,4-difluorocyclohexyl)amino)pyrimidine-4-carboxamide [0028] as a white solid (5.5 g MS(M+1)+=291.1) and was taken as such tonext step.

Step 2[0029]: To a suspension of 2-chloro-6-((4,4-difluorocyclohexyl)amino)pyrimidine-4-carboxamide [0028] (5.5 g, 18.92 mmol) in dichloromethane was added triethylamine (9.57 g, 94.6 mmol) and phosphorus oxychloride (7.25 g, 47.3 mmol) at 0° C. and the reaction mixture was stirred at rt. After 1 h the reaction mixture was quenched with ice (100 g) and extracted with dichloromethane (2×100 mL). The organic layer was dried over anhydrous sodium sulfate, filtered and concentrated under reduced pressure to afford brown oil which was purified by column chromatography using 30% ethyl acetate in hexane as eluent to afford 2-chloro-6-((4,4-difluorocyclohexyl)amino)pyrimidine-4-carbonitrile [0029] as a pale yellow solid (3.6 g, 70% yield). MS(M+1)+=273.1.

Step 3[0030]: To a solution of 2-chloro-6-((4,4-difluorocyclohexyl)amino)pyrimidine-4-carbonitrile [0029] (3.6 g, 13.302 mmol) in tetrahydrofuran was added a solution of lithium aluminium hydride in tetrahydrofuran (9.9 mL, 2M solution, 19.803 mmol) at −15° C. and the reaction mixture was stirred at same temperature. Reaction turned dark brown after LAH addition. After 10 min, the reaction mixture was quenched with saturated aqueous sodium sulfate solution at 0° C. and stirred at rt. The suspension was passed through celite bed, washed with chloroform (50 mL). The filtrate was concentrated under reduced pressure to afford 6-(aminomethyl)-2-chloro-N-(4,4-difluorocyclohexyl)pyrimidin-4-amine [0030] as red oil (4.2 g, MS(M+1)+=277.2) and it was taken as such tonext step.

Step 4[0031]: To a solution of 6-(aminomethyl)-2-chloro-N-(4,4-difluorocyclohexyl)pyrimidin-4-amine [0030] (4.2 g, 15.178 mmol) in dichloromethane were added triethylamine (2.3 g, 22.76 mmol) and boc-anhydride (3.9 g, 18.213 mmol) at 0° C. and the reaction mixture was stirred at same temperature. After 1 h, the reaction mixture was quenched with ice and extracted with dichloromethane (2×100 mL). The combined organic layer was dried over anhydrous sodium sulfate, filtered and concentrated under reduced pressure to afford as brown oil, which was purified by column chromatography using 30% ethyl acetate in hexane as eluent to afford tert-butyl ((2-chloro-6-((4,4-difluorocyclohexyl)amino)pyrimidin-4-yl)methyl)carbamate [0031] as a pale yellow solid (2.3 g). MS(M+1)+=377.2.

Step 5[0032]: To a solution of tert-butyl ((2-chloro-6-((4,4-difluorocyclohexyl)amino)pyrimidin-4-yl)methyl)carbamate [0031] (4.2 g, 15.178 mmol) and ethyl-1H-pyrazole-3-carboxylate [0005] (4.2 g, 15.178 mmol) in acetonitrile was added cesium carbonate (4.2 g, 15.178 mmol) and the reaction mixture was heated at 85° C. in sealed tube. After 2 h, the reaction mixture was filtered, washed with chloroform (50 mL). The combined filtrate was concentrated under reduced pressure to afford pale brown oil which was purified by column chromatography using 35% ethyl acetate in hexane as eluent to afford ethyl 1-(4-(((tert-butoxycarbonyl)amino)methyl)-6-((4,4-difluorocyclohexyl)amino)pyrimidin-2-yl)-1H-pyrazole-3-carboxylate [0032] as a pale yellow solid (2.2 g). MS(M+1)+=481.3.

Step 6[0033]: To a solution of ethyl 1-(4-(((tert-butoxycarbonyl)amino)methyl)-6-((4,4-difluorocyclohexyl)amino)pyrimidin-2-yl)-1H-pyrazole-3-carboxylate [0032] (2.2 g, 4.578 mmol) in tetrahydrofuran was added a solution of lithium aluminum hydride in tetrahydrofuran (3.43 mL, 2 M, 6.867 mmol) at −20° C. and the reaction mixture was stirred at rt. After 30 min, the reaction mixture was quenched with saturated aqueous sodium sulfate solution at 0° C. and stirred at rt for 10 min. The mixture was passed through celite bed, washed with ethyl acetate (50 mL). The combined filtrate was concentrated under reduced pressure to afford tert-butyl ((6-((4,4-difluorocyclohexyl)amino)-2-(3-(hydroxymethyl)-1H-pyrazol-1-yl)pyrimidin-4-yl)methyl)carbamate [0033] as an off-white solid (1.9 g). MS(M+1)+=439.1.

Step 7[0034]: To a solution of tert-butyl ((6-((4,4-difluorocyclohexyl)amino)-2-(3-(hydroxymethyl)-1H-pyrazol-1-yl)pyrimidin-4-yl)methyl)carbamate [0033] (1.9 g, 4.333 mmol) in dichloromethane was added diethylaminosulfur trifluoride (1.0 g, 6.499 mmol) at −20° C. and the reaction mixture was stirred at same temperature for 15 min, quenched with saturated aqueous sodium bicarbonate solution at 0° C. and extracted with dichloromethane (2×50 mL). The combined organic layer was dried over anhydrous sodium sulfate, filtered and concentrated under reduced pressure to afford a red solid which was purified by column chromatography using 35% ethyl acetate in hexane as eluent to afford tert-butyl ((6-((4,4-difluorocyclohexyl)amino)-2-(3-(fluoromethyl)-1H-pyrazol-1-yl)pyrimidin-4-yl)methyl)carbamate[0034] as off-white solid (0.75 g). MS(M+1)+=441.2.

Step 8[0036]: To a solution of tert-butyl ((6-((4,4-difluorocyclohexyl)amino)-2-(3-(fluoromethyl)-1H-pyrazol-1-yl)pyrimidin-4-yl)methyl)carbamate [0034] (0.15 g, 0.340 mmol) in dichloromethane was added dry hydrogen chloride in dioxane (4M) at 0° C. and the reaction mixture was stirred at rt for 1 h, concentrated under reduced pressure and the residue was diluted with dichloromethane (20 mL). To the solution was added triethylamine (~1.5 mL) at 0° C. followed by acetyl chloride (0.054 g, 0.68 mmol). After 10 min, the reaction mixture was quenched with water, extracted with dichloromethane, washed with water and brine solution. The combined organic layer was dried over anhydrous sodium sulfate, filtered and concentrated under reduced pressure to afford N-((6-((4,4-difluorocyclohexyl)amino)-2-(3-(fluoromethyl)-1H-pyrazol-1-yl)pyrimidin-4-yl)methyl)acetamide [0036], Compound 327 as an off-white solid (0.055 g). MS(M+1)+=383.2, $^1$H NMR (400 MHz, DMSO-d6) δ 8.63 (s, 1H), 8.49 (s, 1H), 7.81 (s, 1H), 6.65 (s, 1H), 6.28 (s, 1H), 5.42 (d, JF=48 Hz, 2H), 4.13 (bs, 3H), 2.15-1.90 (m, 9H), 1.62-1.45 (m, 2H).

Example 7

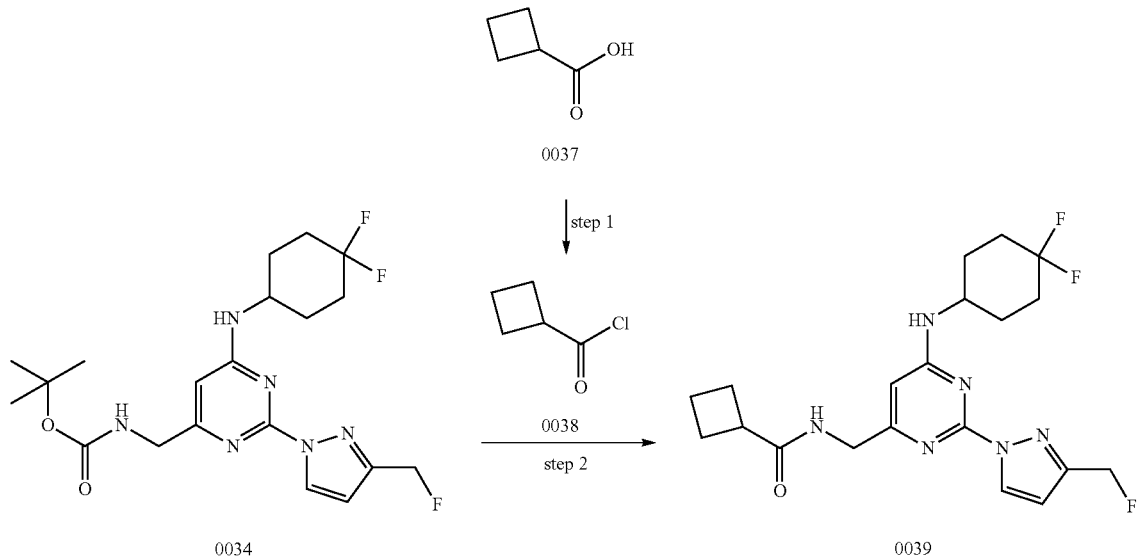

Step 1[0038]: To a solution of cyclobutanecarboxylic acid (0.3 g, 2.99 mmol) in dichloromethane was added oxalyl chloride (1.14 g, 8.98 mmol) and N,N-dimethylformamide (0.02 g, 0.3 mmol) at 0° C. and the reaction mixture was stirred rt. After 1 h, the reaction mixture was concentrated under reduced pressure to afford cyclobutanecarbonyl chloride [0038] as brown oil (0.4 g). This was taken as such to next step.

Step 2[0039]: The procedure is similar to Step 8[0036] in example 6. 0.3 g of tert-butyl ((6-((4,4-difluorocyclohexyl)amino)-2-(3-(fluoromethyl)-1H-pyrazol-1-yl)pyrimidin-4-yl)methyl)carbamate[0034] gave 0.098 g of N-((6-((4,4-difluorocyclohexyl)amino)-2-(3-(fluoromethyl)-1H-pyrazol-1-yl)pyrimidin-4-yl)methyl)cyclobutanecarboxamide [0039], Compound 328 as pale brown solid. MS(M+1)$^+$=423.2; $^1$H NMR (400 MHz, DMSO-d6) δ 8.61 (s, 1H), 8.26 (s, 1H), 7.80 (s, 1H), 6.64 (s, 1H), 6.21 (s, 1H), 5.45 (d, JF=48 Hz, 2H), 4.12 (bs, 3H), 3.19-3.07 (m, 1H), 2.25-2.13 (m, 2H), 2.12-1.85 (m, 9H), 1.85-1.75 (m, 1H), 1.65-1.50 (m, 2H).

Example 8

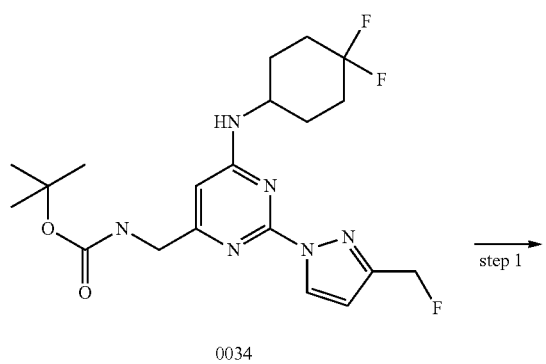

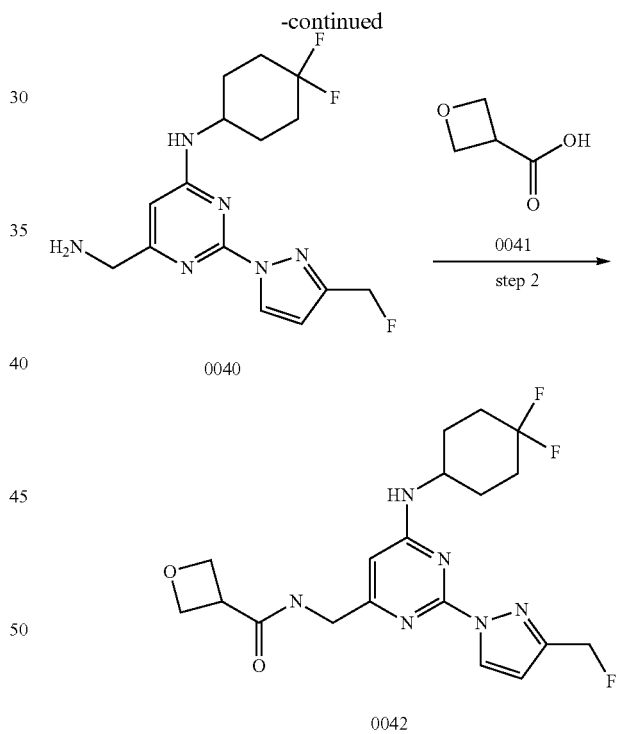

Step 1[0040]: To a solution of tert-butyl ((6-((4,4-difluorocyclohexyl)amino)-2-(3-(fluoromethyl)-1H-pyrazol-1-yl)pyrimidin-4-yl)methyl)carbamate [0034] (0.3 g, 0.68 mmol) in dichloromethane was added 4M HCl in dioxane (5 mL) at 0° C. and the reaction mixture was stirred at rt for 1 h, concentrated under reduced pressure to afford 6-(aminomethyl)-N-(4,4-difluorocyclohexyl)-2-(3-(fluoromethyl)-1H-pyrazol-1-yl)pyrimidin-4-amine [0040] as an off-white solid. This was taken as such to next step.

Step 2[0042]: To a solution of 3-oxetanecarboxylic acid [0041] (0.140 g, 1.38 mmol) in N,N-dimethylformamide was added 1-propanephosphonic acid cyclic anhydride ((1.317 g, 2.07 mmol), triethylamine (0.209 g, 2.07 mmol) at 0° C. and the reaction mixture was stirred at rt. After 15 min, 6-(aminomethyl)-N-(4,4-difluorocyclohexyl)-2-(3-(fluoromethyl)-1H-pyrazol-1-yl)pyrimidin-4-amine [0040] (0.26 g, 0.69 mmol) was added to the reaction mixture at 0° C. and stirred at rt for 16 h. The reaction mixture was quenched with water, extracted with ethyl acetate, washed with water and brine. The combined organic layer was dried over anhydrous sodium sulfate, filtered and concentrated under reduced pressure to afford brown oil, which was purified in the Reveleris flash system using ethyl acetate in hexane followed by methanol in chloroform as eluents in 12 g column. The product was isolated at 07% methanol in chloroform as eluent to afford N-((6-((4,4-difluorocyclohexyl)amino)-2-(3-(fluoromethyl)-1H-pyrazol-1-yl)pyrimidin-4-yl)methyl)oxetane-3-carboxamide, Compound 333 [0042] as a white solid (0.05 g). MS(M+1)$^+$=425.2; $^1$H NMR (400 MHz, DMSO-d6) δ 8.63 (bs, 1H), 8.54 (bs, 1H), 7.82 (s, 1H), 6.66 (s, 1H), 6.24 (s, 1H), 5.45 (d, JF=48 Hz, 1H), 4.69 (d, J=7.9 Hz, 4H), 4.19 (s, 3H), 3.92-3.82 (m, 1H), 2.12-1.92 (m, 7H), 1.57 (bs, 2H).

Example 9

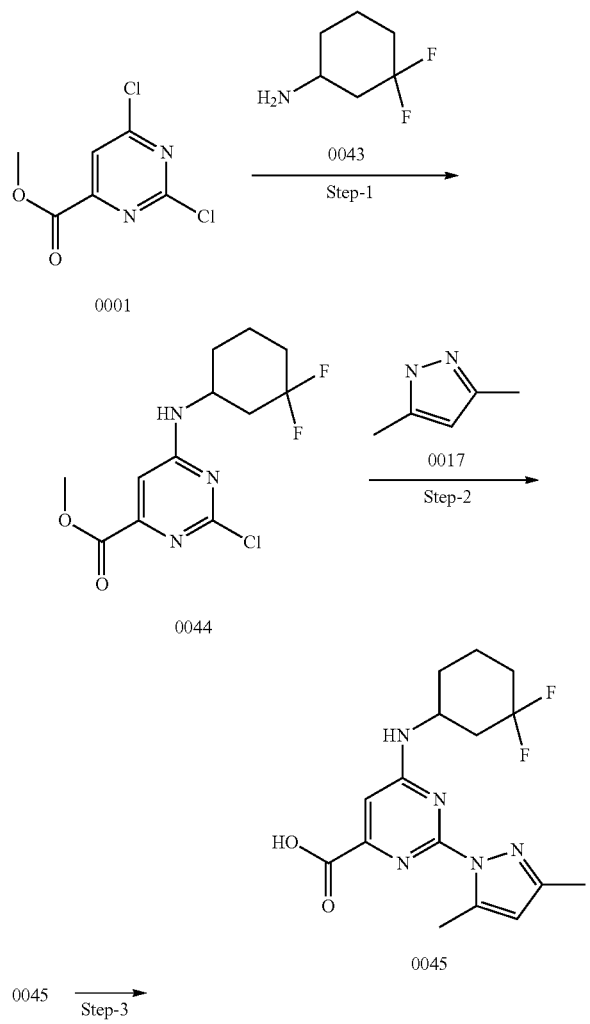

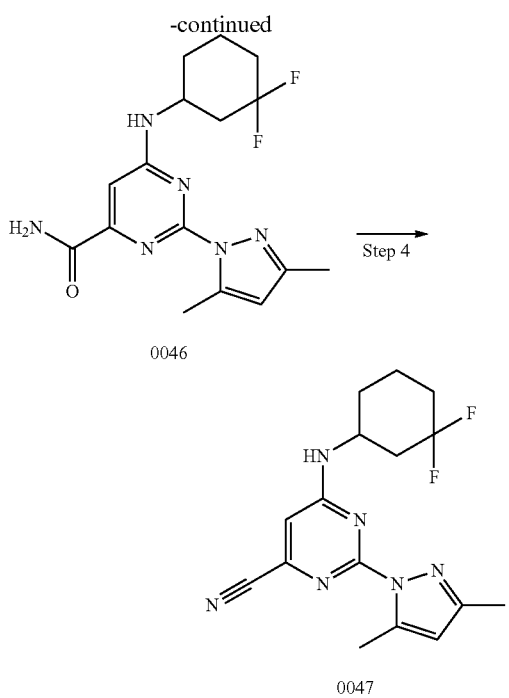

Step 1[0044]: The procedure is similar to step 1[0003] in Example 1. 1 g of methyl-2,4-dichloropyrimidine-6-carboxylate [0001] gave 1.1 g of methyl 2-chloro-6-((3,3-difluorocyclohexyl)amino)pyrimidine-4-carboxylate [0044] as a white solid.

MS(M+1)$^+$=306.7.

Step 2[0045]: The procedure is similar to step 3[0004] in Example 1. 1.1 g of methyl 2-chloro-6-((3,3-difluorocyclohexyl)amino)pyrimidine-4-carboxylate [0044] gave 2 g of 6-((3,3-difluoro cyclohexyl)amino)-2-(3,5-dimethyl-1H-pyrazol-1-yl)pyrimidine-4-carboxylic acid [0045] as yellow solid. MS(M−1)$^−$=350.0. This was taken as such to next step.

Step 3[0046] Compound 350: To a solution of 6-((3,3-difluorocyclohexyl)amino)-2-(3,5-dimethyl-1H-pyrazol-1-yl)pyrimidine-4-carboxylicacid [0045] (1.9 g, 5.407 mmol) in dichloromethane (10 mL) was added oxalyl chloride (2.74 g, 21.63 mmol) and N,N-dimethylformamide (0.04 g, 0.54 mmol) drop wise at 0° C. Then the reaction mixture was stirred at rt for 1 h. The reaction mixture was concentrated under reduced pressure under N2 atm to afford 2.2 g of 6-((3,3-difluorocyclohexyl)amino)-2-(3,5-dimethyl-1H-pyrazol-1-yl)pyrimidine-4-carbonyl chloride. 6-((3,3-difluorocyclopentyl)amino)-2-(3,5-dimethyl-1H-pyrazol-1-yl)pyrimidine-4-carbonyl chloride was dissolved in tetrahydrofuran (10 mL) and the reaction mixture was purged with ammonia gas at −10° C. for 15 min. The reaction mixture was concentrated under reduced pressure to afford crude was purified by column chromatography using 6% methanol in chloroform as a solvent to afford 0.4 g of 6-((3,3-difluorocyclohexyl)amino)-2-(3,5-dimethyl-1H-pyrazol-1-yl)pyrimidine-4-carboxamide (Compound 350) [0046] as an off-white solid.

MS(M+1)$^+$=351.2. $^1$H-NMR (400 MHz, DMSO-d6): δ 8.10 (d, J=7.60 Hz, 1H), 7.80 (s, 1H), 7.73 (s, 1H), 6.97 (s, 1H), 6.09 (s, 1H), 4.09 (bs, 1H), 2.54 (s, 3H), 2.44 (bs, 1H), 2.18 (s, 3H), 2.12-1.70 (m, 5H), 1.55-1.30 (m, 2H).

Step 4[0047] Compound 351: To a solution of 6-((3,3-difluorocyclohexyl)amino)-2-(3,5-dimethyl-1H-pyrazol-1-yl)pyrimidine-4-carboxamide [0046] (0.35 g, 0.99 mmol) in dichloromethane was added triethylamine (0.50 g, 4.99 mmol) and trifluoromethanesulfonic anhydride (0.71 g, 2.49 mmol) at 0° C. and the reaction mixture was stirred at same temperature. After 1 h, the reaction mixture was quenched with ice and extracted with chloroform, washed with water and brine solution. The combined organic layer was dried over anhydrous sodium sulfate, filtered and concentrated under reduced pressure to afford a pale brown solid, was purified in the Reveleris flash system instrument using ethyl acetate in hexane as solvent in 24 g column to afford 0.24 g of 6-((3,3-difluorocyclohexyl)amino)-2-(3,5-dimethyl-1H-pyrazol-1-yl)pyrimidine-4-carbonitrile (Compound 351) [0047] as an off-white solid. MS(M+1)$^+$=333.2. $^1$H NMR (400 MHz, DMSO-d6) δ 8.42 (d, J=7.5 Hz, 1H), 6.85 (s, 1H), 6.12 (s, 1H), 4.07 (bs, 1H), 2.54 (s, 3H), 2.42-2.32 (m, 1H), 2.17 (s, 3H), 2.03-1.70 (m, 5H), 1.50-1.32 (m, 2H).

Example 10 yl)-N-methoxy-N-methylpyrimidine-4-carboxamide [0045] (0.33 g, 0.836 mmol) in tetrahydrofuran (7 mL) at −70° C. was added methyl magnesium bromide ((3 M solution in tetrahydrofuran) 2.23 mL, 6.69 mmol) drop wise. The reaction mixture was stirred at rt for 10 min. The reaction mixture was quenched with saturated solution of ammonium chloride (5 mL), extracted with ethyl acetate (2×20 mL). The combined organic layer was washed with brine (10 mL) and dried over anhydrous sodium sulfate to afford 0.6 g of crude product which was purified by column chromatography using 56% ethyl acetate in pet ether as eluent to afford 1-(6-((3,3-difluorocyclohexyl)amino)-2-(3,5-dimethyl-1H-pyrazol-1-yl)pyrimidin-4-yl)ethan-1-one (Compound 352) [0049] of as a white solid (0.150 g). MS(M+1)$^+$=350.2, $^1$H NMR (400 MHz, DMSO-d6) δ 8.12 (d, J=7.6 Hz, 1H), 6.84 (s, 1H), 6.12 (s, 1H), 4.13 (s, 1H), 2.56 (d, J=9.1 Hz, 6H), 2.20 (s, 3H), 2.05-1.73 (m, 6H), 1.52-1.31 (m, 2H).

Step 3[0050] Compound 353: To a cooled solution of 1-(6-((3,3-difluorocyclohexyl)amino)-2-(3,5-dimethyl-1H-

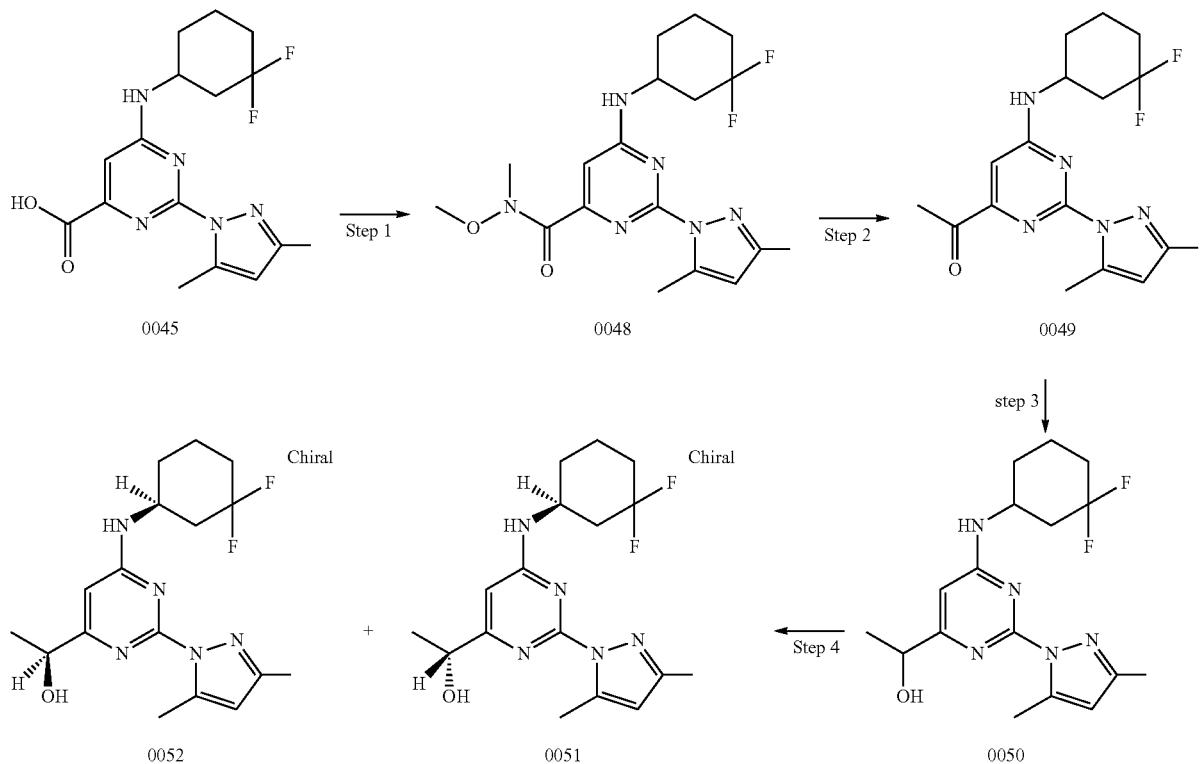

Step 1[0048]: To a solution of 6-((3,3-difluorocyclohexyl) amino)-2-(3,5-dimethyl-1H-pyrazol-1-yl)pyrimidine-4-carboxylic acid [0045](0.52 g, 1.48 mmol) in N,N-dimethylformamide (5 mL) was added N,N-diisopropyl ethylamine (1.28 mL, 7.4 mmol), followed by N,O-dimethylhydroxylamine (0.22 g, 2.22 mmol) hydrochloride and HBTU (0.67 g, 1.776). The reaction mixture was stirred at rt for 3 h. The reaction mixture was quenched with ice, extracted with ethyl acetate (2×20 mL). The combined organic layer was washed with water (20 mL), followed by brine (20 mL), dried over anhydrous sodium sulfate to afford 6-((3,3-difluorocyclohexyl)amino)-2-(3,5-dimethyl-1H-pyrazol-1-yl)-N-methoxy-N-methylpyrimidine-4-carboxamide [0048] as a yellow solid (0.6 g). MS(M+1)$^+$=395.0

Step 2[0049] Compound 352: To a solution of 6-((3,3-difluorocyclohexyl)amino)-2-(3,5-dimethyl-1H-pyrazol-1- pyrazol-1-yl)pyrimidin-4-yl)ethan-1-one [0049] (0.17 g, 0.486 mmol) in methanol (3 mL) was added sodium borohydride (0.018 g, 0.486 mmol). The reaction mixture was stirred at rt for 10 min, concentrated under reduced pressure, dissolved in water (5 mL), neutralized with 1.5 N HCl solutions (10 mL) and extracted with ethyl acetate (2×20 mL). The combined organic layer was washed with brine (10 mL), dried over anhydrous sodium sulfate to afford 1-(6-((3,3-difluorocyclohexyl)amino)-2-(3,5-dimethyl-1H-pyrazol-1-yl)pyrimidin-4-yl)ethan-1-ol (Compound 353) [0050] as a white solid (0.160 g). MS(M+1)$^+$=352.2, $^1$H-NMR (400 MHz, DMSO-d6): δ 7.70 (s, 1H), 6.51 (s, 1H), 6.03 (s, 1H), 5.36 (s, 1H), 4.46 (s, 1H), 4.07 (s, 2H), 3.32 (m, 1H), 2.16 (s, 1H), 1.99 (s, 3H), 1.95-1.91 (m, 3H), 1.80-1.73 (m, 5H), 1.44-1.38 (m, 2H), 1.34-1.28 (m, 5H), Step 4[0051 and 0052] Compound 354 and 355: The isomers were separated by Supercritical Fluid Chromatography (SFC) to afford 0.040 g of (+)-1-(6-(((S)-3,3-difluorocyclohexyl)amino)-2-(3,5-dimethyl-1H-pyrazol-1-yl)pyrimidin-4-yl)ethan-1-ol (Compound 354) [0051] as a yellow solid MS(M+1)$^+$=352.2, $^1$H-NMR (400 MHz, DMSO-d6): δ 7.70 (d, J=6.76 Hz, 1H), 6.51 (s, 1H), 6.03 (s, 1H), 5.36 (d, J=4.12 Hz, 1H), 4.46 (t, J=5.36 Hz, 1H), 4.07 (bs, 1H), 2.56 (s, 2H), 2.49-2.48 (m, 1H), 2.16 (s, 3H), 2.10-1.56 (m, 6H), 1.50-1.49 (m, 1H), 1.48-1.35 (m, 4H), and (−)-1-(6-(((S)-3, 3-difluorocyclohexyl)amino)-2-(3,5-dimethyl-1H-pyrazol-1-yl)pyrimidin-4-yl)ethan-1-ol (Compound 355) [0052] as a yellow solid. MS(M+1)$^+$=352.2, $^1$H-NMR (400 MHz, DMSO-d6): δ 7.70 (bs, 1H), 6.51 (s, 1H), 6.03 (s, 1H), 5.36 (s, 1H), 4.46 (bs, 1H), 4.07 (bs, 2H), 3.32 (m, 1H), 2.48-2.47 (m, 1H), 2.16 (s, 2H), 2.01-1.99 (m, 3H), 1.99-1.56 (m, 4H), 1.56-1.49 (m, 1H), 1.49-1.30 (m, 4H).

Example 11

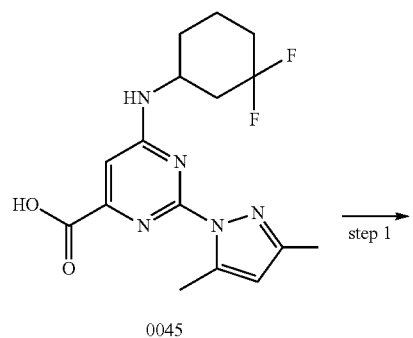

0045

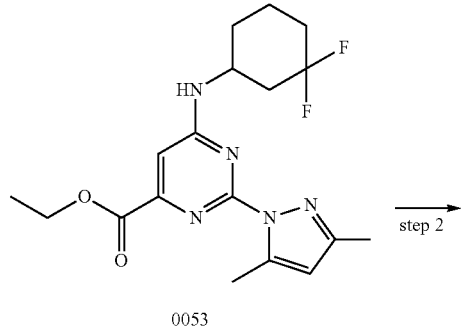

0053

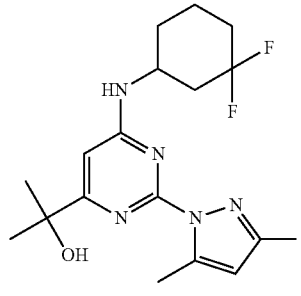

0054

Step 1[0053]: Concentrated sulfuric acid (5 mL, 93.80 mmol) was added to a solution of 6-((3,3-difluorocyclohexyl)amino)-2-(3,5-dimethyl-1H-pyrazol-1-yl)pyrimidine-4-carboxylicacid [0045] (1.1 g, 3.130 mmol) in ethanol (20 mL), after addition the reaction mixture was heated at 75° C. for 5 h, concentrated under reduced pressure, diluted with water (20 mL), cooled to 5° C., basified with solid sodium carbonate till pH~10 and extracted with ethyl acetate (2×100 mL). The combined organic layers were washed with brine (3×300 mL), dried over anhydrous sodium sulfate, filtered and concentrated to afford 1.2 g of ethyl 6-((3,3-difluorocyclohexyl)amino)-2-(3,5-dimethyl-1H-pyrazol-1-yl)pyrimidine-4-carboxylate. This was purified by column chromatography using 20% ethyl acetate in pet ether as eluent to afford ethyl 6-((3,3-difluorocyclohexyl)amino)-2-(3,5-dimethyl-1H-pyrazol-1-yl)pyrimidine-4-carboxylate [0053] as a yellow solid (0.660 g). MS(M+1)$^+$=380.0

Step 2[0054] Compound 356: To a solution of ethyl 6-((3,3-difluorocyclohexyl)amino)-2-(3,5-dimethyl-1H-pyrazol-1-yl)pyrimidine-4-carboxylate [0053] (0.15 g, 0.395 mmol) in tetrahydrofuran (2 mL), was added methyl magnesium bromide (3 M solution in tetrahydrofuran) 0.32 mL, 0.988 mmol)) drop-wise at 0° C. after addition the reaction mixture was stirred at rt for 3 h. The reaction mixture was cooled to 0° C. and quenched with (1.5 N) HCl solutions (5 mL). It was then extracted with ethyl acetate (2×30 mL). The combined organic layer was washed with water (20 mL), followed by brine (20 mL) and dried over anhydrous sodium sulfate to afford crude product which was purified by preparative HPLC to afford 2-(6-((3,3-difluorocyclohexyl)amino)-2-(3,5-dimethyl-1H-pyrazol-1-yl)pyrimidin-4-yl)propan-2-ol (Compound 356) [0054] as an off-white solid (0.070 g). MS(M+1)$^+$=366.2, $^1$H NMR (400 MHz, DMSO-d6) δ 7.68 (bs, 1H), 6.64 (s, 1H), 6.04 (s, 1H), 5.18 (s, 1H), 4.10 (bs, 1H), 2.48 (s, 3H), 2.58-2.45 (m, 1H), 2.17 (s, 3H), 2.08-1.89 (m, 2H), 1.89-1.65 (m, 3H), 1.55-1.43 (m, 1H), 1.37 (s, 6H), 1.33-1.29 (m, 1H).

Example 12

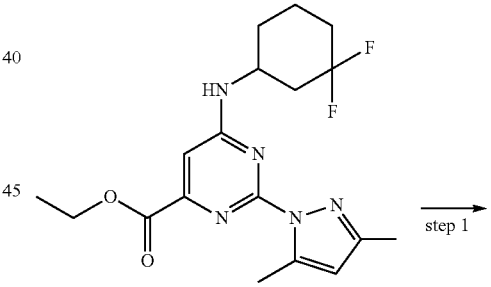

0053

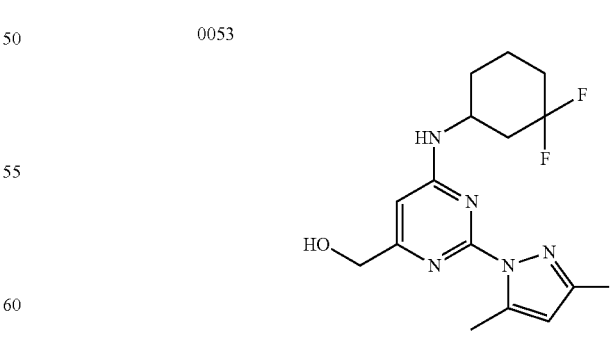

0055

Step 1[0055]: Compound 357 To a solution of ethyl 6-((3,3-difluorocyclohexyl)amino)-2-(3,5-dimethyl-1H-pyrazol-1-yl)pyrimidine-4-carboxylate [0053] (220 g, 0.579 mmol) in tetrahydrofuran (6 mL), was added lithium aluminium hydride (2 M solution in tetrahydrofuran, 0.579 mL, 1.159 mmol) drop-wise at −78° C., after addition the reaction mixture was stirred at −78° C. for 3 h. The reaction mixture was quenched with saturated solution of ammonium chloride solution (10 mL). It was then extracted with ethyl acetate (2×20 mL). The combined organic layer was washed with water (10 mL), followed by brine and dried over anhydrous sodium sulfate to afford (6-((3,3-difluorocyclohexyl)amino)-2-(3,5-dimethyl-1H-pyrazol-1-yl)pyrimidin-4-yl)methanol (Compound 357) [0055] as an off-white solid (0.150 g). MS(M+1)$^+$=338.2, $^1$H NMR (400 MHz, DMSO-d6) δ 7.73 (d, J=7.6 Hz, 1H), 6.50 (s, 1H), 6.04 (s, 1H), 5.45 (t, J=5.8 Hz, 1H), 4.35 (d, J=5.6 Hz, 2H), 4.07 (s, 1H), 2.40 (s, 1H), 2.16 (s, 4H), 2.04-1.91 (m, 2H), 1.88-1.69 (m, 3H), 1.46 (d, J=13.6 Hz, 1H), 1.35 (d, J=7.7 Hz, 1H).

Example 13

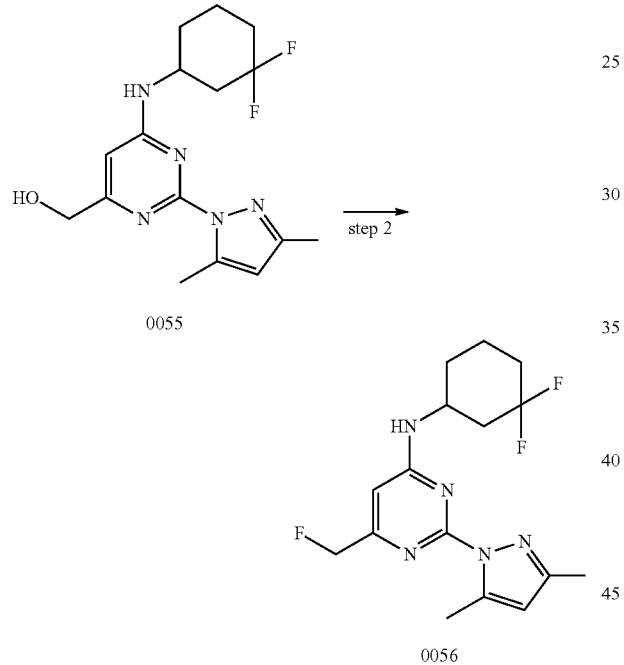

Step 1[0056] Compound 358: To a solution of (6-((3,3-difluorocyclohexyl)amino)-2-(3,5-dimethyl-1H-pyrazol-1-yl)pyrimidin-4-yl)methanol [0055] (0.1 g, 0.296 mmol) in dichloromethane (10 mL) was added diethylaminosulfur trifluoride (0.095 g, 0.592 mmol) drop-wise at 0° C., after addition the reaction mixture was stirred at rt for 18 h. The reaction mixture was diluted with dichloromethane (20 mL). The organic layer was washed with 10% sodium bicarbonate solution (15 mL) to afford crude product which was purified by preparative HPLC to afford N-(3,3-difluorocyclohexyl)-2-(3,5-dimethyl-1H-pyrazol-1-yl)-6-(fluoromethyl)pyrimidin-4-amine (Compound 358) [0056] as a yellow solid (0.050 g). MS(M+1)$^+$=340.2, $^1$H NMR (400 MHz, DMSO-d6) δ 7.89 (d, J=7.5 Hz, 1H), 6.43 (s, 1H), 6.07 (s, 1H), 5.31 (d, JF=46.3 Hz, 2H), 4.09 (bs, 1H), 2.53 (s, 3H), 2.49-2.40 (m, 1H), 2.16 (s, 3H), 2.08-1.92 (m, 2H), 1.92-1.65 (m, 3H), 1.55-1.25 (m, 2H).

Example 14

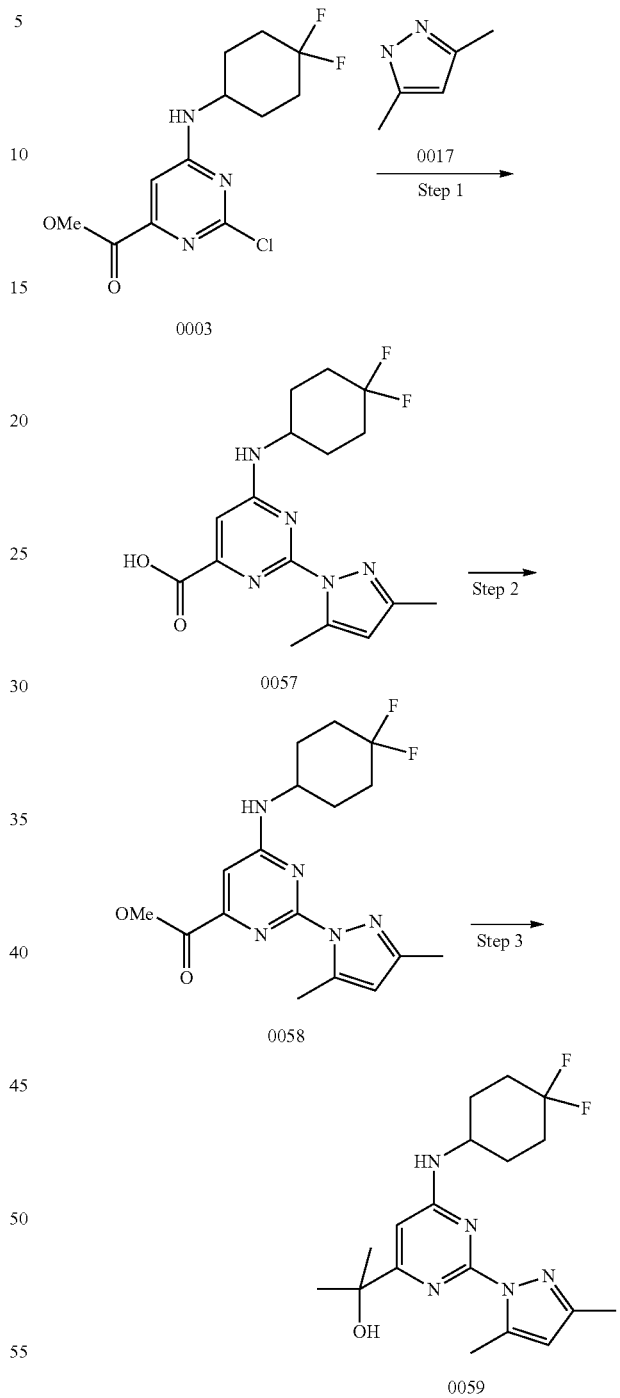

Step 1[0057]: The procedure is similar to step 3[0006] in example 1. 2.2 g of methyl 2-chloro-6-((4,4-difluorocyclohexyl)amino)pyrimidine-4-carboxylate [0003] gave 2.8 g of 6-((4,4-difluorocyclohexyl)amino)-2-(3,5-dimethyl-1H-pyrazol-1-yl)pyrimidine-4-carboxylic acid [0057] as a yellowish solid. MS(M+1)$^+$=352.0.

Step 2[0058]: The procedure is similar to step 4[0007] in example 1, 0.9 g of 6-((4,4-difluorocyclohexyl)amino)-2-(3, 5-dimethyl-1H-pyrazol-1-yl)pyrimidine-4-carboxylic acid [0057] gave 0.71 g of methyl 6-((4,4-difluorocyclohexyl)amino)-2-(3,5-dimethyl-1H-pyrazol-1-yl)pyrimidine-4-carboxylate [0058] as an yellow solid. MS(M+1)$^+$=366.2.

Step 3[0059] The procedure is similar to step 2[0049] in example 10. 0.65 g of methyl 6-((4,4-difluorocyclohexyl)amino)-2-(3,5-dimethyl-1H-pyrazol-1-yl)pyrimidine-4-carboxylate [0058] gave 0.13 g of 2-(6-((4,4-difluorocyclohexyl)amino)-2-(3,5-dimethyl-1H-pyrazol-1-yl)pyrimidin-4-yl)propan-2-ol [0059], Compound 152. MS(M+1)$^+$=366.2, $^1$H-NMR (400 MHz, DMSO-d6): δ 7.62 (s, 1H), 6.64 (s, 1H), 6.03 (s, 1H), 5.17 (s, 1H), 4.05 (bs, 1H), 2.56 (s, 3H), 2.15 (s, 3H), 2.07-1.94 (m, 6H), 1.58-1.55 (m, 2H), 1.37 (s, 6H).

Example 15

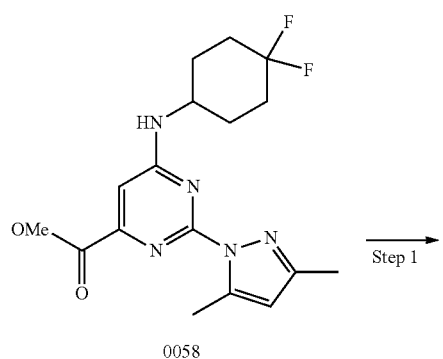

0058

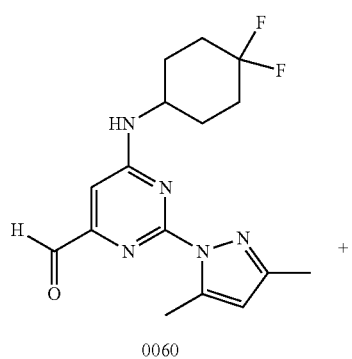

0060

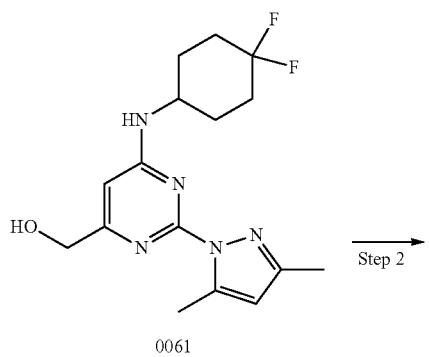

0061

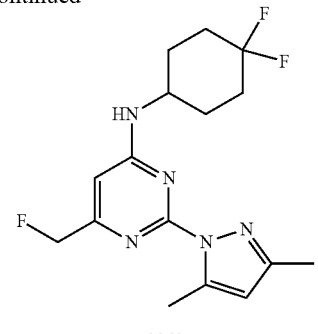

0062

Step 1[0060 and 0061] Lithium aluminum hydride (2M THF solution, 31.62 mmol) was added drop-wise at −78° C. to a solution of ethyl 6-((4,4-difluorocyclohexyl)amino)-2-(3,5-dimethyl-1H-pyrazol-1-yl)pyrimidine-4-carboxylate [0058] (6 g, 15.814 mmol) in tetrahydrofuran (85 mL). After addition the reaction mixture was stirred at −78° C. for 3 h, quenched with water (25 mL) and extracted with ethyl acetate (3×500 mL). The combined organic layer was washed with brine (3×300 mL), dried over anhydrous sodium sulfate, filtered and concentrated under reduced pressure to afford mixture an which was purified by column chromatography using 50% ethyl acetate in pet ether as eluent to afford of 6-((4,4-difluorocyclohexyl)amino)-2-(3,5-dimethyl-1H-pyrazol-1-yl)pyrimidine-4-carbaldehyde [0060] as an yellow solid (1.2 g MS(M+1)$^+$=338.0) and (6-((4,4-difluorocyclohexyl)amino)-2-(3,5-dimethyl-1H-pyrazol-1-yl)pyrimidin-4-yl)methanol [0061], Compound 137 as an yellow solid (2.1 g). MS(M+1)$^+$=336.2, $^1$H NMR (400 MHz, DMSO-d6) δ 7.67 (d, J=7.7 Hz, 1H), 6.52 (s, 1H), 6.04 (s, 1H), 5.44 (t, J=5.9 Hz, 1H), 4.35 (d, J=5.6 Hz, 2H), 4.04 (bs, 1H), 2.56 (s, 3H), 2.16 (s, 3H), 2.10-1.85 (m, 6H), 1.65-1.56 (m, 2H).

Step 2[0062]: The procedure is similar to step 3[0012] in example 2. 0.25 g of (6-((4,4-difluorocyclohexyl)amino)-2-(3,5-dimethyl-1H-pyrazol-1-yl)pyrimidin-4-yl)methanol [0061] gave 0.05 g of N-(4,4-difluorocyclohexyl)-2-(3,5-dimethyl-1H-pyrazol-1-yl)-6-(fluoromethyl)pyrimidin-4-amine [0062], Compound 165 as an off-white solid.

MS(M+1)$^+$=340.2, $^1$H-NMR (400 MHz, DMSO-d6): δ 7.83 (d, J=6.96 Hz, 1H), 6.41 (s, 1H), 6.05 (s, 1H), 5.30 (d, JF=46.3 Hz, 2H), 4.04 (bs, 1H), 2.52 (s, 3H), 2.14 (s, 3H), 2.07-1.94 (m, 6H), 1.57-1.54 (m, 2H),

Example 16

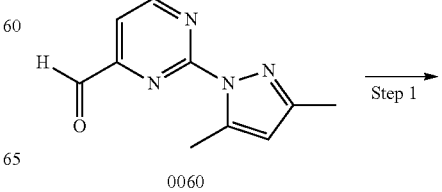

0060

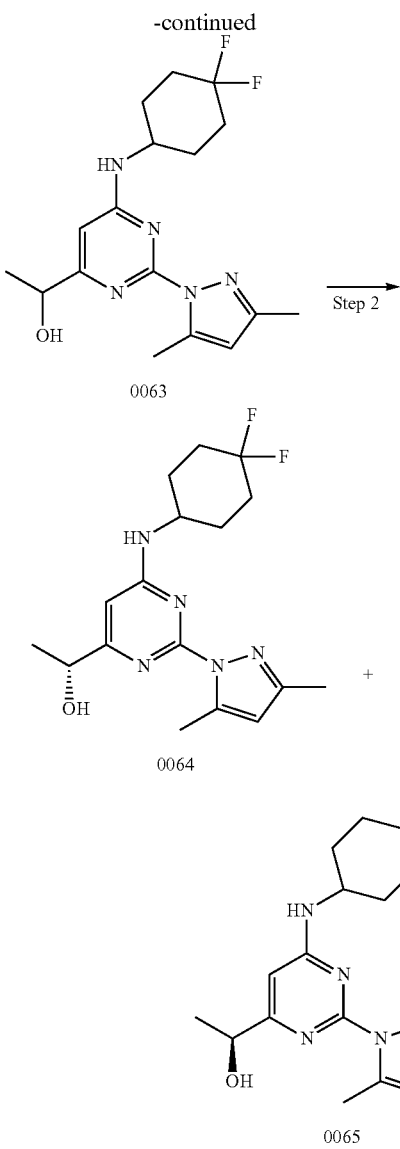

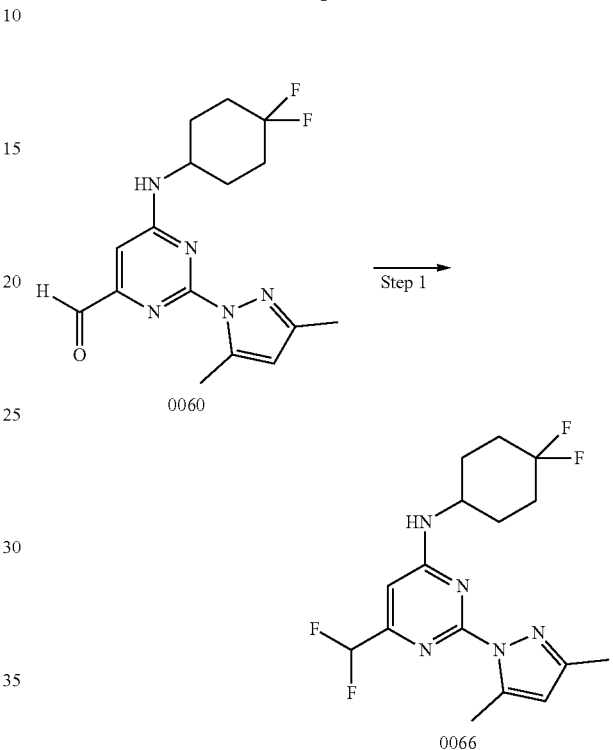

Step 1[0063]: The procedure is similar to step 2[0049] in example 10. 2.8 g of 6-((4,4-difluorocyclohexyl)amino)-2-(3,5-dimethyl-1H-pyrazol-1-yl)pyrimidine-4-carbaldehyde [0060] gave 0.48 g of racemate 1-(6-((4,4-difluorocyclohexyl)amino)-2-(3,5-dimethyl-1H-pyrazol-1-yl)pyrimidin-4-yl)ethan-1-ol [0063], as an off-white solid. MS(M+1)⁺= 352.2, ¹H-NMR (400 MHz, DMSO-d6): δ 7.64 (d, J=7.20 Hz, 1H), 6.53 (s, 1H), 6.03 (s, 1H), 5.37 (s, 1H), 4.34 (bs, 1H), 4.10 (bs, 1H), 2.13 (s, 3H), 2.06-1.85 (m, 6H), 1.65-1.49 (m, 2H), 1.39-1.22 (m, 6H).

Step 2[0064 and 0065]: 0.48 g of 1-(6-((4,4-difluorocyclohexyl)amino)-2-(3,5-dimethyl-1H-pyrazol-1-yl)pyrimidin-4-yl)ethan-1-ol [63] was purified by chiral preparative HPLC to afford 0.12 g of (−)1-(6-((4,4-difluorocyclohexyl)amino)-2-(3,5-dimethyl-1H-pyrazol-1-yl)pyrimidin-4-yl)ethan-1-ol [0064], Compound 198 as an off-white solid. MS(M+1)⁺=352.2. SOR: −9.5°, solvent-methanol, concentration=0.2, Temp—27.5° C. ¹H-NMR (400 MHz, DMSO-d6): δ 7.67 (d, J=7.48 Hz, 1H), 6.54 (s, 1H), 6.04 (s, 1H), 5.39 (s, 1H), 4.47 (s, 1H), 4.05 (bs, 1H), 2.52 (s, 3H), 2.16 (s, 3H), 2.06-1.94 (m, 6H), 1.58-1.55 (m, 2H), 1.31 (d, J=0.60 Hz, 3H), and 0.12 g of (+)1-(6-((4,4-difluorocyclohexyl)amino)-2-(3,5-dimethyl-1H-pyrazol-1-yl)pyrimidin-4-yl)ethan-1-ol [0065], Compound 199 as an off-white solid. MS(M+1)⁺=352.2. SOR: +2.5, Solvent-methanol, Concentration=0.200, Temp—27.3° C. ¹H NMR (400 MHz, DMSO-d6) δ 7.67 (d, J=7.4 Hz, 1H), 6.54 (s, 1H), 6.04 (s, 1H), 5.39 (s, 1H), 4.47 (bs, 1H), 4.05 (bs, 1H), 2.52 (s, 3H), 2.17 (s, 3H), 2.17-1.85 (m, 6H), 1.65-1.57 (m, 2H), 1.33 (d, J=6.6 Hz, 3H).

Example 17

Step 1[0066]: The procedure is similar to step 3 [0012] in example 2. 0.21 g of 6-((4,4-difluorocyclohexyl)amino)-2-(3,5-dimethyl-1H-pyrazol-1-yl)pyrimidine-4-carbaldehyde [11] gave 0.06 g of N-(4,4-difluorocyclohexyl)-6-(difluoromethyl)-2-(3,5-dimethyl-1H-pyrazol-1-yl)pyrimidin-4-amine [0066], Compound 142 as an off-white solid. MS(M+1)⁺=358.2, ¹H-NMR (400 MHz, DMSO-d6): δ 8.10 (d, J=7.04 Hz, 1H), 6.77 (t, JF=54.7 Hz, 1H), 6.60 (s, 1H), 6.10 (s, 1H), 4.08 (bs, 1H), 2.56 (s, 3H), 2.16 (s, 3H), 2.12-1.88 (m, 6H), 1.62-1.53 (m, 2H).

Example 18

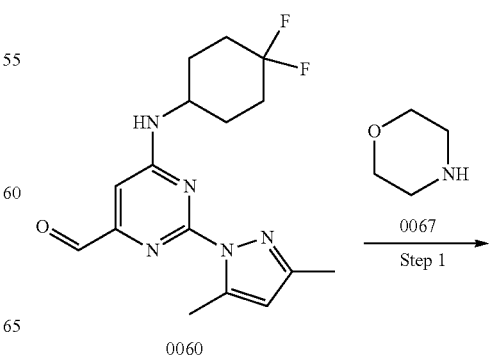

-continued

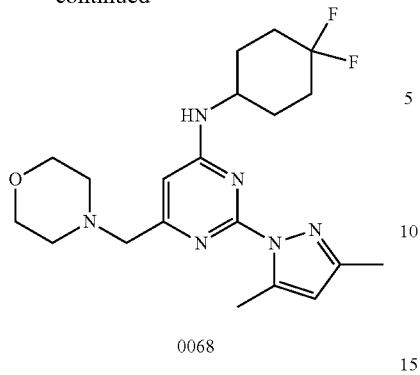

0068

Step 1 [0068]: To a solution of 6-((4,4-difluorocyclohexyl)amino)-2-(3,5-dimethyl-1H-pyrazol-1-yl)pyrimidine-4-carbaldehyde [0060] (0.35 g, 1.043 mmol) and morpholine [0067] (0.09 g, 1.047 mmol) in tetrahydrofuran (15 mL), was added titanium(IV)isopropoxide (0.61 g, 2.08 mmol) at 0° C. After addition the reaction mixture was stirred at rt for 4 h, cooled to 0° C., added ethanol (4 mL) and sodium borohydride in portions. After 16 h the reaction mixture was concentrated under reduced pressure and the residue was basified with sodium bicarbonate solution (25 mL) till pH ~10, extracted with ethyl acetate (3×100 mL), dried over anhydrous sodium sulfate, filtered and concentrated under reduced pressure to afford crude product which was purified by column chromatography using 2% methanol in chloroform as eluent to afford of N-(4,4-difluorocyclohexyl)-2-(3,5-dimethyl-1H-pyrazol-1-yl)-6-(morpholinomethyl)pyrimidin-4-amine [0068], Compound 176 as an off-white solid (0.042 g). MS(M+1)$^+$=407.2, $^1$H NMR (400 MHz, DMSO-d6) δ 7.66 (d, J=7.4 Hz, 1H), 6.50 (s, 1H), 6.04 (s, 1H), 4.03 (bs, 1H), 3.62 (t, J=4.7 Hz, 4H), 3.38 (s, 2H), 2.48 (s, 3H), 2.45 (s, 4H), 2.16 (s, 3H), 2.15-1.88 (m, 6H), 1.65-1.56 (m, 2H).

Example 19

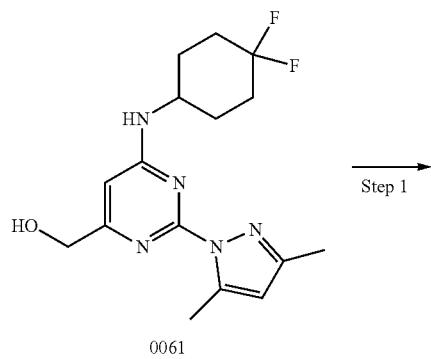

0061

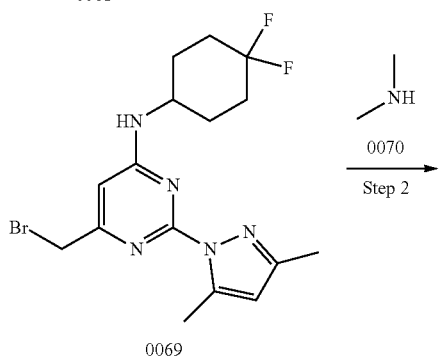

0069

-continued

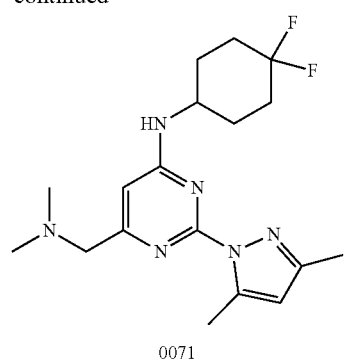

0071

Step 1 [0069]: To a solution of (6-((4,4-difluorocyclohexyl)amino)-2-(3,5-dimethyl-1H-pyrazol-1-yl)pyrimidin-4-yl)methanol [0061] (1.4 g, 4.14 mmol) in dichloromethane (55 mL) was added carbon tetrabromide (1.5 g, 4.564 mmol). The reaction mixture was stirred at rt for 16 h. The reaction mixture was diluted with water (25 mL) and extracted with dichloromethane (2×300 mL). The combined organic layer was washed with brine (25 mL), dried over anhydrous sodium sulfate, filtered and concentrated under reduced pressure to afford 6-(bromomethyl)-N-(4,4-difluorocyclohexyl)-2-(3,5-dimethyl-1H-pyrazol-1-yl)pyrimidin-4-amine [0069] as a brownish gum (1.25 g). MS(M+1 and M+3)$^+$=400.2/402.2

Step 2 [0071] NSSY5107.0001: 0.4 g of 6-(bromomethyl)-N-(4,4-difluorocyclohexyl)-2-(3,5-dimethyl-1H-pyrazol-1-yl)pyrimidin-4-amine [0069] and N,N-dimethylamine [0070] (0.18 g, 3.99 mmol) in tetrahydrofuran was heated at 80° C. to afford 0.028 g of N-(4,4-difluorocyclohexyl)-2-(3,5-dimethyl-1H-pyrazol-1-yl)-6-((dimethylamino)methyl)pyrimidin-4-amine [0071], Compound 177 as an off-white solid. MS(M+1)$^+$=365.2, $^1$H NMR (400 MHz, Chloroform-d) δ 6.44 (s, 1H), 5.99 (s, 1H), 5.21 (bs, 1H), 3.89 (bs, 1H), 3.54 (s, 2H), 2.63 (s, 3H), 2.36 (s, 6H), 2.31 (s, 3H), 2.15-2.07 (m, 4H), 1.99-1.83 (m, 2H), 1.72-1.55 (m, 2H).

Example 20

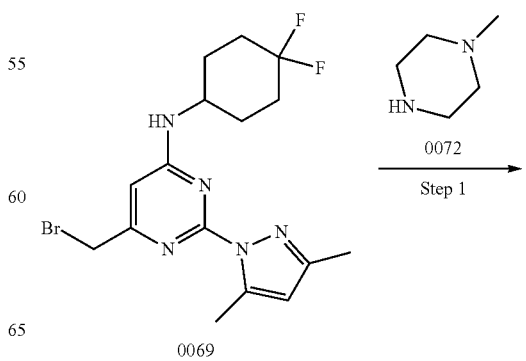

0069

-continued

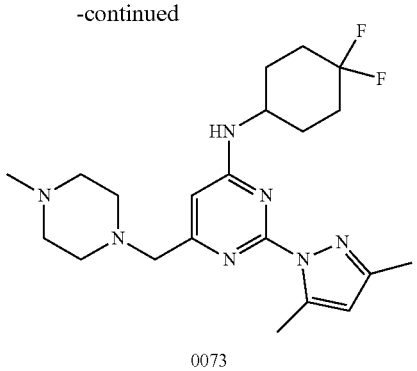

0073

Step 1 [0073]: 0.35 g of 6-(bromomethyl)-N-(4,4-difluorocyclohexyl)-2-(3,5-dimethyl-1H-pyrazol-1-yl)pyrimidin-4-amine [0069] and 1-methylpiperazine [0072] (0.096 g, 0.9618 mmol) in acetonitrile was added triethylamine (2 eq) and stirred at rt to afford 0.04 g of N-(4,4-difluorocyclohexyl)-2-(3,5-dimethyl-1H-pyrazol-1-yl)-6-((4-methylpiperazin-1-yl)methyl)pyrimidin-4-amine [0073], Compound 178 as an off-white solid.

MS(M+1)⁺=420.1, ¹H NMR (400 MHz, DMSO-d6) δ 7.65 (d, J=7.5 Hz, 1H), 6.49 (s, 1H), 6.04 (s, 1H), 4.03 (s, 1H), 3.37 (s, 2H), 2.56 (s, 3H), 2.39 (bs, 8H), 2.19 (s, 3H), 2.16 (s, 3H), 2.11-1.88 (m, 6H), 1.65-1.56 (m, 2H).

Example 21

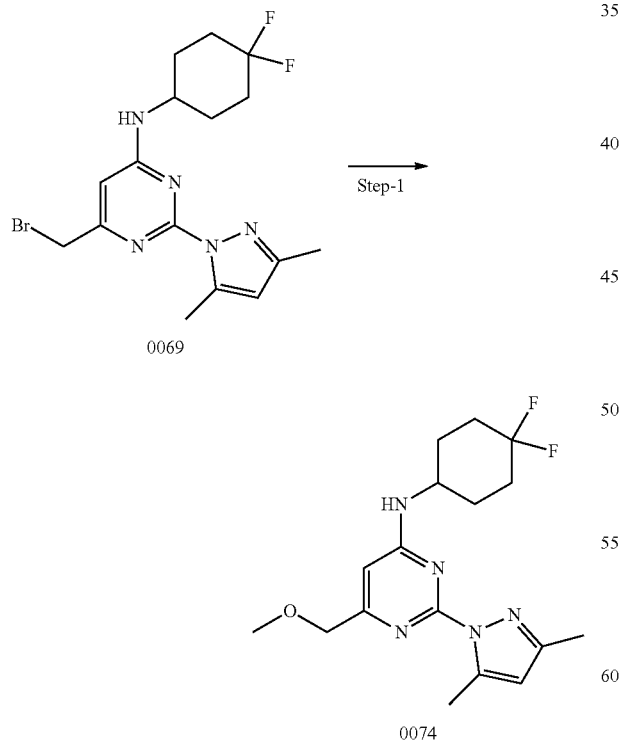

Step 1[0074]: Sodium methoxide (0.33 g, 6.24 mmol) was added to a solution of 6-(bromomethyl)-N-(4,4-difluorocyclohexyl)-2-(3,5-dimethyl-1H-pyrazol-1-yl)pyrimidin-4-amine [0069] (1.25 g, 3.122 mmol) in methanol (60 mL). After addition the reaction mixture was stirred at rt for 48 h, concentrated under reduced pressure, added saturated ammonium chloride solution (25 mL) and extracted with ethyl acetate (3×300 mL). The combined organic layer was washed with brine (50 mL), dried over anhydrous sodium sulfate, filtered and concentrated under reduced pressure to afford crude and which was purified by preparative HPLC to afford N-(4,4-difluorocyclohexyl)-2-(3,5-dimethyl-1H-pyrazol-1-yl)-6-(methoxymethyl)pyrimidin-4-amine [0074] as an off-white solid (0.71 g). MS(M+1)⁺=352.0, ¹H NMR (400 MHz, DMSO-d6) δ 7.70 (d, J=7.6 Hz, 1H), 6.43 (s, 1H), 6.05 (s, 1H), 4.30 (s, 2H), 4.04 (bs, 1H), 3.40 (s, 3H), 2.52 (s, 3H), 2.16 (s, 3H), 2.12-1.88 (m, 6H), 1.62-1.56 (m, 2H).

Example 22

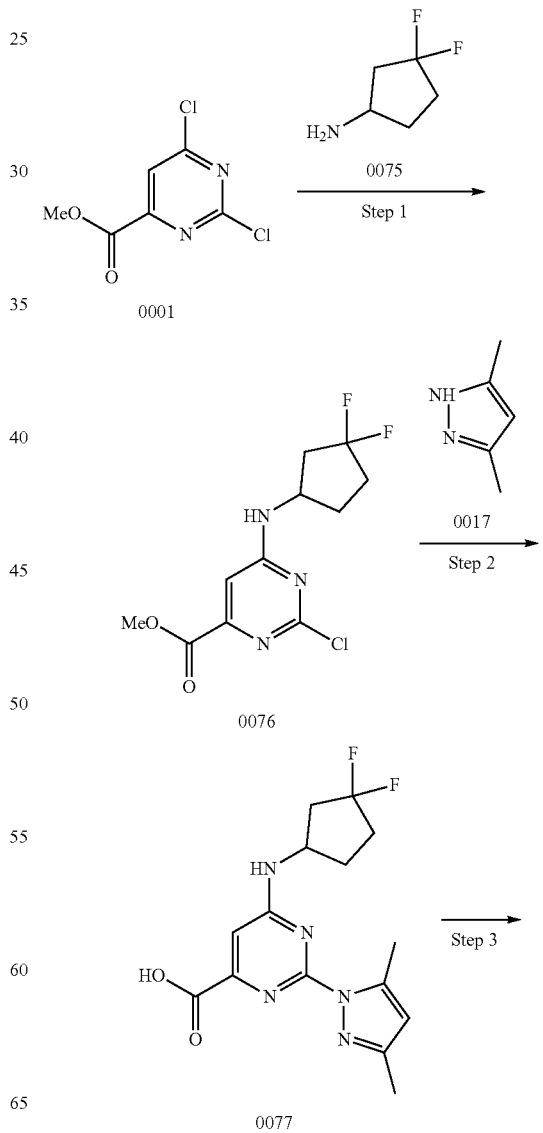

-continued

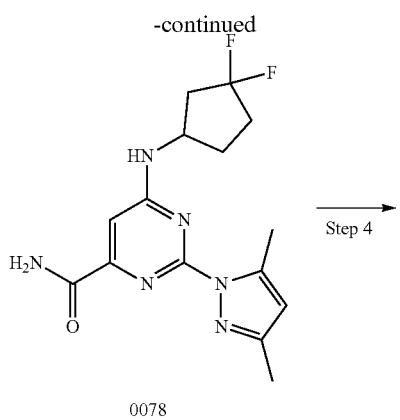

0078

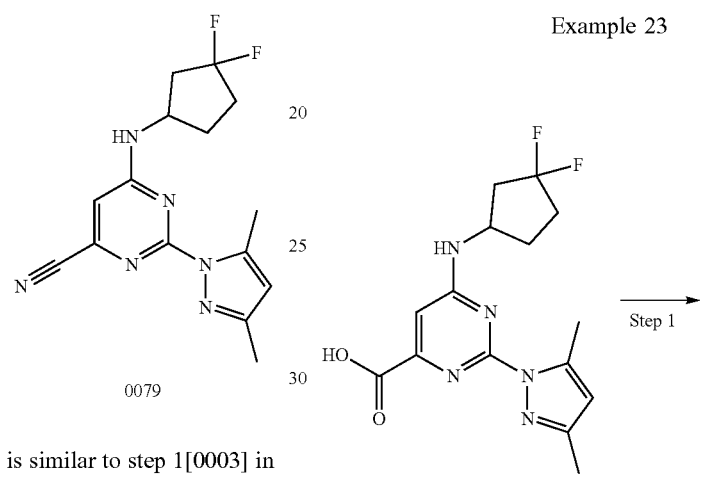

0079

Step 1[0076]: The procedure is similar to step 1[0003] in example 1. 2.0 g of methyl 2,6-dichloropyrimidine-4-carboxylate [0001] gave 2.56 g of methyl 2-chloro-6-((3,3-difluorocyclopentyl)amino)pyrimidine-4-carboxylate [0076] as a pale brown solid.

MS(M+1)$^+$=292.

Step 2[0077]: The procedure is similar to step 3[0006] in example 1. 2.0 g of methyl 2-chloro-6-((3,3-difluorocyclopentyl)amino)pyrimidine-4-carboxylate [0076] gave 2.1 g of 6-((3,3-difluorocyclopentyl)amino)-2-(3,5-dimethyl-1H-pyrazol-1-yl)pyrimidine-4-carboxylic acid [0077] as a yellow solid. MS(M+1)$^+$=338.

Step 3[0078]: To a solution of 6-((3,3-difluorocyclopentyl)amino)-2-(3,5-dimethyl-1H-pyrazol-1-yl)pyrimidine-4-carboxylic acid [0076] (0.5 g, 1.482 mmol) in dichloromethane (10 mL) was added oxalyl chloride (0.313 g, 3.70 mmol) and N,N-dimethylformamide (0.010 g, 0.148 mmol) drop wise at 0° C. Then the reaction mixture was stirred at rt for 1 h and concentrated under reduced pressure under N2 atm to afford 0.56 g of 6-((3,3-difluorocyclopentyl)amino)-2-(3, 5-dimethyl-1H-pyrazol-1-yl)pyrimidine-4-carbonyl chloride. 6-((3,3-difluorocyclopentyl)amino)-2-(3,5-dimethyl-1H-pyrazol-1-yl)pyrimidine-4-carbonyl chloride (0.51 g, 1.40 mmol) was dissolved in tetrahydrofuran (10 mL) and purged with ammonia gas at −10° C. for 15 min. The reaction mixture was then concentrated under reduced pressure to afford crude which was purified by column chromatography using 6% methanol in chloroform as a eluent to afford 6-((3,3-difluorocyclopentyl)amino)-2-(3,5-dimethyl-1H-pyrazol-1-yl)pyrimidine-4-carboxamide [33], Compound 183 as a pale brown solid (0.21 g). MS(M+1)$^+$=337, $^1$H NMR (400 MHz, DMSO-d6): δ 8.27 (d, J=−6.80 Hz, 1H), 7.81 (s, 1H), 7.70 (s, 1H), 6.97 (s, 1H), 6.09 (s, 1H), 4.49-4.50 (m, 1H), 2.58-2.67 (m, 4H), 2.21-2.32 (m, 7H), 1.92-1.82 (m, 1H), Step 4[0079]: The procedure is similar to Step 4[0047] in example 09. 0.18 g of 6-((3,3-difluorocyclopentyl)amino)-2-(3,5-dimethyl-1H-pyrazol-1-yl)pyrimidine-4-carboxamide [0078] gave 0.1 g of 6-((3,3-difluorocyclopentyl)amino)-2-(3,5-dimethyl-1H-pyrazol-1-yl)pyrimidine-4-carbonitrile [0079], Compound 184 as an off-white solid.

MS(M+1)$^+$=319, $^1$H NMR (400 MHz, DMSO-d6) δ 8.33 (d, J=2.4 Hz, 1H), 6.90 (s, 1H), 6.09 (s, 1H), 4.46 (bs, 1H), 2.80-257 (m, 1H), 2.55 (s, 3H), 2.35-2.28 (m 2H), 2.18 (s, 3H), 2.11-2.20 (m, 2H), 1.87-1.70 (m, 1H).

Example 23

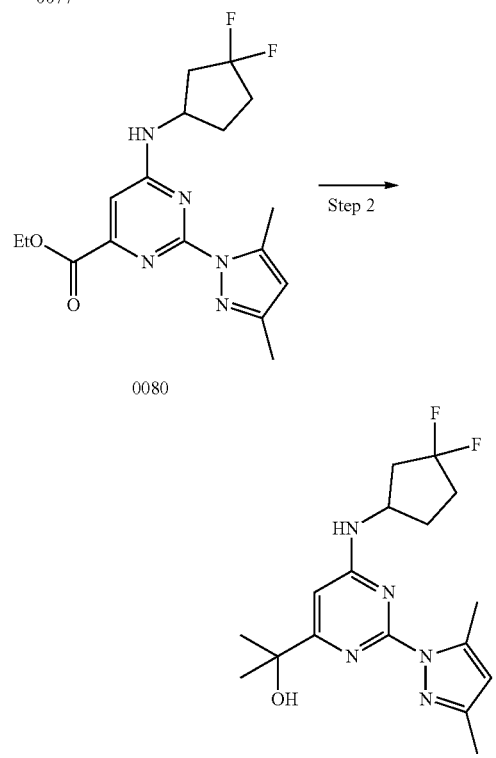

Step 1[0080]: The procedure is similar to step 4[0007] in example 1. 2.1 g of 6-((3,3-difluorocyclopentyl)amino)-2-

(3,5-dimethyl-1H-pyrazol-1-yl)pyrimidine-4-carboxylic acid [0077] gave 1.56 g of ethyl 6-((3,3-difluorocyclopentyl)amino)-2-(3,5-dimethyl-1H-pyrazol-1-yl)pyrimidine-4-carboxylate [0080] as a yellow gummy solid. MS(M+1)⁺=366.

Step 2[0081]: The procedure is similar to step 2[049] in example 10. 0.25 g of ethyl 6-((3,3-difluorocyclopentyl)amino)-2-(3,5-dimethyl-1H-pyrazol-1-yl)pyrimidine-4-carboxylate [0080] gave 0.03 g of 2-(6-((3,3-difluorocyclopentyl)amino)-2-(3,5-dimethyl-1H-pyrazol-1-yl)pyrimidin-4-yl)propan-2-ol [0081], Compound 214 as a yellow solid. MS(M+1)⁺=352, ¹H NMR (400 MHz, DMSO-d6) δ 7.87 (bs, 1H), 6.64 (s, 1H), 6.05 (s, 1H), 5.20 (s, 1H), 4.49 (bs, 1H), 2.59 (m, 2H), 2.34-2.30 (m, 1H), 2.29 (s, 3H), 2.28-2.00 (m, 3H) 1.75 (m, 1H), 1.38 (s, 3H), 1.37 (s, 3H), 1.23 (m, 2H).

Example 24

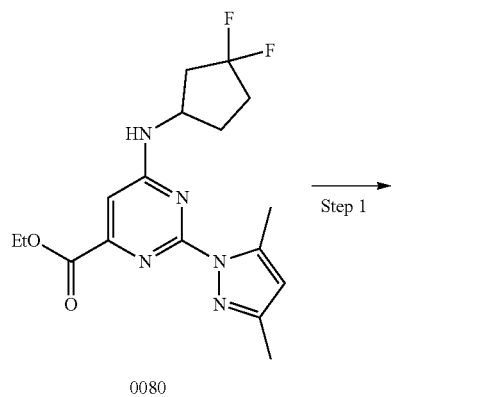

0080

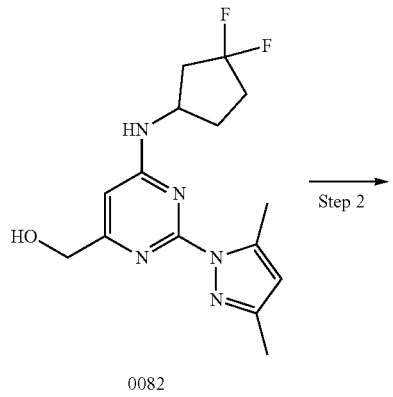

0082

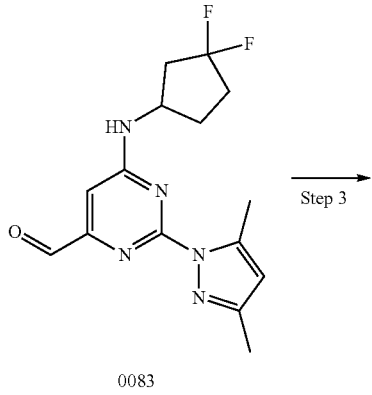

0083

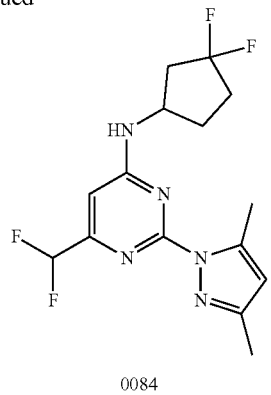

0084

Step 1[0082]: The procedure is similar to step 2 [0019] in Example 4. 0.18 g of ethyl 6-((3,3-difluorocyclopentyl)amino)-2-(3,5-dimethyl-1H-pyrazol-1-yl)pyrimidine-4-carboxylate [0080] gave 0.04 g of (6-((3,3-difluorocyclopentyl)amino)-2-(3,5-dimethyl-1H-pyrazol-1-yl)pyrimidin-4-yl)methanol [0082], Compound 192 as a white solid.

MS(M+1)⁺=324, ¹H NMR (400 MHz, DMSO-d6) δ 7.90 (d, J=7.0 Hz, 1H), 6.51 (s, 1H), 6.04 (s, 1H), 5.45 (t, J=5.8 Hz, 1H), 4.46 (bs, 1H), 4.36 (d, J=5.8 Hz, 2H), 2.58 (s, 3H), 2.37-2.19 (m, 2H), 2.16 (s, 3H), 2.35-1.98 (m, 3H), 1.75 (m, 1H).

Step 2 [0083]:0.3 g of (6-((3,3-difluorocyclopentyl)amino)-2-(3,5-dimethyl-1H-pyrazol-1-yl)pyrimidin-4-yl)methanol [0082] gave 0.3 g of 6-((3,3-difluorocyclopentyl)amino)-2-(3,5-dimethyl-1H-pyrazol-1-yl)pyrimidine-4-carbaldehyde [0083] as a yellow solid (using Dess-Martin periodinane (2 eq) in dichloromethane).

MS(M+1)⁺=322.

Step 3 [0084] The procedure is similar to step 3[0012] in example 2. 0.2 g of 6-((3,3-difluorocyclopentyl)amino)-2-(3,5-dimethyl-1H-pyrazol-1-yl)pyrimidine-4-carbaldehyde [0083] gave 0.02 g of N-(3,3-difluorocyclopentyl)-6-(difluoromethyl)-2-(3,5-dimethyl-1H-pyrazol-1-yl)pyrimidin-4-amine [0084], Compound 168 as a white solid. MS(M+1)⁺=344, ¹H-NMR (400 MHz, DMSO-d6): δ 8.33 (d, J=6.80 Hz, 1H), 6.78 (t, JF=54.40 Hz, 1H), 6.61 (s, 1H), 6.11 (s, 1H), 4.47-4.53 (m, 1H), 2.67-2.68 (m, 1H), 2.52 (s, 3H), 2.22-2.34 (m, 7H), 1.92-1.85 (m, 1H), Example 25

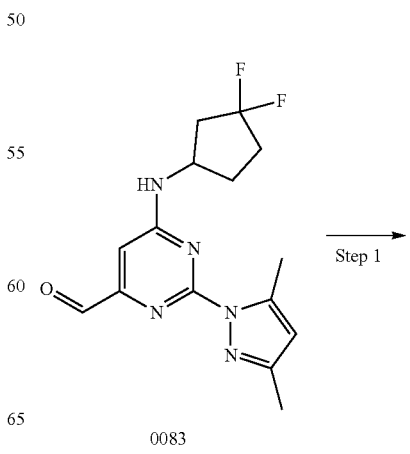

0083

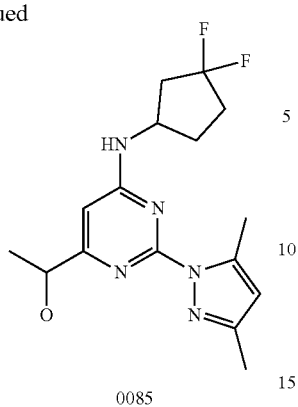

0085

Step 1[0085]: The procedure is similar to step 2[049] in example 10. 0.22 g of 6-((3,3-difluorocyclopentyl)amino)-2-(3,5-dimethyl-1H-pyrazol-1-yl)pyrimidine-4-carbaldehyde [0083] gave 0.05 g of 1-(6-((3,3-difluorocyclopentyl)amino)-2-(3,5-dimethyl-1H-pyrazol-1-yl)pyrimidin-4-yl)ethan-1-ol [0085], Compound 225 as a pale yellow solid. MS(M+1)$^+$=338, $^1$H NMR (400 MHz, DMSO-d6) δ 7.89 (s, 1H), 6.54 (s, 1H), 6.05 (s, 1H), 5.39 (d, J=4.6 Hz, 1H), 4.49 (d, J=6.9 Hz, 2H), 2.65-2.55 (m, 2H), 2.35-2.22 (m, 2H), 2.16 (s, 3H), 2.17 (s, 3H) 1.75 (s, 1H), 1.33 (d, J=6.7 Hz, 3H), 1.23 (d, J=3.8 Hz, 1H).

Example 26

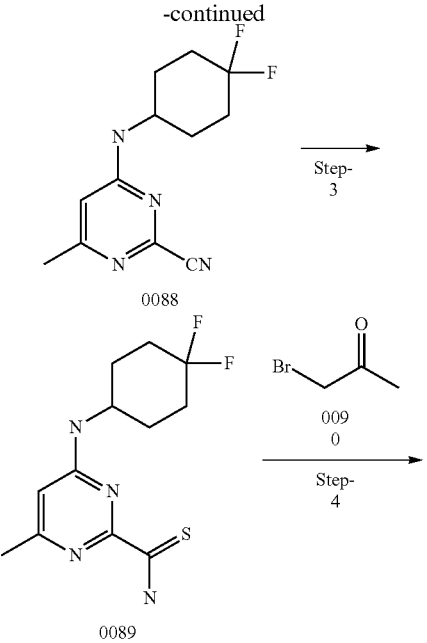

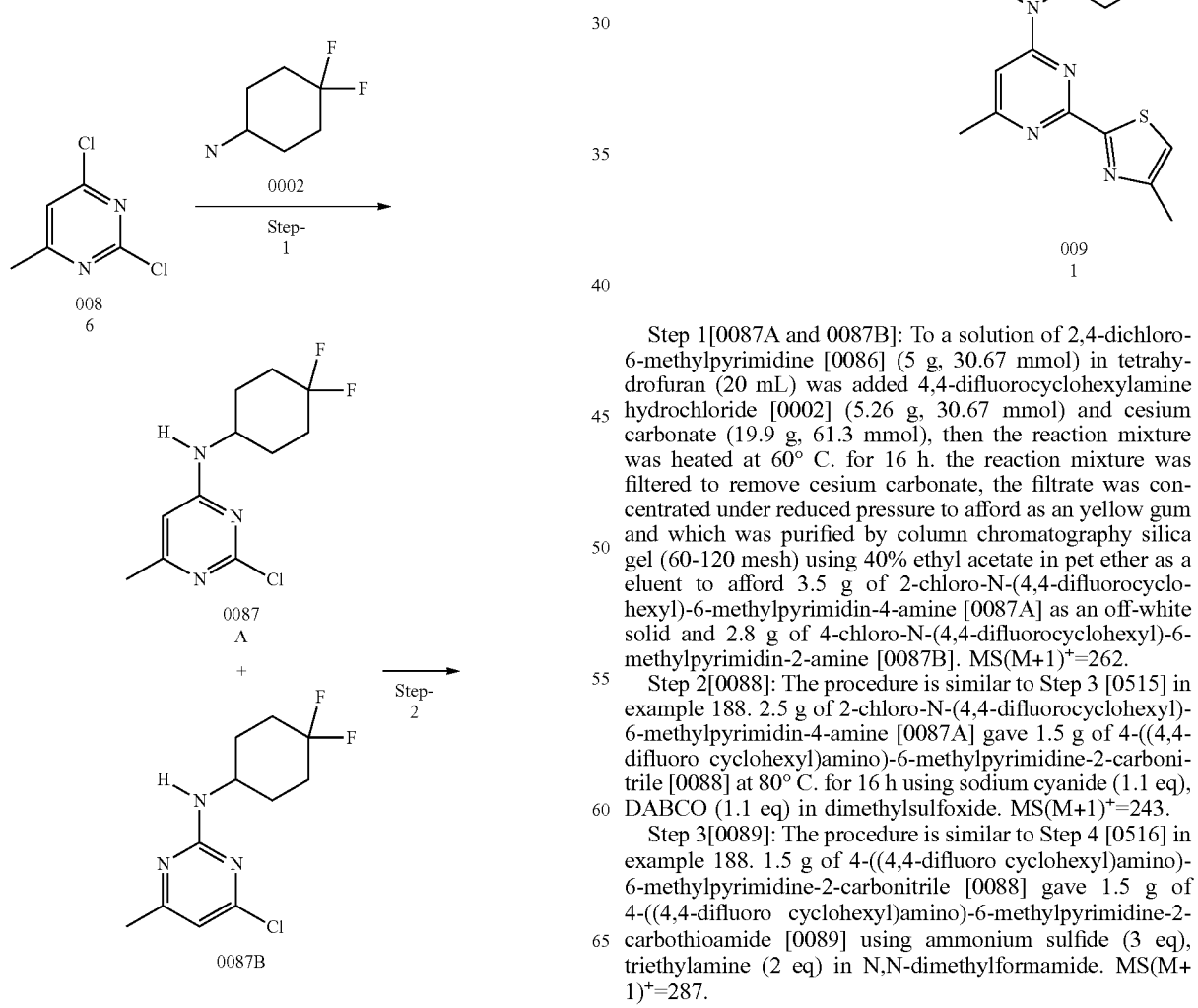

Step 1[0087A and 0087B]: To a solution of 2,4-dichloro-6-methylpyrimidine [0086] (5 g, 30.67 mmol) in tetrahydrofuran (20 mL) was added 4,4-difluorocyclohexylamine hydrochloride [0002] (5.26 g, 30.67 mmol) and cesium carbonate (19.9 g, 61.3 mmol), then the reaction mixture was heated at 60° C. for 16 h. the reaction mixture was filtered to remove cesium carbonate, the filtrate was concentrated under reduced pressure to afford as an yellow gum and which was purified by column chromatography silica gel (60-120 mesh) using 40% ethyl acetate in pet ether as a eluent to afford 3.5 g of 2-chloro-N-(4,4-difluorocyclohexyl)-6-methylpyrimidin-4-amine [0087A] as an off-white solid and 2.8 g of 4-chloro-N-(4,4-difluorocyclohexyl)-6-methylpyrimidin-2-amine [0087B]. MS(M+1)$^+$=262.

Step 2[0088]: The procedure is similar to Step 3 [0515] in example 188. 2.5 g of 2-chloro-N-(4,4-difluorocyclohexyl)-6-methylpyrimidin-4-amine [0087A] gave 1.5 g of 4-((4,4-difluoro cyclohexyl)amino)-6-methylpyrimidine-2-carbonitrile [0088] at 80° C. for 16 h using sodium cyanide (1.1 eq), DABCO (1.1 eq) in dimethylsulfoxide. MS(M+1)$^+$=243.

Step 3[0089]: The procedure is similar to Step 4 [0516] in example 188. 1.5 g of 4-((4,4-difluoro cyclohexyl)amino)-6-methylpyrimidine-2-carbonitrile [0088] gave 1.5 g of 4-((4,4-difluoro cyclohexyl)amino)-6-methylpyrimidine-2-carbothioamide [0089] using ammonium sulfide (3 eq), triethylamine (2 eq) in N,N-dimethylformamide. MS(M+1)$^+$=287.

Step 4[0091]: To a solution of 4-((4,4-difluoro cyclohexyl)amino)-6-methylpyrimidine-2-carbothioamide [0089] (1.5 g, 5.23 mmol) in ethanol (15 mL) was added bromoacetone (0.86 g, 6.28 mmol), then the reaction mixture was stirred at rt in a closed vial for 16 h. the reaction mixture was concentrated to afford as an brownish gum and which was purified by column of silica gel (60-120 mesh) using 3% methanol in chloroform as eluent to afford as an off-white solid 0.700 g, as an HBr salt, which was dissolved in saturated bicarbonate solution and extracted with ethyl acetate (2×70 mL), the combined organic layer was dried over anhydrous sodium sulfate and concentrated under high vacuum to afford 0.41 g of N-(4,4-difluorocyclohexyl)-6-methyl-2-(4-methylthiazol-2-yl)pyrimidin-4-amine [0091], Compound 231 as an off-white solid. MS(M+1)$^+$=325, $^1$H NMR (400 MHz, DMSO-d6) δ 7.52 (bs, 1H), 7.39 (d, J=1.1 Hz, 1H), 6.35 (bs, 1H), 4.01 (bs, 1H), 2.43 (s, 3H), 2.29 (s, 3H), 2.07-1.95 (m, 6H), 1.59-1.52 (m, 2H).

Example 27

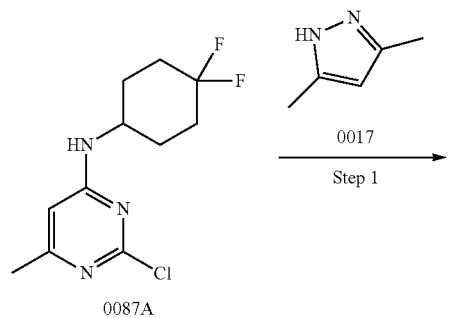

Step 1[0092]: The procedure is similar to step 3[0006] in Example 1. 4 g of 2-chloro-N-(4,4-difluorocyclohexyl)-6-methylpyrimidin-4-amine [0087A] gave 2.6 g of N-(4,4-difluorocyclohexyl)-2-(3,5-dimethyl-1H-pyrazol-1-yl)-6-methylpyrimidin-4-amine [0092], Compound 247 as white solid. MS(M+1)$^+$=322.2, $^1$H NMR (400 MHz, DMSO-d6) δ 7.53 (d, J=7.7 Hz, 1H), 6.21 (s, 1H), 6.03 (s, 1H), 4.01 (bs, 1H), 2.48 (s, 3H), 2.23 (s, 3H), 2.15 (s, 3H), 2.13-1.85 (m, 6H), 1.62-1.47 (m, 2H).

Example 28

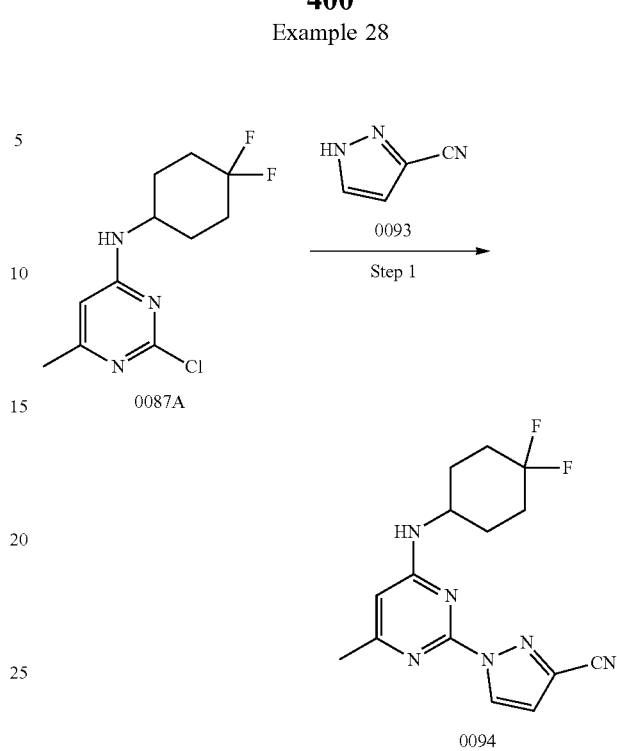

Step 2[0094]: The procedure is similar to step 3[0006] in Example 1. 0.3 g of 2-chloro-N-(4,4-difluorocyclohexyl)-6-methylpyrimidin-4-amine [0087A] gave 0.26 g of 1-(4-((4,4-difluorocyclohexyl)amino)-6-methyl pyrimidin-2-yl)-1H-pyrazole-3-carbonitrile [0094], Compound 212 as white solid. MS(M+1)$^+$=319.2, $^1$H NMR (400 MHz, DMSO-d6) δ 8.81 (s, 1H), 7.81 (s, 1H), 7.19 (s, 1H), 6.32 (s, 1H), 4.16 (bs, 1H), 2.28 (s, 3H), 2.19-1.86 (m, 6H), 1.60-1.45 (m, 2H).

Example 29

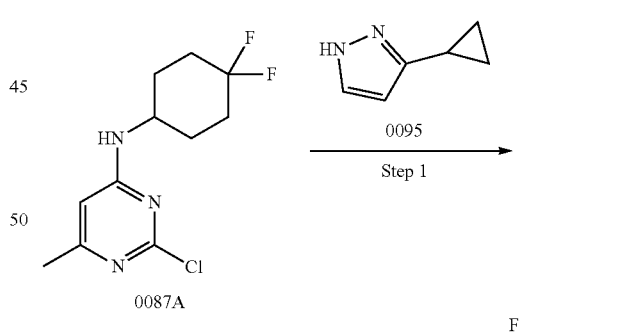

Step 1[0096]: The procedure is step 3[0006] in Example 1. 0.3 g of 2-chloro-N-(4,4-difluorocyclohexyl)-6-methyl-pyrimidin-4-amine [0087A] gave 0.21 g of 2-(3-cyclopropyl-1H-pyrazol-1-yl)-N-(4,4-difluorocyclohexyl)-6-methyl-pyrimidin-4-amine [0096], Compound 203 as off-white solid. MS(M+1)$^+$=334.4, $^1$H NMR (400 MHz, DMSO-d6) δ 8.42 (s, 1H), 7.55 (s, 1H), 6.19 (s, 2H), 4.13 (bs, 1H), 2.25 (s, 3H), 2.14-1.92 (m, 7H), 1.65-1.45 (m, 2H), 1.01-0.87 (m, 2H), 0.79-0.63 (m, 2H).

Example 30

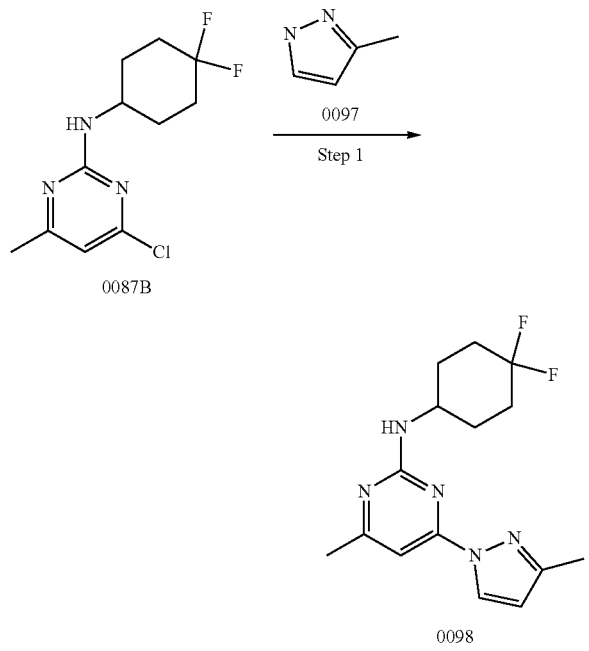

Step 1[0098]: The procedure is step 3[0006] in Example 1. 0.3 g of 4-chloro-N-(4,4-difluorocyclohexyl)-6-methyl-pyrimidin-2-amine [0087B] gave 0.14 g of N-(4,4-difluorocyclohexyl)-4-methyl-6-(3-methyl-1H-pyrazol-1-yl)pyrimidin-2-amine [0098], Compound 120 as a white solid. MS(M+1)$^+$=308, $^1$H NMR (400 MHz, DMSO-d6) δ 8.52 (bs, 1H), 7.35 (bs, 1H), 6.86 (s, 1H), 6.38 (d, J=2.6 Hz, 1H), 3.99 (d, J=9.8 Hz, 1H), 2.29 (s, 3H), 2.26 (s, 3H), 2.10-1.87 (m, 6H), 1.68-1.50 (m, 2H).

Example 31

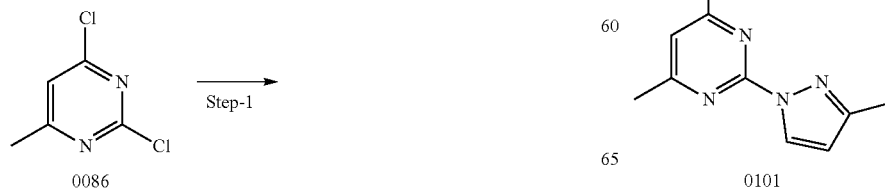

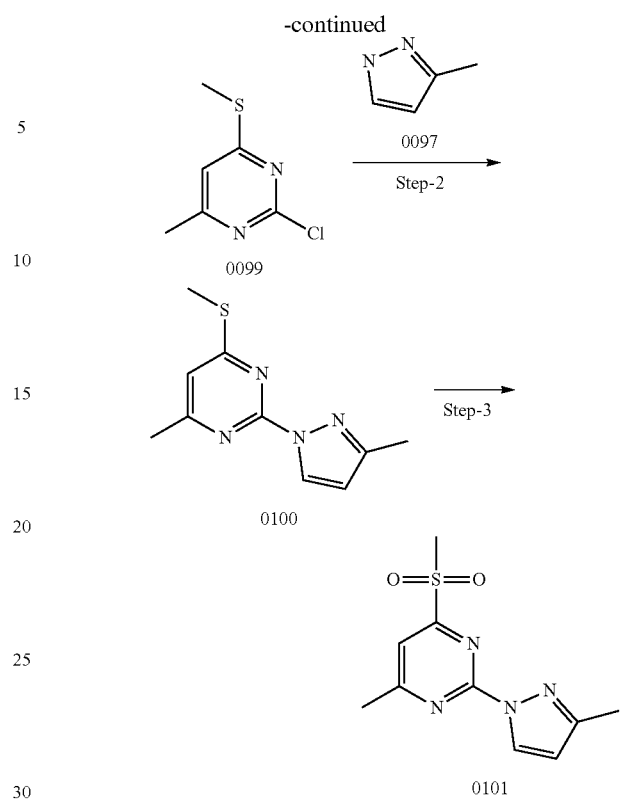

Step 1[0099]: To a stirred solution of 2,4-Dichloro-6-methylpyrimidine [0086] (5 g, 30.674 mmol) in tetrahydrofuran (50 mL) was added sodium thiomethoxide (2.14 g, 30.67 mmol) in portions at −10° C. under nitrogen. The mixture was stirred at −10° C. for 3 h. The solid precipitate was filtered, washed with methanol (20 mL) and dried under vacuum to afford 2-chloro-4-methyl-6-(methylthio)pyrimidine [0099] as an yellow solid (5 g). MS(M+1)$^+$=175.

Step 2[0100]: The procedure is step 3[0006] in Example 1. 2.5 g of 2-chloro-4-methyl-6-(methylthio)pyrimidine [0099] gave 3.0 g of 4-methyl-2-(3-methyl-1H-pyrazol-1-yl)-6-(methylthio)pyrimidine [0100] as a yellow liquid. MS(M+1)$^+$=221.

Step 3[0101]: The procedure is similar to step 2[0378] in example 145. 3.0 g of 4-methyl-2-(3-methyl-1H-pyrazol-1-yl)-6-(methylthio)pyrimidine [0100] gave 1.3 g of 4-methyl-2-(3-methyl-1H-pyrazol-1-yl)-6-(methylsulfonyl)pyrimidine [0101] as a yellow solid using 3-chloroperbenzoic acid (3 eq) in dichloromethane. MS(M+1)$^+$=253.

Example 32

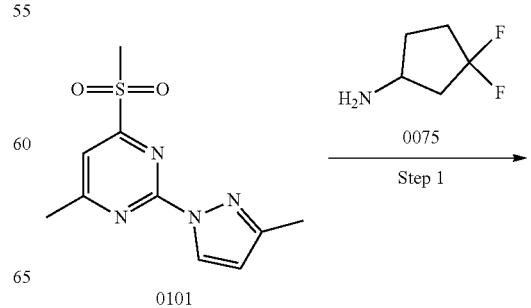

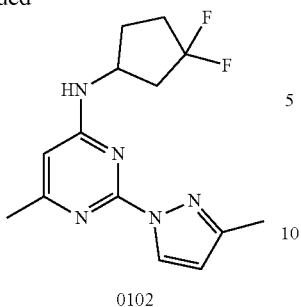

0102

Step 1[0102]: To a solution of 4-methyl-2-(3-methyl-1H-pyrazol-1-yl)-6-(methylsulfonyl)pyrimidine [0101] (0.1 g, 0.396 mmol) in dry tetrahydrofuran (8 mL) was added 3,3-difluoro-N-methylcyclopentan-1-amine [0075] (0.096 g, 0.792 mmol) under N2 atm. The reaction mixture was heated at 100° C. in sealed tube for 16 h. The reaction mixture was concentrated under reduced pressure to afford crude and which was purified by column chromatography using 30% ethyl acetate in hexane as a eluent to afford N-(3,3-difluorocyclopentyl)-6-methyl-2-(3-methyl-1H-pyrazol-1-yl)pyrimidin-4-amine, Compound 150 as a white solid (0.04 g). MS(M+1)$^+$=294, $^1$H-NMR (400 MHz, DMSO-d6): δ 8.41 (s, 1H), 7.79 (bs, 1H), 6.28 (d, J=2.5 Hz, 1H), 6.2 (bs, 1H), 4.51 (bs, 1H), 2.67-2.58 (m, 1H), 2.24 (s, 3H), 2.24 (s, 3H), 2.20 (m, 2H), 2.10-2.06 (m, 2H), 1.77-1.74 (m, 1H).

Example 35

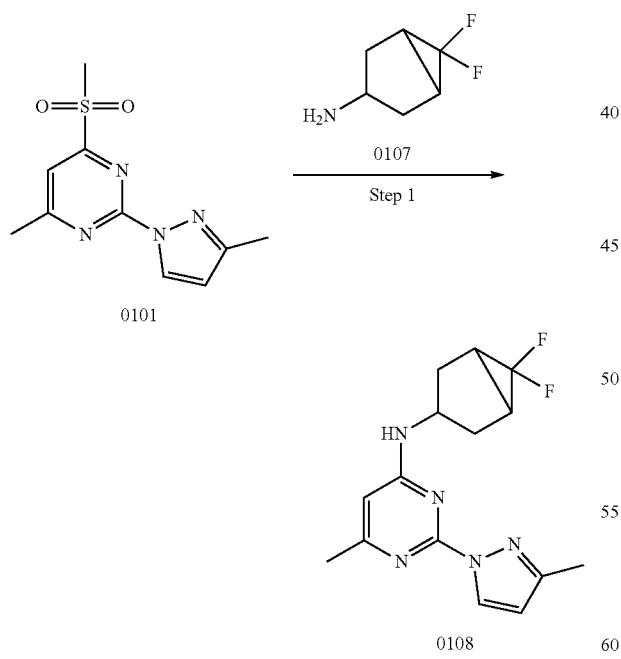

Step 1[0108]: The procedure is similar to step 1[0106] in example 34. 0.15 g of 4-methyl-2-(3-methyl-1H-pyrazol-1-yl)-6-(methylsulfonyl)pyrimidine [0101] gave 0.08 g of N-((1R,5S)-6,6-difluorobicyclo[3.1.0]hexan-3-yl)-6-methyl-2-(3-methyl-1H-pyrazol-1-yl)pyrimidin-4-amine

[0108], Compound 245 as an off-white solid. MS(M+1)$^+$=306, $^1$H NMR (400 MHz, DMSO-d6) δ 8.34 (s, 1H), 7.65 (bs, 1H), 6.30 (d, J=2.6 Hz, 1H), 6.16 (bs, 1H), 4.36 (bs, 1H), 2.45-2.30 (m, 2H), 2.28-2.12 (m, 2H), 2.25 (s, 3H), 2.21 (s, 3H) 1.91 (bs, 2H).

Example 38

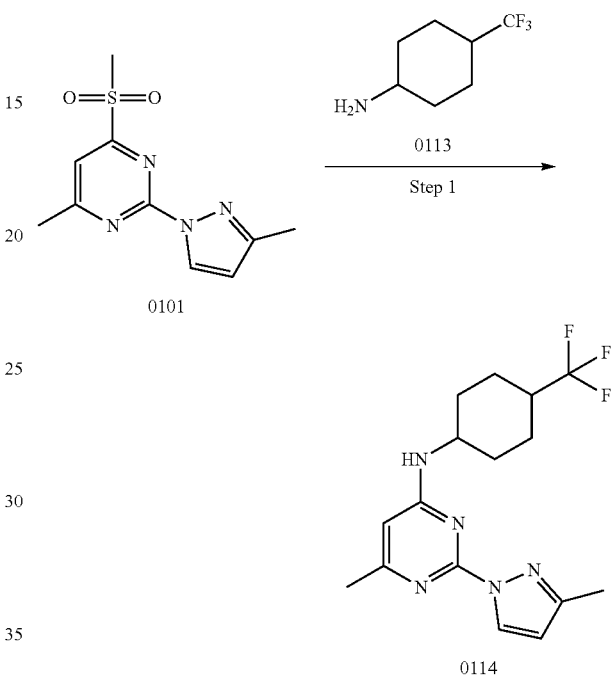

Step 1[0114]: The procedure is similar to step 1[0102] in example 32. 0.12 g of 4-methyl-2-(3-methyl-1H-pyrazol-1-yl)-6-(methylsulfonyl)pyrimidine [0101] gave 0.06 g of 6-methyl-2-(3-methyl-1H-pyrazol-1-yl)-N-(4-(trifluoromethyl)cyclohexyl)pyrimidin-4-amine [0114], Compound 144 as a yellow solid. MS(M+1)$^+$=340, $^1$H NMR (400 MHz, DMSO-d6) δ 8.42 (bs, 1H), 7.50 (bs, 1H), 6.27 (d, J=2.5 Hz, 1H), 6.15 (bs, 1H), 3.89 (bs, 1H), 2.58 (bs, 1H), 2.44 (s, 3H), 2.42 (s, 3H), 2.10-1.95 (m, 2H), 1.91 (d, J=12.2 Hz, 2H), 1.50-1.37 (m, 2H), 1.36-1.20 (m, 2H).

Example 39

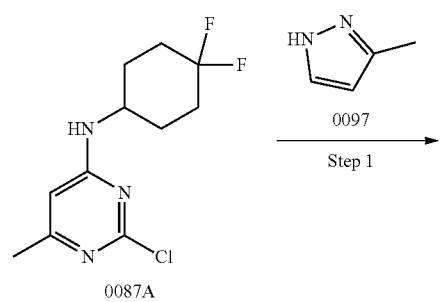

-continued

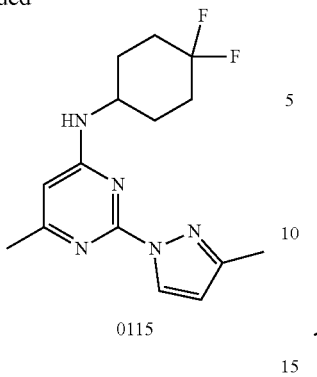

0115

Step 1[0115]: The procedure is similar to step 3[0006] in example 1. 2.0 g of 2-chloro-N-(4,4-difluorocyclohexyl)-6-methylpyrimidin-4-amine [0087A] gave 0.9 g of N-(4,4-difluorocyclohexyl)-6-methyl-2-(3-methyl-1H-pyrazol-1-yl)pyrimidin-4-amine [0115], Compound 148 as an off-white solid. MS(M+1)$^+$=308, $^1$H-NMR (400 MHz, DMSO-d6): δ 8.44 (bs, 1H), 7.79 (bs, 1H), 6.29-6.19 (m, 2H), 4.13-4.08 (m, 1H), 2.25 (s, 3H), 2.24 (s, 3H), 2.05-1.95 (m, 6H), 1.60-1.54 (m, 2H).

Example 40

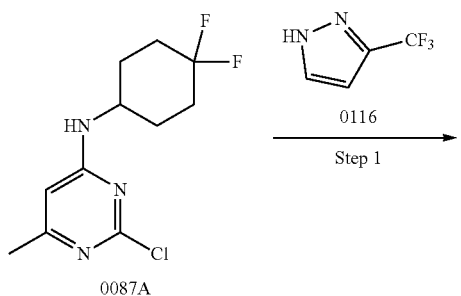

0087A

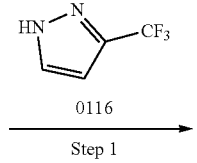

0116

Step 1

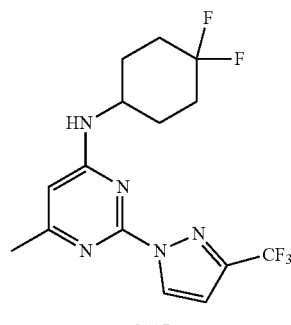

0117

Step 1[0117]: The procedure is similar to step 3[0006] in example 1. 0.2 g 2-chloro-N-(4,4-difluorocyclohexyl)-6-methylpyrimidin-4-amine [0087A] gave 0.18 g of N-(4,4-difluorocyclohexyl)-6-methyl-2-(3-(trifluoromethyl)-1H-pyrazol-1-yl)pyrimidin-4-amine [0117], Compound 200 as an off-white solid. MS(M+1)$^+$=362.0, $^1$H NMR (400 MHz, DMSO-d6) δ 8.70 (d, J=2.5 Hz, 1H), 7.57 (d, J=7.6 Hz, 1H), 6.90 (d, J=2.7 Hz, 1H), 6.40 (s, 1H), 4.04 (bs, 1H), 2.33 (s, 3H), 2.13-1.94 (m, 6H), 1.65 (qd, J=12.2, 11.3, 4.3 Hz, 2H).

Example 41

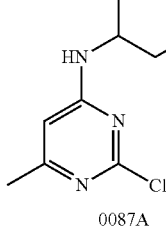

0087A

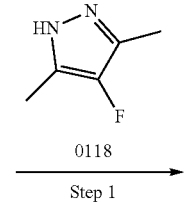

0118

Step 1

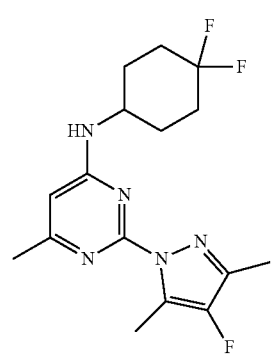

0119

Step 1[0119]: The procedure is similar to step 3[0006] in example 1. 0.2 g 2-chloro-N-(4,4-difluorocyclohexyl)-6-methylpyrimidin-4-amine [0087A] gave 0.12 g of N-(4,4-difluorocyclohexyl)-2-(4-fluoro-3,5-dimethyl-1H-pyrazol-1-yl)-6-methylpyrimidin-4-amine [0119], Compound 201 as a white solid. MS(M+1)$^+$=340.2, $^1$H NMR (400 MHz, DMSO-d6) δ 7.59 (d, J=7.6 Hz, 1H), 6.22 (s, 1H), 4.00 (s, 1H), 2.48 (s, 3H), 2.34-2.14 (m, 6H), 2.12-1.88 (m, 6H), 1.55 (t, J=11.5 Hz, 2H).

Example 42

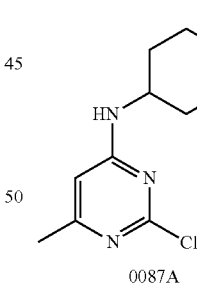

0087A

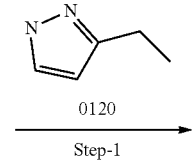

0120

Step-1

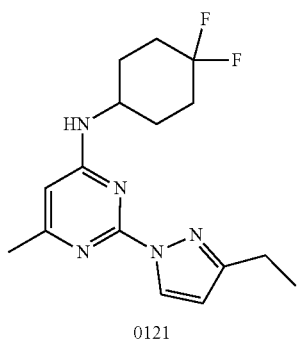

0121

Step 1[0121]: The procedure is similar to The procedure is similar to step 3[0006] in example 1. 0.300 g of 2-chloro-N-(4,4-difluorocyclohexyl)-6-methylpyrimidin-4-amine [0087A] and 0.220 g of 3-ethyl pyrazole [0120] gave 0.08 g of N-(4,4-difluorocyclohexyl)-2-(3-ethyl-1H-pyrazol-1-yl)-6-methylpyrimidin-4-amine [0121], Compound 197 as an white solid, MS(M+1)⁺=336. ¹H NMR (400 MHz, DMSO-d6) δ 8.46 (bs, 1H), 7.56 (bs, 1H), 6.34 (d, J=2.5 Hz, 1H), 6.20 (bs, 1H), 4.14 (s, 1H), 2.63 (q, J=7.6 Hz, 2H), 2.26 (s, 3H), 2.12-1.91 (m, 6H), 1.60-1.52 (m, 2H), 1.21 (t, J=7.7 Hz, 3H).

Example 43

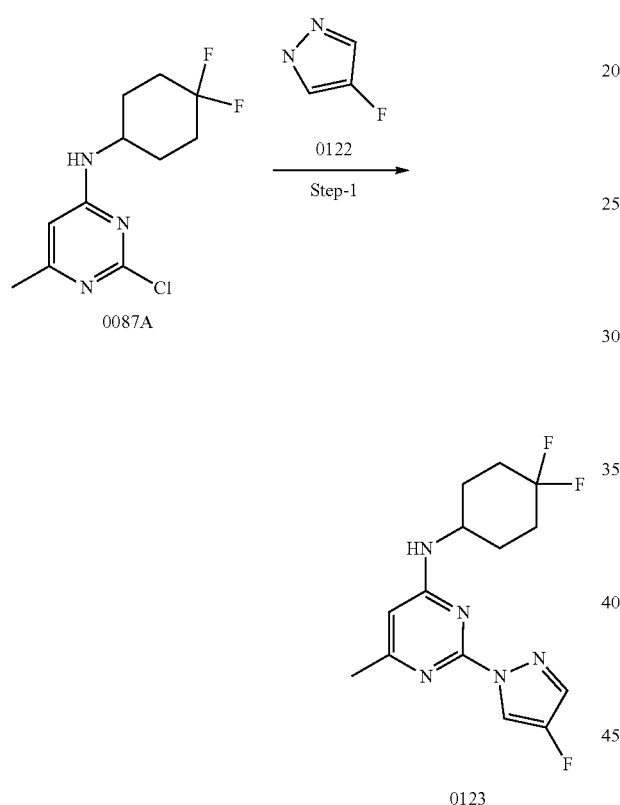

Step 1[0123]: The procedure is similar to step 3[0006] in example 1. 0.300 g of 2-chloro-N-(4,4-difluorocyclohexyl)-6-methylpyrimidin-4-amine [0087A] and 0.148 g of 4-fluoro pyrazole [0122] gave 0.150 g of N-(4,4-difluorocyclohexyl)-2-(4-fluoro-1H-pyrazol-1-yl)-6-methylpyrimidin-4-amine [0123], Compound 196 as an light yellow solid, MS(M+1)⁺=312. ¹H NMR (400 MHz, DMSO-d6) δ 8.64 (bs, 1H), 7.84 (d, J=4.4 Hz, 1H), 7.66 (bs, 1H), 6.23 (bs, 1H), 4.17 (bs, 1H), 2.26 (s, 3H), 2.10-1.95 (m, 6H), 1.60-1.52 (s, 2H).

Example 44

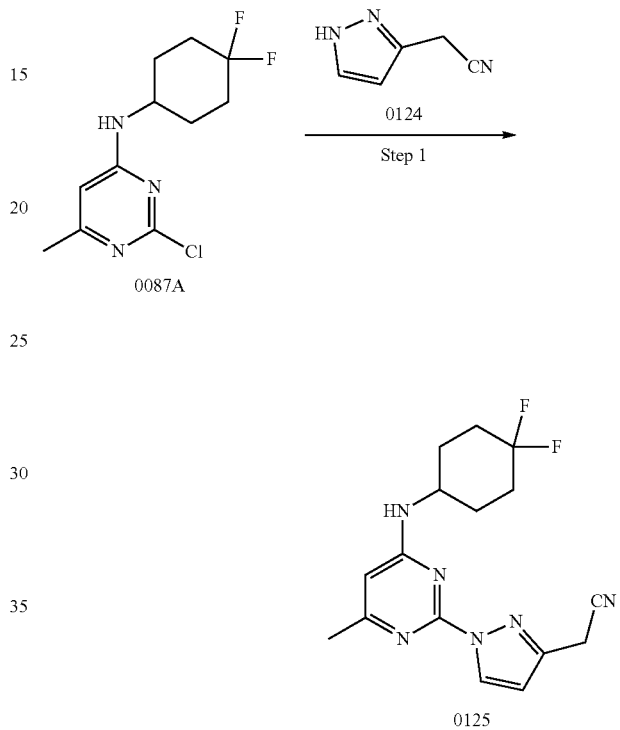

Step 1[0125]: The procedure is similar to step 3[0006] in example 1. 0.15 g 2-chloro-N-(4,4-difluorocyclohexyl)-6-methylpyrimidin-4-amine [0087A] gave 0.1 g of 2-(1-(4-((4,4-difluorocyclohexyl)amino)-6-methylpyrimidin-2-yl)-1H-pyrazol-3-yl)acetonitrile [0125], Compound 208 as a white solid. MS(M+1)⁺=333.1, ¹H NMR (400 MHz, DMSO-d6) δ 8.59 (s, 1H), 7.68 (s, 1H), 6.50 (d, J=2.6 Hz, 1H), 6.24 (s, 1H), 4.11 (s, 3H), 2.28 (s, 3H), 2.01 (d, J=42.1 Hz, 6H), 1.56 (s, 2H).

Example 45

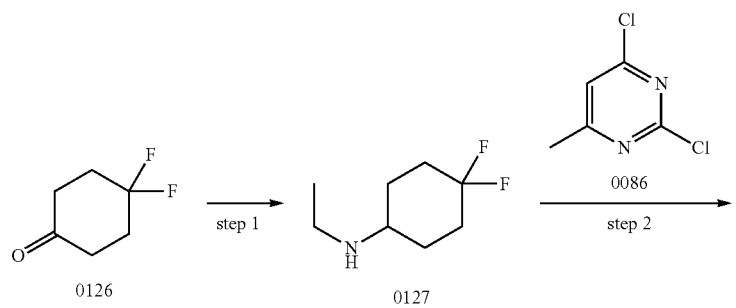

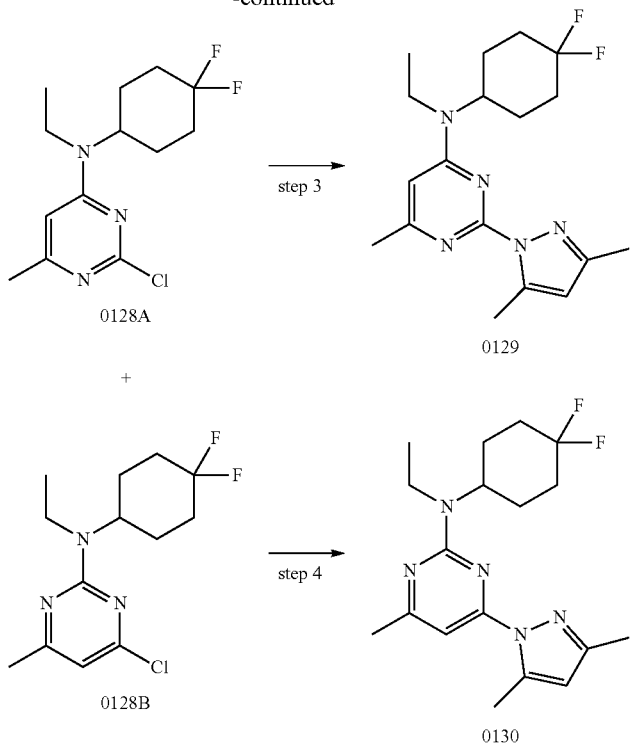

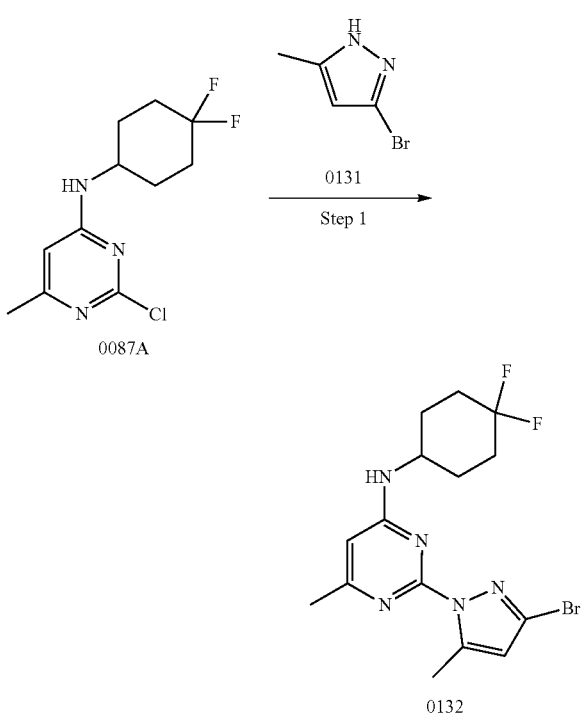

Step 1[0127]: To a mixture of 4,4-difluorocyclohexanone [0126] (2 g, 14.911 mmol), ethylamine (1.34 g, 29.82 mmol) and acetic acid (2.68 g, 44.73 mmol) in 1,2-dichloroethane under N2 atmosphere was added sodium triacetoxyborohydride (6.32 g, 29.82 mmol) portion wise at 0° C. The resultant reaction mixture was slowly warmed to rt. After 16 h, the reaction mixture was basified with 1 N sodium hydroxide solution and extracted with 10% methanol in chloroform. The combined organic layer was washed with brine, dried over anhydrous sodium sulfate, filtered and concentrated under reduced pressure to afford N-ethyl-4,4-difluorocyclohexan-1-amine [0127], as brown oil. (1.5 g, 63% yield), MS(M+1)+=164.2. This is taken as such tonext step.

Step 2[0128A & 0128B]: The procedure is similar to step 1[0106] in example 34 (75° C., acetonitrile). 1.2 g of 2,4-dichloro-6-methylpyrimidine [0127] gave 0.6 g of 2-chloro-N-(4,4-difluorocyclohexyl)-N-ethyl-6-methylpyrimidin-4-amine [0128A] as white solid and 0.28 g of 4-chloro-N-(4,4-difluorocyclohexyl)-N-ethyl-6-methylpyrimidin-2-amine [0128B] as yellow solid. MS(M+1)+= 290.3.

Step 3[0129]: The procedure is similar to step 3[0006] in Example 1. 0.3 g of 2-chloro-N-(4,4-difluorocyclohexyl)-N-ethyl-6-methylpyrimidin-4-amine [0128A] gave 0.17 g of N-(4,4-difluorocyclohexyl)-2-(3,5-dimethyl-1H-pyrazol-1-yl)-N-ethyl-6-methylpyrimidin-4-amine [0129], Compound 161 as yellow gum. MS(M+1)+=350.4. $^1$H NMR (400 MHz, DMSO-d6) δ 6.52 (bs, 1H), 6.05 (s, 1H), 4.58 (bs, 1H), 3.43 (bs, 2H), 2.53 (s, 3H), 2.32 (s, 3H), 2.17 (s, 3H), 2.15-1.85 (m, 4H), 1.83-1.73 (m, 4H), 1.14 (t, J=6.9 Hz, 3H).

Step 4[0130]: The procedure is similar to step 3[0006] in Example 1. 0.2 g 4-chloro-N-(4,4-difluorocyclohexyl)-N-ethyl-6-methylpyrimidin-2-amine [0128B] gave 0.08 g of N-(4,4-difluorocyclohexyl)-4-(3,5-dimethyl-1H-pyrazol-1-yl)-N-ethyl-6-methylpyrimidin-2-amine [0130], Compound 160 as yellow gum. MS(M+1)+=350.4. $^1$H NMR (400 MHz, DMSO-d6) δ 6.95 (s, 1H), 6.14 (s, 1H), 4.64 (bs, 1H), 3.49 (q, J=6.9 Hz, 2H), 2.66 (s, 3H), 2.33 (s, 3H), 2.19 (s, 3H), 2.12 (bs, 2H), 2.05-1.75 (m, 6H), 1.14 (t, J=6.9 Hz, 3H).

Example 46

Step 1[0132]: To a stirred solution of 2-chloro-N-(4,4-difluorocyclohexyl)-6-methylpyrimidin-4-amine [0087A] (0.3 g, 1.146 mmol) in acetonitrile (10 mL) was added 3-bromo-5-methyl-1h-pyrazole (0.276 g, 1.719 mmol) and cesium carbonate (0.74 g, 2.29 mmol). The reaction mixture was irradiated in microwave at 150° C. for 2 h. The reaction mixture was filtered to remove cesium carbonate. Filtrate was concentrated under reduced pressure to afford crude product which was purified by column chromatography using 20% ethyl acetate in pet ether as eluent to afford 0.400 g of 2-(3-bromo-5-methyl-1H-pyrazol-1-yl)-N-(4,4-difluorocyclohexyl)-6-methylpyrimidin-4-amine [0132], Compound 220 as an off-white solid. MS(M+1)$^+$=386.0. $^1$H NMR (400 MHz, DMSO-d6) δ 7.69 (d, J=7.7 Hz, 1H), 6.41 (s, 1H), 6.28 (s, 1H), 4.04 (s, 1H), 2.55 (s, 3H), 2.24 (s, 3H), 2.07-1.92 (m, 6H), 1.59-1.53 (m, 2H).

Example 47

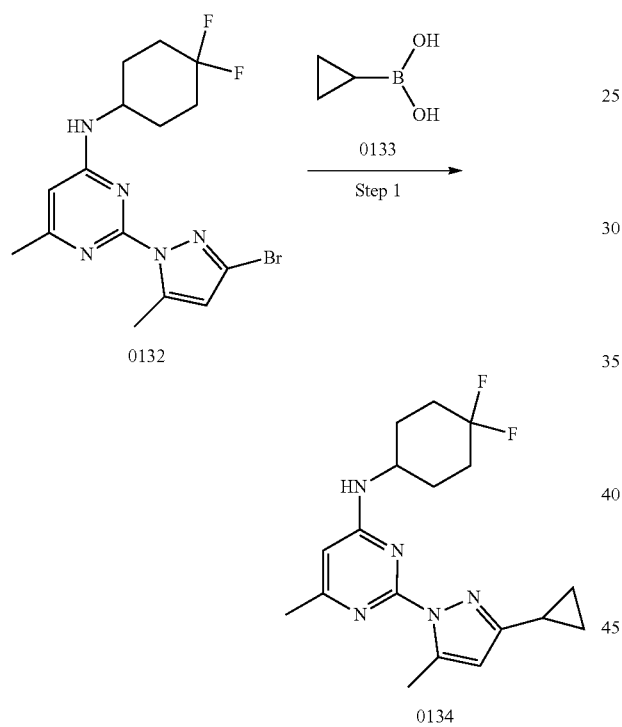

Step 1[0134]: To a stirred solution of 2-(3-bromo-5-methyl-1H-pyrazol-1-yl)-N-(4,4-difluorocyclohexyl)-6-methylpyrimidin-4-amine [0132] (0.25 g, 0.647 mmol) in dioxane (5 mL), was added cyclopropylboronic acid [0133] (0.111 g, 1.29 mmol) and potassium phosphate tribasic (0.274 g, 1.29 mmol). The reaction mixture was degassed for 10 min, added 1,1'-bis(diphenylphosphino)ferrocene]dichloropalladium(II) complex with dichloromethane (0.026 g, 0.032 mmol) and irradiated in microwave at 110° C. for 2 h. After completion the reaction mixture was filtered through celite and the filtrate was concentrated under reduced pressure to afford crude product which was purified by preparative HPLC to afford 0.021 g of 2-(3-cyclopropyl-5-methyl-1H-pyrazol-1-yl)-N-(4,4-difluorocyclohexyl)-6-methylpyrimidin-4-amine [0134], Compound 221 as an off-white solid. MS(M+1)$^+$=348.2, $^1$H NMR (400 MHz, DMSO-d6): δ 7.52 (d, J=7.64 Hz, 1H), 6.20 (m, 1H), 5.90 (s, 1H), 3.98 (m, 1H), 2.30 (s, 3H), 1.93 (s, 3H), 1.84-1.91 (m, 6H), 1.50-1.57 (m, 2H), 0.88 (t, J=6.40 Hz, 2H), 0.85 (t, J=4.48 Hz, 2H).

Example 48

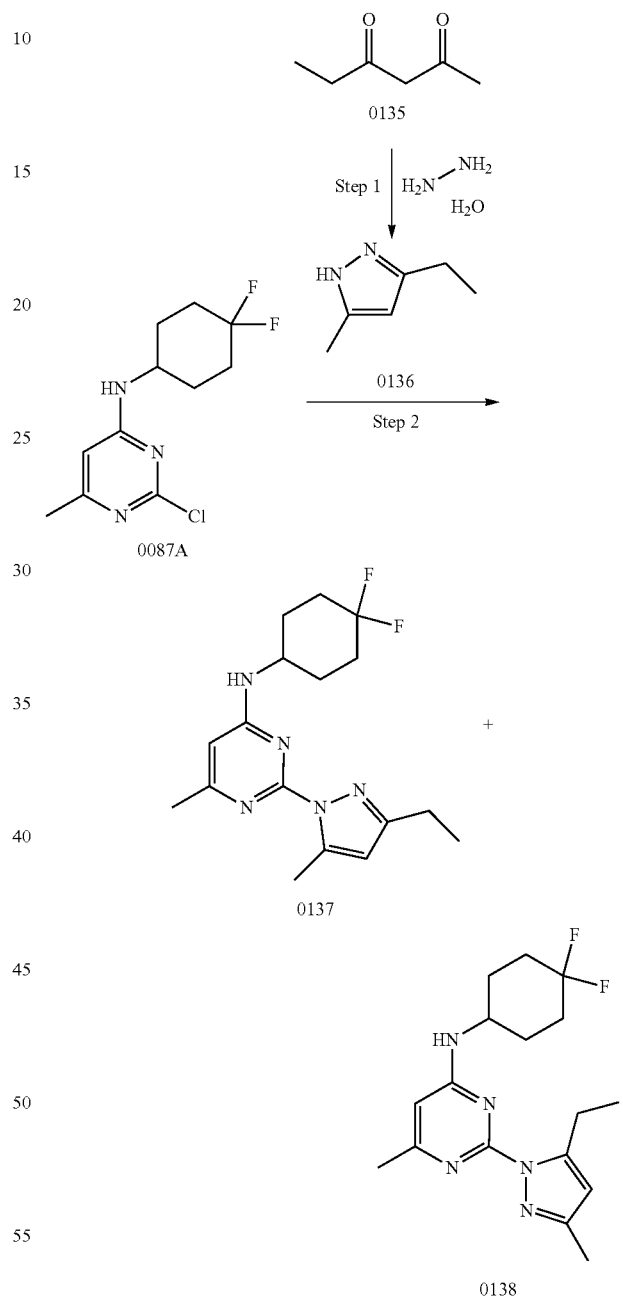

Step 1[0064]: To a stirred solution of hexane-2,4-dione [0135] (1 g, 8.760 mmol) in ethanol (25 mL) was added hydrazine hydrate (0.526 g, 10.51 mmol) drop-wise. The reaction mixture was refluxed at 85° C. for 5 h. The reaction mixture was concentrated under reduced pressure. The residue was diluted with ethyl acetate (50 mL) washed with water (20 mL). The organic extracts was dried over anhydrous sodium sulfate, filtered and concentrated under reduced pressure to afford 0.8 g of 3-ethyl-5-methyl-1H-pyrazole [0136] as colorless liquid. MS(M+1)+=110.8.

Step 2[0137]: To a stirred solution of 3-ethyl-5-methyl-1H-pyrazole [0136] (0.5 g, 4.53 mmol) in acetonitrile (5 mL), was added 2-chloro-N-(4,4-difluorocyclohexyl)-6-methylpyrimidin-4-amine [0087A] (0.59 g, 2.269 mmol) and cesium carbonate (1.47 g, 4.53 mmol). The reaction mixture was irradiated in microwave at 140° C. for 2 h, filtered to remove cesium carbonate and washed several times with chloroform (3×20 mL). The solvent was concentrated under reduced pressure to afford crude product which was purified by preparative HPLC to afford 0.050 g of N-(4,4-difluorocyclohexyl)-2-(3-ethyl-5-methyl-1H-pyrazol-1-yl)-6-methyl pyrimidin-4-amine [0137], Compound 249 as an off-white solid [MS(M+1)+=336.0. 1H-NMR (400 MHz, DMSO-d6): δ 7.55 (d, J=7.20 Hz, 1H), 6.22 (s, 1H), 6.08 (s, 1H), 4.02 (s, 1H), 2.56-2.54 (m, 2H), 2.56 (s, 3H), 2.33 (s, 3H), 2.17-1.88 (m, 6H), 1.59-1.51 (m, 2H), 1.17-1.85 (t, J=7.20 Hz, 3H) and 0.065 g of N-(4,4-difluorocyclohexyl)-2-(5-ethyl-3-methyl-1H-pyrazol-1-yl)-6-methylpyrimidin-4-amine [0138], Compound 260 as an off-white solid MS(M+1)+=336.0/337.0. ¹H NMR (400 MHz, DMSO-d6) δ 7.55 (d, J=7.7 Hz, 1H), 6.23 (s, 1H), 6.06 (s, 1H), 3.98 (s, 1H), 3.01-2.95 (q, J=7.44 Hz, 2H), 2.24 (s, 3H), 2.17 (s, 3H), 2.08-1.87 (m, 6H), 1.58-1.53 (m, 2H), 1.17 (t, J=7.4 Hz, 3H).

Example 50

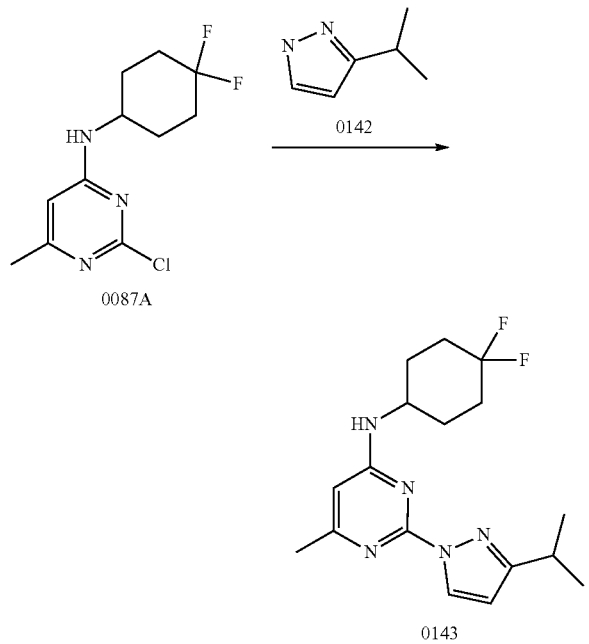

Step 1[0143]: The procedure is similar to step 3[0006] in example 1. 0.250 g of 2-chloro-N-(4,4-difluorocyclohexyl)-6-methylpyrimidin-4-amine [0087A] and 0.210 g of 3-isopropyl-1H-pyrazole [0142] gave 0.200 g of N-(4,4-difluorocyclohexyl)-2-(3-isopropyl-1H-pyrazol-1-yl)-6-methylpyrimidin-4-amine [0143], Compound 218 as an off-white solid which was purified by prep HPLC. MS(M+1)+=336, ¹H NMR (400 MHz, DMSO-d6) δ 8.48 (s, 1H), 7.66 (s, 1H), 6.39 (d, J=2.7 Hz, 1H), 6.21 (bs, 1H), 4.15 (s, 1H), 3.00-2.95 (m, 1H), 2.27 (s, 3H), 2.14-1.88 (m, 6H), 1.60-1.52 (m, 2H), 1.24 (d, J=6.9 Hz, 6H).

Example 51

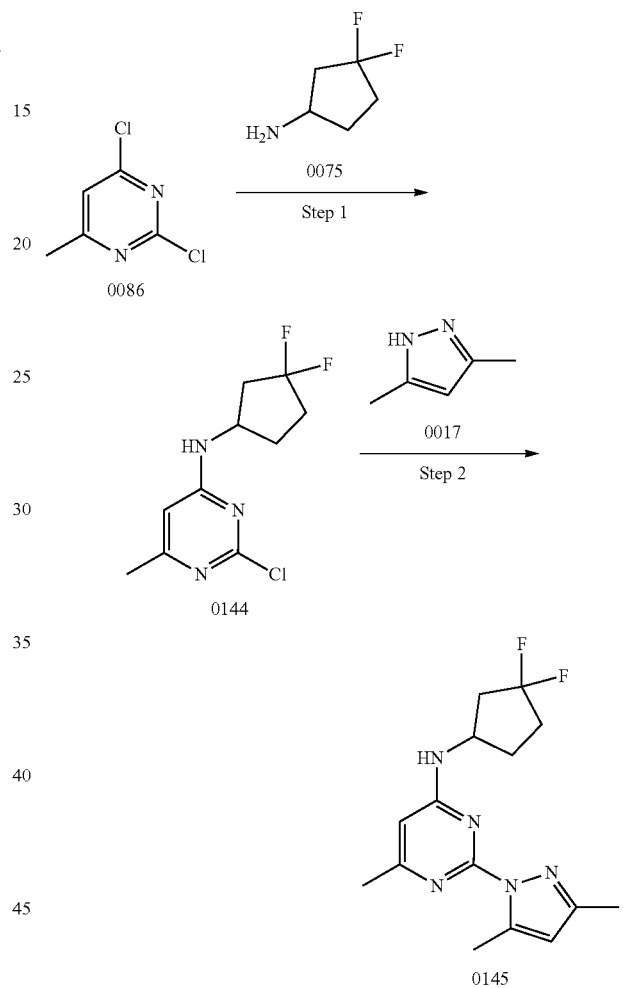

Step 1[0144]: The procedure is similar to step 1[0003] in example 1. 0.3 g of 2,4-dichloro-6-methylpyrimidine [0086] gave 0.2 g of 2-chloro-N-(3,3-difluorocyclopentyl)-6-methylpyrimidin-4-amine [0144] as an off-white solid. MS(M+1)+=247.9.

Step 2 [0145]: 0.25 g of 2-chloro-N-(3,3-difluorocyclopentyl)-6-methylpyrimidin-4-amine [0144] and 0.145 g of 3,5-dimethyl pyrazole in acetonitrile was irradiated at 150° C. to afford 0.1 g of N-(3,3-difluorocyclopentyl)-2-(3,5-dimethyl-1H-pyrazol-1-yl)-6-methylpyrimidin-4-amine [0145] as a white solid. MS(M+1)+=308.2, ¹H NMR (400 MHz, Chloroform-d) δ 6.13 (s, 1H), 6.01 (s, 1H), 5.50 (s, 1H), 4.39 (s, 1H), 2.74-2.54 (m, 4H), 2.44 (d, J=0.6 Hz, 3H), 2.33 (s, 4H), 2.25-1.99 (m, 2H), 1.84 (dq, J=12.5, 7.6 Hz, 2H).

Example 52

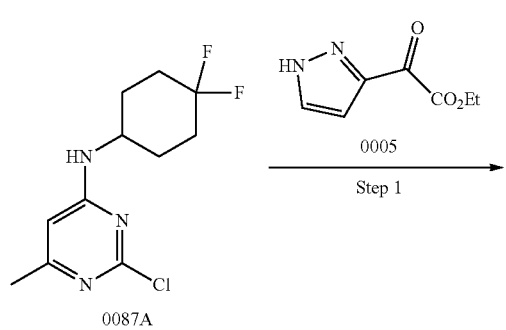

Example 53

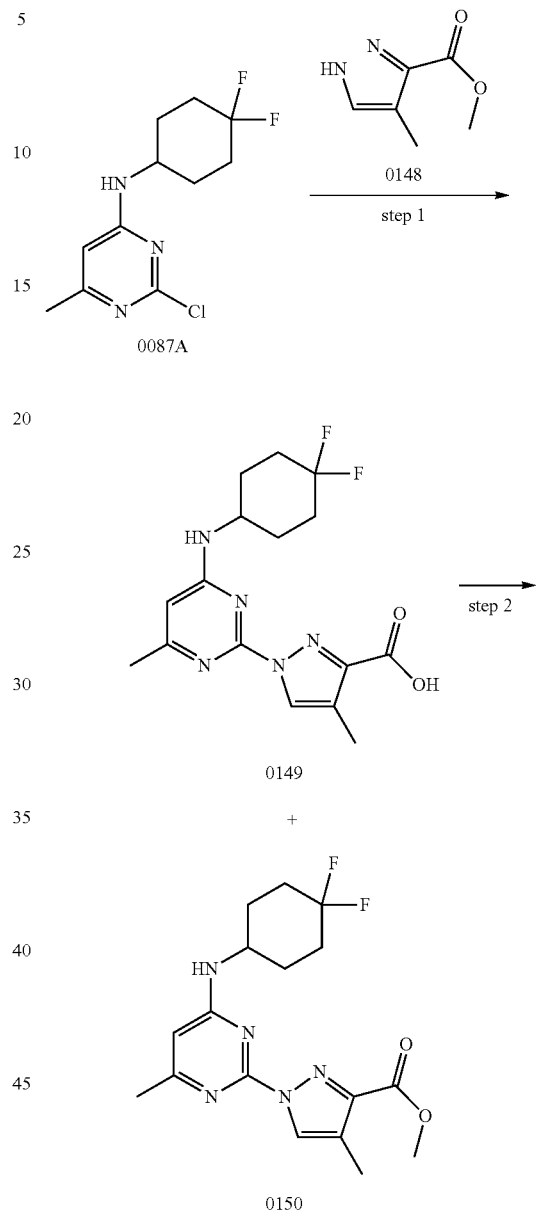

Step 1[0146]: The procedure is similar to step 3 [0006] in example 1. 1 g of 2-chloro-N-(4,4-difluorocyclohexyl)-6-methylpyrimidin-4-amine [0087A] gave 0.7 g of ethyl 1-(4-((4,4-difluorocyclohexyl)amino)-6-methylpyrimidin-2-yl)-1H-pyrazole-3-carboxylate [0146] as a pale yellow solid. MS(M+1)+=366.1.

Step 2[0147]: The procedure is similar to step 2[049] in example 10. 0.15 g of ethyl 1-(4-((4,4-difluorocyclohexyl)amino)-6-methylpyrimidin-2-yl)-1H-pyrazole-3-carboxylate [0146] gave 0.015 g of 2-(1-(4-((4,4-difluorocyclohexyl)amino)-6-methylpyrimidin-2-yl)-1H-pyrazol-3-yl)propan-2-ol [0147], Compound 215 as a white solid. MS(M+1)+=352.39, $^1$H-NMR (400 MHz, DMSO-d6): δ 8.44 (s, 1H), 7.55 (s, 1H), 6.45 (t, J=2.60 Hz, 1H), 6.19 (s, 1H), 5.03 (s, 1H), 4.10-4.09 (m, 1H), 2.26 (s, 3H), 2.05-1.95 (m, 6H), 1.57-1.54 (m, 2H), 1.45 (s, 6H).

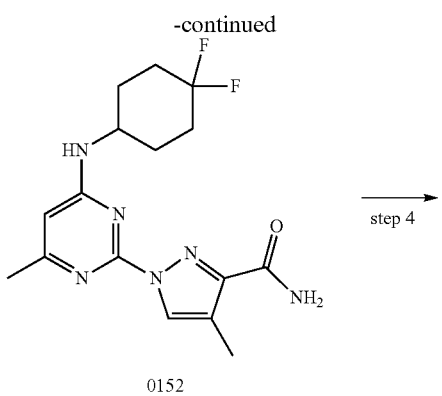

0152

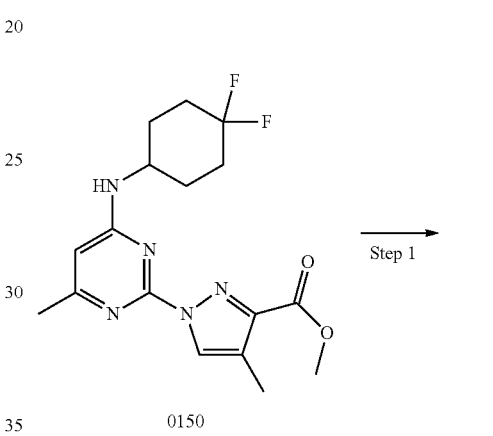

0153

Step 1[0149 & 0150]: The procedure is similar to step 3[0006] in Example 1. 2 g of 2-chloro-N-(4,4-difluorocyclohexyl)-6-methylpyrimidin-4-amine [0087A] gave 1.7 g of methyl 1-(4-((4,4-difluorocyclohexyl)amino)-6-methylpyrimidin-2-yl)-4-methyl-1H-pyrazole-3-carboxylate [0149] as an off-white solid MS(M+1)+=380.0 and 0.4 g of 1-(4-((4,4-difluorocyclohexyl)amino)-6-methylpyrimidin-2-yl)-4-methyl-1H-pyrazole-3-carboxylicacid [0150] as a brown solid. MS(M+1)+=352.3.

Step 2[0151]: To a solution of 1-(4-((4,4-difluorocyclohexyl)amino)-6-methylpyrimidin-2-yl)-4-methyl-1H-pyrazole-3-carboxylic acid [0149] (0.7 g, 1.99 mmol) in dichloromethane was added oxalyl chloride (1.0 g, 7.96 mmol) at 0° C. and the reaction mixture was stirred at rt. After 1 h, the reaction mixture was concentrated under reduced pressure in nitrogen atmosphere to afford 1 g of 1-(4-((4,4-difluorocyclohexyl)amino)-6-methylpyrimidin-2-yl)-4-methyl-1H-pyrazole-3-carbonyl chloride as a brown solid [0151]. MS(M+1)+=366.6 (methyl ester mass). This was taken as such tonext step.

Step 3[0152]: Ammonia gas was purged to a solution of 1-(4-((4,4-difluorocyclohexyl)amino)-6-methylpyrimidin-2-yl)-4-methyl-1H-pyrazole-3-carbonyl chloride [0151] (0.7 g, 1.99 mmol) in tetrahydrofuran at −10° C. for 15 min. After 0.5 h, the reaction mixture was brought to rt and purged with nitrogen for 10 min. The reaction mixture was concentrated under reduced pressure to afford a pale brown solid, which was purified in the Reveleris flash system instrument using methanol in chloroform as solvent in 24 g column. The product spot was isolated at 4% Methanol in chloroform as solvent to afford 0.650 g of 1-(4-((4,4-difluorocyclohexyl)amino)-6-methylpyrimidin-2-yl)-4-methyl-1H-pyrazole-3-carboxamide [0152], as white solid. MS(M+1)+=351.2.

Step 4[0153]:NSSY5282.0001. To a solution of 1-(4-((4,4-difluorocyclohexyl)amino)-6-methylpyrimidin-2-yl)-4-methyl-1H-pyrazole-3-carboxamide [0152] (0.35 g, 0.85 mmol) in dichloromethane was added triethylamine (0.43 g, 4.28 mmol) and trifluoromethanesulfonic anhydride (0.61 g, 2.14 mmol) at 0° C. and the reaction mixture was stirred at same temperature. After 1 h, the reaction mixture was quenched with ice and extracted with chloroform, washed with water and brine solution. The combined organic layer was dried over anhydrous sodium sulfate, filtered and concentrated under reduced pressure to afford a pale brown solid which was purified in the Reveleris flash system instrument using ethyl acetate in hexane as eluent in 24 g column to afford 0.21 g of 1-(4-((4,4-difluorocyclohexyl)amino)-6-methylpyrimidin-2-yl)-4-methyl-1H-pyrazole-3-carbonitrile [0153], Compound 253 as white solid. MS(M+1)+= 333.2. $^1$H NMR (400 MHz, DMSO-d6) δ 8.53 (s, 1H), 7.52 (d, J=7.2 Hz, 1H), 6.37 (s, 1H), 4.05 (bs, 1H), 2.30 (s, 3H), 2.22 (s, 3H), 2.11-1.87 (m, 6H), 1.72-1.56 (m, 2H).

Example 54

0150

0154

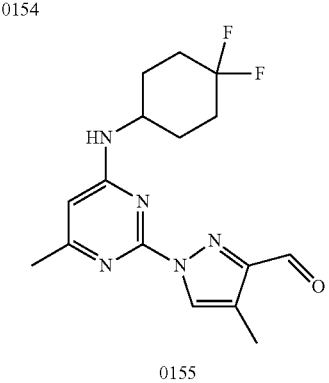

0155

Step 1[0154]: To a solution of 2-chloro-N-(4,4-difluorocyclohexyl)-6-methylpyrimidin-4-amine [0150] (1 g, 2.63 mmol) in tetrahydrofuran was added lithium aluminum hydride (0.2 g, 5.27 mmol) at −78° C. and the reaction mixture was stirred at same temperature. After 2 h, the reaction mixture was quenched with saturated aqueous ammonium chloride at −78° C., brought to rt and stirred for 15 min. The white precipitate formed was filtered off through celite bed and washed with ethyl acetate. The filtrate was washed with water and brine solution. The combined organic layer was dried over anhydrous sodium sulfate, filtered and concentrated under reduced pressure to afford a pale yellow solid, which was purified in the Reveleris flash system instrument using ethyl acetate in hexane as solvent in 24 g column to afford 0.07 g of (1-(4-((4,4-difluorocyclohexyl)amino)-6-methylpyrimidin-2-yl)-4-methyl-1H-pyrazol-3-yl)methanol [0154], Compound 236 as a white solid [MS(M+1)⁺=338.0. ¹H NMR (400 MHz, DMSO-d6) δ 8.22 (s, 1H), 7.24 (d, J=7.6 Hz, 1H), 6.23 (s, 1H), 4.68 (t, J=5.7 Hz, 1H), 4.48 (d, J=5.7 Hz, 2H), 4.02 (bs, 1H), 2.32 (s, 3H), 2.10 (s, 3H), 2.12-1.89 (m, 6H), 1.70-1.55 (m, 2H), and 0.4 g of 1-(4-((4,4-difluorocyclohexyl)amino)-6-methylpyrimidin-2-yl)-4-methyl-1H-pyrazole-3-carbaldehyde [0155] as a white solid. MS(M+1)⁺=336.0.

Example 55

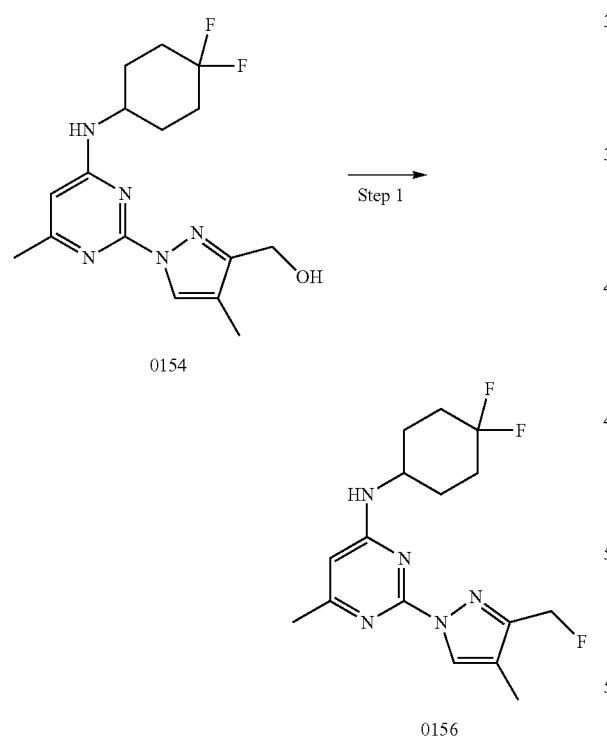

Step 2[0156]:NSSy5293.0001. The procedure is similar to step 3[0012] in Example 2. 0.5 g of (1-(4-((4,4-difluorocyclohexyl)amino)-6-methylpyrimidin-2-yl)-4-methyl-1H-pyrazol-3-yl)methanol [0154] gave 0.15 g of N-(4,4-difluorocyclohexyl)-2-(3-(fluoromethyl)-4-methyl-1H-pyrazol-1-yl)-6-methylpyrimidin-4-amine [0156], Compound 258 as white solid. MS(M+1)⁺=340.2, ¹H NMR (400 MHz, DMSO-d6) δ 8.33 (s, 1H), 7.34 (d, J=7.6 Hz, 1H), 6.28 (s, 1H), 5.49 (s, 1H), 5.37 (s, 1H), 4.04 (bs, 1H), 2.26 (s, 3H), 2.13 (s, 3H), 2.11-1.84 (m, 6H), 1.72-1.58 (m, 2H).

Example 56

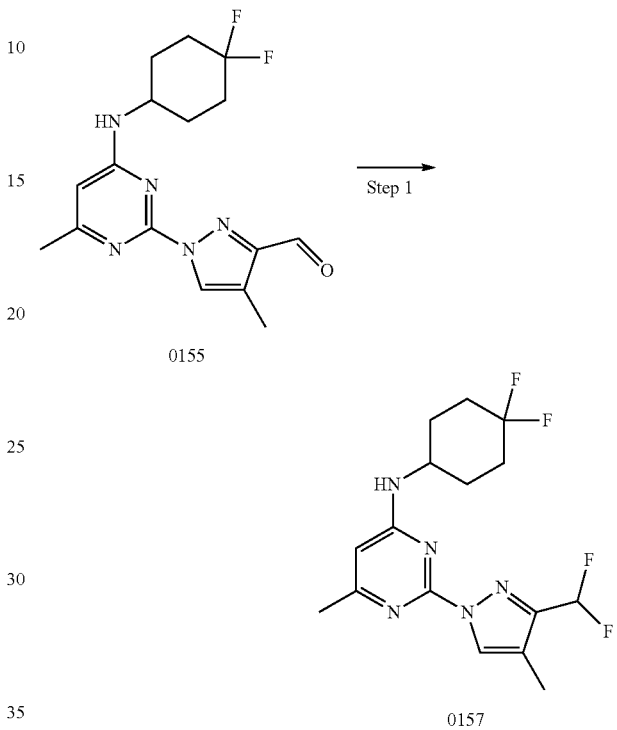

Step 3[0157]: The procedure is similar to step 3 [0012] in Example 2. 0.4 g of 1-(4-((4,4-difluorocyclohexyl)amino)-6-methylpyrimidin-2-yl)-4-methyl-1H-pyrazole-3-carbaldehyde [0155], Compound 246 gave 0.175 g of N-(4,4-difluorocyclohexyl)-2-(3-(difluoromethyl)-4-methyl-1H-pyrazol-1-yl)-6-methylpyrimidin-4-amine [0157] as white solid. MS(M+1)⁺=358.0. ¹H-NMR (400 MHz, DMSO-d6): δ 8.40 (s, 1H), 7.41 (d, J=7.20 Hz, 1H), 7.00 (t, JF=53.60 Hz, 1H), 6.32 (s, 1H), 4.01 (bs, 1H), 2.29 (s, 3H), 2.19 (s, 3H), 2.15-1.90 (m, 6H), 1.72-1.58 (m, 2H).

Example 57

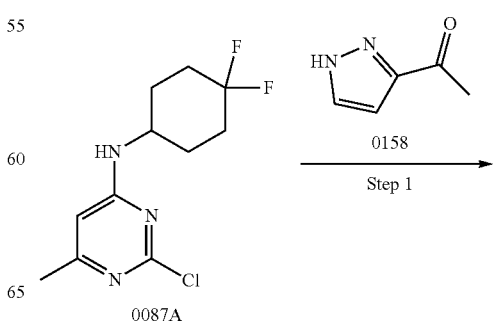

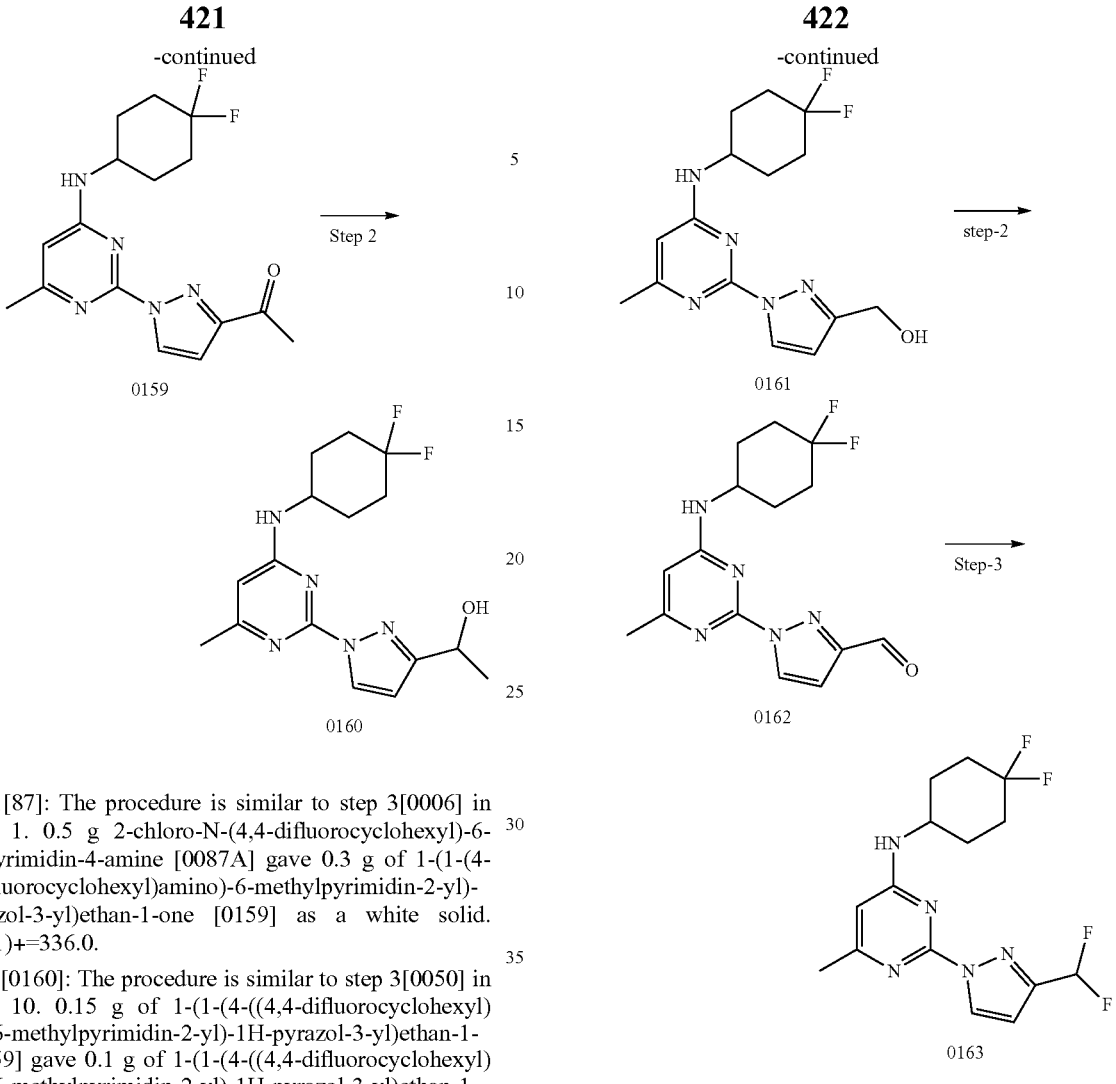

Step 1[87]: The procedure is similar to step 3[0006] in example 1. 0.5 g 2-chloro-N-(4,4-difluorocyclohexyl)-6-methylpyrimidin-4-amine [0087A] gave 0.3 g of 1-(1-(4-((4,4-difluorocyclohexyl)amino)-6-methylpyrimidin-2-yl)-1H-pyrazol-3-yl)ethan-1-one [0159] as a white solid. MS(M+1)+=336.0.

Step 2[0160]: The procedure is similar to step 3[0050] in example 10. 0.15 g of 1-(1-(4-((4,4-difluorocyclohexyl)amino)-6-methylpyrimidin-2-yl)-1H-pyrazol-3-yl)ethan-1-one [0159] gave 0.1 g of 1-(1-(4-((4,4-difluorocyclohexyl)amino)-6-methylpyrimidin-2-yl)-1H-pyrazol-3-yl)ethan-1-ol [0160], Compound 202 as an off-white solid. MS(M+1)$^+$=338.0, $^1$H NMR (400 MHz, DMSO-d6) δ 8.48 (s, 1H), 7.58 (s, 1H), 6.44 (d, J=2.7 Hz, 1H), 6.21 (s, 1H), 5.20 (d, J=4.8 Hz, 1H), 4.88-4.58 (m, 1H), 4.15 (s, 1H), 2.26 (s, 3H), 2.01 (d, J=41.4 Hz, 6H), 1.56 (d, J=9.3 Hz, 2H), 1.39 (d, J=6.5 Hz, 3H).

Example 58

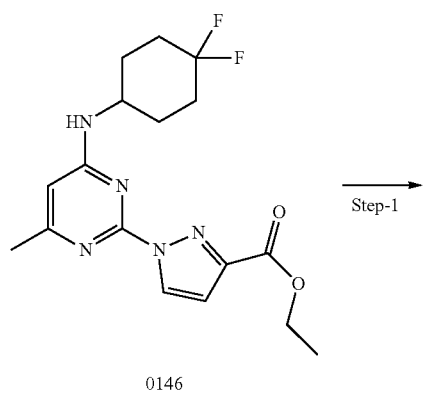

Step 1[0161]. The procedure is similar to step 2 [0019] in Example 4. 1.4 g of ethyl 1-(4-((4,4-difluorocyclohexyl)amino)-6-methylpyrimidin-2-yl)-1H-pyrazole-3-carboxylate [0146] gave 0.98 g of (1-(4-((4,4-difluorocyclohexyl)amino)-6-methylpyrimidin-2-yl)-1H-pyrazol-3-yl)methanol [0161] Compound 204 as an off-white solid.

MS(M+1)$^+$=324, $^1$H NMR (400 MHz, DMSO-d6) δ 8.50 (s, 1H), 7.59 (bs, 1H), 6.45 (s, 1H), 6.21 (bs, 1H), 5.20 (s, 1H), 4.49 (d, J=5.7 Hz, 2H), 4.16 (bs, 1H), 2.26 (s, 3H), 2.15-1.88 (m, 6H), 1.65-1.48 (m, 2H).

Step 2[0162]: 0.9 g of (1-(4-((4,4-difluorocyclohexyl)amino)-6-methylpyrimidin-2-yl)-1H-pyrazol-3-yl)methanol [0161] gave 0.62 g of 1-(4-((4,4-difluorocyclohexyl)amino)-6-methylpyrimidin-2-yl)-1H-pyrazole-3-carbaldehyde [0162] as a white solid, using manganese dioxide (5 eq) in dichloromethane. MS(M+1)+=322.3.

Step 3[0163]: The procedure is similar to step 3 [0012] in Example 2. 0.7 g of 1-(4-((4,4-difluorocyclohexyl)amino)-6-methylpyrimidin-2-yl)-1H-pyrazole-3-carbaldehyde [0162] gave 0.075 g of N-(4,4-difluorocyclohexyl)-2-(3-(difluoromethyl)-1H-pyrazol-1-yl)-6-methylpyrimidin-4-amine [0163] as an off-white solid. MS(M+1)$^+$=344.2, $^1$H NMR (400 MHz, DMSO-d6) δ 8.69 (bs, 1H), 7.72 (bs, 1H), 7.12 (t, JF=54.16 Hz, 1H), 6.77 (s, 1H), 6.29 (bs, 1H), 4.18 (bs, 1H), 2.28 (s, 3H), 2.17-1.83 (m, 6H), 1.65-1.57 (m, 2H).

Example 59

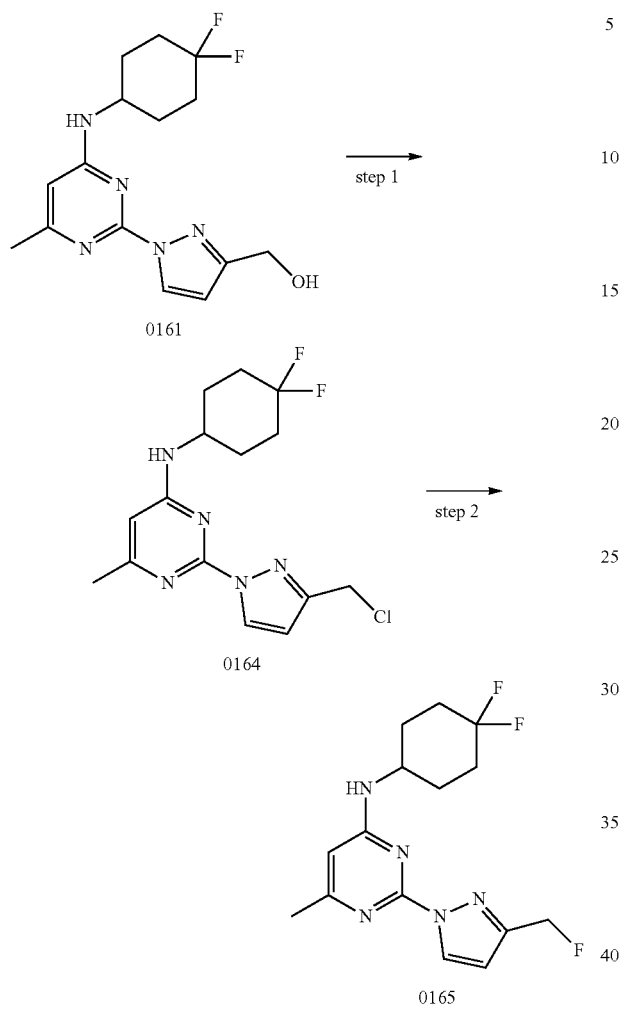

Step 1: Thionyl chloride (0.49 g, 4.17 mmol) was added to a solution of (1-(4-((4,4-difluorocyclohexyl)amino)-6-methylpyrimidin-2-yl)-1H-pyrazol-3-yl)methanol [0161] (0.45 g, 1.39 mmol) in dichloromethane and the reaction mixture was heated at 50° C. After 1 h, the reaction mixture was concentrated under reduced pressure and the residue was triturated with hexane and dried vacuum to afford 0.41 g of 2-(3-(chloromethyl)-1H-pyrazol-1-yl)-N-(4,4-difluorocyclohexyl)-6-methylpyrimidin-4-amine [0164] as off-white solid. MS(M+1)+=342.2. This was taken as such to next step.

Step 2[0165]: A solution of Potassium fluoride (1.08 g, 18.72 mmol), 18-crown-6 (0.12 g, 0.46 mmol) and 2-(3-(chloromethyl)-1H-pyrazol-1-yl)-N-(4,4-difluorocyclohexyl)-6-methylpyrimidin-4-amine [0164] (1.6 g, 4.68 mmol), in acetonitrile was heated at 100° C. in sealed tube. After 24 h, the reaction mixture was quenched with 10% sodium bicarbonate solution until the pH around ~10 and extracted with dichloromethane (3×400 mL), combined organic layer was washed with brine (2×200 mL), dried with anhydrous sodium sulfate, filtrate was concentrated to afford a crude product, which was purified by column chromatography to afford 0.81 g of N-(4,4-difluorocyclohexyl)-2-(3-(fluoromethyl)-1H-pyrazol-1-yl)-6-methylpyrimidin-4-amine [0165], Compound 233 as off-white solid. MS(M+1)+=326.2, $^1$H NMR (400 MHz, DMSO-d6) δ 8.60 (s, 1H), 7.66 (bs, 1H), 6.64 (s, 1H), 6.26 (bs, 1H), 5.45 (d, JF=48 Hz, 2H), 4.17 (bs, 1H), 2.27 (s, 3H), 2.13-1.87 (m, 6H), 1.62-1.57 (m, 2H).

Example 60

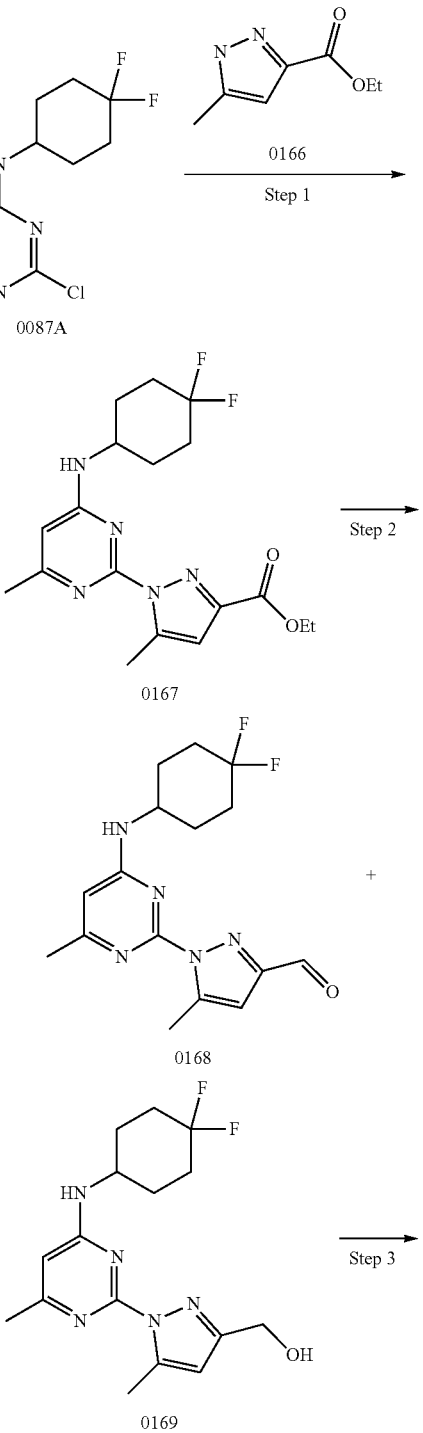

-continued

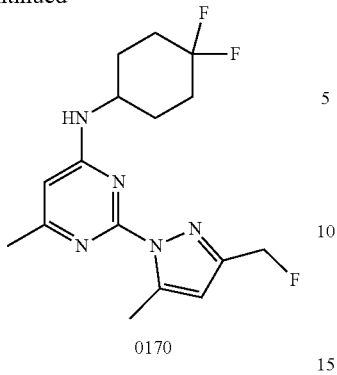

0170

Step 1[0167]: The procedure is similar to step 3[0006] in example 1. 0.5 g 2-chloro-N-(4,4-difluorocyclohexyl)-6-methylpyrimidin-4-amine [0087A] and ethyl 5-methyl-1H-pyrazole-3-carboxylate [0166] (0.35 g, 2.29 mmol) gave 0.7 g of ethyl 1-(4-((4,4-difluorocyclohexyl)amino)-6-methylpyrimidin-2-yl)-5-methyl-1H-pyrazole-3-carboxylate [0167] as a white solid. MS(M+1)+=348.2.

Step 2 [0168 and 0169]: The procedure is similar to step 2[0019] in example 4. 0.7 g ethyl 1-(4-((4,4-difluorocyclohexyl)amino)-6-methylpyrimidin-2-yl)-5-methyl-1H-pyrazole-3-carboxylate [0167] gave 0.1 g of 1-(4-((4,4-difluorocyclohexyl)amino)-6-methylpyrimidin-2-yl)-5-methyl-1H-pyrazole-3-carbaldehyde [0168] as an off-white solid. MS(M+1)+=338.38 and 0.035 g of (1-(4-((4,4-difluorocyclohexyl)amino)-6-methylpyrimidin-2-yl)-5-methyl-1H-pyrazol-3-yl)methanol [0169], Compound 241 as a white solid. MS(M+1)$^+$=336.35, $^1$H NMR (400 MHz, DMSO-d6) δ 7.57 (d, J=7.7 Hz, 1H), 6.24 (s, 1H), 6.20 (s, 1H), 5.09 (t, J=5.9 Hz, 1H), 4.41 (d, J=6.0 Hz, 2H), 4.02 (s, 1H), 2.54 (s, 3H), 2.25 (s, 3H), 2.12-2.02 (m, 2H), 1.95 (d, J=14.0 Hz, 4H), 1.56 (d, J=11.9 Hz, 2H).

Step 3[0170]: The procedure is similar to step 3[0012] in example 2, 0.1 g 1-(4-((4,4-difluorocyclohexyl)amino)-6-methylpyrimidin-2-yl)-5-methyl-1H-pyrazole-3-carbaldehyde [0169] gave 0.018 g of N-(4,4-difluorocyclohexyl)-2-(3-(fluoromethyl)-5-methyl-1H-pyrazol-1-yl)-6-methylpyrimidin-4-amine [0170], Compound 256 as a grey solid. MS(M+1)$^+$=340.4, $^1$H NMR (400 MHz, DMSO-d6) δ 7.37 (d, J=7.8 Hz, 1H), 6.33 (s, 2H), 5.33 (d, JF=48 Hz, 2H), 3.97 (bs, 1H), 2.56 (s, 3H), 2.28 (s, 3H), 2.13-1.88 (m, 6H), 1.62 (q, J=11.6, 9.6 Hz, 2H).

Example 61

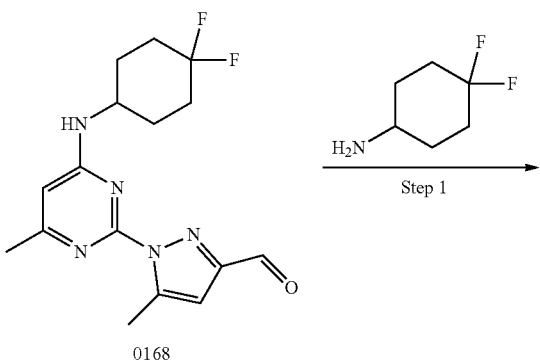

0168

-continued

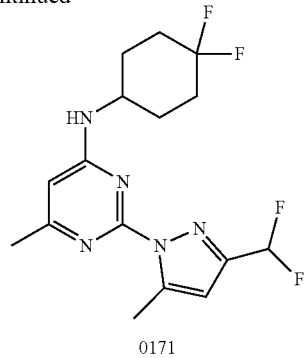

0171

Step 1[0171]: The procedure is similar to step 3 [0012] in example 2. 0.15 g of 1-(4-((4,4-difluorocyclohexyl)amino)-6-methylpyrimidin-2-yl)-5-methyl-1H-pyrazole-3-carbaldehyde [0168] gave 0.075 g of N-(4,4-difluorocyclohexyl)-2-(3-(difluoromethyl)-5-methyl-1H-pyrazol-1-yl)-6-methylpyrimidin-4-amine [0171], Compound 237 as a white solid. MS(M+1)$^+$=358.35, $^1$H NMR (400 MHz, DMSO-d6) δ 7.72 (d, J=7.6 Hz, 1H), 7.02 (t, JF=54 Hz, 1H), 6.52 (s, 1H), 6.31 (s, 1H), 2.58 (s, 3H), 2.28 (s, 3H), 2.09-1.89 (m, 6H), 1.56 (d, J=12.0 Hz, 2H), 1.25 (d, J=6.2 Hz, 1H).

Example 63

Step 1[0175]: The procedure is similar to step 2[0177] in example 62. 0.2 g of 4-chloro-2-(3,5-dimethyl-1H-pyrazol-1-yl)pyrimidine [0173] gave 0.1 g of N-(4,4-difluorocyclohexyl)-2-(3,5-dimethyl-1H-pyrazol-1-yl)pyrimidin-4-amine [0175], Compound 163 as an off-white solid. MS(M+1)$^+$= 308.2, $^1$H-NMR (400 MHz, CDCl3): δ 8.20 (d, J=5.60 Hz, 1H), 6.29 (d, J=5.60 Hz, 1H), 6.02 (s, 1H), 5.53 (s, 1H), 3.88

(s, 1H), 3.22 (s, 3H), 2.34 (s, 3H), 1.97-1.90 (m, 4H), 1.86-1.73 (m, 2H), 1.71-1.65 (m, 2H),

Example 64

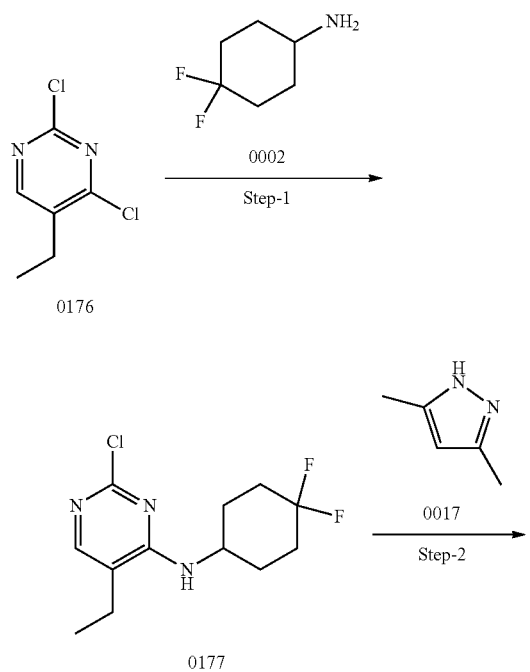

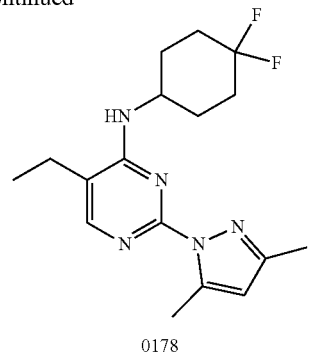

Step 1[0177]: The procedure is similar to step 3[0006] in Example 1. 0.5 g of 2,4-dichloro-5-ethylpyrimidine [0176] gave 0.25 g of 2-chloro-N-(4,4-difluorocyclohexyl)-5-ethylpyrimidin-4-amine [0177] as a light brown gum. MS(M+1)+=276.

Step 2[0178]: The procedure is similar to step 2[0174] in Example 62 (without base). 0.25 g of 2-chloro-N-(4,4-difluorocyclohexyl)-5-ethylpyrimidin-4-amine [0177] gave 0.03 g of N-(4,4-difluorocyclohexyl)-2-(3,5-dimethyl-1H-pyrazol-1-yl)-5-ethylpyrimidin-4-amine [0178], Compound 111 as an off-white solid. MS(M+1)$^+$=336.1, $^1$H NMR (400 MHz, Chloroform-d) δ 8.09 (s, 1H), 6.01 (s, 1H), 4.70 (d, J=7.4 Hz, 1H), 4.17 (d, J=9.8 Hz, 1H), 2.66 (s, 3H), 2.42 (q, J=7.5 Hz, 2H), 2.33 (s, 3H), 2.18 (d, J=10.3 Hz, 4H), 2.01-1.80 (m, 2H), 1.75-1.60 (m, 2H), 1.27 (t, J=7.5 Hz, 3H).

Example 65

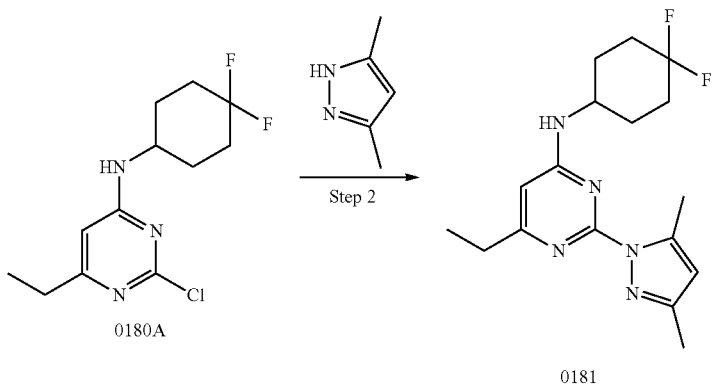

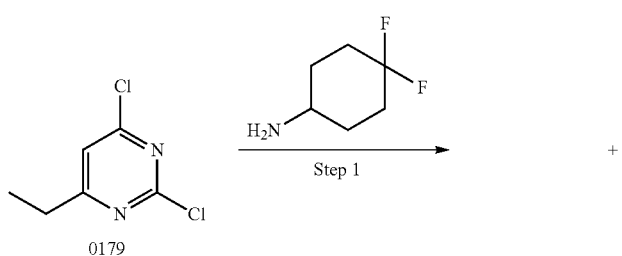

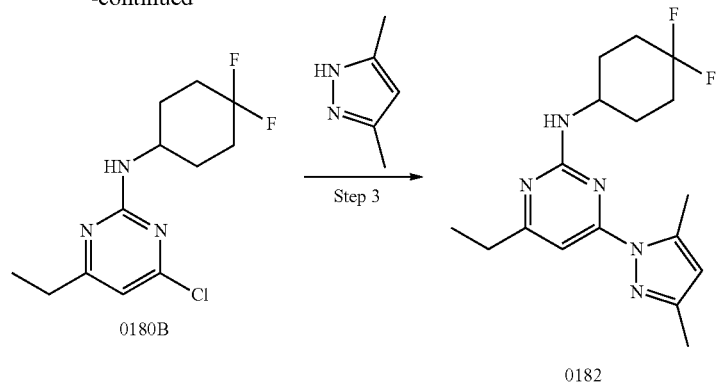

Step 1[0180A & 0180B]: To a solution of 2,4-Dichloro-6-ethylpyrimidine [0179] (1 g, 5.64 mmol) and 4,4-Difluorocyclohexylamine Hydrochloride (0.96 g, 5.64 mmol) in acetonitrile was added cesium carbonate (3.68 g, 11.29 g) and the reaction mixture was heated at 65° C. in sealed tube. After 16 h, the reaction mixture was filtered and the filtrate was concentrated to afford a crude product, which was purified by column chromatography to afford 0.8 g of 2-chloro-N-(4,4-difluorocyclohexyl)-6-ethylpyrimidin-4-amine [0180A] as colorless oil and 0.5 g of 4-chloro-N-(4,4-difluorocyclohexyl)-6-ethylpyrimidin-2-amine [0180B] as colorless oil. MS(M+1)+=276.0.

Step 2[0181]: The procedure is similar to step 3[0006] in Example 1. 0.3 g of 2-chloro-N-(4,4-difluorocyclohexyl)-6-ethylpyrimidin-4-amine [0180A] gave 0.05 g of N-(4,4-difluorocyclohexyl)-2-(3,5-dimethyl-1H-pyrazol-1-yl)-6-ethylpyrimidin-4-amine [0181], Compound 171 as off-white solid. MS(M+1)+=336.4. ¹H NMR (400 MHz, DMSO-d6) δ 7.56 (d, J=7.7 Hz, 1H), 6.23 (s, 1H), 6.04 (s, 1H), 4.03 (bs, 1H), 3.28 (m, 2H), 2.48 (s, 3H), 2.16 (s, 3H), 2.15-1.85 (m, 6H), 1.62-1.49 (m, 2H), 1.18 (t, J=7.5 Hz, 3H).

Step 3[0182]: The procedure is similar to step 3[0006] in Example 1. 0.3 g of 4-chloro-N-(4,4-difluorocyclohexyl)-6-ethylpyrimidin-2-amine [0180B] gave 0.95 g of N-(4,4-difluorocyclohexyl)-4-(3,5-dimethyl-1H-pyrazol-1-yl)-6-ethylpyrimidin-2-amine [0182], Compound 169 as white solid. MS(M+1)+=336.4. ¹H NMR (400 MHz, DMSO-d6) δ 7.35 (bs, 1H), 6.88 (s, 1H), 6.12 (s, 1H), 3.84 (bs, 1H), 2.64 (s, 3H), 2.60-2.53 (m, 2H), 2.18 (s, 3H), 2.10-1.75 (m, 6H), 1.64-1.52 (m, 2H), 1.18 (t, J=7.6 Hz, 3H).

Example 67

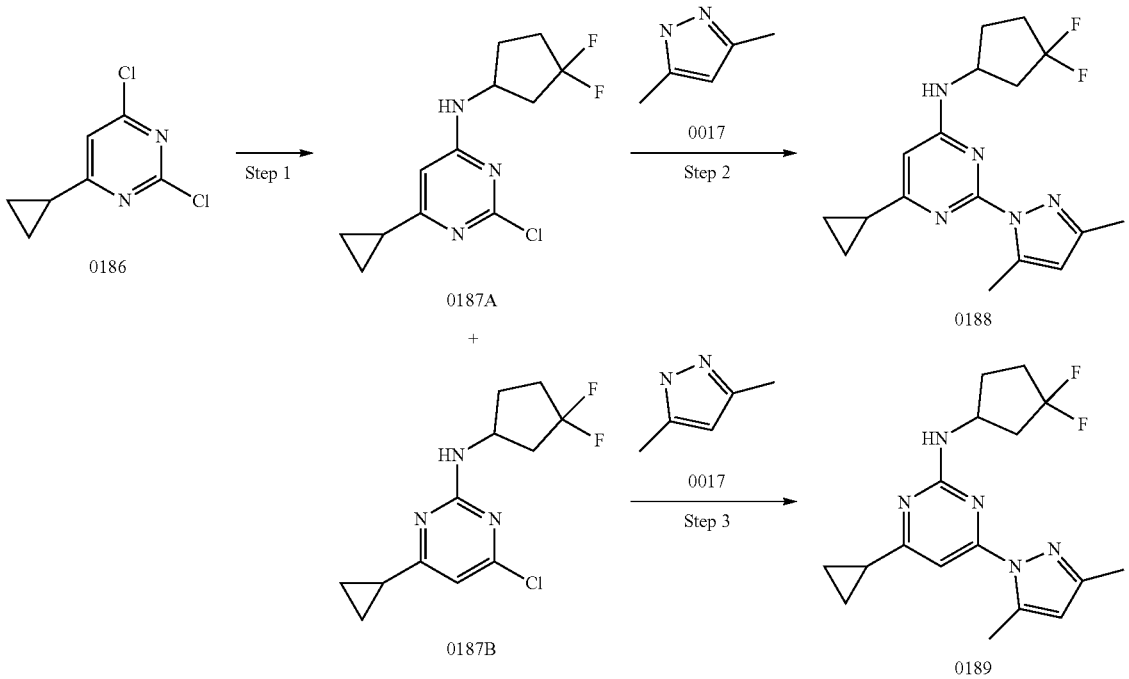

Step 1[0187A and 0187B]: The procedure is similar to Step 1[0180A & 0180B] in example 66. 0.5 g of 2,4-dichloro-6-cyclopropyl pyrimidine [0186] gave 0.3 g of 2-chloro-6-cyclopropyl-N-(3,3-difluorocyclopentyl)pyrimidin-4-amine [0187A] and 0.125 g of 4-chloro-6-cyclopropyl-N-(3,3-difluorocyclopentyl)pyrimidin-2-amine [0187B] both as colorless gums. MS(M+1)+=274.0.

Step 2[0188]: The procedure is similar to step 3[0006] in Example 1. 0.3 g of 2-chloro-6-cyclopropyl-N-(3,3-difluorocyclopentyl)pyrimidin-4-amine [0187A] gave 0.175 g of 6-cyclopropyl-N-(3,3-difluorocyclopentyl)-2-(3,5-dimethyl-1H-pyrazol-1-yl)pyrimidin-4-amine [0188], Compound 217 as white solid. MS(M+1)+=334.2, ¹H NMR (400 MHz, DMSO-d6) δ 7.71 (s, 1H), 6.31 (s, 1H), 6.03 (s, 1H), 4.45 (s, 1H), 2.58 (dt, J=13.6, 6.5 Hz, 1H), 2.45 (s, 3H), 2.31-2.17 (m, 2H), 2.15 (s, 3H), 2.06 (dq, J=16.2, 9.1, 8.0 Hz, 2H), 1.93 (s, 1H), 1.72 (dq, J=12.2, 8.5 Hz, 1H), 0.98-0.90 (m, 3H).

Step 3[0189]: The procedure is similar to step 3[0006] in Example 1. 0.125 g of 4-chloro-6-cyclopropyl-N-(3,3-difluorocyclopentyl)pyrimidin-2-amine [0187B] gave 0.045 g 4-cyclopropyl-N-(3,3-difluorocyclopentyl)-6-(3,5-dimethyl-1H-pyrazol-1-yl)pyrimidin-2-amine [0189], Compound 222 as white solid, MS(M+1)+=334.2. ¹H-NMR (400 MHz, DMSO-d6): δ 7.39 (bs, 1H), 6.99 (s, 1H), 6.13 (s, 1H), 4.29 (q, J=7.20 Hz, 1H), 2.64 (s, 3H), 2.35-2.25 (m, 2H), 2.20 (s, 3H), 2.15-1.98 (m, 4H), 1.85-1.73 (m, 1H), 1.12-0.90 (m, 4H).

Example 69

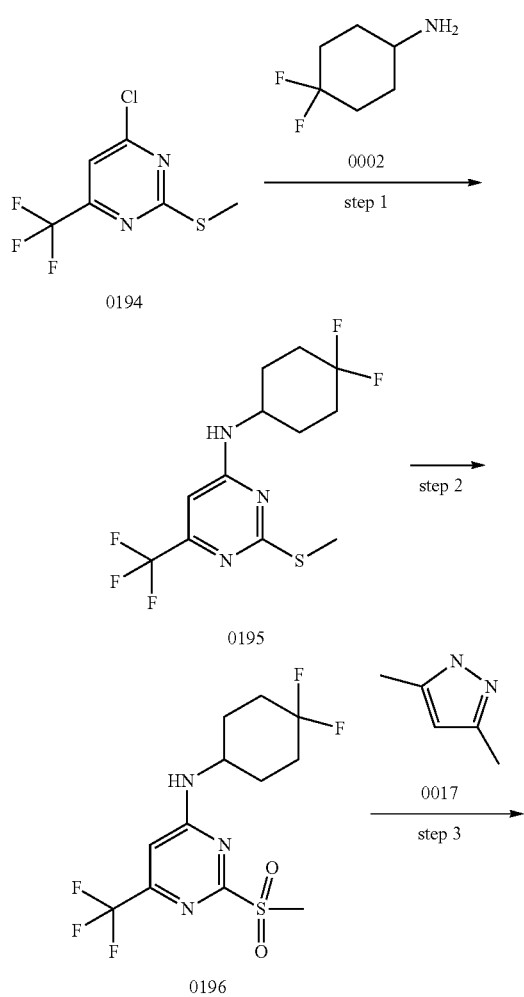

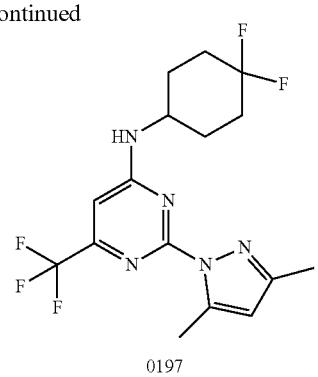

Step 1[0195]: To a solution of 4-chloro-2-(methylsulfanyl)-6-(trifluoromethyl)pyrimidine [0194] (1 g, 4.374 mmol) in acetonitrile (10 mL) was added N,N-diisopropyl ethylamine (0.84 g, 6.56 mmol), followed by 4,4-difluorocyclohexylamine hydrochloride [0002] (0.75 g, 4.374 mmol). The reaction mixture was stirred at rt for 36 h. The reaction mixture was concentrated under reduced pressure. The residue was diluted with ethyl acetate (50 mL). The organic layer was washed with water (10 mL), followed by brine (10 mL). The organic layer was dried over anhydrous sodium sulfate to afford 1.4 g of N-(4,4-difluorocyclohexyl)-2-(methylthio)-6-(trifluoromethyl)pyrimidin-4-amine [0195] as a yellow gum. MS(M+1)+=328.3

Step 2[0196]: To a solution of N-(4,4-difluorocyclohexyl)-2-(methylthio)-6-(trifluoromethyl)pyrimidin-4-amine [0195] (0.55 g, 1.68 mmol) in dichloromethane (10 mL), 3-chloroperbenzoic acid (0.86 g, 5.04 mmol) was added portion-wise at 0° C. The reaction mixture was stirred at rt for 3 h. The reaction mixture was diluted with dichloromethane (50 mL). The organic layer was stirred with saturated solution of sodium thiosulfate solution (20 mL), followed by 10% sodium bicarbonate solution (10 mL), water (10 mL) and brine water (10 mL). The organic layer was dried over anhydrous sodium sulfate to afford 0.6 g of N-(4,4-difluorocyclohexyl)-2-(methylsulfonyl)-6-(trifluoromethyl)pyrimidin-4-amine [0196] as a yellow solid. MS(M+1)+=359.9

Step 3[0197]: To a solution of N-(4,4-difluorocyclohexyl)-2-(methylsulfonyl)-6-(trifluoromethyl)pyrimidin-4-amine [0196] (0.55 g, 1.53 mmol) in acetonitrile (6 mL), was added 3,5-dimethyl pyrazole [0017] (0.22 g, 2.296 mmol) and cesium carbonate (0.748 g, 2.296 mmol). The reaction mixture was irradiated in microwave at 130° C. for 2 h and concentrated under reduced pressure to afford 0.55 g of N-(4,4-difluorocyclohexyl)-2-(3,5-dimethyl-1H-pyrazol-1-yl)-6-(trifluoromethyl)pyrimidin-4-amine. This was purified by column chromatography using 60% ethyl acetate in pet ether as solvent to afford 0.090 g of N-(4,4-difluorocyclohexyl)-2-(3,5-dimethyl-1H-pyrazol-1-yl)-6-(trifluoromethyl)pyrimidin-4-amine [0197], Compound 162 as a white solid. MS(M+1)+=376.6. ¹H NMR (400 MHz, DMSO-d6) δ 8.30 (d, J=7.5 Hz, 1H), 6.74 (s, 1H), 6.13 (s, 1H), 4.09 (bs, 1H), 2.57 (s, 3H), 2.19 (s, 3H), 2.15-1.90 (m, 6H), 1.65-1.52 (m, 2H).

Example 71

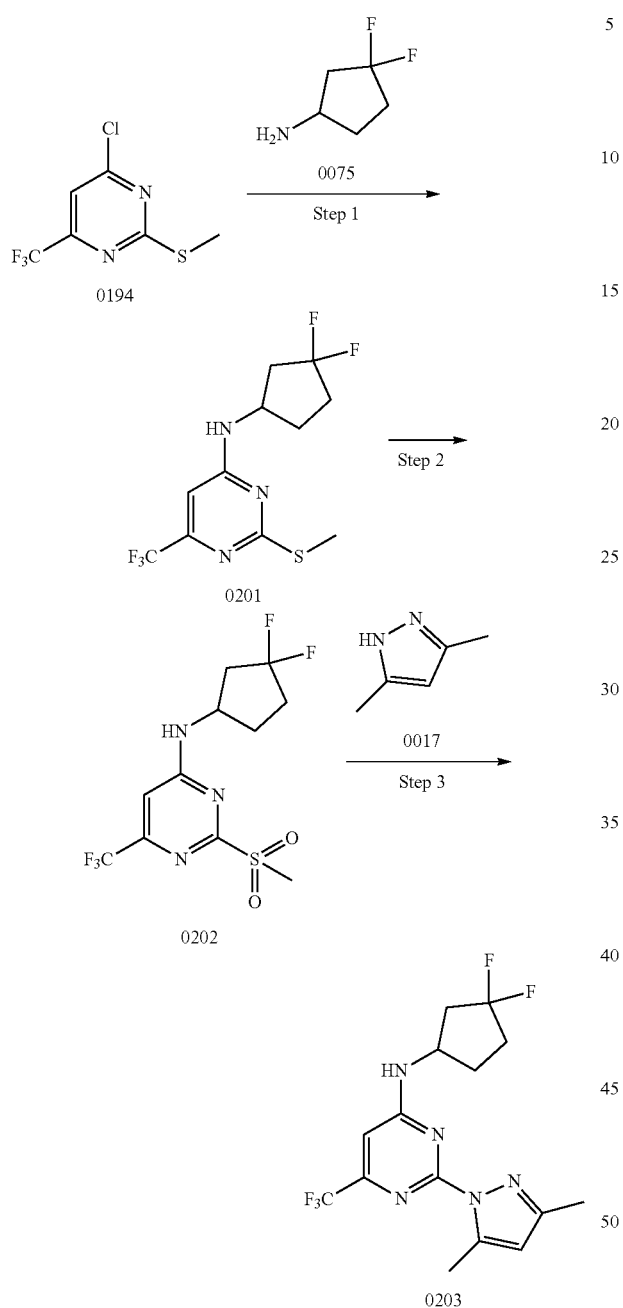

Step 1[0201]: The procedure is similar to Step 1[0195] in example 69. 0.5 g of 4-chloro-2-(methylthio)-6-(trifluoromethyl)pyrimidine [0194] gave 0.4 g of N-(3,3-difluorocyclopentyl)-2-(methylthio)-6-(trifluoromethyl)pyrimidin-4-amine [0201] as an off-white solid. MS(M+1)+=314.1.

Step 2[0202]: The procedure is similar to Step 2[0196] in example 69. 0.4 g N-(3,3-difluorocyclopentyl)-2-(methylthio)-6-(trifluoromethyl)pyrimidin-4-amine [0201] gave 0.35 g of N-(3,3-difluorocyclopentyl)-2-(methylsulfonyl)-6-(trifluoromethyl)pyrimidin-4-amine [0202] as an off-white solid. MS(M+1)+=346.2.

Step 3[0203]: The procedure is similar to Step 3[0197] in example 69. 0.2 g N-(3,3-difluorocyclopentyl)-2-(methylsulfonyl)-6-(trifluoromethyl)pyrimidin-4-amine [0202] gave 0.07 g of N-(3,3-difluorocyclopentyl)-2-(3,5-dimethyl-1H-pyrazol-1-yl)-6-(trifluoromethyl)pyrimidin-4-amine [0203], Compound 167 as a white solid.

MS(M+1)+=362.2, 1H NMR (400 MHz, CDCl3): δ 6.52 (s, 1H), 6.06-5.99 (m, 2H), 4.36 (m, 1H), 2.70-2.65 (m, 4H), 2.39-2.29 (m, 5H), 2.23-2.16 (m, 2H), 2.12-2.09 (m, 1H).

Example 72

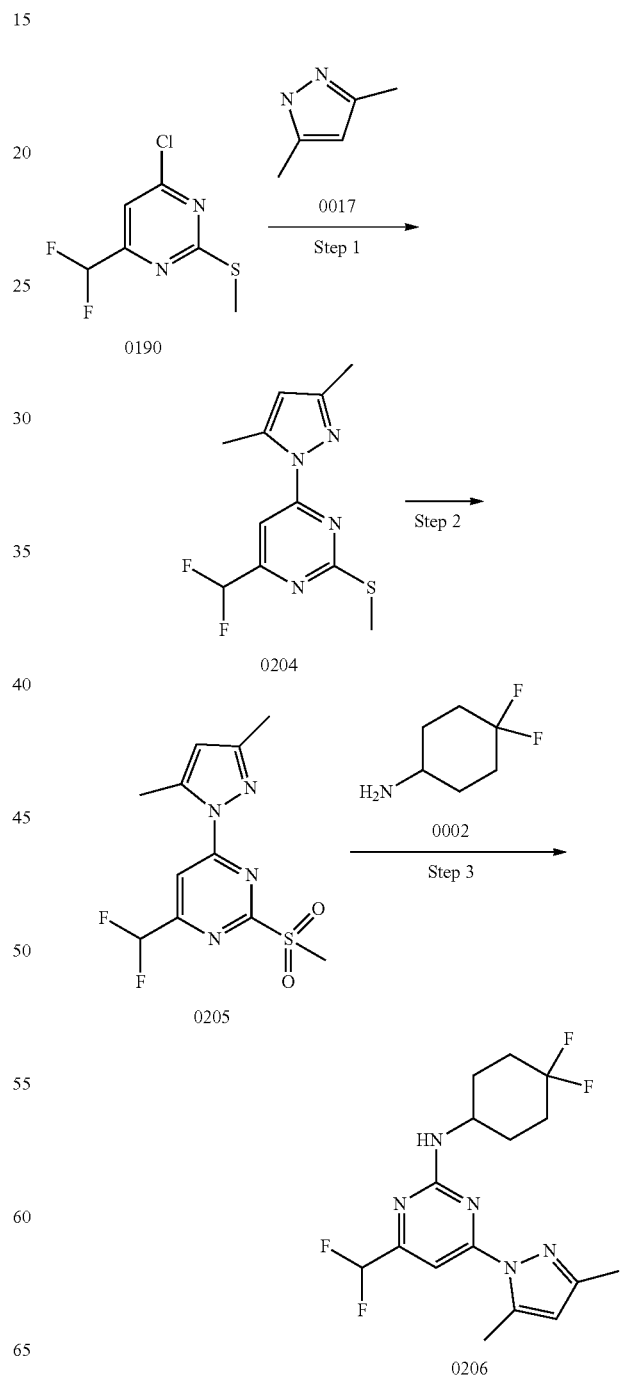

Step 1[0204]: The procedure is similar to Step 1[0195] in example 69. 1.0 g of 4-chloro-6-(difluoromethyl)-2-(methylthio)pyrimidine [0190] gave 0.8 g 4-(difluoromethyl)-6-(3,5-dimethyl-1H-pyrazol-1-yl)-2-(methylthio)pyrimidine [0204] as an off-white solid. MS (M+1)+=271.2.

Step 2[0205]: The procedure is similar to Step 2[0196] in example 69. 1.0 g 4-(difluoromethyl)-6-(3,5-dimethyl-1H-pyrazol-1-yl)-2-(methylthio)pyrimidine [0204] gave 0.7 g of 4-(difluoromethyl)-6-(3,5-dimethyl-1H-pyrazol-1-yl)-2-(methylsulfonyl)pyrimidine [0205] as an off-white solid. MS(M+1)+=303.1.

Step 3[0206]: The procedure is similar to Step 3[0197] in example 69 (DIPEA as base). 0.4 g of 4-(difluoromethyl)-6-(3,5-dimethyl-1H-pyrazol-1-yl)-2-(methylsulfonyl)pyrimidine [0205] gave 0.2 g of N-(4,4-difluorocyclohexyl)-4-(difluoromethyl)-6-(3,5-dimethyl-1H-pyrazol-1-yl)pyrimidin-2-amine [0206] as a white solid. MS(M+1)+=358.2, 1H NMR (400 MHz, DMSO-d6) δ 7.94 (d, J=7.4 Hz, 1H), 7.19 (s, 1H), 6.76 (t, JF=54 Hz, 1H), 6.21 (s, 1H), 2.68 (s, 3H), 2.21 (s, 3H), 2.12-1.89 (m, 6H), 1.60 (d, J=11.8 Hz, 3H).

Example 73

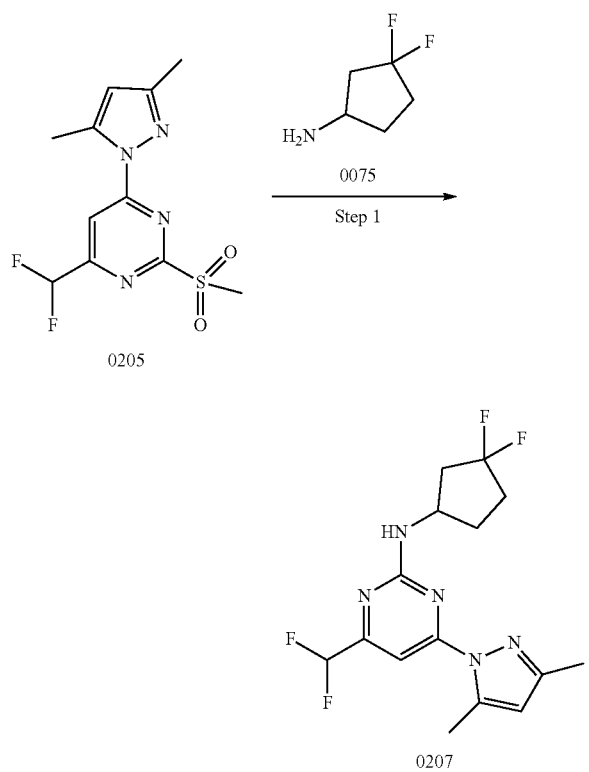

Step 3[0207]: The procedure is similar to Step 3[0197] in example 69 (DIPEA as base). 0.25 g of 4-(difluoromethyl)-6-(3,5-dimethyl-1H-pyrazol-1-yl)-2-(methylsulfonyl)pyrimidine [0205] gave 0.2 g N-(3,3-difluorocyclopentyl)-4-(difluoromethyl)-6-(3,5-dimethyl-1H-pyrazol-1-yl)pyrimidin-2-amine [0207], Compound 181 as a white solid. MS(M+1)+=344.4, 1H NMR (400 MHz, DMSO-d6) δ 8.25-7.72 (m, 1H), 7.22 (s, 1H), 6.77 (t, JF=54.5 Hz, 1H), 6.20 (s, 1H), 4.35 (s, 1H), 2.67 (s, 3H), 2.55 (d, J=8.1 Hz, 1H), 2.42-1.90 (m, 7H), 1.82 (q, J=9.0 Hz, 1H).

Example 74

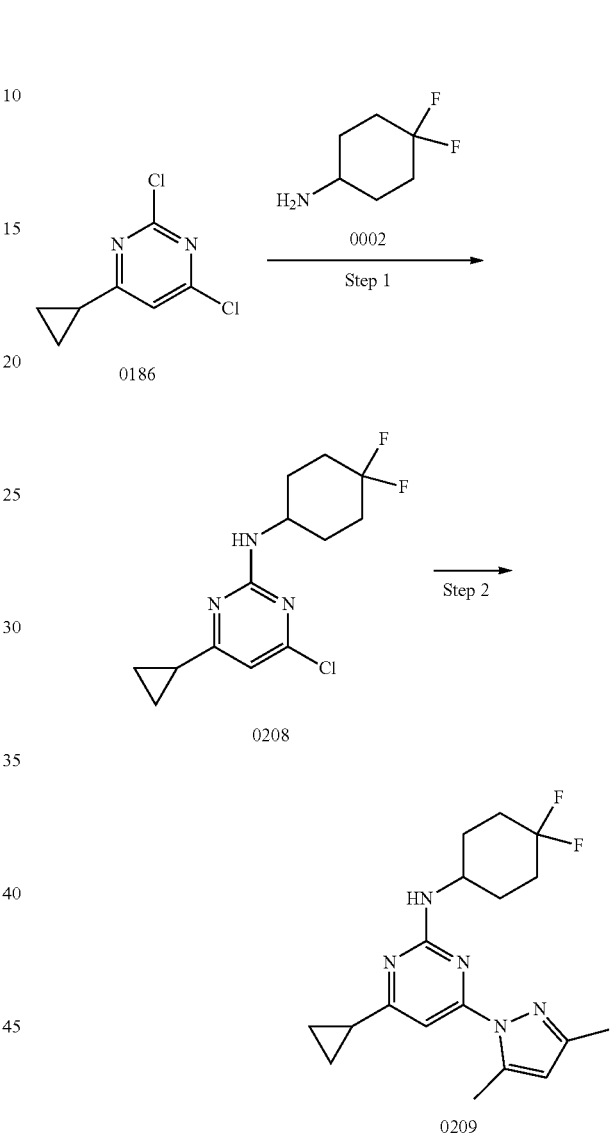

Step 1[0208]: The procedure is similar to Step 3[0197] in example 69. 0.3 g 2,4-dichloro-6-cyclopropylpyrimidine [0186] gave 0.2 g of 4-chloro-6-cyclopropyl-N-(4,4-difluorocyclohexyl)pyrimidin-2-amine [0208] as an off-white solid. MS(M+1)+=288.2.

Step 2[0209]: The procedure is similar to Step 3[0197] in example 69. 0.2 g 4-chloro-6-cyclopropyl-N-(4,4-difluorocyclohexyl)pyrimidin-2-amine [0208] gave 0.04 g of 4-cyclopropyl-N-(4,4-difluorocyclohexyl)-6-(3,5-dimethyl-1H-pyrazol-1-yl)pyrimidin-2-amine [0209], Compound 226 as a white solid. MS(M+1)+=348.2, 1H NMR (400 MHz, DMSO-d6): δ 7.91 (m, 1H), 7.60 (m, 1H), 5.82 (s, 1H), 5.06 (m, 1H), 3.55 (s, 2H), 2.57 (m, 1H), 2.43 (s, 3H), 1.51-1.46 (m, 6H), 1.31-1.32 (m, 2H), 1.29 (s, 6H).

Example 75

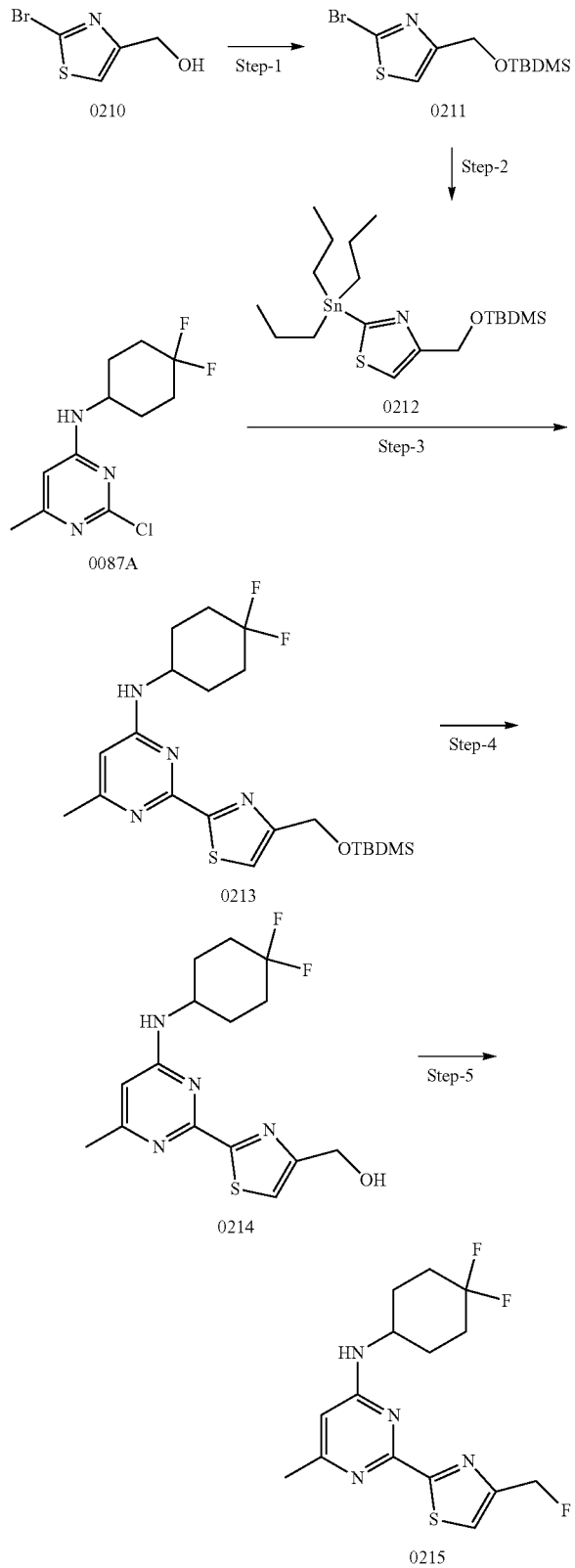

Step 1[0211]: To a solution of 2-Bromo-4-Hydroxymethylthiazole [0210] (2 g, 10.30 mmol) in N,N-dimethylformamide (20 mL) was added tert-butyl dimethylsilyl chloride (3.2 g, 20.6 mmol) and imidazole (2.80 g, 41.2 mmol), then the reaction mixture was stirred at rt for 5 h. After the completion of the reaction, to the reaction mixture was added ice cold water and extracted with ethyl acetate (2×75 mL), the combined organic layer was dried over anhydrous sodium sulfate and concentrated to afford as an colorless liquid and which was purified by column of silica gel (60-120 mesh) using 15% ethyl acetate in hexane as eluent to afford 3 g of 2-bromo-4-(((tert-butyl dimethylsilyl)oxy)methyl)thiazole [0211] as an colorless liquid.

Step 2[0212]: To a solution of 2-bromo-4-(((tert-butyl dimethylsilyl)oxy)methyl)thiazole [0211] (0.3 g, 0.97 mmol) in tetrahydrofuran (10 mL) at −78° C. under N2 was added n-BuLi (2.5 M in hexane) (0.06, 1.07, 1.) and the resulting brown solution was stirred for 30 min before adding tributyltin chloride (0.38 g, 1.16 mmol) and the reaction mixture was allowed to warm to rt and left overnight. After completion, the reaction mixture was quenched with saturated ammonium chloride solution, extracted with ethyl acetate (2×25 mL). The combined organic layer was dried over anhydrous sodium sulfate and concentrated to afford 0.7 g of 4-(((tert-butyldimethylsilyl)oxy)methyl)-2-(tributylstannyl)thiazole [0212] as a light yellow liquid.

Step 3[0213]: To a solution of 2-chloro-N-(4,4-difluorocyclohexyl)-6-methylpyrimidin-4-amine [0087A] (0.3 g, 1.14 mmol) in toluene (10 mL) was added 4-(((tert-butyldimethylsilyl)oxy)methyl)-2-(tributylstannyl) thiazole [00212] (0.71 g, 1.37 mmol1.) and purged nitrogen for 5 min, then added tetrakis(triphenylphosphine)palladium(0) (0.26 g, 0.22 mmol0.) to the reaction mixture and was irradiated in microwave at 130° C. for 2 h. the reaction mixture was filtered through celite bed and the filtrate was concentrated to afford as an brownish gum and which was purified by column of silica gel (60-120 mesh), using 50% ethyl acetate in hexane as eluent to afford 0.140 g of 2-(4-(((tert-butyldimethylsilyl)oxy)methyl)thiazol-2-yl)-N-(4,4-difluorocyclohexyl)-6-methylpyrimidin-4-amine[0213] as an colorless gum. MS(M+1)+=455.

Step 4[0214]: To an ice cooled solution of 2-(4-(((tert-butyldimethylsilyl)oxy)methyl)thiazol-2-yl)-N-(4,4-difluoro cyclohexyl)-6-methylpyrimidin-4-amine [0213] (0.12 g, 0.26 mmol1.) in diethyl ether (10 mL) was added hydrogenchloride (gas) in dioxane, After the completion of the reaction, the solid was filtered and washed with hexane to afford as off-white solid and which was dissolved in saturated sodium bicarbonate solution and extracted with ethyl acetate (2×25 mL), the combined organic layer was dried over anhydrous sodium sulfate and concentrated to afford as an colorless gum and which was purified by column of silica gel (60-120 mesh), using ethyl acetate as eluent to afford 0.055 g of (2-(4-((4,4-difluorocyclohexyl)amino)-6-methylpyrimidin-2-yl)thiazol-4-yl)methanol [0214], Compound 270 as an white solid. MS(M+1)+=341, $^1$H NMR (400 MHz, DMSO-d6) δ 7.53 (s, 2H), 6.35 (s, 1H), 5.39 (t, J=5.7 Hz, 1H), 4.62 (d, J=5.7 Hz, 2H), 4.09 (s, 1H), 2.29 (s, 3H), 2.07-1.95 (m, 6H), 1.59-1.52 (m, 2H).

Step 5[0215]: The procedure is similar to step 3 [0012] in example 2. 0.32 g of (2-(4-((4,4-difluorocyclohexyl)amino)-6-methylpyrimidin-2-yl)thiazol-4-yl)methanol [0214] gave 0.18 g of N-(4,4-difluorocyclohexyl)-2-(4-(fluoromethyl) thiazol-2-yl)-6-methylpyrimidin-4-amine [0215], Compound 273 as an light yellow solid, MS(M+1)+=343. $^1$H NMR (400 MHz, DMSO-d6) δ 7.96 (d, J=3.4 Hz, 1H), 7.57

(bs, 1H), 6.38 (bs, 1H), 5.50 (d, JF=48.5 Hz, 2H), 4.10 (bs, 1H), 2.30 (s, 3H), 2.02-1.95 (m, 6H), 1.61-152 (m, 2H).

Example 76

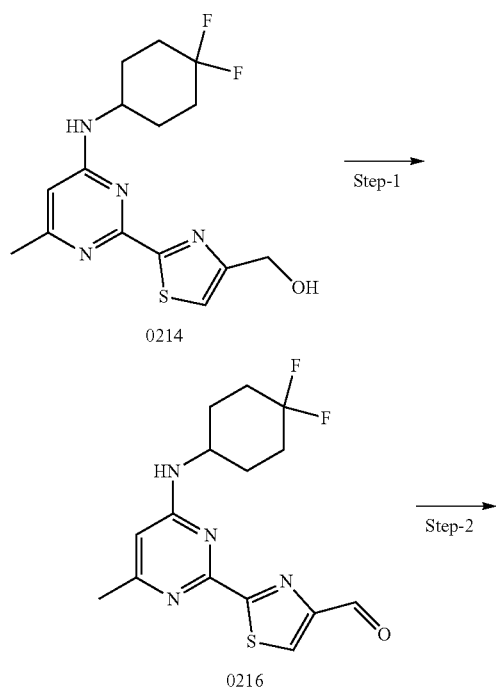

Step 1[0216]: 0.080 g of (2-(4-((4,4-difluorocyclohexyl)amino)-6-methylpyrimidin-2-yl)thiazol-4-yl)methanol [0214] gave 0.080 g of 2-(4-((4,4-difluorocyclohexyl)amino)-6-methylpyrimidin-2-yl)thiazole-4-carbaldehyde [0216] as an light brownish gum, using Dess-Martin periodinane (2 eq) in dichloromethane.

MS(M+1)+=338 and it was taken as such for next step.

Step 2[00217]: The procedure is similar to step 3 [0012] in example 2. 0.080 g of 2-(4-((4,4-difluorocyclohexyl)amino)-6-methylpyrimidin-2-yl)thiazole-4-carbaldehyde [0216] gave 0.032 g of N-(4,4-difluorocyclohexyl)-2-(4-(difluoromethyl)thiazol-2-yl)-6-methylpyrimidin-4-amine [0217], Compound 277 as an light yellow gummy solid.

MS(M+1)$^{+}$=338. $^{1}$H-NMR (400 MHz, DMSO-d6): δ 8.22 (t, J=1.40 Hz, 1H), 7.50 (s, 1H), 7.14 (t, JF=54.52 Hz, 1H), 6.41 (bs, 1H), 4.05 (bs, 1H), 2.32 (s, 3H), 2.09-1.99-1.90 (m, 6H), 1.63-1.57 (m, 2H).

Example 77

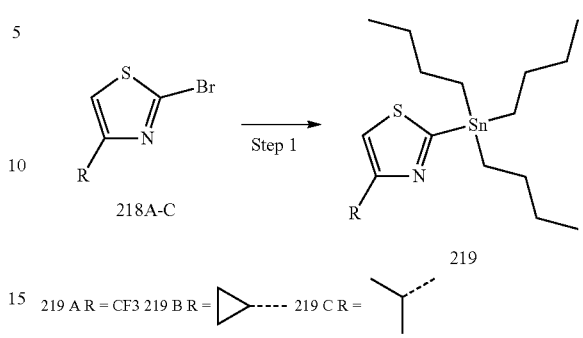

Step 1[219]: To a solution of 2-bromo-4-(trifluoromethyl)thiazole in tetrahydrofuran (10 mL) at −78° C. under N2 atmosphere was added n-Butyl lithium (2.5 M in hexane) and the reaction mixture was stirred at same temperature. After 30 min, tributyltin chloride was added to the reaction mixture at −78° C. and stirred at rt. After 16 h, the reaction mixture was quenched with saturated ammonium chloride solution and extracted with ethyl acetate (2*25 mL). The combined organic layer was dried over sodium sulfate, filtered and concentrated to afford 2-(tributylstannyl)-4-(Rs)-thiazole [219A to C] as a yellow liquid. LCMS inconclusive and it was taken as such for next step.

Example 78

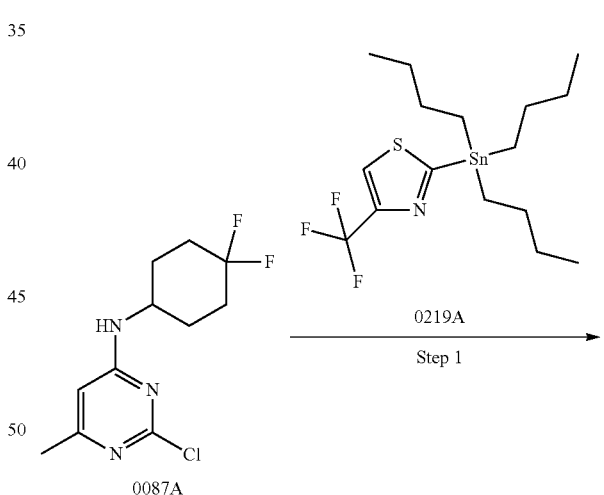

Step 1[0220]: To a solution of 0.2 g of 2-chloro-N-(4,4-difluorocyclohexyl)-6-methylpyrimidin-4-amine [0087A] and 0.7 g of 2-(tributylstannyl)-4-(trifluoromethyl)thiazole in toluene (8 mL), was degassed with nitrogen for 10 min and tetrakis(triphenylphosphine)palladium(0) was added to the reaction mixture and irradiated in microwave at 130° C. After 2 h, the reaction mixture was passed through celite bed and the filtrate was concentrated to afford a crude product, which was purified by column chromatography to afford 0.025 g of N-(4,4-difluoro cyclohexyl)-6-methyl-2-(4-(trifluoromethyl)thiazol-2-yl)pyrimidin-4-amine [0220], Compound 269 as an light yellow solid. MS(M+1)⁺=379. $^1$H NMR (400 MHz, DMSO-d6) δ 8.61 (s, 1H), 7.67 (bs, 1H), 6.41 (bs, 1H), 3.88 (bs, 1H), 2.32 (s, 3H), 2.03-1.95 (d, 6H), 1.60-1.52 (m, 2H).

Example 79

Example 80

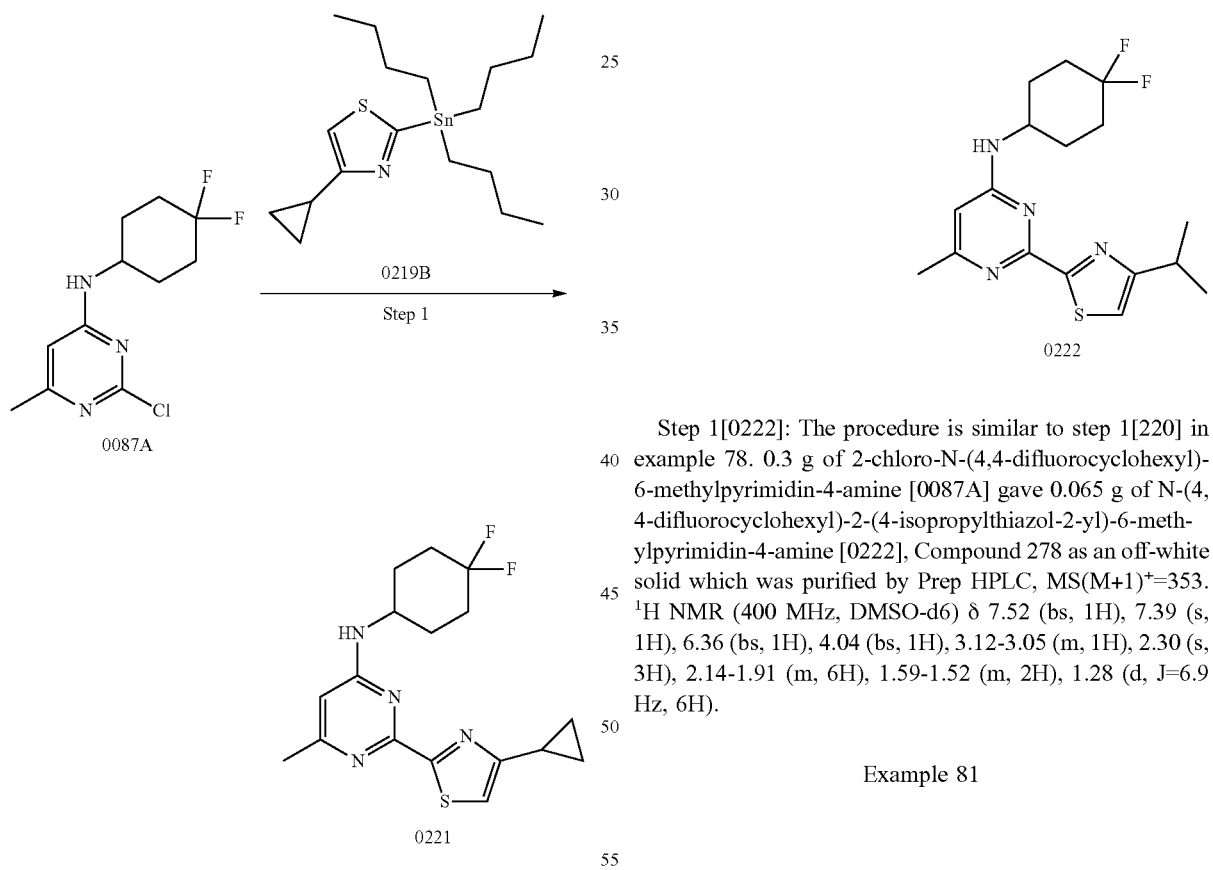

Step 1[0222]: The procedure is similar to step 1[220] in example 78. 0.3 g of 2-chloro-N-(4,4-difluorocyclohexyl)-6-methylpyrimidin-4-amine [0087A] gave 0.065 g of N-(4,4-difluorocyclohexyl)-2-(4-isopropylthiazol-2-yl)-6-methylpyrimidin-4-amine [0222], Compound 278 as an off-white solid which was purified by Prep HPLC, MS(M+1)⁺=353. $^1$H NMR (400 MHz, DMSO-d6) δ 7.52 (bs, 1H), 7.39 (s, 1H), 6.36 (bs, 1H), 4.04 (bs, 1H), 3.12-3.05 (m, 1H), 2.30 (s, 3H), 2.14-1.91 (m, 6H), 1.59-1.52 (m, 2H), 1.28 (d, J=6.9 Hz, 6H).

Example 81

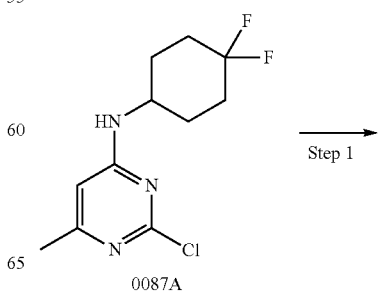

Step 1[0221]: The procedure is similar to step 1[0220] in example 78. 0.2 g of 2-chloro-N-(4,4-difluorocyclohexyl)-6-methylpyrimidin-4-amine [0087A] gave 0.016 g of 2-(4-cyclopropylthiazol-2-yl)-N-(4,4-difluorocyclohexyl)-6-methylpyrimidin-4-amine [0221], Compound 267 as an yellow solid which was purified by Prep HPLC, MS(M+1)⁺=351. $^1$H NMR (400 MHz, DMSO-d6) δ 7.52 (bs, 1H), 7.38 (s, 1H), 6.35 (bs, 1H), 4.04 (bs, 1H), 3.01 (bs, 1H), 2.29 (s, 3H), 2.13-1.91 (m, 6H), 1.60-1.52 (m, 2H), 0.93 (dt, J=8.3, 2.9 Hz, 2H), 0.85 (dt, J=5.2, 2.8 Hz, 2H).

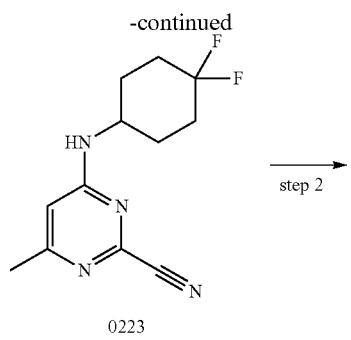

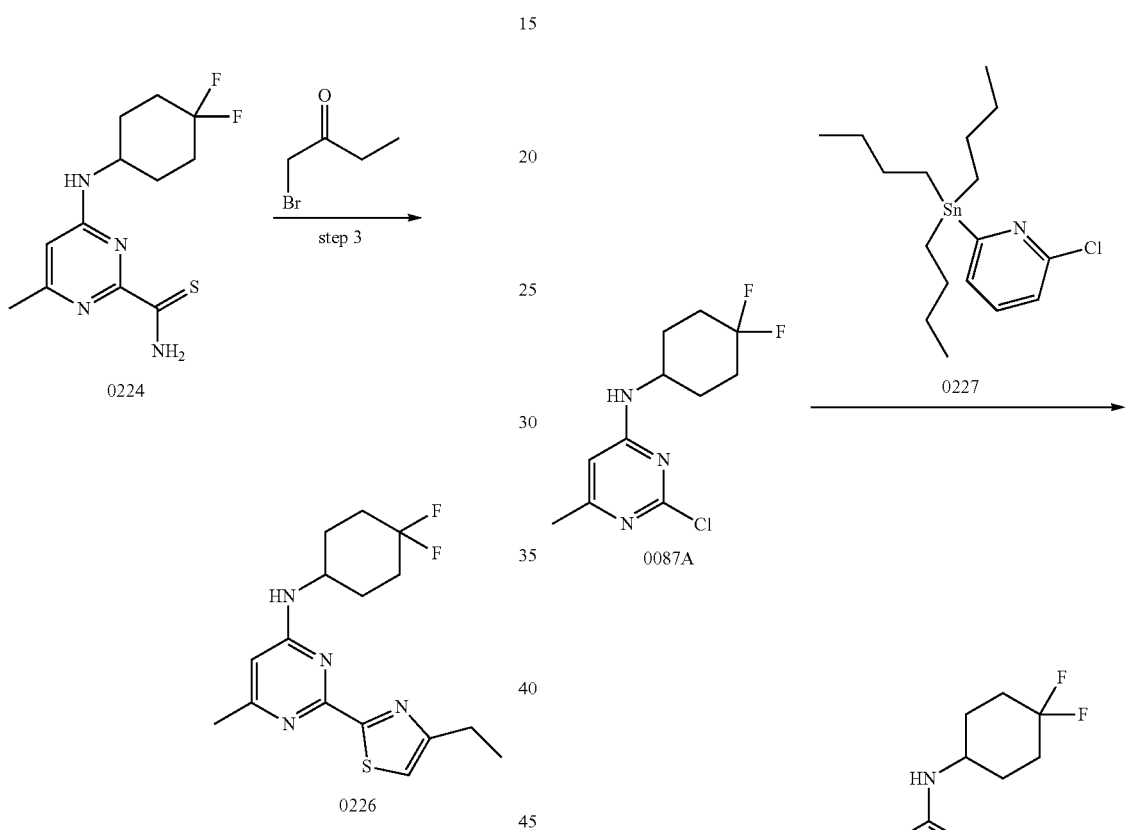

Step 3[0225]: 0.3 g of 4-((4,4-difluorocyclohexyl)amino)-6-methylpyrimidine-2-carbothioamide [0224] and 1.89 g 1-bromobutan-2-one in tetrahydrofuran was heated at 70° C. to afford 0.4 g N-(4,4-difluorocyclohexyl)-2-(4-ethylthiazol-2-yl)-6-methylpyrimidin-4-amine [0225], Compound 279 as a yellow solid. MS(M+1)$^+$=339.0. $^1$H NMR (400 MHz, DMSO-d6) δ 7.51 (s, 1H), 7.40 (s, 1H), 6.35 (s, 1H), 4.07 (bs, 1H), 2.79 (q, J=7.5 Hz, 2H), 2.29 (s, 3H), 2.16-1.86 (m, 6H), 1.65-1.46 (m, 2H), 1.26 (t, J=7.5 Hz, 3H).

Example 82

Step 1[0223]: To a solution of 2-chloro-N-(4,4-difluorocyclohexyl)-6-methylpyrimidin-4-amine [0087A] (0.8 g, 3.056 mmol) and 1,4-diazabicyclo[2.2.2]octane (0.342 g, 3.056 mmol) were dissolved in dimethyl sulfoxide (10 mL) and stirred at rt for 1 h. To the resultant reaction mixture was added sodium cyanide (0.151 g, 3.056 mmol) and stirred at 80° C. for 24 h. The reaction mixture was quenched with water (10 mL) and extracted with ethyl acetate (2×400 mL), the combined organic layer was dried over anhydrous sodium sulfate and concentrated under reduced pressure to afford 0.500 g of 4-((4,4-difluorocyclohexyl)amino)-6-methylpyrimidine-2-carbonitrile [0223] as an off-white solid. MS(M+1)+=253.

Step 2[0224]: The procedure is similar to step 4[0516] in Example 188. 0.4 g of 4-((4,4-difluorocyclohexyl)amino)-6-methylpyrimidine-2-carbonitrile [0223] gave 0.4 g of 4-((4,4-difluorocyclohexyl)amino)-6-methylpyrimidine-2-carbothioamide [0224] as an off-white solid, ammonium sulfide, triethylamine in n,n-dimethylformamide. MS(M+1)$^+$=287.2

Step 1[0282]: The procedure is similar to step 1[0220] in example 78. 0.500 g of 2-chloro-N-(4,4-difluorocyclohexyl)-6-methylpyrimidin-4-amine [0087A] and 1.1 g of 2-chloro-6-(tributylstannyl)pyridine [0227] gave 0.040 g of 2-(6-chloropyridin-2-yl)-N-(4,4-difluorocyclohexyl)-6-methyl pyrimidin-4-amine [0282], Compound 230 as a light yellow solid, which was purified by column of silica gel (60-120 mesh) using 60% ethyl acetate in hexane as eluent. MS(M+1)$^+$=339, $^1$H NMR (400 MHz, DMSO-d6) δ 8.29 (d, J=7.7 Hz, 1H), 7.98 (t, J=7.8 Hz, 1H), 7.59 (d, J=7.7 Hz 1H), 7.48 (bs, 1H), 6.40 (bs, 1H), 4.06 (bs, 1H), 2.33 (s, 3H), 2.17-1.90 (m, 6H), 1.60-1.52 (m, 2H).

Example 83

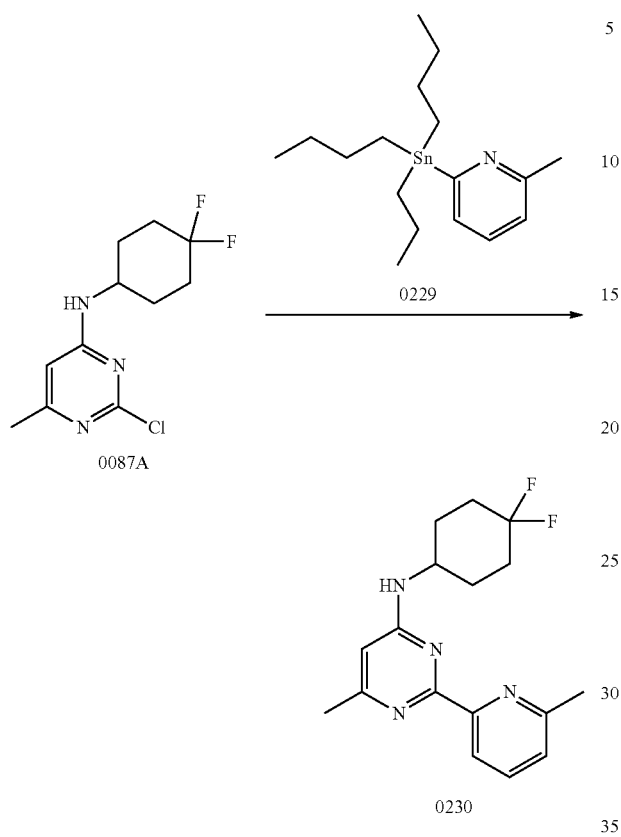

Step 1[0230]: The procedure is similar to step 1[0220] in example 78. 0.400 g of 2-chloro-N-(4,4-difluorocyclohexyl)-6-methylpyrimidin-4-amine [0087A] and 1.16 g of 2-chloro-6-(tributylstannyl)pyridine [0229] gave 0.200 g of N-(4,4-difluorocyclohexyl)-6-methyl-2-(6-methylpyridin-2-yl)pyrimidin-4-amine [0230], Compound 224 as an off-white solid, which was purified by column of silica gel (60-120 mesh) using ethyl acetate as eluent, MS(M+1)$^+$=319, $^1$H NMR (400 MHz, DMSO-d6) δ 8.05 (d, J=7.6 Hz, 1H), 7.77 (t, J=7.7 Hz, 1H), 7.36 (bs, 1H), 7.30 (d, J=7.5 Hz, 1H), 6.36 (bs, 1H), 4.09 (bs, 1H), 2.53 (s, 3H), 2.31 (s, 3H), 2.10-1.95 (m, 6H), 1.60-1.52 (m, 2H).

Example 84

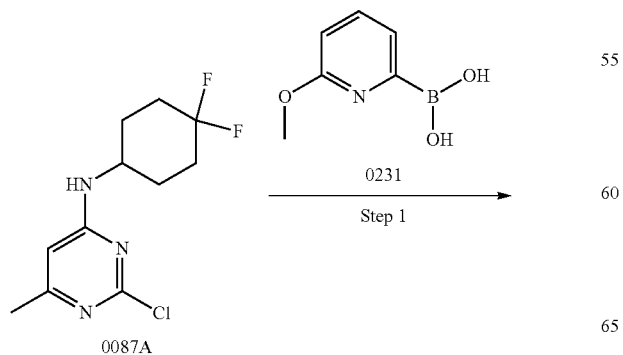

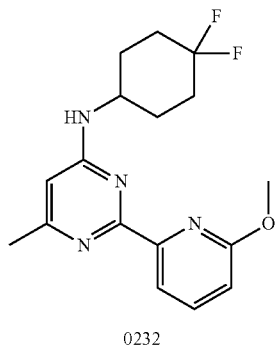

Step 1[0232]: To a stirred solution of 2-chloro-N-(4,4-difluorocyclohexyl)-6-methylpyrimidin-4-amine [0087A] (0.15 g, 0.573 mmol) in a mixture (1:1 ratio) of 1,2-dimethoxyethane and water, were added 6-methoxypyridine-2-boronic acid [0231] (0.18 g, 1.146 mmol), potassium phosphate-tribasic (0.243 g, 1.146 mmol) in a microwave vial. After 5 min added bis(triphenylphosphine)palladium (II) dichloride (0.04 g, 0.057 mmol) in one portion and the reaction mixture was irradiated in microwave at 100° C. for 2 h. After cooling to rt, reaction mixture was diluted with ethyl acetate (20 mL). The insoluble were filtered and filtrate was washed with water (2×50 mL), brine (2×50 mL), dried over anhydrous sodium sulfate, concentrated under reduced pressure to afford crude product which was purified by preparative HPLC to afford 0.11 g of N-(4,4-difluorocyclohexyl)-2-(6-methoxypyridin-2-yl)-6-methylpyrimidin-4-amine [0232], Compound 219 as an off-white solid.

MS(M+1)+=335.2, 1H NMR (400 MHz, DMSO-d6) δ 8.12 (d, J=7.6 Hz, 1H), 6.84 (s, 1H), 6.12 (s, 1H), 4.13 (s, 1H), 4.01 (s, 1H), 2.56 (d, J=9.1 Hz, 6H), 2.20 (s, 3H), 2.05-1.73 (m, 6H), 1.52-1.31 (m, 2H).

Example 87

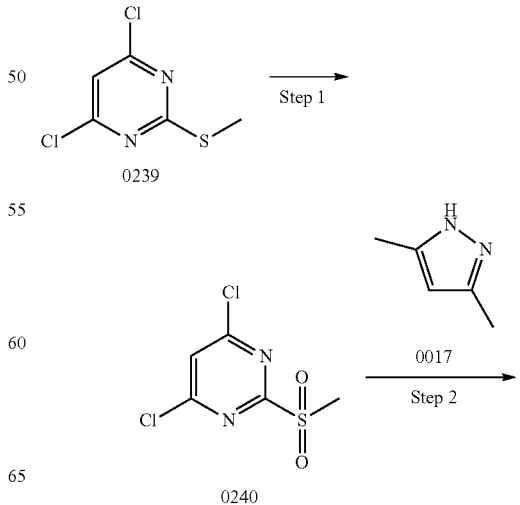

447

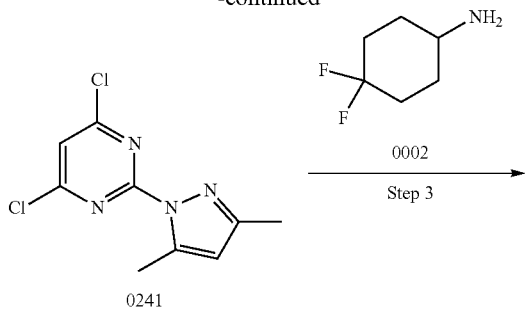

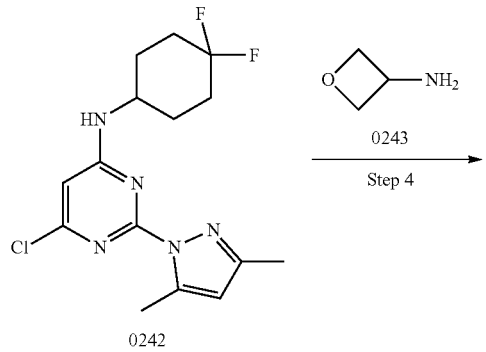

Step 1[0239]: The procedure is similar to step 1[0191] in example 68. 10 g of 4,6-dichloro-2-(methylthio)pyrimidine [0239] gave 8 g of 4,6-dichloro-2-(methylsulfonyl)pyrimidine [0240] as an off-white solid. MS(M+1)+=228.

Step 2[0241]: To a suspension of sodium hydride (35.2 g) in dichloromethane was added 84.6 g of 3,5-dimethyl pyrazole at 0° C. and the reaction mixture was stirred at rt. After 30 min, 200 g of 4,6-dichloro-2-(methylsulfonyl)pyrimidine [0239] (dissolved in dichloromethane) was added drop wise to the reaction mixture at −78° C. and the reaction mixture was stirred at same temperature. After 2 h, the reaction mixture was quenched with water at −78° C. and diluted with dichloromethane. After 5 min, dichloromethane was decanted and washed with brine solution. The organic layer was dried over sodium sulfate, filtered and concentrated under reduced pressure to afford crude product, which was purified by column chromatography to afford 138 g of 4,6-dichloro-2-(3,5-dimethyl-1h-pyrazol-1-yl)pyrimidine [0241] as an off-white solid. MS(M+1)+=244.2.

Step 3[0242]: To a stirred solution of 4,6-dichloro-2-(3,5-dimethyl-1h-pyrazol-1-yl)pyrimidine [0241] (4.9 g, 20.156 mmol) in acetonitrile (50 mL), was added 4,4-difluorocyclohexylamine hydrochloride [0002] (3.45 g, 20.16 mmol) and N,N-diisopropyl ethylamine (7.01 mL, 40.31 mmol). The reaction mixture was heated at 60° C. for 16 h and concentrated under reduced pressure. Water (50

448 mL) was added to the residue and the solid formed was filtered to afford a crude product which was purified by column chromatography using 25% ethyl acetate in pet ether as solvent to afford 3.8 g of 6-chloro-N-(4,4-difluorocyclohexyl)-2-(3,5-dimethyl-1h-pyrazol-1-yl)pyrimidin-4-amine [0242] as a pale brown solid. MS(M+1)+=342.0.

Step 4[0244]: To a stirred solution of 6-chloro-N-(4,4-difluorocyclohexyl)-2-(3,5-dimethyl-1h-pyrazol-1-yl)pyrimidin-4-amine [0242] (0.400 g, 1.17 mmol) in dioxane (10 mL), were added 3-oxetanamine (0.171 g, 2.34 mmol), 4,5-bis(diphenylphosphino)-9,9-dimethylxanthene (0.135 g, 0.234 mmol) and cesium carbonate (0.764 g, 2.34 mmol). The reaction mixture was degassed with nitrogen for 10 min, before adding tris(dibenzylideneacetone)dipalladium(0) (0.38 g, 0.117 mmol) and heated at 95° C. for 16 h. The reaction mixture was filtered through celite and filtrate was concentrated under reduced pressure to afford crude product which was purified by preparative HPLC to afford 0.065 g of N4-(4,4-difluorocyclohexyl)-2-(3,5-dimethyl-1H-pyrazol-1-yl)-N6-(oxetan-3-yl)pyrimidine-4,6-diamine [0244], Compound 243 as an off-white solid. MS(M+1)+=379.0. ¹H NMR (400 MHz, DMSO-d6) δ 7.63 (s, 1H), 6.99 (d, J=7.9 Hz, 1H), 5.99 (s, 1H), 5.25 (s, 1H), 4.78 (s, 3H), 4.47 (s, 2H), 3.82 (s, 1H), 2.55 (s, 3H), 2.14 (s, 3H), 2.07-1.89 (m, 6H), 1.54-1.51 (m, 2H).

Example 88

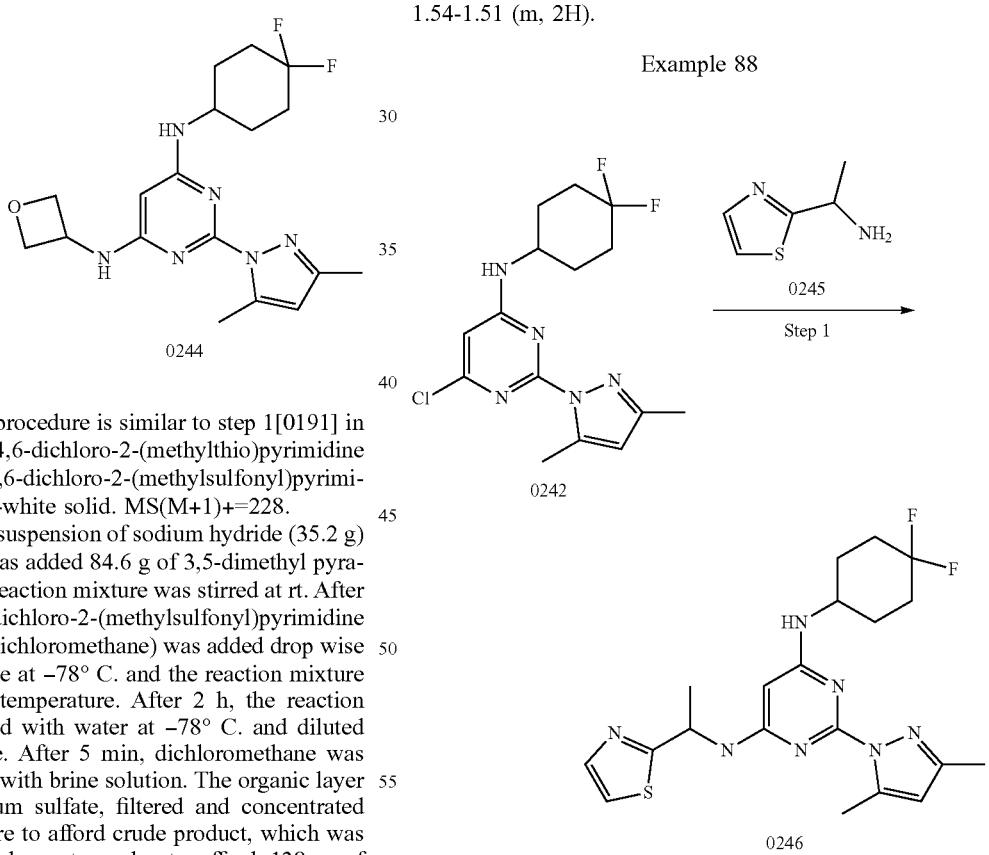

Step 1[0246]: The procedure is similar to step 2[174] in example 62. 0.350 g of 6-chloro-N-(4,4-difluorocyclohexyl)-2-(3,5-dimethyl-1H-pyrazol-1-yl)pyrimidin-4-amine [0242] gave 0.015 g of N4-(4,4-difluorocyclohexyl)-2-(3,5-dimethyl-1H-pyrazol-1-yl)-N6-(1-(thiazol-2-yl)ethyl)pyrimidine-4,6-diamine[0246], Compound 124 as a yellow solid. MS(M+1)+=434.7, ¹H NMR (400 MHz, DMSO-d6) δ 7.72 (s, 1H), 7.66 (d, J=7.3 Hz, 1H), 7.56 (s, 1H), 7.02 (d, J=7.6 Hz, 1H), 5.96 (s, 1H), 5.40 (bs, 2H), 3.72 (bs, 1H), 2.37 (s, 3H), 2.12 (s, 3H), 2.07-1.88 (m, 6H), 1.55 (d, J=6.9 Hz, 5H).

Example 89

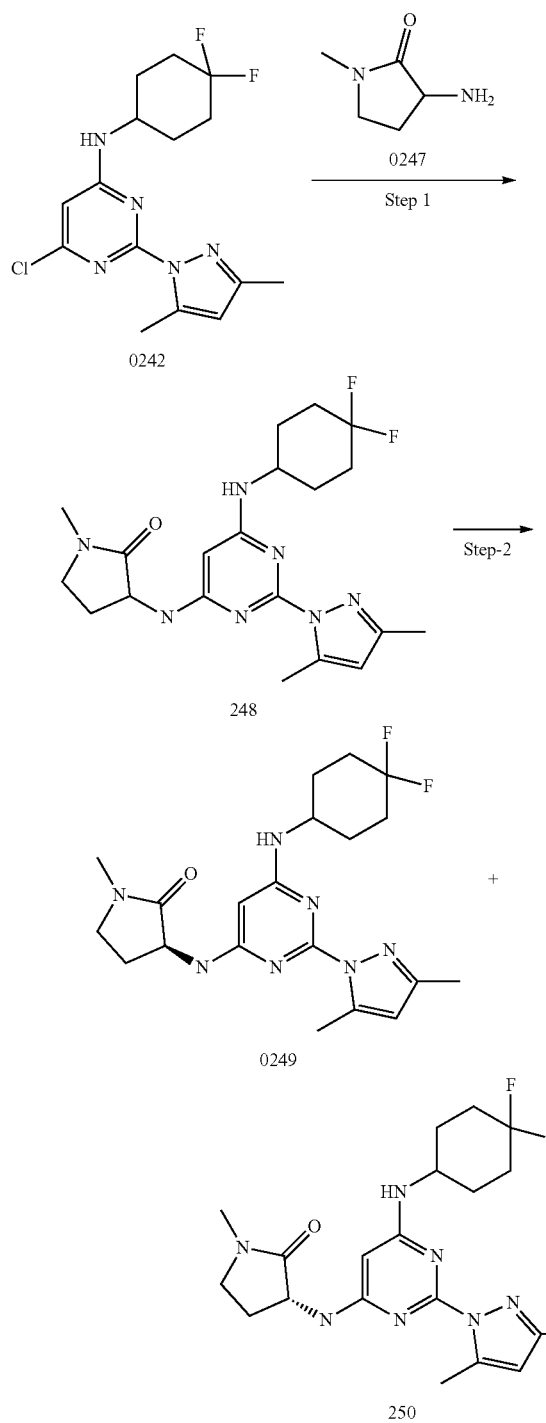

Step 1[0248]: The procedure is similar to step 2[0174] in example 62. 0.350 g of 6-chloro-N-(4,4-difluorocyclohexyl)-2-(3,5-dimethyl-1H-pyrazol-1-yl)pyrimidin-4-amine [0242] gave 0.075 g of 3-((6-((4,4-difluorocyclohexyl) amino)-2-(3,5-dimethyl-1H-pyrazol-1-yl)pyrimidin-4-yl) amino)-1-methylpyrrolidin-2-one [0248], Compound 125 as a yellow solid. MS(M+1)+=420.8 1H NMR (400 MHz, DMSO-d6) δ 7.10 (s, 1H), 6.92 (d, J=7.8 Hz, 1H), 5.99 (s, 1H), 5.42 (s, 1H), 4.50 (s, 1H), 3.83 (s, 1H), 2.76 (s, 3H), 2.48 (s, 3H), 2.14 (s, 3H), 2.06 (s, 2H), 1.91 (d, J=13.4 Hz, 5H), 1.53 (d, J=11.9 Hz, 2H).

Step 2[0249 and 0250]: 3-((6-((4,4-difluorocyclohexyl) amino)-2-(3,5-dimethyl-1H-pyrazol-1-yl)pyrimidin-4-yl) amino)-1-methylpyrrolidin-2-one [0248] which was purified by chiral preparative to afford 0.012 g of (+)-3-((6-((4,4-difluorocyclohexyl)amino)-2-(3,5-dimethyl-1H-pyrazol-1-yl)pyrimidin-4-yl)amino)-1-methylpyrrolidin-2-one [0249], Compound 128 as an off-white solid [MS(M+1)+=420.8, 1H NMR (400 MHz, DMSO-d6) δ 7.09 (d, J=7.48 Hz, 1H), 6.92 (d, J=7.8 Hz, 1H), 5.99 (s, 1H), 5.41 (s, 1H), 4.49 (bs, 1H), 3.83 (bs, 1H), 2.76 (s, 3H), 2.48 (s, 3H), 2.44 (m, 3H), 2.14 (s, 3H), 2.07-1.78 (m, 7H), 1.54-1.50 (m, 2H) and 0.0115 g of (−)-3-((6-((4,4-difluorocyclohexyl)amino)-2-(3,5-dimethyl-1H-pyrazol-1-yl)pyrimidin-4-yl)amino)-1-methylpyrrolidin-2-one [0250], Compound 129 as an off-white solid. MS(M+1)+=420.8, $^1$H NMR (400 MHz, DMSO-d6) δ 7.10 (s, 1H), 6.92 (d, J=7.9 Hz, 1H), 5.99 (s, 1H), 5.41 (s, 1H), 4.50 (s, 1H), 3.81 (s, 1H), 2.75 (s, 3H), 2.52 (s, 3H), 2.44 (m, 3H) 2.14 (s, 3H), 2.06-1.82 (m, 7H), 1.62-1.48 (m, 2H).

Example 90

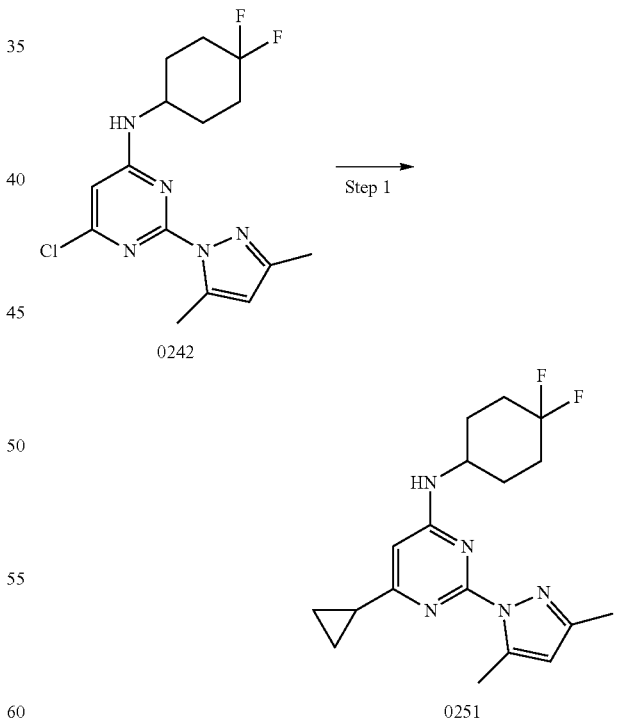

Step 1[0251]: To a solution of indium(III)chloride (0.51 g, 2.34 mmol) in tetrahydrofuran was added cyclopropyl magnesium bromide (1.02 g, 7.02 mmol) at −78° C. and stirred at same temperature. After 30 min, the reaction mixture was brought to rt and cannulated to a vial containing 6-chloro- N-(4,4-difluorocyclohexyl)-2-(3,5-dimethyl-1H-pyrazol-1-yl)pyrimidin-4-amine [0242] (0.8 g, 2.34 mmol) in tetrahydrofuran and heated at 90° C. After 16 h, the reaction mixture was quenched with few drops of methanol, stirred for 10 min, filtered through celite bed which was washed with ethyl acetate. The filtrate was concentrated under reduced pressure and the residue was again dissolved in ethyl acetate and washed with water and brine solution. The combined organic layer was dried over anhydrous sodium sulfate, filtered and concentrated under reduced pressure to afford brown oil, which was purified in the Reveleris flash system instrument using ethyl acetate in hexane as solvent in 25 g column, to afford 0.08 g of 6-cyclopropyl-N-(4,4-difluorocyclohexyl)-2-(3,5-dimethyl-1H-pyrazol-1-yl)pyrimidin-4-amine [0251], Compound 186 as a white solid. MS(M+1)$^+$=348.2, $^1$H-NMR (400 MHz, DMSO-d6): δ 7.49 (s, 1H), 6.31 (s, 1H), 6.02 (s, 1H), 3.99 (bs, 1H), 2.46 (s, 3H), 2.15 (s, 3H), 2.05-1.92 (m, 7H), 1.62-1.50 (m, 2H), 0.99-0.85 (m, 4H).

Example 91

Step 1[0252]: To a stirred solution of 6-chloro-N-(4,4-difluorocyclohexyl)-2-(3,5-dimethyl-1H-pyrazol-1-yl)pyrimidin-4-amine [0242] (1.5 g, 4.388 mmol) and potassium cyanide (0.583 mmol) in acetonitrile (40 mL) were added tributyltin chloride (0.085 g, 0.263 mmol) followed by 1,1'-bis(diphenylphosphino)ferrocene (0.32 g, 0.438 mmol) and tris(dibenzylidene acetone)dipalladium(0) (0.4 g, 0.438 mmol). The mixture was stirred at rt for 30 min and then heated at 80° C. for 24 h. The reaction mixture was diluted with ethyl acetate (250 mL) and water (100 mL). Aqueous layer was extracted with ethyl acetate (2×100 mL). The combined organic layer was washed with water (250 mL), brine solution (100 mL), dried over anhydrous sodium sulfate, filtered and the concentrated under reduced pressure to afford crude and which was purified by column chromatography using 12% ethyl acetate in pet ether as solvent to afford 6-((4,4-difluorocyclohexyl)amino)-2-(3,5-dimethyl-1H-pyrazol-1-yl)pyrimidine-4-carbonitrile [0252] of as an off-white solid (0.43 g). MS(M+1)+=333.2, 1H NMR (400 MHz, DMSO-d6) δ 8.05 (d, J=7.4 Hz, 1H), 7.80 (s, 1H), 7.71 (s, 1H), 6.99 (s, 1H), 6.10 (s, 1H), 2.55 (s, 3H), 2.19 (s, 3H), 2.02 (d, J=39.6 Hz, 6H), 1.58 (d, J=11.9 Hz, 2H).

Step 2[0253]: To a stirred solution of 6-((4,4-difluorocyclohexyl)amino)-2-(3,5-dimethyl-1H-pyrazol-1-yl)pyrimidine-4-carbonitrile [0252] (0.15 g, 0.451 mmol) in a mixture of methanol (5 mL) and water (15 mL) was added potassium hydroxide (0.025 g, 0.451 mmol). The reaction mixture was stirred at rt for 20 h. The reaction mixture was concentrated under reduced pressure. The residue was diluted with ethyl acetate (75 mL) and two layers were separated. Organic layer was washed with water (2×50 mL), brine (3×50 mL), dried over anhydrous sodium sulfate, filtered and concentrated under reduced pressure to afford crude and which was purified by column chromatography using 4% methanol in chloroform as solvent to afford 6-((4,4-difluorocyclohexyl)amino)-2-(3,5-dimethyl-1H-pyrazol-1-yl)pyrimidine-4-carboxamide [0253], Compound 131 as an off-white solid (0.032 g). MS(M+1)$^+$=351.2, $^1$H NMR (400 MHz, DMSO-d6) δ 8.05 (d, J=7.4 Hz, 1H), 7.80 (s, 1H), 7.71 (s, 1H), 6.99 (s, 1H), 6.10 (s, 1H), 4.10 (bs, 1H), 2.55 (s, 3H), 2.19 (s, 3H), 2.10-1.90 (m, 6H), 1.58-1.53 (m, 2H).

Example 92

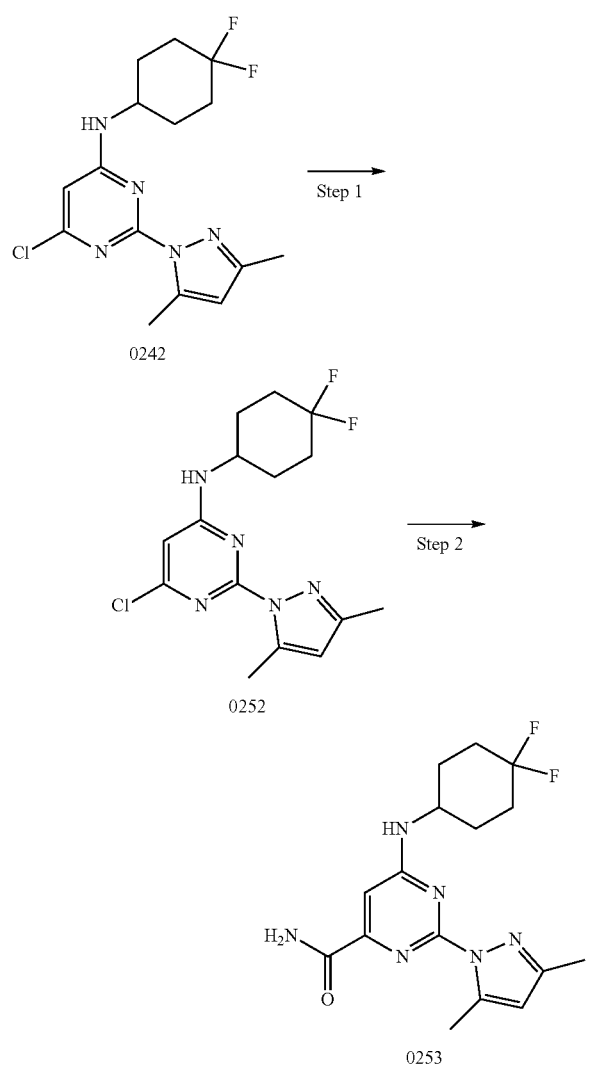

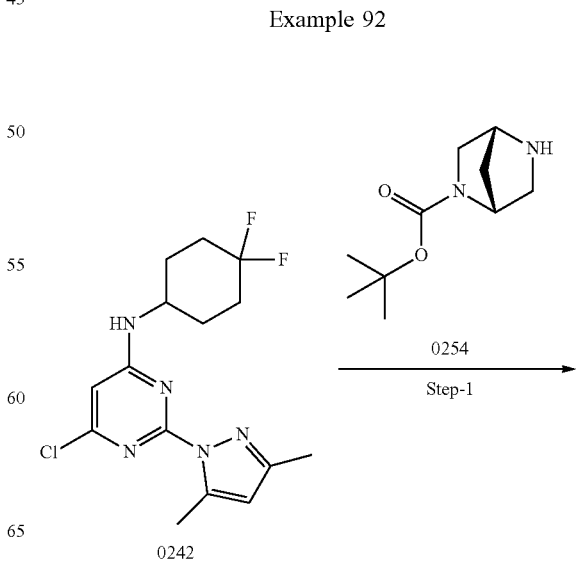

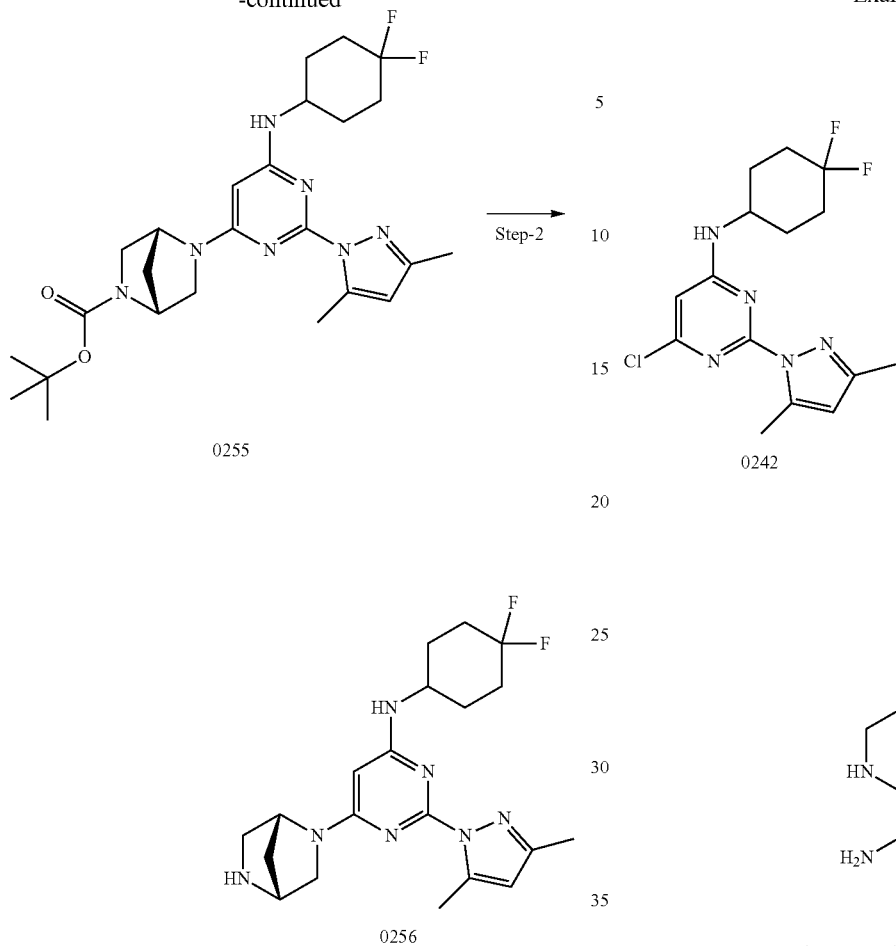
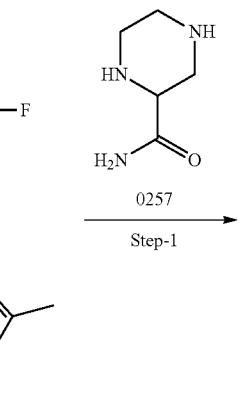
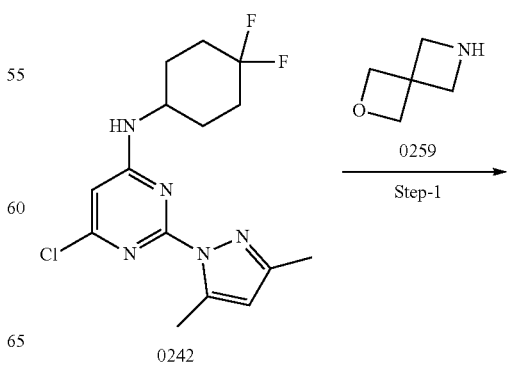

Example 93

Step 1 [0258]: The procedure is similar to Step 2[0174] in example 62. 0.3 g of 6-chloro-N-(4,4-difluorocyclohexyl)-2-(3,5-dimethyl-1H-pyrazol-1-yl)pyrimidin-4-amine [0242] and 0.22 g of piperazine-2-carboxamide [0258] gave 0.055 g of 4-(6-((4,4-difluorocyclohexyl)amino)-2-(3,5-dimethyl-1H-pyrazol-1-yl)pyrimidin-4-yl)piperazine-2-carboxamide [0258], Compound 100. MS(M+1)$^+$=435, $^1$H NMR (400 MHz, DMSO-d6) δ 7.34 (s, 1H), 7.18 (s, 1H), 7.03 (d, J=8.1 Hz, 1H), 6.00 (s, 1H), 5.57 (s, 1H), 4.08 (b, 1H), 3.95-3.80 (m, 2H), 3.19 (dd, J=9.3, 3.4 Hz, 1H), 3.05-2.85 (m, 3H), 2.70-2.60 (m, 2H), 2.49 (s, 3H), 2.15 (s, 3H), 2.07-1.89 (m, 6H), 1.45-1.60 (m, 2H).

Step 1 [0255]: The procedure is similar to Step 2[0174] in example 62. 0.3 g of 6-chloro-N-(4,4-difluorocyclohexyl)-2-(3,5-dimethyl-1H-pyrazol-1-yl)pyrimidin-4-amine [0242] and 0.348 g of (1S,4S)-(−)-2-Boc-2,5-diazabicyclo[2.2.1]heptane [0254] gave 0.075 g of tert-butyl (1R)-5-(6-((4,4-difluorocyclohexyl)amino)-2-(3,5-dimethyl-1H-pyrazol-1-yl)pyrimidin-4-yl)-2,5-diazabicyclo[2.2.1]heptane-2-carboxylate [0255] as an white solid.

Step 2 [0256]: tert-Butyl (1R)-5-(6-((4,4-difluorocyclohexyl)amino)-2-(3,5-dimethyl-1H-pyrazol-1-yl)pyrimidin-4-yl)-2,5-diazabicyclo[2.2.1]heptane-2-carboxylate [0255] was acidified by using Hydrochloric acid in dioxane to afford 6-((4R)-2,5-diazabicyclo [2.2.1]heptan-2-yl)-N-(4,4-difluorocyclohexyl)-2-(3,5-dimethyl-1H-pyrazol-1-yl)pyrimidin-4-amine hydrochloride salt [0256], Compound 103 as an light yellow solid (55 mg). MS(M+1)+=404, MS(M+1)$^+$=404, $^1$H NMR (400 MHz, Methanol-d4) δ 6.30 (s, 1H), 5.21 (s, 1H) 4.66 (s, 1H), 3.99-3.78 (m, 3H), 3.52 (s, 2H), 2.72 (s, 3H), 2.33 (s, 4H), 2.20-2.01 (m, 6H), 1.82-1.65 (m, 2H).

Example 94

-continued

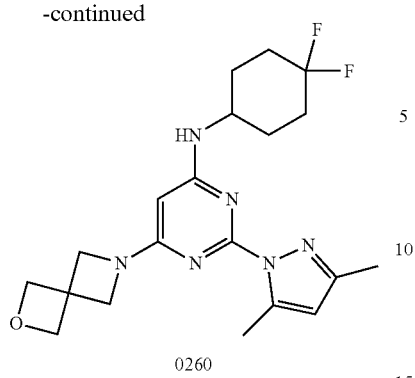

0260

Step 1 [0260] The procedure is similar to Step 3[0006] in example 1 (solvent dimethyl sulfoxide at 100° C.). 0.12 g of 6-chloro-N-(4,4-difluorocyclohexyl)-2-(3,5-dimethyl-1H-pyrazol-1-yl)pyrimidin-4-amine [0242] and 0.069 g of 2-oxa-6-azaspiro(3,3) heptane [0260] gave 0.08 g of N-(4, 4-difluorocyclohexyl)-2-(3,5-dimethyl-1H pyrazol-1-yl)-6-(2-oxa-6-azaspiro[3.3]heptan-6-yl)pyrimidin-4-amine, Compound 105 MS(M+1)$^+$=405, $^1$H NMR (400 MHz, DMSO-d6) δ 7.07 (d, J=8.0 Hz, 1H), 6.00 (s, 1H), 5.19 (s, 1H), 4.72 (s, 4H), 4.11 (s, 4H), 3.86 (bs, 1H), 2.50 (s 3H), 2.14 (s, 3H), 2.15-1.80 (m, 6H), 1.40-1.35 (m, 2H).

Example 95

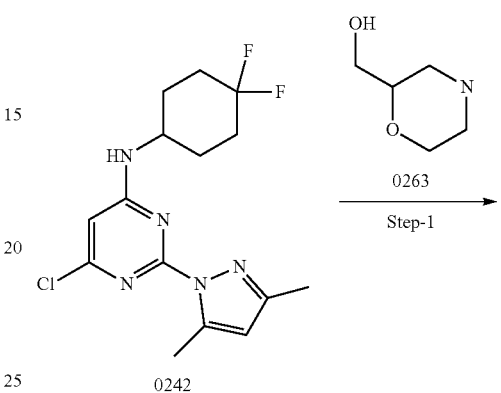

0262

Step 1[0262]: The procedure is similar to Step 3[0006] in example 1 (solvent dimethyl sulfoxide at 100° C.). 0.6 g of 6-chloro-N-(4,4-difluorocyclohexyl)-2-(3,5-dimethyl-1H-pyrazol-1-yl)pyrimidin-4-amine [0242] and 0.309 g of 2-aminopropanamide [0262] gave 0.038 g of 2-((6-((4,4-difluorocyclohexyl)amino)-2-(3,5-dimethyl-1H-pyrazol-1-yl)pyrimidin-4-yl)amino)propanamide, Compound 109 using Cesium carbonate and dimethylsulphoxide at 100° C.

for 48 h. MS(M+1)$^+$=394, $^1$H NMR (400 MHz, DMSO-d6) δ 7.38 (s, 1H), 6.85-7.05 (m, 3H), 5.99 (s, 1H), 5.39 (bs, 1H), 4.24 (bs, 1H), 3.78 (bs, 1H), 2.49 (s, 3H), 2.14 (s, 3H), 2.12-2.00 (m, 2H), 2.0-1.85 (m 4H), 1.61-1.49 (m, 2H), 1.28 (d, J=7.0 Hz, 3H).

Example 96

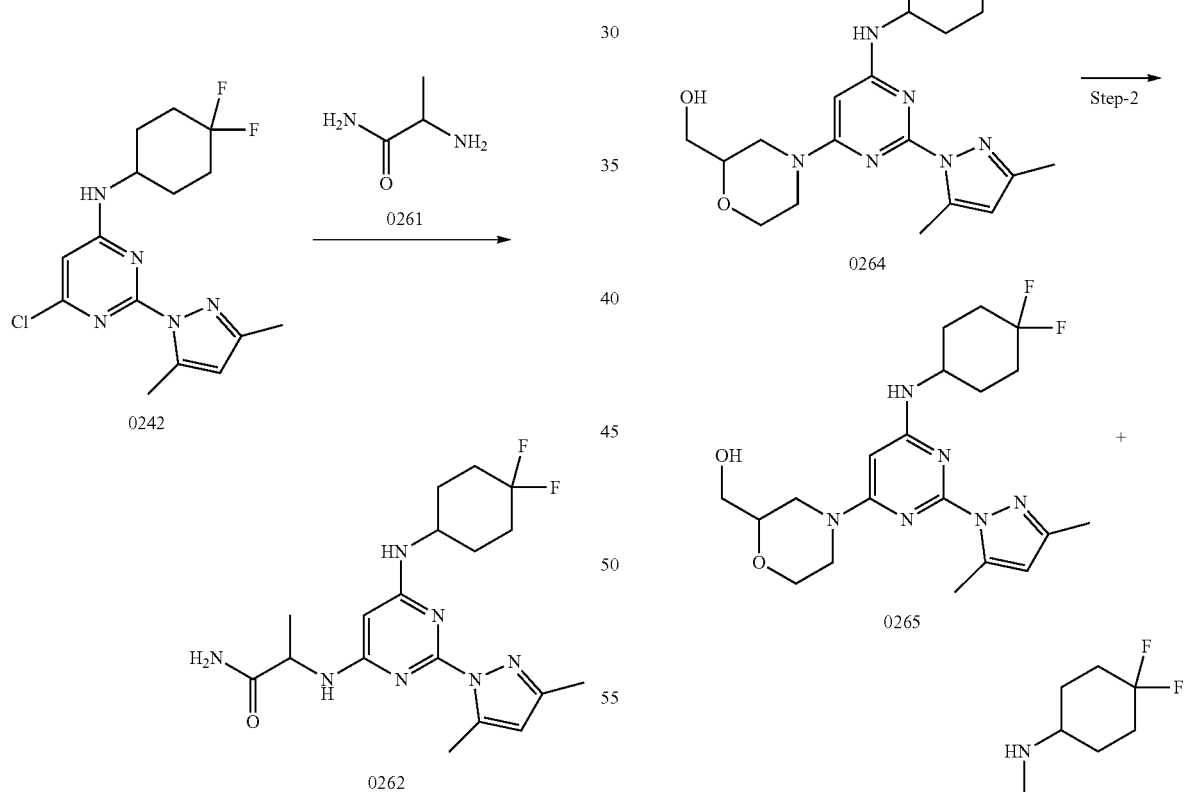

Step 1[0264]: The procedure is similar to Step 3[0006] in example 1 (100° C., dimethylsulfoxide). 0.15 g of 6-chloro-N-(4,4-difluorocyclohexyl)-2-(3,5-dimethyl-1H-pyrazol-1-yl)pyrimidin-4-amine [0242] and 0.102 g of morpholin-2-ylmethanol [0263] gave 0.14 g of racemate (4-(6-((4,4-difluorocyclohexyl)amino)-2-(3,5-dimethyl-1H-pyrazol-1-yl)pyrimidin-4-yl)morpholin-2-yl)methanol [0264], Compound 110. MS(M+1)+=423, $^1$H NMR (400 MHz, DMSO-d6) δ 7.09 (d, J=8.0 Hz, 1H), 6.01 (s, 1H), 5.57 (s, 1H), 4.85 (t, J=5.5 Hz, 1H), 4.19-3.96 (m, 2H), 4.07-3.87 (m, 2H), 3.55-3.40 (m, 4H), 2.95-2.85 (m, 1H), 2.66-2.59 (m, 1H), 2.49 (s, 3H), 2.15 (s, 3H), 2.15-1.85 (m, 6H), 1.60-145 (m, 2H).

Step 2[0265 & 0266]: 0.14 g of racemate (4-(6-((4,4-difluorocyclohexyl)amino)-2-(3,5-dimethyl-1H-pyrazol-1-yl)pyrimidin-4-yl)morpholin-2-yl)methanol [0264] was separated by chiral Prep HPLC to afford 0.050 mg of (+)-(4-(6-((4,4-difluorocyclohexyl)amino)-2-(3,5-dimethyl-1H-pyrazol-1-yl)pyrimidin-4-yl)morpholin-2-yl)methanol [0265], Compound 112. MS(M+1)+=423. SOR: +20.909°, C=0.110, S=MeOH, T=23.4° C. $^1$H NMR (400 MHz, DMSO-d6) δ 7.09 (d, J=8.0 Hz, 1H), 6.01 (s, 1H), 5.57 (s, 1H), 4.85 (t, J=5.5 Hz, 1H), 4.19-3.96 (m, 2H), 4.07-3.87 (m, 2H), 3.55-3.40 (m, 4H), 2.95-2.85 (m, 1H), 2.66-2.59 (m, 1H), 2.49 (s, 3H), 2.15 (s, 3H), 2.15-1.85 (m, 6H), 1.60-145 (m, 2H) and 55 mg of (−)-(4-(6-((4,4-difluorocyclohexyl)amino)-2-(3,5-dimethyl-1H-pyrazol-1-yl)pyrimidin-4-yl)morpholin-2-yl)methanol [0266], Compound 113. MS(M+1)+=423. SOR: −13.889°, C=0.108, S=MeOH, T=23.8° C. $^1$H NMR (400 MHz, DMSO-d6) δ 7.09 (d, J=8.0 Hz, 1H), 6.01 (s, 1H), 5.57 (s, 1H), 4.85 (t, J=5.5 Hz, 1H), 4.19-3.96 (m, 2H), 4.07-3.87 (m, 2H), 3.55-3.40 (m, 4H), 2.95-2.85 (m, 1H), 2.66-2.59 (m, 1H), 2.49 (s, 3H), 2.15 (s, 3H), 2.15-1.85 (m, 6H), 1.60-145 (m, 2H).

Example 98

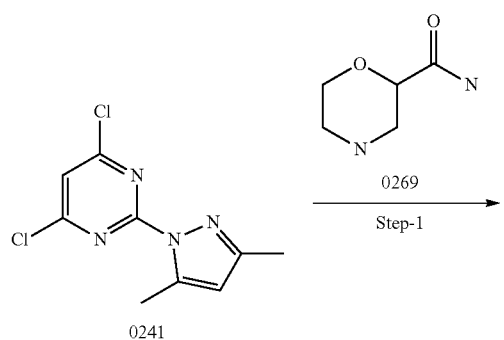

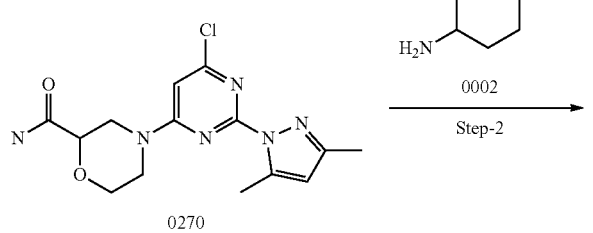

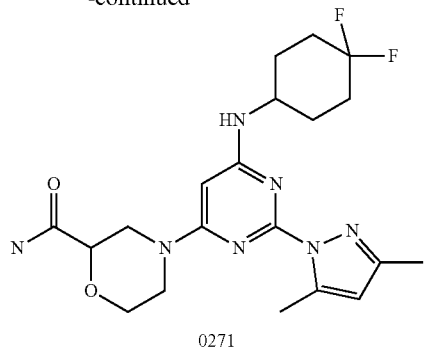

Step 1[0270]: To a solution of 4,6-dichloro-2-(3,5-dimethyl-1H-pyrazol-1-yl)pyrimidine [0241] (1 g, 4.11 mmol) and morpholine-2-carboxamide [0269] (0.53 g, 4.11 mmol) in dimethylsulfoxide (8 mL) was added cesium carbonate (2.68 g, 8.22 mmol) under N2 atmosphere. The resultant reaction mixture was heated at 80° C. in a closed vial for 8 h, quenched with water and extracted with ethyl acetate (2×200 mL). The combined organic layer was washed with brine, dried over anhydrous sodium sulfate, filtered and concentrated under reduced pressure to afford as a yellow gum and which was purified by column chromatography using 5% methanol in chloroform as eluent to afford 4-(6-chloro-2-(3,5-dimethyl-1H-pyrazol-1-yl)pyrimidin-4-yl)morpholine-2-carboxamide [0270] as an off-white solid (0.77 g), MS(M+1)+=337.

Step 2[271]: To a solution of 4-(6-chloro-2-(3,5-dimethyl-1H-pyrazol-1-yl)pyrimidin-4-yl)morpholine-2-carboxamide [0270] (0.28 g, 0.831 mmol) and 4,4-Difluorocyclohexylamine hydrochloride [0002] (0.28 g, 1.66 mmol) in dimethylsulfoxide (6 mL) was added cesium carbonate (0.541 g, 1.66 mmol) under N2 atmosphere. The resultant reaction mixture was heated at 90° C. in a closed vial for 4 days. The reaction mixture was quenched with water, the solid formed was filtered and dried to afford as brown solid and which was purified by prep HPLC to afford 4-(6-((4,4-difluorocyclohexyl)amino)-2-(3,5-dimethyl-1H-pyrazol-1-yl)pyrimidin-4-yl)morpholine-2-carboxamide [271], Compound 115 as an off-white solid (0.05 g). MS(M+1)+=436. $^1$H NMR (400 MHz, DMSO-d6) δ 7.40 (s, 1H), 7.12 (s, 1H), 7.10 (bs 1H), 6.00 (s, 1H), 5.51 (s, 1H), 4.74 (bs, 1H), 4.30 (d, J=11.8 Hz, 1H), 4.01-3.83 (m, 2H), 3.65 (dd, J=11.8, 3.8 Hz, 2H), 3.55-3.35 (m, 2H), 2.47 (s, 3H), 2.14 (s, 3H), 2.09-1.85 (m, 6H), 1.62-1.49 (m, 2H).

Example 99

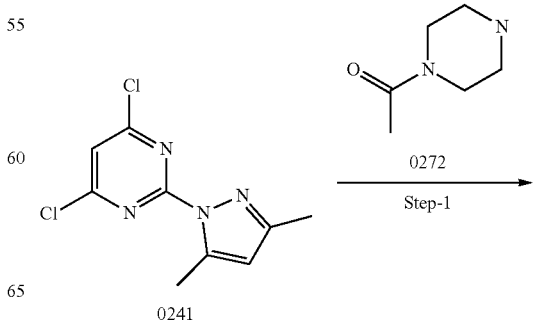

459
-continued

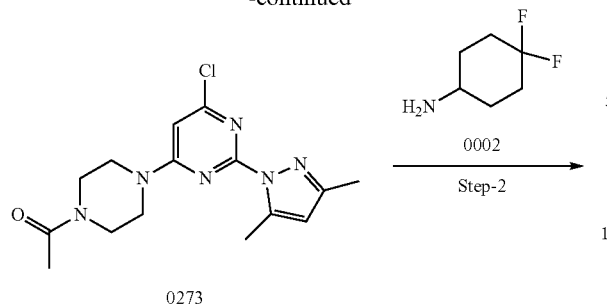

Step 1[0273]: A stirred solution of 4,6-dichloro-2-(3,5-dimethyl-1H-pyrazol-1-yl)pyrimidine [0241] (1.3 g, 5.348 mmol), 1-acetylpiperazine [0272] (0.685 g, 5.348 mmol) and triethylamine (0.82 mL, 5.883 mmol) in acetonitrile (50 mL) was heated at 55° C. for 16 h. The reaction mixture was concentrated under reduced pressure to afford crude product and which was purified by column chromatography using 5% ethyl acetate in hexane as eluent to afford 1-(4-(6-chloro-2-(3,5-dimethyl-1H-pyrazol-1-yl)pyrimidin-4-yl)piperazin-1-yl)ethan-1-one [0273] as an white solid (1.1 g, 64%). MS(M+1)+=335.2.

Step 2[0274]: A stirred suspension of 1-(4-(6-chloro-2-(3,5-dimethyl-1H-pyrazol-1-yl)pyrimidin-4-yl)piperazin-1-yl)ethan-1-one [0273] (0.22 g, 0.657 mmol), 4,4-difluorocyclohexylamine hydrochloride [0002] (0.135 g, 0.788 mmol) and cesium carbonate (0.535 g, 1.642 mmol) in acetonitrile was heated at 150° C. in MW for 5 h. The reaction mixture was concentrated under reduced pressure, added water (10 mL), extracted with chloroform (3*100 mL). The combined organic layer was washed with brine (50 mL), dried over anhydrous sodium sulfate, filtered and concentrated under reduced pressure to afford crude which was purified by column chromatography using 2% methanol in chloroform as eluent to afford 1-(4-(6-((4,4-difluorocyclohexyl)amino)-2-(3,5-dimethyl-1H-pyrazol-1-yl)pyrimidin-4-yl)piperazin-1-yl)ethan-1-one [0274], Compound 102 as an off-white solid (0.043 g, 15%). MS(M+1)+=434, $^1$H NMR (400 MHz, DMSO-d6) δ 7.09 (d, J=8.0 Hz, 1H), 6.01 (s, 1H), 5.57 (s, 1H), 3.88 (bs, 1H), 3.65-3.42 (m, 8H), 2.48 (s, 3H), 2.15 (s, 3H), 2.05 (s, 6H), 1.95-1.85 (m, 3H), 1.65-1.48 (m, 2H).

460
Example 100

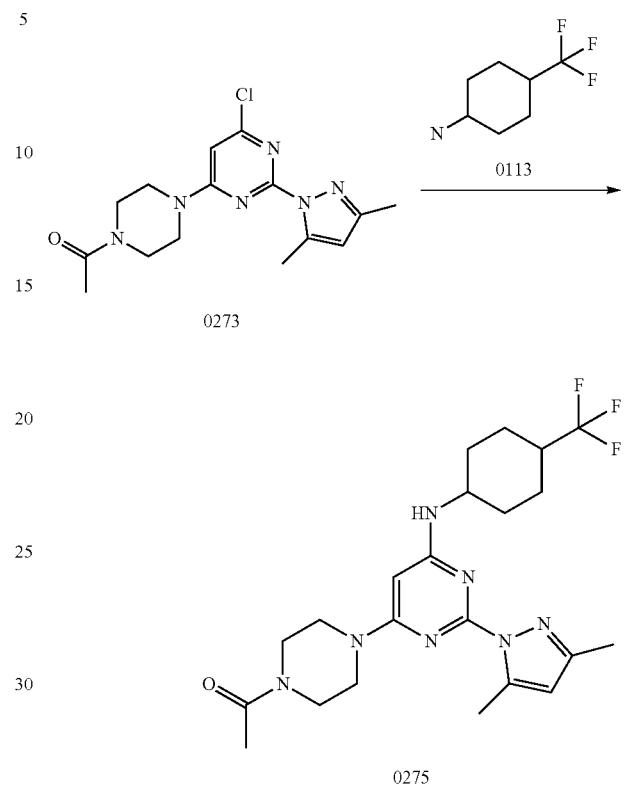

Step 1 [0275]: The procedure is similar to Step 2[0274] in example 99. 0.2 g of 1-(4-(6-chloro-2-(3,5-dimethyl-1H-pyrazol-1-yl)pyrimidin-4-yl)piperazin-1-yl)ethan-1-one [0273] and 0.1 g of 4-(Trifluoromethyl)Cyclohexanamine [0113] gave 0.06 g of 1-(4-(2-(3,5-dimethyl-1H-pyrazol-1-yl)-6-(((4-(trifluoromethyl)cyclohexyl)amino)pyrimidin-4-yl)piperazin-1-yl)ethan-1-one [0275], Compound 149. MS(M+1)+=466, $^1$H NMR (400 MHz, DMSO-d6) δ 7.02 (d, J=7.0 Hz, 1H), 6.00 (s, 1H), 5.56 (s, 1H), 3.54-3.45 (m, 9H), 2.48 (s, 3H), 2.34-2.27 (m, 1H), 2.16 (s, 3H), 2.05 (s, 3H), 2.02-1.86 (m, 4H), 1.42-1.23 (m, 4H).

Example 101

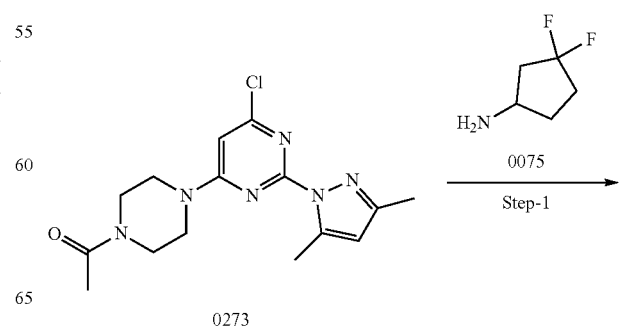

-continued

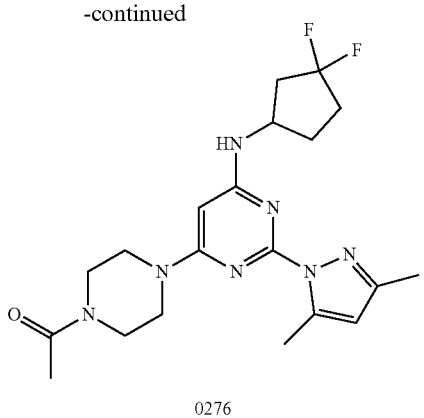

0276

Step 1 [0276]: The procedure is similar to Step 2[0274] in example 99 (Using DIPEA, MW, 180° C.). 0.2 g of 1-(4-(6-chloro-2-(3,5-dimethyl-1H-pyrazol-1-yl)pyrimidin-4-yl)piperazin-1-yl)ethan-1-one [0273] and 0.108 g of 3,3-difluorocyclopentan-1-amine [0075] gave 0.065 g of 1-(4-(6-((3,3-difluorocyclopentyl)amino)-2-(3,5-dimethyl-1H-pyrazol-1-yl)pyrimidin-4-yl)piperazin-1-yl)ethan-1-one [0276], Compound 130. MS(M+1)⁺=420, ¹H NMR (400 MHz, DMSO-d6) δ 7.34 (d, J=7.2 Hz, 1H), 6.03 (s, 1H), 5.58 (d, J=2.3 Hz, 1H), 4.32 (s, 1H), 3.58 (bs, 2H), 3.53 (s, 6H), 2.74-2.56 (m, 1H), 2.48 (s, 3H) 2.35-2.22 (m, 1H), 2.10 (dd, J=45.1, 2.5 Hz, 9H), 1.72 (dt, J=11.9, 8.4 Hz, 1H).

Example 103

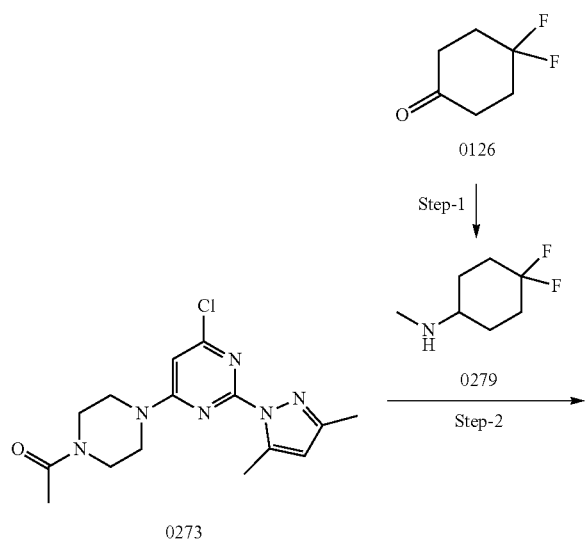

Step 1[0279]: The procedure is similar to Step 1[127] in example 45. 0.5 g of 4,4-Difluoro cyclohexanone [0126] and 0.173 g of methylamine, 2M solution in tetrahydrofuran gave 0.52 g of 4,4-difluoro-N-methylcyclohexan-1-amine [0279]. MS(M+1)+=150.

Step 2[0280]: 0.4 g of 1-(4-(6-chloro-2-(3,5-dimethyl-1H-pyrazol-1-yl)pyrimidin-4-yl)piperazin-1-yl)ethan-1-one [0273] and 0.44 g of 4,4-difluoro-N-methylcyclohexan-1-amine [0279] gave 0.190 g of 1-(4-(6-((4,4-difluoro cyclohexyl)(methyl)amino)-2-(3,5-dimethyl-1H-pyrazol-1-yl)pyrimidin-4-yl)piperazin-1-yl)ethan-1-one [0280], Compound 132 using N,N-diisopropyl ethylamine and acetonitrile in MW at 180° C. for 3 h.

MS(M+1)⁺=150, ¹H NMR (400 MHz, Chloroform-d) δ 6.0 (s, 1H), 5.34 (s, 1H) 4.81 (s, 1H), 3.83 (dd, J=6.5, 4.1 Hz, 2H), 3.75 (dd, J=6.6, 4.2 Hz, 2H), 3.58 (td, J=7.4, 5.2 Hz, 4H), 2.89 (s, 3H), 2.62-2.33 (m, 6H), 2.21 (m, 2H), 2.15 (s, 3H), 1.78 (s, 6H).

Example 104

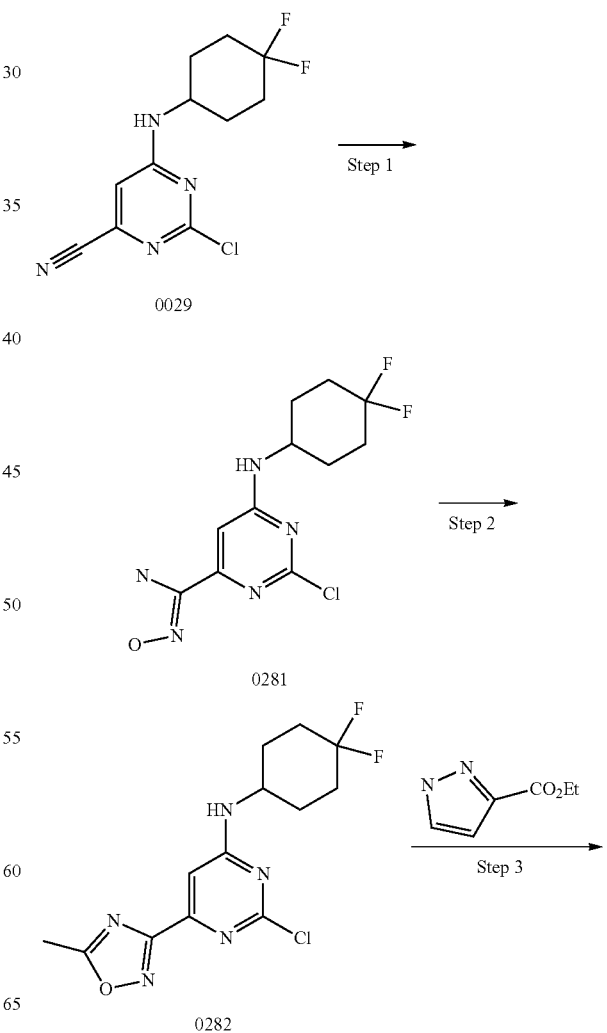

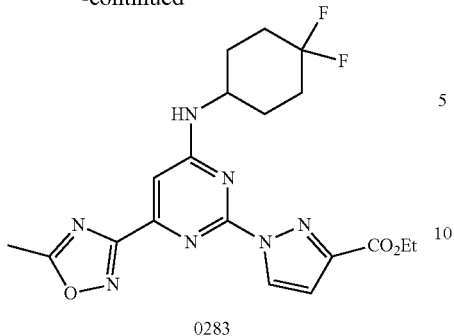

0283

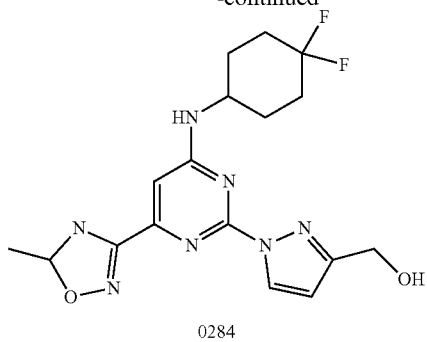

0284

Step 1[0281]: To a solution of 2-chloro-6-((4,4-difluoro-cyclohexyl)amino)pyrimidine-4-carbonitrile [0029] (1.8 g, 6.601 mmol) in tetrahydrofuran (15 mL) was added triethylamine (0.7 g, 6.931 mmol) and followed by slow addition of hydroxylamine hydrochloride (0.486 g, 6.931 mmol) under N2 atm. The resultant reaction mixture was stirred at rt for 16 h. The reaction mixture was diluted with water (30 mL) and extracted with ethyl acetate (2×200 mL). The combined organic layer was washed with brine (20 mL), dried over anhydrous sodium sulfate, filtered and concentrated under reduced pressure to afford 2-chloro-6-((4,4-difluorocyclohexyl)amino)-N'-hydroxypyrimidine-4-carboximidamide [0281] as an off-white solid (1.99 g).

MS(M+1)+=306.

Step 2[0282]: To a stirred solution of 2-chloro-6-((4,4-difluorocyclohexyl)amino)-N'-hydroxypyrimidine-4-carboximidamide [0281] (1.8 g, 5.88 mmol) in acetic anhydride (20 mL) was heated at 100° C. in sealed tube for 24 h. The reaction mixture was concentrated under reduced pressure to afford crude and which was purified by column chromatography using 30% ethyl acetate in pet-ether as a solvent to afford 2-chloro-N-(4,4-difluorocyclohexyl)-6-(5-methyl-1,2,4-oxadiazol-3-yl)pyrimidin-4-amine [0282] as an white solid (0.9 g). MS(M+1)+=330.

Step 3[0283]: 0.9 g of 2-chloro-N-(4,4-difluorocyclohexyl)-6-(5-methyl-1,2,4-oxadiazol-3-yl)pyrimidin-4-amine [56] gave 1.0 g of ethyl 1-(4-((4,4-difluorocyclohexyl)amino)-6-(5-methyl-1,2,4-oxadiazol-3-yl)pyrimidin-2-yl)-1H-pyrazole-3-carboxylate [57] as an off-white solid using CS2CO3, ACN 80° C. 2 h. MS(M+1)+=434.

Example 105

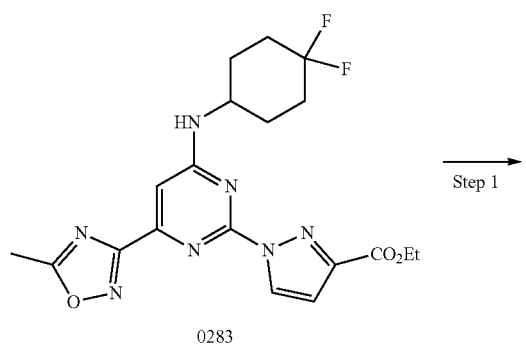

0283

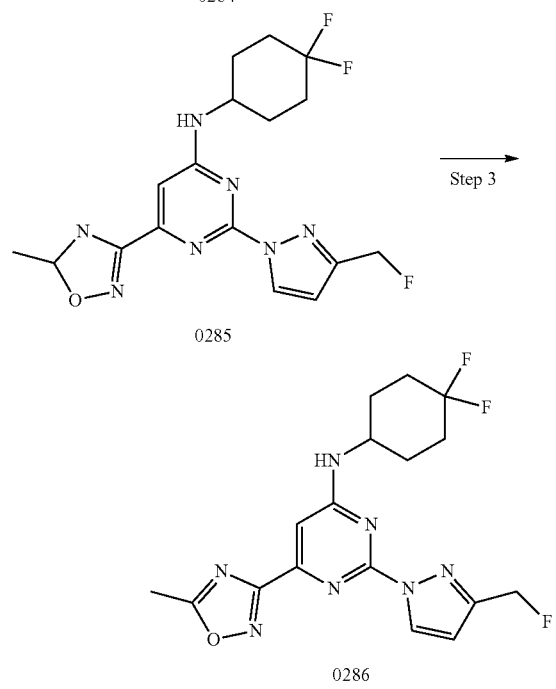

Step 1[0284]: The procedure is similar to step 2[0011] in example 2. 0.8 g of ethyl 1-(4-((4,4-difluorocyclohexyl)amino)-6-(5-methyl-1,2,4-oxadiazol-3-yl)pyrimidin-2-yl)-1H-pyrazole-3-carboxylate [0283] gave 0.9 g of (1-(4-((4,4-difluorocyclohexyl)amino)-6-(5-methyl-4,5-dihydro-1,2,4-oxadiazol-3-yl)pyrimidin-2-yl)-1H-pyrazol-3-yl)methanol [0284] as an white solid. MS(M+1)+=394.

Step 2 [0285]: The procedure is similar to step 3[0012] in example 2. 0.45 g of (1-(4-((4,4-difluorocyclohexyl)amino)-6-(5-methyl-4,5-dihydro-1,2,4-oxadiazol-3-yl)pyrimidin-2-yl)-1H-pyrazol-3-yl)methanol [0284] gave 0.24 g of N-(4,4-difluorocyclohexyl)-2-(3-(fluoromethyl)-1H-pyrazol-1-yl)-6-(5-methyl-4,5-dihydro-1,2,4-oxadiazol-3-yl)pyrimidin-4-amine [0285], Compound 331 as a white solid. MS(M+1)+=396, ¹H-NMR (400 MHz, DMSO-d6): δ 8.79 (s, 1H), 8.05 (bs, 1H), 7.54 (bs, 1H), 6.83 (d, J=11.52 Hz, 1H), 6.70 (s, 1H), 5.76 (s, 1H), 5.46 (d, JF=48.5 Hz, 2H), 4.22 (bs, 1H), 2.07-1.98 (m, 6H), 1.61-1.59 (m, 2H), 1.39 (d, J=4.0 Hz, 3H).

Step 3[0286]: 0.15 g of N-(4,4-difluorocyclohexyl)-2-(3-(fluoromethyl)-1H-pyrazol-1-yl)-6-(5-methyl-4,5-dihydro-1,2,4-oxadiazol-3-yl)pyrimidin-4-amine [0285] gave 0.11 g of N-(4,4-difluorocyclohexyl)-2-(3-(fluoromethyl)-1H-pyrazol-1-yl)-6-(5-methyl-1,2,4-oxadiazol-3-yl)pyrimidin-4-amine [0286], Compound 334 as an off-white solid, using manganese dioxide in dichloromethane. MS(M+1)+=394, $^1$H-NMR (400 MHz, DMSO-d6): δ 8.69 (s, 1H), 8.22 (d, J=7.32 Hz, 1H), 7.14 (s, 1H), 6.70 (s, 1H), 5.48 (d, JF=48.5 Hz, 2H), 4.26 (bs, 1H), 2.70 (s, 3H), 2.09-2.01 (m, 6H), 1.63-1.61 (m, 2H).

Example 106

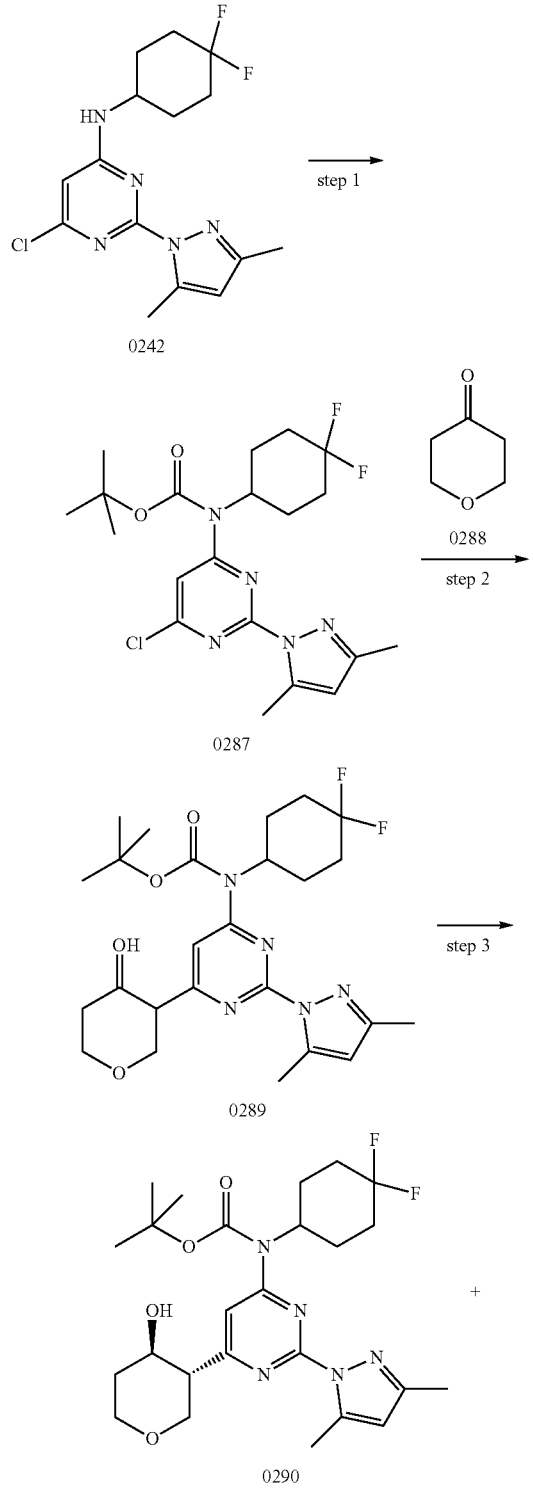

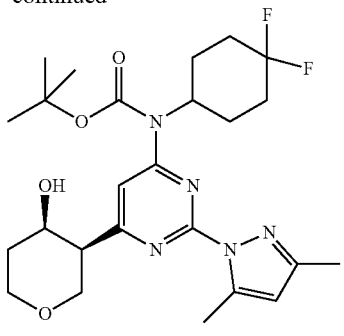

Step 1[0287]: To a solution 6-chloro-N-(4,4-difluorocyclohexyl)-2-(3,5-dimethyl-1H-pyrazol-1-yl)pyrimidin-4-amine [0242] (1 g, 2.92 mmol) in tetrahydrofuran (50 mL) was added boc-anhydride (1.91 g, 8.777 mmol) followed by 4-N,N-dimethylamino pyridine (0.067 g, 0.555 mmol). The reaction mixture was heated at 85° C. for 2 h. The reaction mixture was concentrated under reduced pressure to afford crude product which was purified by column chromatography using 20% ethyl acetate in pet ether as solvent to afford 1.2 g of tert-butyl (6-chloro-2-(3,5-dimethyl-1H-pyrazol-1-yl)pyrimidin-4-yl)(4,4-difluorocyclohexyl)carbamate [0287] as a white solid. MS(M+1)+=342.2

Step 2[0289]: To a solution of tetrahydro-4 h-Pyran-4-One [0288] (1.35 g, 13.577 mmol) in tetrahydrofuran (25 mL) was added lithium bis(trimethylsilyl)amide ((1 M solution in tetrahydrofuran) (13.57 mL, 13.577 mmol) at 0° C. After 30 min tert-butyl (6-chloro-2-(3,5-dimethyl-1H-pyrazol-1-yl)pyrimidin-4-yl)(4,4-difluorocyclohexyl)carbamate [0287] (1.5 g, 3.394 mmol) was added to the reaction mixture at 0° C. drop wise in tetrahydrofuran (5 mL). After addition the reaction was stirred at rt for 1 h. The reaction mixture was quenched with water (25 mL), extracted with ethyl acetate (2×50 mL). The combined organic layer was washed with water (20 mL), followed by brine (20 mL), dried over anhydrous sodium sulfate to afford 2.1 g of tert-butyl (4,4-difluorocyclohexyl)(2-(3,5-dimethyl-1H-pyrazol-1-yl)-6-(4-oxotetrahydro-2H-pyran-3-yl)pyrimidin-4-yl)carbamate [0289] as a yellow solid. MS(M+1)+=506.3

Step 3[0290 and 0291]: To a solution of tert-butyl (4,4-difluorocyclohexyl)(2-(3,5-dimethyl-1H-pyrazol-1-yl)-6-(4-oxotetrahydro-2H-pyran-3-yl)pyrimidin-4-yl)carbamate [0289] (0.5 g, 1.01 mmol) in methanol (5 mL) was added sodium borohydride (38.5 g, 1.01 mmol). The reaction mixture was stirred at rt for 10 min. The reaction mixture was concentrated under reduced pressure. The residue was neutralized with 10% sodium bicarbonate solution (15 mL, extracted with ethyl acetate (2×10 mL). The combined organic layer was washed with water (10 mL), followed by brine (10 mL) and dried over anhydrous sodium sulfate to afford crude product which was purified by preparative HPLC to afford 0.045 g of tert-butyl (4,4-difluorocyclohexyl)(6-((+)-4-hydroxytetrahydro-2H-pyran-3-yl)-2-(3- methyl-1H-pyrazol-1-yl)pyrimidin-4-yl)carbamate [0290] as a yellow solid and 0.130 g of tert-butyl (4,4-difluorocyclohexyl)(6-((−)-4-hydroxytetrahydro-2H-pyran-3-yl)-2-(3-methyl-1H-pyrazol-1-yl)pyrimidin-4-yl)carbamate [0291]. MS (M+1)+=494.2

Example 107

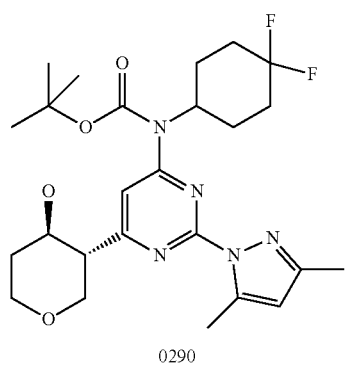

0290

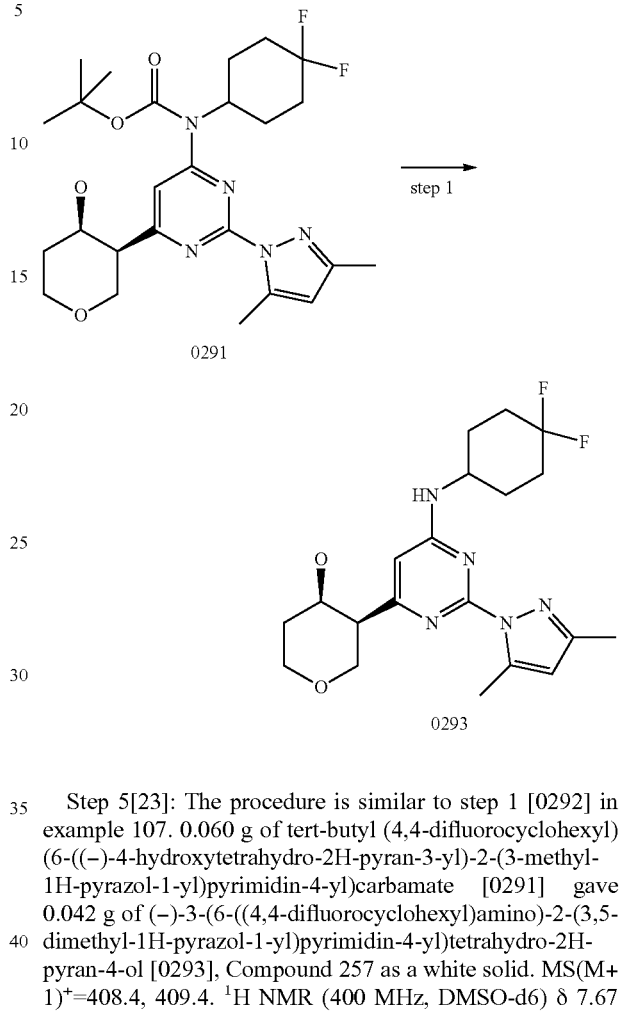

Step 1[0292]: To a cooled solution of tert-butyl (4,4-difluorocyclohexyl)(6-((+)-4-hydroxytetrahydro-2H-pyran-3-yl)-2-(3-methyl-1H-pyrazol-1-yl)pyrimidin-4-yl)carbamate [0290] (0.80 g, 0.157 mmol) in dioxane (5 mL) was added hydrogen chloride gas (5 mL) in dioxane. The reaction mixture was stirred at rt for 2 h. The reaction mixture was concentrated under reduced pressure. The residue was dissolved in water (1 mL). It was then neutralized with 10% sodium bicarbonate solution (20 mL). The aqueous layer was extracted with ethyl acetate (2×20 mL). The combined organic layer was washed with water (10 mL), followed by brine (10 mL) and dried over anhydrous sodium sulfate to afford 0.055 g of (+)-3-(6-((4,4-difluorocyclohexyl)amino)-2-(3,5-dimethyl-1H-pyrazol-1-yl)pyrimidin-4-yl)tetrahydro-2H-pyran-4-ol [0292], Compound 254 as a white solid. MS(M+1)+, 408.4, $^1$H NMR (400 MHz, DMSO-d6) δ 7.60 (bs, 1H), 6.29 (bs, 1H), 6.03 (s, 1H), 4.85 (d, J=5.5 Hz, 1H), 4.04 (bs, 1H), 3.95-3.80 (m, 3H), 3.39 (t, J=11.2, 2H), 2.48 (s, 3H), 2.16 (s, 3H), 2.05-1.80 (m, 7H), 1.63-1.36 (m, 3H).

Step 5[23]: The procedure is similar to step 1 [0292] in example 107. 0.060 g of tert-butyl (4,4-difluorocyclohexyl)(6-((−)-4-hydroxytetrahydro-2H-pyran-3-yl)-2-(3-methyl-1H-pyrazol-1-yl)pyrimidin-4-yl)carbamate [0291] gave 0.042 g of (−)-3-(6-((4,4-difluorocyclohexyl)amino)-2-(3,5-dimethyl-1H-pyrazol-1-yl)pyrimidin-4-yl)tetrahydro-2H-pyran-4-ol [0293], Compound 257 as a white solid. MS(M+1)+=408.4, 409.4. $^1$H NMR (400 MHz, DMSO-d6) δ 7.67 (d, J=7.7 Hz, 1H), 6.24 (bs, 1H), 6.06 (s, 1H), 5.39 (bs, 1H), 4.24 (s, 1H), 4.02 (bs, 1H), 3.97-3.80 (m, 1H), 3.80-3.54 (m, 3H), 2.82 (bs, 1H), 2.53 (s, 3H), 2.16 (s, 3H), 2.10-1.7 (m, 7H), 1.57-1.50 (m, 3H).

Example 109

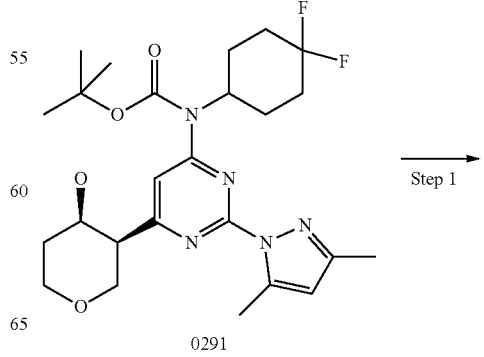

0291

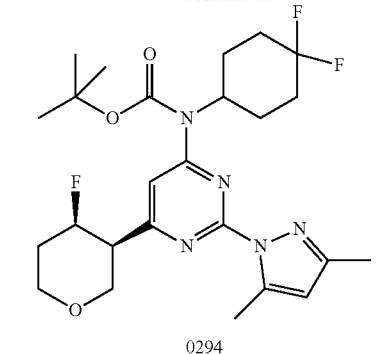 [SMILES: Cc1cc(C)n(-c2nc([C@H]3COCC[C@H]3O)cc(N(C(=O)OC(C)(C)C)C3CCC(F)(F)CC3)n2)n1]

0294

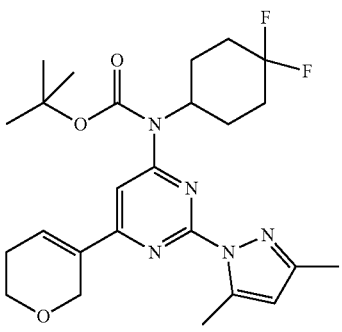

0295

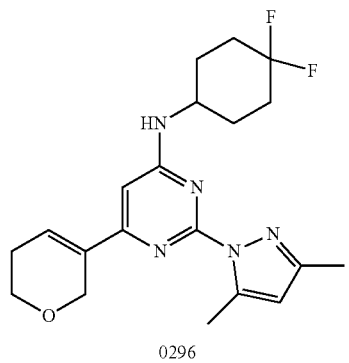

0296

Step 1[0294 and 0295]: To an ice-cold solution of tert-butyl (4,4-difluorocyclohexyl)(2-(3,5-dimethyl-1H-pyrazol-1-yl)-6-(-4-hydroxytetrahydro-2H-pyran-3-yl)pyrimidin-4-yl)carbamate [0291] (0.240 g, 0.472 mmol) in dichloromethane (5 mL) was added diethylaminosulfur trifluoride (0.152 g, 0.945 mmol) drop wise. The reaction mixture was slowly warmed to rt and stirred for 2 h. The reaction mixture was diluted with dichloromethane (20 mL). The organic layer was washed with 10% sodium bicarbonate solution (10 mL), washed with water (10 mL), followed by brine (10 mL). The organic layer was dried over anhydrous sodium sulfate and concentrated under reduced pressure to afford crude product, which was purified by preparative HPLC to afford 0.050 g of tert-butyl (4,4-difluorocyclohexyl)(2-(3,5-dimethyl-1H-pyrazol-1-yl)-6-((3S,4R)-4-fluorotetrahydro-2H-pyran-3-yl)pyrimidin-4-yl)carbamate [0294] as a white solid. MS(M+1)+=410.4 and 0.08 g of tert-butyl (4,4-difluorocyclohexyl)(6-(5,6-dihydro-2H-pyran-3-yl)-2-(3,5-dimethyl-1H-pyrazol-1-yl)pyrimidin-4-yl)carbamate [0295] as a white solid. MS(M+1)+=390.0

Step 2[0296]: To a cooled solution of tert-butyl (4,4-difluorocyclohexyl)(6-(5,6-dihydro-2H-pyran-3-yl)-2-(3,5-dimethyl-1H-pyrazol-1-yl)pyrimidin-4-yl)carbamate [0295] (0.08 g, 0.18 mmol) in dioxane (3 mL) was added hydrogen chloride gas in dioxane (3 mL). The reaction mixture was stirred at rt for 2 h. The reaction mixture was concentrated under reduced pressure. The residue was dissolved in water (1 mL). It was then neutralized with 10% sodium bicarbonate solution. The aqueous layer was extracted with ethyl acetate (2×20 mL). The combined organic layer was washed with water (10 mL), followed by brine (10 mL) and dried over anhydrous sodium sulfate to afford 0.060 g of N-(4,4-difluorocyclohexyl)-6-(5,6-dihydro-2H-pyran-3-yl)-2-(3,5-dimethyl-1H-pyrazol-1-yl)pyrimidin-4-amine [0296], Compound 262 as a white solid. MS(M+1)+=390.2, 391.2. $^1$H NMR (400 MHz, DMSO-d6) δ 7.66 (bs, 1H), 6.93 (bs, 1H), 6.27 (bs, 1H), 6.05 (s, 1H), 4.42 (s, 2H), 4.05 (bs, 1H), 3.74 (t, J=5.4 Hz, 2H), 2.46 (s, 3H), 2.31 (bs, 2H), 2.17 (s, 3H), 2.10-1.85 (m, 6H), 1.60-155 (m, 2H).

Example 110

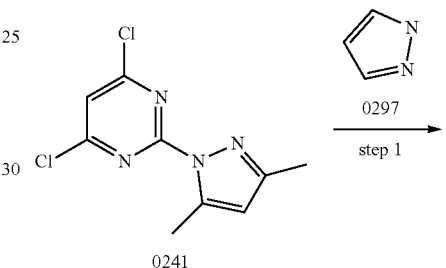

0241

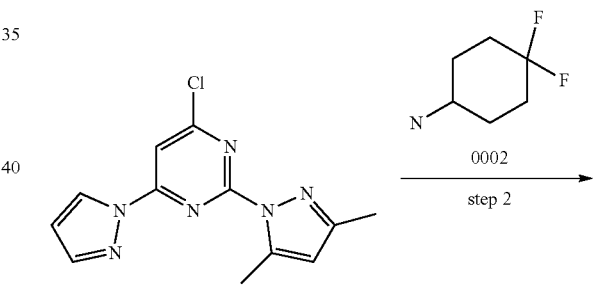

0298

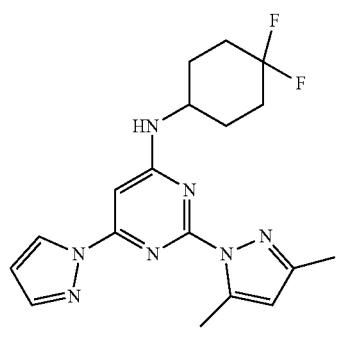

0299

Step 1[0298]: The procedure is similar to Step 2 [0271] in example 98 (16 h). 0.4 g of 4,6-dichloro-2-(3,5-dimethyl-1H-pyrazol-1-yl)pyrimidine [0241] gave 0.350 g of 4-chloro-2-(3,5-dimethyl-1H-pyrazol-1-yl)-6-(1H-pyrazol-1-yl)pyrimidine [0298] as an off-white solid. MS(M+1)+= 275.

Step 2[0299]: The procedure is similar to Step 2 [0271] in example 98 (16 h). 0.15 g of 4-chloro-2-(3,5-dimethyl-1H-pyrazol-1-yl)-6-(1H-pyrazol-1-yl)pyrimidine [0298] gave 0.04 g of N-(4,4-difluorocyclohexyl)-2-(3,5-dimethyl-1H-pyrazol-1-yl)-6-(1H-pyrazol-1-yl)pyrimidin-4-amine [0299], Compound 117 as an off-white solid. MS(M+1)$^+$=374. $^1$H NMR (400 MHz, DMSO-d6) δ 8.50 (s, 1H), 7.98 (s, 1H), 7.87 (s, 1H), 6.85 (s, 1H), 6.59 (s, 1H), 6.13 (d, J=2.8 Hz, 1H), 4.12 (bs, 1H), 2.61 (s, 3H), 2.20 (s, 3H), 2.15-1.85 (m, 6H), 1.68-1.50 (m, 2H).

Example 111

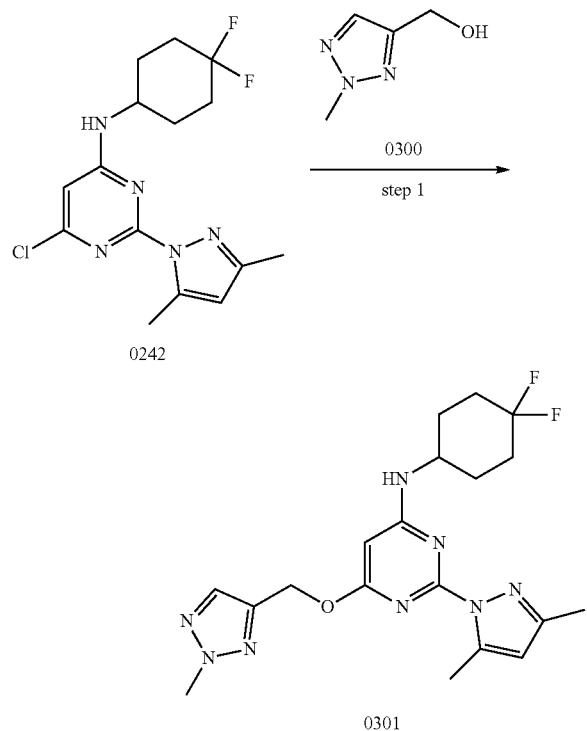

Step 1[0301]: To a stirred solution of 0.500 g of 6-chloro-N-(4,4-difluorocyclohexyl)-2-(3,5-dimethyl-1H-pyrazol-1-yl)pyrimidin-4-amine [0242] in 50% aqueous sodium hydroxide solution (2 mL), was added 0.331 g of (2-methyl-2H-1,2,3-triazol-4-yl)methanol [0300] and tetra butyl ammonium hydrogen sulfate (0.200 g, 0.586 mmol). The reaction mixture was heated at 110° C. for 16 h. The reaction mixture was extracted with ethyl acetate (10 mL), dried over anhydrous sodium sulfate, filtered and concentrated under reduced pressure to afford crude product, which was purified by column chromatography to afford 0.22 g of N-(4,4-difluorocyclohexyl)-2-(3,5-dimethyl-1H-pyrazol-1-yl)-6-((2-methyl-2H-1,2,3-triazol-4-yl)methoxy)pyrimidin-4-amine [0301], Compound 191 as an white solid. MS(M+1)$^+$=419. $^1$H NMR (400 MHz, DMSO-d6) δ 8.05 (bs, 1H), 7.51 (bs, 1H), 6.09 (s, 1H), 5.70 (bs, 1H), 5.36 (s, 2H), 4.14 (s, 3H), 4.01 (bs, 1H), 2.57 (s, 3H), 2.19 (s, 3H), 2.10-1.90 (m, 6H), 1.60-1.53 (m, 2H).

Example 112

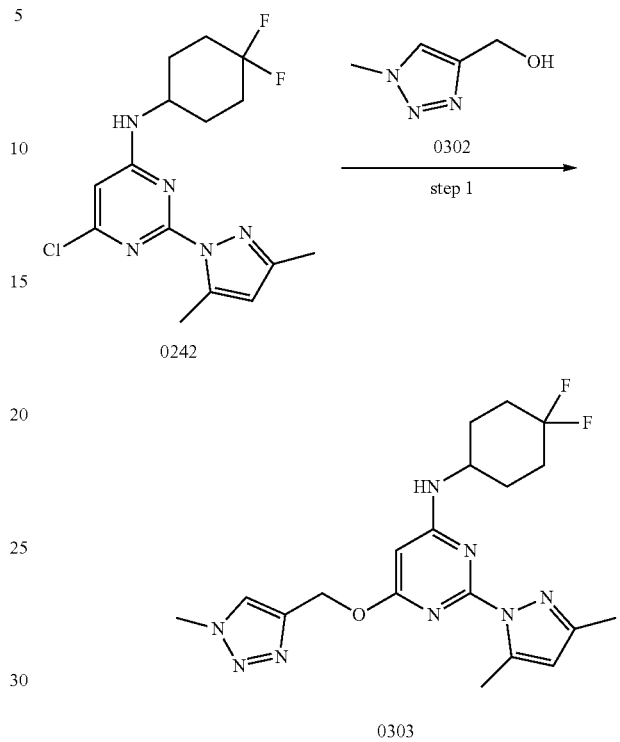

Step 1[0303]: The procedure is similar to step 1[0301] in example 111. 0.250 g of 6-chloro-N-(4,4-difluorocyclohexyl)-2-(3,5-dimethyl-1H-pyrazol-1-yl)pyrimidin-4-amine [0242] and 0.165 g of (1-methyl-1H-1,2,3-triazol-5-yl)methanol [0302] gave 0.150 g of N-(4,4-difluorocyclohexyl)-2-(3,5-dimethyl-1H-pyrazol-1-yl)-6-((1-methyl-1H-1,2,3-triazol-5-yl)methoxy)pyrimidin-4-amine [0303], Compound 126 as an white solid. MS(M+1)$^+$=419. $^1$H NMR (400 MHz, DMSO-d6) δ 8.48 (bs, 1H), 7.48 (bs, 1H), 6.09 (s, 1H), 5.70 (s, 1H), 5.36 (bs, 2H), 4.04 (s, 3H), 4.03 (m, 1H), 2.58 (s, 3H), 2.20 (s, 3H), 2.08-1.91 (m, 6H), 1.50-1.45 (m, 2H).

Example 113

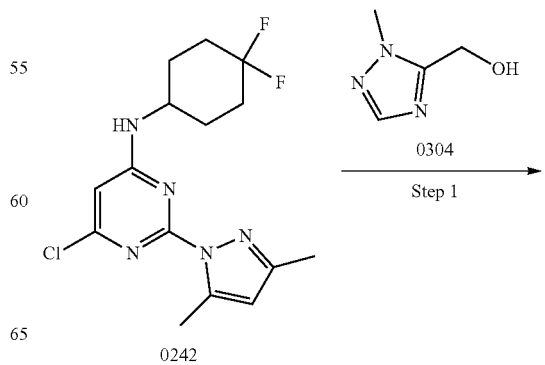

-continued

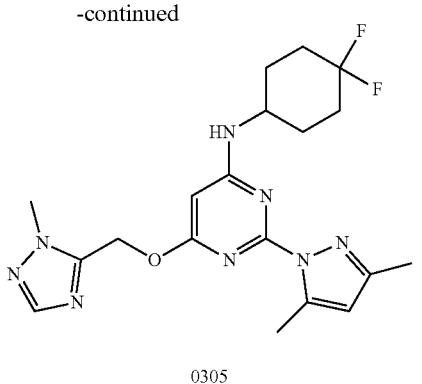

0305

Step 1[0305]: The procedure is similar to step 1[0301] in example 111. 0.150 g of 6-chloro-N-(4,4-difluorocyclohexyl)-2-(3,5-dimethyl-1H-pyrazol-1-yl)pyrimidin-4-amine [0242] gave 0.030 g of N-(4,4-difluorocyclohexyl)-2-(3,5-dimethyl-1H-pyrazol-1-yl)-6-((1-methyl-1H-1,2,4-triazol-5-yl)methoxy)pyrimidin-4-amine[0305], Compound 274.

MS(M+1)$^+$=418.2, $^1$H NMR (400 MHz, DMSO-d6) δ 7.90 (s, 1H), 7.56 (bs, 1H), 6.08 (s, 1H), 5.76 (bs, 1H), 5.47 (s, 2H), 3.99 (s, 4H), 2.55 (s, 3H), 2.17 (s, 3H), 2.12-1.85 (m, 6H), 1.62-1.45 (m, 2H).

Example 114

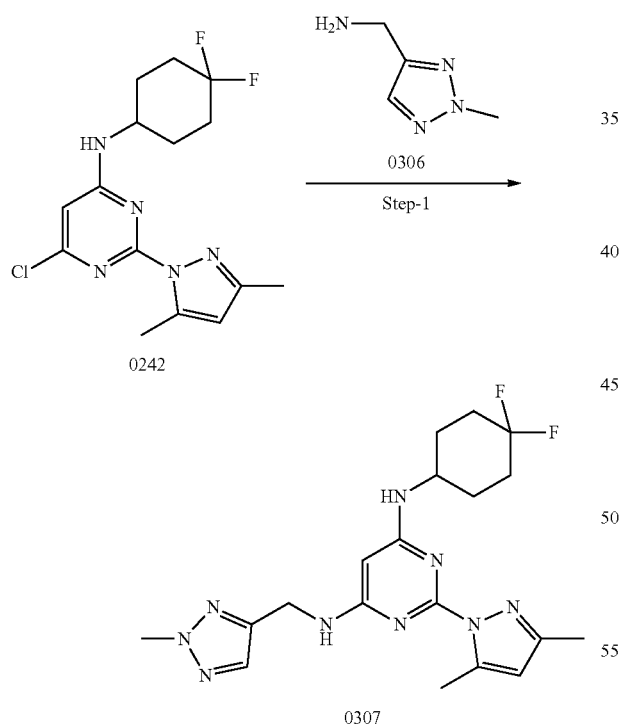

Step 1[0307]: The procedure is similar to step 2[0274] in Example 99. 0.15 g of 6-chloro-N-(4,4-difluorocyclohexyl)-2-(3,5-dimethyl-1H-pyrazol-1-yl)pyrimidin-4-amine [0242] and 0.09 g of (2-methyl-2H-1,2,3-triazol-4-yl)methanamine [0306] gave 0.03 g of N4-(4,4-difluorocyclohexyl)-2-(3,5-dimethyl-1H-pyrazol-1-yl)-N6-((2-methyl-2H-1,2,3-triazol-4-yl)methyl)pyrimidine-4,6-diamine [0307], Compound 235 as a light yellow solid.

MS(M+1)$^+$=418, $^1$H NMR (400 MHz, DMSO-d6) δ 7.70 (s, 1H), 7.32 (t, J=5.8 Hz, 1H), 6.93 (d, J=7.5 Hz, 1H), 5.98 (s, 1H), 5.35 (s, 1H), 4.43-4.39 (m, 2H), 4.08 (s, 3H), 3.80 (bs, 1H), 2.46 (s, 3H), 2.13 (s, 3H), 2.15-1.80 (m, 6H), 1.60-1.43 (m, 2H).

Example 115

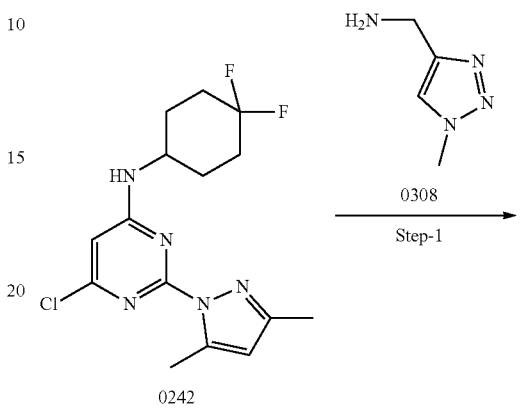

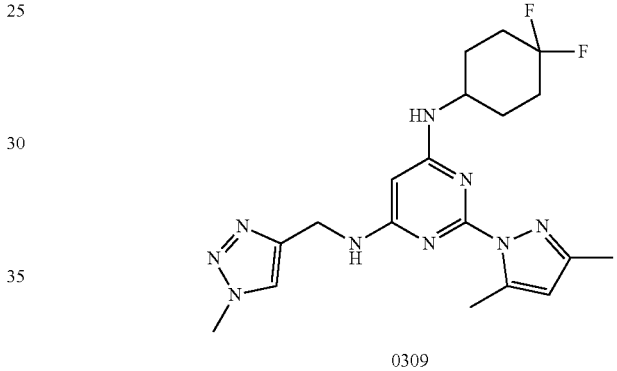

0309

Step 1[0309]: The procedure is similar to step 2[0274] in Example 99. 0.15 g of 6-chloro-N-(4,4-difluorocyclohexyl)-2-(3,5-dimethyl-1H-pyrazol-1-yl)pyrimidin-4-amine [0242] and 0.09 g of (1-methyl-1H-1,2,3-triazol-4-yl)methanamine [0308] gave 0.04 g of N4-(4,4-difluorocyclohexyl)-2-(3,5-dimethyl-1H-pyrazol-1-yl)-N6-((1-methyl-1H-1,2,3-triazol-4-yl)methyl)pyrimidine-4,6-diamine [0309], Compound 233 as an off-white solid.

MS(M+1)$^+$=418, $^1$H NMR (400 MHz, DMSO-d6) δ 8.09 (bs, 1H), 7.33 (t, J=5.9 Hz, 1H), 6.93 (d, J=7.6 Hz, 1H), 6.00 (s, 1H), 5.37 (s, 1H), 4.42 (d, J=5.8 Hz, 2H), 4.00 (s, 3H), 3.81 (bs, 1H), 2.48 (s, 3H), 2.16 (s, 3H), 2.08-1.87 (m, 6H), 1.53-1.48 (m, 2H).

Example 116

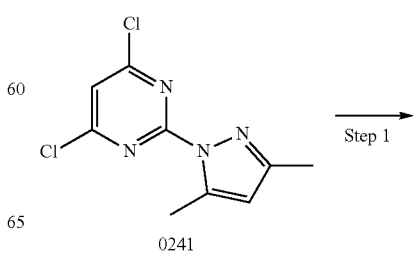

0241

-continued

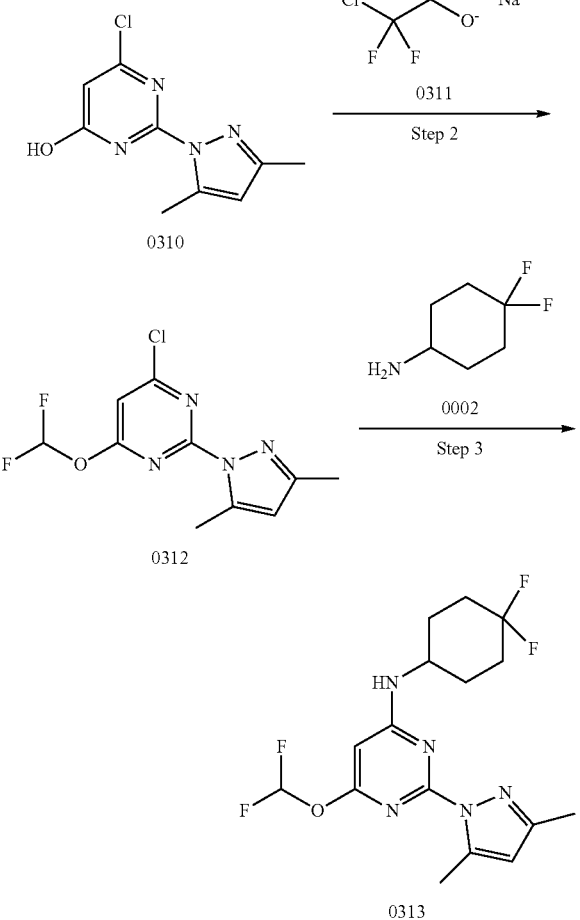

Step 1[0310]: To a stirred solution of 4,6-dichloro-2-(3,5-dimethyl-1H-pyrazol-1-yl)pyrimidine [0241] (2 g, 8.227 mmol) in a mixture of solvent (tetrahydrofuran (20 mL) and water (2 mL)) was added sodium hydroxide (0.65 g, 16.454 mmol). The reaction mixture was stirred at rt for 16 h. The reaction mixture was concentrated under reduced pressure. The residue was dissolved in water, neutralized with 1.5 N HCl solution (~0.5 mL), and extracted with ethyl acetate (3×50 mL). The combined organic extracts were dried over anhydrous sodium sulfate, filtered and concentrated under reduced pressure to afford 0.550 g of 6-chloro-2-(3,5-dimethyl-1H-pyrazol-1-yl)pyrimidin-4-ol [0310] as a white solid. MS(M+1)+=225.2.

Step 2[0312]: To a stirred solution of 6-chloro-2-(3,5-dimethyl-1H-pyrazol-1-yl)pyrimidin-4-ol [0310] (0.50 g, 0.2226 mmol) in acetonitrile (2 mL) was added sodium chlorodifluoroacetate [0311] (0.54 g, 0.356 mmol) and sodium carbonate (0.47 g, 0.445 mmol). The reaction mixture was heated at 90° C. for 5 h. The reaction mixture was partitioned between ethyl acetate (20 mL) and water (5 mL). The organic extracts was dried over anhydrous sodium sulfate, filtered and concentrated under reduced pressure to afford 0.110 g of 4-chloro-6-(difluoromethoxy)-2-(3,5-dimethyl-1H-pyrazol-1-yl)pyrimidine [0312] as an off-white solid. MS(M+1)+=275.2/276.2.

Step 3[0313]: To a stirred solution of 4-chloro-6-(difluoromethoxy)-2-(3,5-dimethyl-1H-pyrazol-1-yl)pyrimidine [0312] (0.1 g, 0.364 mmol) in acetonitrile (3 mL) was added 4,4-difluorocyclohexylamine hydrochloride (0.125 g, 0.728 mmol) and N,N-diisopropyl ethylamine (0.117 g, 0.91 mmol). The reaction mixture was irradiated in microwave at 130° C. for 2 h. The reaction mixture was filtered through celite and the filtrate was concentrated under reduced pressure to afford crude product which was purified by column chromatography using 35% ethyl acetate in pet ether as solvent to afford 0.035 g of N-(4,4-difluorocyclohexyl)-6-(difluoromethoxy)-2-(3,5-dimethyl-1H-pyrazol-1-yl)pyrimidin-4-amine [0313], Compound 209 as a white solid. MS(M+1)+=336.0/337.0. ¹H NMR (400 MHz, DMSO-d6) δ 7.76-7.40 (t, JF=72.8 Hz, 1H), 7.65 (d, 8 Hz, 1H), 6.07 (s, 1H), 5.94 (s, 1H), 3.94 (s, 1H), 2.55 (s, 3H), 2.18 (s, 3H), 2.07-1.95 (m, 6H), 1.63-1.61 (m, 2H).

Example 117

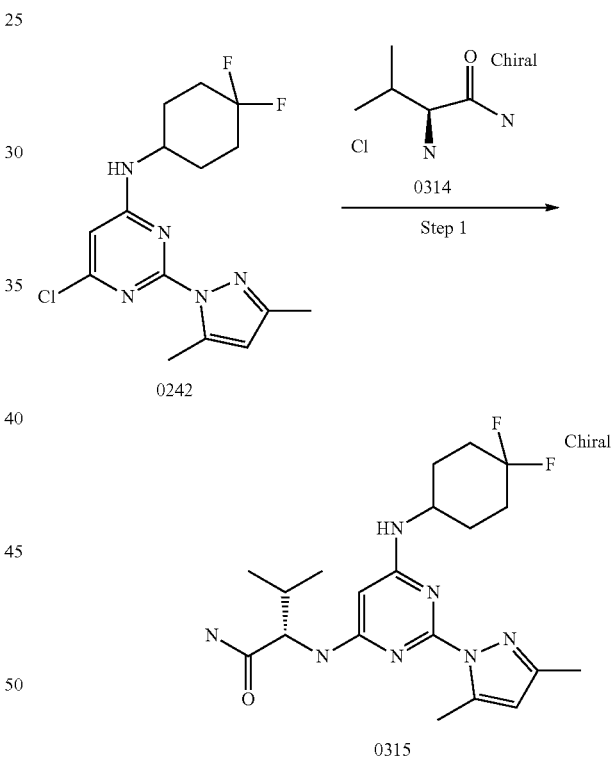

Step 1[55]: The procedure is similar to step 3[0313] in example 116. 0.5 g of 6-chloro-N-(4,4-difluorocyclohexyl)-2-(3,5-dimethyl-1H-pyrazol-1-yl)pyrimidin-4-amine [0242] gave 0.28 g of (R)-2-((6-((4,4-difluorocyclohexyl)amino)-2-(3,5-dimethyl-1H-pyrazol-1-yl)pyrimidin-4-yl)amino)-3-methylbutanamide [0315], Compound 164 0.28 g of as a white solid. MS(M+1)+=422.2. ¹H-NMR (400 MHz, DMSO-d6): δ 7.33 (s, 1H), 7.01 (bs, 1H), 6.93 (bs, 1H), 6.71 (bs, 1H), 5.97 (s, 1H), 5.48 (bs, 1H), 4.23 (bs, 1H), 3.74 (bs, 1H), 2.47 (s, 3H), 2.12 (s, 3H), 2.10-2.00 (m, 3H), 2.00-1.80 (m, 4H), 1.62-1.48 (m, 2H), 0.95 (d, J=0.68 Hz, 6H).

Example 118

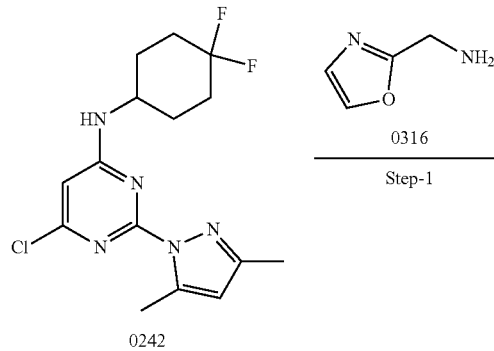

0242

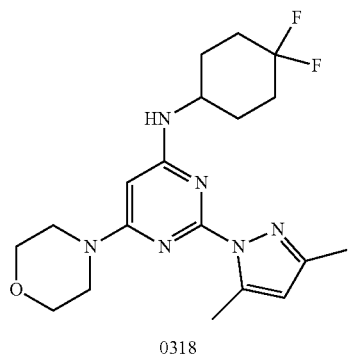

0317

Step 1[0317]: The procedure is similar to step 3[0313] in example 116. 0.3 g of 6-chloro-N-(4,4-difluorocyclohexyl)-2-(3,5-dimethyl-1H-pyrazol-1-yl)pyrimidin-4-amine [0242] gave 0.020 g of N4-(4,4-difluorocyclohexyl)-2-(3,5-dimethyl-1H-pyrazol-1-yl)-N6-(oxazol-2-ylmethyl)pyrimidine-4,6-diamine [0317], Compound 145 as an light brown solid. MS(M+1)$^+$=404, $^1$H NMR (400 MHz, DMSO-d6) δ 8.04 (s, 1H), 7.48 (t, J=6.0 Hz, 1H), 7.15 (s, 1H), 7.02 (d, J=7.9 Hz, 1H), 5.98 (s, 1H), 5.43 (s, 1H), 4.55 (d, J=5.9 Hz, 2H), 3.81 (bs, 1H), 2.42 (s, 3H), 2.13 (s, 3H), 2.06-1.90 (m, 6H), 1.50-1.60 (m, 2H).

Example 119

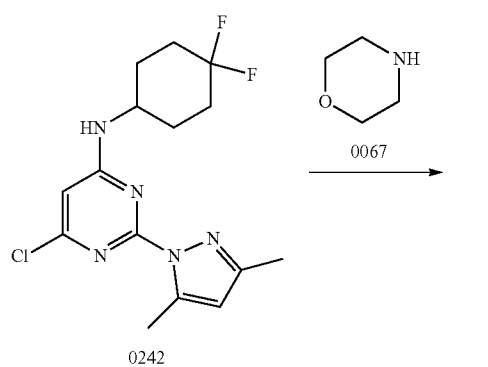

0242

-continued

0318

Step-1 [0318]: To a solution of 6-chloro-N-(4,4-difluorocyclohexyl)-2-(3,5-dimethyl-1H-pyrazol-1-yl)pyrimidin-4-amine [0242] (15 g, 43.88 mmol) in acetonitrile (200 mL) was added morpholine [0067] (15.29 g, 175.54 mmol) and the resultant reaction mixture was heated at 75° C. in sealed tube. The reaction mixture was quenched with water, the obtained solid was filtered dried under vacuum to afford N-(4,4-difluorocyclohexyl)-2-(3,5-dimethyl-1H-pyrazol-1-yl)-6-morpholinopyrimidin-4-amine [0318] Compound 187 as an off-white solid (13.8 g). MS(M+1)$^+$=393, $^1$H-NMR (400 MHz, DMSO-d6): δ 7.09 (d, J=7.92 Hz, 1H), 6.00 (s, 1H), 5.56 (s, 1H), 3.86 (bs, 1H), 3.66 (m, 4H), 3.50 (m, 4H), 2.50 (s, 3H), 2.14 (s, 3H), 2.08-1.89 (m, 6H), 1.54-1.51 (m, 2H).

Example 120

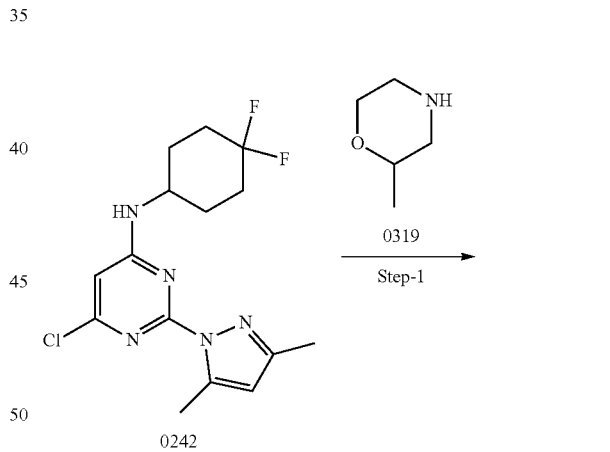

0242

0320

Step 1: The procedure is similar to step 3[0313] in example 116. 0.15 g of 6-chloro-N-(4,4-difluorocyclohexyl)-2-(3,5-dimethyl-1H-pyrazol-1-yl)pyrimidin-4-amine [0242] and 0.088 g of 2-methyl morpholine [0319] gave 0.07 g of N-(4,4-difluorocyclohexyl)-2-(3,5-dimethyl-1H-pyrazol-1-yl)-6-(2-methylmorpholino)pyrimidin-4-amine [0320], Compound 188. MS(M+1)$^+$=407, $^1$H-NMR (400 MHz, DMSO-d6): δ 7.07 (d, J=8.00 Hz, 1H), 6.01 (bs, 1H), 5.57 (s, 1H), 4.07-3.89 (m, 2H), 3.89-3.88 (m, 2H), 3.54-3.48 (m, 2H), 2.89-2.83 (m, 1H), 2.57-2.54 (m, 1H), 2.50 (s, 3H), 2.14 (s, 3H), 2.49-2.08 (m, 6H), 1.50-1.49 (m, 2H), 1.12 (d, J=Hz, 3H).

Example 121

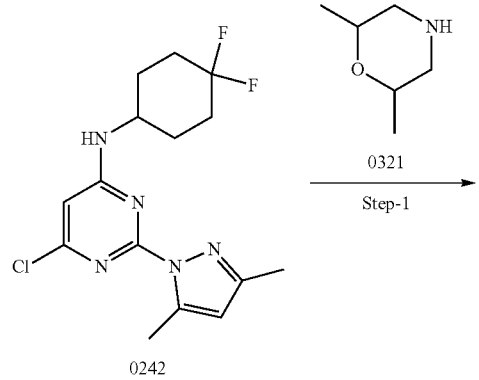

0242

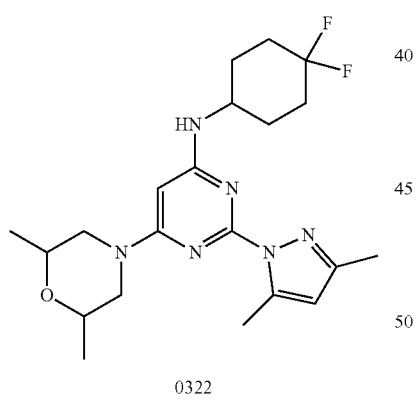

0322

Step 1 [0322]: The procedure is similar to Step 2[0274] in example 99. 0.15 g of 6-chloro-N-(4,4-difluorocyclohexyl)-2-(3,5-dimethyl-1H-pyrazol-1-yl)pyrimidin-4-amine [0242] and 0.101 g of 2,6-dimethyl morpholine [0321] gave 0.07 g of N-(4,4-difluorocyclohexyl)-2-(3,5-dimethyl-1H-pyrazol-1-yl)-6-(2,6-dimethylmorpholino)pyrimidin-4-amine [0322], Compound 190. MS(M+1)$^+$=421, $^1$H NMR (400 MHz, DMSO-d6) δ 7.07 (d, J=8.0 Hz, 1H), 6.01 (s, 1H), 5.57 (s, 1H), 4.08 (bs, 2H), 3.87 (bs, 1H), 3.57-3.58 (m, 2H), 2.48 (s, 3H), 2.12 (s, 3H), 2.12-1.85 (m, 6H), 1.60-1.49 (m, 2H), 1.15 (d, J=6.2 Hz, 6H). (angular Proton (2H) missing)

Example 122

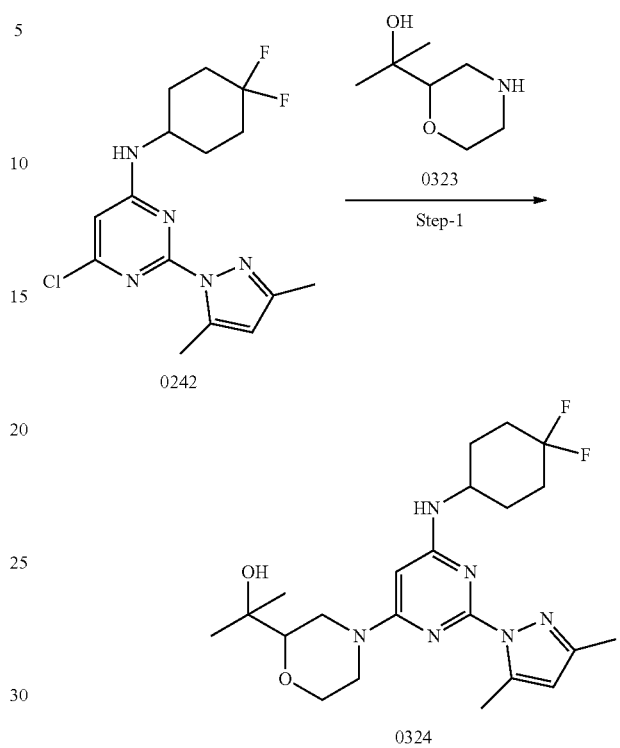

Step 1 [0324]: The procedure is similar to Step 2[0274] in example 99. 0.15 g of 6-chloro-N-(4,4-difluorocyclohexyl)-2-(3,5-dimethyl-1H-pyrazol-1-yl)pyrimidin-4-amine [0242] and 0.127 g of 2-(morpholin-2-yl)propan-2-ol [0323] gave 0.050 g of 2-(4-(6-((4,4-difluorocyclohexyl)amino)-2-(3,5-dimethyl-1H-pyrazol-1-yl)pyrimidin-4-yl)morpholin-2-yl)propan-2-ol [0324], Compound 227. MS(M+1)$^+$=451, $^1$H NMR (400 MHz, DMSO-d6) δ 7.08 (d, J=7.9 Hz, 1H), 6.01 (s, 1H), 5.57 (s, 1H), 4.56 (s, 1H), 4.21 (bs, 1H), 4.11-3.82 (m, 3H), 3.49-340 (m, 1H), 3.16 (dd, J=10.8, 2.4 Hz, 1H), 2.84 (t, J=11.7 Hz, 1H), 2.70-2.60 (m, 1H), 2.58 (s, 3H), 2.15 (s, 3H), 2.07-1.82 (m, 6H), 1.54-1.47 (m 2H), 1.16 (s, 3H), 1.10 (s, 3H).

Example 123

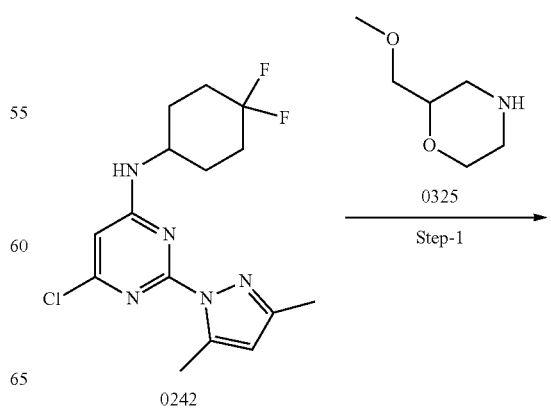

-continued

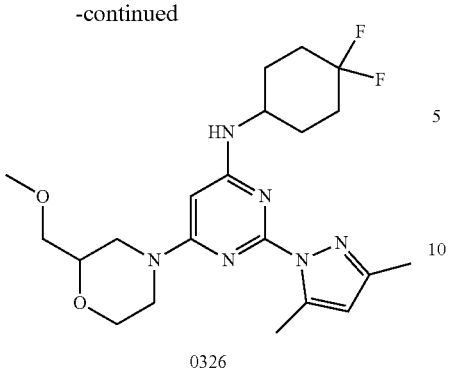

0326

Step 1[0326]: The procedure is similar to Step 2[0274] in example 99. 0.2 g of 6-chloro-N-(4,4-difluorocyclohexyl)-2-(3,5-dimethyl-1H-pyrazol-1-yl)pyrimidin-4-amine [0242] and 0.196 g of 2-(methoxymethyl)morpholine [0325] gave 0.050 g of N-(4,4-difluorocyclohexyl)-2-(3,5-dimethyl-1H-pyrazol-1-yl)-6-(2-(methoxymethyl)morpholino)pyrimidin-4-amine [0326], Compound 194. MS(M+1)⁺=437, ¹H NMR (400 MHz, DMSO-d6) δ 7.10 (d, J=8.0 Hz, 1H), 6.01 (s, 1H), 5.57 (s, 1H), 3.80-4.12 (m, 4H), 3.65-3.55 (m, 1H), 3.55-3.49 (m, 1H), 3.45-3.35 (m, 2H), 3.29 (s, 3H), 2.95-2.82 (m, 1H), 2.72-2.61 (m, 1H), 2.48 (s, 3H), 2.14 (s, 3H), 2.10-2.0 (m, 3H), 1.95-2.0 (m, 3H), 1.54-1.45 (m, 2H).

Example 124

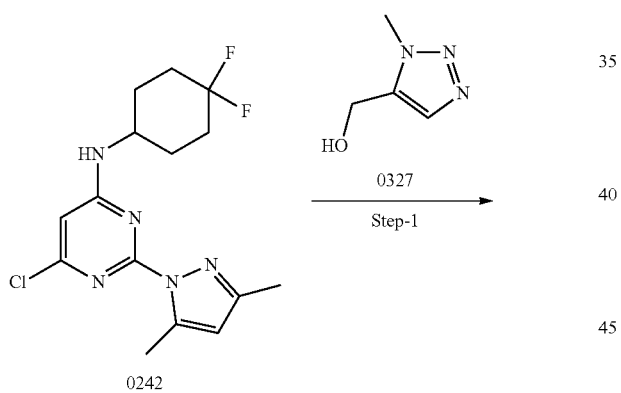

0242

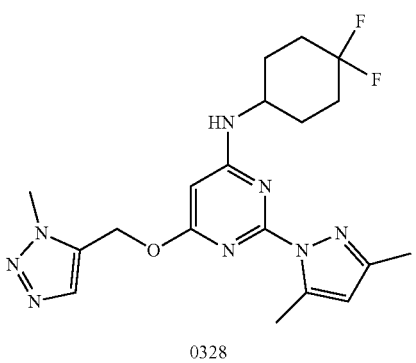

0328

Step 1[0328]: The procedure is similar to step 1[0301] in example 111. 0.25 g of 6-chloro-N-(4,4-difluorocyclohexyl)-2-(3,5-dimethyl-1H-pyrazol-1-yl)pyrimidin-4-amine [0242] and 0.16 g of (1-methyl-1H-1,2,3-triazol-5-yl)methanol [0327] gave 0.15 g of N-(4,4-difluorocyclohexyl)-2-(3, 5-dimethyl-1H-pyrazol-1-yl)-6-((1-methyl-1H-1,2,3-triazol-5-yl)methoxy)pyrimidin-4-amine [0328], Compound 189 as an white solid, LCMS(MH+)=419, ¹H NMR (400 MHz, DMSO-d6) δ 7.88 (s, 1H), 7.53 (bs, 1H), 6.08 (s, 1H), 5.71 (bs, 1H), 5.47 (s, 2H), 4.11 (s, 3H), 3.43 (bs, 1H), 2.56 (s, 3H), 2.18 (s, 3H), 2.11-1.86 (m, 6H), 1.50-1.45 (m, 2H).

Example 126

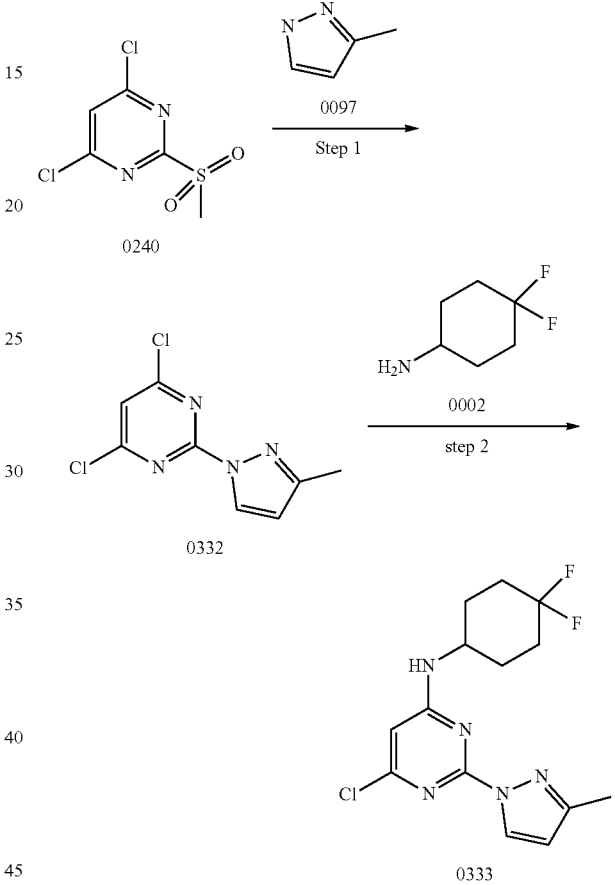

Step 1[0332]: To a suspension of sodium hydride (1.76 g, 44.039 mmol) in dry dichloromethane was added methyl pyrazole [0097] (3.61 g, 44.039 mmol) portion wise under N2 atm. The reaction mixture was stirred at rt for 30 min, then cooled to –78° C., was added a solution of 4,6-dichloro-2-(methylsulfonyl)pyrimidine [0240] (10 g, 44.039 mmol) in dichloromethane drop wise. After addition the reaction mixture was stirred at –78° C. After 1 h, the reaction mixture was quenched with water at –78° C., slowly brought to rt and extracted with dichloromethane. The combined organic layers were washed with brine, dried over anhydrous sodium sulfate and concentrated to afford a yellow solid, which was purified using ethyl acetate in hexane as solvent in column (60-120 silica gel) to afford 3 g of 4,6-dichloro-2-(3-methyl-1H-pyrazol-1-yl)pyrimidine[0332] as white solid. MS(M+1)+=230.0.

Step 2[0333]: 5 g of 4,6-dichloro-2-(methylsulfonyl)pyrimidine[0332] and 4.1 g of 4,4-difluorocyclohexylamine hydrochloride [0002] gave 3 g 6-chloro-N-(4,4-difluorocyclohexyl)-2-(3-methyl-1H-pyrazol-1-yl)pyrimidin-4-amine [0333] as off-white solid (Using DIPEA, ACN 60° C., 16 h). MS(M+1)=328.2.

Example 127

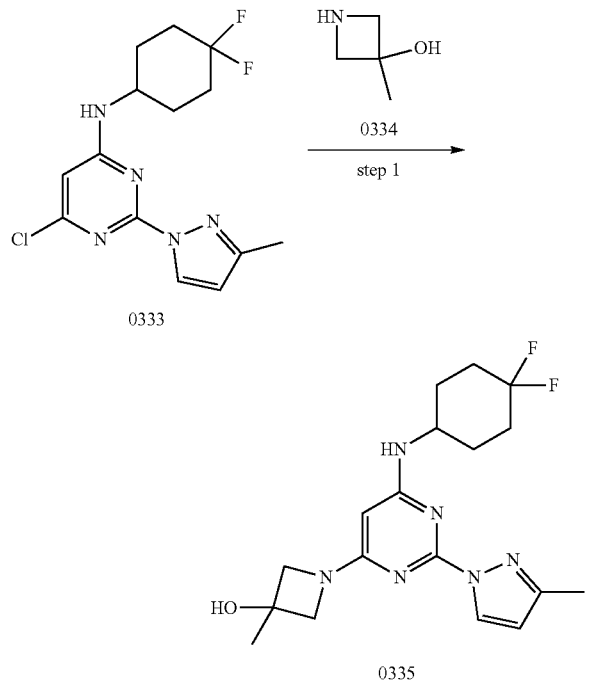

Step 3[0335]: The procedure is similar to step 4 [0244] in example 87. 0.3 g of 6-chloro-N-(4,4-difluorocyclohexyl)-2-(3-methyl-1H-pyrazol-1-yl)pyrimidin-4-amine [0333] gave 0.11 g of 1-(6-((4,4-difluorocyclohexyl)amino)-2-(3-methyl-1H-pyrazol-1-yl)pyrimidin-4-yl)-3-methylazetidin-3-ol [0335], Compound 140 as white solid. MS(M+1)$^+$=379.2, $^1$H NMR (400 MHz, DMSO-d6) δ 8.38 (s, 1H), 7.04 (d, J=7.9 Hz, 1H), 6.25 (d, J=2.5 Hz, 1H), 5.63 (s, 1H), 5.17 (s, 1H), 3.99 (bs, 1H), 3.82 (q, J=8.36 Hz, 4H), 2.24 (s, 3H), 2.12-1.85 (m, 6H), 1.62-1.49 (m, 2H), 1.43 (s, 3H).

Example 128

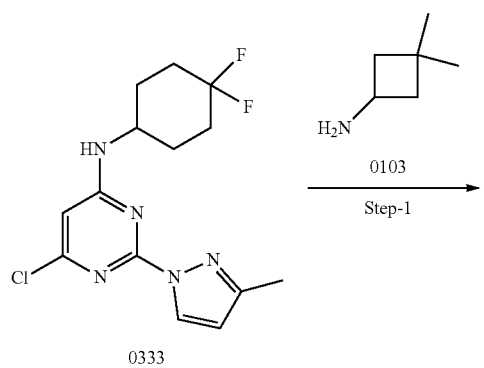

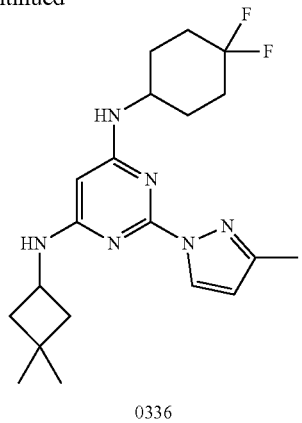

Step 3[0336]: The procedure is similar to step 3[0313] in Example 116 (at 160° C.). 0.2 g of 6-chloro-N-(4,4-difluorocyclohexyl)-2-(3-methyl-1H-pyrazol-1-yl)pyrimidin-4-amine [0333] gave 0.058 g of N4-(4,4-difluorocyclohexyl)-N6-(3,3-dimethylcyclobutyl)-2-(3-methyl-1H-pyrazol-1-yl)pyrimidine-4,6-diamine [0336], Compound 156 as off-white sold. MS(M+1)$^+$=391.4. $^1$H NMR (400 MHz, DMSO-d6) δ 8.36 (d, J=2.7 Hz, 1H), 7.14 (d, J=6.6 Hz, 1H), 6.91 (d, J=7.7 Hz, 1H), 6.24 (d, J=2.4 Hz, 1H), 5.17 (s, 1H), 3.90 (bs, 2H), 2.23 (s, 3H), 2.18-2.12 (m, 2H), 2.12-1.85 (m, 6H), 1.74 (d, J=8.84 Hz, 2H), 1.62-1.48 (m, 2H), 1.24 (s, 3H), 1.08 (s, 3H).

Example 129

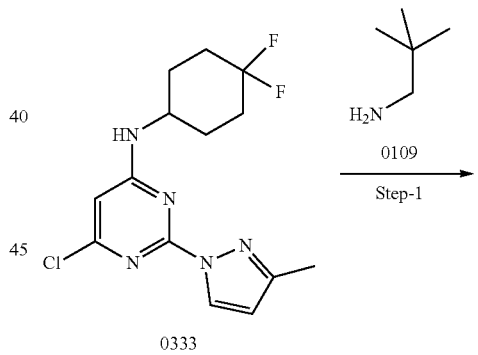

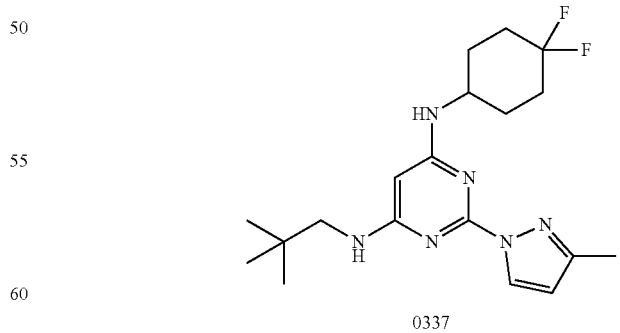

Step 3[0337]: The procedure is similar to step 3[0313] in Example 116 (at 160° C.). 0.2 g of 6-chloro-N-(4,4-difluorocyclohexyl)-2-(3-methyl-1H-pyrazol-1-yl)pyrimidin-4-amine [0333] gave 0.140 g of N4-(4,4-difluorocyclohexyl)-

2-(3-methyl-1H-pyrazol-1-yl)-N6-neopentylpyrimidine-4,6-diamine [0337], Compound 146 as off-white solid. MS(M+1)+=379.2. ¹H NMR (400 MHz, DMSO-d6) δ 8.37 (d, J=2.6 Hz, 1H), 6.90-6.71 (m, 2H), 6.24 (d, J=2.5 Hz, 1H), 5.37 (s, 1H), 3.80 (bs, 1H), 3.06 (bs, 2H), 2.24 (s, 3H), 2.15-1.85 (m, 6H), 1.62-1.48 (m, 2H), 0.92 (s, 9H).

Example 130

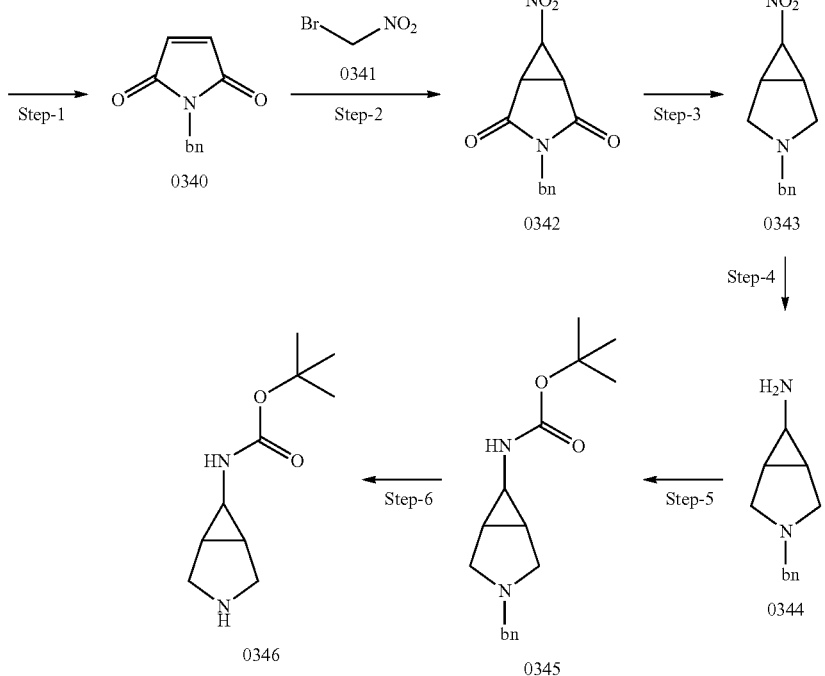

Step 1[0340]: A stirred solution of maleic anhydride [0338] (10 g, 101.981 mmol) and benzyl amine [0339] (11.15 g, 101.981 mmol) in acetic acid (100 mL) was heated at 120° C. for 18 h. The reaction mixture was concentrated under reduced pressure to afford crude product which was purified by column chromatography using 10% ethyl acetate in hexane as eluent to obtain 1-benzyl-1H-pyrrole-2,5-dione [0340] as off-white solid (10 g, 52%).

Step 2[0342]: To a stirred suspension of 1-benzyl-1H-pyrrole-2,5-dione [0340] (13.377 g, 71.461 mmol) and potassium carbonate (9.876 g, 71.461 mmol) in acetonitrile (200 mL) was added a solution of bromonitromethane [0341] (10 g, 71.461 mmol) in acetonitrile (50 mL) under nitrogen atmosphere. Then the reaction mixture was stirred at rt for 18 h. The reaction mixture was filtered and washed with acetonitrile. The combined filtrate was concentrated under reduced pressure to afford crude product which was purified by column chromatography using 15% ethyl acetate in hexane as eluent to obtain 3-benzyl-6-nitro-3-azabicyclo[3.1.0]hexane-2,4-dione [0342] as white solid (6.5 g, 37%).

Step 3[0343]: To a stirred solution of 3-benzyl-6-nitro-3-azabicyclo[3.1.0]hexane-2,4-dione [0342] (8 g, 32.891 mmol) in tetrahydrofuran (100 mL) was added borane dimethyl sulfide complex (13.13 g, 162.455 mmol) at 0° C. under nitrogen. The reaction mixture was allowed slowly to warm to rt and then heated at 65° C. The reaction mixture was cooled to 0° C., quenched with methanol (50 mL) and concentrated under reduced pressure. The residue was diluted with water (100 mL) and extracted with ethyl acetate (3×100 mL). The combined organic layer was washed with brine, dried over anhydrous sodium sulfate, filtered and concentrated under reduced pressure to afford 3-benzyl-6-nitro-3-azabicyclo[3.1.0]hexane [0343] as a colorless gum (5 g, 71%).

Step 4[0344]: To a stirred solution of 3-benzyl-6-nitro-3-azabicyclo[3.1.0]hexane [0343] (0.5 g, 2.291 mmol) in methanol (20 mL) was added Raney-nickel (0.03 g, 0.229 mmol) followed by hydrazine hydrate (1.147 g, 22.909 mmol). Then the mixture was heated at 60° C. for 8 h. The catalyst was filtered and washed with methanol (20 mL). The combined organic layer was concentrated under reduced pressure to afford crude product which was purified by column chromatography using 2% methanol in chloroform as eluent to obtain 3-benzyl-3-azabicyclo[3.1.0]hexan-6-amine [0344] as colorless liquid (0.2 g, 46%). MS(M+1)+=189.1.

Step 5[0345]. 0.5 g of 3-benzyl-3-azabicyclo[3.1.0]hexan-6-amine [0344] gave 0.5 g of tert-Butyl(3-benzyl-3-azabicyclo[3.1.0]hexan-6-yl)carbamate [0345], using triethylamine, boc-anhydride in tetrahydrofuran. MS(M+1)+=289.1.

Step 6[0346]: To a degassed solution of tert-Butyl (3-benzyl-3-azabicyclo[3.1.0]hexan-6-yl) carbamate [0345] (0.2 g, 0.694 mmol) in methanol (10 mL) was added palladium on carbon (0.04 g, 10% W/W) in a tiny clave hydrogen reactor. The mixture was hydrogenated under 50 psi hydrogen gas pressure for 18 h. The reaction mixture was filtered through a bed of celite and washed with methanol (20 mL). The combined filtrate was concentrated under reduced pressure to afford tert-butyl (3-azabicyclo[3.1.0]hexan-6-yl) carbamate [0346] as brownish liquid (0.1 g, 72%). It was taken as such for next step without further purification.

Example 131

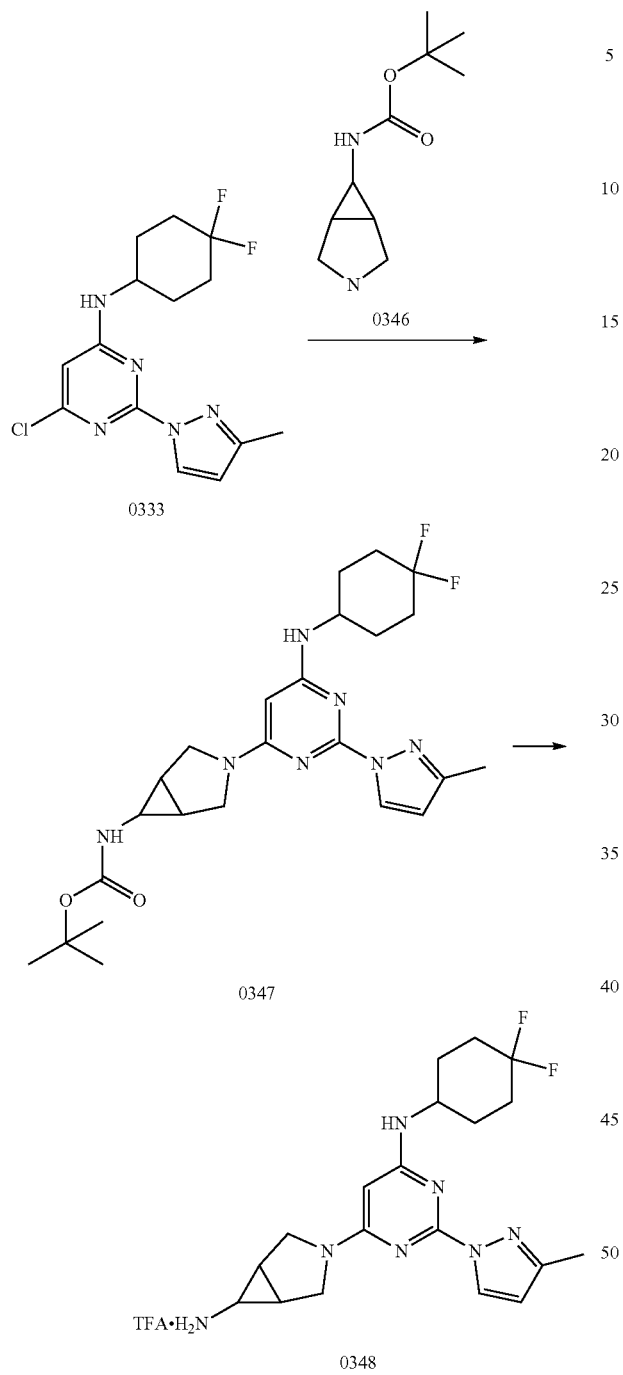

Step 1[0347] The procedure is similar to Step 3[0313] in example 116 (at 180° C.). 0.2 g of 6-chloro-N-(4,4-difluorocyclohexyl)-2-(3-methyl-1H-pyrazol-1-yl)pyrimidin-4-amine [0333] and 0.1 g of tert-butyl (3-azabicyclo[3.1.0] hexan-6-yl) carbamate [0346] gave 0.2 g of tert-Butyl (3-(6-((4,4-difluorocyclohexyl)amino)-2-(3-methyl-1H-pyrazol-1-yl)pyrimidin-4-yl)-3-azabicyclo [3.1.0]hexan-6-yl)carbamate [0347]. MS(M+1)+=490.2.

Step 2[0348]: A stirred solution of tert-Butyl (3-(6-((4,4-difluorocyclohexyl)amino)-2-(3-methyl-1H-pyrazol-1-yl) pyrimidin-4-yl)-3-azabicyclo[3.1.0]hexan-6-yl)carbamate [0347] (0.2 g, 0.409 mmol) in dichloromethane (5 mL) was cooled to 0° C. Trifluoroacetic acid (0.235 g, 2.042 mmol) was added and the mixture was stirred at rt for 18 h. The reaction mixture was concentrated under reduced pressure to afford crude which was purified by column chromatography using 2% methanol in chloroform as eluent to afford 3-(6-((4,4-difluorocyclohexyl)amino)-2-(3-methyl-1H-pyrazol-1-yl)pyrimidin-4-yl)-3-azabicyclo[3.1.0] hexan-6-amine [0348], Compound 155 as white solid (60 mg, 37%). MS(M+1)+=390, $^1$H NMR (400 MHz, Acetone-d6) δ 8.48 (d, J=2.6 Hz, 1H), 6.34 (d, J=2.6 Hz, 1H), 4.03 (bs, 3H), 3.67 (d, J=11.3 Hz, 2H), 3.40 (t, J=2.4 Hz, 1H), 2.66 (s, 2H), 2.31 (s, 3H), 2.12 (s, 3H), 2.12-1.88 (m, 6H), 1.65-1.55 (m, 2H).

Example 133

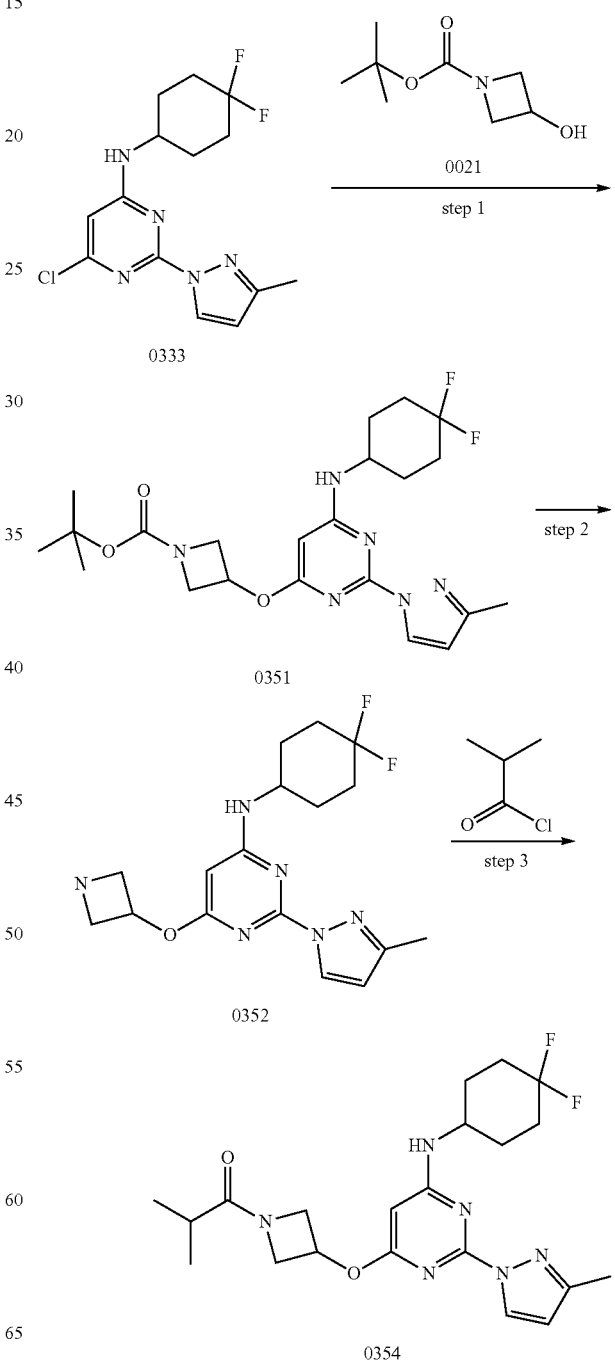

Step 1[0351]: To a stirred solution of 6-chloro-N-(4,4-difluorocyclohexyl)-2-(3-methyl-1H-pyrazol-1-yl)pyrimidin-4-amine [0333] (4.1 g, 12.509 mmol) and tert-butyl 3-hydroxyazetidine-1-carboxylate [0021] (4.3 g, 25.018 mmol) in dioxane (40 mL) was added cesium carbonate (6.11 g, 18.763 mmol). The reaction mixture was heated at 100° C. in a sealed tube for 18 h. The reaction mixture was concentrated under reduced pressure. The residue was dissolved in ethyl acetate (50 mL). The organic layer was washed with water (20 mL), followed by brine (20 mL) and dried over anhydrous sodium sulfate to afford crude product which was purified by column chromatography using 45% ethyl acetate in pet ether as solvent to afford 2.1 g of tert-butyl 3-((6-((4,4-difluorocyclohexyl)amino)-2-(3-methyl-1H-pyrazol-1-yl)pyrimidin-4-yl)oxy)azetidine-1-carboxylate [0351] as a yellow solid.

MS(M+1)+=465.0.

Step 2[0352]: To a cooled solution of tert-butyl 3-((6-((4,4-difluorocyclohexyl)amino)-2-(3-methyl-1H-pyrazol-1-yl)pyrimidin-4-yl)oxy)azetidine-1-carboxylate [0351] (2.1 g, 4.52 mmol) in dioxane (10 mL) was added hydrogen chloride gas in dioxane (10 mL). The reaction mixture was stirred at rt for 1 h. The reaction mixture was concentrated under reduced pressure to afford 2.1 g of 6-(azetidin-3-yloxy)-N-(4,4-difluorocyclohexyl)-2-(3-methyl-1H-pyrazol-1-yl)pyrimidin-4-amine [0352] as a yellow color gum.

Step 3[0354]: To a cooled solution of 6-(azetidin-3-yloxy)-N-(4,4-difluorocyclohexyl)-2-(3-methyl-1H-pyrazol-1-yl)pyrimidin-4-amine [0352] (0.25 g, 0.686 mmol) in dichloromethane (3 mL) was added triethylamine (0.1 mL, 0.754 mmol), followed by iso-butyryl chloride [0353] (73 g, 0.686 mmol). The reaction mixture was stirred at rt for 1 h and diluted with dichloromethane (20 mL). The organic layer was washed with 10% sodium bicarbonate solution (10 mL), followed by water (10 mL) and brine (10 mL). The organic layer was dried over anhydrous sodium sulfate to afford 0.2 g of crude product which was purified by preparative HPLC to afford 0.06 g of 1-(3-((6-((4,4-difluorocyclohexyl)amino)-2-(3-methyl-1H-pyrazol-1-yl)pyrimidin-4-yl)oxy)azetidin-1-yl)-2-methylpropan-1-one [0354], Compound 210 as a white solid. MS(M+1)+=435.5, $^1$H NMR (400 MHz, DMSO-d6) δ 8.44 (d, J=2.4 Hz, 1H), 7.34 (d, J=7.6 Hz, 1H), 6.30 (d, J=2.5 Hz, 1H), 5.74 (s, 1H), 5.40-5.35 (m, 1H), 4.58-3.57 (m, 5H), 2.27 (s, 3H), 2.05-1.85 (m, 7H), 1.60-1.50 (m, 2H), 1.01 (d, J=6.9 Hz, 6H).

Example 134

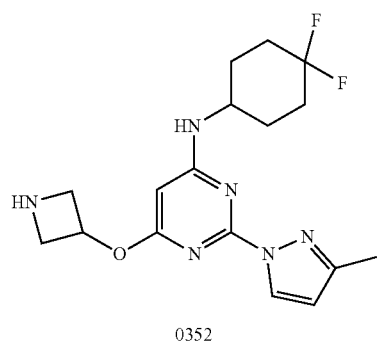 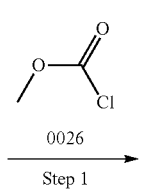

0352    0026    Step 1

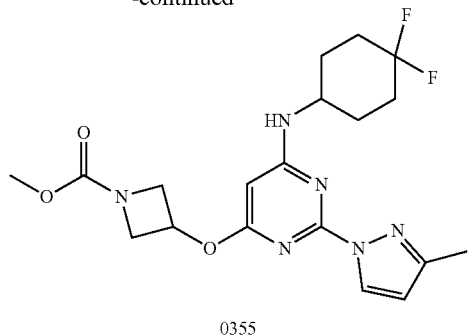

0355

Step 1[77]: The procedure is similar to step 3[0354] in example 133. 0.8 g of 6-(azetidin-3-yloxy)-N-(4,4-difluorocyclohexyl)-2-(3-methyl-1H-pyrazol-1-yl)pyrimidin-4-amine [0352] and 0.2 g of methyl chloroformate [0026] gave 0.32 g of 3-((6-((4,4-difluorocyclohexyl)amino)-2-(3-methyl-1H-pyrazol-1-yl)pyrimidin-4-yl)oxy)azetidine-1-carboxylate [0355], Compound 205 as a white solid. MS(M+1)+=423.4. 1H NMR (400 MHz, DMSO-d6): δ 8.38 (d, J=2.40 Hz, 1H), 7.31 (d, J=7.60 Hz, 1H), 6.29 (d, J=2.80 Hz, 1H), 5.72 (s, 1H), 5.41-5.38 (m, 1H), 4.37-4.33 (m, 2H), 3.94-3.91 (m, 3H), 3.60 (s, 3H), 2.33 (s, 3H), 2.32-2.09 (m, 6H), 2.05-2.04 (m, 2H).

Example 135

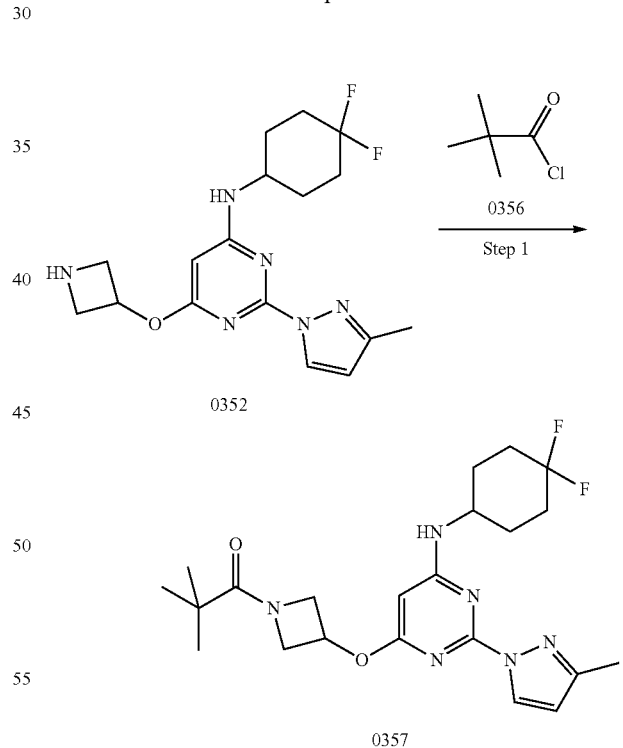

0352

0356
Step 1

0357

Step 1[0357]: The procedure is similar to step 3[0354] in example 133. 0.8 g of 6-(azetidin-3-yloxy)-N-(4,4-difluorocyclohexyl)-2-(3-methyl-1H-pyrazol-1-yl)pyrimidin-4-amine [0352] and 0.26 g of pivaloyl chloride [0356] gave 0.4 g of 1-(3-((6-((4,4-difluorocyclohexyl)amino)-2-(3-methyl-1H-pyrazol-1-yl)oxy)azetidin-1-yl)-2,2-dimethylpropan-1-one [0357], Compound 211 as a white solid. MS(M+1)+=449.4. $^1$H NMR (400 MHz, DMSO-d6) δ

8.40 (d, J=2.6 Hz, 1H), 7.31 (d, J=7.7 Hz, 1H), 6.29 (d, J=2.6 Hz, 1H), 5.73 (s, 1H), 5.39 (tt, J=6.6, 4.1 Hz, 1H), 4.52 (s, 2H), 4.07 (d, J=7.9 Hz, 2H), 3.93 (s, 1H), 2.27 (s, 3H), 2.09-1.89 (m, 6H), 1.62 (d, J=11.4 Hz, 2H), 1.14 (s, 9H).

Example 136

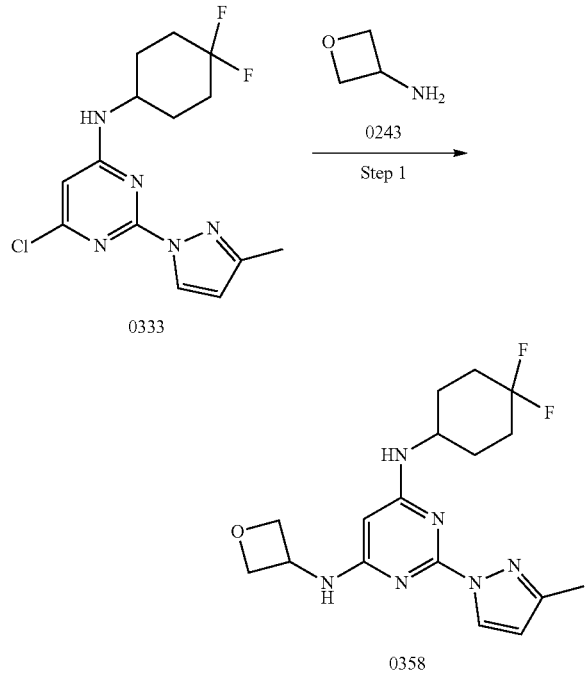

Step 1[45]: The procedure is similar to step 4 [0244] in example 87. 0.4 g of 6-chloro-N-(4,4-difluorocyclohexyl)-2-(3-methyl-1H-pyrazol-1-yl)pyrimidin-4-amine [0333] and 0.178 g of 3-Oxetanamine [0243] gave 0.07 g of N4-(4,4-difluorocyclohexyl)-2-(3-methyl-1H-pyrazol-1-yl)-N6-(oxetan-3-yl)pyrimidine-4,6-diamine [0358], Compound 141 as yellow solid. MS(M+1)⁺=364.8. ¹H NMR (400 MHz, DMSO-d6) δ 8.37 (s, 1H), 7.66 (d, J=5.8 Hz, 1H), 7.01 (d, J=7.8 Hz, 1H), 6.25 (d, J=2.5 Hz, 1H), 5.22 (bs, 1H), 4.79 (t, J=6.5 Hz, 3H), 4.48 (t, J=5.64 Hz, 2H), 3.87 (bs, 1H), 2.24 (s, 3H), 2.15-1.85 (m, 6H), 1.54-1.45 (m, 2H).

Example 137

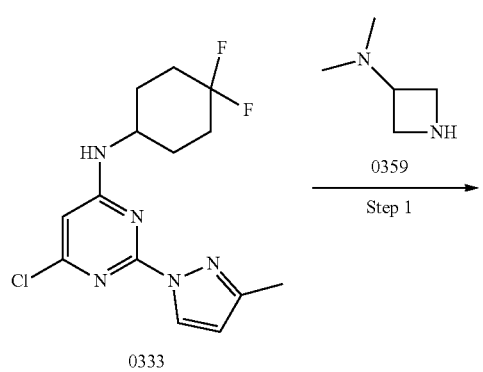

-continued

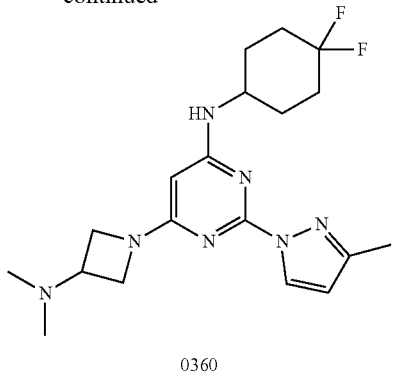

Step 1[0360]: The procedure is similar to step 4 [0244] in example 87. 0.2 g of 6-chloro-N-(4,4-difluorocyclohexyl)-2-(3-methyl-1H-pyrazol-1-yl)pyrimidin-4-amine [0333] and 0.22 g of N,N-dimethylazetidin-3-amine dihydrochloride [0359] gave 0.08 g of N-(4,4-difluorocyclohexyl)-6-(3-(dimethylamino)azetidin-1-yl)-2-(3-methyl-1H-pyrazol-1-yl)pyrimidin-4-amine [0360], Compound 143 as a yellow solid. MS(M+1)⁺=392.1, ¹H NMR (400 MHz, DMSO-d6) δ 8.38 (s, 1H), 7.05 (d, J=8.0 Hz, 1H), 6.25 (d, J=2.6 Hz, 1H), 5.17 (s, 1H), 3.99 (t, J=7.8 Hz, 2H), 3.74 (dd, J=8.7, 5.2 Hz, 2H), 3.20-3.12 (m, 1H), 2.24 (s, 3H), 2.12 (s, 6H), 2.05-1.88 (m, 6H), 1.78 (bs, 1H) 1.60-1.48 (m, 2H).

Example 138

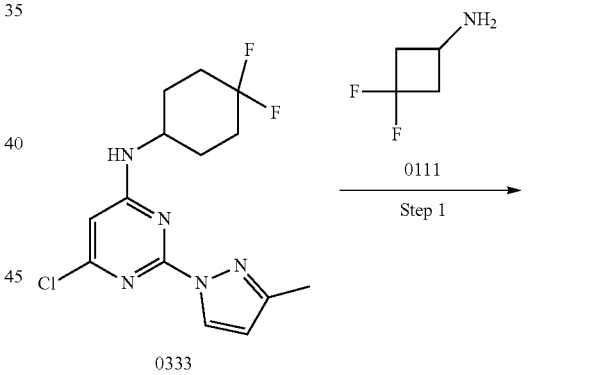

Step 1[0361]: To a solution of 6-chloro-N-(4,4-difluorocyclohexyl)-2-(3-methyl-1H-pyrazol-1-yl)pyrimidin-4- amine [0333] (0.3 g, 0.915 mmol) in acetonitrile (6 mL) was added 3,3-difluorocyclobutanamine hydrochloride [0111] (0.26 g, 1.83 mmol) and N,N-diisopropyl ethylamine (0.236 g, 1.83 mmol). The reaction mixture was heated at 180° C. under microwave for 5 h. The reaction mixture was concentrated under reduced pressure to afford crude product which was purified by column chromatography using 40% ethyl acetate in pet ether to afford 0.130 g of N4-(3,3-difluorocyclobutyl)-N6-(4,4-difluorocyclohexyl)-2-(3-methyl-1H-pyrazol-1-yl)pyrimidine-4,6-diamine [0361], Compound 147 as a white solid. MS(M+1)$^+$=399.2. $^1$H NMR (400 MHz, DMSO-d6) δ 8.37 (s, 1H), 7.42 (d, J=6.1 Hz, 1H), 6.99 (d, J=7.9 Hz, 1H), 6.24 (d, J=2.5 Hz, 1H), 5.24 (s, 1H), 4.08 (bs, 1H), 3.89 (bs, 1H), 3.10-2.90 (m, 2H), 2.64-2.53 (m, 2H), 2.23 (s, 3H), 2.15-1.84 (m, 6H), 1.60-1.49 (m, 2H).

Example 139

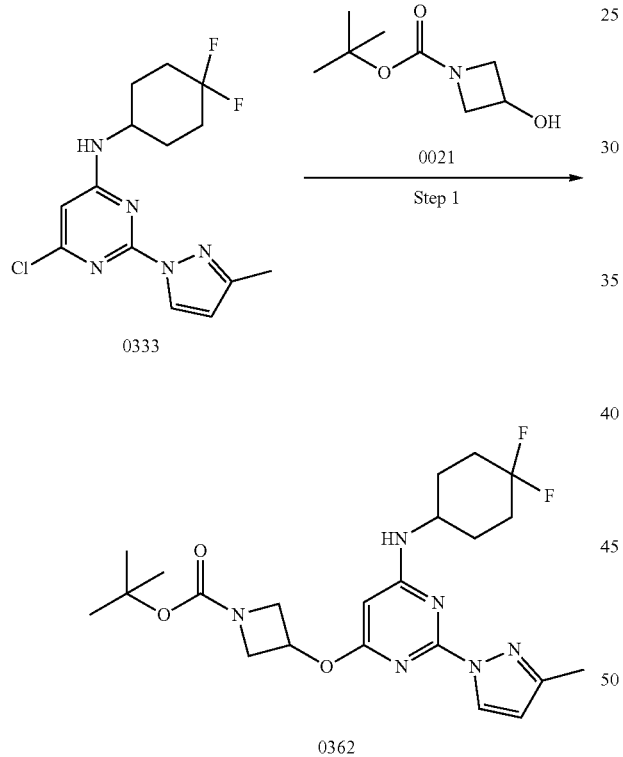

Step 2[0362]: 0.3 g of 6-chloro-N-(4,4-difluorocyclohexyl)-2-(3-methyl-1H-pyrazol-1-yl)pyrimidin-4-amine [0333] and 0.3 g of tert-butyl 3-hydroxyazetidine-1-carboxylate [0021] gave 0.05 g of tert-butyl 3-((6-((4,4-difluorocyclohexyl)amino)-2-(3-methyl-1H-pyrazol-1-yl)pyrimidin-4-yl)oxy)azetidine-1-carboxylate [0362], Compound 151 as a yellow solid. (Using CS2CO3, Dioxane, 100° C., 18 h) MS(M+1)$^+$=465.0, $^1$H NMR (400 MHz, DMSO-d6) δ 8.44 (s, 1H), 7.63 (bs, 1H), 6.32 (d, J=2.5 Hz, 1H), 5.70 (s, 1H), 5.33 (s, 1H), 4.28 (bs, 2H), 3.83 (d, J=7.6 Hz, 2H), 2.26 (s, 3H), 2.15-1.85 (m, 7H), 1.60-1.49 (m, 2H), 1.39 (s, 9H).

Example 140

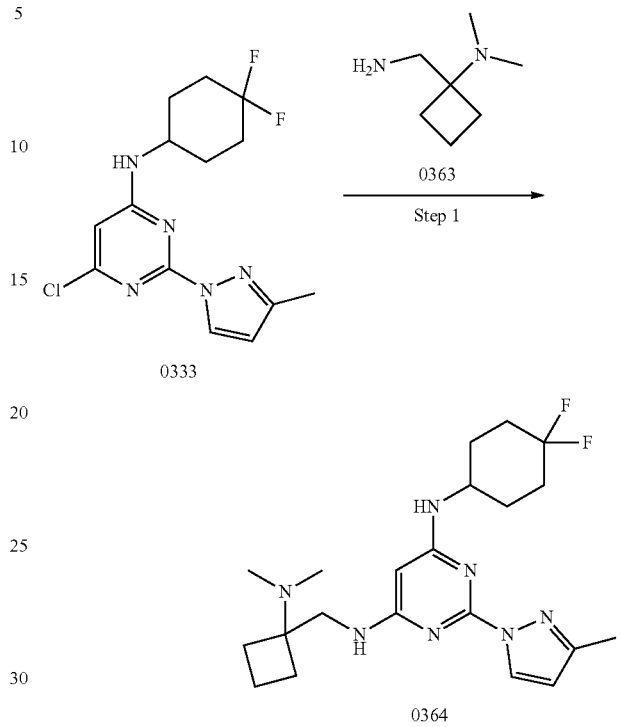

Step 1[0364]: The procedure is similar to step 1[0361] in example 138. 0.2 g of 6-chloro-N-(4,4-difluorocyclohexyl)-2-(3-methyl-1H-pyrazol-1-yl)pyrimidin-4-amine [0333] and 0.156 g of 1-(aminomethyl)-N,N-dimethylcyclobutane-1-amine[0363] gave 0.08 g of N4-(4,4-difluorocyclohexyl)-N6-((1-(dimethylamino)cyclobutyl)methyl)-2-(3-methyl-1H-pyrazol-1-yl)pyrimidine-4,6-diamine [0364], Compound 157 as a white solid.

MS(M+1)$^+$=420.1, $^1$H-NMR (400 MHz, DMSO-d6): δ 8.39 (s, 1H), 6.93 (bs, 1H), 6.27 (s, 1H), 5.41 (s, 1H), 3.81-3.4 (m, 3H), 2.33-2.16 (m, 8H), 2.15-1.98 (m, 5H), 1.97-1.85 (m, 4H), 1.84-1.60 (m, 5H), 1.60-1.49 (m, 2H).

Example 141

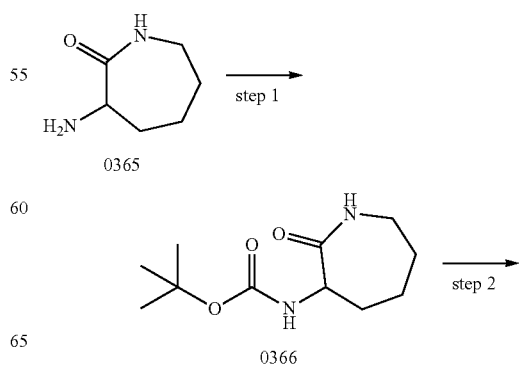

-continued

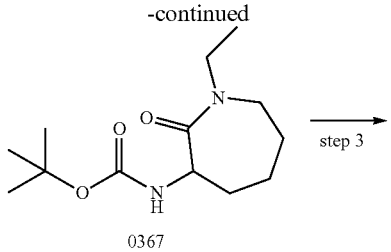

0367

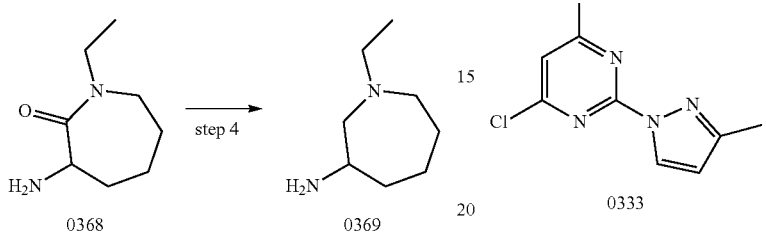

0368　　0369

Step 1[0366]: To a solution of dl-α-amino-ε-caprolactam [0365] (3 g, 23.405 mmol) in dichloromethane (30 mL) was added triethylamine (2.36 g, 23.405 mmol) and followed by slow addition of boc-anhydride (5.1 g, 23.405 mmol) at 0° C. under N2 atm. The resultant reaction mixture was stirred at rt for 16 h. The reaction mixture was concentrated under reduced pressure to afford 4.2 g of tert-butyl (2-oxoazepan-3-yl)carbamate [0366] as a white solid. MS(M+1)+=229.

Step 2[0367]: To a solution of tert-butyl (2-oxoazepan-3-yl)carbamate [0366] in N,N-dimethylformamide (8 mL) was added sodium hydride (0.197 g, 4.81 mmol), the resultant reaction mixture was stirred at rt for 30 min. Then was added iodoethane and stirred at rt for 3 h. The reaction mixture was quenched with ice-cold water (20 mL). The white solid formed was filtered, washed with water and dried under vacuum to afford 0.7 g of tert-butyl (1-ethyl-2-oxoazepan-3-yl)carbamate [0367] as a white solid. MS(M+1)+=257.

Step 3 [0368]: To a cooled solution of tert-butyl (1-ethyl-2-oxoazepan-3-yl)carbamate [0367] (0.7 g, 2.73 mmol) in dioxane (10 mL) was added HCl in dioxane (20 mL) at 0° C. The resultant reaction mixture was slowly warmed to rt and stirred for 8 h. The reaction mixture was concentrated under reduced pressure to afford crude product which was triturated with diethyl ether to afford 0.51 g of 3-amino-1-ethylazepan-2-one [0368] as a yellow solid. MS(M+1)+=157.

Step 4[0369]: To a suspension of 3-amino-1-ethylazepan-2-one [0368] in tetrahydrofuran (10 mL) was added borane dimethyl sulfide complex (1.44 g, 17.922 mmol) drop wise under N2 atm. The resultant reaction mixture was heated at 70° C. for 16 h. The reaction mixture was basified with 10% sodium bicarbonate solution (10 mL) to adjust the pH (8-9). Then the aqueous layer was extracted with ethyl acetate (2×50 mL). The combined extract was washed with brine (20 mL), dried over anhydrous sodium sulfate, filtered and concentrated under reduced pressure to afford 1-ethylazepan-3-amine [0369] as a yellow liquid (0.54 g). MS(M+1)+=143.

Example 142

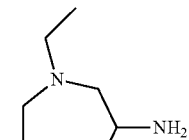

0333　　0369

0370

Step 1[0370]: The procedure is similar to step 1[0361] in example 138. 0.2 g of 6-chloro-N-(4,4-difluorocyclohexyl)-2-(3-methyl-1H-pyrazol-1-yl)pyrimidin-4-amine [0333] and 0.17 g of 1-ethylazepan-3-amine [0369] gave 0.02 g of N4-(4,4-difluorocyclohexyl)-N6-(1-ethylazepan-3-yl)-2-(3-methyl-1H-pyrazol-1-yl)pyrimidine-4,6-diamine [0370], Compound 158 as a yellow solid. MS(M+1)+=434.4. $^1$H NMR (400 MHz, DMSO-d6) δ 8.38 (s, 1H), 6.91 (bs, 1H), 6.54 (bs, 1H), 6.27 (bs, 1H), 5.34 (bs, 1H), 3.87 (bs, 2H), 2.25 (s, 3H), 2.05 (bs, 4H), 1.91 (s, 7H), 1.73-1.49 (m, 9H), 1.10-0.98 (bs, 3H).

Example 143

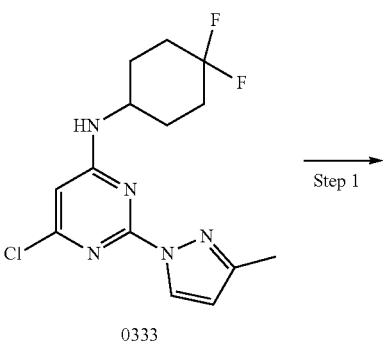

0333

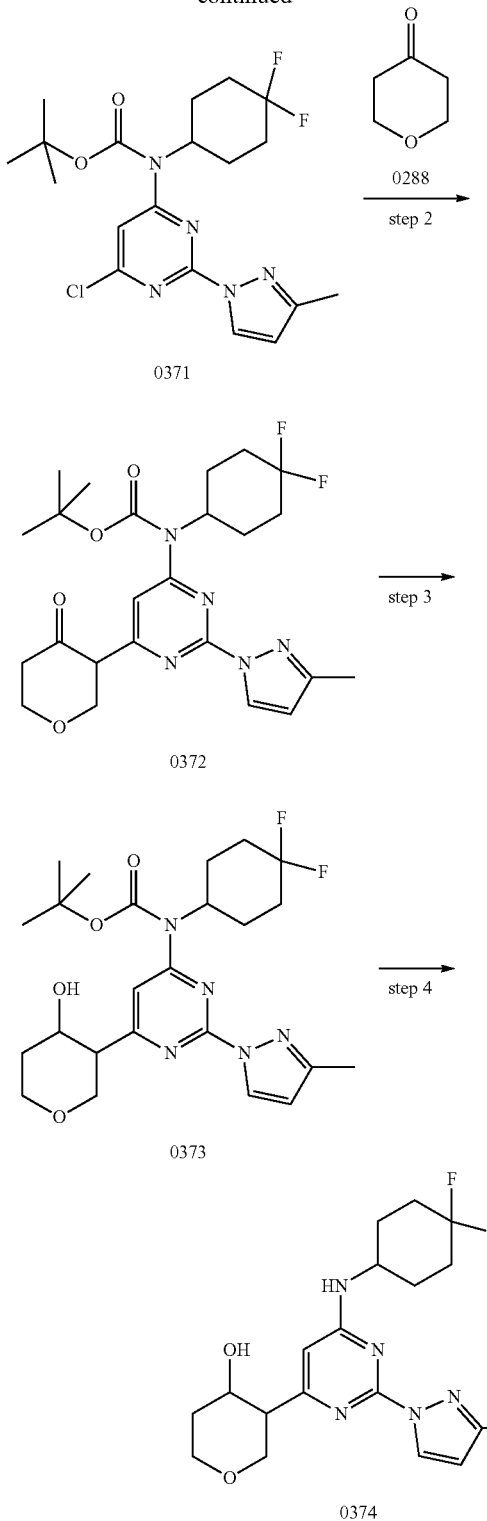

Step 1[0371]: To a solution of 6-chloro-N-(4,4-difluorocyclohexyl)-2-(3-methyl-1H-pyrazol-1-yl)pyrimidin-4-amine [0333] (0.5 g, 1.52 mmol) in tetrahydrofuran (50 mL) was added boc-anhydride (998 g, 4.57 mmol) followed by 4-N,N-dimethylamino pyridine (35 g, 0.289 mmol). The reaction mixture was heated at 85° C. for 1 h. The reaction mixture was concentrated under reduced pressure to afford 0.8 g crude product which was purified by column chromatography using 15% ethyl acetate in pet ether as solvent to afford 0.6 g of tert-butyl (6-chloro-2-(3-methyl-1H-pyrazol-1-yl)pyrimidin-4-yl)(4,4-difluorocyclohexyl)carbamate [0371] as a white solid. MS(M+1)+=428.3

Step 2[0372]: To a solution of tetrahydro-4h-pyran-4-One [0288] (0.46 g, 4.67 mmol) in tetrahydrofuran (10 mL) was added lithium bis(trimethylsilyl)amide (1 M solution in tetrahydrofuran) (4.6 mL, 4.67 mmol) at 0° C. After 30 min, tert-butyl (6-chloro-2-(3-methyl-1H-pyrazol-1-yl)pyrimidin-4-yl)(4,4-difluorocyclohexyl)carbamate [0371] (0.5 g, 1.168 mmol) was added to the reaction mixture at 0° C., drop wise in tetrahydrofuran (5 mL). After addition the reaction was stirred at rt for 18 h, quenched with water (5 mL) and extracted with ethyl acetate (2×50 mL). The combined organic layer was washed with water (25 mL), brine (25 mL), dried over anhydrous sodium sulfate and concentrated to afford crude product which was purified by preparative HPLC to afford 0.1 g of tert-butyl (4,4-difluorocyclohexyl)(2-(3-methyl-1H-pyrazol-1-yl)-6-(4-oxotetrahydro-2H-pyran-3-yl)pyrimidin-4-yl)carbamate [0372] as a yellow solid. MS(M+1)+=492.2.

Step 3[0373]: To a solution of tert-butyl (4,4-difluorocyclohexyl)(2-(3-methyl-1H-pyrazol-1-yl)-6-(4-oxotetrahydro-2H-pyran-3-yl)pyrimidin-4-yl)carbamate [0372] (0.5 g, 0.101 mmol) in methanol (1 mL) was added sodium borohydride (0.038 g, 0.101 mmol). The reaction mixture was stirred at rt for 10 min, concentrated under reduced pressure, added with 10% sodium bicarbonate (5 mL) and extracted with ethyl acetate (2×10 mL). The combined organic layer was washed with water (10 mL), followed by brine (10 mL) and dried over anhydrous sodium sulfate to afford crude product which was purified by preparative HPLC to afford 0.02 g of tert-butyl (4,4-difluorocyclohexyl)(6-(4-hydroxytetrahydro-2H-pyran-3-yl)-2-(3-methyl-1H-pyrazol-1-yl)pyrimidin-4-yl)carbamate [0373] as a white solid. MS(M+1)+=494.2

Step 4[0374]: To a cooled solution of tert-butyl (4,4-difluorocyclohexyl)(6-(4-hydroxytetrahydro-2H-pyran-3-yl)-2-(3-methyl-1H-pyrazol-1-yl)pyrimidin-4-yl)carbamate [0373] (0.05 g, 0.101 mmol) in dioxane (2 mL) was added hydrogen chloride gas in dioxane (2 mL). The reaction mixture was stirred at rt for 2 h. The reaction mixture was concentrated under reduced pressure. The residue was dissolved in water (1 mL) and neutralized with 10% sodium bicarbonate (5 mL) solution. The aqueous layer was extracted with ethyl acetate (2=x=20 mL). The combined organic layer was washed with water (5 mL), followed by brine (5 mL) and dried over anhydrous sodium sulfate to afford 0.035 g of 3-(6-((4,4-difluorocyclohexyl)amino)-2-(3-methyl-1H-pyrazol-1-yl)pyrimidin-4-yl)tetrahydro-2H-pyran-4-ol [0374], Compound 232 as a white solid. MS(M+1)+=394.5, 395.5. $^1$H NMR (400 MHz, DMSO-d6) δ 8.47 (s, 1H), 7.68 (d, J=7.6 Hz, 1H), 6.31 (d, J=2.5 Hz, 1H), 6.21 (bs, 1H), 5.29 (bs, 1H), 4.26 (bs, 1H), 4.15 (bs, 1H), 3.88-3.85 (m, 1H), 3.78-3.71 (m, 2H), 3.64-3.61 (m, 1H), 2.90-2.75 (m, 1H), 2.26 (s, 3H), 2.06-1.85 (s, 6H), 1.85-1.73 (m, 1H), 1.65-1.49 (m, 3H).

Example 144

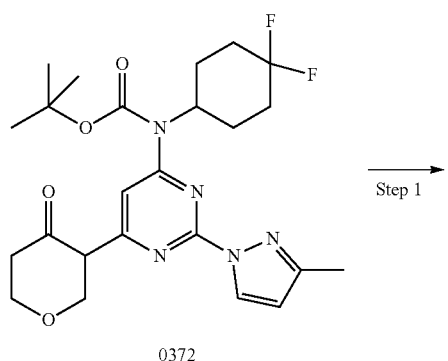

0372

0375

0376

Step 1[0375]: To an ice-cold solution of tert-butyl (4,4-difluorocyclohexyl)(2-(3-methyl-1H-pyrazol-1-yl)-6-(4-oxotetrahydro-2H-pyran-3-yl)pyrimidin-4-yl)carbamate [0372] (0.08 g, 0.162 mmol) in dichloromethane (1 mL) was added diethylaminosulfur trifluoride (0.043 mL, 0.325 mmol) drop wise. The reaction mixture was slowly warmed to rt, stirred for 1 h, quenched with 10% sodium bicarbonate solution (10 mL) and extracted with ethyl acetate (2×20 mL). The combined organic layer was washed with brine (5 mL), dried over anhydrous sodium sulfate and concentrated under reduced pressure to afford 0.05 g of tert-butyl (4,4-difluorocyclohexyl)(6-(4,4-difluorotetrahydro-2H-pyran-3-yl)-2-(3-methyl-1H-pyrazol-1-yl)pyrimidin-4-yl)carbamate [0375] as a yellow solid. MS(M+1)+=514.5

Step 2[0376]: To a cooled solution of tert-butyl (4,4-difluorocyclohexyl)(6-(4,4-difluorotetrahydro-2H-pyran-3-yl)-2-(3-methyl-1H-pyrazol-1-yl)pyrimidin-4-yl)carbamate [0375] (0.04 g, 0.077 mmol) in dioxane (2 mL) was added hydrogen chloride gas in dioxane (2 mL). The reaction mixture was stirred at rt for 2 h and concentrated under reduced pressure. The residue was dissolved in water (1 mL) and neutralized with 10% sodium bicarbonate solution (10 mL). The aqueous layer was extracted with ethyl acetate (2×20 mL). The combined organic layer was washed with water (10 mL), followed by brine (10 mL) and dried over anhydrous sodium sulfate to afford 0.03 g of N-(4,4-difluorocyclohexyl)-6-(4,4-difluorotetrahydro-2H-pyran-3-yl)-2-(3-methyl-1H-pyrazol-1-yl)pyrimidin-4-amine [0376] as a white solid. Compound 242 MS(M+1)+=414.5, 415. 1H NMR (400 MHz, DMSO-d6) δ 8.46 (s, 1H), 7.76 (s, 1H), 6.41 (s, 1H), 6.36-6.26 (m, 1H), 4.17 (s, 2H), 3.99 (s, 2H), 3.64 (s, 1H), 2.55 (s, 1H), 2.26 (s, 2H), 2.18 (s, 1H), 2.05 (s, 2H), 1.96 (s, 2H), 1.56 (s, 2H).

Example 145

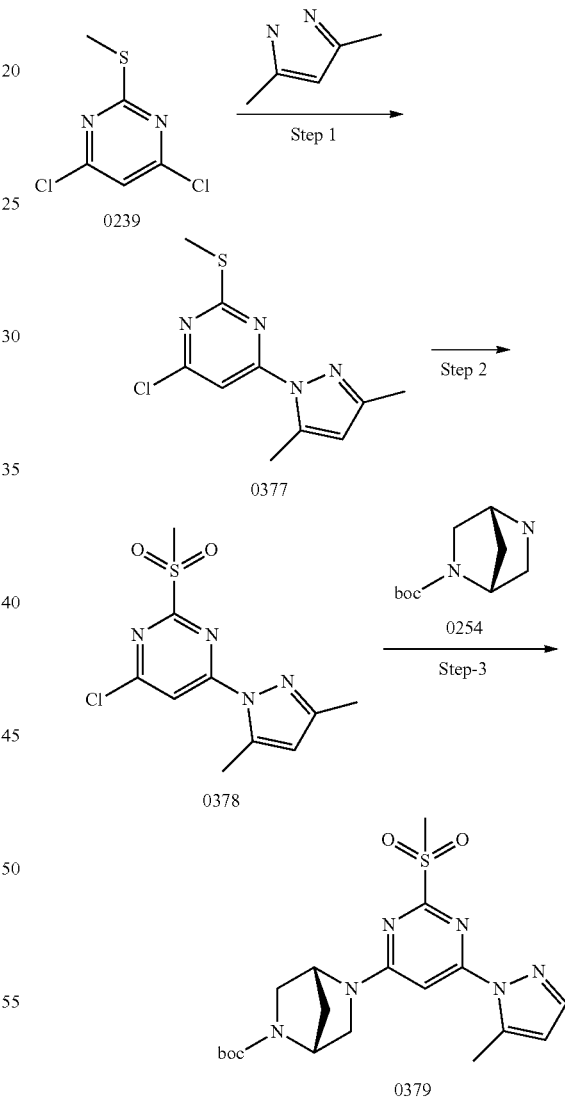

0239

0377

0378

0379

Step 1[0377]: To a suspension of 4,6-dichloro-2-(methylthio)pyrimidine [0029] (10 g, 51.26 mmol) in N,N-dimethylformamide (50 mL) was added 3,5-dimethyl pyrazole [0017] (4.9 g, 51.26 mmol), followed by cesium carbonate (25.05 g, 76.89 mmol) and the reaction mixture was heated at 80° C. After 16 h, the reaction mixture was filtered and washed with chloroform. The filtrate was concentrated under reduced pressure and the residue was triturated with water. The solid formed was filtered, washed with water and dried under vacuum to afford 10 g of 4-chloro-6-(3,5-dimethyl-1H-pyrazol-1-yl)-2-(methylthio)pyrimidine [0377] as an off-white solid. MS(M+1)+=255.2.

Step 2[0378]: To a solution of 4-chloro-6-(3,5-dimethyl-1H-pyrazol-1-yl)-2-(methylthio)pyrimidine [0377] (10 g, 39.255 mmol) in dichloromethane (250 mL) was added 3-chloroperbenzoic acid (20.3 g, 117.36 mmol) in portionwise at 0° C. The reaction mixture was slowly warmed to rt. After 6 h, the reaction mixture was diluted with dichloromethane, washed with saturated sodium thiosulfate solution and followed by 10% sodium bicarbonate solution. The organic layer was dried over anhydrous sodium sulfate, filtered and concentrated under reduced pressure to afford 9 g of 4-chloro-6-(3,5-dimethyl-1H-pyrazol-1-yl)-2-(methylsulfonyl)pyrimidine [0378] as an off-white solid. MS(M+1)+=287.0.

Step 3[0379]: To the solution of 4-chloro-6-(3,5-dimethyl-1H-pyrazol-1-yl)-2-(methylsulfonyl)pyrimidine [0378] (2 g, 6.97 mmol) and N-Boc-2,5-Diaza-Bicyclo[2.2.1]Heptane [0254] (1.38 g, 6.97 mmol) in N,N-dimethylformamide was added cesium carbonate (3.4 g, 10.46 mmol) in closed vial and the reaction mixture was heated at 60° C. After 1 h, the reaction mixture was added water and stirred for 10 min. The solid formed was filtered off and the filtrate was washed with water followed by brine. The organic layer was dried over anhydrous sodium sulfate, filtered and concentrated under reduced pressure to afford a white solid, which was purified in the Reveleris flash system instrument using ethyl acetate in hexane as solvent to afford 1.8 g of t-butyl (1R,4R)-5-(6-(3,5-dimethyl-1H-pyrazol-1-yl)-2-(methylsulfonyl)pyrimidin-4-yl)-2,5-diazabicyclo[2.2.1]heptane-2-carboxylate [0379] as white solid. MS(M+1)+=449.3.

Example 146

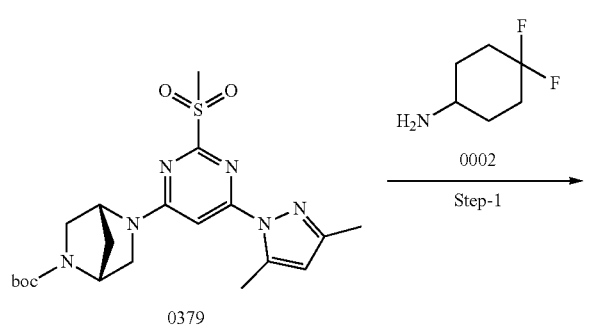

0379

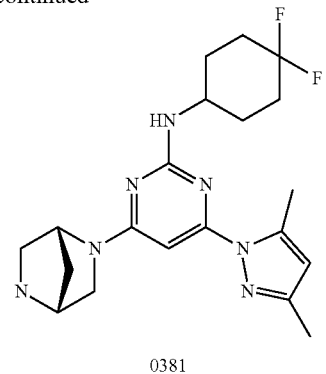

0381

Step 1[0380]: To the solution of t-butyl (1R,4R)-5-(6-(3,5-dimethyl-1H-pyrazol-1-yl)-2-(methylsulfonyl)pyrimidin-4-yl)-2,5-diazabicyclo[2.2.1]heptane-2-carboxylate [0379] (0.4 g, 0.891 mmol) and 4,4-difluorocyclohexylamine hydrochloride [0002] (0.153 g, 0.891 mmol) in dimethylsulfoxide was added cesium carbonate (0.581 g, 1.783 mmol) in closed vial and the reaction mixture was heated at 100° C. After 1 h, the reaction mixture was quenched with water and stirred for 10 min. The solid formed was filtered, washed with water and hexane to afford a white solid which was purified in the Reveleris flash system using ethyl acetate in hexane as eluent to afford 0.08 g of tert-butyl (1R,4R)-5-(2-((4,4-difluorocyclohexyl)amino)-6-(3,5-dimethyl-1H-pyrazol-1-yl)pyrimidin-4-yl)-2,5-diazabicyclo[2.2.1]heptane-2-carboxylate [0380] as white solid. MS(M+1)+= 504.5.

Step 2[0381]: To a cooled solution of hydrogen chloride gas in in dioxane (1.87 g, 51.39 mmol) was added tert-butyl (+)-5-(2-((4,4-difluorocyclohexyl)amino)-6-(3,5-dimethyl-1H-pyrazol-1-yl)pyrimidin-4-yl)-2,5-diazabicyclo[2.2.1]heptane-2-carboxylate [0380], (0.07 g, 0.139 mmol) and the reaction mixture was slowly warmed to rt. After 30 min, the reaction mixture was concentrated under reduced pressure to afford a yellow gum which was triturated with diethyl ether and decanted. The residue was dried under vacuum to afford 0.05 g of 4-((1R,4R)-2,5-diazabicyclo[2.2.1]heptan-2-yl)-N-(4,4-difluorocyclohexyl)-6-(3,5-dimethyl-1H-pyrazol-1-yl)pyrimidin-2-amine [0381], Compound 104 as a yellow solid. MS(M+1)+=404.4. $^1$H NMR (400 MHz, DMSO-d6) δ 9.57 (bs, 1H), 9.06 (bs, 1H), 6.12 (s, 1H), 4.95 (bs, 1H), 4.49 (s, 1H), 3.87 (m, 1H), 3.32 (m, 4H), 3.24 (m, 2H), 2.61 (s, 3H), 2.19 (s, 3H), 2.08 (m, 3H), 1.93 (m, 4H), 1.59 (m, 2H).

Example 147

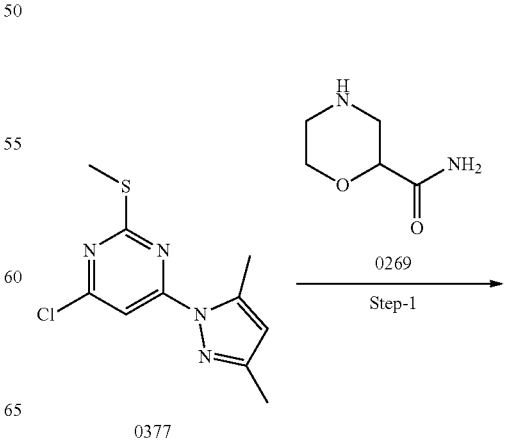

0377

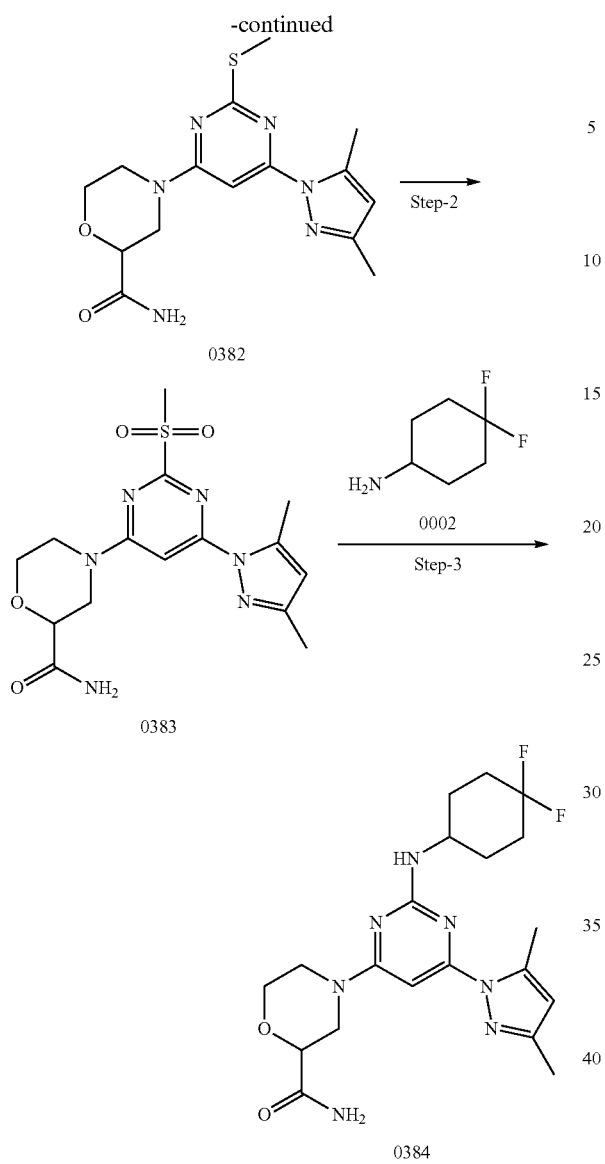

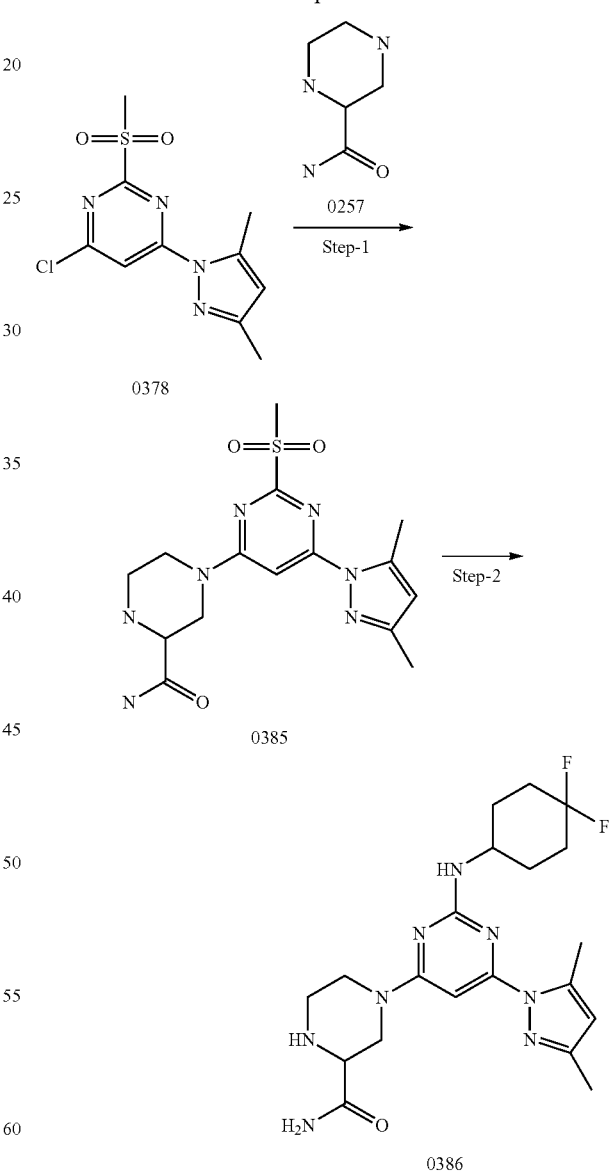

Step 1[0382]: To a solution of 4-chloro-6-(3,5-dimethyl-1H-pyrazol-1-yl)-2-(methylthio)pyrimidine [0377] (1 g, 3.92 mmol) and morpholine-2-carboxamide [0269] (0.76 g, 5.88 mmol) in DMSO (8 mL) was added cesium carbonate (2.55 g, 7.85 mmol) then the reaction mixture was heated at 80° C. in a closed vial for 16 h. After the completion of the reaction, the reaction mixture was quenched with ice-cold water and extracted with ethyl acetate (2×70 mL). The combined organic layer was dried over anhydrous sodium sulfate and concentrated to afford as an brownish gum and which was purified by column of silica gel (60-120 mesh) using 85% ethyl acetate in hexane as eluent to afford 0.6 g of 4-(6-(3,5-dimethyl-1H-pyrazol-1-yl)-2-(methylthio)pyrimidin-4-yl)morpholine-2-carboxamide [0382] as an off-white solid. MS(M+1)+=349.

Step 2[0383]: The procedure is similar to Step 2[0378] in example 145. 0.6 g of 4-(6-(3,5-dimethyl-1H-pyrazol-1-yl)-2-(methylthio)pyrimidin-4-yl)morpholine-2-carboxamide [0382] gave 0.4 g of 4-(6-(3,5-dimethyl-1H-pyrazol-1-yl)-2-(methylsulfonyl)pyrimidin-4-yl)morpholine-2-carboxamide [0383] as an white solid, MS(M+1)+=381.

Step 3[0384]: To a solution of 4-(6-(3,5-dimethyl-1H-pyrazol-1-yl)-2-(methylsulfonyl)pyrimidin-4-yl)morpholine-2-carboxamide [0383] (0.2 g, 0.525 mmol) and 4,4-difluoro cyclohexylamine hydrochloride [0002] (0.18 g, 1.05 mmol) in ethanol (8 mL) was added N,N-diisopropyl ethylamine (0.27 g, 2.10 mmol). The reaction mixture was heated at 90° C. in a closed vial (20 mL) for 5 days. The reaction mixture was concentrated to afford as an brownish gum, which was purified by column using 2% methanol in chloroform as eluent to afford 35 g of 4-(2-((4,4-difluoro-cyclohexyl)amino)-6-(3,5-dimethyl-1H-pyrazol-1-yl)pyrimidin-4-yl)morpholine-2-carboxamide [0384], Compound 114 as an off-white solid. MS(M+1)+=436, $^1$H-NMR (400 MHz, DMSO-d6): δ 7.38 (m, 1H), 7.16 (bs, 1H), 6.78 (d, J=7.56 Hz, 1H), 6.30 (s, 1H), 6.05 (s, 1H), 4.90 (bs, 1H), 4.26 (bs, 1H), 3.85 (dd, J=7.00, 27.24 Hz, 2H), 3.63 (s, 1H), 3.50-3.44 (m, 2H), 2.59 (s, 3H), 2.16 (s, 3H), 2.15-1.80 (m, 6H), 1.61-1.55 (m, 2H).

Example 148

Step 1 [0385]: To a solution of 4-chloro-6-(3,5-dimethyl-1H-pyrazol-1-yl)-2-(methylsulfonyl)pyrimidine [0378] (3 g, 10.46 mmol) and piperazine-2-carboxamide [0257] (1.48 g, 11.50 mmol1.) in N,N-dimethylformamide (15 mL) was added cesium carbonate (5.11 g, 15.69 mmol) and the reaction mixture was heated at 80° C. for 1 h. The reaction mixture was quenched with ice-cold water, the obtained solid was filtered, washed with hexane, dried under high vacuum to afford unidentified off-white solid. The aqueous layer was extracted with chloroform (3×100 mL), the combined organic layer was dried over anhydrous sodium sulfate and concentrated to afford 1.5 g as an brownish gum, which was purified by column of silica gel (60-120 mesh) using 21% methanol in chloroform as eluent to afford 4-(6-(3,5-dimethyl-1H-pyrazol-1-yl)-2-(methylsulfonyl)pyrimidin-4-yl)piperazine-2-carboxamide [0385] as an off-white gum. MS(M+1)+=380.

Step 2[0386]: To a solution of 4-(6-(3,5-dimethyl-1H-pyrazol-1-yl)-2-(methylsulfonyl)pyrimidin-4-yl)piperazine-2-carboxamide [0385] (0.5 g, 1.31 mmol) and 4,4-difluorocyclohexylamine hydrochloride [0002] (0.45 g, 2.63 mmol) in dimethylsulfoxide (10 mL) was added cesium carbonate (1.28 g, 3.95 mmol) and the reaction mixture was heated at 100° C. in a closed vial (20 mL) for 16 h. The reaction mixture was quenched with ice-cold water and extracted with ethyl acetate (2×100 mL). The combined organic layer was dried over anhydrous sodium sulfate and concentrated to afford 0.041 g of 4-(2-((4,4-difluorocyclohexyl)amino)-6-(3,5-dimethyl-1H-pyrazol-1-yl)pyrimidin-4-yl)piperazine-2-carboxamide [0386], Compound 106 as an brownish gum. MS(M+1)+=435, $^1$H-NMR (400 MHz, DMSO-d6): δ 7.33 (bs, 1H), 7.17 (bs, 1H), 6.78 (bs, H), 6.37 (s, 1H), 6.06 (s, 1H), 4.23 (bs, 1H), 3.96 (bs, 1H), 3.84 (bs, 1H), 3.19-3.17 (m, 1H), 2.96-2.92 (m, 4H), 2.68-2.61 (m, 5H), 2.18 (s, 3H), 2.09-2.06 (m, 2H), 1.91-1.85 (m, 3H), 1.59-1.56 (m, 3H).

Example 149

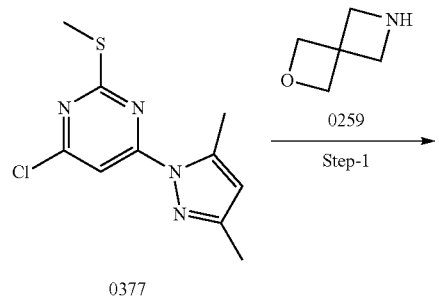

0377

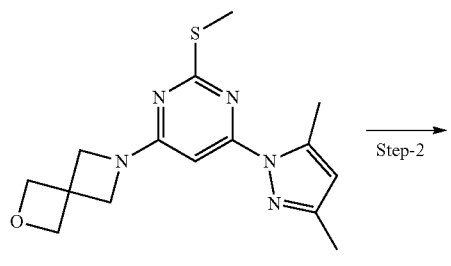

0387

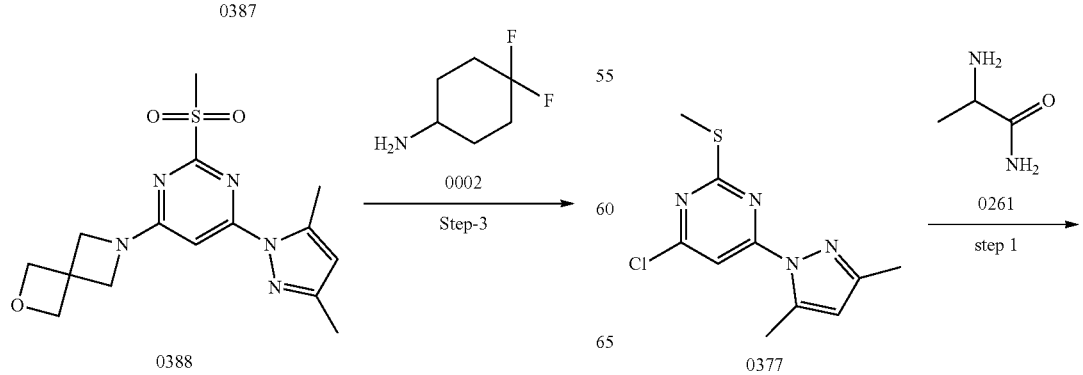

0388

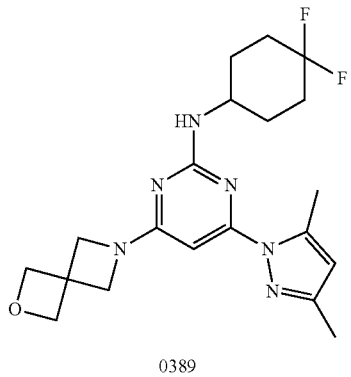

0389

Step 1[0387]: The procedure is similar to Step 1 [0377] in example 145. 0.5 g of 4-chloro-6-(3,5-dimethyl-1H-pyrazol-1-yl)-2-(methylthio)pyrimidine [0377] and 0.194 g of 2-oxa-6-azaspiro[3.3]heptane [0259] gave 0.5 g of 6-(6-(3,5-dimethyl-1H-pyrazol-1-yl)-2-(methylthio)pyrimidin-4-yl)-2-oxa-6-azaspiro[3.3]heptane [0387] as an white solid. MS(M+1)+=318.

Step 2[0388]: The procedure is similar to Step 2[0378] in example 145. 0.5 g of 6-(6-(3,5-dimethyl-1H-pyrazol-1-yl)-2-(methylthio)pyrimidin-4-yl)-2-oxa-6-azaspiro[3.3]heptane [0387] gave 0.52 g of 6-(6-(3,5-dimethyl-1H-pyrazol-1-yl)-2-(methylsulfonyl)pyrimidin-4-yl)-2-oxa-6-azaspiro [3.3] heptane [0388] as an brownish gum, MS(M+1)+=350.

Step 3[0389]: The procedure is similar to Step 1 [0382] in example 147 (at 100° C.). 0.45 g of 6-(6-(3,5-dimethyl-1H-pyrazol-1-yl)-2-(methylsulfonyl)pyrimidin-4-yl)-2-oxa-6-azaspiro [3.3] heptane [0388] gave 0.055 g of N-(4,4-difluorocyclohexyl)-4-(3,5-dimethyl-1H-pyrazol-1-yl)-6-(2-oxa-6-azaspiro[3.3]heptan-6-yl)pyrimidin-2-amine [0389], Compound 108 as an white solid. MS(M+1)+=405, $^1$H-NMR (400 MHz, DMSO-d6): δ 6.94 (bs, 1H), 6.06 (s, 1H), 5.96 (s, 1H), 4.70 (s, 4H), 4.16 (s, 4H), 3.83 (bs, 1H), 2.59 (s, 3H), 2.16 (s, 3H), 2.10-1.82 (m, 6H), 1.56-1.53 (m, 2H).

Example 150

507
-continued

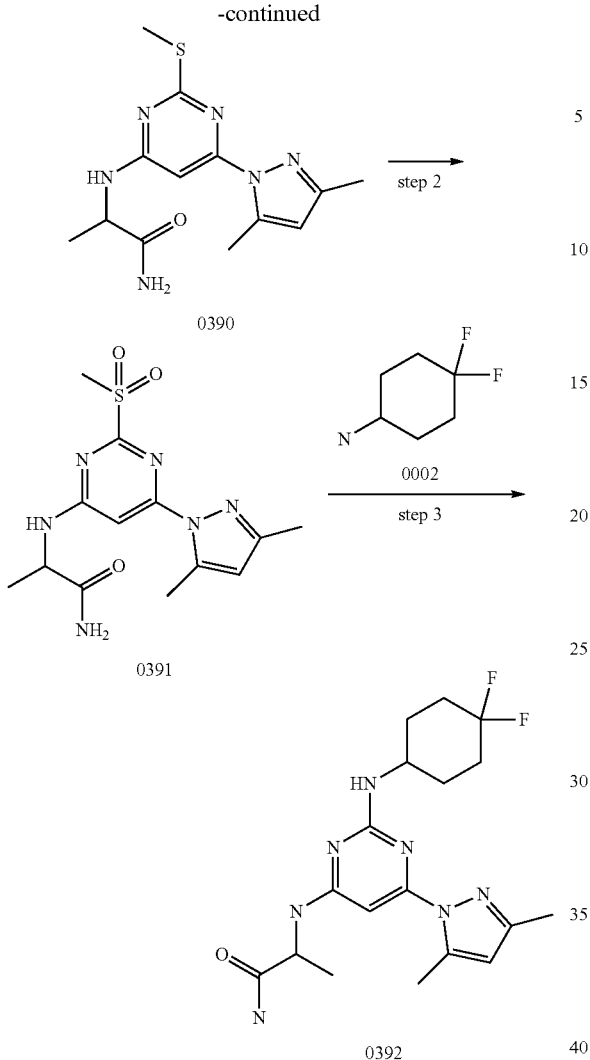

Step 1[0390]: To a solution of 4-chloro-6-(3,5-dimethyl-1H-pyrazol-1-yl)-2-(methylthio)pyrimidine [0377] (4 g, 15.702 mmol) in N,N-dimethyl formamide (40 mL) was added 2-amino propanamide (1.38 g, 15.702 mmol), followed by cesium carbonate (7.67 g, 23.553 mmol) and the reaction mixture was heated at 80° C. for 16 h. The reaction mixture was quenched with ice. The solid formed was filtered to afford crude product which was purified by column chromatography using 50% ethyl acetate in hexane as solvent to afford 2.5 g of 2-((6-(3,5-dimethyl-1H-pyrazol-1-yl)-2-(methylthio)pyrimidin-4-yl)amino)propanamide [0390] as a yellow solid. MS(M+1)+=307.3

Step 2[0391]: The procedure is similar to step 2[0378] in example 145. 2.7 g of 2-((6-(3,5-dimethyl-1H-pyrazol-1-yl)-2-(methylthio)pyrimidin-4-yl)amino)propanamide [0390] gave 0.62 g of 2-((6-(3,5-dimethyl-1H-pyrazol-1-yl)-2-(methylsulfonyl)pyrimidin-4-yl)amino)propanamide [0391] as a yellow solid. MS(M+1)+=339.2

Step 3[100]: The procedure is similar to Step 1 [0382] in example 147 (at 100° C.). 0.37 g of 2-((6-(3,5-dimethyl-1H-pyrazol-1-yl)-2-(methylsulfonyl)pyrimidin-4-yl)amino)propanamide [0391] gave 0.05 g of 2-((2-((4,4-difluorocyclohexyl)amino)-6-(3,5-dimethyl-1H-pyrazol-1-yl)pyrimidin-4-yl)amino)propanamide [0392], Compound 107 as an off-white solid. MS(M+1)+=394.3. $^1$H NMR (400 MHz, DMSO-d6) δ 7.45-6.81 (m, 3H), 6.63 (d, J=7.5 Hz, 1H), 6.24 (s, 1H), 6.03 (s, 1H), 4.34 (bs, 1H), 3.83 (bs, 1H), 2.59 (s, 3H), 2.16 (s, 3H), 2.12-1.75 (m, 6H), 1.65-1.45 (m, 2H), 1.28 (d, J=7.1 Hz, 3H).

508
Example 151

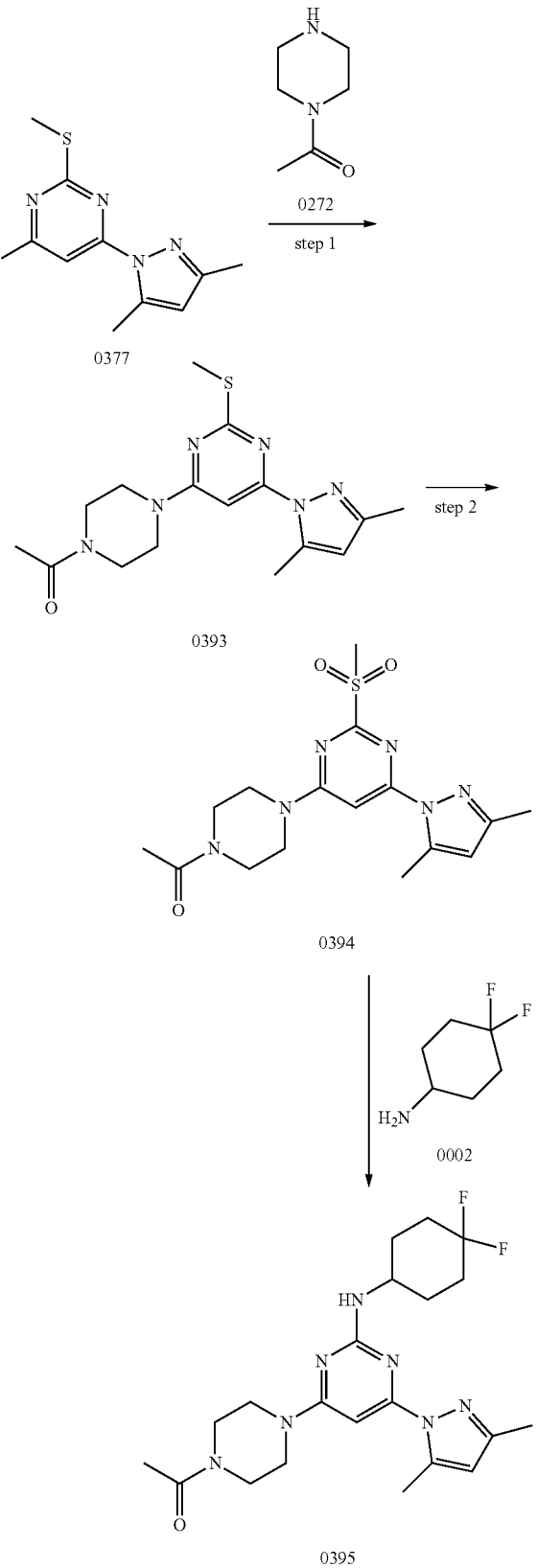

Step 1[0393]: To a solution of 4-chloro-6-(3,5-dimethyl-1H-pyrazol-1-yl)-2-(methylthio)pyrimidine [0377] (10 g, 39.255 mmol) in N,N-dimethylformamide (80 mL) was added 1-acetylpiperazine (5.03 g, 39.255 mmol) and cesium carbonate (19.18 g, 58.88 mmol). The reaction mixture was heated at 60° C. in a closed vial in a thermal block for 8 h. The reaction mixture was quenched with ice. The solid formed was filtered to afford 10.3 g of 1-(4-(6-(3,5-dimethyl-1H-pyrazol-1-yl)-2-(methylthio)pyrimidin-4-yl)piperazin-1-yl)ethan-1-one [0393] as a yellow solid. MS(M+1)+= 347.4.

Step 2[0394]: To a stirred solution of 1-(4-(6-(3,5-dimethyl-1H-pyrazol-1-yl)-2-(methylthio)pyrimidin-4-yl)piperazin-1-yl)ethan-1-one [0393] (5 g, 14.431 mmol) in dichloromethane (50 mL), 3-chloroperbenzoic acid (6.22 g, 36.079 mmol) was added portion-wise at 0° C. The reaction mixture was stirred at rt for 3 h, diluted with dichloromethane (50 mL), washed with saturated solution of sodium thiosulfate (25 mL), followed by 10% sodium bicarbonate solution (20 mL), water (20 mL) and brine (20 mL). The organic layer was dried over anhydrous sodium sulfate to afford 4.5 g of 1-(4-(6-(3,5-dimethyl-1H-pyrazol-1-yl)-2-(methylsulfonyl)pyrimidin-4-yl)piperazin-1-yl)ethan-1-one [0394] as a yellow solid. MS(M+1)+=379.0.

Step 3[0395]: 1 The procedure is similar to step 1[0382] in example 147 (at 100° C.). 0.5 g of 1-(4-(6-(3,5-dimethyl-1H-pyrazol-1-yl)-2-(methylsulfonyl)pyrimidin-4-yl)piperazin-1-yl)ethan-1-one [0394] gave 0.070 g of 1-(4-(2-((4,4-difluorocyclohexyl)amino)-6-(3,5-dimethyl-1H-pyrazol-1-yl)pyrimidin-4-yl)piperazin-1-yl)ethan-1-one [0395], Compound 101 as a white solid. MS(M+1)$^+$=434.4. $^1$H NMR (400 MHz, DMSO-d6) δ 6.84 (d, J=6.84 Hz, 1H), 6.38 (s, 1H), 6.07 (s, 1H), 3.86 (s, 1H), 3.63 (s, 2H), 3.54-3.47 (m, 6H), 2.61 (s, 3H), 2.18 (s, 3H), 2.04 (s, 5H), 1.99-1.85 (m, 4H), 1.58-1.55 (m, 2H).

Example 152

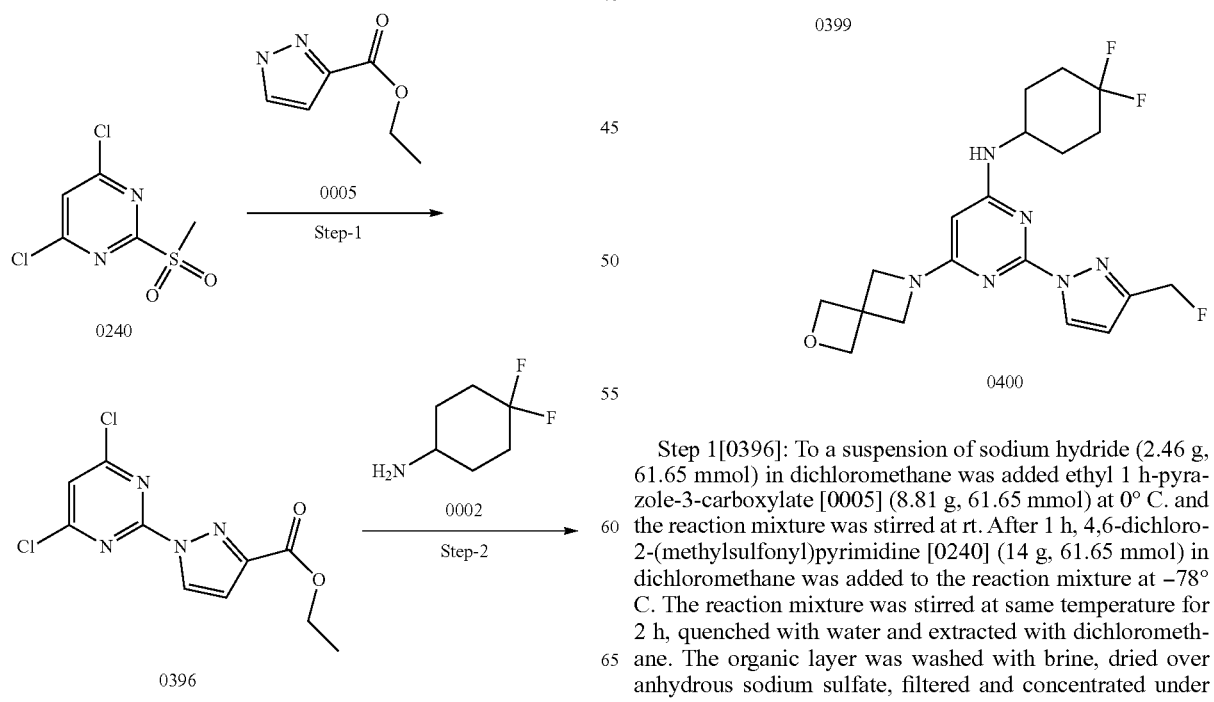

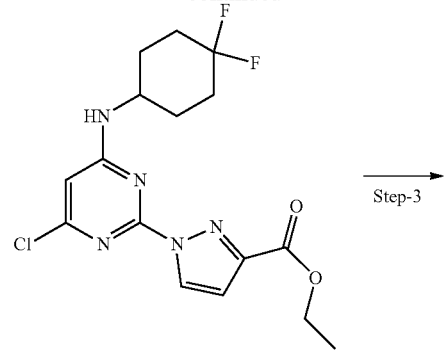

0397

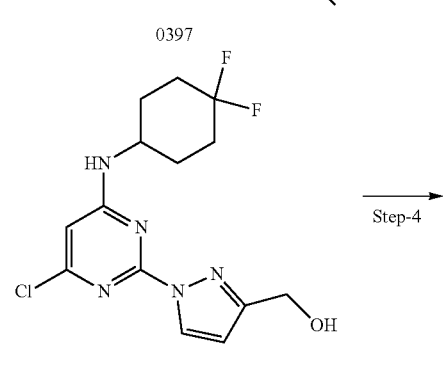

0398

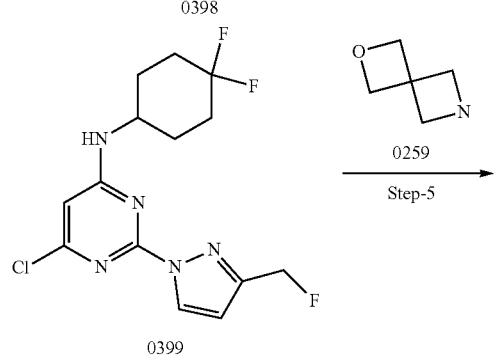

0399

0400

Step 1[0396]: To a suspension of sodium hydride (2.46 g, 61.65 mmol) in dichloromethane was added ethyl 1 h-pyrazole-3-carboxylate [0005] (8.81 g, 61.65 mmol) at 0° C. and the reaction mixture was stirred at rt. After 1 h, 4,6-dichloro-2-(methylsulfonyl)pyrimidine [0240] (14 g, 61.65 mmol) in dichloromethane was added to the reaction mixture at −78° C. The reaction mixture was stirred at same temperature for 2 h, quenched with water and extracted with dichloromethane. The organic layer was washed with brine, dried over anhydrous sodium sulfate, filtered and concentrated under reduced pressure to afford 16.5 g of ethyl 1-(4,6-dichloropyrimidin-2-yl)-1H-pyrazole-3-carboxylate [0396] as an off-white solid. MS(M+1)+=288.2.

Step 2[0397]: 16 g of 1-(4,6-dichloropyrimidin-2-yl)-1H-pyrazole-3-carboxylate [0396] gave 21 g of ethyl 1-(4-chloro-6-((4,4-difluorocyclohexyl)amino)pyrimidin-2-yl)-1H-pyrazole-3-carboxylate [0397] as an off-white solid (Using DIPEA, ACN, rt, 16 h)

Step 3[0398]: To an ice cooled solution of ethyl 1-(4-chloro-6-((4,4-difluorocyclohexyl)amino)pyrimidin-2-yl)-1H-pyrazole-3-carboxylate [0397] in tetrahydrofuran (20 mL) was added lithium borohydride. The reaction mixture was slowly brought to rt (1 h). After completion, the reaction mixture was quenched with water and extracted with ethyl acetate (2×50 mL). The combined organic layer was dried over anhydrous sodium sulfate and concentrated to afford 0.7 g of methyl (1-(4-chloro-6-((4,4-difluorocyclohexyl)amino)pyrimidin-2-yl)-1H-pyrazol-3-yl)methanol [0398] as an off-white solid. MS(M+1)+=344.

Step 4[0399]: To an ice cooled solution of methyl (1-(4-chloro-6-((4,4difluorocyclohexyl)amino)pyrimidin-2-yl)-1H-pyrazol-3-yl)methanol [0398] in dichloromethane (15 mL) was added diethylamino sulphur trifluoride. The reaction mixture was slowly warmed to rt and stirred for 30 min. After completion, the reaction mixture was quenched with saturated bicarbonate solution and extracted dichloromethane (2×75 mL). The combined organic layer was dried over anhydrous sodium sulfate and concentrated to afford as an light brownish gum and which was purified by column chromatography using 40% ethyl acetate in hexane as to afford 0.450 g of 6-chloro-N-(4,4-difluorocyclohexyl)-2-(3-(fluoromethyl)-1H-pyrazol-1-yl)pyrimidin-4-amine [0399] as an off-white gum. MS(M+1)+=346.

Step 5[0400]: To a solution of 6-chloro-N-(4,4-difluorocyclohexyl)-2-(3-(fluoromethyl)-1H-pyrazol-1-yl)pyrimidin-4-amine [0399] in acetonitrile (10 mL) was added 2-oxa-6-azaspiro(3,3)heptane [0259] and cesium carbonate. The reaction mixture was irradiated at 100° C. in MW for 1 h. After the completion, the reaction mixture was filtered to remove cesium carbonate. The filtrate was concentrated to afford brownish gum and which was purified by column chromatography using 75% ethyl acetate in hexane to afford N-(4,4-difluorocyclohexyl)-2-(3-(fluoromethyl)-1H-pyrazol-1-yl)-6-(2-oxa-6-azaspiro[3.3]heptan-6-yl)pyrimidin-4-amine [0246], Compound 338 as an off-white solid 0.21 g, MS(M+1)$^+$=409. $^1$H NMR (400 MHz, DMSO-d6) δ 8.51 (s, 1H), 7.17 (d, J=7.9 Hz, 1H), 6.60 (d, J=2.5 Hz, 1H), 5.49 (d, JF=48.5 Hz, 2H), 5.22 (s, 1H), 4.73 (s, 4H), 4.15 (s, 4H), 2.08-1.88 (m, 6H), 1.54-1.52 (m, 2H).

Example 153

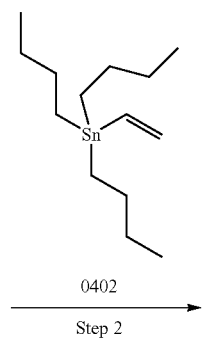

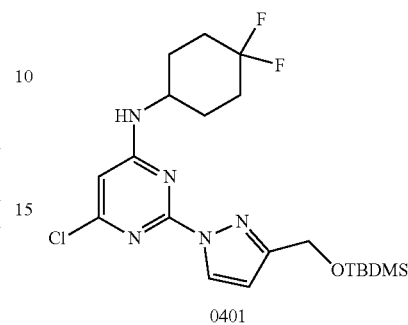

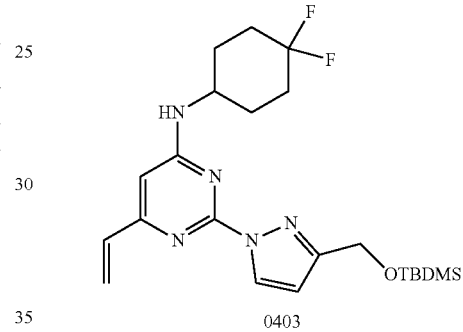

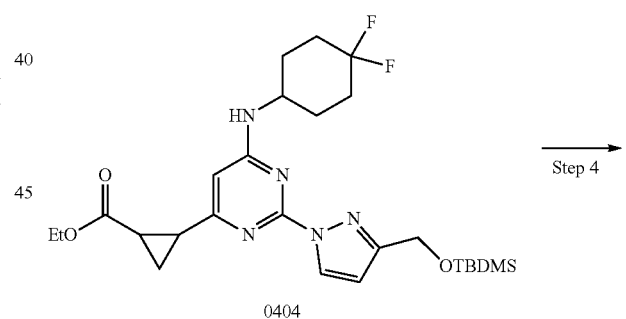

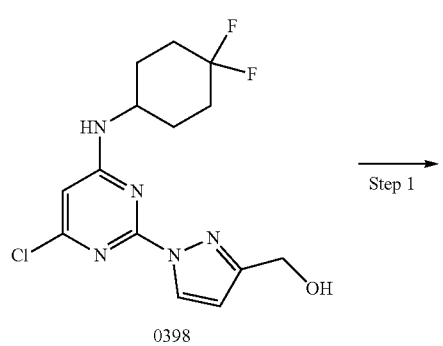

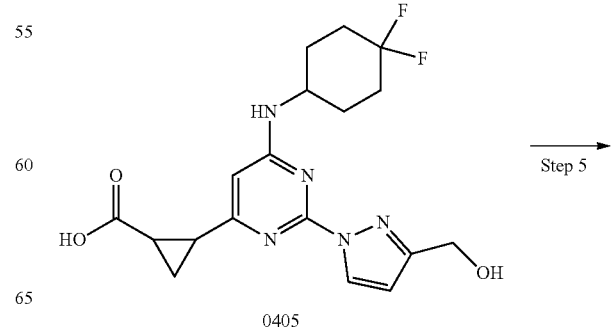

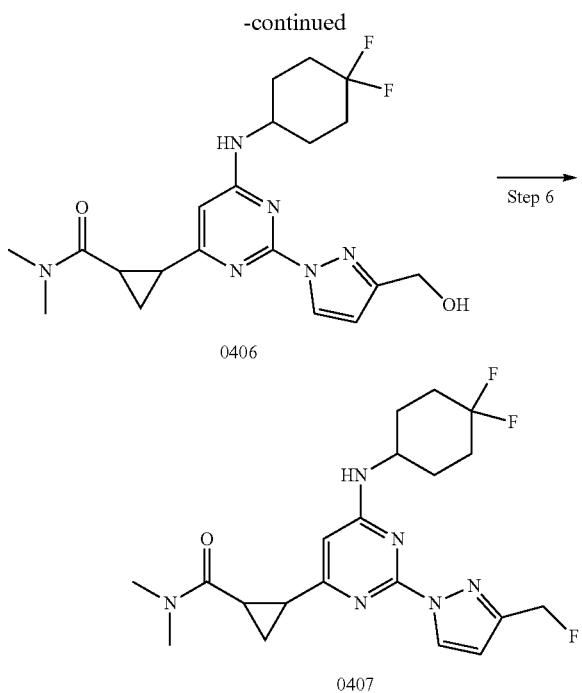

Step 1[0401]: To a stirred solution of (1-(4-chloro-6-((4,4-difluorocyclohexyl)amino)pyrimidin-2-yl)-1H-pyrazol-3-yl)methanol [0398] (3.4 g, 9.89 mmol) and imidazole (1.753 g, 14.836 mmol) in dichloromethane (50 mL) was added tert-butyl dimethylsilyl chloride (1.8 g, 11.868 mmol) in portions at 0° C. The reaction mixture was slowly brought to rt for 4 h, concentrated under reduced pressure to afford crude product which was purified by column chromatography using 15% ethyl acetate in hexane as eluent to afford 2-(3-(((tert-butyldimethylsilyl)oxy)methyl)-1H-pyrazol-1-yl)-6-chloro-N-(4,4-difluorocyclohexyl)pyrimidin-4-amine [0401] as yellowish solid (3.6 g, 67%).

MS(M+1)+=459.1.

Step 2[0403]: To a degassed solution of 2-(3-(((tert-butyldimethylsilyl)oxy)methyl)-1H-pyrazol-1-yl)-6-chloro-N-(4,4-difluorocyclohexyl)pyrimidin-4-amine [0401] (3.5 g, 7.614 mmol) and tributyl(vinyl)tin [0402] (3.747 g, 11.462 mmol) in 1,2-dichloroethane (50 mL) was added bis(triphenylphosphine)palladium(II) dichloride (0.268 g, 0.682 mmol). The reaction mixture was heated to 80° C. for 16 h, quenched with water (50 mL) and extracted with ethyl acetate (2×100 mL). The combined organic layer was washed with brine (50 mL), dried over anhydrous sodium sulfate, filtered and concentrated under reduced pressure to afford crude product which was purified by column chromatography using 10% ethyl acetate in hexane as eluent to afford 2-(3-(((tert-butyldimethylsilyl)oxy)methyl)-1H-pyrazol-1-yl)-N-(4,4-difluorocyclohexyl)-6-vinylpyrimidin-4-amine [0403] as off-white solid (2.56 g). MS(M+1)+=450.61

Step 3 [0404]: To a stirred solution of 2-(3-(((tert-butyldimethylsilyl)oxy)methyl)-1H-pyrazol-1-yl)-N-(4,4-difluorocyclohexyl)-6-vinylpyrimidin-4-amine [0403] (2.56 g, 5.694 mmol) and ethyl diazoacetate (0.975 g, 8.540 mmol) in toluene (30 mL) was heated at 100° C. for 16 h. The reaction mixture was concentrated under reduced pressure to afford crude product which was purified by column chromatography using 15% ethyl acetate in hexane as eluent to afford ethyl 2-(2-(3-(((tert-butyldimethylsilyl)oxy)methyl)-1H-pyrazol-1-yl)-6-((4,4-difluorocyclohexyl)amino)pyrimidin-4-yl)cyclopropane-1-carboxylate [0404] as an off-white solid (0.5 g, 16%). MS(M+1)+=536.7

Step 4 [0405]: To a stirred solution of ethyl 2-(2-(3-(((tert-butyldimethylsilyl)oxy)methyl)-1H-pyrazol-1-yl)-6-((4,4-difluorocyclohexyl)amino)pyrimidin-4-yl)cyclopropane-1-carboxylate [0404] (0.5 g, 0.933 mmol) in a mixture of tetrahydrofuran (10 mL) and water (5 mL) was added lithium hydroxide monohydrate (0.196 g, 4.666 mmol) and the reaction mixture was stirred at rt for 18 h. The reaction mixture was acidified (pH-4-5) with aqueous hydrochloric acid (1N, 5 mL) and concentrated to dryness to afford 2-(6-((4,4-difluorocyclohexyl)amino)-2-(3-(hydroxymethyl)-1H-pyrazol-1-yl)pyrimidin-4-yl)cyclopropane-1-carboxylic acid [0405] as a white solid (0.36 g). MS(M+1)+=340.4

Step 5 [0406]: To a stirred solution of 2-(6-((4,4-difluorocyclohexyl)amino)-2-(3-(hydroxymethyl)-1H-pyrazol-1-yl)pyrimidin-4-yl)cyclopropane-1-carboxylic acid [0405] (0.366 g, 0.933 mmol) in tetrahydrofuran (4 mL) in a pressure tube was added triethyl amine (0.33 mL, 2.326 mmol) followed by N-(3-dimethylaminopropyl)-N'-ethylcarbodiimide (0.267 g, 1.396 mmol) and 1-hydroxybenzotriazole hydrate (0.154 g, 1.116 mmol) at 0° C. The reaction mixture was stirred at 0° C. for 15 min. Then a solution of dimethyl amine in tetrahydrofuran (4.65 mL, 2M) was added. The mixture was stirred with slow warming to rt for 24 h. The reaction mixture was quenched with water (20 mL) and the product was extracted with chloroform (3×50 mL). The combined organic layer was washed with brine (25 mL), dried over anhydrous sodium sulfate, filtered and concentrated under reduced pressure to afford crude product which was purified by column chromatography using 2% methanol in chloroform as eluent to afford 2-(6-((4,4-difluorocyclohexyl)amino)-2-(3-(hydroxymethyl)-1H-pyrazol-1-yl)pyrimidin-4-yl)-N,N-dimethylcyclopropane-1-carboxamide [0406] as off-white solid (0.15 g). MS(M+1)+=421.46.

Step 6 [0407]: The procedure is similar to step 3[0012] in example 2. 0.15 g 2-(6-((4,4-difluorocyclohexyl)amino)-2-(3-(hydroxymethyl)-1H-pyrazol-1-yl)pyrimidin-4-yl)-N,N-dimethylcyclopropane-1-carboxamide [0406] gave 0.02 g of 2-(6-((4,4-difluorocyclohexyl)amino)-2-(3-(fluoromethyl)-1H-pyrazol-1-yl)pyrimidin-4-yl)-N,N-dimethylcyclopropane-1-carboxamide [0407], Compound 308 as an off-white solid.

MS(M+1)+=423.45, $^1$H NMR (400 MHz, DMSO-d6) δ 8.61 (s, 1H), 7.71 (s, 1H), 6.63 (d, J=3.1 Hz, 1H), 6.38 (s, 1H), 5.50 (s, 1H), 5.45 (d, JF=48 Hz, 1H), 4.16 (s, 1H), 3.09 (s, 3H), 2.86 (s, 3H), 2.42 (bs, 1H), 2.29 (s, 1H), 2.19-1.82 (m, 6H), 1.71-1.44 (m, 3H), 1.36 (s, 1H).

Example 154

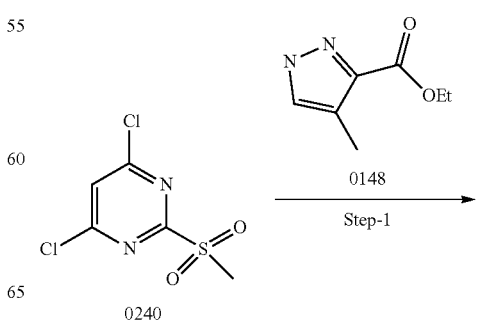

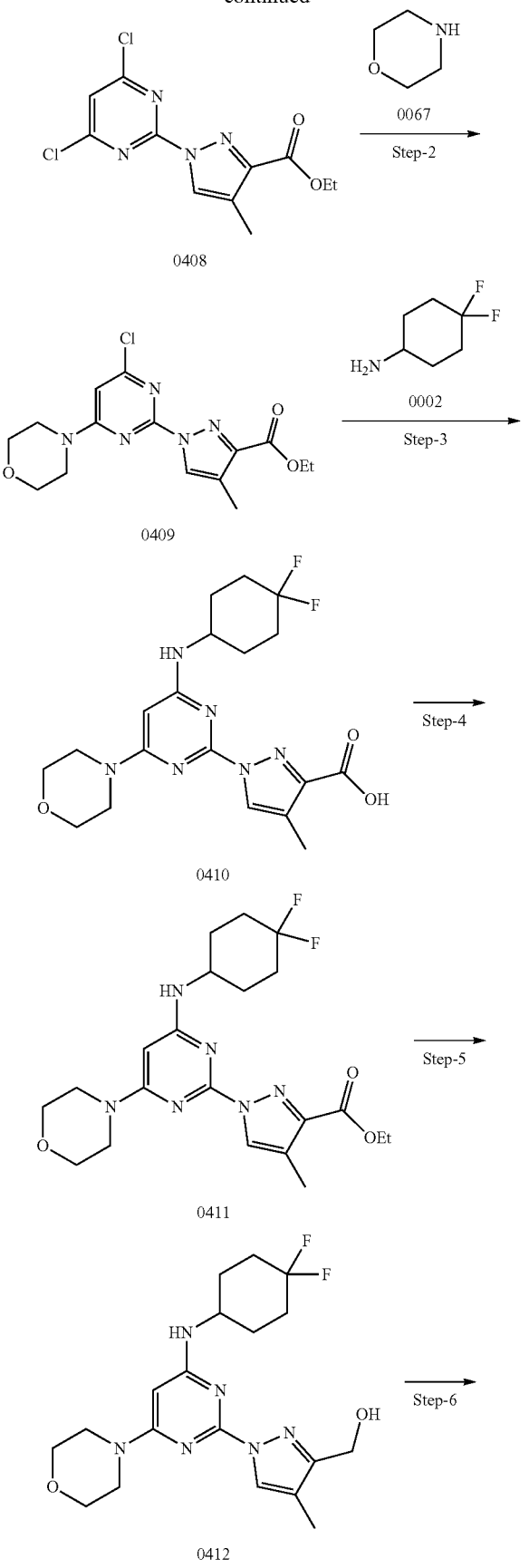
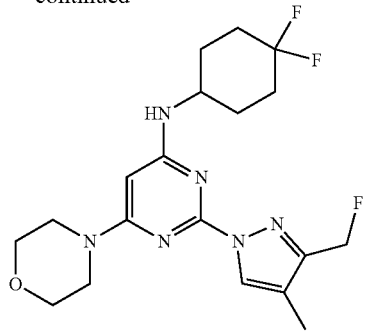

Step 1[0408]: The procedure is similar to step 2 [0241] in example 87. 5 g of 4,6-dichloro-2-(methylsulfonyl)pyrimidine [0240] and 3.3 g of ethyl 4-methyl-1H-pyrazole-3-carboxylate [0148] gave 4.1 g of ethyl 1-(4,6-dichloropyrimidin-2-yl)-4-methyl-1H-pyrazole-3-carboxylate [0408] as off-white solid. MS(M+1)+=302.2.

Step 2[0409]: The procedure is similar to Step 1[0106] in example 34 (acetonitrile as solvent). 2.1 g of ethyl 1-(4,6-dichloropyrimidin-2-yl)-4-methyl-1H-pyrazole-3-carboxylate [0408] gave 1.65 g of ethyl 1-(4-chloro-6-morpholinopyrimidin-2-yl)-4-methyl-1H-pyrazole-3-carboxylate [0409]. MS(M+1)+=352.2.

Step 3 [0410]: The procedure is similar to Step 4[0244] in example 87. 1.5 g of ethyl 1-(4-chloro-6-morpholinopyrimidin-2-yl)-4-methyl-1H-pyrazole-3-carboxylate [0409] and 4,4-difluorocyclohexan-1-amine [0002] gave 1.6 g (crude) 1-(4-(((4,4-difluorocyclohexyl)amino)-6-morpholinopyrimidin-2-yl)-4-methyl-1H-pyrazole-3-carboxylic acid [0410] as brown solid. MS(M+1)+=422.2. This was taken as such to next step.

Step 4[0411]: The procedure is similar to Step 4[0007] in example 1. 1.6 g of 1-(4-((4,4-difluorocyclohexyl)amino)-6-morpholinopyrimidin-2-yl)-4-methyl-1H-pyrazole-3-carboxylic acid [0410] gave 1.35 g of Ethyl 1-(4-((4,4-difluorocyclohexyl)amino)-6-morpholinopyrimidin-2-yl)-4-methyl-1H-pyrazole-3-carboxylate [0411], MS(M+1)+=451.1.

Step 4[0412]: The procedure is similar to Step 2[0019] in example 4. 1.35 g of ethyl 1-(4-((4,4-difluorocyclohexyl)amino)-6-morpholinopyrimidin-2-yl)-4-methyl-1H-pyrazole-3-carboxylate [0411] gave 0.985 g of 4(1-(4-((4,4-difluorocyclohexyl)amino)-6-morpholinopyrimidin-2-yl)-4-methyl-1H-pyrazol-3-yl)methanol [0412], MS(M+1)+=409.1.

Step 5[0413]: The procedure is similar to Step 3[0012] in example 2. 0.46 g of 4(1-(4-((4,4-difluorocyclohexyl)amino)-6-morpholinopyrimidin-2-yl)-4-methyl-1H-pyrazol-3-yl)methanol [0412] gave 0.985 g of N-(4,4-difluorocyclohexyl)-2-(3-(fluoromethyl)-4-methyl-1H-pyrazol-1-yl)-6-morpholinopyrimidin-4-amine [0413], Compound 281.

MS(M+1)+=411.2, MR=146.4-154.0° C., $^1$H NMR (400 MHz, DMSO-d6) δ 8.37 (s, 1H), 7.16 (d, J=8.0 Hz, 1H), 5.56 (s, 1H), 5.44 (d, JF=48 Hz, 2H), 4.01 (bs, 1H), 3.72-3.65 (m, 4H), 3.51 (bs, 4H), 2.11 (s, 3H), 2.12-1.88 (m, 6H), 1.62-1.54 (m, 2H).

517

Example 155

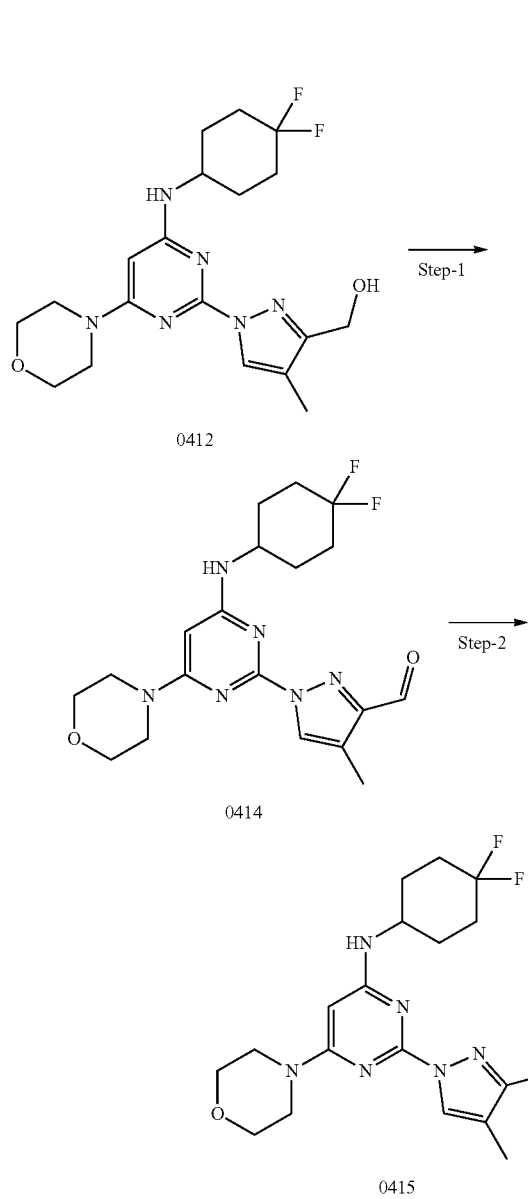

Step 1[0414]: 0.51 g of 4(1-(4-((4,4-difluorocyclohexyl)amino)-6-morpholinopyrimidin-2-yl)-4-methyl-1H-pyrazol-3-yl)methanol [0412] gave 0.38 g of 1-(4-((4,4-difluorocyclohexyl)amino)-6-morpholinopyrimidin-2-yl)-4-methyl-1H-pyrazole-3-carbaldehyde [0414], using manganese dioxide in dichloromethane. MS(M+1)+=407.

Step 2[0415]: The procedure is similar to Step 3[0012] in example 2. 0.37 g of 1-(4-((4,4-difluorocyclohexyl)amino)-6-morpholinopyrimidin-2-yl)-4-methyl-1H-pyrazole-3-carbaldehyde [0414] gave 0.08 g of N-(4,4-difluorocyclohexyl)-2-(3-(difluoromethyl)-4-methyl-1H-pyrazol-1-yl)-6-morpholinopyrimidin-4-amine [0415], Compound 282.

MS(M+1)$^+$=429, $^1$H NMR (400 MHz, DMSO-d6) δ 8.47 (s, 1H), 7.59 (s, 1H), 7.08 (t, JF=53.34 Hz, 1H), 5.96 (d, J=8.12 Hz, 1H), 4.11 (bs, 1H), 3.74 (s, 4H), 3.52 (s, 4H), 2.16 (s, 3H), 2.12-1.88 (m, 6H), 1.36 (bs, 2H).

518

Example 156

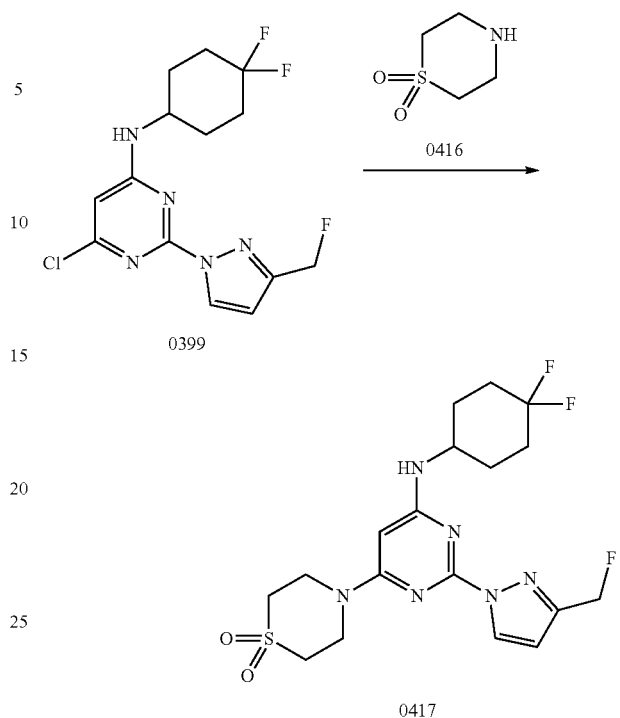

Step 3[Step-1]: To a solution of 6-chloro-N-(4,4-difluorocyclohexyl)-2-(3-(fluoromethyl)-1H-pyrazol-1-yl)pyrimidin-4-amine [0399] (0.4 g, 1.156 mmol) in dimethylsulfoxide (8 mL) was added thiomorpholine 1,1-dioxide [0416] (0.18 g, 1.18 mmol) and followed by triethylamine (0.24 g, 1.735 mmol) under N2 atm. The resultant reaction mixture was irradiated in MW at 120° C. for 2 h. The reaction mixture was quenched with ice cold water (30 mL), and extracted with ethyl acetate (2×80 mL). The combined organic extract was washed with brine (3×50 mL), dried over anhydrous sodium sulfate, filtered and concentrated under reduced pressure to afford as a yellow liquid and which was purified by column chromatography using 76% ethyl acetate in hexane as an eluent to afford 4-(6-((4,4-difluorocyclohexyl)amino)-2-(3-(fluoromethyl)-1H-pyrazol-1-yl)pyrimidin-4-yl)thiomorpholine [0417], Compound 283 as an off-white solid (0.1 g). MS(M+1)$^+$=445, $^1$H NMR (400 MHz, DMSO-d6) δ 8.59 (s, 1H), 7.27 (d, J=7.7 Hz, 1H), 6.61 (d, J=3.0 Hz, 1H), 5.74 (s, 1H), 5.42 (d, JF=48 Hz, 2H), 4.06 (m, 4H), 3.93 (bs, 1H), 3.17 (m, 4H), 2.10-1.89 (m, 6H), 1.56 (m, 2H).

Example 157

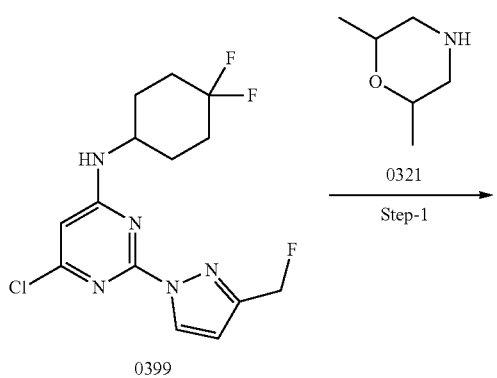

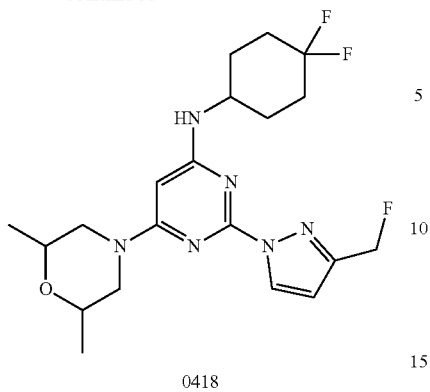

0418

Step 1[0418]: To a solution of 6-chloro-N-(4,4-difluoro-cyclohexyl)-2-(3-(fluoromethyl)-1H-pyrazol-1-yl)pyrimidin-4-amine [0418] (0.3 g, 0.86 mmol) in acetonitrile (12 mL) was added 2,6-dimethyl morpholine [0321] (0.19 g, 1.73 mmol) and followed by N,N-diisopropyl ethylamine (0.33 g, 2.60 mmol) under N2 atm. The resultant reaction mixture was heated at 90° C. for 4 h. The reaction mixture was quenched with ice cold water (30 mL) and extracted with ethyl acetate (2×80 mL). The combined organic extract was washed with brine (3×50 mL), dried over anhydrous sodium sulfate, filtered and concentrated under reduced pressure to afford brown solid, which was purified by column chromatography using 35% ethyl acetate in hexane as an eluent to afford N-(4,4-difluorocyclohexyl)-6-(2,6-dimethylmorpholino)-2-(3-(fluoromethyl)-1H-pyrazol-1-yl) pyrimidin-4-amine [0418], Compound 294 as an off-white solid (0.085 g).

MS(M+1)+=425, ¹H NMR (400 MHz, DMSO-d6) δ 8.57 (d, J=2.6 Hz, 1H), 8.31 (s, 1H), 7.12 (d, J=8.1 Hz, 1H), 6.59 (s, 1H), 5.56 (s, 1H), 5.45 (d, JF=48 Hz, 2H), 4.10-3.81 (m, 2H), 3.66 (d, J=13.0 Hz, 2H), 3.29-3.14 (m, 2H), 2.10-1.89 (m, 6H), 1.65-1.54 (m, 2H), 1.15 (d, J=6.3 Hz, 6H).

Example 158

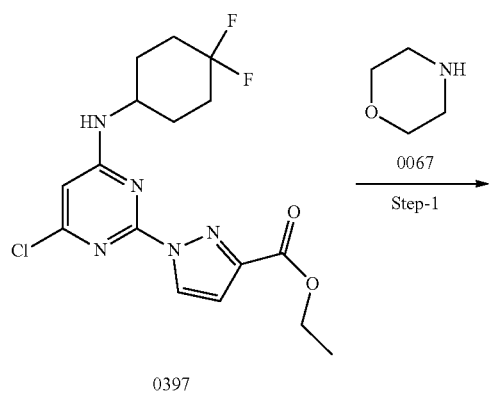

0397

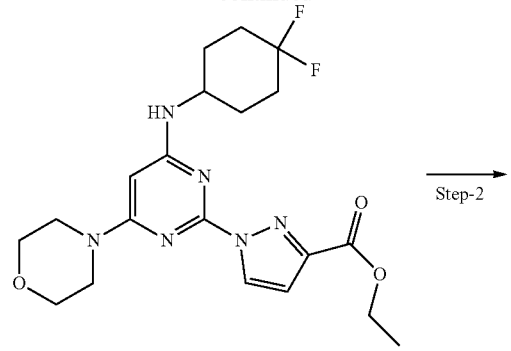

0419

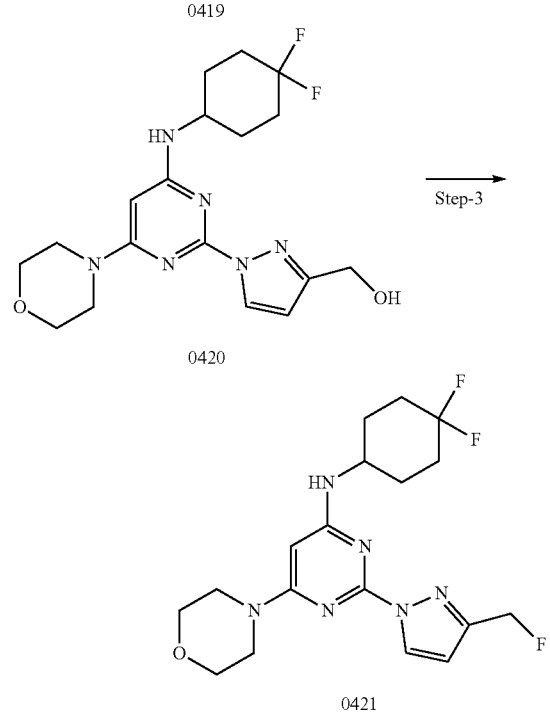

0420

0421

Step 1[0419]: 2 g of ethyl 1-(4-chloro-6-((4,4-difluoro-cyclohexyl)amino)pyrimidin-2-yl)-1H-pyrazole-3-carboxylate [0397] and 1.80 g of morpholine [0067] gave 1.85 g of ethyl 1-(4-((4,4-difluorocyclohexyl)amino)-6-morpholinopyrimidin-2-yl)-1H-pyrazole-3-carboxylate [0419] (Using acetonitrile, MW, 100° C., 1 h) MS(M+1)+=437 and it was taken as such for next step without further purification.

Step 2[0420]: The procedure is similar to Step 2[0019] in example 4. 1.85 g of ethyl 1-(4-((4,4-difluorocyclohexyl)amino)-6-morpholinopyrimidin-2-yl)-1H-pyrazole-3-carboxylate [0419] gave 1.56 g of (1-(4-((4,4-difluorocyclohexyl)amino)-6-morpholinopyrimidin-2-yl)-1H-pyrazol-3-yl)methanol [0420]. MS(M+1)+=395.

Step 3[0421]: The procedure is similar to Step 3[0012] in example 2. 0.5 g of (1-(4-((4,4-difluorocyclohexyl)amino)-6-morpholinopyrimidin-2-yl)-1H-pyrazol-3-yl)methanol [0420] gave 0.1 g of N-(4,4-difluorocyclohexyl)-2-(3-(fluoromethyl)-1H-pyrazol-1-yl)-6-morpholinopyrimidin-4-amine [0421], Compound 280. MS(M+1)+=397, ¹H NMR (400 MHz, DMSO-d6) δ 8.57 (d, J=2.6 Hz, 1H), 7.19 (d, J=8.1 Hz, 1H), 6.60 (t, J=1.8 Hz, 1H), 5.59 (s, 1H), 5.42 (d, JF=48 Hz, 2H), 3.93 (bs, 1H), 3.69 (t, J=4.7 Hz, 4H), 3.52 (m, 4H), 2.13-1.85 (m, 6H), 1.55 (m, 2H).

Example 159

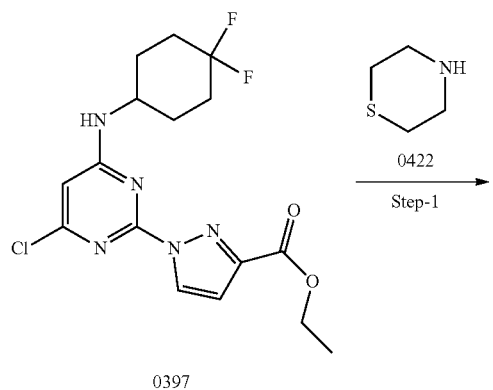

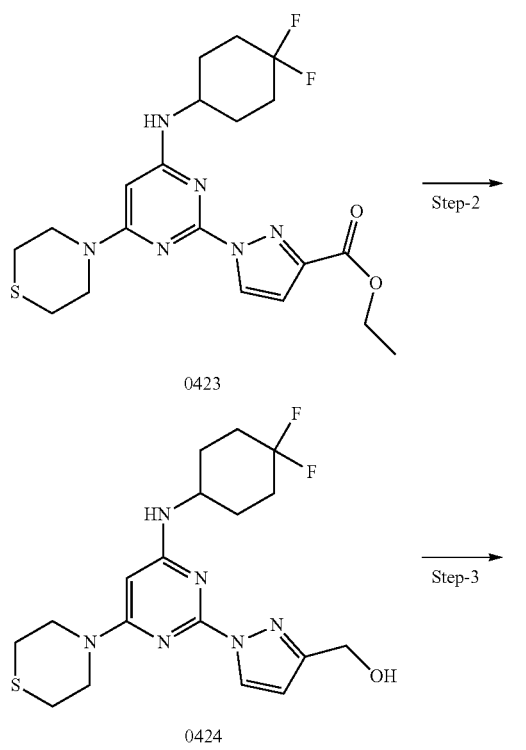

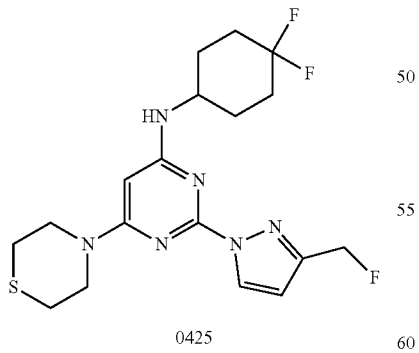

Step 1[0423]: The procedure is similar to Step 1[270] in example 98. 1 g of ethyl 1-(4-chloro-6-((4,4-difluorocyclohexyl)amino)pyrimidin-2-yl)-1H-pyrazole-3-carboxylate [0397] and 0.4 g of thiomorpholine [0422] gave 0.98 g of ethyl 1-(4-((4,4-difluorocyclohexyl)amino)-6-thiomorpholino pyrimidin-2-yl)-1H-pyrazole-3-carboxylate [0423] MS(M+1)+=453 and it was taken as such for next step without further purification.

Step 2[0424]: The procedure is similar to Step 2[0019] in example 4. 0.97 g of ethyl 1-(4-((4,4-difluorocyclohexyl)amino)-6-thiomorpholinopyrimidin-2-yl)-1H-pyrazole-3-carboxylate [0423] gave 0.78 g of (1-(4-((4,4-difluorocyclohexyl)amino)-6-thiomorpholinopyrimidin-2-yl)-1H-pyrazol-3-yl)methanol [0424]. MS(M+1)+=411.

Step 3[0425]: The procedure is similar to Step 3[0012] in example 2. 0.45 g of (1-(4-((4,4-difluorocyclohexyl)amino)-6-thiomorpholinopyrimidin-2-yl)-1H-pyrazol-3-yl)methanol [0424] gave 0.112 g of N-(4,4-difluorocyclohexyl)-2-(3-(fluoromethyl)-1H-pyrazol-1-yl)-6-thiomorpholinopyrimidin-4-amine [0425], Compound 284.

MS(M+1)$^+$=413, $^1$H NMR (400 MHz, DMSO-d6) δ 8.55 (s, 1H), 7.13 (d, J=8.0 Hz, 1H), 6.59 (s, 1H), 5.58 (s, 1H), 5.40 (d, JF=48.4 Hz, 2H), 4.01 (bs, 1H), 3.90 (s, 4H), 2.74-2.56 (m, 4H), 2.15-1.85 (m, 6H), 1.62-1.44 (m, 2H).

Example 160

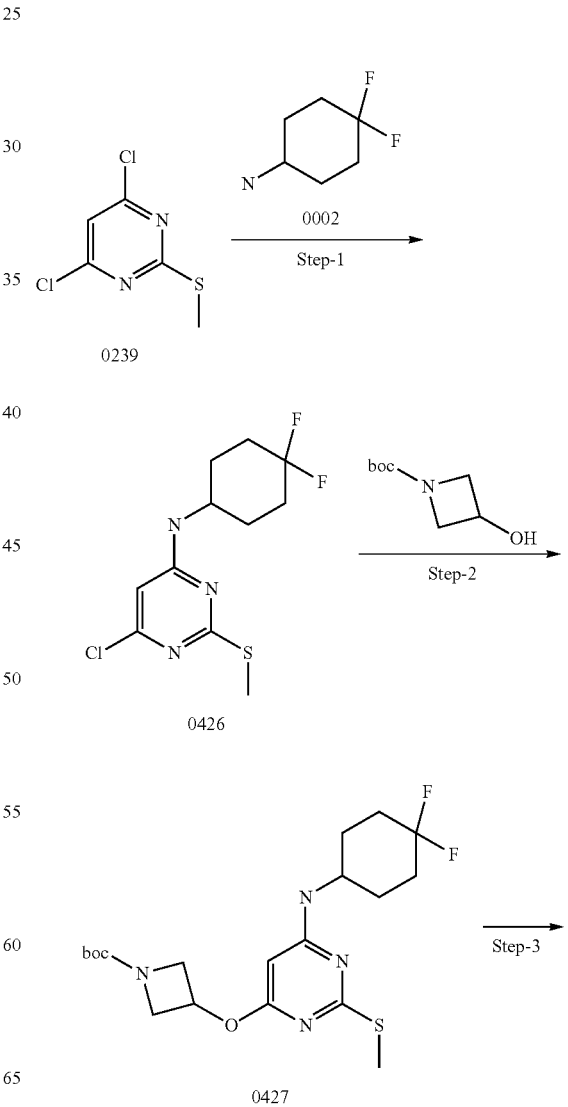

523
-continued

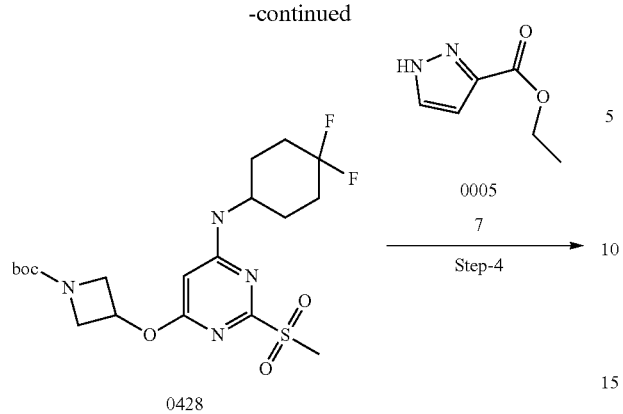

0428

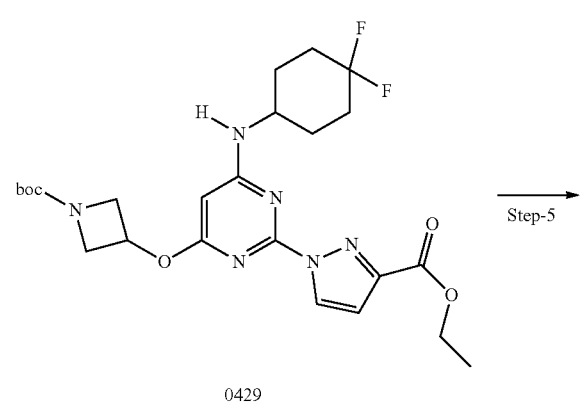

0429

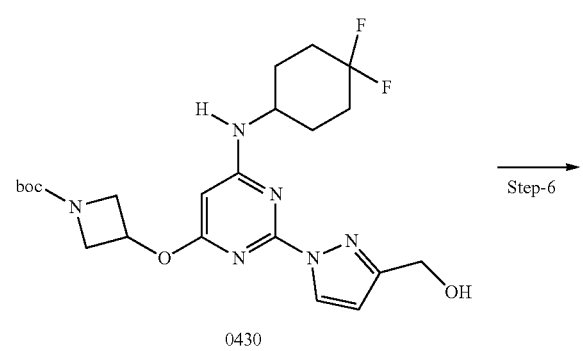

0430

0431

524
-continued

0432

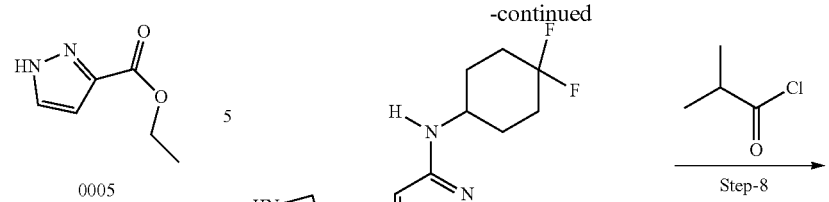

0433

Step 1[0426]: To a solution of 4,6-dichloro-2-(methyl-thio)pyrimidine [0239] (150 g, 768.94 mmol) in acetonitrile (1500 mL) was added 4,4-difluorocyclohexylamine hydrochloride [0002] (158.35 g, 922.733 mmol) and cesium carbonate (526 g, 1614 mmol). The reaction mixture was heated at 75° C. for 16 h. The reaction mixture was filtered to remove cesium carbonate. The filtrate was concentrated under reduced pressure to afford 210 g of 6-chloro-N-(4,4-difluorocyclohexyl)-2-(methylthio)pyrimidin-4-amine [0426] as a pale yellow solid. MS(M+1)+=294.0/295.0.

Step 2[0427]: To a stirred solution of 6-chloro-N-(4,4-difluorocyclohexyl)-2-(methylthio)pyrimidin-4-amine [0426] (100 g, 340.40 mmol) in acetonitrile (1500 mL), was added 1-boc-3-(hydroxy)azetidine (117.9 g, 680.81 mmol) and cesium carbonate (166.37 g, 510.60 mmol). The reaction mixture was heated to 85° C. for 16 h. The reaction mixture was filtered and washed with ethyl acetate (250 mL). The filtrate was concentrated under reduced pressure to afford crude product, which was purified by column chromatography using 7% ethyl acetate in pet ether as solvent to afford 100 g of tert-butyl 3-((6-((4,4-difluorocyclohexyl)amino)-2-(methylthio)pyrimidin-4-yl)oxy)azetidine-1-carboxylate [0427] as an off-white solid. MS(M+1)+=431.6, 432.4.

Step 3[0428]: To a stirred solution of tert-butyl 3-((6-((4,4-difluorocyclohexyl)amino)-2-(methylthio)pyrimidin-4-yl)oxy)azetidine-1-carboxylate [0427] (1.2 g, 2.78 mmol) in tetrahydrofuran (20 mL) was added m-chloroperbenzoic acid (1.44 g, 8.316 mmol) at 0° C. The reaction mixture was stirred at rt for 30 min. The reaction mixture was quenched with aqueous sodium thiosulfate (15 mL) and extracted with ethyl acetate (25 mL). The organic layer was washed with saturated sodium bicarbonate (2×25 mL), water (25 mL) and brine solution (25 mL). The organic layer was dried over anhydrous sodium sulfate, filtered and concentrated under reduced pressure to afford 1.2 g of tert-butyl 3-((6-((4,4-difluorocyclohexyl)amino)-2-(methylsulfonyl)pyrimidin-4-yl)oxy)azetidine-1-carboxylate [0428] as a white solid. MS(M+1)+=463.9.

Step 4[0429]: To a stirred solution of tert-butyl 3-((6-((4,4-difluorocyclohexyl)amino)-2-(methylsulfonyl)pyrimidin-4-yl)oxy)azetidine-1-carboxylate [0428] (2 g, 4.32 mmol) in acetonitrile (15 mL) was added ethyl 1 h-pyrazole-3-carboxylate (1.23 g, 8.648 mmol) and followed by cesium carbonate (2.81 g, 8.64 mmol) under N2 atm. The resultant reaction mixture was heated at 85° C. for 16 h. The reaction mixture was filtered to remove cesium carbonate. The obtained filtrate was concentrated under reduced pressure to afford crude product, which was triturated with pet ether to afford 1.8 g of ethyl 1-(4-((1-(tert-butoxycarbonyl)azetidin-3-yl)oxy)-6-((4,4-difluorocyclohexyl)amino)pyrimidin-2-yl)-1H-pyrazole-3-carboxylate [0429] as an off-white solid. MS(M+1)+=523.

Step 5[0430]: To a stirred solution of ethyl 1-(4-((1-(tert-butoxycarbonyl)azetidin-3-yl)oxy)-6-((4,4-difluorocyclohexyl)amino)pyrimidin-2-yl)-1H-pyrazole-3-carboxylate [0429] (80 g, 153.095 mmol) in tetrahydrofuran (800 mL), was added lithium aluminium hydride ((2 M solution in tetrahydrofuran) 114 mL, 229.64 mmol) at −20° C. The reaction mixture was stirred at same temperature for 30 min and quenched with saturated sodium sulfate. The solid was filtered off and the filtrate was dried over anhydrous sodium sulfate and concentrated under reduced pressure to afford crude product, which was purified by column chromatography using 65% ethyl acetate in pet ether as solvent to afford 31 g of tert-butyl 3-((6-((4,4-difluorocyclohexyl)amino)-2-(3-(hydroxymethyl)-1H-pyrazol-1-yl)pyrimidin-4-yl)oxy)azetidine-1-carboxylate [0430] as an off-white solid. MS(M+1)+=481.2.

Step 6[0431]: To a stirred solution of tert-butyl 3-((6-((4,4-difluorocyclohexyl)amino)-2-(3-(hydroxymethyl)-1H-pyrazol-1-yl)pyrimidin-4-yl)oxy)azetidine-1-carboxylate [0430] (10 g, 20.811 mmol) in dichloromethane (100 mL), was added diethylaminosulfurdiethylaminosulfur trifluoride (4.39 mL, 33.297 mmol) at −20° C. The reaction mixture was stirred at same temperature for 15 min. The reaction mixture was quenched with saturated sodium bicarbonate solution (15 mL), and then extracted with dichloromethane (2×100 mL). The organic layer was washed with brine solution (50 mL), dried over anhydrous sodium sulfate, filtered and concentrated under reduced pressure to afford 10.5 g crude product, which was purified by column chromatography using 42% ethyl acetate in pet ether as solvent to afford 3.8 g of tert-butyl 3-((6-((4,4-difluorocyclohexyl)amino)-2-(3-(fluoromethyl)-1H-pyrazol-1-yl)pyrimidin-4-yl)oxy)azetidine-1-carboxylate [0431] as an off-white solid. MS(M+1)+=483.3.

Step 7 [0432]: To a stirred solution of tert-butyl 3-((6-((4,4-difluorocyclohexyl)amino)-2-(3-(fluoromethyl)-1H-pyrazol-1-yl)pyrimidin-4-yl)oxy)azetidine-1-carboxylate [0431] (14 g, 29.015 mmol) in dicholoromethane (140 mL), was added trifluoroacetic acid (41 g, 362.69 mmol) at 0° C. The reaction mixture was stirred at rt for 6 h. The reaction mixture was concentrated under reduced pressure, to the residue water (15 mL) was added and neutralized with saturated sodium bicarbonate solution (25 mL), extracted with ethyl acetate (2×250 mL), the combined organic extracts were washed with brine (25 mL), dried over anhydrous sodium sulfate, filtered and concentrated under reduced pressure to afford 14.2 g of 1-(3-((6-((4,4-difluorocyclohexyl)amino)-2-(3-(fluoromethyl)-1H-pyrazol-1-yl)pyrimidin-4-yl)oxy)azetidin-1-yl)-2-methylpropan-1-one [0432] as an off-white solid. MS(M+1)+=382.8.

Step 8[0433]: To a stirred solution of 1-(3-((6-((4,4-difluorocyclohexyl)amino)-2-(3-(fluoromethyl)-1H-pyrazol-1-yl)pyrimidin-4-yl)oxy)azetidin-1-yl)-2-methylpropan-1-one [0432] (14.2 g, 37.135 mmol) in dicholoromethane (150 mL), was added triethylamine (10.35 mL, 74.27 mmol) and iso-butyryl chloride [0353] (7.9 g, 74.27 mmol) at 0° C. The reaction mixture was stirred at same temperature for 15 min and partitioned between dicholoromethane (500 mL) and water (50 mL). The organic layer was washed with brine (50 mL), dried over anhydrous sodium sulfate, filtered and concentrated under reduced pressure to afford crude product, which was purified by column chromatography using 28% ethyl acetate in pet ether as solvent to afford 11.4 g of 1-(3-((6-((4,4-difluorocyclohexyl)amino)-2-(3-(fluoromethyl)-1H-pyrazol-1-yl)pyrimidin-4-yl)oxy)azetidin-1-yl)-2-methylpropan-1-one [0433], Compound 290 as a white solid. MS(M+1)+=453.2. $^1$H NMR (400 MHz, DMSO-d6) δ 8.54 (d, J=2.4 Hz, 1H), 7.42 (d, J=7.6 Hz, 1H), 6.61 (s, 1H), 5.80 (s, 1H), 5.49-5.37 (d, JF=48.0 Hz, 2H), 5.44-5.41 (m, 1H), 4.46 (bs, 3H), 3.95 (bs, 3H), 2.15-1.90 (m, 6H), 1.67-1.55 (m, 2H), 0.98 (d, J=6.8 Hz, 6H).

Example 161

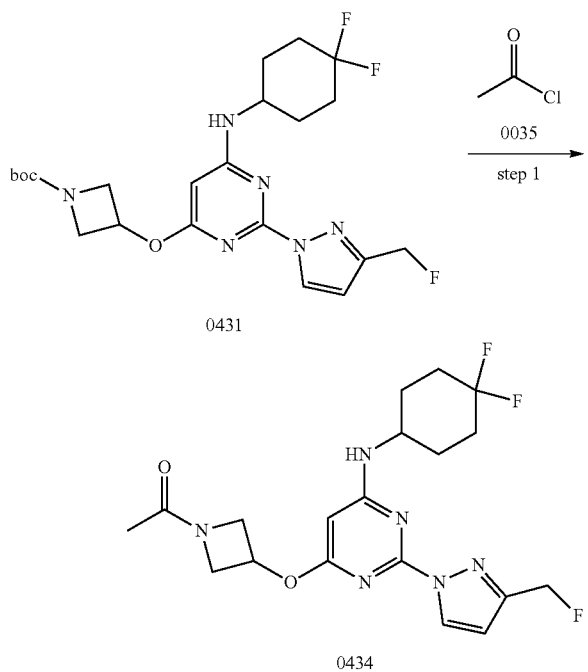

Step 1[0434]: To a solution of tert-butyl3-((6-((4,4-difluorocyclohexyl)amino)-2-(3-(fluoromethyl)-1H-pyrazol-1-yl)pyrimidin-4-yl)oxy)azetidine-1-carboxylate [0431] (0.25 g, 0.51 mmol) in dichloromethane was added trifluoroacetic acid (0.59 g, 1.03 mmol) at 0° C. and the reaction mixture was stirred at rt. After 16 h, triethylamine (~1.5 mL, until reaction mixture become basic) was added to the reaction mixture at 0° C., followed by acetyl chloride [0035] (0.082 g, 1.036 mmol) and reaction mixture was stirred at rt. After 10 min, the reaction mixture was quenched with water, extracted with chloroform, washed with water and brine solution. The combined organic layer was dried over anhydrous sodium sulfate, filtered and concentrated under reduced pressure to afford colorless oil, which was purified in the Reveleris flash system instrument using ethyl acetate in hexane as solvent in 12 g column, to afford 0.11 g of 1-(3-((6-((4,4-difluorocyclohexyl)amino)-2-(3-(fluoromethyl)-1H-pyrazol-1-yl)pyrimidin-4-yl)oxy)azetidin-1-yl)ethan-1-one [0434], Compound 289 as white solid. MS(M+1)+=425.2. $^1$H NMR (400 MHz, DMSO-d6) δ 8.59 (bs, 1H), 7.66 (bs, 1H), 6.67 (s, 1H), 5.75 (bs, 1H), 5.45 (d, JF=48 Hz, 3H), 4.56 (bs, 1H), 4.28 (bs, 1H), 4.13 (dd, J=9.9, 4.0 Hz, 2H), 3.83 (dd, J=10.8, 4.0 Hz, 1H), 2.15-1.88 (m, 6H), 1.80 (s, 3H), 1.65-1.52 (m, 2H).

Example 162

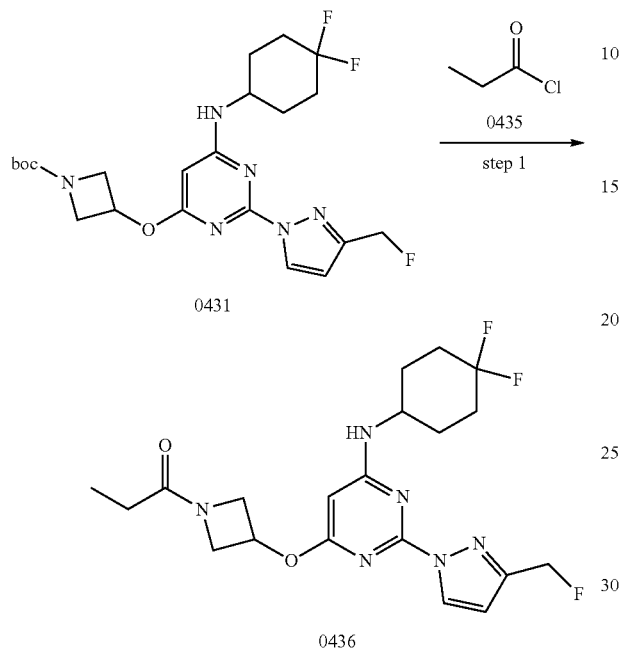

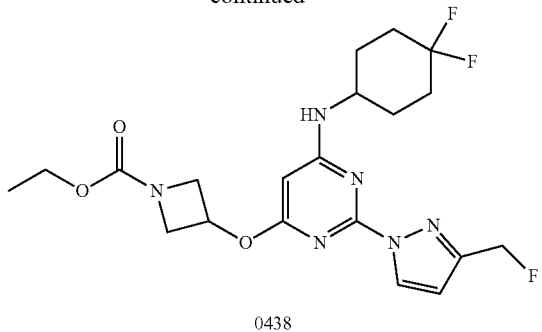

Step 1[0438]: The procedure is similar to step 1[0434] in example 161. 0.25 g of tert-butyl 3-((6-((4,4-difluorocyclohexyl)amino)-2-(3-(fluoromethyl)-1H-pyrazol-1-yl)pyrimidin-4-yl)oxy)azetidine-1-carboxylate [0431] gave 0.13 g of ethyl 3-((6-((4,4-difluorocyclohexyl)amino)-2-(3-(fluoromethyl)-1H-pyrazol-1-yl)pyrimidin-4-yl)oxy)azetidine-1-carboxylate[0438], Compound 287 as white solid. MS(M+1)+=455.2, $^1$H NMR (400 MHz, DMSO-d6) δ 8.52 (d, J=2.4 Hz, 1H), 7.42 (d, J=7.2 Hz, 1H), 6.61 (s, 1H), 5.80 (s, 1H), 5.45 (d, JF=48 Hz, 2H), 5.43-5.38 (m, 1H), 4.42-4.30 (m, 2H), 4.03 (q, J=7.1 Hz, 2H), 3.91 (dd, J=10.3, 4.2 Hz, 3H), 2.15-1.90 (m, 6H), 1.72-1.55 (m, 2H), 1.19 (t, J=7.1 Hz, 3H).

Step 1[0436]: The procedure is similar to step 1[0434] in example 161. 0.25 g of tert-butyl3-((6-((4,4-difluorocyclohexyl)amino)-2-(3-(fluoromethyl)-1H-pyrazol-1-yl)pyrimidin-4-yl)oxy)azetidine-1-carboxylate [0431] and 0.096 g of propionyl chloride [0435] gave 0.12 g of 1-(3-((6-((4,4-difluorocyclohexyl)amino)-2-(3-(fluoromethyl)-1H-pyrazol-1-yl)pyrimidin-4-yl)oxy)azetidin-1-yl)propan-1-one [0436], Compound 288 as white solid. MS(M+1)$^+$=439.7. $^1$H NMR (400 MHz, DMSO-d6) δ 8.53 (d, J=2.4 Hz, 1H), 7.43 (d, J=7.6 Hz, 1H), 6.60 (s, 1H), 5.80 (s, 1H), 5.48 (d, JF=48 Hz, 2H), 5.42-5.38 (m, 1H), 4.55 (bs, 2H), 4.10 (bs, 3H), 2.18-1.82 (m, 8H), 1.72-1.56 (m, 2H), 1.00 (t, J=7.5 Hz, 3H).

Example 163

Example 164

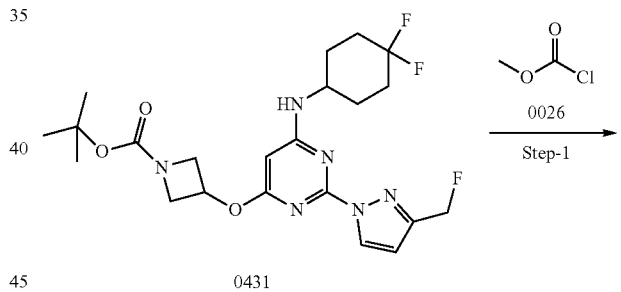

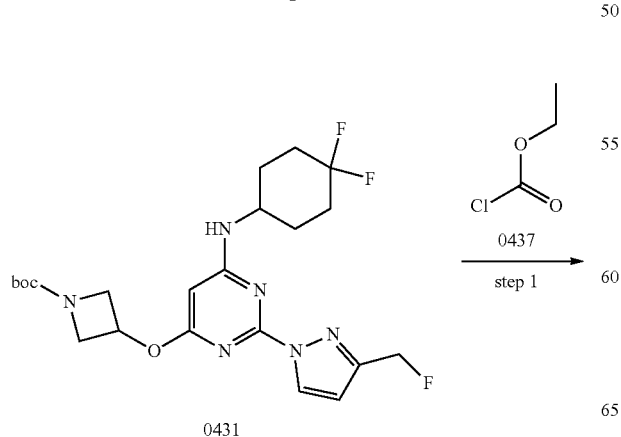

Step 1 [0439]: The procedure is similar to step 1[0434] in example 161. 0.25 g of tert-butyl 3-((6-((4,4-difluorocyclohexyl)amino)-2-(3-(fluoromethyl)-1H-pyrazol-1-yl)pyrimidin-4-yl)oxy)azetidine-1-carboxylate [0431] and 0.097 g of methyl chloroformate [0026] gave 0.13 g of methyl 3-((6-

529

((4,4-difluorocyclohexyl)amino)-2-(3-(fluoromethyl)-1H-pyrazol-1-yl)pyrimidin-4-yl)oxy)azetidine-1-carboxylate [0439], Compound 291. MS(M+1)⁺=441, ¹H NMR (400 MHz, DMSO-d6) δ 8.52 (d, J=2.7 Hz, 1H), 7.42 (d, J=7.7 Hz, 1H), 6.61 (d, J=2.6 Hz, 1H), 5.79 (s, 1H), 5.43 (d, JF=48 Hz, 2H), 5.46-5.38 (m, 1H), 4.36 (dd, J=9.8, 6.6 Hz, 2H), 3.94 (dd, J=10.0, 4.3 Hz, 3H), 3.60 (s, 3H), 2.15-1.90 (m, 6H), 1.70-1.55 (m, 2H).

Example 165

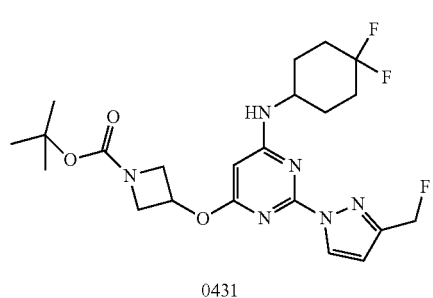

0431

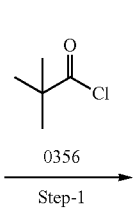

0356

Step-1

530

-continued

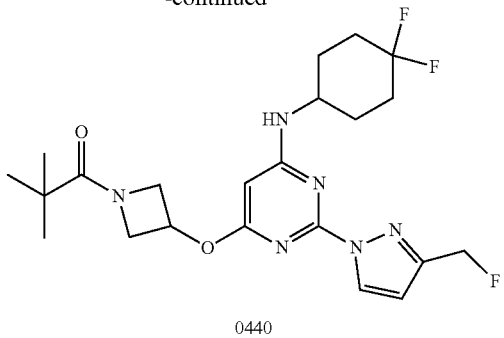

0440

Step 1 [0440]: The procedure is similar to step 1[0434] in example 161. 0.25 g of tert-butyl 3-((6-((4,4-difluorocyclohexyl)amino)-2-(3-(fluoromethyl)-1H-pyrazol-1-yl)pyrimidin-4-yl)oxy)azetidine-1-carboxylate [0431] and 0.124 g of Pivaloyl Chloride [0356] gave 0.13 g of 1-(3-((6-((4,4-difluorocyclohexyl)amino)-2-(3-(fluoromethyl)-1H-pyrazol-1-yl)pyrimidin-4-yl)oxy)azetidin-1-yl)-2,2-dimethyl-propan-1-one [0440], Compound 293. MS(M+1)⁺=467, ¹H NMR (400 MHz, DMSO-d6) δ 8.54 (d, J=2.6 Hz, 1H), 7.42 (d, J=7.7 Hz, 1H), 6.67-6.54 (m, 1H), 5.80 (s, 1H), 5.43 (d, JF=48 Hz, 2H) 5.46-5.38 (m, 1H), 4.53 (bs, 2H), 4.10 (bs, 2H), 3.90 (bs, 1H), 2.13-1.88 (m, 6H), 1.68-1.55 (m, 2H), 1.15 (s, 9H).

Example 166

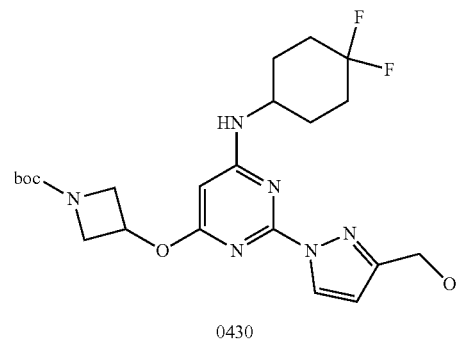

0430

TFA/MDC

Step-1

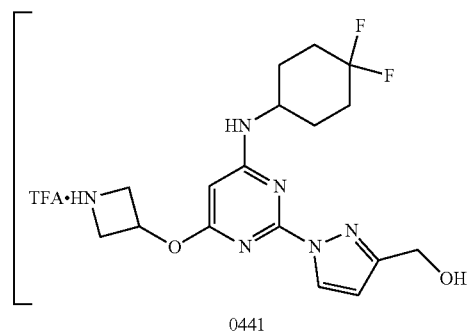

0441

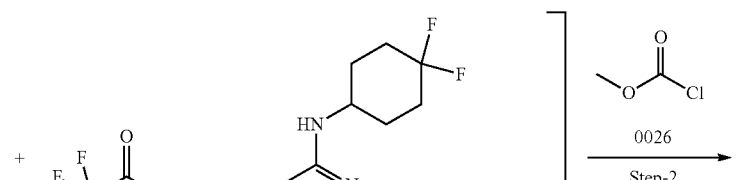

0442

0026

Step-2

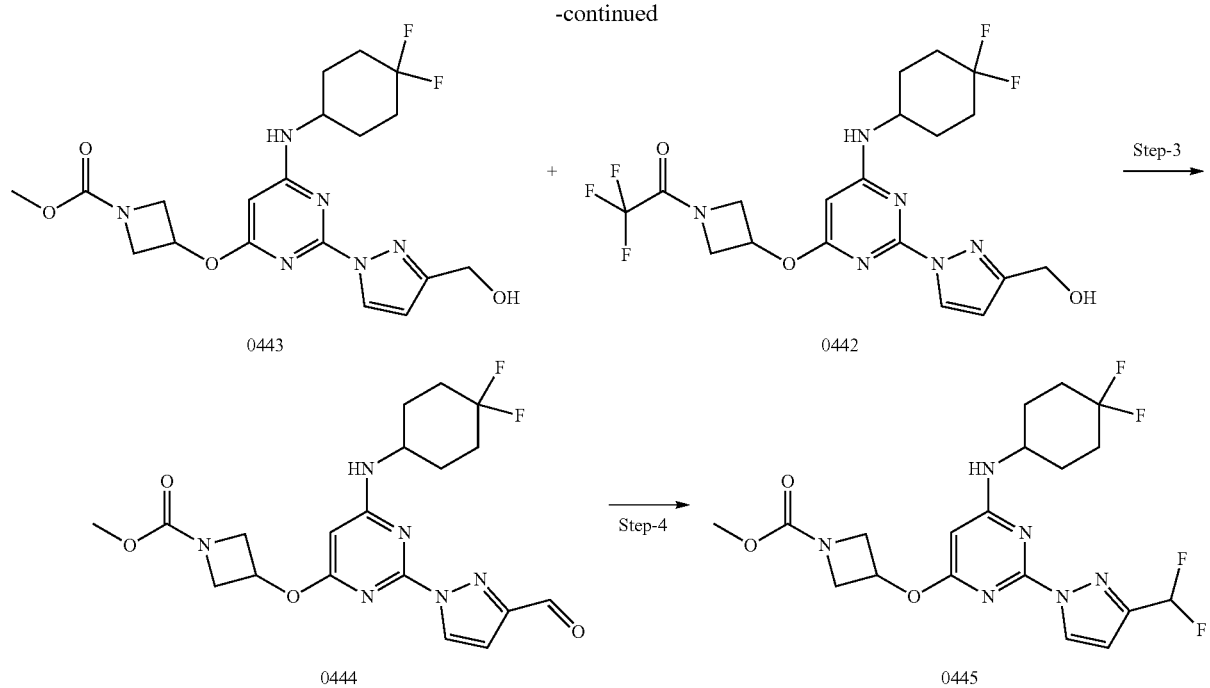

Step 1[0441 and 0442]: The procedure is similar to step 4[0025] in example 5. 1 g of tert-butyl 3-((6-((4,4-difluorocyclohexyl)amino)-2-(3-(hydroxymethyl)-1H-pyrazol-1-yl)pyrimidin-4-yl)oxy)azetidine-1-carboxylate [0430] gave a mixture of (1-(4-(azetidin-3-yloxy)-6-((4,4-difluorocyclohexyl)amino)pyrimidin-2-yl)-1H-pyrazol-3-yl)methanol [0441] and 1-(3-((6-((4,4-difluorocyclohexyl)amino)-2-(3-(hydroxymethyl)-1H-pyrazol-1-yl)pyrimidin-4-yl)oxy)azetidin-1-yl)-2,2,2-trifluoroethan-1-one [0442] and taken as such for next step without isolation.

Step 2[0443 and 0442] (0442): The procedure is similar to Step 5[0027] in example 5. A mixture of (1-(4-(azetidin-3-yloxy)-6-((4,4-difluorocyclohexyl)amino)pyrimidin-2-yl)-1H-pyrazol-3-yl)methanol [0441], 1-(3-((6-((4,4-difluorocyclohexyl)amino)-2-(3-(hydroxymethyl)-1H-pyrazol-1-yl)pyrimidin-4-yl)oxy)azetidin-1-yl)-2,2,2-trifluoroethan-1-one [0442] and 1.05 g of methyl chloroformate [0026] gave 0.2 g of methyl 3-((6-((4,4-difluorocyclohexyl)amino)-2-(3-(hydroxymethyl)-1H-pyrazol-1-yl)pyrimidin-4-yl)oxy)azetidine-1-carboxylate [0443]. MS(M+1)+=439, and 0.175 g of 1-(3-((6-((4,4-difluorocyclohexyl)amino)-2-(3-(hydroxymethyl)-1H-pyrazol-1-yl)pyrimidin-4-yl)oxy)azetidin-1-yl)-2,2,2-trifluoroethan-1-one [0442], Compound 319. MS(M+1)+=477, ¹H NMR (400 MHz, DMSO-d6) δ 8.45 (d, J=2.7 Hz, 1H), 7.37 (d, J=7.7 Hz, 1H), 6.46 (d, J=2.7 Hz, 1H), 5.77 (s, 1H), 5.52 (tt, J=6.7, 4.3 Hz, 1H), 4.86 (m, 2H), 4.59-4.50 (m, 1H), 4.52 (d, J=5.8 Hz, 2H), 4.43 (m, 1H), 4.12 (m, 1H), 2.21-1.83 (m, 6H), 1.63 (d, J=11.4 Hz, 2H).

Step 3[0444]: To a solution of methyl 3-((6-((4,4-difluorocyclohexyl)amino)-2-(3-(hydroxymethyl)-1H-pyrazol-1-yl)pyrimidin-4-yl)oxy)azetidine-1-carboxylate [0443] (0.3 g, 0.684 mmol) in dichloromethane (7 mL) was added manganese dioxide (0.29 g, 3.42 mmol) and the resultant reaction mixture was stirred at rt for 20 h. The reaction mixture was filtered and the filtrate was concentrated to afford methyl 3-((6-((4,4-difluorocyclohexyl)amino)-2-(3-formyl-1H-pyrazol-1-yl)pyrimidin-4-yl)oxy)azetidine-1-carboxylate [0444] as an off-white solid (0.24 g). MS(M+1)+=437.

Step 4[0445]: The procedure is similar to Step 3[0012] in example 2. 0.18 g of methyl 3-((6-((4,4-difluorocyclohexyl)amino)-2-(3-formyl-1H-pyrazol-1-yl)pyrimidin-4-yl)oxy)azetidine-1-carboxylate [0444] gave 0.09 g of methyl 3-((6-((4,4-difluorocyclohexyl)amino)-2-(3-(difluoromethyl)-1H-pyrazol-1-yl)pyrimidin-4-yl)oxy)azetidine-1-carboxylate [0445], Compound 295. MS(M+1)+=459, ¹H NMR (400 MHz, DMSO-d6) δ 8.59 (d, J=2.8 Hz, 1H), 7.00 (t, JF=54.8 Hz, 1H) 6.72 (d, J=2.7 Hz, 1H), 5.81 (s, 1H), 5.39 (tt, J=6.7, 4.2 Hz, 1H), 4.35 (ddd, J=9.7, 6.6, 1.2 Hz, 2H), 4.13-3.80 (m, 3H), 3.59 (s, 3H), 2.10-1.80 (m, 6H), 1.73-1.50 (m, 2H).

Example 167

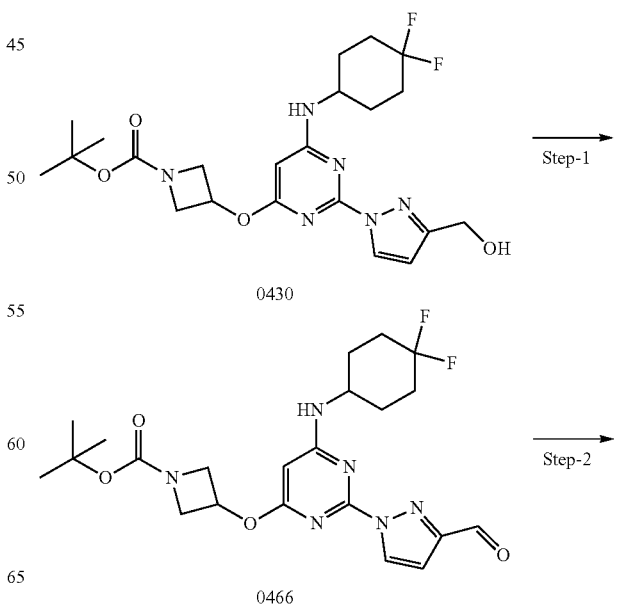

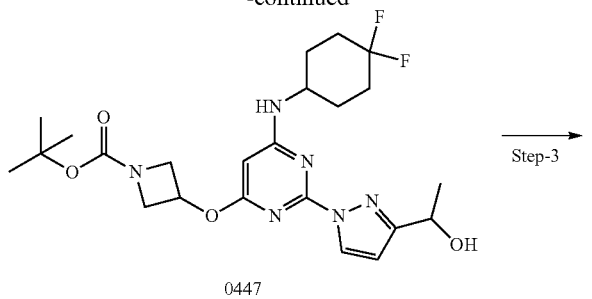

0447

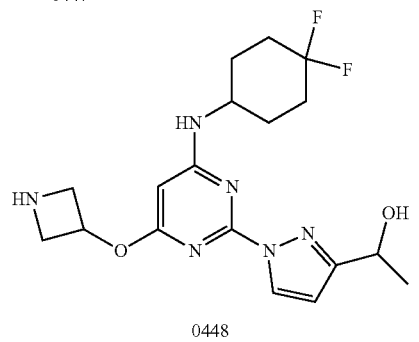

0448

Step 1[0466]: The procedure is similar to Step 3[0444] in example 166. 1 g of tert-butyl 3-((6-((4,4-difluorocyclohexyl)amino)-2-(3-(hydroxymethyl)-1H-pyrazol-1-yl)pyrimidin-4-yl)oxy)azetidine-1-carboxylate [0430] gave 0.78 g of tert-butyl 3-((6-((4,4-difluorocyclohexyl)amino)-2-(3-formyl-1H-pyrazol-1-yl)pyrimidin-4-yl)oxy) azetidine-1-carboxylate [0466]. MS(M+1)+=479.

Step 2[0447]: The procedure is similar to Step 2[049] in example 10. 0.78 g of tert-butyl 3-((6-((4,4-difluorocyclohexyl)amino)-2-(3-formyl-1H-pyrazol-1-yl)pyrimidin-4-yl)oxy) azetidine-1-carboxylate [0466] gave 0.3 g of tert-butyl 3-((6-((4,4-difluorocyclohexyl)amino)-2-(3-(1-hydroxyethyl)-1H-pyrazol-1-yl)pyrimidin-4-yl)oxy)azetidine-1-carboxylate [0447]. MS(M+1)+=495.

Step 3[0448]: To an ice cooled solution of tert-butyl 3-((6-((4,4-difluorocyclohexyl)amino)-2-(3-(1-hydroxyethyl)-1H-pyrazol-1-yl)pyrimidin-4-yl)oxy)azetidine-1-carboxylate [0447] (0.3 g, 0.606 mmol) in methanol (7 mL) was purged dry hydrogen chloride gas for 10 min. The reaction mixture was concentrated to afford 1-(1-(4-(azetidin-3-yloxy)-6-((4,4-difluorocyclohexyl)amino)pyrimidin-2-yl)-1H-pyrazol-3-yl)ethan-1-ol hydrochloride salt [0448] as a yellow solid (0.33 g). MS(M+1)+=396.

Example 168

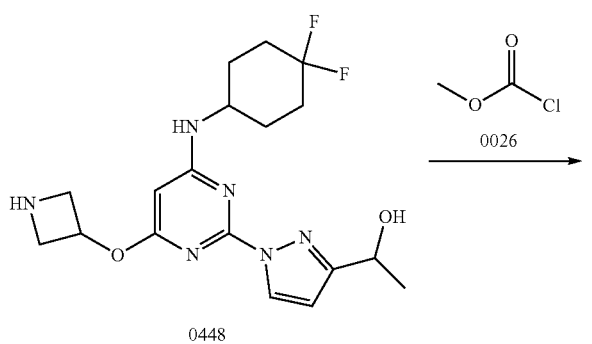

0448

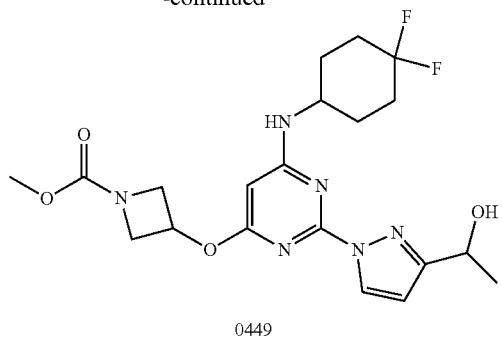

0449

Step 1 [0449]: The procedure is similar to Step 8[0433] in example 160. 0.18 g of 1-(1-(4-(azetidin-3-yloxy)-6-((4,4-difluorocyclohexyl)amino)pyrimidin-2-yl)-1H-pyrazol-3-yl)ethan-1-ol Hydrochloride salt [0448] and 0.047 g of methyl chloroformate [0026] gave 0.075 g of methyl 3-((6-((4,4-difluorocyclohexyl)amino)-2-(3-(1-hydroxyethyl)-1H-pyrazol-1-yl)pyrimidin-4-yl)oxy)azetidine-1-carboxylate [0449], Compound 307. MS (M+1)+=453, $^1$H NMR (400 MHz, Chloroform-d) δ 8.36 (d, J=2.6 Hz, 1H), 6.48 (d, J=2.7 Hz, 1H), 5.60 (s, 1H), 5.40 (m, 1H), 3.32 (s, 1H), 5.14 (m, 1H), 4.53-4.33 (m, 2H), 4.11 (dd, J=10.1, 4.3 Hz, 2H), 3.72 (s, 3H), 3.58 (s, 1H), 2.28 (s, 1H), 2.24-2.03 (m, 5H), 2.00-1.80 (m, 2H), 1.75-1.50 (m, 3H).

Example 169

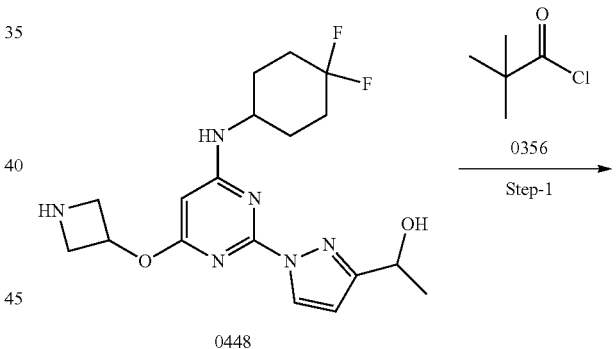

0448

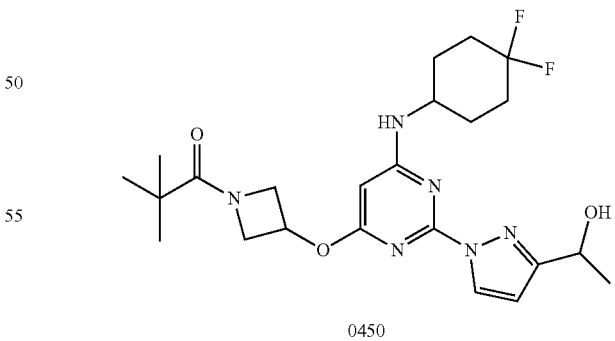

0450

Step 4[0450]: The procedure is similar to Step 8[0433] in example 160. 0.33 g of 1-(1-(4-(azetidin-3-yloxy)-6-((4,4-difluorocyclohexyl)amino)pyrimidin-2-yl)-1H-pyrazol-3-yl)ethan-1-ol Hydrochloride salt [0448] and 0.11 g of pivaloyl chloride [0356] gave 0.17 g of 1-(3-((6-((4,4-difluorocyclohexyl)amino)-2-(3-(1-hydroxyethyl)-1H- pyrazol-1-yl)pyrimidin-4-yl)oxy)azetidin-1-yl)-2,2-dimethylpropan-1-one [0450], Compound 315. MS(M+1)$^+$= 479, $^1$H NMR (400 MHz, DMSO-d6) δ 8.48 (s, 1H), 7.64 (m, 1H), 6.47 (d, J=2.5 Hz, 1H), 5.71-5.68 (m, 1H), 5.36 (s, 1H), 5.27-5.18 (m, 1H), 4.93-4.66 (m, 2H), 4.29 (m, 2H), 3.83 (m, 1H), 2.26-1.80 (m, 6H), 1.55 (m, 2H), 1.39 (d, J=6.5 Hz, 3H), 1.12 (s, 9H).

Example 170

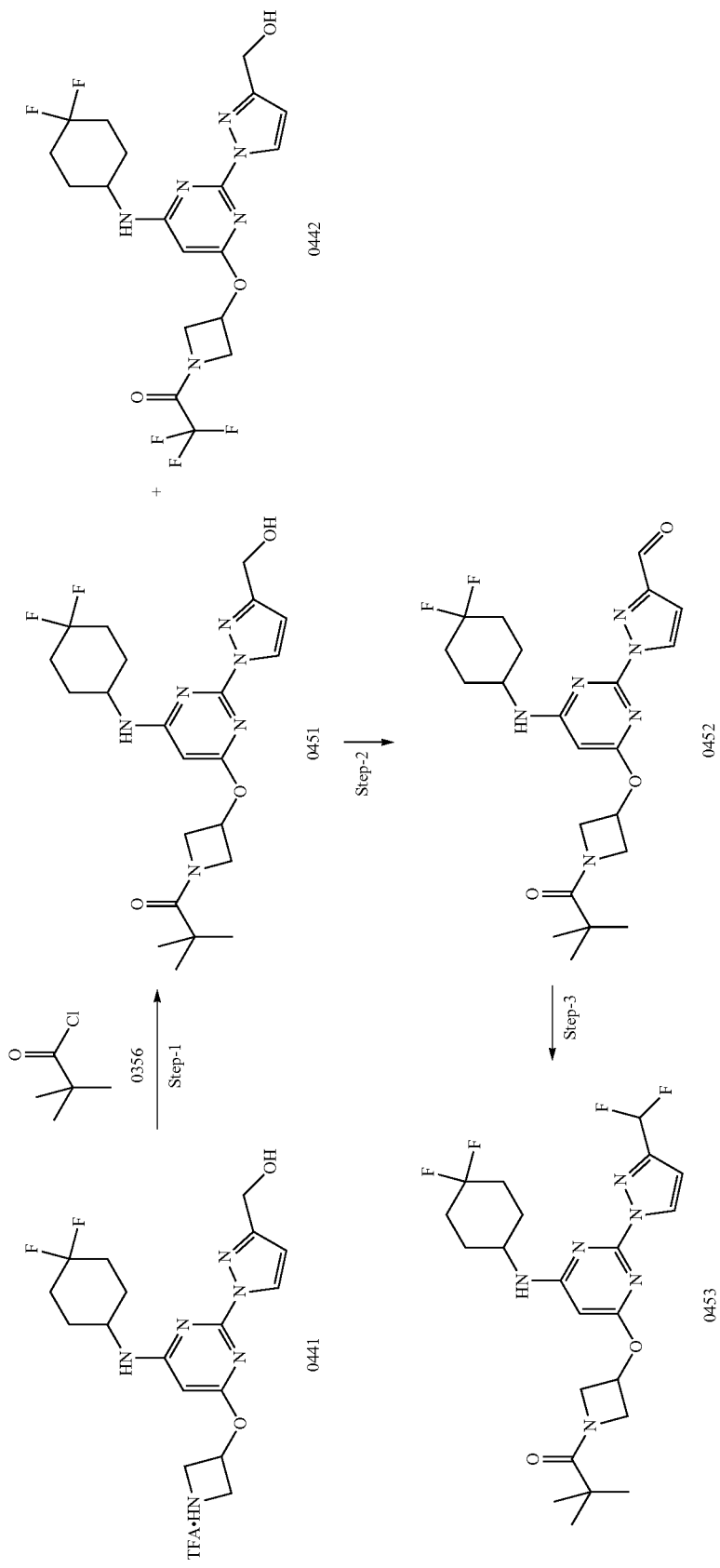

Step 1[0451 and 0442]: The procedure is similar to Step 2[0443 and 0442] in example 166. A mixture of (1-(4-(azetidin-3-yloxy)-6-((4,4-difluorocyclohexyl)amino)pyrimidin-2-yl)-1H-pyrazol-3-yl)methanol [0441], 1-(3-((6-((4,4-difluorocyclohexyl)amino)-2-(3-(hydroxymethyl)-1H-pyrazol-1-yl)pyrimidin-4-yl)oxy)azetidin-1-yl)-2,2,2-trifluoroethan-1-one [0442] and 1.05 g of Pivaloyl Chloride [0356] gave 0.5 g of 1-(3-((6-((4,4-difluorocyclohexyl)amino)-2-(3-(hydroxymethyl)-1H-pyrazol-1-yl)pyrimidin-4-yl)oxy)azetidin-1-yl)-2,2-dimethylpropan-1-one [0451]. MS(M+1)+=465 and 0.177 g of 1-(3-((6-((4,4-difluorocyclohexyl)amino)-2-(3-(hydroxymethyl)-1H-pyrazol-1-yl)pyrimidin-4-yl)oxy)azetidin-1-yl)-2,2,2-trifluoroethan-1-one [0442]. MS(M+1)+=477.

Step 2[0452] The procedure is similar to Step 3[0444] in example 166. 0.5 g of 1-(3-((6-((4,4-difluorocyclohexyl)amino)-2-(3-(hydroxymethyl)-1H-pyrazol-1-yl)pyrimidin-4-yl)oxy)azetidin-1-yl)-2,2-dimethylpropan-1-one [0451] gave 0.3 g of 1-(4-((4,4-difluorocyclohexyl)amino)-6-((1-pivaloylazetidin-3-yl)oxy)pyrimidin-2-yl)-1H-pyrazole-3-carbaldehyde [0452]. MS(M+1)+=463.2.

Step 3[0453]: The procedure is similar to Step 3[0012] in example 2. 0.2 g of 1-(4-((4,4-difluorocyclohexyl)amino)-6-((1-pivaloylazetidin-3-yl)oxy)pyrimidin-2-yl)-1H-pyrazole-3-carbaldehyde [0452] gave 0.13 g of 1-(3-((6-((4,4-difluorocyclohexyl)amino)-2-(3-(difluoromethyl)-1H-pyrazol-1-yl)pyrimidin-4-yl)oxy)azetidin-1-yl)-2,2-dimethylpropan-1-one [0453], Compound 298. MS(M+1)+= 485.2, MR=186.7-189.6° C., $^1$H NMR (400 MHz, DMSO-d6) δ 8.62 (s, 1H), 7.50 (d, J=74.8 Hz, 1H), 7.03 (t, JF=54 Hz, 1H), 6.74 (s, 1H), 5.83 (s, 1H), 5.42-5.36 (m, 1H), 4.53 (bs, 2H), 4.10 (bs, 2H), 3.94 (bs, 1H), 2.19-1.77 (m, 6H), 1.60-1.52 (m, 2H), 1.11 (s, 9H).

Step 1[0454] The procedure is similar to Step 3[0444] in example 166. 0.2 g of 1-(3-((6-((4,4-difluorocyclohexyl)amino)-2-(3-(hydroxymethyl)-1H-pyrazol-1-yl)pyrimidin-4-yl)oxy)azetidin-1-yl)-2,2,2-trifluoroethan-1-one [0442] gave 0.2 g of 1-(4-((4,4-difluorocyclohexyl)amino)-6-((1-(2,2,2-trifluoroacetyl)azetidin-3-yl)oxy)pyrimidin-2-yl)-1H-pyrazole-3-carbaldehyde [0454]. MS(M+1)+=475.2.

Step 2[0455]: The procedure is similar to Step 3[0012] in example 2. 0.2 g of 1-(4-((4,4-difluorocyclohexyl)amino)-6-((1-(2,2,2-trifluoroacetyl)azetidin-3-yl)oxy)pyrimidin-2-yl)-1H-pyrazole-3-carbaldehyde [0454] gave 0.1 g of 1-(3-((6-((4,4-difluorocyclohexyl)amino)-2-(3-(difluoromethyl)-1H-pyrazol-1-yl)pyrimidin-4-yl)oxy)azetidin-1-yl)-2,2,2-trifluoroethan-1-one [0455], Compound 299. MS (M+1)+= 497 0.2, MR=164.7-170.8° C., $^1$H NMR (400 MHz, DMSO-d6) δ 8.62 (d, J=2.8 Hz, 1H), 7.53 (d, J=7.6 Hz, 1H), 7.03 (t, JF=54 Hz, 1H), 6.74 (d, J=2.8 Hz, 1H), 5.86 (s, 1H), 5.60-5.30 (m, 1H), 4.86 (bs, 1H), 4.56 (bs, 1H), 4.45 (bs, 1H), 4.13 (bs, 1H), 3.95 (bs, 1H), 2.18-1.82 (m, 6H), 1.64 (t, J=10.8 Hz, 2H).

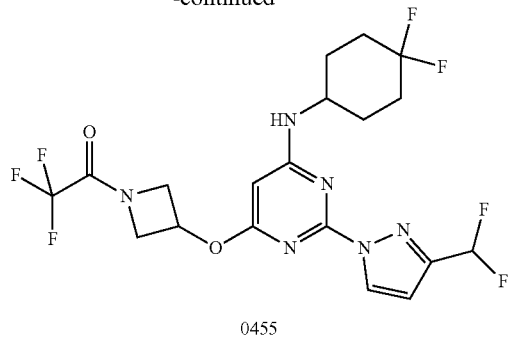

0455

Example 171

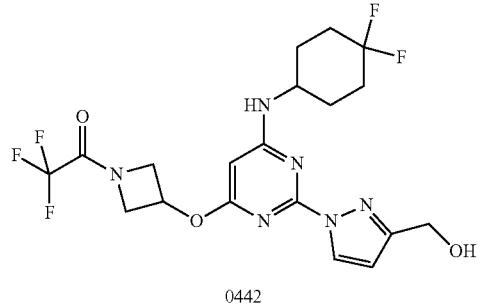

0442

Step-1

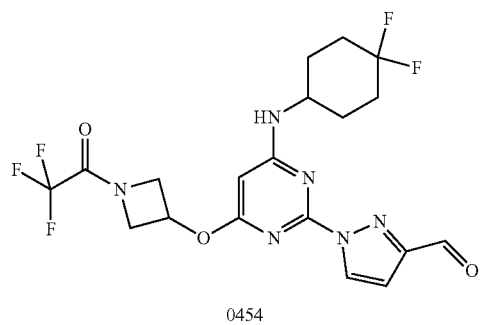

0454

Step-2

Example 172

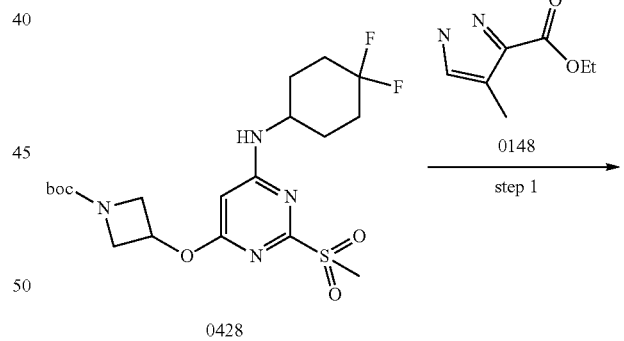

0428 step 1
0148

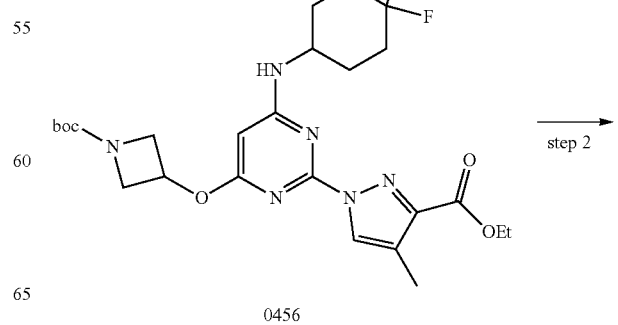

0456 step 2

541

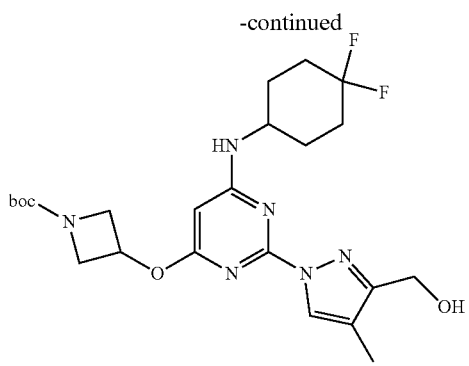

0457

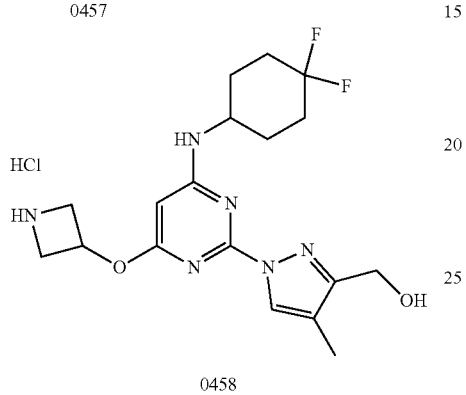

0458

542

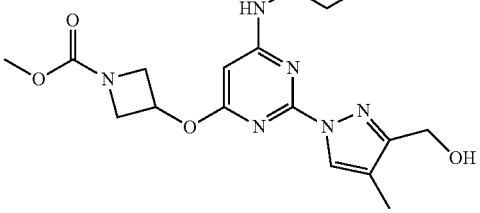

0459

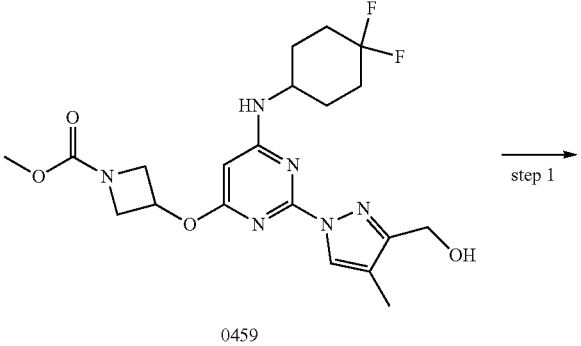

0460

Step 1[0456]: The procedure is similar to step 2 [0274] in Example 99 (at 120° C.). 5 g of tert-butyl 3-((6-((4,4-difluorocyclohexyl)amino)-2-(methylsulfonyl)pyrimidin-4-yl)oxy)azetidine-1-carboxylate [0428] gave 3 g of Ethyl 1-(4-(((1-(tert-butoxycarbonyl)azetidin-3-yl)oxy)-6-((4,4-difluorocyclohexyl)amino)pyrimidin-2-yl)-4-methyl-1H-pyrazole-3-carboxylate [0456] as off-white solid. MS(M+1)+=537.2.

Step 2[0457]: The procedure is similar to step 2[0019] in Example 4. 6 g of Ethyl 1-(4-(((1-(tert-butoxycarbonyl)azetidin-3-yl)oxy)-6-((4,4-difluorocyclohexyl)amino)pyrimidin-2-yl)-4-methyl-1H-pyrazole-3-carboxylate [0456] gave 5 g of tert-Butyl 3-((6-((4,4-difluorocyclohexyl)amino)-2-(3-(hydroxymethyl)-4-methyl-1H-pyrazol-1-yl)pyrimidin-4-yl)oxy)azetidine-1-carboxylate [0457] as off-white solid. MS(M+1)+=495.2.

Step 3[0458]: The procedure is similar to step 1[0292] in Example 107. 5 g of tert-Butyl 3-((6-((4,4-difluorocyclohexyl)amino)-2-(3-(hydroxymethyl)-4-methyl-1H-pyrazol-1-yl)pyrimidin-4-yl)oxy)azetidine-1-carboxylate [0457] gave 3.5 g of (1-(4-(azetidin-3-yloxy)-6-((4,4-difluorocyclohexyl)amino)pyrimidin-2-yl)-4-methyl-1H-pyrazol-3-yl)methanol HCl [0458] as an brown solid. MS(M+1)+=395.2.

Example 173

Step 1[0459]: The procedure is similar to step 8[0433] in Example 160. 1 g of (1-(4-(azetidin-3-yloxy)-6-((4,4-difluorocyclohexyl)amino)pyrimidin-2-yl)-4-methyl-1H-pyrazol-3-yl)methanol.HCl [0458] gave 0.6 g of Methyl 3-((6-((4,4-difluorocyclohexyl)amino)-2-(3-(hydroxymethyl)-4-methyl-1H-pyrazol-1-yl)pyrimidin-4-yl)oxy)azetidine-1-carboxylate [0459] as an off-white solid. MS(M+1)+=453.2

Step 2[0460]: The procedure is similar to step 3[0012] in Example 2. 0.6 g of methyl 3-((6-((4,4-difluorocyclohexyl)amino)-2-(3-(hydroxymethyl)-4-methyl-1H-pyrazol-1-yl)pyrimidin-4-yl)oxy)azetidine-1-carboxylate [0459] gave 0.3 g of methyl 3-((6-((4,4-difluorocyclohexyl)amino)-2-(3-(fluoromethyl)-4-methyl-1H-pyrazol-1-yl)pyrimidin-4-yl)oxy)azetidine-1-carboxylate [0460], Compound 310 as white solid. MS(M+1)+=455.2, $^1$H NMR (400 MHz, DMSO-d6) δ 8.31 (s, 1H), 7.37 (d, J=7.7 Hz, 1H), 5.76 (s, 1H), 5.45 (d, JF=48 Hz, 3H), 4.36 (ddd, J=9.6, 6.6, 1.1 Hz, 2H), 3.93 (ddd, J=9.6, 4.3, 1.1 Hz, 3H), 3.60 (s, 3H), 2.14 (s, 3H), 2.11-1.88 (m, 6H), 1.70-1.54 (m, 2H).

Example 174

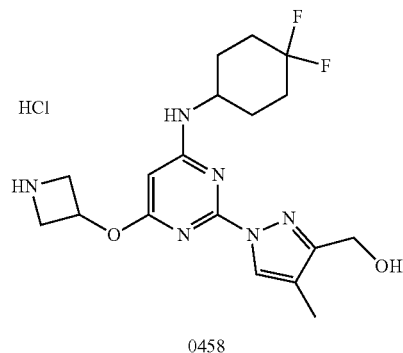

0458

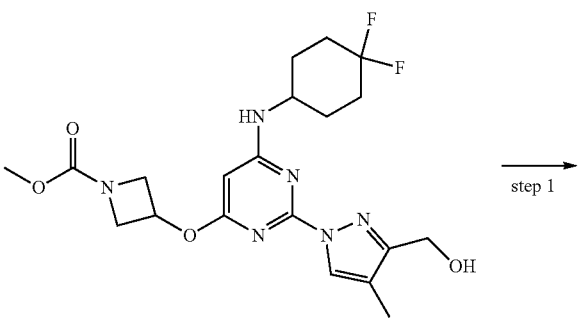

0459

543

-continued

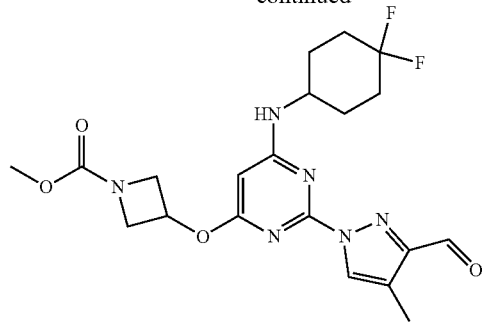

0461

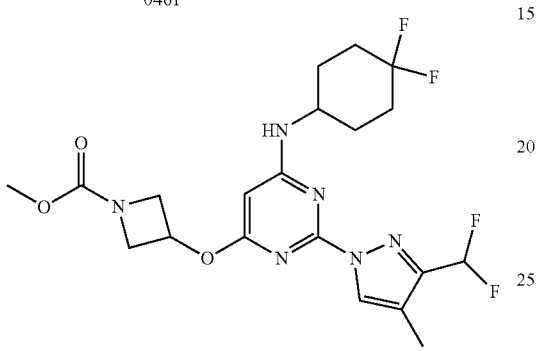

0462

Step 1[0461]: The procedure is similar to step 3[0444] in Example 166. 0.3 g of methyl 3-((6-((4,4-difluorocyclohexyl)amino)-2-(3-(hydroxymethyl)-4-methyl-1H-pyrazol-1-yl)pyrimidin-4-yl)oxy)azetidine-1-carboxylate [0459] gave 0.2 g of Methyl 3-((6-((4,4-difluorocyclohexyl)amino)-2-(3-formyl-4-methyl-1H-pyrazol-1-yl)pyrimidin-4-yl)oxy)azetidine-1-carboxylate [0461] as off-white solid. MS(M+1)+=451.2.

Step 2[0462]: The procedure is similar to step 3[0012] in Example 2. 0.2 g of methyl 3-((6-((4,4-difluorocyclohexyl)amino)-2-(3-formyl-4-methyl-1H-pyrazol-1-yl)pyrimidin-4-yl)oxy)azetidine-1-carboxylate [0459] gave 0.075 g of methyl 3-((6-((4,4-difluorocyclohexyl)amino)-2-(3-(difluoromethyl)-4-methyl-1H-pyrazol-1-yl)pyrimidin-4-yl)oxy)azetidine-1-carboxylate [0462], Compound 318 as an white solid. MS(M+1)+=473.2, $^1$H NMR (400 MHz, DMSO-d6) δ 8.39 (s, 1H), 7.45 (d, J=7.8 Hz, 1H), 6.70 (t, JF=54 Hz, 1H), 5.79 (s, 1H), 5.40 (dd, J=7.4, 3.7 Hz, 1H), 4.37 (dd, J=9.9, 6.8 Hz, 2H), 3.93 (dd, J=9.7, 4.4 Hz, 3H), 3.60 (s, 3H), 2.19 (s, 3H), 2.14-1.83 (m, 6H), 1.64 (t, J=10.9 Hz, 2H).

Example 175

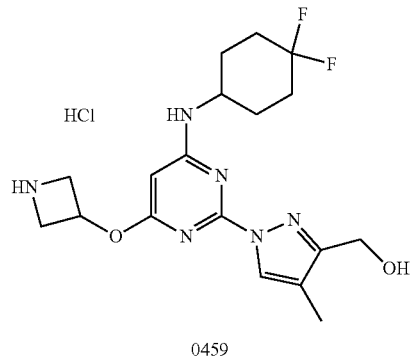 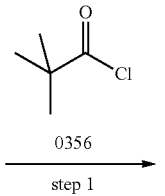

0459

544

-continued

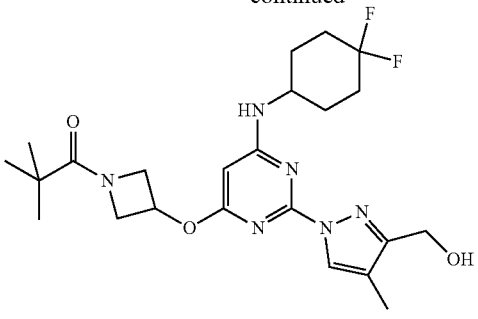

0463

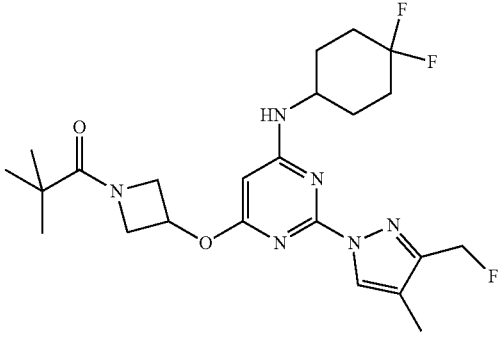

0464

Step 1[0463]: The procedure is similar to step 8[0433] in Example 160. 1.1 g of (1-(4-(azetidin-3-yloxy)-6-((4,4-difluorocyclohexyl)amino)pyrimidin-2-yl)-4-methyl-1H-pyrazol-3-yl)methanol.HCl [0459] gave 0.6 g of 1-(3-((6-((4,4-difluorocyclohexyl)amino)-2-(3-(hydroxymethyl)-4-methyl-1H-pyrazol-1-yl)pyrimidin-4-yl)oxy)azetidin-1-yl)-2,2-dimethylpropan-1-one [0463] as off-white solid. MS(M+1)+=479.2.

Step 2[0464]: The procedure is similar to step 3[0012] in Example 2. 0.3 g of 1-(3-((6-((4,4-difluorocyclohexyl)amino)-2-(3-(hydroxymethyl)-4-methyl-1H-pyrazol-1-yl)pyrimidin-4-yl)oxy)azetidin-1-yl)-2,2-dimethylpropan-1-one [0463] gave 0.125 g of 1-(3-((6-((4,4-difluorocyclohexyl)amino)-2-(3-(fluoromethyl)-4-methyl-1H-pyrazol-1-yl)pyrimidin-4-yl)oxy)azetidin-1-yl)-2,2-dimethylpropan-1-one [0464], Compound 309 as white solid. MS(M+1)+=481.2, $^1$H NMR (400 MHz, DMSO-d6) δ 8.33 (s, 1H), 7.37 (d, J=7.6 Hz, 1H), 5.76 (s, 1H), 5.48 (s, 1H), 5.46 (bs, 3H), 4.53 (s, 2H), 4.08 (d, J=10.0 Hz, 2H), 2.14 (d, J=1.2 Hz, 3H), 1.94 (td, J=12.8, 12.0, 7.1 Hz, 7H), 1.63 (d, J=11.2 Hz, 2H), 1.14 (d, J=1.9 Hz, 9H).

Example 176

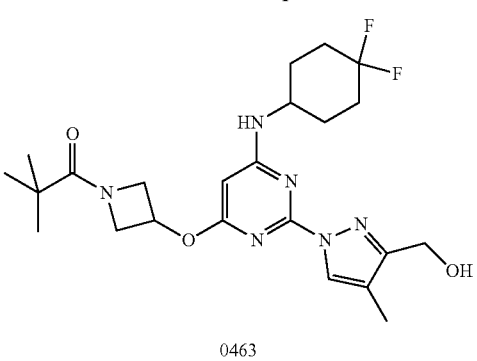

0463

-continued

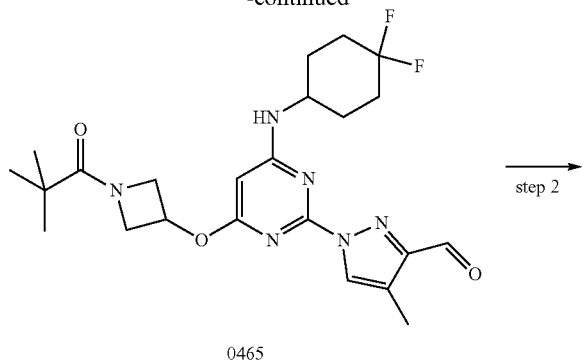

0465

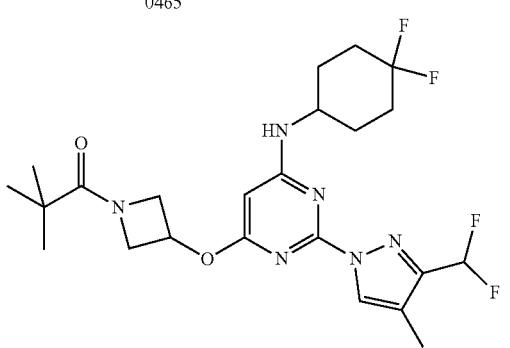

0466

Step 1[0465]: The procedure is similar to step 3[0444] in Example 166. 0.25 g of 1-(3-((6-((4,4-difluorocyclohexyl)amino)-2-(3-(hydroxymethyl)-4-methyl-1H-pyrazol-1-yl)pyrimidin-4-yl)oxy)azetidin-1-yl)-2,2-dimethylpropan-1-one [0463] gave 0.2 g 1-(4-((4,4-Difluorocyclohexyl)amino)-6-((1-pivaloylazetidin-3-yl)oxy)pyrimidin-2-yl)-4-methyl-1H-pyrazole-3-carbaldehyde [0465] as off-white solid. MS(M+1)+=477.2.

Step 2[0466]: The procedure is similar to step 3[0012] in Example 2. 0.25 g of 1-(4-((4,4-difluorocyclohexyl)amino)-6-((1-pivaloylazetidin-3-yl)oxy)pyrimidin-2-yl)-4-methyl-1H-pyrazole-3-carbaldehyde [0465] gave 0.07 g of 1-(3-((6-((4,4-difluorocyclohexyl)amino)-2-(3-(difluoromethyl)-4-methyl-1H-pyrazol-1-yl)pyrimidin-4-yl)oxy)azetidin-1-yl)-2,2-dimethylpropan-1-one [0466], Compound 317 as white solid. MS(M+1)$^+$=499.2, $^1$H NMR (400 MHz, DMSO-d6) δ 8.41 (s, 1H), 7.45 (d, J=7.9 Hz, 1H), 6.9 (t, JF=54 Hz, 1H), 5.80 (s, 1H), 5.43-5.36 (m, 1H), 4.54 (bs, 2H), 4.09 (bs, 2H), 3.94 (bs, 1H), 2.27-2.15 (m, 3H), 2.13-1.88 (m, 6H), 1.64 (t, J=11.1 Hz, 2H), 1.15 (d, J=1.5 Hz, 9H).

Example 177

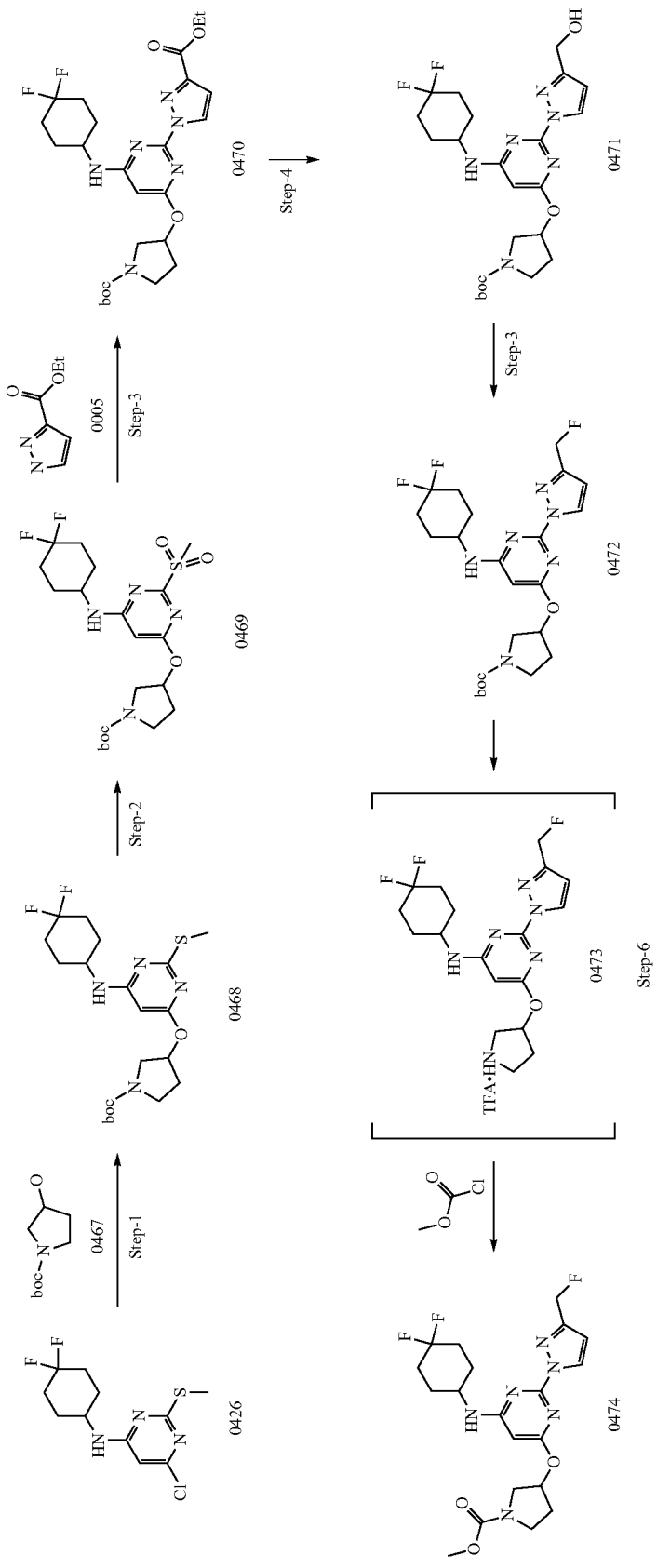

Step 1[0468]: The procedure is similar to Step 1[270] in example 98. 2.5 g of 6-chloro-N-(4,4-difluorocyclohexyl)-2-(methylthio)pyrimidin-4-amine [0426] and 2.39 g of 1-Boc-3-Hydroxypyrrolidine [0467] gave 1.25 g of tert-butyl 3-((6-((4,4-difluorocyclohexyl)amino)-2-(methylthio)pyrimidin-4-yl)oxy)pyrrolidine-1-carboxylate [0468] MS(M+1)+=445.

Step 2[0469]: The procedure is similar to Step 2[0378] in example 145. 1.25 g of tert-butyl 3-((6-((4,4-difluorocyclohexyl)amino)-2-(methylthio)pyrimidin-4-yl)oxy)pyrrolidine-1-carboxylate [0468] gave 1.3 g of tert-butyl 3-((6-((4,4-difluorocyclohexyl)amino)-2-(methylsulfonyl)pyrimidin-4-yl)oxy)pyrrolidine-1-carboxylate [0469] MS(M+1)+=477.

Step 3[0470]: The procedure is similar to Step 2[0274] in example 99 (at 120° C.). 1.3 g of tert-butyl 3-((6-((4,4-difluorocyclohexyl)amino)-2-(methylsulfonyl)pyrimidin-4-yl)oxy)pyrrolidine-1-carboxylate [0469] and 0.708 g of Ethyl 1h-Pyrazole-3-Carboxylate [0005] gave 1.3 g of ethyl 1-(4-((1-(tert-butoxycarbonyl)pyrrolidin-3-yl)oxy)-6-((4,4-difluorocyclohexyl)amino)pyrimidin-2-yl)-1H-pyrazole-3-carboxylate [0470].

MS(M+1)+=537.

Step 4[0471]: The procedure is similar to Step 2[0019] in example 4. 1.3 g of ethyl 1-(4-((1-(tert-butoxycarbonyl)pyrrolidin-3-yl)oxy)-6-((4,4-difluorocyclohexyl)amino)pyrimidin-2-yl)-1H-pyrazole-3-carboxylate [0470] gave 1 g of tert-butyl 3-((6-((4,4-difluorocyclohexyl)amino)-2-(3-(hydroxymethyl)-1H-pyrazol-1-yl)pyrimidin-4-yl)oxy)pyrrolidine-1-carboxylate [0471]. MS(M+1)+=495.

Step 5[0472]: The procedure is similar to step 3[0012] in Example 2. 0.7 g of tert-butyl 3-((6-((4,4-difluorocyclohexyl)amino)-2-(3-(hydroxymethyl)-1H-pyrazol-1-yl)pyrimidin-4-yl)oxy) pyrrolidine-1-carboxylate [0471] gave 0.25 g of tert-butyl 3-((6-((4,4-difluorocyclohexyl)amino)-2-(3-(fluoromethyl)-1H-pyrazol-1-yl)pyrimidin-4-yl)oxy)pyrrolidine-1-carboxylate [0472]. MS(M+1)+=497.

Step 6[0474]: The procedure is similar to Step 1[0434] in example 161. 0.25 g of tert-butyl 3-((6-((4,4-difluorocyclohexyl)amino)-2-(3-(fluoromethyl)-1H-pyrazol-1-yl)pyrimidin-4-yl)oxy)pyrrolidine-1-carboxylate [0472] and 0.095 g of methyl chloroformate [0026] gave 0.12 g of methyl 3-((6-((4,4-difluorocyclohexyl)amino)-2-(3-(fluoromethyl)-1H-pyrazol-1-yl)pyrimidin-4-yl)oxy)pyrrolidine-1-carboxylate [0474], Compound 297.

MS(M+1)+=455, $^1$H NMR (400 MHz, DMSO-d6) δ 8.55 (d, J=2.7 Hz, 1H), 7.34 (d, J=7.7 Hz, 1H), 6.61 (dd, J=2.8, 1.2 Hz, 1H), 5.76 (s, 1H), 5.56 (m, 1H), 5.43 (d, JF=48 Hz, 2H), 3.93 (bs, 1H), 3.69 (dd, J=12.2, 4.8 Hz, 1H), 3.62 (s, 3H), 3.53-3.38 (m, 3H), 2.23 (m, 1H), 2.11-1.93 (m, 7H), 1.62 (m, 2H).

Example 178

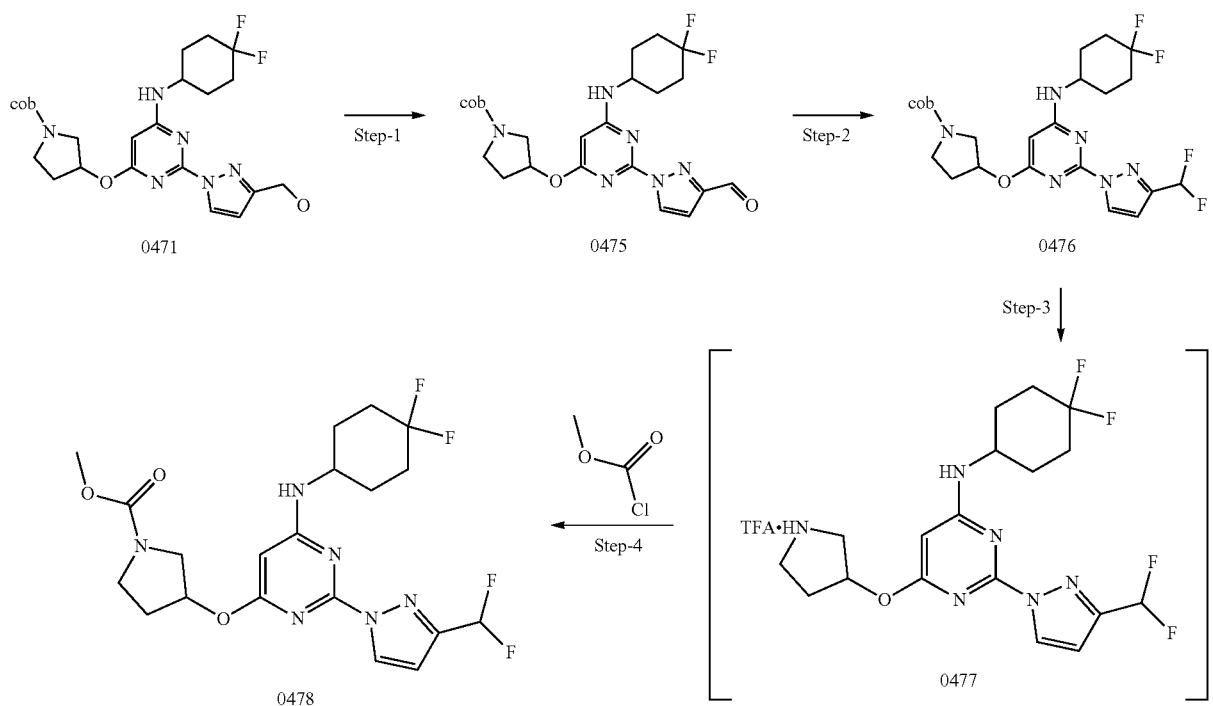

Step 1[0475]: The procedure is similar to Step 3[0444] in example 166. 0.6 g of tert-butyl 3-((6-((4,4-difluorocyclohexyl)amino)-2-(3-(hydroxymethyl)-1H-pyrazol-1-yl)pyrimidin-4-yl)oxy) pyrrolidine-1-carboxylate [0471] gave 0.25 g of tert-butyl 3-((6-((4,4-difluorocyclohexyl)amino)-2-(3-formyl-1H-pyrazol-1-yl)pyrimidin-4-yl)oxy)pyrrolidine-1-carboxylate [0475]. MS(M+1)+=493.

Step 2[0476]: The procedure is similar to step 3[0012] in Example 2. 0.4 g of tert-butyl 3-((6-((4,4-difluorocyclohexyl)amino)-2-(3-formyl-1H-pyrazol-1-yl)pyrimidin-4-yl)oxy)pyrrolidine-1-carboxylate [0475] gave 0.24 g of tert-butyl 3-((6-((4,4-difluorocyclohexyl)amino)-2-(3-(difluoromethyl)-1H-pyrazol-1-yl)pyrimidin-4-yl)oxy) pyrrolidine-1-carboxylate [0476]. MS(M+1)+=515.

Step 3 and 4[0477 and 0478]: The procedure is similar to Step 1[0434] in example 161. 0.4 g of tert-butyl 3-((6-((4,4-difluorocyclohexyl)amino)-2-(3-(difluoromethyl)-1H-pyrazol-1-yl)pyrimidin-4-yl)oxy)pyrrolidine-1-carboxylate

[0476] and 0.068 g of methyl chloroformate [0026] gave 0.1 g of methyl 3-((6-(((4,4-difluorocyclohexyl)amino)-2-(3-(difluoromethyl)-1H-pyrazol-1-yl)pyrimidin-4-yl)oxy)pyrrolidine-1-carboxylate [0478], Compound 305. MS(M+1)$^+$= 473, $^1$H NMR (400 MHz, DMSO-d6-80° C.) δ 8.63 (d, J=2.4 Hz, 1H), 7.41 (d, J=7.6 Hz, 1H), 7.03 (t, JF=54.4 Hz, 1H), 6.73 (d, J=2.4 Hz, 1H), 5.80 (s, 1H), 5.57 (m, 1H), 3.94 (bs, 1H), 3.69 (dd, J=12.2, 4.8 Hz, 1H), 3.6 (s, 3H), 3.55-3.39 (m, 3H), 2.30-2.15 (m, 1H), 2.11-1.93 (m, 7H), 1.62 (m, 2H).

Example 179

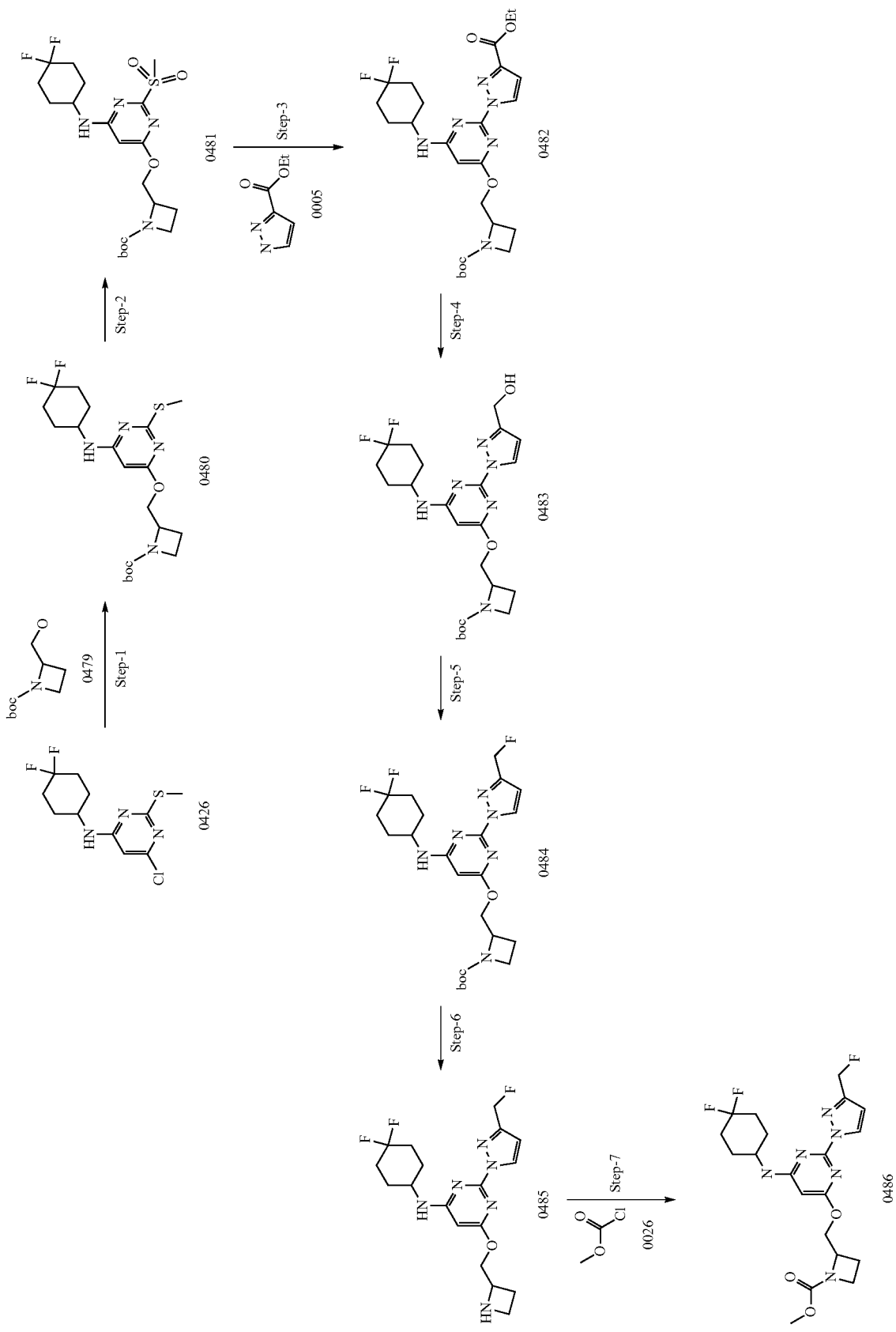

Step 1[0480]: The procedure is similar to Step 1[270] in example 98. 3 g of 6-chloro-N-(4,4-difluorocyclohexyl)-2-(methylthio)pyrimidin-4-amine [0426] and 2.8 g of 12-Hydroxymethyl-azetidine-1-Carboxylic acid tert-butyl ester [0479] gave 1.4 g of tert-butyl 2-(((6-((4,4-difluorocyclohexyl)amino)-2-(methylthio)pyrimidin-4-yl)oxy)methyl)azetidine-1-carboxylate [0480]. MS(M+1)+=445.

Step 2[0481]: The procedure is similar to Step 2[0378] in example 145. 1.4 g of tert-butyl 2-(((6-((4,4-difluorocyclohexyl)amino)-2-(methylthio)pyrimidin-4-yl)oxy)methyl)azetidine-1-carboxylate [0480] gave 1.3 g of tert-butyl 2-(((6-((4,4-difluorocyclohexyl)amino)-2-(methylsulfonyl)pyrimidin-4-yl)oxy)methyl)azetidine-1-carboxylate [0481]. MS(M+1)+=477.

Step 3[0482]: The procedure is similar to Step 2[0274] in example 99 (at 120° C.). 1.3 g of tert-butyl 2-(((6-((4,4-difluorocyclohexyl)amino)-2-(methylsulfonyl)pyrimidin-4-yl)oxy)methyl)azetidine-1-carboxylate [0481] and 0.585 g of Ethyl 1h-Pyrazole-3-Carboxylate gave 1.4 g of ethyl 1-(4-(((1-(tert-butoxycarbonyl)azetidin-2-yl)methoxy)-6-((4,4-difluorocyclohexyl)amino)pyrimidin-2-yl)-1H-pyrazole-3-carboxylate [0482]. MS(M+1)+=537.

Step 4[0483]: The procedure is similar to Step 2[0019] in example 4. 1.4 g of ethyl 1-(4-((1-(tert-butoxycarbonyl)azetidin-2-yl)methoxy)-6-((4,4-difluorocyclohexyl)amino)pyrimidin-2-yl)-1H-pyrazole-3-carboxylate [0482] gave 1.25 g of tert-butyl 2-(((6-((4,4-difluorocyclohexyl)amino)-2-(3-(hydroxymethyl)-1H-pyrazol-1-yl)pyrimidin-4-yl)oxy)methyl)azetidine-1-carboxylate [0483], MS(M+1)+=495.

Step 5[0484]: The procedure is similar to step 3[0012] in Example 2. 0.65 g of tert-butyl 2-(((6-((4,4-difluorocyclohexyl)amino)-2-(3-(hydroxymethyl)-1H-pyrazol-1-yl)pyrimidin-4-yl)oxy)methyl)azetidine-1-carboxylate [0483] gave 0.24 g of tert-butyl 2-(((6-((4,4-difluorocyclohexyl)amino)-2-(3-(fluoromethyl)-1H-pyrazol-1-yl)pyrimidin-4-yl)oxy)methyl)azetidine-1-carboxylate [0484]. MS(M+1)+=497.

Step 6 and 7[0485 and 0486]: The procedure is similar to Step 1[0434] in example 161. 0.24 g of tert-butyl 2-(((6-((4,4-difluorocyclohexyl)amino)-2-(3-(fluoromethyl)-1H-pyrazol-1-yl)pyrimidin-4-yl)oxy)methyl)azetidine-1-carboxylate [0484] and 0.054 g of methyl chloroformate [0026] gave 0.1 g of methyl 2-(((6-((4,4-difluorocyclohexyl)amino)-2-(3-(fluoromethyl)-1H-pyrazol-1-yl)pyrimidin-4-yl)oxy)methyl)azetidine-1-carboxylate [0486], Compound 306. MS(M+1)$^+$=455, $^1$H NMR (400 MHz, DMSO-d6-80° C.) δ 8.55 (d, J=2.4 Hz, 1H), 7.31 (d, J=8.4 Hz, 1H), 6.60 (m, 1H), 5.80 (s, 1H), 5.38 (d, JF=48 Hz, 2H), 4.45-4.26 (m, 3H), 3.90 (bs, 1H), 3.87-3.80 (m, 2H), 3.55 (s, 3H), 2.40-2.30 (m, 1H), 2.20-2.10 (m, 1H), 2.11-1.93 (m, 6H), 1.62 (m, 2H).

Example 180

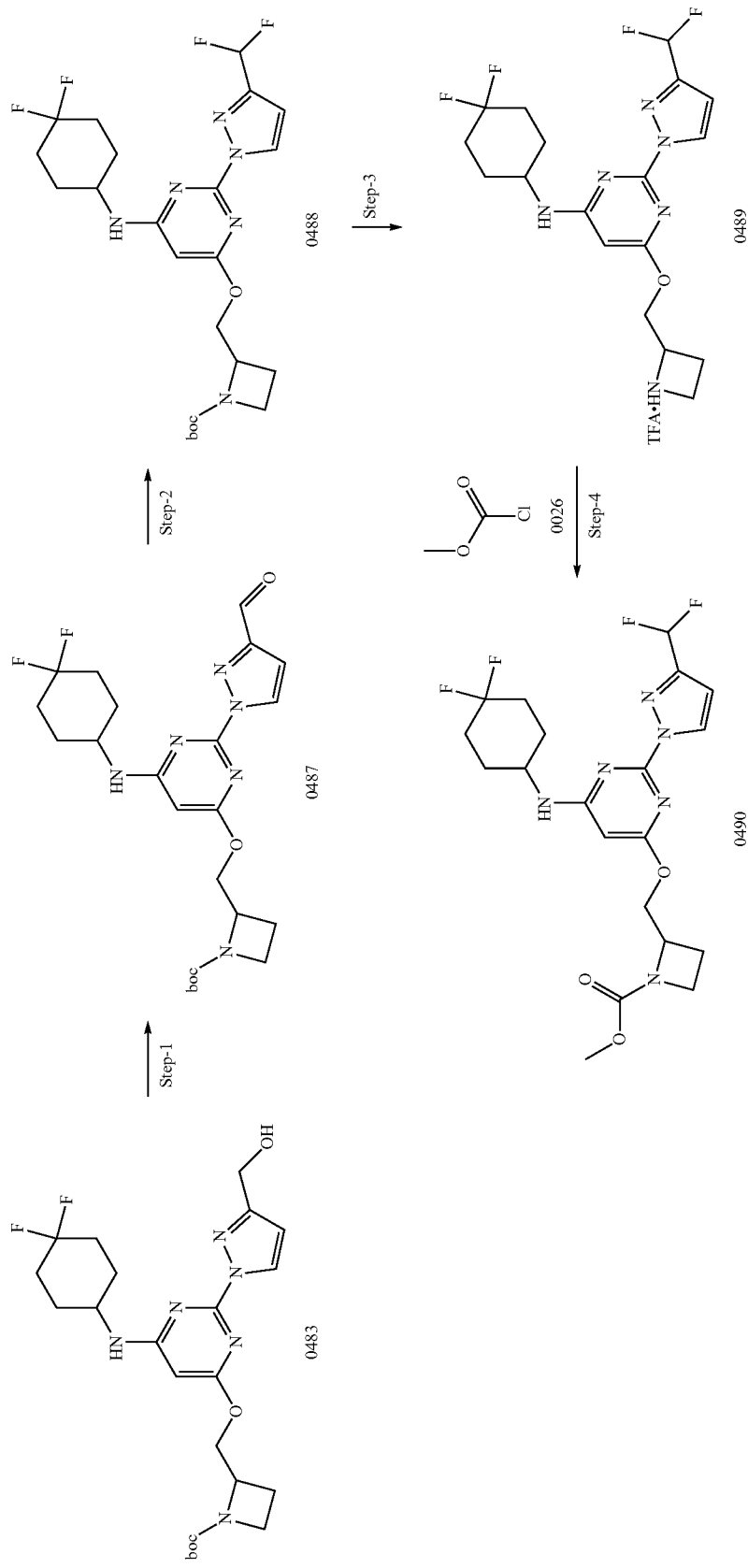

Step 1[0487]: The procedure is similar to Step 3[0444] in example 166. 0.5 g of tert-butyl 2-(((6-((4,4-difluorocyclohexyl)amino)-2-(3-(hydroxymethyl)-1H-pyrazol-1-yl)pyrimidin-4-yl)oxy)methyl)azetidine-1-carboxylate [0483] gave 0.4 g of tert-butyl 2-(((6-((4,4-difluorocyclohexyl)amino)-2-(3-formyl-1H-pyrazol-1-yl)pyrimidin-4-yl)oxy)methyl)azetidine-1-carboxylate [0487]. MS(M+1)+=493.

Step 2[0488]: The procedure is similar to step 3[0012] in Example 2. 0.4 g of tert-butyl 2-(((6-((4,4-difluorocyclohexyl)amino)-2-(3-formyl-1H-pyrazol-1-yl)pyrimidin-4-yl)oxy)methyl)azetidine-1-carboxylate [0487] gave 0.21 g of tert-butyl 2-(((6-((4,4-difluorocyclohexyl)amino)-2-(3-(difluoromethyl)-1H-pyrazol-1-yl)pyrimidin-4-yl)oxy)methyl)azetidine-1-carboxylate [0488]. MS(M+1)+=515.

Step 3 and 4[0489 and 0490]: The procedure is similar to Step 1[0434] in example 161. 0.2 g of tert-butyl 2-(((6-((4,4-difluorocyclohexyl)amino)-2-(3-(difluoromethyl)-1H-pyrazol-1-yl)pyrimidin-4-yl)oxy)methyl)azetidine-1-carboxylate [0488] and 0.073 g of methyl chloroformate [0026] gave 0.09 g of methyl 2-(((6-((4,4-difluorocyclohexyl)amino)-2-(3-(difluoromethyl)-1H-pyrazol-1-yl)pyrimidin-4-yl)oxy)methyl)azetidine-1-carboxylate [0490], Compound 314. MS(M+1)$^+$=473, $^1$H NMR (400 MHz, DMSO-d6) δ 8.70 (s, 1H), 7.66 (bs, 1H), 7.13 (t, JF=54.4 Hz, 1H), 6.79 (d, J=2.9 Hz, 1H), 5.81 (bs, 1H), 4.50 (m, 3H), 4.01 (bs, 1H), 3.83 (bs, 2H), 3.54 (s, 3H), 2.29 (m, 1H), 2.20-1.80 (m, 7H), 1.65-1.45 (m, 2H), Example 181

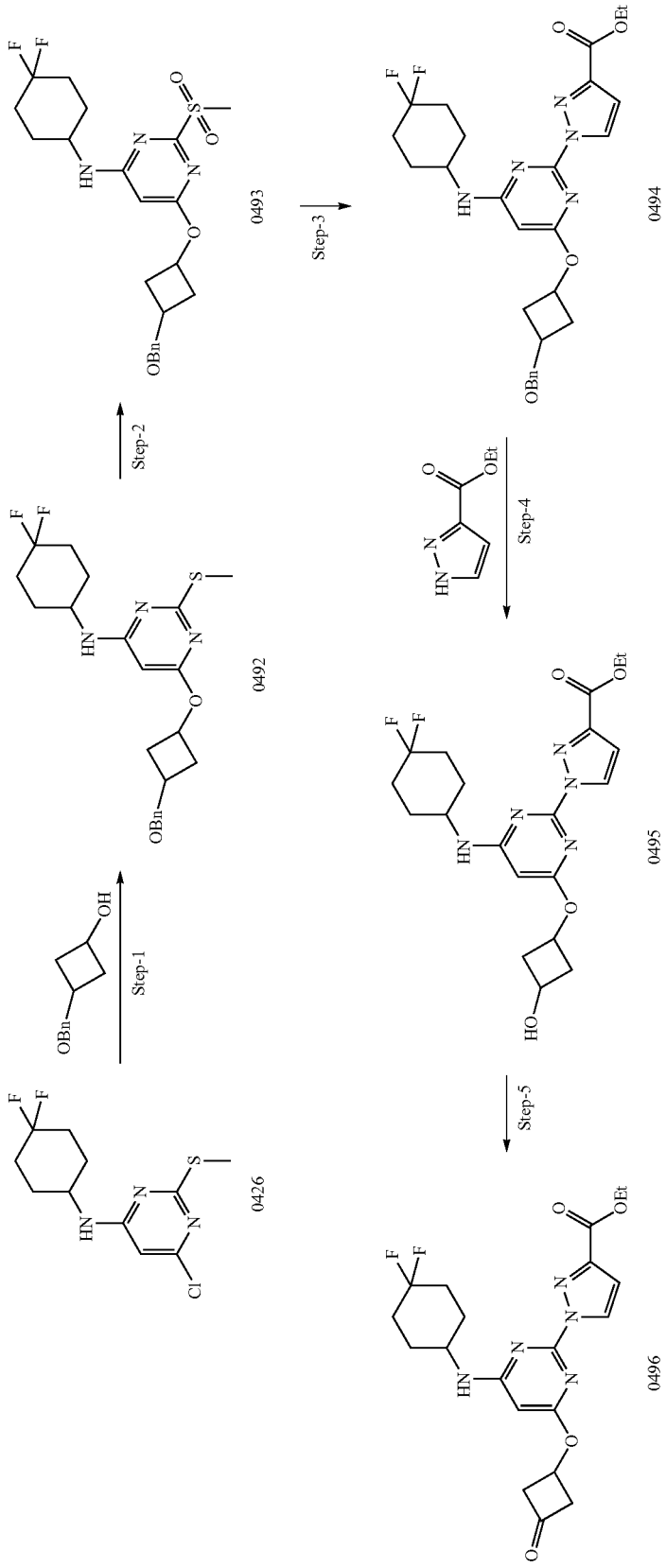

Step 1[0492]: The procedure is similar to Step 1[270] in example 98. 13 g of 6-chloro-N-(4,4-difluorocyclohexyl)-2-(methylthio)pyrimidin-4-amine [0426] and 4 g of 3-(benzyloxy)cyclobutan-1-ol [0491] gave 4 g of 6-(3-(benzyloxy)cyclobutoxy)-N-(4,4-difluorocyclohexyl)-2-(methylthio)pyrimidin-4-amine [0492] MS(M+1)+=436.

Step 2[0493]: The procedure is similar to Step 2[0378] in example 145. 3 g of 6-(3-(benzyloxy)cyclobutoxy)-N-(4,4-difluorocyclohexyl)-2-(methylthio)pyrimidin-4-amine [0492] gave 3 g of 6-(3-(benzyloxy)cyclobutoxy)-N-(4,4-difluorocyclohexyl)-2-(methylsulfonyl)pyrimidin-4-amine [0493] MS(M+1)+=468.

Step 3[0494]: The procedure is similar to Step 2[0274] in example 99 (at 120° C.). 3 g of 6-(3-(benzyloxy)cyclobutoxy)-N-(4,4-difluorocyclohexyl)-2-(methylsulfonyl)pyrimidin-4-amine [0493] and 1.37 g of ethyl 1h-Pyrazole-3-carboxylate gave 3 g of ethyl 1-(4-(3-(benzyloxy)cyclobutoxy)-6-((4,4-difluorocyclohexyl)amino)pyrimidin-2-yl)-1H-pyrazole-3-carboxylate [0494], MS(M+1)+=528.

Step 4[0495]: To a solution of ethyl 1-(4-(3-(benzyloxy)cyclobutoxy)-6-((4,4-difluorocyclohexyl)amino)pyrimidin-2-yl)-1H-pyrazole-3-carboxylate [0494] (3 g, 5.686 mmol) in methanol was added palladium on carbon (10%) (0.6 g) under N2 atm. The resultant reaction mixture was hydrogenated at 3 kg/Cm3 hydrogen pressure for 24 h. The reaction mixture was filtered through celite bed and washed with methanol. The filtrate was concentrated under reduced pressure to afford as a colorless gum and which was purified by column chromatography using 50% ethyl acetate in hexane as a eluent to afford ethyl 1-(4-((4,4-difluorocyclohexyl)amino)-6-(3-hydroxycyclobutoxy)pyrimidin-2-yl)-1H-pyrazole-3-carboxylate [0495] as an white solid (2.0 g). MS(M+1)+=438.

Step 5[0496]: The procedure is similar to Step 3[0444] in example 166] (Using Dess-Martin periodinane). 1.5 g of ethyl 1-(4-((4,4-difluorocyclohexyl)amino)-6-(3-hydroxycyclobutoxy)pyrimidin-2-yl)-1H-pyrazole-3-carboxylate [0495] gave 1.56 g of ethyl 1-(4-((4,4-difluorocyclohexyl)amino)-6-(3-oxo cyclobutoxy)pyrimidin-2-yl)-1H-pyrazole-3-carboxylate [0496] MS(M+1)+=436.

Example 182

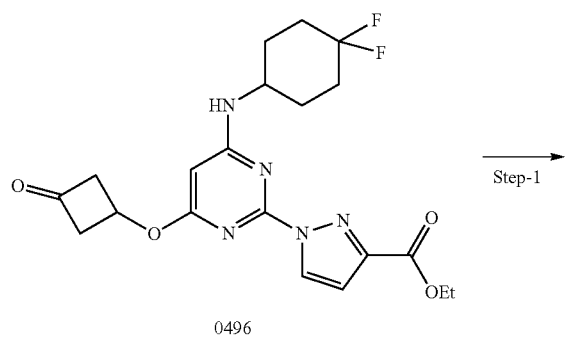

Step 1[0497]: The procedure is similar to step 3[0012] in Example 2. 0.6 g of ethyl 1-(4-((4,4-difluorocyclohexyl)amino)-6-(3-oxocyclobutoxy)pyrimidin-2-yl)-1H-pyrazole-3-carboxylate [0496] gave 0.33 g of ethyl 1-(4-(3,3-difluorocyclobutoxy)-6-((4,4-difluorocyclohexyl)amino)pyrimidin-2-yl)-1H-pyrazole-3-carboxylate [0497]. MS(M+1)+=458.

Step 2[0498]: The procedure is similar to Step 2[0019] in example 4. 0.33 g of ethyl 1-(4-(3,3-difluorocyclobutoxy)-6-((4,4-difluorocyclohexyl)amino)pyrimidin-2-yl)-1H-pyrazole-3-carboxylate [0497] gave 0.26 g of (1-(4-(3,3-difluorocyclobutoxy)-6-((4,4-difluoro cyclohexyl)amino)pyrimidin-2-yl)-1H-pyrazol-3-yl)methanol [0498]. MS(M+1)+=416.

Step 3 [0499]: The procedure is similar to step 3[0012] in Example 2. 0.26 g of (1-(4-(3,3-difluorocyclobutoxy)-6-((4,4-difluorocyclohexyl)amino)pyrimidin-2-yl)-1H-pyrazol-3-yl)methanol [0498] gave 0.11 g of 6-(3,3-difluorocyclobutoxy)-N-(4,4-difluorocyclohexyl)-2-(3-(fluoromethyl)-1H-pyrazol-1-yl)pyrimidin-4-amine [0499], Compound 347. MS(M+1)+=418, 1H NMR (400 MHz, DMSO-d6) δ 8.54 (d, J=2.7 Hz, 1H), 7.39 (d, J=7.7 Hz, 1H), 6.61 (s, 1H), 5.78 (s, 1H), 5.43 (d, JF=48.5 Hz, 2H), 5.18 (dd, J=7.9, 4.9 Hz, 1H), 3.95 (bs, 1H), 3.18 (ddt, J=15.4, 11.8, 7.8 Hz, 2H), 2.75 (qd, J=14.2, 4.9 Hz, 2H), 2.10-1.89 (m, 6H), 1.71-1.55 (m, 2H).

Example 183

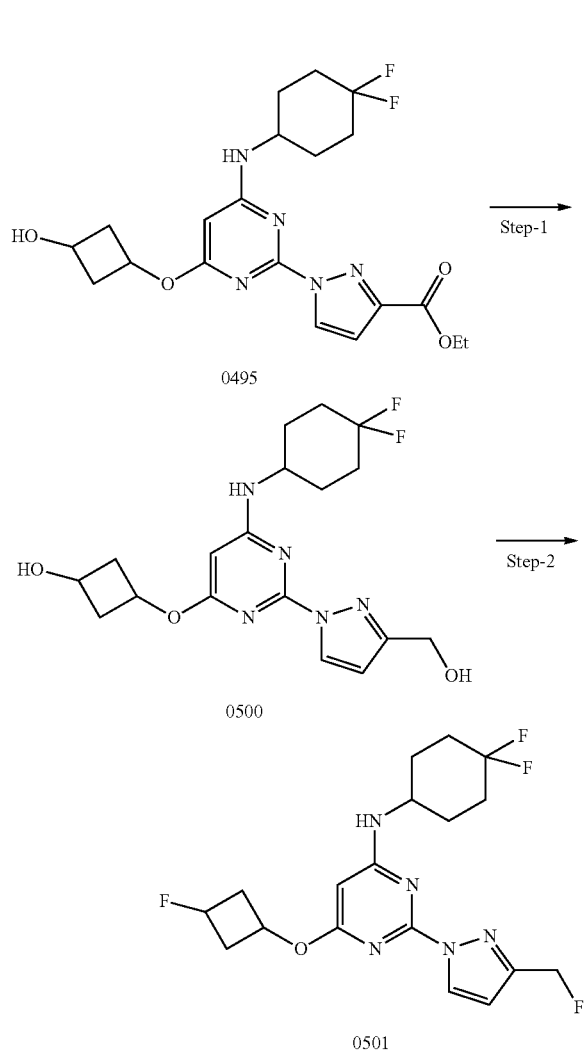

Step 1[0500]: The procedure is similar to Step 2[0019] in example 4. 0.3 g of ethyl 1-(4-((4,4-difluorocyclohexyl)amino)-6-(3-hydroxycyclobutoxy)pyrimidin-2-yl)-1H-pyrazole-3-carboxylate [0495] gave 0.25 g of 3-((6-((4,4-difluorocyclohexyl)amino)-2-(3-(hydroxymethyl)-1H-pyrazol-1-yl)pyrimidin-4-yl)oxy)cyclobutan-1-ol [0500].

MS(M+1)+=396.

Step 2[0501]: The procedure is similar to step 3[0012] in Example 2. 0.25 g of 3-((6-((4,4-difluorocyclohexyl)amino)-2-(3-(hydroxymethyl)-1H-pyrazol-1-yl)pyrimidin-4-yl)oxy)cyclobutan-1-ol [0500] gave 0.1 g of N-(4,4-difluorocyclohexyl)-6-(3-fluorocyclobutoxy)-2-(3-(fluoromethyl)-1H-pyrazol-1-yl)pyrimidin-4-amine [0501], Compound 346. MS(M+1)+=400, 1H-NMR (400 MHz, DMSO-d6): δ 8.56 (s, 1H), 7.60 (bs, 1H), 6.65 (d, J=1.44 Hz, 1H), 5.69 (bs, 1H), 5.47 (d, JF=48.5 Hz, 2H), 5.45-5.37 (m, 1H), 5.30-5.25 (m, 1H), 4.15 (bs, 1H), 2.68-2.67 (m, 2H), 2.56-2.55 (m, 2H), 2.12-1.89 (m, 6H), 1.65-1.50 (m, 2H).

Example 184

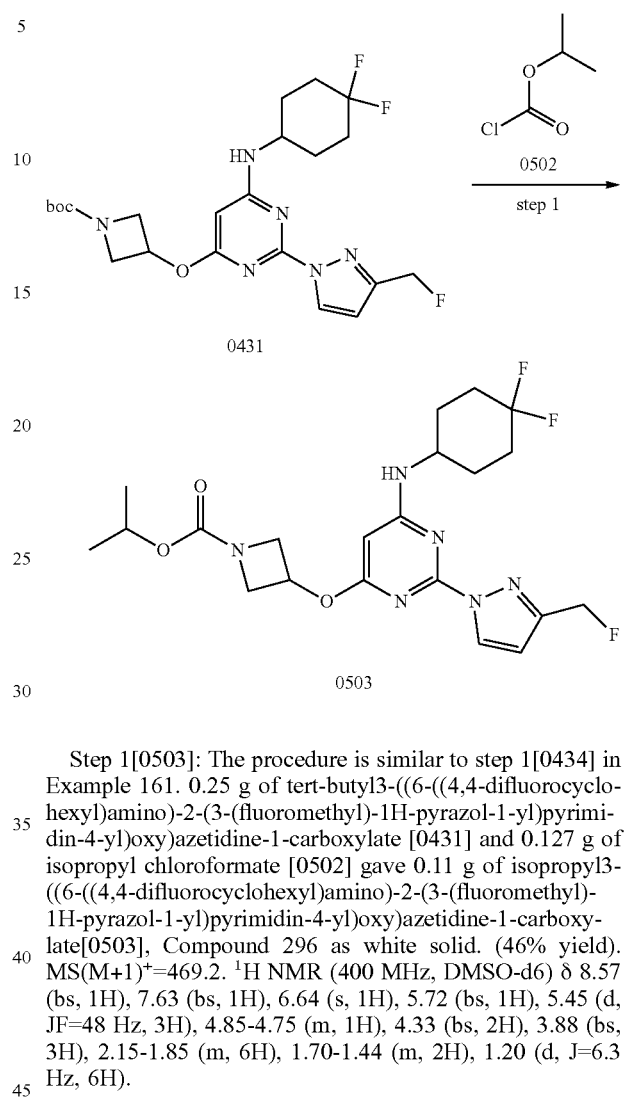

Step 1[0503]: The procedure is similar to step 1[0434] in Example 161. 0.25 g of tert-butyl3-((6-((4,4-difluorocyclohexyl)amino)-2-(3-(fluoromethyl)-1H-pyrazol-1-yl)pyrimidin-4-yl)oxy)azetidine-1-carboxylate [0431] and 0.127 g of isopropyl chloroformate [0502] gave 0.11 g of isopropyl3-((6-((4,4-difluorocyclohexyl)amino)-2-(3-(fluoromethyl)-1H-pyrazol-1-yl)pyrimidin-4-yl)oxy)azetidine-1-carboxylate[0503], Compound 296 as white solid. (46% yield). MS(M+1)+=469.2. 1H NMR (400 MHz, DMSO-d6) δ 8.57 (bs, 1H), 7.63 (bs, 1H), 6.64 (s, 1H), 5.72 (bs, 1H), 5.45 (d, JF=48 Hz, 3H), 4.85-4.75 (m, 1H), 4.33 (bs, 2H), 3.88 (bs, 3H), 2.15-1.85 (m, 6H), 1.70-1.44 (m, 2H), 1.20 (d, J=6.3 Hz, 6H).

Example 186

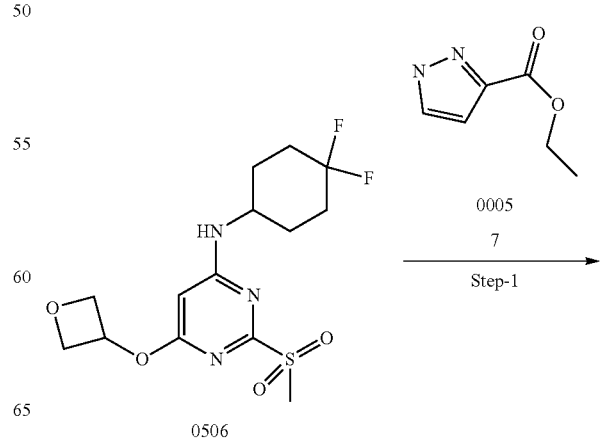

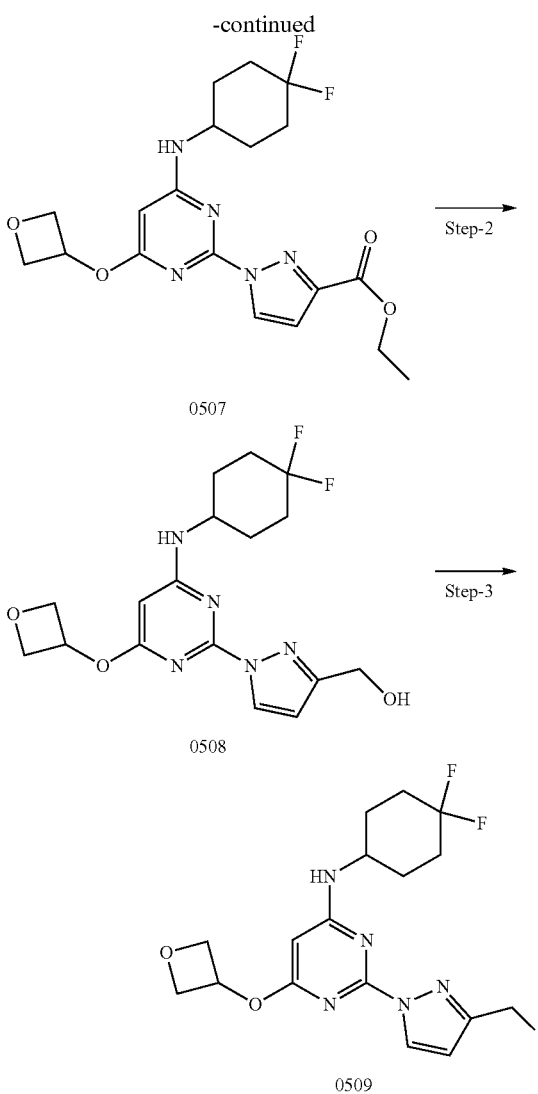

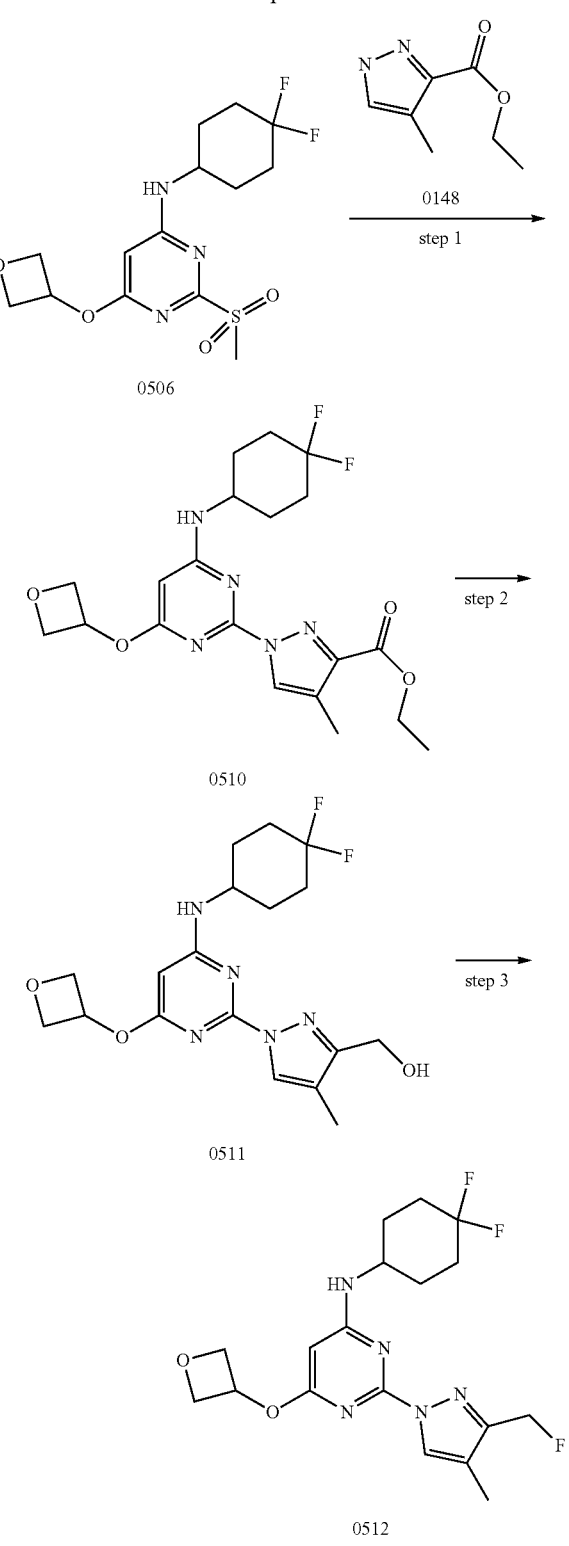

yloxy)pyrimidin-4-amine [0509], Compound 285 MS(M+1)+=384, $^1$H-NMR (400 MHz, DMSO-d6): δ 8.50 (d, J=2.40 Hz, 1H), 7.41 (d, J=7.60 Hz, 1H), 6.60 (t, J=1.20 Hz, 1H), 5.78 (s, 1H), 5.64 (t, J=6.00 Hz, 1H), 5.41 (d, JF=48.5 Hz, 2H), 4.90 (m, 2H), 4.60 (m, 2H), 4.01 (m, 1H), 2.10-1.98 (m, 6H), 1.95-1.61 (m, 2H).

Example 187

Step 1[0507]: The procedure is similar to Step 1 [270] in example 98 (at 80° C. in MW for 1 h) 0.4 g of N-(4,4-difluoro cyclohexyl)-2-(methylsulfonyl)-6-(oxetan-3-yloxy) pyrimidin-4-amine[0506] and 0.23 g of ethyl 1h-Pyrazole-3-carboxylate [005] gave 0.35 g of ethyl 1-(4-((4,4-difluorocyclohexyl)amino)-6-(oxetan-3-yloxy)pyrimidin-2-yl)-1H-pyrazole-3-carboxylate [0507], MS(M+1)+=332.

Step 2[0508]: To an ice cooled solution of ethyl 1-(4-((4,4-difluorocyclohexyl)amino)-6-(oxetan-3-yloxy)pyrimidin-2-yl)-1H-pyrazole-3-carboxylate [0507] (0.35 g, 0.826 mmol) in tetrahydrofuran (10 mL) was added 2M solution of lithium aluminium hydride in tetrahydrofuran (0.062 g, 1.65 mmol), after completion of addition the reaction mixture was slowly warmed to rt and stirred for 10 min. The reaction mixture was quenched with saturated ammonium chloride solution and extracted with ethyl acetate (2×30 mL), the combined organic layer was dried over anhydrous sodium sulfate and concentrated to afford (1-(4-((4,4-difluorocyclohexyl)amino)-6-(oxetan-3-yloxy)pyrimidin-2-yl)-1H-pyrazol-3-yl)methanol [0508] as an off-white gum 0.350 g, MS(M+1)+=325.

Step 3[0509]: The procedure is similar to step 3[0012] in Example 2. 0.35 g of (1-(4-((4,4-difluorocyclohexyl) amino)-6-(oxetan-3-yloxy)pyrimidin-2-yl)-1H-pyrazol-3-yl)methanol [0508] gave 0.1 g of N-(4,4-difluorocyclohexyl)-2-(3-(fluoromethyl)-1H-pyrazol-1-yl)-6-(oxetan-3-

569

Step 1[0510]: The procedure is similar to Step 2 [0274] in example 99 (at 100° C.). 0.5 g of N-(4,4-difluoro cyclohexyl)-2-(methylsulfonyl)-6-(oxetan-3-yloxy)pyrimidin-4-amine [0506] and 0.318 g of ethyl 4-methylpyrazole-3-carboxylate [0148] gave 0.5 g of ethyl 1-(4-((4,4-difluorocyclohexyl)amino)-6-(oxetan-3-yloxy)pyrimidin-2-yl)-4-methyl-1H-pyrazole-3-carboxylate [0510] as an off-white solid. MS(M+1)+=438.

Step 2[0511]: The procedure is similar to Step 2 [0019] in example 4. 0.5 g of ethyl 1-(4-((4,4-difluorocyclohexyl)amino)-6-(oxetan-3-yloxy)pyrimidin-2-yl)-4-methyl-1H-pyrazole-3-carboxylate [0510] gave 0.4 g of (1-(4-((4,4-difluorocyclohexyl)amino)-6-(oxetan-3-yloxy)pyrimidin-2-yl)-4-methyl-1H-pyrazol-3-yl)methanol [0511] as a brown solid. MS(M+1)+=396.

Step 3[0512]: The procedure is similar to Step 3 [0012] in example 2. 0.4 g of (1-(4-((4,4-difluorocyclohexyl)amino)-6-(oxetan-3-yloxy)pyrimidin-2-yl)-4-methyl-1H-pyrazol-3-yl)methanol [0511] gave 0.12 g of N-(4,4-difluorocyclohexyl)-2-(3-(fluoromethyl)-4-methyl-1H-pyrazol-1-yl)-6-(oxetan-3-yloxy)pyrimidin-4-amine [0512], Compound 304 as a white solid. MS(M+1)$^+$=398, $^1$H NMR (400 MHz, DMSO-d6) δ 8.35 (bs, 1H), 7.61 (bs, 1H), 5.61 (bs, 2H), 5.42 (d, JF=48.5 Hz, 2H), 4.95-4.88 (m, 2H), 4.58 (dd, J=7.5, 5.3 Hz, 2H), 4.14 (bs, 1H), 2.13 (bs, 3H), 2.09-1.85 (m, 6H), 1.59-1.52 (m, 2H).

Example 188

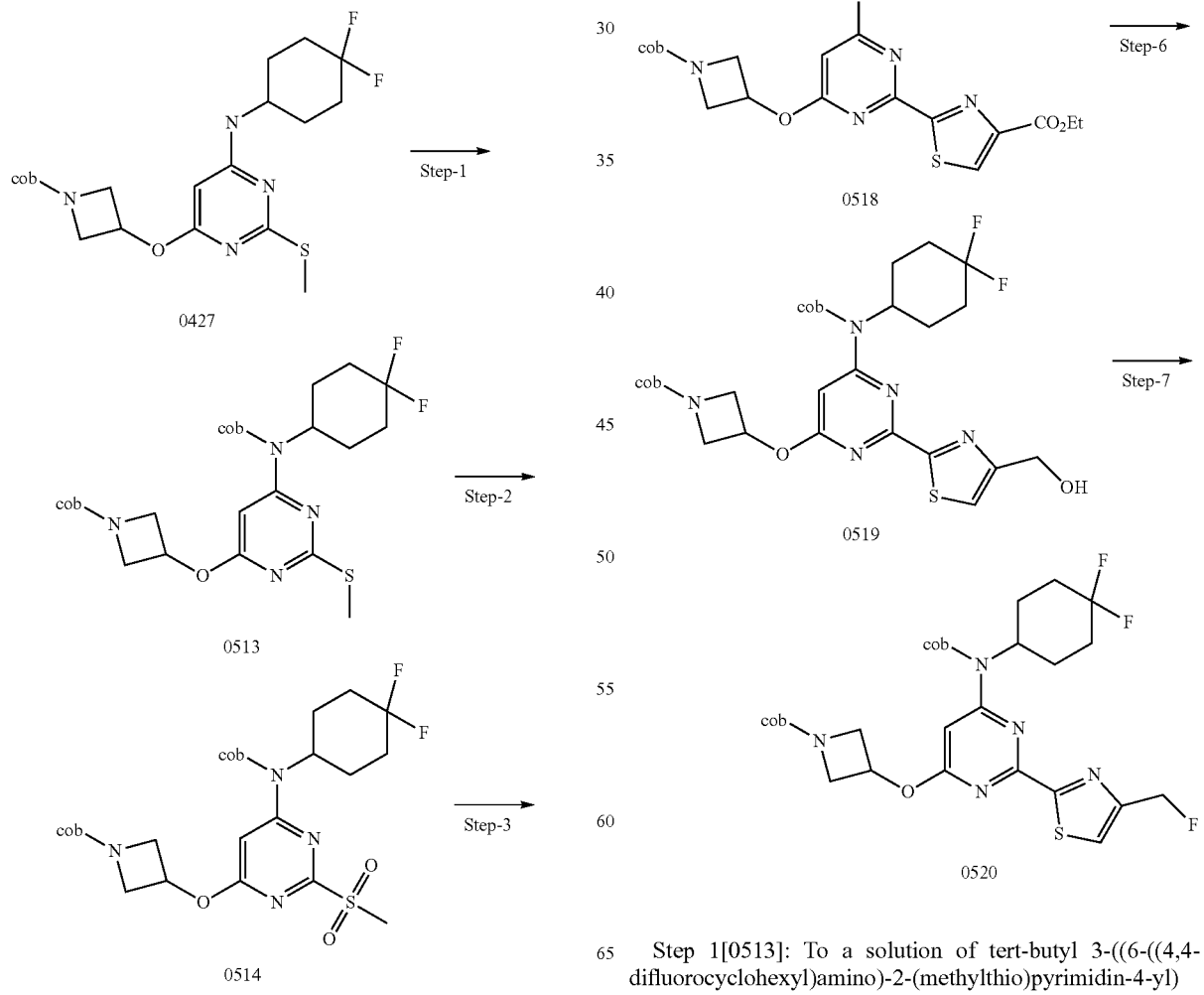

Step 1[0513]: To a solution of tert-butyl 3-((6-((4,4-difluorocyclohexyl)amino)-2-(methylthio)pyrimidin-4-yl)oxy)azetidine-1-carboxylate [0427] (5 g, 11.613 mmol) in tetrahydrofuran was added 4-N,N-dimethylamino pyridine (0.42 g, 3.484 mmol) and boc-anhydride (12.6 g, 58.069 mmol) at 0° C. and the reaction mixture was stirred at rt. After 16 h, the reaction mixture was concentrated under reduced pressure to afford a brown oil, which was purified in the Reveleris flash system instrument using ethyl acetate in hexane as solvent in 0.120 g column to afford tert-butyl 3-((6-((tert-butoxycarbonyl)(4,4-difluorocyclohexyl) amino)-2-(methylthio)pyrimidin-4-yl)oxy)azetidine-1-carboxylate [0513] as pale yellow oil. (5.8 g, 95% yield). MS(M+1)+=531.1.

Step 2[0514]: The procedure is similar to step 2 [0378] in example 145. 5.8 g of tert-butyl 3-((6-((tert-butoxycarbonyl)(4,4-difluorocyclohexyl)amino)-2-(methylthio)pyrimidin-4-yl)oxy)azetidine-1-carboxylate [0513] gave 6 g of tert-butyl 3-((6-((tert-butoxycarbonyl)(4,4-difluorocyclohexyl) amino)-2-(methylsulfonyl)pyrimidin-4-yl)oxy)azetidine-1carboxylate [0514] as off-white solid. (98% yield). MS(M+1)+=563.9.

Step 3[0515]: To a solution of tert-butyl 3-((6-((tert-butoxycarbonyl)(4,4-difluorocyclohexyl)amino)-2-(methylthio)pyrimidin-4-yl)oxy)azetidine-1-carboxylate [0514], (6 g, 10.66 mmol) in dimethyl sulfoxide was added 1,4-diazabicyclo[2.2.2]octane (1.31 g, 11.730 mmol) followed by sodium cyanide (0.58 g, 11.730 mmol) at 10° C. Then reaction mixture was stirred at rt. After 10 min, the reaction mixture was quenched with ice and stirred for 15 min. The solid formed was filtered, washed with water and dried under vacuum to afford tert-butyl 3-((6-((tert-butoxycarbonyl)(4,4-difluorocyclohexyl)amino)-2-cyanopyrimidin-4-yl)oxy)azetidine-1-carboxylate [0515] as off-white solid. (5 g, 92% yield). MS(M+1)+=509.6.

Step 4[0516]: To a solution of tert-butyl 3-((6-((tert-butoxycarbonyl)(4,4-difluorocyclohexyl)amino)-2-cyanopyrimidin-4-yl)oxy)azetidine-1-carboxylate [0515] (5 g, 9.81 mmol) in N,N-dimethylformamide was added triethylamine (1.98 g, 19.62 mmol) and ammonium sulfide in water (20%) (1.33 g, 19.625 mmol) and the reaction mixture was stirred at rt. After 5 min, the reaction mixture was quenched with ice and then extracted with ethyl acetate, washed with water and brine solution. The organic layer was dried over anhydrous sodium sulfate, filtered and concentrated under reduced pressure to afford tert-butyl 3-((6-((tert-butoxycarbonyl)(4,4-difluorocyclohexyl)amino)-2-carbamothioylpyrimidin-4-yl)oxy) azetidine-1-carboxylate [0516], as orange solid. (4.5 g, 85% yield). MS(M+1)+=544.6.

Step 5[0518]: To a solution of tert-butyl 3-((6-((tert-butoxycarbonyl)(4,4-difluorocyclohexyl)amino)-2-carbamothioylpyrimidin-4-yl)oxy)azetidine-1-carboxylate [0516] (5 g, 9.197 mmol) and ethyl bromopyruvate [0517] (3.58 g, 18.394 mmol) in tetrahydrofuran was stirred at rt. After 4 h, the reaction mixture was quenched with water and extracted with ethyl acetate. The combined organic layer was washed with brine, dried over anhydrous sodium sulfate, filtered and concentrated to afford a brown gum, which was purified in the Reveleris flash system instrument using ethyl acetate in hexane as solvent in 24 g column, to afford ethyl 2-(4-((tert-butoxycarbonyl)(4,4-difluorocyclohexyl) amino)-6-((1-(tert-butoxycarbonyl)azetidin-3-yl)oxy)pyrimidin-2-yl)thiazole-4-carboxylate [0518] as a yellow solid. (2.2 g, 40% yield). MS(M+1)+=640.2.

Step 6[0519]: To a stirred solution of ethyl 2-(4-((tert-butoxycarbonyl)(4,4-difluorocyclohexyl)amino)-6-((1-(tert-butoxycarbonyl)azetidin-3-yl)oxy)pyrimidin-2-yl)thiazole-4-carboxylate [0518] (2.2 g, 3.439 mmol) in tetrahydrofuran was added Lithium aluminum hydride (0.300 g, 7.909 mmol) at -78° C. and stirred at same temperature. After 3 h, the reaction mixture was slowly warmed to -10° C. After 1 h, the reaction mixture was quenched with saturated ammonium chloride solution drop wise at -10° C. and stirred at rt for 10 min. The reaction mixture was filtered through celite bed, washed with tetrahydrofuran and the filtrate was concentrated to afford tert-butyl 3-((6-((tert-butoxycarbonyl)(4,4-difluorocyclohexyl)amino)-2-(4-(hydroxymethyl)thiazol-2-yl)pyrimidin-4-yl)oxy)azetidine-1-carboxylate [0519] a yellow solid. (1.5 g, crude). MS(M+1)+=598.0.

Step 7[0520]: The procedure is similar to step 3 [0012] in example 2. 1.5 g of tert-butyl 3-((6-((tert-butoxycarbonyl)(4,4-difluorocyclohexyl)amino)-2-(4-(hydroxymethyl)thiazol-2-yl)pyrimidin-4-yl)oxy)azetidine-1-carboxylate [0519], 1.2 g gave tert-butyl 3-((6-((tert-butoxycarbonyl)(4,4-difluorocyclohexyl)amino)-2-(4-(fluoromethyl)thiazol-2-yl)pyrimidin-4-yl)oxy)azetidine-1-carboxylate [0520] as orange solid (0.6 g, 50% yield). MS(M+1)$^+$=600.1.

Example 189

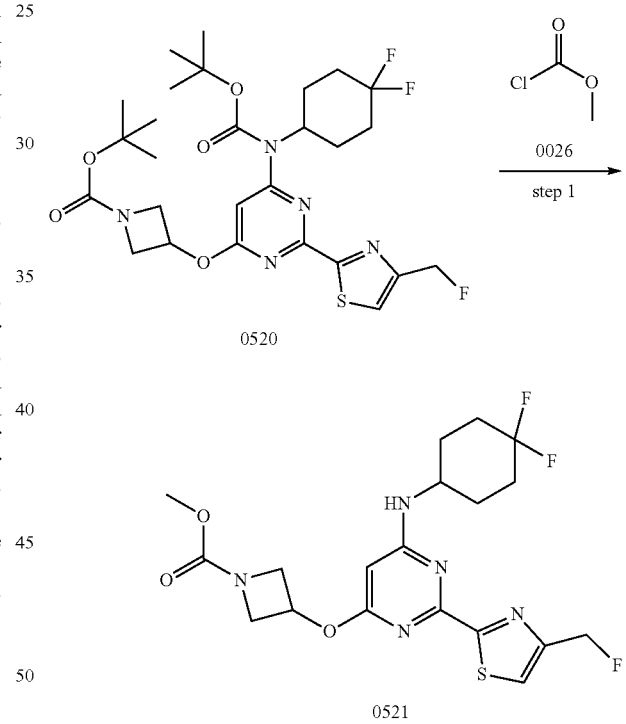

Step 1[0521]: The procedure is similar to step 8 [0036] in Example 6 (using TFA). 0.27 g of tert-butyl 3-((6-((tert-butoxycarbonyl)(4,4-difluorocyclohexyl)amino)-2-(4-(fluoromethyl)thiazol-2-yl)pyrimidin-4-yl)oxy)azetidine-1-carboxylate[0520] and 0.08 g of methyl chloroformate [0026] gave 0.130 g of methyl 3-((6-((tert-butoxycarbonyl)(4,4-difluorocyclohexyl)amino)-2-(4-(fluoromethyl)thiazol-2-yl) pyrimidin-4-yl)oxy)azetidine-1-carboxylate [0521], Compound 313 as a yellow solid (65% yield). MS(M+1)$^+$=458.2. $^1$H NMR (400 MHz, DMSO-d6) δ 8.01 (d, J=3.3 Hz, 1H), 7.62 (bs, 1H), 5.90 (bs, 1H), 5.50 (d, JF=48 Hz, 2H), 5.38 (bs, 1H), 4.35 (bs, 3H), 3.94 (bs, 2H), 3.58 (s, 3H), 2.15-1.88 (m, 6H), 1.65-1.50 (m, 2H).

Example 190

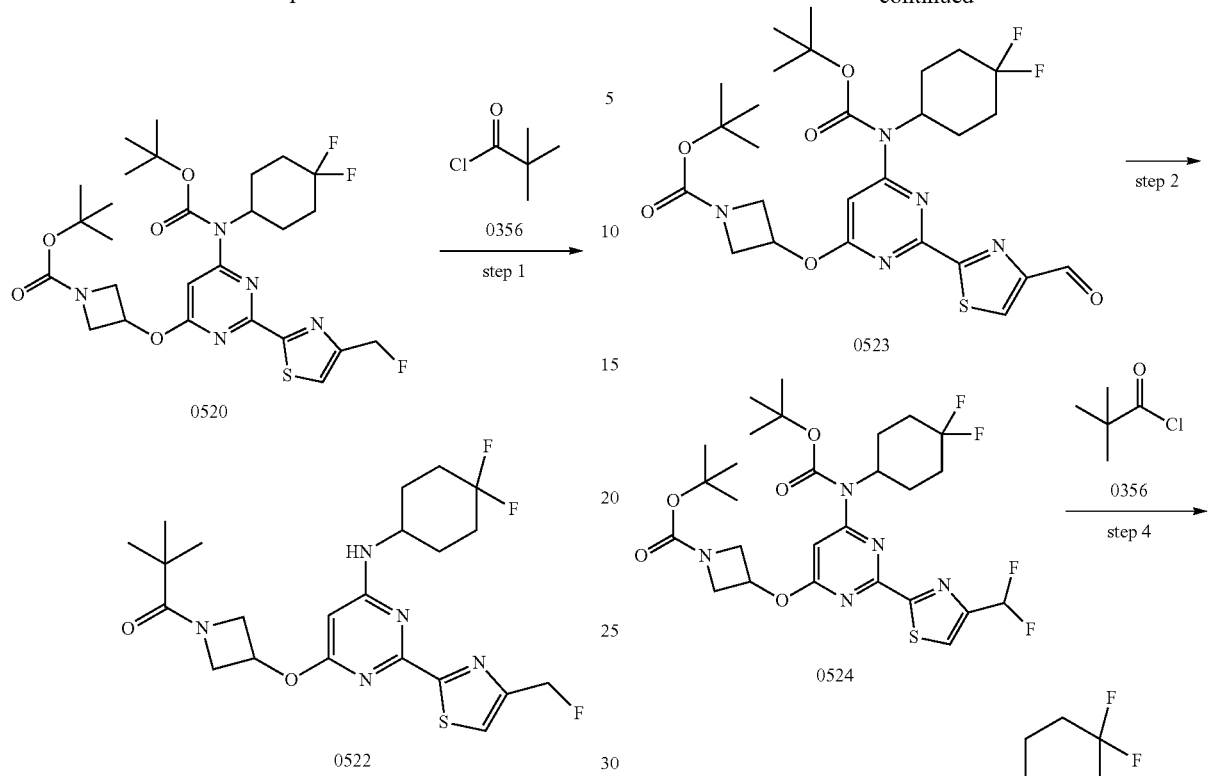

Step 1[0522]: The procedure is similar to step 8 [0036] in Example 6 (using TFA). 0.25 g of tert-butyl 3-((6-((tert-butoxycarbonyl)(4,4-difluorocyclohexyl)amino)-2-(4-(fluoromethyl)thiazol-2-yl)pyrimidin-4-yl)oxy)azetidine-1-carboxylate [0520] and 0.1 g of pivaloyl chloride [0356] gave 0.15 g of 1-(3-((6-((4,4-difluorocyclohexyl)amino)-2-(4-(fluoromethyl)thiazol-2-yl)pyrimidin-4-yl)oxy)azetidin-1-yl)-2,2-dimethylpropan-1-one [0522], Compound 316 as an off-white solid. MS(M+1)+=484.2. $^1$H NMR (400 MHz, DMSO-d6) δ 7.92 (s, 1H), 7.35 (d, J=7.2 Hz, 1H), 5.90 (s, 1H), 5.55 (d, JF=48 Hz, 2H), 5.43-5.35 (m, 1H), 4.53 (bs, 2H), 4.08 (bs, 2H), 3.93 (bs, 1H), 2.15-1.90 (m, 6H), 1.70-1.58 (m, 2H), 1.14 (s, 9H).

Example 191

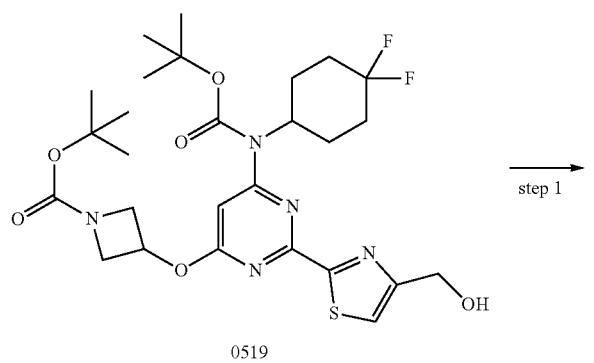

Step 1[0523]: To a solution of tert-butyl 3-((6-((tert-butoxycarbonyl)(4,4-difluorocyclohexyl)amino)-2-(4-(hydroxymethyl)thiazol-2-yl)pyrimidin-4-yl)oxy)azetidine-1-carboxylate [0519] (2.5 g, 4.182 mmol) in dichloromethane (30 mL) was added manganese dioxide (3.63 g, 41.828 mmol) under N2 atm. The resultant reaction mixture was stirred at rt for 16 h. The reaction mixture was filtered through celite bed, and washed with tetrahydrofuran, filtrate was concentrated under reduced pressure to afford crude product, which was triturated with ethyl acetate to afford 1.5 g of tert-butyl 3-((6-((tert-butoxycarbonyl)(4,4-difluorocyclohexyl)amino)-2-(4-formylthiazol-2-yl)pyrimidin-4-yl)oxy)azetidine-1-carboxylate [0523] as a yellow solid. MS(M+1)+=596.2.

Step 2[0524]: To a solution of tert-butyl 3-((6-((tert-butoxycarbonyl)(4,4-difluorocyclohexyl)amino)-2-(4-formylthiazol-2-yl)pyrimidin-4-yl)oxy)azetidine-1-carboxylate [0523] (0.7 g, 1.175 mmol) in dichloromethane (50 mL) was added diethylaminosulfurdiethylaminosulfur trifluoride (0.37 g, 2.35 mmol) at −20° C. The reaction mixture was allowed to rt for 16 h. The reaction mixture was quenched with saturated sodium bicarbonate solution (20 mL) at 0° C. and extracted with dichloromethane (50 mL), washed with water (20 mL) and brine solution (20 mL). The organic layer was dried over anhydrous sodium sulfate, filtered and concentrated under reduced pressure to afford crude product, which was purified by column chromatography using 40% ethyl acetate in pet ether as solvent to afford 0.35 g of tert-butyl 3-((6-((tert-butoxycarbonyl)(4,4-difluorocyclohexyl)amino)-2-(4-(difluoromethyl)thiazol-2-yl)pyrimidin-4-yl)oxy)azetidine-1-carboxylate [0524] as a white solid. MS(M+1)+=618.1.

Step 4[0525]: The procedure is similar to step 8 [0036] in Example 6 (using HCl gas). 0.17 g of tert-butyl 3-((6-((tert-butoxycarbonyl)(4,4-difluorocyclohexyl)amino)-2-(4-(difluoromethyl)thiazol-2-yl)pyrimidin-4-yl)oxy)azetidine-1-carboxylate [0524] and 0.06 g of pivaloyl chloride gave 0.075 g of 1-(3-((6-((4,4-difluorocyclohexyl)amino)-2-(4-(difluoromethyl)thiazol-2-yl)pyrimidin-4-yl)oxy)azetidin-1-yl)-2,2-dimethylpropan-1-one [0525], Compound 329 as a white solid. MS(M+1)+=502.2. $^1$H NMR (400 MHz, DMSO-d6) δ 8.20 (s, 1H), 7.41 (d, J=7.2 Hz, 1H), 7.09 (t, JF=54.8 Hz, 1H), 5.92 (s, 1H), 5.42-5.35 (m, 1H), 4.52 (bs, 2H), 4.09 (bs, 2H), 3.91 (bs, 1H), 2.22-1.88 (m, 6H), 1.72-1.56 (m, 2H), 1.15 (s, 9H).

Example 192

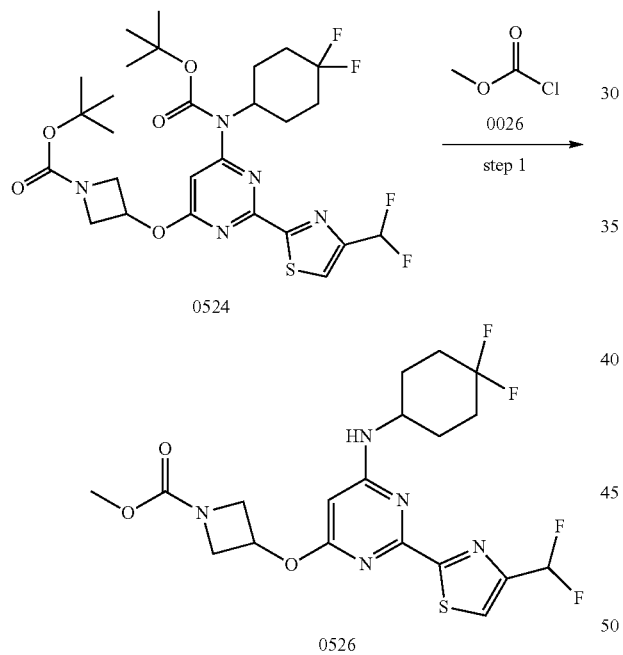

Step 1[0526]: The procedure is similar to step 8 [0036] in Example 6 (using HCl gas). 0.17 g of tert-butyl 3-((6-((tert-butoxycarbonyl)(4,4-difluorocyclohexyl)amino)-2-(4-(difluoromethyl)thiazol-2-yl)pyrimidin-4-yl)oxy)azetidine-1-carboxylate [0524] and 0.13 g of methyl chloroformate [0026] gave 0.060 g of methyl 3-((6-((4,4-difluorocyclohexyl)amino)-2-(4-(difluoromethyl)thiazol-2-yl)pyrimidin-4-yl)oxy)azetidine-1-carboxylate [0526], Compound 330 as an off-white solid. MS(M+1)+=476.0. $^1$H NMR (400 MHz, DMSO-d6) δ 8.28 (s, 1H), 7.75 (bs, 1H), 7.17 (t, JF=55 Hz, 1H), 5.93 (bs, 1H), 5.37 (s, 1H), 4.10 (bs, 1H), 4.36 (s, 2H), 3.94 (s, 2H), 3.58 (s, 3H), 2.15-1.85 (m, 6H), 1.62-1.48 (m, 2H).

Example 193

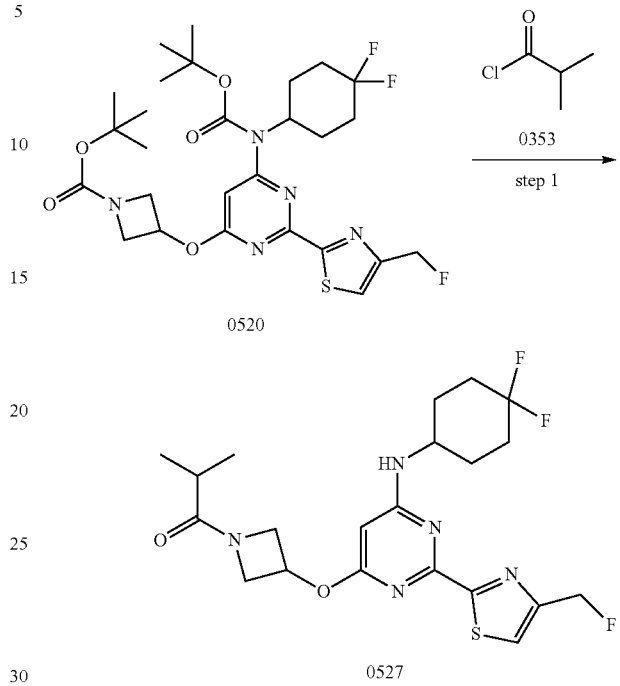

Step 1[0527]: The procedure is similar to step 8 [0036] in Example 6 (using TFA). 0.2 g of tert-butyl 3-((6-((tert-butoxycarbonyl)(4,4-difluorocyclohexyl)amino)-2-(4-(fluoromethyl)thiazol-2-yl)pyrimidin-4-yl)oxy)azetidine-1-carboxylate [0520] and 0.07 g of iso-butyryl chloride [0353] gave 0.11 g of 1-(3-((6-((4,4-difluorocyclohexyl)amino)-2-(4-(fluoromethyl)thiazol-2-yl)pyrimidin-4-yl)oxy)azetidin-1-yl)-2-methylpropan-1-one [0527], Compound 342 as a yellow solid. MS(M+1)+=470.2. $^1$H NMR (400 MHz, DMSO-d6) δ 8.02 (d, J=3.2 Hz, 1H), 7.64 (bs, 1H), 5.91 (bs, 1H), 5.55 (d, JF=48 Hz, 2H), 5.40 (bs, 1H), 4.58 (t, J=9.36 Hz, 1H), 4.01 (bs, 2H), 4.28 (dd, J=10.8, 6.8 Hz, 1H), 4.18 (dd, J=9.8, 4.1 Hz, 1H), 3.84 (dd, J=10.7, 4.2 Hz, 1H), 2.15-1.90 (m, 6H), 1.65-1.53 (m, 2H), 0.99 (t, J=6.9 Hz, 6H).

Example 194

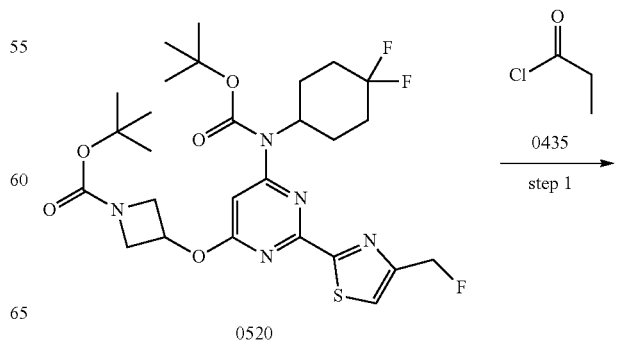

-continued

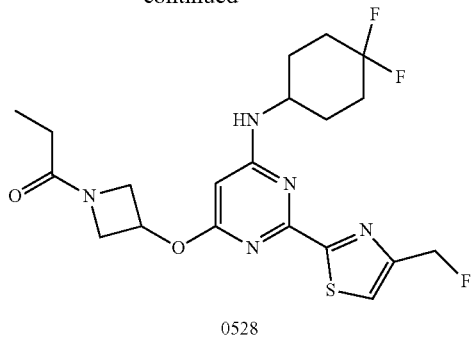

0528

Step 1[0528]: The procedure is similar to step 8 [0036] in Example 6 (using TFA). 0.25 g of tert-butyl 3-((6-((tert-butoxycarbonyl)(4,4-difluorocyclohexyl)amino)-2-(4-(fluoromethyl)thiazol-2-yl)pyrimidin-4-yl)oxy)azetidine-1-carboxylate [0520] and 0.07 g of propionyl chloride [0435] gave 0.15 g of 1-(3-((6-((4,4-difluorocyclohexyl)amino)-2-(4-(fluoromethyl)thiazol-2-yl)pyrimidin-4-yl)oxy)azetidin-1-yl)propan-1-one [0528], Compound 341 as a yellow solid. MS(M+1)+=456.2. $^1$H NMR (400 MHz, DMSO-d6) δ 7.92 (s, 1H), 7.35 (d, JF=7.6 Hz, 1H), 5.91 (s, 1H), 5.55 (d, JF=48 Hz, 2H), 5.45-5.35 (m, 1H), 4.44 (bs, 2H), 3.92 (bs, 3H), 2.11-1.90 (m, 8H), 1.72-1.55 (m, 2H), 1.00 (t, J=7.3 Hz, 3H).

Example 195

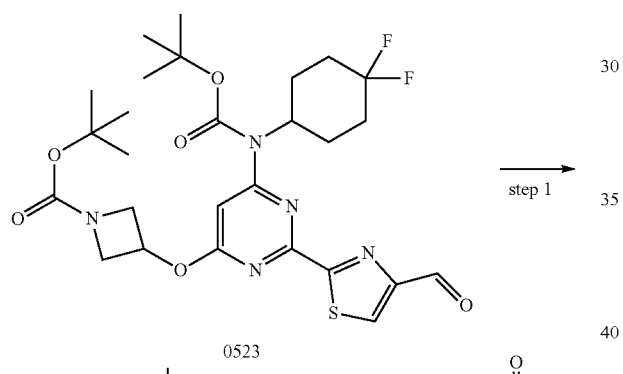

0523

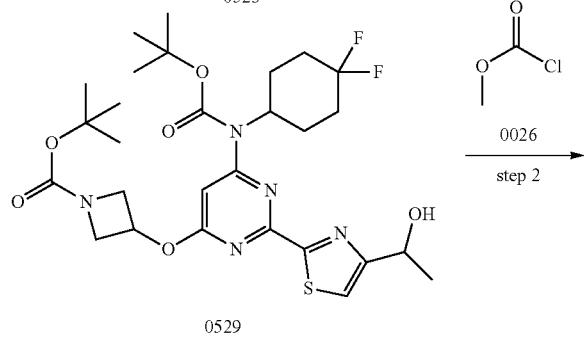

0529

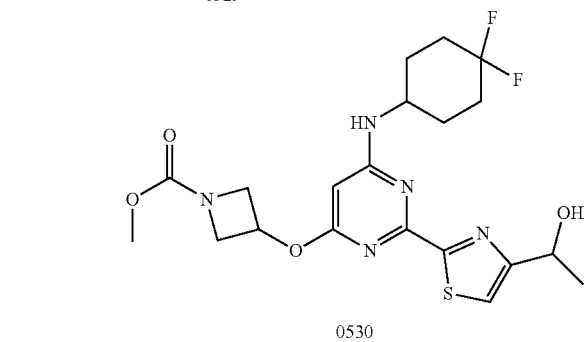

0530

Step 1[0529]: To a solution of tert-butyl 3-((6-((tert-butoxycarbonyl)(4,4-difluorocyclohexyl)amino)-2-(4-formylthiazol-2-yl)pyrimidin-4-yl)oxy)azetidine-1-carboxylate [0523] (0.9 g, 1.510 mmol) in tetrahydrofuran (5 mL) was added methyl magnesium bromide (0.9 g, 7.55 mmol) drop-wise at −15° C. (ice+acetone) under inert atm. Resultant reaction mixture was allowed to stir at same −15° C. to rt for 4 h. The reaction mixture was quenched with saturated ammonium chloride solution (10 mL) and product was extracted with dichloromethane (3×30 ml). The combined organic layer were washed with brine (10 mL), dried over anhydrous sodium sulfate and concentrated under reduced pressure to afford crude product, which was purified by column chromatography using 70% ethyl acetate in pet ether as solvent to afford 0.320 g of tert-butyl 3-((6-((tert-butoxycarbonyl)(4,4-difluorocyclohexyl)amino)-2-(4-(1-hydroxyethyl)thiazol-2-yl)pyrimidin-4-yl)oxy)azetidine-1-carboxylate [0529] as an off-white solid. MS(M+1)+=612.4.

Step 2[0530]: The procedure is similar to step 8 [0036] in Example 6 (using HCl gas). 0.17 g of tert-butyl 3-((6-((tert-butoxycarbonyl)(4,4-difluorocyclohexyl)amino)-2-(4-(1-hydroxyethyl)thiazol-2-yl)pyrimidin-4-yl)oxy)azetidine-1-carboxylate [0529] and 0.05 g of Methyl chloroformate gave 0.055 g of methyl 3-((6-((4,4-difluorocyclohexyl)amino)-2-(4-(1-hydroxyethyl)thiazol-2-yl)pyrimidin-4-yl)oxy)azetidine-1-carboxylate [0530], Compound 344 as a yellow solid. MS(M+1)+=470.2. $^1$H NMR (400 MHz, DMSO-d6) δ 7.68 (bs, 1H), 7.56 (s, 1H), 5.88 (bs, 1H), 5.39 (d, J=4.44 Hz, 1H), 5.35 (s, 1H), 4.87 (t, J=6.1 Hz, 1H), 4.34 (bs, 2H), 4.01 (bs, 1H), 3.94 (s, 2H), 3.58 (s, 3H), 2.12-1.88 (m, 6H), 1.62-1.50 (m, 2H), 1.42 (d, J=6.5 Hz, 3H).

Example 196

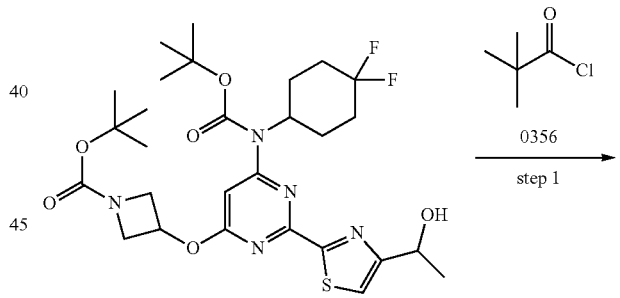

0529

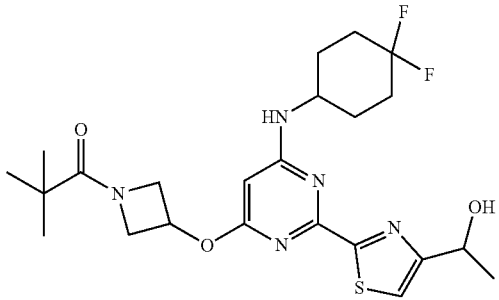

0531

Step 1[0531]: The procedure is similar to step 8 [0036] in Example 6 (using TFA). 0.17 g of tert-butyl 3-((6-((tert-butoxycarbonyl)(4,4-difluorocyclohexyl)amino)-2-(4-(1-hydroxyethyl)thiazol-2-yl)pyrimidin-4-yl)oxy)azetidine-1- carboxylate [0529] and 0.07 g of pivaloyl chloride gave 0.025 g of [0531], Compound 337 as an off-white solid.

MS(M+1)+=496.2. ¹H NMR (400 MHz, DMSO-d6) δ 7.58 (bs, 1H), 7.56 (s, 1H), 5.89 (s, 1H), 5.38 (d, J=4.76 Hz, 1H), 5.35 (b, 1H), 4.87 (t, J=5.36 Hz, 1H), 4.82 (bs, 1H), 4.42-4.25 (m, 2H), 3.83 (bs, 2H), 2.12-1.87 (m, 6H), 1.65-1.50 (m, 2H), 1.48-1.32 (m, 4H), 1.12 (s, 8H).

Example 197

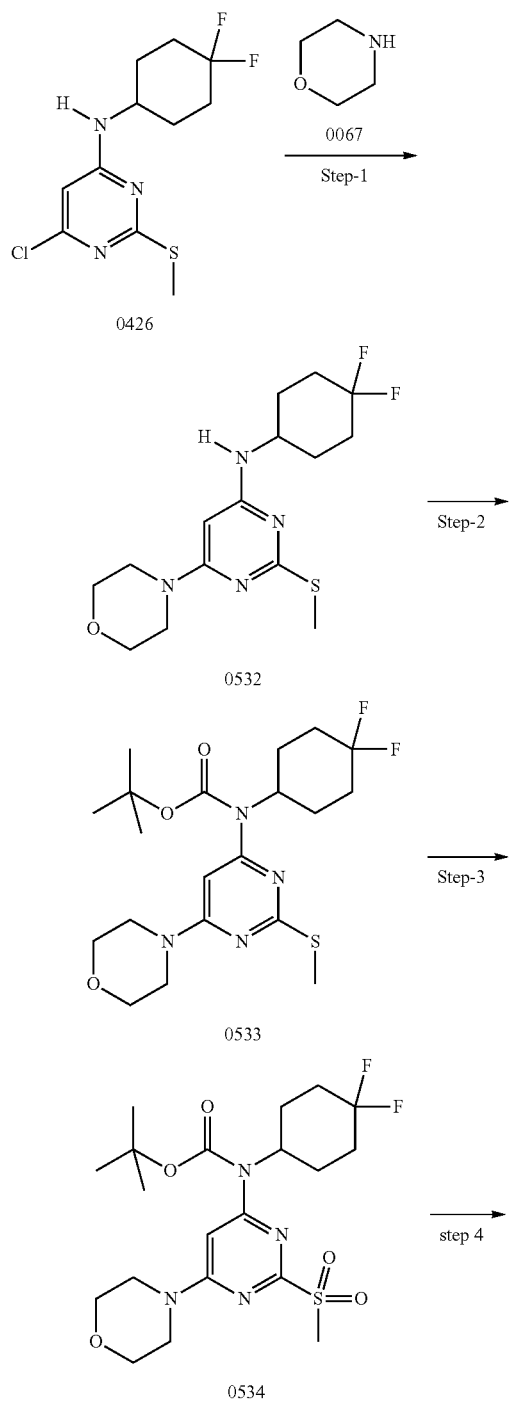

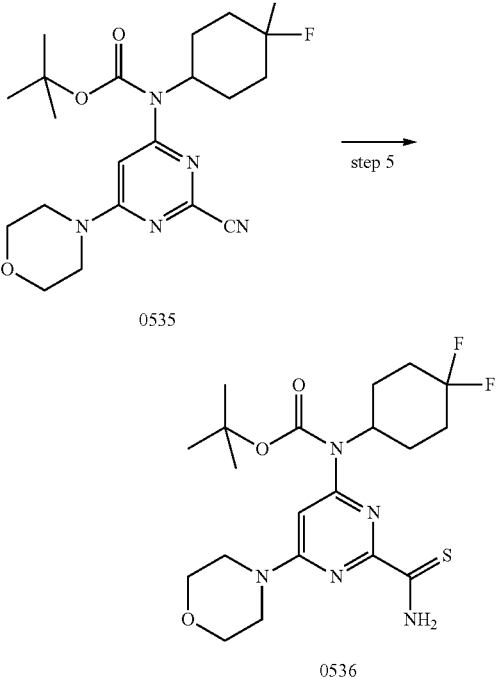

Step 1 [0532]: To a solution of 6-chloro-N-(4,4-difluorocyclohexyl)-2-(methylthio)pyrimidin-4-amine [0426] (1.4 g, 4.76 mmol) and morpholine [67] (0.83 mL, 9.53 mmol) in acetonitrile (20 mL) was heated at 85° C. in a sealed tube for 16 h. After completion of the reaction, the reaction mixture was filtered to remove cesium carbonate and the filtrate was concentrated and the resulting residue which was purified by column chromatography using 30% ethyl acetate in hexane as eluent to afford N-(4,4-difluorocyclohexyl)-2-(methylthio)-6-morpholinopyrimidin-4-amine [0532] as an off-white solid (1.5 g 93% yield). MS(M+1)+=345.2.

Step 2 [0533]: To a solution of N-(4,4-difluorocyclohexyl)-2-(methylthio)-6-morpholino pyrimidin-4-amine [0532] (1 g, 2.90 mmol) in tetrahydrofuran (15 mL) was added 4-N,N-dimethylamino pyridine (0.1 g, 0.87 mmol0), triethyl amine (1.2 ml, 8.71 mmol) and boc-anhydride (3.16 g, 14.51 mmol). The reaction mixture was heated at 80° C. for 16 h, After completion of the reaction, the reaction mixture was quenched with water and extracted with ethyl acetate (2×75 mL), the combined organic layer was dried over anhydrous sodium sulfate and concentrated to afford tert-butyl (4,4-difluorocyclohexyl)(2-(methylthio)-6-morpholino pyrimidin-4-yl)carbamate [0533] as a yellow gum (1.1 g 85%).

MS(M+1)+=445.2

Step 3 [0534]: To an ice cooled solution of tert-butyl (4,4-difluorocyclohexyl)(2-(methylthio)-6-morpholinopyrimidin-4-yl)carbamate [0533] (1.1 g, 2.47 mmol) in dichloromethane (20 mL) was added 3-chloroperbenzoic acid (m-chloroperbenzoic acid) (1.28 g, 7.42 mmol), then the reaction mixture was stirred at rt for 30 min. After the completion, the reaction mixture was quenched with saturated bicarbonate solution and extracted with dichloromethane (2×75 mL), the combined organic layer was dried over anhydrous sodium sulfate and concentrated to afford tert-butyl (4,4-difluorocyclohexyl)(2-(methylsulfonyl)-6-morpholinopyrimidin-4-yl)carbamate [0534] as an off-white gum (0.9 g 76% yield). MS(M+1)+=477.3

Step 4 [0535]: To a solution of tert-butyl (4,4-difluorocyclohexyl)(2-(methylsulfonyl)-6-morpholinopyrimidin-4- yl)carbamate [0534] in dimethylsulfoxide (10 mL) was added 1,4-diazabicyclo[2.2.2]octane (0.23 g, 2.077 mmol1.) followed by sodium cyanide (0.102 g, 2.077 mmol). The reaction mixture was stirred at rt. After the completion, the reaction mixture was quenched with water, the obtained solid was filtered and dried under high vacuum to afford tert-butyl (2-cyano-6-morpholinopyrimidin-4-yl)(4,4-difluoro cyclohexyl)carbamate [0535] as an light brown solid (0.4 g 50% yield). MS(M+1)+=324.3.

Step 5 [0536]: To a solution of tert-butyl (2-cyano-6-morpholinopyrimidin-4-yl)(4,4-difluoro cyclohexyl)carbamate [0535] (0.4 g, mmol) in N,N-dimethylformamide (10 mL) was added triethylamine (0.26 mL, 1.88 mmol) and ammonium sulfide in water (20%) (0.64 g, 1.88 mmol) and the reaction mixture was stirred at rt for 10 min. After the completion, the reaction mixture was quenched with water, the obtained solid was filtered and dried under high vacuum to afford tert-butyl (2-carbamothioyl-6-morpholinopyrimidin-4-yl) (4,4-difluoro cyclohexyl) carbamate [0536] as a light brown solid (0.4 g, 93%). MS(M+1)+=458.2

Example 198

Step 1 [0537]: To a solution of tert-butyl (2-carbamothioyl-6-morpholinopyrimidin-4-yl)(4,4-di fluorocyclohexyl)carbamate [0536] (0.4 g, 0.87 mmol) in ethanol (10 mL) was added bromoacetone [0090] (0.155 g, 1.13 mmol). The reaction mixture was stirred at rt. After completion of the reaction, the reaction mixture was concentrated and the resulting residue was quenched with saturated bicarbonate solution and extracted with ethyl acetate (2×50 mL), the combined organic layer was dried over anhydrous sodium sulfate and concentrated to afford brownish gum and which was purified by column chromatography using 42% ethyl acetate in hexane as eluent to afford tert-butyl (4,4-difluorocyclohexyl)(2-(4-methylthiazol-2-yl)-6-morpholinopyrimidin-4-yl)carbamate [0537] as an off-white solid (0.3 g 69% yield). MS(M+1)+=496.2.

Step 2 [0538]: To an ice cooled solution of tert-butyl (4,4-difluorocyclohexyl)(2-(4-methyl thiazol-2-yl)-6-morpholino pyrimidin-4-yl)carbamate [0537] (0.3 g, 0.605 mmol) in dichloromethane was added trifluoroacetic acid (0.187 ml, 2.42 mmol), then the reaction mixture was stirred at rt. After the completion of the reaction, the reaction mixture was concentrated and the resulting residue was basified with saturated bicarbonate solution and extracted with ethyl acetate (2×70 mL), the combined organic layer was dried over anhydrous sodium sulfate and concentrated and which was purified by column chromatography to afford N-(4,4-difluorocyclohexyl)-2-(4-methylthiazol-2-yl)-6-morpholinopyrimidin-4-amine [0538], Compound 320 as an off-white solid (0.105 g). MS(M+1)+=396.3. ¹H NMR (400 MHz, DMSO-d6) δ 7.34 (d, J=1.2 Hz, 1H), 7.05 (d, J=8.0 Hz, 1H), 5.66 (s, 1H), 3.89 (bs, 1H), 3.69 (dd, J=5.8, 3.8 Hz, 4H), 3.58-3.48 (m, 4H), 2.42 (s, 3H), 2.11-1.90 (m, 6H), 1.59-1.52 (m, 2H).

Example 199

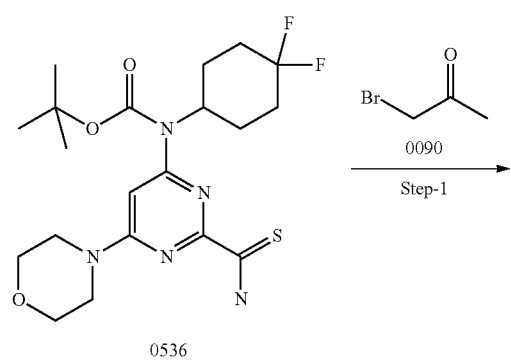

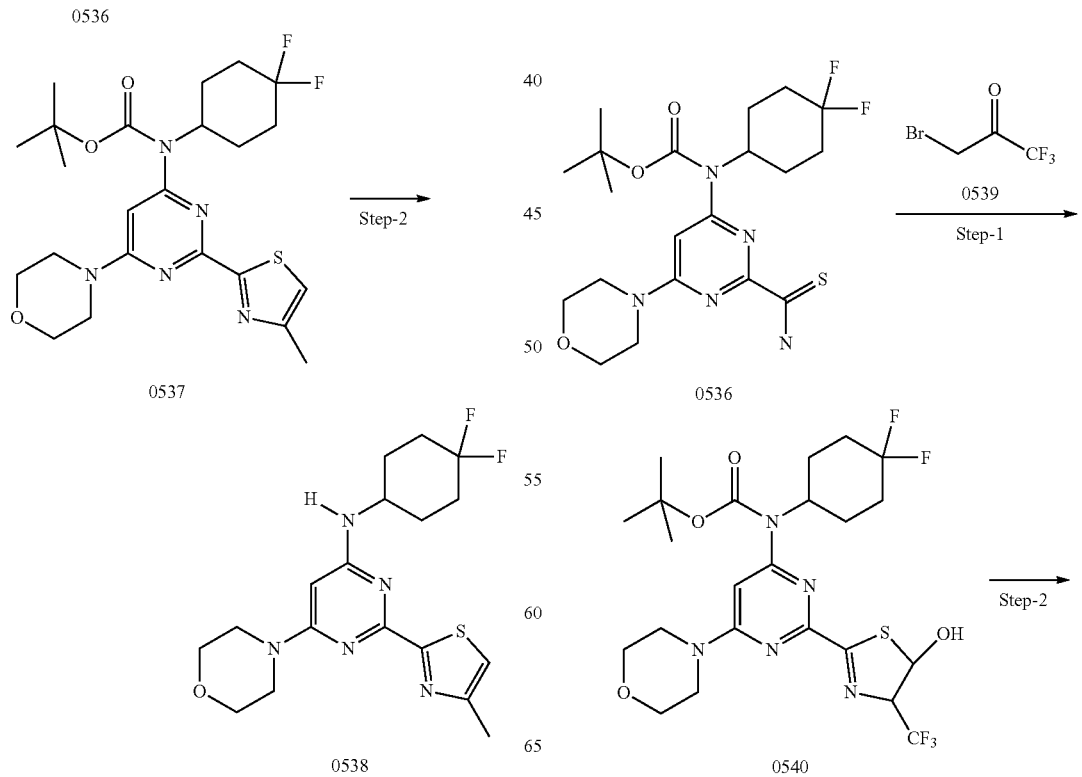

ethyl)thiazol-2-yl)pyrimidin-4-amine [0542], Compound 332 as an off-white solid (0.175 g, 53% yield). MS(M+1)⁺=450.4. ¹H-NMR (400 MHz, DMSO-d6): δ 7.93 (d, J=3.28 Hz, 1H), 7.12 (d, J=7.60 Hz, 1H), 5.69 (s, 1H), 5.48 (d, JF=48.5 Hz, 2H), 3.90 (s, 1H), 3.70 (m, 4H), 3.52 (m, 4H), 1.95-1.56 (m, 6H), 1.24 (s, 2H), Example 200

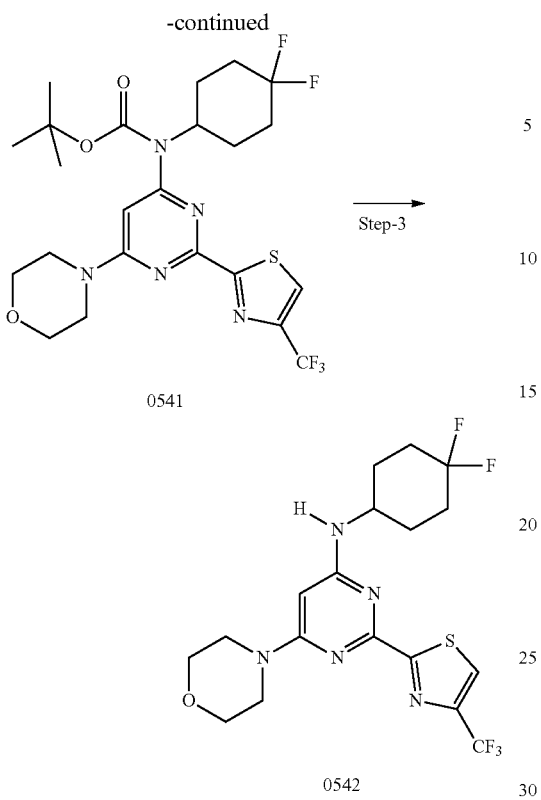

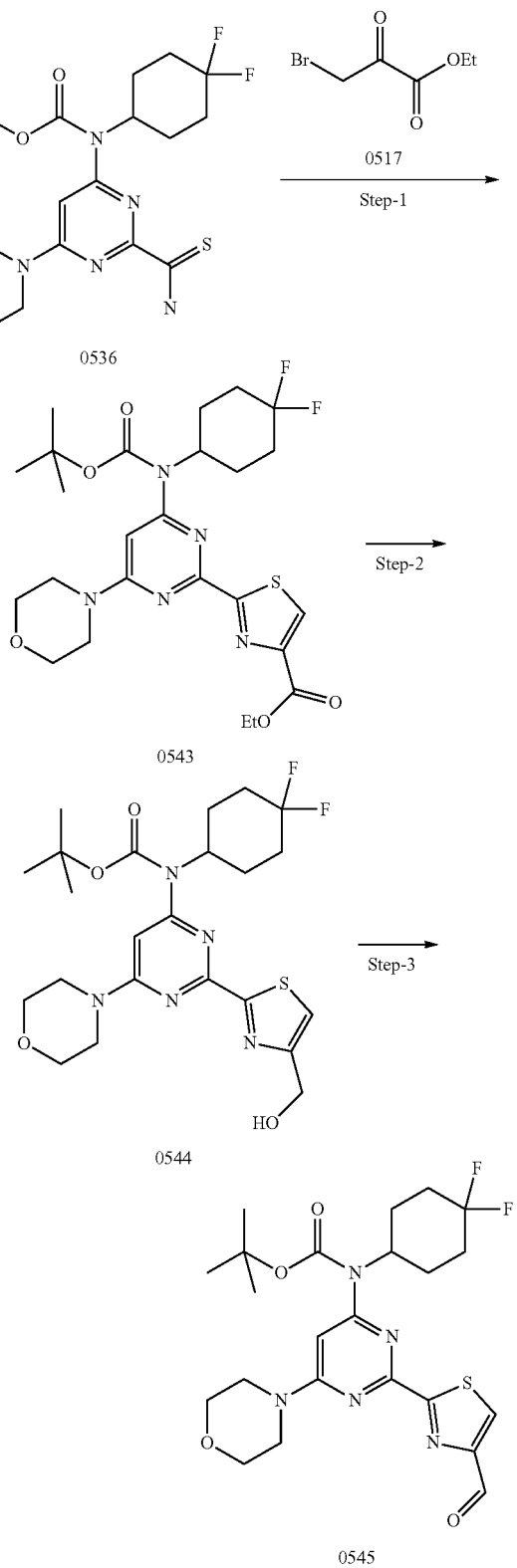

Step 1 [0540]: To a solution of tert-butyl (2-carbamothioyl-6-morpholinopyrimidin-4-yl)(4,4-difluoro cyclohexyl) carbamate [0536] (0.5 g, 1.09 mmol) in tetrahydrofuran (10 mL) was added 3-bromo-1,1,1-trifluoroacetone [0539] (0.313 g, 1.63 mmol), then the reaction mixture was stirred at rt. After the completion of the reaction, the reaction mixture was concentrated to afford N-(4,4-difluorocyclohexyl)-2-(4-methylthiazol-2-yl)-6-morpholinopyrimidin-4-amine [0540] as an off-white gum (0.6 g) and it was taken as such for next step. MS(M+1)+=568.2.

Step 2 [0541]: To a solution of N-(4,4-difluorocyclohexyl)-2-(4-methylthiazol-2-yl)-6-morpholinopyrimidin-4-amine [0540] (0.6 g, 1.05 mmol) in dichloromethane (10 mL) was added triethylamine (0.29 mL, 2.11 mmol) and trifluoroacetic anhydride (0.29 mL, 2.11 mmol), then the reaction mixture was stirred at rt. After the completion of the reaction, the reaction mixture was quenched with water and extracted dichloromethane (2×35 mL), the combined organic layer was dried over anhydrous sodium sulfate and concentrated to afford as an light brownish gum which was purified by column of silica gel (60-120 mesh), using 35% ethyl acetate in hexane as eluent to afford tert-butyl (4,4-difluorocyclohexyl)(6-morpholino-2-(4-(trifluoromethyl)thiazol-2-yl)pyrimidin-4-yl)carbamate [0541] as an off-white solid. (0.4 g, 68% Yield). MS(M+1)+=550.4

Step 3 [0542]: To a solution of tert-butyl (4,4-difluorocyclohexyl)(6-morpholino-2-(4-(trifluoromethyl)thiazol-2-yl)pyrimidin-4-yl)carbamate [0541] (0.4 g, 0.72 mmol) in dichloromethane (10 mL) was added trifluoroacetic acid (1 mL, 13.02 mmol), then the reaction mixture was stirred at rt. After the completion of the reaction, the reaction mixture was concentrated and the resulting residue was quenched with 10% sodium bicarbonate solution and extracted with ethyl acetate (2×40 mL), the combined organic layer was dried over anhydrous sodium sulfate and concentrated as an brownish gum and which was purified by column chromatography using 30% ethyl acetate in hexane as to afford N-(4,4-difluorocyclohexyl)-6-morpholino-2-(4-(trifluorom- Step 1 [0543]: To a solution of tert-butyl (2-carbamothioyl-6-morpholinopyrimidin-4-yl)(4,4-difluoro cyclohexyl) carbamate [0536] (2.8 g, 6.11 mmol) in tetrahydrofuran (30 mL) was added ethyl bromopyruvate [0517] (1.79 g, 9.17 mmol), then the reaction mixture was stirred at rt for 4 h. After the completion of the reaction, the reaction mixture was concentrated. The residue was dissolved in ethyl acetate and washed with 10% sodium bicarbonate solution. The organic layer was concentrated to afford as an off-white solid which was triturated with methanol. The obtained solid was filtered and dried under high vacuum to afford ethyl 2-(4-((tert-butoxycarbonyl)(4,4-difluorocyclohexyl)amino)-6-morpholino pyrimidin-2-yl)thiazole-4-carboxylate [0543] as an off-white solid. (2 g, 60% Yield). MS(M+1)+=554.2.

Step 2 [0544]: To a solution of ethyl 2-(4-((tert-butoxycarbonyl)(4,4-difluorocyclohexyl)amino)-6-morpholino pyrimidin-2-yl)thiazole-4-carboxylate [0543] (1.5 g, 2.70 mmol) in tetrahydrofuran (20 mL) was added lithium borohydride (0.177 g, 8.12 mmol), then the reaction mixture was stirred at rt for 1 h. After the completion of the reaction, the reaction mixture was quenched with water and extracted with ethyl acetate (2×50 mL), the combined organic layer was dried over anhydrous sodium sulfate and concentrated to afford tert-butyl (4,4-difluorocyclohexyl)(2-(4-(hydroxymethyl) thiazol-2-yl)-6-morpholinopyrimidin-4-yl) carbamate [0544] as an off-white solid. (1 g, 72% Yield). MS(M+1)+=512.2.

Step 3 [0545]: To an ice cooled solution of tert-butyl (4,4-difluorocyclohexyl)(2-(4-(hydroxymethyl)thiazol-2-yl)-6-morpholinopyrimidin-4-yl)carbamate [0544] (1 g, 1.95 mmol) in dichloromethane (20 mL) was added Dess-Martin periodinane (1.28 g, 2.93 mmol), then the reaction mixture was stirred at rt for 30 min. After the completion of the reaction, the reaction mixture was quenched with saturated bicarbonate solution and extracted dichloromethane (2×75 mL). The combined organic layer was dried over anhydrous sodium sulfate and concentrated to afford tert-butyl (4,4-difluorocyclohexyl)(2-(4-formylthiazol-2-yl)-6-morpholinopyrimidin-4-yl)carbamate [0545] as an off-white solid. (0.9 g, 90% Yield). MS(M+1)+=510.4.

Example 201

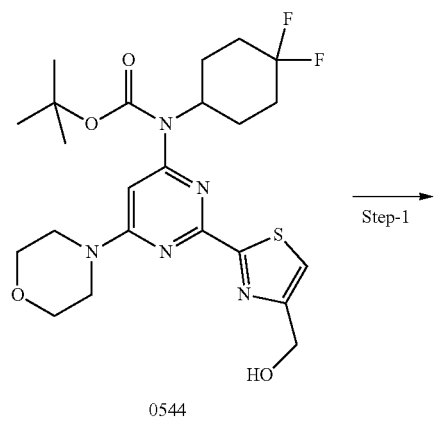

0544

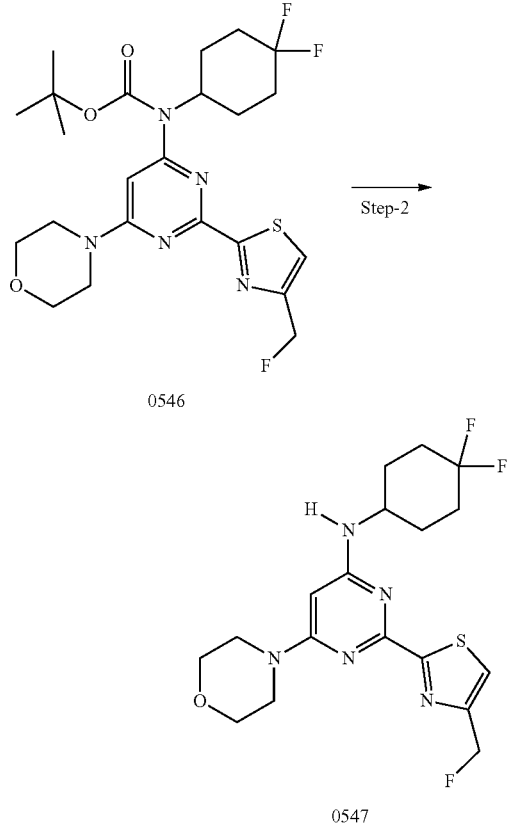

0546

0547

Step 1[0546]: To an ice cooled solution of tert-butyl (4,4-difluorocyclohexyl)(2-(4-(hydroxymethyl)thiazol-2-yl)-6-morpholinopyrimidin-4-yl)carbamate [00544] (0.4 g, 0.78 mmol) in dichloromethane (10 mL) was added diethylaminosulfur trifluoride (0.25 g, 1.56 mmol). The reaction mixture was slowly warmed to rt and stirred for 30 min. After completion of the reaction, the reaction mixture was quenched with saturated bicarbonate solution and extracted dichloromethane (2×75 mL). The combined organic layer was dried over anhydrous sodium sulfate and concentrated to afford 0.31 g of tert-butyl (4,4-difluorocyclohexyl)(2-(4-(fluoromethyl)thiazol-2-yl)-6-morpholinopyrimidin-4-yl) carbamate [0546] as an light brownish gum and which was taken as such for next step.
MS(M+1)+=514.4.

Step 2 [0547]: To an ice cooled solution of tert-butyl (4,4-difluorocyclohexyl)(2-(4-(fluoromethyl)thiazol-2-yl)-6-morpholinopyrimidin-4-yl)carbamate [0546] (0.31 g, 0.60 mmol) in dichloromethane (10 mL) was added trifluoroacetic acid (1.2 g, 10.41 mmol). The reaction mixture was slowly warmed to rt and stirred 16 h. After the completion of the reaction, the reaction mixture was concentrated and the resulting residue was quenched with 10% sodium bicarbonate solution and extracted with ethyl acetate (2×40 mL), the combined organic layer was dried over anhydrous sodium sulfate and concentrated to afford as an brownish gum and which was purified by column chromatography using 35% ethyl acetate in hexane as to afford N-(4,4-difluorocyclohexyl)-2-(4-(fluoromethyl)thiazol-2-yl)-6-morpholinopyrimidin-4-amine [0547], Compound 336 as an off-white solid. (0.115 g, 46%, Yield). MS(M+1)+, 414.2. 
$^1$H-NMR (400 MHz, DMSO-d6): δ 7.93 (d, J=3.28 Hz, 1H), 7.12 (d, J=7.60 Hz, 1H), 5.69 (s, 1H), 5.48 (d, JF=48.5 Hz, 2H), 3.90 (s, 1H), 3.70 (m, 4H), 3.52 (m, 4H), 1.95-1.56 (m, 6H), 1.24 (s, 2H),

Example 202

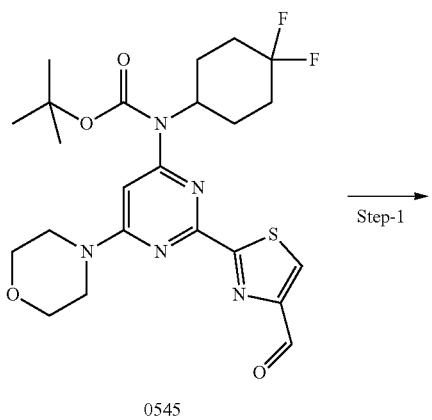

0545

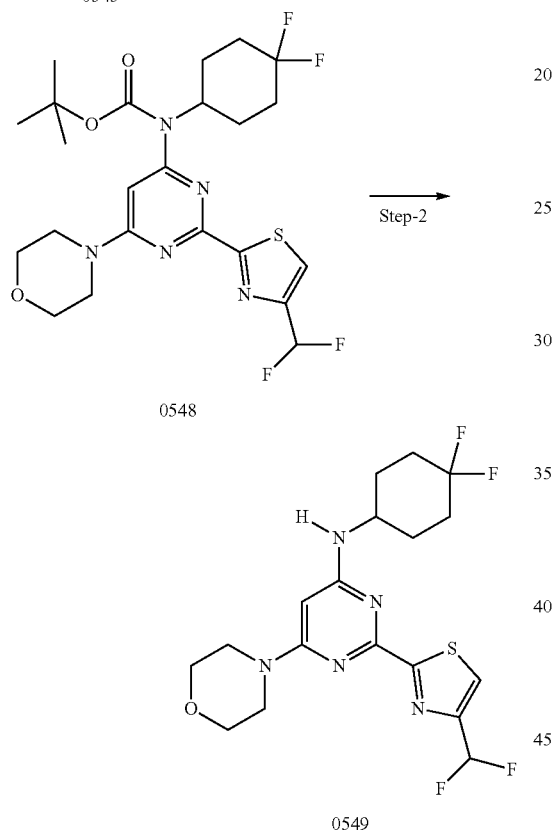

Step 1 [0548]: To an ice cooled solution of tert-butyl (4,4-difluorocyclohexyl)(2-(4-formylthiazol-2-yl)-6-morpholinopyrimidin-4-yl)carbamate [0545] (0.5 g, 0.98 mmol) in dichloromethane (10 mL) was added diethylamino sulfur trifluoride (0.31 g, 1.961 mmol), then the reaction mixture was slowly warmed to rt and stirred for 30 min. After the completion of the reaction, the reaction mixture was quenched with saturated bicarbonate solution and extracted dichloromethane (2×75 mL), the combined organic layer was dried over anhydrous sodium sulfate and concentrated to afford tert-butyl (4,4-difluorocyclohexyl)(2-(4-(difluoromethyl)thiazol-2-yl)-6-morpholinopyrimidin-4-yl)carbamate [0548] as an light brownish gum (0.45 g) and which was taken as such for next step. MS(M+1)+=532.2.

Step 2 [0549]: To an ice cooled solution of tert-butyl (4,4-difluorocyclohexyl)(2-(4-(difluoromethyl)thiazol-2-yl)-6-morpholinopyrimidin-4-yl)carbamate [0548] (0.45 g, 0.84 mmol) in dichloromethane (10 mL) was added trifluoroacetic acid (1.5 g, 13.02 mmol). The reaction mixture was slowly warmed to rt and stirred for 16 h. After the completion of the reaction, the reaction mixture was concentrated and neutralized with 10% sodium bicarbonate solution and extracted with ethyl acetate, the combined organic layer was dried over anhydrous sodium sulfate and concentrated to afford as an brownish gum and which was purified by column chromatography using 80% ethyl acetate in hexane to afford N-(4,4-difluorocyclohexyl)-2-(4-(difluoromethyl) thiazol-2-yl)-6-morpholinopyrimidin-4-amine [0549], Compound 339 as an off-white solid. (0.22 g, 60%, Yield). MS(M+1)+=432.2. ¹H-NMR (400 MHz, DMSO-d6): δ 8.20 (s, 1H), 7.18 (bs, 1H), 7.16 (t, JF=54.52 Hz, 1H), 5.70 (s, 1H), 3.88 (bs, 1H), 3.70 (s, 4H), 3.53 (s, 4H), 2.08-1.93 (m, 6H), 1.57-1.52 (m, 2H).

Example 203

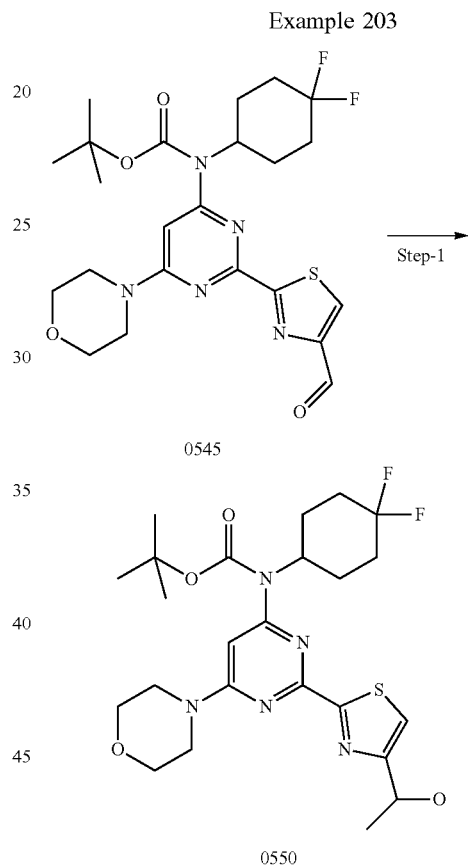

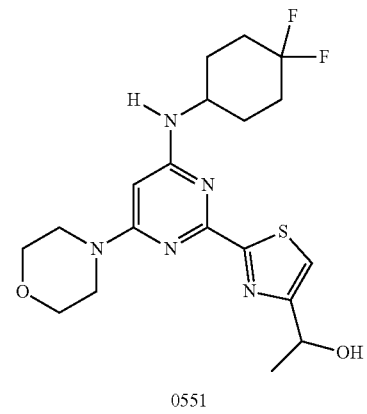

0551

Step 1 [0550]: To an ice cooled solution of tert-butyl (4,4-difluorocyclohexyl)(2-(4-formylthiazol-2-yl)-6-morpholinopyrimidin-4-yl)carbamate [0545] (0.3 g, 0.58 mmol) in tetrahydrofuran (10 mL) was added 2M solution of methyl magnesium bromide in tetrahydrofuran (0.14 g, 1.17 mmol). After completion of addition, the reaction mixture was slowly warmed to rt and stirred at rt for 1 h. After the completion of the reaction, the reaction mixture was quenched with water and extracted with ethyl acetate (2×50 mL), the combined organic layer was dried over anhydrous sodium sulfate and concentrated to afford tert-butyl (4,4-difluorocyclohexyl)(2-(4-(1-hydroxyethyl)thiazol-2-yl)-6-morpholinopyrimidin-4-yl)carbamate [0550] as an off-white gum (0.25 g) and which was taken as such for next step. MS(M+1)+=526.2.

Step 2 [551]: To an ice cooled solution of tert-butyl (4,4-difluorocyclohexyl)(2-(4-(1-hydroxyethyl)thiazol-2-yl)-6-morpholinopyrimidin-4-yl)carbamate [0550] (0.25 g, 0.47 mmol) in dichloromethane (10 mL) was added 4N hydrochloric acid in dioxane (0.93 g, 25.6 mmol5). The reaction mixture was slowly warmed to rt and stirred for 16 h. After the completion of the reaction, the reaction mixture was concentrated and neutralized with 10% sodium bicarbonate solution and extracted with ethyl acetate, the combined organic layer was dried over anhydrous sodium sulfate and concentrated to afford as an brownish gum and which was purified by column chromatography using ethyl acetate as eluent to afford 1-(2-(4-((4,4-difluorocyclohexyl)amino)-6-morpholinopyrimidin-2-yl)thiazol-4-yl)ethan-1-ol [0551], Compound 340 as a light yellow solid. (0.065 g, 32%, Yield). MS(M+1)⁺=426.4. ¹H-NMR (400 MHz, DMSO-d6): δ 7.47 (d, J=0.72 Hz, 1H), 7.09 (d, J=7.84 Hz, 1H), 5.67 (s, 1H), 5.34 (d, J=4.76 Hz, 1H), 4.87-4.84 (m, 1H), 3.99 (s, 1H), 3.68 (m, 4H), 3.52 (m, 4H), 2.08-1.92 (m, 6H), 1.61-1.56 (m, 2H), 1.42 (d, J=6.52 Hz, 3H), Example 204

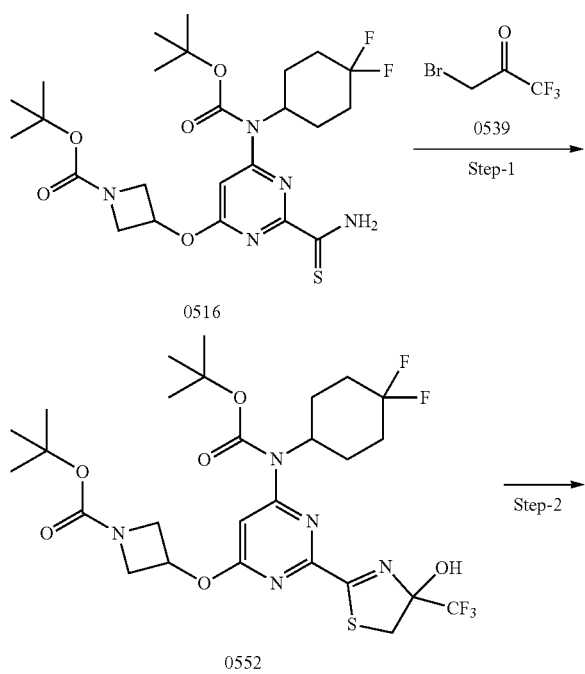

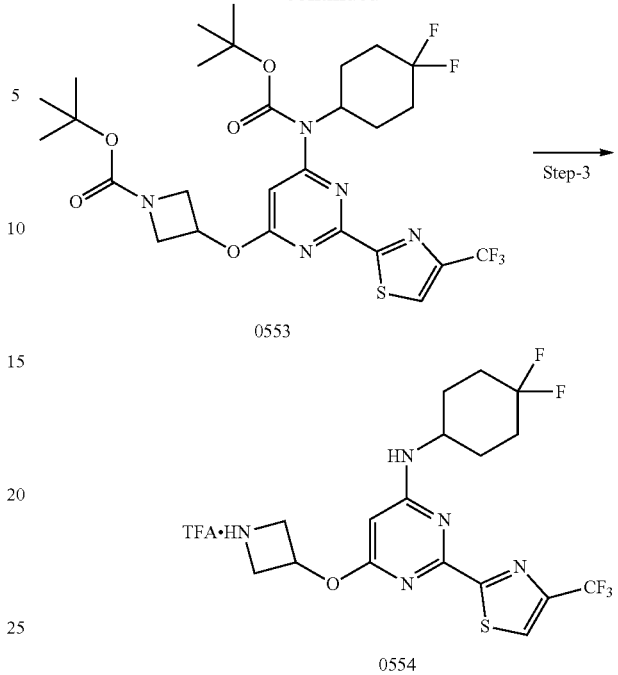

Step 1 [0552]: To a solution of tert-butyl 3-((6-((tert-butoxycarbonyl)(4,4-difluorocyclohexyl)amino)-2-carbamothioylpyrimidin-4-yl)oxy)azetidine-1-carboxylate [0516] (0.5 g, 0.919 mmol) in tetrahydrofuran (10 mL) was added 3-bromo-1,1,1-trifluoroacetone [0539] (0.21 g, 1.10 mmol). The reaction mixture was stirred at rt for 5 h. After the completion of the reaction, the reaction mixture was concentrated to afford 0.6 g of tert-butyl 3-((6-((tert-butoxycarbonyl)(4,4-difluorocyclohexyl)amino)-2-(2-hydroxy-4-(trifluoromethyl)-2,3-dihydrothiazol-2-yl)pyrimidin-4-yl)oxy)azetidine-1-carboxylate [0552] as an off-white gum. MS(M+1)+=654.2.

Step 2 [0553]: To an ice cooled solution of tert-butyl 3-((6-((tert-butoxycarbonyl)(4,4-difluorocyclohexyl)amino)-2-(2-hydroxy-4-(trifluoromethyl)-2,3-dihydrothiazol-2-yl)pyrimidin-4-yl)oxy)azetidine-1-carboxylate [0552] in dichloromethane (10 mL) (0.6 g, 0.917 mmol) was added triethylamine (0.18 g, 1.83 mmol) and trifluoroacetic anhydride (0.385 g, 1.83 mmol). The reaction mixture was stirred at rt for 30 min. After the completion of the reaction, the reaction mixture was quenched with water and extracted dichloromethane (2×35 mL), the combined organic layer was dried over anhydrous sodium sulfate and concentrated to afford as an light brownish gum and which was purified by column of silica gel (60-120 mesh), using 30% ethyl acetate in hexane as eluent to afford tert-butyl 3-((6-((tert-butoxycarbonyl)(4,4-difluorocyclohexyl)amino)-2-(2-hydroxy-4-(trifluoromethyl)-2,3-dihydrothiazol-2-yl)pyrimidin-4-yl)oxy)azetidine-1-carboxylate [0553] as an off-white solid. (0.5 g, 86%, Yield). MS(M+1)+=636.4.

Step 3 [0554]: To an ice cooled solution of tert-butyl 3-((6-((tert-butoxycarbonyl)(4,4-difluorocyclohexyl)amino)-2-(2-hydroxy-4-(trifluoromethyl)-2,3-dihydrothiazol-2-yl)pyrimidin-4-yl)oxy)azetidine-1-carboxylate [0553] (0.5 g, 0.786 mmol) in dichloromethane (10 mL) was added trifluoroacetic acid (1.5 g, 13.02 mmol). The reaction mixture was slowly warmed to rt and stirred for 16 h. After the completion of the reaction, the reaction mixture was concentrated to afford crude 6-(azetidin-3-yloxy)-N-(4,4-difluorocyclohexyl)-2-(4-(trifluoromethyl) thiazol-2-yl)pyrimidin-4-amine [0554] as an off-white gum (0.42 g) which was taken as such to next step. MS(M+1)+=436.4.

Example 205

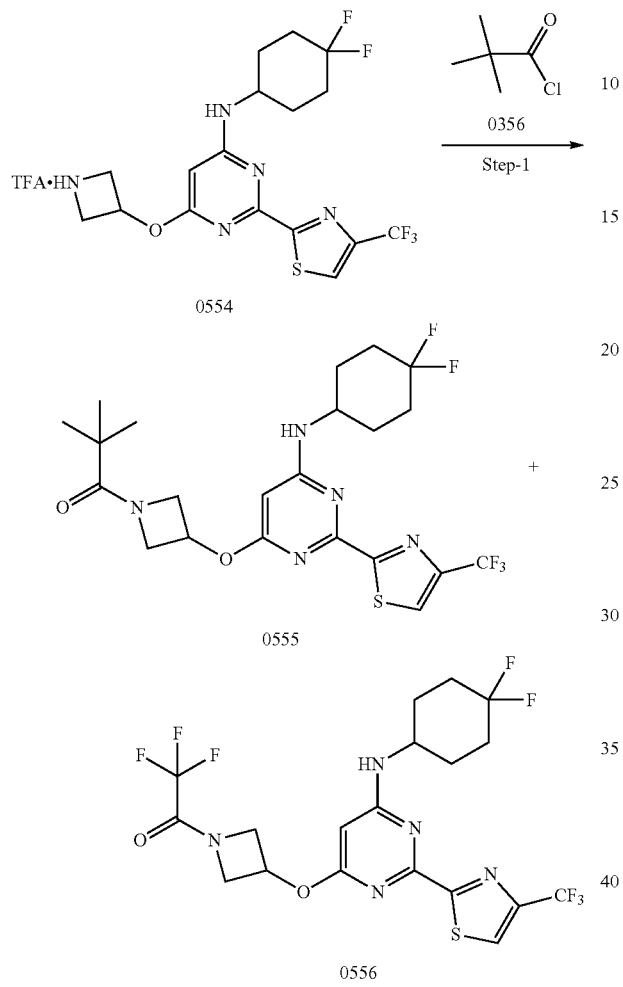

Step 4[0555 & 0556]: To an ice cooled solution of ethyl acetate (2×40 mL), 6-(azetidin-3-yloxy)-N-(4,4-difluorocyclohexyl)-2-(4-(trifluoromethyl) thiazol-2-yl)pyrimidin-4-amine [0554] (0.42 g, 0.786 mmol) in dichloromethane (10 mL) was added triethylamine (0.11 g, 0.943 mmol) and pivaloyl chloride (0.11 g, 0.943 mmol). The reaction mixture was stirred at rt for 30 min. After the completion of the reaction, the reaction mixture was quenched with water and extracted with dichloromethane (2×40 mL), the combined organic layer was dried over anhydrous sodium sulfate and concentrated to afford as an brownish gum and which was purified by column chromatography, fraction-1 was eluted 20% ethyl acetate in hexane as to afford 1-(3-((6-((4,4-difluorocyclohexyl)amino)-2-(4-(trifluoromethyl)thiazol-2-yl)pyrimidin-4-yl)oxy)azetidin-1-yl)-2,2-dimethylpropan-1-one [0555], Compound 322 as an light yellow solid (0.05 g), MS(M+1)+=520, ¹H NMR (400 MHz, DMSO-d6) δ 8.66 (d, J=0.9 Hz, 1H), 7.77 (d, J=73.7 Hz, 1H), 6.01 (s, 1H), 5.38 (bs, 1H), 4.55 (m, 2H), 4.12 (m, 2H), 3.91 (bs, 1H), 2.01-1.92 (m, 6H), 1.59-1.52 (m, 2H), 1.12 (s, 9H). Fraction-2 was eluted 35% ethyl acetate in hexane as to afford 1-(3-((6-((4,4-difluorocyclohexyl)amino)-2-(4-(trifluoromethyl)thiazol-2-yl)pyrimidin-4-yl)oxy)azetidin-1-yl)-2,2,2-trifluoroethan-1-one [0556], Compound 323 as an off-white solid (0.045 g). MS(M+1)+=532. ¹H NMR (400 MHz, DMSO-d6) δ 8.66 (s, 1H), 7.80 (d, J=8.09 Hz, 1H), 5.99 (s, 1H), 5.49 (t, J=6.3 Hz, 1H), 4.85 (bs, 1H), 4.61-4.38 (m, 2H), 4.15 (dd, J=11.4, 4.1 Hz, 1H), 3.63 (s, 1H), 2.13-1.90 (m, 6H), 1.58-1.52 (m, 2H).

Example 206

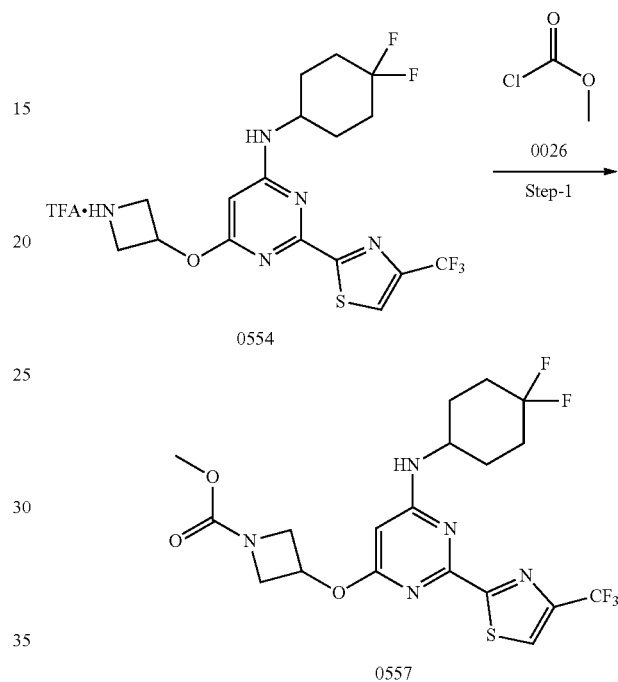

Step 1 [0557]: The procedure is similar to step 5 [0027] in example 5. 0.300 g of 6-(azetidin-3-yloxy)-N-(4,4-difluorocyclohexyl)-2-(4-(trifluoromethyl)thiazol-2-yl)pyrimidin-4-amine [0554] gave 0.042 g of methyl 3-((6-((4,4-difluorocyclohexyl)amino)-2-(4-(trifluoromethyl)thiazol-2-yl)pyrimidin-4-yl)oxy)azetidine-1-carboxylate [0557], Compound 324 as an off-white solid. MS(M+1)+=494, ¹H-NMR (400 MHz, DMSO-d6): δ 8.65 (s, 1H), 7.87 (bs, 1H), 5.97 (bs, 1H), 5.38 (s, 1H), 4.01 (bs, 1H), 4.36 (bs, 2H), 3.96 (bs, 2H), 3.58 (s, 3H), 2.06-1.59 (m, 6H), 1.56-1.24 (m, 2H).

Example 207

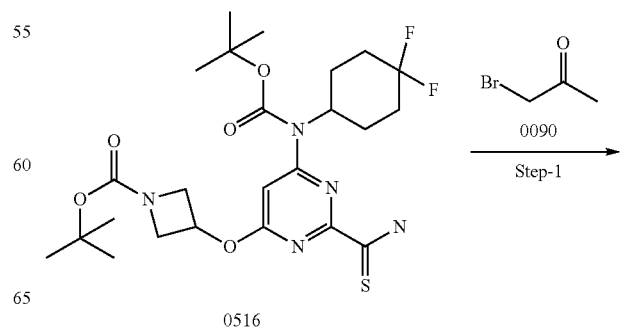

Example 208

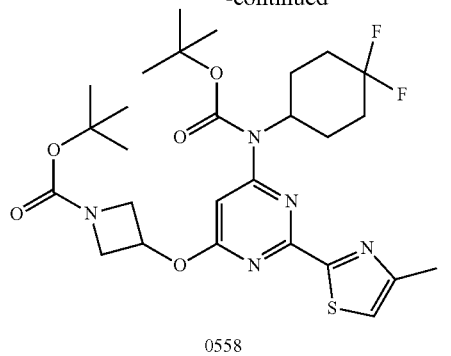

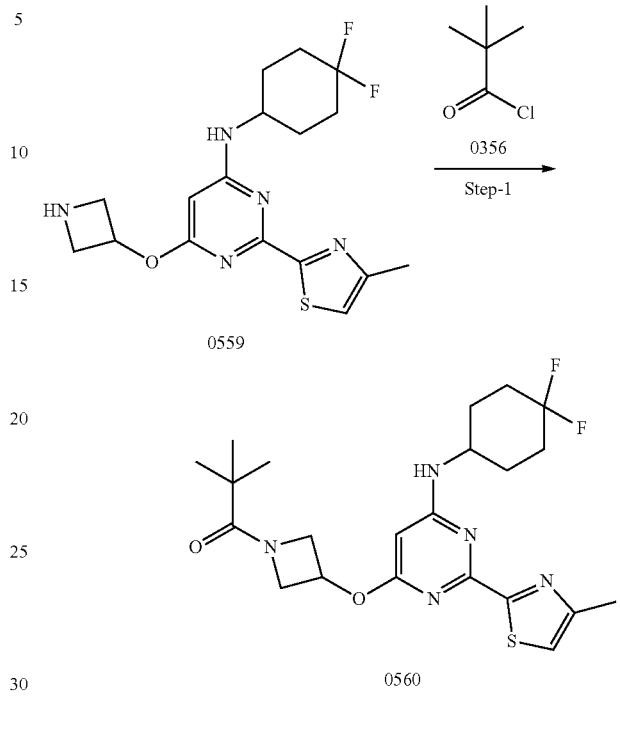

Step 1[0558]: To a solution of tert-butyl 3-((6-(((tert-butoxycarbonyl)(4,4-difluorocyclohexyl)amino)-2-carbamothioylpyrimidin-4-yl)oxy)azetidine-1-carboxylate [0516] (1 g, 1.83 mmol) in tetrahydrofuran (20 mL) was added Bromoacetone (0.377 g, 2.75 mmol) then the reaction mixture was stirred at rt for 16 h. After the completion of the reaction, the reaction mixture was quenched with water and extracted with ethyl acetate (2×50 mL), the combined organic layer was dried over anhydrous sodium sulfate and concentrated to afford as an light brownish gum and which was purified by column chromatography using 38% ethyl acetate in hexane as eluent to afford tert-butyl 3-((6-(((tert-butoxycarbonyl)(4,4-difluorocyclohexyl)amino)-2-(4-methylthiazol-2-yl)pyrimidin-4-yl)oxy)azetidine-1-carboxylate [0558] as an off-white solid. (0.55 g), MS(M+1)+=582.

Step 2[0559]: To an ice cooled solution of tert-butyl 3-((6-(((tert-butoxycarbonyl)(4,4-difluorocyclohexyl)amino)-2-(4-methylthiazol-2-yl)pyrimidin-4-yl)oxy)azetidine-1-carboxylate [0558] (0.55 g, 0.94 mmol) in dichloromethane (20 mL) was added trifluoroacetic acid (1.08 g, 9.45 mmol), then the reaction mixture was stirred at rt. After the completion of the reaction, the reaction mixture was concentrated and the resulting residue was quenched with 10% sodium bicarbonate solution and extracted with ethyl acetate (2×40 mL), the combined organic layer was dried over anhydrous sodium sulfate and concentrated to afford 6-(azetidin-3-yloxy)-N-(4,4-difluorocyclohexyl)-2-(4-methylthiazol-2-yl)pyrimidin-4-amine [0559] as an off-white gum 0.35 g. MS(M+1)+=382.

Step 3[0560]: To an ice cooled solution of 6-(azetidin-3-yloxy)-N-(4,4-difluoro cyclohexyl)-2-(4-methylthiazol-2-yl)pyrimidin-4-amine [0559] (0.3 g, 0.78 mmol) in dichloromethane (10 mL) was added triethylamine (0.119 g, 1.17 mmol) and methyl chloroformate (0.096 g, 1.02 mmol). The reaction mixture was stirred at rt for 30 min. After completion of the reaction, the reaction mixture was quenched with water and extracted with dichloromethane (2×30 mL), the combined organic layer was dried over anhydrous sodium sulfate and concentrated to afford 0.350 g as a brownish gum which was purified by column chromatography using 65% ethyl acetate in hexane as eluent to afford methyl 3-((6-((4,4-difluorocyclohexyl)amino)-2-(4-methylthiazol-2-yl)pyrimidin-4-yl)oxy)azetidine-1-carboxylate [0560], Compound 311 as an light brown solid. (0.055 g, 16% Yield), MS(M+1)+=440, $^1$H NMR (400 MHz, DMSO-d6) δ 7.60 (bs, 1H), 7.44 (s, 1H), 5.87 (bs, 1H), 5.36 (bs, 1H), 4.77 (bs, 1H), 4.30 (bs, 2H), 3.88 (bs, 2H), 2.44 (s, 3H), 2.11-1.92 (m, 6H), 1.59-152 (m, 2H), 1.12 (s, 9H).

Example 209

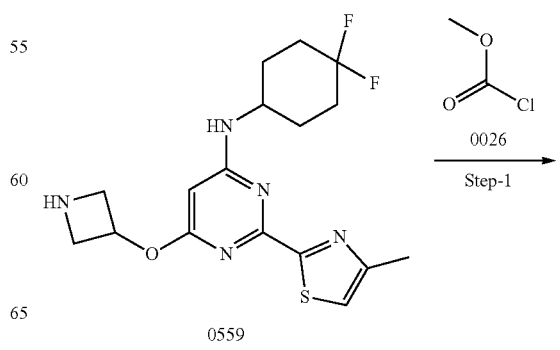

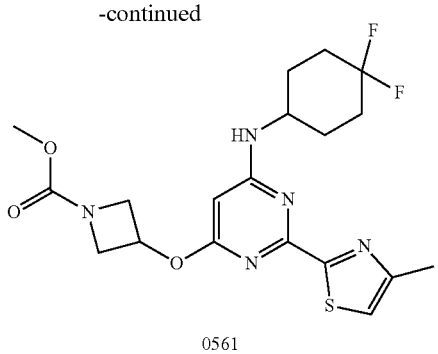

0561

Step 1[0561]: The procedure is similar to step 5 [0027] in example 5. 0.350 g of 6-(azetidin-3-yloxy)-N-(4,4-difluorocyclohexyl)-2-(4-methylthiazol-2-yl)pyrimidin-4-amine [0559] gave 0.260 g of 1-(3-((6-((4,4-difluorocyclohexyl)amino)-2-(4-methylthiazol-2-yl)pyrimidin-4-yl)oxy)azetidin-1-yl)-2,2-dimethylpropan-1-one [0561], Compound 303 as an off-white solid. MS(M+1)⁺=440. ¹H NMR (400 MHz, DMSO-d6) δ 7.57 (bs, 1H), 7.44 (d, J=1.1 Hz, 1H), 5.86 (bs, 1H), 5.35 (bs, 1H), 4.38-4.32 (m, 2H), 3.99-3.95 (m, 2H), 3.58 (s, 3H), 3.33 (bs, 1H), 2.44 (s, 3H), 2.22-1.85 (m, 6H), 1.59-1.52 (m, 2H).

Example 210

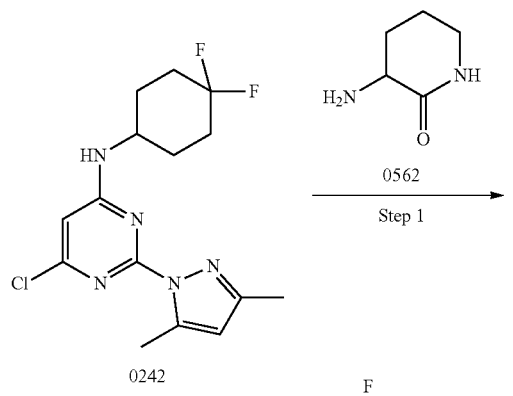

0242

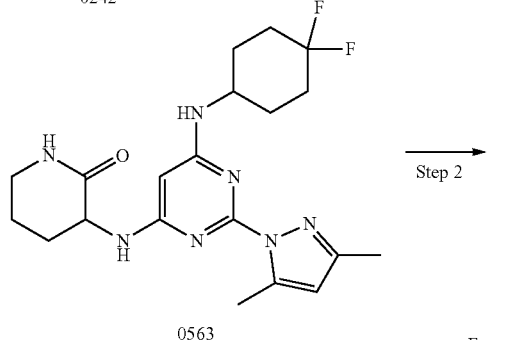

0563

0564

Step 1 [0563]: The procedure is similar to step 1 [0361] in example 138. 0.4 g of 6-chloro-N-(4,4-difluorocyclohexyl)-2-(3,5-dimethyl-1H-pyrazol-1-yl)pyrimidin-4-amine [0242] and 3-amino-2-piperidone [0562] (0.26 g, 2.34 mmol) gave 0.16 g of 3-((6-((4,4-difluorocyclohexyl)amino)-2-(3,5-dimethyl-1H-pyrazol-1-yl)pyrimidin-4-yl)amino)piperidin-2-one [0563] as a white solid. MS(M+1)+=419.

Step 3 [0564]: To a solution of 3-((6-((4,4-difluorocyclohexyl)amino)-2-(3,5-dimethyl-1H-pyrazol-1-yl)pyrimidin-4-yl)amino)piperidin-2-one [0563] (0.1 g, 0.23 mmol) in N,N-dimethylformamide (5 mL) was added sodium hydride (0.01 g, 0.26 mmol). The resultant reaction mixture was stirred at rt for 30 min, added iodomethane (0.037 g, 0.26 mmol) and stirred at rt for 1 h. The reaction mixture was quenched in ice and extracted with ethyl acetate (2×20 mL). The combined organic layer was washed with water (10 mL), followed by brine (10 mL) and dried over anhydrous sodium sulfate to afford crude product which was purified by preparative HPLC to afford 0.035 g of 3-((6-((4,4-difluorocyclohexyl)amino)-2-(3,5-dimethyl-1H-pyrazol-1-yl)pyrimidin-4-yl)amino)-1-methylpiperidin-2-one [0564], Compound 133 as a white solid. MS(M+1)+=434.2, 1H NMR (400 MHz, DMSO-d6): δ 6.97 (d, J=8.00 Hz, 1H), 6.87 (d, J=7.80 Hz, 1H), 5.97 (s, 1H), 5.39 (s, 1H), 4.32 (s, 1H), 3.78 (s, 1H), 3.25-3.32 (m, 2H), 2.81 (s, 1H), 2.46 (s, 3H), 2.13 (s, 3H), 2.04-2.06 (m, 3H), 1.82-1.87 (m, 7H), 1.52 (m, 2H).

Example 211

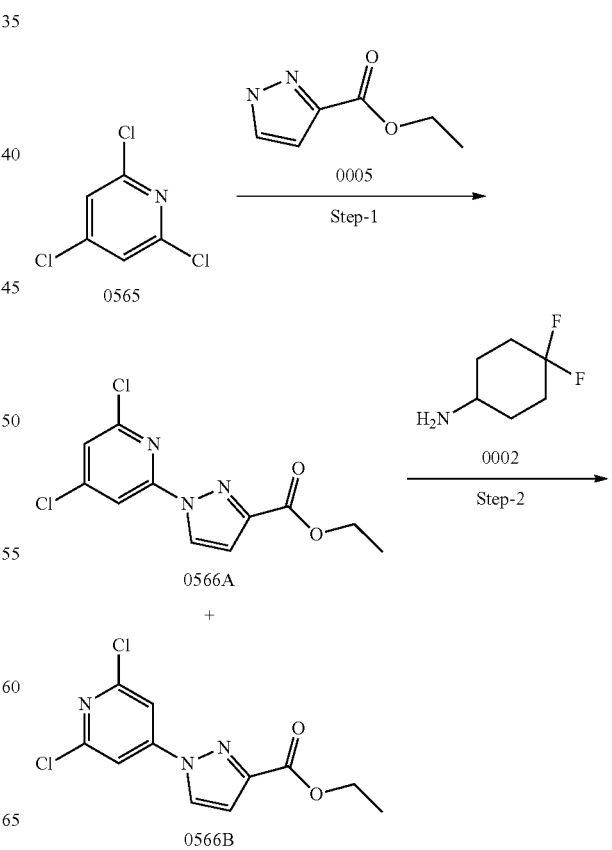

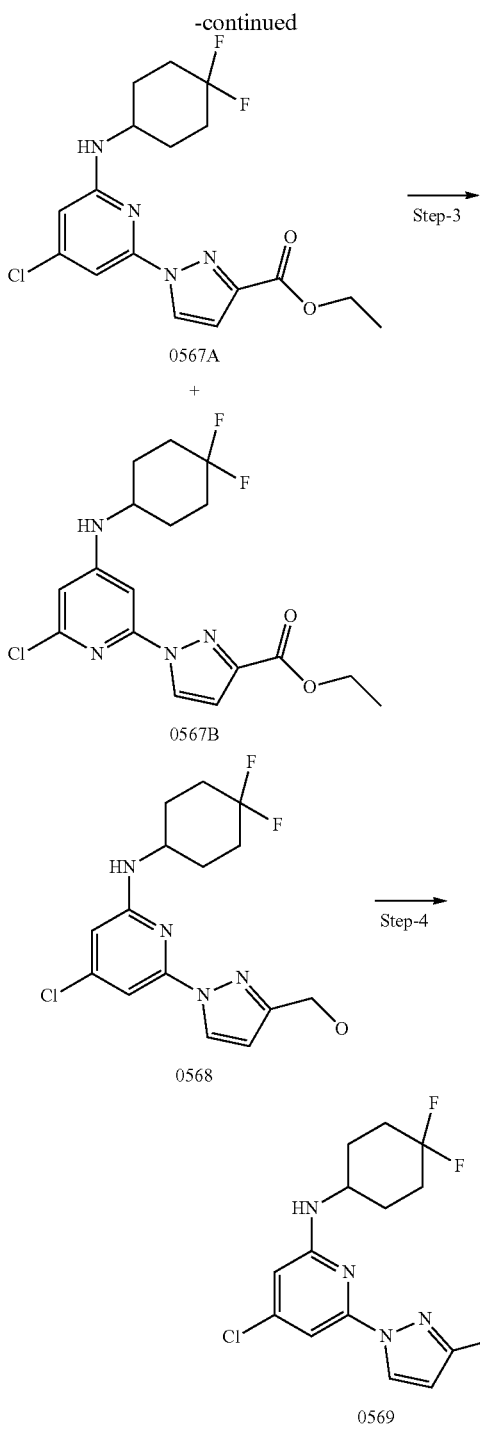

of ethyl 1-(4,6-dichloropyridin-2-yl)-1H-pyrazole-3-carboxylate [0566A] as a white solid. MS(M+1)+=286.0.

Step 2[0567A]: To a stirred solution of ethyl 1-(4,6-dichloropyridin-2-yl)-1H-pyrazole-3-carboxylate [0566A] (2 g, 6.99 mmol) in dioxane (20 mL) were added 4,4-difluorocyclohexylamine hydrochloride (1.19 g, 6.990 mmol) cesium carbonate (3.41 g, 10.48 mmol) and 4,5-bis(diphenylphosphino)-9,9-dimethylxanthene (0.606 g, 1.04 mmol). Then the reaction mixture was purged with N2 for 5 min before adding palladium (II) acetate (0.158 g, 0.699 mmol). The reaction mixture was irradiated in microwave at 100° C. for 2 h. The reaction mixture was filtered through celite, filtrate was concentrated under reduced pressure to afford 3.3 g of ethyl 1-(6-chloro-4-((4,4-difluorocyclohexyl)amino)pyridin-2-yl)-1H-pyrazole-3-carboxylate. This was purified by column chromatography using 11% ethyl acetate in pet ether as solvent to afford 0.450 g of ethyl 1-(4-chloro-6-((4,4-difluorocyclohexyl)amino)pyridin-2-yl)-1H-pyrazole-3-carboxylate [0567A] as an off-white solid. MS(M+1)+=385.2.

Step 3[0568]: The procedure is similar to step 2[0011] in example 2. 0.450 g of ethyl 1-(4-chloro-6-((4,4-difluorocyclohexyl)amino)pyridin-2-yl)-1H-pyrazole-3-carboxylate [0567A] gave 0.350 g of (1-(4-chloro-6-((4,4-difluorocyclohexyl)amino)pyridin-2-yl)-1H-pyrazol-3-yl)methanol [0568] as an off-white solid. MS(M+1)+=343.1.

Step 4[0569]: The procedure is similar to step 3[0012] in example 2. 0.350 g of (1-(4-chloro-6-((4,4-difluorocyclohexyl)amino)pyridin-2-yl)-1H-pyrazol-3-yl)methanol [0568] gave 0.19 g of 4-chloro-N-(4,4-difluorocyclohexyl)-6-(3-(fluoromethyl)-1H-pyrazol-1-yl)pyridin-2-amine [0569] as an off-white solid. MS(M+1)+=345.1.

Example 212

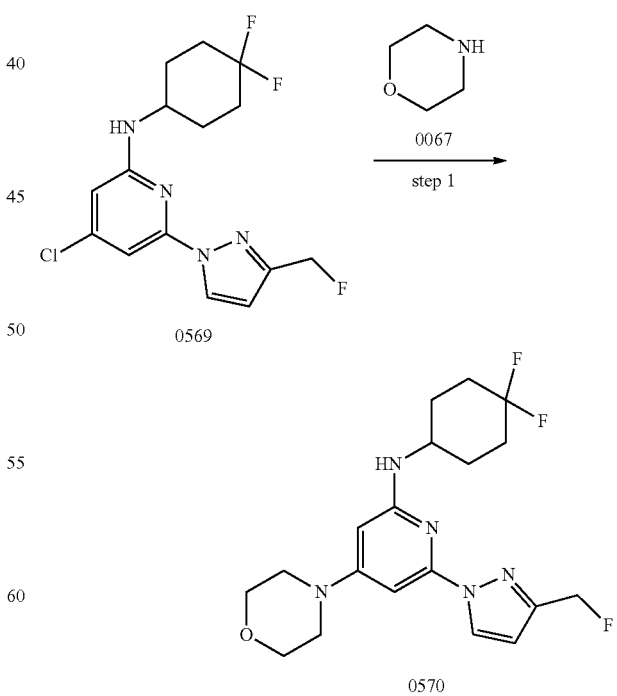

Step 1[0570]: To a stirred solution of 4-chloro-N-(4,4-difluorocyclohexyl)-6-(3-(fluoromethyl)-1H-pyrazol-1-yl)

pyridin-2-amine [0569] (0.120 g, 0.348 mmol) in toluene (3 mL), was added morpholine [0067] (36 g, 0.417 mmol), sodium-tert-butoxide (0.066 g, 0.692 mmol) and BINAP [rac-2,2'-bis(diphenylphosphino)-1,1'-binaphthyl] (0.033 g, 0.055 mmol). The reaction mixture was purged with N2 for 10 min before adding bis(dibenzylideneacetone)palladium (0.016 g, 0.0278 mmol). The reaction mixture was irradiated in microwave at 100° C. for 2 h. The reaction mixture was filtered through celite, and then the filtrate was concentrated under reduced pressure to afford 0.067 g N-(4,4-difluorocyclohexyl)-6-(3-(fluoromethyl)-1H-pyrazol-1-yl)-4-morpholinopyridin-2-amine [0570], Compound 292 as a pale brown solid. MS(M+1)$^+$=395.5. $^1$H NMR (400 MHz, DMSO-d6) δ 8.51 (d, J=2.5 Hz, 1H), 6.65 (d, J=1.8 Hz, 1H), 6.64 (s, 1H), 6.46 (d, J=7.6 Hz, 1H), 5.80 (d, J=1.9 Hz, 1H), 5.47-5.35 (d, JF=48.4 Hz, 2H), 3.96 (bs, 1H), 3.71 (t, J=4.8 Hz, 4H), 3.20 (t, J=4.9 Hz, 4H), 2.03-1.93 (m, 6H), 1.54-1.51 (m, 2H).

Example 213

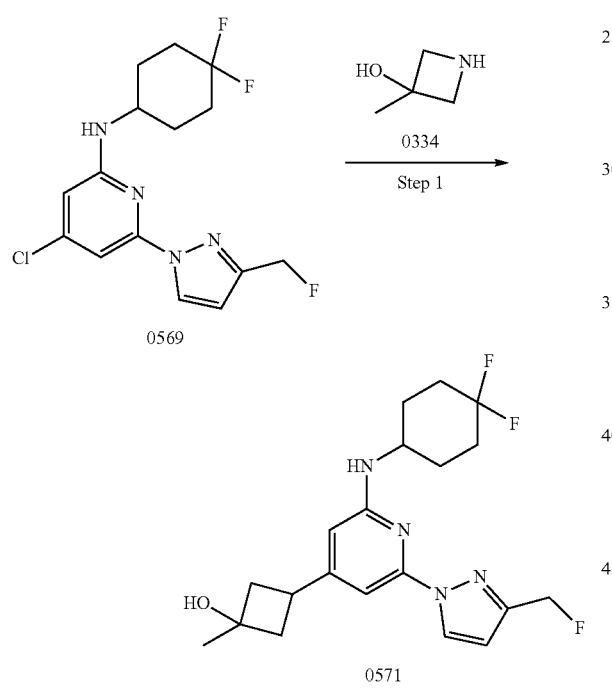

Step 1[0571]: To a stirred solution of 4-chloro-N-(4,4-difluorocyclohexyl)-6-(3-(fluoromethyl)-1H-pyrazol-1-yl)pyridin-2-amine [0569] (0.20 g, 0.058 mmol) in toluene (1 mL), was added 3-methylazetidin-3-ol hydrochloride [0334] (0.06 g, 0.069 mmol) and potassium tert-butoxide (0.020 g, 0174 mmol). The reaction mixture was purged N2 for 10 min and finally added 2-(2'-di-tert-butylphosphine)biphenyl palladium(II) acetate (0.06 g, 0.0174 mmol). The reaction mixture was irradiated in microwave at 120° C. for 2 h. The reaction mixture was filtered through celite and filtrate was concentrated under reduced pressure to afford 0.027 g of 1-(2-((4,4-difluorocyclohexyl)amino)-6-(3-(fluoromethyl)-1H-pyrazol-1-yl)pyridin-4-yl)-3-methylazetidin-3-ol [0571], Compound 326 as an off-white solid. MS(M+1)$^+$=396.2. $^1$H-NMR (400 MHz, DMSO-d6): δ 8.51 (s, 1H), 6.60 (s, 1H), 6.42 (d, J=7.56 Hz, 1H), 6.18 (s, 1H), 5.55 (d, JF=64.25 Hz, 2H), 5.36 (d, J=2.32 Hz, 2H), 3.95 (bs, 1H), 3.80 (d, J=7.60 Hz, 2H), 3.70 (d, J=7.68 Hz, 2H), 2.12-1.88 (m, 6H), 1.6-1.48 (m, 2H), 1.44 (s, 3H).

Example 214

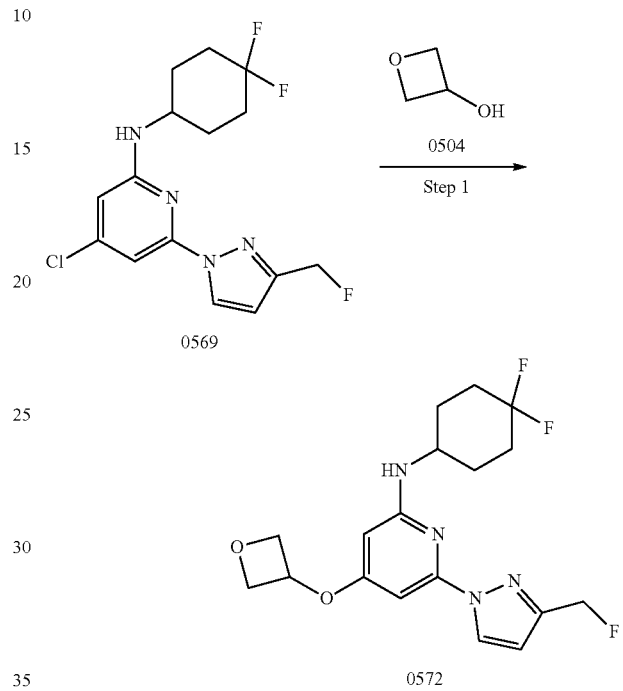

Step 1[0572]: The procedure is similar to step 2[0274] in example 99 (at 100° C.). 0.2 g of 4-chloro-N-(4,4-difluorocyclohexyl)-6-(3-(fluoromethyl)-1H-pyrazol-1-yl)pyridin-2-amine [0569] gave 0.053 g of N-(4,4-difluorocyclohexyl)-6-(3-(fluoromethyl)-1H-pyrazol-1-yl)-4-(oxetan-3-yloxy)pyridin-2-amine [00572], Compound 302 as an off-white solid. MS(M+1)$^+$=383.2. $^1$H NMR (400 MHz, DMSO-d6) δ 8.54 (d, J=2.5 Hz, 1H), 6.83 (d, J=7.5 Hz, 1H), 6.63 (s, 1H), 6.47 (d, J=1.9 Hz, 1H), 5.70 (d, J=1.9 Hz, 1H), 5.48-5.36 (d, JF=48.4 Hz, 2H), 5.31 (t, J=5.2 Hz, 1H), 4.89 (t, J=6.7 Hz, 2H), 4.56 (dd, J=7.5, 4.8 Hz, 2H), 3.98 (bs, 1H), 2.07-1.94 (m, 6H), 1.52-1.53 (m, 2H).

Example 215

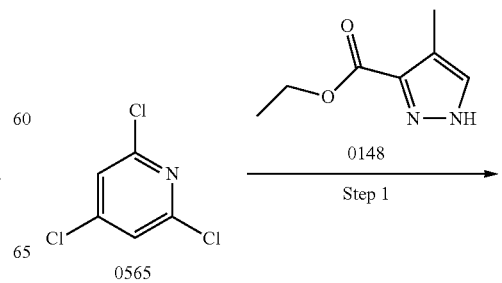

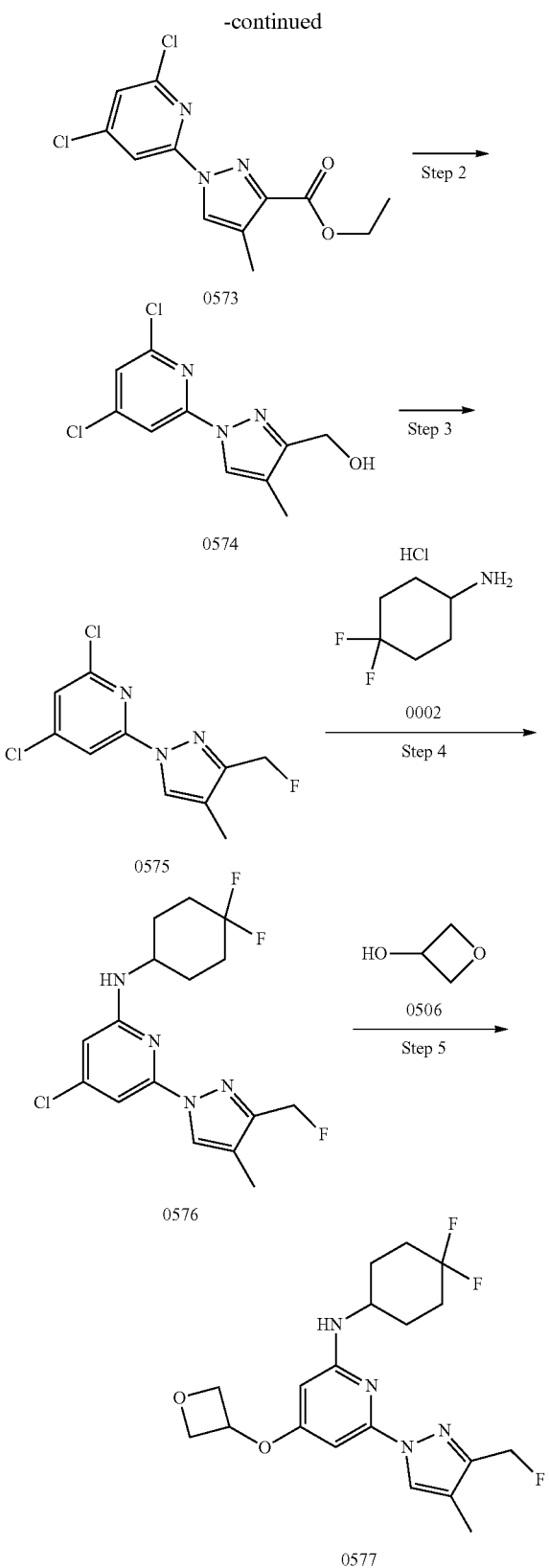

The reaction mixture was filtered to remove cesium carbonate, filtrate was concentrated under reduced pressure to afford crude product, which was purified by column chromatography using 8% ethyl acetate in pet ether as solvent to afford of ethyl 1-(4,6-dichloropyridin-2-yl)-4-methyl-1H-pyrazole-3-carboxylate [0573] as a white solid. MS(M+1)+=301.1.

Step 2[0574]: To a stirred solution of ethyl 1-(4,6-dichloropyridin-2-yl)-4-methyl-1H-pyrazole-3-carboxylate [0573] (1.5 g, 4.99 mmol) in tetrahydrofuran (15 mL), was added lithium borohydride (0.326 g, 14.992 mmol) at 0° C. The reaction mixture was stirred at rt for 5 h. The reaction mixture was quenched with ice, extracted with ethyl acetate (2×100 mL), the combined organic layer was dried over anhydrous sodium sulfate, filtered and concentrated under reduced pressure to afford crude product, which was purified by column chromatography using 8% ethyl acetate in pet ether as solvent to afford 1.12 g of (1-(4,6-dichloropyridin-2-yl)-4-methyl-1H-pyrazol-3-yl)methanol [0574] as an off-white solid. MS(M+1)+=259.1.

Step 3[0575]: To a stirred solution of (1-(4,6-dichloropyridin-2-yl)-4-methyl-1H-pyrazol-3-yl)methanol [0574] (1.12 g, 4.33 mmol) in dichloromethane (10 mL) was added diethylaminosulfur trifluoride (1.11 g, 6.94 mmol) at −20° C. The reaction mixture was stirred at rt for 15 min. The reaction mixture was quenched with saturated sodium bicarbonate solution (10 mL), extracted with dichloromethane (2×50 mL) the combined organic layer was dried over anhydrous sodium sulfate, filtered and concentrated under reduced pressure to afford a crude product, which was purified by column chromatography using 4% ethyl acetate in pet ether as solvent to afford 0.660 g of 2,4-dichloro-6-(3-(fluoromethyl)-4-methyl-1H-pyrazol-1-yl)pyridine [0575] as a white solid. MS(M+1)+=261.0.

Step 4[0576]: To a stirred solution of 2,4-dichloro-6-(3-(fluoromethyl)-4-methyl-1H-pyrazol-1-yl)pyridine [0575] (0.650 g, 2.499 mmol) in acetonitrile (10 mL), was added 4,4-difluorocyclohexylamine hydrochloride [0002] (0.470 g, 2.749 mmol), cesium carbonate (1.62 g, 4.99 mmol), and 4,5-bis(diphenylphosphino)-9,9-dimethylxanthene (0.216 g, 0.374 mmol). The reaction mixture was purged with N2 for 10 min, and added by palladium (II) acetate (0.056 g, 0.249 mmol). The reaction mixture was irradiated in microwave at 100° C. for 2 h. The reaction mixture was filtered, filtrate was concentrated under reduced pressure to afford crude product, which was purified by column chromatography using 12% ethyl acetate in pet ether as solvent to afford 0.220 g of 4-chloro-N-(4,4-difluorocyclohexyl)-6-(3-(fluoromethyl)-4-methyl-1H-pyrazol-1-yl)pyridin-2-amine [0576] as a white solid. MS(M+1)+=359.1.

Step 5 [0577]: To a stirred solution of 4-chloro-N-(4,4-difluorocyclohexyl)-6-(3-(fluoromethyl)-4-methyl-1H-pyrazol-1-yl)pyridin-2-amine [0576] (0.200 g, 0.55 mmol) in acetonitrile (5 mL), was added 3-hydroxyoxetane [0506] (0.049 g, 0.668 mmol), and cesium carbonate (0.363 g, 1.11 mmol). The reaction mixture was irradiated in microwave at 150° C. for 2 h. The reaction mixture was filtered through celite, filtrate was concentrated under reduced pressure to afford crude product, which was purified by column chromatography using 31% ethyl acetate in pet ether as solvent to afford 0.032 g of N-(4,4-difluorocyclohexyl)-6-(3-(fluoromethyl)-4-methyl-1H-pyrazol-1-yl)-4-(oxetan-3-yloxy)pyridin-2-amine [0577], Compound 345 as an off-white solid. MS(M+1)+=397.2. $^1$H NMR (400 MHz, DMSO-d6) δ 8.34 (s, 1H), 6.80 (d, J=7.4 Hz, 1H), 6.43 (d, J=1.8 Hz, 1H), 5.68 (s, 1H), 5.45 (d, JF=48.5 Hz, 2H), 5.33-5.30 (m, 1H), 4.89 (t, J=6.7 Hz, 2H), 4.56 (t, J=7.4 Hz, 2H), 3.99 (bs, 1H), 2.13 (s, 3H), 2.12-1.90 (m, 6H), 1.58-1.45 (m, 2H).

Step 1[0573]: To a stirred solution of 2,4,6-trichloropyridine [0565] (15 g, 82.22 mmol) in acetonitrile (150 mL), was added ethyl 4-methylpyrazole-3-carboxylate [0148] (13.94 g, 90.442 mmol) and cesium carbonate (40.18 g, 123.3 mmol). The reaction mixture was stirred at rt for 16 h.

Example 216

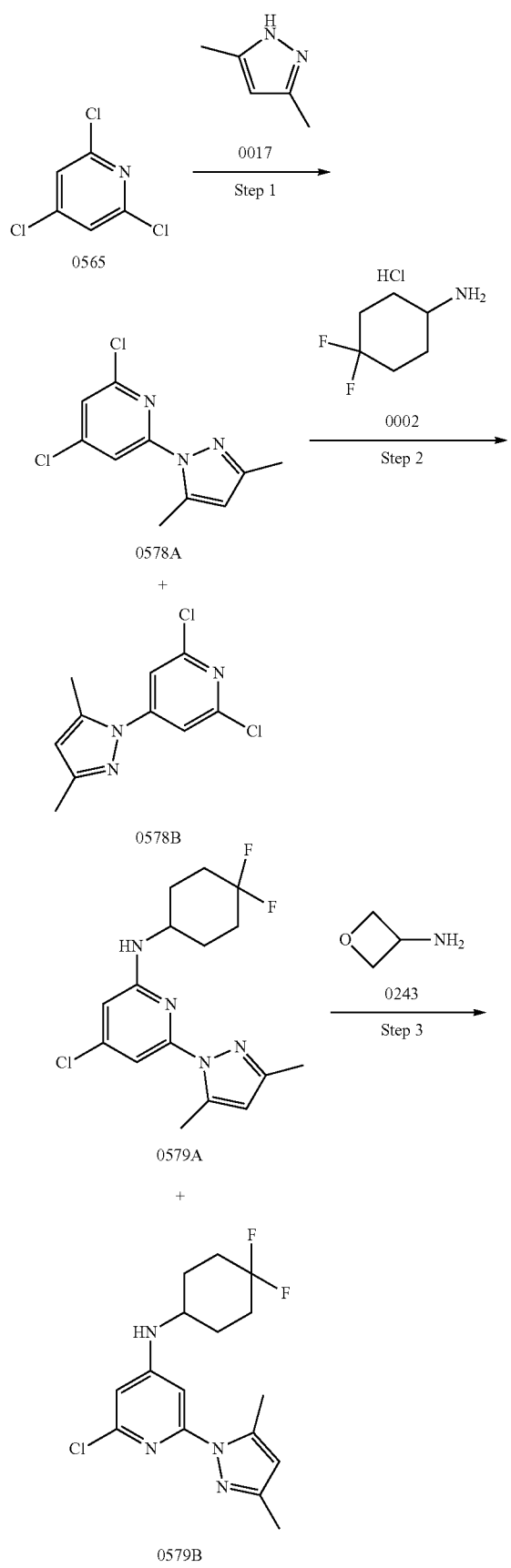

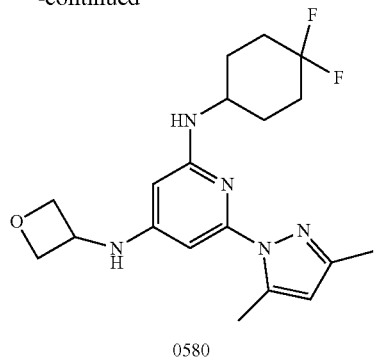

Step 1 [0578A and 0578B]: To a stirred solution of 2,4,6-trichloropyridine [0565] (25 g, 137.033 mmol) in acetonitrile (400 mL) was added 3,5-dimethylpyrazole [0017] (15.8 g, 164.44 mmol) and cesium carbonate (89 g, 274 mmol). The reaction mixture was heated at 75° C. for 16 h. The reaction mixture was concentrated under reduced pressure. The residue was diluted with water (200 mL) and stirred for 10 min. The solid formed was filtered, washed with water and dried under vacuum to afford crude product, which was purified by column chromatography using 1.5% ethyl acetate in pet ether as solvent to afford 11 g of 2,4-dichloro-6-(3,5-dimethyl-1H-pyrazol-1-yl)pyridine 2,4-dichloro-6-(3,5-dimethyl-1H-pyrazol-1-yl)pyridine [0578A] as a white solid and 8 g of 2,6-dichloro-4-(3,5-dimethyl-1H-pyrazol-1-yl)pyridine [0578B] as a white solid. MS(M+1)+=242.1.

Step 2 [0579A and 0579B]: To a stirred solution of 2,4-dichloro-6-(3,5-dimethyl-1H-pyrazol-1-yl)pyridine 2,4-dichloro-6-(3,5-dimethyl-1H-pyrazol-1-yl)pyridine [0578A] (1 g, 4.13 mmol) in dioxane (10 mL), were added 4,4-difluorocyclohexylamine hydrochloride [0002] (0.850 g, 4.956 mmol), 4,5-bis(diphenylphosphino)-9,9-dimethylxanthene (0.286 g, 0.495 mmol) and cesium carbonate (2.69 g, 8.26 mmol). The reaction mixture was degassed for 10 min, and then added palladium (II) acetate (0.074 g, 0.33 mmol). The reaction mixture was irradiated in microwave at 100° C. for 3 h. The reaction mixture was passed through celite, washed with chloroform (20 mL) and then the filtrate was concentrated under reduced pressure to afford crude product, which was purified by column chromatography using 5% ethyl acetate in pet ether as solvent to afford 0.950 g of 4-chloro-N-(4,4-difluorocyclohexyl)-6-(3,5-dimethyl-1H-pyrazol-1-yl)pyridin-2-amine [0579A] and 0.6 g of 2-chloro-N-(4,4-difluorocyclohexyl)-6-(3,5-dimethyl-1H-pyrazol-1-yl)pyridin-4-amine [0579B] as a yellow solid. MS(M+1)+=341.2

Step 3 [0580]: To a stirred solution of 4-chloro-N-(4,4-difluorocyclohexyl)-6-(3,5-dimethyl-1H-pyrazol-1-yl)pyridin-2-amine [0579A] (0.3 g, 0.88 mmol) in dioxane (10 mL), were added 3-oxetanamine [0243] (0.128 g, 1.76 mmol), 4,5-bis(diphenylphosphino)-9,9-dimethylxanthene (0.061 g, 0.105 mmol) and cesium carbonate (0.537 g, 1.76 mmol). The reaction mixture was degassed for 10 min, then added tris(dibenzylideneacetone)dipalladium(0) (0.080 g, 0.088 mmol). The reaction mixture was heated at 95° C. for 16 h. The reaction mixture was filtered through celite, filtrate was concentrated under reduced pressure to afford crude product, which was purified by preparative HPLC to afford 0.060 g of N2-(4,4-difluorocyclohexyl)-6-(3,5-dimethyl-1H-pyrazol-1-yl)-N4-(oxetan-3-yl)pyridine-2,4-diamine [0580], Compound 228 as an off-white solid. MS(M+1)+= 378.2. $^1$H-NMR (400 MHz, DMSO-d6): δ 6.96 (d, J=4 Hz, 1H), 6.28 (d, J=1.6 Hz, 1H), 6.26 (s, 1H), 5.97 (s, 1H) 5.32 (d, J=1.52 Hz, 1H), 4.83-4.79 (t, J=6.4 Hz, 2H), 4.54-4.46 (m, 1H), 4.43-4.40 (t, J=5.92 Hz, 2H), 3.82 (s, 1H), 2.53 (s, 3H), 2.15 (s, 3H), 2.10-1.81 (m, 6H), 1.53-1.47 (m, 2H).

Example 217

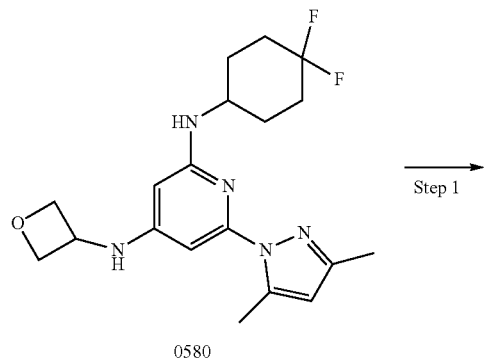

Step 1[0581 and 0582]: To a suspension of sodium hydride (0.036 g, 0.908 mmol) in N, N-dimethylformamide (0.5 mL), was added N2-(4,4-difluorocyclohexyl)-6-(3,5-dimethyl-1H-pyrazol-1-yl)-N4-(oxetan-3-yl)pyridine-2,4-diamine [0580] (0.170 g, 0.45 mmol) drop wise at 0° C. The reaction mixture was stirred at rt for 15 min. After 15 min iodomethane (0.076 g, 0.054 mmol) was added to the reaction mixture. The reaction mixture was stirred at rt for 3 h. The reaction mixture was quenched with ice cold water, extracted with ethyl acetate (2×10 mL), the combined organic extracts were dried over anhydrous sodium sulfate, concentrated under reduced pressure to afford crude product, which was purified by column chromatography using 25% ethyl acetate in pet ether as solvent to afford 0.080 g of N2-(4,4-difluorocyclohexyl)-6-(3,5-dimethyl-1H-pyrazol-1-yl)-N4-methyl-N4-(oxetan-3-yl)pyridine-2,4-diamine [0581], Compound 238 as an off-white solid MS(M+1)+=392.4. $^1$H NMR (400 MHz, DMSO-d6) δ 6.35-6.33 (m, 2H), 6.00 (s, 1H), 5.48 (d, J=2.0 Hz, 1H), 4.93-4.72 (m, 3H), 4.70-4.51 (m, 2H), 3.85 (s, 1H), 2.91 (s, 3H), 2.53 (s, 3H), 2.17 (s, 3H), 2.07-1.86 (m, 6H), 1.54-1.46 (m, 2H) and 0.008 g of N2-(4,4-difluorocyclohexyl)-6-(3,5-dimethyl-1H-pyrazol-1-yl)-N2,N4-dimethyl-N4-(oxetan-3-yl)pyridine-2,4-diamine [0582], Compound 240 as pale yellow gummy liquid. MS(M+1)+=406.4. $^1$H NMR (400 MHz, DMSO-d6) δ 6.39 (d, J=1.8 Hz, 1H), 6.02 (s, 1H), 5.53 (d, J=2.0 Hz, 1H), 4.98-4.93 (m, 1H), 4.80 (t, J=6.8 Hz, 2H), 4.66 (t, J=6.6 Hz, 2H), 4.59-4.53 (m, 1H), 3.51 (s, 1H), 3.00 (s, 3H), 2.81 (s, 3H), 2.56 (s, 3H), 2.17 (s, 3H), 2.12-1.93 (m, 5H), 1.76-1.67 (m, 2H).

Example 218

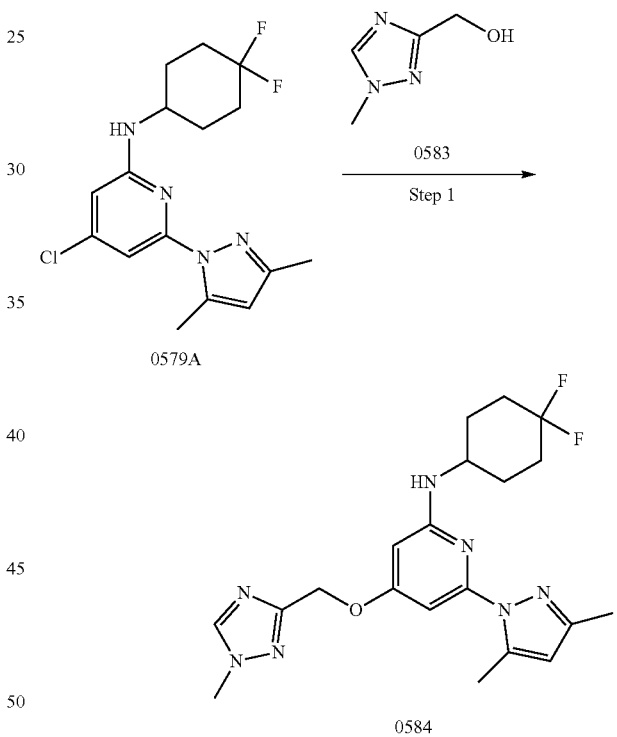

Step 1[0584]: To a stirred solution of 4-chloro-N-(4,4-difluorocyclohexyl)-6-(3,5-dimethyl-1H-pyrazol-1-yl)pyridin-2-amine [0579A] (0.200 g, 0.586 mmol) in 50% aqueous sodium hydroxide solution (2 mL), was added (1-methyl-1h-1,2,4-triazol-3-yl)methanol [0583] (0.079 g, 0.704 mmol) and tetra butyl ammonium hydrogen sulfate (0.200 g, 0.586 mmol). The reaction mixture was heated at 110° C. for 16 h. The reaction mixture was extracted with ethyl acetate (10 mL), dried over anhydrous sodium sulfate, filtered and concentrated under reduced pressure to afford crude product, which was purified by column chromatography using 51% ethyl acetate in pet ether as solvent to afford 0.018 g of N-(4,4-difluorocyclohexyl)-6-(3,5-dimethyl-1h- pyrazol-1-yl)-4-((1-methyl-1H-1,2,4-triazol-3-yl)methoxy)pyridin-2-amine [0584], Compound 275 as an off-white solid.

MS(M+1)$^+$=418.2. $^1$H NMR (400 MHz, DMSO-d6) δ 8.49 (s, 1H), 6.72 (d, J=7.7 Hz, 1H), 6.59 (d, J=2.0 Hz, 1H), 6.03 (s, 1H), 5.99 (d, J=2.0 Hz, 1H), 5.08 (s, 2H), 3.87 (s, 4H), 2.57 (s, 3H), 2.16 (s, 3H), 2.08-1.84 (m, 6H), 1.56-1.48 (m, 2H).

Example 219

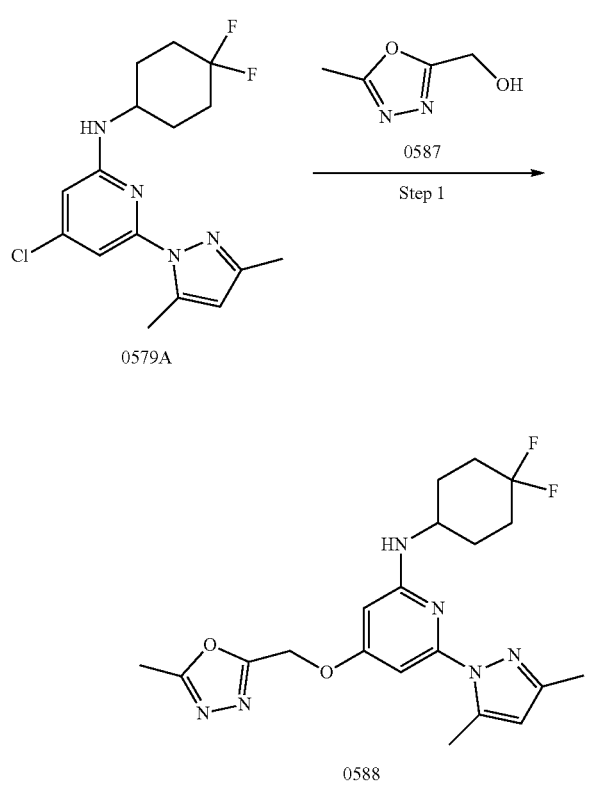

Step 1[0588]: To a solution of 4-chloro-N-(4,4-difluorocyclohexyl)-6-(3,5-dimethyl-1H-pyrazol-1-yl)pyridin-2-amine [0579A] (0.3 g, 0.880 mmol) in acetonitrile (10 mL) were added (5-methyl [1,3,4]-oxadiazol-2-yl) methanol (0.2 g, 1.760 mmol) and Cesium carbonate (0.86 g, 2.640 mmol) under N2 atm. The resultant reaction mixture was irradiated at 150° C. After 2 h, the reaction mixture was filtered and washed with chloroform, the obtained filtrate was concentrated under reduced pressure to afford a yellow liquid, which was purified in the Reveleris flash system instrument using ethyl acetate in hexane as solvent in 12 g column, to afford 0.035 g of N-(4,4-difluorocyclohexyl)-6-(3,5-dimethyl-1H-pyrazol-1-yl)-4-((5-methyl-1,3,4-oxadiazol-2-yl)methoxy)pyridin-2-amine [0588], Compound 261 as off-white solid. MS(M+1)$^+$=419.0, $^1$H NMR (400 MHz, DMSO-d6) δ 6.81 (d, J=7.5 Hz, 1H), 6.62 (d, J=2.0 Hz, 1H), 6.04 (s, 1H), 5.97 (d, J=2.0 Hz, 1H), 5.39 (s, 2H), 3.87 (bs, 1H), 2.58 (s, 3H), 2.54 (s, 3H), 2.17 (s, 3H), 2.15-1.85 (m, 6H), 1.58-1.45 (m, 2H).

Example 220

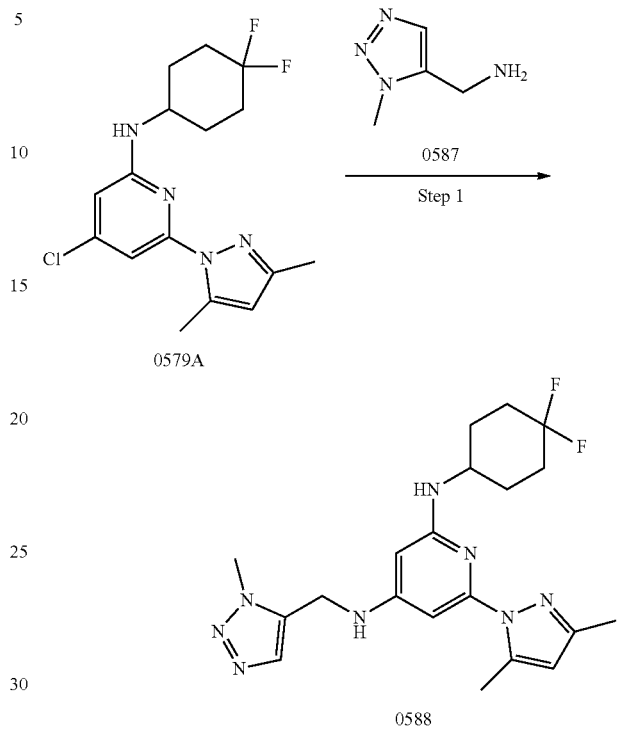

Step 1[0588]: The procedure is similar to step 3[0580] in example 216. 0.25 g of chloro-N-(4,4-difluorocyclohexyl)-6-(3,5-dimethyl-1H-pyrazol-1-yl)pyridin-2-amine [0579A] and 0.25 g of (1-methyl-1H-1,2,3-triazol-5-yl)methanamine [0587] gave 0.03 g of N2-(4,4-difluorocyclohexyl)-6-(3,5-dimethyl-1H-pyrazol-1-yl)-N4-((1-methyl-1H-1,2,3-triazol-5-yl)methyl)pyridine-2,4-diamine [0588], Compound 250 as yellow solid.

MS(M+1)$^+$=417.0, $^1$H NMR (400 MHz, DMSO-d6) δ 7.62 (s, 1H), 6.80 (t, J=5.7 Hz, 1H), 6.39 (d, J=1.7 Hz, 1H), 6.26 (d, J=7.5 Hz, 1H), 5.97 (s, 1H), 5.52 (d, J=1.7 Hz, 1H), 4.39 (d, J=5.7 Hz, 2H), 4.01 (s, 3H), 3.81 (bs, 1H), 2.54 (s, 3H), 2.15 (s, 3H), 2.10-1.98 (m, 2H), 2.00-1.78 (m, 4H), 1.52-1.40 (m, 2H).

Example 221

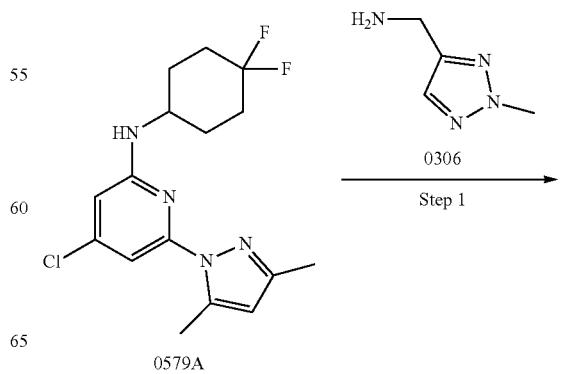

-continued

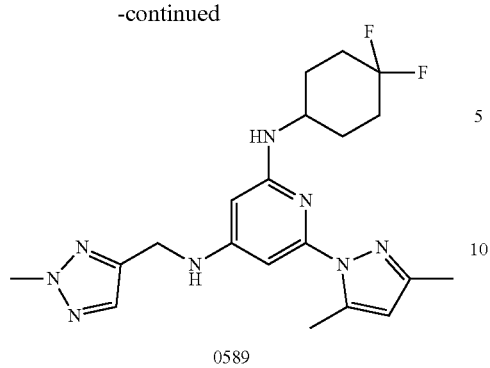

0589

Step 1[0589]: The procedure is similar to step 3[0580] in example 216. 0.3 g of chloro-N-(4,4-difluorocyclohexyl)-6-(3,5-dimethyl-1H-pyrazol-1-yl)pyridin-2-amine [579A] and 0.197 g of (2-methyl-2H-1,2,3-triazol-4-yl)methanamine [0306] gave 0.042 g of N2-(4,4-difluorocyclohexyl)-6-(3,5-dimethyl-1H-pyrazol-1-yl)-N4-((2-methyl-2H-1,2,3-triazol-4-yl)methyl)pyridine-2,4-diamine [0589], Compound 248 as yellow solid. MS(M+1)$^+$=417.0, $^1$H NMR (400 MHz, DMSO-d6) δ 7.61 (s, 1H), 6.76 (t, J=5.9 Hz, 1H), 6.36 (d, J=1.8 Hz, 1H), 6.25 (d, J=7.6 Hz, 1H), 5.97 (s, 1H), 5.53 (d, J=1.8 Hz, 1H), 4.28 (d, J=5.9 Hz, 2H), 4.11 (s, 3H), 3.80 (bs, 1H), 2.14 (s, 3H), 2.09-1.78 (m, 6H), 1.56-1.40 (m, 2H).

Example 222

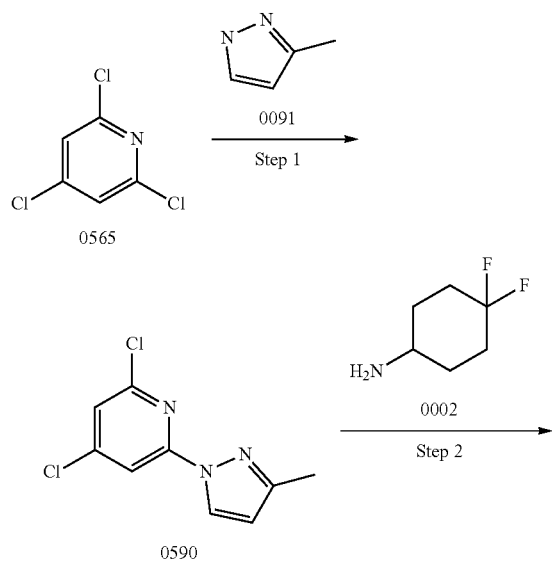

-continued

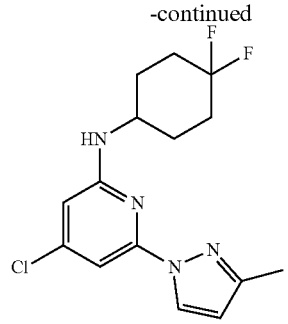

0591

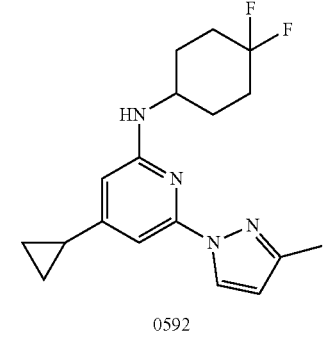

0592

Step 1[0590]: The procedure is similar to step 1[0270] in example 98. 5 g of 2,4,6-trichloropyridine [0565] and 2.2 g of 3-methylpyrazole [0091] gave 2.2 g of 2,4-dichloro-6-(3-methyl-1H-pyrazol-1-yl)pyridine [0590] as white solid. MS(M+1)+=229.2.

Step 2[0591]: The procedure is similar to step 3[0580] in example 216. 1 g of 2,4-dichloro-6-(3-methyl-1H-pyrazol-1-yl)pyridine [0590] and 0.82 g of 4,4-difluorocyclohexylamine hydrochloride [0002] gave 0.6 g of 4-chloro-N-(4,4-difluorocyclohexyl)-6-(3-methyl-1H-pyrazol-1-yl)pyridin-2-amine [0591] as off-white solid. MS(M+1)+=327.2.

Step 3[0592]: The procedure is similar to step 1[0251] in example 90. 0.28 g of 6-chloro-N-(4,4-difluorocyclohexyl)-2-(3,5-dimethyl-1H-pyrazol-1-yl)pyrimidin-4-amine [0591] gave 0.115 g of 6-cyclopropyl-N-(4,4-difluorocyclohexyl)-2-(3,5-dimethyl-1H-pyrazol-1-yl)pyrimidin-4-amine [0592], Compound 182 as white solid MS(M+1)$^+$=333.2. $^1$H NMR (400 MHz, DMSO-d6) δ 8.39 (d, J=2.4 Hz, 1H), 6.62 (d, J=1.12 Hz, 1H), 6.60 (s, 1H), 6.27 (d, J=2.4 Hz, 1H), 6.09 (d, J=1.3 Hz, 1H), 3.95 (bs, 1H), 2.26 (s, 3H), 2.12-1.90 (m, 6H), 1.92-1.85 (m, 1H), 1.62-1.55 (m, 2H), 1.03-0.92 (m, 2H), 0.76-0.67 (m, 2H).

Example 223

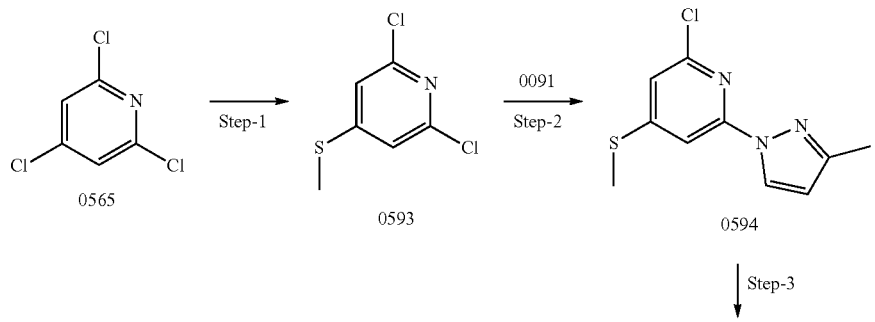

Step-3

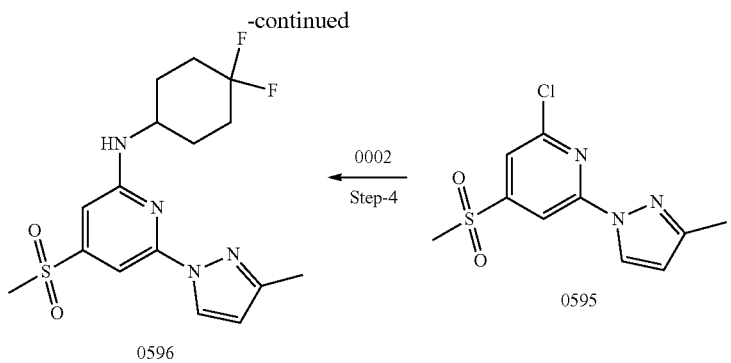

Step 1[0593]: To a cooled (−10° C.) solution of 2,4,6-trichloropyridine [0565] (2 g, 10.96 mmol) in tetrahydrofuran (10 mL) was added sodium thiomethoxide (0.762 g, 10.96 mmol) portion wise under N2 atm. The resultant reaction mixture was stirred at −10° C. After 3 h, the reaction mixture was quenched with water (10 mL) and extracted with ethyl acetate (2×100 mL). The combined organic layer was washed with brine, dried over anhydrous sodium sulfate, filtered and concentrated under reduced pressure to afford as a colorless liquid, which was purified in the Reveleris flash system instrument using ethyl acetate in hexane as solvent in 12 g column to afford 0.9 g of 2,6-dichloro-4-(methylthio)pyridine [0593] as a white solid. MS(M+1)+=195.0.

Step 2[0594]: This procedure is similar to step 1[0270] in example 98. 0.25 g of 2,6-dichloro-4-(methylthio)pyridine [0594] and 0.1 g of 3-methylpyrazole [0091] gave 0.1 g of 2-chloro-6-(3-methyl-1H-pyrazol-1-yl)-4-(methylthio)pyridine [0594] as white solid. MS(M+1)+=240.0.

Step 3[0595]: This procedure is similar to step 2[0378] in example 145. 0.5 g of 2-chloro-6-(3-methyl-1H-pyrazol-1-yl)-4-(methylthio)pyridine [0594] gave 0.52 g of 2-chloro-6-(3-methyl-1H-pyrazol-1-yl)-4-(methylsulfonyl)pyridine [0595] as a white solid. MS(M+1)+=272.0.

Step 4[0596]: The procedure is similar to step 3[0580] in example 216. 0.2 g of 2-chloro-6-(3-methyl-1H-pyrazol-1-yl)-4-(methylsulfonyl)pyridine [0595] gave 0.063 g of N-(4,4-difluorocyclohexyl)-6-(3-methyl-1H-pyrazol-1-yl)-4-(methylsulfonyl)pyridin-2-amine [0596], Compound 153 as a white solid. MS(M+1)+=371.2, 1H NMR (400 MHz, DMSO-d6) δ 8.50 (d, J=2.6 Hz, 1H), 7.52 (d, J=7.4 Hz, 1H), 7.23 (s, 1H), 6.82 (s, 1H), 6.38 (d, J=2.6 Hz, 1H), 4.09 (m, 1H), 3.27 (s, 3H), 2.29 (s, 3H), 2.13-1.96 (m, 6H), 1.61-1.52 (m, 2H).

Example 224

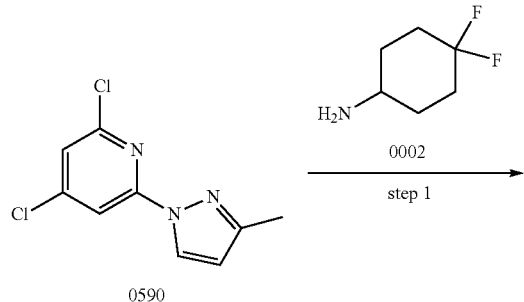

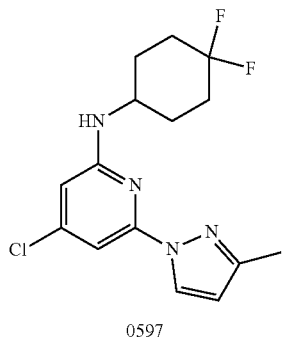

Step 1[0597]: This procedure is similar to Step 3[0580] in example 216. 1 g of 2,4-dichloro-6-(3-methyl-1H-pyrazol-1-yl)pyridine [0590] and 0.822 g of 4,4-difluorocyclohexylamine hydrochloride [0002] gave 0.6 g of 4-chloro-N-(4,4-difluorocyclohexyl)-6-(3-methyl-1H-pyrazol-1-yl)pyridin-2-amine [0597], Compound 179 as an off-white solid. MS(M+1)+=327.0, 1H NMR (400 MHz, DMSO-d6) δ 8.43 (d, J=2.5 Hz, 1H), 7.11 (d, J=7.5 Hz, 1H), 6.88 (d, J=1.5 Hz, 1H), 6.39 (d, J=1.6 Hz, 1H), 6.33 (d, J=1.6 Hz, 1H) 3.99 (s, 1H), 2.26 (s, 3H), 2.13-1.90 (m, 6H), 1.57-1.45 (m, 2H).

Example 225

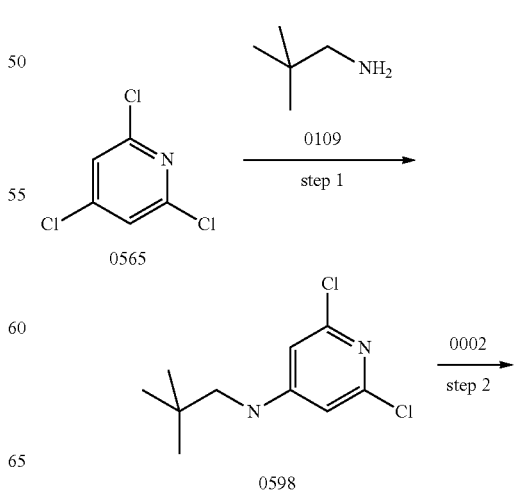

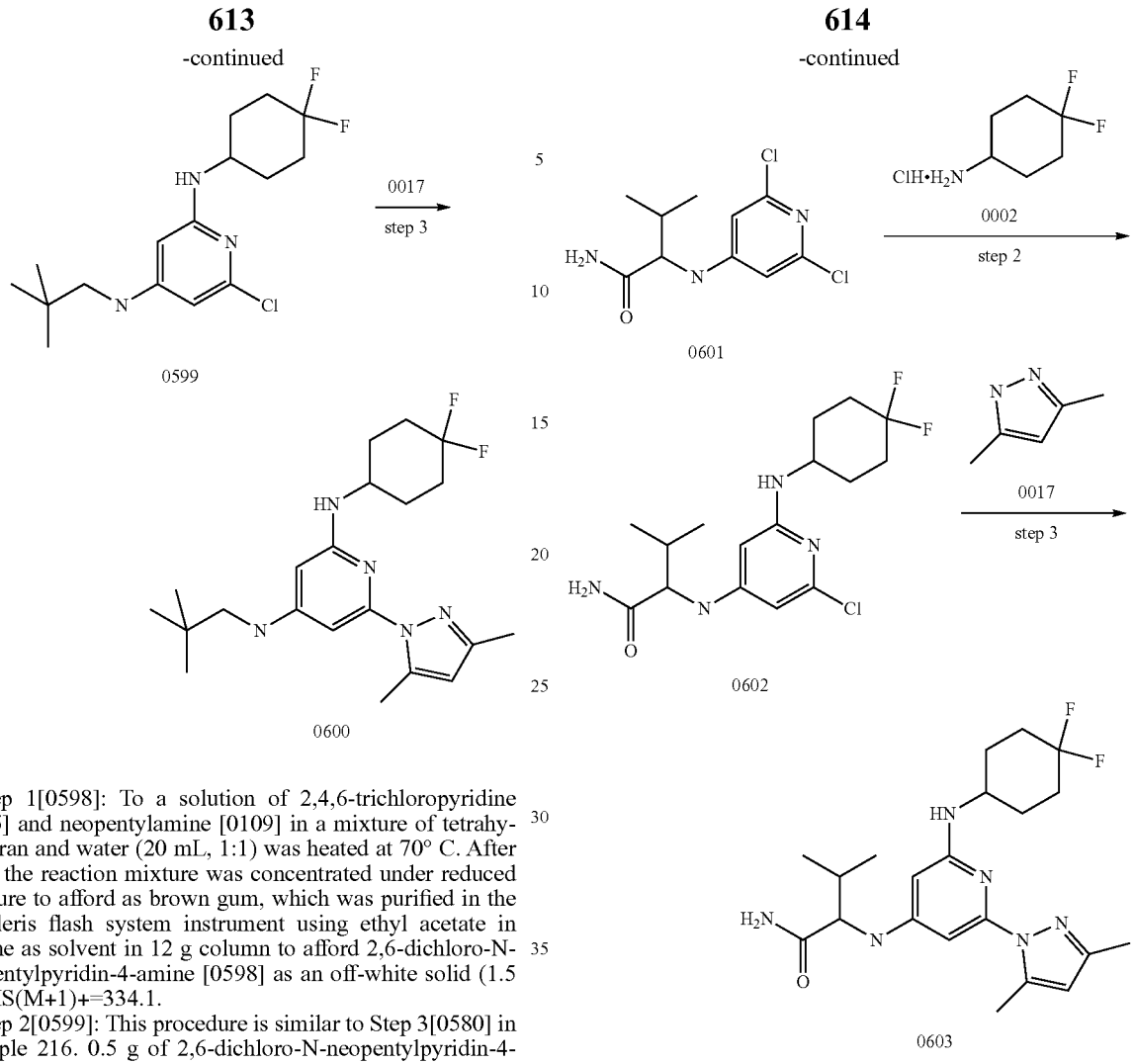

Step 1[0598]: To a solution of 2,4,6-trichloropyridine [0565] and neopentylamine [0109] in a mixture of tetrahydrofuran and water (20 mL, 1:1) was heated at 70° C. After 18 h, the reaction mixture was concentrated under reduced pressure to afford as brown gum, which was purified in the Reveleris flash system instrument using ethyl acetate in hexane as solvent in 12 g column to afford 2,6-dichloro-N-neopentylpyridin-4-amine [0598] as an off-white solid (1.5 g). MS(M+1)+=334.1.

Step 2[0599]: This procedure is similar to Step 3[0580] in example 216. 0.5 g of 2,6-dichloro-N-neopentylpyridin-4-amine [0598] gave 0.1 g of 2-chloro-6-(3,5-dimethyl-1H-pyrazol-1-yl)-N-neopentylpyridin-4-amine [0599] as an off-white solid. MS(M+1)+=332.1.

Step 3[0600]: This procedure is similar to Step 3[0006] in example 1. 0.1 g of 2-chloro-6-(3,5-dimethyl-1H-pyrazol-1-yl)-N-neopentylpyridin-4-amine [0599], Compound 234 gave 0.015 g of N2-(4,4-difluorocyclohexyl)-6-(3,5-dimethyl-1H-pyrazol-1-yl)-N4-neopentylpyridine-2,4-diamine [0600] as brown solid. MS(M+1)+=392.2, $^1$H NMR (400 MHz, Chloroform-d) δ 6.29 (s, 1H), 5.98 (d, J=7.3 Hz, 1H), 5.44 (s, 1H), 3.67 (s, 1H), 2.99 (s, 2H), 2.60 (s, 3H), 2.30-2.20 (m, 6H), 2.08 (bs, 4H), 1.91 (bs, 2H), 1.03 (s, 9H).

Example 226

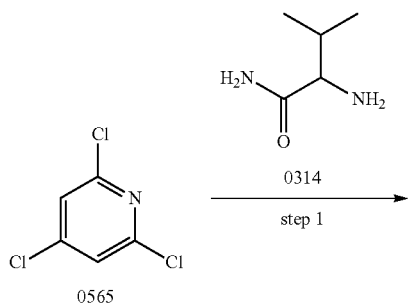

Step 1[0601]: To a solution of 2,4,6-trichloropyridine [0565] (0.35 g, 1.918 mmol) in tetrahydrofuran (12 mL) was added L-valinamide hydrochloride [0314] (0.3 g, 1.918 mmol) and cesium carbonate (1.37 g, 4.2 mmol), after addition the reaction mixture was stirred at 60° C. for 28 h. The reaction mixture was diluted with water, product was extracted with ethyl acetate (2×100 mL), combined organic layer was washed with brine (100 mL), dried over anhydrous sodium sulfate filtered and concentrated under reduced pressure to afford crude product, which was purified by column chromatography using 25% ethyl acetate in pet ether as solvent to afford 0.11 g of 2-((2,6-dichloropyridin-4-yl)amino)-3-methylbutanamide [0601] as a brown solid. MS(M+1)+=262.4

Step 2[602]: The procedure is similar to step 4[0244] in example 87 (10 h, 100° C.). 0.19 g of [0601] and 0.15 g of 4,4-difluorocyclohexylamine hydrochloride [0002] gave 0.09 g of 2-((2-chloro-6-((4,4-difluorocyclohexyl)amino)pyridin-4-yl)amino)-3-methylbutanamide [0602] as a brown solid. MS(M+1)+=362.7.

Step 3[0603]: The procedure is similar to step 3[0580] in example 216 (10 h, 110° C.). 0.15 g of [0602] and 0.08 g of 3,5-dimethyl pyrazole [0017] gave 0.018 g of 2-((2-((4,4-difluorocyclohexyl)amino)-6-(3,5-dimethyl-1H-pyrazol-1-yl)pyridin-4-yl)amino)-3-methylbutanamide [0603], Compound 239 as an off-white solid. MS(M+1)+=421.2, $^1$H NMR (400 MHz, DMSO-d6) δ 8.10 (s, 2H), 7.86 (s, 1H), 7.59 (s, 1H), 7.14 (d, J=7.5 Hz, 1H), 6.91 (s, 1H), 6.41 (s, 1H), 6.08 (s, 1H), 3.88 (bs, 1H), 3.53 (d, J=5.2 Hz, 1H), 2.60

(s, 3H), 2.17 (s, 3H), 2.10-1.88 (m, 6H), 1.62-1.53 (m, 2H), 0.95 (dd, J=10.4, 6.9 Hz, 6H).

Example 227

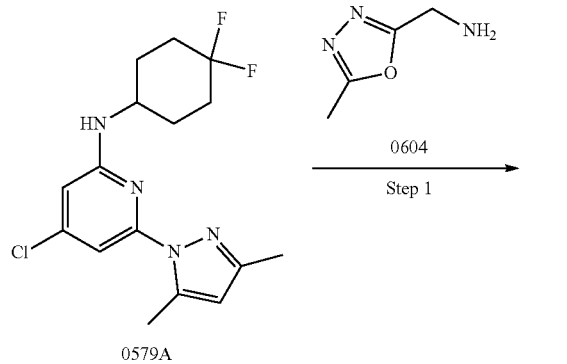

Step 1[0605]: The procedure is similar to step 4[0244] in example 87 (10 h, 110° C.). 0.31 g of 4-chloro-N-(4,4-difluorocyclohexyl)-6-(3,5-dimethyl-1H-pyrazol-1-yl)pyridin-2-amine [0579A] and 0.16 g of c-(5-Methyl-[1,3,4] oxadiazol-2-Y1)-methylamine [0604] gave 0.068 g of N2-(4,4-difluorocyclohexyl)-6-(3,5-dimethyl-1H-pyrazol-1-yl)-N4-((5-methyl-1,3,4-oxadiazol-2-yl)methyl)pyridine-2,4-diamine [0605], Compound 252 as an off-white solid. MS(M+1)$^+$=417.9, $^1$H NMR (400 MHz, DMSO-d6) δ 6.97 (s, 1H), 6.36-6.32 (m, 2H), 5.97 (s, 1H), 5.55 (s, 1H), 4.48 (d, J=6.2 Hz, 2H), 3.80 (bs, 1H), 2.53 (s, 3H), 2.47 (s, 3H), 2.14 (s, 3H), 2.10-1.88 (m, 6H), 1.62-1.48 (m, 2H).

Example 228

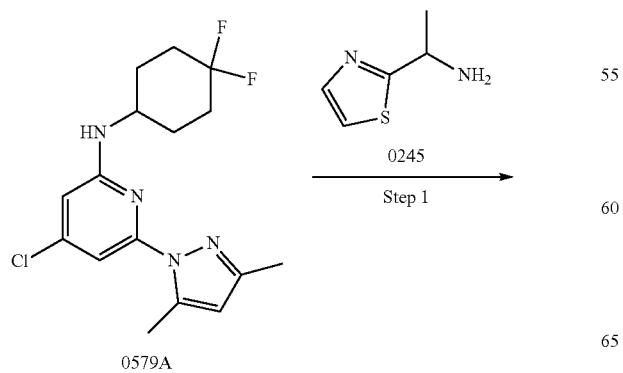

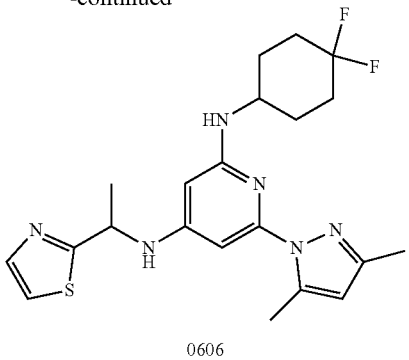

Step 1 [0606]: The procedure is similar to step 4[0244] in example 87 (20 h, 110° C.). 0.32 g of 4-chloro-N-(4,4-difluorocyclohexyl)-6-(3,5-dimethyl-1H-pyrazol-1-yl)pyridin-2-amine [0579A] and 0.12 g of 1-thiazol-2-yl-ethylamine [0245] gave 0.058 g of N2-(4,4-difluorocyclohexyl)-6-(3,5-dimethyl-1H-pyrazol-1-yl)-N4-(1-(thiazol-2-yl)ethyl)pyridine-2,4-diamine [0606], Compound 255 as an off-white solid. MS(M+1)$^+$=433.2, $^1$H NMR (400 MHz, DMSO-d6) δ 7.74 (d, J=3.3 Hz, 1H), 7.58 (d, J=3.2 Hz, 1H), 7.04 (d, J=6.6 Hz, 1H), 6.42 (d, J=1.7 Hz, 1H), 6.30 (d, J=7.6 Hz, 1H), 5.97 (s, 1H), 5.44 (d, J=1.8 Hz, 1H), 4.80 (p, J=6.7 Hz, 1H), 3.77 (bs, 1H), 2.52 (s, 3H), 2.15 (s, 3H), 2.10-1.88 (m, 6H), 1.53 (d, J=6.8 Hz, 3H), 1.45 (bs, 2H).

Example 229

Step 1[0607]: The procedure is similar to step 4[0244] in example 87 (at 100° C. for 20 h). 0.25 g of 4-chloro-N-(4,4-difluorocyclohexyl)-6-(3,5-dimethyl-1H-pyrazol-1-yl)pyridin-2-amine [0579A] and 0.08 g of oxazol-2-yl-methylamine [0316] gave 0.042 g of N2-(4,4-difluorocyclohexyl)-6-(3,5-dimethyl-1H-pyrazol-1-yl)-N4-(oxazol-2-ylmethyl)pyridine-2,4-diamine [0607], Compound 259 as an off-white solid.

MS(M+1)⁺=403.2, ¹H NMR (400 MHz, DMSO-d6) δ 8.07 (s, 1H), 7.17 (s, 1H), 6.94 (t, J=6.3 Hz, 1H), 6.37 (d, J=1.8 Hz, 1H), 6.30 (d, J=7.7 Hz, 1H), 5.97 (s, 1H), 5.54 (d, J=1.8 Hz, 1H), 4.39 (d, J=6.3 Hz, 2H), 3.80 (bs, 1H), 2.53 (s, 3H), 2.15 (s, 3H), 2.10-1.88 (m, 6H), 1.65-1.48 (m, 2H).

Example 230

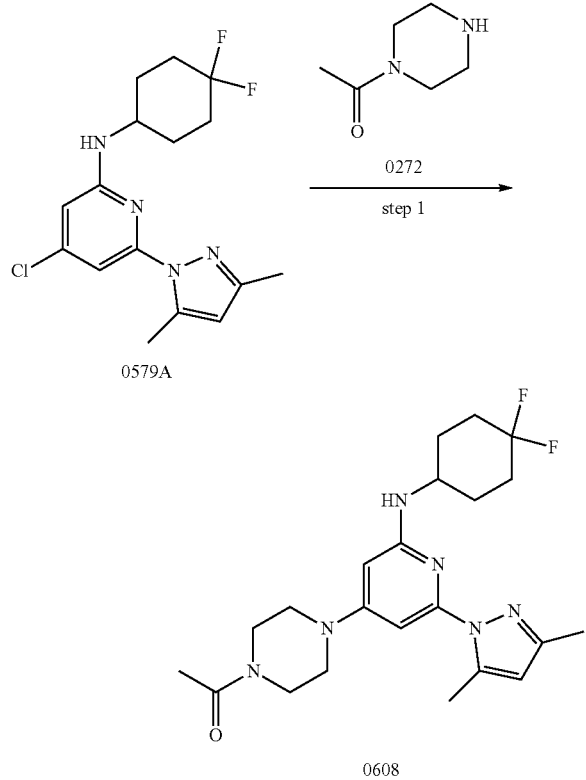

Step 1[0177]: To a stirred solution of 4-chloro-N-(4,4-difluorocyclohexyl)-6-(3,5-dimethyl-1H-pyrazol-1-yl)pyridin-2-amine [0579A] (0.48 g, 1.40 mmol) in dioxane was added 1-acetylpiperazine [0272] (0.27 g, 2.11 mmol), cesium carbonate (1.4 g, 1.97 mmol), 4,5-bis(diphenylphosphino)-9,9-dimethylxanthene (0.326 g, 0.563 mmol) and the reaction mixture was purged with nitrogen for 5 min. Then tris(dibenzylideneacetone)dipalladium (0.386 g, 0.422 mmol) was added to the reaction mixture and the reaction mixture was heated at 90° C. in sealed tube. After 16 h, the reaction mixture was passed through celite bed, washed with chloroform and the filtrate was concentrated under reduced pressure to afford as a brown oil, which was purified in the Reveleris flash system instrument using ethyl acetate in hexane as solvent in 25 g column, to afford 1-(4-(2-((4,4-difluorocyclohexyl)amino)-6-(3,5-dimethyl-1H-pyrazol-1-yl)pyridin-4-yl)piperazin-1-yl)ethan-1-one [0608], Compound 134 as yellow solid (0.18 g). MS(M+1)⁺=433.3, ¹H NMR (400 MHz, DMSO-d6) δ 6.54 (d, J=1.9 Hz, 1H), 6.39 (d, J=7.8 Hz, 1H), 6.00 (s, 1H), 5.78 (s, 1H), 3.87 (bs, 1H), 3.56 (s, 4H), 3.27 (d, J=4 Hz, 2H), 3.21 (d, J=4.28 Hz, 2H), 2.54 (s, 3H), 2.16 (s, 3H), 2.04 (s, 5H), 1.98-1.80 (m, 4H), 1.62-1.48 (m, 2H).

Example 231

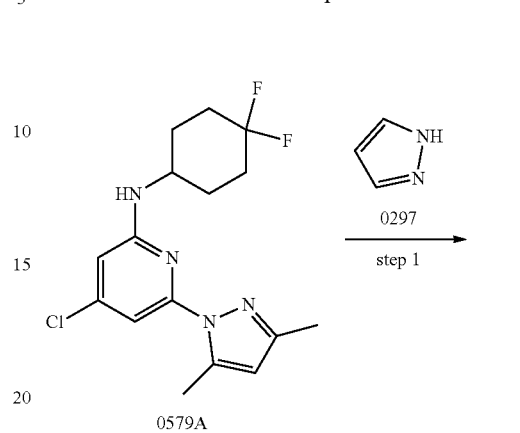

Step 1[0609]: The procedure is similar to step 4[0244] in example 87. 0.3 g of 4-chloro-N-(4,4-difluorocyclohexyl)-6-(3,5-dimethyl-1H-pyrazol-1-yl)pyridin-2-amine [0579A] gave 0.03 g of N-(4,4-difluorocyclohexyl)-6-(3,5-dimethyl-1H-pyrazol-1-yl)-4-(1H-pyrazol-1-yl)pyridin-2-amine [0609], Compound 127 as a white solid. MS(M+1)⁺=373.7, ¹H-NMR (400 MHz, DMSO-d6): δ 8.52 (d, J=2.60 Hz, 1H), 7.79 (d, J=1.60 Hz, 1H), 7.35 (d, J=1.64 Hz, 1H), 7.03 (d, J=7.52 Hz, 1H), 6.80 (d, J=1.68 Hz, 1H), 6.57-6.56 (m, 1H), 6.08 (s, 1H), 3.93-3.91 (m, 1H), 2.61 (s, 3H), 2.19 (s, 3H), 2.09-2.07 (m, 2H), 2.00-1.90 (m, 4H), 1.54-1.60 (m, 2H).

Example 232

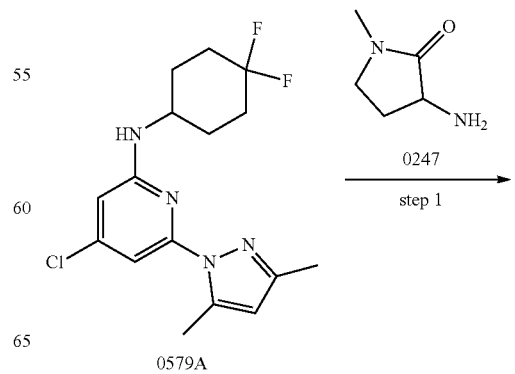

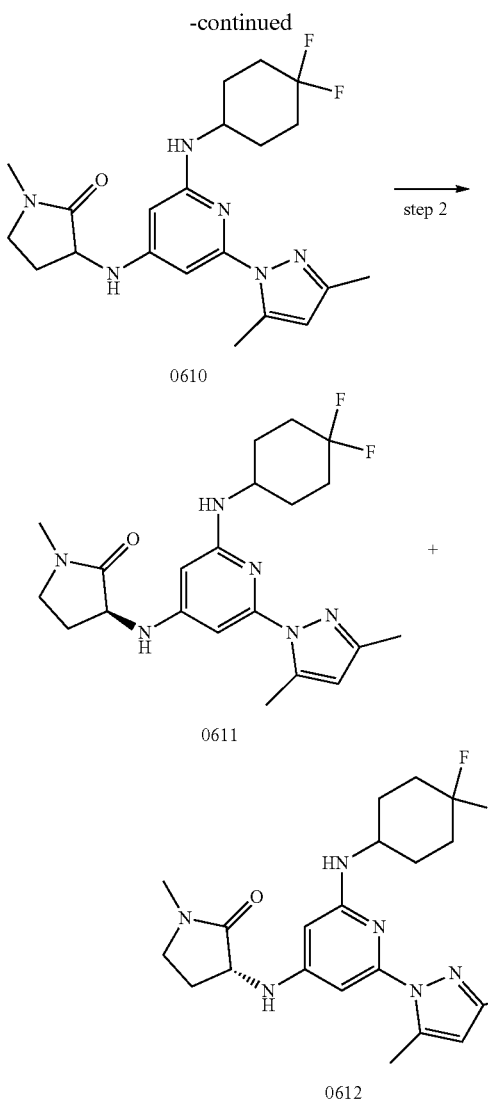

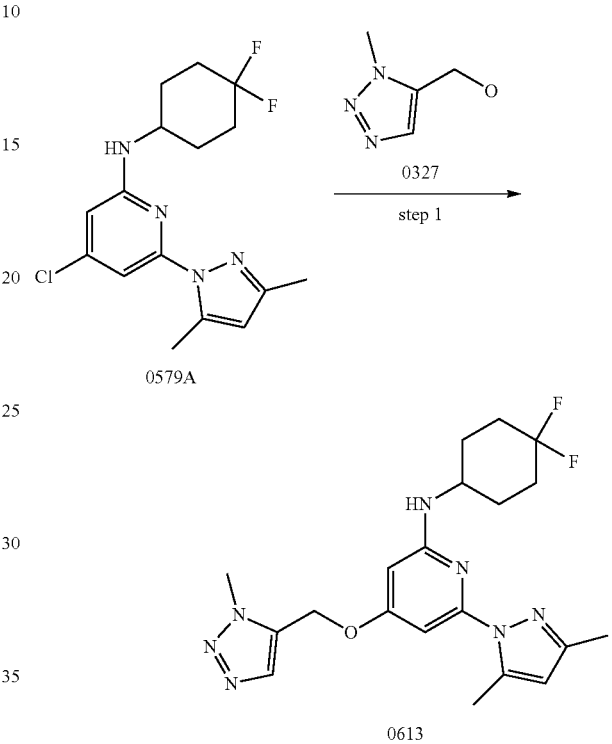

Step 1[0610]: The procedure is similar to step 4[0244] in example 87. 0.3 g of 4-chloro-N-(4,4-difluorocyclohexyl)-6-(3,5-dimethyl-1H-pyrazol-1-yl)pyridin-2-amine [0579A] gave 0.04 g of racemate 3-((2-((4,4-difluorocyclohexyl)amino)-6-(3,5-dimethyl-1H-pyrazol-1-yl)pyridin-4-yl)amino)-1-methylpyrrolidin-2-one [0610], Compound 135 as a brown solid. MS(M+1)⁺=419.2. ¹H NMR (400 MHz, DMSO-d6) δ 6.43 (d, J=7.1 Hz, 1H), 6.37 (s, 1H), 6.20 (d, J=7.6 Hz, 1H), 5.97 (s, 1H), 5.58 (s, 1H), 4.10-4.05 (m, 1H), 3.82 (bs, 1H), 3.31 (m, 2H) 2.77 (s, 3H), 2.53 (s, 3H), 2.42 (m, 1H), 2.15 (s, 3H), 2.06 (m, 2H), 1.92 (m, 4H), 1.76 (m, 1H), 1.51-1.41 (m, 2H).

Step 2[0611 and 0612]: Enantiomers were separated by chiral prep HPLC to afford 0.029 g of (+)-3-((2-((4,4-difluorocyclohexyl)amino)-6-(3,5-dimethyl-1H-pyrazol-1-yl)pyridin-4-yl)amino)-1-methylpyrrolidin-2-one [0611], Compound 138 as a yellow solid. ¹H NMR (400 MHz, DMSO-d6) δ 6.42 (d, J=7.4 Hz, 1H), 6.36 (d, J=1.7 Hz, 1H), 6.19 (d, J=7.7 Hz, 1H), 5.96 (s, 1H), 5.58 (d, J=1.8 Hz, 1H), 4.07 (q, J=8.5 Hz, 1H), 3.81 (bs, 1H), 3.33 (s, 3H), 3.30 (d, J=1.4 Hz, 1H), 2.76 (s, 3H), 2.53 (s, 3H), 2.43 (m, 1H), 2.14 (s, 3H), 2.05-1.91 (m, 2H), 1.88-1.80 (m, 4H), 1.78-1.71 (m, 1H), 1.50 (m, 2H), and 0.023 g of (−)-3-((2-((4,4-difluorocyclohexyl)amino)-6-(3,5-dimethyl-1H-pyrazol-1-yl)pyridin-4-yl)amino)-1-methylpyrrolidin-2-one [0612], Compound 139 as a yellow solid. ¹H NMR (400 MHz, DMSO-d6) δ 6.42 (d, J=7.3 Hz, 1H), 6.36 (d, J=1.6 Hz, 1H), 6.19 (d, J=7.8 Hz, 1H), 5.96 (s, 1H), 5.58 (d, J=1.8 Hz, 1H), 4.07 (q, J=8.5 Hz, 1H), 3.79 (bs, 1H), 2.76 (s, 3H), 2.53 (s, 3H), 2.48-2.38 (m, 2H), 2.14 (s, 3H), 2.12-1.88 (m, 6H), 1.85-1.73 (m, 1H), 1.58-1.48 (m, 2H), 0.88-0.75 (m, 1H).

Example 233

Step 1[0613]: The procedure is similar to step 1[0301] in example 111. 0.3 g of 4-chloro-N-(4,4-difluorocyclohexyl)-6-(3,5-dimethyl-1H-pyrazol-1-yl)pyridin-2-amine [0579A] gave 0.050 g of N-(4,4-difluorocyclohexyl)-6-(3,5-dimethyl-1H-pyrazol-1-yl)-4-((1-methyl-1H-1,2,3-triazol-5-yl)methoxy)pyridin-2-amine [0613], Compound 268 as a white solid. MS(M+1)⁺=418.2. ¹H NMR (400 MHz, DMSO-d6) δ 7.82 (s, 1H), 6.74 (d, J=7.6 Hz, 1H), 6.63 (d, J=2.0 Hz, 1H), 6.03 (s, 1H), 5.96 (d, J=1.6 Hz, 1H), 5.31 (s, 2H), 4.04 (s, 3H), 3.87 (bs, 1H), 2.57 (s, 3H), 2.16 (s, 3H), 2.09-1.85 (m, 6H), 1.62-1.45 (m, 2H).

Example 234

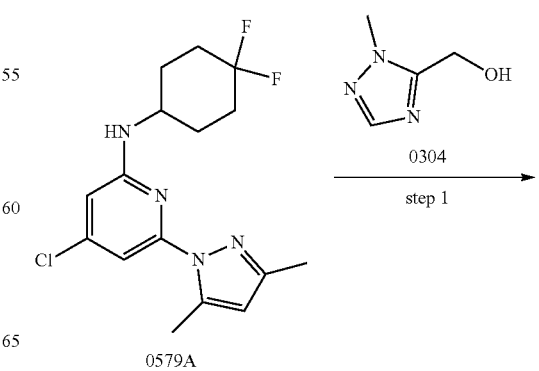

-continued

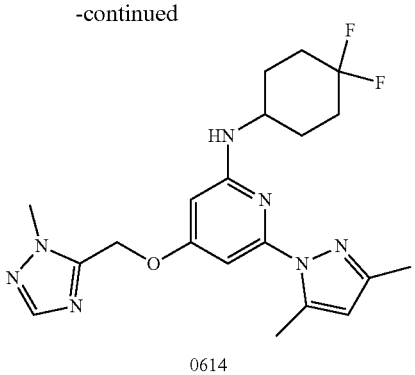

0614

Step 1[0614]: To a suspension of 4-chloro-N-(4,4-difluorocyclohexyl)-6-(3,5-dimethyl-1H-pyrazol-1-yl)pyridin-2-amine [0579A] (0.15 g, 0.44 mmol) and (1-methyl-1H-1,2,4-triazol-5-yl)methanol [0304] (0.14 g, 1.17 mmol) in 50% aq. sodium hydroxide solution (2 mL) was added tetrabutyl ammonium hydrogen Sulfate (0.14 g, 0.44 mmol), then the reaction mixture was heated at 100° C. in a closed vial for 16 h. After the completion of the reaction, the reaction mixture was extracted with ethyl acetate (2×40 mL), the combined organic layer was dried over anhydrous sodium sulfate and concentrated to afford crude and which was purified by column of silica gel (60-120 mesh), using 25% ethyl acetate in hexane as eluent gave 0.03 g of N-(4,4-difluorocyclohexyl)-6-(3,5-dimethyl-1H-pyrazol-1-yl)-4-((1-methyl-1H-1,2,4-triazol-5-yl)methoxy)pyridin-2-amine [0614], Compound 271 as a white solid. MS(M+1)$^+$=419.6, $^1$H-NMR (400 MHz, DMSO-d6): δ 7.95 (s, 1H), 6.77 (d, J=7.60 Hz, 1H), 6.62 (d, J=1.96 Hz, 1H), 6.03 (s, 1H), 5.97 (d, J=1.96 Hz, 1H), 5.31 (s, 1H), 3.89 (s, 1H), 3.85-3.84 (m, 1H), 2.57 (s, 3H), 2.15 (s, 3H), 2.07-1.92 (m, 6H), 1.52-1.47 (m, 2H).

Example 235

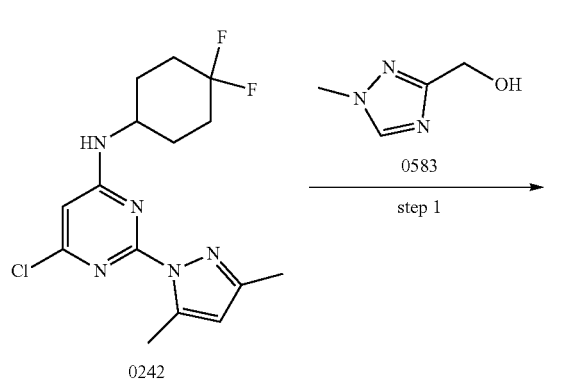

Step 1[0615]: The procedure is similar to step 1[0614] in example 234. 0.3 g of 4-chloro-N-(4,4-difluorocyclohexyl)-6-(3,5-dimethyl-1H-pyrazol-1-yl)pyridin-2-amine [0242] gave 0.065 g of N-(4,4-difluorocyclohexyl)-2-(3,5-dimethyl-1H-pyrazol-1-yl)-6-((1-methyl-1H-1,2,4-triazol-3-yl)methoxy)pyrimidin-4-amine [0615] as a white solid (0.065 g). MS(M+1)$^+$=419.6, $^1$H NMR (400 MHz, DMSO-d6) δ 8.46 (s, 1H), 7.53 (bs, 1H), 6.06 (s, 1H), 5.75 (bs, 1H), 5.31 (s, 2H), 4.01 (bs, 1H), 3.86 (s, 3H), 2.54 (s, 3H), 2.17 (s, 3H), 2.12-1.85 (m, 6H), 1.62-1.50 (m, 2H).

Example 236

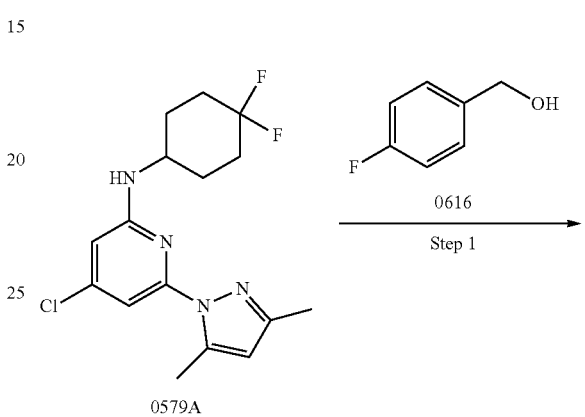

Step 1[0617]: To a suspension of 4-chloro-N-(4,4-difluorocyclohexyl)-6-(3,5-dimethyl-1H-pyrazol-1-yl)pyridin-2-amine [0579A] (0.2 g, 0.58 mmol) and 4-fluorobenzyl alcohol [0616] (0.14 g, 1.17 mmol) in 50% aq. sodium hydroxide solution (2 mL) was added tetrabutyl ammonium hydrogen Sulfate (0.11 g, 0.35 mmol), then the reaction mixture was heated at 100° C. in a closed vial for 16 h. After the completion of the reaction, the reaction mixture was extracted with ethyl acetate (2×40 mL), the combined organic layer was dried over anhydrous sodium sulfate and concentrated to afford crude and which was purified by column of silica gel (60-120 mesh), using 25% ethyl acetate in hexane as eluent to afford N-(4,4-difluorocyclohexyl)-6-(3,5-dimethyl-1H-pyrazol-1-yl)-4-((4-fluorobenzyl)oxy)pyridin-2-amine [0617], Compound 263 as an off-white gum (0.075 g).

MS(M+1)$^+$=431, $^1$H NMR (400 MHz, DMSO-d6) δ 7.50 (t, 2H), 7.24 (t, J=8.6 Hz, 2H), 6.69 (d, J=7.7 Hz, 1H), 6.61 (s, 1H), 6.03 (s, 1H), 5.95 (s, 1H), 5.11 (s, 2H), 3.86 (bs, 1H), 2.58 (s, 3H), 2.16 (s, 3H), 2.01-1.90 (m, 6H), 1.59-1.52 (m, 2H).

Example 237

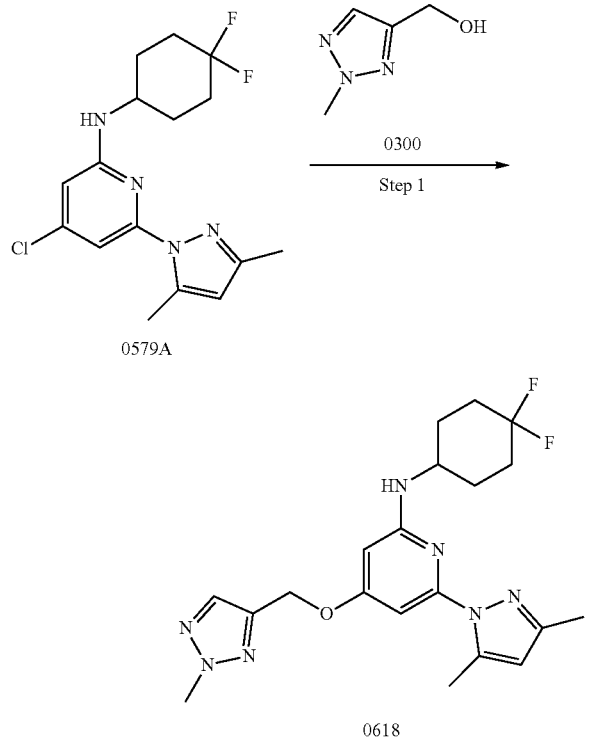

Step 1[0618]: The procedure is similar to step 1[0614] in example 234. 0.2 g of 4-chloro-N-(4,4-difluorocyclohexyl)-6-(3,5-dimethyl-1H-pyrazol-1-yl)pyridin-2-amine [0579A] and 0.133 g of (2-methyl-2H-1,2,3-triazol-4-yl)methanol [0300] gave 0.07 g of N-(4,4-difluorocyclohexyl)-6-(3,5-dimethyl-1H-pyrazol-1-yl)-4-((2-methyl-2H-1,2,3-triazol-4-yl)methoxy)pyridin-2-amine [0618], Compound 251 as an off-white solid. MS(M+1)$^+$=418, $^1$H-NMR (400 MHz, DMSO-d6): δ 7.84 (s, 1H), 6.70 (d, J=7.60 Hz, 1H), 6.59 (d, J=2.00 Hz, 1H), 6.02 (s, 1H), 5.96 (s, 1H), 5.16 (s, 2H), 4.16 (s, 3H), 3.85 (bs, 1H), 2.57 (s, 3H), 2.15 (s, 3H), 2.07-1.87 (m, 6H), 1.52-1.50 (m, 2H).

Example 238

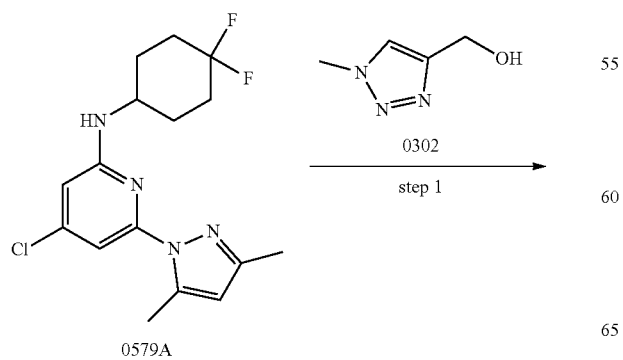

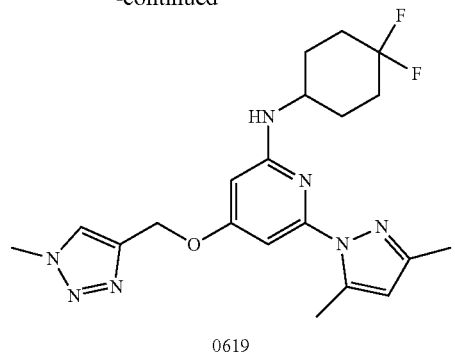

Step 1[0619]: The procedure is similar to step 1[0614] in example 234. 0.2 g of 4-chloro-N-(4,4-difluorocyclohexyl)-6-(3,5-dimethyl-1H-pyrazol-1-yl)pyridin-2-amine [0579A] and 0.265 g of (1-methyl-1H-1,2,3-triazol-4-yl)methanol [0302] gave 0.1 g of N-(4,4-difluorocyclohexyl)-6-(3,5-dimethyl-1H-pyrazol-1-yl)-4-((1-methyl-1H-1,2,3-triazol-4-yl)methoxy)pyridin-2-amine [0619], Compound 244 as an off-white solid. MS(M+1)$^+$=418, $^1$H NMR (400 MHz, DMSO-d6) δ 8.17 (s, 1H), 6.71 (d, J=7.5 Hz, 1H), 6.59 (d, J=2.0 Hz, 1H), 6.06-5.98 (m, 2H), 5.16 (s, 2H), 4.06 (s, 3H), 3.87 (bs, 1H), 2.58 (s, 3H), 2.16 (s, 3H), 2.11-1.89 (m, 6H), 1.59-1.52 (m, 2H).

Example 239

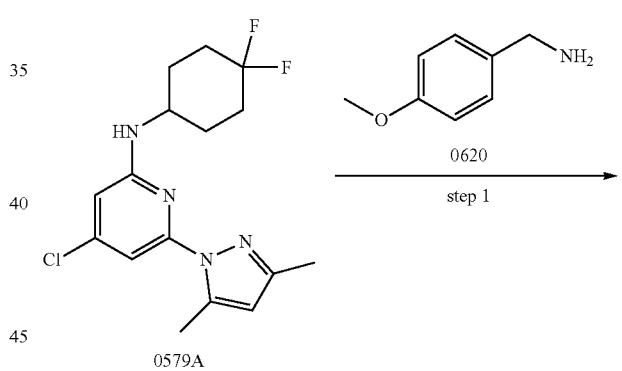

Step 1[0621]: The procedure is similar to step 4[0244] in example 87. 0.2 g of 4-chloro-N-(4,4-difluorocyclohexyl)-6-(3,5-dimethyl-1H-pyrazol-1-yl)pyridin-2-amine [0579A] gave 0.035 g of N2-(4,4-difluorocyclohexyl)-6-(3,5-dimethyl-1H-pyrazol-1-yl)-N4-(4-methoxybenzyl)pyridine-2,4-diamine [0621], Compound 264 as off-white solid.

MS(M+1)+=442.2. ¹H NMR (400 MHz, DMSO-d6) δ 7.34-7.13 (m, 2H), 7.02-6.85 (m, 2H), 6.80 (t, J=6.1 Hz, 1H), 6.35 (d, J=1.8 Hz, 1H), 6.16 (d, J=7.7 Hz, 1H), 5.95 (s, 1H), 5.45 (d, J=1.9 Hz, 1H), 4.18 (d, J=5.9 Hz, 2H), 3.76 (bs, 1H), 3.72 (s, 3H), 2.51 (s, 3H), 2.13 (s, 3H), 2.09-1.75 (m, 6H), 1.46 (q, J=12.0, 10.4 Hz, 2H).

Example 240

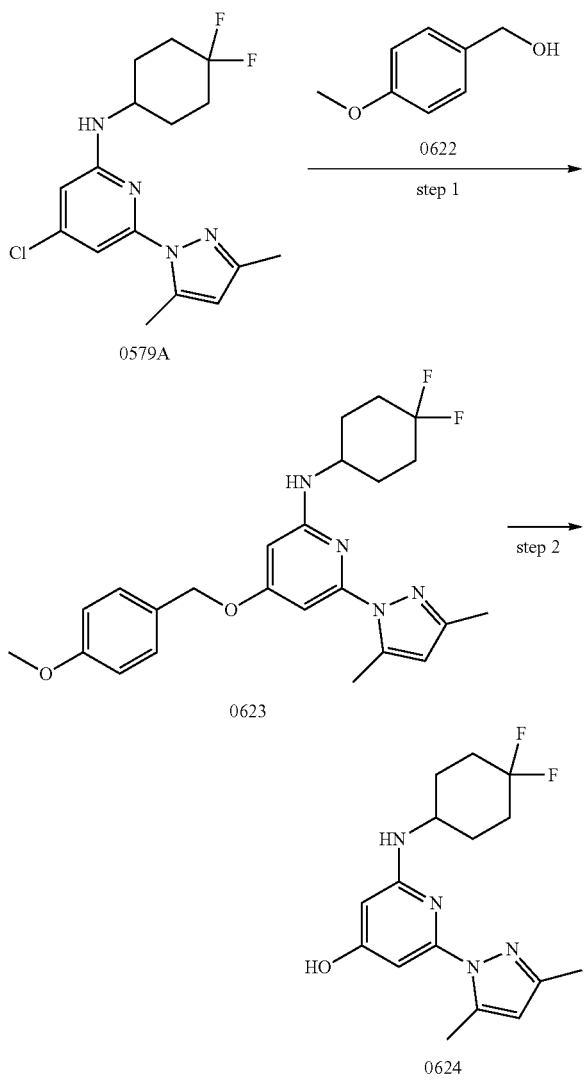

Step 1[0623]: To a suspension of sodium hydride in tetrahydrofuran (2 mL) in a micro wave vial was added a solution of 4-methoxybenzyl alcohol [0622] (0.15 g, 1.1 mmol) in tetrahydrofuran at 0° C. under nitrogen. The solution was stirred at 0° C. for half an hour. 4-chloro-N-(4,4-difluorocyclohexyl)-6-(3,5-dimethyl-1H-pyrazol-1-yl)pyridin-2-amine [0579A] (025 g, 0.73 mmol) was added and the reaction mixture was heated at 150° C. The reaction mixture was quenched with ice, then extracted with ethyl acetate (2×25 mL). The combined organic layer was dried over sodium sulfate, filtered and concentrated under reduced pressure to afford crude product and which was purified by column chromatography using 25% ethyl acetate in pet ether as solvent to afford N-(4,4-Difluorocyclohexyl)-6-(3,5-dimethyl-1H-pyrazol-1-yl)-4-((4-methoxybenzyl)oxy)pyridin-2-amine [0623] as an off-white solid (0.05 g). MS(M+1)+=443.2.

Step 2[0624]: A solution of N-(4,4-difluorocyclohexyl)-6-(3,5-dimethyl-1H-pyrazol-1-yl)-4-((4-methoxybenzyl)oxy)pyridin-2-amine [0623] (0.05 g, 0.11 mmol) in methanol (3 mL) was degassed with nitrogen for 5 min. Palladium on carbon (10%) (0.02 g) was added and the mixture was hydrogenated with hydrogen (63 psi) at rt for 2 h. The reaction mixture was filtered through celite, filtrate was concentrated under reduced pressure to afford crude product which was purified by column chromatography using 40% ethyl acetate in pet ether as solvent to afford of 2-((4,4-difluorocyclohexyl)amino)-6-(3,5-dimethyl-1H-pyrazol-1-yl)pyridin-4-ol [0624], Compound 276 as an white solid (0.012 g). MS(M+1)+=323.1, 1H NMR (400 MHz, Chloroform-d) δ 6.76 (d, J=1.8 Hz, 1H), 6.00 (s, 1H), 5.74 (d, J=1.8 Hz, 1H), 4.49 (s, 1H), 3.72 (s, 1H), 2.55 (s, 3H), 2.29 (s, 3H), 2.11 (td, J=13.7, 11.4, 5.5 Hz, 5H), 1.87 (d, J=27.4 Hz, 2H), 1.65-1.53 (m, 2H).

Example 241

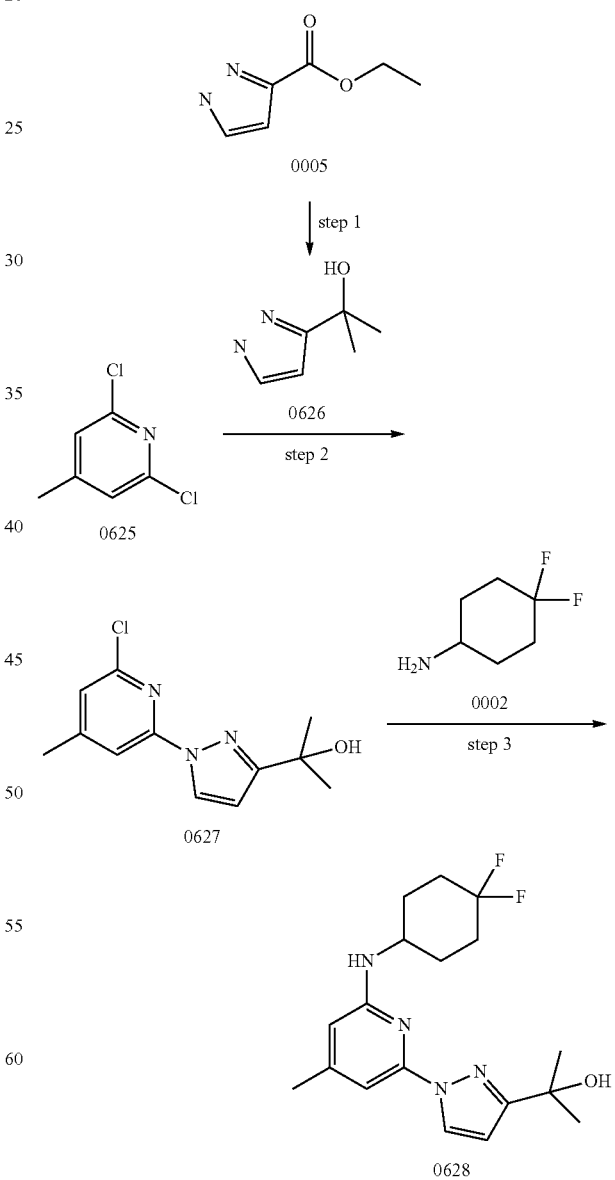

Step 1[0626]: To a stirred solution of ethyl 1h-pyrazole-3-carboxylate [0005] (1 g, 6.99 mmol) in tetrahydrofuran (15 mL), methyl magnesium bromide (2.5 g, 2097 mmol) was added at 0° C. The reaction mixture was stirred at rt for 16 h. The reaction mixture was quenched with saturated solution of sodium bisulfate (15 mL), then the reaction mixture was filtered and separated the organic layer, then the aqueous was basified with saturated solution of sodium bicarbonate (20 mL), and then extracted with ethyl acetate (2×200 mL). The combined organic layer was washed with brine solution (25 mL), dried over sodium sulfate, filtered and concentrated under reduced pressure to afford 0.650 g of 2-(1h-pyrazol-3-yl)propan-2-ol [0626] as colorless gum. MS(M+1)+=127.2.

Step 2[0627]: This procedure is similar to Step 1[0270] in example 98. 0.5 g of 2,6-dichloro-4-methyl pyridine [0625] and 0.77 g of 2-(1H-pyrazol-3-yl)propan-2-ol [0626] gave 0.6 g of 2-(1-(6-chloro-4-methylpyridin-2-yl)-1H-pyrazol-3-yl)propan-2-ol [0627] as a yellow liquid. MS(M+1)+=252.0.

Step 3[0628]: This procedure is similar to Step 1[0570] in example 212. 0.35 g of 2-(1-(6-chloro-4-methylpyridin-2-yl)-1H-pyrazol-3-yl)propan-2-ol [0627] and 0.47 g of 4,4-difluorocyclohexylamine hydrochloride [0628] gave 0.06 g of 2-(1-(6-((4,4-difluorocyclohexyl)amino)-4-methylpyridin-2-yl)-1H-pyrazol-3-yl)propan-2-ol [0628], Compound 265 as white solid. MS(M+1)+=351.0, $^1$H NMR (400 MHz, DMSO-d6) δ 8.39 (d, J=2.5 Hz, 1H), 6.80 (s, 1H), 6.66 (d, J=7.4 Hz, 1H), 6.45 (d, J=2.6 Hz, 1H), 6.18 (s, 1H), 5.02 (s, 1H), 3.97 (bs, 1H), 2.22 (s, 3H), 2.13-1.87 (m, 6H), 1.68-1.50 (m 2H), 1.47 (s, 6H).

Example 242

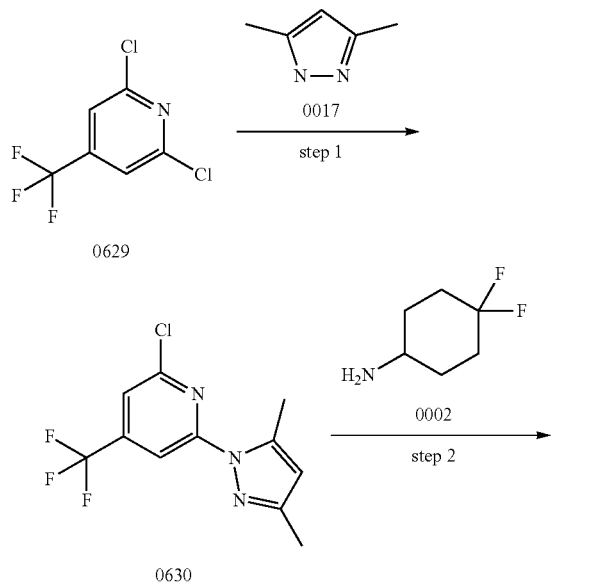

Step 1[0630]: This procedure is similar to Step 1[0270] in example 98. 0.5 g of 2,6-dichloro-4-(trifluoromethyl)pyridine [0629] and 0.24 g of 3,5-dimethyl pyrazole [0630] gave 0.48 g (crude) of 4-(tert-butyl)-2-chloro-6-(3,5-dimethyl-1H-pyrazol-1-yl)pyridine [0603] as a yellow liquid. MS(M+1)+=276.2. This was taken as such tonext step.

Step 2[0631] NSSy5088: This procedure is similar to Step 3[0580] in example 216. 0.48 g (crude) of 4-(tert-butyl)-2-chloro-6-(3,5-dimethyl-1H-pyrazol-1-yl)pyridine [0630] and 0.35 g of 4,4-difluorocyclohexylamine hydrochloride [0002] gave 0.28 g of N-(4,4-difluorocyclohexyl)-6-(3,5-dimethyl-1H-pyrazol-1-yl)-4-(trifluoromethyl)pyridin-2-amine [0631], Compound 170 as a white solid. MS(M+1)+=375.2, $^1$H NMR (400 MHz, DMSO-d6) δ 7.39 (d, J=7.5 Hz, 1H), 7.07 (s, 1H), 6.62 (s, 1H), 6.11 (s, 1H), 3.93 (bs, 1H), 2.63 (s, 3H), 2.19 (s, 3H), 2.11-1.86 (m, 6H), 1.50-1.58 (m, 2H).

Example 243

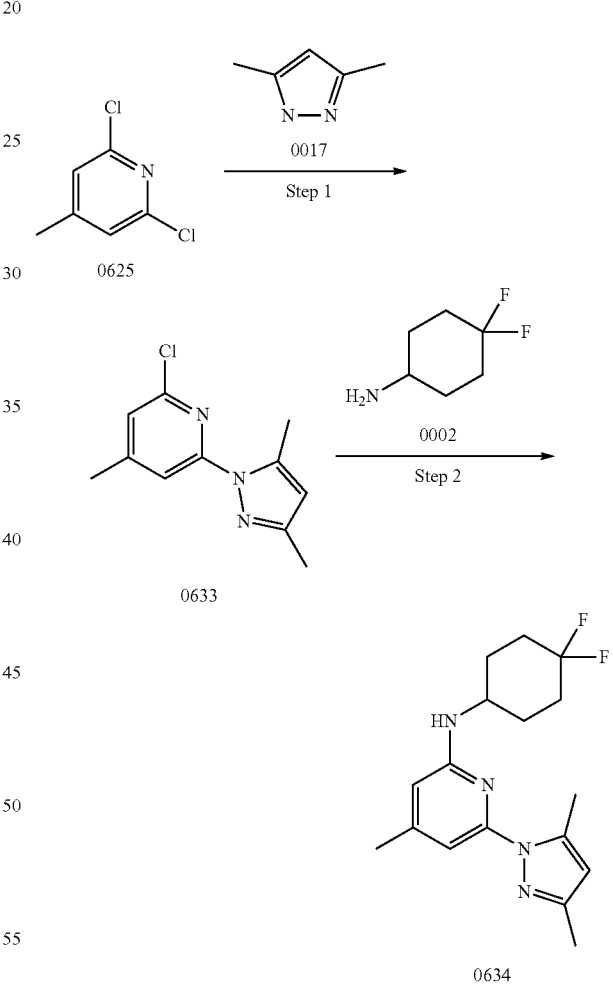

Step 1[0633]: This procedure is similar to Step 1[0270] in example 98. 1 g of 2,6-dichloro-4-methyl pyridine [0625] and 0.65 g of 3,5-dimethyl pyrazole [0017] gave 0.6 g of 2-chloro-6-(3,5-dimethyl-1H-pyrazol-1-yl)-4-methylpyridine [0633] as white solid. MS(M+1)+=222.0.

Step 2[0634]. This procedure is similar to Step 3[0580] in example 216. 0.2 g of 2-chloro-6-(3,5-dimethyl-1H-pyrazol-1-yl)-4-methylpyridine [0633] and 0.46 g of 4,4-difluorocyclohexylamine hydrochloride [0002] gave 0.05 g of N-(4, 4-difluorocyclohexyl)-6-(3,5-dimethyl-1H-pyrazol-1-yl)-4-methylpyridin-2-amine [0634], Compound 159 as a white solid. MS(M+1)+=321.2, ¹H NMR (400 MHz, DMSO-d6) δ 6.74 (s, 1H), 6.63 (d, J=7.5 Hz, 1H), 6.16 (s, 1H), 6.01 (s, 1H), 3.86 (bs, 1H), 2.56 (s, 3H), 2.17 (s, 3H), 2.15 (s, 3H), 2.15-2.00 (m, 2H), 1.99-1.86 (m, 4H), 1.58-1.45 (m, 2H).

Example 245

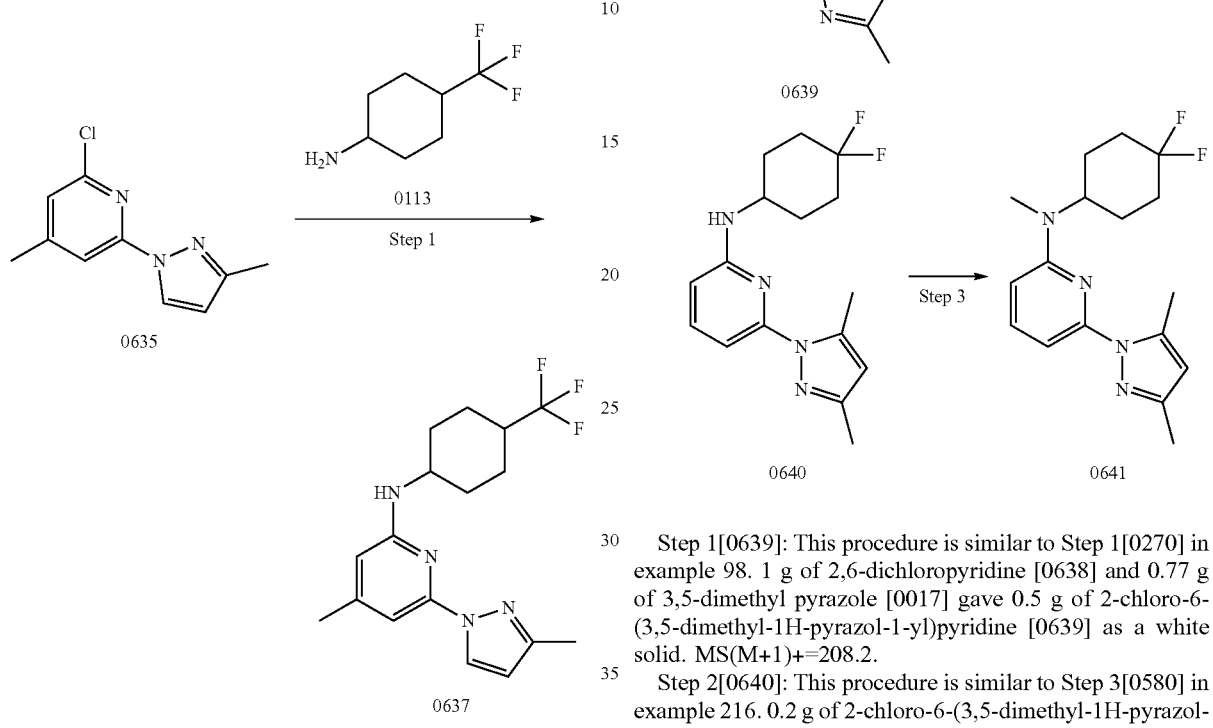

Step 1[0637]: The procedure is similar to Step 1[0570] in example 212. 0.2 g of 2-chloro-4-methyl-6-(3-methyl-1H-pyrazol-1-yl)pyridine [0635] and 0.3 g of 4-(trifluoromethyl)cyclohexanamine [0113] gave 0.04 g of 4-methyl-6-(3-methyl-1H-pyrazol-1-yl)-N-(4-(trifluoromethyl)cyclohexyl)pyridin-2-amine [0637], Compound 180 as an off-white solid. MS(M+1)+=339.2, ¹H NMR (400 MHz, DMSO-d6) δ 8.36 (d, J=2.5 Hz, 1H), 6.76 (s, 1H), 6.56 (d, J=7.6 Hz, 1H), 6.26 (d, J=2.5 Hz, 1H), 6.14 (s, 1H), 3.76-3.64 (m, 1H), 2.28 (s, 3H), 2.24 (s, 3H), 2.10 (d, J=10.8 Hz, 2H), 1.94 (d, J=12 Hz, 2H), 1.45 (qd, J=12.9, 3.3 Hz, 2H), 1.23 (qd, J=12.9, 3.4 Hz, 2H).

Example 246

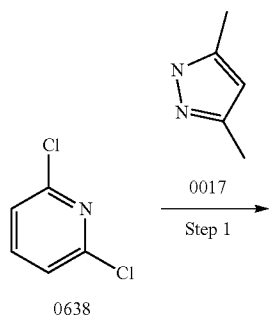

Step 1[0639]: This procedure is similar to Step 1[0270] in example 98. 1 g of 2,6-dichloropyridine [0638] and 0.77 g of 3,5-dimethyl pyrazole [0017] gave 0.5 g of 2-chloro-6-(3,5-dimethyl-1H-pyrazol-1-yl)pyridine [0639] as a white solid. MS(M+1)+=208.2.

Step 2[0640]: This procedure is similar to Step 3[0580] in example 216. 0.2 g of 2-chloro-6-(3,5-dimethyl-1H-pyrazol-1-yl)pyridine [0639] and 0.19 g of 4,4-difluorocyclohexylamine hydrochloride [0002] gave 0.06 g of N-(4,4-difluorocyclohexyl)-6-(3,5-dimethyl-1H-pyrazol-1-yl)pyridin-2-amine [0640], Compound 154 as a white solid. MS(M+1)+=307.2, ¹H-NMR (400 MHz, DMSO-d6): δ 7.46 (t, J=7.96 Hz, 1H), 7.27 (bs, 1H), 6.77 (d, J=7.52 Hz, 1H), 6.35 (d, J=8.16 Hz, 1H), 6.04 (s, 1H), 3.89-3.88 (m, 1H), 2.59 (s, 3H), 2.17 (s, 3H), 2.04-1.99 (m, 2H), 1.91-1.90 (m, 4H), 1.58-1.52 (m, 2H).

Step 3[0641]: To a solution of N-(4,4-difluorocyclohexyl)-6-(3,5-dimethyl-1H-pyrazol-1-yl)pyridin-2-amine [0640] (0.15 g, 0.48 mmol) in tetrahydrofuran (10 mL) was added Lithium bis(trimethylsilyl)amide (0.16 g, 0.97 mmol) drop wise at 0° C. Then the reaction mixture was stirred at rt for 30 min, then iodomethane (0.13 g, 0.97 mmol) was added to the reaction mixture at 0° C. and stirred at rt. After 16 h, the reaction mixture was quenched with ice and extracted with ethyl acetate (2×25 mL). The combined organic layer was washed with brine (10 mL), dried over anhydrous sodium sulfate, filtered and concentrated under reduced pressure to afford a yellow liquid which was purified in the Releris flash system instrument using ethyl acetate in hexane as solvent in 12 g column, to afford of N-(4,4-difluorocyclohexyl)-6-(3,5-dimethyl-1H-pyrazol-1-yl)-N-methylpyridin-2-amine [0641], Compound 166 as a white solid (0.14 g). MS(M+1)+=321.2, ¹H NMR (400 MHz, DMSO-d6) δ 7.62 (t, J=8.1 Hz, 1H), 6.99 (d, J=7.7 Hz, 1H), 6.55 (d, J=8.5 Hz, 1H), 6.06 (s, 1H), 4.52 (bs, 1H), 2.86 (s, 3H), 2.62 (s, 3H), 2.18 (s, 3H), 2.13-1.88 (m, 4H), 1.86-1.63 (m, 4H).

Example 247

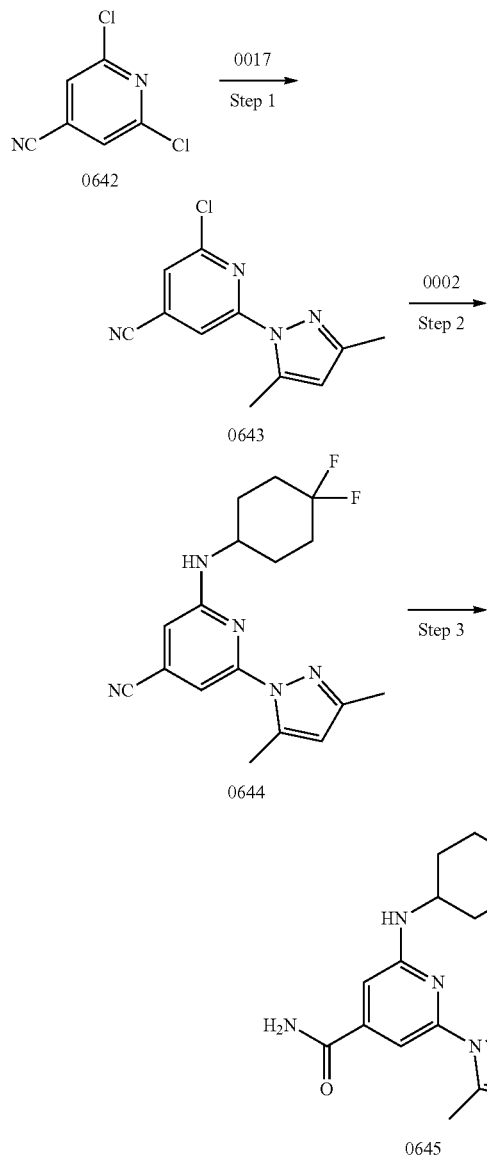

Step 1 [0643]: To a stirred suspension of 2,6-dichloroisonicotinonitrile [0642] (2 g, 11.560 mmol), 3,5-dimethyl pyrazole [0017] (1.222 g, 12.717 mmol) and cesium carbonate (5.650 g, 17.341 mmol) in acetonitrile was heated at 75° C. for 20 h. The reaction mixture was filtered, washed with ethyl acetate. The combined filtrate was concentrated under reduced pressure to afford crude which was purified by column chromatography using 5% ethyl acetate in hexane as eluent to afford 1 g of 2-chloro-6-(3,5-dimethyl-1H-pyrazol-1-yl)isonicotinonitrile [0643] as a white solid. MS(M+1)+=233.1

Step 2[0644]: This procedure is similar to Step 3[0580] in example 216. 0.3 g of 2-chloro-6-(3,5-dimethyl-1H-pyrazol-1-yl)isonicotinonitrile [0643] and 0.26 g of 4,4-difluorocyclohexylamine hydrochloride [0002] gave 0.12 g of 2-((4,4-difluorocyclohexyl)amino)-6-(3,5-dimethyl-1H-pyrazol-1-yl)isonicotinonitrile [0644], Compound 174 as off-white solid. MS(M+1)+=322.3, ¹H-NMR (400 MHz, CDCl3): δ 7.39 (d, J=1.20 Hz, 1H), 6.39 (d, J=0.80 Hz, 1H), 6.01 (d, J=Hz, 1H), 4.62 (d, J=7.60 Hz, 1H), 3.86 (d, J=7.20 Hz, 2H), 2.64 (s, 3H), 2.29 (s, 3H), 1.97-1.90 (m, 4H), 1.89-1.84 (m, 2H), 1.83-1.65 (m, 1H).

Step 3[0645] NSSy5101. To a solution of 2-((4,4-difluorocyclohexyl)amino)-6-(3,5-dimethyl-1H-pyrazol-1-yl)isonicotinonitrile [0644] (0.1 g, 0.30 mmol) in tetrahydrofuran:water (1:1) was added potassium hydroxide (0.084 g, 1.50 mmol) and the reaction mixture was heated at 60° C. After 8 h, the reaction mixture was concentrated under reduced pressure and the residue was diluted with water and extracted with chloroform. The combined organic layer was washed with brine and dried over anhydrous sodium sulfate, filtered and concentrated under reduced pressure to afford brown oil. The crude was purified in the Reveleris flash system instrument using methanol in chloroform as solvent in 12 g column to afford 0.021 g 2-((4,4-difluorocyclohexyl)amino)-6-(3,5-dimethyl-1H-pyrazol-1-yl)isonicotinamide [0645], Compound 175 as orange solid. MS(M+1)+=350.2, 1H NMR (400 MHz, DMSO-d6) δ 8.06 (s, 1H), 7.48 (s, 1H), 7.24 (d, J=1.2 Hz, 1H), 6.99 (d, J=7.7 Hz, 1H), 6.73 (d, J=1.2 Hz, 1H), 6.06 (s, 1H), 3.90 (d, J=9.2 Hz, 1H), 2.59 (s, 3H), 2.18 (s, 3H), 2.12-1.74 (m, 6H), 1.74-1.30 (m, 2H).

Example 248

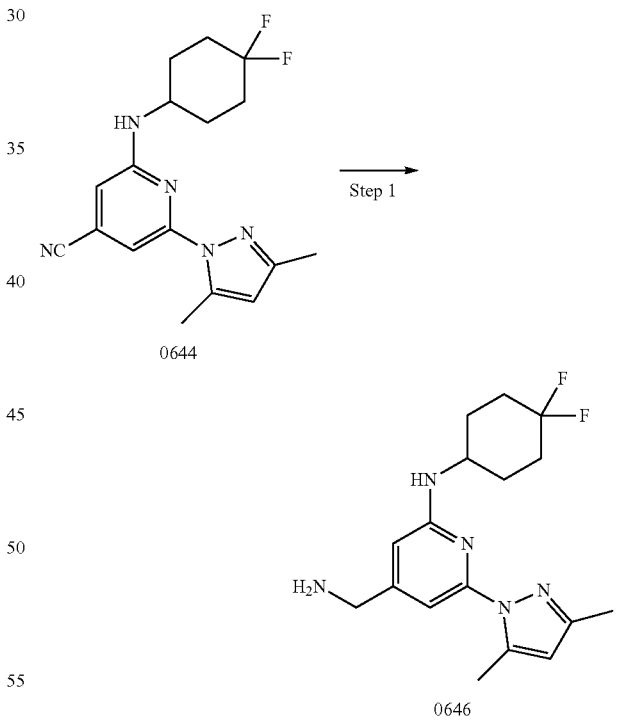

Step 1[0646]: This procedure is similar to Step 2[0019] in example 4. 0.1 g of 2-((4,4-difluorocyclohexyl)amino)-6-(3,5-dimethyl-1H-pyrazol-1-yl)isonicotinonitrile [0644] gave 0.026 g of 4-(aminomethyl)-N-(4,4-difluorocyclohexyl)-6-(3,5-dimethyl-1H-pyrazol-1-yl)pyridin-2-amine [0646], Compound 195 as brown solid. MS(M+1)+=336.2, ¹H NMR (400 MHz, DMSO-d6) δ 8.34 (s, 3H), 7.05 (s, 1H), 6.36 (s, 1H), 6.08 (s, 1H), 3.94 (q, J=5.9 Hz, 3H), 2.60 (s, 3H), 2.18 (s, 3H), 2.10-1.86 (m, 6H), 1.63-1.47 (m, 2H).

Example 249

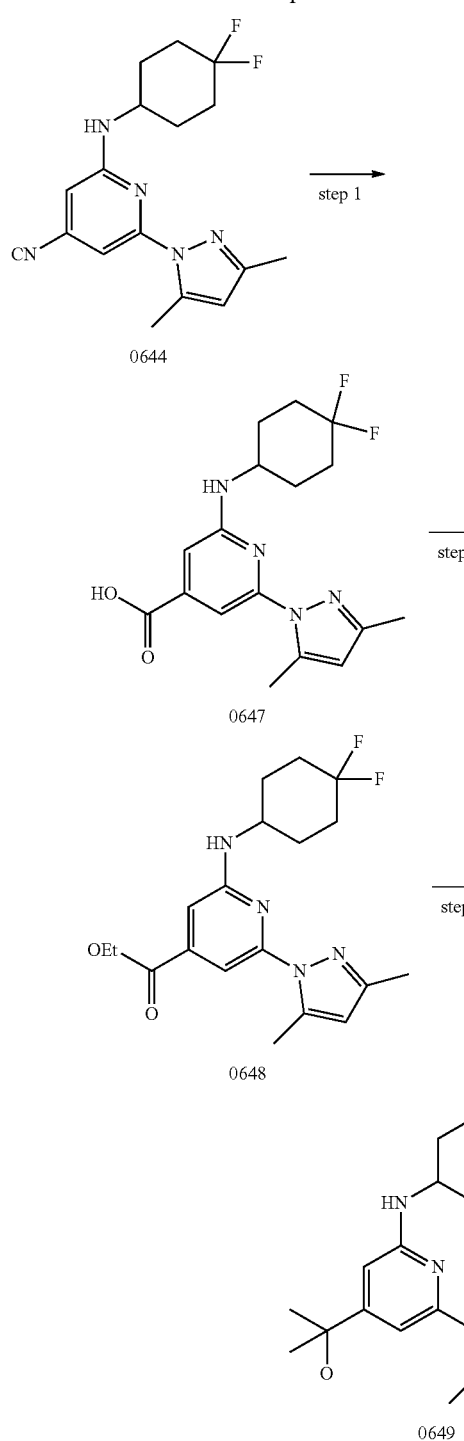

Step 1[0647]: To a suspension of 2-((4,4-difluorocyclohexyl)amino)-6-(3,5-dimethyl-1H-pyrazol-1-yl)isonicotinonitrile [0647] (0.5 g, 1.51 mmol) in conc. hydrochloric acid (10 mL) was heated at 100° C. for 24 h. The reaction mixture was diluted with water and extracted with chloroform (3×50 mL). The combined organic layer was dried over anhydrous sodium sulfate, filtered and concentrated under reduced pressure to afford crude product which was purified by column chromatography using 2% methanol in chloroform as eluent to obtain 2-((4,4-difluorocyclohexyl)amino)-6-(3,5-dimethyl-1H-pyrazol-1-yl)isonicotinic acid [0647] (0.25 g, 47%) as off-white solid. MS(M+1)+=351.2.

Step 2[0648]: To a stirred solution of 2-((4,4-difluorocyclohexyl)amino)-6-(3,5-dimethyl-1H-pyrazol-1-yl)isonicotinic acid [0647] (0.25 g, 0.714 mmol) in ethanol (10 mL) was added conc. sulfuric acid and the mixture was heated at 80° C. for 18 h. The reaction mixture was concentrated under reduced pressure to remove ethanol. The residue was basified with aq. sodium bicarbonate solution. The product was extracted with chloroform (3×25 mL). The combined organic layer was dried over anhydrous sodium sulfate, filtered and concentrated under reduced pressure to afford ethyl 2-((4,4-difluorocyclohexyl)amino)-6-(3,5-dimethyl-1H-pyrazol-1-yl)isonicotinate [0648] (0.15 g, 55%) as an off-white solid. MS(M+1)+=378.4.

Step 3[0649]: This procedure is similar to Step 1[0529] in example 195. 0.2 g of ethyl 2-((4,4-difluorocyclohexyl)amino)-6-(3,5-dimethyl-1H-pyrazol-1-yl)isonicotinate [0648] gave 0.06 g of 2-(2-((4,4-difluorocyclohexyl)amino)-6-(3,5-dimethyl-1H-pyrazol-1-yl)pyridin-4-yl)propan-2-ol [0649], Compound 206 as an off-white solid. MS(M+1)$^+$= 365.2, $^1$H NMR (400 MHz, Chloroform-d) δ 7.12 (d, J=1.3 Hz, 1H), 6.44 (d, J=1.3 Hz, 1H), 5.98 (s, 1H), 3.89 (s, 1H), 2.61 (s, 3H), 2.31 (s, 3H), 2.24-2.05 (m, 4H), 2.03-1.75 (m, 4H), 1.64-1.45 (m, 8H).

Example 250

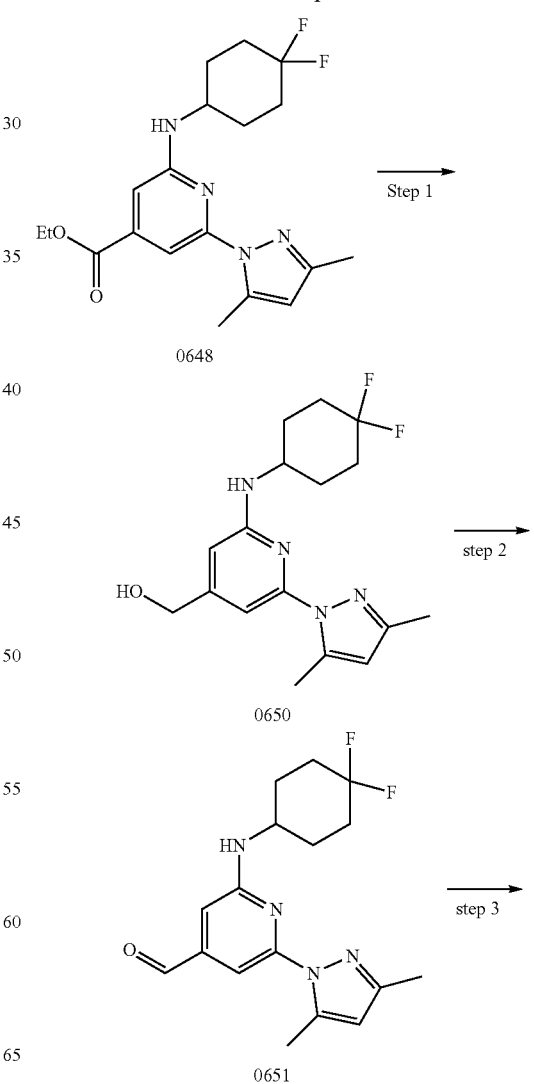

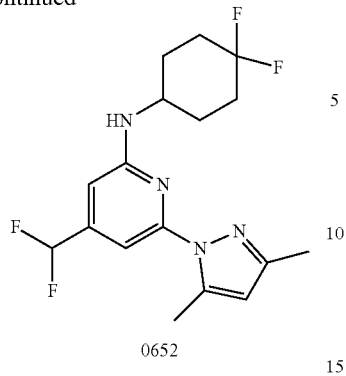

0652

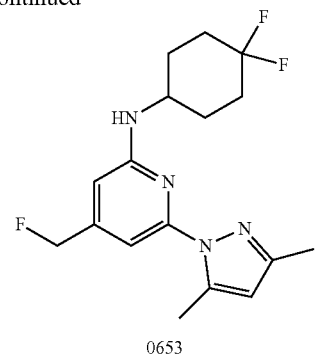

0653

Step 1 [0650]: The procedure is similar to step 2[0019] in example 4 [at −78° C.]. 0.1 g of ethyl 2-((4,4-difluorocyclohexyl)amino)-6-(3,5-dimethyl-1H-pyrazol-1-yl)isonicotinate [0648] gave 0.055 g of (2-((4,4-difluorocyclohexyl)amino)-6-(3,5-dimethyl-1H-pyrazol-1-yl)pyridin-4-yl)methanol [0650], Compound 185 as an off-white solid. MS(M+1)⁺=337.4, ¹H NMR (400 MHz, DMSO-d6) δ 6.85 (s, 1H), 6.73 (d, J=7.6 Hz, 1H), 6.36 (s, 1H), 6.03 (s, 1H), 5.29 (s, 1H), 4.42 (s, 2H), 3.89 (d, J=9.1 Hz, 1H), 2.58 (s, 3H), 2.17 (s, 3H), 2.13-1.86 (m, 6H), 1.54 (q, J=11.6, 10.9 Hz, 2H).

Step 2[0651]: This procedure is similar to Step 3[0444] in example 166. 0.25 g of (2-((4,4-difluorocyclohexyl)amino)-6-(3,5-dimethyl-1H-pyrazol-1-yl)pyridin-4-yl)methanol [0650] gave 0.1 g of 2-((4,4-difluorocyclohexyl)amino)-6-(3,5-dimethyl-1H-pyrazol-1-yl)isonicotinaldehyde [0651] as an off-white solid. MS(M+1)+=335.2.

Step 3[0652]: This procedure is similar to Step 3[0012] in example 2. 0.1 g of 2-((4,4-difluorocyclohexyl)amino)-6-(3,5-dimethyl-1H-pyrazol-1-yl)isonicotinaldehyde [0651] gave 0.04 g of N-(4,4-difluorocyclohexyl)-4-(difluoromethyl)-6-(3,5-dimethyl-1H-pyrazol-1-yl)pyridin-2-amine [0652], Compound 213 as an off-white solid. MS(M+1)⁺=357.1, ¹H NMR (400 MHz, Chloroform-d) δ 7.25 (s, 1H), 6.41 (s, 1H), 6.36 (s, 1H), 6.01 (s, 1H), 4.53 (s, 1H), 3.90 (s, 1H), 2.65 (s, 3H), 2.31 (s, 3H), 2.23-2.11 (m, 4H), 2.00-1.81 (m, 2H), 1.75-1.55 (m, 2H).

Example 251

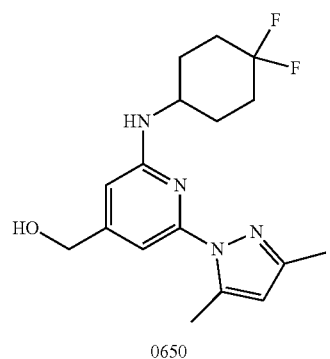

0650 step 1

Step 1[0653]: This procedure is similar to Step 3[0012] in example 2. 0.25 g of (2-((4,4-difluoro cyclohexyl)amino)-6-(3,5-dimethyl-1H-pyrazol-1-yl)pyridin-4-yl)methanol [0650] gave 0.01 g of N-(4,4-difluorocyclohexyl)-6-(3,5-dimethyl-1H-pyrazol-1-yl)-4-(fluoromethyl)pyridin-2-amine [0653], Compound 229 as brown solid. MS(M+1)⁺= 339.1, ¹H NMR (400 MHz, Chloroform-d) δ 6.87 (s, 1H), 6.45 (s, 1H), 6.09 (s, 1H), 5.48 (s, 1H), 5.36 (s, 1H), 3.81 (s, 2H), 2.62 (s, 3H), 2.38 (s, 3H), 2.23 (bs, 2H), 2.11 (bs, 2H), 1.94 (s, 2H), 1.79 (bs, 2H).

Example 252

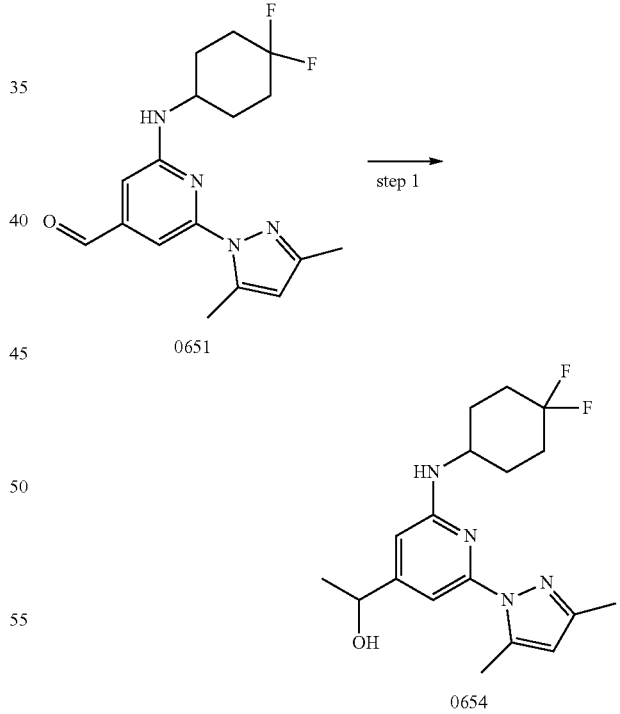

0651 step 1

0654

Step 1[0654]: This procedure is similar to Step 2[0049] in example 10. 0.1 g of 2-((4,4-difluorocyclohexyl)amino)-6-(3,5-dimethyl-1H-pyrazol-1-yl)isonicotinaldehyde [0651] gave 0.05 g of 1-(2-((4,4-difluorocyclohexyl)amino)-6-(3,5-dimethyl-1H-pyrazol-1-yl)pyridin-4-yl)ethan-1-ol [0654], Compound 207 as off-white solid. MS(M+1)⁺=351.1, ¹H NMR (400 MHz, Chloroform-d) δ 7.04 (s, 1H), 6.32 (s, 1H), 5.98 (s, 1H), 4.83 (q, J=6.5 Hz, 1H), 4.45 (s, 1H), 3.87 (s, 1H), 2.61 (s, 3H), 2.30 (s, 3H), 2.24-2.04 (m, 4H), 2.03-1.79 (m, 2H), 1.8-1.55 (m, 2H), 1.50 (d, J=6.5 Hz, 3H).

Example 253

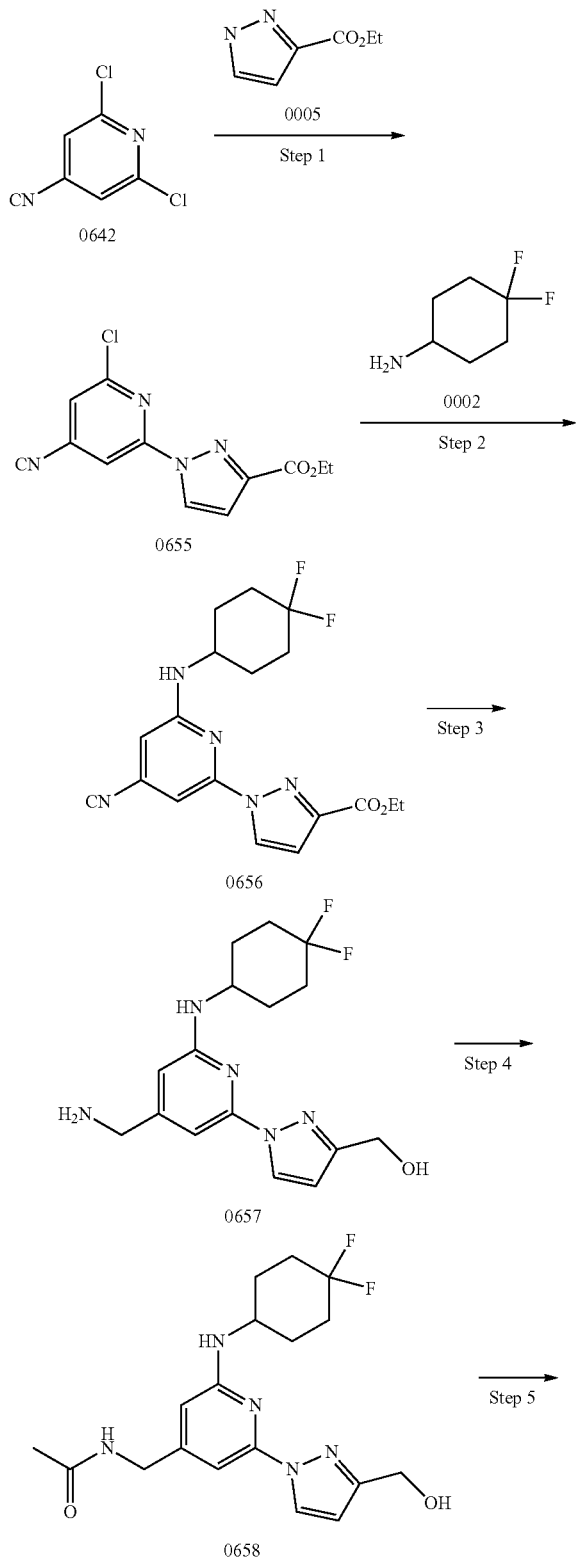

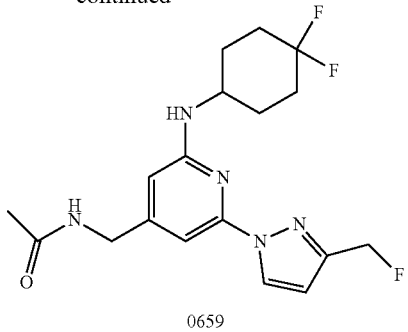

Step 1[0655]: The procedure is similar to step 1[0270] in example 98 [at 50° C. for 6 h]. 6 g of 2,6-dichloroisonicotinonitrile [0642] and 4.9 g of ethyl 1H-pyrazole-3-carboxylate [0005] gave 7.2 g of ethyl 1-(6-chloro-4-cyanopyridin-2-yl)-1H-pyrazole-3-carboxylate [0655] as an off-white solid. MS(M+1)+=277.0.

Step 2[0656]: The procedure is similar to step 3[0580] in example 216 (at 90° C. for 16 h). 2.5 g of ethyl 1-(6-chloro-4-cyanopyridin-2-yl)-1H-pyrazole-3-carboxylate [0655] and 1.5 g of 4,4-difluorocyclohexan-1-amine [0002] gave 1.74 g of ethyl 1-(4-cyano-6-((4,4-difluorocyclohexyl)amino)pyridin-2-yl)-1H-pyrazole-3-carboxylate [0656] as a yellow solid. MS(M+1)+=376.4/377.3

Step 3[0657]: The procedure is similar to step 2[0019] in example 4. 1 g of ethyl 1-(4-cyano-6-((4,4-difluorocyclohexyl)amino)pyridin-2-yl)-1H-pyrazole-3-carboxylate [0656] gave 0.55 g of (1-(4-(aminomethyl)-6-((4,4-difluorocyclohexyl)amino)pyridin-2-yl)-1H-pyrazol-3-yl)methanol [0657] as a brownish solid. MS(M+1)+=338.2

Step 4[0658]: To a solution of (1-(4-(aminomethyl)-6-((4,4-difluorocyclohexyl)amino)pyridin-2-yl)-1H-pyrazol-3-yl)methanol [0657] (0.55 g, 1.63 mmol), in dichloromethane (15 mL) was added acetyl chloride (0.29 g, 4.07 mmol) in drop wise and followed by triethylamine (0.65 g, 6.52 mmol) at 0° C. After addition the reaction mixture was stirred at rt for 1 h. The reaction mixture was diluted with water (10 mL) and extracted with ethyl acetate (2×50 mL). The combined organic layer was washed with brine (10 mL), dried over sodium sulfate, filtered and concentrated under reduced pressure to afford crude product and which was dissolved in methanol:water(1:1) followed by addition of potassium carbonate (0.5 g, 1.18 mmol) and stirred at rt for 15 min. The reaction mixture was concentrated under reduced pressure to afford crude product and which was purified by column chromatography using 5% methanol in chloroform as solvent to afford of N-((2-((4,4-difluorocyclohexyl)amino)-6-(3-(hydroxymethyl)-1H-pyrazol-1-yl)pyridin-4-yl)methyl)acetamide [0658] as a brown solid (0.38 g). MS(M+1)+=380.2

Step 5[0659]: The procedure is similar to step 3[0012] in example 2. 0.38 g of N-((2-((4,4-difluorocyclohexyl)amino)-6-(3-(hydroxymethyl)-1H-pyrazol-1-yl)pyridin-4-yl)methyl)acetamide [0658] gave 0.038 g of N-((2-((4,4-difluorocyclohexyl)amino)-6-(3-(fluoromethyl)-1H-pyrazol-1-yl)pyridin-4-yl)methyl)acetamide [0659], Compound 312 as a white solid. MS(M+1)+=382.3, $^1$H NMR (400 MHz, DMSO-d6) δ 8.55 (d, J=2.5 Hz, 1H), 8.42 (t, J=6.1 Hz, 1H), 6.91 (s, 1H), 6.89 (s, 1H), 6.63 (s, 1H), 6.28 (s, 1H), 5.45 (d, JF=48 Hz, 2H), 4.16 (d, J=6.1 Hz, 2H), 4.01 (bs, 1H), 2.26-1.92 (m, 6H), 1.89 (s, 3H), 1.62-1.54 (m, 2H).

Example 254

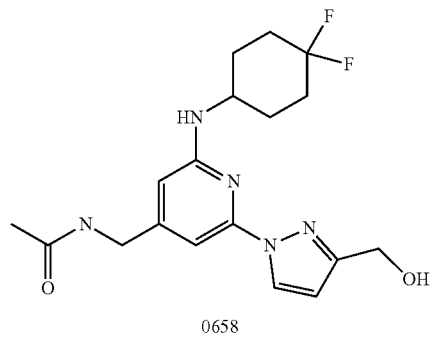

Example 255

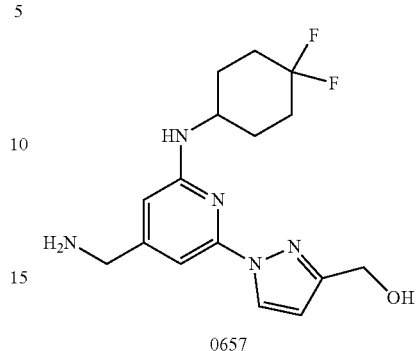

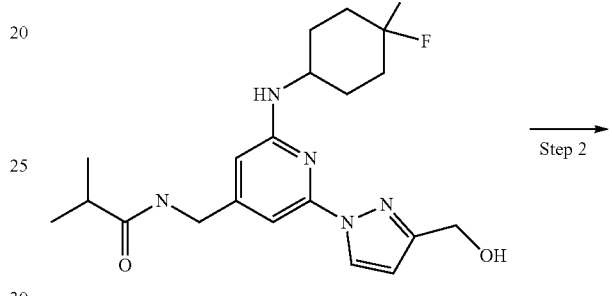

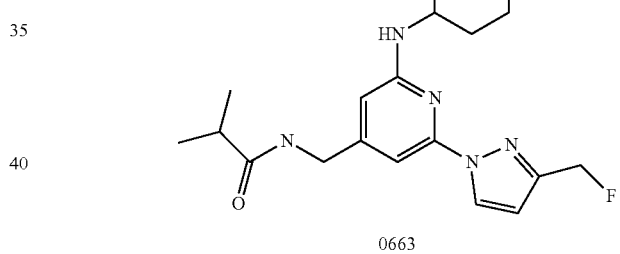

Step 1[0660]: The procedure is similar to step 3[0444] in example 166. 0.35 g of N-((2-((4,4-difluorocyclohexyl)amino)-6-(3-(hydroxymethyl)-1H-pyrazol-1-yl)pyridin-4-yl)methyl)acetamide [0658] gave 0.29 g of N-((2-((4,4-difluorocyclohexyl)amino)-6-(3-formyl-1H-pyrazol-1-yl)pyridin-4-yl)methyl)acetamide [0660] as a brown solid.

MS(M+1)+=378.39

Step 2 [0661]: The procedure is similar to step 3[0012] in example 2. 0.29 g of N-((2-((4,4-difluorocyclohexyl)amino)-6-(3-formyl-1H-pyrazol-1-yl)pyridin-4-yl)methyl)acetamide [0660] gave 0.058 g of N-((2-((4,4-difluorocyclohexyl)amino)-6-(3-(difluoromethyl)-1H-pyrazol-1-yl)pyridin-4-yl)methyl)acetamide [0661], Compound 301 as an yellowish solid. MS(M+1)$^+$=400.2, $^1$H-NMR (400 MHz, DMSO-d6): δ 8.64 (d, J=2.44 Hz, 1H), 8.42 (t, J=6.00 Hz, 1H), 7.11 (t, JF=54 Hz, 1H), 6.97 (s, 1H), 6.95 (s, 1H), 6.77 (d, J=2.48 Hz, 1H), 6.33 (s, 1H), 4.18 (d, J=6.00 Hz, 2H), 4.03 (bs, 1H), 2.06-1.98 (m, 6H), 1.90 (s, 3H), 1.59-1.56 (m, 2H).

Step 1[0662]: The procedure is similar to step 4[0658] in example 253. 0.5 g of (1-(4-(aminomethyl)-6-((4,4-difluorocyclohexyl)amino)pyridin-2-yl)-1H-pyrazol-3-yl)methanol [0657] gave 0.3 g of N-((2-((4,4-difluorocyclohexyl)amino)-6-(3-(hydroxymethyl)-1H-pyrazol-1-yl)pyridin-4-yl)methyl)isobutyramide [0662] as a brown solid. MS(M+1)+=408.2.

Step 2[0663]: The procedure is similar to step 3[0012] in example 2. 0.3 g of N-((2-((4,4-difluorocyclohexyl)amino)-6-(3-(hydroxymethyl)-1H-pyrazol-1-yl)pyridin-4-yl)methyl)isobutyramide [0662] gave 0.1 g of N-((2-((4,4-difluorocyclohexyl)amino)-6-(3-(fluoromethyl)-1H-pyrazol-1-yl)pyridin-4-yl)methyl)isobutyramide [0663], Compound 348 as an off-white solid. MS(M+1)+=410.2, 1H NMR (400 MHz, DMSO-d6): δ 8.56 (d, J=2.20 Hz, 1H), 8.32 (t, J=5.84 Hz, 1H), 6.91 (d, J=8.04 Hz, 2H), 6.64 (s, 1H), 6.26 (s, 1H), 5.49 (s, 1H), 5.37 (s, 1H), 4.18 (d, J=5.84 Hz, 2H), 4.02-4.01 (m, 1H), 2.45-2.43 (m, 2H), 2.07-1.97 (m, 6H), 1.56-1.54 (m, 2H), 1.06 (d, J=6.84 Hz, 6H).

Example 256

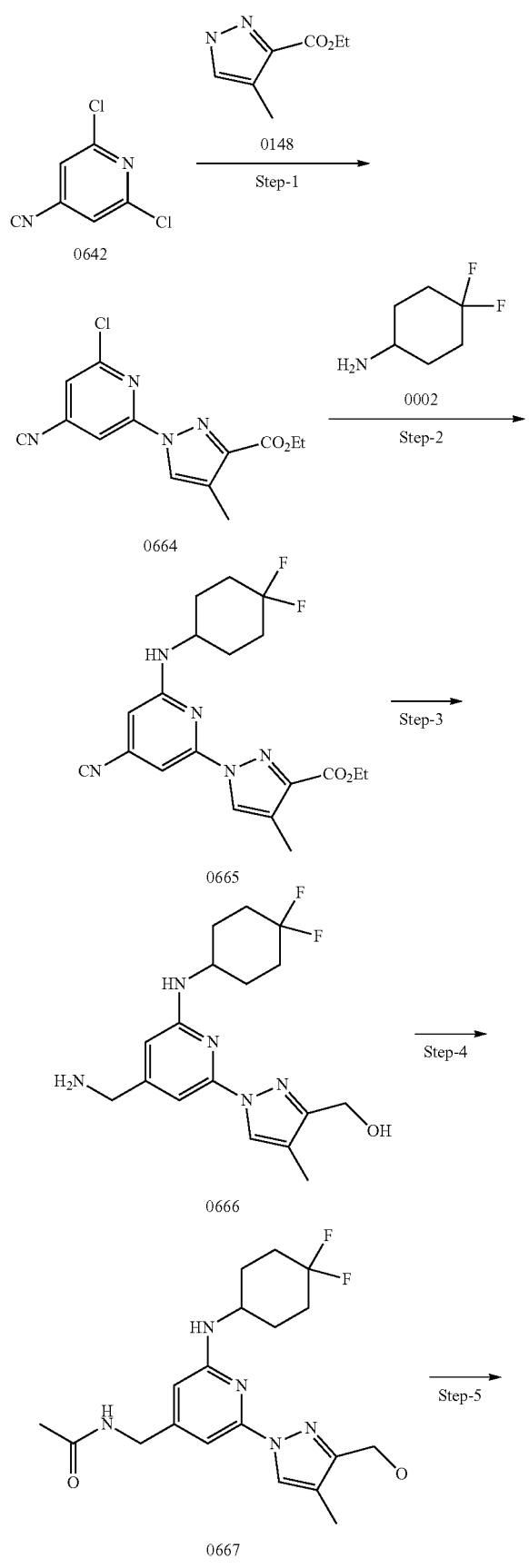

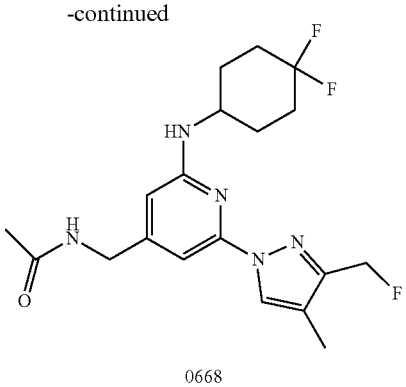

Step 1[0664]: The procedure is similar to step 1[0270] in example 98 [at rt for 16 h]. 10 g of 2,6-dichloroisonicotinonitrile [0642] gave 5 g of ethyl 1-(6-chloro-4-cyanopyridin-2-yl)-4-methyl-1H-pyrazole-3-carboxylate [0664] as a brownish solid. MS(M+1)+=291.0

Step 2[0665]: The procedure is similar to step 3[0580] in example 216 [at 80° C. for 12 h]. 5 g of ethyl 1-(6-chloro-4-cyanopyridin-2-yl)-4-methyl-1H-pyrazole-3-[0664] gave 1.3 g of ethyl 1-(4-cyano-6-((4,4-difluorocyclohexyl)amino)pyridin-2-yl)-4-methyl-1H-pyrazole-3-carboxylate [0665] as an off-white solid. MS(M+1)+=389.4

Step 3[0666]: The procedure is similar to step 2[0019] in example 4. 1 g of ethyl 1-(4-cyano-6-((4,4-difluorocyclohexyl)amino)pyridin-2-yl)-4-methyl-1H-pyrazole-3-carboxylate [0665] gave 0.61 g of (1-(4-(aminomethyl)-6-((4,4-difluorocyclohexyl)amino)pyridin-2-yl)-4-methyl-1H-pyrazol-3-yl)methanol [0666] as a brownish solid. MS(M+1)+=351.3.

Step 4[0667]: The procedure is similar to step 4[0658] in example 253. 0.7 g of (1-(4-(aminomethyl)-6-((4,4-difluorocyclohexyl)amino)pyridin-2-yl)-4-methyl-1H-pyrazol-3-yl)methanol [0666] gave 0.4 g of N-((2-((4,4-difluorocyclohexyl)amino)-6-(3-(hydroxymethyl)-4-methyl-1H-pyrazol-1-yl)pyridin-4-yl)methyl)acetamide [0667] as an off-white solid. MS(M+1)+=393.4.

Step 5[0668]. The procedure is similar to step 3[0012] in example 2. 0.15 g of N-((2-((4,4-difluorocyclohexyl)amino)-6-(3-(hydroxymethyl)-4-methyl-1H-pyrazol-1-yl)pyridin-4-yl)methyl)acetamide [0667] gave 0.12 g of N-((2-((4,4-difluorocyclohexyl)amino)-6-(3-(fluoromethyl)-4-methyl-1H-pyrazol-1-yl)pyridin-4-yl)methyl)acetamide. This was purified by column chromatography using 1% methanol in chloroform as solvent to afford 0.028 g of N-((2-((4,4-difluorocyclohexyl)amino)-6-(3-(fluoromethyl)-4-methyl-1H-pyrazol-1-yl)pyridin-4-yl)methyl)acetamide [0668], Compound 349 as an off-white solid. MS(M+1)+=396.2, $^1$H-NMR (400 MHz, DMSO-d6): δ 8.42 (t, J=5.88 Hz, 1H), 8.36 (s, 1H), 6.88 (s, 1H), 6.86 (s, 1H), 6.26 (s, 1H), 5.45 (d, JF=48 Hz, 2H), 4.16 (d, J=5.96 Hz, 2H), 4.02 (bs, 1H), 2.18 (s, 3H), 2.09-2.06 (m, 6H), 1.90 (s, 3H), 1.50-1.28 (m, 2H).

Example 257

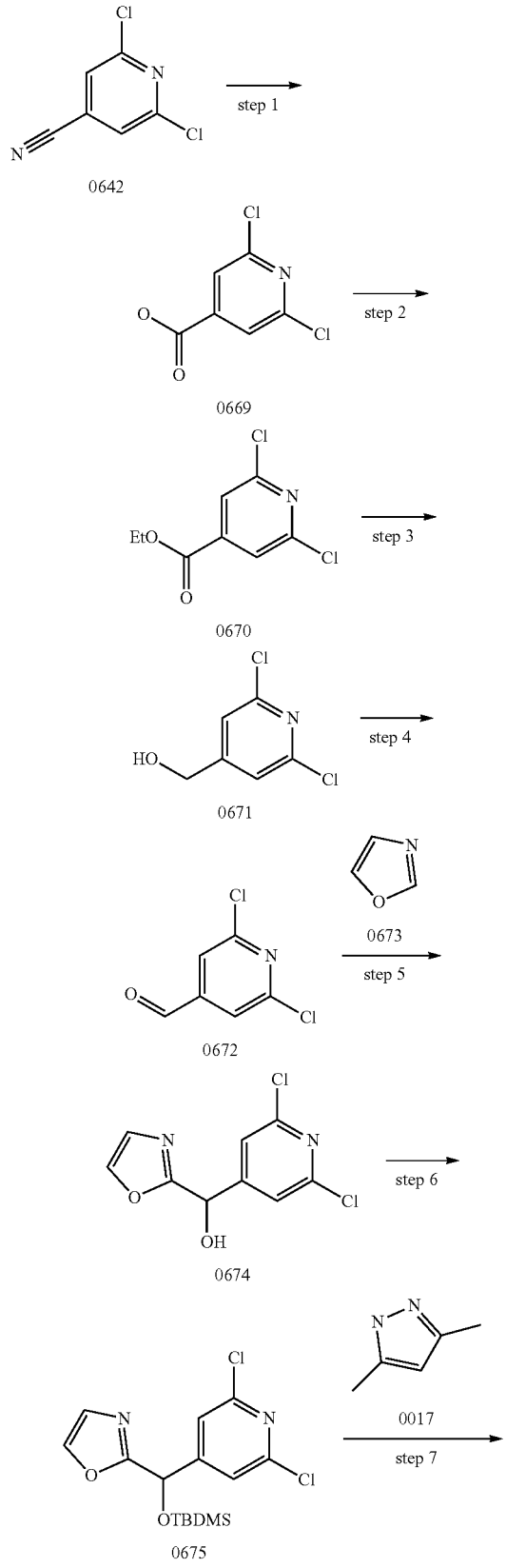

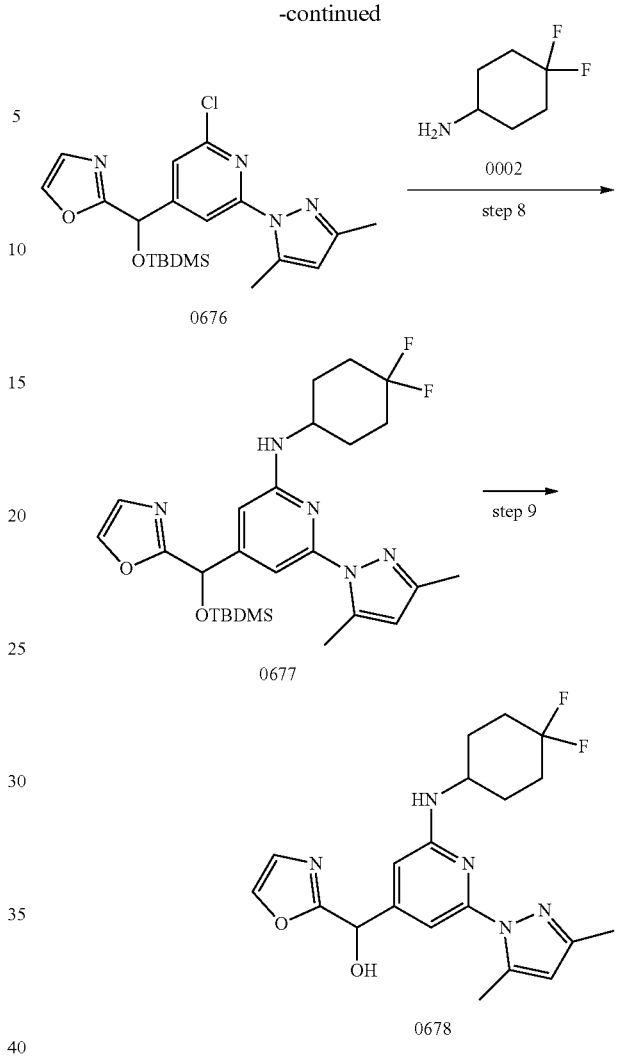

Step 1[0669]: To a stirred solution of 2,6-dichloroisonicotinonitrile [0642] (15.0 g, 86.70 mmol) was taken in concentrated hydro chloric acid (120 mL) and heated to 110° C. for 3 h. The reaction mixture was cooled to rt and diluted slowly with ice cold water (300 mL). White solid thus precipitated was filtered, washed with ice cold water (100 mL) and dried under reduced pressure to afford 2,6-dichloroisonicotinic acid [0669] as a white solid (14.18 g, 90%). MS(M+1)+=190.1.

Step 2 [0670]: To a stirred solution of 2,6-dichloroisonicotinic acid [0669] (14.18 g, 73.85 mmol) in ethanol (125 mL) was added concentrated sulfuric acid (0.2 mL, 3.7 mmol). The resultant reaction mixture was heated at 90° C. for 6 h. The reaction mixture was concentrated under reduced pressure. The residue was diluted with ice-water (50 mL) and neutralized with solid sodium bicarbonate. White solid was slowly precipitated out which was filtered, washed with water (200 mL) and dried under reduced pressure to afford ethyl 2,6-dichloroisonicotinate [0670] as a white solid (11.2 g, 68%). MS(M+1)+=221.0.

Step 3 [0671]: The procedure is similar to step 2[0011] in example 2. 14.1 g of ethyl 2,6-dichloroisonicotinate [0670] gave 11.1 g of (2,6-dichloropyridin-4-yl)methanol [0671] MS(M+1)+=179.0.

Step 4 [0672]: To a stirred solution of 2,6-dichloropyridin-4-yl)methanol [0671] (8.6 g, 48.31 mmol) in a mixture of dichloromethane (150 mL) and tetrahydrofuran (20 mL) was added manganese dioxide (21.01 g, 241.55 mmol) under inert atmosphere. The reaction mixture was stirred at rt for 20 h. The reaction mixture was filtered over celite and filtrate was concentrated under reduced pressure to afford crude product which was purified by column chromatography using 15% ethyl acetate in pet ether as eluent to afford 2,6-dichloroisonicotinaldehyde [0672] as a white solid (4.9 g). MS(M+1)+=177.0.

Step 5 [0674]: To a stirred solution of oxazole [0673] (2.69 mL, 42.0 mmol) in tetrahydrofuran (30 mL), was added n-butyl lithium (2.5M in hexane, 16.79 mL, 42.0 mmol) slowly under inert atmosphere at −78° C. and stirred at −78° C. for 30 mins. After 30 min to the reaction mixture was added a solution of 2,6-dichloroisonicotinaldehyde [0672] (4.1 g, 24.158 mmol) in tetrahydrofuran (20 mL) at −78° C. and stirring was continued for 40 min. The reaction mixture was quenched with saturated ammonium chloride solution (10 mL) at −78° C. The reaction mixture was extracted with ethyl acetate (2×50 mL). The combined organic layers were washed with brine solution (25 mL), dried over anhydrous sodium sulfate, filtered and concentrated under reduced pressure to afford crude product which was purified by column chromatography using 60% ethyl acetate in pet ether as eluent to afford (2,6-dichloropyridin-4-yl)(oxazol-2-yl)methanol [0674] as a white solid (5.7 g). MS(M+1)+=245.

Step 6 [0675]: To a stirred solution of (2,6-dichloropyridin-4-yl)(oxazol-2-yl)methanol [0674] (5.7 g, 23.25 mmol) in dichloromethane (60 mL) was added imidazole (2.37 g, 34.87 mmol) under inert atmosphere at 0° C. and stirred for 1 h. Then tert-butyldimethylsilyl chloride (4.18 g, 27.91 mmol) was added to the reaction mixture at 0° C. and reaction mixture was slowly warmed to rt for 16 h. The reaction mixture was quenched with water (10 mL) and product was extracted with ethyl acetate (2×75 mL). The combined organic layer was washed with brine solution (25 mL), dried over anhydrous sodium sulfate, filtered and concentrated under reduced pressure to afford crude product which was purified by column chromatography using 20% ethyl acetate in pet ether as eluent to afford 2-(((tert-butyldimethylsilyl)oxy)(2,6-dichloropyridin-4-yl)methyl) oxazole[0675] as colorless liquid (6 g). MS(M+1)+=360.2.

Step 7 [0676]: To a stirred solution of 3,5-dimethyl-1H-pyrazole [0017] (0.64 g, 6.67 mmol) in tetrahydrofuran (20 mL) was added sodium hydride (0.26 g, 6.67 mmol) under inert atmosphere at 0° C. and stirred at same 0° C. for 30 mins. Then to the resultant reaction mixture was added a solution of (2-(((tert-butyldimethylsilyl)oxy)(2,6-dichloropyridin-4-yl)methyl)oxazole) [0675] (2.0 g, 5.56 mmol) in tetrahydrofuran (10 mL) at 0° C. The reaction mixture was heated at 60° C. for 16 h. The reaction mixture was quenched with ice cold water (20 mL). The product was extracted with ethyl acetate (2×50 mL). The combined organic layer was washed with brine solution (20 mL), dried over anhydrous sodium sulfate, filtered and concentrated under reduced pressure to afford crude product which was purified by column chromatography using 35% ethyl acetate in pet ether as eluent to afford 2-(((tert-butyldimethylsilyl)oxy)(2-chloro-6-(3,5-dimethyl-1H-pyrazol-1-yl)pyridin-4-yl)methyl)oxazole [0676] as an off-white solid (0.57 g). MS(M+1)+=420.2.

Step 8 [0677]: The procedure is similar to step 3[0580] in example 216. 0.5 g of 2-(((tert-butyldimethylsilyl)oxy)(2-chloro-6-(3,5-dimethyl-1H-pyrazol-1-yl)pyridin-4-yl) methyl)oxazole [0676] and 4,4-difluorocyclohexylamine hydrochloride [0002] (0.245 g, 1.432 mmol) gave 0.28 g of 4-(((tert-butyldimethylsilyl)oxy)(oxazol-2-yl)methyl)-N-(4, 4-difluorocyclohexyl)-6-(3,5-dimethyl-1H-pyrazol-1-yl)pyridin-2-amine [0677] as an yellow solid. MS(M+1)+=518.6.

Step 9 [0678]: To a stirred solution of (((tert-butyldimethylsilyl)oxy)(oxazol-2-yl)methyl)-N-(4,4-difluorocyclohexyl)-6-(3,5-dimethyl-1H-pyrazol-1-yl)pyridin-2-amine [0677] (0.3 g, 0.58 mmol) in tetrahydrofuran (10 mL) was added tetrabutylammonium fluoride (1M solution in THF, 1.16 mL, 1.15 mmol) drop wise at 0° C. under inert atmosphere and the resultant reaction mixture was allowed to stir at rt for 1 h. The reaction mixture was quenched with ice cold water (5 mL) and product was extracted with ethyl acetate (2×20 mL). The combined organic layer was washed with brine solution (10 mL), dried over anhydrous sodium sulfate, filtered and concentrated under reduced pressure to afford crude product which was purified by column chromatography using ethyl acetate in pet ether as eluent to afford (2-((4,4-difluorocyclohexyl)amino)-6-(3,5-dimethyl-1H-pyrazol-1-yl)pyridin-4-yl)(oxazol-2-yl)methanol [0678], Compound 343 as an yellow solid (0.19 g).

MS(M+1)+=404.2, $^1$H-NMR (400 MHz, DMSO-d6): δ 8.29 (d, J=0.96 Hz, 1H), 7.99 (t, J=0.92 Hz, 1H), 6.92 (d, J=0.48 Hz, 1H), 6.81 (d, J=7.52 Hz, 1H), 6.44 (s, 1H), 6.03 (m, 2H), 5.52 (d, J=4.76 Hz, 1H), 3.89-3.88 (m, 1H), 2.57 (s, 3H), 2.16 (s, 3H), 2.08-1.99 (m, 2H), 1.96-1.93 (m, 4H), 1.57-1.49 (m, 2H),

Example 258

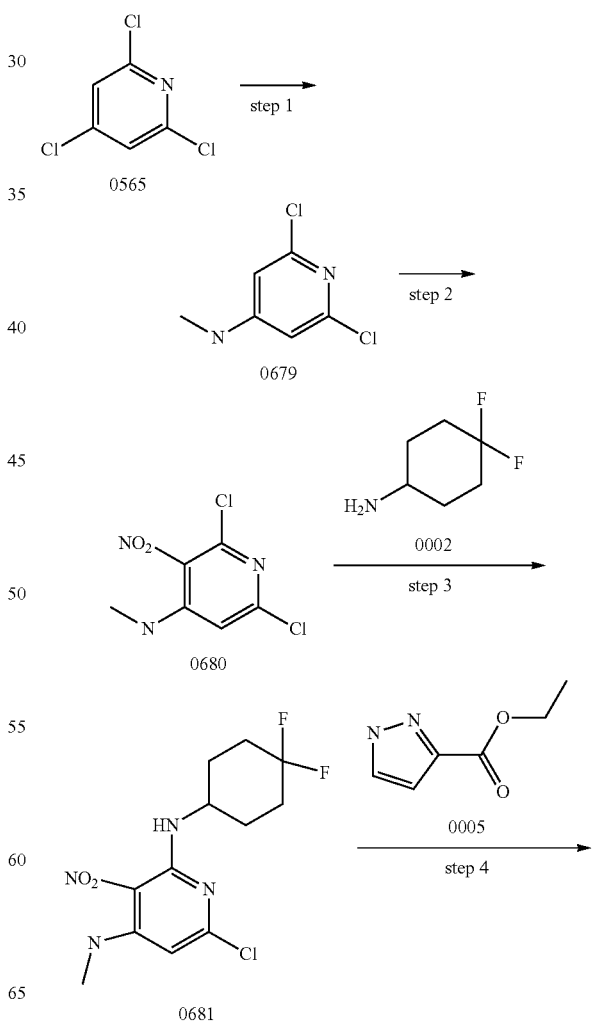

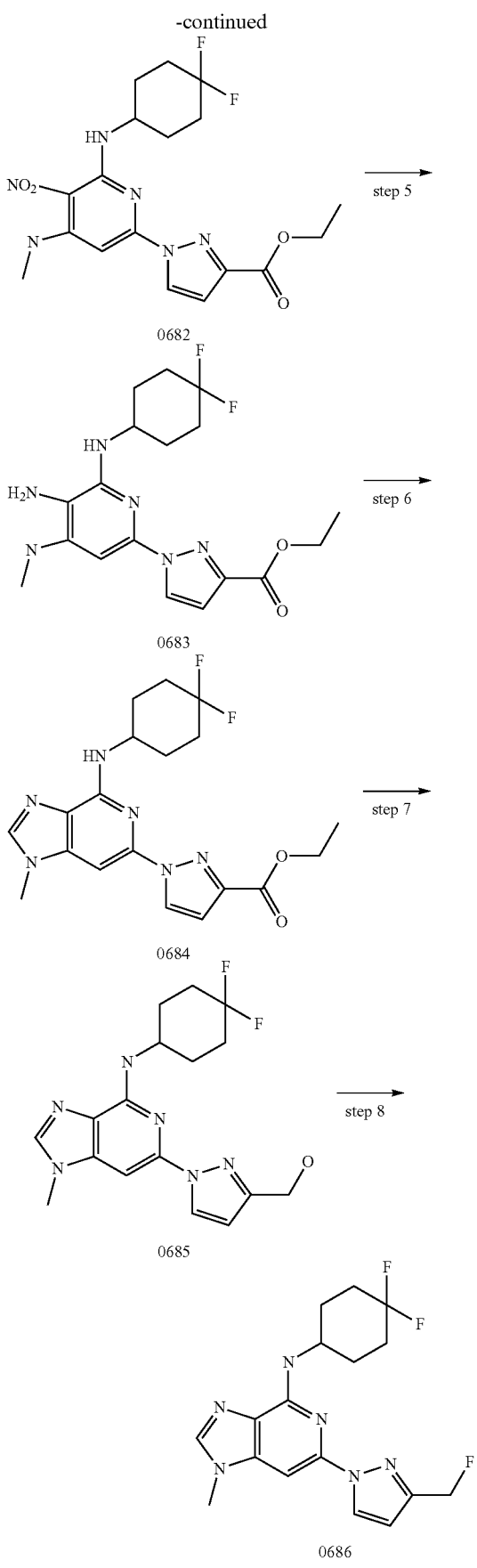

Step 1 [0679]: To a solution of 2,4,6-trichloropyridine [0565] (15 g, 82.22 mmol) in ethanol was added methylamine 30% solution in ethanol (15.32 g, 493.32 mmol) at 0° C. and the reaction mixture was stirred at rt in sealed tube. After 2 days, the reaction mixture was concentrated under reduced pressure and triturated with water, the solid formed was filtered and dried under vacuum to afford an off-white solid, which was triturated with dichloromethane and stirred for 10 min. The solid was filtered, washed with dichloromethane and dried under vacuum to afford 2,6-dichloro-N-methylpyridin-4-amine [0679] as a white solid. (7 g, 48% yield). MS(M+1)+=178.1.

Step 2 [0680]: To a solution of 2,6-dichloro-N-methylpyridin-4-amine [0679] (8 g, 45.189 mmol) in concentrated sulfuric acid (184 g, 1876.06 mmol) was added nitric acid (2.84 g, 45.189 mmol) slowly drop wise at 0° C. and the reaction mixture was stirred at same temperature. After 1 h, the reaction mixture was cooled to 0° C. and quenched with ice and stirred for 10 min. The solid formed was filtered, washed with water and dried under vacuum to afford 2,6-dichloro-N-methyl-3-nitropyridin-4-amine [0680] as a pale yellow solid. (9.5 g, 95% yield). MS(M+1)+=223.1.

Step 3 [0681]: To a suspension of sodium hydride (1.80 g, 45.0388 mmol) in tetrahydrofuran was added 4,4-difluorocyclohexylamine hydrochloride [0002] (3.86 g, 22.519 mmol) at 0° C. and the reaction mixture was stirred at rt for 30 min. Then 2,6-dichloro-N-methyl-3-nitropyridin-4-amine [0680] (5 g, 22.519 mmol) was added to the reaction mixture at 0° C. and the reaction mixture was stirred at rt. After 72 h, the reaction mixture was quenched with ice and stirred for 10 min. The solid formed was filtered and dried under vacuum to afford a yellow solid, which was purified in the Reveleris flash system instrument using ethyl acetate in hexane followed by methanol in chloroform as solvent in 24 g column to afford 6-chloro-N2-(4,4-difluorocyclohexyl)-N4-methyl-3-nitropyridine-2,4-diamine [0681] as an yellow solid, 2.5 g. MS(M+1)+=321.2.

Step 4 [0682]: To a suspension of sodium hydride (0.467 g, 11.69 mmol) in tetrahydrofuran was added ethyl 1h-pyrazole-3-carboxylate [0005] (1.33 g, 9.35 mmol) at 0° C. and the reaction mixture was stirred at rt for 30 min. Then 6-chloro-N2-(4,4-difluorocyclohexyl)-N4-methyl-3-nitropyridine-2,4-diamine [0681] (2.5 g, 7.79 mmol) was added to the reaction mixture at 0° C. and the reaction mixture was heated at 65° C. After 120 h, the reaction mixture was quenched with ice and stirred at rt. The solid formed was filtered washed with water and dried under vacuum to afford a yellow solid, which was purified in the Reveleris flash system instrument using methanol in chloroform as solvent in 80 g column to afford ethyl1-(6-((4,4-difluorocyclohexyl)amino)-4-(methylamino)-5-nitropyridin-2-yl)-1H-pyrazole-3-carboxylate [0682] as an yellow solid. (1.3 g, 40% yield). MS(M+1)+=425.2.

Step 5 [0683]: To a suspension of ethyl1-(6-((4,4-difluorocyclohexyl)amino)-4-(methylamino)-5-nitropyridin-2-yl)-1H-pyrazole-3-carboxylate [0682] (1.3 g, 3.06 mmol) in dichloromethane and methanol was added Raney nickel (0.7 g, 5.35 mmol) and the reaction mixture was stirred at rt under hydrogen atmosphere. After 72 h, the reaction mixture was filtered through celite bed, washed with dichloromethane. The filtrate was concentrated under reduced pressure to afford ethyl 1-(5-amino-6-((4,4-difluorocyclohexyl)amino)-4-(methylamino)pyridin-2-yl)-1H-pyrazole-3-carboxylate [0683] as a purple solid (1.1 g). MS(M+1)+=395.6.

Step 6 [0684]: To a solution of ethyl 1-(5-amino-6-((4,4-difluorocyclohexyl)amino)-4-(methylamino)pyridin-2-yl)-1H-pyrazole-3-carboxylate [0683] (1.0 g) in formic acid (20 vol) was stirred at rt. After 120 h, the reaction mixture was concentrated under reduced pressure and the residue was neutralized with sodium bicarbonate solution, extracted with ethyl acetate, washed with water and brine solution. The combined organic layer was concentrated under reduced pressure to afford a purple solid, which was purified in the Reveleris flash system instrument using ethyl acetate in hexane as solvent in 12 g column to afford ethyl 1-(4-((4, 4-difluorocyclohexyl)amino)-1-methyl-1H-imidazo[4,5-c] pyridin-6-yl)-1H-pyrazole-3-carboxylate [0684] as a purple solid (0.75 g). MS(M+1)+=405.2.

Step 7[0685]: The procedure is similar to step 2[0019] in example 4. 0.75 g of ethyl 1-(4-((4,4-difluorocyclohexyl) amino)-1-methyl-1H-imidazo [4,5-c]pyridin-6-yl)-1H-pyrazole-3-carboxylate [0684] gave 0.65 g of (1-(4-((4,4-difluorocyclohexyl)amino)-1-methyl-1H-imidazo[4,5-c]pyridin-6-yl)-1H-pyrazol-3-yl)methanol [0685] as a purple solid. MS(M+1)+=363.1.

Step 8[0686]: The procedure is similar to step 3[0012] in example 2. 0.65 g of (1-(4-((4,4-difluorocyclohexyl)amino)-1-methyl-1H-imidazo [4,5-c]pyridin-6-yl)-1H-pyrazol-3-yl) methanol [0685] gave 0.165 g of N-(4,4-difluorocyclohexyl)-6-(3-(fluoromethyl)-1H-pyrazol-1-yl)-1-methyl-1H-imidazo[4,5-c]pyridin-4-amine [0686], Compound 286 as a white solid. (30% yield). MS(M+1)+=365.2, ¹H NMR (400 MHz, DMSO-d6) δ 8.63 (d, J=2.5 Hz, 1H), 8.05 (s, 1H), 7.22 (s, 1H), 7.01 (d, J=7.9 Hz, 1H), 6.63 (t, J=2 Hz, 1H), 5.40 (d, JF=48.4 Hz, 2H), 4.32 (bs, 1H), 3.80 (s, 3H), 2.17-1.93 (m, 6H), 1.84-1.62 (m, 2H).

Example 259

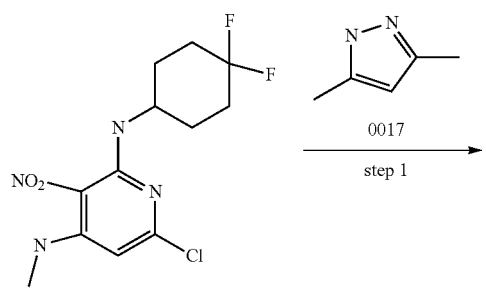

0681

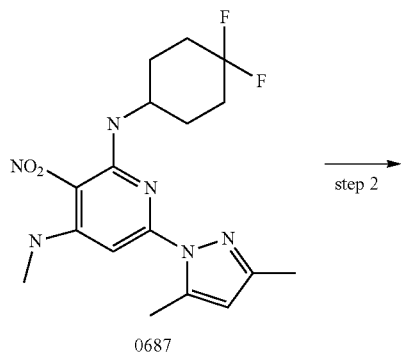

0687

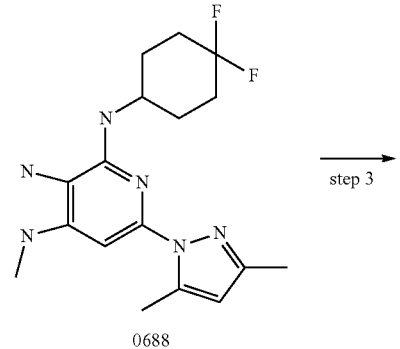

0688

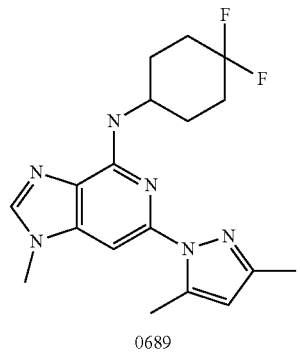

0689

Step 1[0687]: The procedure is similar to step 4[0682] in example 258. 4 g of 6-chloro-N2-(4,4-difluorocyclohexyl)-N4-methyl-3-nitropyridine-2,4-diamine [0681] gave 1 g of N2-(4,4-difluorocyclohexyl)-6-(3,5-di methyl-1H-pyrazol-1-yl)-N4-methyl-3-nitropyridine-2,4-diamine [0687] as an yellow solid(crude). MS(M+1)+=381.3.

Step 2[0688]: The procedure is similar to step 5[0683] in example 258. 0.5 g of N2-(4,4-difluorocyclohexyl)-6-(3,5-dimethyl-1H-pyrazol-1-yl)-N4-methyl-3-nitropyridine-2,4-diamine [0687] gave 0.4 g of N2-(4,4-difluorocyclohexyl)-6-(3,5-dimethyl-1H-pyrazol-1-yl)-N4methylpyridine-2,3,4-triamine [0688] as an yellow solid. MS(M+1)+=351.3.

Step 3[0689]: The procedure is similar to step 6[0684] in example 258. 0.22 g of N2-(4,4-difluorocyclohexyl)-6-(3,5-dimethyl-1H-pyrazol-1-yl)-N4-methylpyridine-2,3,4-triamine [0688] gave 0.052 g of N-(4,4-difluorocyclohexyl)-6-(3,5-dimethyl-1H-pyrazol-1-yl)-1-methyl-1H-imidazo[4,5-c]pyridin-4-amine [0689], Compound 266 as an off-white. MS(M+1)+=361.6. ¹H NMR (400 MHz, DMSO-d6) δ 8.16 (s, 1H), 7.11 (s, 1H), 6.94 (bs, 1H), 6.04 (s, 1H), 4.17 (bs, 1H), 2.60 (s, 3H), 2.48 (s, 3H), 2.20 (s, 3H), 2.15-1.90 (m, 6H), 1.75-1.63 (m, 2H).

Example 260

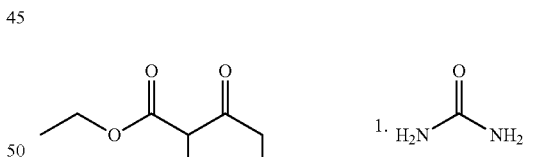

0690

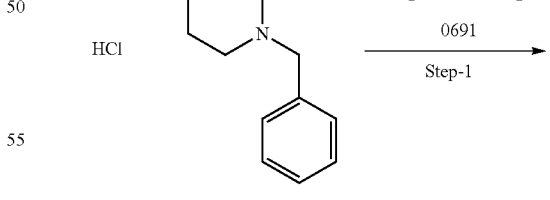

0692

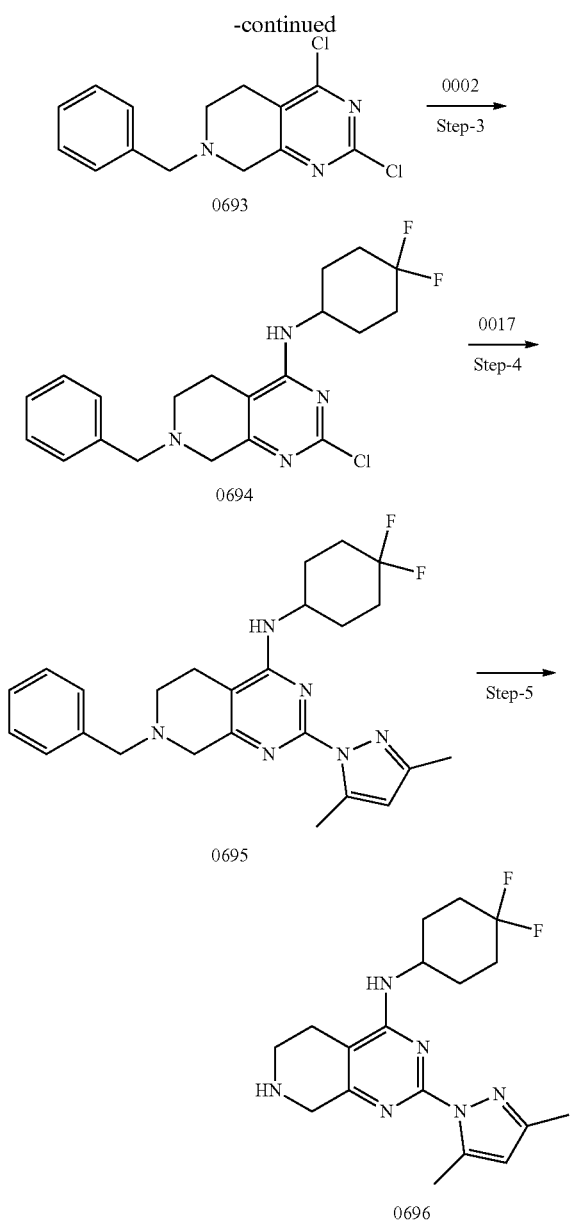

resultant residue was purified by column of silica gel (60-120 mesh), using 20% ethyl acetate in hexane as eluent to afford 7-benzyl-2,4-dichloro-5,6,7,8-tetrahydropyrido[3,4-d]pyrimidine [0693] as an light brown liquid (4.5 g). MS(M+1)$^+$=294.

Step 3[0694]: To a solution of 7-benzyl-2,4-dichloro-5,6,7,8-tetrahydropyrido[3,4-d]pyrimidine [0693] (0.58 g, 1.97 mmol) and 4,4-difluorocyclohexylamine hydrochloride [0002] (0.33 g, 1.97 mmol) in ethanol (10 mL) was added N,N-diisopropyl ethylamine (0.38 g, 2.95 mmol) and the reaction mixture was heated at 90° C. in a closed vial (20 mL) for 16 h. After the completion of the reaction, the reaction mixture was concentrated to dryness and the residue was purified by column of silica gel (60-120 mesh), using 40% ethyl acetate in hexane as eluent to afford 7-benzyl-2-chloro-N-(4,4-difluorocyclohexyl)-5,6,7,8-tetrahydropyrido[3,4-d]pyrimidin-4-amine [0694] as an yellow gummy solid (0.421 g). MS(M+1)$^+$=393.

Step 4[0695]: The procedure is similar to step 3 [0580] in example 216 [at 90° C. for 16 h]. 0.42 g of 7-benzyl-2-chloro-N-(4,4-difluorocyclohexyl)-5,6,7,8-tetrahydropyrido[3,4-d]pyrimidin-4-amine [0694] gave 0.31 g of 7-benzyl-N-(4,4-difluorocyclohexyl)-2-(3,5-dimethyl-1H-pyrazol-1-yl)-5,6,7,8-tetrahydropyrido[3,4-d]pyrimidin-4-amine [0695], Compound 119 as an off-white solid. MS(M+1)$^+$=453, $^1$H-NMR (400 MHz, DMSO-d6): δ 7.35-7.28 (m, 4H), 7.30-7.24 (m, 1H), 6.73 (d, J=7.84 Hz, 1H), 6.00 (s, 1H), 4.12 (m, 1H), 3.66 (s, 2H), 2.66-2.51 (m, 2H), (2.49 (s, 3H), 2.47-2.44 (m, 2H), 2.12 (s, 3H), 2.12-1.70 (m, 6H), 1.67-1.64 (m, 2H), 2H are merging with solvent.

Step 5[0696]: To a solution of 7-benzyl-N-(4,4-difluorocyclohexyl)-2-(3,5-dimethyl-1H-pyrazol-1-yl)-5,6,7,8-tetrahydropyrido[3,4-d]pyrimidin-4-amine [0695] (0.12 g, 0.265 mmol) in dichloromethane (10 mL) at 0° C. was added 1-chloroethyl chloroformate (0.075 g, 0.53 mmol), then the reaction mixture was heated at 45° C. for 8 h. After the completion of the reaction, the reaction mixture was concentrated to dryness and the resulting residue was dissolved in methanol (10 mL) and refluxed for 1 h and concentrated to dryness to afford an off-white gum and which was triturated with dichloromethane, the obtained solid was filtered and washed with hexane, dried under high vacuum to afford N-(4,4-difluorocyclohexyl)-2-(3,5-dimethyl-1H-pyrazol-1-yl)-5,6,7,8-tetrahydropyrido [3,4-d]pyrimidin-4-amine hydrochloride salt [0696] as an off-white solid (0.061 g).

MS(M+1)$^+$=363, $^1$H NMR (400 MHz, DMSO-d6) δ 9.72 (s, 2H), 7.46 (d, J=7.3 Hz, 1H), 6.15 (s, 1H), 4.13 (d, J=4.5 Hz, 3H), 3.42 (d, J=6.0 Hz, 2H), 2.70 (d, J=5.9 Hz, 2H), 2.57 (s, 3H), 2.20 (s, 3H), 2.10 (d, J=8.6 Hz, 2H), 1.95 (d, J=14.2 Hz, 3H), 1.73 (m, 2H).

Example 261

Step 1[0692]: To a suspension of ethyl 1-benzyl-3-oxo-4-piperidinecarboxylate hydrochloride [0690] (15 g, 50.37 mmol) in ethanol was added urea [0691] (15.12 g, 251.8 mmol) and sodium methoxide (35.3 g, 654.8 mmol) and the reaction mixture was refluxed at 90° C. under nitrogen atmosphere for 16 h. After the completion of the reaction, the reaction mixture was cooled to 0° C. and the pH of the suspension was adjusted to 6.0 by addition of aqueous hydrochloric acid (1 N solution). The mixture was stirred at rt for 15 min and the solid formed was filtered, washed with hexanes and dried under vacuum to afford 7-benzyl-5,6,7,8-tetrahydropyrido[3,4-d]pyrimidine-2,4(1H,3H)-dione [0692] as an off-white solid (8 g). MS(M+1)$^+$=258.

Step 2[0693]: A suspension of 7-benzyl-5,6,7,8-tetrahydropyrido[3,4-d]pyrimidine-2,4(1H,3H)-dione [0692] (8 g, 31.09 mmol) in phosphorus oxychloride (253 g, 1650 mmol) was heated at 110° C. under nitrogen atmosphere for 48 h. After the completion of the reaction, the reaction mixture was concentrated to remove phosphorus oxychloride and the

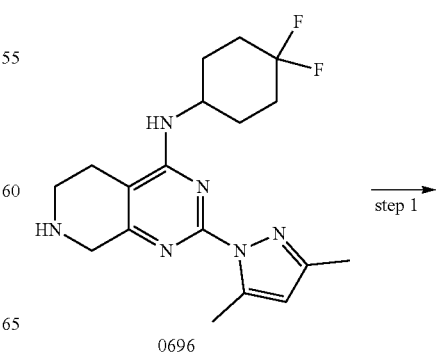

-continued

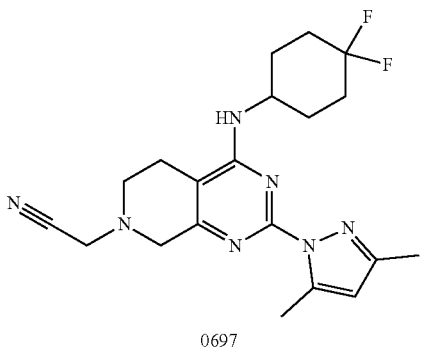

0697

Step 1[0697]: To a solution of N-(4,4-difluorocyclohexyl)-2-(3,5-dimethyl-1H-pyrazol-1-yl)-5,6,7,8-tetrahydropyrido [3,4-d]pyrimidin-4-amine hydrochloride salt [0696] in acetonitrile (5 mL) was added bromoacetonitrile and followed by cesium carbonate, then the reaction mixture was stirred at 80° C. for 16 h. the reaction mixture was filtered and the filtrate was concentrated to afford as a brownish gum, which was purified by column of silica gel (60-120 mesh), using ethyl acetate as eluent to afford 2-(4-((4,4-difluorocyclohexyl)amino)-2-(3,5-dimethyl-1H-pyrazol-1-yl)-5,8-dihydropyrido [3,4-d]pyrimidin-7(6H)-yl) acetonitrile [0697], Compound 122 as an Light brown solid (0.016 g). MS(M+1)$^+$=402, $^1$H-NMR (400 MHz, DMSO-d6): δ 6.81 (d, J=7.92 Hz, 1H), 6.03 (s, 1H), 4.13 (s, 1H), 4.13 (s, 2H), 3.49 (s, 2H), 2.80 (t, J=5.48 Hz, 2H), 2.54 (S, 3H), 2.49-2.49 (m, 2H), 2.15 (s, 3H), 2.08-1.91 (m, 6H), 1.68-1.65 (m, 2H), Example 262

Step 1[0698]: The procedure is similar to step 1[0697] in example 261. 0.07 g of N-(4,4-difluorocyclohexyl)-2-(3,5-dimethyl-1H-pyrazol-1-yl)-5,6,7,8-tetrahydropyrido [3,4-d]pyrimidin-4-amine hydrochloride salt [0696] gave 0.035 g of 2-(4-((4,4-difluorocyclohexyl)amino)-2-(3,5-dimethyl-1H-pyrazol-1-yl)-5,8-dihydropyrido[3,4-d]pyrimidin-7(6H)-yl)acetamide [0698], Compound 121 as an white solid. MS(M+1)$^+$=420, $^1$H NMR (400 MHz, DMSO-d6) δ 7.30 (s, 1H) 7.14 (s, 1H), 6.78 (d, J=8.0 Hz, 1H), 6.03 (s, 1H), 4.14 (bs, 1H), 3.48 (s, 2H), 3.08 (s, 2H), 2.77 (t, J=5.7 Hz, 2H), 2.54 (s, 3H), 2.16 (s, 3H), 2.15-1.85 (m, 8H), 1.69-1.75 (m, 2H).

Example 263

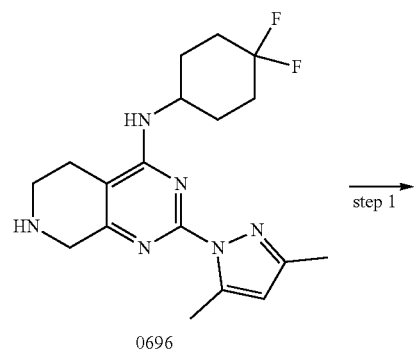

0696

Step 1[0699]: The procedure is similar to step 1[0697] in example 261 [at 80° C. for 16 h]. 0.07 g of N-(4,4-difluorocyclohexyl)-2-(3,5-dimethyl-1H-pyrazol-1-yl)-5,6,7,8-tetrahydropyrido [3,4-d]pyrimidin-4-amine hydrochloride salt [0696] gave 0.022 g of N-(4,4-difluoro cyclohexyl)-2-(3,5-dimethyl-1H-pyrazol-1-yl)-7-isopropyl-5,6,7,8-tetrahydropyrido[3,4-d]pyrimidin-4-amine [0699], Compound 123 as an brownish gum. MS(M+1)$^+$=405, $^1$H NMR (400 MHz, DMSO-d6) δ 6.72 (d, J=7.9 Hz, 1H), 6.03 (s, 1H), 4.12 (d, J=6.8 Hz, 1H), 3.45 (s, 2H), 2.87 (p, J=6.5 Hz, 1H), 2.73 (t, J=5.7 Hz, 2H), 2.54 (s, 3H), 2.41 (t, J=5.7 Hz, 2H), 2.16 (s, 3H), 2.00 (m, 6H), 1.68 (m, 2H), 1.06 (d, J=6.5 Hz, 6H).

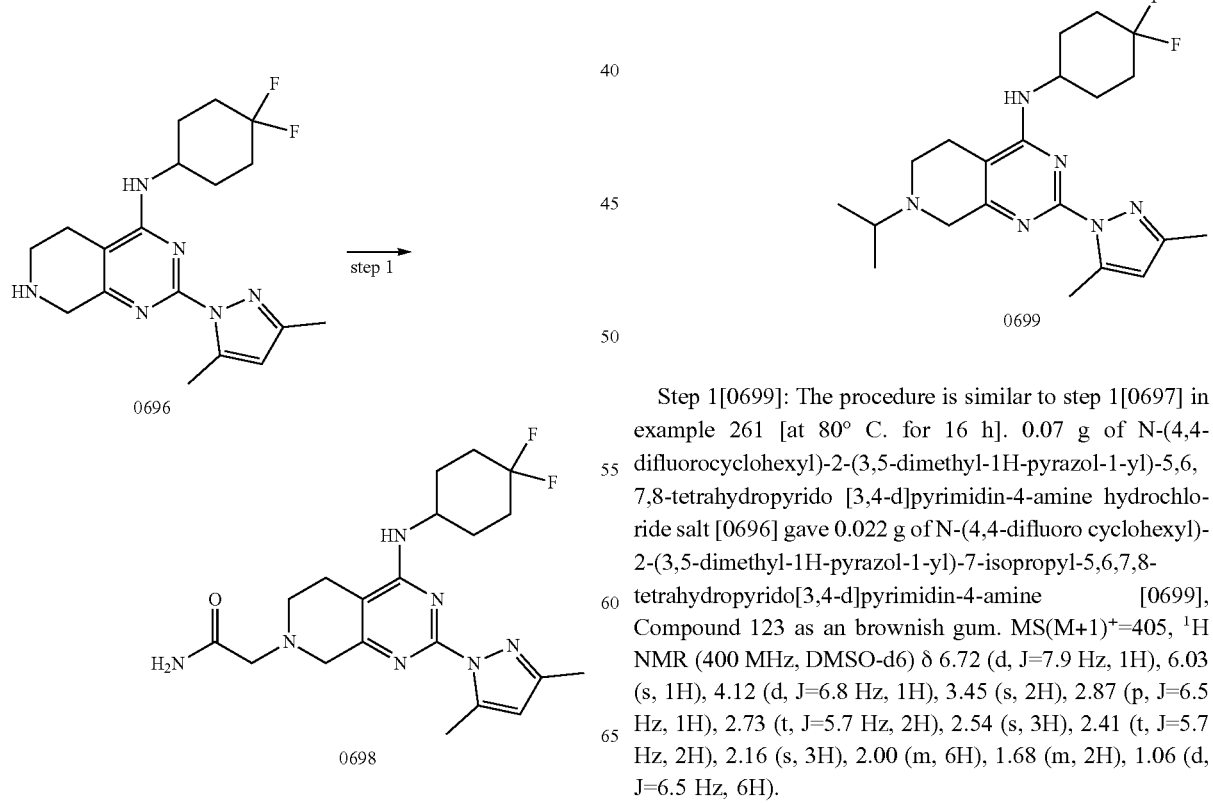

Example 264

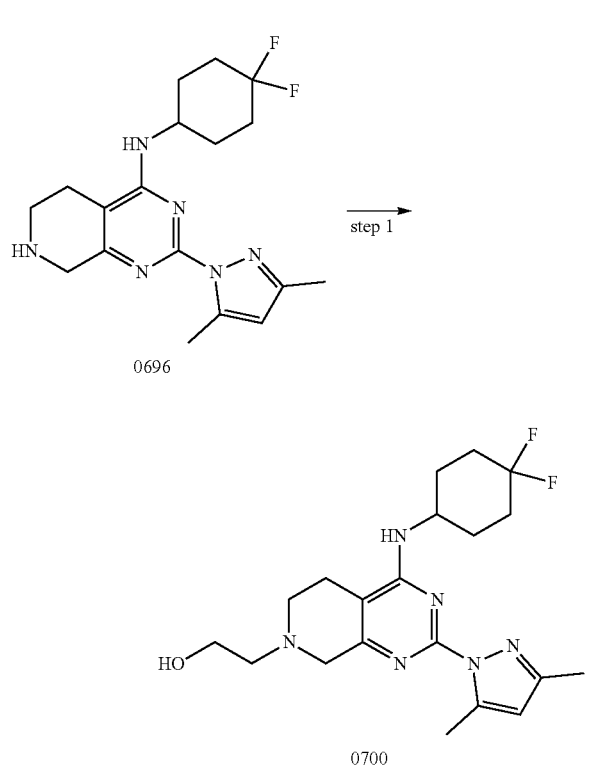

Step 1[0700]: The procedure is similar to step 1[0697] in example 261 [at 70° C. for 16 h]. 0.06 g of N-(4,4-difluorocyclohexyl)-2-(3,5-dimethyl-1H-pyrazol-1-yl)-5,6,7,8-tetrahydropyrido [3,4-d]pyrimidin-4-amine hydrochloride salt [0696] gave 0.026 g of 2-(4-((4,4-difluorocyclohexyl)amino)-2-(3,5-dimethyl-1H-pyrazol-1-yl)-5,8-dihydropyrido[3,4-d]pyrimidin-7(6H)-yl)ethan-1-ol [0700], Compound 118 as an light yellow solid. MS(M+1)+= 407, $^1$H NMR (400 MHz, DMSO-d6) δ 6.74 (d, J=7.9 Hz, 1H), 6.03 (s, 1H), 4.51 (t, J=5.4 Hz, 1H), 4.13 (s, 1H), 3.59 (q, J=5.8 Hz, 2H), 3.44 (s, 2H), 2.75 (t, J=5.8 Hz, 2H), 2.58 (t, J=6.0 Hz, 2H), 2.50 (s, 3H), 2.43 (s, 2H), 2.15 (s, 3H), 2.15-1.85 (m, 6H), 1.74-1.60 (m, 2H).

Example 264

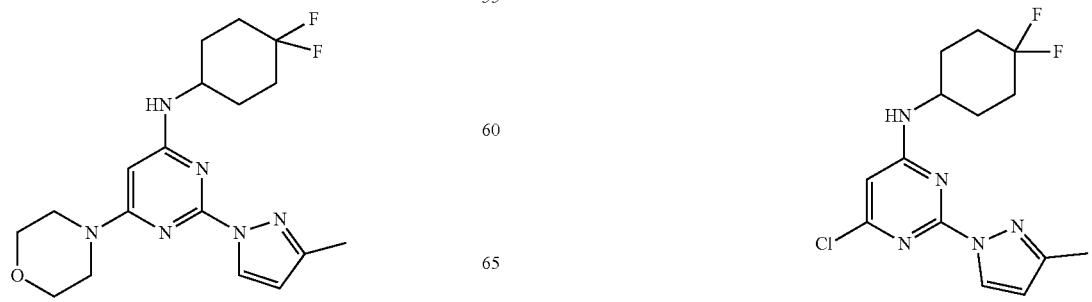

Step 1:

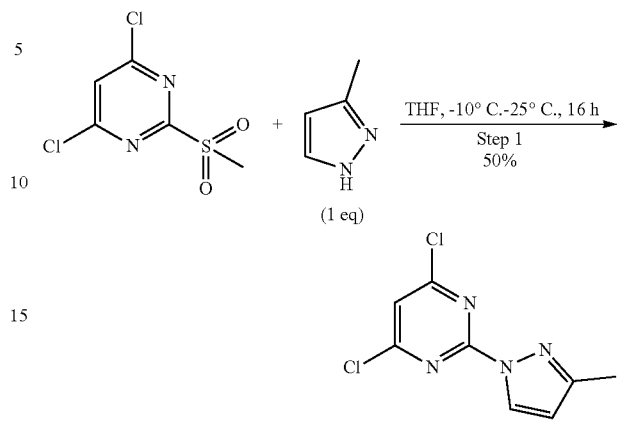

A round-bottomed flask equipped with a teflon-coated stir bar was charged with 4,6-dichloro-2-(methylsulfonyl)pyrimidine (20.0 g, 88.080 mmol, 1.0 eq) in tetrahydrofuran at −10° C. and 3-methyl-1H-pyrazole (7.23 g, 88.080 mmol, 1.0 equiv.) was added dropwise over a period of five minutes via syringe. The reaction mixture was stirred for 16 hours at 25° C. and completion of reaction was determined by TLC. The reaction mixture was portioned between water (500 mL) and ethyl acetate (500 mL). The organic layer was separated and the aqueous layer was extracted with ethyl acetate (2*100 mL). The combined organic layer was dried over sodium sulfate, filtered, and concentrated under reduced pressure to afford crude product which was purified by column chromatography (ethyl acetate/hexane as solvent system) to afford 4,6-dichloro-2-(3-methyl-1H-pyrazol-1-yl)pyrimidine (10.0 g, 43.859 mmol, 50% yield) as a white solid pure form. MS (MH+): m/z=229.1.

Step 2:

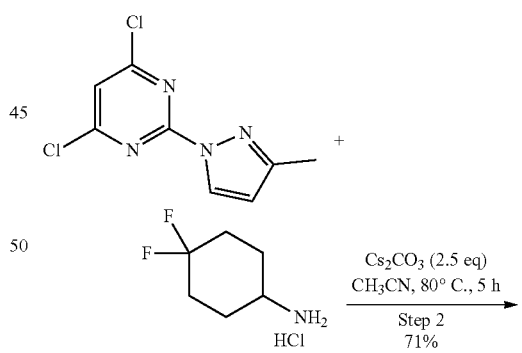

A round-bottomed flask equipped with a teflon-coated stir bar was charged with 2,4-dichloro-6-methylpyrimidine (11.0 g, 48.24 mmol, 1.0 equiv.), 4,4-difluorocyclohexan-1-amine hydrochloride (9.89 g, 57.89 mmol, 1.2 equiv.), and $CS_2CO_3$ (39.19 g, 120.61 mmol, 2.5 equiv.) in acetonitrile (200 mL). The reaction mixture was stirred for five hours at 80° C. and the completion of reaction was determined by TLC. The reaction mixture was cooled to room temperature and partitioned between water (100 mL) and ethyl acetate (200 mL). The organic layer was separated and the aqueous layer was extracted ethyl acetate (2×100 mL). The combined organic layer was dried over sodium sulfate, filtered, and concentrated under reduced pressure to afford crude product which was purified by column chromatography (ethyl acetate/hexane as solvent system) to afford 6-chloro-N-(4,4-difluorocyclohexyl)-2-(3-methyl-1H-pyrazol-1-yl)pyrimidin-4-amine (11.0 g, 33.62 mmol, 71%) as an off-white solid. MS (MH+): m/z=328.1.

Step 3:

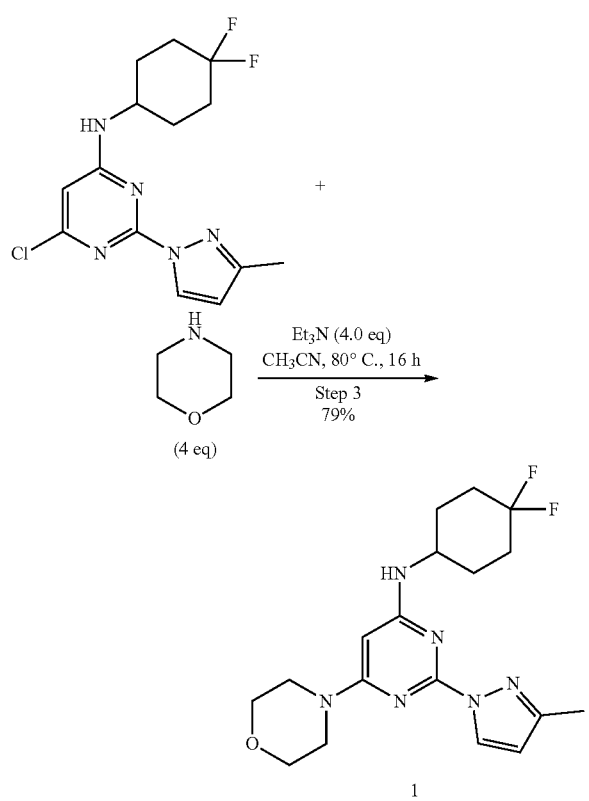

A round-bottomed flask equipped with a teflon-coated stir bar was charged with 6-chloro-N-(4,4-difluorocyclohexyl)-2-(3-methyl-1H-pyrazol-1-yl)pyrimidin-4-amine 5 (14.0 g, 42.79 mmol, 1.0 eq), morpholine (14.91 mL, 171.19 mmol, 4.0 eq), and triethylamine (23.89 mL, 171.19 mmol, 4.0 eq) in acetonitrile (200 mL). The reaction mixture was stirred for 16 hours at 80° C. and completion of reaction was determined by TLC. The reaction mixture was cooled to room temperature and partitioned between water (100 mL) and ethyl acetate (300 mL).

The organic layer was separated and the aqueous layer was extracted ethyl acetate (2×100 mL). The combined organic layer was dried over sodium sulfate, filtered, and concentrated under reduced pressure to afford crude product which was purified by column chromatography (ethyl acetate/hexane as solvent system) to afford N-(4,4-difluorocyclohexyl)-2-(3-methyl-1H-pyrazol-1-yl)-6-morpholinopyrimidin-4-amine (Compound 359) (12.8 g, 33.84 mmol, 79% yield) as an off-white solid. MS (MH+): m/z=379.2. Analytical Data: $^1$H NMR (400 MHz, DMSO-D6): δ 8.41 (d, J=2 Hz, 1H), 7.07 (d, J=8.3 Hz, 1H), 6.25 (d, J=2.4 Hz, 1H), 5.53 (s, 1H), 3.9 (bs, 1H), 3.67 (t, J=4.4 Hz, 4H), 3.49 (S, 4H), 2.23 (s, 3H), 2.23-1.97 (m, 3H), 1.92-1.90 (m, 3H), 1.55-1.53 (m, 2H).

Example 265

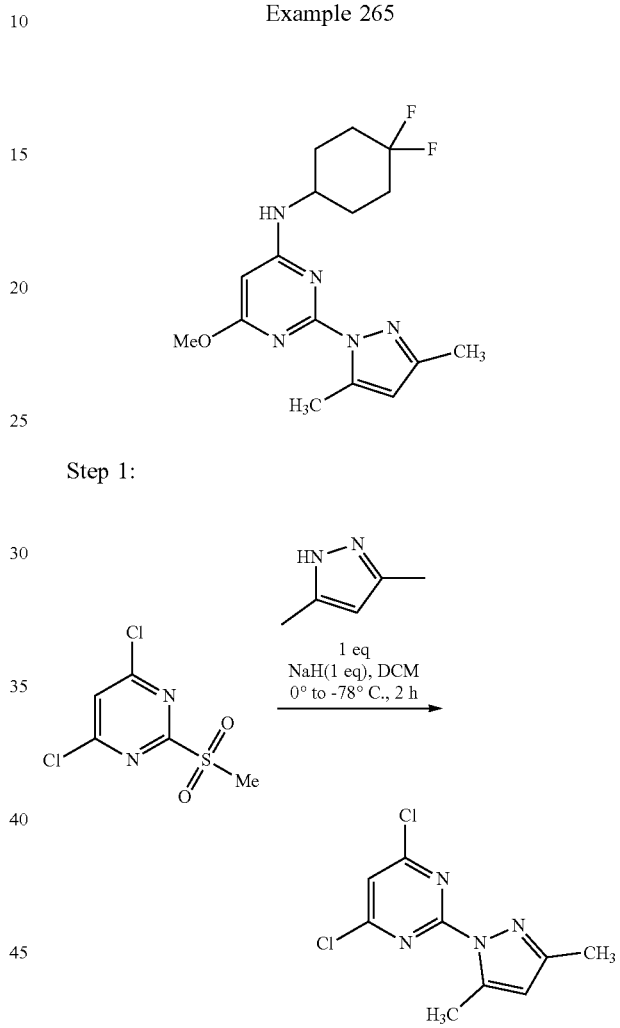

Step 1:

A 5000-mL four-necked, flame-dried, round-bottomed flask, equipped with a teflon-coated stir blade (5 cm) attached with glass rod (neck 1), stopper (neck 2), and addition funnel with stopper (neck 3) and a nitrogen gas inlet-outlet U-tube adaptor filled with oil (Neck 4), was charged with a suspension of sodium hydride (35.2 g, 880 mmol, 1 equiv.) in dichloromethane (1000 mL) was added 3,5-dimethylpyrazole (84.6 g, 880 mmol, 1 equiv.) at 0° C. and the reaction mixture was stirred at room temperature. After 30 min, 4,6-dichloro-2-(methylsulfonyl)pyrimidine (200 g, 880 mmol, 1 equiv.) (dissolved in dichloromethane (1000 mL)) was added dropwise through dropping funnel to the reaction mixture at −78° C. The reaction mixture was stirred at same temperature and the completion of reaction was determined by TLC and UPLC. After 2 h, the reaction mixture was quenched with water at −78° C. and diluted with dichloromethane. After 5 min, dichloromethane was decanted and washed with brine solution. The organic layer was dried over sodium sulfate, filtered, and concentrated under reduced pressure to afford crude product, which was purified by column chromatography using ethyl acetate and pet-ether as solvent to afford 4,6-dichloro-2-(3,5-dimethyl-1h-pyrazol-1-yl)pyrimidine (138 g, 567.71 mmol, 65%) as an off-white solid. MS (MH+): m/z=244.2.

Step 2:

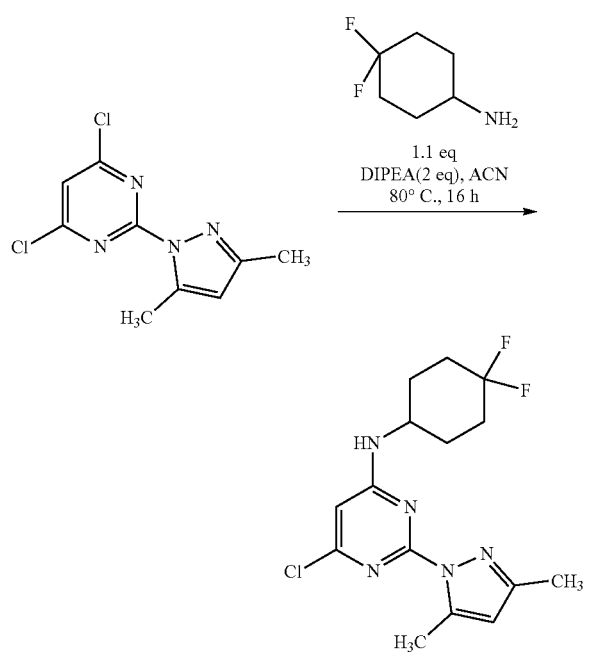

A 2000-mL three-necked, flame-dried, round-bottomed flask, equipped with a teflon-coated stir bar (5 cm), one septa (neck 1), stopper (neck 3) and reflux condenser equipped with nitrogen gas inlet-outlet U-tube adaptor filled with oil (Neck 2), was charged with a solution of 4,6-dichloro-2-(3,5-dimethyl-1h-pyrazol-1-yl)pyrimidine (136 g, 559.4 mmol, 1 equiv.) in acetonitrile (1500 mL) followed by 4,4-difluorocyclohexylamine hydrochloride (105.6 g, 615.4 mmol, 1.1 equiv.) and N,N-diisopropyl ethylamine (194.88 mL, 1118.8 mmol, 2 equiv). The reaction mixture was heated at 80° C. for 16 h. The completion of reaction was determined by TLC and UPLC. The reaction mixture was concentrated and the residue was triturated with water (500 mL). The resulting solid was filtered, washed with pet-ether, dried under vacuum to afford 6-chloro-N-(4,4-difluorocyclohexyl)-2-(3,5-dimethyl-1h-pyrazol-1-yl)pyrimidin-4-amine (191 g, 556 mmol, >95%) as an off-white solid. MS (MH+): m/z=342.0.

Step 3:

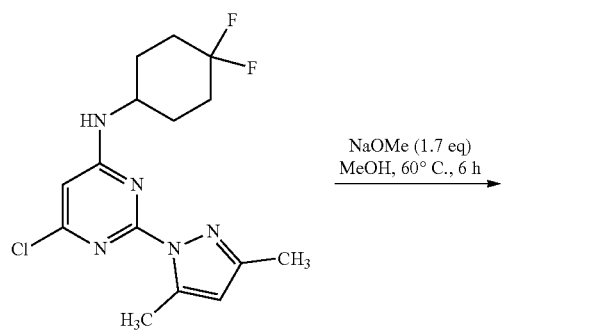

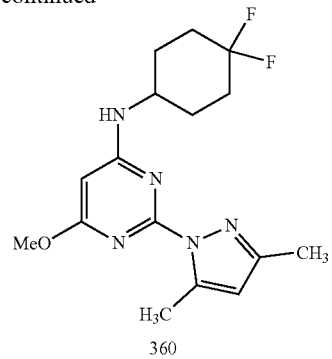

360

A 250 mL three-necked, flame-dried, round-bottomed flask, equipped with a teflon-coated stir bar (2 cm), one septa (neck 1), stopper (neck 3) and reflux condenser equipped with nitrogen gas inlet-outlet U-tube adaptor filled with oil (Neck 2), was charged with a solution of 6-chloro-N-(4,4-difluorocyclohexyl)-2-(3,5-dimethyl-1h-pyrazol-1-yl)pyrimidin-4-amine (20 g, 58.51 mmol, 1 equiv.) in methanol followed by sodium methoxide (21% in methanol, 5.37 g, 99.47 mmol, 1.7 equiv.). The reaction was heated to 60° C., and completion of reaction was determined by TLC and UPLC. After 5 h, the reaction mixture was concentrated under reduced pressure and the residue was diluted with ethyl acetate, washed with water, and washed with brine solution. The organic layer was dried over sodium sulfate, filtered, and concentrated under reduced pressure to afford the crude product which was purified by column chromatography using ethyl acetate in pet-ether as solvent system to afford N-(4,4-difluorocyclohexyl)-2-(3,5-dimethyl-1H-pyrazol-1-yl)-6-methoxypyrimidin-4-amine (Compound 360) [16 g (11 g (99% pure)+5 g (92% pure), 47.41 mmol, ~80%) as a white solid. MS (MH+): m/z=338.1. Analytical Data: $^1$H-NMR (400 MHz, DMSO-d$_6$): δ 7.45 (bs, 1H), 6.06 (s, 1H), 5.72 (s, 1H), 4.01 (bs, 1H), 3.85 (s, 3H), 2.55 (s, 3H), 2.17 (s, 3H), 2.11-1.82 (m, 6H), 1.60-1.55 (m, 2H).

Example 266

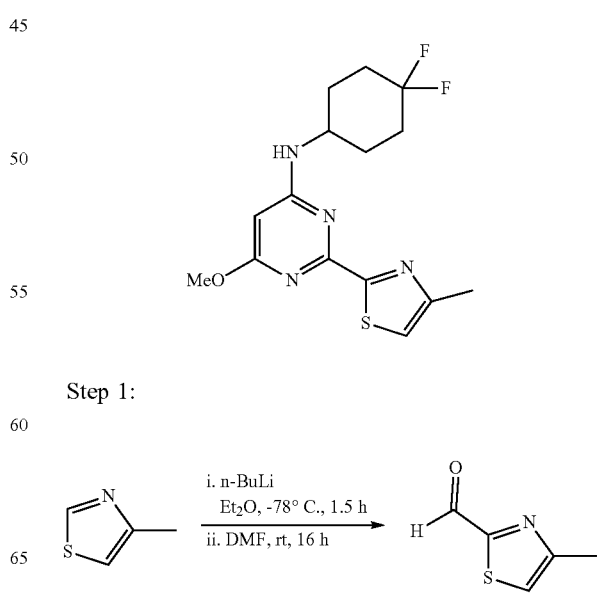

Step 1:

A three-necked round bottomed flask equipped with a teflon-coated stir bar was charged with diethyl ether (250 mL) and n-BuLi (241.98 mL, 604.96 mmol, 2.5M in hexane) was transferred at −78° C. A solution of 4-methylthiazole (50.0 g, 504.13 mmol) in diethyl ether (200 mL) was added over a period of 30 min. The reaction mixture was turned into pale yellow suspension. After 1.5 hours, DMF (58.54 mL, 756.20 mmol) was added and stirred at room temperature for 16 h. The progress of the reaction was monitored by TLC. After completion of the reaction, the mixture was poured into cold aq. HCl (400 mL, 4N) under stirring and separated the two layers. The organic layer was washed with cold aq. HCl (2×80 mL, 4N)). The combined aq. layers were slowly basified with $K_2CO_3$ (pH 7) and extracted with diethyl ether (3×150 mL). The combined organic layers were dried over sodium sulfate and evaporated to dryness at room temperature under vacuum to afford 4-methylthiazole-2-carbaldehyde (60.0 g, crude) as a pale yellow liquid. This crude material was used in the next step without further purification.

Step 2:

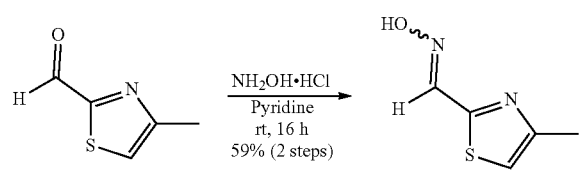

A two-necked round bottomed flask equipped with a teflon-coated stir bar was charged with 4-methylthiazole-2-carbaldehyde (60.0 g, crude) in pyridine (38.04 ml, 472.40 mmol). Hydroxylamine hydrochloride (32.82 g, 472.40 mmol) was added in portions over a period of 15 min. The reaction mixture was stirred at room temperature for 16 h under nitrogen atmosphere. The progress of the reaction was monitored by TLC. After completion of the reaction, the mixture was poured into ice cold water and stirred for 20 min, the obtained solid was filtered and dried under vacuum to afford 4-methylthiazole-2-carbaldehyde oxime (40.0 g, 281.69 mmol, 59% for two steps) as an off white solid. MS (MH+): m/z=143.0.

Step 3:

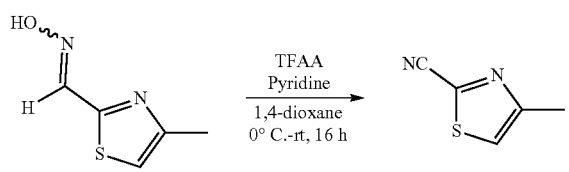

A two-necked round bottomed flask equipped with a teflon-coated stir bar was charged with a solution of 4-methylthiazole-2-carbaldehyde oxime (35.0 g, 246.44 mmol) and pyridine (87.33 mL, 1084.35 mmol) in 1,4-dioxane (140 mL). Trifluoroacetic anhydride (51.38 mL, 369.66 mmol) was added slowly at −10° C. and allowed to stir at room temperature for 16 h. The progress of the reaction was monitored by TLC. After completion of the reaction, the mixture was diluted with water (250 mL) and extracted with diethyl ether (3×350 mL). The combined organic layers were washed with water (2×250 mL), brine (100 mL) dried over sodium sulphate and concentrated under reduced pressure to afford 4-methylthiazole-2-carbonitrile (35.0 g, crude) as light brown liquid. This crude material was used in the next step without further purification. Analytical Data: $^1$H-NMR (400 MHz, DMSO-$d_6$): δ 7.90 (s, 1H), 2.51 (s, 3H).

Step 4:

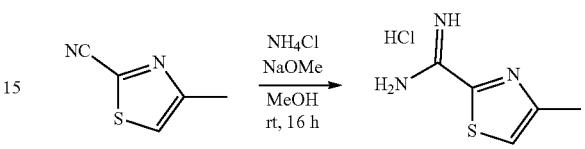

A two-necked round bottomed flask equipped with a teflon-coated stir bar was charged with 4-methylthiazole-2-carbonitrile (35.0 g, crude) in methanol (280 mL) and sodium methoxide (16.77 g, 310.45 mmol) was added. After stirring at room temperature for 3 h, ammonium chloride (30.19 g, 564.66 mmol) was added and stirred for another 16 h. The progress of the reaction was monitored by TLC. After completion of the reaction, the mixture was filtered and washed with methanol. The filtrate was concentrated under reduced pressure and the residue was triturated with diethyl ether (150 mL). The formed solid was filtered and dried under vacuum to afford 4-methylthiazole-2-carboximidamide hydrochloride (35.0 g, crude) as an off-white solid. This crude material was used in the next step without further purification. MS (MH+): m/z=142.0.

Step 5:

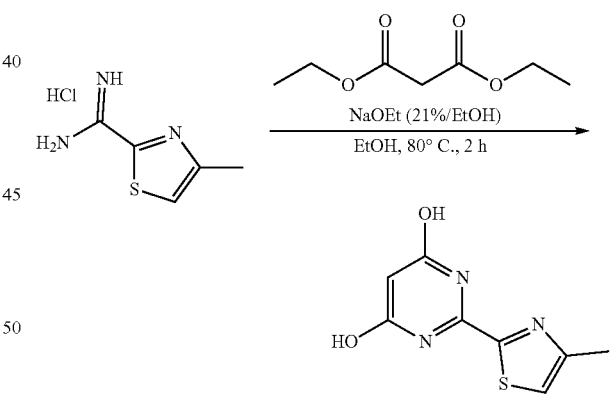

A two-necked round bottomed flask equipped with a teflon-coated stir bar was charged with 4-methylthiazole-2-carboximidamide hydrochloride (35.0 g, crude) in ethanol (350 mL) and diethyl malonate (150.81 mL, 988.64 mmol). Sodium ethoxide (320 mL, 988.64 mmol, 21% in EtOH) was added dropwise at room temperature and heated to 85° C. After 3 hours, the reaction mixture was concentrated under reduced pressure. Water (20 mL) was added and acidified with 1.5 N HCl (pH 2-3). The obtained solid was filtered and dried under vacuum to afford 2-(4-methylthiazol-2-yl)pyrimidine-4,6-diol (29.0 g, crude) as pale yellow solid. This crude material was used in the next step without further purification. MS (MH+): m/z=210.0.

Step 6:

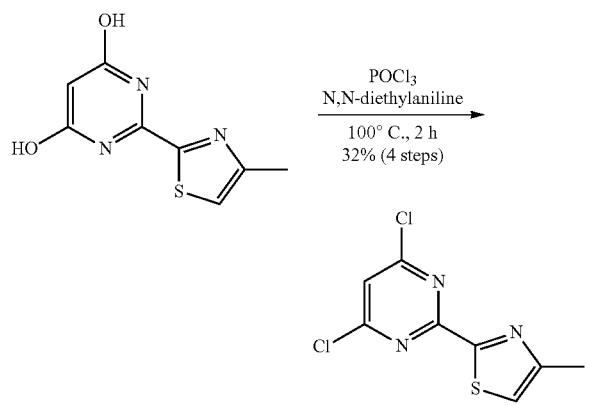

A two-necked round bottomed flask equipped with a teflon-coated stir bar was charged with a suspension of 2-(4-methylthiazol-2-yl)pyrimidine-4,6-diol (29.0 g, crude) and POCl₃ (290 mL). N,N-diethylaniline (37.84 mL, 235.85 mmol) was added at room temperature and heated reflux at 100° C. for 2 h. The progress of the reaction was monitored by TLC. Excess POCl₃ was removed by distillation. The residue was diluted with 500 mL cold water, neutralized with saturated sodium bicarbonate solution, extracted with diethyl ether (2×500 mL). The combined organic layers were washed with water (3×200 mL), brine (100 mL), dried over sodium sulfate and concentrated under reduced pressure. The residue was triturated with n-pentane (100 mL). The obtained solid was filtered and dried under vacuum to afford 2-(4,6-dichloropyrimidin-2-yl)-4-methylthiazole 7 (19.5 g, 79.59 mmol, 32% for four steps) as a pale yellow solid. MS (MH+): m/z=245.9.

Step 7:

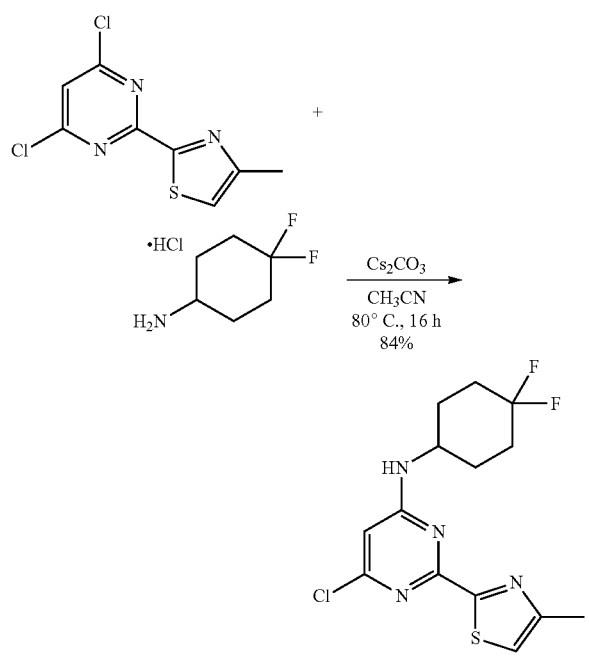

A two necked round bottomed flask equipped with a teflon-coated stir bar was charged with a suspension of 2-(4,6-dichloropyrimidin-2-yl)-4-methylthiazole (19.0 g, 77.56 mmol) and 4,4-difluorocyclohexan-1-amine hydrochloride (13.30 g, 77.56 mmol) in acetonitrile (190 mL). Cesium carbonate (37.89 g, 116.34 mmol) was added and the reaction mixture was heated at 80° C. for 16 h. The progress of the reaction was monitored by TLC. The reaction mixture was cooled to room temperature, filtered, and the solid was washed with ethyl acetate (500 mL). The filtrate was washed with water (2×100 mL), brine (100 mL), dried over sodium sulfate, and concentrated under reduced pressure. The residue was purified by column chromatography (60-120 silica gel) eluted with 15% EtOAc in hexane. Relevant fractions containing the required compound were combined and evaporated to dryness under reduced pressure to afford 6-chloro-N-(4,4-difluorocyclohexyl)-2-(4-methylthiazol-2-yl)pyrimidin-4-amine (22.5 g, 65.25 mmol, 84%) as off-white foam solid. MS (MH+): m/z=344.9.

Step 8:

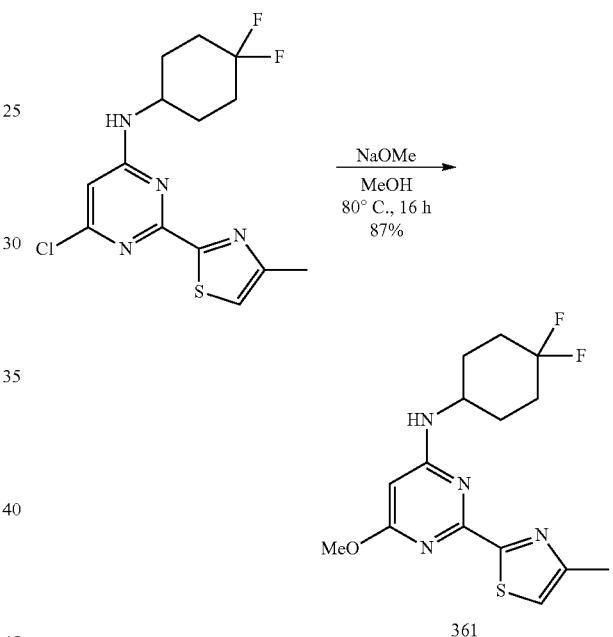

361

A two-necked round bottomed flask equipped with a teflon-coated stir bar was charged with 6-chloro-N-(4,4-difluorocyclohexyl)-2-(4-methylthiazol-2-yl)pyrimidin-4-amine (27.0 g, 78.47 mmol) in methanol (450 mL). Sodium methoxide (21.19 g, 392.36 mmol) was added and heated to 80° C. for 16 h. The progress of the reaction was monitored by TLC. Excess methanol was removed under reduced pressure and the residue was diluted with 10% aqueous ammonium chloride solution (100 mL) and extracted with ethyl acetate (3×150 mL). The combined organic layers were washed with water (2×100 mL), brine (100 mL), dried over sodium sulphate and concentrated under reduced pressure. The residue was purified by column chromatography (60-120 silica gel) eluting with 35-40% of EtOAc in hexane. Relevant fractions containing the target compound were combined and evaporated to dryness under reduced pressure to afford N-(4,4-difluorocyclohexyl)-6-methoxy-2-(4-methylthiazol-2-yl)pyrimidin-4-amine (Compound 361) (23.4 g, 68.82 mmol, 87%) as an off-white solid. MS (MH+): m/z=341.0. Analytical Data: ¹H-NMR (400 MHz, DMSO-d$_6$): δ 7.41 (s, 1H), 7.40 (s, 1H), 5.81 (s, 1H), 3.87 (s, 3H), 2.43 (s, 3H), 2.08-1.89 (m, 6H), 1.61-1.52 (m, 2H).

Example 267

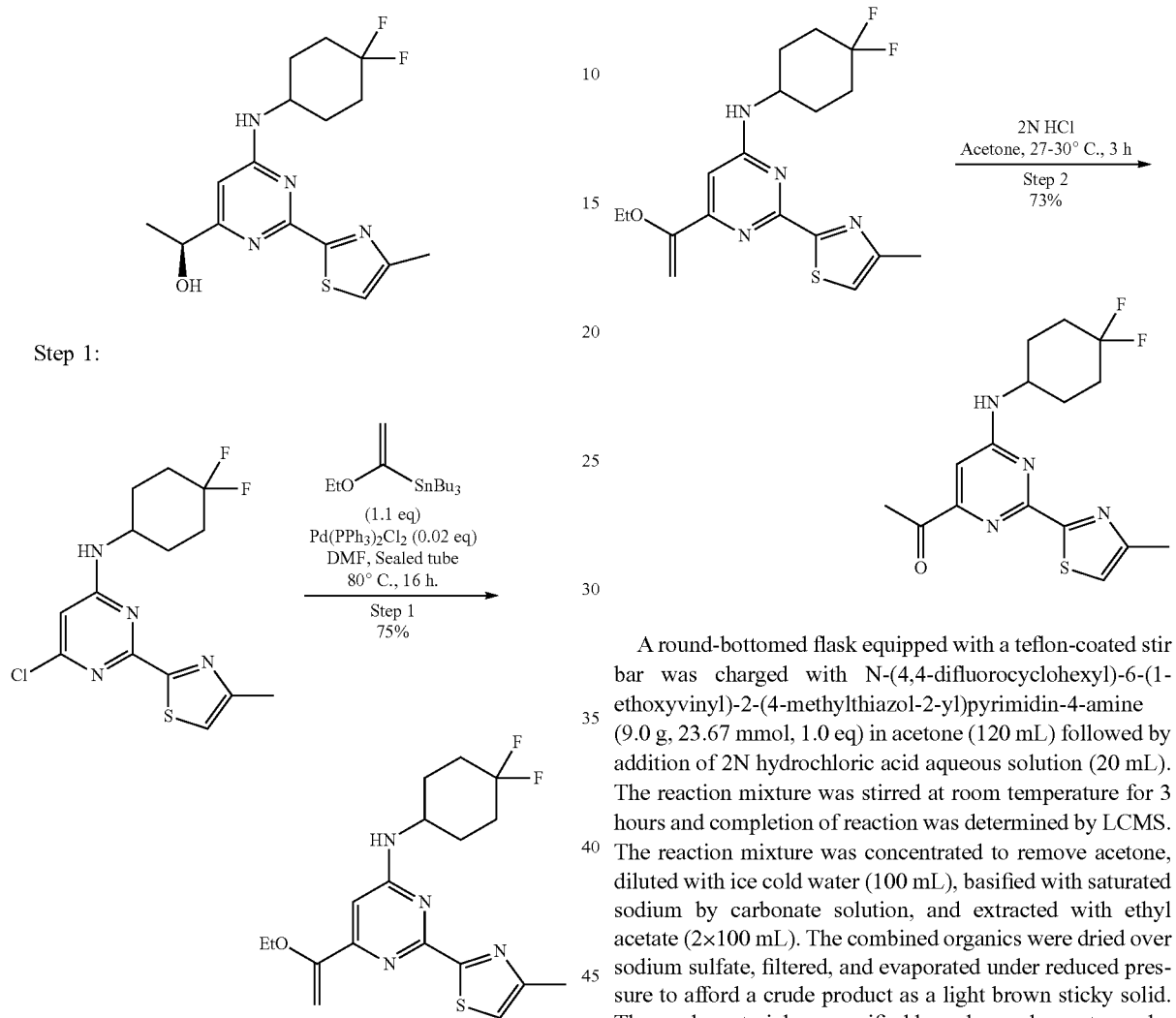

Step 1:

A 250-mL sealed tube, equipped with a teflon-coated stir bar (2 cm), was charged with a solution of 6-chloro-N-(4,4-difluorocyclohexyl)-2-(4-methylthiazol-2-yl)pyrimidin-4-amine (4.9 g, 14.24 mmol, 1.0 eq) and tributyl(1-ethoxyvinyl)stannane (5.65 g, 15.66 mmol, 1.1 eq) in N,N-dimethylformamide (60 mL). The reaction mixture was degassed using argon gas for 5-10 min, followed by addition of bis(triphenylphosphine)palladium(II) dichloride (0.2 g, 0.28 mmol, 0.02 eq). The reaction mixture was sealed and heated at 80° C. for 16 h (completion of reaction was determined by LCMS) and cooled to room temperature. The reaction mixture was diluted with water (300 mL) and extracted with ethyl acetate (2×150 mL). The combined organics were dried over sodium sulfate, filtered, and evaporated to afford a crude product as a light brown sticky solid. The crude material was purified by column chromatography (ethyl acetate/hexane as solvent system) to afford N-(4,4-difluorocyclohexyl)-6-(1-ethoxyvinyl)-2-(4-methylthiazol-2-yl)pyrimidin-4-amine (4.1 g, 10.78 mmol, 75%) as an off-white solid. MS (MH+): m/z=381.0.

Step 2:

A round-bottomed flask equipped with a teflon-coated stir bar was charged with N-(4,4-difluorocyclohexyl)-6-(1-ethoxyvinyl)-2-(4-methylthiazol-2-yl)pyrimidin-4-amine (9.0 g, 23.67 mmol, 1.0 eq) in acetone (120 mL) followed by addition of 2N hydrochloric acid aqueous solution (20 mL). The reaction mixture was stirred at room temperature for 3 hours and completion of reaction was determined by LCMS. The reaction mixture was concentrated to remove acetone, diluted with ice cold water (100 mL), basified with saturated sodium by carbonate solution, and extracted with ethyl acetate (2×100 mL). The combined organics were dried over sodium sulfate, filtered, and evaporated under reduced pressure to afford a crude product as a light brown sticky solid. The crude material was purified by column chromatography (ethyl acetate/hexane as solvent system) to afford 1-(6-((4,4-difluorocyclohexyl)amino)-2-(4-methylthiazol-2-yl)pyrimidin-4-yl)ethan-1-one (6.1 g, 17.32 mmol, 73%) as an off-white solid. MS (MH+): m/z=353.0.

Step 3:

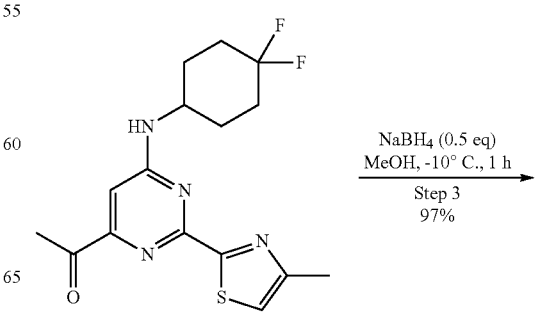

-continued

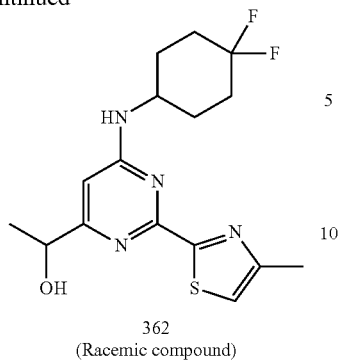

362
(Racemic compound)

A round-bottomed flask equipped with a teflon-coated stir bar was charged with 1-(6-((4,4-difluorocyclohexyl)amino)-2-(4-methylthiazol-2-yl)pyrimidin-4-yl)ethan-1-one (5.6 g, 15.90 mmol, 1.0 eq) in methanol (80 mL) at −10° C. followed by sodium borohydride (0.302 g, 7.95 mmol, 0.5 eq). The reaction mixture was stirred at same temperature for 1 hour and completion of reaction was determined by LCMS. The reaction mixture was quenched with water and concentrated under reduced pressure to remove methanol. The residue was diluted with ice cold water (100 mL) and extracted with ethyl acetate (2×100 mL). The combined organics were dried over sodium sulfate, filtered, and evaporated under reduced pressure to afford 1-(6-((4,4-difluorocyclohexyl)amino)-2-(4-methylthiazol-2-yl)pyrimidin-4-yl)ethan-1-ol 4 (5.5 g, 15.53 mmol, 97%) as an off-white solid of racemic mixture. MS (MH+): m/z=355.0.

Step 4:

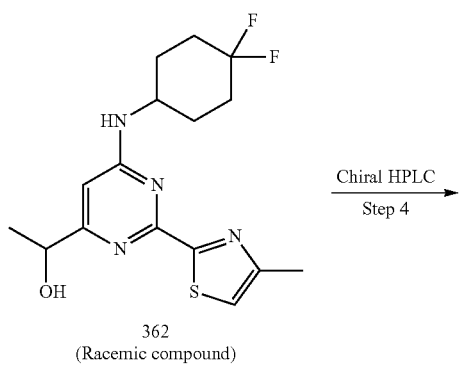

-continued

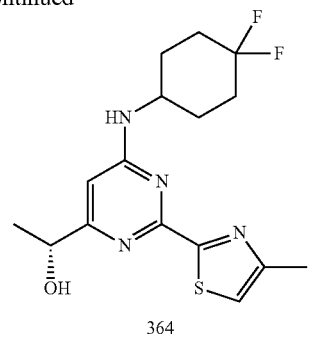

364

The racemic compound 1-(6-((4,4-difluorocyclohexyl)amino)-2-(4-methylthiazol-2-yl)pyrimidin-4-yl)ethan-1-ol Compound 362 (5.5 g) was purified by chiral HPLC (Column: Chiralpak-IC (250*20*5.0μ); Mobile phase-A: N-Hexane (0.1% DEA), Mobile phase-B: IPA:DCM (90:10) isocratic: 50:50 (A:B); Flow rate: 15.0 ml/min; 120/inj; Run time: 15 min) to afford (S)-1-(6-((4,4-difluorocyclohexyl)amino)-2-(4-methylthiazol-2-yl)pyrimidin-4-yl)ethan-1-ol Compound 363 (2.1 g, 5.93 mmol, 38%) as an off-white solid from first eluting fractions (Peak-1, RT=4.24 min.). MS (MH+): m/z=355.0. $^1$H NMR (400 MHz, DMSO-d$_6$): δ 7.59-7.57 (d, J=6.0 Hz, 1H), 7.37 (s, 1H), 6.64 (s, 1H), 5.37-5.36 (d, J=4.4 Hz, 1H), 4.52-4.50 (t, J=11.2 Hz, 5.6 Hz, 1H), 4.05 (bs, 1H), 2.43 (s, 3H), 2.10-1.96 (m, 6H), 1.62-1.59 (m, 2H), 1.35-1.33 (d, J=6.4 Hz, 3H). Other enantiomer: (R)-1-(6-((4,4-difluorocyclohexyl)amino)-2-(4-methylthiazol-2-yl)pyrimidin-4-yl)ethan-1-ol Compound 364 (2.05 g, 5.78 mmol, 37%) as an off-white solid from second eluting fractions (Peak-2, RT=6.45 min.). MS (MH+): m/z=355.0. $^1$H NMR (400 MHz, DMSO-d$_6$): δ 7.60-7.59 (d, J=5.6 Hz, 1H), 7.37 (s, 1H), 6.64 (s, 1H), 5.38 (bs, 1H), 4.52-4.51 (d, J=6.8 Hz, 1H), 4.10 (bs, 1H), 2.43 (s, 3H), 2.10-1.91 (m, 6H), 1.65-1.57 (m, 2H), 1.35-1.34 (d, J=6.8 Hz, 3H).

Example 268

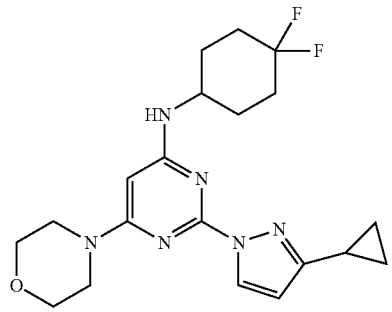 [SMILES: FC1(F)CCC(Nc2cc(N3CCOCC3)nc(-n3ccc(C4CC4)n3)n2)CC1]

Step 1:

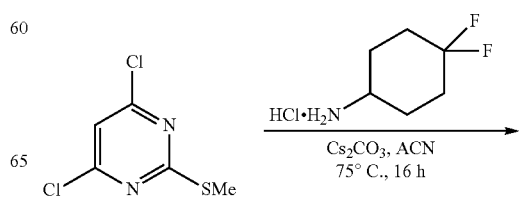

-continued

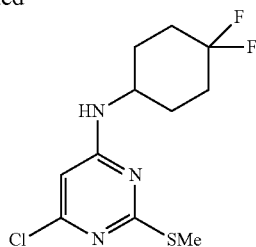

A 1000-mL three-necked, flame-dried, round-bottomed flask, equipped with a teflon-coated stir bar (3 cm), one septa (neck 1), stopper (neck 3) and reflux condenser equipped with nitrogen gas inlet-outlet U-tube adaptor filled with oil (Neck 2), was charged with a solution of 4,6-dichloro-2-(methylthio)pyrimidine (150 g, 768.94 mmol, 1.0 equiv.) in acetonitrile (1500 mL) followed by 4,4-difluorocyclohexylamine hydrochloride (158.35 g, 922.733 mmol) and cesium carbonate (526 g, 1614 mmol, 2.1 equiv.). The reaction mixture was heated at 75° C. for 16 h. The reaction mixture was filtered to remove cesium carbonate, then the filtrate was concentrated under reduced pressure to afford 210 g (93% yield) of 6-chloro-N-(4,4-difluorocyclohexyl)-2-(methylthio)pyrimidin-4-amine as a pale yellow solid. MS (MH+): m/z=294.0.

Step 2:

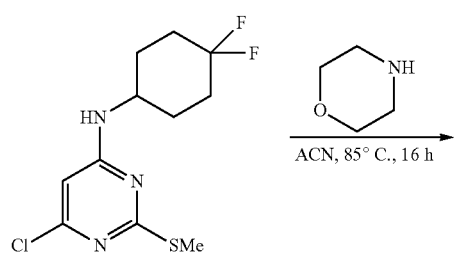

A solution of 6-chloro-N-(4,4-difluorocyclohexyl)-2-(methylthio)pyrimidin-4-amine (60 g, 204.24 mmol, 1.0 equiv.) and morpholine (35.6 mL, 408.48 mmol, 2.0 equiv.) in acetonitrile (600 mL) was heated at 85° C. in a sealed tube for 16 h. After completion of the reaction, the reaction mixture was concentrated, and the resulting residue was quenched with ice cold water. The obtained solid was filtered and washed with water (500 mL), hexane (250 mL), dried under high vacuum to afford N-(4,4-difluorocyclohexyl)-2-(methylthio)-6-morpholinopyrimidin-4-amine as an off-white solid (62 g, 88% yield). MS (MH+): m/z=345.2.

Step 3:

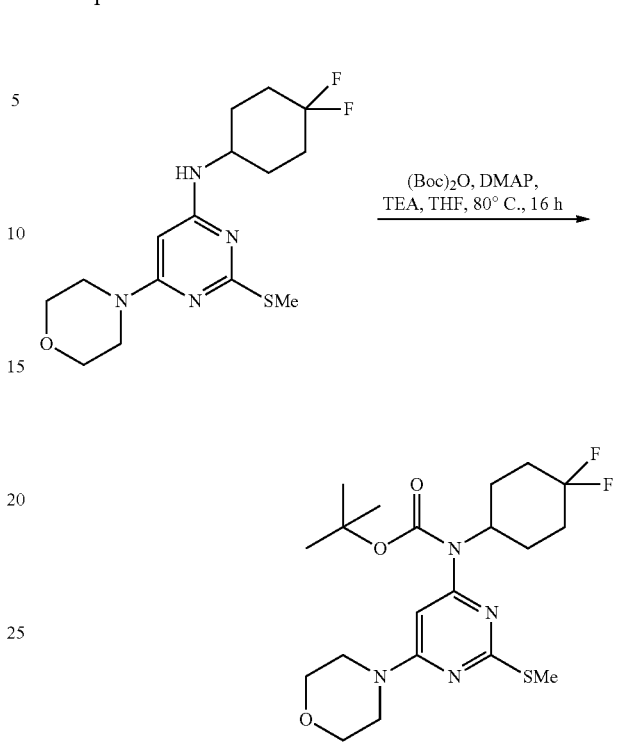

A 100-mL three-necked, flame-dried, round-bottomed flask, equipped with a teflon-coated stir bar (3 cm), one septa (neck 1), stopper (neck 3) and reflux condenser equipped with nitrogen gas inlet-outlet U-tube adaptor filled with oil (Neck 2), was charged with a solution of N-(4,4-difluorocyclohexyl)-2-(methylthio)-6-morpholino pyrimidin-4-amine (1 g, 2.90 mmol) in tetrahydrofuran (15 mL) followed by 4-N,N-dimethylaminopyridine (0.1 g, 0.87 mmol, 0.3 equiv.), triethylamine (1.2 mL, 8.71 mmol, 3.0 equiv.) and Boc anhydride (3.16 g, 14.51 mmol, 5.0 equiv.) then the reaction mixture was heated at 80° C. for 16 h. After completion of the reaction, the reaction mixture was quenched with water and extracted with ethyl acetate (2×75 mL). The combined organic layer was dried over anhydrous sodium sulfate and concentrated to afford tert-butyl (4,4-difluorocyclohexyl)(2-(methylthio)-6-morpholino pyrimidin-4-yl)carbamate as a yellow gum (1.1 g, 85%). MS (MH+): m/z=445.2.

Step 4:

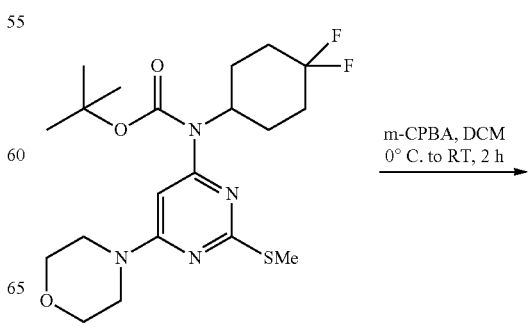

-continued

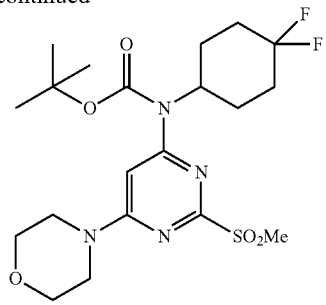

A 100-mL single neck round bottom flask, connected with reflux condenser equipped with nitrogen gas inlet-outlet U-tube adaptor filled with oil, a teflon-coated stir bar (1 cm), was charged with a solution of tert-butyl (4,4-difluorocyclohexyl)(2-(methylthio)-6-morpholinopyrimidin-4-yl)carbamate (50 g, 112.47 mmol) in dichloromethane (600 mL) followed by 3-chloroperbenzoic acid (m-chloroperbenzoic acid) (58.2 g, 337.42 mmol, 3.0 equiv.) at 0° C. The reaction mixture was slowly warmed to rt and stirred for 30 min. After the completion of the reaction, the reaction mixture was quenched with saturated bicarbonate solution and extracted with dichloromethane (2×250 mL). The combined organic layer was dried over anhydrous sodium sulfate and concentrated to afford tert-butyl (4,4-difluorocyclohexyl)(2-(methylsulfonyl)-6-morpholinopyrimidin-4-yl)carbamate as an off-white gum (52 g, 97% yield). MS (MH+): m/z=477.3.

Step 5:

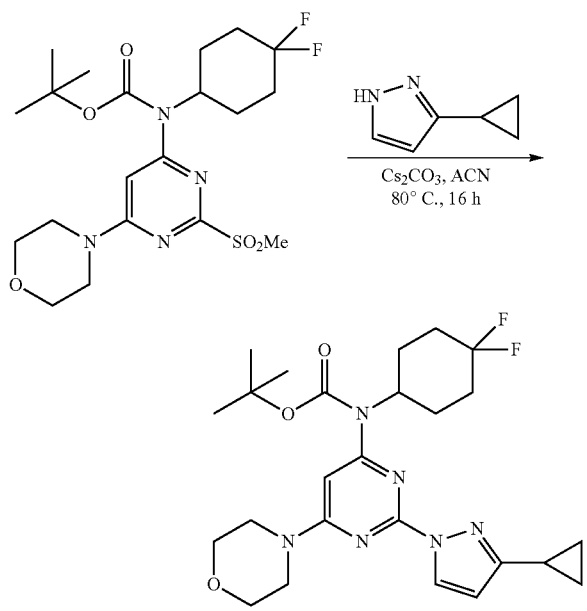

A 100-mL single neck round bottom flask, connected with reflux condenser equipped with nitrogen gas inlet-outlet U-tube adaptor filled with oil, a teflon-coated stir bar (2 cm), was charged with a solution of tert-butyl (4,4-difluorocyclohexyl)(2-(methylsulfonyl)-6-morpholinopyrimidin-4-yl) carbamate (0.9 g, 1.88 mmol) in acetonitrile (10 mL) followed by 3-cyclopropyl-1H-pyrazole (0.3 g, 2.83 mmol, 1.5 equiv.) and cesium carbonate (1.23 g, 3.77 mmol, 2.0 equiv.). The reaction mixture was heated at 80° C. for 16 hours, and completion of reaction was determined by TLC and LCMS. The reaction mixture was filtered and the filtrate was concentrated. The crude product was purified through column chromatography using 60-120 silica gel with ethyl acetate-pet ether as solvent system. The isolated material was dried under vacuum to afford tert-butyl (2-(3-cyclopropyl-1H-pyrazol-1-yl)-6-morpholinopyrimidin-4-yl)(4,4-difluorocyclohexyl)carbamate as an off-white solid (0.8 g, 84%). MS (MH+): m/z=505.

Step 6:

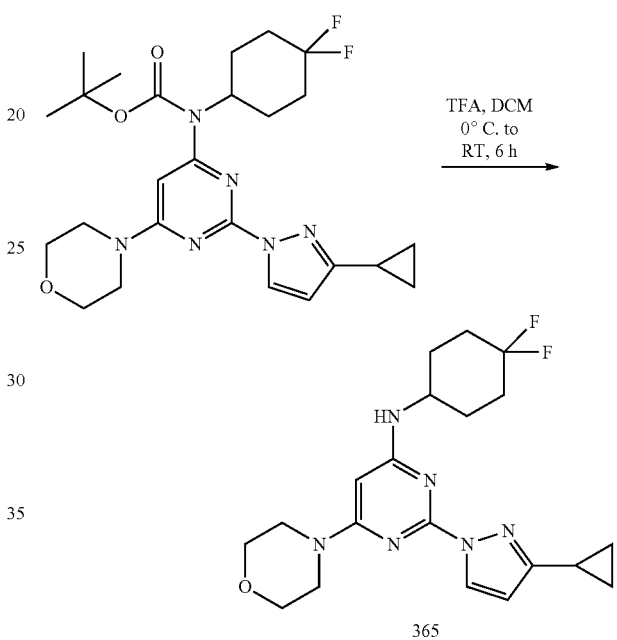

A 100-mL three-necked, flame-dried, round-bottomed flask, equipped with a teflon-coated stir bar (2 cm), one septa (necks 1), stopper (neck 3) and nitrogen gas inlet-outlet U-tube adaptor filled with oil (Neck 2), was charged with a solution tert-butyl (2-(3-cyclopropyl-1H-pyrazol-1-yl)-6-morpholinopyrimidin-4-yl)(4,4-difluorocyclohexyl)carbamate (1.2 g, 1.98 mmol, 1 eq) in dichloromethane (40 mL) followed by trifluoroacetic acid (2.5 mL, 32.55 mmol, 16.4 eq) at 0° C. The reaction mixture was slowly warmed to rt and stirred at same temperature for 6 hours. The completion of reaction was determined by TLC and UPLC. The reaction mixture was concentrated and the resulting residue was quenched with 10% saturated sodium bicarbonate solution, extracted with ethyl acetate (2×100 mL), and concentrated under reduced pressure to afford crude product. The crude product was purified through column chromatography using 60-120 silica gel, ethyl acetate-pet ether as solvent system. The resulting solid was dried under vacuum to afford 2-(3-cyclopropyl-1H-pyrazol-1-yl)-N-(4,4-difluorocyclohexyl)-6-morpholinopyrimidin-4-amine (Compound 365) (0.73 g, 90%). MS (MH+): m/z=405. Analytical Data: $^1$H-NMR (400 MHz, DMSO-d$_6$): δ 8.39 (d, J=2.4 Hz, 1H), 7.08 (d, J=8.0 Hz, 1H), 6.14 (d, J=2.80 Hz, 1H), 5.53 (s, 1H), 3.88

(s, 1H), 3.69-3.67 (m, 4H), 3.50 (m, 4H), 1.99-1.90 (m, 7H), 1.56-1.54 (m, 2H), 0.93-0.89 (m, 2H), 0.72-0.71 (m, 2H).

Example 269

N-(4,4-difluorocyclohexyl)-2-(3-methyl-1H-pyrazol-1-yl)-6-morpholinopyrimidin-4-amine Step 1:

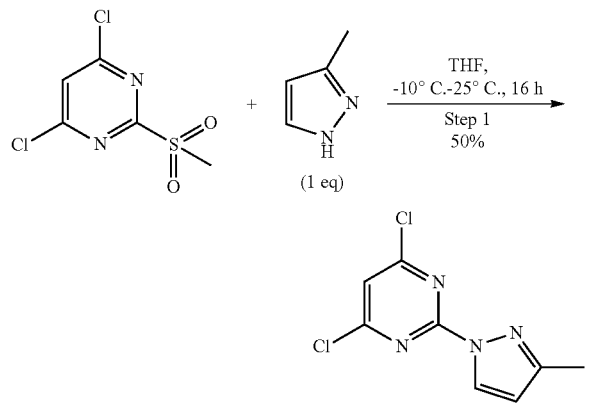

A round-bottomed flask equipped with a teflon-coated stir bar was charged with 4,6-dichloro-2-(methylsulfonyl)pyrimidine (20.0 g, 88.080 mmol, 1.0 eq) in tetrahydrofuran at −10° C. and 3-methyl-1H-pyrazole (7.23 g, 88.080 mmol, 1.0 equiv.) was added dropwise over a period of five minutes via syringe. The reaction mixture was stirred for 16 hours at 25° C. and completion of reaction was determined by TLC. The reaction mixture was portioned between water (500 mL) and ethyl acetate (500 mL). The organic layer was separated and the aqueous layer was extracted with ethyl acetate (2*100 mL). The combined organic layer was dried over sodium sulfate, filtered, and concentrated under reduced pressure to afford crude product which was purified by column chromatography (ethyl acetate/hexane as solvent system) to afford 4,6-dichloro-2-(3-methyl-1H-pyrazol-1-yl)pyrimidine (10.0 g, 43.859 mmol, 50% yield) as a white solid pure form. MS (MH+): m/z=229.1.

Step 2:

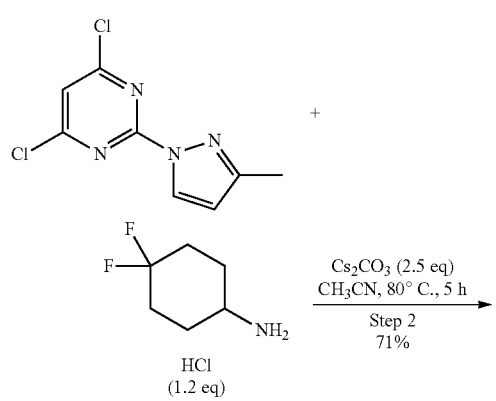

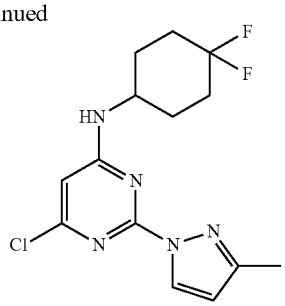

A round-bottomed flask equipped with a teflon-coated stir bar was charged with 2,4-dichloro-6-methylpyrimidine (11.0 g, 48.24 mmol, 1.0 equiv.), 4,4-difluorocyclohexan-1-amine hydrochloride (9.89 g, 57.89 mmol, 1.2 equiv.), and $Cs_2CO_3$ (39.19 g, 120.61 mmol, 2.5 equiv.) in acetonitrile (200 mL). The reaction mixture was stirred for five hours at 80° C. and the completion of reaction was determined by TLC. The reaction mixture was cooled to room temperature and partitioned between water (100 mL) and ethyl acetate (200 mL). The organic layer was separated and the aqueous layer was extracted ethyl acetate (2×100 mL). The combined organic layer was dried over sodium sulfate, filtered, and concentrated under reduced pressure to afford crude product which was purified by column chromatography (ethyl acetate/hexane as solvent system) to afford 6-chloro-N-(4,4-difluorocyclohexyl)-2-(3-methyl-1H-pyrazol-1-yl)pyrimidin-4-amine (11.0 g, 33.62 mmol, 71%) as an off-white solid. MS (MH+): m/z=328.1.

Step 3:

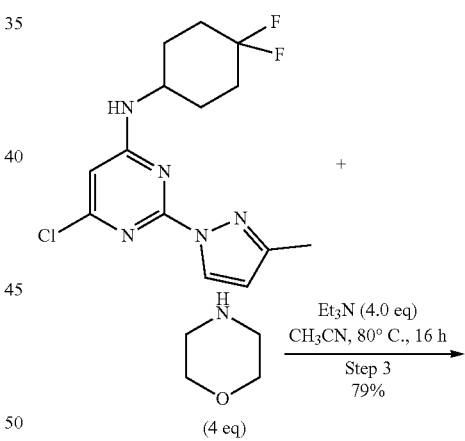

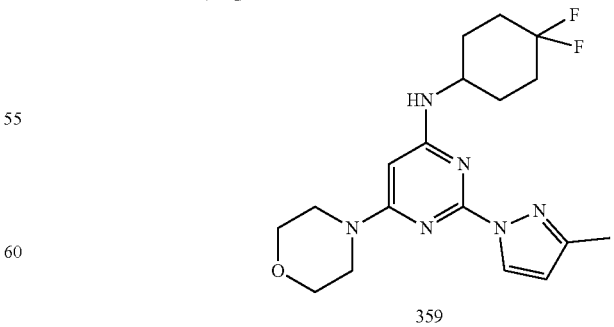

A round-bottomed flask equipped with a teflon-coated stir bar was charged with 6-chloro-N-(4,4-difluorocyclohexyl)-2-(3-methyl-1H-pyrazol-1-yl)pyrimidin-4-amine (14.0 g, 42.79 mmol, 1.0 eq), morpholine (14.91 mL, 171.19 mmol, 4.0 eq), and triethylamine (23.89 mL, 171.19 mmol, 4.0 eq) in acetonitrile (200 mL). The reaction mixture was stirred for 16 hours at 80° C. and completion of reaction was determined by TLC. The reaction mixture was cooled to room temperature and partitioned between water (100 mL) and ethyl acetate (300 mL).

The organic layer was separated and the aqueous layer was extracted ethyl acetate (2×100 mL). The combined organic layer was dried over sodium sulfate, filtered, and concentrated under reduced pressure to afford crude product which was purified by column chromatography (ethyl acetate/hexane as solvent system) to afford N-(4,4-difluoro-cyclohexyl)-2-(3-methyl-1H-pyrazol-1-yl)-6-morpholin-opyrimidin-4-amine (359) (12.8 g, 33.84 mmol, 79% yield) as an off-white solid. MS (MH+): m/z=379.2. Analytical Data: $^1$H NMR (400 MHz, DMSO-D6): δ 8.41 (d, J=2 Hz, 1H), 7.07 (d, J=8.3 Hz, 1H), 6.25 (d, J=2.4 Hz, 1H), 5.53 (s, 1H), 3.9 (bs, 1H), 3.67 (t, J=4.4 Hz, 4H), 3.49 (S, 4H), 2.23 (s, 3H), 2.23-1.97 (m, 3H), 1.92-1.90 (m, 3H), 1.55-1.53 (m, 2H).

Example 270

N-(4,4-difluorocyclohexyl)-2-(3,5-dimethyl-1H-pyrazol-1-yl)-6-methoxypyrimidin-4-amine Step 1:

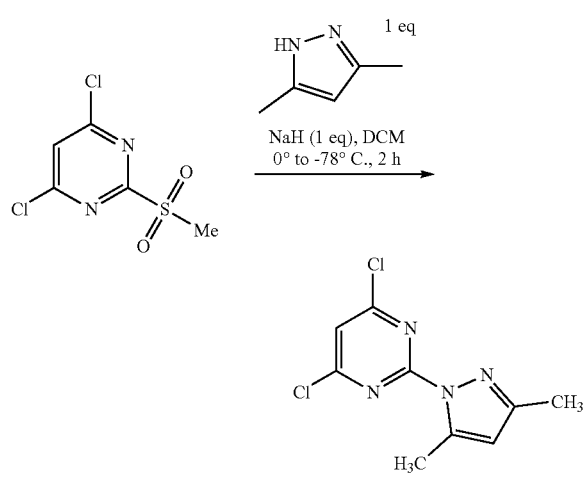

A 5000-mL four-necked, flame-dried, round-bottomed flask, equipped with a teflon-coated stir blade (5 cm) attached with glass rod (neck 1), stopper (neck 2), and addition funnel with stopper (neck 3) and a nitrogen gas inlet-outlet U-tube adaptor filled with oil (Neck 4), was charged with a suspension of sodium hydride (35.2 g, 880 mmol, 1 equiv.) in dichloromethane (1000 mL) was added 3,5-dimethylpyrazole (84.6 g, 880 mmol, 1 equiv.) at 0° C. and the reaction mixture was stirred at room temperature. After 30 min, 4,6-dichloro-2-(methylsulfonyl)pyrimidine (200 g, 880 mmol, 1 equiv.) (dissolved in dichloromethane (1000 mL)) was added dropwise through dropping funnel to the reaction mixture at −78° C. The reaction mixture was stirred at same temperature and the completion of reaction was determined by TLC and UPLC. After 2 h, the reaction mixture was quenched with water at −78° C. and diluted with dichloromethane. After 5 min, dichloromethane was decanted and washed with brine solution. The organic layer was dried over sodium sulfate, filtered, and concentrated under reduced pressure to afford crude product, which was purified by column chromatography using ethyl acetate and pet-ether as solvent to afford 4,6-dichloro-2-(3,5-dimethyl-1h-pyrazol-1-yl)pyrimidine (138 g, 567.71 mmol, 65%) as an off-white solid. MS (MH+): m/z=244.2.

Step 2:

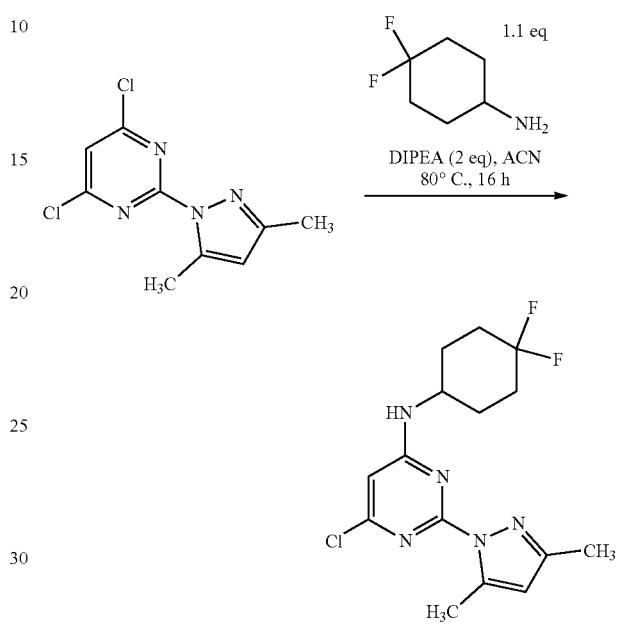

A 2000-mL three-necked, flame-dried, round-bottomed flask, equipped with a teflon-coated stir bar (5 cm), one septa (neck 1), stopper (neck 3) and reflux condenser equipped with nitrogen gas inlet-outlet U-tube adaptor filled with oil (Neck 2), was charged with a solution of 4,6-dichloro-2-(3,5-dimethyl-1h-pyrazol-1-yl)pyrimidine (136 g, 559.4 mmol, 1 equiv.) in acetonitrile (1500 mL) followed by 4,4-difluo-rocyclohexylamine hydrochloride (105.6 g, 615.4 mmol, 1.1 equiv.) and N,N-diisopropyl ethylamine (194.88 mL, 1118.8 mmol, 2 equiv). The reaction mixture was heated at 80° C. for 16 h. The completion of reaction was determined by TLC and UPLC. The reaction mixture was concentrated and the residue was triturated with water (500 mL). The resulting solid was filtered, washed with pet-ether, dried under vacuum to afford 6-chloro-N-(4,4-difluorocyclohexyl)-2-(3,5-dimethyl-1h-pyrazol-1-yl)pyrimidin-4-amine (191 g, 556 mmol, >95%) as an off-white solid. MS (MH+): m/z=342.0.

Step 3:

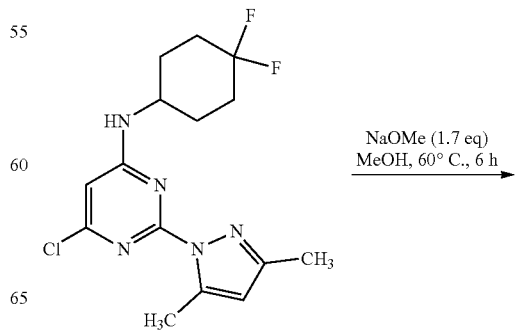

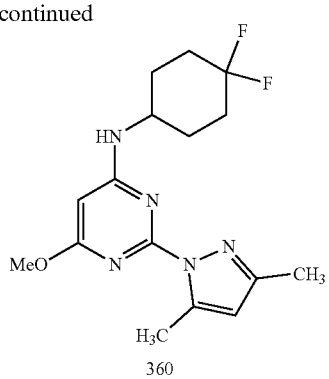

360

A 250 mL three-necked, flame-dried, round-bottomed flask, equipped with a teflon-coated stir bar (2 cm), one septa (neck 1), stopper (neck 3) and reflux condenser equipped with nitrogen gas inlet-outlet U-tube adaptor filled with oil (Neck 2), was charged with a solution of 6-chloro-N-(4,4-difluorocyclohexyl)-2-(3,5-dimethyl-1h-pyrazol-1-yl)pyrimidin-4-amine (20 g, 58.51 mmol, 1 equiv.) in methanol followed by sodium methoxide (21% in methanol, 5.37 g, 99.47 mmol, 1.7 equiv.). The reaction was heated to 60° C., and completion of reaction was determined by TLC and UPLC. After 5 h, the reaction mixture was concentrated under reduced pressure and the residue was diluted with ethyl acetate, washed with water, and washed with brine solution. The organic layer was dried over sodium sulfate, filtered, and concentrated under reduced pressure to afford the crude product which was purified by column chromatography using ethyl acetate in pet-ether as solvent system to afford N-(4,4-difluorocyclohexyl)-2-(3,5-dimethyl-1H-pyrazol-1-yl)-6-methoxypyrimidin-4-amine (360) [16 g (11 g (99% pure)+5 g (92% pure), 47.41 mmol, ~80%) as a white solid. MS (MH+): m/z=338.1. Analytical Data: $^1$H-NMR (400 MHz, DMSO-d$_6$): δ 7.45 (bs, 1H), 6.06 (s, 1H), 5.72 (s, 1H), 4.01 (bs, 1H), 3.85 (s, 3H), 2.55 (s, 3H), 2.17 (s, 3H), 2.11-1.82 (m, 6H), 1.60-1.55 (m, 2H).

Example 271

N-(4,4-difluorocyclohexyl)-6-methoxy-2-(4-methylthiazol-2-yl)pyrimidin-4-amine

Step 1:

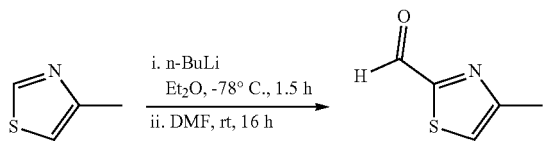

A three-necked round bottomed flask equipped with a teflon-coated stir bar was charged with diethyl ether (250 mL) and n-BuLi (241.98 mL, 604.96 mmol, 2.5M in hexane) was transferred at −78° C. A solution of 4-methylthiazole (50.0 g, 504.13 mmol) in diethyl ether (200 mL) was added over a period of 30 min. The reaction mixture was turned into pale yellow suspension. After 1.5 hours, DMF (58.54 mL, 756.20 mmol) was added and stirred at room temperature for 16 h. The progress of the reaction was monitored by TLC. After completion of the reaction, the mixture was poured into cold aq. HCl (400 mL, 4N) under stirring and separated the two layers. The organic layer was washed with cold aq. HCl (2×80 mL, 4N)). The combined aq. layers were slowly basified with K$_2$CO$_3$ (pH 7) and extracted with diethyl ether (3×150 mL). The combined organic layers were dried over sodium sulfate and evaporated to dryness at room temperature under vacuum to afford 4-methylthiazole-2-carbaldehyde (60.0 g, crude) as a pale yellow liquid. This crude material was used in the next step without further purification.

Step 2:

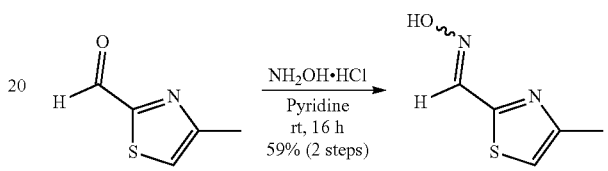

A two-necked round bottomed flask equipped with a teflon-coated stir bar was charged with 4-methylthiazole-2-carbaldehyde (60.0 g, crude) in pyridine (38.04 ml, 472.40 mmol). Hydroxylamine hydrochloride (32.82 g, 472.40 mmol) was added in portions over a period of 15 min. The reaction mixture was stirred at room temperature for 16 h under nitrogen atmosphere. The progress of the reaction was monitored by TLC. After completion of the reaction, the mixture was poured into ice cold water and stirred for 20 min, the obtained solid was filtered and dried under vacuum to afford 4-methylthiazole-2-carbaldehyde oxime (40.0 g, 281.69 mmol, 59% for two steps) as an off white solid. MS (MH+): m/z=143.0.

Step 3:

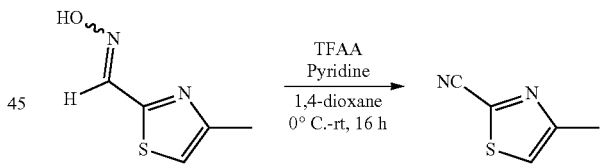

A two-necked round bottomed flask equipped with a teflon-coated stir bar was charged with a solution of 4-methylthiazole-2-carbaldehyde oxime (35.0 g, 246.44 mmol) and pyridine (87.33 mL, 1084.35 mmol) in 1,4-dioxane (140 mL). Trifluoroacetic anhydride (51.38 mL, 369.66 mmol) was added slowly at −10° C. and allowed to stir at room temperature for 16 h. The progress of the reaction was monitored by TLC. After completion of the reaction, the mixture was diluted with water (250 mL) and extracted with diethyl ether (3×350 mL). The combined organic layers were washed with water (2×250 mL), brine (100 mL) dried over sodium sulphate and concentrated under reduced pressure to afford 4-methylthiazole-2-carbonitrile (35.0 g, crude) as light brown liquid. This crude material was used in the next step without further purification. Analytical Data: $^1$H-NMR (400 MHz, DMSO-d$_6$): δ 7.90 (s, 1H), 2.51 (s, 3H).

Step 4:

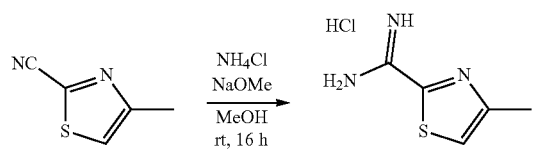

A two-necked round bottomed flask equipped with a teflon-coated stir bar was charged with 4-methylthiazole-2-carbonitrile (35.0 g, crude) in methanol (280 mL) and sodium methoxide (16.77 g, 310.45 mmol) was added. After stirring at room temperature for 3 h, ammonium chloride (30.19 g, 564.66 mmol) was added and stirred for another 16 h. The progress of the reaction was monitored by TLC. After completion of the reaction, the mixture was filtered and washed with methanol. The filtrate was concentrated under reduced pressure and the residue was triturated with diethyl ether (150 mL). The formed solid was filtered and dried under vacuum to afford 4-methylthiazole-2-carboximidamide hydrochloride (35.0 g, crude) as an off-white solid. This crude material was used in the next step without further purification. MS (MH+): m/z=142.0.

Step 5:

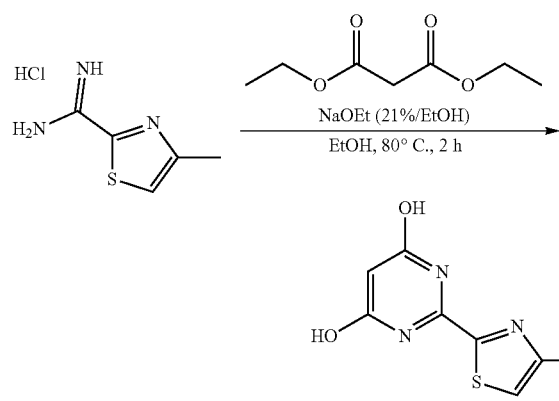

A two-necked round bottomed flask equipped with a teflon-coated stir bar was charged with 4-methylthiazole-2-carboximidamide hydrochloride (35.0 g, crude) in ethanol (350 mL) and diethyl malonate (150.81 mL, 988.64 mmol). Sodium ethoxide (320 mL, 988.64 mmol, 21% in EtOH) was added dropwise at room temperature and heated to 85° C. After 3 hours, the reaction mixture was concentrated under reduced pressure. Water (20 mL) was added and acidified with 1.5 N HCl (pH 2-3). The obtained solid was filtered and dried under vacuum to afford 2-(4-methylthiazol-2-yl)pyrimidine-4,6-diol (29.0 g, crude) as pale yellow solid. This crude material was used in the next step without further purification. MS (MH+): m/z=210.0.

Step 6:

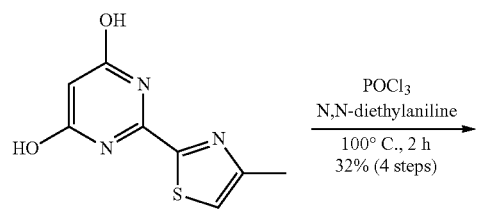

-continued

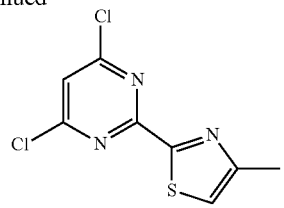

A two-necked round bottomed flask equipped with a teflon-coated stir bar was charged with a suspension of 2-(4-methylthiazol-2-yl)pyrimidine-4,6-diol (29.0 g, crude) and POCl₃ (290 mL). N,N-diethylaniline (37.84 mL, 235.85 mmol) was added at room temperature and heated reflux at 100° C. for 2 h. The progress of the reaction was monitored by TLC. Excess POCl₃ was removed by distillation. The residue was diluted with 500 mL cold water, neutralized with saturated sodium bicarbonate solution, extracted with diethyl ether (2×500 mL). The combined organic layers were washed with water (3×200 mL), brine (100 mL), dried over sodium sulfate and concentrated under reduced pressure. The residue was triturated with n-pentane (100 mL). The obtained solid was filtered and dried under vacuum to afford 2-(4,6-dichloropyrimidin-2-yl)-4-methylthiazole 7 (19.5 g, 79.59 mmol, 32% for four steps) as a pale yellow solid. MS (MH+): m/z=245.9.

Step 7:

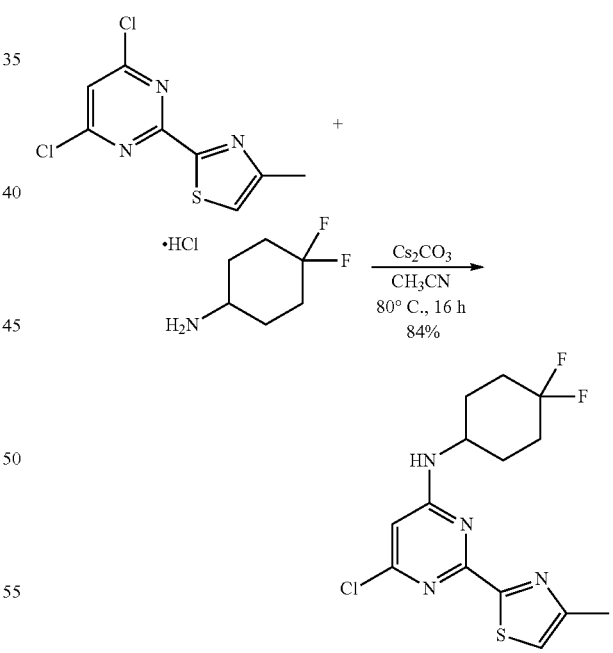

A two necked round bottomed flask equipped with a teflon-coated stir bar was charged with a suspension of 2-(4,6-dichloropyrimidin-2-yl)-4-methylthiazole (19.0 g, 77.56 mmol) and 4,4-difluorocyclohexan-1-amine hydrochloride (13.30 g, 77.56 mmol) in acetonitrile (190 mL). Cesium carbonate (37.89 g, 116.34 mmol) was added and the reaction mixture was heated at 80° C. for 16 h. The progress of the reaction was monitored by TLC. The reaction mixture was cooled to room temperature, filtered, and the solid was washed with ethyl acetate (500 mL). The filtrate was washed with water (2×100 mL), brine (100 mL), dried over sodium sulfate, and concentrated under reduced pressure. The residue was purified by column chromatography (60-120 silica gel) eluted with 15% EtOAc in hexane. Relevant fractions containing the required compound were combined and evaporated to dryness under reduced pressure to afford 6-chloro-N-(4,4-difluorocyclohexyl)-2-(4-methylthiazol-2-yl)pyrimidin-4-amine (22.5 g, 65.25 mmol, 84%) as off-white foam solid. MS (MH+): m/z=344.9.

Step 8:

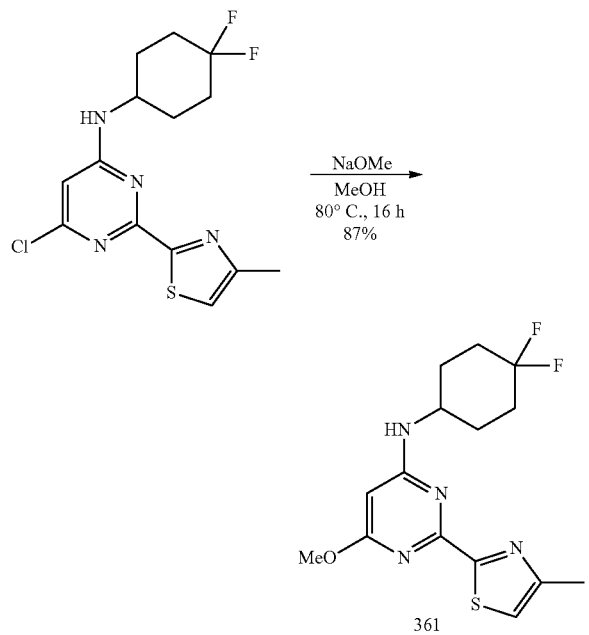

361

A two-necked round bottomed flask equipped with a teflon-coated stir bar was charged with 6-chloro-N-(4,4-difluorocyclohexyl)-2-(4-methylthiazol-2-yl)pyrimidin-4-amine (27.0 g, 78.47 mmol) in methanol (450 mL). Sodium methoxide (21.19 g, 392.36 mmol) was added and heated to 80° C. for 16 h. The progress of the reaction was monitored by TLC. Excess methanol was removed under reduced pressure and the residue was diluted with 10% aqueous ammonium chloride solution (100 mL) and extracted with ethyl acetate (3×150 mL). The combined organic layers were washed with water (2×100 mL), brine (100 mL), dried over sodium sulphate and concentrated under reduced pressure. The residue was purified by column chromatography (60-120 silica gel) eluting with 35-40% of EtOAc in hexane. Relevant fractions containing the target compound were combined and evaporated to dryness under reduced pressure to afford N-(4,4-difluorocyclohexyl)-6-methoxy-2-(4-methylthiazol-2-yl)pyrimidin-4-amine (361) (23.4 g, 68.82 mmol, 87%) as an off-white solid. MS (MH+): m/z=341.0. Analytical Data: $^1$H-NMR (400 MHz, DMSO-$d_6$): δ 7.41 (s, 1H), 7.40 (s, 1H), 5.81 (s, 1H), 3.87 (s, 3H), 2.43 (s, 3H), 2.08-1.89 (m, 6H), 1.61-1.52 (m, 2H).

Example 272

(S)-1-(6-((4,4-difluorocyclohexyl)amino)-2-(4-methylthiazol-2-yl)pyrimidin-4-yl)ethan-1-ol Step 1:

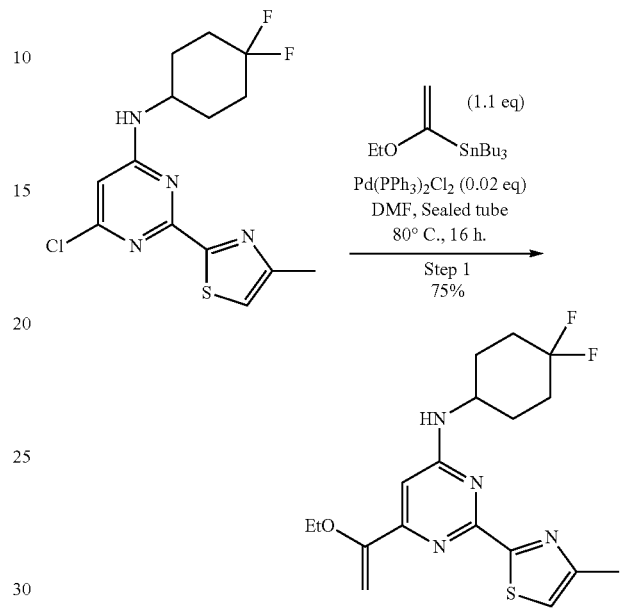

A 250-mL sealed tube, equipped with a teflon-coated stir bar (2 cm), was charged with a solution of 6-chloro-N-(4,4-difluorocyclohexyl)-2-(4-methylthiazol-2-yl)pyrimidin-4-amine (4.9 g, 14.24 mmol, 1.0 eq) and tributyl(1-ethoxyvinyl)stannane (5.65 g, 15.66 mmol, 1.1 eq) in N,N-dimethylformamide (60 mL). The reaction mixture was degassed using argon gas for 5-10 min, followed by addition of bis(triphenylphosphine)palladium(II) dichloride (0.2 g, 0.28 mmol, 0.02 eq). The reaction mixture was sealed and heated at 80° C. for 16 h (completion of reaction was determined by LCMS) and cooled to room temperature. The reaction mixture was diluted with water (300 mL) and extracted with ethyl acetate (2×150 mL). The combined organics were dried over sodium sulfate, filtered, and evaporated to afford a crude product as a light brown sticky solid. The crude material was purified by column chromatography (ethyl acetate/hexane as solvent system) to afford N-(4,4-difluorocyclohexyl)-6-(1-ethoxyvinyl)-2-(4-methylthiazol-2-yl)pyrimidin-4-amine (4.1 g, 10.78 mmol, 75%) as an off-white solid. MS (MH+): m/z=381.0.

Step 2:

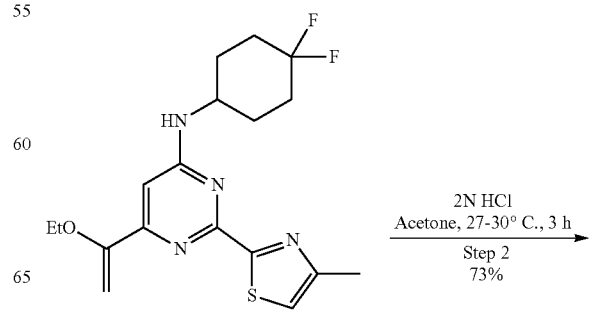

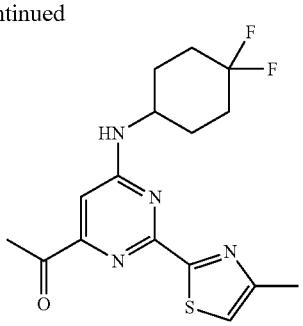

A round-bottomed flask equipped with a teflon-coated stir bar was charged with N-(4,4-difluorocyclohexyl)-6-(1-ethoxyvinyl)-2-(4-methylthiazol-2-yl)pyrimidin-4-amine (9.0 g, 23.67 mmol, 1.0 eq) in acetone (120 mL) followed by addition of 2N hydrochloric acid aqueous solution (20 mL). The reaction mixture was stirred at room temperature for 3 hours and completion of reaction was determined by LCMS. The reaction mixture was concentrated to remove acetone, diluted with ice cold water (100 mL), basified with saturated sodium by carbonate solution, and extracted with ethyl acetate (2×100 mL). The combined organics were dried over sodium sulfate, filtered, and evaporated under reduced pressure to afford a crude product as a light brown sticky solid. The crude material was purified by column chromatography (ethyl acetate/hexane as solvent system) to afford 1-(6-((4,4-difluorocyclohexyl)amino)-2-(4-methylthiazol-2-yl)pyrimidin-4-yl)ethan-1-one (6.1 g, 17.32 mmol, 73%) as an off-white solid. MS (MH+): m/z=353.0.

Step 3:

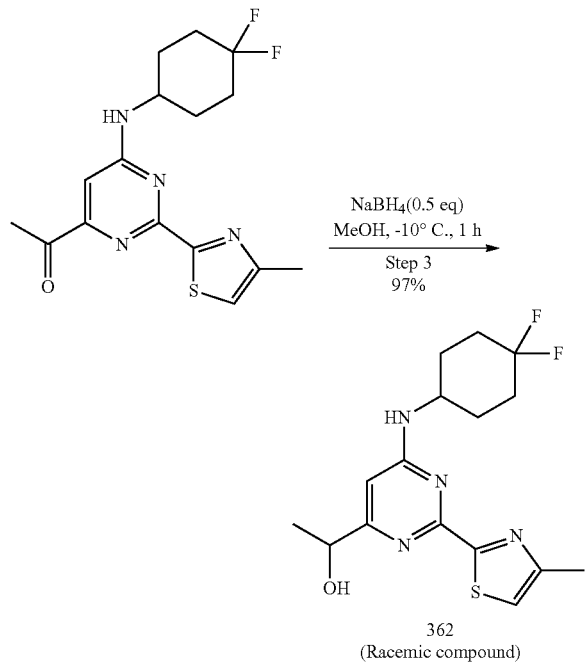

A round-bottomed flask equipped with a teflon-coated stir bar was charged with 1-(6-((4,4-difluorocyclohexyl)amino)-2-(4-methylthiazol-2-yl)pyrimidin-4-yl)ethan-1-one (5.6 g, 15.90 mmol, 1.0 eq) in methanol (80 mL) at −10° C. followed by sodium borohydride (0.302 g, 7.95 mmol, 0.5 eq). The reaction mixture was stirred at same temperature for 1 hour and completion of reaction was determined by LCMS. The reaction mixture was quenched with water and concentrated under reduced pressure to remove methanol. The residue was diluted with ice cold water (100 mL) and extracted with ethyl acetate (2×100 mL). The combined organics were dried over sodium sulfate, filtered, and evaporated under reduced pressure to afford 1-(6-((4,4-difluorocyclohexyl)amino)-2-(4-methylthiazol-2-yl)pyrimidin-4-yl)ethan-1-ol 4 (5.5 g, 15.53 mmol, 97%) as an off-white solid of racemic mixture. MS (MH+): m/z=355.0.

Step 4:

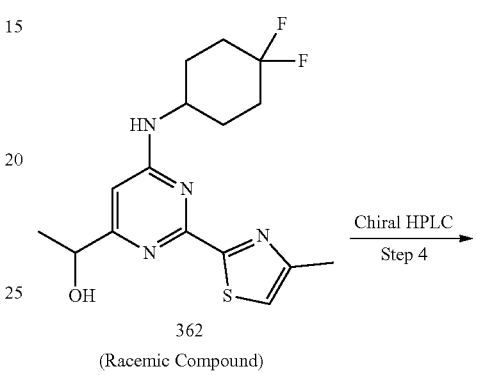

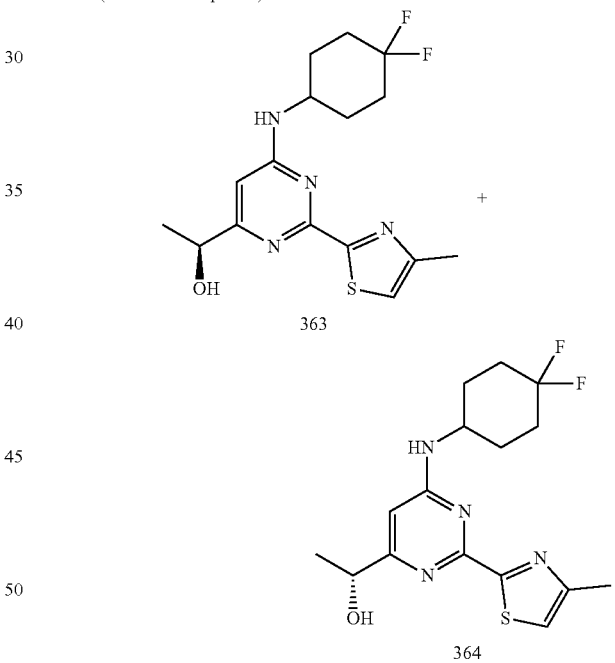

The racemic compound 1-(6-((4,4-difluorocyclohexyl)amino)-2-(4-methylthiazol-2-yl)pyrimidin-4-yl)ethan-1-ol 362 (5.5 g) was purified by chiral HPLC (Column: Chiralpak-IC (250*20*5.0μ); Mobile phase-A: N-Hexane (0.1% DEA), Mobile phase-B: IPA:DCM (90:10) isocratic: 50:50 (A:B); Flow rate: 15.0 ml/min; 120/inj; Run time: 15 min) to afford (S)-1-(6-((4,4-difluorocyclohexyl)amino)-2-(4-methylthiazol-2-yl)pyrimidin-4-yl)ethan-1-ol 363 (2.1 g, 5.93 mmol, 38%) as an off-white solid from first eluting fractions (Peak-1, RT=4.24 min.). MS (MH+): m/z=355.0. $^1$H NMR (400 MHz, DMSO-d$_6$): δ 7.59-7.57 (d, J=6.0 Hz, 1H), 7.37 (s, 1H), 6.64 (s, 1H), 5.37-5.36 (d, J=4.4 Hz, 1H), 4.52-4.50 (t, J=11.2 Hz, 5.6 Hz, 1H), 4.05 (bs, 1H), 2.43 (s, 3H), 2.10-1.96 (m, 6H), 1.62-1.59 (m, 2H), 1.35-1.33 (d, J=6.4 Hz, 3H). Other enantiomer: (R)-1-(6-((4,4-difluorocyclohexyl)amino)-2-(4-methylthiazol-2-yl)pyrimidin-4-yl)ethan-1-ol 364 (2.05 g, 5.78 mmol, 37%) as an off-white solid from second eluting fractions (Peak-2, RT=6.45 min.). MS (MH+): m/z=355.0. $^1$H NMR (400 MHz, DMSO-d$_6$): δ 7.60-7.59 (d, J=5.6 Hz, 1H), 7.37 (s, 1H), 6.64 (s, 1H), 5.38 (bs, 1H), 4.52-4.51 (d, J=6.8 Hz, 1H), 4.10 (bs, 1H), 2.43 (s, 3H), 2.10-1.91 (m, 6H), 1.65-1.57 (m, 2H), 1.35-1.34 (d, J=6.8 Hz, 3H).

Example 273

2-(3-cyclopropyl-1H-pyrazol-1-yl)-N-(4,4-difluorocyclohexyl)-6-morpholinopyrimidin-4-amine Step 1:

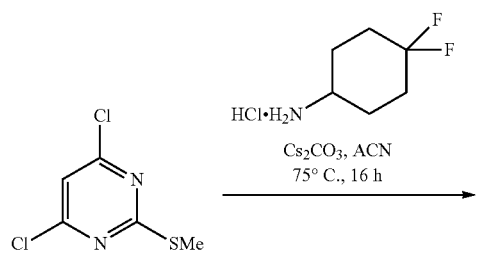

A 1000-mL three-necked, flame-dried, round-bottomed flask, equipped with a teflon-coated stir bar (3 cm), one septa (neck 1), stopper (neck 3) and reflux condenser equipped with nitrogen gas inlet-outlet U-tube adaptor filled with oil (Neck 2), was charged with a solution of 4,6-dichloro-2-(methylthio)pyrimidine (150 g, 768.94 mmol, 1.0 equiv.) in acetonitrile (1500 mL) followed by 4,4-difluorocyclohexylamine hydrochloride (158.35 g, 922.733 mmol) and cesium carbonate (526 g, 1614 mmol, 2.1 equiv.). The reaction mixture was heated at 75° C. for 16 h. The reaction mixture was filtered to remove cesium carbonate, then the filtrate was concentrated under reduced pressure to afford 210 g (93% yield) of 6-chloro-N-(4,4-difluorocyclohexyl)-2-(methylthio)pyrimidin-4-amine as a pale yellow solid. MS (MH+): m/z=294.0.

Step 2:

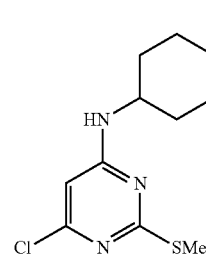

-continued

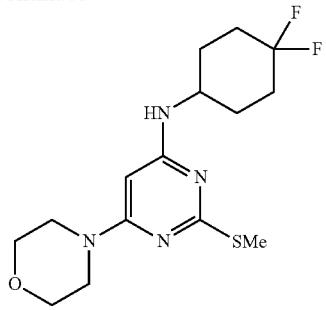

A solution of 6-chloro-N-(4,4-difluorocyclohexyl)-2-(methylthio)pyrimidin-4-amine (60 g, 204.24 mmol, 1.0 equiv.) and morpholine (35.6 mL, 408.48 mmol, 2.0 equiv.) in acetonitrile (600 mL) was heated at 85° C. in a sealed tube for 16 h. After completion of the reaction, the reaction mixture was concentrated, and the resulting residue was quenched with ice cold water. The obtained solid was filtered and washed with water (500 mL), hexane (250 mL), dried under high vacuum to afford N-(4,4-difluorocyclohexyl)-2-(methylthio)-6-morpholinopyrimidin-4-amine as an off-white solid (62 g, 88% yield). MS (MH+): m/z=345.2.

Step 3:

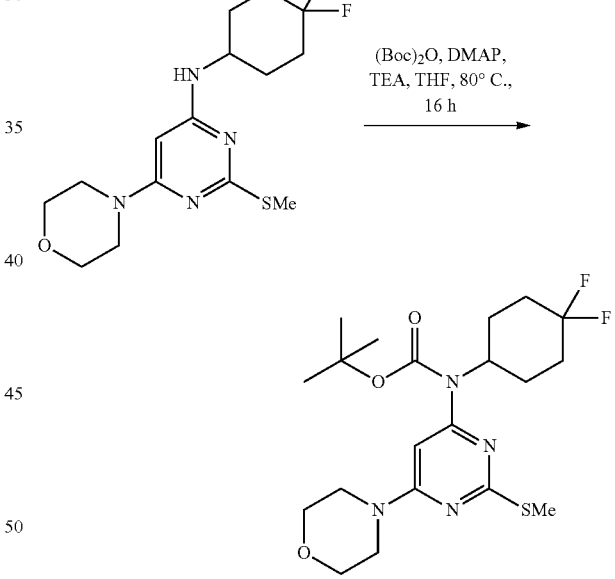

A 100-mL three-necked, flame-dried, round-bottomed flask, equipped with a teflon-coated stir bar (3 cm), one septa (neck 1), stopper (neck 3) and reflux condenser equipped with nitrogen gas inlet-outlet U-tube adaptor filled with oil (Neck 2), was charged with a solution of N-(4,4-difluorocyclohexyl)-2-(methylthio)-6-morpholino pyrimidin-4-amine (1 g, 2.90 mmol) in tetrahydrofuran (15 mL) followed by 4-N,N-dimethylaminopyridine (0.1 g, 0.87 mmol, 0.3 equiv.), triethylamine (1.2 mL, 8.71 mmol, 3.0 equiv.) and Boc anhydride (3.16 g, 14.51 mmol, 5.0 equiv.) then the reaction mixture was heated at 80° C. for 16 h. After completion of the reaction, the reaction mixture was quenched with water and extracted with ethyl acetate (2×75 mL). The combined organic layer was dried over anhydrous sodium sulfate and concentrated to afford tert-butyl (4,4-difluorocyclohexyl)(2-(methylthio)-6-morpholino pyrimidin-4-yl)carbamate as a yellow gum (1.1 g, 85%). MS (MH+): m/z=445.2.

Step 4:

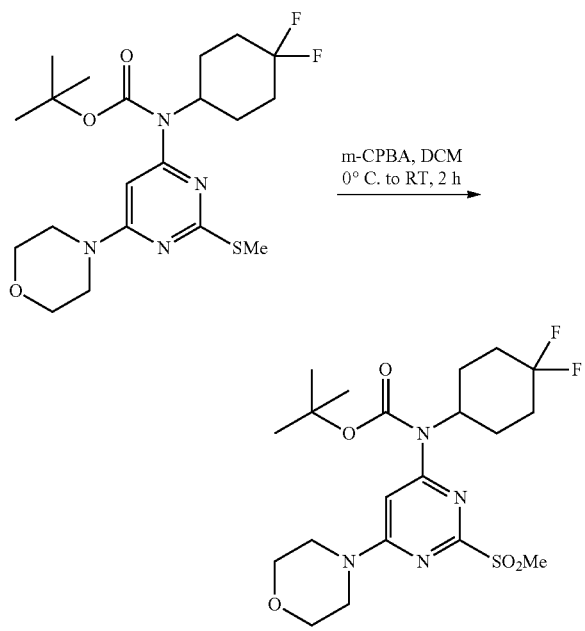

A 100-mL single neck round bottom flask, connected with reflux condenser equipped with nitrogen gas inlet-outlet U-tube adaptor filled with oil, a teflon-coated stir bar (1 cm), was charged with a solution of tert-butyl (4,4-difluorocyclohexyl)(2-(methylthio)-6-morpholinopyrimidin-4-yl)carbamate (50 g, 112.47 mmol) in dichloromethane (600 mL) followed by 3-chloroperbenzoic acid (m-chloroperbenzoic acid) (58.2 g, 337.42 mmol, 3.0 equiv.) at 0° C. The reaction mixture was slowly warmed to rt and stirred for 30 min. After the completion of the reaction, the reaction mixture was quenched with saturated bicarbonate solution and extracted with dichloromethane (2×250 mL). The combined organic layer was dried over anhydrous sodium sulfate and concentrated to afford tert-butyl (4,4-difluorocyclohexyl)(2-(methylsulfonyl)-6-morpholinopyrimidin-4-yl)carbamate as an off-white gum (52 g, 97% yield). MS (MH+): m/z=477.3.

Step 5:

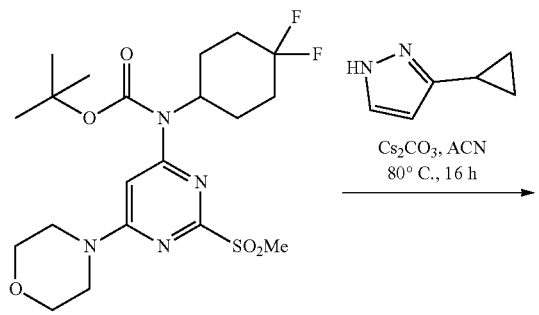

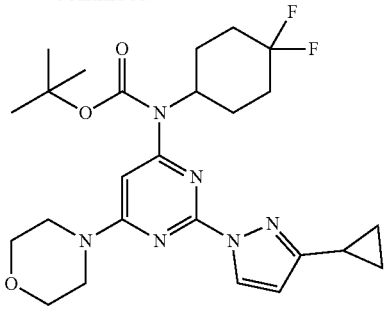

A 100-mL single neck round bottom flask, connected with reflux condenser equipped with nitrogen gas inlet-outlet U-tube adaptor filled with oil, a teflon-coated stir bar (2 cm), was charged with a solution of tert-butyl (4,4-difluorocyclohexyl)(2-(methylsulfonyl)-6-morpholinopyrimidin-4-yl)carbamate (0.9 g, 1.88 mmol) in acetonitrile (10 mL) followed by 3-cyclopropyl-1H-pyrazole (0.3 g, 2.83 mmol, 1.5 equiv.) and cesium carbonate (1.23 g, 3.77 mmol, 2.0 equiv.). The reaction mixture was heated at 80° C. for 16 hours, and completion of reaction was determined by TLC and LCMS. The reaction mixture was filtered and the filtrate was concentrated. The crude product was purified through column chromatography using 60-120 silica gel with ethyl acetate-pet ether as solvent system. The isolated material was dried under vacuum to afford tert-butyl (2-(3-cyclopropyl-1H-pyrazol-1-yl)-6-morpholinopyrimidin-4-yl)(4,4-difluorocyclohexyl)carbamate as an off-white solid (0.8 g, 84%). MS (MH+): m/z=505.

Step 6:

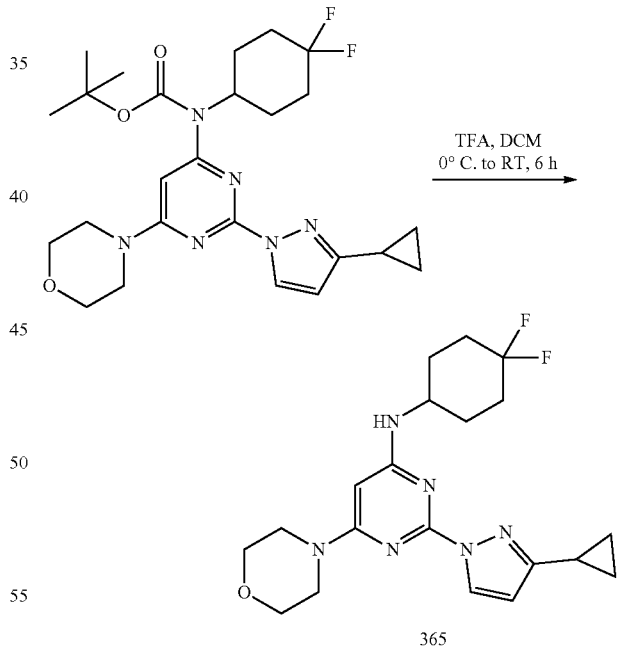

365

A 100-mL three-necked, flame-dried, round-bottomed flask, equipped with a teflon-coated stir bar (2 cm), one septa (necks 1), stopper (neck 3) and nitrogen gas inlet-outlet U-tube adaptor filled with oil (Neck 2), was charged with a solution tert-butyl (2-(3-cyclopropyl-1H-pyrazol-1-yl)-6-morpholinopyrimidin-4-yl)(4,4-difluorocyclohexyl)carbamate (1.2 g, 1.98 mmol, 1 eq) in dichloromethane (40 mL) followed by trifluoroacetic acid (2.5 mL, 32.55 mmol, 16.4 eq) at 0° C. The reaction mixture was slowly warmed to rt and stirred at same temperature for 6 hours. The completion of reaction was determined by TLC and UPLC. The reaction mixture was concentrated and the resulting residue was quenched with 10% saturated sodium bicarbonate solution, extracted with ethyl acetate (2×100 mL), and concentrated under reduced pressure to afford crude product. The crude product was purified through column chromatography using 60-120 silica gel, ethyl acetate-pet ether as solvent system. The resulting solid was dried under vacuum to afford 2-(3-cyclopropyl-1H-pyrazol-1-yl)-N-(4,4-difluorocyclohexyl)-6-morpholinopyrimidin-4-amine 365 (0.73 g, 90%). MS (MH+): m/z=405. Analytical Data: $^1$H-NMR (400 MHz, DMSO-d$_6$): δ 8.39 (d, J=2.4 Hz, 1H), 7.08 (d, J=8.0 Hz, 1H), 6.14 (d, J=2.80 Hz, 1H), 5.53 (s, 1H), 3.88 (s, 1H), 3.69-3.67 (m, 4H), 3.50 (m, 4H), 1.99-1.90 (m, 7H), 1.56-1.54 (m, 2H), 0.93-0.89 (m, 2H), 0.72-0.71 (m, 2H).

Example 274

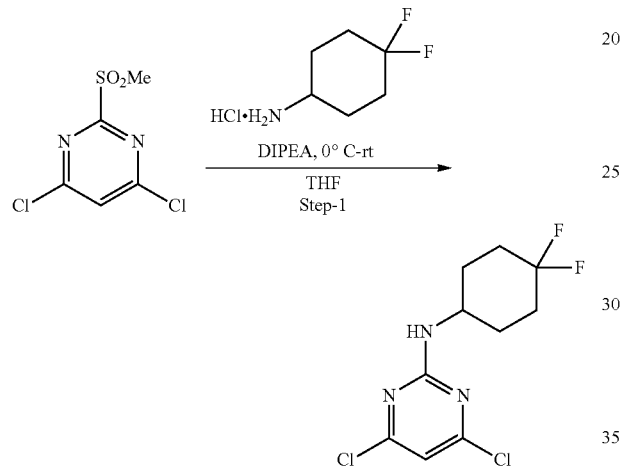

Step 1: To a stirred solution of 4,6-Dichloro-2-(Methylsulfonyl)Pyrimidine (10 g, 44.039 mmol) in tetrahydrofuran (100 mL) was added 4,4-difluorocyclohexylamine hydrochloride (9.06 g, 52.84 mmol) and N, N-di-isopropyl ethylamine (9.2 mL, 52.84 mmol) at 0° C. The reaction mixture was stirred at rt for 5 h. The reaction mixture was quenched with water (25 mL) and extracted with ethyl acetate (2×250 mL). The combined organic layer was washed with brine solution (50 mL), the organic extracts was dried over sodium sulfate, filtered and concentrated under reduced pressure to afford crude product as a pale yellowish gum. The crude product was purified by column chromatography (60-120 mesh) using ethyl acetate in pet ether as solvent to afford 4,6-dichloro-N-(4,4-difluorocyclohexyl)pyrimidin-2-amine as off-white solid (4 g, 32%). MS (M, M+2)$^+$=282.0, 284.1.

Example-838

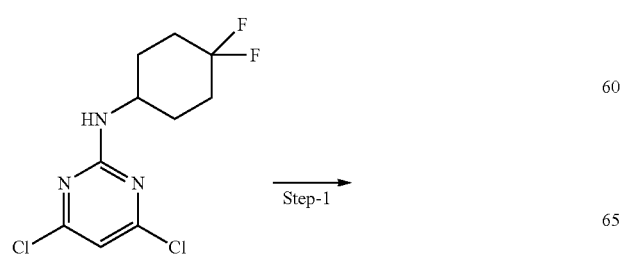

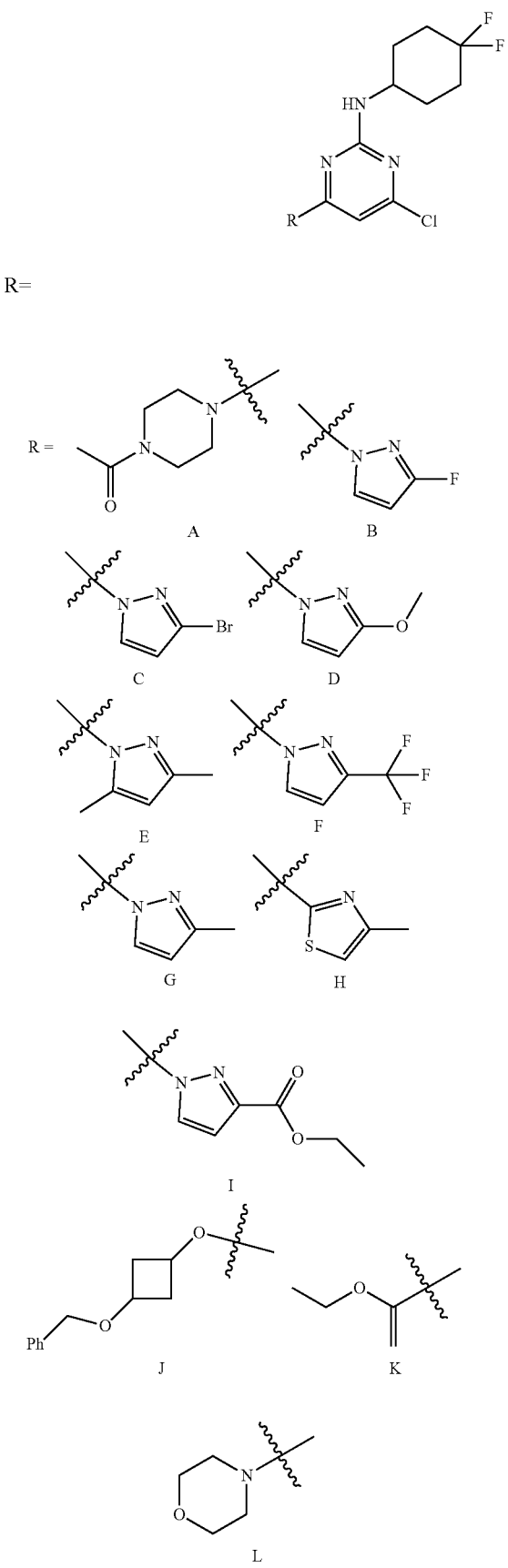

TABLE 1A

Step 1:

| Compound No | R | Condition | Yield (%) |
|---|---|---|---|
| A | 4-acetylpiperazin-1-yl | TEA, THF, 65° C., 2 h | 81 |
| B | 3-fluoro-1H-pyrazol-1-yl | Cs$_2$CO$_3$, ACN, 80° C., 8 h | 71 |
| C | 3-bromo-1H-pyrazol-1-yl | Cs$_2$CO$_3$, ACN, 80° C., 16 h | 80 |
| D | 3-methoxy-1H-pyrazol-1-yl | Cs$_2$CO$_3$, ACN, 80° C., 16 h | 78 |
| E | 3,5-dimethyl-1H-pyrazol-1-yl | Cs$_2$CO$_3$, ACN, 70° C., 16 h | 68 |
| F | 3-(trifluoromethyl)-1H-pyrazol-1-yl | Cs$_2$CO$_3$, ACN, 70° C., 16 h | 75 |
| G | 3-methyl-1H-pyrazol-1-yl | Cs$_2$CO$_3$, ACN, 70° C., 16 h | 47 |
| H | 4-methylthiazol-2-yl | Pd(PPh$_3$)$_2$Cl$_2$, Toluene, 100° C., 16 h | 80 |
| I | ethyl 1H-pyrazole-3-carboxylate-1-yl | Cs$_2$CO$_3$, ACN, rt, 5 h | 57 |
| J | 3-(benzyloxy)cyclobutoxy | K$^+$(CH$_3$)$_3$CO$^-$, THF, 80° C., 16 h | 55 |

TABLE 1A-continued

Step 1:

| Compound No | R | Condition | Yield (%) |
|---|---|---|---|
| K | ethoxy vinyl group | Pd(PPh₃)₂Cl₂, Toluene, 80° C., 16 h | 75 |
| L | morpholinyl group | ACN, 75° C., 16 h | 78 |

Step 1[A]: To a stirred solution of 4,6-dichloro-N-(4,4-difluorocyclohexyl)pyrimidin-2-amine (2 g, 7.08 mmol) in acetonitrile (20 mL) was added 1-acetylpiperazine (0.90 g, 7.08 mmol) and triethylamine (0.86 g, 1.18 mL, 8.50 mmol). The reaction mixture was heated at 65° C. for 2 h. The reaction mixture was concentrated and the residue was triturated with water, the solid formed was filtered off, washed with hexane, dried under high vacuum to afford 1-(4-(6-chloro-2-((4,4-difluorocyclohexyl)amino)pyrimidin-4-yl)piperazin-1-yl)ethan-1-one [A] as a white solid (2.1 g, 81%). MS (M+1)⁺=374.2.

Step 1[B]: To a stirred solution of 4,6-dichloro-N-(4,4-difluorocyclohexyl)pyrimidin-2-amine (1 g, 3.54 mmol) in acetonitrile (10 mL) was added 3-fluoro pyrazole (0.36 g, 4.25 mmol) and cesium carbonate (2.30 g, 7.089 mmol). The reaction mixture was heated at 80° C. for 8 h. The reaction mixture was filtered and the filtrate was concentrated to afford crude product and which was purified by column chromatography (60-120 mesh) using 22% ethyl acetate in pet ether as solvent to afford 4,6-dichloro-N-(4,4-difluorocyclohexyl)pyrimidin-2-amine [B] as an off-white solid (4 g, 32%). MS (M, M+2)⁺=282.0, 284.1.

Step 1[C, D, E, F, G, I, J, L]: The procedure is similar to Step 1[B] in Example-838.

Step 1[H]: To a solution of 4,6-dichloro-N-(4,4-difluorocyclohexyl)pyrimidin-2-amine (0.8 g, 2.83 mmol) in toluene (10 mL) was added 4-methyl-2-(tributylstannyl) thiazole (1.65 g, 4.25 mmol). The reaction mixture was purged with N₂ for 5 min, then added bis (triphenylphosphine) Palladium (II) dichloride (0.19 g, 0.28 mmol) and the reaction mixture was heated at 100° C. for 16 h. The reaction mixture was filtered through celite bed and the filtrate was concentrated under reduced pressure to afford crude product and which was purified by flash chromatography using ethyl acetate and pet-ether as solvent system to afford 4-chloro-N-(4,4-difluorocyclohexyl)-6-(4-methylthiazol-2-yl)pyrimidin-2-amine [H] as a white solid (0.8 g, 80%). MS (M+1)⁺=345.1.

Step 1[K]: The procedure is similar to Step 1[H] in Example-838.

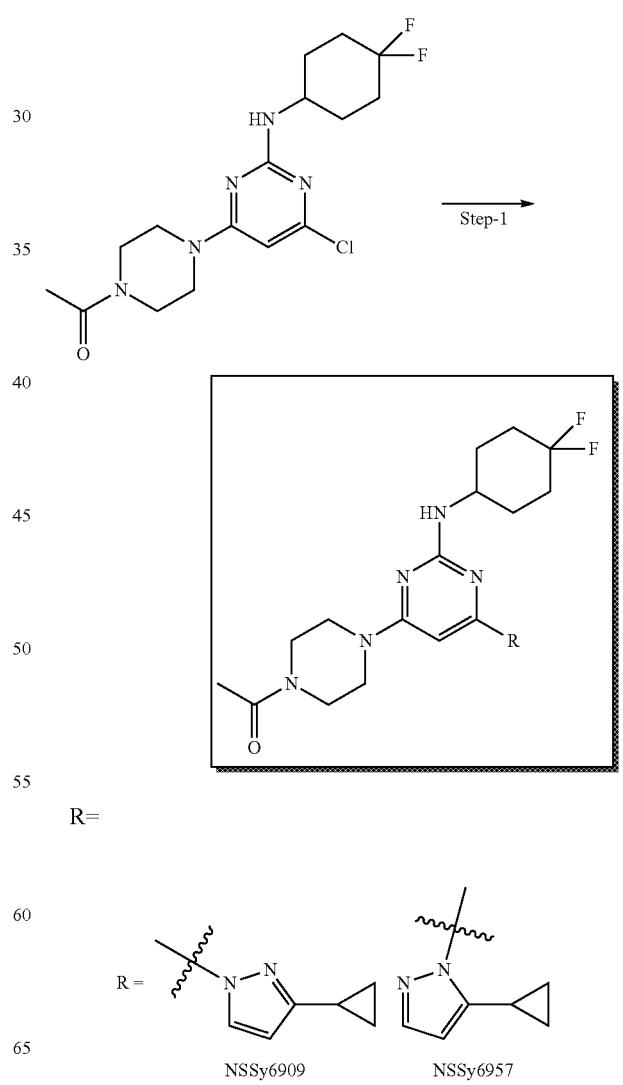

Example-839

R=

NSSy6909    NSSy6957

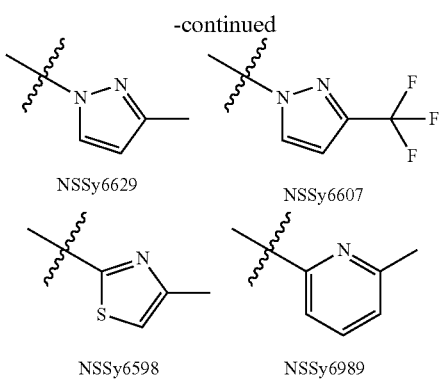

product, which was purified by grace instrument using 80% ethyl acetate in pet-ether to afford 1-(4-(6-(3-cyclopropyl-1H-pyrazol-1-yl)-2-((4,4-difluorocyclohexyl)amino)pyrimidin-4-yl)piperazin-1-yl)ethan-1-one as off-white solid (0.095 g, 53%). MS (M+1)$^+$=446.2; $^1$H-NMR (400 MHz, DMSO-d$_6$): δ 8.38 (s, 1H), 6.88 (s, 1H), 6.37 (d, J=7.80 Hz, 1H), 6.21 (d, J=2.44 Hz, 1H), 3.95-3.93 (m, 1H), 3.66 (m, 2H), 3.57-3.54 (m, 6H), 2.07-1.91 (m, 10H), 1.60-1.57 (m, 2H), 0.96-0.88 (m, 2H), 0.75-0.73 (m, 2H) and 1-(4-(6-(5-cyclopropyl-1H-pyrazol-1-yl)-2-((4,4-difluorocyclohexyl)amino)pyrimidin-4-yl)piperazin-1-yl)ethan-1-one as an off-white solid (0.0053 g, 3%). MS (M+1)$^+$=446.2; $^1$H-NMR (400 MHz, DMSO-d$_6$): δ 7.53 (s, 1H), 6.90-6.88 (m, 1H), 6.40 (s, 1H), 6.08 (s, 1H), 3.86-3.81 (m, 1H), 3.65-3.52 (m, 4H), 3.47 (m, 4H), 2.08-2.05 (m, 6H), 1.91-1.83 (m, 4H), 1.62-1.57 (m, 2H), 0.99-0.94 (m, 2H), 0.68 (m, 2H).

TABLE 2A

| Compound No | R | Condition | Yield (%) |
|---|---|---|---|
| NSSy6909 | 3-cyclopropyl-pyrazole | Cs$_2$CO$_3$, ACN, 130° C., 2 h, MW | 53 |
| NSSy6957 | 5-cyclopropyl-pyrazole | Cs$_2$CO$_3$, ACN, 130° C., 2 h, MW | 03 |
| NSSy6629 | 3-methyl-pyrazole | Xanthphos, Pd$_2$(dba)$_3$, Cs$_2$CO$_3$, dioxane, 90° C., 24 h | 16 |
| NSSy6607 | 3-(trifluoromethyl)-pyrazole | Cs$_2$CO$_3$, ACN, 130° C., 2 h, MW | 13 |
| NSSy6598 | 4-methylthiazole | Pd$_2$(dba)$_3$, Toluene, 100° C., 16 h | 22 |
| NSSy6989 | 6-methylpyridine | Pd(PPh$_3$)$_4$, o-xylene, 180° C., 30 min, MW | 52 |

Step 1[NSSy6909 and NSSy6957]: To a solution of 1-(4-(6-chloro-2-((4,4-difluorocyclohexyl)amino)pyrimidin-4-yl)piperazin-1-yl)ethan-1-one (0.15 g, 0.40 mmol) and 3-cyclopropyl-1H-pyrazole (0.08 g, 0.80 mmol) in acetonitrile (5 mL) was added cesium carbonate (0.26 g, 0.80 mmol) and the reaction mixture was irradiated under microwave at 130° C. for 2 h. The reaction mixture was filtered and the filtrate was concentrated to afford crude Step 1[NSSy6629]: To a solution of 1-(4-(6-chloro-2-((4,4-difluorocyclohexyl)amino)pyrimidin-4-yl)piperazin-1-yl)ethan-1-one (0.3 g, 0.802 mmol) and 3-methylpyrazole (0.098 g, 1.20 mmol) in dioxane (10 mL) was added cesium carbonate (0.39 g, 1.20 mmol), followed by 4,5-Bis(diphenylphosphino)-9,9-dimethylxanthene (0.18 g, 0.32 mmol) and the reaction mixture was purged with N$_2$ gas for 5 min. Then tris (dibenzylideneacetone)dipalladium (0) (0.22 g, 0.24 mmol) was added and the reaction mixture was heated at 90° C. for 24 h. The reaction mixture was filtered through celite bed, washed with ethyl acetate and the filtrate was concentrated under reduced pressure to afford crude product, which was purified by flash chromatography using ethyl acetate and pet-ether as solvent system to afford 1-(4-(2-((4,4-difluorocyclohexyl)amino)-6-(3-methyl-1H-pyrazol-1-yl)pyrimidin-4-yl)piperazin-1-yl)ethan-1-one as an off-white solid (0.052 g, 16%). MS (M+1)$^+$=420.2; $^1$H-NMR (400 MHz, DMSO-d$_6$): δ 7.40 (s, 1H), 6.91 (d, J=7.60 Hz, 1H), 6.26 (s, 1H), 4.73 (s, 4H), 4.21 (s, 4H), 3.87 (s, 1H), 2.43 (s, 3H), 2.10-1.93 (m, 6H), 1.62-1.59 (m, 2H).

Step 1[NSSy6607]: The procedure is similar to Step 1[NSSy6909] in Example-839. MS (M+1)$^+$=474.2; $^1$H-NMR (400 MHz, DMSO-d$_6$): δ 7.40 (s, 1H), δ 7.1 (s, 1H), 6.91 (d, J=7.60 Hz, 1H), 6.26 (s, 1H), 4.73 (s, 4H), 4.21 (s, 4H), 3.87 (s, 1H), 2.43 (s, 3H), 2.10-1.93 (m, 6H), 1.62-1.59 (m, 2H).

Step 1[NSSy6598]: To a solution of 1-(4-(6-chloro-2-((4,4-difluoro cyclohexyl)amino)pyrimidin-4-yl) piperazin-1-yl) ethan-1-one (0.3 g, 0.8 mmol) in toluene (10 mL) was added 4-methyl-2-(tributylstannyl) thiazole (0.62 g, 1.60 mmol). The reaction mixture was purged with N$_2$ for 5 min, then added bis (triphenylphosphine) Palladium (II) dichloride (0.22 g, 0.32 mmol) and the reaction mixture was heated at 100° C. for 16 h. The reaction mixture was filtered through celite bed and the filtrate was concentrated under reduced pressure to afford crude product, which was purified by flash chromatography using ethyl acetate and pet-ether as solvent system to afford 1-(4-(2-((4,4-difluorocyclohexyl)amino)-6-(4-methylthiazol-2-yl)pyrimidin-4-yl)piperazin-1-yl)ethan-1-one as an white solid (0.08 g, 22%). MS (M+1)$^+$=437.1; $^1$H-NMR (400 MHz, DMSO-d$_6$): δ 7.40 (s, 1H), 6.91 (s, 1H), 6.68 (s, 1H), 3.89 (d, J=6.00 Hz, 1H), 3.70 (s, 2H), 3.61 (s, 2H), 3.54 (s, 4H), 2.43 (s, 3H), 2.10-2.06 (m, 2H), 2.05 (s, 3H), 1.96-1.89 (m, 4H), 1.66-1.58 (m, 2H).

Step 1[NSSy6989]: To a solution of 1-(4-(6-chloro-2-((4,4-difluorocyclohexyl)amino)pyrimidin-4-yl)piperazin-1-yl)ethan-1-one (0.15 g, 0.401 mmol) in o-xylene (4 mL) was added 2-methyl-6-(tributylstannyl)pyridine (0.306 g, 0.80 mmol) and tetrakis(triphenylphosphine)palladium(0) (0.09 g, 0.080 mmol). The reaction mixture was irradiated under MW at 180° C. for 30 min. The reaction mixture was concentrated under reduced pressure and the residue was dissolved in ethyl acetate, filtered through celite bed and the filtrate was concentrated to afford crude product and which was purified by flash chromatography using ethyl acetate and pet-ether as solvent system to afford 1-(4-(2-((4,4-difluorocyclohexyl)amino)-6-(6-methylpyridin-2-yl)pyrimidin-4-yl)piperazin-1-yl)ethan-1-one as an off-white solid (0.09 g, 52%). MS (M+1)$^+$=431.0; $^1$H-NMR (400 MHz, DMSO-d$_6$): δ 8.10 (d, J=6.80 Hz, 1H), 7.82-7.78 (m, 1H), 7.32 (d, J=7.60 Hz, 1H), 6.99 (s, 1H), 6.73 (s, 1H), 4.01 (m, 1H), 3.69-3.60 (m, 4H), 3.56-3.55 (m, 4H), 2.50 (s, 3H), 2.50-1.94 (m, 9H), 1.64-1.61 (m, 2H).

Example-840

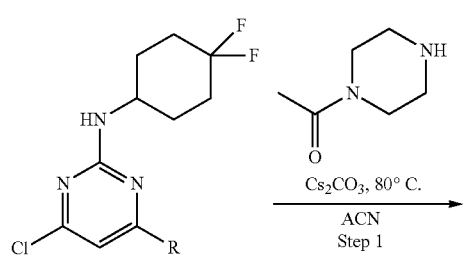

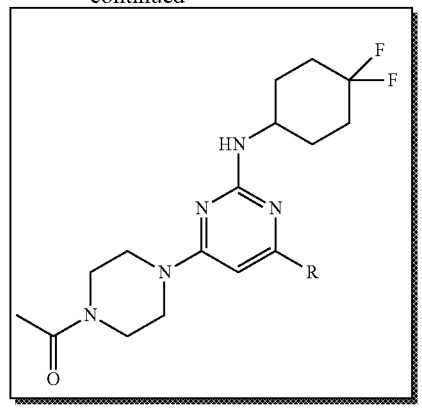

R=

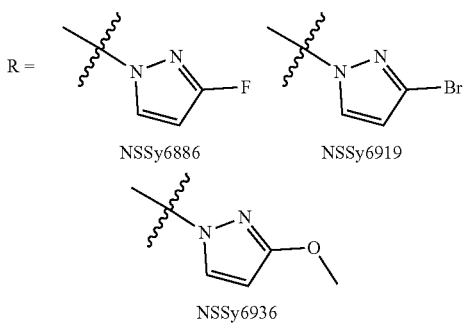

TABLE 3A

| Step 1: The Procedure is similar to Step 1[B] in Example-838 | | | |
|---|---|---|---|
| Compound No | R | Condition | Yield (%) |
| NSSy6886 | ![pyrazole-F] | Cs$_2$CO$_3$, ACN, 80° C., 3 h | 75 |
| NSSy6919 | ![pyrazole-Br] | Cs$_2$CO$_3$, ACN, 80° C., 16 h | 80 |
| NSSy6936 | ![pyrazole-OMe] | Cs$_2$CO$_3$, ACN, 80° C., 32 h | 80 |

Step 1[NSSy6886]: MS (M+1)$^+$=424; $^1$H-NMR (400 MHz, DMSO-d$_6$): δ 8.36 (s, 1H), 6.98 (s, 1H), 6.36-6.34 (m, 1H), 6.28 (s, 1H), 3.92 (s, 1H), 3.67-3.52 (m, 8H), 2.12-1.85 (m, 9H), 1.62-1.57 (m, 2H).

Step 1[NSSy6919]: MS (M, M+2)$^+$=484, 486; $^1$H-NMR (400 MHz, DMSO-d$_6$): δ 8.60 (s, 1H), 7.01 (s, 1H), 6.70 (s, 1H), 6.38 (s, 1H), 4.01 (s, 1H), 3.69 (s, 2H), 3.60 (s, 2H), 3.52 (s, 4H), 2.05-1.91 (m, 9H), 1.62-1.57 (m, 2H).

Step 1[NSSy6936]: MS (M+1)$^+$=436.2; $^1$H-NMR (400 MHz, DMSO-d$_6$): δ 8.36 (s, 1H), 6.85 (d, J=4.36 Hz, 1H), 6.27 (s, 1H), 6.06 (s, 1H), 4.00 (s, 1H), 3.90 (s, 3H), 3.65-3.54 (m, 8H), 2.09-1.91 (m, 9H), 1.63-1.57 (m, 2H).

Example-841

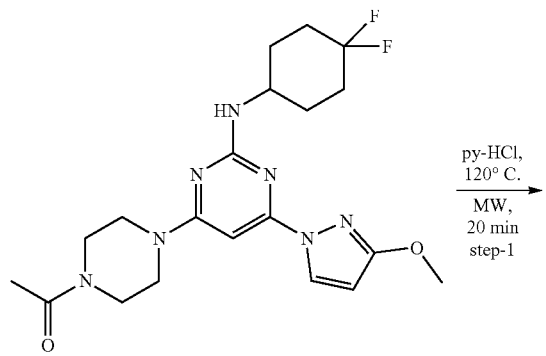

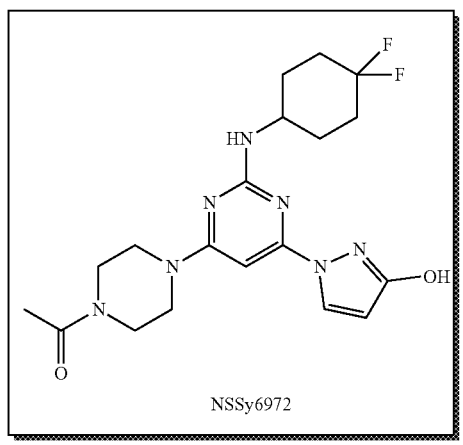

Step 1[NSSy6972]: A mixture of 1-(4-(2-((4,4-difluorocyclohexyl)amino)-6-(3-methoxy-1H-pyrazol-1-yl)pyrimidin-4-yl)piperazin-1-yl)ethan-1-one (0.15 g, 3.44 mmol) in Pyridine Hydrochloride (0.199 g, 1.72 mmol) was irradiated under microwave at 150° C. for 40 min. The crude reaction mixture was purified by Prep HPLC to afford 1-(4-(2-((4,4-difluorocyclohexyl)amino)-6-(3-hydroxy-1H-pyrazol-1-yl) pyrimidin-4-yl) piperazin-1-yl) ethan-1-one as a white solid (0.038 g, 26%). MS (M+1)$^+$=422; $^1$H-NMR (400 MHz, DMSO-d$_6$): δ 10.49 (s, 1H), 8.25 (s, 1H), 6.80 (d, J=6.4 Hz, 1H), 6.17 (s, 1H), 5.84 (d, J=2.80 Hz, 1H), 4.01 (s, 1H), 3.54 (s, 8H), 2.08-1.91 (m, 9H), 1.62-1.57 (m, 2H).

Example-842

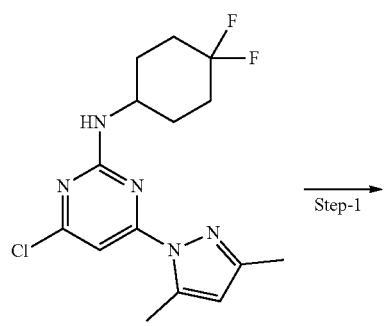

-continued

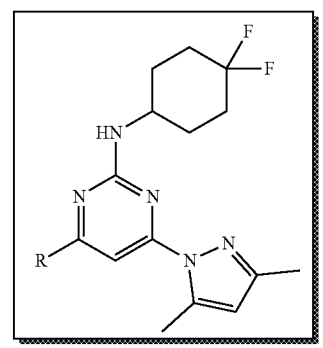

R=

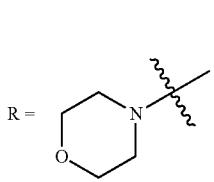
NSSy6389

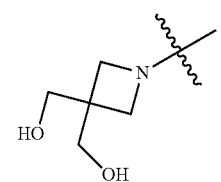
NSSy6564

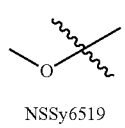
NSSy6519

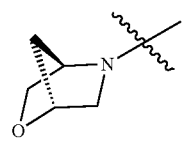
NSSy6638

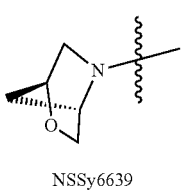
NSSy6639

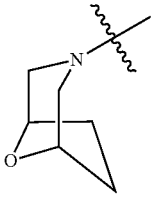
NSSy6644

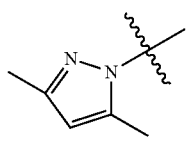
NSSy6654

TABLE 4

| Step 1: | | | |
|---|---|---|---|
| Compound No | R | Condition | Yield (%) |
| NSSy6389 | 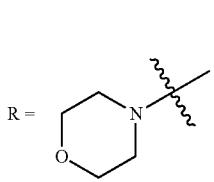 | ACN, 75° C., 16 h | 61 |

TABLE 4-continued

Step 1:

| Compound No | R | Condition | Yield (%) |
|---|---|---|---|
| NSSy6564 | azetidine with CH2OH, CH2OH substituents | Cs2CO3, ACN, 75° C., 3 h, | 50 |
| NSSy6519 | methoxy group | NaOMe, MeOH, 50° C., 16 h, | 92 |
| NSSy6638 | oxa-bridged bicyclic amine | Cs2CO3, ACN, 80° C., 16 h, | 32 |
| NSSy6639 | oxa-bridged bicyclic amine (isomer) | Cs2CO3, ACN, 80° C., 16 h, | 82 |
| NSSy6644 | oxa-bridged bicyclic amine | Cs2CO3, ACN, 80° C., 16 h, | 56 |
| NSSy6654 | 3,5-dimethylpyrazole | Cs2CO3, ACN, 80° C., 16 h, | 10 |

Step 1[NSSy6389]: The Procedure is similar to Step 1[B] in Example-838. MS (M+1)$^+$=393.1; $^1$H-NMR (400 MHz, DMSO-d$_6$): δ 6.79 (d, J=7.20 Hz, 1H), 6.36 (s, 1H), 6.06 (s, 1H), 3.85 (s, 1H), 3.64 (s, 4H), 3.52 (s, 4H), 2.60 (s, 3H), 2.16 (s, 3H), 2.07-2.05 (m, 2H), 1.93-1.91 (m, 4H), 1.58-1.55 (m, 2H).

Step 1[NSSy6564]: The Procedure is similar to Step 1[B] in Example-838. MS (M+1)$^+$=423.2; $^1$H-NMR (400 MHz, DMSO-d$_6$): δ 6.84 (s, 1H), 6.05 (s, 1H), 5.94 (s, 1H), 4.83 (t, J=5.20 Hz, 2H), 4.72 (s, 1H), 4.15 (s, 1H), 3.81 (s, 1H), 3.69 (s, 4H), 3.52 (s, 4H), 2.61 (s, 3H), 2.17 (s, 3H), 2.06-1.91 (m, 6H), 1.57-1.54 (m, 3H).

Step 1[NSSy6519]: To a solution of 4-chloro-N-(4,4-difluorocyclohexyl)-6-(3,5-dimethyl-1H-pyrazol-1-yl)pyrimidin-2-amine (0.05 g, 0.146 mmol) in methanol (2 mL) was added sodium methoxide (0.01 g, 0.219 mmol). The reaction mixture was heated at 50° C. for 16 h. The reaction mixture was concentrated and the resulting residue was dissolved in water, extracted with ethyl acetate (2×20 mL). The combined organic layer was dried over sodium sulfate and concentrated to afford N-(4,4-difluorocyclohexyl)-4-(3,5-dimethyl-1H-pyrazol-1-yl)-6-methoxy pyrimidin-2-amine as an off-white solid (0.045 g, 92%). MS (M+1)$^+$=338.1; $^1$H-NMR (400 MHz, DMSO-d$_6$): δ 7.38 (s, 1H), 6.34 (s, 1H), 6.11 (s, 1H), 3.86 (s, 4H), 2.64 (s, 3H), 2.18 (s, 3H), 2.15-1.85 (m, 6H), 1.65-1.52 (m, 2H).

Step 1[NSSy6638]: The Procedure is similar to Step 1[B] in Example-838. MS (M+1)$^+$=405.6; $^1$H-NMR (400 MHz, DMSO-d$_6$): δ 6.79 (s, 1H), 6.09 (s, 2H), 4.88 (s, 2H), 3.85-3.76 (m, 2H), 3.67-3.65 (m, 2H), 3.46-3.43 (m, 1H), 3.20 (s, 1H), 2.61 (s, 3H), 2.17 (s, 3H), 2.15-2.02 (m, 2H), 1.98-1.80 (m, 6H), 1.65-1.50 (m, 2H).

Step 1[NSSy6639]: The Procedure is similar to Step 1[B] in Example-838. MS (M+1)$^+$=405.6; $^1$H-NMR (400 MHz, DMSO-d$_6$): δ 6.30 (s, 1H), 6.15 (s, 1H), 6.01 (s, 1H), 4.90 (s, 1H), 4.65 (s, 1H), 3.88 (s, 1H), 3.79 (d, J=6.80 Hz, 1H), 3.70 (d, J=7.20 Hz, 1H), 3.46 (d, J=10.00 Hz, 1H), 3.30 (d, J=10.00 Hz, 1H), 2.62 (s, 3H), 0.00 (s, 3H), 2.13-2.03 (m, 2H), 2.13-1.92 (m, 3H), 1.90-1.78 (m, 3H), 1.70-1.60 (m, 2H).

Step 1[NSSy6644]: The Procedure is similar to Step 1[B] in Example-838. MS (M+1)$^+$=419.2; $^1$H-NMR (400 MHz, DMSO-d$_6$): δ 6.78 (s, 1H), 6.29 (s, 1H), 6.06 (s, 1H), 4.40 (s, 2H), 3.86 (s, 1H), 3.02-2.99 (m, 2H), 2.60 (s, 3H), 2.16 (s, 3H), 2.08-2.06 (m, 2H), 1.93-1.81 (m, 6H), 1.69-1.67 (m, 2H), 1.58-1.56 (m, 2H).

Step 1[NSSy6654]: The Procedure is similar to Step 1[B] in Example-838. MS (M+1)$^+$=402.5; $^1$H-NMR (400 MHz, DMSO-d$_6$): δ 7.47 (s, 1H), 7.45 (s, 1H), 6.16 (s, 1H), 3.90 (s, 1H), 2.69 (s, 6H), 2.22 (s, 6H), 2.15-1.85 (m, 6H), 1.62-1.55 (m, 2H).

Example-843

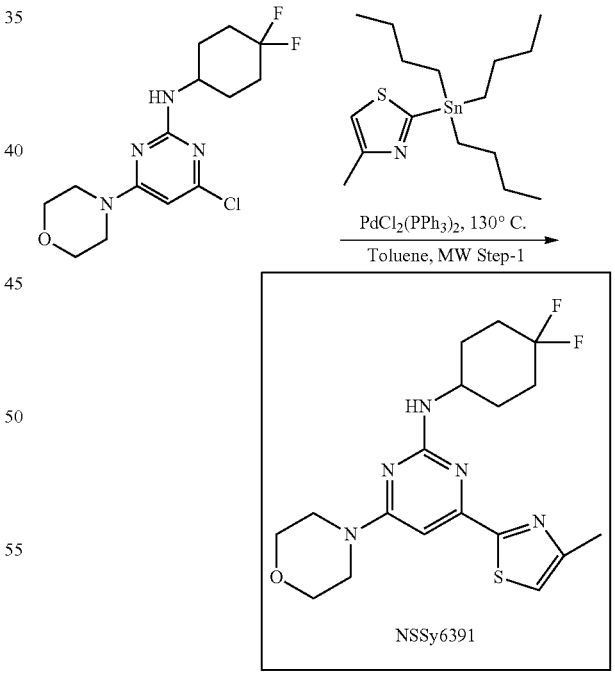

Step 1[NSSy6391]: The Procedure is similar to Step 1[H] in Example-838. 0.25 g of 4-chloro-N-(4,4-difluorocyclohexyl)-6-morpholinopyrimidin-2-amine gave N-(4,4-difluorocyclohexyl)-4-(4-methylthiazol-2-yl)-6-morpholinopyrimidin-2-amine as an off-white solid (0.09 g, 31%). MS (M+1)$^+$=396.1; $^1$H-NMR (400 MHz, DMSO-d$_6$): δ 7.39 (s, 1H), 6.87 (s, 1H), 6.66 (s, 1H), 3.87 (s, 1H), 3.66 (m, 4H), 3.58 (m, 4H), 2.32 (s, 3H), 2.06-1.91 (m, 6H), 1.61-1.59 (m, 2H).

Example-853

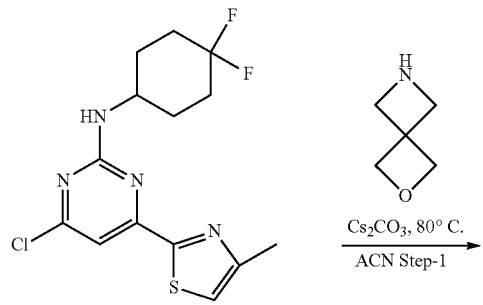

Step 1[NSSy6558]: The Procedure is similar to Step 1[B] in Example-838. 0.095 g of 4-chloro-N-(4,4-difluorocyclohexyl)-6-(4-methylthiazol-2-yl)pyrimidin-2-amine gave N-(4,4-difluorocyclohexyl)-4-(4-methylthiazol-2-yl)-6-(2-oxa-6-azaspiro [3.3] heptan-6-yl)pyrimidin-2-amine as an off-white solid (0.07 g, 72%). MS (M+1)⁺=408.1; ¹H-NMR (400 MHz, DMSO-d₆): δ 7.40 (s, 1H), 6.91 (d, J=7.60 Hz, 1H), 6.26 (s, 1H), 4.73 (s, 4H), 4.21 (s, 4H), 3.87 (s, 1H), 2.43 (s, 3H), 2.10-1.93 (m, 6H), 1.62-1.59 (m, 2H).

Example-854

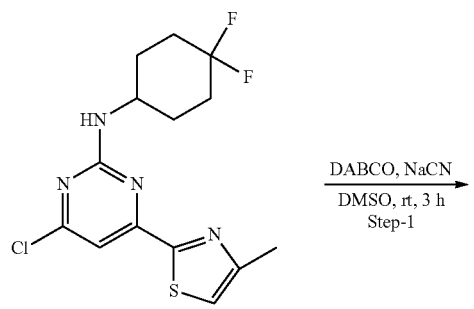

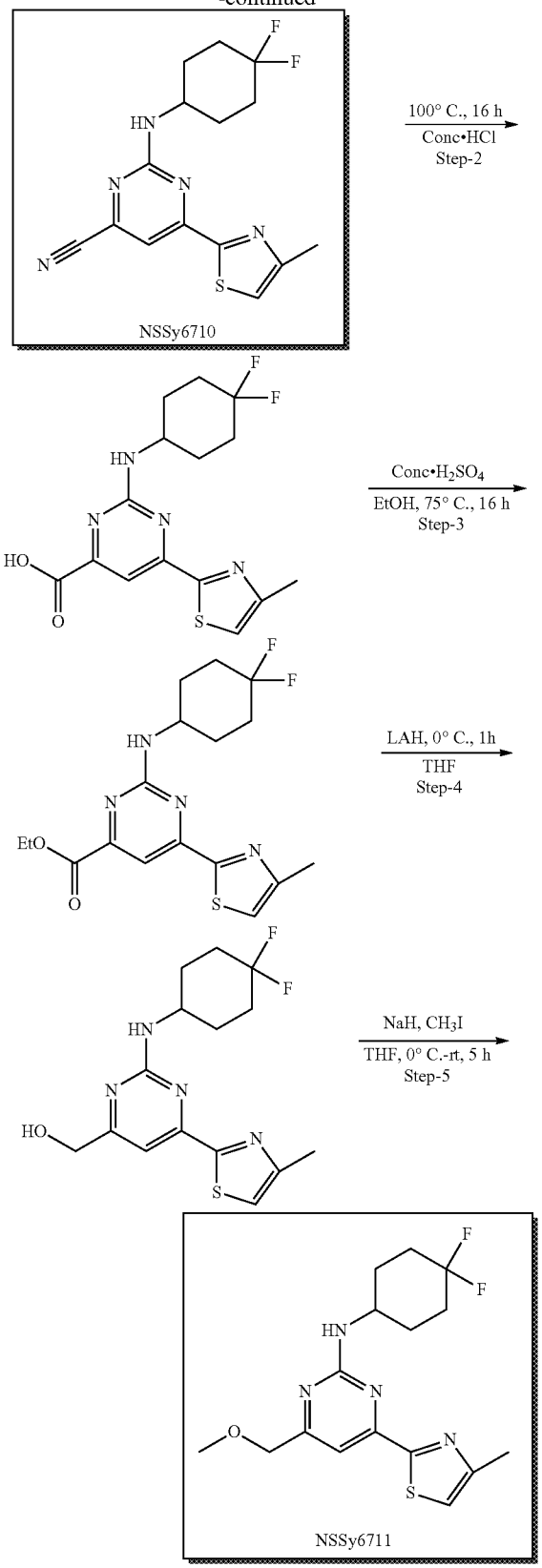

Step 1[NSSy6710]: To a stirred solution of 4-chloro-N-(4,4-difluoro cyclo hexyl)-6-(4-methylthiazol-2-yl)pyrimidin-2-amine (0.8 g, 2.32 mmol) in dimethylsulphoxide (10 mL) was added 1,4-diazabicyclo[2.2.2]octane (0.286 g, 2.55 mmol) and sodium cyanide (0.126 g, 2.55 mmol) at rt for 2 h. The reaction mixture was quenched with ice cold water and extracted with ethyl acetate (2×50 mL). The combined organic layer was dried over sodium sulfate and concentrated to afford crude product, which was purified by flash chromatography using 28% ethyl acetate in pet-ether as solvent system to afford 2-((4,4-difluorocyclohexyl)amino)-6-(4-methylthiazol-2-yl)pyrimidine-4-carbonitrile as an yellow solid (0.23 g, 29%). MS (M+1)$^+$=336.1; $^1$H-NMR (400 MHz, DMSO-d$_6$): δ 8.20 (s, 1H), 7.65 (s, 1H), 7.59 (s, 1H), 3.99 (bs, 1H), 2.47 (s, 3H), 2.33 (s, 3H), 2.06-1.95 (m, 6H), 1.64-1.62 (m, 2H).

Step 2: To a solution of 2-((4,4-difluorocyclohexyl) amino)-6-(4-methyl thiazol-2-yl)pyrimidine-4-carbonitrile (0.20 g, 0.59 mmol) in Conc Hydrochloric acid was heated at 100° C. for 16 h. The reaction mixture was allowed to cool down, and concentrated under reduced pressure to afford 2-((4,4-difluorocyclohexyl)amino)-6-(4-methylthiazol-2-yl) pyrimidine-4-carboxylic acid as a brown solid (0.2 g, 90%). MS (M+1)$^+$=336.1

Step 3: To a stirred solution of 2-((4,4-difluorocyclohexyl)amino)-6-(4-methylthiazol-2-yl)pyrimidine-4-carboxylic acid (0.2 g, 0.21 mmol) in ethanol (10 mL) was added 0.5 mL Conc sulphuric acid and the reaction mixture was heated at 75° C. for 16 h. The reaction mixture was concentrated under reduced pressure and the residue was quenched with saturated bicarbonate solution and extracted with ethyl acetate (2×50 mL). The combined organic layer was dried over sodium sulfate and concentrated to afford ethyl 2-((4,4-difluorocyclohexyl)amino)-6-(4-methylthiazol-2-yl)pyrimidine-4-carboxylate as an off-white gum (0.19 g, 92%). MS (M+1)$^+$=383.1.

Step 4: To an ice-cooled solution of ethyl 2-((4,4-difluorocyclohexyl)amino)-6-(4-methylthiazol-2-yl)pyrimidine-4-carboxylate (0.2 g, 0.52 mmol) in tetrahydrofuran (10 mL) was added Lithium aluminium hydride (2M in THF) and stirred at 0° C. for 1 h. The reaction mixture was quenched with ice cooled water and extracted with ethyl acetate (3×20 mL). The combined organic layer was dried over sodium sulfate and concentrated to afford (2-((4,4-difluoro cyclohexyl)amino)-6-(4-methylthiazol-2-yl)pyrimidin-4-yl) methanol as an off-white gum (0.12 g, 67%). MS (M+1)$^+$= 341.1.

Step 5[NSSy6711]: To an ice cooled solution of sodium hydride (0.014 g, 0.35 mmol) in THF (3 mL) was added a solution of (2-((4,4-difluorocyclohexyl)amino)-6-(4-methylthiazol-2-yl)pyrimidin-4-yl)methanol (0.1 g, 0.29 mmol) in tetrahydrofuran (2 mL) and stirred at 0° C. for 15 min. Iodomethane (0.045 g, 0.32 mmol) was added to the reaction mixture at 0° C. and slowly warmed to rt and stirred at rt for 5 h. The reaction mixture was quenched with ice cooled water and extracted with ethyl acetate (3×20 mL). The combined organic layer was dried over sodium sulfate and concentrated to afford N-(4,4-difluoro cyclohexyl)-4-(methoxymethyl)-6-(4-methylthiazol-2-yl)pyrimidin-2-amine as an off-white solid (15 mg, 14%). MS (M+1)$^+$= 355.1; $^1$H-NMR (400 MHz, DMSO-d$_6$): δ 6.99 (s, 1H), 6.66 (s, 1H), 6.43 (s, 1H) 5.50 (s, 1H), 5.38 (s, 1H), 3.98 (s, 1H), 3.68 (s, 2H), 3.59 (s, 2H), 3.54-3.52 (m, 4H), 2.06-2.04 (m, 6H), 1.94 (s, 3H), 1.54-1.61 (m, 2H)

Example-855

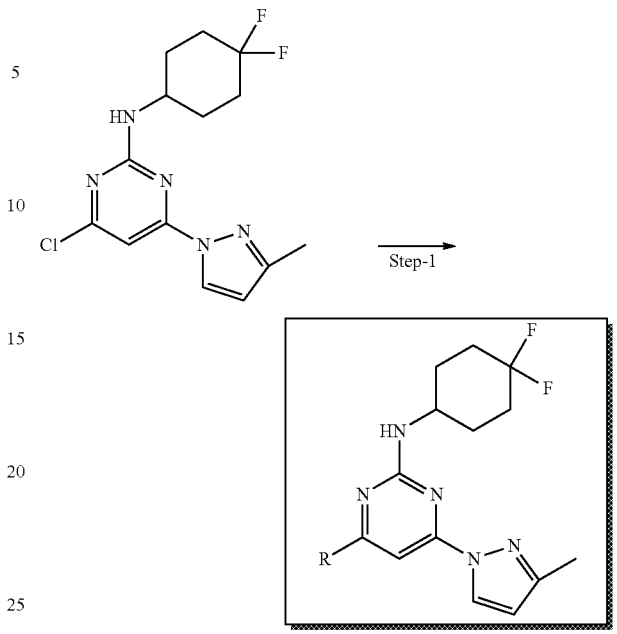

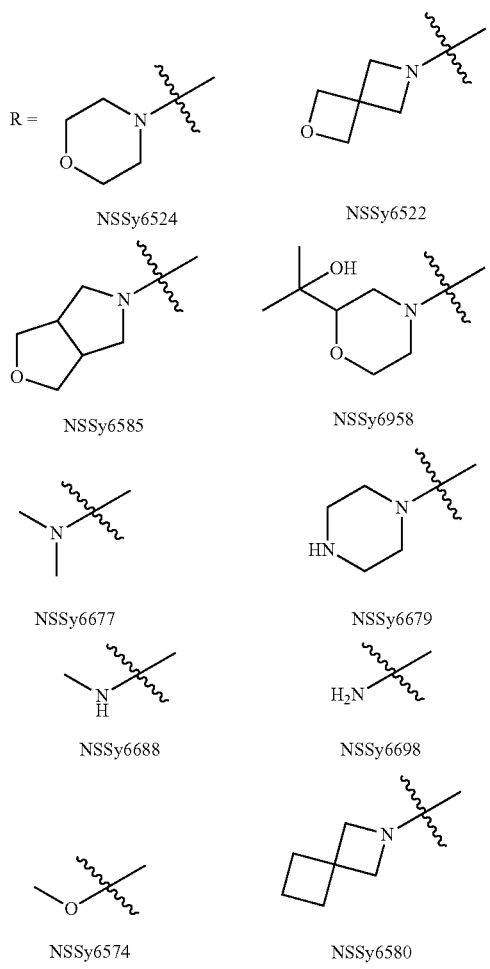

R=

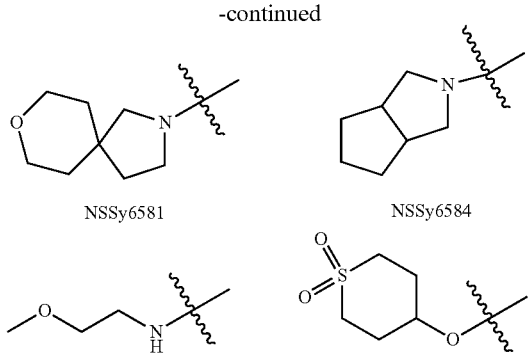
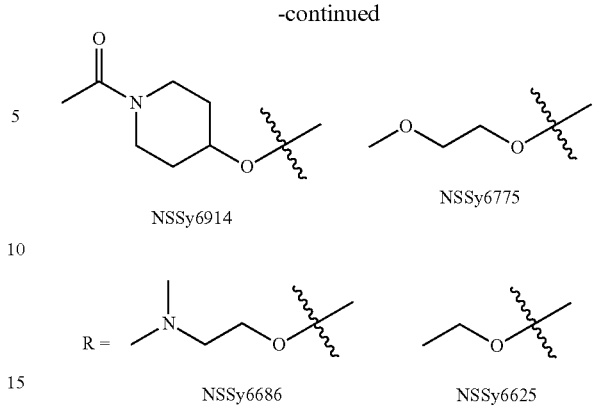
TABLE 5
| Step 1: | | | |
|---|---|---|---|
| Compound No | R | Condition | Yield (%) |
| NSSy6524 | (morpholine) | ACN, 75° C., 16 h | 75 |
| NSSy6522 | (2-oxa-6-azaspiro[3.3]heptane) | Cs$_2$CO$_3$, ACN, 75° C., 16 h | 96 |
| NSSy6585 | (hexahydrofuro[3,4-c]pyrrole) | Cs$_2$CO$_3$, ACN, 75° C., 16 h | 40 |
| NSSy6958 | (2-(2-hydroxypropan-2-yl)morpholine) | Cs$_2$CO$_3$, ACN, 90° C., 16 h | 58 |
| NSSy6677 | (dimethylamine) | Cs$_2$CO$_3$, ACN, 80° C., 16 h | 23 |
| NSSy6679 | (piperazine) | ACN, 100° C., 2 h | 43 |
| NSSy6688 | (methylamine) | Cs$_2$CO$_3$, ACN, 75° C., 16 h | 27 |
| NSSy6698 | (amine) | Aq. NH$_3$, 100° C., 16 h | 76 |

TABLE 5-continued

Step 1:

| Compound No | R | Condition | Yield (%) |
|---|---|---|---|
| NSSy6574 | methoxy group | NaOMe, MeOH, 50° C., 16 h | 78 |
| NSSy6580 | 2-azaspiro[3.3]heptane | Cs₂CO₃, ACN, 75° C., 4 h | 55 |
| NSSy6581 | 2-oxa-7-azaspiro[4.5]decane | Cs₂CO₃, ACN, 75° C., 4 h | 62 |
| NSSy6584 | octahydrocyclopenta[c]pyrrole | Cs₂CO₃, ACN, 70° C., 5 h | 25 |
| NSSy6700 | 2-methoxyethylamine | Cs₂CO₃, ACN, 80° C., 16 h | 38 |
| NSSy6913 | 1,1-dioxotetrahydro-2H-thiopyran-4-yloxy | K⁺(CH₃)₃CO⁻, THF, 70° C., 16 h | 35 |
| NSSy6914 | 1-acetylpiperidin-4-yloxy | K⁺(CH₃)₃CO⁻, THF, 70° C., 16 h | 28 |
| NSSy6675 | 2-methoxyethoxy | K⁺(CH₃)₃CO⁻, THF, 70° C., 16 h | 24 |
| NSSy6686 | 2-(dimethylamino)ethoxy | K⁺(CH₃)₃CO⁻, THF, 70° C., 16 h | 60 |
| NSSy6625 | ethoxy | NaOEt, EtOH, 70° C., 6 h | 26 |

Step 1[NSSy6524]: The Procedure is similar to Step 1[B] in Example-838. MS (M+1)⁺=379.2; ¹H-NMR (400 MHz, DMSO-d₆): δ 8.40 (s, 1H), 6.88 (s, 1H), 6.37 (s, 1H), 6.33 (s, 1H), 3.98 (s, 1H), 3.66 (s, 4H), 3.57 (s, 4H), 2.26 (s, 3H), 2.15-1.85 (m, 6H), 1.60-1.57 (m, 2H).

Step 1[NSSy6522]: The Procedure is similar to Step 1[B] in Example-838. MS (M+1)⁺=391.0; ¹H-NMR (400 MHz, DMSO-d₆): δ 8.42 (s, 1H), 6.92 (d, J=7.20 Hz, 1H), 6.32 (s, 1H), 5.95 (s, 1H), 4.72 (s, 4H), 4.18 (s, 4H), 3.95 (s, 1H), 2.26 (s, 3H), 2.08-1.89 (m, 6H), 1.59-1.56 (m, 2H).

Step 1[NSSy6585]: The Procedure is similar to Step 1[B] in Example-838. MS (M+1)⁺=405.2; ¹H-NMR (400 MHz, DMSO-d₆): δ 8.51 (s, 1H), 6.43 (s, 1H), 6.26 (s, 1H), 4.20-3.40 (m, 10H), 3.06 (s, 3H), 2.28 (s, 3H), 2.15-1.85 (m, 6H), 1.68-1.55 (m, 2H).

Step 1[NSSy6958]: The Procedure is similar to Step 1[B] in Example-838. MS (M+1)⁺=437.2; ¹H-NMR (400 MHz, DMSO-d₆): δ 8.36 (d, J=2.40 Hz, 1H), 6.51 (d, J=7.60 Hz, 1H), 6.38 (s, 1H), 6.29 (s, 1H), 4.36-4.35 (m, 1H), 4.24 (s, 1H), 4.16-4.15 (m, 1H), 3.99-3.92 (m, 2H), 3.55-3.49 (m, 1H), 3.18 (dd, J=2.80, 10.80 Hz, 1H), 3.04 (s, 2H), 2.98-2.91 (m, 1H), 2.84-2.78 (m, 1H), 2.28 (s, 3H), 2.10-1.89 (m, 6H), 1.68-1.64 (m, 2H), 1.19 (s, 3H), 1.14 (s, 3H).

Step 1[NSSy6677]: The Procedure is similar to Step 1[B] in Example-838. MS (M+1)⁺=337.2; ¹H-NMR (400 MHz, DMSO-d₆): δ 8.37 (s, 1H), 6.73 (d, J=6.40 Hz, 1H), 6.30 (s, 1H), 6.24 (s, 1H), 3.93 (s, 1H), 3.05 (s, 6H), 2.26 (s, 3H), 2.15-1.85 (m, 6H), 1.65-1.52 (m, 2H).

Step 1[NSSy6679]: The Procedure is similar to Step 1[B] in Example-838. MS (M+1)⁺=378.0; ¹H-NMR (400 MHz, DMSO-d₆): δ 8.37 (s, 1H), 6.78 (d, J=6.40 Hz, 1H), 6.36-6.24 (m, 2H), 4.09-3.92 (m, 1H), 3.59-3.41 (m, 4H), 3.17 (s, 1H), 2.72-2.64 (m, 4H), 2.25 (s, 3H), 2.08-1.90 (m, 6H), 1.62-1.57 (m, 2H)

Step 1[NSSy6688]: The Procedure is similar to Step 1[B] in Example-838. MS (M+1)⁺=323.2; ¹H-NMR (400 MHz, DMSO-d₆): δ 8.32 (d, J=2.40 Hz, 1H), 6.61 (s, 1H), 6.25 (d, J=2.40 Hz, 1H), 6.22-6.18 (m, 2H), 3.95 (s, 1H), 2.85 (s, 3H), 2.26 (s, 3H), 1.85-2.12 (m, 6H), 1.60-1.75 (m, 2H).

Step 1[NSSy6698]: A solution of 4-chloro-N-(4,4-difluorocyclohexyl)-6-(3-methyl-1H-pyrazol-1-yl)pyrimidin-2-amine (0.13 g, 0.39 mmol) in aqueous ammonia was heated in a sealed tube at 100° C. for 16 h. The reaction mixture was extracted with ethyl acetate (2×20 mL). The combined organic layer was dried over sodium sulfate and concentrated to afford crude which was purified by column chromatography using ethyl acetate as eluent to afford N2-(4,4-difluorocyclohexyl)-6-(3-methyl-1H-pyrazol-1-yl)pyrimidine-2,4-diamine as an white solid (91 mg, 76%). MS (M+1)⁺=309.2; ¹H-NMR (400 MHz, DMSO-d₆): δ 8.34 (s, 1H), 6.62 (d, J=6.80 Hz, 1H), 6.51 (s, 2H), 6.28 (s, 1H), 6.22-6.17 (m, 1H), 3.93 (s, 1H), 2.24 (s, 3H), 2.15-1.85 (m, 6H), 1.52-1.48 (m, 2H).

Step 1[NSSy6574]: The Procedure is similar to Step 1[NSSy6519] in Example-842. MS (M+1)⁺=324.2; ¹H-NMR (400 MHz, DMSO-d₆): δ 8.38 (s, 1H), 6.95 (s, 1H), 6.42-6.25 (m, 2H), 4.00 (s, 1H), 3.90 (s, 3H), 2.28 (s, 3H), 2.15-1.85 (m, 6H), 1.75-1.62 (m, 2H).

Step 1[NSSy6580]: The Procedure is similar to Step 1[B] in Example-838. MS (M+1)⁺=389.2; ¹H-NMR (400 MHz, DMSO-d₆): δ 8.39 (s, 1H), 6.86 (d, J=7.16 Hz, 1H), 6.31 (s, 1H), 5.92 (s, 1H), 3.96 (s, 4H), 2.26 (s, 3H), 2.20-2.16 (m, 4H), 2.15-1.75 (m, 7H), 1.65-1.50 (m, 2H).

Step 1[NSSy6581]: The Procedure is similar to Step 1[B] in Example-2. MS (M+1)⁺=433.1; ¹H-NMR (400 MHz, DMSO-d₆): δ 8.35 (s, 1H), 6.27 (s, 2H), 6.16 (s, 1H), 3.94 (s, 1H), 3.70-3.50 (m, 5H), 3.38 (s, 2H), 2.28 (s, 3H), 2.15-1.85 (m, 8H), 1.75-1.50 (m, 7H).

Step 1[NSSy6584]: The Procedure is similar to Step 1[B] in Example-838. MS (M+1)⁺=403.3; ¹H-NMR (400 MHz, DMSO-d₆): δ 8.37 (bs, 1H), 6.73 (s, 1H), 6.30 (s, 1H), 6.09 (s, 1H), 3.93 (s, 1H), 3.63 (s, 2H), 3.23 (s, 2H), 2.72 (s, 2H), 2.25 (s, 3H), 2.04-1.92 (m, 6H), 1.71-1.81 (m, 2H), 1.69-1.62 (m, 1H), 1.55-1.58 (m, 3H), 1.14 (s, 2H).

Step 1[NSSy6700]: The Procedure is similar to Step 1[B] in Example-838. MS (M+1)⁺=367.2; ¹H-NMR (400 MHz, DMSO-d₆): δ 8.33 (s, 1H), 7.18-7.15 (bs, 1H), 6.70 (s, 1H), 6.28 (s, 1H), 6.19 (s, 1H), 3.90 (s, 1H), 3.44 (s, 4H), 3.26 (s, 3H), 2.32 (s, 3H), 2.04-1.90 (m, 6H), 1.61-1.59 (m, 2H).

Step 1[NSSy6913]: The Procedure is similar to Step 1[B] in Example-838. MS (M+1)⁺=442.2; ¹H-NMR (400 MHz, DMSO-d₆): δ 8.38 (s, 1H), 7.09 (d, J=7.20 Hz, 1H), 6.42 (s, 1H), 6.34 (s, 1H), 5.35-5.33 (m, 1H), 3.97 (s, 1H), 3.25-3.20 (m, 2H), 3.15-3.12 (m, 2H), 2.33-2.29 (m, 8H), 2.08-1.91 (m, 6H), 1.71-1.66 (m, 2H).

Step 1[NSSy6914]: The Procedure is similar to Step 1[B] in Example-838. MS (M+1)⁺=435.2; ¹H-NMR (400 MHz, DMSO-d₆): δ 8.38 (s, 1H), 7.05 (d, J=7.60 Hz, 1H), 6.33 (s, 1H), 5.28-5.24 (m, 1H), 3.96 (s, 1H), 3.75 (s, 2H), 3.35-3.33 (m, 2H), 2.27 (s, 3H), 2.11-1.89 (m, 1H), 1.73-1.64 (m, 4H).

Step 1[NSSy6675]: The Procedure is similar to Step 1[B] in Example-838. MS (M+1)⁺=368.0; ¹H-NMR (400 MHz, DMSO-d₆—80° C.): δ 8.37 (d, J=2.40 Hz, 1H), 6.91 (s, 1H), 6.34 (s, 1H), 6.32 (d, J=2.40 Hz, 1H), 4.45 (t, J=4.80 Hz, 2H), 3.97 (s, 1H), 3.68 (t, J=4.80 Hz, 2H), 3.33 (s, 3H), 2.28 (s, 3H), 2.04-1.93 (m, 6H), 1.89-1.66 (m, 2H).

Step 1[NSSy6686]: The Procedure is similar to Step 1[B] in Example-838. MS (M+1)⁺=381.2; ¹H-NMR (400 MHz, DMSO-d₆): δ 8.37 (d, J=2.40 Hz, 1H), 6.90 (d, J=6.40 Hz, 1H), 6.32 (d, J=3.20 Hz, 2H), 4.41 (t, J=6.00 Hz, 2H), 3.98 (s, 1H), 2.67-2.64 (m, 2H), 2.27-2.25 (m, 8H), 1.85-2.85 (m, 6H), 1.74-1.66 (m, 2H).

Step 1[NSSy6625]: The Procedure is similar to Step 1[NSSy6519] in Example-842. MS (M+1)⁺=338.0; ¹H-NMR (400 MHz, DMSO-d₆): δ 8.51 (s, 1H), 7.36 (s, 1H), 6.37 (d, J=2.40 Hz, 1H), 6.27 (m, 1H), 4.34 (m, 2H), 4.01 (m, 1H), 2.27 (s, 3H), 2.06-1.93 (m, 6H), 1.62-1.60 (m, 2H), 1.23 (m, 3H).

Example-856

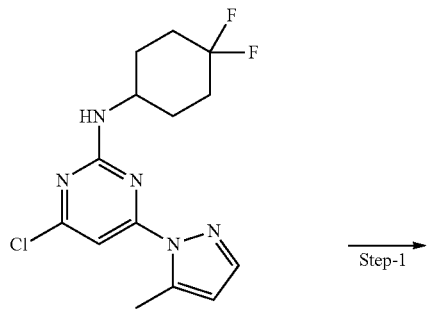

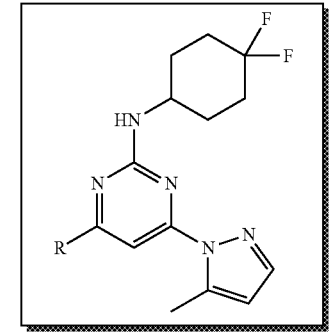

R=

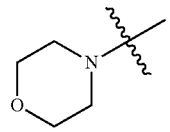 [SMILES: *N1CCOCC1]    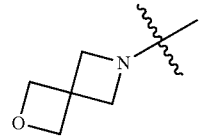

NSSy6525            NSSy6523

TABLE 6

Step 1:

| Compound No | R | Condition | Yield (%) |
|---|---|---|---|
| NSSy6525 | morpholine | ACN, 75° C., 16 h | 82 |
| NSSy6523 | 2-oxa-6-azaspiro[3.3]heptane | Cs₂CO₃, ACN, 75° C., 16 h | 73 |

Step 1[NSSy6525]: The Procedure is similar to Step 1[B] in Example-838. MS (M+1)+=379.2; 1H-NMR (400 MHz, DMSO-d₆): δ 7.58 (s, 1H), 6.88 (s, 1H), 6.43 (s, 1H), 6.27 (s, 1H), 3.86 (s, 1H), 3.66 (s, 4H), 3.52 (s, 4H), 2.65 (s, 3H), 2.08-1.88 (m, 6H), 1.63-1.54 (m, 2H).

Step 1[NSSy6523]: The Procedure is similar to Step 1[B] in Example-838. MS (M+1)+=391.2; ¹H-NMR (400 MHz, DMSO-d₆): δ 7.57 (s, 1H), 6.99 (bs, 1H), 6.26 (s, 1H), 6.03 (s, 1H), 4.72 (s, 4H), 4.16 (s, 4H), 3.85 (s, 1H), 2.65 (s, 3H), 2.08-1.93 (m, 6H), 1.58-1.55 (m, 2H).

Example-857

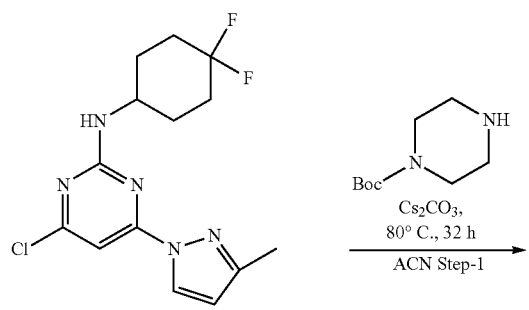

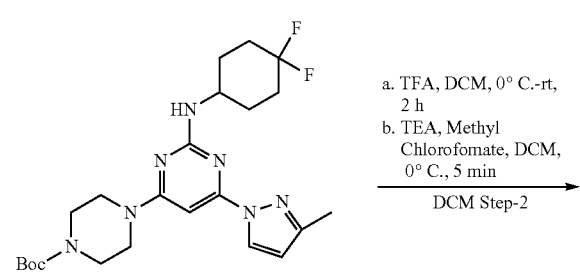

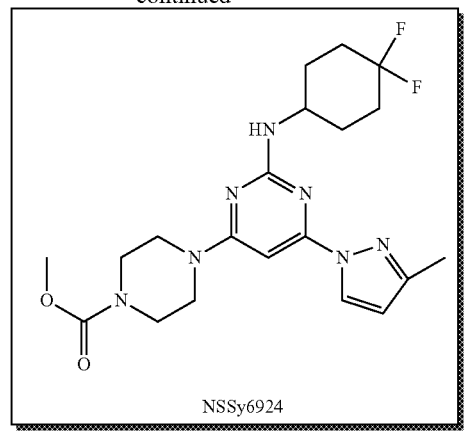

NSSy6924

Step 1: The Procedure is similar to Step 1[B] in Example-838. 0.2 g of 4-chloro-N-(4,4-difluorocyclohexyl)-6-(3-methyl-1H-pyrazol-1-yl)pyrimidin-2-amine gave tert-butyl 4-(2-((4,4-difluorocyclohexyl)amino)-6-(3-methyl-1H-pyrazol-1-yl)pyrimidin-4-yl) piperazine-1-carboxylate as a white solid (0.27 g, 93%). MS (M+1)⁺=478.

Step 2[NSSy6924]: To a stirred solution of tert-butyl 4-(2-((4,4-difluorocyclohexyl)amino)-6-(3-methyl-1H-pyrazol-1-yl)pyrimidin-4-yl) piperazine-1-carboxylate (0.15 g, 0.402 mmol) in dichloromethane (5 mL) was added trifluoroacetic acid (0.073 mL, 0.94 mmol) at 0° C. and the mixture was stirred at rt for 2 h. The reaction mixture was concentrated under reduced pressure to afford crude N-(4,4-difluorocyclohexyl)-4-(3-methyl-1H-pyrazol-1-yl)-6-(piperazin-1-yl)pyrimidin-2-amine which was dissolved in dichloromethane (5 mL) and added triethylamine (2 mL, 14.30 mmol) and methyl chloroformate (0.18 g, 0.81 mmol) at 0° C. The reaction mixture was stirred at same temperature for 10 min, partitioned between dichloromethane (10 mL) and water (3 mL). The organic layer was dried over anhydrous sodium sulfate, filtered and concentrated under reduced pressure. The crude was purified by column chromatography using 60% ethyl acetate in pet ether as eluent to afford methyl 4-(2-((4,4-difluorocyclohexyl)amino)-6-(3-methyl-1H-pyrazol-1-yl)pyrimidin-4-yl)piperazine-1-carboxylate as a white solid (0.105 g, 77%). MS (M+1)⁺=436.2; ¹H-NMR (400 MHz, DMSO-d₆): δ 8.45 (s, 1H), 6.90 (s, 1H), 6.38 (s, 1H), 6.32 (s, 1H), 3.96 (s, 1H), 3.64 (s, 7H), 3.47 (s, 4H), 2.27 (s, 3H), 2.15-1.91 (m, 6H), 1.62-1.57 (m, 2H).

Example-858

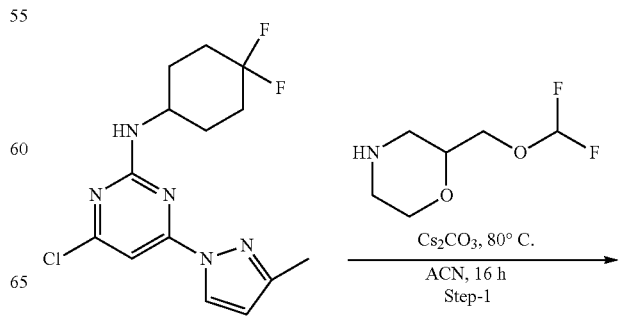

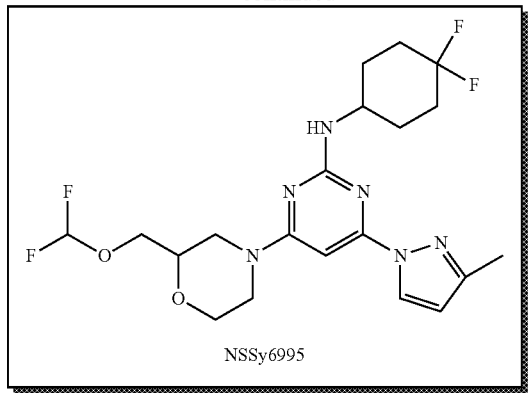

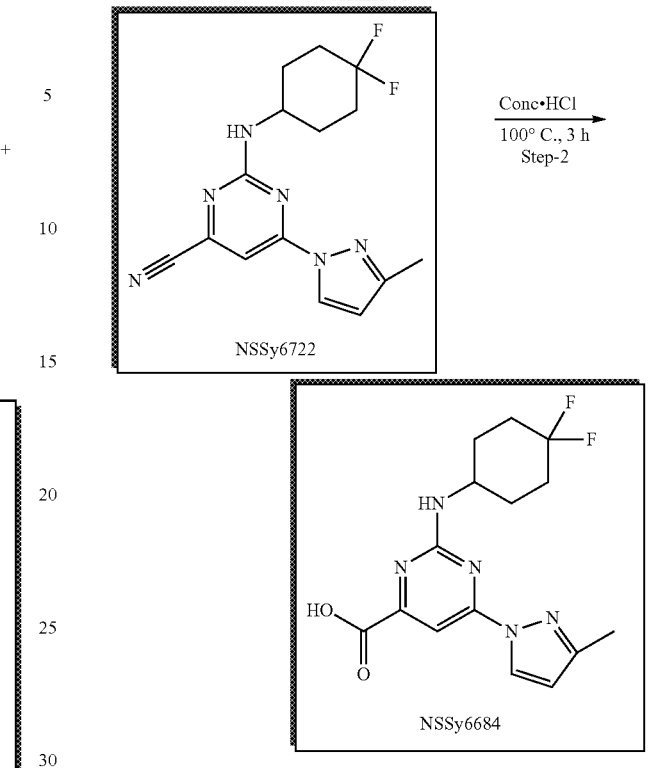

Step 1[NSSy6995 and NSSy6986]: The Procedure is similar to Step 1[B] in Example-838. 0.13 g of 4-chloro-N-(4,4-difluorocyclohexyl)-6-(3-methyl-1H-pyrazol-1-yl)pyrimidin-2-amine gave N-(4,4-difluorocyclohexyl)-4(2-(((difluoromethoxy)methyl) morpholino)-6-(3-methyl-1H-pyrazol-1-yl)pyrimidin-2-amine as a white solid (0.045 g, 25%). MS (M+1)$^+$=459.1; $^1$H-NMR (400 MHz, DMSO-d$_6$): δ 8.37 (s, 1H), 6.65 (t, J=76.4 Hz, 1H), 6.57 (d, J=8.0 Hz, 1H), 6.42 (s, 1H), 6.30 (s, 1H), 4.26 (s, 1H), 4.13 (s, 1H), 3.98-3.95 (m, 4H), 3.73-3.70 (m, 1H), 3.57 (t, J=3.20 Hz, 1H), 3.20-3.18 (m, 1H), 2.89-2.83 (m, 1H), 2.28 (s, 3H), 2.01-1.88 (m, 6H), 1.67-1.65 (m, 2H) and (4-(2-((4,4-difluorocyclohexyl)amino)-6-(3-methyl-1H-pyrazol-1-yl)pyrimidin-4-yl)morpholin-2-yl)methanol as an white solid (0.056 g, 35%). MS (M+1)$^+$=409.2; $^1$H-NMR (400 MHz, DMSO-d$_6$): δ 8.37 (s, 1H), 6.54 (d, J=7.60 Hz, 1H), 6.40 (s, 1H), 6.30 (s, 1H), 4.55 (m, 1H), 4.24 (s, 1H), 4.14 (s, 1H), 3.95-3.92 (m, 2H), 3.54-3.46 (m, 4H), 2.97 (m, 1H), 2.79 (t, J=3.20 Hz, 1H), 2.33 (s, 3H), 2.10-1.91 (m, 6H), 1.67-1.64 (m, 2H).

Step 1[NSSy6722]: The Procedure is similar to Step 1[NSSy6710] in Example-854. 0.3 g of 4-chloro-N-(4,4-difluorocyclohexyl)-6-(3-methyl-1H-pyrazol-1-yl)pyrimidin-2-amine gave 2-((4,4-difluorocyclohexyl)amino)-6-(3-methyl-1H-pyrazol-1-yl)pyrimidine-4-carbonitrile as an off-white solid (0.052 g, 75%). MS (M+1)$^+$=319; $^1$H-NMR (400 MHz, DMSO-d$_6$): δ 8.64 (s, 1H), 8.14 (d, J=6.40 Hz, 1H), 7.36 (s, 1H), 6.50 (s, 1H), 4.04-3.94 (m, 1H), 2.33 (s, 3H), 2.13-1.91 (m, 6H), 1.26-1.23 (m, 2H).

Step 2[NSSy6684]: The Procedure is similar to Step 2[NSSy6711] in Example-854. 0.22 g of 2-((4,4-difluorocyclohexyl)amino)-6-(3-methyl-1H-pyrazol-1-yl)pyrimidine-4-carbonitrile gave 2-((4,4-difluorocyclohexyl)amino)-6-(3-methyl-1H-pyrazol-1-yl)pyrimidine-4-carboxylic acid as an off-white solid (0.07 g, 30%). MS (M+1)$^+$=338.1; $^1$H-NMR (400 MHz, DMSO-d$_6$): δ 13.58 (s, 1H), 8.62 (s, 1H), 7.93 (s, 1H), 7.53-7.41 (m, 1H), 6.46-6.40 (m, 2H), 4.01 (m, 1H), 2.30 (s, 3H), 2.07-1.93 (m, 6H), 1.63-1.60 (m, 2H).

Example-859

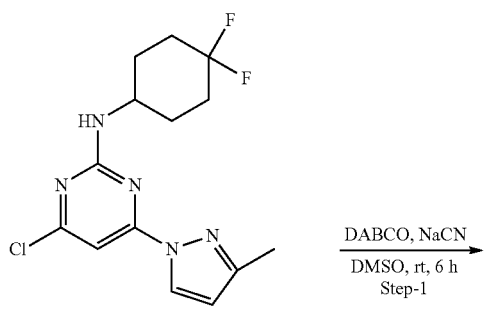

Example-860

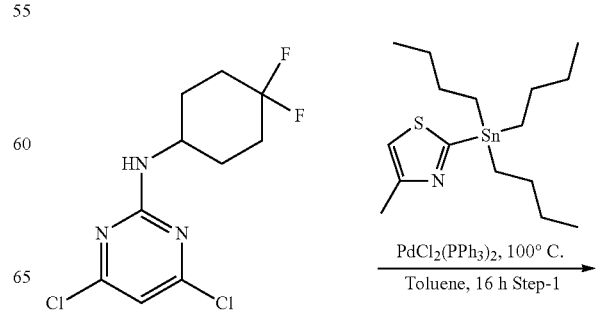

-continued

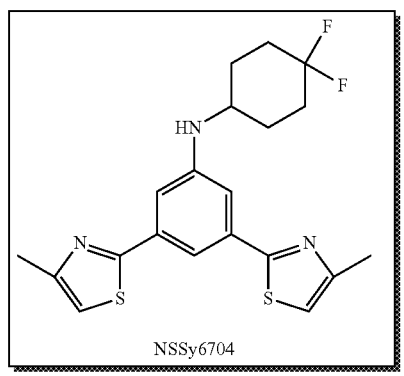

Step 2[NSSy6704]: The Procedure is similar to Step 1[H] in Example-838. 0.8 g of 4,6-dichloro-N-(4,4-difluorocyclohexyl)pyrimidin-2-amine gave N-(4,4-difluorocyclohexyl)-4,6-bis(4-methylthiazol-2-yl)pyrimidin-2-amine as an yellow solid (0.3 g, 26%). MS (M+1)$^+$=408.1; $^1$H-NMR (400 MHz, DMSO-d$_6$): δ 7.85-7.83 (m, 2H), 7.77 (s, 1H), 7.57 (s, 1H), 3.95 (s, 1H), 3.26 (s, 3H), 2.32 (s, 3H) 2.03-1.90 (m, 6H), 1.73-1.68 (m, 2H).

Example-861

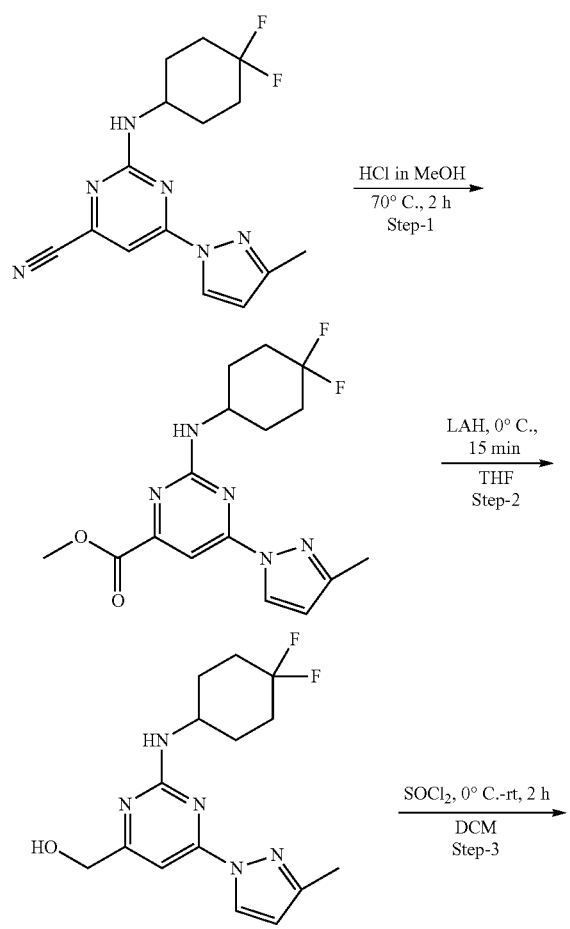

-continued

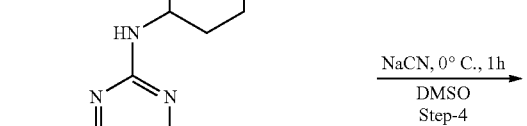

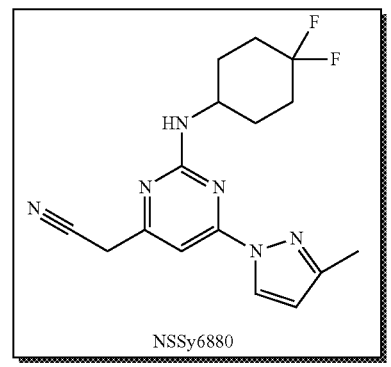

Step 1: To solution of 2-((4,4-difluorocyclohexyl)amino)-6-(3-methyl-1H-pyrazol-1-yl)pyrimidine-4-carbonitrile (1.8 g, 5.65 mmol) in 3M hydrochloric acid in methanol was heated at 70° C. The reaction mixture was concentrated and the resulting residue was quenched with 10% sodium bicarbonate solution and extracted with ethyl acetate (2×60 mL). The combined organic layer was dried over sodium sulfate and concentrated to afford crude and which was purified by column chromatography using 30% ethyl acetate in pet ether as eluent to afford methyl 2-((4,4-difluorocyclohexyl)amino)-6-(3-methyl-1H-pyrazol-1-yl)pyrimidine-4-carboxylate as an off-white gum (1.2 g, 60%). MS (M+1)$^+$= 352.1.

Step 2: The Procedure is similar to Step 4[NSSy6711] in Example-854. 1.2 g of methyl 2-((4,4-difluorocyclohexyl)amino)-6-(3-methyl-1H-pyrazol-1-yl)pyrimidine-4-carboxylate gave (2-((4,4-difluorocyclohexyl)amino)-6-(3-methyl-1H-pyrazol-1-yl)pyrimidin-4-yl) methanol as an off-white gum (0.6 g, 54%). MS (M+1)$^+$=324.

Step 3: To an ice cooled solution of (2-((4,4-difluorocyclohexyl)amino)-6-(3-methyl-1H-pyrazol-1-yl)pyrimidin-4-yl) methanol (0.65 g, 2.01 mmol) in dichloromethane (15 mL) was added thionyl chloride (0.48 g, 4.02 mmol). The reaction mixture was slowly warmed to rt and stirred for 2 h. The reaction mixture was quenched with 10% sodium bicarbonate solution and extracted with ethyl acetate (2×35 mL). The combined organic layer was dried over sodium sulfate and concentrated to afford crude which was purified by column chromatography using 20% ethyl acetate in pet ether as eluent to afford 4-(chloromethyl)-N-(4,4-difluorocyclohexyl)-6-(3-methyl-1H-pyrazol-1-yl)pyrimidin-2-amine (0.25 g, 36) as off-white gum. MS (M+1)$^+$=342.3.

Step 4[NSSy6800]: To an ice cooled solution of 4-(chloromethyl)-N-(4,4-difluorocyclohexyl)-6-(3-methyl-1H-pyrazol-1-yl)pyrimidin-2-amine (0.1 g, 0.29 mmol) in dimethyl sulphoxide (4 mL) was added sodium cyanide. The reaction mixture was slowly warmed to rt and stirred for 1 h. The reaction mixture was quenched with water and extracted with ethyl acetate (2×35 mL). The combined organic layer was dried over sodium sulfate and concentrated to afford crude and that was purified by grace instrument using 30% ethyl acetate in pet ether as an eluent to afford 2-(2-((4,4-difluorocyclohexyl)amino)-6-(3-methyl-1H-pyrazol-1-yl)pyrimidin-4-yl)acetonitrile as white solid (0.06 g, 65%). MS (M+1)$^+$=333.2; $^1$H-NMR (400 MHz, DMSO-d$_6$): δ 8.60 (s, 1H), 7.70 (s, 1H), 7.06 (d, J=42.40 Hz, 1H), 6.44 (d, J=2.80 Hz, 1H), 4.11 (s, 2H), 2.33 (s, 3H), 2.06-1.92 (m, 6H), 1.63-1.60 (m, 2H).

Example-862

Step 1[NSSy6744]: To an ice cooled solution of (2-((4,4-difluorocyclohexyl)amino)-6-(3-methyl-1H-pyrazol-1-yl)pyrimidin-4-yl) methanol (0.2 g, 0.61 mmol) in tetrahydrofuran (8 mL) was added sodium hydride (0.037 g, 0.92 mmol) and the reaction mixture was stirred at rt for 30 min. After 30 min, added a solution of iodomethane (0.096 g, 0.68 mmol) in tetrahydrofuran (2 mL) to the above reaction mixture at 0° C. and stirred at same temperature for 2 h. The reaction mixture was quenched with water and extracted with ethyl acetate (2×35 mL). The combined organic layer was dried over sodium sulfate and concentrated to afford crude and that was purified by Prep TLC using 30% ethyl acetate in pet ether as an eluent to afford N-(4,4-difluorocyclohexyl)-4-(methoxymethyl)-6-(3-methyl-1H-pyrazol-1-yl)pyrimidin-2-amine as an off-white solid (0.042 g, 20%). MS (M+1)$^+$=338.2; $^1$H-NMR (400 MHz, DMSO-d$_6$): δ 8.57 (m, 1H), 7.47 (m, 1H), 7.01 (s, 1H), 6.41 (s, 1H), 4.34 (s, 2H), 3.98 (m, 1H), 3.40 (s, 3H), 2.29 (s, 3H), 2.05-1.91 (m, 6H), 1.61-1.59 (m, 2H).

Example-863

Step 1[NSSy6783]: To a solution of 4-(chloromethyl)-N-(4,4-difluorocyclohexyl)-6-(3-methyl-1H-pyrazol-1-yl)pyrimidin-2-amine (0.1 g, 0.29 mmol) in acetonitrile (8 mL) was added cesium carbonate (0.38 g, 1.17 mmol) and dimethyl amine (0.079 g, 1.75 mmol). The reaction mixture was heated at 70° C. in a closed vial for 16 h. The reaction mixture was filtered and the filtrate was concentrated to afford crude which was purified by Prep HPLC to afford N-(4,4-difluorocyclohexyl)-4-((dimethylamino)methyl)-6-(3-methyl-1H-pyrazol-1-yl)pyrimidin-2-amine as light brown solid (0.06 g, 60%). MS (M+1)$^+$=351.2; $^1$H-NMR (400 MHz, DMSO-d$_6$): δ 8.55 (m, 1H), 7.44-7.42 (m, 1H), 7.08 (s, 1H), 6.41 (s, 1H), 4.00 (m, 1H), 2.33 (s, 3H), 2.28 (s, 3H), 2.24 (m, 2H), 1.95-1.88 (m, 6H), 1.61-1.59 (m, 2H).

Example-864

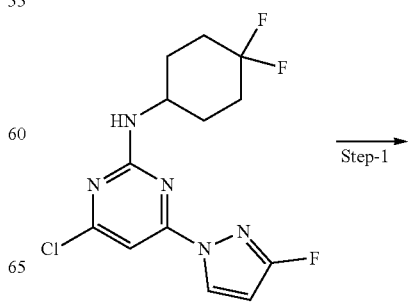

721
-continued

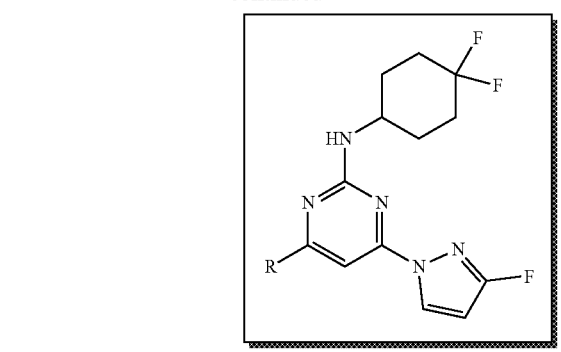

R=

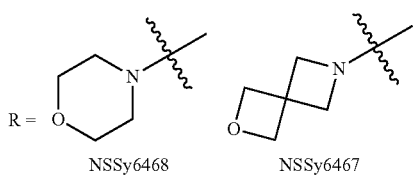 [SMILES: *N1CCOCC1 ; *N1CC2(COC2)C1]

TABLE 7

| Compound No | R | Condition | Yield (%) |
| --- | --- | --- | --- |
| NSSy6468 | ![morpholine] | Cs₂CO₃, ACN, 75° C., 16 h | 66 |
| NSSy6467 | ![oxa-azaspiro] | Cs₂CO₃, ACN, 75° C., 8 h | 59 |

Step 1[NSSy6468]: The procedure is similar to Step 1[B] in Example-838. MS (M+1)⁺=382.4; ¹H-NMR (400 MHz, DMSO-d₆): δ 8.40 (s, 1H), 6.47 (d, J=6.80 Hz, 1H), 6.27-6.23 (m, 2H), 3.96 (s, 1H), 3.68 (s, 4H), 3.59 (s, 4H), 2.15-1.85 (m, 6H), 1.65-1.55 (m, 2H).

Step 1[NSSy6467]: The procedure is similar to Step 1[B] in Example-838. MS (M+1)⁺=394.4; ¹H-NMR (400 MHz, DMSO-d₆): δ 8.54 (s, 1H), 7.03 (s, 1H), 6.35 (s, 1H), 5.85 (s, 1H), 4.72 (s, 4H), 4.19 (s, 4H), 4.05 (s, 4H), 2.15-1.85 (m, 6H), 1.65-1.50 (m, 2H).

722
Example-865

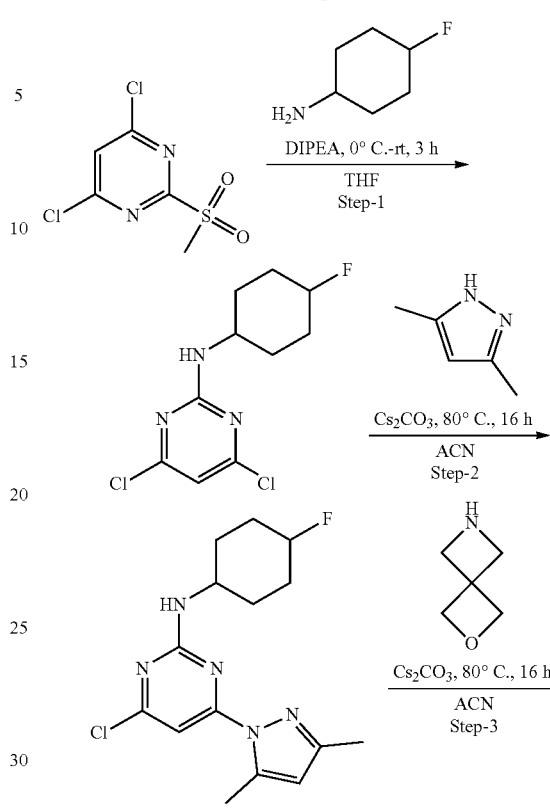

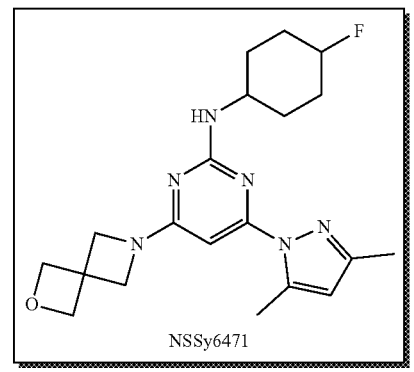

Step 1: The procedure is similar to Step 1[A] in Example-838. 0.4 g of 4,6-dichloro-2-(methylsulfonyl)pyrimidine gave 4,6-dichloro-N-(4-fluorocyclohexyl)pyrimidin-2-amine as a colourless gum (0.18 g, 34%). MS (M+1)⁺=264.12.

Step 2: The procedure is similar to Step 1[B] in Example-838. 0.18 g of 4,6-dichloro-N-(4-fluorocyclohexyl)pyrimidin-2-amine gave 4-chloro-6-(3,5-dimethyl-1H-pyrazol-1-yl)-N-(4-fluorocyclohexyl)pyrimidin-2-amine as a white solid (0.15 g, 68%). MS (M+1)⁺=323.8.

Step 3[NSSy6471]: The procedure is similar to Step 1[B] in Example-838. 0.15 g of 4-chloro-6-(3,5-dimethyl-1H-pyrazol-1-yl)-N-(4-fluorocyclohexyl)pyrimidin-2-amine gave 4-(3,5-dimethyl-1H-pyrazol-1-yl)-N-(4-fluoro cyclohexyl)-6-(2-oxa-6-azaspiro[3.3]heptan-6-yl)pyrimidin-2-amine as a white solid (0.14 g, 78%). MS (M+1)⁺=386.5; ¹H-NMR (400 MHz, DMSO-d₆): δ 6.87 (bs, 1H), 6.06 (s, 1H), 5.95 (s, 1H), 4.84 (s, 4H), 4.15 (s, 4H), 3.33 (bs, 1H), 2.60 (s, 3H), 2.17 (s, 3H), 2.08-1.85 (m, 3H), 1.82-1.65 (m, 2H), 1.65-1.42 (m, 3H), 1.42-1.28 (m, 1H).

Example-866

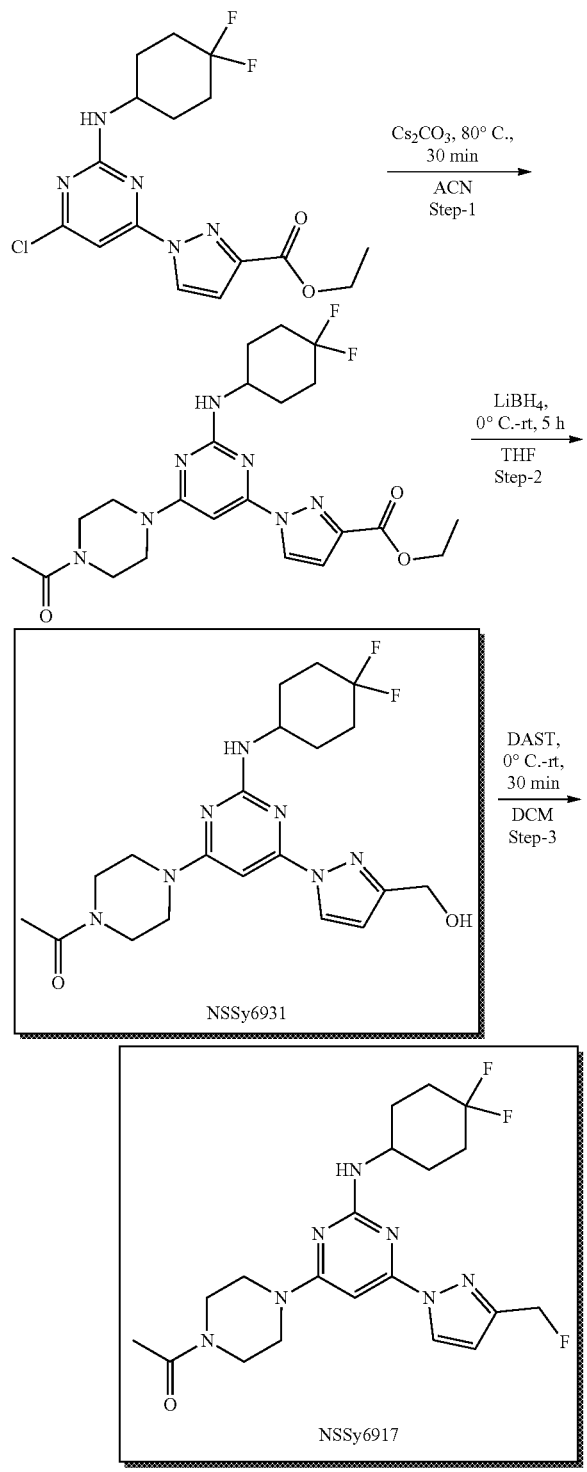

Step 1: The procedure is similar to Step 1[B] in Example-838. 0.8 g of ethyl 1-(6-chloro-2-((4,4-difluorocyclohexyl)amino)pyrimidin-4-yl)-1H-pyrazole-3-carboxylate gave ethyl 1-(6-(4-acetylpiperazin-1-yl)-2-((4,4-difluoro cyclohexyl)amino)pyrimidin-4-yl)-1H-pyrazole-3-carboxylate as a white solid (0.6 g, 66%). MS (M+1)+=477.5.

Step 2[NSSy6931]: To an ice cooled solution of ethyl 1-(6-(4-acetylpiperazin-1-yl)-2-((4,4-difluorocyclohexyl)amino)pyrimidin-4-yl)-1H-pyrazole-3-carboxylate (0.5 g, 1.04 mmol) in THF (20 mL) was added Lithium borohydride (0.068 g, 3.14 mmol) and stirred at rt for 5 h. The reaction mixture was quenched with water and extracted with ethyl acetate (2×50 mL), the combined organic layer was dried over sodium sulfate and concentrated to afford crude product, which was purified by flash chromatography using 60% ethyl acetate in hexane as eluent to afford 1-(4-(2-((4,4-difluorocyclohexyl)amino)-6-(3-(hydroxymethyl)-1H-pyrazol-1-yl)pyrimidin-4-yl)piperazin-1-yl)ethan-1-one as a white solid (0.033 g, 7%). MS (M+1)+=435.5; 1H-NMR (400 MHz, DMSO-d6): δ 8.46 (s, 1H), 6.91 (s, 1H), 6.53-6.38 (m, 2H), 5.23-5.20 (m, 1H), 4.50-4.48 (m, 2H), 3.97 (s, 1H), 3.66 (s, 2H), 3.56-3.53 (m, 6H), 2.07-2.04 (m, 6H), 1.99 (s, 3H), 1.93-1.91 (m, 2H).

Step 3[NSSy6917]: To an ice cooled solution of 1-(4-(2-((4,4-difluorocyclohexyl)amino)-6-(3-(hydroxymethyl)-1H-pyrazol-1-yl)pyrimidin-4-yl)piperazin-1-yl)ethan-1-one (0.15 g, 0.34 mmol) in DCM (10 mL) was added diethylaminosulphur trifluoride (0.11 g, 0.09 mL, 0.38 mmol), then the reaction mixture was slowly warmed to rt and stirred for 30 mins. Then the reaction mixture was quenched with 10% sodium bicarbonate solution and extracted with dichloromethane (2×50 mL). The combined organic layer was washed with brine, dried over sodium sulfate, filtered and concentrated under reduced pressure to afford crude product, which was purified by flash chromatography using ethyl acetate and pet-ether as solvent system to afford as an off-white solid (0.04 g, 27%). MS (M+1)+=437.9; 1H-NMR (400 MHz, DMSO-d6): δ 6.99 (bs, 1H), 6.66 (s, 1H), 6.43 (s, 1H) 5.50 (s, 1H), 5.38 (s, 1H), 3.98 (s, 1H), 3.68 (s, 2H), 3.59 (s, 2H), 3.54-3.52 (m, 4H), 2.06-2.04 (m, 6H), 1.94 (s, 3H), 1.54-1.61 (m, 2H).

Example-867

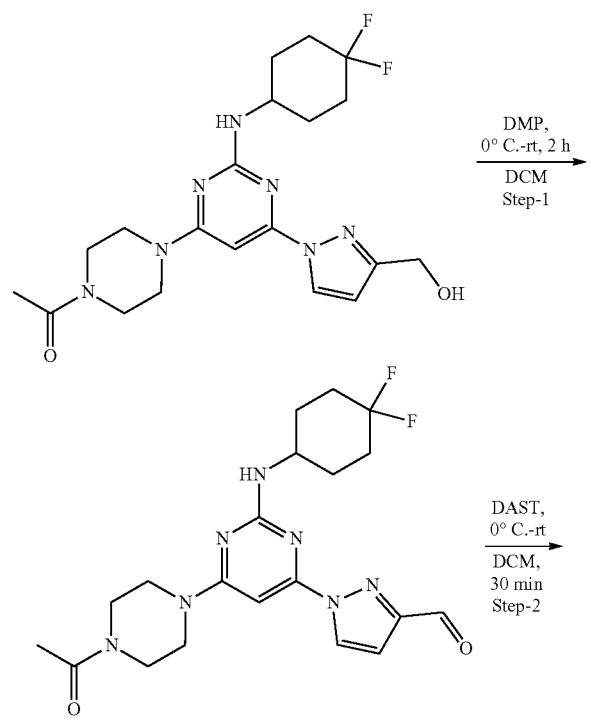

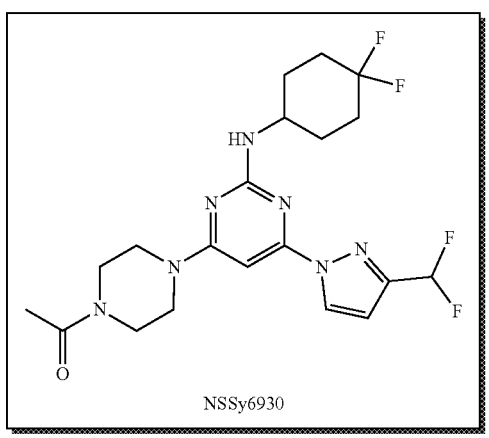

NSSy6930

Step 1: To an ice-cooled solution of 1-(4-(2-((4,4-difluorocyclohexyl)amino)-6-(3-(hydroxymethyl)-1H-pyrazol-1-yl)pyrimidin-4-yl) piperazin-1-yl) ethan-1-one (0.18 g, 0.41 mmol) in DCM (10 mL) was added dess-Martin periodinane (0.54 g, 1.24 mmol). The reaction mixture was stirred at 0° C. and slowly warmed to rt and stirred for 2 h. The reaction mixture was quenched with saturated sodium thio sulfate solution and extracted with dichloromethane (2×20 mL). The combined organic layer was washed with 10% sodium bicarbonate, water, brine and dried over sodium sulfate and concentrated to afford 1-(6-(4-acetylpiperazin-1-yl)-2-((4,4-difluorocyclohexyl)amino)pyrimidin-4-yl)-1H-pyrazole-3-carbaldehyde as an off-white solid (0.16 g, 88%). MS (M+1)+=434.2.

Step 2[NSSy6930]: The procedure is similar to Step 3[NSSy6917] in Example-21. 0.15 g of 1-(6-(4-acetylpiperazin-1-yl)-2-((4,4-difluorocyclohexyl)amino)pyrimidin-4-yl)-1H-pyrazole-3-carbaldehyde gave 1-(4-(2-((4,4-difluorocyclohexyl)amino)-6-(3-(difluoromethyl)-1H-pyrazol-1-yl)pyrimidin-4-yl)piperazin-1-yl)ethan-1-one as a white solid (0.035 g, 22%). MS (M+1)+=455.9; 1H-NMR (400 MHz, DMSO-d6): δ 8.80 (s, 1H), 7.05 (s, 1H) 7.26-6.99 (m, 1H), 6.80 (s, 1H), 6.44 (s, 1H), 3.98 (bs, 1H), 3.68 (s, 2H), 3.59 (s, 2H), 3.54-3.53 (m, 4H), 2.08-2.05 (m, 6H), 1.94-1.91 (m, 3H), 1.61-1.58 (m, 2H).

Example-868

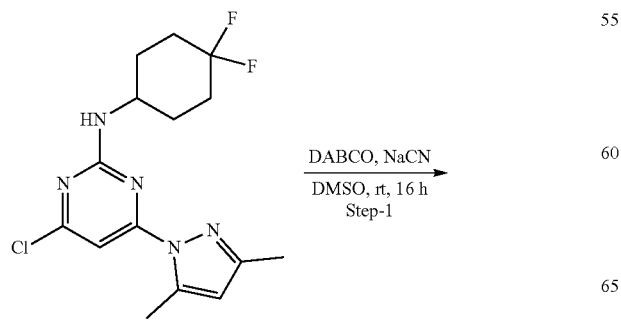

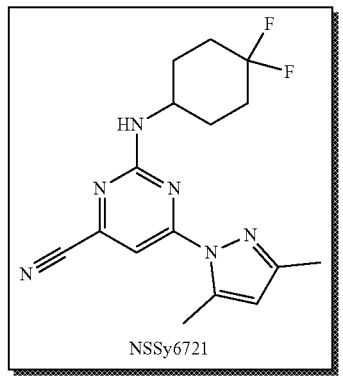

NSSy6721

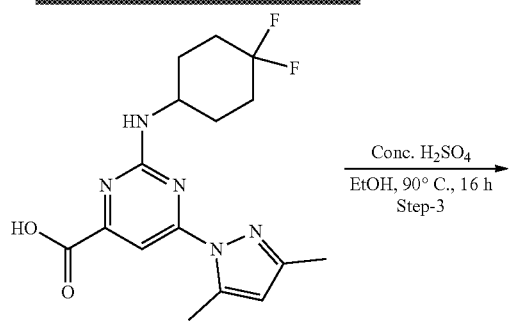

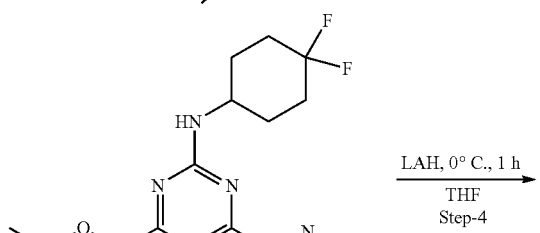

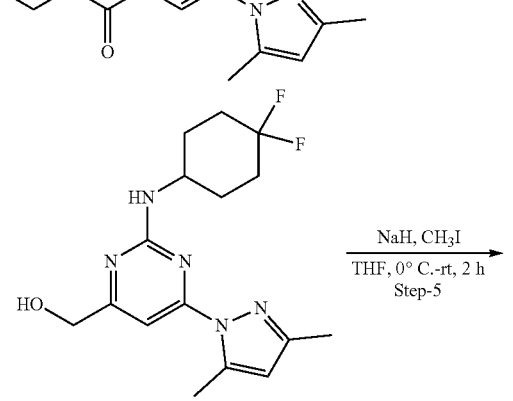

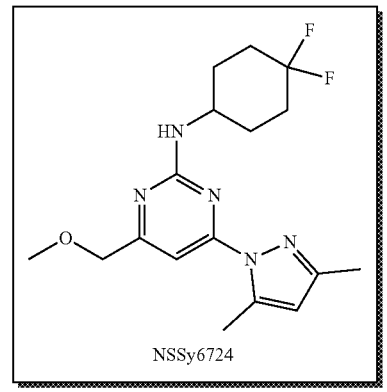

NSSy6724

Step 1[NSSy6721]: The procedure is similar to Step 1[NSSy6710] in Example-854. 0.3 g of 4-chloro-N-(4,4-difluorocyclohexyl)-6-(3,5-dimethyl-1H-pyrazol-1-yl)pyrimidin-2-amine gave 2-((4,4-difluorocyclohexyl)amino)-6-(3,5-dimethyl-1H-pyrazol-1-yl)pyrimidine-4-carbonitrile as an off-white solid (0.3 g, 86%). MS (M+1)+=333.0; 1H-NMR (400 MHz, DMSO-d6): δ 8.13 (s, 1H), 7.37 (s, 1H), 6.25 (s, 1H), 3.84 (s, 1H), 2.66 (s, 3H), 2.20 (s, 3H), 2.07-1.93 (m, 6H), 1.60-1.58 (m, 2H).

Step 2: The procedure is similar to Step 2[NSSy6711] in Example-854. 0.25 g of 2-((4,4-difluorocyclohexyl)amino)-6-(3,5-dimethyl-1H-pyrazol-1-yl)pyrimidine-4-carbonitrile gave 2-((4,4-difluorocyclohexyl)amino)-6-(3,5-dimethyl-1H-pyrazol-1-yl)pyrimidine-4-carboxylic acid as a white solid (0.3 g, 50%). MS (M+1)+=352.0.

Step 3: The procedure is similar to Step 3[NSSy6711] in Example-854. 0.2 g of 2-((4,4-difluorocyclohexyl)amino)-6-(3,5-dimethyl-1H-pyrazol-1-yl)pyrimidine-4-carboxylic acid gave ethyl 2-((4,4-difluorocyclohexyl)amino)-6-(3,5-dimethyl-1H-pyrazol-1-yl)pyrimidine-4-carboxylate as an off-white solid (0.21 g, 95%). MS (M+1)+=380.0.

Step 4: The procedure is similar to Step 4[NSSy6711] in Example-854. 0.21 g of ethyl 2-((4,4-difluorocyclohexyl)amino)-6-(3,5-dimethyl-1H-pyrazol-1-yl)pyrimidine-4-carboxylate gave (2-((4,4-difluorocyclohexyl)amino)-6-(3,5-dimethyl-1H-pyrazol-1-yl)pyrimidin-4-yl) methanol as an off-white solid (0.1 g, 55%). MS (M+1)+=338.0.

Step 5[NSSy6724]: The procedure is similar to Step 5[NSSy6711] in Example-854. 0.1 g of (2-((4,4-difluorocyclohexyl)amino)-6-(3,5-dimethyl-1H-pyrazol-1-yl)pyrimidin-4-yl) methanol gave N-(4,4-difluorocyclohexyl)-4-(3,5-dimethyl-1H-pyrazol-1-yl)-6-methoxymethyl)pyrimidin-2-amine as an off-white solid (0.05 g, 50%). MS (M+1)+=352.0; 1H-NMR (400 MHz, DMSO-d6): δ 7.47 (s, 1H), 7.05 (s, 1H), 6.14 (s, 1H), 4.29 (s, 2H), 3.85-3.84 (m, 1H), 3.38 (s, 3H), 2.66 (s, 3H), 2.19 (s, 3H), 2.09-2.07 (m, 2H), 1.95-1.83 (m, 4H), 1.62-1.54 (m, 2H).

Example-869

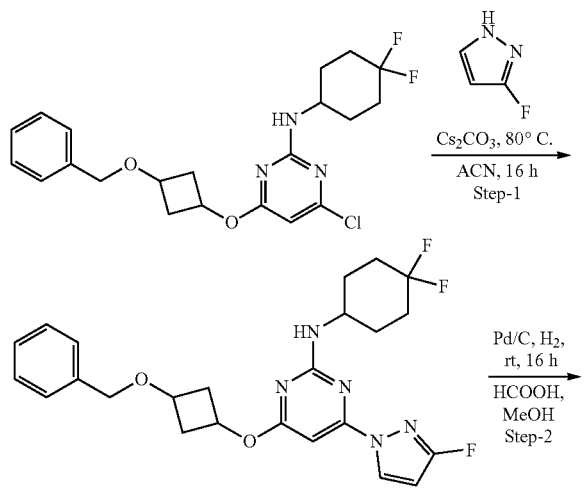

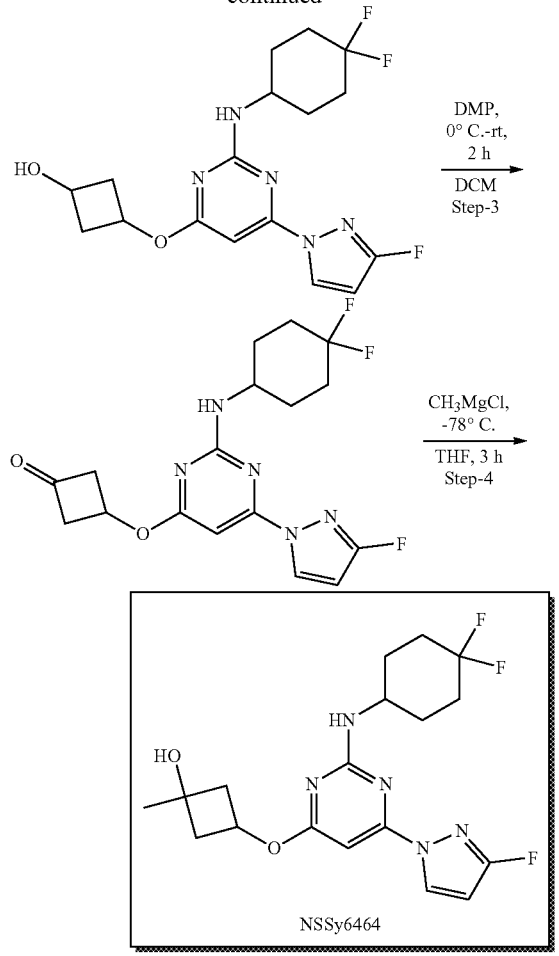

Step 1: The procedure is similar to Step 1[B] in Example-838. 0.5 g of 4-(3-(benzyloxy)cyclobutoxy)-6-chloro-N-(4,4-difluorocyclohexyl)pyrimidin-2-amine gave 4-(3-(benzyloxy)cyclobutoxy)-N-(4,4-difluorocyclohexyl)-6-(3-Fluoro-1H-pyrazol-1-yl)pyrimidin-2-amine as yellowish gum (0.54 g, 98%). MS (M+1)+=474.1.

Step 2: To a stirred solution of 4-(3-(benzyloxy)cyclobutoxy)-N-(4,4-difluorocyclohexyl)-6-(3-fluoro-1H-pyrazol-1-yl)pyrimidin-2-amine (0.45 g, 0.95 mmol) in methanol (5 mL) was added Formic acid (0.2 mL) and followed by palladium on carbon (10%, 0.05 g). The reaction mixture was stirred at rt for 16 h. The reaction mixture was filtered through celite, filtrate was concentrated under reduced pressure, and residue was quenched with saturated bicarbonate solution and extracted with ethyl acetate (2×50 mL). The combined organic layer was dried over sodium sulfate, filtered and concentrated under reduced pressure to afford 3-((2-((4,4-difluorocyclohexyl)amino)-6-(3-fluoro-1H-pyrazol-1-yl)pyrimidin-4-yl)oxy)cyclobutan-1-ol as a colourless gum (0.35 g, 97%). MS (M+1)+=384.1.

Step 3: The procedure is similar to Step 1[NSSy6930] in Example-867. 0.35 g of 3-((2-((4,4-difluorocyclohexyl)amino)-6-(3-fluoro-1H-pyrazol-1-yl)pyrimidin-4-yl)oxy)cyclobutan-1-ol gave of 3-((2-((4,4-difluorocyclohexyl)amino)-6-(3-fluoro-1H-pyrazol-1-yl)pyrimidin-4-yl)oxy)cyclobutan-1-one as a white solid (0.1 g, 29%). MS (M+1)+=382.1.

Step 4[NSSy6464]: To a pre-cooled (−78° C.) solution of 3-((2-((4,4-difluorocyclohexyl)amino)-6-(3-fluoro-1H-pyrazol-1-yl)pyrimidin-4-yl)oxy)cyclobutan-1-one (0.1 g, 0.26 mmol) in tetrahydrofuran (10 mL) was added methylmagnesium bromide (1.4 M solution in THF:Toluene)(0.09 g, 0.78 mmol) and stirred at −78° C. for 2 h. The reaction mixture was quenched with saturated aqueous ammonium chloride solution and extracted with ethyl acetate (2×20 mL). The combined organic layer was dried over sodium sulfate and concentrated under reduced pressure to afford crude product, which was purified by preparative HPLC to afford 3-((2-((4,4-difluorocyclohexyl)amino)-6-(3-fluoro-1H-pyrazol-1-yl)pyrimidin-4-yl)oxy)-1-methylcyclobutan-1-ol as an off-white solid (5.1 mg, 5%). MS (M+1)+=398.2; 1H-NMR (400 MHz, DMSO-d6): δ 8.37 (s, 1H), 6.88 (s, 1H), 6.24 (s, 1H), 5.52 (s, 1H), 4.54-4.53 (m, 1H), 3.67-3.66 (m, 4H), 3.65-3.40 (m, 4H), 3.36 (s, 1H), 1.98 (s, 3H), 1.87-1.81 (m, 3H), 1.64-1.55 (m, 1H).

Example-870

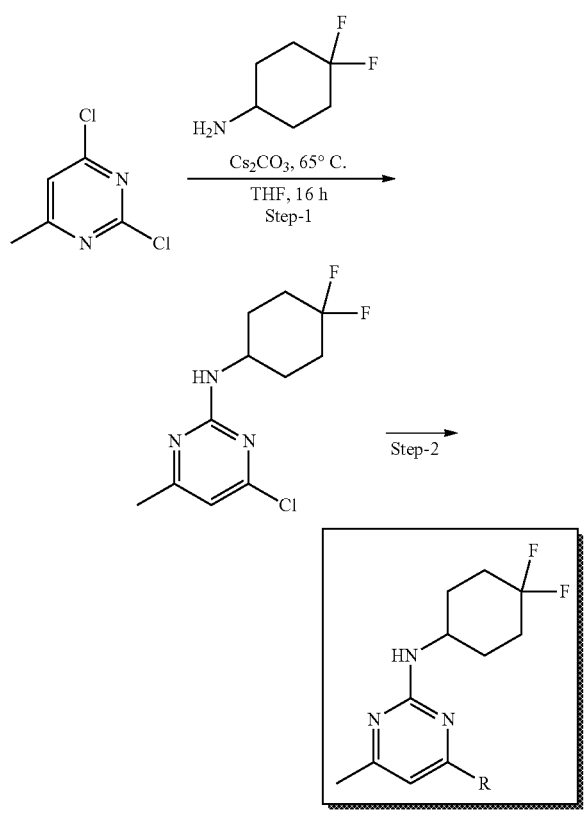

R=

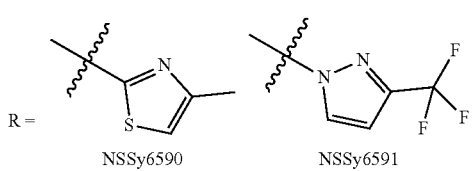

NSSy6590  NSSy6591

-continued

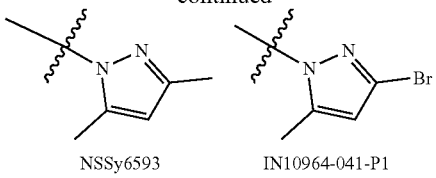

NSSy6593  IN10964-041-P1

Step 1: The procedure is similar to Step 1[B] in Example-838. 3.0 g of 2,4-dichloro-6-methylpyrimidine gave 2-chloro-N-(4,4-difluorocyclohexyl)-6-methylpyrimidin-4-amine as an off-white solid (2.5 g, 52%). MS (M+1)+=262.9.

TABLE 8

| | Step 2: | | |
|---|---|---|---|
| Compound No | R | Condition | Yield (%) |
| NSSy6590 | (4-methylthiazol-2-yl) | Pd(PPh₃)₂Cl₂, toluene, 100° C., 16 h | 27 |
| NSSy6591 | (3-(trifluoromethyl)-1H-pyrazol-1-yl) | Cs₂CO₃, ACN, 80° C., 16 h | 87 |
| NSSy6593 | (3,5-dimethyl-1H-pyrazol-1-yl) | Cs₂CO₃, ACN, 80° C., 16 h | 72 |
| IN10964-041-P1 | (3-bromo-5-methyl-1H-pyrazol-1-yl) | Cs₂CO₃, ACN, 100° C., 2 h | 81 |

Step 2[NSSy6590]: The procedure is similar to Step 1[NSSy6989] in Example-839. MS (M+1)+=325.0; 1H-NMR (400 MHz, DMSO-d6): δ 7.48 (d, J=0.80 Hz, 1H), 7.36 (s, 1H), 7.11 (s, 1H), 3.93-3.88 (m, 1H), 2.44 (s, 3H), 2.34 (s, 3H), 2.17-1.86 (m, 6H), 1.67-1.49 (m, 2H).

Step 2[NSSy6591]: The procedure is similar to Step 1[B] in Example-838. MS (M+1)+=362.2; 1H-NMR (400 MHz, DMSO-d6): δ 8.91 (bs, 1H), 7.64 (bs, 1H), 7.09 (s, 1H), 6.98 (s, 1H), 4.04 (s, 1H), 2.36 (s, 3H), 2.20-1.80 (m, 6H), 1.70-1.5 (m, 2H).

Step 2[NSSy6593]: The procedure is similar to Step 1[B] in Example-838. MS (M+1)+=322.0; 1H-NMR (400 MHz, DMSO-d6): δ 7.38 (s, 1H), 6.89 (s, 1H), 6.13 (s, 1H), 3.86 (s, 1H), 2.65 (s, 3H), 2.28 (s, 3H), 2.19 (s, 3H), 2.15-1.85 (m, 6H), 1.65-1.52 (m, 2H).

Step 2[IN10964-041-P1]: The procedure is similar to Step 1[B] in Example-838. MS (M+1)+=387.9; 1H-NMR (400

MHz, DMSO-d6): δ 7.55 (s, 1H), 6.87 (s, 1H), 6.52 (s, 1H), 3.85 (s, 1H), 2.68 (s, 3H), 2.31 (s, 3H), 2.10-1.80 (m, 6H), 1.61-1.50 (m, 2H).

Example-871

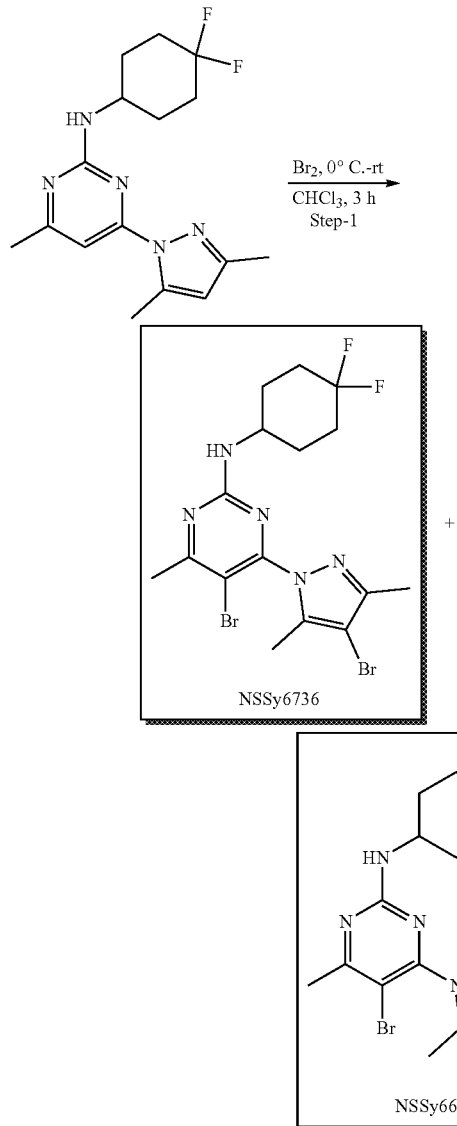

Step 1[NSSy6736 and NSSy6678]: To a stirred solution of N-(4,4-difluorocyclohexyl)-4-(3,5-dimethyl-1H-pyrazol-1-yl)-6-methylpyrimidin-2-amine (0.54 g, 1.68 mmol) in chloroform (8 mL) was added bromine (0.29 g, 1.84 mmol) dropwise at 0° C. and stirred at rt for 3 h. The reaction mixture was diluted with chloroform, washed with water, dried over anhydrous sodium sulfate, concentrated under reduced pressure to afford crude product and which was purified by flash column chromatography using ethyl acetate in pet-ether as solvent to afford 5-bromo-4-(4-bromo-3,5-dimethyl-1H-pyrazol-1-yl)-N-(4,4-difluorocyclohexyl)-6-methylpyrimidin-2-amine as an off-white solid (0.14 g, 17%). MS (M+1)$^+$=479.0; $^1$H-NMR (400 MHz, DMSO-d$_6$): δ 7.84 (s, 1H), 3.92-3.79 (m, 1H), 2.23 (s, 3H), 2.62 (s, 3H), 2.23 (s, 3H), 2.18 (s, 3H), 2.02-1.88 (m, 6H), 1.58-1.56 (m, 2H) and 5-bromo-N-(4,4-difluorocyclohexyl)-4-(3,5-dimethyl-1H-pyrazol-1-yl)-6-methylpyrimidin-2-amine as an off-white solid (0.07 g, 10%). MS (M+1)$^+$=400.0; $^1$H-NMR (400 MHz, DMSO-d$_6$): δ 7.48 (s, 1H), 6.90 (s, 1H), 3.85-3.82 (m, 1H), 2.75 (s, 3H), 2.30 (s, 3H), 2.22 (s, 3H), 2.10-1.62 (m, 6H), 1.58-1.53 (m, 2H).

Example-872

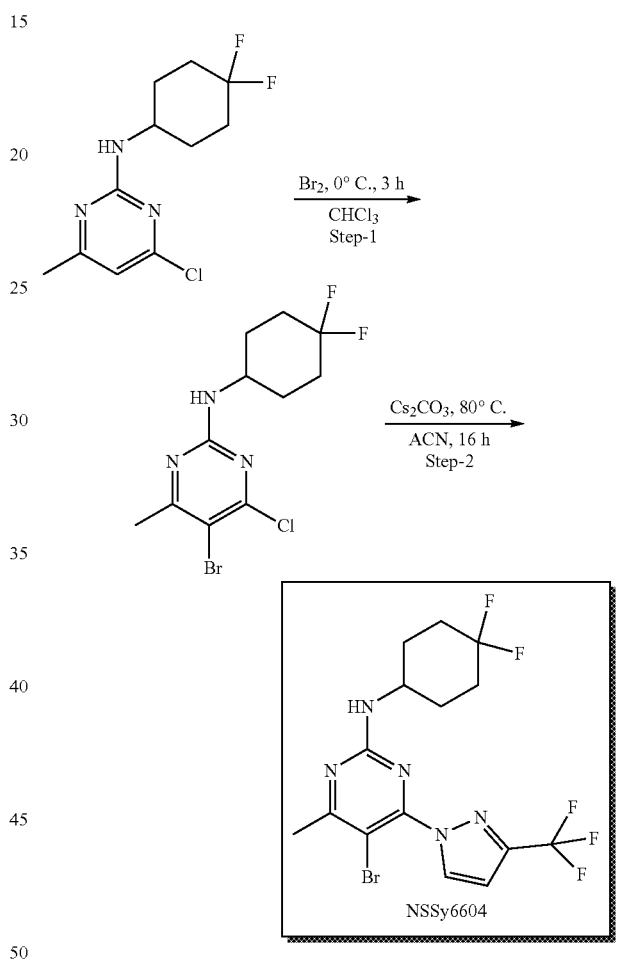

Step 1: The procedure is similar to Step 1[NSSy6736] in Example-26. 0.6 g of 4-chloro-N-(4,4-difluorocyclohexyl)-6-methylpyrimidin-2-amine gave 5-bromo-4-chloro-N-(4,4-difluorocyclohexyl)-6-methylpyrimidin-2-amine as an off-white solid (0.25 g, 32%). MS (M+1)+=342.0.

Step 2[NSSy6604]: The procedure is similar to Step 1[B] in Example-838. 0.25 g of 5-bromo-4-chloro-N-(4,4-difluorocyclohexyl)-6-methylpyrimidin-2-amine gave 5-bromo-N-(4,4-difluorocyclohexyl)-4-methyl-6-(3-(trifluoromethyl)-1H-pyrazol-1-yl)pyrimidin-2-amine as a colourless gum (0.14 g, 43%). MS (M+1)+=440.0; 1H-NMR (400 MHz, DMSO-d6): δ 8.55-8.47 (m, 1H), 7.91 (s, 1H), 7.05 (s, 1H), 3.93 (s, 1H), 2.51 (s, 3H), 2.15-1.85 (m, 6H), 1.68-1.52 (m, 2H).

Example-28

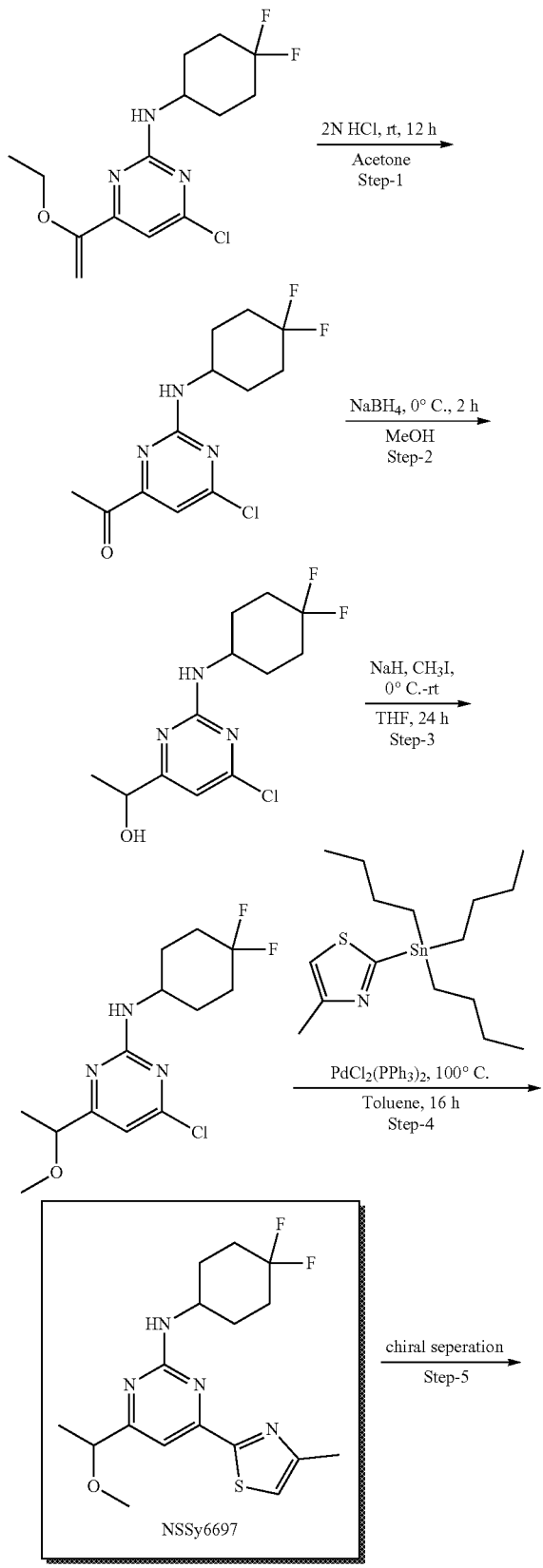

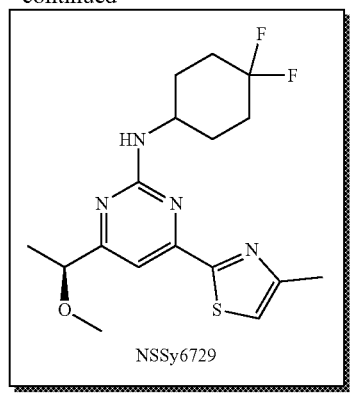

Step 1: To a stirred solution of 4-chloro-N-(4,4-difluorocyclohexyl)-6-(1-ethoxyvinyl)pyrimidin-2-amine (0.4 g, 1.25 mmol) in acetone (20 mL) was added aqueous hydrochloric acid (2N) (2 mL). The reaction mixture was allowed to stir at rt for 12 h. The reaction mixture was concentrated to remove acetone, diluted with ice-cold water, basified with saturated sodium bicarbonate solution and extracted with ethyl acetate (2×25 mL). The combined organic layer was concentrated under reduced pressure to afford crude product and which was purified by column chromatography using ethyl acetate in pet-ether as solvent to afford 1-(6-chloro-2-((4,4-difluorocyclohexyl)amino)pyrimidin-4-yl)ethan-1-one as an off-white solid (0.35 g, 97%). MS (M+1)+=290.1.

Step 2: The procedure is similar to Step 2[NSSy6931] in Example-21. 0.35 g of 1-(6-chloro-2-((4,4-difluorocyclohexyl)amino)pyrimidin-4-yl)ethan-1-one gave 1-(6-chloro-2-((4,4-difluorocyclohexyl)amino)pyrimidin-4-yl)ethan-1-ol as an white solid (0.31 g, 88%). MS (M+1)+=292.1.

Step 3: The procedure is similar to Step 5[NSSy6711] in Example-854. 0.31 g of 1-(6-chloro-2-((4,4-difluorocyclohexyl)amino)pyrimidin-4-yl) ethan-1-ol gave 0.27 g of 4-chloro-N-(4,4-difluorocyclohexyl)-6-(1-methoxyethyl)pyrimidin-2-amine as an off-white solid (0.27 g, 87%). MS (M+1)+=306.1.

Step 4[NSSy6697]: The procedure is similar to Step 1[H] in Example-838. 0.25 g of 4-chloro-N-(4,4-difluorocyclohexyl)-6-(1-methoxyethyl)pyrimidin-2-amine gave N-(4,4-difluorocyclohexyl)-4-(1-methoxyethyl)-6-(4-methylthiazol-2-yl)pyrimidin-2-amine as an off-white solid (0.15 g, 50%). MS (M+1)+=369.1; 1H-NMR (400 MHz, DMSO-d6): δ 7.51 (s, 2H), 7.24 (s, 1H), 4.19-4.18 (m, 1H), 3.92 (s, 1H), 3.28 (s, 3H), 2.46 (s, 3H), 2.15-1.85 (m, 6H), 1.72-1.60 (m, 2H), 1.36 (d, J=6.40 Hz, 3H).

Step 5[NSSy6729]: Racemate of N-(4,4-difluorocyclohexyl)-4-(1-methoxy ethyl)-6-(4-methylthiazol-2-yl)pyrimidin-2-amine was separated by chiral HPLC to afford (S)—N-(4,4-difluorocyclohexyl)-4-(1-methoxyethyl)-6-(4-methylthiazol-2-yl)pyrimidin-2-amine as an off-white solid. MS (M+1)+=369.1; 1H-NMR (400 MHz, DMSO-d6): δ 7.51 (s, 2H), 7.24 (s, 1H), 4.19-4.18 (m, 1H), 3.92 (s, 1H), 3.28 (s, 3H), 2.46 (s, 3H), 2.15-1.85 (m, 6H), 1.72-1.60 (m, 2H), 1.36 (d, J=6.40 Hz, 3H).

Example-874
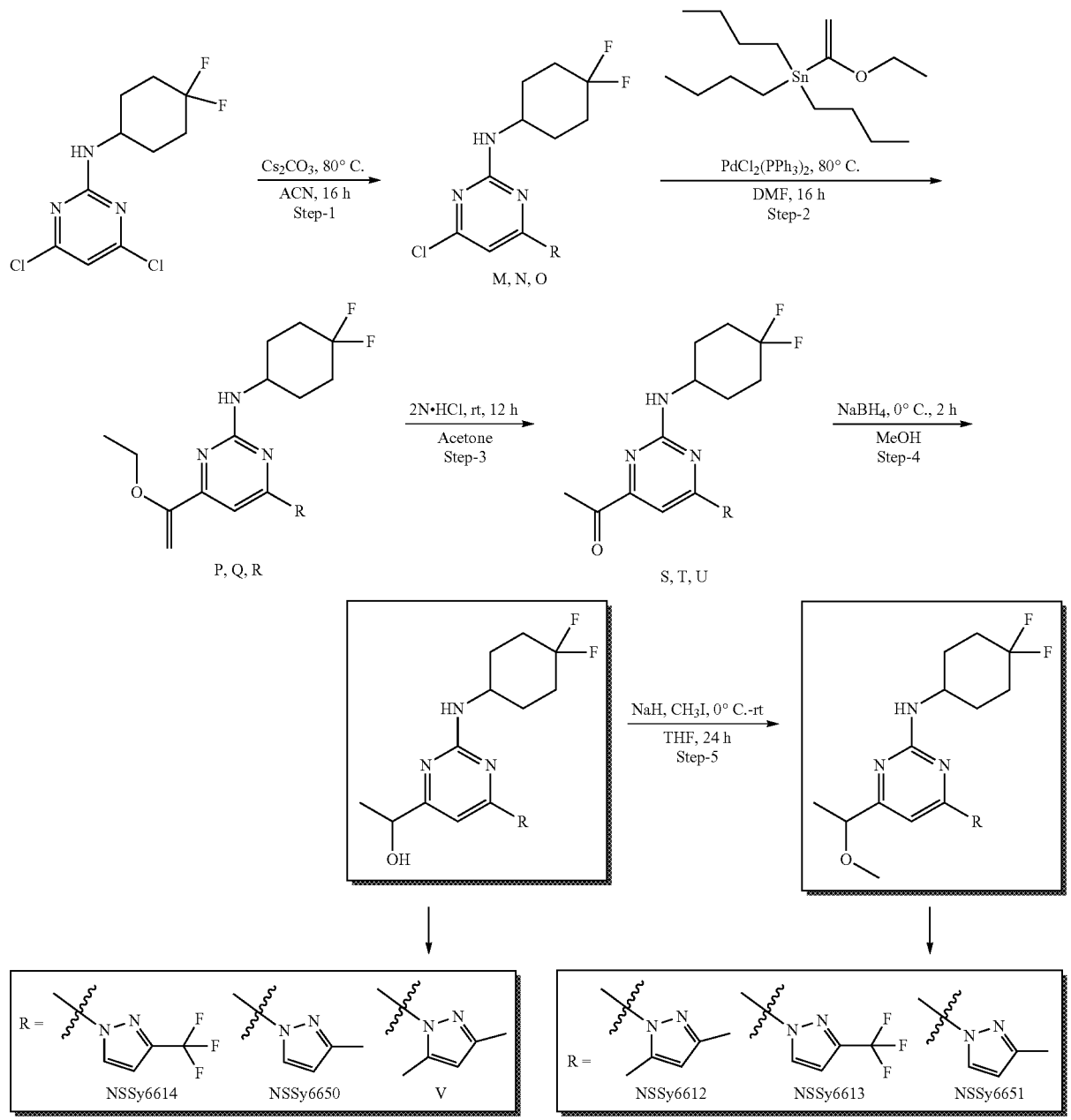
TABLE 9
| Step 1: The procedure is similar to Step 1[B] in Example-838. | | | | |
|---|---|---|---|---|
| Compound No | R | Condition | Yield (%) | MS (M + 1)+ |
| M | 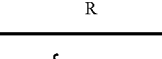 | Cs₂CO₃, ACN, 70° C., 16 h | 70 | 342.1 |

TABLE 9-continued

Step 1: The procedure is similar to Step 1[B] in Example-838.

| Compound No | R | Condition | Yield (%) | MS (M + 1)⁺ |
|---|---|---|---|---|
| N | [pyrazole with CF₃] | Cs₂CO₃, ACN, 75° C., 16 h | 83 | 382.7 |
| O | [3-methylpyrazole] | Cs₂CO₃, ACN, 75° C., 16 h | 47 | 328.1 |

TABLE 10

Step 2: The procedure is similar to Step 1[H] in Example-838.

| Compound No | R | Condition | Yield (%) | MS (M + 1)⁺ |
|---|---|---|---|---|
| P | [3,5-dimethylpyrazole] | Pd(PPh₃)₂Cl₂, DMF, 80° C., 16 h | 52 | 378 |
| Q | [pyrazole with CF₃] | Pd(PPh₃)₂Cl₂, DMF, 80° C., 16 h | 69 | 418.0 |
| R | [3-methylpyrazole] | Pd(PPh₃)₂Cl₂, DMF, 80° C., 16 h | 68 | 364.2 |

TABLE 11

Step 3: The procedure is similar to Step 1[NSSy6697] in Example-873.

| Compound No | R | Condition | Yield (%) | MS (M + 1)⁺ |
|---|---|---|---|---|
| S | [3,5-dimethylpyrazole] | 2N HCl•Acetone, rt, 12 h | 94 | 350.0 |
| T | [pyrazole with CF₃] | 2N HCl•Acetone, rt, 12 h | 85 | 390.0 |
| U | [3-methylpyrazole] | 2N, HCl•Acetone, rt, 12 h | 63 | 336.0 |

TABLE 12

Step 4: The procedure is similar to Step 2[NSSy6931] in Example-21.

| Compound No | R | Condition | Yield (%) | MS (M + 1)⁺ |
|---|---|---|---|---|
| V | 3,5-dimethyl-pyrazol-1-yl | NaBH₄, MeOH, 0° C., 2 h | 90 | 352.0 |
| NSSy6614 | 3-(trifluoromethyl)pyrazol-1-yl | NaBH₄, MeOH, 0° C., 2 h | 47 | 392.1 |
| NSSy6650 | 3-methyl-pyrazol-1-yl | NaBH₄, MeOH, 0° C., 2 h | 91 | 338.1 |

Step 4[NSSY6614]: $^1$H-NMR (400 MHz, DMSO-d$_6$): δ 8.74 (s, 1H), 7.60 (s, 1H), 7.23 (s, 1H), 7.10 (s, 1H), 5.55 (d, J=4.80 Hz, 1H), 4.52 (s, 1H), 4.05 (s, 1H), 2.15-1.85 (m, 6H), 1.68-1.52 (m, 2H), 1.37-1.36 (m, 3H).

Step 4[NSSY6650]: $^1$H-NMR (400 MHz, DMSO-d$_6$): δ 8.54 (s, 1H), 7.36 (s, 1H), 7.14 (s, 1H), 6.39 (s, 1H), 5.42 (d, J=4.80 Hz, 1H), 3.93 (s, 1H), 2.24 (s, 3H), 2.15-1.85 (m, 6H), 1.52-1.49 (m, 2H).

TABLE 13

Step 5: The procedure is similar to Step 5[NSSy6711] in Example-854.

| Compound No | R | Condition | Yield (%) | MS (M + 1)⁺ |
|---|---|---|---|---|
| NSSy6612 | 3,5-dimethyl-pyrazol-1-yl | NaH, CH₃I, 0° C.-rt, 16 h | 46 | 336.2 |
| NSSy6613 | 3-(trifluoromethyl)pyrazol-1-yl | NaH, CH₃I, 0° C.-rt, 16 h | 38 | 406.1 |
| NSSy6651 | 3-methyl-pyrazol-1-yl | NaH, CH₃I, 0° C.-rt, 16 h | 45 | 352.2 |

Step 5[NSSy6612]: $^1$H-NMR (400 MHz, DMSO-d$_6$): δ 7.52 (s, 1H), 7.04 (s, 1H), 6.15 (s, 1H), 4.12 (d, J=6.00 Hz, 1H), 3.86 (s, 1H), 3.26 (s, 3H), 2.67 (s, 3H), 2.20 (s, 3H), 2.15-1.85 (m, 6H), 1.65-1.53 (m, 2H), 1.34 (d, J=6.40 Hz, 3H).

Step 5[NSSy6613]: 1H-NMR (400 MHz, DMSO-d6): δ 8.79 (s, 1H), 7.71 (s, 1H), 7.07 (d, J=19.60 Hz, 2H), 4.20 (s, 1H), 4.05 (s, 1H), 3.28 (s, 3H), 2.15-1.90 (m, 6H), 1.65-1.55 (m, 2H), 1.36-1.34 (m, 3H).

Step 5[NSSy6651]: 1H-NMR (400 MHz, DMSO-d6): δ 8.45 (s, 1H), 7.04 (s, 1H), 6.99 (s, 1H), 6.36 (s, 1H), 4.18 (d, J=6.40 Hz, 1H), 3.99 (s, 1H), 3.32 (s, 3H), 2.30 (s, 3H), 2.15-1.85 (m, 6H), 1.75-1.63 (m, 2H), 1.39-1.37 (m, 3H).

Example-875

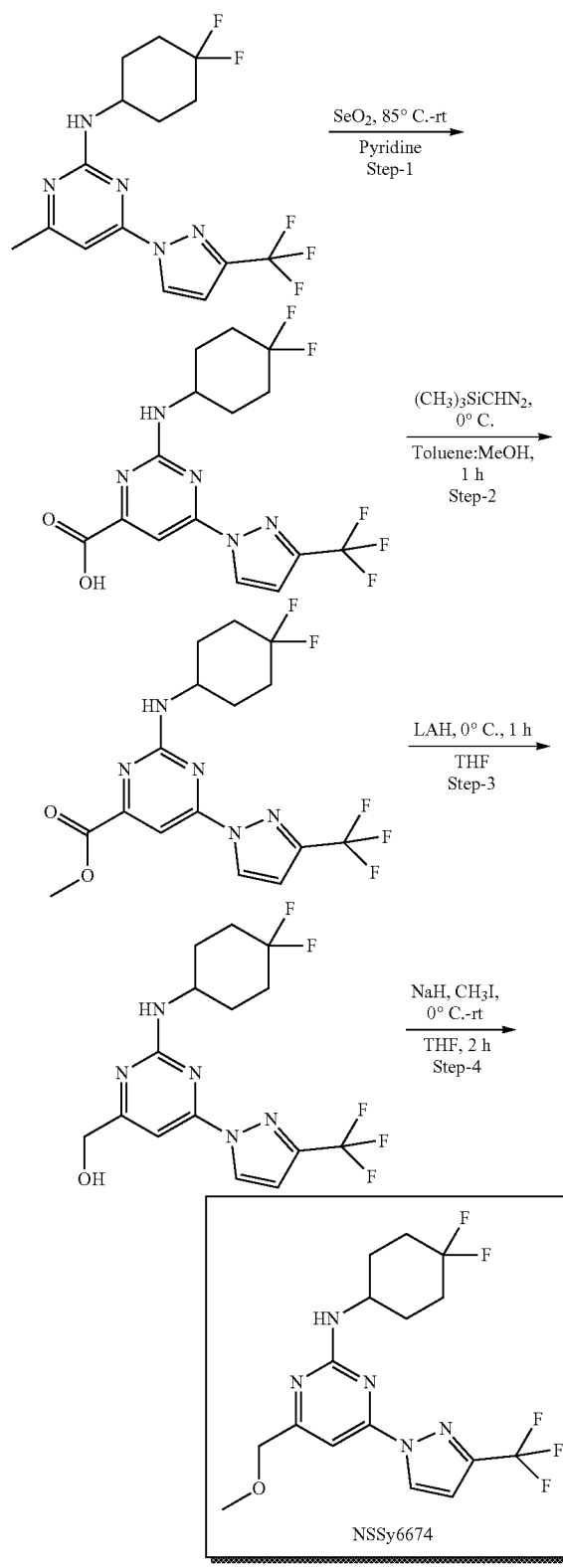

Step 1: To a solution of N-(4,4-difluorocyclohexyl)-4-methyl-6-(3-(trifluoromethyl)-1H-pyrazol-1-yl)pyrimidin-2-amine (0.3 g, 0.83 mmol) in pyridine (4 mL) was added selenium dioxide (0.27 g, 2.49 mmol) and the reaction mixture was heated at 55° C. for 2 h, then at 85° C. for 5 h, the reaction was allowed to stir at room temperature for 16 h. The reaction mixture was concentrated under reduced pressure and the residue was triturated with water, filtered and dried under vacuum to afford 2-((4,4-difluorocyclohexyl)amino)-6-(3-(trifluoromethyl)-1H-pyrazol-1-yl)pyrimidine-4-carboxylic acid as a pale brown solid (0.25 g). MS (M+1)+=392.2.

Step 2: To a suspension of 2-((4,4-difluorocyclohexyl)amino)-6-(3-(trifluoromethyl)-1H-pyrazol-1-yl)pyrimidine-4-carboxylic acid (0.25 g, 0.638 mmol) in Toluene (7 mL) and methanol (3 mL) was added (Trimethylsilyl)diazomethane (0.11 mL, 0.76 mmol), 2.0 M in hexane) at 0° C. and the reaction mixture was stirred at room temperature for 1 h. The reaction mixture was quenched with water and concentrated under reduced pressure to afford crude product, which was diluted with ethyl acetate, washed with water and brine solution. The organic layer was dried over sodium sulfate, filtered and concentrated under reduced pressure to afford methyl 2-((4,4-difluorocyclohexyl)amino)-6-(3-(trifluoromethyl)-1H-pyrazol-1-yl)pyrimidine-4-carboxylate as a brown gum (0.2 g). MS (M+1)+=406.4.

Step 3: The Procedure is similar to Step 4[NSSy6711] in Example-854. 0.18 g of methyl 2-((4,4-difluorocyclohexyl)amino)-6-(3-(trifluoromethyl)-1H-pyrazol-1-yl)pyrimidine-4-carboxylate gave (2-((4,4-difluorocyclohexyl)amino)-6-(3-(trifluoromethyl)-1H-pyrazol-1-yl)pyrimidin-4-yl) methanol as an off-white solid (0.15 g, 93%). MS (M+1)+= 378.4.

Step 4[NSSy6674]: The Procedure is similar to Step 5[NSSy6711] in Example-854. 0.18 g of (2-((4,4-difluorocyclohexyl)amino)-6-(3-(trifluoromethyl)-1H-pyrazol-1-yl)pyrimidin-4-yl) methanol gave N-(4,4-difluorocyclohexyl)-4-(methoxymethyl)-6-(3-(trifluoromethyl)-1H-pyrazol-1-yl)pyrimidin-2-amine as an off-white solid (0.15 g, 43%). MS (M+1)+=392.3; 1H-NMR (400 MHz, DMSO-d6): δ 8.75 (d, J=1.60 Hz, 1H), 7.26 (d, J=6.80 Hz, 1H), 7.11 (d, J=Hz, 1H), 6.98 (d, J=2.80 Hz, 1H), 4.39 (s, 2H), 4.04 (s, 1H), 3.44 (s, 3H), 2.04-1.94 (m, 6H), 1.75-1.67 (m, 2H).

Example-876

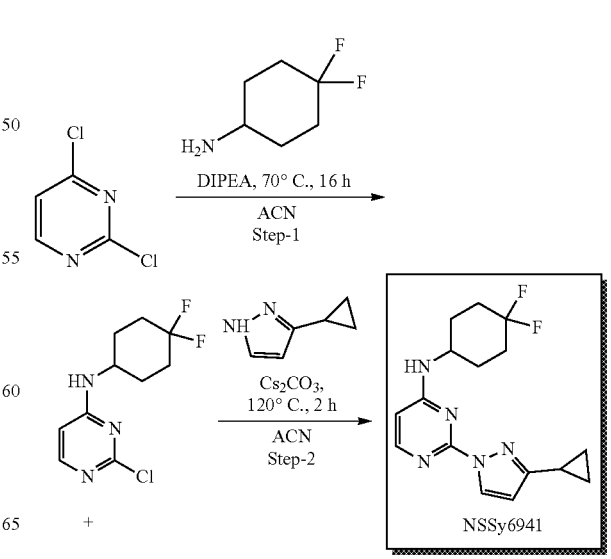

743
-continued

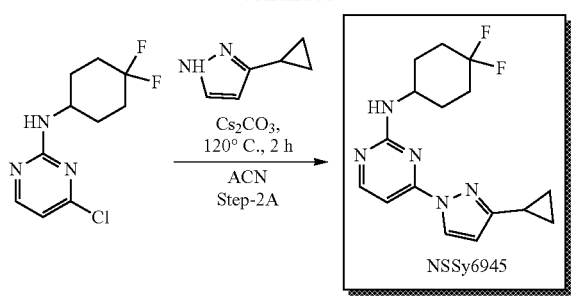

744
-continued

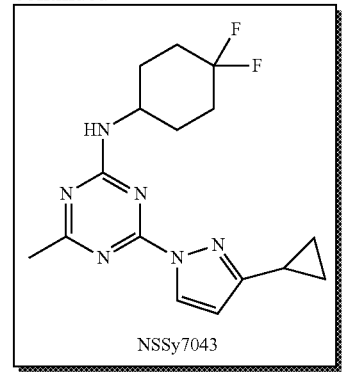

Step 1: The procedure is similar to Step 1[B] in Example-838. 1 g of 2,4-dichloropyrimidine gave 0.7 g of 2-chloro-N-(4,4-difluorocyclohexyl)pyrimidin-4-amine as an off-white solid and 0.06 g of 4-chloro-N-(4,4-difluorocyclohexyl)pyrimidin-2-amine as an off-white solid. MS (M+1)+=248.1.

Step 2[NSSy6941]: The procedure is similar to Step 1[B] in Example-838. 0.2 g of 2-chloro-N-(4,4-difluorocyclohexyl)pyrimidin-4-amine gave 2-(3-cyclopropyl-1H-pyrazol-1-yl)-N-(4,4-difluorocyclohexyl)pyrimidin-4-amine as a white solid (0.12 g, 50%). MS (M+1)+=320.1; 1H-NMR (400 MHz, DMSO-d6): δ 8.43 (s, 1H), 8.02 (s, 1H), 7.70 (s, 1H), 6.35 (s, 1H), 6.22 (s, 1H), 3.92-4.14 (m, 1H), 2.06-1.97 (m, 7H), 1.59-1.56 (m, 2H), 0.94-0.87 (m, 2H), 0.69-0.74 (m, 2H).

Step 2A [NSSy6945]: The procedure is similar to Step 1[B] in Example-838. 0.06 g of 4-chloro-N-(4,4-difluorocyclohexyl)pyrimidin-2-amine gave 4-(3-cyclopropyl-1H-pyrazol-1-yl)-N-(4,4-difluorocyclohexyl)pyrimidin-2-amine as white solid (0.031 g, 42%). MS (M+1)+=320.1; 1H-NMR (400 MHz, DMSO-d6): δ 8.55 (s, 1H), 8.32 (s, 1H), 7.41 (s, 1H), 6.93 (s, 1H), 6.33 (s, 1H), 3.99 (s, 1H), 2.15-1.85 (m, 7H), 1.68-1.55 (m, 2H), 0.97-0.94 (m, 2H), 0.77-0.75 (m, 2H).

Step 1: The procedure is similar to Step 1[B] in Example-838. 0.3 g of 2,4-dichloro-6-methyl-1,3,5-triazine gave 4-chloro-N-(4,4-difluorocyclohexyl)-6-methyl-1,3,5-triazin-2-amine as white solid (0.3 g, 60%). MS (M+1)+=263.1.

Step 2[NSSy7043]: The procedure is similar to Step 1[B] in Example-838. 0.15 g of 4-chloro-N-(4,4-difluorocyclohexyl)-6-methyl-1,3,5-triazin-2-amine gave 4-(3-cyclopropyl-1H-pyrazol-1-yl)-N-(4,4-difluorocyclohexyl)-6-methyl-1,3,5-triazin-2-amine as white solid (0.15 g, 78%). MS (M+1)+=335.1; 1H-NMR (400 MHz, DMSO-d6): δ 8.55-8.39 (m, 1H), 8.26 (d, J=8.00 Hz, 1H), 6.31 (s, 1H), 4.08 (s, 1H), 2.36 (s, 3H), 2.15-1.85 (m, 6H), 1.66-1.57 (m, 2H), 0.98 (s, 2H), 0.97 (s, 2H).

Example-878

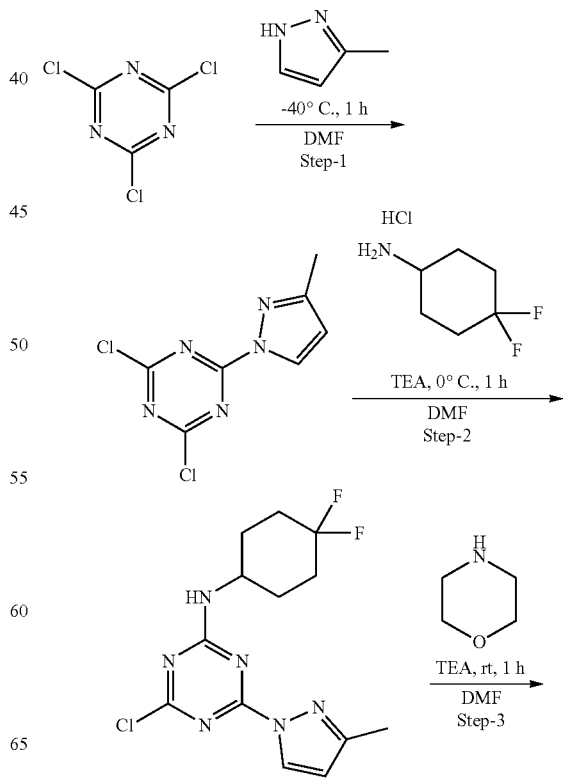

Example-877

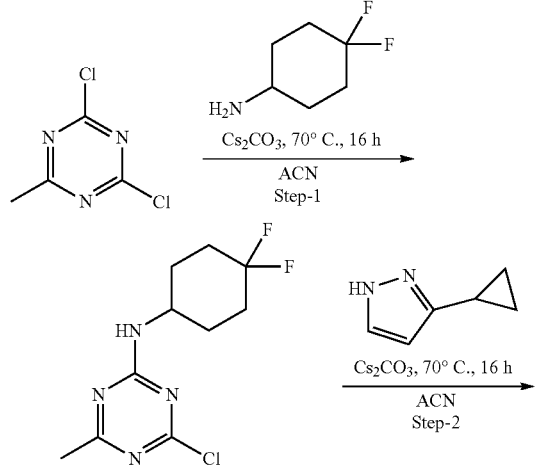

-continued

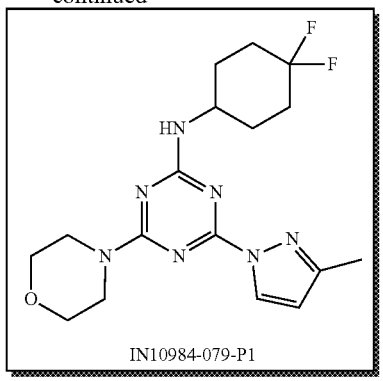

Step 1: To a solution of 2,4,6-trichloro-1,3,5-triazine (2 g, 10.84 mmol) in DMF (5 mL) was added 3-methyl pyrazole (0.88 mL, 10.84 mmol) at −40° C. and stirred at same temperature for 1 h. The reaction mixture was poured into ice cold Water and extract with dichloromethane (2×20 mL). The combined organic layer washed with brine water (10 mL) and dried over sodium sulfate and concentrated under reduced pressure to afford crude and which was purified by column chromatography using 5% ethyl acetate in hexane as eluent to afford 2,4-dichloro-6-(3-methyl-1H-pyrazol-1-yl)-1,3,5-triazine as an yellow solid (0.25 g, 10%). MS (M+1)$^+$=230.1.

Step 2: To an ice cooled solution of 2,4-dichloro-6-(3-methyl-1H-pyrazol-1-yl)-1,3,5-triazine in DMF was added 4,4-Difluorocyclohexylamine hydrochloride and triethylamine and stirred at 0° C. for 1 h. The reaction mixture was poured into ice cooled water, the obtained solid was filtered and dried under high vacuum to afford 4-chloro-N-(4,4-difluorocyclohexyl)-6-(3-methyl-1H-pyrazol-1-yl)-1,3,5-triazin-2-amine as an white solid (0.3 g, 83%). MS (M+1)+=329.1.

Step 3[IN10984-079-P1]: The procedure is similar to Step 2[IN10984-079-P1] in Example-878. 0.3 g of 4-chloro-N-(4,4-difluorocyclohexyl)-6-(3-methyl-1H-pyrazol-1-yl)-1,3,5-triazin-2-amine gave N-(4,4-difluorocyclohexyl)-4-(3-methyl-1H-pyrazol-1-yl)-6-morpholino-1,3,5-triazin-2-amine as an off-white solid (0.13 g, 37%). MS (M+1)+=380.2; 1H-NMR (400 MHz, MeOD): δ 8.48 (d, J=15.60 Hz, 1H), 6.31 (s, 1H), 4.01 (s, 1H), 3.88 (s, 4H), 3.72 (s, 4H), 2.34 (s, 3H), 2.06-1.93 (m, 7H), 1.69-1.67 (m, 2H).

Example-879

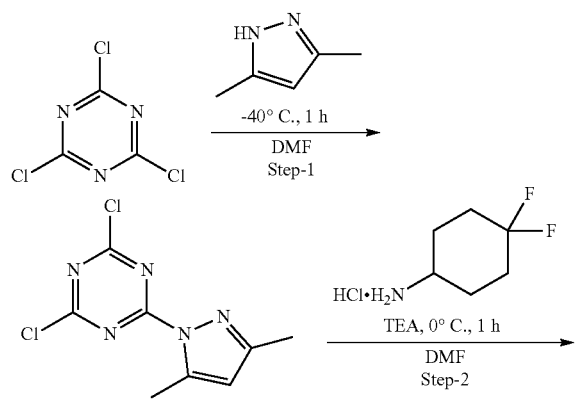

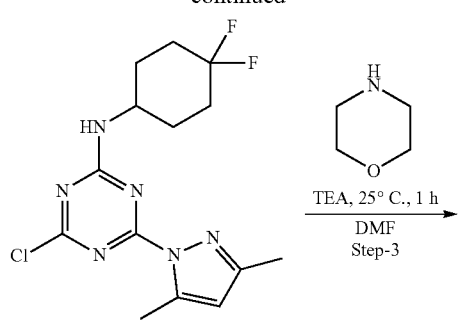

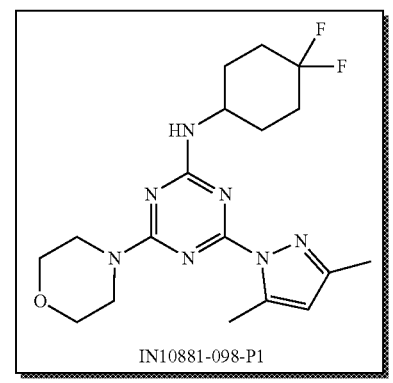

Step 1: The procedure is similar to Step 1[IN10984-079-P1] in Example-878. 1 g of 2,4,6-trichloro-1,3,5-triazine gave 2,4-dichloro-6-(3,5-dimethyl-1H-pyrazol-1-yl)-1,3,5-triazine (0.2 g, 15%). MS (M+1)+=243.9.

Step 2: The procedure is similar to Step 2[IN10984-079-P1] in Example-878. 0.2 g of 2,4-dichloro-6-(3,5-dimethyl-1H-pyrazol-1-yl)-1,3,5-triazine gave 4-chloro-N-(4,4-difluorocyclohexyl)-6-(3,5-dimethyl-1H-pyrazol-1-yl)-1,3,5-triazin-2-amine. (0.2 g, 71%). MS (M+1)+=343.

Step 3[IN10881-098-P1]: The procedure is similar to Step 2[IN10984-079-P1] in Example-878. 0.2 g of 4-chloro-N-(4,4-difluorocyclohexyl)-6-(3,5-dimethyl-1H-pyrazol-1-yl)-1,3,5-triazin-2-amine gave N-(4,4-difluorocyclohexyl)-4-(3,5-dimethyl-1H-pyrazol-1-yl)-6-morpholino-1,3,5-triazin-2-amine (0.1 g, 43%). MS (M+1)+=343.0; 1H-NMR (400 MHz, DMSO-d6): δ 7.88 (d, J=8.00 Hz, 1H), 6.09 (d, J=8.00 Hz, 1H), 3.97 (s, 1H), 3.80-3.63 (m, 8H), 2.56 (s, 3H), 2.15 (d, J=10.80 Hz, 3H), 2.10-1.80 (m, 6H), 1.62-1.50 (m, 2H).

Example-880

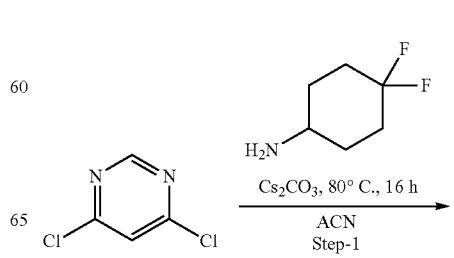

-continued

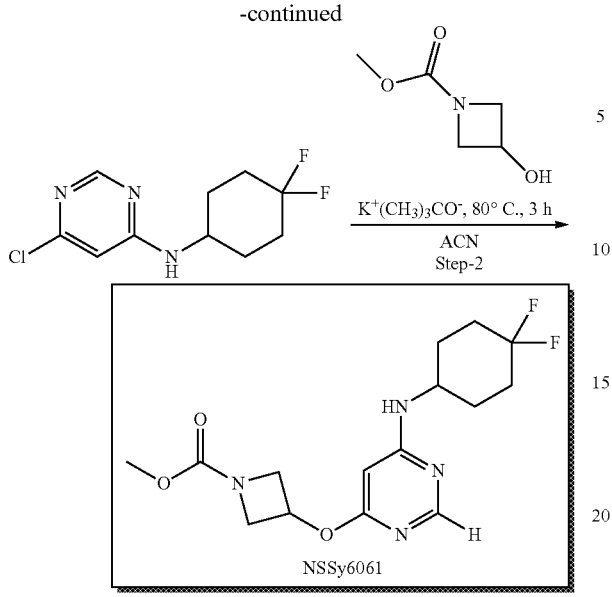

NSSy6061

Step 1: The procedure is similar to Step 1[B] in Example-838. 1 g of 4,6-dichloropyrimidine gave 6-chloro-N-(4,4-difluorocyclohexyl)pyrimidin-4-amine as a yellow solid (1.5 g, 90%). MS (M+1)+=248.0.

Step 2[NSSy6061]: The procedure is similar to Step 1[B] in Example-838. 0.4 g of 6-chloro-N-(4,4-difluorocyclohexyl)pyrimidin-4-amine gave methyl 3-((6-((4,4-difluorocyclohexyl)amino)pyrimidin-4-yl)oxy) azetidine-1-carboxylate as white solid (0.06 g, 10%). MS (M+1)+=343.0; 1H-NMR (400 MHz, DMSO-d6): δ 8.14 (s, 1H), 7.28 (s, 1H), 5.80 (s, 1H), 5.27 (s, 1H), 4.27 (s, 2H), 3.85 (s, 1H), 3.84 (s, 2H), 3.56 (s, 3H), 2.02-1.89 (m, 6H), 1.54-1.46 (m, 2H).

Example-881

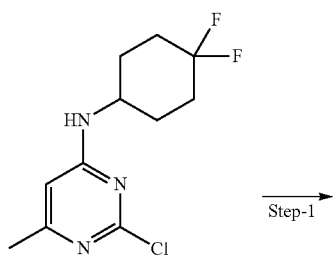

Step-1

-continued

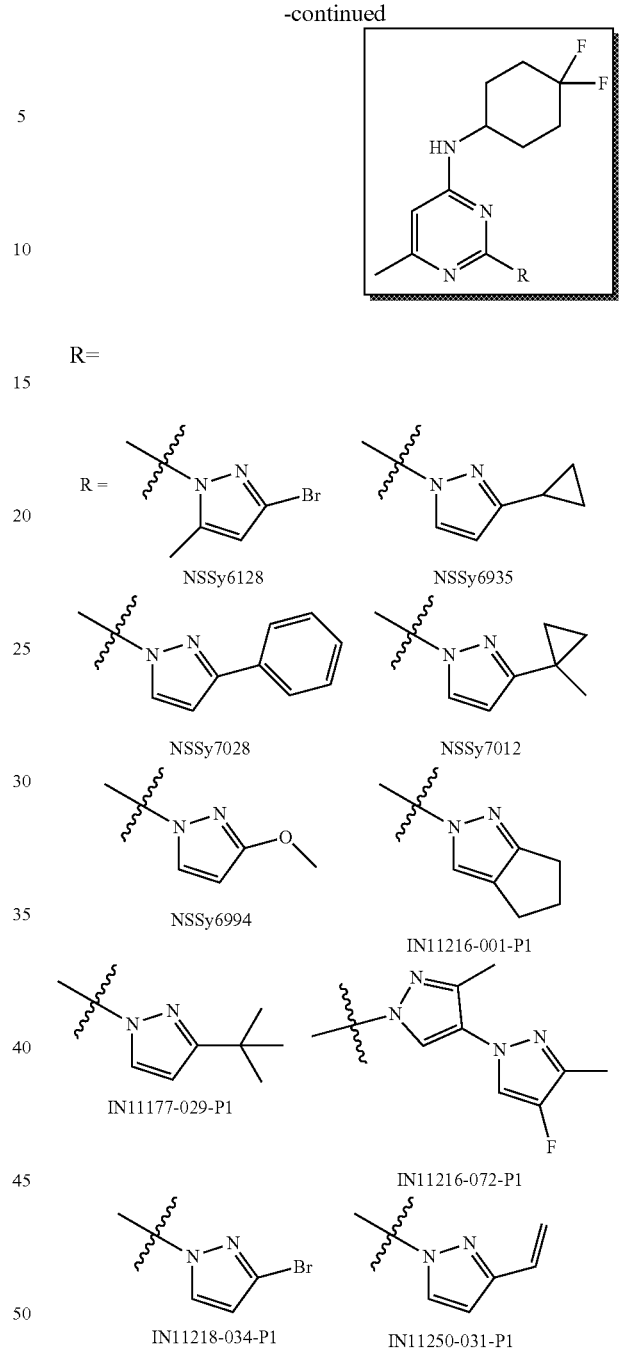

TABLE 14

| Step 1: | | | |
|---|---|---|---|
| Compound No | R | Condition | Yield (%) |
| NSSy6128 | (pyrazole with Br and methyl) | Cs$_2$CO$_3$, ACN, 150° C., MW, 2 h | 33 |

TABLE 14-continued

Step 1:

| Compound No | R | Condition | Yield (%) |
|---|---|---|---|
| NSSy6935 | [pyrazole with cyclopropyl] | Cs$_2$CO$_3$, ACN, 120° C., MW, 8 h | 87 |
| NSSy7028 | [pyrazole with phenyl] | Cs$_2$CO$_3$, ACN, 80° C., Sealed tube 1 h | 58 |
| NSSy7012 | [pyrazole with 1-methylcyclopropyl] | Cs$_2$CO$_3$, ACN, 130° C., MW, 1 h | 45 |
| NSSy6994 | [pyrazole with methoxy] | Cs$_2$CO$_3$, ACN, 130° C., MW, 1 h | 66 |
| IN11216-001-P1 | [cyclopentapyrazole] | K$^+$(CH$_3$)$_3$CO$^−$, NMP, 110° C., 16 h | 35 |
| IN11177-029-P1 | [pyrazole with tert-butyl] | K$^+$(CH$_3$)$_3$CO$^−$, NMP, 110° C., 16 h | 60 |
| IN11216-072-P1 | [bis-pyrazole with 4-F, 5-methyl] | 4-fluoro-5-methyl-1H-pyrazole, Cs$_2$CO$_3$, ACN, 100° C., 16 h | 18 |
| IN11218-034-P1 | [pyrazole with Br] | Cs$_2$CO$_3$, ACN, 70° C., 3 days | 98 |
| IN11218-031-P1 | [pyrazole with vinyl] | Step a: 3-bromo pyrazole, Cs$_2$CO$_3$, ACN, 70° C., 3 days<br>Step b: tributyl (vinyl) stannane, CsF, Pd(PPh$_3$)$_4$, Cy$_3$P, 1,4-dioxane, 120° C., MW, 2 h. | 98/99 |

Step 1[NSSy6128]: The procedure is similar to Step 1[NSy6909] in Example-839. MS (M, M+2)+=386.0, 388.0; 1H-NMR (400 MHz, DMSO-d6): δ 7.68 (d, J=7.20 Hz, 1H), 6.43 (d, J=14.00 Hz, 1H), 6.26 (d, J=21.60 Hz, 1H), 4.03-3.88 (m, 1H), 2.55 (s, 3H), 2.27 (s, 3H), 2.05-1.92 (m, 6H), 1.59-1.48 (m, 2H).

Step 1[NSSy6935]: The procedure is similar to Step 1[NSy6909] in Example-839. MS (M+1)+=334.2; 1H-NMR (400 MHz, DMSO-d6): δ 8.42 (s, 1H), 7.55 (s, 1H), 6.19 (s, 2H), 4.13 (s, 1H), 2.26 (s, 3H), 2.01-1.94 (m, 7H), 1.61-1.53 (m, 2H), 0.95-0.91 (m, 2H), 0.74-0.72 (m, 2H).

Step 1[NSSy7028]: The procedure is similar to Step 1[B] in Example-838. MS (M+1)+=370.0; 1H-NMR (400 MHz, DMSO-d6): δ 8.65 (s, 1H), 7.94 (d, J=7.60 Hz, 1H), 7.64 (s, 1H), 7.49-7.45 (m, 2H), 7.40-7.36 (m, 2H), 7.02 (d, J=2.40 Hz, 1H), 6.25 (s, 1H), 4.19 (s, 1H), 2.31 (s, 3H), 2.08-1.99 (m, 6H), 1.60-1.58 (m, 2H).

Step 1[NSSy7012]: The procedure is similar to Step 1[NSy6909] in Example-839. MS (M+1)+=348.0; 1H-NMR (400 MHz, DMSO-d6): δ 8.43 (s, 1H), 7.54 (s, 1H), 6.25 (d, J=2.80 Hz, 1H), 6.19 (s, 1H), 4.14 (s, 1H), 2.33 (s, 3H), 2.06-1.95 (m, 6H), 1.58-1.55 (m, 2H), 1.43 (s, 3H), 0.95-0.94 (m, 2H), 0.77-0.75 (m, 2H).

Step 1[NSSy6994]: The procedure is similar to Step 1[NSy6909] in Example-839. MS (M+1)+=324.0; 1H-NMR (400 MHz, DMSO-d6): δ 8.43 (s, 1H), 7.53 (s, 1H), 6.20 (d, J=28.84 Hz, 1H), 6.01 (d, J=2.72 Hz, 1H), 4.01 (s, 1H), 3.95 (s, 3H), 2.47 (s, 3H), 2.06-1.96 (m, 6H), 1.57-1.55 (m, 2H).

Step 1[IN11216-001-P1]: The procedure is similar to Step 1[B] in Example-838. MS (M+1)+=369.2; 1H-NMR (400 MHz, DMSO-d6): δ 8.18 (s, 1H), 7.46 (d, J=6.00 Hz, 1H), 6.17 (s, 1H), 4.13 (s, 1H), 2.67-2.62 (m, 4H), 2.37-2.33 (m, 2H), 2.23 (s, 3H), 2.12-1.88 (m, 6H), 1.62-1.50 (m, 2H).

Step 1[IN11177-029-P1]: The procedure is similar to Step 1[B] in Example-838. MS (M+1)+=350.0; 1H-NMR (400 MHz, DMSO-d6): δ 8.44 (bs, 1H), 7.54 (bs, 1H), 6.40 (d, J=2.4 Hz, 1H), 6.20 (bs, 1H), 4.11 (bs, 1H), 2.33 (s, 3H), 2.08-1.95 (m, 6H), 1.58-1.55 (m, 2H), 1.29 (s, 9H).

Step 1[IN11216-072-P1]: The procedure is similar to Step 1[B] in Example-838. MS (M+1)+=406.2; 1H-NMR (400 MHz, DMSO-d6): δ 8.09 (s, 1H), 7.70 (d, J=8.00 Hz, 1H), 6.36 (d, J=1.60 Hz, 1H), 6.28 (s, 1H), 4.04 (s, 1H), 2.60 (s, 3H), 2.30 (s, 6H), 2.12-1.90 (m, 6H), 1.61-1.55 (m, 2H).

Step 1[IN11218-034-P1]: The procedure is similar to Step 1[B] in Example-838. MS (M+1)+=372.1; 1H-NMR (400 MHz, CDCl3): δ 8.42 (d, J=2.40 Hz, 1H), 6.45 (d, J=2.40 Hz, 1H), 6.08 (s, 1H), 5.21-5.10 (m, 1H), 3.80 (s, 1H), 2.42 (s, 3H), 2.28-1.98 (m, 6H), 1.71-1.61 (m, 2H).

Step 1[IN11250-031-P1]: The procedure is similar to Step 1[NSSy6989] in Example-839. MS (M+1)+=320.2; 1H-NMR (400 MHz, DMSO-d6): δ 8.52 (s, 1H), 7.64 (s, 1H), 6.79-6.76 (m, 2H), 6.23 (s, 1H), 5.91 (s, 1H), 5.86 (s, 1H), 5.42 (d, J=12.00 Hz, 1H), 4.04-4.02 (m, 1H), 2.26 (s, 3H), 1.99-2.06 (m, 6H), 1.56-1.58 (m, 2H).

Example-882

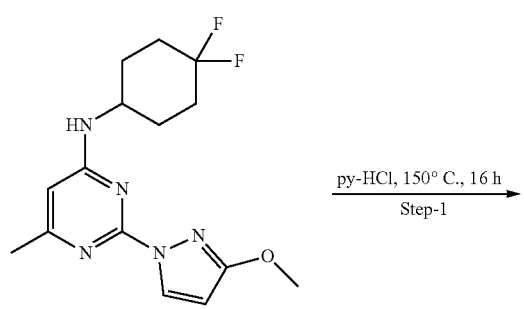

py-HCl, 150° C., 16 h
Step-1

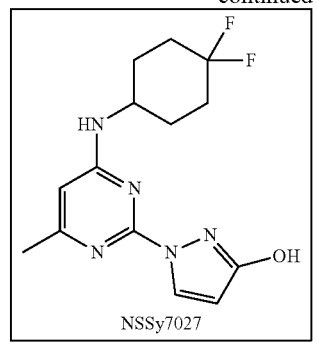

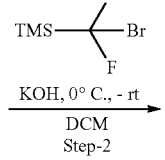

KOH, 0° C., - rt
DCM
Step-2

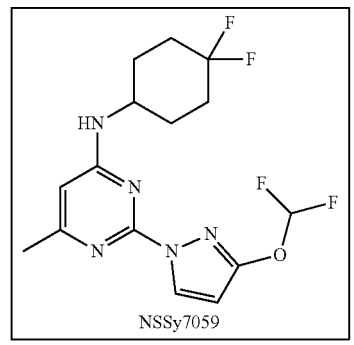

Step 1[NSSy7027]: The procedure is similar to Step 1[NSSy6972] in Example-841. 0.1 g of N-(4,4-difluorocyclohexyl)-2-(3-methoxy-1H-pyrazol-1-yl)-6-methylpyrimidin-4-amine gave 1-(4-((4,4-difluorocyclohexyl)amino)-6-methylpyrimidin-2-yl)-1H-pyrazol-3-ol as brown solid (0.021 g, 54%). MS (M+1)$^+$=310.0; $^1$H-NMR (400 MHz, DMSO-d$_6$): δ 10.43 (d, J=10.8 Hz, 1H), 8.31 (s, 1H), 7.45 (d, J=7.6 Hz, 1H), 6.14 (s, 1H), 5.81 (s, 1H), 4.13 (s, 1H), 2.21 (s, 3H), 2.08-1.95 (m, 6H), 1.57-1.55 (m, 2H).

Step 2[NSSy7059]: To an ice cooled solution of 1-(4-((4,4-difluorocyclohexyl)amino)-6-methylpyrimidin-2-yl)-1H-pyrazol-3-ol (0.03 g, 0.097 mmol) in dichloromethane (5 mL) was added Potassium hydroxide in 20% in water (0.032 g, 0.58 mmol) and (bromodifluoromethyl)trimethylsilane (0.039 g, 0.19 mmol), slowly warmed to room temperature. After 1 h, the reaction mixture was quenched with water and extracted with dichloromethane (2×10 mL). The combined organic layer was dried over sodium sulfate, filtered and concentrated to afford crude product, which was purified by Prep HPLC using 15% ethyl acetate in hexane as eluent to afford N-(4,4-difluorocyclohexyl)-2-(3(difluoromethoxy)-1H-pyrazol-1-yl)-6-methylpyrimidin-4-amine as an off-white solid (8 mg, 23%). MS (M+1)+=360.0; 1H-NMR (400 MHz, DMSO-d6): δ 8.57 (s, 1H), 7.66 (s, 1H), 7.43 (t, J=72.8 Hz, 1H), 6.31 (d, J=2.4 Hz, 1H), 6.23 (s, 1H), 4.12 (s, 1H), 2.26 (s, 3H), 2.07-1.97 (m, 6H), 1.57-1.55 (m, 2H).

Example-883

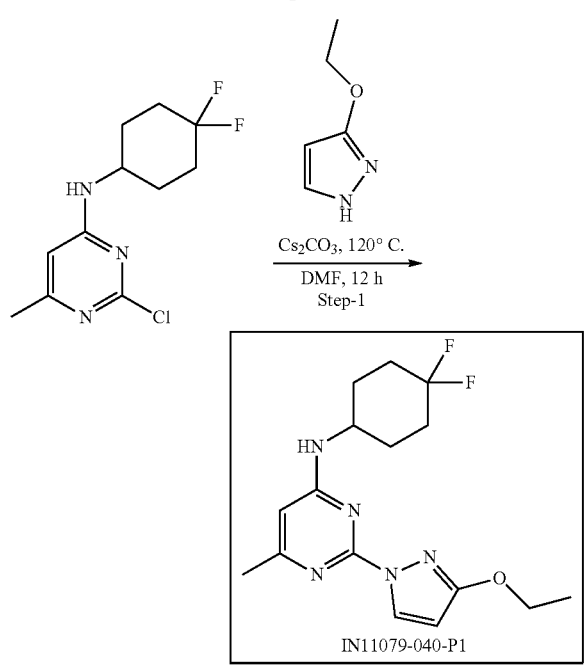

Step 1[IN11079-040-P1]: The procedure is similar to Step 1[B] in Example-838. 0.2 g of 2-chloro-N-(4,4-difluorocyclohexyl)-6-methylpyrimidin-4-amine gave N-(4,4-difluorocyclohexyl)-2-(3-ethoxy-1H-pyrazol-1-yl)-6-methylpyrimidin-4-amine as a white solid (0.07 g, 27%). MS (M+1)$^+$= 338.0; $^1$H-NMR (400 MHz, DMSO-d$_6$): δ 8.40 (s, 1H), 7.49 (s, 1H), 6.16 (s, 1H), 5.99 (d, J=3.20 Hz, 1H), 4.22 (q, J=6.80 Hz, 2H), 4.10 (s, 1H), 2.24 (s, 3H), 2.12-1.88 (m, 6H), 1.62-1.50 (m, 2H), 1.33 (t, J=6.80 Hz, 3H).

Example-884

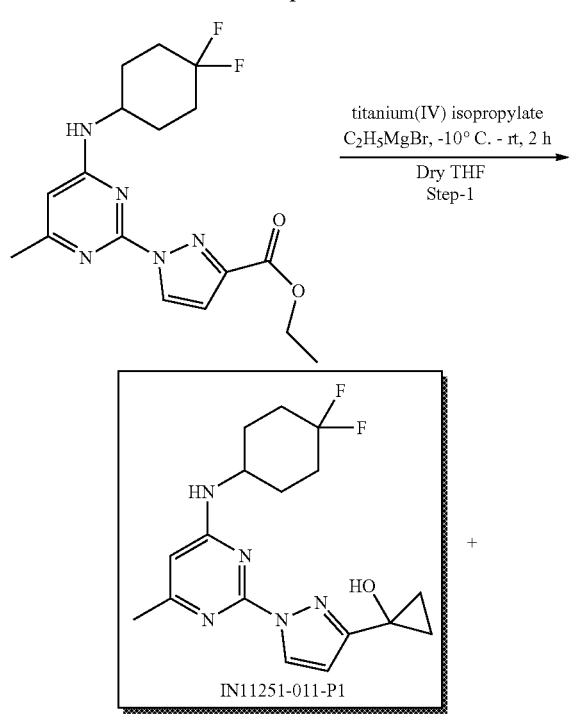

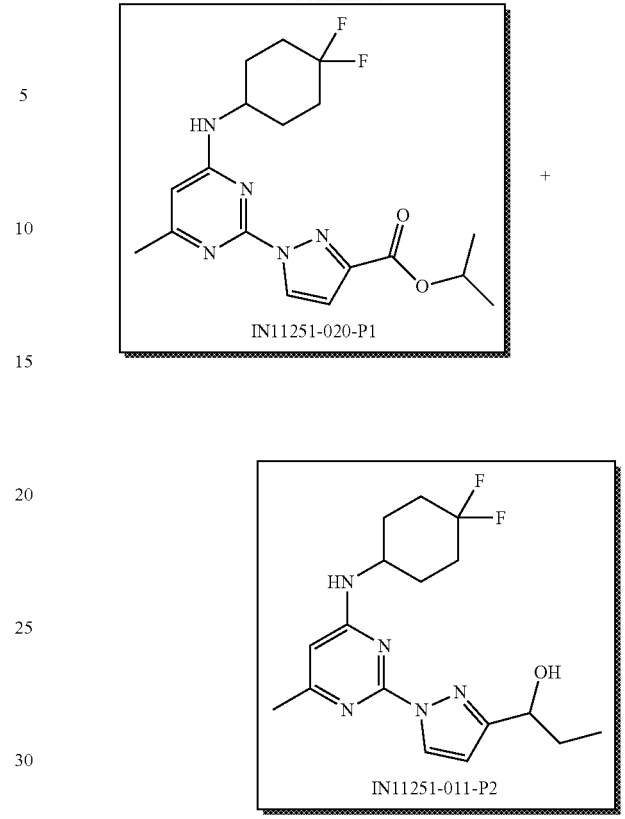

Step 1[IN11251-011-P1, IN11251-020-P1 and IN11251-011-P2]: To a solution of ethyl 1-(4-((4,4-difluorocyclohexyl)amino)-6-methylpyrimidin-2-yl)-1H-pyrazole-3-carboxylate (0.2 g, 0.54 mmol) in THF (10 mL) at −10° C. was added Titanium(IV) isopropylate (0.15 g, 0.54 mmol) and ethyl magnesium bromide (0.21 g, 1.64 mmol). The reaction mixture was slowly warmed to rt and stirred at rt for 2 h. The reaction mixture was quenched with saturated ammonium chloride solution and extracted with ethyl acetate (2×50 mL). The combined organic layer was dried over sodium sulfate and concentrated to afford crude and which was purified by Prep HPLC to afford 1-(1-(4-((4,4-difluorocyclohexyl)amino)-6-methylpyrimidin-2-yl)-1H-pyrazol-3-yl)cyclopropan-1-ol as an off-white solid (0.04 g). MS (M+1)+=350.2; 1H-NMR (400 MHz, DMSO-d6): δ 8.46 (s, 1H), 7.54 (s, 1H), 6.46 (d, J=2.8 Hz, 1H), 6.19 (s, 1H), 6.06 (s, 1H), 4.20 (m, 1H), 2.25 (s, 3H), 2.09-1.95 (m, 7H), 1.57-1.55 (m, 2H), 1.01 (d, J=1.6 Hz, 3H) and isopropyl 1-(4-((4,4-difluorocyclohexyl)amino)-6-methylpyrimidin-2-yl)-1H-pyrazole-3-carboxylate as an off-white solid (0.045 g). MS (M+1)+=380.2; 1H-NMR (400 MHz, DMSO-d6): δ 8.67 (s, 1H), 7.73 (s, 1H), 6.92 (d, J=2.80 Hz, 1H), 6.30 (s, 1H), 5.14-5.17 (m, 1H), 4.18 (s, 1H), 2.33 (s, 3H), 2.12-1.90 (m, 6H), 1.60-1.50 (m, 2H), 1.35 (s, 6H) and 1-(1-(4-((4,4-difluorocyclohexyl)amino)-6-methylpyrimidin-2-yl)-1H-pyrazol-3-yl)propan-1-ol as an off-white solid (0.03 g). MS (M+1)+=352.2; 1H-NMR (400 MHz, DMSO-d6): δ 8.47 (s, 1H), 7.56 (s, 1H), 7.49 (s, 1H), 6.00 (s, 1H), 5.14 (d, J=4.80 Hz, 1H), 5.13 (s, 1H), 4.51 (q, J=6.40 Hz, 2H), 4.14 (s, 1H), 2.26 (s, 3H), 2.10-1.90 (m, 6H), 1.74-1.67 (m, 2H), 1.60-1.50 (m, 2H), 0.86 (t, J=7.20 Hz, 3H).

Example-885

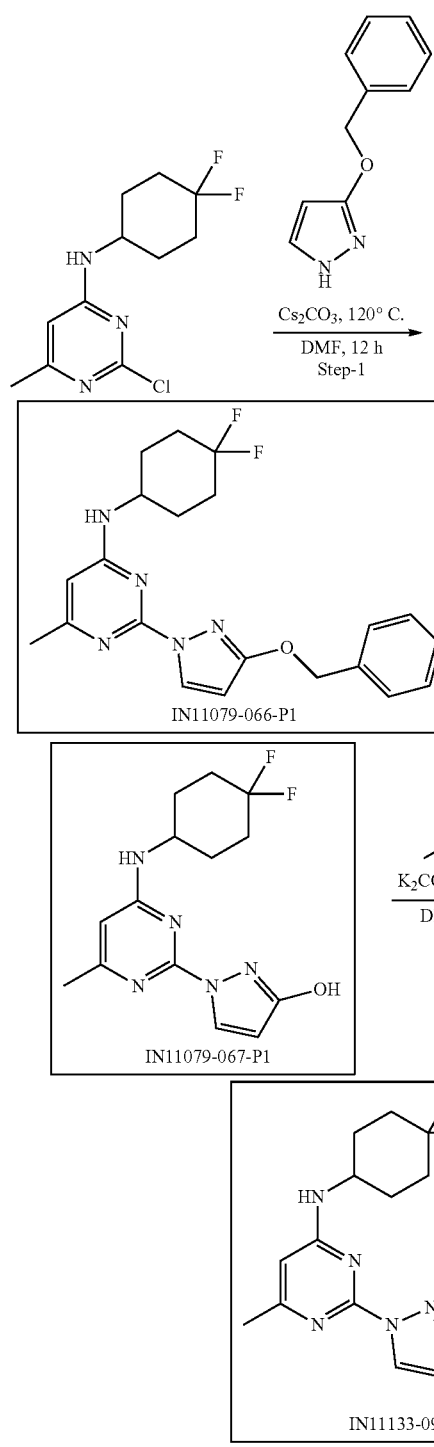

Example-886

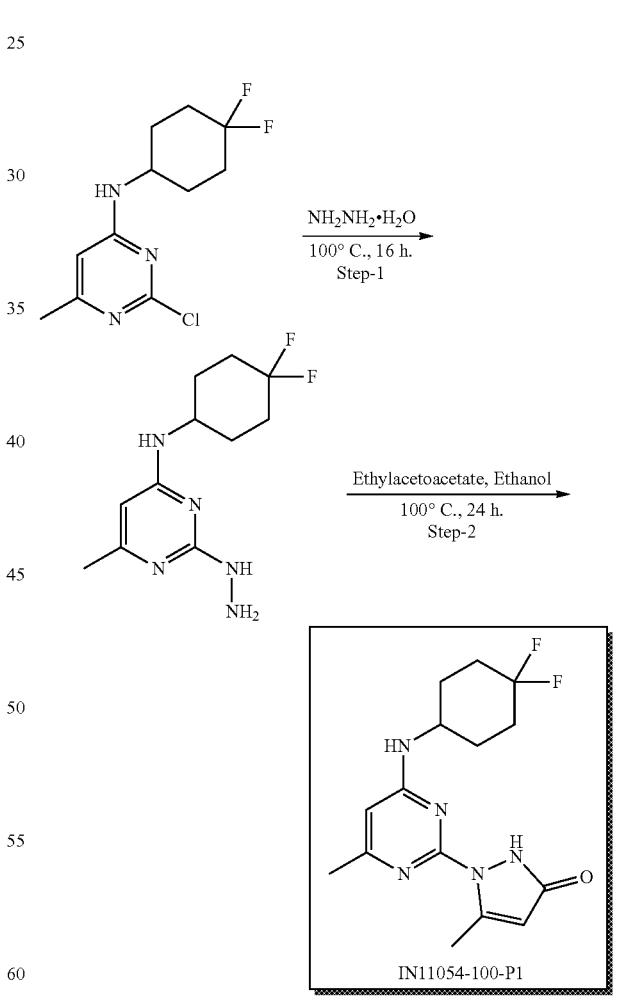

Step 1[IN11079-066-P1]: The procedure is similar to Step 1[B] in Example-838. 0.35 g of 2-chloro-N-(4,4-difluorocyclohexyl)-6-methylpyrimidin-4-amine gave 2-(3-(benzyloxy)-1H-pyrazol-1-yl)-N-(4,4-difluorocyclohexyl)-6-methyl pyrimidin-4-amine as a white solid (0.2 g, 37%). MS (M+1)+=400.1; 1H-NMR (400 MHz, DMSO-d6): δ 8.43 (s, 1H), 7.48 (s, 3H), 7.36-7.33 (m, 3H), 6.17 (s, 1H), 6.07 (d, J=3.20 Hz, 1H), 5.27 (s, 2H), 4.12 (s, 1H), 2.33 (s, 3H), 2.12-1.85 (m, 6H), 1.62-1.50 (m, 2H).

Step 2[IN11079-067-P1]: The procedure is similar to Step 2[NSSy6464] in Example-869. 0.22 g of 2-(3-(benzyloxy)-1H-pyrazol-1-yl)-N-(4,4-difluorocyclohexyl)-6-methylpyrimidin-4-amine gave 1-(4-((4,4-difluorocyclohexyl)amino)-6-methylpyrimidin-2-yl)-1H-pyrazol-3-ol as a white solid (0.09 g, 53%). MS (M+1)+=308.2; 1H-NMR (400 MHz, DMSO-d6): δ 8.30 (s, 1H), 7.43 (d, J=7.60 Hz, 1H), 6.14 (s, 1H), 5.81 (d, J=2.40 Hz, 1H), 4.11 (s, 1H), 2.21 (s, 3H), 2.15-1.85 (m, 6H), 1.60-1.50 (m, 2H).

Step 3[IN11133-094-P1]: The procedure is similar to Step 1[B] in Example-838. 0.065 g of 1-(4-((4,4-difluorocyclohexyl)amino)-6-methylpyrimidin-2-yl)-1H-pyrazol-3-ol gave N-(4,4-difluorocyclohexyl)-2-(3-isopropoxy-1H-pyrazol-1-yl)-6-methylpyrimidin-4-amine as an off-white solid (0.04 g, 39%). MS (M+1)+=352.2; 1H-NMR (400 MHz, DMSO-d6): δ 8.39 (s, 1H), 7.49 (s, 1H), 6.15 (bs, 1H), 5.98 (d, J=1.6 Hz, 1H), 4.88-4.83 (m, 1H), 4.15 (m, 1H), 2.24 (s, 3H), 2.05-1.96 (m, 6H), 1.57-1.55 (m, 2H), 1.31-1.30 (m, 6H).

Example-886

Step 1: To a solution of 2-chloro-N-(4,4-difluorocyclohexyl)-6-methyl pyrimidin-4-amine (0.5 g, 1.90 mmol) in ethanol (2 mL) was added hydrazinehydrate (10 mL) and the reaction mixture was heated at 100° C. for 16 h. The reaction mixture was cooled to rt and concentrated under reduced pressure. The resultant residue was diluted with ethyl acetate and washed with water, dried over sodium sulfate and concentrated under reduced pressure to afford N-(4,4-difluorocyclohexyl)-2-hydrazineyl-6-methylpyrimidin-4-amine as an off-white solid (0.5 g). MS (M+1)+=258.1.

Step 2[IN11054-100-P1]: To a solution of N-(4,4-difluorocyclohexyl)-2-hydrazineyl-6-methylpyrimidin-4-amine (0.05 g, 0.19 mmol) in ethanol (2 mL) was added Ethylacetoacetate (0.056 g, 0.38 mmol) and the reaction mixture was heated at 100° C. for 24 h. The reaction mixture was cooled to rt and concentrated under reduced pressure and the resultant residue was diluted with ethyl acetate and washed with water dried over sodium sulfate and concentrated under reduced pressure to afford 1-(4-((4,4-difluorocyclohexyl)amino)-6-methylpyrimidin-2-yl)-5-methyl-1,2-dihydro-3H-pyrazol-3-one as an off-white solid (0.05 g). MS (M+1)+= 324.1; 1H-NMR (400 MHz, DMSO-d6): δ 7.65 (bs, 1H), 6.26 (s, 1H), 5.32 (s, 1H), 3.95 (bs, 1H), 2.29 (s, 3H), 2.13 (s, 3H), 2.03-1.97 (m, 6H), 1.67-1.62 (m, 2H).

Example-887

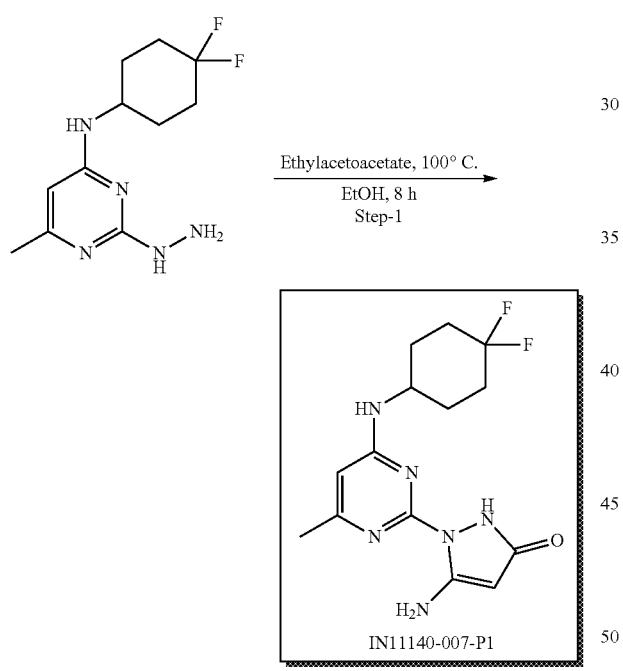

Step 1[IN11140-007-P1]: The procedure is similar to Step 2[IN11054-090-P1] in Example-886. 0.1 g of N-(4,4-difluorocyclohexyl)-2-hydrazineyl-6-methylpyrimidin-4-amine gave 5-amino-1-(4-((4,4-difluorocyclohexyl)amino)-6-methylpyrimidin-2-yl)-1,2-dihydro-3H-pyrazol-3-one as a white solid (0.05 g, 41%). MS (M+1)+=325.1; 1H-NMR (400 MHz, DMSO-d6): δ 9.25 (s, 1H), 7.05 (s, 2H), 6.03 (s, 1H), 4.22 (s, 1H), 4.02-3.90 (m, 2H), 2.23 (s, 3H), 2.15-1.90 (m, 6H), 1.40 (m, 2H).

Example-888

Intentionally Omitted

Example-889

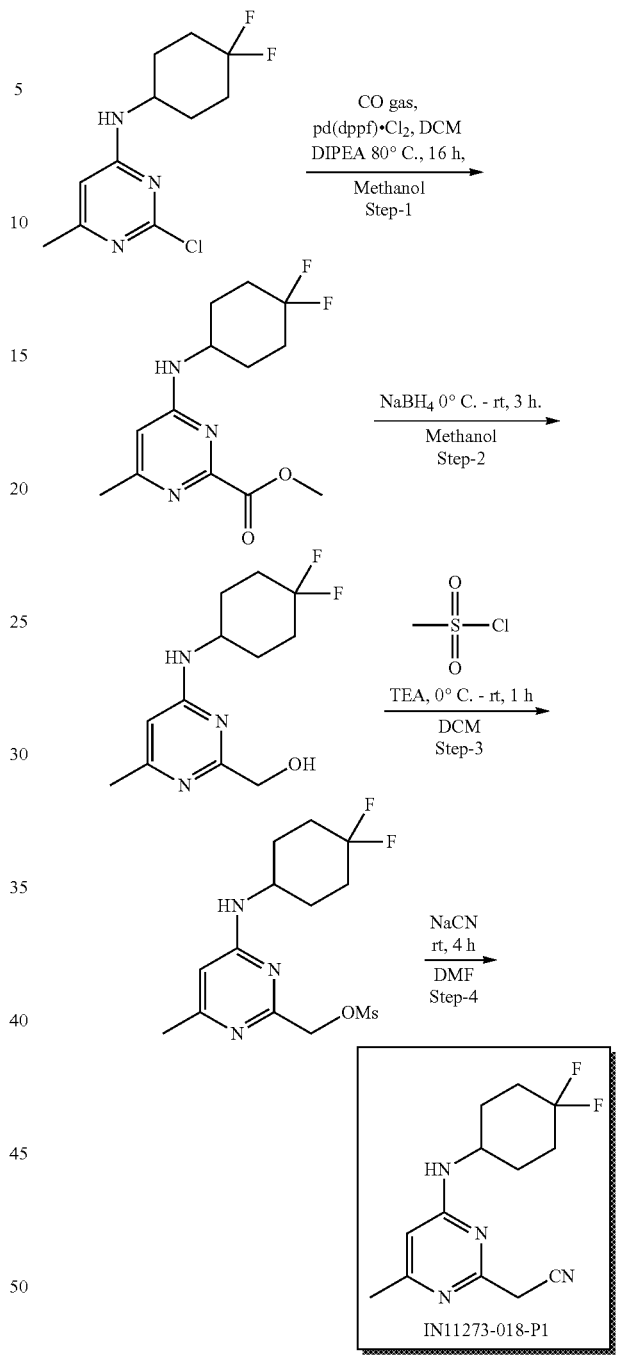

Step 1: To stirred solution of 2-chloro-N-(4,4-difluorocyclohexyl)-6-methylpyrimidin-4-amine (2.6 g, 9.95 mmol) in methanol (40 mL) was added [1,1'-Bis(diphenylphosphino)ferrocene]dichloropalladium(II), complex with DCM (0.813 g, 0.995 mmol) and N, N-Diisopropylethylamine (5.05 mL, 29.85 mmol) in a Steel bomb and purged with nitrogen gas for about 5 min. The Steel bomb was sealed and filled with carbon monoxide gas at 100 psi and the reaction mixture was heated to 80° C. for 16 h. The reaction mixture was degassed for complete removal of CO gas and reaction mixture was concentrated under reduced pressure to obtain crude brown liquid and which was purified by column chromatography using 75% ethyl acetate in hexane as eluent to afford methyl 4-((4,4-difluorocyclohexyl)amino)-6-methylpyrimidine-2-carboxylate as a white solid (1.5 g, 53%). MS (M+1)+=286.2.

Step 2: The procedure is similar to Step 2[NSSy6931] in Example-21. 1 g of methyl 4-((4,4-difluorocyclohexyl)amino)-6-methylpyrimidine-2-carboxylate gave (4-((4,4-difluorocyclohexyl)amino)-6-methylpyrimidin-2-yl) methanol as an off-white solid (0.68 g, 75%). MS (M+1)+=258.2.

Step 3: To a stirred solution of (4-((4,4-difluorocyclohexyl)amino)-6-methyl pyrimidin-2-yl)methanol (0.68 g, 2.64 mmol) in DCM (15 mL) was added trimethylamine (0.75 mL, 5.28 mmol) followed by methanesulfonyl chloride (0.31 mL, 3.97 mmol) at 0° C. and the reaction mixture was allowed to stir at rt for 1 h. The reaction mixture was diluted DCM (150 mL) and washed with saturated sodium bicarbonate solution, the organic solution was dried over sodium sulfate and concentrated under reduced pressure to afford (4-((4,4-difluorocyclohexyl)amino)-6-methylpyrimidin-2-yl)methyl methanesulfonate as an light brown liquid (0.7 g, crude). MS (M+1)+=236.2.

Step 4[IN11273-018-P1]: The procedure is similar to Step 4[NSSy6800] in Example-861. 0.5 g of (4-((4,4-difluorocyclohexyl)amino)-6-methylpyrimidin-2-yl)methyl methanesulfonate gave 2-(4-((4,4-difluorocyclohexyl)amino)-6-methylpyrimidin-2-yl) acetonitrile as yellow solid (0.26 g, 65%). MS (M+1)+=267.2; 1H-NMR (400 MHz, DMSO-d6): δ 7.40 (d, J=7.20 Hz, 1H), 6.25 (s, 1H), 3.97 (s, 2H), 2.20 (s, 3H), 2.06-1.91 (m, 6H), 1.58-1.55 (m, 2H).

Example-890

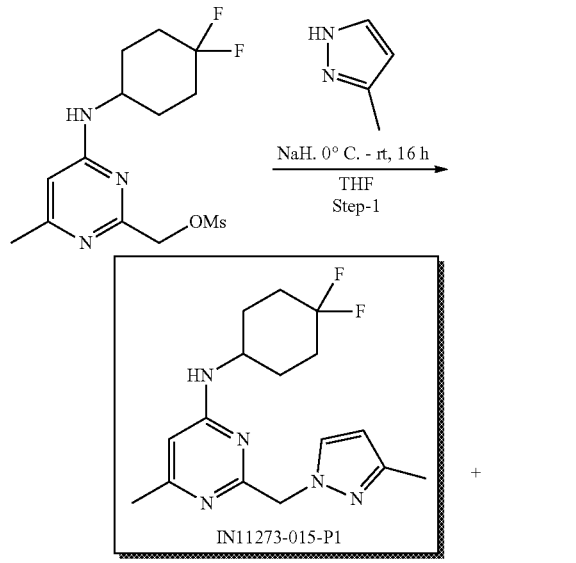

Step 1[IN11273-015-P1 and IN11273-015-P2]: The procedure is similar to Step 5[NSSy6711] in Example-854. 0.36 g of 2-(4-((4,4-difluorocyclohexyl)amino)-6-methylpyrimidin-2-yl) acetonitrile gave N-(4,4-difluorocyclohexyl)-6-methyl-2-((3-methyl-1H-pyrazol-1-yl)methyl)pyrimidin-4-amine as an off-white solid (0.044 g). MS (M+1)+=322.2; 1H-NMR (400 MHz, DMSO-d6): δ 7.20 (d, J=6.80 Hz, 1H), 6.17 (s, 1H), 6.02 (s, 1H), 5.11 (s, 2H), 3.60-3.71 (m, 1H), 2.29 (s, 3H), 2.17 (s, 3H), 1.79-2.02 (m, 6H), 1.40-1.33 (m, 2H) and N-(4,4-difluorocyclohexyl)-6-methyl-2-((5-methyl-1H-pyrazol-1-yl)methyl)pyrimidin-4-amine as an white solid (0.062 g). MS (M+1)+=322.2; 1H-NMR (400 MHz, DMSO-d6): δ 7.62 (d, J=2.00 Hz, 1H), 7.22-7.21 (m, 1H), 6.18 (s, 1H), 6.00 (d, J=2.00 Hz, 1H), 5.06 (s, 2H), 3.73 (s, 1H), 2.17 (s, 3H), 2.16 (s, 3H), 2.11-1.85 (m, 6H), 1.82-1.45 (m, 2H).

Example-891

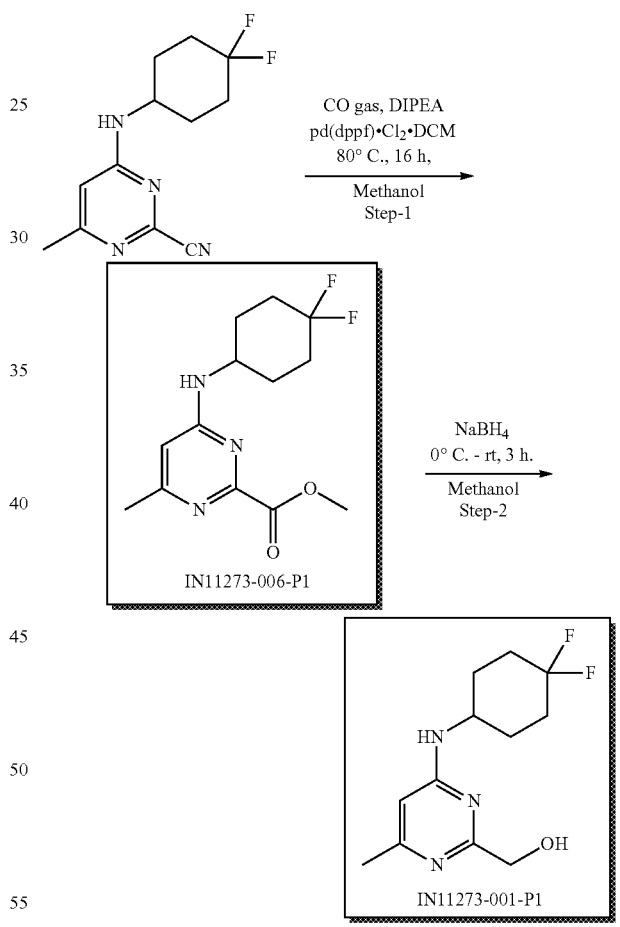

Step 1[IN11273-006-P1]: The procedure is similar to Step 1[IN11273-018-P1] in Example-889. 2.6 g of 2-chloro-N-(4,4-difluorocyclohexyl)-6-methylpyrimidin-4-amine gave methyl 4-((4,4-difluorocyclohexyl)amino)-6-methylpyrimidine-2-carboxylate as a yellow solid (1.5 g, 53%). MS (M+1)+=286.2; 1H-NMR (400 MHz, DMSO-d6): δ 7.57 (s, 1H), 6.44 (s, 1H), 4.12-4.01 (m, 1H), 3.80 (s, 3H), 2.26 (s, 3H), 2.06-1.90 (m, 6H), 1.58-1.50 (m, 2H).

Step 2[IN11273-001-P1]: The procedure is similar to Step 2[NSSy6931] in Example-21. 0.58 g of methyl 4-((4,4- difluorocyclohexyl)amino)-6-methylpyrimidine-2-carboxylate gave (4-((4,4-difluorocyclohexyl)amino)-6-methylpyrimidin-2-yl) methanol as a yellow solid (0.44 g, 84%). MS (M+1)+=258.2; 1H-NMR (400 MHz, DMSO-d6): δ 7.22 (d, J=7.6 Hz, 1H), 6.19 (s, 1H), 4.61 (t, J=5.6 Hz, 1H), 4.28 (d, J=6.0 Hz, 2H), 2.20 (s, 3H), 2.09-1.89 (m, 6H), 1.57-1.48 (m, 2H).

Example-892

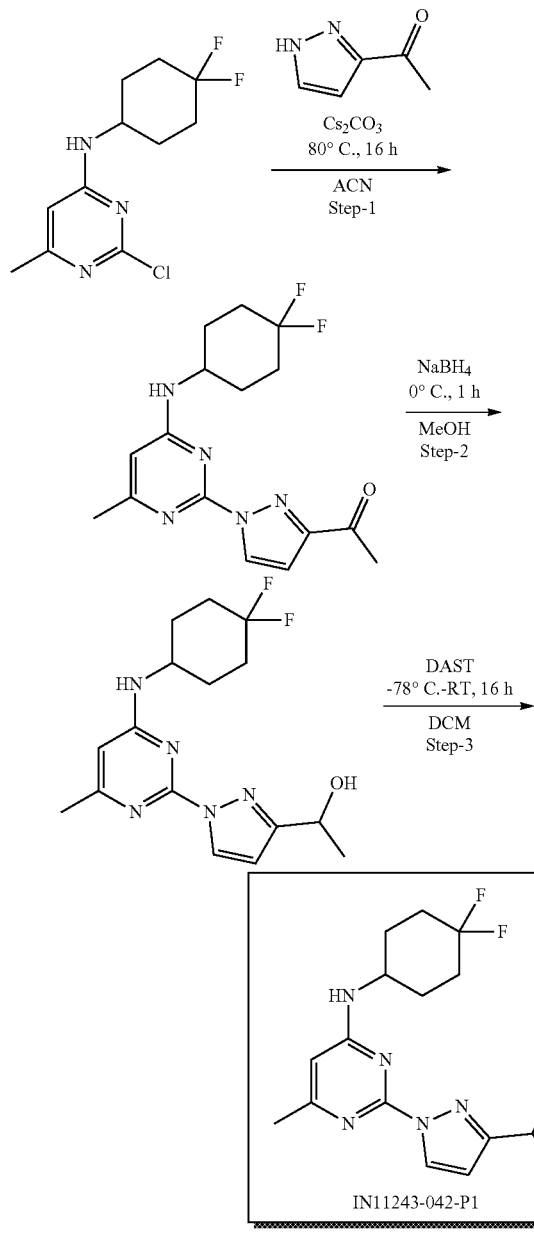

Step 1: The procedure is similar to Step 1[B] in Example-838. 0.8 g of 2-chloro-N-(4,4-difluorocyclohexyl)-6-methylpyrimidin-4-amine gave 1-(1-(4-((4,4-difluorocyclohexyl)amino)-6-methylpyrimidin-2-yl)-1H-pyrazol-3-yl) ethan-1-one as a yellow solid (0.41 g, 40%). MS (M+1)+=336.2.

Step 2: The procedure is similar to Step 2[NSSy6931] in Example-21. 0.15 g of 1-(1-(4-((4,4-difluorocyclohexyl)amino)-6-methylpyrimidin-2-yl)-1H-pyrazol-3-yl)ethan-1-one gave 1-(1-(4-((4,4-difluorocyclohexyl)amino)-6-methylpyrimidin-2-yl)-1H-pyrazol-3-yl)ethan-1-ol as an off-white solid (0.115 g, 76%). MS (M+1)+=338.2.

Step 3[IN11243-042-P1]: The procedure is similar to Step 3[NSSy6917] in Example-21. 0.1 g of 1-(1-(4-((4,4-difluorocyclohexyl)amino)-6-methylpyrimidin-2-yl)-1H-pyrazol-3-yl) ethan-1-ol gave N-(4,4-difluorocyclohexyl)-2-(3-(1-fluoroethyl)-1H-pyrazol-1-yl)-6-methylpyrimidin-4-amine as an off-white solid (0.04 g, 40%). MS (M+1)+=340.2; 1H-NMR (400 MHz, DMSO-d6): δ 8.57 (bs, 1H), 6.61 (d, J=2.0 Hz, 1H), 6.25 (s, 1H), 5.84-5.67 (m, 1H), 4.14 (s, 1H), 2.27 (s, 3H), 2.07-1.96 (m, 6H), 1.64-1.62 (m, 3H), 1.58-1.56 (m, 2H).

Example-893

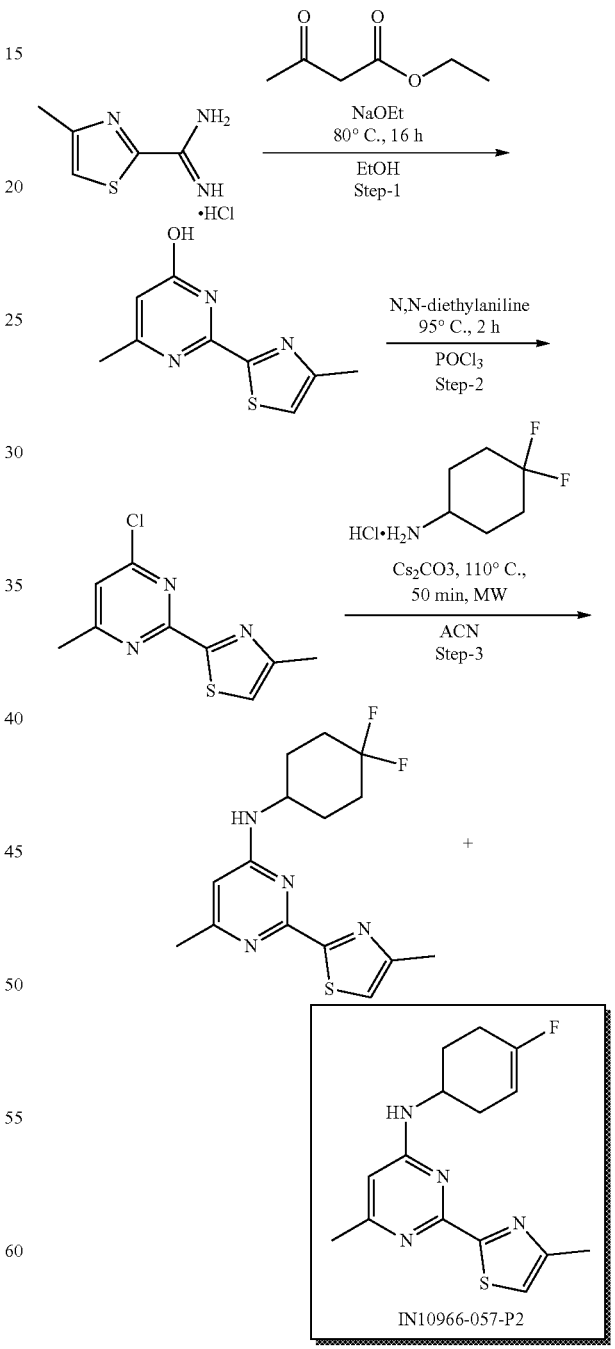

Step 1: To a solution of 4-methylthiazole-2-carboximidamide hydrogen chloride (5 g, 35.4 mmol) in ethanol (50 mL) was added ethyl 3-oxobutanoate (6.75 mL, 53.1 mmol)

and sodium ethoxide (12 g, 177.0 mmol). The reaction mixture was heated at 80° C. for 16 h. The reaction mixture was concentrated under reduced pressure and the resulting residue was diluted with water and washed with ethyl acetate. The aqueous layer was acidified with diluted HCl, pH up to 5, then extracted into ethyl acetate (2×30 mL). The combined organic layer was dried over sodium sulfate and concentrated to afford 6-methyl-2-(4-methylthiazol-2-yl)pyrimidin-4-ol as an off-white solid (3.2 g, 43.6%). MS (M+1)+=208.

Step 2: To a solution of 6-methyl-2-(4-methylthiazol-2-yl)pyrimidin-4-ol (3.8 g, 18.9 mmol) in Phosphorous Oxychloride (39.35 mL, 434.7 mmol) was added N, N-diethylaniline (5.15 mL, 32.13 mmol). The reaction mixture was heated at 95° C. for 2 h. The reaction mixture was poured into ice cold water and extracted with ethyl acetate (2×20 mL). The combined organic layer was dried over sodium sulfate and concentrated to afford crude and which was purified by column chromatography using 20% ethyl acetate in hexane as eluent to afford 2-(4-chloro-6-methylpyrimidin-2-yl)-4-methylthiazole as an off-white solid (2 g, 47%). MS (M+1)+=226.

Step 3[IN10966-057-P2]: The procedure is similar to Step 1[NSSy6909] in Example-839. 0.4 g of 2-(4-chloro-6-methylpyrimidin-2-yl)-4-methylthiazole gave N-(4,4-difluorocyclohexyl)-6-methyl-2-(4-methylthiazol-2-yl)pyrimidin-4-amine (0.17 g) MS (M+1)+=325.0; and N-(4-fluorocyclohex-3-en-1-yl)-6-methyl-2-(4-methylthiazol-2-yl)pyrimidin-4-amine as an off-white solid (0.110 g). MS (M+1)+=305.0; 1H-NMR (400 MHz, DMSO-d6): δ 7.47 (d, J=7.20 Hz, 1H), 7.37 (s, 1H), 6.35 (s, 1H), 5.21 (d, J=17.20 Hz, 1H), 4.20 (s, 1H), 2.43 (s, 4H), 2.28 (s, 5H), 2.10-1.90 (m, 2H), 1.75 (s, 1H).

Example-613

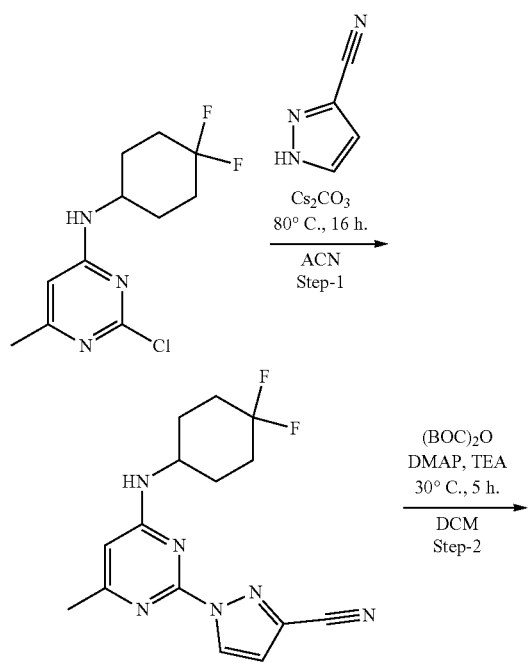

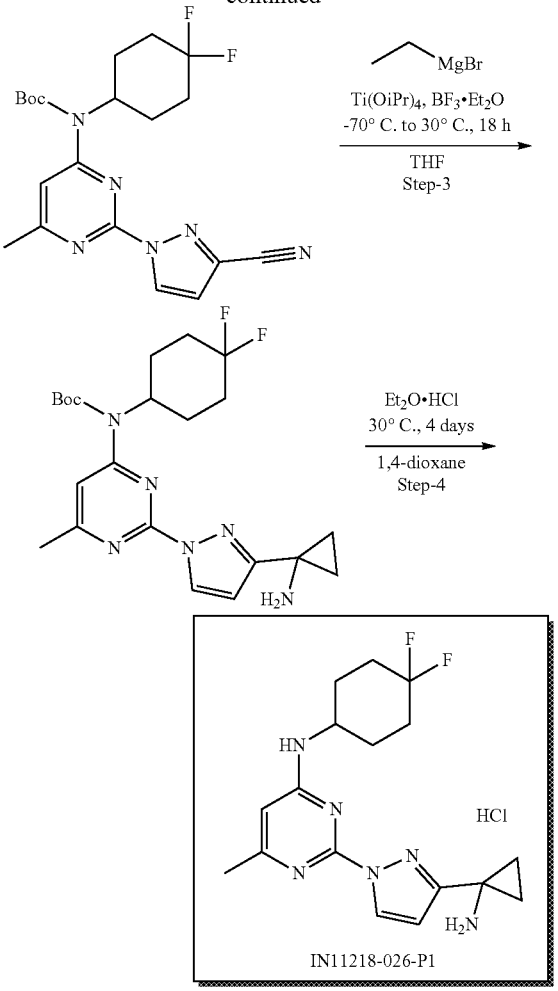

Step 1: The procedure is similar to Step 1[B] in Example-2. 1 g of 2-chloro-N-(4,4-difluorocyclohexyl)-6-methylpyrimidin-4-amine gave 1-(4-((4,4-difluorocyclohexyl)amino)-6-methylpyrimidin-2-yl)-1H-pyrazole-3-carbonitrile as an off-white solid (1 g, 82%). MS (M+1)+=319.2.

Step 2: To a solution of 1-(4-((4,4-difluorocyclohexyl)amino)-6-methyl pyrimidin-2-yl)-1H-pyrazole-3-carbonitrile (0.3 g, 0.94 mmol) in DCM (10 mL) was added ditertiary butyl dicarbonate (0.65 mL) and N, N-dimethyl amino pyridine (0.115 g, 0.94 mmol). The reaction mixture was stirred at rt for 5 h. The reaction mixture was quenched with water and extracted with DCM (2×25 mL). The combined organic layer was dried over sodium sulfate and concentrated to afford crude and which was purified by column chromatography using 10% ethyl acetate in hexane as eluent to afford tert-butyl (2-(3-cyano-1H-pyrazol-1-yl)-6-methylpyrimidin-4-yl)(4,4-difluorocyclohexyl) carbamate as yellow solid (0.27 g, 70%). MS (M+1)+=419.2.

Step 3: To a solution of tert-butyl (2-(3-cyano-1H-pyrazol-1-yl)-6-methylpyrimidin-4-yl)(4,4-difluorocyclohexyl) carbamate and Titanium isopropoxide at −78° C. was added 3M Ethylmagnesium bromide in diethyl ether. The reaction mixture was slowly warmed to rt and stirred for 17 h. Borontrifluoride diethyl etherate was added slowly and stirred at rt for 1 h. The reaction mixture was quenched with 5 mL of 1 N dilute HCl and then basified with aqueous 10%

NaOH solution (5 mL). The reaction mixture was extracted with ethyl acetate (3×30 mL). The combined organic layers was dried over sodium sulfate and evaporated to dryness to afford crude and which was purified by column chromatography using 4% methanol in dichloromethane as eluent to afford tert-butyl (2-(3-(1-aminocyclopropyl)-1H-pyrazol-1-yl)-6-methylpyrimidin-4-yl)(4,4-difluorocyclohexyl)carbamate as brown solid (0.16 g). MS (M+1)⁺=449.3.

Step 4[IN11218-026-P1]: To a solution of tert-butyl (2-(3-(1-aminocyclopropyl)-1H-pyrazol-1-yl)-6-methylpyrimidin-4-yl)(4,4-difluoro cyclohexyl)carbamate (0.1 g, 0.223 mmol) in dioxane (5 mL) was added 2M HCl in ether (15 mL) and the reaction mixture was stirred at rt for 4 days. The reaction mixture was concentrated and the resulting residue was washed with diethyl ether and dried under high vacuum to afford 2-(3-(1-aminocyclopropyl)-1H-pyrazol-1-yl)-N-(4,4-difluorocyclohexyl)-6-methylpyrimidin-4-amine hydrogen chloride as a pale brown solid (0.05 g). MS (M+1)⁺=349.3; ¹H-NMR (400 MHz, MeOD): δ 8.76 (s, 1H), 6.67 (s, 1H), 6.45 (s, 1H), 4.35 (s, 1H), 2.57 (s, 3H), 2.15-1.85 (m, 8H), 1.65-1.55 (m, 3H), 1.57 (s, 4H).

Example-614

Intentionally Omitted:

Example-615

Intentionally Omitted:

Example-616

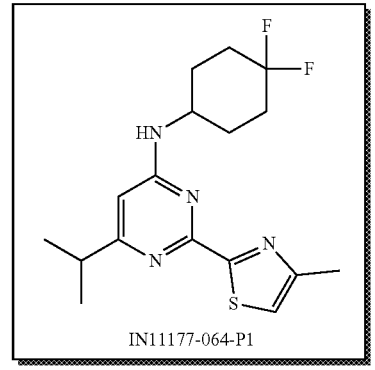

IN11177-064-P1

Step 1: The procedure is similar to Step 1[IN10966-057-P2] in Example-893. 0.6 g of 4-methylthiazole-2-carboximidamide hydrochloride gave 6-isopropyl-2-(4-methylthiazol-2-yl)pyrimidin-4-ol (0.2 g, crude). MS (M+1)⁺=236.

Step 2: The procedure is similar to Step 2[IN10966-057-P2] in Example-893. 0.2 g of 6-isopropyl-2-(4-methylthiazol-2-yl)pyrimidin-4-ol gave 2-(4-chloro-6-isopropyl pyrimidin-2-yl)-4-methylthiazole (0.08 g, 37%). MS (M+1)+=254.

Step 3[IN11177-064-P1]: The procedure is similar to Step 1[B] in Example-838. 0.07 g of 2-(4-chloro-6-isopropyl pyrimidin-2-yl)-4-methylthiazole N-(4,4-difluorocyclohexyl)-6-isopropyl-2-(4-methylthiazol-2-yl)pyrimidin-4-amine (0.06 g, 58%). MS (M+1)+=353.0; 1H-NMR (400 MHz, DMSO-d6): δ 7.48 (bs, 1H), 7.37 (d, J=0.8 Hz, 1H), 6.35 (s, 1H), 4.07 (m, 1H), 2.82-2.75 (m, 1H), 2.44 (s, 3H), 2.10-1.91 (m, 8H), 1.63-1.56 (m, 2H), 1.34-1.15 (m, 6H).

Example-617

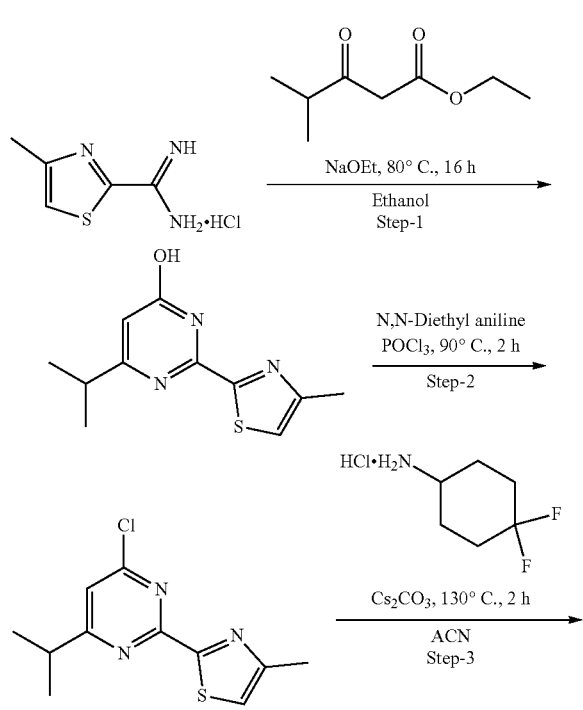

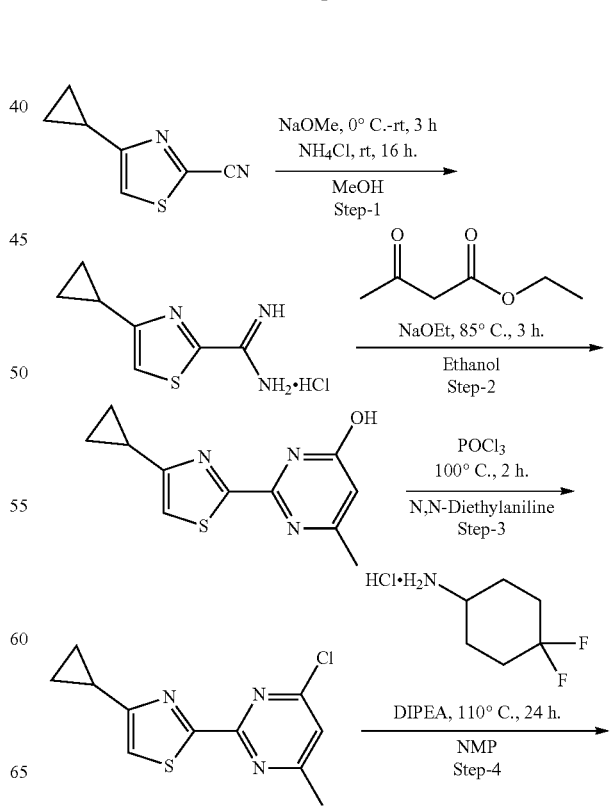

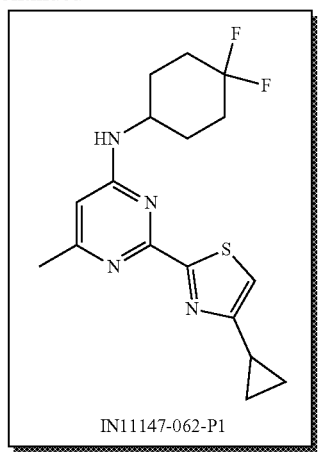

IN11147-062-P1

Step 1: 1.7 g of 4-cyclopropylthiazole-2-carbonitrile gave 4-cyclopropylthiazole-2-carboximidamide hydrochloride as a white solid (2.4 g, crude). MS (M+1)+=168.1.

Step 2: The procedure is similar to Step 1[IN10966-057-P2] in Example-893. 0.6 g of 4-cyclopropylthiazole-2-carboximidamide hydrochloride gave 2-(4-cyclopropylthiazol-2-yl)-6-methylpyrimidin-4-ol as an off-white solid (0.45 g, 65%). MS (M+1)+=234.1.

Step 3: The procedure is similar to Step 2[IN10966-057-P2] in Example-893. 0.45 g of 2-(4-cyclopropylthiazol-2-yl)-6-methylpyrimidin-4-ol gave 2-(4-chloro-6-methylpyrimidin-2-yl)-4-cyclopropylthiazole as a light brown solid (0.36 g, 74%). MS (M+1)+=252.0.

Step 4[IN11147-062-P1]: The procedure is similar to Step 1[B] in Example-838. 0.1 g of 2-(4-chloro-6-methylpyrimidin-2-yl)-4-cyclopropylthiazole gave 2-(4-cyclopropylthiazol-2-yl)-N-(4,4-difluorocyclohexyl)-6-methylpyrimidin-4-amine as an off-white solid (0.07 g, 53%). MS (M+1)+=351.2; ¹H-NMR (400 MHz, DMSO-$d_6$): δ 7.50 (bs, 1H), 7.37 (s, 1H), 6.34 (s, 1H), 4.04 (bs, 1H), 2.33-2.15 (m, 3H), 2.06-1.89 (m, 7H), 1.62-1.55 (m, 2H), 0.94-0.82 (m, 4H).

Example-618

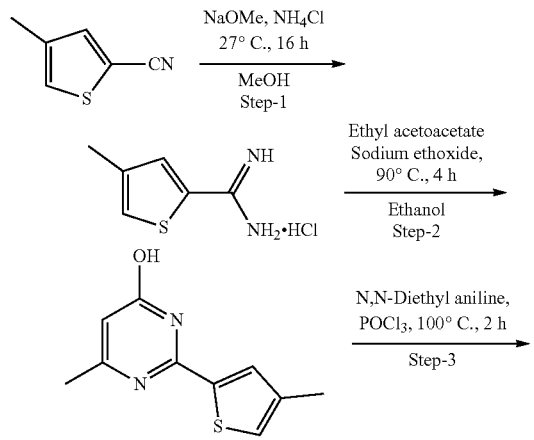

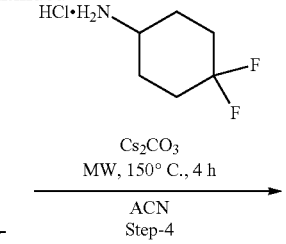

Cs₂CO₃
MW, 150° C., 4 h
ACN
Step-4

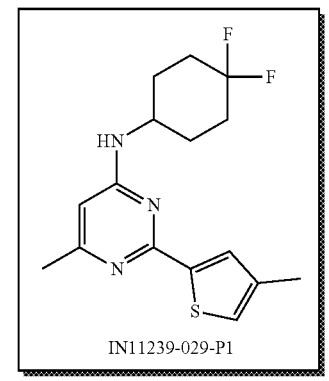

IN11239-029-P1

Step 1: 0.6 g of 4-methyl thiophene-2-carbonitrile gave 4-methylthiophene-2-carboximid amide hydrochloride as a white solid (0.85 g). MS (M+1)+=141.1.

Step 2: The procedure is similar to Step 1[IN10966-057-P2] in Example-893. 0.85 g of 4-methyl thiophene-2-carboximid amide hydrochloride gave 6-methyl-2-(4-methyl thiophen-2-yl)pyrimidin-4-ol as an off-white solid (0.4 g). MS (M+1)+=207.1.

Step 3: The procedure is similar to Step 2[IN10966-057-P2] in Example-893. 0.21 g of 6-methyl-2-(4-methyl thiophen-2-yl)pyrimidin-4-ol gave 4-chloro-6-methyl-2-(4-methylthiophen-2-yl)pyrimidine as a light brown solid (0.23 g). MS (M+1)+=225.1.

Step 4[IN11239-029-P1]: The procedure is similar to Step 1[NSSy6909] in Example-839. 0.23 g of 4-chloro-6-methyl-2-(4-methylthiophen-2-yl)pyrimidine gave N-(4,4-difluorocyclohexyl)-6-methyl-2-(4-methylthiophen-2-yl)pyrimidin-4-amine as an off-white solid (0.025 g, 7%). MS (M+1)+=324.1; 1H-NMR (400 MHz, DMSO-d6): δ 7.62 (s, 1H), 7.24 (d, J=6.0 Hz, 1H), 7.19 (s, 1H), 6.18 (s, 1H), 4.04 (s, 1H), 2.22 (s, 6H), 2.06-1.96 (m, 8H), 1.58-1.56 (m, 2H).

Example-619

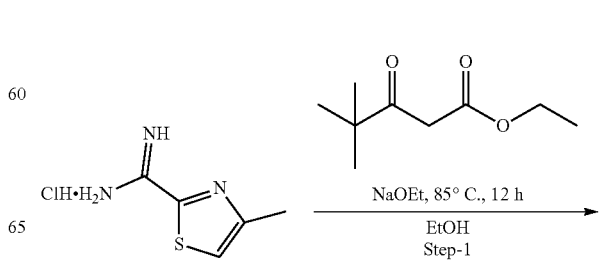

NaOEt, 85° C., 12 h
EtOH
Step-1

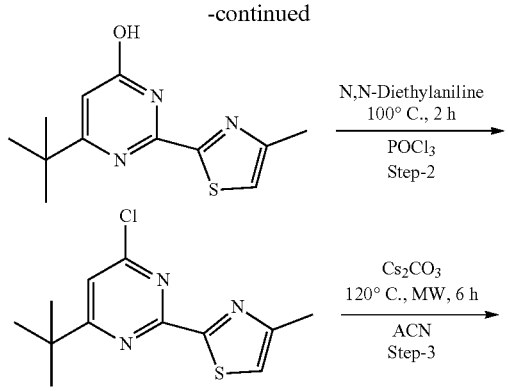

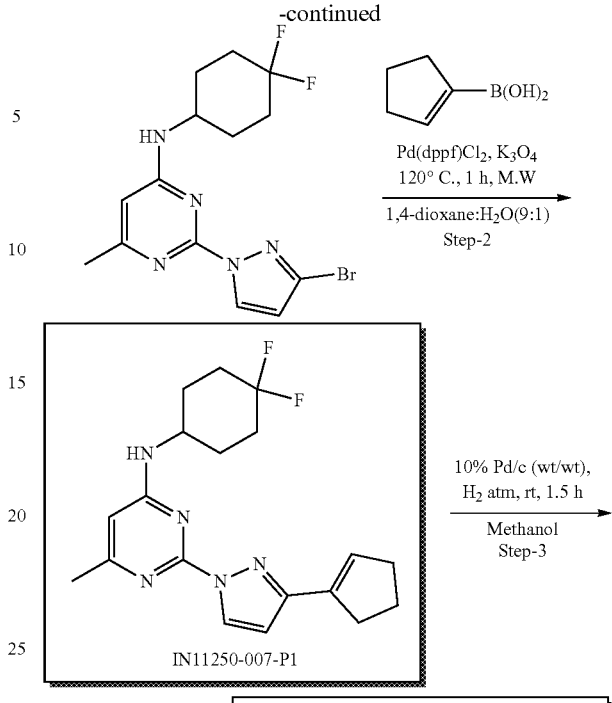

Step 1: The procedure is similar to Step 1[IN10966-057-P2] in Exampl-48. 1 g of 4-methylthiazole-2-carboximidamide hydrochloride gave 6-(tert-butyl)-2-(4-methylthiazol-2-yl)pyrimidin-4-ol as a yellow liquid (0.68 g, 48%). MS (M+1)+=250.2.

Step 2: The procedure is similar to Step 2[IN10966-057-P2] in Example-893. 0.67 g of 6-(tert-butyl)-2-(4-methylthiazol-2-yl)pyrimidin-4-ol gave 2-(4-(tert-butyl)-6-chloropyrimidin-2-yl)-4-methylthiazole as an off-white solid (0.35 g, 49%). MS (M+1)+=268.1.

Step 3[IN11220-039-P1]: The procedure is similar to Step 1[NSSy6909] in Example-839. 0.25 g of 2-(4-(tert-butyl)-6-chloropyrimidin-2-yl)-4-methylthiazole gave 6-(tert-butyl)-N-(4,4-difluorocyclohexyl)-2-(4-methylthiazol-2-yl)pyrimidin-4-amine as an off-white solid (0.1 g, 30%). MS (M+1)+=367.2; 1H-NMR (400 MHz, DMSO-d6): δ 7.49-7.48 (m, 1H), 7.36 (d, J=1.20 Hz, 1H), 6.45 (s, 1H), 4.10-4.09 (m, 1H), 2.44 (s, 3H), 2.10-1.99 (m, 6H), 1.97-1.59 (m, 2H), 1.25 (s, 9H).

Example-620

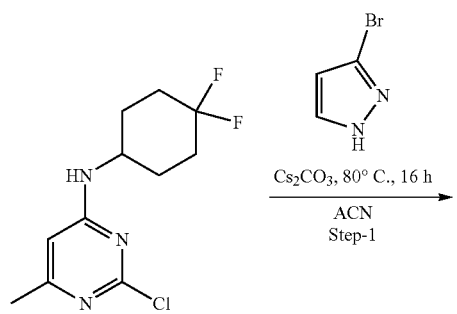

Step 1: The procedure is similar to Step 1[B] in Example-838. 0.5 g of 2-chloro-N-(4,4-difluorocyclohexyl)-6-methylpyrimidin-4-amine gave 2-(3-bromo-1H-pyrazol-1-yl)-N-(4,4-difluorocyclohexyl)-6-methylpyrimidin-4-amine as an off-white solid (1 g as crude). MS (M+1)+=372.2.

Step 2[IN11250-007-P1]: To a solution of 2-(3-bromo-1H-pyrazol-1-yl)-N-(4,4-difluorocyclohexyl)-6-methylpyrimidin-4-amine (0.2 g, 0.53 mmol) in dioxane:water (10 mL) was added cyclopent-1-en-1-ylboronic acid (0.09 g, 0.80 mmol) and potassium phosphate (0.34 g, 1.59 mmol) and purged nitrogen for 10 min. Pd(dppf)Cl2 (0.043 g, 0.053 mmol) was added and the reaction mixture was heated at 120° C. for 1 h in MW. The reaction mixture was filtered and the filtrate was concentrated to afford crude and which was purified by Prep HPLC to afford 2-(3-(cyclopent-1-en-1-yl)-1H-pyrazol-1-yl)-N-(4,4-difluorocyclohexyl)-6-methylpyrimidin-4-amine as an off-white solid (0.022 g, 11%). MS (M+1)+=360.2; 1H-NMR (400 MHz, DMSO-d6): δ 8.51 (bs, 1H), 7.58 (bs, 1H), 6.68 (d, J=2.8 Hz, 1H), 6.30 (t, J=2.00 Hz, 1H), 6.22 (bs, 1H), 2.70-2.67 (m, 3H), 2.27 (s, 3H), 2.09-1.91 (m, 9H), 1.58-1.56 (m, 3H).

Step 3[IN11250-017-P1]: The procedure is similar to Step 2[NSSy6464] in Example-869. 0.08 g of 2-(3-(cyclopent-1-en-1-yl)-1H-pyrazol-1-yl)-N-(4,4-difluorocyclohexyl)-6-methylpyrimidin-4-amine gave 2-(3-cyclopentyl-1H-pyrazol-1-yl)-N-(4,4-difluorocyclohexyl)-6-methylpyrimidin-4-amine as an off-white solid (0.03 g, 37.5%). MS (M+1)+= 362.2; 1H-NMR (400 MHz, DMSO-d6): δ 8.44 (s, 1H), 7.54 (s, 1H), 6.34 (d, J=2.8 Hz, 1H), 6.20 (bs, 1H), 4.08 (bs, 1H), 3.31-3.07 (m, 1H), 2.26 (s, 3H), 2.09-1.96 (m, 9H), 1.73-1.58 (m, 9H).

Example-621

Omitted Intentionally

Example-622

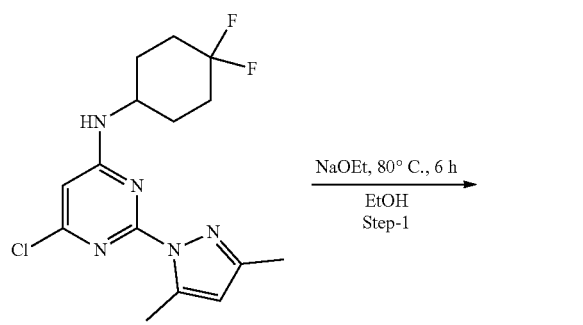

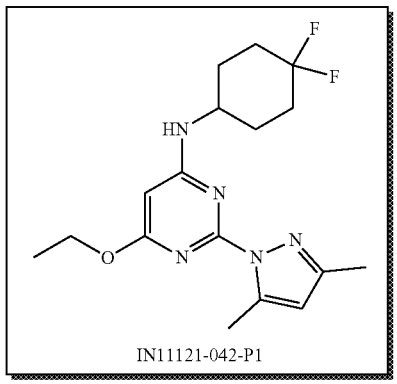

Step 1[IN11121-042-P1]: The procedure is similar to Step 1[NSSy6519] in Example-842. 0.3 g of 6-chloro-N-(4,4-difluorocyclohexyl)-2-(3,5-dimethyl-1H-pyrazol-1-yl)pyrimidin-4-amine gave N-(4,4-difluorocyclohexyl)-2-(3,5-dimethyl-1H-pyrazol-1-yl)-6-ethoxypyrimidin-4-amine as an off-white solid (0.11 g, 36%). MS (M+1)+=352.1; 1H-NMR (400 MHz, DMSO-d6): δ 7.41 (s, 1H), 6.05 (s, 1H), 5.68 (s, 1H), 4.27 (q, J=40.00 Hz, 2H), 3.90 (s, 1H), 2.54 (s, 3H), 2.16 (s, 3H), 2.10-1.85 (m, 6H), 1.60-1.48 (m, 2H), 1.29 (t, J=7.20 Hz, 3H)

Example-623

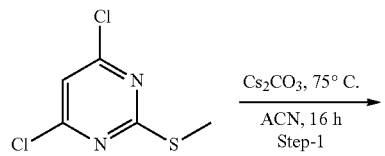

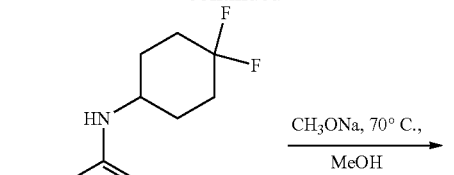

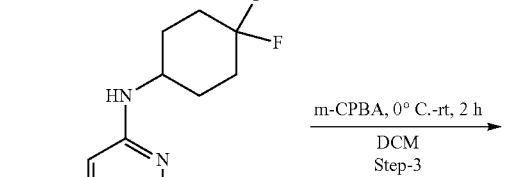

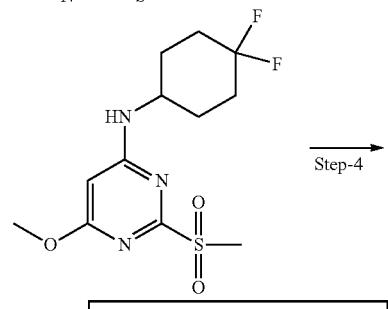

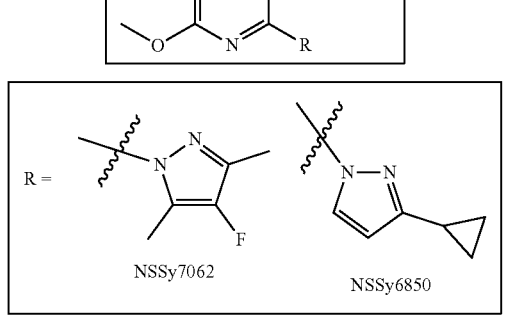

Step 1: The procedure is similar to Step 1[B] in Example-838. 7 g of 4,6-dichloro-2-(methylthio)pyrimidine gave 6-chloro-N-(4,4-difluorocyclohexyl)-2-(methylthio)pyrimidin-4-amine as a yellow solid (10.2 g, 96%). MS (M+1)+= 294.2.

Step 2: The procedure is similar to Step 1[NSSy6519] in Example-842. 0.5 g of 6-chloro-N-(4,4-difluorocyclohexyl)-2-(methylthio)pyrimidin-4-amine gave N-(4,4-difluorocyclohexyl)-6-methoxy-2-(methylthio)pyrimidin-4-amine as yellowish gum (0.35 g, 71%). MS (M+1)+=290.0.

Step 3: To a stirred solution of N-(4,4-difluorocyclohexyl)-6-methoxy-2-(methylthio)pyrimidin-4-amine (0.35 g, 1.20 mmol) in Dichloromethane (10 mL) was added 3-Chloroperbenzoic acid (0.62 g, 3.62 mmol) at 0° C. The reaction mixture was stirred at room temperature. After 2 h, the reaction mixture was quenched with saturated sodium bicarbonate solution and extracted with DCM (50 mL). The organic layer was washed with saturated sodium thiosulfate solution and brine, then dried over sodium sulfate, filtered and concentrated under reduced pressure to afford N-(4,4-difluorocyclohexyl)-6-methoxy-2-(methylsulfonyl)pyrimidin-4-amine as a white solid (0.37 g, 95%). MS (M+1)+= 322.1.

TABLE 15

Step 4: The procedure is similar to Step 1[B] in Example

| Compound No | R | Condition | Yield (%) |
|---|---|---|---|
| NSSy7062 | 3,5-dimethyl-4-fluoro-pyrazol-1-yl | Cs$_2$CO$_3$, ACN, 80° C., 16 h | 71 |
| NSSy6850 | 3-cyclopropyl-pyrazol-1-yl | Cs$_2$CO$_3$, ACN, 80° C., 16 h | 12 |

Step 4[NSSy7062]: MS (M+1)$^+$=356.1; $^1$H-NMR (400 MHz, DMSO-d$_6$): δ 7.51 (s, 1H), 5.71 (s, 1H), 3.85 (s, 3H), 2.53 (s, 3H), 2.20 (s, 3H), 2.15-1.85 (m, 6H), 1.60-1.50 (m, 2H).

Step 4[NSSy6850]: MS (M+1)$^+$=350.1; $^1$H-NMR (400 MHz, DMSO-d$_6$): δ 8.42 (s, 1H), 7.48 (s, 1H), 6.20 (s, 1H), 5.68 (s, 1H), 3.87 (s, 1H), 2.08-2.02 (m, 3H), 1.97-1.91 (m, 4H), 1.58 (d, J=15.20, Hz, 2H), 0.94 (q, J=2.00 Hz, 2H), 0.73 (q, J=0.80 Hz, 2H).

Example-624

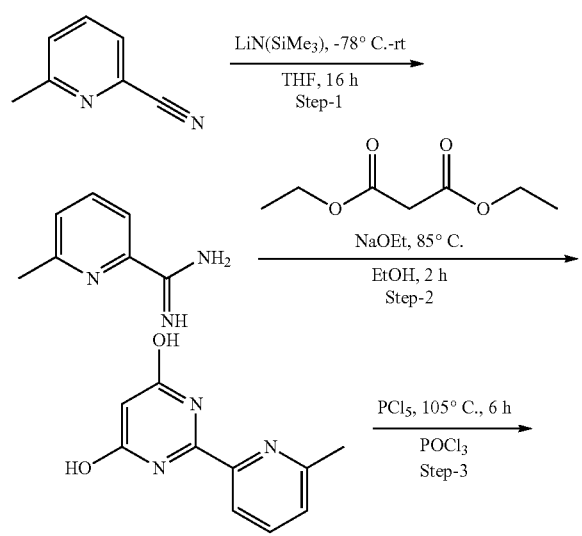

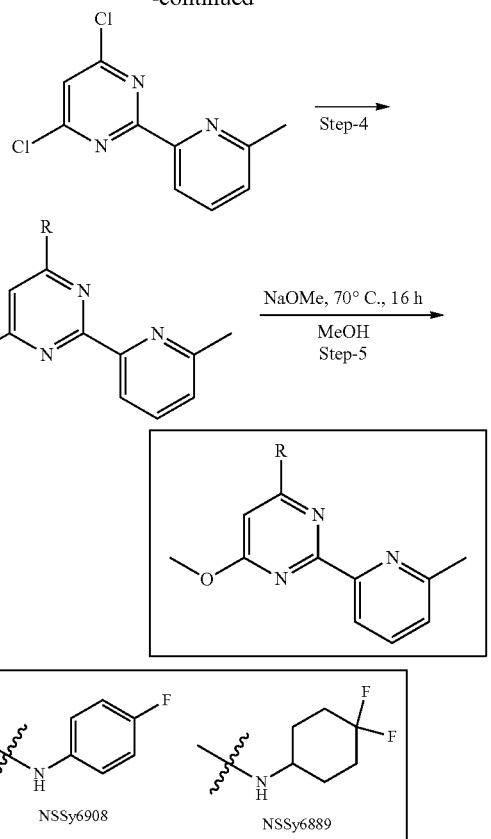

Step 1: To a pre (−78° C.) cooled solution of 6-methyl-2-Pyridinecarbonitrile (5 g, 42.32 mmol) in Tetrahydrofuran (50 mL) was added Lithium bis(trimethylsilyl)amide (14.16 g, 84.64 mmol) and slowly warmed to rt and continued for 16 h. After that 1.5 N HCl solution (50 mL) was added to the reaction mixture and stirred for 1 h. Then extracted with ethyl acetate (100 mL), the aqueous layer was basified and extracted with chloroform (3×100 mL). The chloroform was dried over sodium sulfate, filtered and concentrated under reduced pressure to afford 6-methylpicolinimidamide as an off-white solid (3.5 g, 40%). MS (M+1)+=136.1.

Step 2: The procedure is similar to Step 1[IN10966-057-P2] in Example-893. 3.5 g of 6-methylpicolinimidamide gave 2-(6-methylpyridin-2-yl)pyrimidine-4,6-diol as red solid (3.5 g, 67%). MS (M+1)+=204.1.

Step 3: To a suspension of 2-(6-methylpyridin-2-yl)pyrimidine-4,6-diol (3.5 g, 17.2 mmol) in Phosphorus oxychloride (16.06 mL, 172.2 mmol) was added Phosphorus Pentachloride (3.58 g, 17.2 mmol) and heated at 105° C. After 6 h, the reaction mixture was cooled to room temperature and quenched with ice and basified using saturated sodium bicarbonate solution to pH=7. The reaction mixture was extracted with ethyl acetate and washed with brine solution. The organic layer was dried over sodium sulfate, filtered and concentrated under reduced pressure to afford crude product, which was purified using ethyl acetate in pet-ether as solvent to afford 4,6-dichloro-2-(6-methylpyridin-2-yl)pyrimidine as yellow solid (1.3 g, 32%). MS (M+1)$^+$=242.2.

TABLE 16

Step 4:

| Compound No | R | Condition | Yield (%) | MS (M+1)+ |
|---|---|---|---|---|
| W | 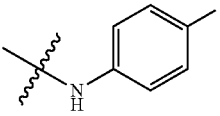 | DIPEA, ACN, 80 °C., 16h, sealed tube. | 86 | 315.1 |
| X | 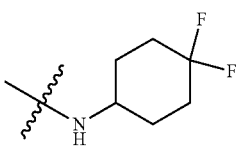 [SMILES: *NC1CCC(F)(F)CC1] | Cs₂CO₃, ACN, 80 °C., 16h, sealed tube | 95 | 339.4 |

Step 4[W]: The procedure is similar to Step 1[B] in Example-838.

Step 4[X]: The procedure is similar to Step 1[B] in Example-838.

TABLE 17

Step 5: The procedure is similar to Step 1[NSSy6519] in Example-842.

| Compound No | R | Condition | Yield (%) | MS (M+1)+ |
|---|---|---|---|---|
| NSSy6889 | 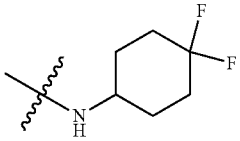 [SMILES: *NC1CCC(F)(F)CC1] | NaOMe, MeOH, 75 °C., 16h. | 67 | 335.2 |

Step 5[NSSy6889]: $^1$H-NMR (400 MHz, DMSO-d$_6$): δ 8.07 (d, J=7.60 Hz, 1H), 7.79 (t, J=7.60 Hz, 1H), 7.32 (d, J=7.60 Hz, 2H), 5.82 (s, 1H), 3.90 (s, 1H), 2.53 (s, 1H), 2.06-1.94 (m, 6H), 1.59-1.57 (m, 2H).

Example-625

Intentionally Omitted

Example-626

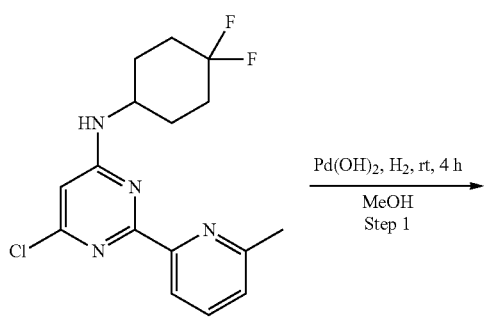

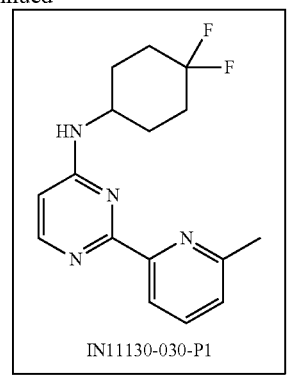

IN11130-030-P1

Step 1[IN11130-030-P1]: The procedure is similar to Step 2[NSSy6464] in Example-869. 0.14 g of 6-chloro-N-(4,4-difluorocyclohexyl)-2-(6-methylpyridin-2-yl)pyrimidin-4-amine gave N-(4,4-difluorocyclohexyl)-2-(6-methylpyridin-2-yl)pyrimidin-4-amine as an off-white solid (0.07 g, 56%). MS (M+1)+=305.0; $^1$H-NMR (400 MHz, DMSO-d$_6$): δ 8.41 (d, J=6.0 Hz, 1H), 8.25-8.17 (m, 1H), 7.73-7.69 (m, 1H), 7.25 (d, J=8.0 Hz, 1H), 6.34 (d, J=5.6 Hz, 1H), 5.15 (m, 1H), 3.89 (m, 1H), 2.70 (s, 3H), 2.31-2.09 (m, 4H), 2.13-1.88 (m, 2H), 1.75-1.65 (m, 2H).

Example-627

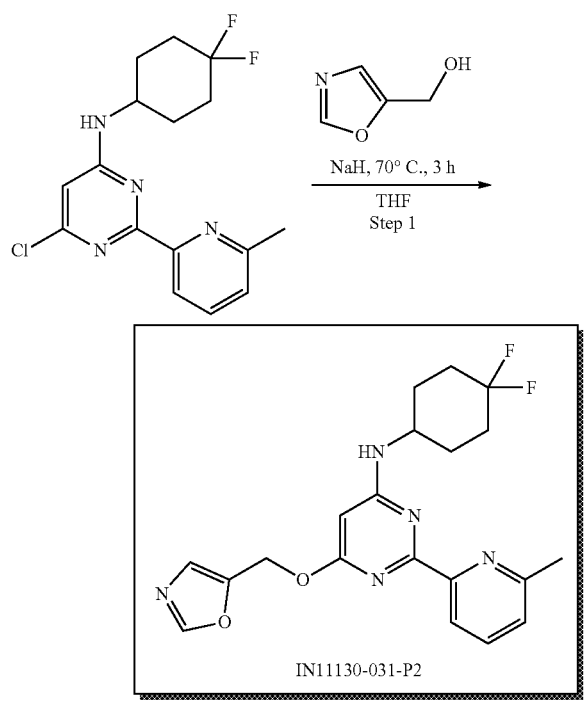

Step 1[IN11130-031-P2]: The procedure is similar to Step 5[NSSy6711] in Example-854. 0.14 g of 6-chloro-N-(4,4-difluorocyclohexyl)-2-(6-methylpyridin-2-yl)pyrimidin-4-amine gave N-(4,4-difluorocyclohexyl)-2-(6-methylpyridin-2-yl)-6-(oxazol-5-ylmethoxy)pyrimidin-4-amine as an off-white solid (0.06 g, 36%). MS (M+1)$^+$=402.1; $^1$H-NMR (400 MHz, DMSO-$d_6$): δ 8.39 (s, 1H), 8.12 (d, J=7.6 Hz, 1H), 7.81 (t, J=7.6 Hz, 1H), 7.47-7.42 (m, 2H), 7.35 (d, J=7.6 Hz, 1H), 5.86 (s, 1H), 5.49 (s, 2H), 4.01 (m, 1H), 2.55 (s, 3H), 2.08-1.93 (m, 6H), 1.61-1.56 (m, 2H).

Example-628

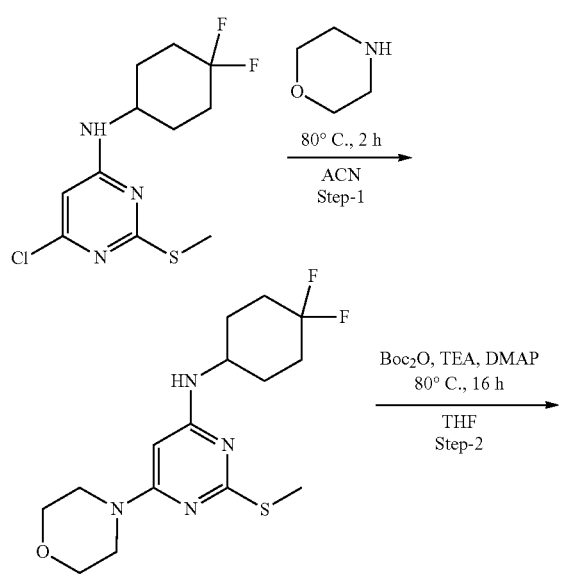

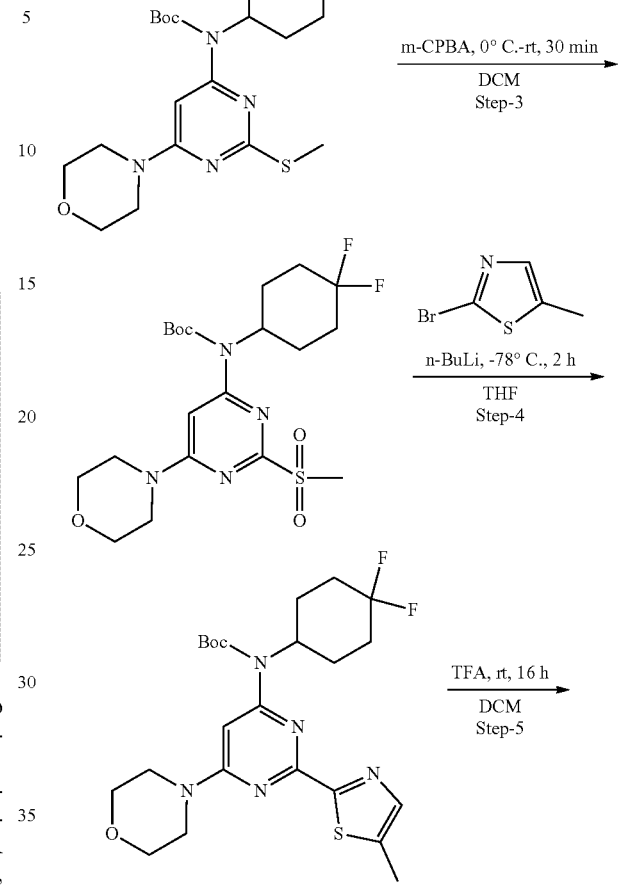

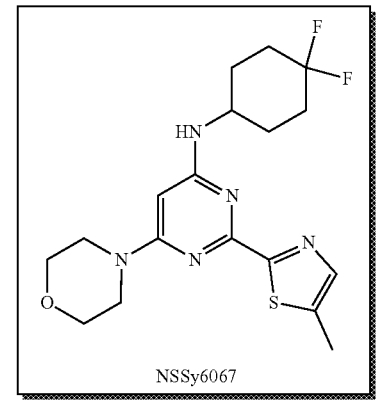

Step 1: The procedure is similar to Step 1[B] in Example-838. 1.4 g of 6-chloro-N-(4,4-difluorocyclohexyl)-2-(methylthio)pyrimidin-4-amine gave N-(4,4-difluorocyclohexyl)-2-(methylthio)-6-morpholinopyrimidin-4-amine as an off-white solid (1.5 g, 93%). MS (M+1)+=345.2.

Step 2: To a solution of N-(4,4-difluorocyclohexyl)-2-(methylthio)-6-morpholino pyrimidin-4-amine (1 g, 2.90 mmol) in tetrahydrofuran (15 mL) was added 4-N, N-Dimethylamino pyridine (0.1 g, 0.87 mmol), triethyl amine (1.2 mL, 8.71 mmol) and Boc-anhydride (3.16 g, 14.51 mmol). The reaction mixture was heated at 80° C. for 16 h. The reaction mixture was quenched with water and extracted with ethyl acetate (2×75 mL), the combined organic layer was dried over anhydrous sodium sulfate and concentrated to afford tert-butyl (4,4-difluorocyclohexyl)(2-(methylthio)-6-morpholino pyrimidin-4-yl)carbamate as an yellowish gum (1.1 g, 85%). MS (M+1)+=445.2.

Step 3: The procedure is similar to Step 3[NSSy7062] in Example-623. 1.1 g of tert-butyl (4,4-difluorocyclohexyl) (2-(methylthio)-6-morpholinopyrimidin-4-yl) carbamate gave tert-butyl (4,4-difluorocyclohexyl) (2-(methylsulfonyl)-6-morpholino pyrimidin-4-yl) carbamate as an off-white gum (0.9 g, 76%). MS (M+1)+=477.3.

Step 4: To a stirred solution of Tetrahydrofuran (5 mL) was added n-butyl lithium (2.5M solution in hexane)(0.62 mL, 1.57 mmol) dropwise at −78° C., followed by dropwise addition of 2-Bromo-5-Methyl-1,3-Thiazole (0.2 g, 1.15 mmol) in THF. The reaction mixture was stirred at same temperature for 1 h. After 1 h tert-butyl (4,4-difluorocyclohexyl) (2-(methylsulfonyl)-6-morpholino pyrimidin-4-yl) carbamate (0.5 g, 1.04 mmol) in THF added dropwise to the reaction mixture and stirred at same temperature for 2 h. The reaction mixture was quenched with saturated ammonium chloride solution (10 mL) and extracted with ethyl acetate. The combined organic layer was washed with brine solution, dried over sodium sulfate, filtered and concentrated under reduced pressure to afford crude product, which was purified by flash chromatography to afford tert-butyl(4,4-difluorocyclohexyl)(2-(5-methylthiazol-2-yl)-6-morpholinopyrimidin-4-yl)carbamate as an off-white solid (0.15 g, 28%). MS (M+1)+=496.0.

Step 4[NSSy6067]: To an ice cooled solution of tert-butyl (4,4-difluorocyclohexyl) (2-(5-methylthiazol-2-yl)-6-morpholinopyrimidin-4-yl) carbamate (0.15 g, 0.30 mmol) in dichloromethane was added trifluoroacetic acid (0.2 mL, 2.60 mmol). The reaction mixture was stirred at room temperature for 16 h. The reaction mixture was concentrated and the resulting residue was basified with saturated sodium bicarbonate solution and extracted with ethyl acetate (2×70 mL), the combined organic layer was dried over anhydrous sodium sulfate, filtered and concentrated under reduced pressure to afford crude product, which was purified by column chromatography to afford N-(4,4-difluorocyclohexyl)-2-(5-methylthiazol-2-yl)-6-morpholinopyrimidin-4-amine as an off-white solid (0.055 g, 55%). MS (M+1)+= 396.0; 1H-NMR (400 MHz, DMSO-$d_6$): δ 7.60 (s, 1H), 7.01 (d, J=8.00 Hz, 1H), 5.65 (s, 1H), 3.94 (s, 1H), 3.70-3.68 (m, 4H), 3.50 (s, 4H), 2.47 (s, 3H), 2.08-1.92 (m, 6H), 1.61-1.55 (m, 2H).

Example-629

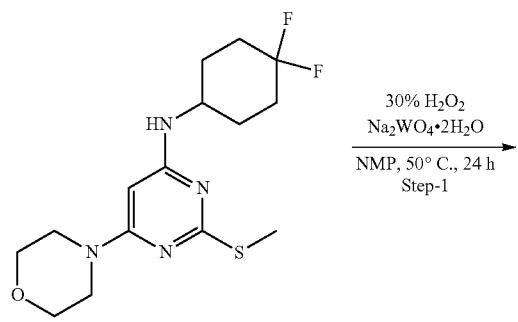

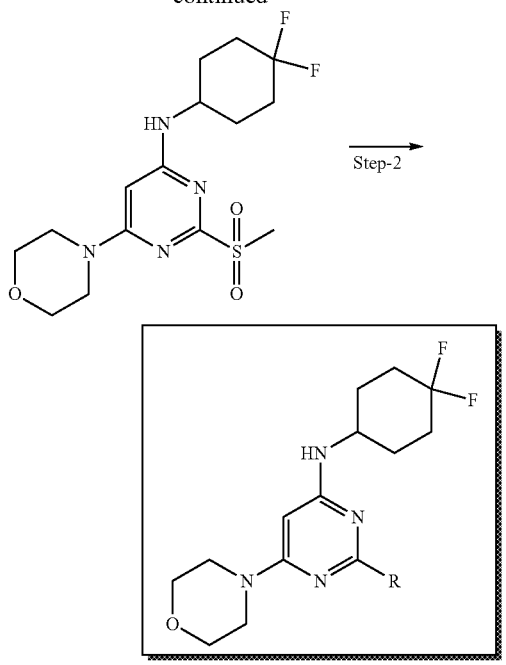

R=

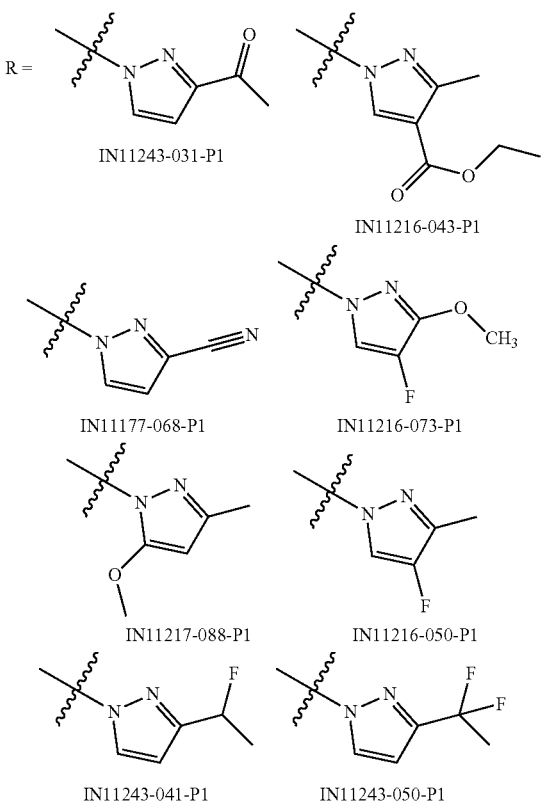

Step 1: To a solution of N-(4,4-difluorocyclohexyl)-2-(methylthio)-6-morpholinopyrimidin-4-amine (1 g, 2.90 mmol) in NMP (10.0 mL) was charged Sodium Tungstate Dihydrate (0.19 g, 0.58 mmol) at room temperature. The reaction mass temperature was then raised to 70-75° C. and 30% $H_2O_2$ (1 mL) was added drop wise over a period of 5.0 mins, the reaction mixture was stirred for 24 h at 50° C. The reaction was cooled to room temperature, ice cold water (50 mL) was added slowly to the reaction mixture and the mixture was stirred for 1 h, the resulting solid was collected by filtration and washed with water (2×50 mL), dried under vacuum at 50° C. to afford N-(4,4-difluorocyclohexyl)-2-(methylsulfonyl)-6-morpholinopyrimidin-4-amine as an off-white solid (0.8 g, 73%). MS (M+1)$^+$=377.1.

Step 2[IN11243-031-P1]: The procedure is similar to Step 1[B] in Example-838. 1H-NMR (400 MHz, DMSO-d6): δ 8.64 (d, J=2.80 Hz, 1H), 7.25 (d, J=7.60 Hz, 1H), 6.86 (d, J=3.20 Hz, 1H), 5.64 (s, 1H), 4.01-4.10 (m, 1H), 3.70-3.69 (m, 4H), 3.55-3.50 (m, 4H), 2.56 (s, 3H), 2.32-1.94 (m, 6H), 1.61-1.53 (m, 2H).

Step 2[IN11216-043-P1]: The procedure is similar to Step 1[B] in Example-838. 1H-NMR (400 MHz, DMSO-d6): δ 8.82 (s, 1H), 7.21 (d, J=8.00 Hz, 1H), 5.60 (s, 1H), 4.25-4.22

TABLE 18

| Compound No | R | Condition | Yield (%) | MS (M+1)$^+$ |
|---|---|---|---|---|
| IN11243-031-P1 | (pyrazole with acetyl) | $Cs_2CO_3$, ACN, 80 °C., 16h, | 50 | 407.2 |
| IN11216-043-P1 | (pyrazole with methyl and ethyl ester) | $Cs_2CO_3$, ACN, 80 °C., 16h, | 70 | 451.1 |
| IN11177-068-P1 | (pyrazole with CN) | $Cs_2CO_3$, ACN, 130 °C., 1h, MW | 29 | 390 |
| IN11216-073-P1 | (pyrazole with OCH$_3$ and F) | $Cs_2CO_3$, ACN, 80 °C., 16h, | 27 | 413.2 |
| IN11217-088-P1 | (pyrazole with methyl and OMe) | NaH, DMF, 80 °C., 4h | 35 | 409.3 |
| IN11216-050-P1 | (pyrazole with methyl and F) | $Cs_2CO_3$, ACN, 80 °C., 16h, | 20 | 397.2 |
| IN11243-041-P1 | (pyrazole with CHF-CH$_3$) | Step a: $Cs_2CO_3$, ACN, 80 °C., 16h, Step b: NaBH$_4$, MeOH, 0 °C., 1h Step c: DAST, −78 °C-rt, 16h | 50/70.8/50 | 407.2/409.3/411.3 |
| IN11243-050-P2 | (pyrazole with CHF-CH$_3$) | Step a: $Cs_2CO_3$, ACN, 80 °C., 16h, Step b: Deoxo-fluoro, EtOH, 90 °c, 48h | 50/7.14 | 407.2/429.2 |

(m, 2H), 4.01-3.99 (m, 1H), 3.69-3.68 (m, 4H), 3.52-3.42 (m, 4H), 2.41 (s, 3H), 2.05-1.90 (m, 6H), 1.61-1.52 (m, 2H), 1.29-1.28 (m, 3H).

Step 2[IN11177-068-P1]: The procedure is similar to Step 1[NSSy6909] in Example-839. 1H-NMR (400 MHz, DMSO-d6): δ 8.77 (d, J=2.00 Hz, 1H), 7.29 (d, J=7.60 Hz, 1H), 7.16 (s, 1H), 5.64 (s, 1H), 4.01-3.90 (m, 1H), 3.69-3.52 (m, 4H), 3.55-3.50 (m, 4H), 2.07-1.93 (m, 6H), 1.60-1.51 (m, 2H).

Step 2[IN11216-073-P1]: The procedure is similar to Step 1[B] in Example-838. 1H-NMR (400 MHz, DMSO-d6): δ 8.54 (d, J=4.40 Hz, 1H), 7.09 (d, J=8.00 Hz, 1H), 5.50 (s, 1H), 3.94 (s, 3H), 3.89 (s, 1H), 3.68-3.67 (m, 4H), 3.50-3.40 (m, 4H), 2.09-1.89 (m, 6H), 1.59-1.50 (m, 2H).

Step 2[IN11217-088-P1]: 1H-NMR (400 MHz, DMSO-d6): δ 7.02 (d, J=8.00 Hz, 1H), 5.71 (s, 1H), 5.53 (s, 1H), 3.79 (s, 1H), 3.78 (s, 3H), 3.71-3.66 (m, 4H), 3.45-3.40 (m, 4H), 3.33 (s, 3H), 2.13-1.90 (m, 6H), 1.58-1.53 (m, 2H).

Step 2[IN11216-050-P1]: The procedure is similar to Step 1[B] in Example-838. 1H-NMR (400 MHz, DMSO-d6): δ 8.50 (d, J=4.80 Hz, 1H), 7.10 (d, J=7.60 Hz, 1H), 5.53 (s, 1H), 4.04-4.02 (m, 1H), 3.67-3.60 (m, 4H), 3.49-3.48 (m, 4H), 2.22 (s, 3H), 2.04-1.89 (m, 6H), 1.58-1.52 (m, 2H).

Step 2[IN11243-041-P1]: Step a: The procedure is similar to Step 1[B] in Example-838. Step b: The procedure is similar to Step 2[NSSy6931] in Example-21. Step c: The procedure is similar to Step 3[NSSy6917] in Example-21. 1H-NMR (400 MHz, DMSO-d6): δ 8.54 (d, J=2.40 Hz, 1H), 7.16 (d, J=8.00 Hz, 1H), 6.58 (s, 1H), 5.74 (d, J=62.80 Hz, 1H), 5.58 (s, 1H), 3.91-3.90 (m, 1H), 3.69-3.68 (m, 4H), 3.52-3.41 (m, 4H), 2.02 (s, 3H), 2.01-1.67 (m, 6H), 1.59-1.51 (m, 2H).

Step 2[IN11243-050-P2]: Step a: The procedure is similar to Step 1[B] in Example-838. Step b: The procedure is similar to Step 3[NSSy6917] in Example-21. 1H-NMR (400 MHz, DMSO-d6): δ 8.61 (d, J=2.40 Hz, 1H), 7.22 (d, J=8.40 Hz, 1H), 6.68 (d, J=2.40 Hz, 1H), 5.61 (s, 1H), 4.11-4.00 (m, 1H), 3.70-3.69 (m, 4H), 3.53-3.52 (m, 4H), 2.05 (s, 3H), 2.03-1.91 (m, 7H), 1.57-1.54 (m, 2H).

Example-630

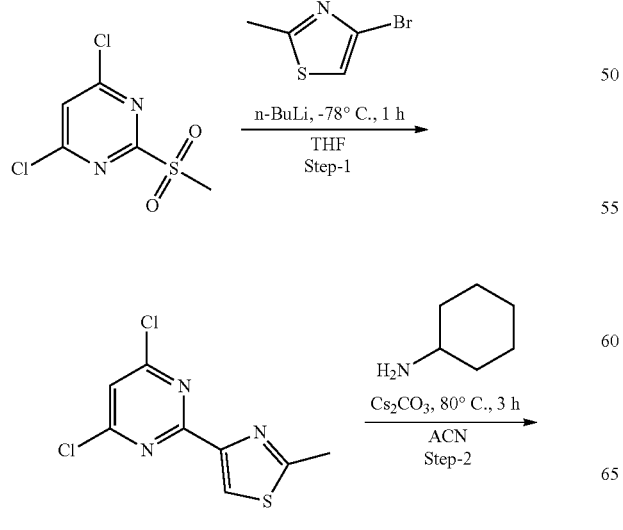

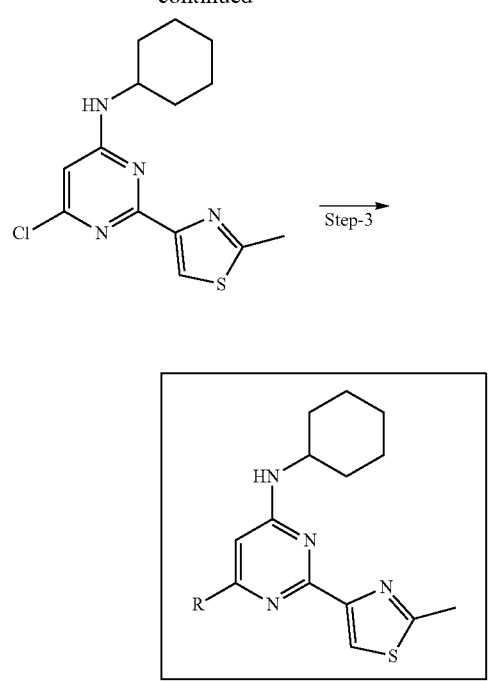

R=

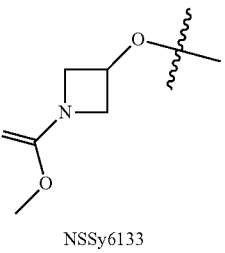

Step 1: The procedure is similar to Step 4[NSSy6067] in Example-628. 1.5 g of 4,6-dichloro-2-(methylsulfonyl)pyrimidine gave 4-(4,6-dichloropyrimidin-2-yl)-2-methylthiazole as a yellow solid (0.5 g, 30%). MS (M+1)+=248.0.

Step 2: The procedure is similar to Step 1[B] in Example-838. 0.25 g of 4-(4,6-dichloropyrimidin-2-yl)-2-methylthiazole as yellow solid gave 6-chloro-N-cyclohexyl-2-(2-methylthiazol-4-yl)pyrimidin-4-amine as a yellow solid (0.3 g, 90%). MS (M+1)+=309.0.

TABLE 19

Step 3:

| Compound No | R | Condition | Yield (%) | MS (M+1)+ |
|---|---|---|---|---|
| NSSy6134 | (thiomorpholine 1,1-dioxide) | Pd₂(dba)₃, Xanthphos, Cs₂CO₃, Dioxane, 90 °C., 16h | 35 | 408.2 |
| NSSy6140 | (2-oxa-6-azaspiro[3.3]heptane) | Cs₂CO₃, ACN, 80 °C., 16h sealed tube | 41 | 408.2 |
| NSSy6133 | (methyl 3-oxyazetidine-1-carboxylate) | K⁺(CH₃)₃CO⁻, 80 °C., ACN, 5h | 42 | 404.2 |

Step 3[NSSy6134]: The procedure is similar to Step 1[NSSy6629] in Example-839. 1H-NMR (400 MHz, DMSO-d6): δ 8.16 (s, 1H), 6.81 (s, 1H), 5.68 (s, 1H), 4.02 (s, 4H), 3.13 (s, 4H), 2.67 (s, 1H), 1.89-1.86 (m, 2H), 1.73-1.70 (m, 2H), 1.60-1.57 (m, 1H), 1.36-1.20 (m, 6H).

Step 3[NSSy6140]: The procedure is similar to Step 1[B] in Example-838. 1H-NMR (400 MHz, DMSO-d6): δ 8.12 (s, 1H), 6.89 (s, 1H), 5.19 (s, 1H), 4.71 (s, 4H), 4.10 (s, 4H), 3.92 (s, 1H), 2.68 (s, 3H), 2.04-1.92 (m, 6H), 1.54-1.52 (m, 2H).

Step 3[NSSy6133]: The procedure is similar to Step 1[B] in Example-838. 1H-NMR (400 MHz, DMSO-d6): δ 8.19 (s, 1H), 7.26 (s, 1H), 5.66 (s, 1H), 5.29 (s, 1H), 4.34 (s, 2H), 3.91-3.90 (m, 2H), 3.58 (s, 3H), 1.73-1.70 (m, 2H), 1.39-1.36 (m, 2H), 1.33-1.30 (m, 1H), 1.23-1.20 (m, 2H).

Example-631

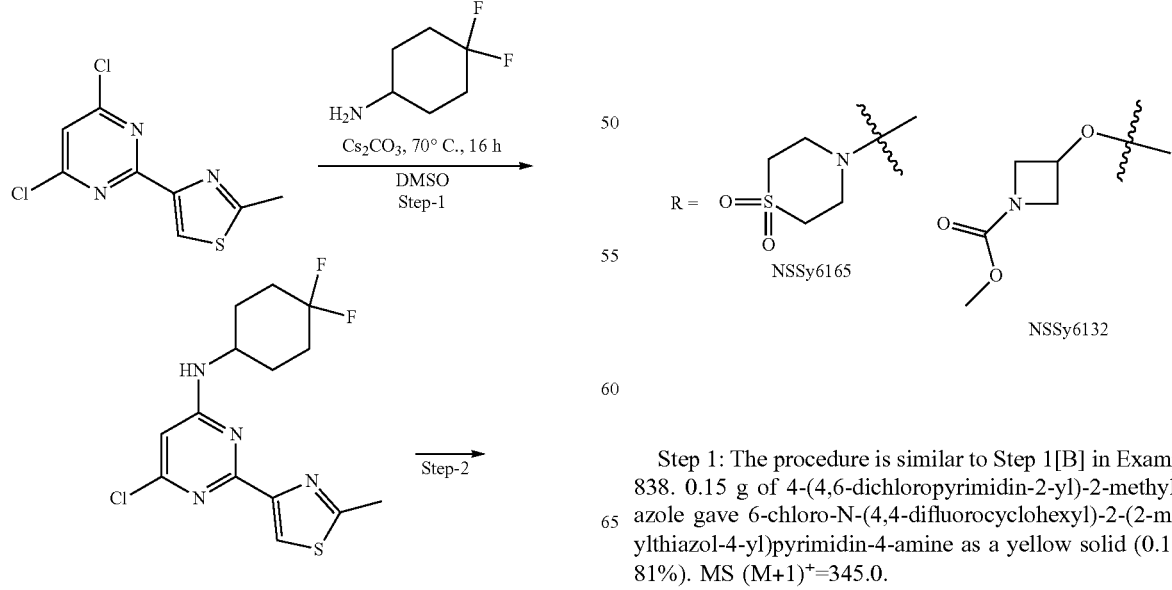

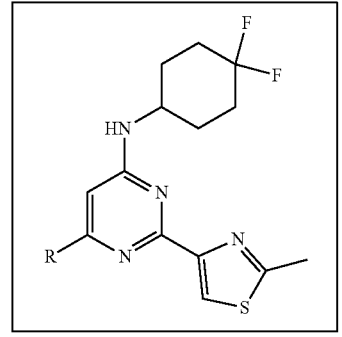

Step 1: The procedure is similar to Step 1[B] in Example-838. 0.15 g of 4-(4,6-dichloropyrimidin-2-yl)-2-methylthiazole gave 6-chloro-N-(4,4-difluorocyclohexyl)-2-(2-methylthiazol-4-yl)pyrimidin-4-amine as a yellow solid (0.17 g, 81%). MS (M+1)+=345.0.

TABLE 20

Step 2:

| Compound No | R | Condition | Yield (%) | MS (M+1)+ |
|---|---|---|---|---|
| NSSy6165 | | Pd2(dba)3, Xanthphos, Cs2CO3, Dioxane, 90 °C., 16h | 14 | 444.0 |
| NSSy6132 | | Cs2CO3, ACN, 80 °C., 5h sealed tube | 14 | 440.2 |

Step 2[NSSy6165]: The procedure is similar to Step 1[NSSy6629] in Example-839. 1H-NMR (400 MHz, DMSO-d6): δ 8.20 (s, 1H), 7.00 (s, 1H), 5.71 (s, 1H), 4.03 (s, 4H), 3.98 (s, 1H), 3.14 (s, 4H), 2.67 (s, 3H), 2.05-1.91 (m, 6H), 1.59-1.57 (m, 2H).

Step 2[NSSy6132]: The procedure is similar to Step 1[B] in Example-838. 1H-NMR (400 MHz, DMSO-d6): δ 8.24 (s, 1H), 7.40 (s, 1H), 5.72 (s, 1H), 5.39 (s, 1H), 4.34 (s, 2H), 3.92-3.91 (m, 2H), 3.58 (s, 3H), 2.68 (s, 3H), 2.04-1.93 (m, 6H), 1.56-1.54 (m, 2H).

Example-632

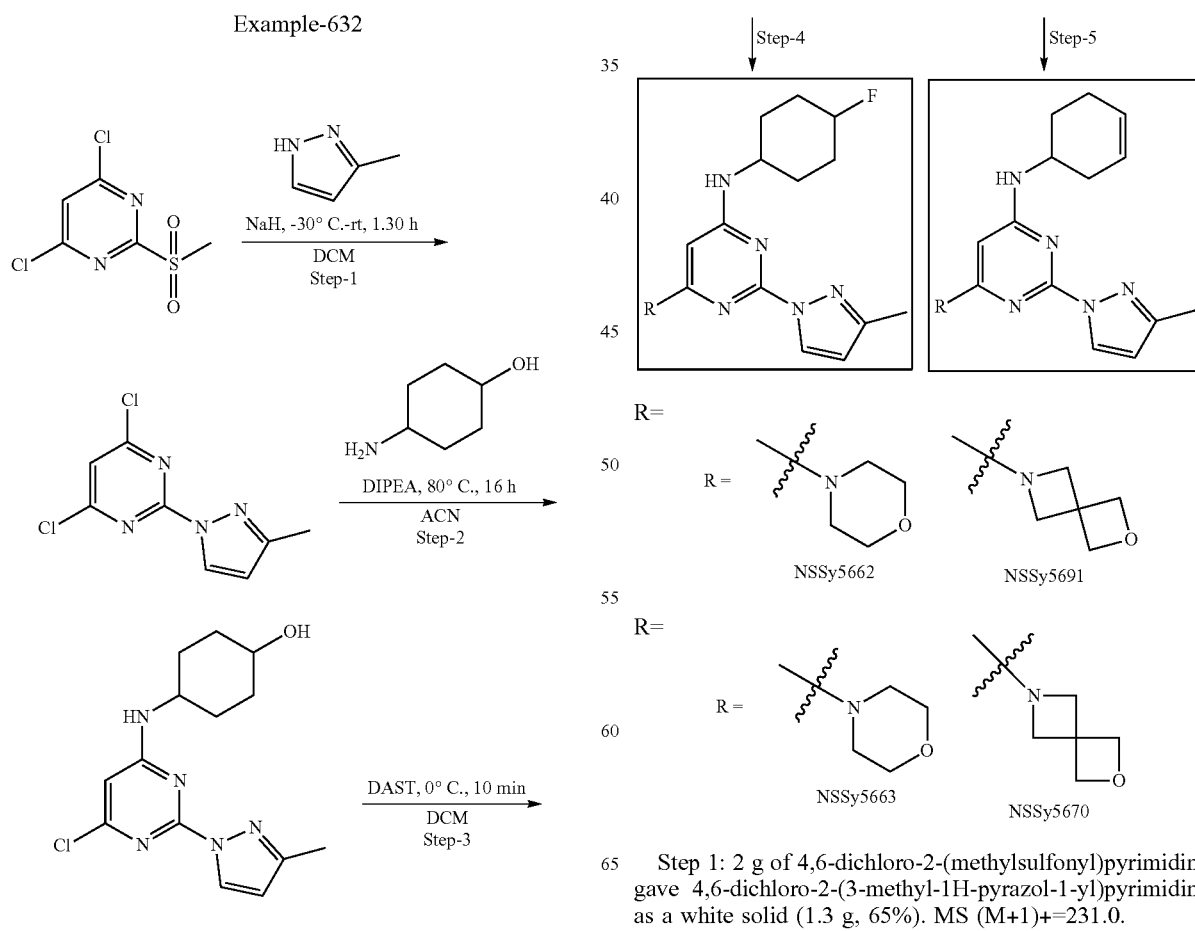

Step 1: 2 g of 4,6-dichloro-2-(methylsulfonyl)pyrimidine gave 4,6-dichloro-2-(3-methyl-1H-pyrazol-1-yl)pyrimidine as a white solid (1.3 g, 65%). MS (M+1)+=231.0.

Step 2: The procedure is similar to Step 1[B] in Example-838. 1.3 g of 4,6-dichloro-2-(3-methyl-1H-pyrazol-1-yl)pyrimidine gave 1 g of 4-((6-chloro-2-(3-methyl-1H-pyrazol-1-yl)pyrimidin-4-yl)amino)cyclohexan-1-ol as an off-white solid (1 g, 58%). MS (M+1)+=308.0.

Step 3: The procedure is similar to Step 3[NSSy6917] in Example-21. 1 g of 4-((6-chloro-2-(3-methyl-1H-pyrazol-1-yl)pyrimidin-4-yl)amino)cyclohexan-1-ol gave 6-chloro-N-(4-fluorocyclohexyl)-2-(3-methyl-1H-pyrazol-1-yl)pyrimidin-4-amine as an off-white solid (0.06 g, 6%). MS (M+1)+= 310.0 and 6-chloro-N-(cyclohex-3-en-1-yl)-2-(3-methyl-1H-pyrazol-1-yl)pyrimidin-4-amine as an off-white solid (0.6 g, 60%). MS (M+1)+=290.0.

Step 5[NSSy5663]: The procedure is similar to Step 1[B] in Example-838. 1H-NMR (400 MHz, DMSO-d6): δ 8.38 (d, J=2.40 Hz, 1H), 6.98 (d, J=8.00 Hz, 1H), 6.25 (d, J=2.40 Hz, 1H), 5.68 (d, J=14.40 Hz, 2H), 5.54 (s, 1H), 3.96 (m, 1H), 3.69-3.67 (m, 4H), 3.66 (m, 4H), 2.37-2.33 (m, 1H), 2.24 (s, 3H), 2.14-1.97 (m, 2H), 1.90-1.87 (m, 2H), 1.52-1.47 (m, 1H).

Step 5[NSSy5670]: The procedure is similar to Step 1[B] in Example-838. 1H-NMR (400 MHz, DMSO-d6): δ 8.32 (d, J=2.40 Hz, 1H), 6.96 (d, J=8.00 Hz, 1H), 6.24 (d, J=2.40 Hz, 1H), 5.69-5.61 (m, 2H), 5.16 (s, 1H), 4.71 (m, 4H), 4.08-4.07 (m, 4H), 3.90 (m, 1H), 2.35-2.33 (m, 1H), 2.32 (s, 3H), 2.23-2.13 (m, 2H), 2.07-1.96 (m, 2H), 1.50 (m, 1H).

TABLE 21

| | | Step 4: | | |
|---|---|---|---|---|
| Compound No | R | Condition | Yield (%) | MS (M+1)+ |
| NSSy5662 | 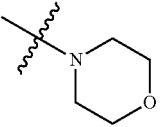 [SMILES: *N1CCOCC1] | ACN, 80 °C., 16h | 50 | 361.0 |
| NSSy5691 | 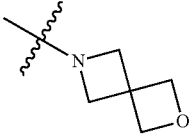 [SMILES: *N1CC2(COC2)C1] | Cs2CO3, ACN, 80 °C., 16h, sealed tube | 40 | 373.0 |

Step 4[NSSy5662]: The procedure is similar to Step 1[B] in Example-838. 1H-NMR (400 MHz, DMSO-d6): δ 8.40 (d, J=2.00 Hz, 1H), 6.98 (d, J=8.00 Hz, 1H), 6.25 (d, J=2.40 Hz, 1H), 5.52 (s, 1H), 4.67-4.53 (m, 1H), 3.69-3.67 (m, 4H), 3.50 (m, 4H), 2.17 (s, 3H), 2.03-1.92 (m, 4H), 1.76-1.71 (m, 2H), 1.63-1.57 (m, 3H).

Step 4[NSSy5691]: The procedure is similar to Step 1[B] in Example-838. 1H-NMR (400 MHz, DMSO-d6): δ 8.35 (s, 1H), 7.03-6.96 (m, 1H), 6.25 (d, J=2.00 Hz, 1H), 5.16 (s, 1H), 4.85-4.72 (m, 5H), 4.13-4.04 (m, 4H), 3.92-3.81 (m, 1H), 2.24 (s, 3H), 1.99-1.92 (m, 6H), 1.67-1.55 (m, 2H).

Example-633

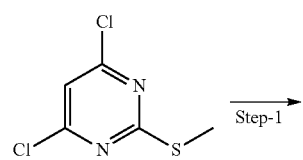

TABLE 22

| | | Step 5: | | |
|---|---|---|---|---|
| Compound No | R | Condition | Yield (%) | MS (M+1)+ |
| NSSy5663 | 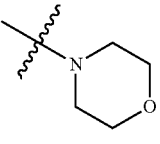 [SMILES: *N1CCOCC1] | ACN, 80 °C., 16h | 38 | 341.0 |
| NSSy5670 | 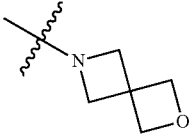 | Cs2CO3, ACN, 80 °C., 16h, sealed tube | 47 | 353.0 |

791 -continued

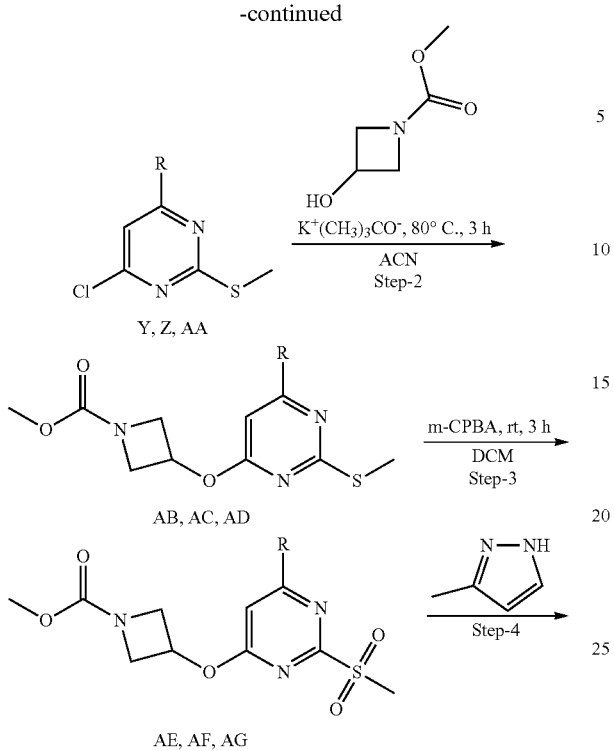

Y, Z, AA

AB, AC, AD

AE, AF, AG

792 -continued

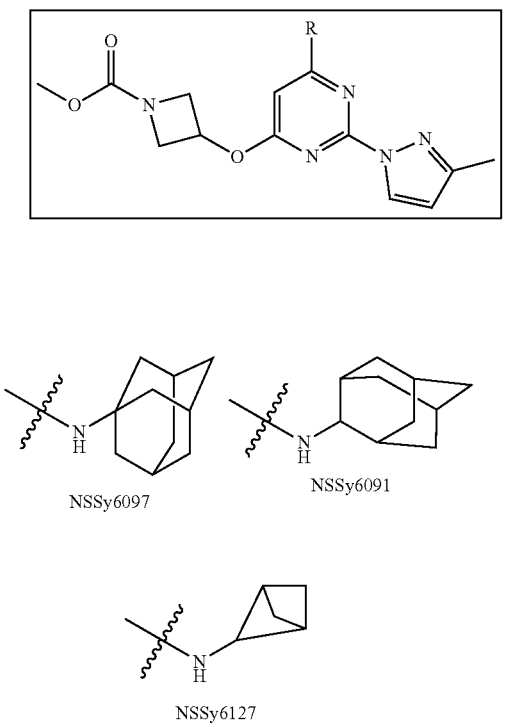

R =

NSSy6097

NSSy6091

NSSy6127

TABLE 23

Step 1: The procedure is similar to Step 1[B] in Example-838.

| Compound No | R | Condition | Yield (%) | MS (M+1)+ |
|---|---|---|---|---|
| Y | (1-adamantyl-NH) | Cs₂CO₃, ACN, 70 °C., 16h | 90 | 310.0 |
| Z | (2-adamantyl-NH) | Cs₂CO₃, ACN, 75 °C., 16h | 92 | 310.0 |
| AA | (bicyclopentyl-NH) | Cs₂CO₃, ACN, 75 °C., 16h | 90 | 242.0 |

TABLE 24

Step 2: The procedure is similar to Step 1[B] in Example-838.

| Compound No | R | Condition | Yield (%) | MS (M+1)+ |
|---|---|---|---|---|
| AB | (1-adamantyl-NH) | K+(CH₃)₃CO−, 80 °C., ACN, 3h | 68 | 405.0 |

TABLE 24-continued

Step 2: The procedure is similar to Step 1[B] in Example-838.

| Compound No | R | Condition | Yield (%) | MS (M+1)+ |
|---|---|---|---|---|
| AC | adamantyl-NH- | K+(CH3)3CO−, 80 °C., ACN, 3h | 61 | 405.0 |
| AD | bicycloalkyl-NH- | K+(CH3)3CO−, 80 °C., ACN, 3h | 32 | 337.0 |

TABLE 25

Step 3: The procedure is similar to Step 3[NSSy7062] in Example-623.

| Compound No | R | Condition | Yield (%) | MS (M+1)+ |
|---|---|---|---|---|
| AE | adamantyl-NH- | m-CPBA, DCM, 0 °C.-rt, 3h | 80 | 437.0 |
| AF | adamantyl-NH- | m-CPBA, DCM, 0 °C.-rt, 3h | 75 | 437.0 |
| AG | bicycloalkyl-NH- | m-CPBA, DCM, 0 °C.-rt, 3h | 82 | 369.0 |

TABLE 26

Step 4: The procedure is similar to Step 1[B] in Example-838.

| Compound No | R | Condition | Yield (%) | MS (M+1)+ |
|---|---|---|---|---|
| NSSy6097 | adamantyl-NH- | Cs2CO3, ACN, 70 °C., 16h | 11 | 439.0 |
| NSSy6091 | adamantyl-NH- | Cs2CO3, ACN, 75 °C., 16h | 10 | 439.0 |
| NSSy6127 | bicycloalkyl-NH- | Cs2CO3, DMSO, 75 °C., 16h | 16 | 371.0 |

Step 4[NSSy6097]: 1H-NMR (400 MHz, DMSO-d6): δ 8.32 (d, J=2.40 Hz, 1H), 7.14 (s, 1H), 6.34 (d, J=2.40 Hz, 1H), 5.70 (s, 1H), 5.32 (m, 1H), 4.33 (m, 2H), 3.91-3.90 (m, 2H), 3.58 (s, 3H), 2.26 (s, 3H), 2.09 (m, 9H), 1.69 (m, 6H).

Step 4[NSSy6091]: 1H-NMR (400 MHz, DMSO-d6): δ 8.38 (s, 1H), 7.42 (d, J=7.60 Hz, 1H), 6.32 (d, J=2.00 Hz, 1H), 5.85-5.79 (m, 1H), 5.35 (s, 1H), 4.10-4.08 (m, 2H), 3.97-3.93 (m, 2H), 3.56 (s, 3H), 2.13 (s, 3H), 2.05-2.03 (m, 2H), 2.00-1.95 (m, 2H), 1.85-1.82 (m, 6H), 1.72-1.51 (m, 2H), 1.54-1.51 (m, 2H).

Step 4[NSSy6127]: 1H-NMR (400 MHz, DMSO-d6): δ 8.38 (d, J=2.52 Hz, 1H), 8.37 (m, 1H), 6.33 (d, J=2.52 Hz, 1H), 5.69 (s, 1H), 5.37 (s, 1H), 4.35 (m, 2H), 3.93-3.92 (m, 2H), 3.58 (s, 3H), 2.34 (s, 3H), 2.33-2.08 (m, 6H).

Example-634

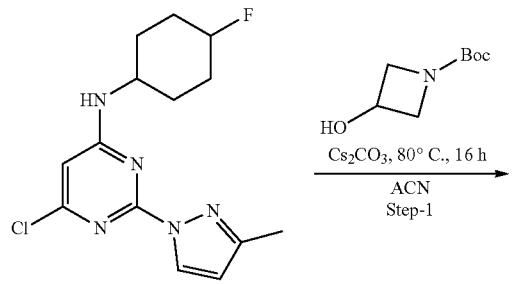

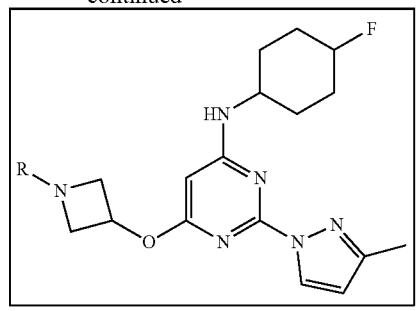

R=

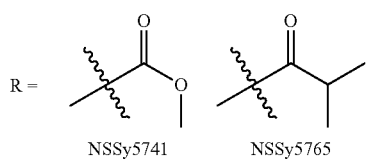

Step 1: The procedure is similar to Step 1[B] in Example-838. 0.6 g of 6-chloro-N-(4-fluorocyclohexyl)-2-(3-methyl-1H-pyrazol-1-yl)pyrimidin-4-amine gave tert-butyl 3-((6-((4-fluorocyclohexyl)amino)-2-(3-methyl-1H-pyrazol-1-yl)pyrimidin-4-yl)oxy) azetidine-1-carboxylate as an off-white solid (0.3 g, 35%). MS (M+1)$^+$=447.2.

TABLE 27

| Step 2: The procedure is similar to Step 2[NSSy6924] in Example-857. | | | | |
|---|---|---|---|---|
| Compound No | R | Condition | Yield (%) | MS (M+1)$^+$ |
| NSSy5741 | ![structure] | (a) TFA, 0 °C., rt, 16h, (b) TEA, 0 °C.-rt | 26 | 405.1 |
| NSSy5765 | ![structure] | (a) TFA, 0 °C., rt, 16h, (b) TEA, 0 °C.-rt | 17 | 417.0 |

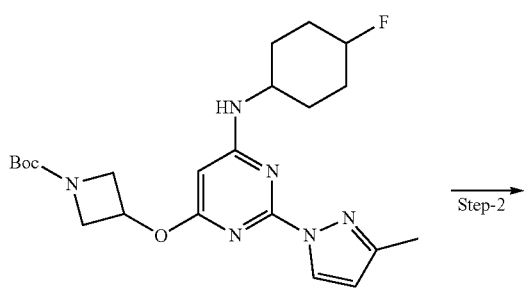

Step 2[NSSy5741]: 1H-NMR (400 MHz, DMSO-d6): δ 8.40 (s, 1H), 7.63-7.50 (m, 1H), 6.31 (s, 1H), 5.76-5.72 (m, 1H), 5.35 (s, 2H), 4.34 (s, 2H), 3.91 (s, 2H), 3.91 (s, 1H), 2.25 (s, 3H), 2.02-1.92 (m, 3H), 1.57-1.50 (m, 2H).

Step 2[NSSy5765]: 1H-NMR (400 MHz, DMSO-d6): δ 8.41 (d, J=2.00 Hz, 1H), 7.61 (s, 1H), 6.31 (d, J=2.40 Hz, 1H), 5.69 (s, 1H), 5.36 (s, 1H), 4.92 (m, 1H), 4.65 (m, 1H), 4.26 (m, 1H), 3.80 (m, 1H), 2.02 (s, 3H), 1.91-2.02 (m, 3H), 1.51-1.75 (m, 5H), 0.97 (t, J=6.80 Hz, 6H).

Example-635

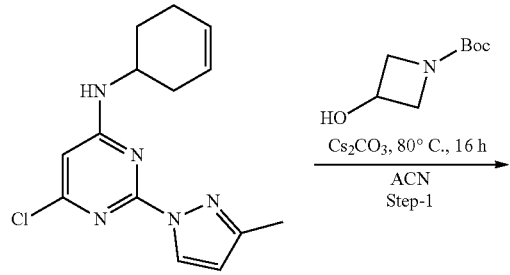

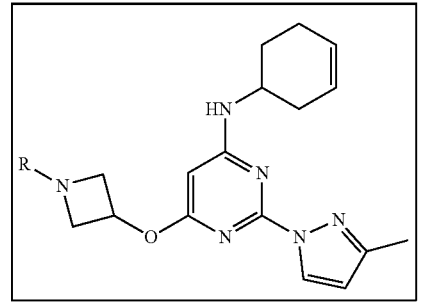

R=

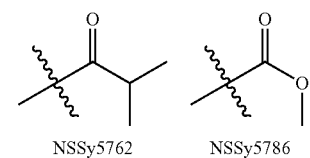

Step 1: The procedure is similar to Step 1[B] in Example-838. 0.3 g of 6-chloro-N-(cyclohex-3-en-1-yl)-2-(3-methyl-1H-pyrazol-1-yl)pyrimidin-4-amine gave tert-butyl 3-((6-(cyclohex-3-en-1-ylamino)-2-(3-methyl-1H-pyrazol-1-yl)pyrimidin-4-yl)oxy)azetidine-1-carboxylate as an off-white solid (0.4 g, 72%). MS (M+1)$^+$=427.0.

TABLE 28

Step 2: The procedure is similar to Step 2[NSSy6924] in Example-857.

| Compound No | R | Condition | Yield (%) | MS (M+1)$^+$ |
|---|---|---|---|---|
| NSSy5786 | (isopropyl ketone) | a. TFA, 0 °C., rt, 16h  b. TEA, 0 °C.-rt | 19 | 385.0 |
| NSSy5762 | (methyl ester) | a. TFA, 0 °C., rt, 16h  b. TEA, 0 °C.-rt | 19 | 397.0 |

Step 2[NSSy5762]: $^1$H-NMR (400 MHz, DMSO-d$_6$): δ 8.42 (d, J=2.40 Hz, 1H), 7.52 (s, 1H), 6.33 (d, J=2.80 Hz, 1H), 5.69-5.67 (m, 3H), 5.39-5.37 (m, 1H), 4.61 (m, 1H), 4.26 (m, 2H), 3.83 (d, J=10.80 Hz, 1H), 2.35 (m, 1H), 2.27 (s, 3H), 2.16 (m, 2H), 1.92-1.89 (m, 2H), 1.51 (m, 1H), 0.99 (d, J=6.80 Hz, 6H).

Step 2[NSSy5786]: $^1$H-NMR (400 MHz, DMSO-d$_6$): δ 8.39 (d, J=2.52 Hz, 1H), 7.50 (m, 1H), 6.32 (d, J=2.52 Hz, 1H), 5.68-5.66 (m, 3H), 5.36 (m, 1H), 4.35-4.20 (m, 3H), 3.92-3.85 (m, 2H), 3.57 (s, 3H), 2.50 (m, 1H), 2.21 (s, 3H), 2.10 (m, 2H), 1.95 (m, 2H), 1.50 (m, 1H).

Example-636

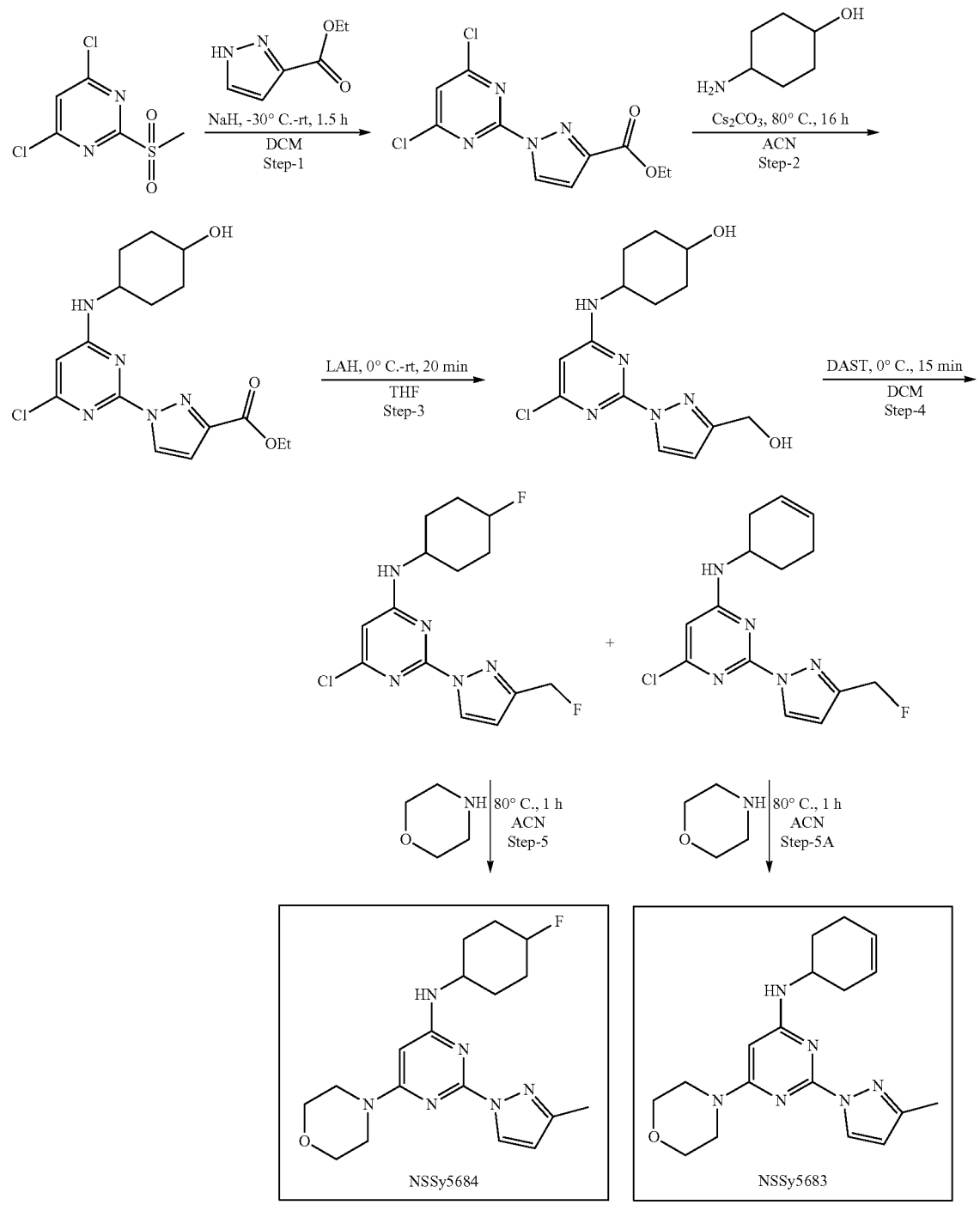

Step 1: 14 g of 4,6-dichloro-2-(methylsulfonyl)pyrimidine gave ethyl 1-(4,6-dichloropyrimidin-2-yl)-1H-pyrazole-3-carboxylate as an off-white solid (16.5 g, 90%). MS (M+1)+=288.0.

Step 2: The procedure is similar to Step 1[B] in Example-838. 1.5 g of ethyl 1-(4,6-dichloropyrimidin-2-yl)-1H-pyrazole-3-carboxylate gave ethyl 1-(4-chloro-6-((4-hydroxycyclohexyl)amino)pyrimidin-2-yl)-1H-pyrazole-3-carboxylate as an off-white solid (1.9 g, 90%). MS (M+1)+=366.0.

Step 3: The procedure is similar to Step 4[NSSy6711] in Example-854. 6.7 g of ethyl 1-(4-chloro-6-((4-hydroxycyclohexyl)amino)pyrimidin-2-yl)-1H-pyrazole-3-carboxylate gave 4-((6-chloro-2-(3-(hydroxymethyl)-1H-pyrazol-1-yl)pyrimidin-4-yl)amino)cyclohexan-1-ol as an off-white solid (4 g, 70%). MS (M+1)+=324.2.

Step 4: The procedure is similar to Step 3[NSSy6917] in Example-21. 2 g of 4-((6-chloro-2-(3-(hydroxymethyl)-1H-pyrazol-1-yl)pyrimidin-4-yl)amino)cyclo hexan-1-ol gave 6-chloro-N-(4-fluorocyclohexyl)-2-(3-(fluoromethyl)-1H-pyrazol-1-yl)pyrimidin-4-amine as white gum (0.15 g, 8%). MS (M+1)+=328.0; and 6-chloro-N-(cyclohex-3-en-1-yl)-2-(3-(fluoromethyl)-1H-pyrazol-1-yl)pyrimidin-4-amine as white gum (0.55 g, 30%). MS (M+1)+=308.0.

Step 5[NSSy5684]: The procedure is similar to Step 1[B] in Example-838. 0.06 g of 6-chloro-N-(4-fluorocyclohexyl)-2-(3-(fluoromethyl)-1H-pyrazol-1-yl)pyrimidin-4-amine gave N-(4-fluorocyclohexyl)-2-(3-methyl-1H-pyrazol-1-yl)-6-morpholinopyrimidin-4-amine as an off-white solid (0.035 g, 50%). MS (M+1)+=361.0; 1H-NMR (400 MHz, DMSO-d6): δ 8.40 (d, J=2.00 Hz, 1H), 6.98 (d, J=8.00 Hz, 1H), 6.25 (d, J=2.40 Hz, 1H), 5.52 (s, 1H), 4.67-4.53 (m, 1H), 3.69-3.67 (m, 4H), 3.50 (m, 4H), 2.17 (s, 3H), 2.03-1.92 (m, 4H), 1.76-1.71 (m, 2H), 1.63-1.57 (m, 3H).

Step 5A [NSSy5683]: The procedure is similar to Step 1[B] in Example-838. 0.2 g of 6-chloro-N-(cyclohex-3-en-1-yl)-2-(3-(fluoromethyl)-1H-pyrazol-1-yl)pyrimidin-4-amine gave N-(cyclohex-3-en-1-yl)-2-(3-methyl-1H-pyrazol-1-yl)-6-morpholinopyrimidin-4-amine as an off-white solid (0.09 g, 38%). MS (M+1)+=341.0; 1H-NMR (400 MHz, DMSO-d6): δ 8.38 (d, J=2.40 Hz, 1H), 6.98 (d, J=8.00 Hz, 1H), 6.25 (d, J=2.40 Hz, 1H), 5.68 (d, J=14.40 Hz, 2H), 5.54 (s, 1H), 3.96 (m, 1H), 3.69-3.67 (m, 4H), 3.66 (m, 4H), 2.37-2.33 (m, 1H), 2.24 (s, 3H), 2.14-1.97 (m, 2H), 1.90-1.87 (m, 2H), 1.52-1.47 (m, 1H).

Example-637

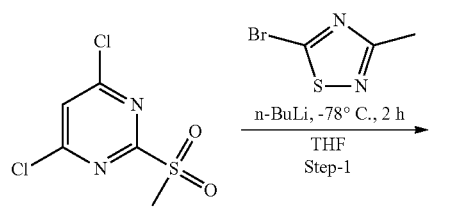

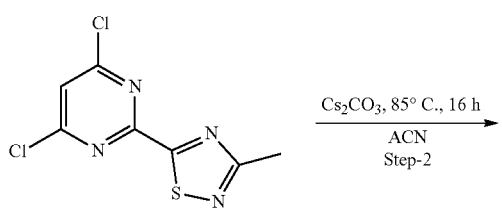

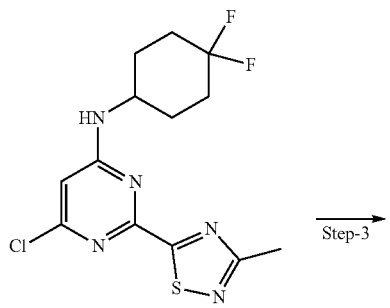

-continued

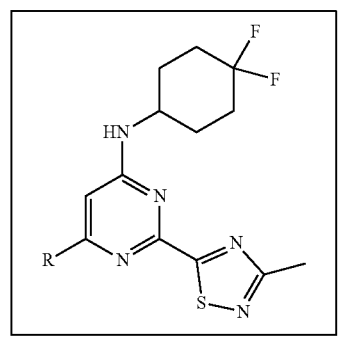

R=

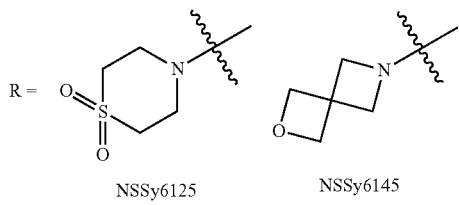

NSSy6125    NSSy6145

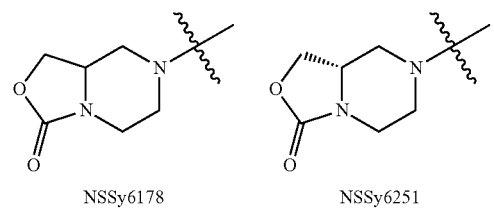

NSSy6178    NSSy6251

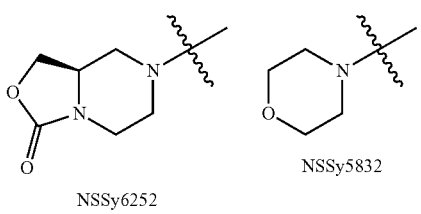

NSSy6252    NSSy5832

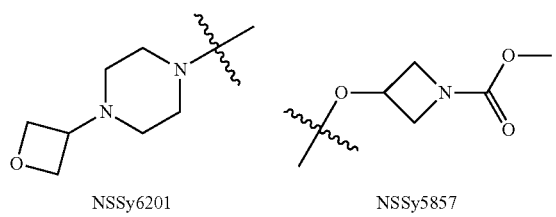

NSSy6201    NSSy5857

Step 1: The procedure is similar to Step 4[NSSy6067] in Example-628. 2 g of 4,6-dichloro-2-(methylsulfonyl)pyrimidine gave 5-(4,6-dichloropyrimidin-2-yl)-3-methyl-1,2,4-thiadiazole as yellow solid (1.32 g, 62%). MS (M+1)+=248.9.

Step 2: The procedure is similar to Step 1[B] in Example-838. 1 g of 5-(4,6-dichloropyrimidin-2-yl)-3-methyl-1,2,4-thiadiazole gave 6-chloro-N-(4,4-difluorocyclohexyl)-2-(3-methyl-1,2,4-thiadiazol-5-yl)pyrimidin-4-amine as a yellow solid (1.2 g, 85%). MS (M+1)+=346.1.

TABLE 29

Step 3:

| Compound No | R | Condition | Yield (%) | MS (M+1)+ |
|---|---|---|---|---|
| NSSy6125 | thiomorpholine 1,1-dioxide | Pd₂(dba)₃, Xanthphos, Cs₂CO₃, Dioxane, 90 °C., 16h | 13 | 445.2 |
| NSSy6145 | 2-oxa-6-azaspiro[3.3]heptane | Cs₂CO₃, ACN, 80 °C., 5h | 57 | 409.0 |
| NSSy6178 | hexahydrooxazolo[3,4-a]pyrazin-3-one | Pd₂(dba)₃, X-Phos, Cs₂CO₃, Dioxane, 100 °C., 16h | 25 | 371.0 |
| NSSy6251 | hexahydrooxazolo[3,4-a]pyrazin-3-one | Pd₂(dba)₃, X-Phos, Cs₂CO₃, Dioxane, 100 °C. 16h Chiral of 112 | — | 371.0 |
| NSSy6252 | hexahydrooxazolo[3,4-a]pyrazin-3-one | Pd₂(dba)₃, X-Phos, Cs₂CO₃, Dioxane, 100 °C., 16h Chiral of 112 | — | 371.0 |
| NSSy5832 | morpholine | Cs₂CO₃, ACN, 80 °C., 5h | 57 | 397.2 |
| NSSy6201 | 1-(oxetan-3-yl)piperazine | Cs₂CO₃, TEA, ACN, 80 °C., 16h | 15 | 452.2 |
| NSSy5857 | tert-butyl 3-oxyazetidine-1-carboxylate | K+(CH₃)₃CO−, 80 °C., ACN, 3h | 80 | 441.3 |

Step 3[NSSy6125]: The procedure is similar to Step 1[NSSy6629] in Example-839. 1H-NMR (400 MHz, DMSO-d6): δ 7.32 (d, J=7.76 Hz, 1H), 5.89 (s, 1H), 4.07 (s, 4H), 3.92 (s, 1H), 3.19 (s, 4H), 2.65 (s, 3H), 2.13-1.92 (m, 6H), 1.62-1.54 (m, 2H).

Step 3[NSSy6145]: The procedure is similar to Step 1[B] in Example-838. 1H-NMR (400 MHz, DMSO-d6): δ 7.19 (d, J=7.60 Hz, 1H), 5.36 (s, 1H), 4.73 (s, 4H), 4.16 (s, 4H), 3.86 (s, 1H), 2.65 (s, 3H), 2.06-1.91 (m, 6H), 1.59-1.52 (m, 2H).

Step 3[NSSy6178]: The procedure is similar to Step 1[NSSy6629] in Example-839. 1H-NMR (400 MHz, DMSO-d6): δ 7.27 (d, J=7.92 Hz, 1H), 5.80 (s, 1H), 4.55 (s, 1H), 4.45 (t, J=8.52 Hz, 1H), 4.35 (s, 1H), 4.08-4.05 (m, 1H), 3.88-3.84 (m, 2H), 3.68 (d, J=10.80 Hz, 1H), 3.09-3.02 (m, 1H), 2.94-2.81 (m, 2H), 2.65 (s, 3H), 2.07-1.92 (m, 6H), 1.62-1.56 (m, 2H).

Step 3[NSSy6251]: The procedure is similar to Step 1[NSSy6629] in Example-839. 1H-NMR (400 MHz, DMSO-d6): δ 7.26 (d, J=8.00 Hz, 1H), 5.80 (s, 1H), 4.54 (s, 1H), 4.35-4.25 (m, 1H), 4.44 (t, J=8.40 Hz, 1H), 4.08-4.04 (m, 1H), 3.91-3.85 (m, 2H), 3.70-3.69 (m, 1H), 3.09-3.02 (m, 1H), 2.93-2.81 (m, 2H), 2.65 (s, 3H), 2.15-1.85 (m, 6H), 1.62-1.57 (m, 2H).

Step 3[NSSy6252]: The procedure is similar to Step 1[NSSy6629] in Example-839. 1H-NMR (400 MHz, DMSO-d6): δ 7.26 (d, J=7.60 Hz, 1H), 5.80 (s, 1H), 4.55 (s, 1H), 4.44 (t, J=8.40 Hz, 1H), 4.33 (s, 1H), 4.08-4.04 (m, 1H), 3.90-3.86 (m, 2H), 3.57 (d, J=28.00 Hz, 1H), 3.09-3.02 (m, 1H), 2.93-2.81 (m, 2H), 2.65 (s, 3H), 2.07-1.92 (m, 6H), 1.62-1.57 (m, 2H).

Step 3[NSSy5832]: The procedure is similar to Step 1[B] in Example-838. 1H-NMR (400 MHz, DMSO-d6): δ 7.22 (d, J=8.00 Hz, 1H), 5.73 (s, 1H), 3.88 (s, 1H), 3.70-3.68 (m, 4H), 3.52 (s, 4H), 2.64 (s, 3H), 2.08-2.01 (m, 3H), 1.95-1.92 (m, 3H), 1.60-1.53 (m, 2H).

Step 3[NSSy6201]: The procedure is similar to Step 1[B] in Example-838. 1H-NMR (400 MHz, DMSO-d6): δ 7.18 (d, J=8.04 Hz, 1H), 5.74 (s, 1H), 4.59-4.56 (m, 2H), 4.50-4.47 (m, 2H), 3.90 (s, 1H), 3.57 (s, 4H), 3.46-3.43 (m, 1H), 2.65 (s, 3H), 2.35 (s, 4H), 2.06-1.93 (m, 6H), 1.58-1.55 (m, 2H).

Step 3[NSSy5857]: The procedure is similar to Step 1[B] in Example-838. 1H-NMR (400 MHz, DMSO-d6): δ 7.48 (d, J=7.52 Hz, 1H), 5.95 (s, 1H), 5.41-5.36 (m, 1H), 4.37-4.33 (m, 2H), 3.96-3.93 (m, 2H), 3.60 (s, 3H), 3.09 (s, 1H), 2.67 (s, 3H), 2.10-1.91 (m, 6H), 1.67-1.62 (m, 2H).

Example-638

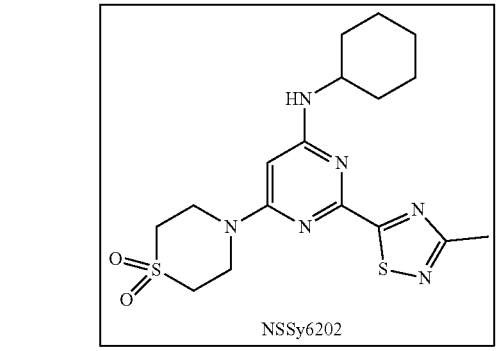

NSSy6202

Step 1: The procedure is similar to Step 1[B] in Example-838. 1 g of 5-(4,6-dichloropyrimidin-2-yl)-3-methyl-1,2,4-thiadiazole gave 6-chloro-N-cyclohexyl-2-(3-methyl-1,2,4-thiadiazol-5-yl)pyrimidin-4-amine as a white solid (1.05 g, 84%). MS (M+1)+=310.1.

Step 2[NSSy6202]: The procedure is similar to Step 1[NSSy6629] in Example-839. 0.3 g of 6-chloro-N-cyclohexyl-2-(3-methyl-1,2,4-thiadiazol-5-yl)pyrimidin-4-amine gave 4-(6-(cyclohexylamino)-2-(3-methyl-1,2,4-thiadiazol-5-yl)pyrimidin-4-yl)thiomorpholine 1,1-dioxide as an off-white solid (0.048 g, 12%). MS (M+1)+=409.6; 1H-NMR (400 MHz, DMSO-d6): δ 7.14 (d, J=8.00 Hz, 1H), 5.86 (s, 1H), 2.65 (s, 3H), 1.90-1.87 (m, 2H), 1.74-1.71 (m, 2H), 1.62-1.59 (m, 1H), 1.38-1.32 (m, 2H), 1.25-1.19 (m, 3H).

Example-639

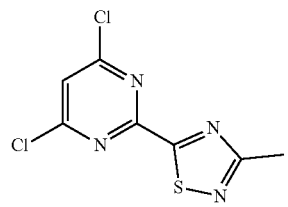

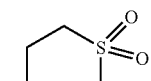

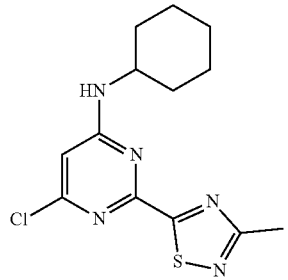

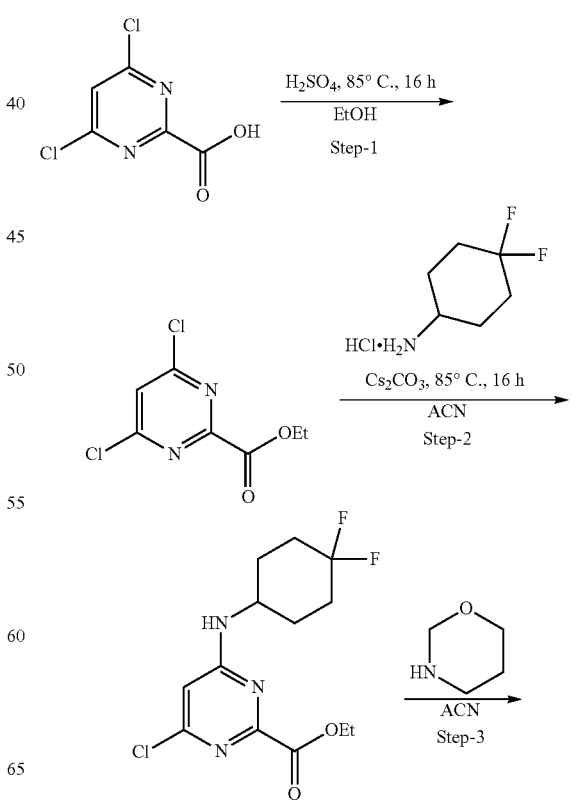

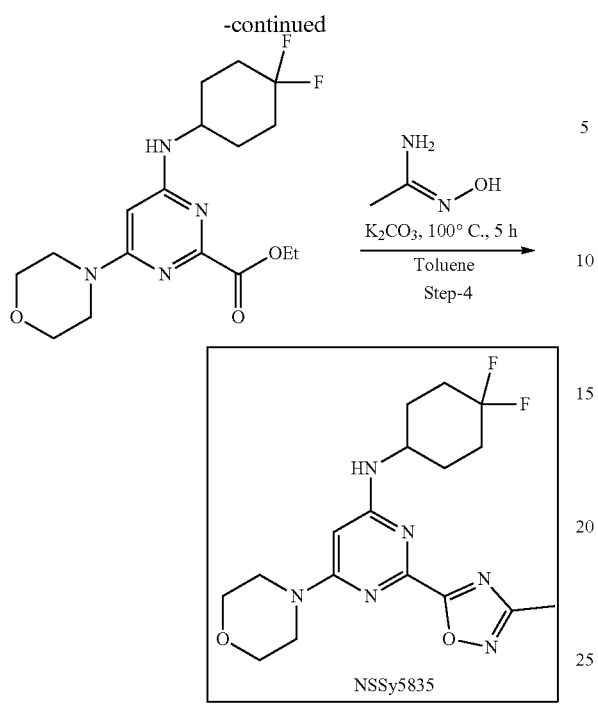

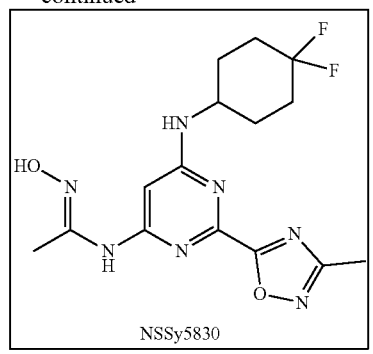

Step 1: The procedure is similar to Step 3[NSSy6711] in Example-854. 1 g of 4,6-dichloropyrimidine-2-carboxylic acid gave ethyl 4,6-dichloropyrimidine-2-carboxylate as green oil (0.9 g, 81%). MS (M+1)+=223.1.

Step 2: The procedure is similar to Step 1[B] in Example-838. 1 g of ethyl 4,6-dichloropyrimidine-2-carboxylate gave ethyl 4-chloro-6-((4,4-difluorocyclohexyl)amino)pyrimidine-2-carboxylate as colourless gum (0.6 g, 42%). MS (M+1)+=320.0.

Step 3: The procedure is similar to Step 1[B] in Example-838. 0.25 g of ethyl 4-chloro-6-((4,4-difluorocyclohexyl)amino)pyrimidine-2-carboxylate gave ethyl 4-((4,4-difluorocyclohexyl)amino)-6-morpholinopyrimidine-2-carboxylate as colourless gum (0.17 g, 60%). MS (M+1)+= 371.1.

Step 4[NSSy5835]: The procedure is similar to Step 1[B] in Example-838. 0.17 g of ethyl 4-((4,4-difluorocyclohexyl)amino)-6-morpholinopyrimidine-2-carboxylate gave N-(4,4-difluorocyclohexyl)-2-(3-methyl-1,2,4-oxadiazol-5-yl)-6-morpholinopyrimidin-4-amine as an off-white solid (0.035 g, 20%). MS (M+1)+=381.2; 1H-NMR (400 MHz, DMSO-d6): δ 7.27-7.25 (m, 1H), 5.77 (s, 1H), 3.89 (s, 1H), 3.69-3.67 (m, 2H), 3.51-3.50 (m, 4H), 2.42-2.41 (m, 3H), 2.05-1.90 (m, 6H), 1.59-1.51 (m, 2H).

Example-640

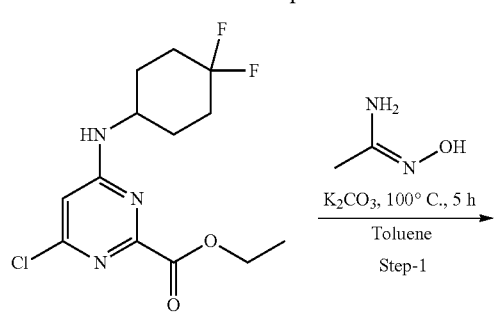

Step 1[NSSy5830]: The procedure is similar to Step 1[B] in Example-838. 0.15 g of ethyl 4-chloro-6-((4,4-difluorocyclohexyl)amino)pyrimidine-2-carboxylate gave (E)-N-(6-((4,4-difluorocyclohexyl)amino)-2-(3-methyl-1,2,4-oxadiazol-5-yl)pyrimidin-4-yl)-N'-hydroxyacetimidamide as a white solid (0.06 g, 35%). MS (M+1)+=368.0; 1H-NMR (400 MHz, DMSO-d6): δ 7.67 (s, 1H), 6.50-6.42 (m, 3H), 4.11 (s, 1H), 2.42 (s, 3H), 2.04-1.91 (m, 6H), 1.80 (s, 3H), 1.58-1.55 (m, 2H).

Example-641

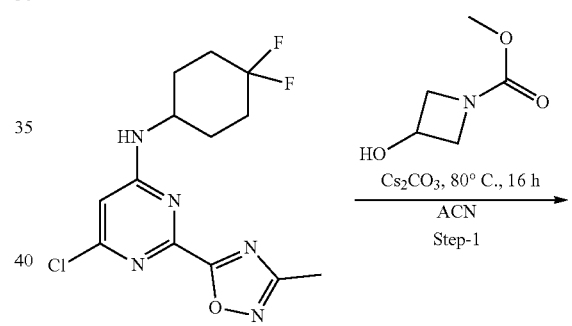

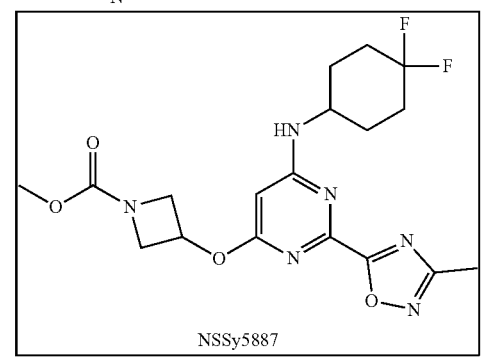

Step 1[NSSy5887]: The procedure is similar to Step 1[B] in Example-838. 0.10 g of 6-chloro-N-(4,4-difluorocyclohexyl)-2-(3-methyl-1,2,4-oxadiazol-5-yl)pyrimidin-4-amine gave methyl 3-((6-((4,4-difluorocyclohexyl)amino)-2-(3-methyl-1,2,4-oxadiazol-5-yl)pyrimidin-4-yl)oxy)azetidine-1-carboxylate as an off-white solid (0.06 g, 50%). MS (M+1)+=425.5; 1H-NMR (400 MHz, DMSO-d6): δ 7.91 (s, 1H), 6.11 (s, 1H), 5.36 (s, 2H), 4.32 (s, 1H), 4.11-4.10 (m, 2H), 3.49 (s, 3H), 2.44 (s, 3H), 2.05-1.93 (m, 6H), 1.57-1.54 (m, 2H).

Example-642

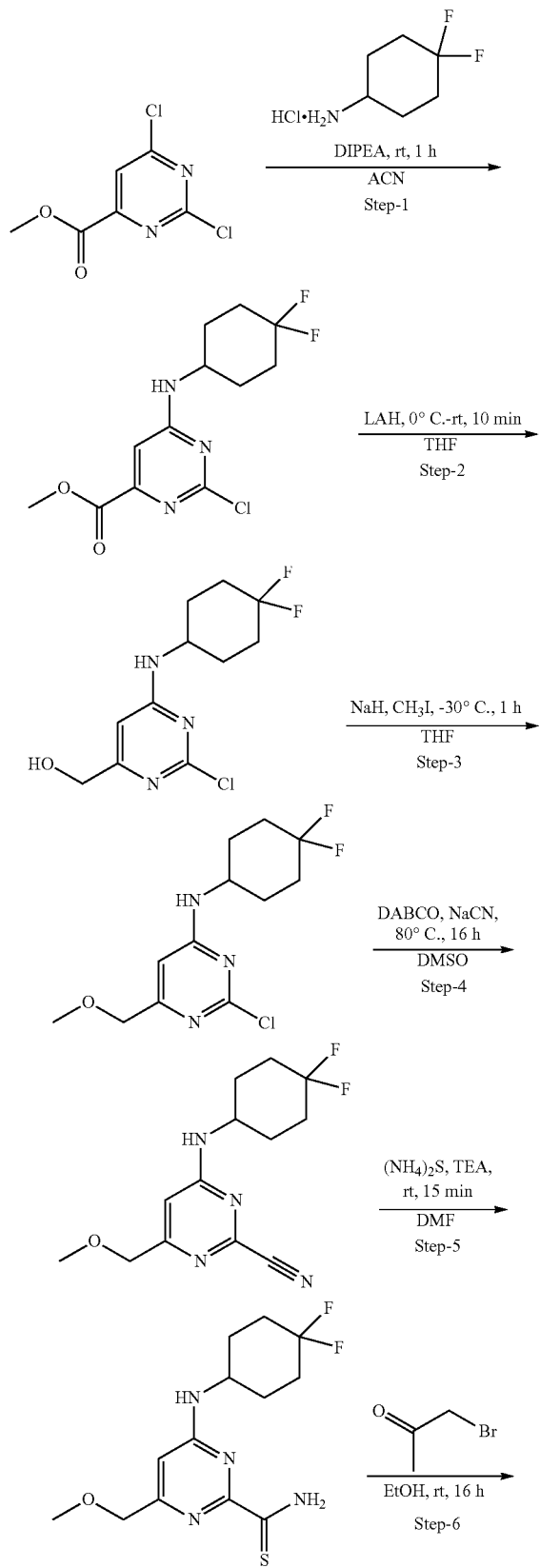

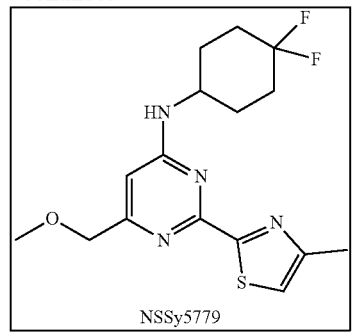

Step 1: The procedure is similar to Step 1[A] in Example-838. 5 g of methyl 2,6-dichloropyrimidine-4-carboxylate gave methyl 2-chloro-6-((4,4-difluorocyclohexyl)amino)pyrimidine-4-carboxylate as yellow solid (4.8 g, 66%). MS (M+1)+=306.1.

Step 2: The procedure is similar to Step 4[NSSy6711] in Example-854. 2 g of methyl 2-chloro-6-((4,4-difluorocyclohexyl)amino)pyrimidine-4-carboxylate gave (2-chloro-6-((4,4-difluorocyclohexyl)amino)pyrimidin-4-yl) methanol as white solid (1.6 g, 88%). MS (M+1)+=278.2.

Step 3: The procedure is similar to Step 5[NSSy6711] in Example-854. 1.1 g (2-chloro-6-((4,4-difluorocyclohexyl)amino)pyrimidin-4-yl) methanol gave 2-chloro-N-(4,4-difluorocyclohexyl)-6-(methoxymethyl)pyrimidin-4-amine as a colourless gum (0.77 g, 46%). MS (M+1)+=292.1.

Step 4: The procedure is similar to Step 1[NSSy6710] in Example-854. 0.38 g of 2-chloro-N-(4,4-difluorocyclohexyl)-6-(methoxymethyl)pyrimidin-4-amine gave 4-((4,4-difluorocyclohexyl)amino)-6-(methoxymethyl)pyrimidine-2-carbonitrile as brown gum (0.3, 75%). MS (M+1)+=283.0.

Step 5: To a cooled solution of 4-((4,4-difluorocyclohexyl)amino)-6-(methoxymethyl)pyrimidine-2-carbonitrile (0.4 g, 1.41 mmol) in N, N-dimethylformamide (5 mL) was added triethylamine (0.286 g, 2.83 mmol) and ammonium sulphide in water (20%) (0.96 g, 2.83 mmol) and stirred at room temperature. After 15 min, the reaction mixture was quenched with water and extracted with ethyl acetate (2×25 mL). The combined organic layer was dried over sodium sulfate, filtered and concentrated to afford 4-((4,4-difluorocyclohexyl)amino)-6-(methoxymethyl)pyrimidine-2-carbothioamide as a light brown solid (0.25 g, 55%). MS (M+1)+=317.0.

Step 6[NSSy5779]: To a solution of 4-((4,4-difluorocyclohexyl)amino)-6-(methoxymethyl)pyrimidine-2-carbothioamide (0.25 g, 0.79 mmol) in ethanol (10 mL) was added bromoacetone (0.129 g, 0.94 mmol). The reaction mixture was stirred at room temperature in a closed vial for 16 h. The reaction mixture was concentrated and the resulting residue was quenched with saturated bi-carbonate solution, extracted with ethyl acetate (2×50 mL). The combined organic layer was dried over sodium sulfate, filtered and concentrated to afford crude product, which was purified by column chromatography (60-120 mesh silica gel), using 80% ethyl acetate in pet ether as eluent to afford N-(4,4-difluorocyclohexyl)-6-(methoxymethyl)-2-(4-methylthiazol-2-yl)pyrimidin-4-amine as an off-white solid (0.051 g, 18%). MS (M+1)+=355.0; 1H-NMR (400 MHz, DMSO-d6): δ 7.63 (s, 1H), 7.39 (s, 1H), 6.52 (s, 1H), 4.34 (s, 2H), 4.10 (m, 1H), 4.10 (s, 3H), 2.32 (s, 3H), 1.97-1.77 (m, 6H), 1.61-1.56 (m, 2H).

Example-643

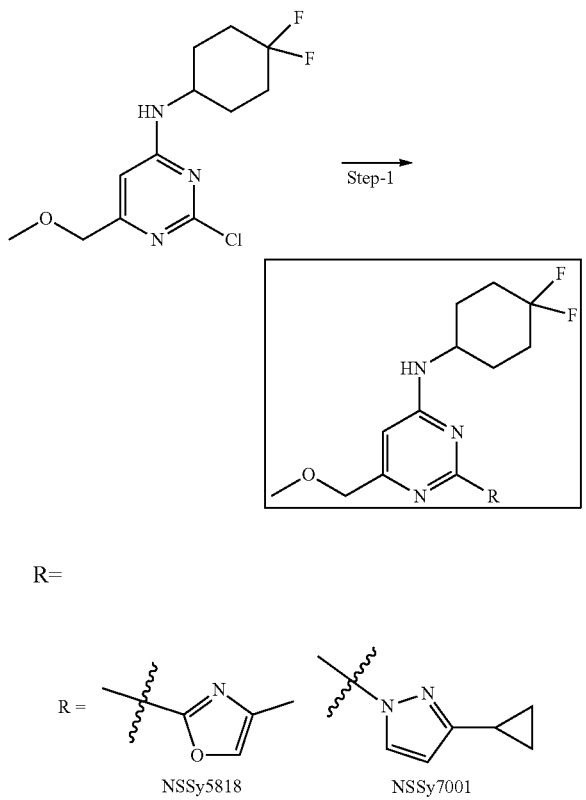

R=

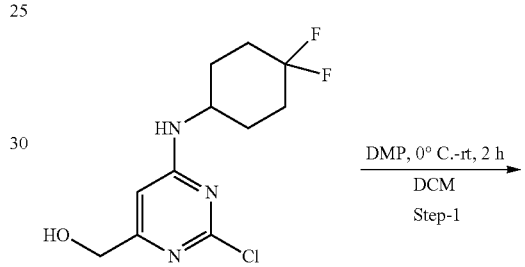

NSSy5818         NSSy7001 quenched with water and extracted with ethyl acetate (2×50 mL). The combined organic layer was dried over sodium sulfate, filtered and concentrated to afford a crude product, which was purified by column chromatography using 70% ethyl acetate in pet ether as a eluent to afford N-(4,4-difluorocyclohexyl)-6-(methoxymethyl)-2-(4-methyloxazol-2-yl)pyrimidin-4-amine as an light brownish gum (0.0017 g, 17%). MS (M+1)+=339.0; 1H-NMR (400 MHz, DMSO-d6): δ 7.94 (d, J=1.20 Hz, 1H), 7.65 (s, 1H), 6.57 (s, 1H), 4.34 (s, 2H), 4.17 (m, 1H), 3.40 (s, 3H), 2.17 (s, 3H), 2.06-1.95 (m, 6H), 1.63-1.58 (m, 2H).

Step 1[NSSy7001]: The procedure is similar to Step 1[NSSy6909] in Example-839. 0.77 g of 2-chloro-N-(4,4-difluorocyclohexyl)-6-(methoxymethyl)pyrimidin-4-amine gave 2-(3-cyclopropyl-1H-pyrazol-1-yl)-N-(4,4-difluorocyclohexyl)-6-(methoxymethyl)pyrimidin-4-amine as a white solid (0.4 g, 42%). MS (M+1)+=364.2; 1H-NMR (400 MHz, DMSO-d6): δ 8.43 (s, 1H), 7.67 (s, 1H), 6.39 (s, 1H), 6.19 (s, 1H), 4.30 (s, 2H), 4.15 (s, 1H), 3.32 (s, 3H), 2.07-1.94 (m, 7H), 1.65-1.55 (m, 2H), 0.93-0.90 (m, 2H), 0.74-0.70 (m, 2H).

Example-644

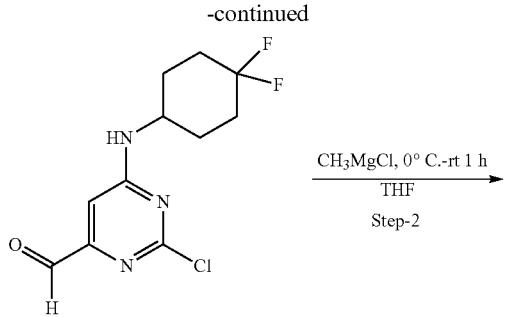

TABLE 30

| | | Step 1: | | |
|---|---|---|---|---|
| Compound No | R | Condition | Yield (%) | MS (M+1)+ |
| NSSy5818 | 4-methyloxazolyl | n-BuLi, ZnCl2 (0.5 M in THF), Pd (PPh3)4, THF, 80 °C., 2h | 7 | 339.0 |
| NSSy7001 | 3-cyclopropylpyrazolyl | Cs2CO3, ACN, 120 °C. 3h, MW | 42 | 364.2 |

Step 1[NSSy5818]: n-Butyl lithium (1.6M, 1.1 mL) was added drop wise to a stirred solution of 4-methyl oxazole (0.12 g, 1.44 mmol) in THF (2 mL) at −78° C. After 10 min, a solution of Zinc chloride (0.5 mol, 8.89 mL) was added dropwise. The reaction mixture was stirred for 15 min at −78° C. then the reaction mixture was warmed to room temperature. The reaction mixture was added to a microwave vial containing the 2-chloro-N-(4,4-difluorocyclohexyl)-6-(methoxymethyl)pyrimidin-4-amine (0.22 g, 0.75 mmol) and Tetrakis (triphenylphosphine) palladium (0) (0.08 g, 0.075 mmol) under nitrogen atmosphere. The reaction mixture was irradiated under microwave at 80° C. After 2 h, the reaction mixture was filtered and the filtrate was

813

-continued

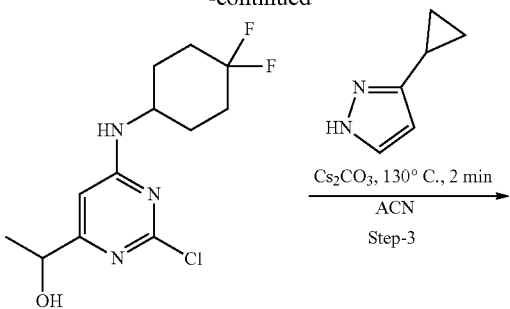

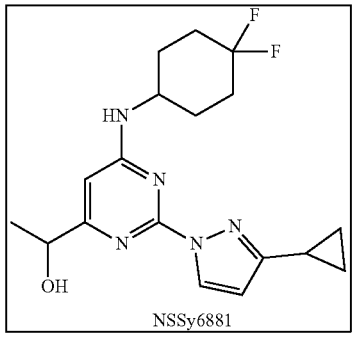

Step 1: The procedure is similar to Step 1[NSSy6930] in Example-867. 0.85 g of (2-chloro-6-((4,4-difluorocyclohexyl)amino)pyrimidin-4-yl) methanol gave 2-chloro-6-((4,4-difluorocyclohexyl)amino)pyrimidine-4-carbaldehyde as an off-white solid (0.6 g, 70%). MS (M+1)+=276.0.

Step 2: The procedure is similar to Step 4[NSSy6464] in Example-869. 0.6 g of 2-chloro-6-((4,4-difluorocyclohexyl)amino)pyrimidine-4-carbaldehyde gave 1-(2-chloro-6-((4,4-difluorocyclohexyl)amino)pyrimidin-4-yl) ethan-1-ol as a white solid (0.2 g, 31%). MS (M+1)+=292.0.

Step 3[NSSy6881]: The procedure is similar to Step 1[B] in Example-838. 0.15 g of 1-(2-chloro-6-((4,4-difluorocyclohexyl)amino)pyrimidin-4-yl) ethan-1-ol gave 1-(2-(3-cyclopropyl-1H-pyrazol-1-yl)-6-((4,4-difluorocyclohexyl)amino)pyrimidin-4-yl) ethan-1-ol as an off-white solid (0.06 g, 32%). MS (M+1)+=364.0; 1H-NMR (400 MHz, DMSO-d6): δ 8.44 (s, 1H), 7.67 (d, J=17.60 Hz, 1H), 6.51 (s, 1H), 6.18 (d, J=2.40 Hz, 1H), 5.36 (d, J=4.00 Hz, 1H), 4.49-4.47 (m, 1H), 4.16 (d, J=9.20 Hz, 1H), 2.06-1.97 (m, 6H), 1.59-1.57 (m, 2H), 1.35-1.24 (m, 3H), 0.94-0.92 (m, 2H), 0.82-0.80 (m, 2H).

Example-645

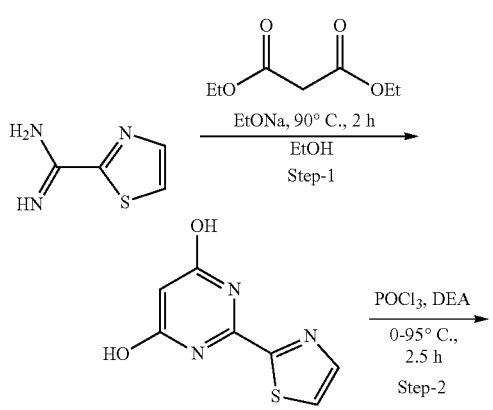

814

-continued

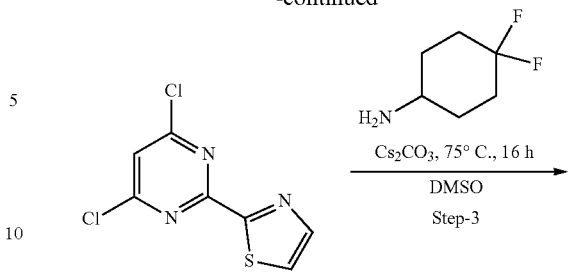

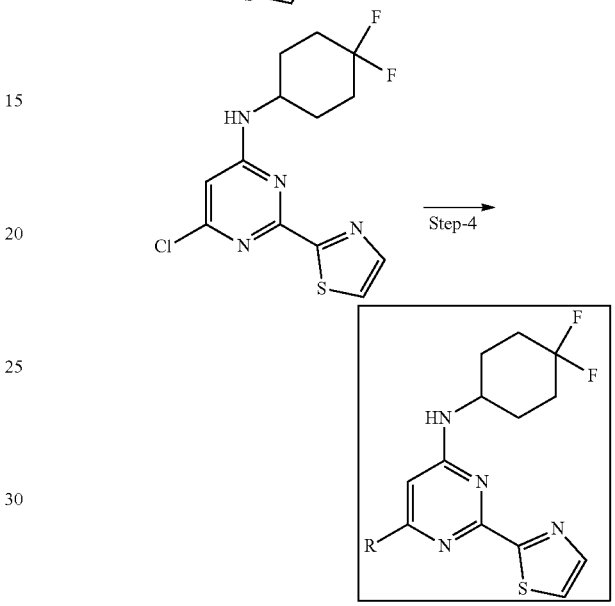

R=

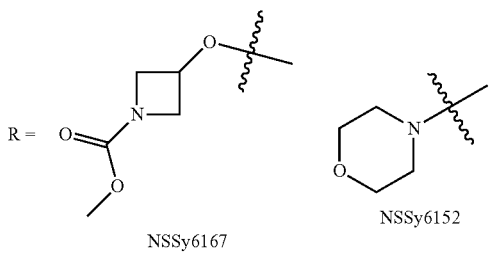

Step 1: The procedure is similar to Step 1[IN10966-057-P2] in Example-893. 4 g of thiazole-2-carboximidamide gave 2-(thiazol-2-yl)pyrimidine-4,6-diol as an off-white solid (3.6 g, 58%). MS (M+1)+=196.0.

Step 2: To a suspension of 2-(thiazol-2-yl)pyrimidine-4,6-diol (3.5 g, 17.93 mmol) in Phosphorus oxychloride (13.19 g, 86.06 mmol) was added N, N-Diethylaniline (4.6 g, 30.48 mmol) at 0° C. and the reaction mixture was heated at 95° C. for 2.5 h. The reaction mixture was concentrated under reduced pressure and the residue was diluted with ethyl acetate (50 mL), slowly added to an ice cooled saturated sodium bi-carbonate solution and stirred for 10 min, extracted with ethyl acetate, washed with water and brine solution. The organic layer was dried over sodium sulfate, filtered and concentrated under reduced pressure to afford 2-(4,6-dichloropyrimidin-2-yl) thiazole, as a brown solid (3.0 g, 72.11%). MS (M+1)+=233.0.

Step 3: The procedure is similar to Step 1[B] in Example-838. 2 g of 2-(4,6-dichloropyrimidin-2-yl) thiazole gave 6-chloro-N-(4,4-difluorocyclohexyl)-2-(thiazol-2-yl)pyrimidin-4-amine as an off-white solid (2.2 g, 79%). MS (M+1)+=331.0.

TABLE 31

Step 4:

| Compound No | R | Condition | Yield (%) | MS (M + 1)+ |
|---|---|---|---|---|
| NSSy6167 | 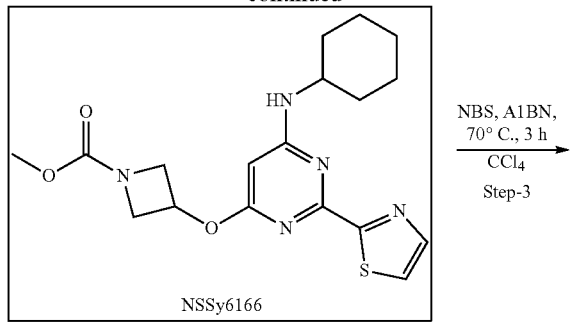 | K+(CH3)3CO-, 80° C., ACN, 5 h | 70 | 426.0 |
| NSSy6152 | 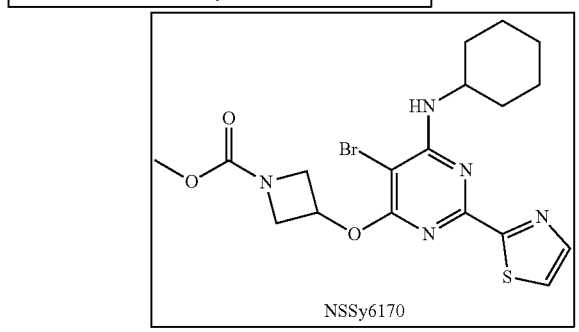 | Cs2CO3, DMSO, 90° C., 16 h | 30 | 382.0 |

Step 4[NSSy6167]: The procedure is similar to Step 1[B] in Example-838. 1H-NMR (400 MHz, DMSO-d6): δ 8.00 (d, J=2.96 Hz, 1H), 7.90 (d, J=3.12 Hz, 1H), 7.63-7.57 (m, 1H), 5.86 (s, 1H), 5.69 (d, J=6.52 Hz, 1H), 5.36 (s, 1H), 4.42-4.35 (m, 2H), 4.11-4.05 (m, 2H), 3.59 (s, 3H), 2.07-1.93 (m, 6H), 1.59-1.57 (m, 2H).

Step 4[NSSy6152]: The procedure is similar to Step 1[B] in Example-838. 1H-NMR (400 MHz, DMSO-d6): δ 7.93 (d, J=1.24 Hz, 1H), 7.81 (d, J=1.24 Hz, 1H), 7.06 (d, J=7.80 Hz, 1H), 5.68 (s, 1H), 4.01-3.92 (m, 1H), 3.70-3.69 (m, 4H), 3.41-3.34 (m, 4H), 2.09-1.93 (m, 6H), 1.59-1.56 (m, 2H).

Example-646

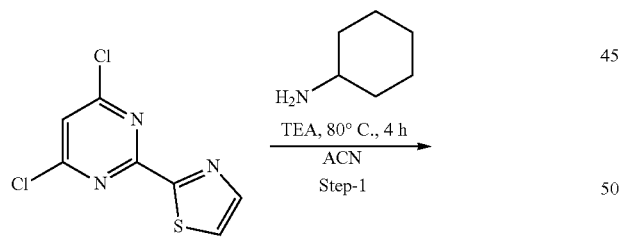

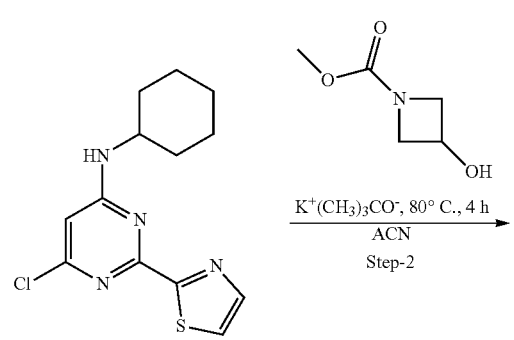

-continued

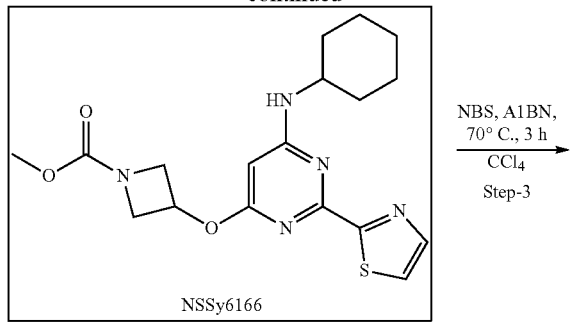

Step 1: The procedure is similar to Step 1[A] in Example-838. 1 g of 2-(4,6-dichloropyrimidin-2-yl) thiazole gave 6-chloro-N-cyclohexyl-2-(thiazol-2-yl)pyrimidin-4-amine as an off-white solid (1 g, 83%). MS (M+1)+=295.0.

Step 2[NSSy6166]: The procedure is similar to Step 1[B] in Example-838. 1 g of 6-chloro-N-cyclohexyl-2-(thiazol-2-yl)pyrimidin-4-amine gave methyl 3-((6-(cyclohexylamino)-2-(thiazol-2-yl)pyrimidin-4-yl)oxy) azetidine-1-carboxylate as an off-white gum (1 g, 76%). MS (M+1)+= 390.0; 1H-NMR (400 MHz, DMSO-d6): δ 7.99 (d, J=3.08 Hz, 1H), 7.88 (d, J=3.04 Hz, 1H), 7.42 (s, 1H), 5.81 (s, 1H), 5.35 (s, 1H), 4.35 (m, 3H), 3.94 (m, 2H), 3.54 (s, 3H), 1.74-1.71 (m, 2H), 1.59 (m, 2H), 1.37-1.34 (m, 1H), 1.31-1.20 (m, 5H).

Step 3[NSSy6170]: To a solution of methyl 3-((6-(cyclohexylamino)-2-(thiazol-2-yl)pyrimidin-4-yl)oxy)azetidine- 1-carboxylate (0.03 g, 0.07 mmol) in carbon tetrachloride (3 mL) was added 2,2-Azobisisobutyronitrile (AIBN) (0.001 g, 0.007 mmol) followed by N-Bromosuccinimide (0.013 g, 0.07 mmol) and the reaction mixture was heated at 70° C. After 2 h, the reaction mixture was diluted with water and extracted with dichloromethane. The combined organic layer was dried over sodium sulfate, filtered and concentrated to afford crude product, which was purified by column chromatography using 55% ethyl acetate in pet ether as eluent to afford methyl 3-((5-bromo-6-(cyclohexylamino)-2-(thiazol-2-yl)pyrimidin-4-yl)oxy)azetidine-1-carboxylate as an off-white solid (0.15 g, 62%). MS (M, M+2)+=468.0 and 470.0; 1H-NMR (400 MHz, DMSO-d6): δ 8.01 (d, J=3.20 Hz, 1H), 7.92 (d, J=3.20 Hz, 1H), 6.75 (d, J=8.00 Hz, 1H), 5.45-5.40 (m, 1H), 4.40-4.36 (m, 1H), 4.06-3.97 (m, 3H), 2.16 (s, 3H), 1.89-1.86 (m, 2H), 1.78-1.75 (m, 2H), 1.66-1.62 (m, 2H), 1.49-1.29 (m, 4H), 1.20-1.14 (m, 1H).

Example-647

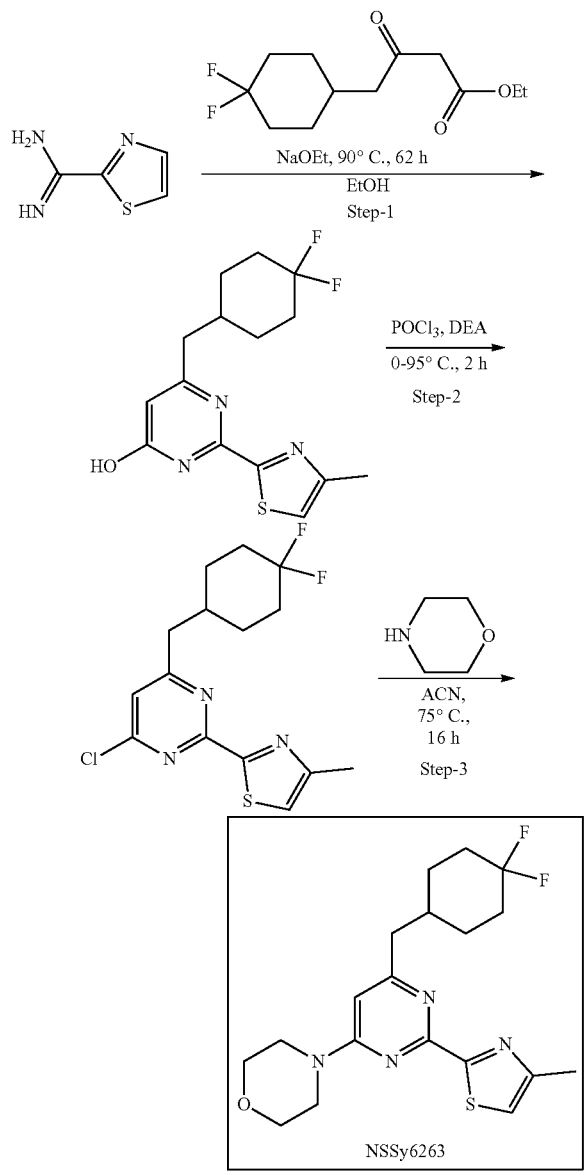

Step 1: The Procedure is similar to Step 1[A] in Example-838. 1.5 g of thiazole-2-carboximidamide gave 6-((4,4-difluorocyclohexyl)methyl)-2-(4-methylthiazol-2-yl)pyrimidin-4-ol as an off-white solid (0.15 g, 5%). MS (M+1)=326.1.

Step 2: To an ice cooled solution of 6-((4,4-difluorocyclohexyl)methyl)-2-(4-methylthiazol-2-yl)pyrimidin-4-ol (0.15 g, 0.461 mmol) in Phosphorus oxychloride (0.35 g, 2.3 mmol) was added N, N-Diethylaniline (0.11 g, 0.78 mmol) and the reaction mixture was heated at 90° C. for 2 h. The reaction mixture was diluted with ethyl acetate and poured into ice cold bicarbonate solution, it was allowed to keep 5 min, extracted with ethyl acetate, washed with water and brine solution. The organic layer was dried over sodium sulfate, filtered and concentrated under reduced pressure to afford 2-(4-chloro-6-((4,4-difluorocyclohexyl)methyl)pyrimidin-2-yl)-4-methylthiazole as a brown gum (0.15 g, 94%). MS (M+1)+=344.5.

Step 3[NSSy6263]: The Procedure is similar to Step 1[B] in Example-838. 0.1 g of 2-(4-chloro-6-((4,4-difluorocyclohexyl)methyl)pyrimidin-2-yl)-4-methylthiazole gave 4-(6-((4,4-difluorocyclohexyl)methyl)-2-(4-methylthiazol-2-yl)pyrimidin-4-yl)morpholine as an off-white solid (0.044 g, 40%). MS (M+1)+=395.2; 1H-NMR (400 MHz, DMSO-d6-80° C.): δ 7.41 (s, 1H), 6.74 (s, 1H), 3.70-3.33 (m, 8H), 2.67-2.51 (m, 2H), 2.00-1.94 (m, 4H), 1.83-1.74 (m, 4H), 1.28-1.24 (m, 3H).

Example-648

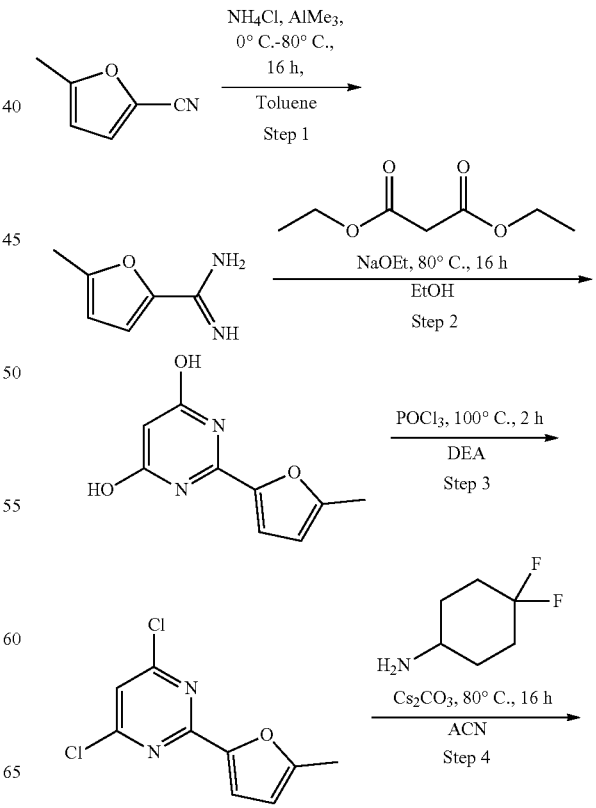

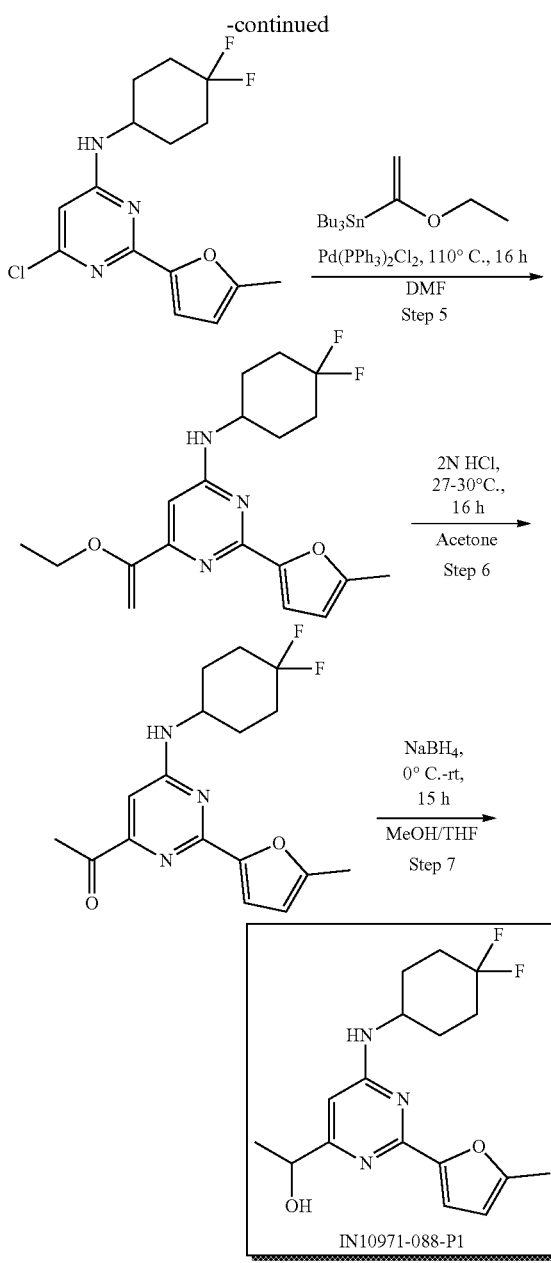

Step 5: The procedure is similar to Step 1[H] in Example-838. 0.22 g of 6-chloro-N-(4,4-difluorocyclohexyl)-2-(5-methylfuran-2-yl)pyrimidin-4-amine gave N-(4,4-difluorocyclohexyl)-6-(1-ethoxyvinyl)-2-(5-methylfuran-2-yl)pyrimidin-4-amine as an off-white solid (0.16 g, crude). MS (M+1)+=364.2.

Step 6: The procedure is similar to Step 1[NSSy6697] in Example-873. 0.16 g of N-(4,4-difluorocyclohexyl)-6-(1-ethoxyvinyl)-2-(5-methylfuran-2-yl)pyrimidin-4-amine gave 1-(6-((4,4-difluorocyclohexyl)amino)-2-(5-methylfuran-2-yl)pyrimidin-4-yl) ethan-1-one as an off-white solid (0.08 g, 54%). MS (M+1)+=336.2.

Step 7[IN10971-088-P1]: The procedure is similar to Step 2[NSSy6931] in Example-21. 0.08 g of 1-(6-((4,4-difluorocyclohexyl)amino)-2-(5-methylfuran-2-yl) pyrimidin-4-yl) ethan-1-one gave 1-(6-((4,4-difluorocyclohexyl)amino)-2-(5-methylfuran-2-yl)pyrimidin-4-yl) ethan-1-ol as an off-white solid (0.05 g, 62%). MS (M+1)+=338.2; 1H-NMR (400 MHz, MeOD): δ 7.08 (d, J=4.40 Hz, 1H), 6.46 (s, 1H), 6.18 (d, J=2.80 Hz, 1H), 4.63 (q, J=6.80 Hz, 1H), 4.08 (s, 1H), 2.39 (s, 3H), 2.15-1.85 (m, 6H), 1.70-1.60 (m, 2H), 1.50-1.49 (m, 3H).

Example-649

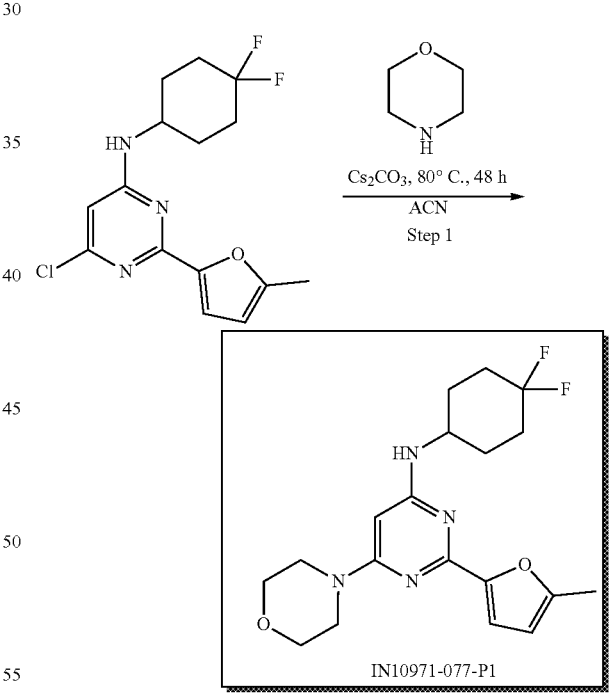

Step 1: The procedure is similar to Step 3[IN11237-001-P1] in Example-614. 1 g of 5-methylfuran-2-carbonitrile gave 5-methylfuran-2-carboximidamide as a white solid (1.5 g, crude). MS (M+1)+=125.1.

Step 2: The procedure is similar to Step 1[IN10966-057-P2] in Example-893. 1 g of 5-methylfuran-2-carboximidamide gave 2-(5-methylfuran-2-yl)pyrimidine-4,6-diol as an off-white solid (0.7 g, crude). MS (M+1)+=193.0.

Step 3: The procedure is similar to Step 2[IN10966-057-P2] in Example-893. 1.1 g of 2-(5-methylfuran-2-yl)pyrimidine-4,6-diol gave 4,6-dichloro-2-(5-methylfuran-2-yl)pyrimidine as brownish gum (1 g, 76%). MS (M+1)+=229.

Step 4: The procedure is similar to Step 1[B] in Example-838. 0.5 g of 4,6-dichloro-2-(5-methylfuran-2-yl)pyrimidine gave 6-chloro-N-(4,4-difluorocyclohexyl)-2-(5-methylfuran-2-yl)pyrimidin-4-amine as an off-white solid (0.42 g, 58%). MS (M+1)+=328.

Step 1[IN10971-077-P1]: The procedure is similar to Step 1[B] in Example-838. 0.2 g of 6-chloro-N-(4,4-difluorocyclohexyl)-2-(5-methylfuran-2-yl)pyrimidin-4-amine gave N-(4,4-difluorocyclohexyl)-2-(5-methylfuran-2-yl)-6-morpholinopyrimidin-4-amine as a white solid (0.14 g, 60%). MS (M+1)+=379; 1H-NMR (400 MHz, MeOD): δ 6.99 (d, J=3.20 Hz, 1H), 6.14 (s, 1H), 5.52 (s, 1H), 3.88 (s, 1H), 3.76-3.74 (m, 4H), 3.56-3.54 (m, 4H), 2.36 (s, 3H), 2.15-1.90 (m, 6H), 1.65-1.55 (m, 2H).

Example-650

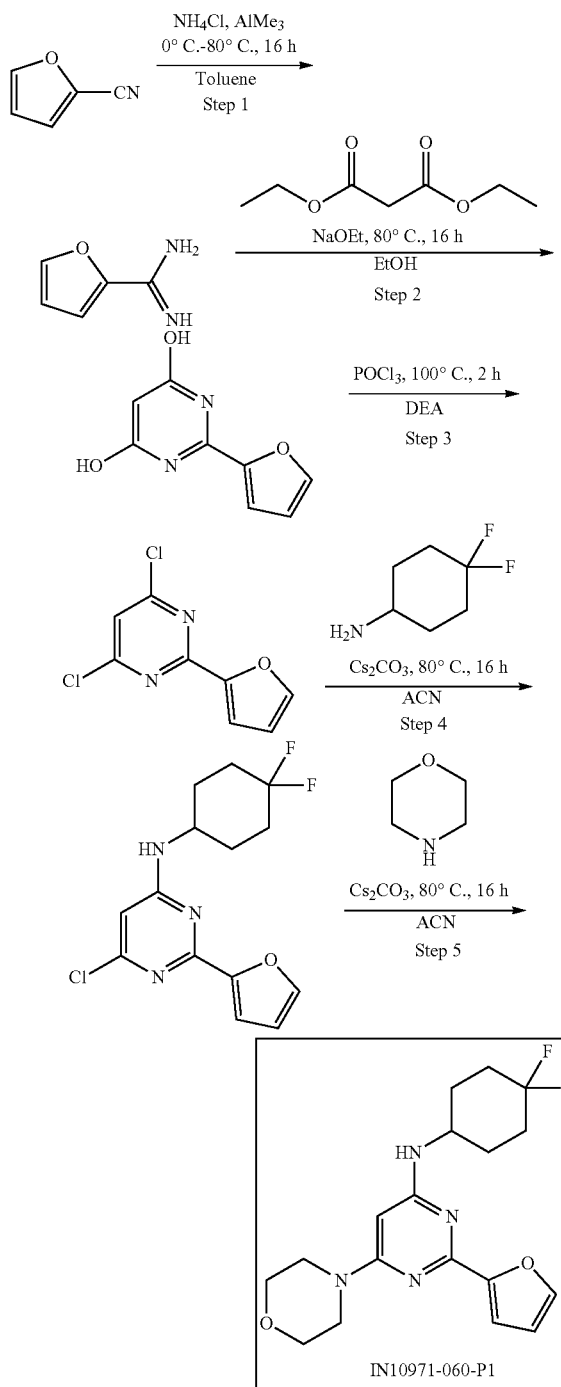

Step 1: The procedure is similar to Step 3[IN11237-001-P1] in Example-614. 1 g of furan-2-carbonitrile gave furan-2-carboximidamide as a white solid (1.5 g, crude). MS (M+1)+=111.1.

Step 2: The procedure is similar to Step 1[IN10966-057-P2] in Example-893. 0.8 g of furan-2-carboximidamide gave 2-(furan-2-yl)pyrimidine-4,6-diol as an off-white solid (0.6 g, crude). MS (M+1)+=179.1.

Step 3: The procedure is similar to Step 2[IN10966-057-P2] in Example-893. 0.6 g of 2-(furan-2-yl)pyrimidine-4,6-diol gave 4,6-dichloro-2-(furan-2-yl)pyrimidine as a light brown solid (0.4 g, 55%). MS (M+1)+=216.9.

Step 4: The procedure is similar to Step 1[B] in Example-838. 0.4 g of 4,6-dichloro-2-(furan-2-yl)pyrimidine gave 6-chloro-N-(4,4-difluorocyclohexyl)-2-(furan-2-yl)pyrimidin-4-amine as an off-white solid (0.4 g, 54%). MS (M+1)+=314.

Step 5[IN10971-060-P1]: The procedure is similar to Step 1[B] in Example-838. 0.4 g of 6-chloro-N-(4,4-difluorocyclohexyl)-2-(furan-2-yl)pyrimidin-4-amine gave N-(4,4-difluorocyclohexyl)-2-(furan-2-yl)-6-morpholinopyrimidin-4-amine as a white solid (0.35 g, 75%). MS (M+1)+=365.1; 1H-NMR (400 MHz, CD3OD): δ 7.60 (d, J=1.2 Hz, 1H), 7.10 (d, J=3.2 Hz, 1H), 6.53 (d, J=3.4 Hz, 1H), 5.54 (s, 1H), 3.92-3.90 (m, 1H), 3.76-3.74 (m, 4H), 3.57-3.55 (m, 4H), 2.12-1.87 (m, 6H), 1.66-1.58 (m, 2H).

Example-651

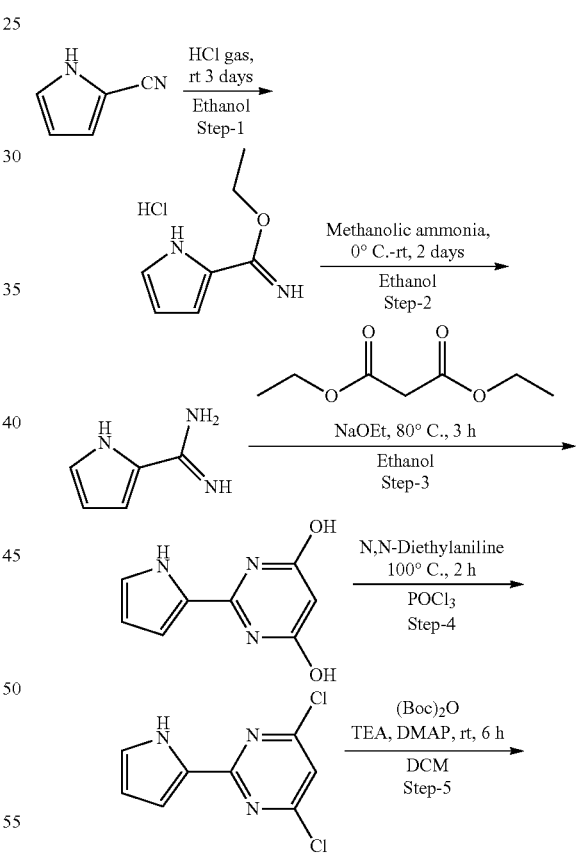

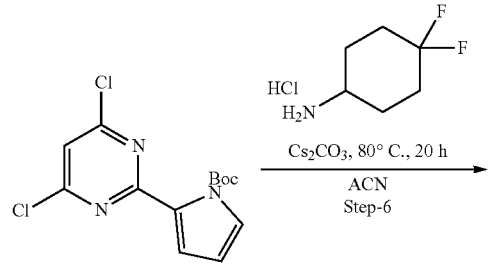

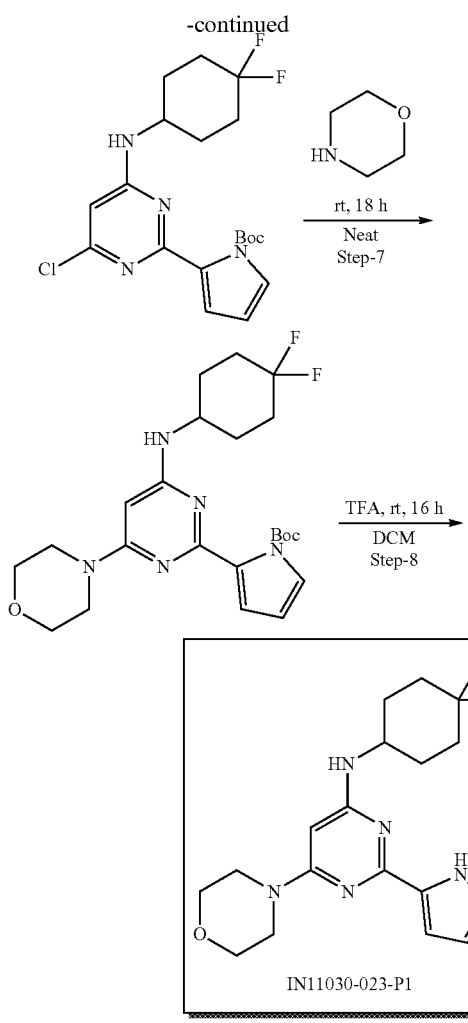

Step 1: To an ice cooled solution of 1H-pyrrole-2-carbonitrile (0.5 g, 5.42 mmol) in ethanol (5 mL) was purged with dry HCl gas for 2 h. The reaction mixture was slowly warmed to rt and stirred at rt in a closed condition for 3 days. The reaction mixture was concentrated and the resulting residue was triturated with diethyl ether to afford ethyl 1H-pyrrole-2-carbimidate as a grey solid (0.8 g, crude). MS (M+1)+=139.1.

Step 2: In a 100 mL sealed tube was charged with ethyl 1H-pyrrole-2-carbimidate (0.7 g, 6.41 mmol) and 30 mL of ammonia in methanol at 0° C. The sealed tube cap was fixed tightly and stirred at rt for 2 days. The reaction mixture was concentrated under vacuum to afford 1H-pyrrole-2-carboximidamide as a brown solid (0.55 g, crude). MS (M+1)+=110.1.

Step 3: The procedure is similar to Step 1[IN10966-057-P2] in Example-893. 0.7 g of 1H-pyrrole-2-carboximidamide gave 2-(1H-pyrrol-2-yl)pyrimidine-4,6-diol as an off-white solid (0.55 g, crude). MS (M+1)+=178.1.

Step 4: The procedure is similar to Step 2[IN10966-057-P2] in Example-893. 0.3 g of 2-(1H-pyrrol-2-yl)pyrimidine-4,6-diol gave 4,6-dichloro-2-(1H-pyrrol-2-yl)pyrimidine as brownish gum (0.12 g, 33%). MS (M+1)+=215.

Step 5: The procedure is similar to Step 2[IN11218-026-P1] in Example-613. 0.12 g of 4,6-dichloro-2-(1H-pyrrol-2-yl)pyrimidine gave tert-butyl 2-(4,6-dichloropyrimidin-2-yl)-1H-pyrrole-1-carboxylate as an off-white solid (0.2 g). MS (M+1)+=315.

Step 6: The procedure is similar to Step 1[B] in Example-838. 0.2 g of tert-butyl 2-(4,6-dichloropyrimidin-2-yl)-1H-pyrrole-1-carboxylate gave tert-butyl 2-(4-chloro-6-((4,4-difluorocyclohexyl)amino)pyrimidin-2-yl)-1H-pyrrole-1-carboxylate as an off-white solid (0.2 g). MS (M+1)+=413.4.

Step 7: The procedure is similar to Step 1[B] in Example-838. 0.2 g of tert-butyl 2-(4-chloro-6-((4,4-difluorocyclohexyl)amino)pyrimidin-2-yl)-1H-pyrrole-1-carboxylate gave tert-butyl 2-(4-((4,4-difluorocyclohexyl)amino)-6-morpholinopyrimidin-2-yl)-1H-pyrrole-1-carboxylate as a light yellow solid (0.11 g, Crude). MS (M+1)+=464.2.

Step 8[IN11030-023-P1]: The procedure is similar to Step 5[NSSy6067] in Example-628. 0.1 g of tert-butyl 2-(4-((4,4-difluorocyclohexyl)amino)-6-morpholinopyrimidin-2-yl)-1H-pyrrole-1-carboxylate gave N-(4,4-difluorocyclohexyl)-6-morpholino-2-(1H-pyrrol-2-yl)pyrimidin-4-amine as an off-white solid (0.022 g, 22%). MS (M+1)+=364.2; 1H-NMR (400 MHz, DMSO-d6): δ 6.83 (s, 1H), 6.70 (s, 1H), 6.50 (s, 1H), 6.08 (d, J=2.40 Hz, 1H), 5.43 (s, 1H), 4.02 (s, 1H), 3.68 (s, 4H), 3.49 (s, 4H), 2.10-1.85 (m, 6H), 1.58-1.48 (m, 2H).

Example-652

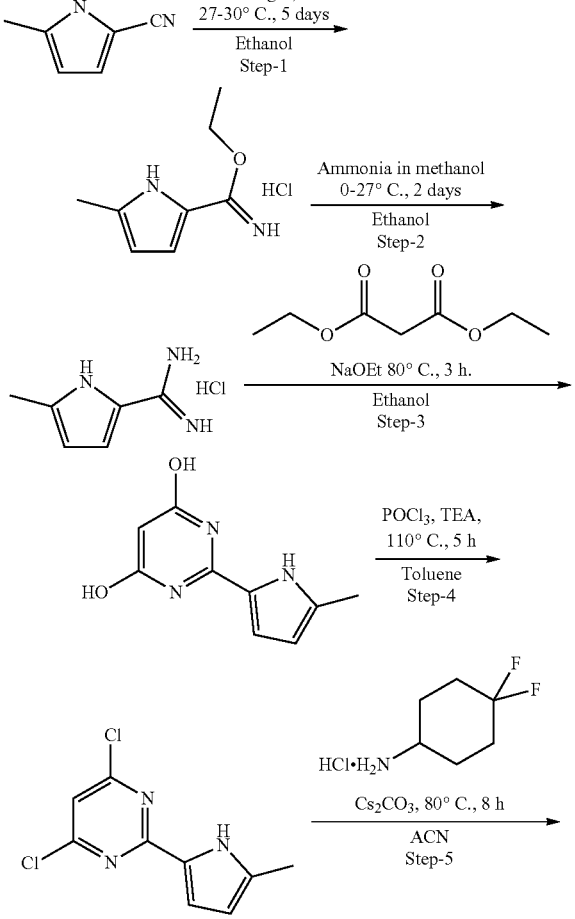

825

-continued

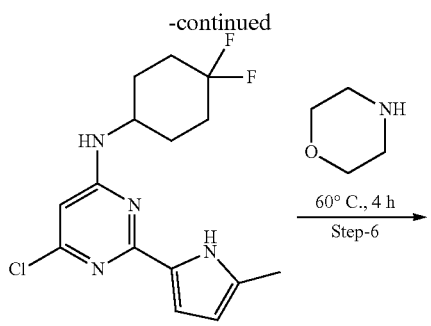

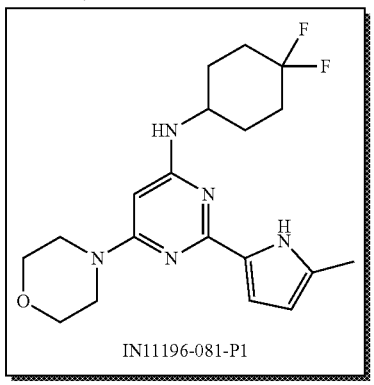
IN11196-081-P1

Step 1: The procedure is similar to Step 1[IN11030-023-P1] in Example-651. 2 g of 5-methyl-1H-pyrrole-2-carbonitrile gave ethyl 5-methyl-1H-pyrrole-2-carbimidate as an off-white solid (2.2 g, crude). MS (M+1)+=153.2.

Step 2: The procedure is similar to Step 2[IN11030-023-P1] in Example-651. 2.2 g of ethyl 5-methyl-1H-pyrrole-2-carbimidate gave 5-methyl-1H-pyrrole-2-carboximidamide as an off-white solid (2.5 g, crude). MS (M+1)+=124.2.

Step 3: The procedure is similar to Step 1[IN10966-057-P2] in Example-893. 1.2 g of 5-methyl-1H-pyrrole-2-carboximidamide gave 2-(5-methyl-1H-pyrrol-2-yl)pyrimidine-4,6-diol as an off-white solid (1.4 g, crude). MS (M+1)+=192.2.

Step 4: The procedure is similar to Step 2[IN10966-057-P2] in Example-893. 1.4 g of 2-(5-methyl-1H-pyrrol-2-yl)pyrimidine-4,6-diol gave 4,6-dichloro-2-(5-methyl-1H-pyrrol-2-yl)pyrimidine as a light brown solid (0.7 g, crude). MS (M+1)+=228.1.

Step 5: The procedure is similar to Step 1[B] in Example-838. 0.3 g of 4,6-dichloro-2-(5-methyl-1H-pyrrol-2-yl)pyrimidine gave 6-chloro-N-(4,4-difluorocyclohexyl)-2-(5-methyl-1H-pyrrol-2-yl)pyrimidin-4-amine as an off-white solid (0.25 g, 80%). MS (M+1)+=327.1.

Step 6[IN11196-081-P1]: The procedure is similar to Step 1[B] in Example-838. 0.1 g of 6-chloro-N-(4,4-difluorocyclohexyl)-2-(5-methyl-1H-pyrrol-2-yl)pyrimidin-4-amine gave N-(4,4-difluorocyclohexyl)-2-(5-methyl-1H-pyrrol-2-yl)-6-morpholino pyrimidin-4-amine as an off-white solid (0.025 g, 21%). MS (M+1)+=378.2; 1H-NMR (400 MHz, DMSO-d6): δ 10.70 (s, 1H), 6.59 (t, J=2.40 Hz, 1H), 6.54 (d, J=7.60 Hz, 1H), 5.78 (s, 1H), 5.40 (s, 1H), 4.01 (s, 1H), 3.68 (s, 4H), 3.50 (s, 4H), 2.25 (s, 3H), 2.10-1.85 (m, 6H), 1.60-1.48 (m, 2H).

Example-653

Intentionally Omitted

826

Example-654

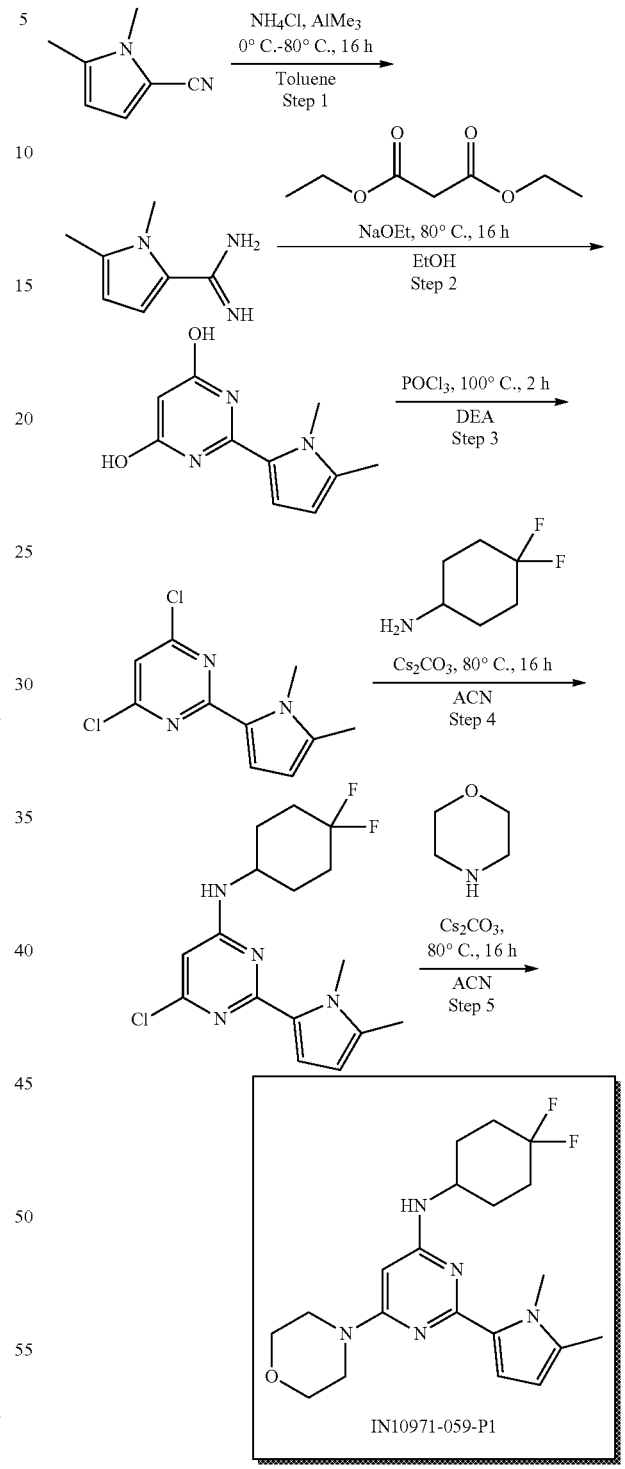

Step 1: The procedure is similar to Step 3[IN11237-001-P1] in Example-614. 2 g of 1,5-dimethyl-1H-pyrrole-2-carbonitrile gave 1,5-dimethyl-1H-pyrrole-2-carboximidamide as an off-white solid (3 g, crude). MS (M+1)+=138.2.

Step 2: The procedure is similar to Step 1[IN10966-057-P2] in Example-893. 3 g of 1,5-dimethyl-1H-pyrrole-2- carboximidamide gave 2-(1,5-dimethyl-1H-pyrrol-2-yl)pyrimidine-4,6-diol as an off-white solid (3 g, 84%). MS (M+1)+=206.

Step 3: The procedure is similar to Step 2[IN10966-057-P2] in Example-893. 1 g of 2-(1,5-dimethyl-1H-pyrrol-2-yl)pyrimidine-4,6-diol gave 4,6-dichloro-2-(1,5-dimethyl-1H-pyrrol-2-yl)pyrimidine as a light brown solid (0.7 g, 59%). MS (M+1)+=241.9.

Step 4: The procedure is similar to Step 1[B] in Example-838. 0.5 g of 4,6-dichloro-2-(1,5-dimethyl-1H-pyrrol-2-yl)pyrimidine gave 6-chloro-N-(4,4-difluoro cyclohexyl)-2-(1,5-dimethyl-1H-pyrrol-2-yl)pyrimidin-4-amine as an off-white solid (0.4 g, 56%). MS (M+1)+=341.

Step 5[IN10971-059-P1]: The procedure is similar to Step 1[B] in Example-838. 0.4 g of 6-chloro-N-(4,4-difluorocyclohexyl)-2-(1,5-dimethyl-1H-pyrrol-2-yl)pyrimidin-4-amine gave N-(4,4-difluorocyclohexyl)-2-(1,5-dimethyl-1H-pyrrol-2-yl)-6-morpholino pyrimidin-4-amine as an off-white solid (0.25 g, 54%). MS (M+1)+=392.1; 1H-NMR (400 MHz, MeOD): δ 6.86 (d, J=4.00 Hz, 1H), 5.96 (d, J=4.00 Hz, 1H), 5.57 (s, 1H), 3.88 (s, 4H), 3.78-3.71 (m, 4H), 3.65 (s, 4H), 2.28 (s, 3H), 2.13-1.95 (m, 6H), 1.70-1.64 (m, 3H).

Example-655

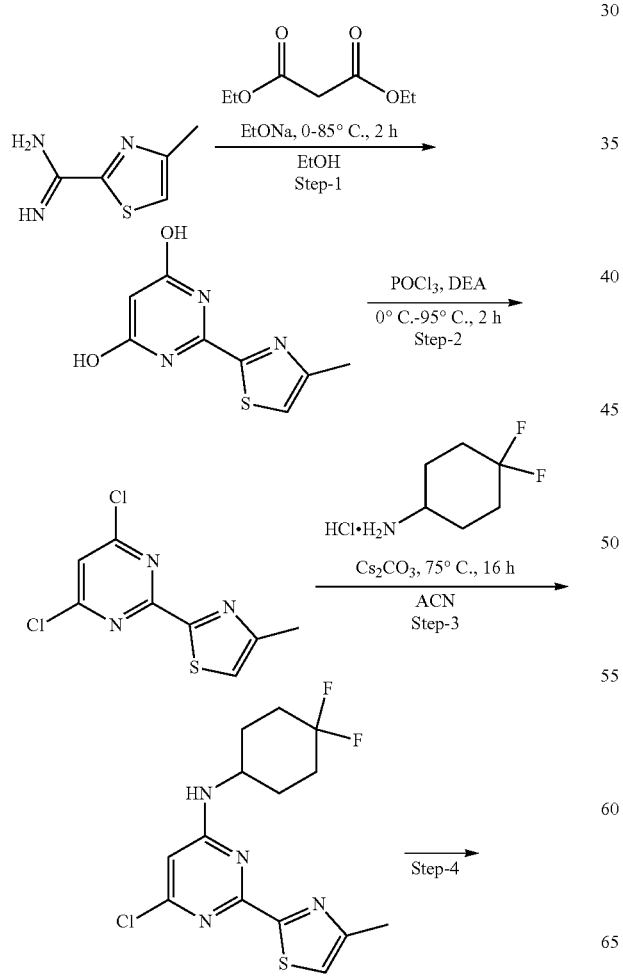

-continued

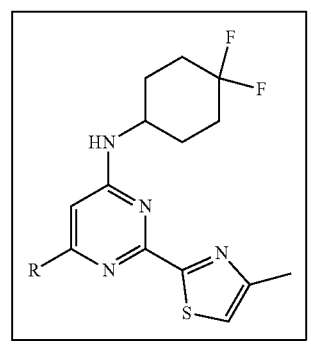

| Compound No | R |
|---|---|
| NSSy5774 | |
| NSSy5787 | |
| NSSy5789 | |
| NSSy5792 | |
| NSSy5795 | |
| NSSy6055 | |
| NSSy6062 | |

-continued

| Compound No | R |
|---|---|
| NSSy6093 | (3-methyl-2-oxopiperazin-1-yl) |
| NSSy6116 | (2-oxa-5-azabicyclo[2.2.1]heptan-5-yl) |
| NSSy6129 | (3-oxa-8-azabicyclo[3.2.1]octan-8-yl) |
| NSSy5796 | (2-(methoxymethyl)morpholino) |
| NSSy6171 | ((1S,4S)-2-oxa-5-azabicyclo[2.2.1]heptan-5-yl) |
| NSSy6111 | (1,1-dioxidothiomorpholino) |
| NSSy5740 | (3-hydroxy-3-methylcyclobutoxy) |
| NSSy6253 | ((1,1-dioxidotetrahydro-2H-thiopyran-4-yl)oxy) |
| NSSy5730 | methyl (3-methoxycyclobutyl)(methyl)carbamate |

-continued

| Compound No | R |
|---|---|
| NSSy6007 | (4,5,6,7-tetrahydro-[1,2,3]triazolo[1,5-a]pyridin-4-yl)oxy |
| NSSy6258 | ((1-acetylpiperidin-4-yl)oxy) |
| NSSy6056 | H |
| IN10882-020-P1 | (3-(hydroxymethyl)pyrrolidin-1-yl) |
| IN10882-014-P1 | (pyrrolidin-1-yl) |
| IN11030-032-P1 | (2,2,6,6-tetrafluoromorpholino) |
| IN10864-066-P1 | (3-(hydroxymethyl)-4-methylpiperazin-1-yl) |
| IN10864-060-P1 | (3-(methoxymethyl)-4-methylpiperazin-1-yl) |
| IN10864-031-P1 | (4-isopropylpiperazin-1-yl) |

831
-continued

| Compound No | R |
|---|---|
| IN10964-007-P1 | (isopropoxymethyl morpholine) |
| IN11059-047-P1 | (oxazolylmethoxy) |
| IN11125-013-P1 | (isoxazol-3-ylmethoxy) |
| IN11055-049-P1 | (methylamino) |
| IN11055-046-P1 | (dimethylamino) |
| IN11055-016-P1 | (isopropoxy) |
| IN10864-043-P1 | (2,2-dimethylmorpholine) |
| IN10864-034-P1 | (1,4-oxazepane) |
| IN10864-033-P1 | (4-fluoropiperidine) |
| IN10876-013-P1 | (3-methoxypiperidine) |
| IN11059-052-P1 | (methylsulfonamidoethoxy) |

832
-continued

| Compound No | R |
|---|---|
| IN11039-009-P1 | (methyl carbamate ethoxy) |
| IN10973-025-P1 | (methyl pyrrolidine-1-carboxylate-3-yloxy) |
| IN10880-014-P1 | (4-methylpiperazine) |
| IN10880-018-P1 | (2-ethylmorpholine) |
| IN10880-032-P1 | (4-acetamidopiperidine) |
| IN10880-033-P1 | (2-(BocNHmethyl)morpholine) |
| IN10882-040-P1 | (oxetan-3-ylamino) |
| IN10882-043-P1 | (N-methyl oxetan-3-ylamino) |

-continued

| Compound No | R |
|---|---|
| IN10881-099-P1 | (methoxymethyl-morpholin-N-yl) |
| IN10881-090-P1 | (N-methyl-N-cyclopropylamino) |
| IN10881-092-P1 | (2-((diethylamino)methyl)morpholin-4-yl) |
| IN10881-021-P1 | (piperidin-1-yl) |
| IN11140-052-P1 | ((2-chlorooxazol-5-yl)methoxy) |
| IN11079-014-P1 | (3-methoxytetrahydrofuran) |
| IN11079-007-P1 | (tetrahydro-2H-pyran-4-yloxy) |
| IN11079-033-P1 | (oxetan-3-yloxy) |
| IN11054-039-P1 | (methylthio) |
| IN11054-046-P2 | (methylsulfinyl) |

-continued

| Compound No | R |
|---|---|
| IN11054-046-P1 | (methylsulfonyl) |
| IN10881-023-P2 | (4-hydroxypiperidin-1-yl) |
| IN10881-020-P1 | (4-(dimethylamino)piperidin-1-yl) |
| IN10881-025-P1 | ((morpholin-2-yl)methoxy) |
| IN10881-027-P1 | (3-(hydroxymethyl)morpholin-4-yl) |
| IN10987-056-P1 | (5-methyl-2,5-diazabicyclo[2.2.1]heptan-2-yl) |
| IN10987-050-P1 | (2,5-diazabicyclo[2.2.1]heptan-2-yl) |
| IN11107-015-P1 | (methoxy) |
| IN10880-29-P1 | (cyano) |
| IN11218-030-P1 | (phenyl) |
| IN11196-080-P1 | (pyridin-2-yl) |

Step 1: The Procedure is similar to Step 1[IN10966-057-P2] in Example-893. 2 g of 4-methylthiazole-2-carboximidamide gave 2-(4-methylthiazol-2-yl)pyrimidine-4,6-diol as an off-white solid (2.3 g, 97%). MS (M+1)+=210.1

Step 2: The Procedure is similar to Step 2[IN10966-057-P2] in Example-893. 0.5 g of 2-(4-methylthiazol-2-yl)pyrimidine-4,6-diol gave 2-(4,6-dichloropyrimidin-2-yl)-4-methylthiazole as a light brown solid (0.45 g, 77%). MS (M+1)+=246.0, 248.0.

Step 3: The Procedure is similar to Step 1[B] in Example-838. 0.20 g of 2-(4,6-dichloropyrimidin-2-yl)-4-methylthiazole gave 6-chloro-N-(4,4-difluorocyclohexyl)-2-(4-methylthiazol-2-yl)pyrimidin-4-amine as an off-white solid (0.27 g, 96%). MS (M+1)+=345.1.

TABLE 32

Step 4:

| Compound No | R | Condition | Yield (%) |
|---|---|---|---|
| NSSy5774 | (oxazolidinone-fused piperazine) | Cs₂CO₃, ACN, 120° C., 16 h, | 21 |
| NSSy5787 | 4-(oxetan-3-yl)piperidine | Cs₂CO₃, ACN, 100° C., 16 h, | 35 |
| NSSy5789 | 2-(methoxymethyl)morpholine | Cs₂CO₃, ACN, 120° C., 16 h, | 72 |
| NSSy5796 | (S)-2-(methoxymethyl)morpholine | Cs₂CO₃, ACN, 120° C., 16 h, | — |
| NSSy5795 | (R)-2-(methoxymethyl)morpholine | Cs₂CO₃, ACN, 120° C., 16 h, | — |
| NSSy6055 | 4-acetylpiperazine | Cs₂CO₃, ACN, 140° C., 3 h, MW | 30 |
| NSSy6062 | thiomorpholine 1,1-dioxide | Xanthphos, Pd₂(dba)₃, Cs₂CO₃, dioxane, 90° C., 16 h | 30 |
| NSSy6093 | 1-methyl-3-oxopiperazine | Cs₂CO₃, ACN, 120° C., 16 h, | 25 |

TABLE 32-continued

Step 4:

| Compound No | R | Condition | Yield (%) |
|---|---|---|---|
| NSSy6116 | (2-oxa-5-azabicyclo[2.2.1]heptane group) | Cs$_2$CO$_3$, ACN, 80° C., 16 h, | 35 |
| NSSy6129 | (3-oxa-8-azabicyclo[3.2.1]octane group) | Cs$_2$CO$_3$, ACN, 80° C., 16 h, | 17 |
| NSSy5792 | (4-(oxetan-3-yl)piperazin-1-yl group) | Cs$_2$CO$_3$, TEA:ACN (1:1), 80° C., 16 h, | 12 |
| NSSy6171 | (2-oxa-5-azabicyclic group with H stereochem) | Cs$_2$CO$_3$, DMSO, 80° C., 16 h, | 42 |
| NSSy6111 | (1,1-dioxothiomorpholin-4-yl group) | Xanthphos, Pd$_2$(dba)$_3$, Cs$_2$CO$_3$, dioxane, 90° C., 16 h | 21 |
| NSSy5740 | (3-hydroxy-3-methylcyclobutoxy group) | K$^+$(CH$_3$)$_3$CO$^-$, THF, 70° C., 16 h | 30 |
| NSSy6253 | (1,1-dioxotetrahydro-2H-thiopyran-4-yloxy group) | K$^+$(CH$_3$)$_3$CO$^-$, THF, 70° C., 16 h | 68 |
| NSSy5730 | (3-(methoxycarbonyl(methyl)amino)cyclobutoxy group) | Cs$_2$CO$_3$, ACN, 80° C., 16 h, | 18 |

TABLE 32-continued

Step 4:

| Compound No | R | Condition | Yield (%) |
|---|---|---|---|
| NSSy6007 | 4,5,6,7-tetrahydro-[1,2,3]triazolo[1,5-a]pyridin-4-yloxy | NaOH, TBAHS, H₂O, 70° C., 16 h | 26 |
| NSSy6258 | 1-acetylpiperidin-4-yloxy | K⁺(CH₃)₃CO⁻, THF, 80° C., 16 h | 49 |
| NSSy6056 | H | Pd/C, 50° C., 16 h | 28 |
| IN10882-020-P1 | 3-(hydroxymethyl)cyclopentyl | THF, 65° C., 48 h | 97 |
| IN10882-014-P1 | pyrrolidin-1-yl | THF, 65° C., 48 h | 60 |
| IN11030-032-P1 | 2,2,6,6-tetrafluoromorpholin-4-yl | Xanthphos, Pd(OAc)₂, Cs₂CO₃, dioxane, 95° C., 16 h | 29 |
| IN11055-015-P1 | ethoxy | NaOEt, EtOH, 80° C., 12 h | 51 |
| IN10864-066-P1 | 3-(hydroxymethyl)-4-methylpiperazin-1-yl | TEA, ACN, 80° C., 5 days | 31 |
| IN10864-060-P1 | 3-(methoxymethyl)-4-methylpiperazin-1-yl | TEA, ACN, 80° C., 5 days | 25 |

TABLE 32-continued

Step 4:

| Compound No | R | Condition | Yield (%) |
|---|---|---|---|
| IN10864-031-P1 | 4-isopropylpiperazinyl | TEA, THF, 65° C., 48 h | 68 |
| IN10964-007-P1 | 2-(isopropoxymethyl)morpholinyl | TEA, ACN, 85° C., 35 h | 26 |
| IN11059-047-P1 | (oxazol-5-yl)methoxy | NaH, THF, 70° C., 1 h | 29 |
| IN11125-013-P1 | (isoxazol-3-yl)methoxy | NaH, THF, 70° C., 1 h | 56 |
| IN11055-049-P1 | methylamino | Methyl amine, MeOH, 85° C., 12 h | 15 |
| IN11055-046-P1 | dimethylamino | Dimethyl amine hydrochloride, DIPEA, ACN, 65° C., 12 h | 48 |
| IN11055-016-P1 | isopropoxy | Sodium metal, IPA, 90° C., 5 h | 56 |
| IN10864-043-P1 | 2,2-dimethylmorpholinyl | TEA, THF, 70° C., 48 h | 95 |
| IN10864-034-P1 | 1,4-oxazepan-4-yl | TEA, THF:DMF (1:2), 80° C., 48 h | 50 |
| IN10864-033-P1 | 4-fluoropiperidinyl | TEA, THF, 70° C., 24 h | 72 |

TABLE 32-continued

Step 4:

| Compound No | R | Condition | Yield (%) |
|---|---|---|---|
| IN10876-013-P1 | 3-methoxypiperidin-1-yl | TEA, THF, 90° C., 72 h | 27 |
| IN11059-052-P1 | 2-(methylsulfonamido)ethoxy | Step a: 2-aminoethan-1-ol, NaH, THF:TEA(1:20), 70° C., 1 h<br>Step b: Methanesulfonyl chloride, TEA, DCM, 0° C.-rt, 1 h | 93/29 |
| IN11039-009-P1 | 2-((methoxycarbonyl)amino)ethoxy | Step a: tert-butyl (2-hydroxyethyl)carbamate, NaH, THF, 70° C., 16 h<br>Step b: TFA, DCM, rt, 2 h<br>Step c: Methylchloroformate, K$_2$CO$_3$, ACN, 60° C., 16 h | 49/70/54 |
| IN10973-025-P1 | 1-(methoxycarbonyl)pyrrolidin-3-yloxy | Cs$_2$CO$_3$, ACN, 80° C., 16 h | 68 |
| IN10880-014-P1 | 4-methylpiperazin-1-yl | THF, 60° C., 16 h | 76 |
| IN10880-018-P1 | 2-ethylmorpholin-4-yl | THF, 80° C., 16 h | 65 |
| IN10880-032-P1 | 4-acetamidopiperidin-1-yl | TEA, ACN, 80° C., 36 h | 25 |
| IN10880-033-P1 | 2-((Boc-amino)methyl)morpholin-4-yl | TEA, ACN, 80° C., 36 h | 43 |
| IN10882-040-P1 | oxetan-3-ylamino | DIPEA, 100° C., 15 min, MW | 22 |

TABLE 32-continued

Step 4:

| Compound No | R | Condition | Yield (%) |
|---|---|---|---|
| IN10882-043-P1 | *N-methyl-N-(oxetan-3-yl)amino* | DIPEA, 100° C., 15 min, MW | 56 |
| IN10881-099-P1 | *3-(methoxymethyl)morpholino* | DIPEA, 110° C., 20 min, MW | 35 |
| IN10881-090-P1 | *N-cyclopropyl-N-methylamino* | DIPEA, 110° C., 20 min, MW | 36 |
| IN10881-092-P1 | *2-((diethylamino)methyl)morpholino* | TEA, ACN, 110° C., 12 h | 72 |
| IN10881-021-P1 | *piperidin-1-yl* | TEA, THF, 65° C., 48 h | 32 |
| IN11140-052-P1 | *(2-chlorooxazol-5-yl)methoxy* | Step a: oxazol-5-ylmethanol, Cs$_2$CO$_3$, ACN, 90° C., 16 h<br>Step b: LiHMDS, Hexachloroethane, THF, −78° C., 16 h | 51/60 |
| IN11079-014-P1 | *(tetrahydrofuran-3-yl)oxy* | tetrahydrofuran-3-ol, Sodium Metal 60° C., 4 h | 61 |
| IN11079-007-P1 | *(tetrahydro-2H-pyran-4-yl)oxy* | tetrahydro-2H-pyran-4-ol, Sodium Metal, 60° C., 3 h | 61 |

TABLE 32-continued

Step 4:

| Compound No | R | Condition | Yield (%) |
|---|---|---|---|
| IN11079-033-P1 | oxetan-3-yl-O- | oxetan-3-ol, Sodium Metal, 60° C., 6 h | 60 |
| IN11054-039-P1 | -S-CH3 | NaSMe, EtOH, 65° C., 3 h | 90 |
| IN11054-046-P2 | -S(O)-CH3 | m-CPBA, DCM, rt, 16 h, | 18 |
| IN11054-046-P1 | -S(O)2-CH3 | m-CPBA, DCM, rt, 16 h, | 20 |
| IN10881-023-P2 | 4-hydroxypiperidin-1-yl | TEA, THF, 65° C., 48 h | 33 |
| IN10881-020-P1 | 4-(dimethylamino)piperidin-1-yl | TEA, THF, 65° C., 48 h | 29 |
| IN10881-025-P1 | (morpholin-2-yl)methoxy | TEA, THF, 65° C., 12 h | 33 |
| IN10881-027-P1 | 3-(hydroxymethyl)morpholin-4-yl | TEA, ACN, 65° C., 12 h | 25 |
| IN10987-056-P1 | (1S,4S)-5-methyl-2,5-diazabicyclo[2.2.1]heptan-2-yl | Step a: Tert-butyl (1S, 4S)-2, 5-diazabicyclo[2.2.1]heptane-2-carboxylate, TEA, ACN, 80° C., 16 h<br>Step b: LAH, THF, 0° C.-80° C., 16 h | 44/37 |
| IN10987-050-P1 | (1S,4S)-2,5-diazabicyclo[2.2.1]heptan-2-yl | Step a: Tert-butyl (1S, 4S)-2, 5-diazabicyclo[2.2.1]heptane-2-carboxylate, TEA, ACN, 80° C., 16 h<br>Step b: HCl in Ether, 0° C.-30° C., 16 h. | 44/41 |
| IN10880-029-P1 | -CN | Zn(CN)$_2$, Pd(PPh$_3$)$_4$, DMF, 130° C., 24 h | 21 |

TABLE 32-continued

Step 4:

| Compound No | R | Condition | Yield (%) |
|---|---|---|---|
| IN11218-030-P1 | phenyl group | Phenyl boronic acid, Pd(Ph₃P)₄, K₂CO₃, 1,4-dioxane, 100° C., 24 h | 30 |
| IN11196-080-P1 | 2-pyridyl group | 2-(Tributylstannyl)pyridine, Pd(PPh₃)₂Cl₂, 1,4-Dioxane, 110° C., 16 h | 28 |

Step 4[NSSy5774]: The Procedure is similar to Step 1[B] in Example-838. MS (M+1)+=451.1; 1H-NMR (400 MHz, DMSO-d6): δ 7.36 (s, 1H), 7.10 (s. 1H), 5.73 (s, 1H), 4.57-4.55 (m, 1H), 4.46-4.44 (m, 1H), 4.42 (s, 1H), 4.07-4.04 (m, 1H), 3.90 (s, 2H), 3.69 (s, 1H), 3.04-3.01 (m, 1H), 2.90-2.77 (m, 2H), 2.42 (s, 3H), 2.07-1.92 (m, 6H), 1.61-1.56 (m, 2H).

Step 4[NSSy5787]: The Procedure is similar to Step 1[B] in Example-838. MS (M+1)+=450.0; 1H-NMR (400 MHz, DMSO-d6): δ 7.33 (d, J=0.96 Hz, 1H), 6.93 (d, J=7.88 Hz, 1H), 5.66 (s, 1H), 4.63-4.60 (m, 2H), 4.39-4.33 (m, 4H), 3.92 (m, 1H), 2.86-2.81 (m, 2H), 2.75-2.71 (m, 1H), 2.42 (s, 3H), 2.08-2.00 (m, 3H), 1.94-1.91 (m, 4H), 1.67-1.64 (m, 2H), 1.60-1.52 (m, 2H), 1.04-0.94 (m, 2H).

Step 4[NSSy5789]: The Procedure is similar to Step 1[B] in Example-838. MS (M+1)+=440.0; 1H-NMR (400 MHz, DMSO-d6): δ 7.33 (s, 1H), 7.04 (s, 1H), 5.66 (s, 1H), 4.09-4.06 (m, 2H), 3.95-3.92 (m, 2H), 3.62-3.39 (m, 4H), 3.29 (s, 3H), 2.91 (s, 1H), 2.67-2.64 (m, 1H), 2.41 (s, 3H), 2.07-1.91 (m, 6H), 1.60-1.54 (m, 2H) and isomers was separated by Chiral HPLC to afford [NSSy5796]. MS (M+1)+=440.0; 1H-NMR (400 MHz, DMSO-d6): δ 7.33 (s, 1H), 7.04 (s, 1H), 5.66 (s, 1H), 4.09-4.06 (m, 2H), 3.95-3.92 (m, 2H), 3.62-3.39 (m, 4H), 3.29 (s, 3H), 2.91 (s, 1H), 2.67-2.64 (m, 1H), 2.41 (s, 3H), 2.07-1.91 (m, 6H), 1.60-1.54 (m, 2H) and [NSSy5795]. MS (M+1)+=440.0; 1H-NMR (400 MHz, DMSO-d6): δ 7.33 (s, 1H), 7.04 (s, 1H), 5.66 (s, 1H), 4.09-4.06 (m, 2H), 3.95-3.92 (m, 2H), 3.62-3.39 (m, 4H), 3.29 (s, 3H), 2.91 (s, 1H), 2.67-2.64 (m, 1H), 2.41 (s, 3H), 2.07-1.91 (m, 6H), 1.60-1.54 (m, 2H).

Step 4[NSSy6055]: The Procedure is similar to Step 1[NSSy6909] in Example-839. MS (M+1)+=437.0; 1H-NMR (400 MHz, DMSO-d6): δ 7.35 (s, 1H), 7.06 (d, J=8.04 Hz, 1H), 5.67 (s, 1H), 3.91 (s, 1H), 3.61 (s, 2H), 3.54-3.50 (m, 4H), 2.43 (s, 3H), 2.30-1.80 (m, 9H), 1.60-1.50 (m, 2H).

Step 4[NSSy6062]: The Procedure is similar to Step 1[NSSy6629] in Example-839. MS (M+1)+=444.0; 1H-NMR (400 MHz, DMSO-d6): δ 7.36 (s, 1H), 7.15 (d, J=8.0 Hz, 1H), 5.82 (s, 1H), 4.07-4.01 (m, 4H), 3.89 (s, 1H), 3.18-3.16 (m, 4H), 2.42 (s, 3H), 2.20-1.80 (m, 6H), 1.60-1.40 (m, 2H).

Step 4[NSSy6093]: The Procedure is similar to Step 1[B] in Example-838. MS (M+1)+=423.4; 1H-NMR (400 MHz, DMSO-d6): δ 7.35 (s, 1H), 7.09 (s, 1H), 5.66 (s, 1H), 4.09 (s, 2H), 3.86-3.84 (m, 3H), 3.44-3.42 (m, 2H), 2.90 (s, 3H), 2.42 (s, 3H), 2.06-1.92 (m, 6H), 1.58-1.55 (m, 2H).

Step 4[NSSy6116]: The Procedure is similar to Step 1[B] in Example-838. MS (M+1)+=408.2; 1H-NMR (400 MHz, DMSO-d6): δ 7.33 (d, J=0.80 Hz, 1H), 6.97 (d, J=7.60 Hz, 1H), 5.40 (s, 1H), 4.96-4.95 (m, 1H), 4.69 (s, 1H), 3.87-3.79 (m, 1H), 3.79-3.65 (m, 1H), 3.43-3.31 (m, 1H), 3.24-3.17 (m, 1H), 2.50 (s, 3H), 2.09-1.92 (m, 7H), 1.87-1.80 (m, 2H), 1.61-1.55 (m, 2H).

Step 4[NSSy6129]: The Procedure is similar to Step 1[B] in Example-838. MS (M+1)+=422.2; 1H-NMR (400 MHz, DMSO-d6): δ 7.34 (d, J=0.80 Hz, 1H), 7.01 (d, J=7.80 Hz, 1H), 5.57 (s, 1H), 4.44 (s, 2H), 3.88-3.86 (m, 2H), 3.01-2.97 (m, 2H), 2.42 (s, 3H), 2.08-1.94 (m, 3H), 1.92-1.70 (m, 8H), 1.61-1.51 (m, 2H).

Step 4[NSSy5792]: The Procedure is similar to Step 1[B] in Example-838. MS (M+1)+=451.0; 1H-NMR (400 MHz, DMSO-d6): δ 7.34 (s, 1H), 7.01 (d, J=7.76 Hz, 1H), 5.67 (s, 1H), 4.59-4.56 (m, 2H), 4.50-4.47 (m, 2H), 3.90-3.88 (m, 1H), 3.56 (m, 4H), 3.43 (t, J=5.68 Hz, 1H), 2.34 (s, 3H), 2.08-2.06 (m, 4H), 2.00-1.92 (m, 6H), 1.60-1.55 (m, 2H).

Step 4[NSSy6171]: The Procedure is similar to Step 1[B] in Example-838. MS (M+1)+=408.1; 1H-NMR (400 MHz, DMSO-d6): δ 7.33 (s, 1H), 6.98 (d, J=8.0 Hz, 1H), 5.39 (s, 1H), 4.95 (s, 1H), 4.68 (s, 1H), 3.90 (s, 1H), 3.86 (d, J=16.0 Hz, 1H), 3.79 (d, J=8.0 Hz, 1H), 3.35 (bs, 1H), 3.21 (s, 1H), 2.08 (s, 3H), 2.06-1.91 (m, 6H), 1.86 (s, 2H) 1.57-1.55 (m, 2H).

Step 4[NSSy6111]: The Procedure is similar to Step 1[NSSy6629] in Example-839. MS (M+1)+=427.2; 1H-NMR (400 MHz, DMSO-d6): δ 8.44 (s, 1H), 7.18 (d, J=8.0 Hz, 1H), 6.27 (s, 2H), 5.69 (s, 1H), 4.05 (s, 4H), 3.98 (s, 1H), 3.17-3.16 (m, 4H), 2.24 (s, 3H), 2.08-1.90 (m, 6H), 1.57-1.54 (m, 2H).

Step 4[NSSy5740]: The Procedure is similar to Step 1[B] in Example-838. MS (M+1)+=411.2; 1H-NMR (400 MHz, DMSO-d6): δ 7.43 (s, 1H), 7.40 (s, 1H), 5.77 (s, 1H), 5.15 (s, 1H), 4.72 (s, 1H), 4.02 (s, 1H), 2.55-2.50 (m, 2H), 2.42 (s, 3H), 2.15-2.10 (m, 2H), 2.07-1.93 (m, 6H), 1.58-1.55 (m, 2H), 1.27 (s, 3H).

Step 4[NSSy6253]: The Procedure is similar to Step 1[B] in Example-838. MS (M+1)+=459.2; 1H-NMR (400 MHz, DMSO-d6): δ 7.35 (s, 1H), 7.22 (d, J=7.20 Hz, 1H), 5.89 (s, 1H), 5.38-5.34 (m, 1H), 3.23-3.12 (m, 4H), 2.45 (s, 3H), 2.37-2.31 (m, 4H), 2.15-1.90 (m, 6H), 1.66-1.60 (m, 2H).

Step 4[NSSy5730]: The Procedure is similar to Step 1[B] in Example-838. MS (M+1)+=468.2; 1H-NMR (400 MHz, DMSO-d6): δ 7.45 (s, 2H), 5.78 (s, 1H), 4.81 (s, 1H), 4.24

(bs, 1H), 3.59 (s, 3H), 2.81 (s, 3H), 2.54 (bs, 1H), 2.39 (s, 3H), 2.32-2.18 (m, 1H), 2.05-1.92 (m, 6H), 1.59-1.57 (m, 2H).

Step 4[NSSy6007]: The Procedure is similar to Step 1[NSSy5828] in Example-799. MS (M+1)+=448.0; 1H-NMR (400 MHz, DMSO-d6): δ 7.91 (s, 1H), 7.51 (bs, 1H), 7.46 (s, 1H), 6.34 (s, 1H), 5.82 (s, 1H), 4.59-4.54 (m, 1H), 4.32-4.25 (m, 1H), 2.46 (s, 3H), 2.30-1.80 (m, 11H), 1.60-1.50 (m, 2H).

Step 4[NSSy6258]: The Procedure is similar to Step 1[B] in Example-838. MS (M+1)+=452.0; 1H-NMR (400 MHz, DMSO-d6): δ 7.42 (d, J=0.80 Hz, 2H), 5.82 (s, 1H), 5.24 (s, 1H), 3.84-3.81 (m, 1H), 3.70-3.66 (m, 1H), 3.31 (s, 1H), 3.28-3.26 (m, 2H), 2.43 (s, 3H), 2.03-1.93 (m, 11H), 1.58-1.56 (m, 4H).

Step 4[NSSy6056]: To a stirred solution of 6-chloro-N-(4,4-difluorocyclohexyl)-2-(4-methylthiazol-2-yl)pyrimidin-4-amine (0.25 g, 0.725 mmol) in methanol (5 mL) was added 10% palladium on carbon and the reaction mixture was heated at 50° C. for 6 h. The reaction mixture was filtered through celite, the filtrate was concentrated under reduced pressure to afford crude and which was purified by column chromatography using 75% ethyl acetate in pet ether as solvent to afford N-(4,4-difluorocyclohexyl)-2-(4-methylthiazol-2-yl)pyrimidin-4-amine as an off-white solid (135 mg, 28%). MS (M+1)+=311.0; 1H-NMR (400 MHz, DMSO-d6): δ 8.15 (d, J=6.00 Hz, 1H), 7.32 (s, 1H), 6.51 (d, J=6.00 Hz, 1H), 4.02 (s, 2H), 2.45 (s, 3H), 2.12-1.93 (m, 6H), 1.71-1.65 (m, 2H).

Step 4[IN10882-020-P1]: The Procedure is similar to Step 1[B] in Example-838. 1H-NMR (400 MHz, DMSO-d6): δ 7.31 (s, 1H), 6.85 (d, J=7.60 Hz, 1H), 5.34 (s, 1H), 4.71 (t, J=5.20 Hz, 1H), 3.90 (s, 1H), 3.60-3.35 (m, 5H), 3.90 (s, 1H), 2.41 (s, 4H), 2.15-1.85 (m, 7H), 1.72 (m, 1H), 1.62-1.50 (m, 2H).

Step 4[IN10882-014-P1]: The Procedure is similar to Step 1[B] in Example-838. 1H-NMR (400 MHz, DMSO-d6): δ 7.32 (s, 1H), 6.89 (d, J=7.60 Hz, 1H), 5.35 (s, 1H), 3.88 (s, 1H), 3.40 (s, 4H), 2.41 (s, 3H), 2.50-2.00 (m, 2H), 1.95-1.85 (m, 8H), 1.60-1.50 (m, 2H).

Step 4[IN11030-032-P1]: The Procedure is similar to Step 1[NSSy6629] in Example-839. 1H-NMR (400 MHz, DMSO-d6): δ 7.40 (s, 1H), 7.35 (s, 1H), 5.94 (s, 1H), 4.50-4.35 (m, 4H), 2.50 (s, 4H), 2.18-2.09 (m, 6H), 1.65-1.52 (m, 2H).

Step 4[IN11055-015-P1]: The Procedure is similar to Step 1[NSSy6519] in Example-842. 1H-NMR (400 MHz, DMSO-d6): δ 7.40 (s, 2H), 5.80 (s, 1H), 4.32 (q, J=7.60 Hz, 2H), 3.80 (s, 1H), 2.43 (s, 3H), 2.15-1.85 (m, 6H), 1.60-1.50 (m, 2H), 1.32 (t, J=6.80 Hz, 3H).

Step 4[IN10864-066-P1]: The Procedure is similar to Step 1[B] in Example-838. 1H-NMR (400 MHz, CD3OD): δ 7.21 (s, 1H), 5.65 (s, 1H), 4.40-4.20 (m, 2H), 4.10 (s, 1H), 3.79 (dd, J=3.20, 11.40 Hz, 1H), 3.65 (dd, J=5.60, 11.60 Hz, 1H), 3.15-3.05 (m, 1H), 3.00-2.88 (m, 2H), 2.50 (s, 3H), 2.49 (s, 4H), 2.36 (s, 1H), 2.15-1.85 (m, 7H), 1.68-1.55 (m, 2H).

Step 4[IN10864-060-P1]: The Procedure is similar to Step 1[B] in Example-838. 1H-NMR (400 MHz, DMSO-d6): δ 7.34 (s, 1H), 7.03 (d, J=8.00 Hz, 1H), 5.65 (s, 1H), 4.09 (s, 2H), 3.90 (s, 1H), 3.58-3.34 (m, 1H), 3.31 (s, 4H), 3.05-2.95 (m, 1H), 2.85-2.75 (m, 2H), 2.45 (s, 3H), 2.40-2.38 (m, 5H), 2.10-1.85 (m, 6H), 1.60-1.50 (m, 2H).

Step 4[IN10864-031-P1]: The Procedure is similar to Step 1[A] in Example-838. 1H-NMR (400 MHz, DMSO-d6): δ 7.32 (s, 1H), 6.95 (d, J=7.60 Hz, 1H), 5.64 (s, 1H), 3.89 (s, 1H), 3.51 (s, 4H), 2.72-2.67 (m, 1H), 2.41 (s, 3H), 2.15-1.85 (m, 6H), 1.65-1.50 (m, 2H), 1.00 (d, J=6.00 Hz, 6H).

Step 4[IN10964-007-P1]: The Procedure is similar to Step 1[B] in Example-838. 1H-NMR (400 MHz, DMSO-d6): δ 7.35 (s, 1H), 7.07 (d, J=7.60 Hz, 1H), 5.65 (s, 1H), 4.18-4.02 (m, 2H), 3.85 (d, J=40.00 Hz, 2H), 3.62-3.40 (m, 6H), 2.41 (s, 3H), 2.12-1.85 (m, 6H), 1.60-1.50 (m, 2H), 1.08 (d, J=6.40 Hz, 6H), Step 4[IN11059-047-P1]: The Procedure is similar to Step 2[IN10991-021-P1] in Example-694. 1H-NMR (400 MHz, DMSO-d6): δ 8.40 (s, 1H), 7.51 (s, 1H), 7.45 (s, 1H), 7.37 (s, 1H), 5.87 (s, 1H), 5.46 (s, 2H), 2.43 (s, 3H), 2.12-1.85 (m, 6H), 1.62-1.50 (m, 2H).

Step 4[IN11125-013-P1]: The Procedure is similar to Step 2[IN10991-021-P1] in Example-694. 1H-NMR (400 MHz, DMSO-d6): δ 8.40 (d, J=1.6 Hz, 1H), 7.05 (s, 1H), 6.53 (d, J=2.0 Hz, 1H), 5.72 (s, 1H), 5.60 (s, 2H), 5.29 (bs, 1H), 3.57 (bs, 1H), 2.56 (s, 3H), 2.17-2.04 (m, 4H), 1.98-1.84 (m, 2H), 1.70-1.62 (m, 2H).

Step 4[IN11055-049-P1]: The Procedure is similar to Step 1[B] in Example-838. 1H-NMR (400 MHz, CD3OD): δ 7.21 (s, 1H), 5.41 (s, 1H), 5.40 (s, 1H), 4.05-3.90 (m, 1H), 2.86 (s, 3H), 2.47 (s, 3H), 2.11-1.91 (m, 7H), 1.67-1.62 (m, 2H).

Step 4[IN11055-046-P1]: The Procedure is similar to Step 1[B] in Example-838. 1H-NMR (400 MHz, DMSO-d6): δ 7.32 (s, 1H), 6.90 (d, J=8.00 Hz, 1H), 5.50 (s, 1H), 3.90 (s, 1H), 3.03 (s, 6H), 2.41 (s, 3H), 2.12-1.88 (m, 6H), 1.62-1.50 (m, 2H).

Step 4[IN11055-016-P1]: The Procedure is similar to Step 5[IN10963-068-P1] in Example-694. 1H-NMR (400 MHz, DMSO-d6): δ 7.40 (s, 2H), 5.76 (s, 1H), 5.27-5.25 (m, 1H), 3.80 (s, 1H), 2.33 (s, 3H), 2.15-1.85 (m, 6H), 1.65-1.50 (m, 2H), 1.28 (d, J=12.40 Hz, 6H).

Step 4[IN10864-043-P1]: The Procedure is similar to Step 1[A] in Example-838. 1H-NMR (400 MHz, DMSO-d6): δ 7.33 (d, J=0.8 Hz, 1H), 6.97 (d, J=7.6 Hz, 1H), 5.65 (s, 1H), 3.91-3.88 (m, 1H), 3.71-3.69 (m, 2H), 3.52-3.38 (m, 2H), 3.38 (s, 2H), 2.41 (s, 3H), 2.12-1.91 (m, 6H), 1.61-1.53 (m, 2H), 1.18 (s, 6H).

Step 4[IN10864-034-P1]: The Procedure is similar to Step 1[A] in Example-838. 1H-NMR (400 MHz, DMSO-d6): δ 7.31 (s, 1H), 6.93-6.90 (m, 1H), 5.55 (s, 1H), 3.90 (m, 1H), 3.76-3.62 (m, 8H), 2.41 (s, 3H), 2.06-1.88 (m, 8H), 1.58-1.55 (m, 2H).

Step 4[IN10864-033-P1]: The Procedure is similar to Step 1[A] in Example-838. 1H-NMR (400 MHz, DMSO-d6): δ 7.33 (s, 1H), 6.96 (d, J=8.40 Hz, 1H), 5.71 (s, 1H), 4.97-4.84 (m, 1H), 4.00-3.70 (m, 2H), 3.55-3.36 (m, 2H), 2.42 (s, 7H), 2.15-1.73 (m, 9H), 1.82-1.50 (m, 4H).

Step 4[IN10876-013-P1]: The Procedure is similar to Step 1[A] in Example-838. 1H-NMR (400 MHz, DMSO-d6): δ 7.32 (s, 1H), 6.91 (d, J=7.6 Hz, 1H), 5.66 (s, 1H), 3.96-3.92 (m, 2H), 3.70 (bs, 1H), 2.41 (s, 4H), 2.06-1.94 (m, 9H), 1.72-1.69 (m, 2H), 1.60-1.36 (m, 6H).

Step 4[IN11059-052-P1]: Step a: The Procedure is similar to Step 2[IN10991-021-P1] in Example-694. Step b: The Procedure is similar to Step 3[IN11273-018-P1] in Example-889. 1H-NMR (400 MHz, DMSO-d6): δ 7.45 (bs, 1H), 7.42 (s, 1H), 7.28 (t, J=6.0 Hz, 1H), 5.83 (s, 1H), 4.35 (t, J=5.6 Hz, 2H), 3.36-3.30 (m, 2H), 2.95 (s, 3H), 2.44 (s, 3H), 2.09-1.91 (m, 7H), 1.62-1.56 (m, 2H).

Step 4[IN11039-009-P1]: Step a: The Procedure is similar to Step 2[IN10991-021-P1] in Example-694. Step b: The Procedure is similar to Step 5[NSSy6067] in Example-628. Step c: The Procedure is similar to Step 1[B] in Example-838. 1H-NMR (400 MHz, MeOD): δ 7.26 (s, 1H), 5.78 (s, 1H), 4.41 (t, J=6.00 Hz, 2H), 4.05 (s, 1H), 3.61 (s, 3H), 3.47 (t, J=5.60 Hz, 2H), 2.50 (s, 3H), 2.15-2.00 (m, 6H), 1.70-1.56 (m, 2H).

Step 4[IN10973-025-P1]: The Procedure is similar to Step 1[B] in Example-838. 1H-NMR (400 MHz, DMSO-d6): δ 7.47 (s, 1H), 7.42 (s, 1H), 5.84 (s, 1H), 5.54 (s, 1H), 3.70-3.52 (m, 5H), 3.48-3.30 (m, 3H), 2.43 (s, 3H), 2.30-1.85 (m, 8H), 1.65-1.50 (m, 2H).

Step 4[IN10880-014-P1]: The Procedure is similar to Step 1[B] in Example-838. 1H-NMR (400 MHz, DMSO-d6): δ 7.33 (s, 1H), 6.99 (d, J=8.00 Hz, 1H), 5.66 (s, 1H), 3.88 (s, 1H), 3.53 (s, 4H), 2.41 (s, 3H), 2.38 (s, 4H), 2.22 (s, 3H), 2.10-1.85 (m, 6H), 1.60-1.50 (m, 2H).

Step 4[IN10880-018-P1]: The Procedure is similar to Step 1[B] in Example-838. 1H-NMR (400 MHz, DMSO-d6): δ 7.34 (s, 1H), 7.05 (d, J=8.00 Hz, 1H), 6.41 (s, 1H), 4.11-4.10 (m, 2H), 3.95-3.85 (m, 2H), 3.53-3.48 (m, 1H), 2.91-2.85 (m, 1H), 2.61-2.55 (m, 1H), 2.41 (s, 3H), 2.15-1.85 (m, 6H), 1.60-1.45 (m, 4H), 0.95 (t, J=7.20 Hz, 3H).

Step 4[IN10880-032-P1]: The Procedure is similar to Step 1[A] in Example-838. 1H-NMR (400 MHz, DMSO-d6): δ 7.80 (d, J=7.6 Hz, 1H), 7.33 (s, 1H), 6.93 (d, J=8.0 Hz, 1H), 5.68 (s, 1H), 4.24-4.21 (m, 2H), 3.91-3.81 (m, 2H), 3.01-2.95 (m, 2H), 2.42 (s, 3H), 2.09-1.91 (m, 6H), 1.80 (s, 3H), 1.60-1.55 (m, 2H), 1.36-1.29 (m, 4H).

Step 4[IN10880-033-P1]: The Procedure is similar to Step 1[B] in Example-838. 1H-NMR (400 MHz, DMSO-d6): δ 7.34 (s, 1H), 7.05 (d, J=7.20 Hz, 1H), 6.95 (s, 1H), 5.64 (s, 1H), 4.20 (d, J=12.00 Hz, 1H), 4.03-3.92 (m, 3H), 3.53-3.44 (m, 2H), 3.07 (t, J=5.20 Hz, 2H), 2.94-2.89 (m, 1H), 2.62-2.56 (m, 1H), 2.42 (s, 3H), 2.15-1.85 (m, 6H), 1.62-1.52 (m, 2H), 1.40 (s, 9H).

Step 4[IN10882-040-P1]: The Procedure is similar to Step 1[NSSy6909] in Example-839. 1H-NMR (400 MHz, CD3OD): δ 7.58 (s, 1H), 5.70 (s, 1H), 5.00-4.94 (m, 1H), 4.33-4.29 (m, 1H), 3.73-3.63 (m, 3H), 2.55 (s, 3H), 2.17-1.90 (m, 7H), 1.74-1.65 (m, 2H).

Step 4[IN10882-043-P1]: The Procedure is similar to Step 1[NSSy6909] in Example-3. 1H-NMR (400 MHz, CD3OD): δ 7.61 (s, 1H), 5.59 (s, 1H), 5.02-4.89 (m, 2H), 4.22-4.18 (m, 1H), 3.98-3.92 (m, 1H), 3.92-3.66 (m, 1H), 3.07 (s, 3H), 2.55 (m, 3H), 2.17-1.95 (m, 6H), 1.76-1.66 (m, 2H).

Step 4[IN10881-099-P1]: The Procedure is similar to Step 1[NSSy6909] in Example-839. 1H-NMR (400 MHz, DMSO-d6): δ 7.34 (d, J=1.20 Hz, 1H), 7.07 (d, J=8.00 Hz, 1H), 5.63 (s, 1H), 4.50-4.42 (m, 1H), 3.96-3.90 (m, 2H), 3.70-3.65 (m, 1H), 3.55-3.46 (m, 2H), 3.29 (s, 3H), 3.08-3.07 (m, 1H), 2.41 (s, 3H), 2.09-1.92 (m, 7H), 1.57-1.55 (m, 2H).

Step 4[IN10881-090-P1]: The Procedure is similar to Step 1[NSSy6909] in Example-839. 1H-NMR (400 MHz, DMSO-d6): δ 7.33 (s, 1H), 7.05 (d, J=7.20 Hz, 1H), 5.91 (s, 1H), 3.90 (s, 1H), 3.08 (s, 3H), 2.41 (s, 3H), 2.10-1.85 (m, 6H), 1.62-1.50 (m, 2H), 1.35 (s, 1H), 0.86 (d, J=6.00 Hz, 2H), 0.65 (s, 2H).

Step 4[IN10881-092-P1]: The Procedure is similar to Step 1[B] in Example-838. 1H-NMR (400 MHz, DMSO-d6): δ 7.35 (s, 1H), 7.10 (d, J=8.00 Hz, 1H), 5.66 (s, 1H), 4.30 (s, 1H), 4.11-4.08 (m, 1H), 3.95 (d, J=10.00 Hz, 2H), 3.70-3.40 (m, 3H), 2.90 (t, J=10.80 Hz, 2H), 2.80-2.60 (m, 3H), 2.41 (s, 3H), 2.06-1.91 (m, 7H), 1.60-1.49 (m, 2H), 1.05 (s, 7H).

Step 4[IN10881-021-P1]: The Procedure is similar to Step 1[A] in Example-838. 1H-NMR (400 MHz, DMSO-d6): δ 7.30 (s, 1H), 6.92 (d, J=8.0 Hz, 1H), 5.64 (s, 1H), 3.88 (m, 1H), 3.55 (m, 4H), 2.41 (s, 3H), 2.08-1.91 (m, 6H), 1.63-1.53 (m, 8H).

Step 4[IN11140-052-P1]: Step a: The Procedure is similar to Step 1[B] in Example-838. Step b: The Procedure is similar to Step 4[NSSy6067] in Example-628. 1H-NMR (400 MHz, DMSO-d6): δ 7.54 (bs, 1H), 7.48-7.45 (m, 2H), 5.88 (m, 1H), 5.43 (s, 2H), 4.10 (m, 1H), 2.45 (s, 3H), 2.08-1.93 (m, 6H), 1.61-1.56 (m, 2H).

Step 4[IN11079-014-P1]: The Procedure is similar to Step 5[IN10963-068-P1] in Example-697. 1H-NMR (400 MHz, MeOD): δ 7.41 (s, 1H), 5.82 (s, 1H), 5.53 (s, 1H), 3.96-3.92 (m, 1H), 3.88-3.75 (m, 3H), 2.43 (s, 3H), 2.30-2.20 (m, 4H), 2.15-1.85 (m, 6H), 1.60-1.50 (m, 2H).

Step 4[IN11079-007-P1]: The Procedure is similar to Step 5[IN10963-068-P1] in Example-697. 1H-NMR (400 MHz, DMSO-d6): δ 7.40 (s, 2H), 5.81 (s, 1H), 5.20 (s, 1H), 3.86 (t, J=4.80 Hz, 2H), 3.51 (t, J=9.20 Hz, 2H), 2.43 (s, 3H), 2.12-1.85 (m, 9H), 1.55-1.66 (m, 4H).

Step 4[IN11079-033-P1]: The Procedure is similar to Step 5[IN10963-068-P1] in Example-697. 1H-NMR (400 MHz, DMSO-d6): δ 7.55 (s, 1H), 7.42 (s, 1H), 5.85 (s, 1H), 5.59 (t, J=5.60 Hz, 1H), 4.89 (t, J=6.80 Hz, 2H), 4.58 (t, J=6.00 Hz, 2H), 3.95 (s, 1H), 2.43 (s, 3H), 2.15-1.85 (m, 6H), 1.52-1.48 (m, 2H).

Step 4[IN11054-039-P1]: The Procedure is similar to Step 1[IN10965-089-P1] in Example-705. 1H-NMR (400 MHz, CDCl3): δ 7.03 (s, 1H), 6.15 (s, 1H), 5.19 (bs, 1H), 3.66 (bs, 1H), 2.55 (s, 6H), 2.18-2.00 (m, 4H), 1.99-1.86 (m, 2H), 1.70-1.65 (m, 2H).

Step 4[IN11054-046-P2]: The Procedure is similar to Step 3[NSSy7062] in Example-623. 1H-NMR (400 MHz, DMSO-d6): δ 8.18 (d, J=6.80 Hz, 1H), 7.49 (s, 1H), 7.03 (s, 1H), 4.20-4.15 (m, 1H), 2.82 (s, 3H), 2.45 (s, 3H), 2.07-1.96 (m, 6H), 1.66-1.63 (m, 2H).

Step 4[IN11054-046-P1]: The Procedure is similar to Step 3[NSSy7062] in Example-623. 1H-NMR (400 MHz, DMSO-d6): δ 8.71 (d, J=9.20 Hz, 1H), 7.66 (s, 1H), 7.37 (s, 1H), 4.00 (s, 1H), 3.90 (s, 3H), 2.55 (s, 3H), 2.15-1.80 (m, 8H).

Step 4[IN10881-023-P2]: The Procedure is similar to Step 1[A] in Example-838. 1H-NMR (400 MHz, DMSO-d6): δ 7.33 (s, 1H), 6.92 (d, J=7.6 Hz, 1H), 5.64 (s, 1H), 4.92 (d, J=1.6 Hz, 1H), 4.17 (m, 1H), 3.98-3.95 (m, 2H), 3.48-3.46 (m, 1H), 2.98-2.93 (m, 1H), 2.78-2.73 (m, 1H), 2.42 (s, 3H), 2.06-1.92 (m, 6H), 1.74-1.73 (m, 2H), 1.57-1.54 (m, 2H), 1.41-1.39 (m, 2H).

Step 4[IN10881-020-P1]: The Procedure is similar to Step 1[A] in Example-838. 1H-NMR (400 MHz, DMSO-d6): δ 7.32 (s, 1H), 6.93 (d, J=7.60 Hz, 1H), 5.67 (s, 1H), 4.32 (d, J=11.60 Hz, 2H), 3.89 (s, 1H), 2.84 (t, J=12.40 Hz, 2H), 2.42 (s, 4H), 2.22 (s, 6H), 2.15-1.80 (m, 8H), 1.62-1.50 (m, 2H), 1.42-1.35 (m, 2H).

Step 4[IN10881-025-P1]: The Procedure is similar to Step 1[A] in Example-838. 1H-NMR (400 MHz, DMSO-d6): δ 7.35 (s, 1H), 7.06 (d, J=8.00 Hz, 1H), 5.66 (s, 1H), 4.87 (t, J=5.20 Hz, 1H), 4.20 (s, 1H), 3.95 (d, J=9.20 Hz, 2H), 3.55-3.40 (m, 4H), 2.91-2.86 (m, 1H), 2.70-2.60 (m, 1H), 2.42 (s, 3H), 2.15-1.85 (m, 6H), 1.60-1.50 (m, 2H).

Step 4[IN10881-027-P1]: The Procedure is similar to Step 1[A] in Example-838. 1H-NMR (400 MHz, DMSO-d6): δ 7.50 (s, 1H), 7.43 (s, 1H), 5.83 (s, 1H), 4.19 (t, J=5.60 Hz, 2H), 3.86-3.82 (m, 1H), 3.70 (d, J=11.20 Hz, 1H), 3.50-3.40 (m, 1H), 3.28-3.23 (m, 1H), 3.15 (s, 1H), 2.90-2.80 (m, 2H), 2.44 (s, 3H), 2.09-1.90 (m, 7H), 1.65-1.50 (m, 2H), 1.34 (s, 1H).

Step 4[IN10987-056-P1]: Step a: The Procedure is similar to Step 1[A] in Example-838. Step b: The Procedure is similar to Step 4[NSSy6711] in Example-854. 1H-NMR (400 MHz, DMSO-d6): δ 7.32 (s, 1H), 6.92 (d, J=7.20 Hz, 1H), 5.35 (s, 1H), 4.70 (s, 1H), 3.85 (s, 1H), 3.47 (s, 2H), 3.03 (d, J=148.40 Hz, 1H), 2.75 (d, J=60.00 Hz, 1H), 2.41 (s, 4H), 2.30 (s, 3H), 2.15-1.82 (m, 7H), 1.68-1.50 (m, 3H).

Step 4[IN10987-050-P1]: Step a: The Procedure is similar to Step 1[A] in Example-838. Step b: The Procedure is similar to Step 5[NSSy6067] in Example-628. 1H-NMR (400 MHz, DMSO-d6): δ 7.31 (s, 1H), 6.86 (d, J=7.60 Hz, 1H), 5.35 (s, 1H), 5.30 (s, 1H), 4.70 (s, 1H), 3.90 (s, 1H), 3.66 (s, 1H), 3.38 (s, 1H), 2.90 (d, J=8.80 Hz, 2H), 2.77 (d, J=9.20 Hz, 1H), 2.41 (s, 3H), 2.06-1.91 (m, 6H), 1.57-1.50 (m, 4H).

Step 4[IN10880-029-P1]: The Procedure is similar to Step 3[NSSy5933] in Example-808. 1H-NMR (400 MHz, DMSO-d6): δ 8.32 (s, 1H), 7.52 (s, 1H), 6.95 (s, 1H), 4.08 (s, 1H), 2.50 (s, 3H), 2.11-1.88 (m, 6H), 1.70-1.52 (m, 2H).

Step 4[IN11218-030-P1]: The Procedure is similar to Step 2[IN11250-007-P1] in Example-620. 1H-NMR (400 MHz, DMSO-d6): δ 8.17 (s, 2H), 7.72 (s, 1H), 7.60-7.50 (m, 3H), 7.48 (s, 1H), 6.98 (s, 1H), 4.15 (s, 1H), 2.47 (s, 3H), 2.15-1.90 (m, 6H), 1.70-1.55 (m, 2H).

Step 4[IN11196-080-P1]: The Procedure is similar to Step 1[H] in Example-838. 1H-NMR (400 MHz, DMSO-d6): δ 8.72 (s, 1H), 8.41 (d, J=8.00 Hz, 1H), 8.03 (t, J=6.40 Hz, 1H), 7.85 (s, 1H), 7.55-7.52 (m, 2H), 7.46 (s, 1H), 4.19 (s, 1H), 2.48 (s, 3H), 2.15-1.90 (m, 6H), 1.62-1.60 (m, 2H).

Example-656

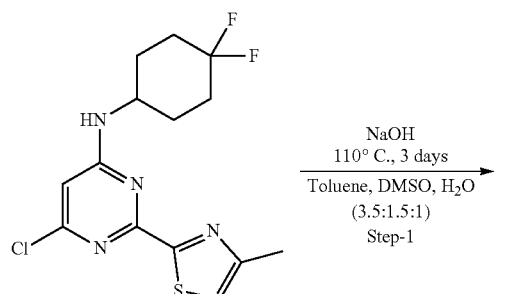

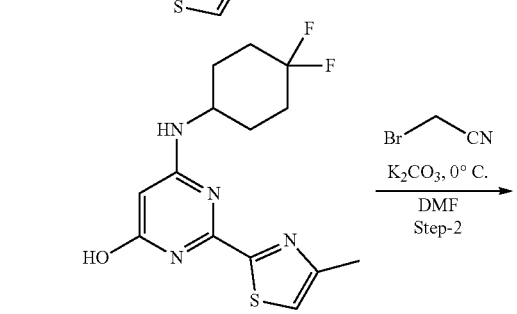

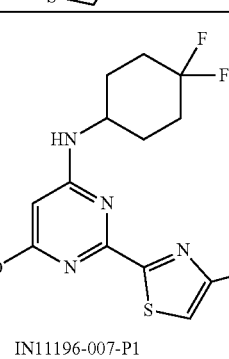

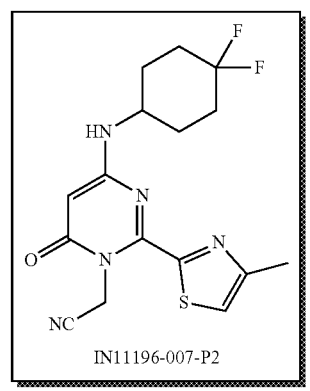

Step 1: To a stirred solution of 6-chloro-N-(4,4-difluorocyclohexyl)-2-(4-methylthiazol-2-yl)pyrimidin-4-amine (0.3 g, 0.87 mmol) in mixture of solvents Toluene:DMSO:Water (3.5:1.5:1) was added sodium hydroxide (0.14 g, 3.48 mmol). The reaction mixture was stirred at 110° C. for 24 h. Added 4 eq of sodium hydroxide and stirred at 110° C. for 48 h. The reaction mixture was diluted with water (50 mL), acidified with 1N HCl and extracted with ethyl acetate (2×25 mL). The combined organics were dried over sodium sulfate, filtered and evaporated to afford 6-((4,4-difluorocyclohexyl)amino)-2-(4-methylthiazol-2-yl)pyrimidin-4-ol as an off-white solid (0.17 g, 59%). MS (M+1)+=327.2.

Step 2[IN11196-007-P1 and IN11196-007-P2]: The procedure is similar to Step 1[A] in Example-838. 0.16 g of 6-((4,4-difluorocyclohexyl)amino)-2-(4-methylthiazol-2-yl)pyrimidin-4-ol gave 2-((6-((4,4-difluorocyclohexyl)amino)-2-(4-methylthiazol-2-yl)pyrimidin-4-yl)oxy)acetonitrile as an off-white solid (0.03 g, 16%). MS (M+1)+=366.1; 1H-NMR (400 MHz, DMSO-d6): δ 7.66 (s, 1H), 7.47 (s, 1H), 5.95 (s, 1H), 5.25 (s, 2H), 4.01 (s, 1H), 2.45 (s, 3H), 2.12-1.85 (m, 6H), 1.62-1.52 (m, 2H) and 2-(4-((4,4-difluorocyclohexyl)amino)-2-(4-methylthiazol-2-yl)-6-oxopyrimidin-1(6H)-yl)acetonitrile as white solid (0.04 g, 22%). MS (M+1)+=366.2; 1H-NMR (400 MHz, DMSO-d6): δ 7.72 (s, 1H), 7.38 (bs, 1H), 5.57 (s, 2H), 5.25 (s, 1H), 3.51 (s, 1H), 3.41 (s, 3H), 2.08-1.93 (m, 6H), 1.61-1.53 (m, 2H).

Example-657

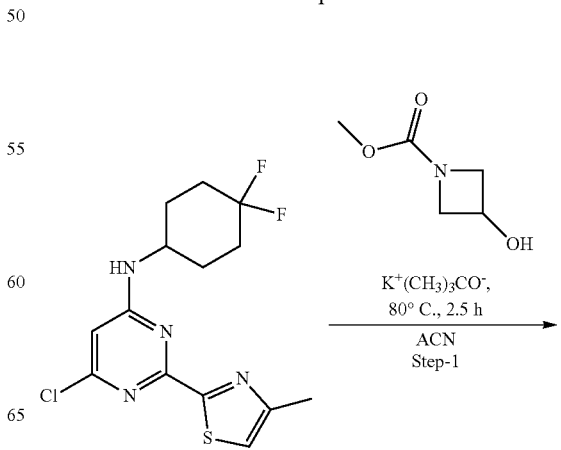

857

-continued

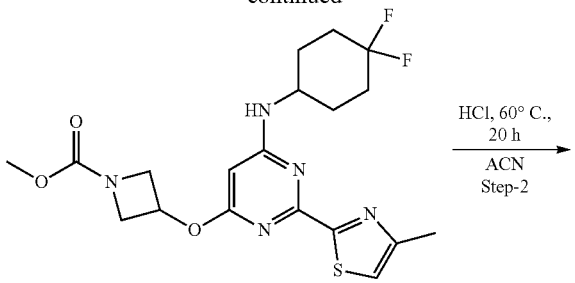

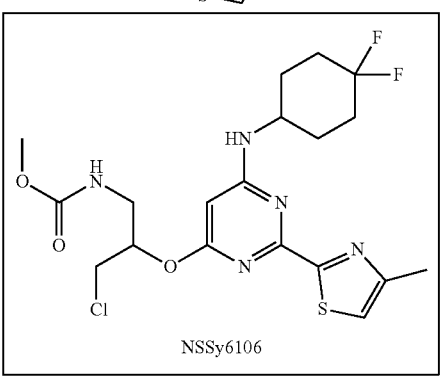

Step 1: The Procedure is similar to Step 1[B] in Example-838. 25 g of 6-chloro-N-(4,4-difluorocyclohexyl)-2-(4-methylthiazol-2-yl)pyrimidin-4-amine gave methyl 3-((6-((4,4-difluorocyclohexyl)amino)-2-(4-methylthiazol-2-yl)pyrimidin-4-yl)oxy) azetidine-1-carboxylate (16 g, 50%). MS (M+1)+=440.

Step 2[NSSy6106]: To a solution of acetonitrile and hydrochloric acid (0.1N) was added methyl 3-((6-((4,4-difluorocyclohexyl)amino)-2-(4-methylthiazol-2-yl)pyrimidin-4-yl)oxy) azetidine-1-carboxylate (0.6 g, 1.36 mmol) and the reaction mixture was heated at 60° C. for 20 h. The reaction mixture was concentrated to reduce the volume, then cooled at −78° C. and dried in freeze drier to afford methyl (3-chloro-2-((6-((4,4-difluorocyclohexyl)amino)-2-(4-methylthiazol-2-yl)pyrimidin-4-yl)oxy)propyl)carbamate as yellow solid (0.3 g, 45%). MS (M+1)+=476.2; 1H-NMR (400 MHz, DMSO-d6): δ 9.72 (d, J=6.4 Hz, 0.5H), 9.33 (d, J=8.4 Hz, 0.5H), 7.96 (s, 0.5H), 7.91 (s, 0.5H), 7.61 (s, 1H), 7.27 (t, J=51.2 Hz, 0.17H), 6.67 (s, 0.5H), 6.37 (s, 0.5H), 5.36-5.28 (m, 1H), 5.11-5.06 (m, 1H), 4.72-4.65 (m, 1H), 4.17 (s, 0.5H), 3.80 (bs, 0.5H), 3.54 (s, 5H), 2.56 (s, 3H), 2.25-1.85 (m, 6H), 1.78-1.56 (m, 2H).

Example-658

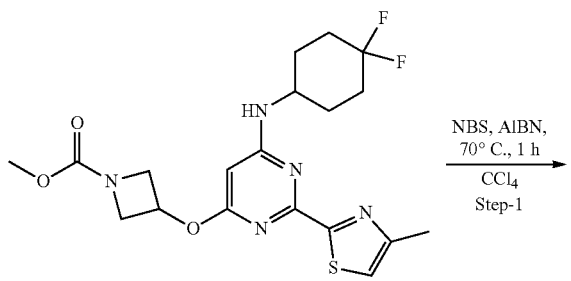

858

-continued

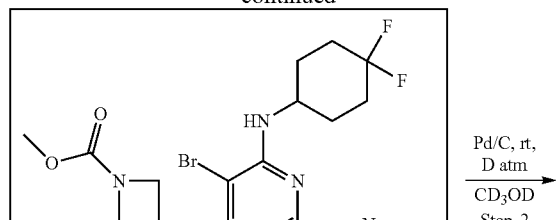

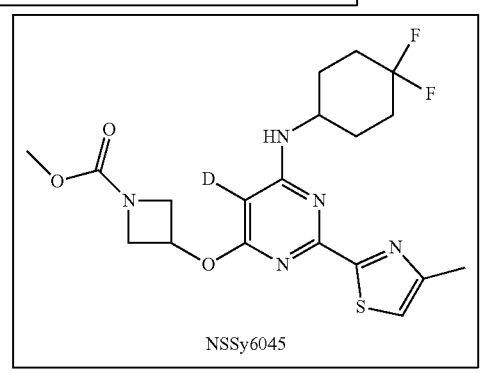

Step 1[NSSy5868]: To a solution of methyl 3-((6-((4,4-difluorocyclohexyl)amino)-2-(4-methylthiazol-2-yl)pyrimidin4yl)oxy) azetidine-1-carboxylate (2.3 g, 5.23 mmol) in carbon tetrachloride was added 2,2-Azobisisobutyronitrile (AIBN) (0.08 g, 0.52 mmol) followed by N-bromosuccinimide (0.93 g, 5.23 mmol) and the reaction mixture was heated at 70° C. for 1 h. The reaction mixture was diluted with water, extracted with dichloromethane. The combined organic layer was washed with water and brine solution, dried over sodium sulfate. The reaction mixture was filtered and concentrated under reduced pressure to afford crude and which was purified by Reveleris flash system instrument by using 45% ethyl acetate in pet ether as eluent afford methyl 3-((5-bromo-6-((4,4-difluorocyclohexyl)amino)-2-(4-methylthiazol-2-yl)pyrimidin-4-yl)oxy) azetidine-1-carboxylate as pale yellow solid (2.6 g, 82%). MS (M, M+2)+=518, 520; 1H-NMR (400 MHz, DMSO-d6): δ 7.48 (s, 1H), 6.95 (s, 1H), 5.40-5.36 (m, 1H), 4.39-4.36 (m, 2H), 4.20-4.17 (m, 1H), 3.99-3.96 (m, 2H), 3.58 (s, 3H), 2.46 (s, 3H), 2.10-1.91 (m, 6H), 1.67-1.62 (m, 2H).

Step 2[NSSy6045]: To a solution of methyl 3-((5-bromo-6-((4,4-difluorocyclohexyl)amino)-2-(4-methylthiazol-2-yl)pyrimidin-4-yl)oxy) azetidine-1-carboxylate (0.2 g, 0.38 mmol) in CD3OD was purged with nitrogen for 2 min, then added palladium carbon and stirred under deuterium atmosphere at 5 kg pressure in tiny clave for 16 h. The reaction mixture was filtered through celite bed, washed with ethyl acetate. The filtrate was concentrated under reduced pressure to afford crude which was purified by Reveleris flash system instrument using 40% ethyl acetate in pet ether as eluent to afford Deuterated methyl 3-((6-((4,4-difluorocyclohexyl)amino)-2-(4-methylthiazol-2-yl)pyrimidin-4-yl-5-d)oxy) azetidine-1-carboxylate as pale yellow solid (70 mg, 36%). MS (M+1)+=441.0; 1H-NMR (400 MHz, DMSO-d6): δ 7.62 (bs, 1H), 7.43 (s, 1H), 5.35 (s, 1H), 4.44-4.35 (m, 2H), 4.00-3.85 (m, 2H), 3.58 (s, 3H), 2.43 (s, 3H), 2.30-1.80 (m, 11H), 1.60-1.50 (m, 2H).

Example-659

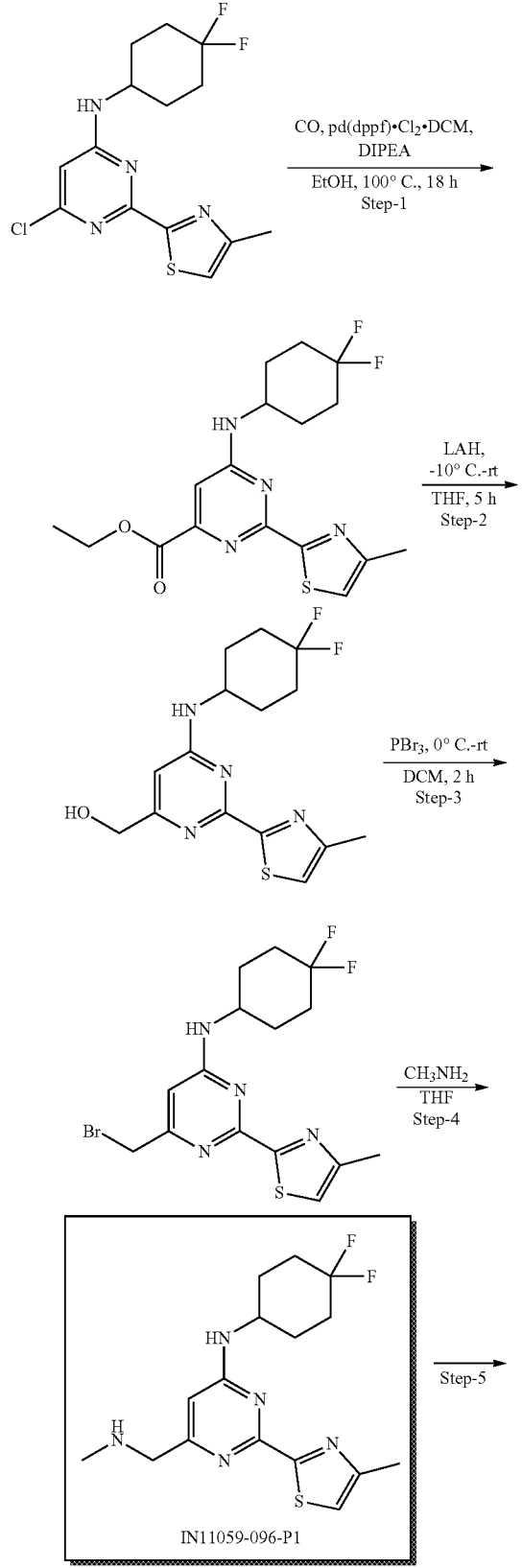

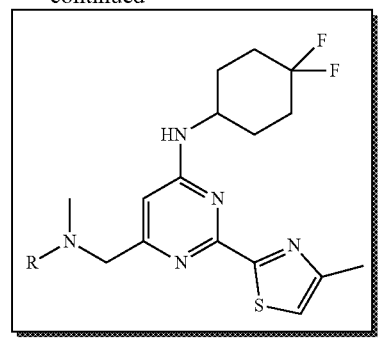

R=

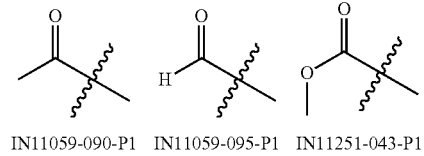

| IN11059-090-P1 | IN11059-095-P1 | IN11251-043-P1 |

Step 1: To stirred solution of 6-chloro-N-(4,4-difluorocyclohexyl)-2-(4-methylthiazol-2-yl)pyrimidin-4-amine (4 g, 11.62 mmol) in ethanol (50 mL) was added [1,1'-Bis(diphenylphosphino)ferrocene]dichloropalladium(II), complex with DCM (0.95 g, 1.16 mmol) and N, N-Diisopropylethylamine (12.2 mL, 69.72 mmol) in a Steel bomb and purged with N2 for about 10 min. The Steel bomb was sealed and filled with carbon monoxide gas at 100 Psi and the reaction mixture was heated to 100° C. for 18 h. The reaction mixture was cooled to rt, degassed the steel bomb and reaction mixture was concentrated under reduced pressure to obtain brown liquid and which was purified by column chromatography using 45% ethyl acetate in hexane as eluent to afford ethyl 6-((4,4-difluorocyclohexyl)amino)-2-(4-methylthiazol-2-yl)pyrimidine-4-carboxylate as an yellow solid (2 g, 45%). MS (M+1)+=383.1.

Step 2: The Procedure is similar to Step 4[NSSy6711] in Example-854. 4 g of ethyl 6-((4,4-difluorocyclohexyl)amino)-2-(4-methylthiazol-2-yl)pyrimidine-4-carboxylate gave (6-((4,4-difluorocyclohexyl)amino)-2-(4-methylthiazol-2-yl)pyrimidin-4-yl) methanol as an off-white solid (2 g, 45%). MS (M+1)+=383.1.

Step 3: To a stirred solution of (6-((4,4-difluorocyclohexyl)amino)-2-(4-methylthiazol-2-yl)pyrimidin-4-yl) methanol (1 g, 2.94 mmol) in dichloromethane (50 mL) at 0° C. was added Phosphorus tribromide (1.4 mL, 14.70 mmol) dropwise for about 5 min and the reaction mixture was warmed to rt and stirred for about 2 h. The reaction mixture was poured in ice cold water (150 mL) and extracted with DCM (3×150 mL). The combined organic layer was washed with saturated aqueous sodium bicarbonate solution (3×75 mL) followed by brine (100 mL) and dried over sodium sulfate and evaporated to dryness to afford 6-(bromomethyl)-N-(4,4-difluorocyclohexyl)-2-(4-methylthiazol-2-yl)pyrimidin-4-amine as an off-white solid (0.69 g, 58%). MS (M+1)+=405.0.

Step 4[IN11059-096-P1]: To a stirred 6-(bromomethyl)-N-(4,4-difluorocyclohexyl)-2-(4-methylthiazol-2-yl)pyrimidin-4-amine (0.69 g, 1.72 mmol) in a Sealed tube was added Methylamine solution (2.0 M in THF) (17.2 mL, 34.4 mmol) at rt and the reaction mixture sealed and stirred at rt for about 16 h. The reaction was then concentrated under reduced pressure and the product was washed with n-pentane and dried in vacuum to afford N-(4,4-difluorocyclohexyl)-6-((methylamino)methyl)-2-(4-methylthiazol-2-yl)pyrimidin-4-amine as an off-white solid (0.41 g, 54%). MS (M+1)+=354; 1H-NMR (400 MHz, DMSO-d6): δ 7.56 (s, 1H), 7.38 (s, 1H), 6.56 (s, 1H), 4.09 (s, 1H), 3.57 (s, 2H), 2.49 (s, 3H), 2.33 (s, 4H), 2.15-1.85 (m, 6H), 1.65-1.51 (m, 2H).

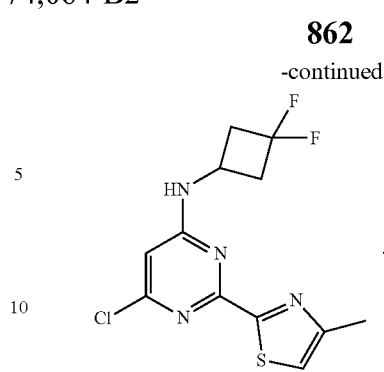

TABLE 33

| | | Step 5: | |
|---|---|---|---|
| Compound No | R | Condition | Yield (%) |
| IN11059-090-P1 | (acetyl group) | Acetyl chloride, TEA, DCM, 0° C.-rt, 30 min | 41 |
| IN11059-095-P1 | (formyl group) | Ethylformate, DIPEA, THF, 70° C., 16 h | 23 |
| IN11251-043-P1 | (methoxycarbonyl group) | Methyl Chloroformate, TEA, DCM, 0° C.-rt, 2 h | 20 |

[IN11059-090-P1]: The procedure is similar to Step 3[IN11273-018-P1] in Example-889. MS (M+1)+=396.1; 1H-NMR (400 MHz, DMSO-d6, 100° C.): δ 7.32 (s, 2H), 6.34 (s, 1H), 4.43 (s, 2H), 4.05 (s, 1H), 3.10 (s, 3H), 2.46 (s, 3H), 2.09 (s, 3H), 2.10-1.85 (m, 6H), 1.75-1.62 (m, 2H).

[IN11059-095-P1]: The procedure is similar to Step 3[IN11273-018-P1] in Example-889. MS (M+1)+=382.1; 1H-NMR (400 MHz, DMSO-d6): δ 8.22 (d, J=4.4 Hz, 1H), 7.70-7.64 (bs, 1H), 7.41 (s, 1H), 6.33 (bs, 1H), 4.41 (s, 1H), 4.34 (s, 1H), 4.11 (bs, 1H), 3.01 (s, 1H), 2.77 (s, 2H), 2.44 (s, 3H), 2.09-1.96 (m, 6H), 1.62-1.59 (m, 2H).

[IN11251-043-P1]: The procedure is similar to Step 3[IN11273-018-P1] in Example-889. MS (M+1)+=411.2; 1H-NMR (400 MHz, DMSO-d6): δ 7.29 (d, J=0.80 Hz, 1H), 7.08 (s, 1H), 6.86 (d, J=6.40 Hz, 1H), 6.39 (s, 1H), 4.37 (s, 2H), 3.90 (s, 1H), 3.66 (s, 3H), 2.86 (s, 3H), 2.41 (s, 3H), 2.09-1.90 (m, 6H), 1.63-1.56 (m, 2H).

Example-660

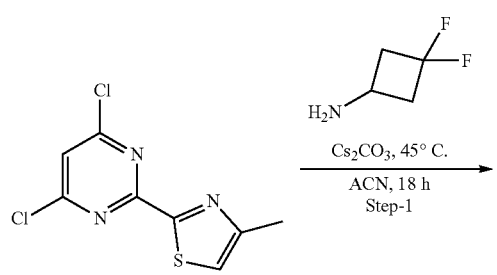

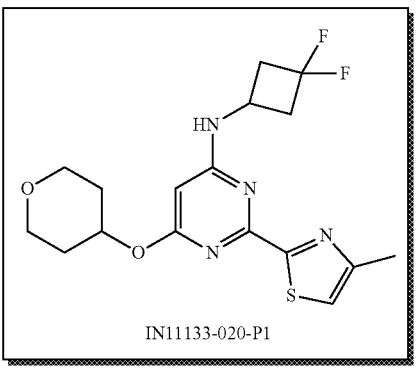

Step 1: The Procedure is similar to Step 1[B] in Example-838. 0.3 g of 2-(4,6-dichloropyrimidin-2-yl)-4-methylthiazole gave 6-chloro-N-(3,3-difluorocyclobutyl)-2-(4-methylthiazol-2-yl)pyrimidin-4-amine as an off-white solid (0.22 g, 57%). MS (M+1)+=317.

Step 2[IN11133-020-P1]: The Procedure is similar to Step 1[B] in Example-838. 0.14 g of 6-chloro-N-(3,3-difluorocyclobutyl)-2-(4-methylthiazol-2-yl)pyrimidin-4-amine gave N-(3,3-difluorocyclobutyl)-2-(4-methylthiazol-2-yl)-6-((tetrahydro-2H-pyran-4-yl)oxy) pyrimidin-4-amine as an off-white solid (0.02 g, 8%). MS (M+1)+=383.1; 1H-NMR (400 MHz, CD3OD): δ 7.27 (d, J=0.80 Hz, 1H), 5.73 (s, 1H), 5.44-5.40 (m, 1H), 4.30 (s, 1H), 4.00-3.90 (m, 2H), 3.70-3.60 (m, 2H), 3.12-2.98 (m, 2H), 2.65-2.52 (m, 2H), 2.50 (s, 3H), 2.10-2.00 (m, 2H), 1.80-1.68 (m, 2H).

Example-661

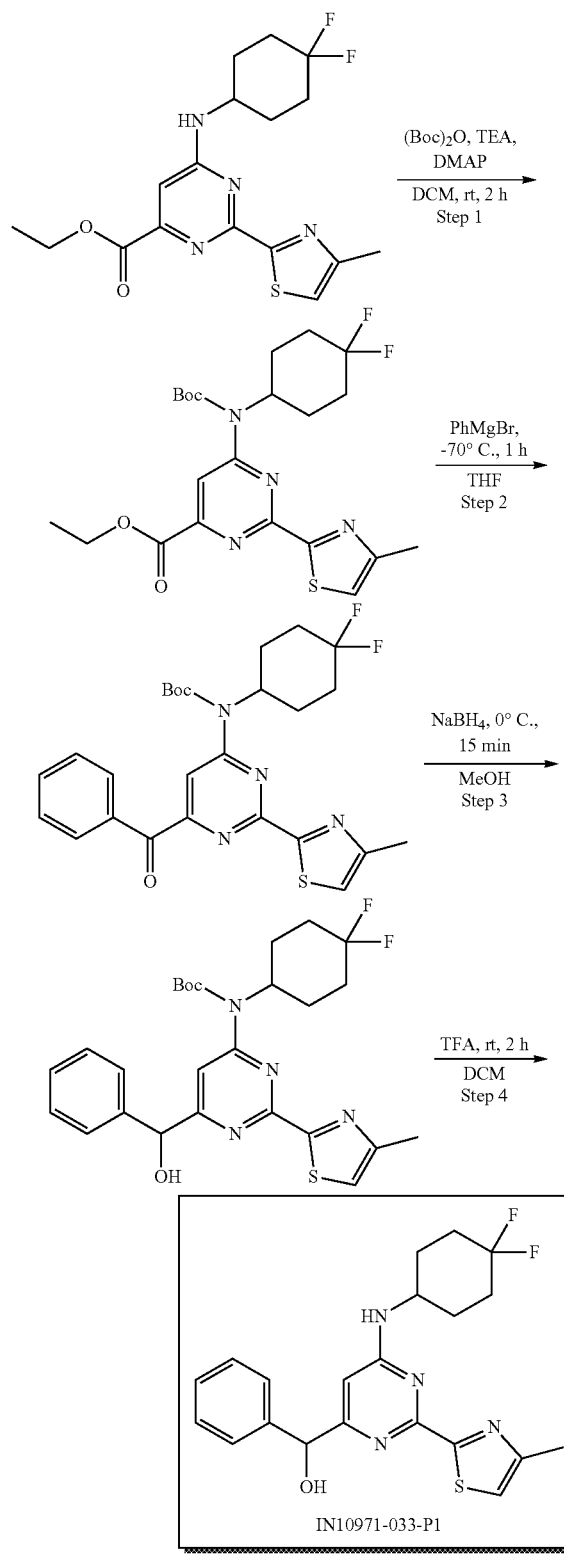

Step 1: The Procedure is similar to Step 2[IN11218-026-P1] in Example-613. 0.1 g of ethyl 6-((4,4-difluorocyclohexyl)amino)-2-(4-methylthiazol-2-yl)pyrimidine-4-carboxylate gave ethyl 6-((tert-butoxycarbonyl) (4,4-difluorocyclohexyl)amino)-2-(4-methylthiazol-2-yl)pyrimidine-4-carboxylate as an off-white solid (0.08 g, 63%). MS (M+1)+=483.

Step 2: The Procedure is similar to Step 4[NSSy6464] in Example-869. 0.08 g of ethyl 6-((tert-butoxycarbonyl) (4,4-difluorocyclohexyl)amino)-2-(4-methylthiazol-2-yl)pyrimidine-4-carboxylate gave tert-butyl (6-benzoyl-2-(4-methylthiazol-2-yl)pyrimidin-4-yl) (4,4-difluorocyclohexyl) carbamate as an off-white solid (0.07 g, 82%). MS (M+1)+= 515.

Step 3: The Procedure is similar to Step 2[NSSy6931] in Example-21. 0.07 g of tert-butyl (6-benzoyl-2-(4-methylthiazol-2-yl)pyrimidin-4-yl) (4,4-difluorocyclohexyl) carbamate gave tert-butyl (4,4-difluorocyclohexyl) (6-(hydroxy (phenyl)methyl)-2-(4-methylthiazol-2-yl)pyrimidin-4-yl) carbamate as an off-white solid (0.06 g, 85%). MS (M+1)+= 517.

Step 4[IN10971-033-P1]: The Procedure is similar to Step 5[NSSy6067] in Example-628. 0.06 g of tert-butyl (4,4-difluorocyclohexyl) (6-(hydroxy (phenyl)methyl)-2-(4-methylthiazol-2-yl)pyrimidin-4-yl) carbamate gave (6-((4,4-difluorocyclohexyl)amino)-2-(4-methylthiazol-2-yl) pyrimidin-4-yl) (phenyl) methanol as an off-white solid (0.035 g, 72%). MS (M+1)+=417; 1H-NMR (400 MHz, CD3OD): δ 7.46 (d, J=7.2 Hz, 2H), 7.34-7.30 (m, 2H), 7.26-7.22 (m, 2H), 6.53 (s, 1H), 5.60 (s, 1H), 4.22 (bs, 1H), 2.60 (s, 3H), 2.07-1.89 (m, 7H), 1.65-1.60 (m, 3H).

Example-662

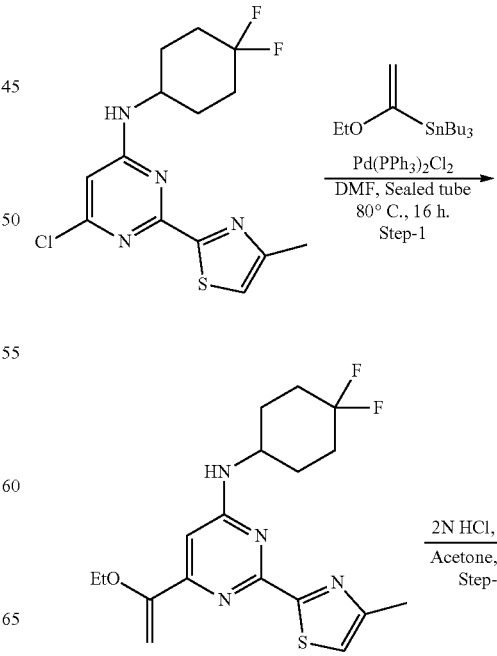

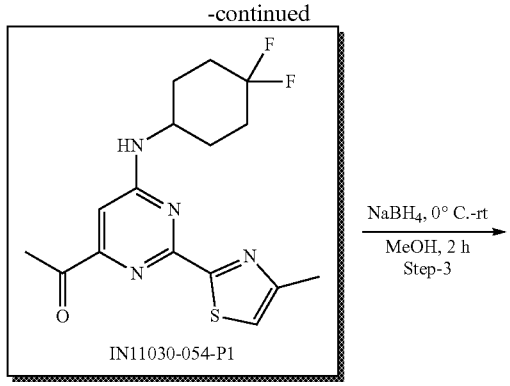
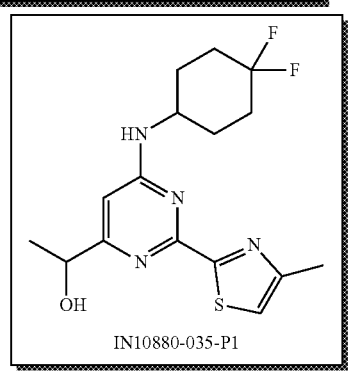
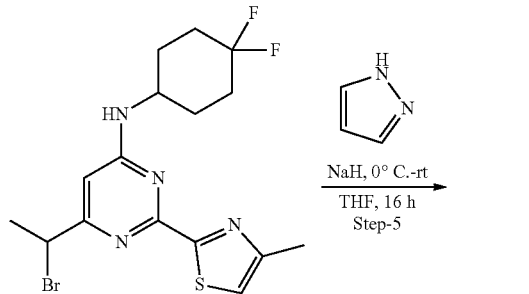
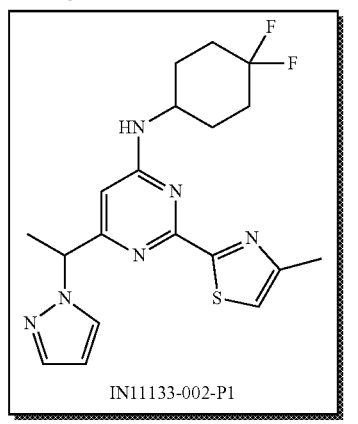

Step 1: The Procedure is similar to Step 1[H] in Example-838. 2.5 g of 6-chloro-N-(4,4-difluorocyclohexyl)-2-(4-methylthiazol-2-yl)pyrimidin-4-amine gave N-(4,4-difluorocyclohexyl)-6-(1-ethoxyvinyl)-2-(4-methylthiazol-2-yl)pyrimidin-4-amine as an off-white solid (1.9 g, 69%). MS (M+1)+=381.

Step 2[IN11030-054-P1]: The Procedure is similar to Step 1[NSSy6697] in Example-873. 1.8 g of N-(4,4-difluorocyclohexyl)-6-(1-ethoxyvinyl)-2-(4-methylthiazol-2-yl)pyrimidin-4-amine gave 1-(6-((4,4-difluorocyclohexyl)amino)-2-(4-methylthiazol-2-yl)pyrimidin-4-yl) ethan-1-one as an off-white solid (1.35 g, 81%). MS (M+1)+=353.1; 1H-NMR (400 MHz, DMSO-d6): δ 8.00 (d, J=6.00 Hz, 1H), 7.47 (d, J=1.2 Hz, 1H), 6.95 (s, 1H), 4.15 (bs, 1H), 2.60 (s, 3H), 2.47 (s, 3H), 2.07-1.93 (m, 6H), 1.67-1.59 (m, 2H).

Step 3[IN10880-035-P1]: The Procedure is similar to Step 2[NSSy6931] in Example-21. 1.4 g of 1-(6-((4,4-difluorocyclohexyl)amino)-2-(4-methylthiazol-2-yl)pyrimidin-4-yl) ethan-1-one gave 1-(6-((4,4-difluorocyclohexyl)amino)-2-(4-methylthiazol-2-yl)pyrimidin-4-yl) ethan-1-ol as an off-white solid (1.2 g, 85%). MS (M+1)+=355.2; 1H-NMR (400 MHz, DMSO-d6): δ 7.60 (s, 1H), 7.38 (s, 1H), 6.64 (s, 1H), 5.40 (s, 1H), 4.51 (d, J=6.40 Hz, 1H), 4.11 (s, 1H), 2.15-1.88 (m, 6H), 1.65-1.55 (m, 2H), 1.48-1.42 (m, 3H), 2.32 (s, 3H).

Step 4: The Procedure is similar to Step 3[IN11059-090-P1] in Example-659. 1.1 g of 1-(6-((4,4-difluorocyclohexyl)amino)-2-(4-methylthiazol-2-yl)pyrimidin-4-yl) ethan-1-ol gave 6-(1-bromoethyl)-N-(4,4-difluorocyclohexyl)-2-(4-methylthiazol-2-yl)pyrimidin-4-amine as a yellow solid (0.95 g). MS (M+1)+=416.9.

Step 5[IN11133-002-P1]: The Procedure is similar to Step 5[NSSy6711] in Example-854. 0.2 g of 6-(1-bromoethyl)-N-(4,4-difluorocyclohexyl)-2-(4-methylthiazol-2-yl)pyrimidin-4-amine gave 6-(1-(1H-pyrazol-1-yl)ethyl)-N-(4,4-difluorocyclohexyl)-2-(4-methylthiazol-2-yl)pyrimidin-4-amine as an off-white solid (0.045 g). MS (M+1)+=405.1; 1H-NMR (400 MHz, DMSO-d6): δ 7.93 (d, J=2.00 Hz, 1H), 7.64 (bs, 1H), 7.55 (s, 1H), 7.41 (s, 1H), 6.35 (t, J=2.00 Hz, 1H), 5.82-5.80 (m, 1H), 5.50-5.45 (m, 1H), 4.10-4.00 (m, 1H), 2.44 (m, 3H), 2.04-1.80 (m, 6H), 1.81 (d, J=6.8 Hz, 3H), 1.80-1.54 (m, 2H).

Example-663

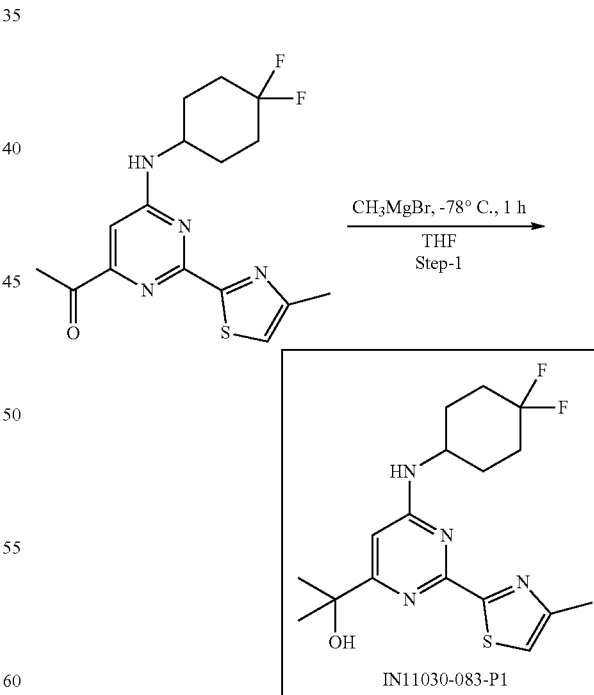

Step 1[IN11030-083-P1]: The Procedure is similar to Step 4[NSSy6464] in Example-869. 0.3 g of 1-(6-((4,4-difluorocyclohexyl)amino)-2-(4-methylthiazol-2-yl)pyrimidin-4-yl) ethan-1-one gave 2-(6-((4,4-difluorocyclohexyl)amino)-2-(4-methylthiazol-2-yl)pyrimidin-4-yl) propan-2-ol as an off-white solid (0.03 g). MS (M+1)⁺=369.1; ¹H-NMR (400 MHz, DMSO-d₆): δ 7.56 (bs, 1H), 7.37 (s, 1H), 6.76 (s, 1H), 5.17 (s, 1H), 4.15 (bs, 1H), 2.44 (s, 3H), 2.08-1.97 (m, 6H), 1.62-1.59 (m, 2H), 1.40 (s, 6H).

Example-664

Omitted Intentionally

Example-665

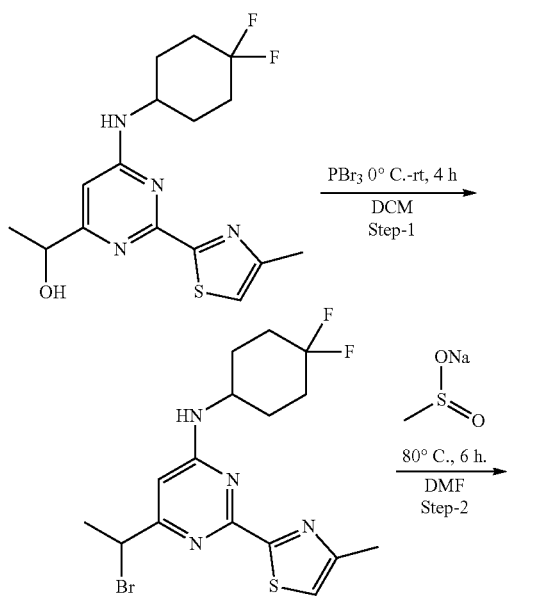

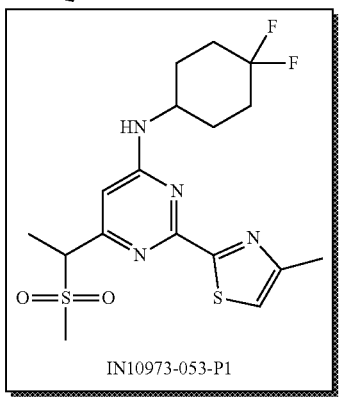

Step 1: The Procedure is similar to Step 3[IN11059-090-P1] in Example-659. 0.16 g of 1-(6-((4,4-difluorocyclohexyl)amino)-2-(4-methylthiazol-2-yl)pyrimidin-4-yl) ethan-1-ol gave 6-(1-bromoethyl)-N-(4,4-difluorocyclohexyl)-2-(4-methylthiazol-2-yl)pyrimidin-4-amine as a yellow solid (0.09 g). MS (M+1)+=416.9.

Step 2[IN10973-053-P1]: The Procedure is similar to Step 3[IN11273-018-P1] in Example-889. 0.08 g of 6-(1-bromoethyl)-N-(4,4-difluorocyclohexyl)-2-(4-methylthiazol-2-yl)pyrimidin-4-amine gave N-(4,4-difluorocyclohexyl)-6-(1-(methylsulfonyl)ethyl)-2-(4-methylthiazol-2-yl)pyrimidin-4-amine as an off-white solid (0.06 g). MS (M+1)+=417.0; 1H-NMR (400 MHz, DMSO-d6): δ 7.86 (d, J=5.2 Hz, 1H), 7.44 (s, 1H), 6.57 (s, 1H), 4.46 (d, J=6.4 Hz, 1H), 4.13 (bs, 1H), 3.09 (s, 3H), 2.44 (s, 3H), 2.11-1.99 (m, 6H), 1.65-1.60 (m, 5H).

Example-666

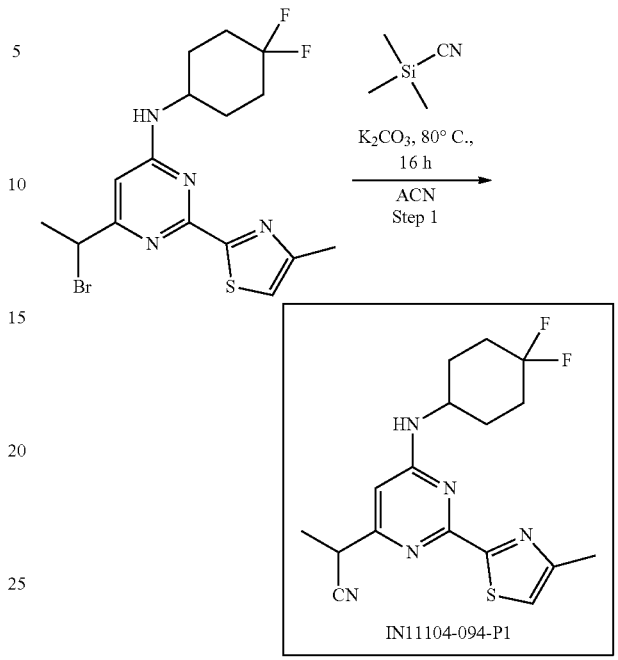

Step 1[IN11104-094-P1]: The Procedure is similar to Step 1[B] in Example-838. 0.2 g of 6-(1-bromoethyl)-N-(4,4-difluorocyclohexyl)-2-(4-methylthiazol-2-yl)pyrimidin-4-amine gave 2-(6-((4,4-difluorocyclohexyl)amino)-2-(4-methylthiazol-2-yl)pyrimidin-4-yl) propanenitrile as an off-white solid (0.09 g, 51%). MS (M+1)⁺=363.8; ¹H-NMR (400 MHz, DMSO-d₆): δ 7.87 (s, 1H), 7.44 (s, 1H), 6.59 (s, 1H), 4.24-4.22 (m, 1H), 4.13 (s, 1H), 2.45 (s, 3H), 2.00 (s, 6H), 1.67-1.52 (m, 5H).

Example-667

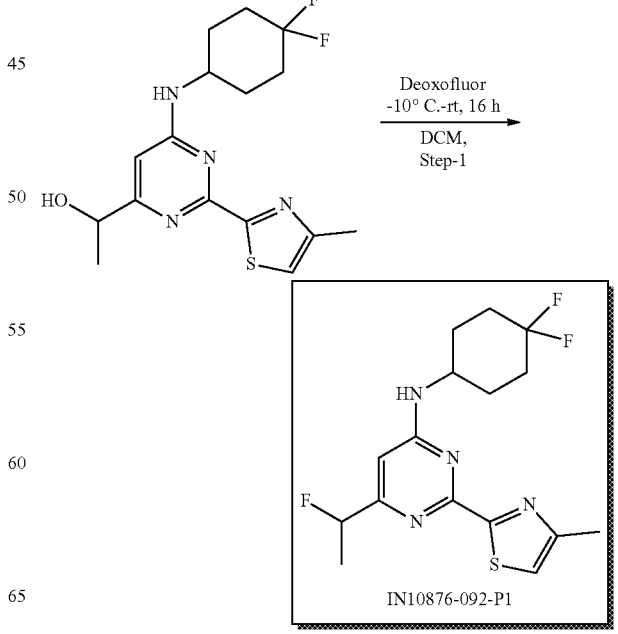

Step 1[IN10876-092-P1]: The Procedure is similar to Step 3[NSSy6917] in Example-21. 0.1 g of 1-(6-((4,4-difluorocyclohexyl)amino)-2-(4-methylthiazol-2-yl)pyrimidin-4-yl) ethan-1-ol gave N-(4,4-difluorocyclohexyl)-6-(1-fluoroethyl)-2-(4-methylthiazol-2-yl)pyrimidin-4-amine as an off-white solid (0.025 g, 24%). MS (M+1)$^+$=357.0; $^1$H-NMR (400 MHz, DMSO-d$_6$): δ 7.78 (s, 1H), 7.43 (s, 1H), 6.55 (s, 1H), 5.50-5.45 (m, 1H), 4.12 (s, 1H), 2.44 (s, 3H), 2.00-1.75 (m, 6H), 1.70-1.50 (m, 5H).

Example-668

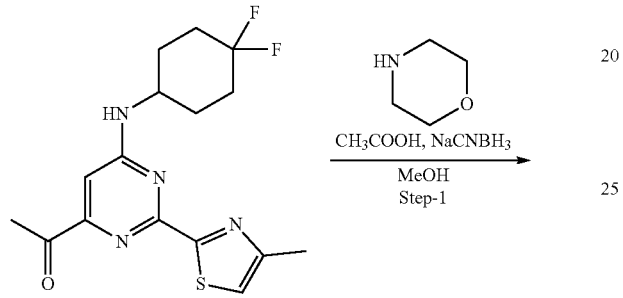

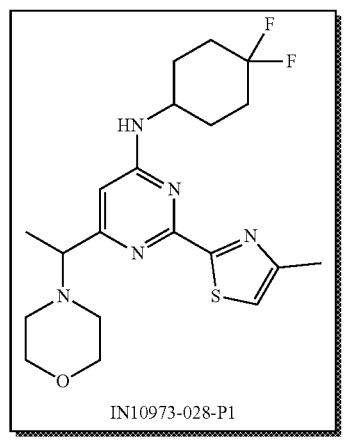

Step 1[IN10973-028-P1]: To a solution of 1-(6-((4,4-difluorocyclohexyl)amino)-2-(4-methylthiazol-2-yl)pyrimidin-4-yl) ethan-1-one and morpholine in methanol was added acetic acid. The reaction mixture was stirred at rt for 4 h. Sodium cyano borohydride was added and continued to stir at rt for 16 h. The Reaction mixture was evaporated to dryness, added ice cold water and stirred for 10 minutes. The obtained solid was filtered and dried under vacuum to afford crude and which was purified by column chromatography using ethyl acetate as eluent to afford N-(4,4-difluorocyclohexyl)-2-(4-methylthiazol-2-yl)-6-(1-morpholinoethyl)pyrimidin-4-amine as an off-white solid (0.04 g, 33%). MS (M+1)$^+$=424.1; $^1$H-NMR (400 MHz, DMSO-d$_6$): δ 7.56 (s, 1H), 7.38 (s, 1H), 6.56 (s, 1H), 4.01 (s, 1H), 3.59 (t, J=4.40 Hz, 4H), 2.49 (s, 5H), 2.32-1.97 (m, 6H), 1.68-1.52 (m, 2H), 1.33-1.22 (m, 6H).

Example-669

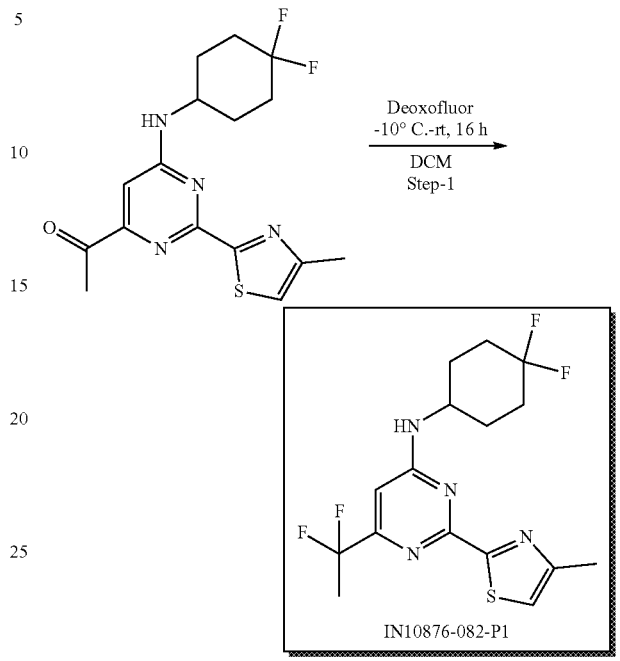

Step 2[IN10876-082-P1]: The Procedure is similar to Step 3[NSSy6917] in Example-21. 0.4 g of 1-(6-((4,4-difluorocyclohexyl)amino)-2-(4-methylthiazol-2-yl)pyrimidin-4-yl) ethan-1-one gave N-(4,4-difluorocyclohexyl)-6-(1,1-difluoroethyl)-2-(4-methylthiazol-2-yl)pyrimidin-4-amine as an off-white solid (0.085 g, 20%). MS (M+1)$^+$=375.0; $^1$H-NMR (400 MHz, DMSO-d$_6$): δ 8.01 (d, J=6.80 Hz, 1H), 7.47 (s, 1H), 6.72 (s, 1H), 4.15 (s, 1H), 2.45 (s, 3H), 2.15-1.85 (m, 7H), 1.65-1.55 (m, 2H), 1.33 (s, 2H).

Example-670

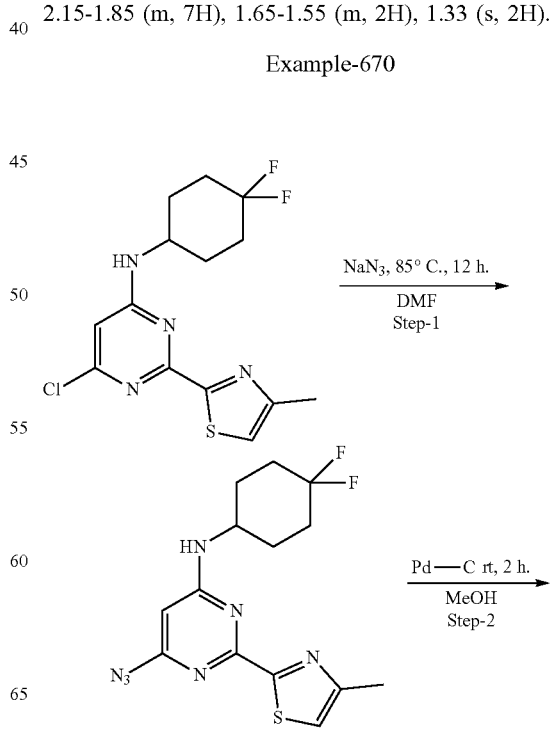

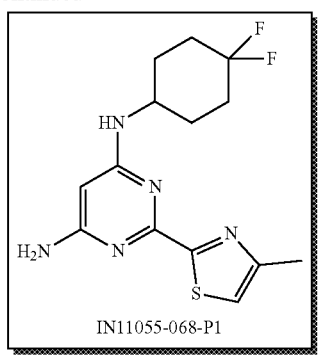

IN11055-068-P1

Step 1: To a solution of 6-chloro-N-(4,4-difluorocyclohexyl)-2-(4-methylthiazol-2-yl)pyrimidin-4-amine (0.2 g, 0.581 mmol) in dry DMF (1 mL) was added sodium azide (0.075 g, 1.162 mmol) and heated at 85° C. for 12 h. The reaction mixture was quenched with ice cold water, the obtained solid was filtered and dried under high vacuum to afford 6-azido-N-(4,4-difluorocyclohexyl)-2-(4-methylthiazol-2-yl)pyrimidin-4-amine as an off-white solid (0.2 g, 98%).

Step 2[IN11055-068-P1]: The Procedure is similar to Step 2[NSSy6464] in Example-869. 0.2 g of 6-azido-N-(4,4-difluorocyclohexyl)-2-(4-methylthiazol-2-yl)pyrimidin-4-amine gave N4-(4,4-difluorocyclohexyl)-2-(4-methylthiazol-2-yl)pyrimidine-4,6-diamine as an off-white solid (0.08 g, 43%). MS (M+1)+=326.0; 1H-NMR (400 MHz, DMSO-d6): δ 7.30 (d, J=0.80 Hz, 1H), 6.81 (d, J=7.60 Hz, 1H), 6.31 (s, 2H), 5.42 (s, 1H), 3.78 (s, 1H), 2.43 (s, 3H), 2.10-1.82 (m, 6H), 1.61-1.50 (m, 2H).

Example-671

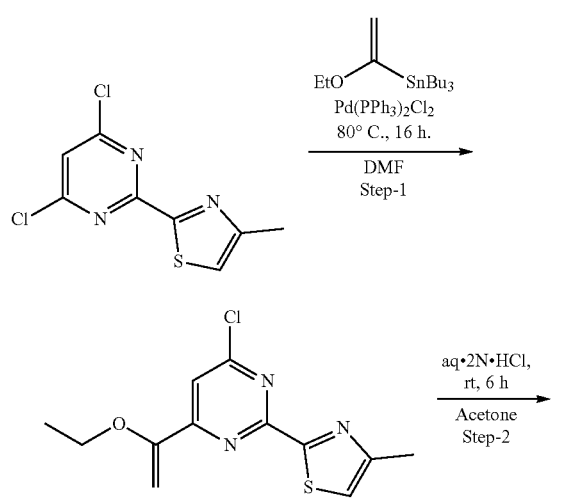

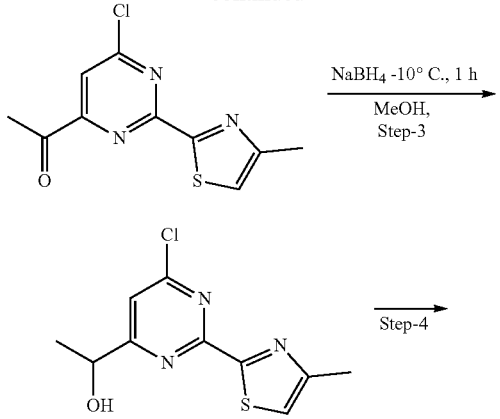

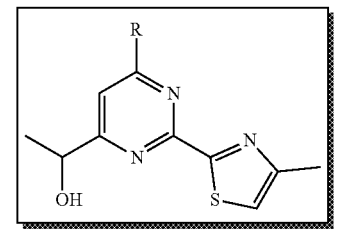

R=

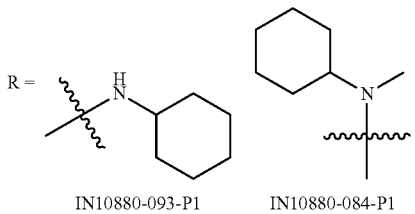

IN10880-093-P1    IN10880-084-P1

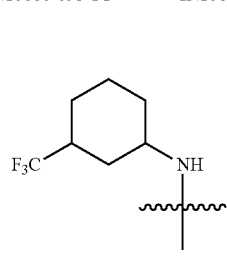 [SMILES: *NC1CCCC(C(F)(F)F)C1]

IN10880-085-P1

Step 1: The Procedure is similar to Step 1[H] in Example-838. 0.3 g of 2-(4,6-dichloropyrimidin-2-yl)-4-methylthiazole gave 2-(4-chloro-6-(1-ethoxyvinyl)pyrimidin-2-yl)-4-methylthiazole as an off-white solid (0.23 g, 67%). MS (M+1)+=282.

Step 2: The Procedure is similar to Step 1[NSSy6697] in Example-873. 0.23 g of 2-(4-chloro-6-(1-ethoxyvinyl)pyrimidin-2-yl)-4-methylthiazole gave 1-(6-chloro-2-(4-methylthiazol-2-yl)pyrimidin-4-yl) ethan-1-one as an off-white solid (0.17 g, 82%). MS (M+1)+=254.

Step 3: The Procedure is similar to Step 2[NSSy6931] in Example-21. 0.17 g of 1-(6-chloro-2-(4-methylthiazol-2-yl)pyrimidin-4-yl) ethan-1-one gave 1-(6-chloro-2-(4-methylthiazol-2-yl)pyrimidin-4-yl) ethan-1-ol as an off-white solid (0.16 g, 93%). MS (M+1)+=255.9.

TABLE 34

Step 4:

| Compound No | R | Condition | Yield (%) |
|---|---|---|---|
| IN10880-093-P1 | ![structure: N-cyclohexyl] | Cyclohexanamine, rt, 16 h, Neat | 70 |
| IN10880-084-P1 | ![structure: N-methyl-N-cyclohexyl] | 2-Methylcyclohexan-1-amine, rt, 16 h, Neat | 57 |
| IN10880-085-P1 | ![structure: 3-CF3 cyclohexyl NH] | 3-(Trifluoromethyl)cyclohexan-1-amine, rt, 16 h, Neat | 42 |

Step 4[IN10880-093-P1]: MS (M+1)+=319.1; 1 H-NMR (400 MHz, DMSO-d6): δ 7.48 (s, 1H), 7.36 (s, 1H), 6.60 (s, 1H), 5.37 (s, 1H), 4.49 (s, 1H), 3.91 (s, 1H), 2.43 (s, 3H), 1.95-1.55 (m, 5H), 1.40-1.10 (m, 8H).

Step 4[IN10880-084-P1]: MS (M+1)+=333.1; 1H-NMR (400 MHz, DMSO-d6): δ 7.39 (s, 1H), 6.72 (s, 1H), 5.43 (d, J=4.80 Hz, 1H), 4.59-4.55 (m, 1H), 2.96 (s, 3H), 2.44 (s, 3H), 1.84 (d, J=28.00 Hz, 2H), 1.70-1.50 (m, 5H), 1.45-1.30 (m, 5H), 1.30-1.20 (m, 2H).

Step 4[IN10880-085-P1]: MS (M+1)+=387.0; 1H-NMR (400 MHz, DMSO-d6): δ 7.57 (bs, 1H), 7.37-7.36 (m, 1H), 6.59 (s, 1H), 5.40 (d, J=4.4 Hz, 1H), 4.50-4.45 (m, 1H), 3.92 (bs, 1H), 2.42 (s, 3H), 2.25-2.17 (m, 1H), 1.99-1.97 (m, 1H), 1.85-1.76 (m, 2H), 1.63-1.56 (m, 2H), 1.50-1.44 (m, 1H), 1.34-1.32 (m, 3H), 1.22-1.14 (m, 2H).

Example-672

Intentionally Omitted

Example-673

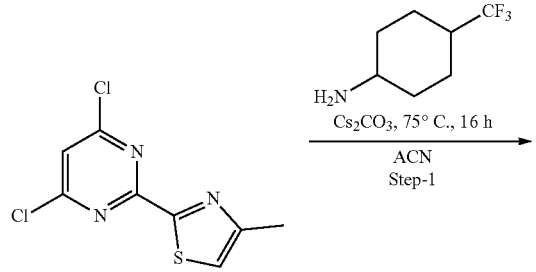

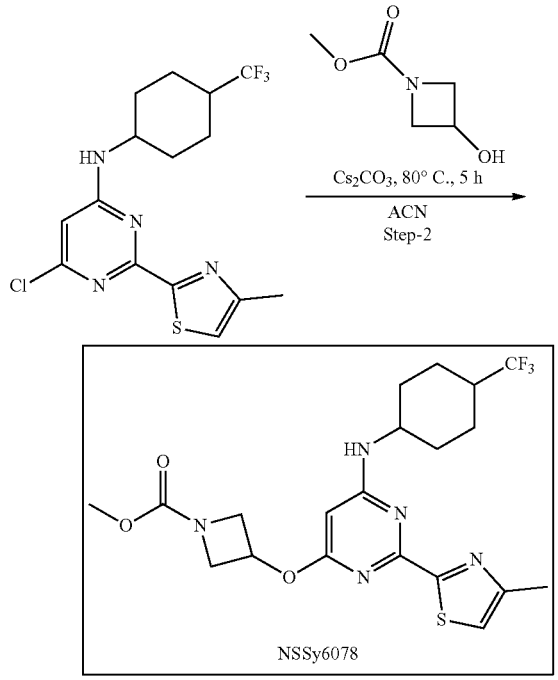

Step 1: The Procedure is similar to Step 1[B] in Example-838. 0.3 g of 2-(4,6-dichloropyrimidin-2-yl)-4-methylthiazole gave 6-chloro-2-(4-methylthiazol-2-yl)-N-(4-(trifluoromethyl)cyclohexyl)pyrimidin-4-amine as an off-white solid (0.3 g, 70%). MS (M+1)+=377.4.

Step 2[NSSy6078]: The Procedure is similar to Step 1[B] in Example-838. 0.45 g of 6-chloro-2-(4-methylthiazol-2-yl)-N-(4-(trifluoromethyl)cyclohexyl)pyrimidin-4-amine gave methyl 3-((2-(4-methylthiazol-2-yl)-6-((4-(trifluoromethyl)cyclohexyl)amino)pyrimidin-4-yl)oxy) azetidine-1-carboxylate as an off-white solid (0.18 g, 32%). MS (M+

1)+=472.2; 1H-NMR (400 MHz, DMSO-d6): δ 7.34 (s, 1H), 7.24 (d, J=4.00 Hz, 1H), 5.88 (s, 1H), 5.39-5.36 (m, 1H), 4.37-4.32 (m, 2H), 4.08 (s, 1H), 4.01 (s, 2H), 3.60 (s, 3H), 2.44 (s, 3H), 2.32-2.31 (m, 1H), 1.8 (d, J=8, 2H), 1.74-1.69 (m, 6H).

Example-674

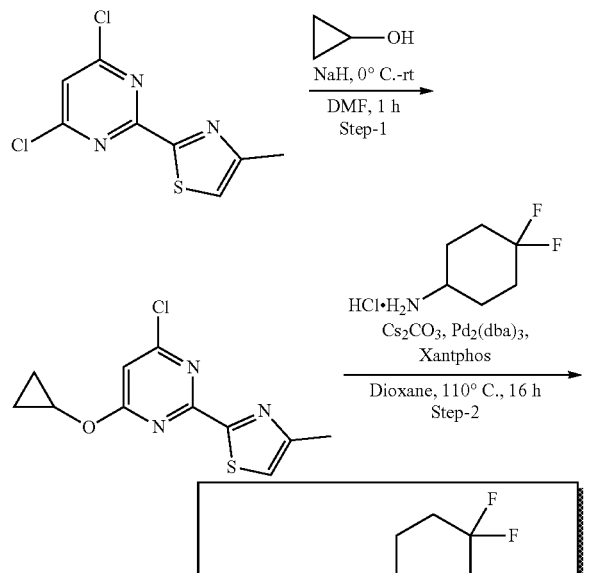

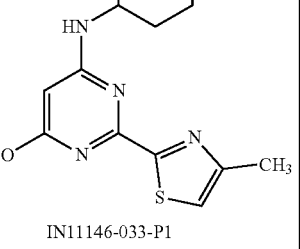

IN11146-033-P1

Step 1: The Procedure is similar to Step 5[NSSy6711] in Example-854. 0.5 g of 2-(4,6-dichloropyrimidin-2-yl)-4-methylthiazole gave 2-(4-chloro-6-cyclopropoxypyrimidin-2-yl)-4-methylthiazole as an off-white solid (0.32 g, 58.8%). MS (M+1)+=268.

Step 2[IN11146-033-P1]: The Procedure is similar to Step 1[NSSy6629] in Example-839. 0.32 g of 2-(4-chloro-6-cyclopropoxypyrimidin-2-yl)-4-methylthiazole gave 6-cyclopropoxy-N-(4,4-difluorocyclohexyl)-2-(4-methylthiazol-2-yl)pyrimidin-4-amine as an off-white solid (0.03 g, 6.8%). MS (M+1)+=367.0; 1H-NMR (400 MHz, MeOD): δ 7.52 (s, 1H), 7.40 (s, 1H), 5.99 (s, 1H), 4.07 (s, 1H), 2.43 (s, 3H), 2.10-1.90 (m, 6H), 1.65-1.52 (m, 2H), 0.86 (s, 1H), 0.82 (d, J=18.00 Hz, 2H), 0.75 (s, 2H).

Example-675

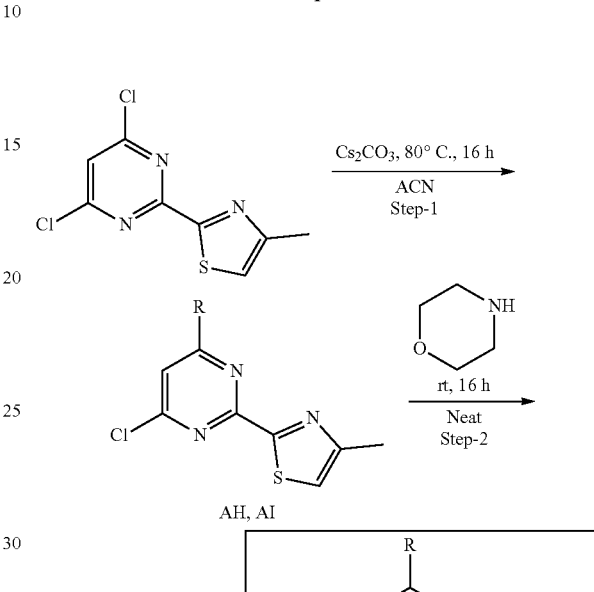

AH, AI

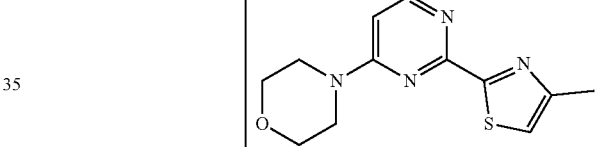

R=

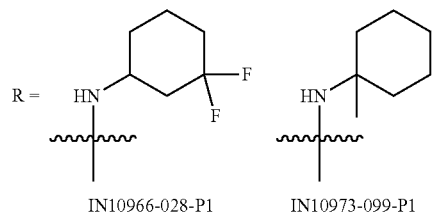

IN10966-028-P1    IN10973-099-P1

TABLE 35

| Step 1: The Procedure is similar to Step 1[B] in Example-838. | | | | |
|---|---|---|---|---|
| Compound No | R | Condition | Yield (%) | MS (M + 1)+ |
| AH | ![HN-cyclohexyl-F,F] | Cs₂CO₃, ACN, 80° C., 16 h | 25 | 345.1 |

TABLE 35-continued

Step 1: The Procedure is similar to Step 1[B] in Example-838.

| Compound No | R | Condition | Yield (%) | MS (M + 1)+ |
|---|---|---|---|---|
| AI | (1-methylcyclohexyl)amine group | Cs$_2$CO$_3$, ACN, 80° C., 20 h | 76 | 323.1 |

TABLE 36

Step 2: The Procedure is similar to Step 1[B] in Example-838.

| Compound No | R | Condition | Yield (%) | MS (M + 1)+ |
|---|---|---|---|---|
| IN10966-028-P1 | (4,4-difluorocyclohexyl)amine | Morpholine, rt, 16 h, Neat | 88 | 396.1 |
| IN10973-099-P1 | (1-methylcyclohexyl)amine | Morpholine, rt, 24 h, Neat | 86 | 374.2 |

[IN10966-028-P1]: 1H-NMR (400 MHz, DMSO-d6): δ 7.35 (s, 1H), 7.06 (d, J=8.00 Hz, 1H), 5.64 (s, 1H), 3.98 (s, 1H), 3.68 (s, 4H), 3.50 (s, 4H), 2.42 (s, 3H), 1.93-1.49 (m, 6H), 1.30-1.23 (m, 2H).

[IN10973-099-P1]: 1H-NMR (400 MHz, DMSO-d6): δ 7.31 (s, 1H), 6.38 (s, 1H), 5.79 (s, 1H), 3.70-3.67 (m, 4H), 3.45-3.43 (m, 4H), 3.16 (s, 3H), 2.85-2.18 (m, 2H), 1.50-1.38 (m, 9H), 1.30-1.20 (m, 2H).

Example-676

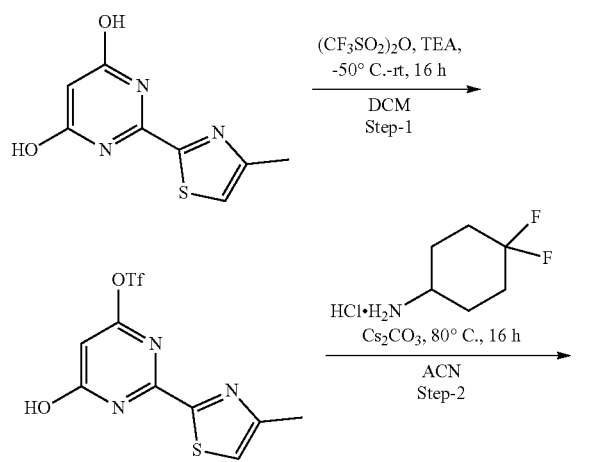

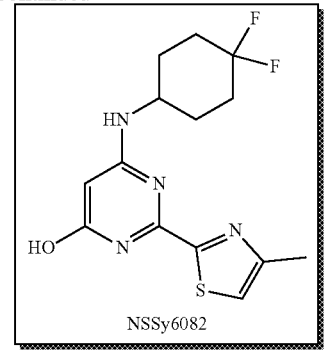

NSSy6082

Step 1: To a stirred solution of 2-(4-methylthiazol-2-yl)pyrimidine-4,6-diol (1 g, 4.77 mmol) in dichloromethane (18 mL) was added trifluoromethanesulfonic anhydride (1.0 mL) at −50° C. and followed by trimethylamine (1.3 mL). The reaction mixture was slowly warmed to room temperature and stirred at rt for 16 h. The reaction mixture was concentrated under reduced pressure to remove excess triflic anhydride and the residue was quenched with 10% sodium bicarbonate and extracted with ethyl acetate, washed with water and brine solution. The organic layer was dried over sodium sulfate, filtered and concentrated under reduced pressure to afford 6-hydroxy-2-(4-methylthiazol-2-yl)pyrimidin-4-yl trifluoromethanesulfonate as brown solid (1.4 g, 86%). MS (M+1)+=342.2.

Step 2[NSSy6082]: The Procedure is similar to Step 1[B] in Example-838. 0.3 g of 6-hydroxy-2-(4-methylthiazol-2-yl)pyrimidin-4-yl trifluoromethane sulfonate gave 6-((4,4-difluorocyclohexyl)amino)-2-(4-methyl thiazol-2-yl)pyrimidin-4-ol (0.04 g, 14%). MS (M+1)+=327.2; 1H-NMR (400 MHz, DMSO-d6): δ 11.42 (s, 1H), 7.56 (s, 1H), 7.13 (s, 1H), 5.26 (s, 1H), 2.44 (s, 3H), 2.32-2.31 (m, 1H), 1.89-1.87 (m, 2H), 1.74-1.69 (m, 6H).

Example-677

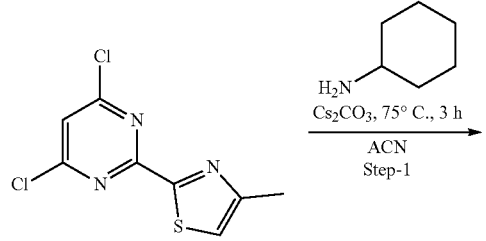

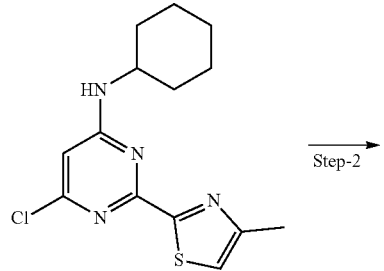

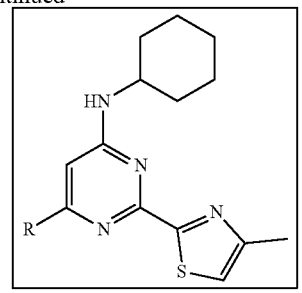

R=

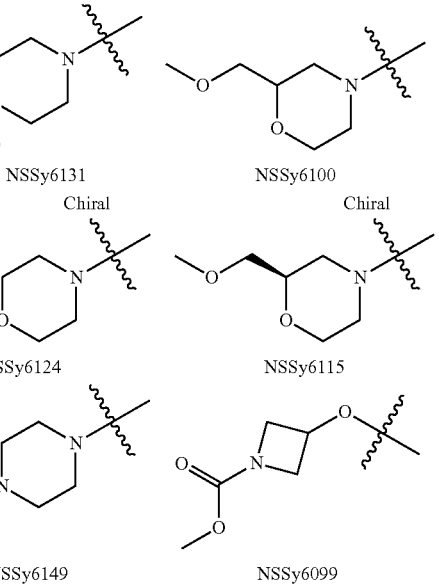

Step 1: The Procedure is similar to Step 1[B] in Example-838. 2 g of 2-(4,6-dichloropyrimidin-2-yl)-4-methylthiazole gave 6-chloro-N-cyclohexyl-2-(4-methylthiazol-2-yl)pyrimidin-4-amine as an off-white solid (2 g, 80%). MS (M+1)+=309.5.

TABLE 37

| | Step 1: | | |
|---|---|---|---|
| Compound No | R | Condition | Yield (%) |
| NSSy6131 | (thiomorpholine-1,1-dioxide) | Xanthphos, Pd$_2$(dba)$_3$, Cs$_2$CO$_3$, dioxane, 90° C., 16 h | 24 |
| NSSy6100 | (methoxymethyl morpholine) | Cs$_2$CO$_3$, ACN, 90° C., 16 h | 48 |

TABLE 37-continued

Step 1:

| Compound No | R | Condition | Yield (%) |
|---|---|---|---|
| NSSy6124 | Chiral, methoxymethyl morpholine | Cs₂CO₃, ACN, 90° C., 16 h | — |
| NSSy6115 | Chiral, methoxymethyl morpholine | Cs₂CO₃, ACN, 90° C., 16 h | — |
| NSSy6149 | oxetanyl piperazine | Cs₂CO₃, TEA:ACN (1:1), 75° C., 2 days | 13 |
| NSSy6099 | methyl carbamate azetidinyloxy | K⁺(CH₃)₃CO⁻, THF, 75° C., 3 h | 56 |

Step 2[NSSy6131]: The Procedure is similar to Step 1[NSSy6629] in Example-839. MS (M+1)+=408.2; 1H-NMR (400 MHz, DMSO-d6-80° C.): δ 7.34 (s, 1H), 6.94 (d, J=8.00 Hz, 1H), 5.77 (s, 1H), 4.05 (s, 4H), 3.06 (s, 4H), 2.41 (s, 3H), 1.89-1.86 (m, 2H), 1.73-1.69 (m, 2H), 1.60-1.57 (m, 1H), 1.35-1.13 (m, 6H).

Step 2[NSSy6100]: The Procedure is similar to Step 1[B] in Example-838. MS (M+1)+=404.2; 1H-NMR (400 MHz, DMSO-d6): δ 7.32 (s, 1H), 6.86 (d, J=6.80 Hz, 1H), 4.12-4.04 (m, 2H), 3.94-3.92 (m, 1H), 3.55-3.41 (m, 3H), 3.32-3.29 (m, 4H), 2.86 (m, 1H), 2.68-2.62 (m, 1H), 2.41 (s, 3H), 1.34-1.19 (m, 5H) and isomers was separated by Chiral HPLC to afford [NSSy6124]. MS (M+1)+=404.2; 1H-NMR (400 MHz, DMSO-d6): δ 7.33 (s, 1H), 6.89 (d, J=8.16 Hz, 1H), 5.63 (s, 1H), 4.25-4.05 (m, 2H), 3.94-3.80 (m, 1H), 3.50 (s, 4H), 3.30 (s, 3H), 2.89 (t, J=11.96 Hz, 1H), 2.69-2.68 (m, 1H), 2.42 (s, 3H), 1.89-1.87 (m, 2H), 1.74-1.70 (m, 2H), 1.61-1.58 (m, 1H), 1.36-1.15 (m, 6H) and [NSSy6115]. MS (M+1)+=404.2; 1H-NMR (400 MHz, DMSO-d6): δ 7.30 (s, 1H), 6.87 (d, J=8.00 Hz, 1H), 5.63 (s, 1H), 4.05-3.93 (m, 3H), 3.51-3.41 (m, 4H), 3.30 (s, 3H), 2.90-2.87 (m, 1H), 2.69-2.51 (m, 1H), 2.42 (s, 3H), 1.89-1.87 (m, 2H), 1.74-1.70 (m, 2H), 1.61 (m, 1H), 1.36-1.18 (m, 6H).

Step 2[NSSy6149]: The Procedure is similar to Step 1[B] in Example-838. MS (M+1)+=415.2; 1H-NMR (400 MHz, DMSO-d6-80° C.): δ 7.31 (s, 1H), 6.81 (d, J=8.00 Hz, 1H), 5.61 (s, 1H), 4.57-4.54 (m, 2H), 4.85-4.45 (m, 2H), 3.53 (s, 4H), 3.48-3.41 (m, 1H), 2.40 (s, 3H), 2.32 (s, 4H), 1.88-1.85 (m, 2H), 1.74-1.69 (m, 3H), 1.60-1.57 (s, 1H), 1.34-1.13 (m, 6H).

Step 2[NSSy6099]: The Procedure is similar to Step 1[B] in Example-838. MS (M+1)+=404.2; 1H-NMR (400 MHz, DMSO-d6): δ 7.43 (s, 2H), 5.79 (s, 1H), 5.34 (s, 1H), 4.33 (s, 2H), 3.91 (s, 2H), 3.58 (s, 3H), 2.43 (s, 3H), 1.89 (s, 2H), 1.73 (s, 2H), 1.60 (s, 1H), 1.36-1.16 (m, 5H).

Example-678

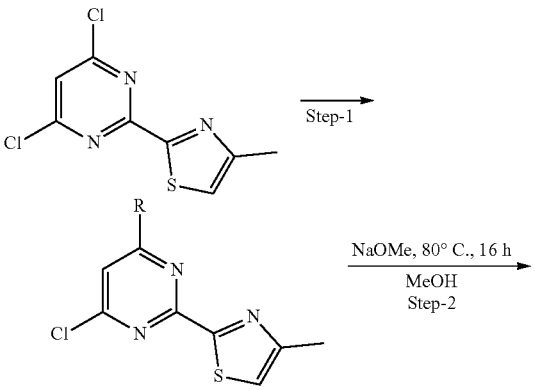

883
-continued
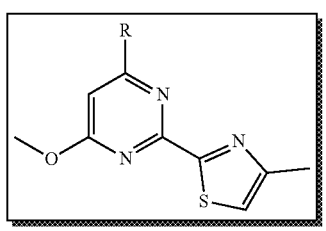
R=
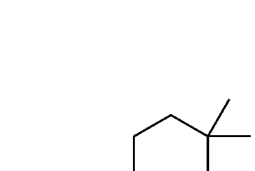 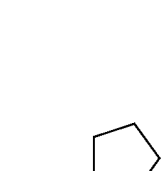
IN11055-069-P1     IN11055-066-P1
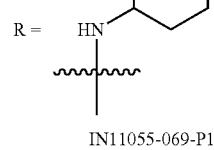 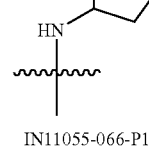
IN11104-084-P2     IN11137-018-P1
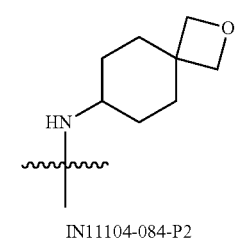 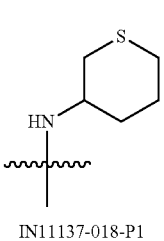
IN11059-023-P1     IN11106-027-P1
884
-continued
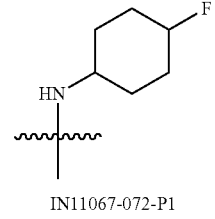 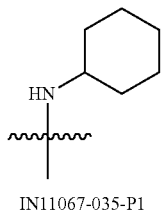 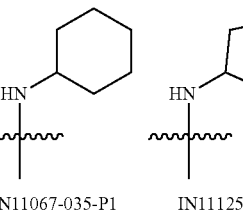
IN11067-072-P1   IN11067-035-P1   IN11125-028-P1
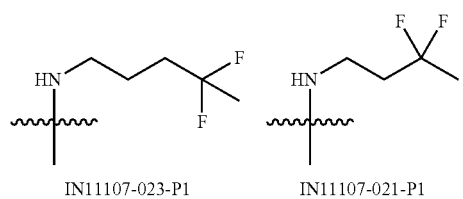
IN11107-023-P1          IN11107-021-P1
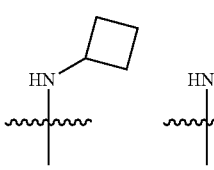 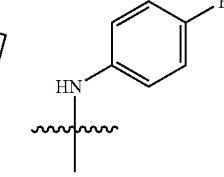
IN11111-003-P1     IN11059-059-P1
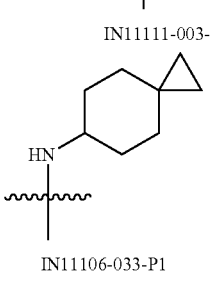 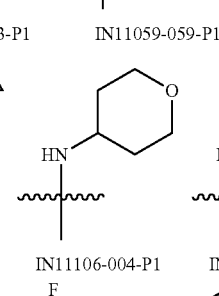
IN11106-033-P1   IN11106-004-P1   IN11079-070-P1
 
IN11133-014-P1     IN11055-087-P1
TABLE 38
| Step 1: | | | | |
|---|---|---|---|---|
| Compound No | R | Condition | Yield (%) | MS (M + 1)+ |
| AJ |  | Cs$_2$CO$_3$, ACN, 80° C., 16 h | 72 | 337.0 |
| AK |  | Cs$_2$CO$_3$, ACN, 80° C., 16 h | 71 | 295.0 |

TABLE 38-continued

| | Step 1: | | | |
|---|---|---|---|---|
| Compound No | R | Condition | Yield (%) | MS (M + 1)+ |
| AL | 2-oxa-spiro[3.5]non-7-yl-NH- | Cs₂CO₃, ACN, 80° C., 16 h | — | 351.0 |
| AM | tetrahydrothiopyran-3-yl-NH- | Cs₂CO₃, ACN, 80° C., 16 h | 60 | 327.0 |
| AN | 2,4-difluorophenyl-NH- | Cs₂CO₃, ACN, 80° C., 16 h | 49 | 339.0 |
| AO | tetrahydropyran-3-yl-NH- | Cs₂CO₃, ACN, 80° C., 16 h | 75 | 311.0 |
| AP | 4-fluorocyclohexyl-NH- | Cs₂CO₃, ACN, 80° C., 16 h | 67 | 327.0 |
| AQ | cyclohexyl-NH- | Cs₂CO₃, ACN, 80° C., 16 h | 95 | 308.9 |
| AR | 3,3-difluorocyclopentyl-NH- | Cs₂CO₃, ACN, 80° C., 16 h | 22 | 331.0 |
| AS | 4,4-difluoropentyl-NH- | Cs₂CO₃, ACN, rt, 16 h | 59 | 333.0 |

TABLE 38-continued
| Step 1: | | | | |
|---|---|---|---|---|
| Compound No | R | Condition | Yield (%) | MS (M + 1)+ |
| AT | 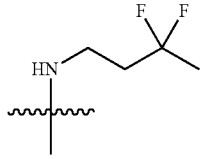 [SMILES: *NCCC(C)(F)F] | Cs₂CO₃, ACN, rt, 16 h | 73 | 319.0 |
| AU | 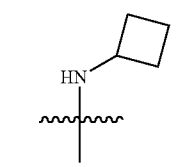 [SMILES: *NC1CCC1] | Cs₂CO₃, ACN, 80° C., 16 h | 83 | 281.0 |
| AV | 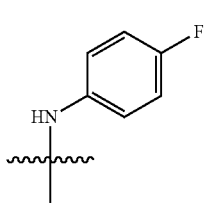 [SMILES: *Nc1ccc(F)cc1] | H₂SO₄, IPA, 80° C., 16 h | 40 | 320.9 |
| AW | 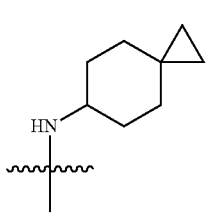 [SMILES: *NC1CCC2(CC1)CC2] | Cs₂CO₃, ACN, 80° C., 16 h | 66 | 335.0 |
| AX | 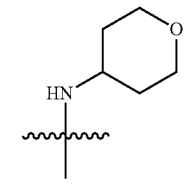 | Cs₂CO₃, ACN, 80° C., 16 h | 75 | 311.0 |
| AY | 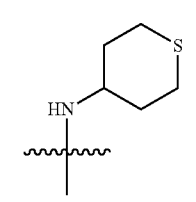 [SMILES: *NC1CCSCC1] | Cs₂CO₃, ACN, 80° C., 16 h | 75 | 327.0 |
| AZ | 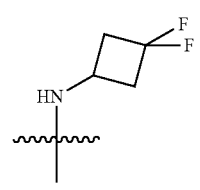 [SMILES: *NC1CC(F)(F)C1] | Cs₂CO₃, ACN, 80° C., 16 h | 54 | 317.0 |
| BA | 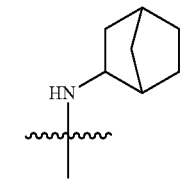 [SMILES: *NC1CC2CCC1C2] | Cs₂CO₃, ACN, 80° C., 16 h | 46 | 321 |

TABLE 39

| | | | Step 1: | | |
|---|---|---|---|---|---|
| Compound No | R | | Condition | Yield (%) | MS (M + 1)+ |
| IN11055-069-P1 | 4,4-dimethylcyclohexyl-HN- | | NaOMe, 80° C., 16 h, MeOH | 40 | 333.1 |
| IN11055-066-P1 | cyclopentyl-HN- | | NaOMe, 80° C., 16 h, MeOH | 27 | 291.1 |
| IN11104-084-P2 | 2-oxaspiro[3.5]nonyl-HN- | | NaOMe, 80° C., 16 h, MeOH | 87 | 347.0 |
| IN11137-018-P1 | tetrahydrothiopyran-3-yl-HN- | | NaOMe, 80° C., 16 h, MeOH | 50 | 323.0 |
| IN11106-027-P1 | tetrahydropyran-3-yl-HN- | | NaOMe, 80° C., 16 h, MeOH | 26 | 307.0 |
| IN11067-072-P1 | 4-fluorocyclohexyl-HN- | | NaOMe, 80° C., 16 h, MeOH | 88 | 323.0 |
| IN11067-035-P1 | cyclohexyl-HN- | | NaOMe, 80° C., 16 h, MeOH | 37 | 305.0 |
| IN11125-028-P1 | 3,3-difluorocyclopentyl-HN- | | NaOMe, 80° C., 16 h, MeOH | 59 | 327.0 |

TABLE 39-continued

Step 1:

| Compound No | R | Condition | Yield (%) | MS (M + 1)+ |
|---|---|---|---|---|
| IN11107-023-P1 | HN-CH₂CH₂C(CH₃)(F)F (4-fluoro-4-methylpentyl amine linkage) | NaOMe, 80° C., 16 h, MeOH | 60 | 329.1 |
| IN11107-021-P1 | HN-CH₂CH₂C(F)₂CH₃ | NaOMe, 80° C., 16 h, MeOH | 63 | 315.0 |
| IN11111-003-P1 | HN-cyclobutyl | NaOMe, 80° C., 16 h, MeOH | 48 | 277.0 |
| IN11106-033-P1 | HN-spiro[5.2]cyclohexyl-cyclopropyl | NaOMe, 80° C., 16 h, MeOH | 63 | 331.0 |
| IN11106-004-P1 | HN-(tetrahydro-2H-pyran-4-yl) | NaOMe, 80° C., 16 h, MeOH | 43 | 307.0 |
| IN11079-072-P1 | HN-(tetrahydro-2H-thiopyran-4-yl) | NaOMe, 80° C., 16 h, MeOH | 47 | 323.0 |
| IN11133-014-P1 | HN-(3,3-difluorocyclobutyl) | NaOMe, 80° C., 16 h, MeOH | 72 | 313.0 |
| IN11055-087-P1 | HN-(norbornan-2-yl) | NaOMe, 80° C., 16 h, MeOH | 67 | 317.1 |

Step 2[IN11055-069-P1]: To a stirred solution of 6-chloro-N-(4,4-dimethylcyclohexyl)-2-(4-methylthiazol-2-yl)pyrimidin-4-amine (0.2 g, 0.59 mmol) in methanol (10 mL) was added sodium methoxide (0.202 g, 2.975 mmol). The reaction mixture was heated to reflux at 80° C. for 16 h. The reaction mixture was quenched with water (10 mL)

and extracted with (3×30 mL) of ethyl acetate. The combined organic layers were dried over sodium sulfate, concentrated under reduced pressure to afford crude product, which was purified by flash column chromatography using 50% ethyl acetate in pet-ether to afford N-(4,4-dimethylcyclohexyl)-6-methoxy-2-(4-methylthiazol-2-yl)pyrimidin-4-amine as an off-white solid (0.08 g, 40%). MS (M+1)+=333.1; 1H-NMR (400 MHz, DMSO-d6): δ 7.45 (s, 1H), 7.30 (s, 1H), 5.75 (s, 1H), 3.91 (s, 3H), 3.90 (s, 1H), 2.46 (s, 3H), 3.90 (s, 2H), 1.45-1.20 (m, 6H), 0.92 (s, 6H).

Step 2[IN11055-066-P1]: 1H-NMR (400 MHz, DMSO-d6): δ 7.40 (s, 2H), 5.73 (s, 1H), 4.20 (s, 1H), 3.87 (s, 3H), 2.43 (s, 3H), 2.00-1.82 (m, 2H), 1.70-1.40 (m, 6H).

Step 2[IN11104-084-P2]: 1H-NMR (400 MHz, DMSO-d6): δ 7.40 (s, 1H), 7.23 (s, 1H), 5.75 (s, 1H), 4.32 (s, 1H), 3.90 (s, 2H), 4.02 (s, 3H), 3.90 (s, 3H), 2.05 (d, J=24.00 Hz, 2H), 1.75-1.65 (m, 2H), 1.60-1.50 (m, 2H), 1.25-1.15 (m, 4H).

Step 2[IN11137-018-P1]: 1H-NMR (400 MHz, DMSO-d6): δ 7.41 (s, 2H), 5.80 (s, 1H), 4.05 (s, 1H), 3.87 (s, 3H), 3.90 (s, 1H), 2.44 (s, 4H), 2.12-2.09 (m, 1H), 1.94-1.90 (m, 1H), 1.75 (s, 1H), 1.44-1.41 (m, 1H).

Step 2[IN11106-027-P1]: 1H-NMR (400 MHz, CD3OD): δ 7.26 (d, J=0.8 Hz, 1H), 5.78 (s, 1H), 3.98-3.97 (m, 1H), 3.95 (s, 3H), 3.79-3.76 (m, 1H), 3.54-3.48 (m, 1H), 2.49 (s, 3H), 2.07-2.03 (m, 1H), 1.81-1.60 (m, 4H), 1.33-1.23 (m, 2H).

Step 2[IN11067-072-P1]: 1H-NMR (400 MHz, DMSO-d6): δ 7.40 (s, 1H), 7.37 (s, 1H), 5.79 (s, 1H), 4.86-4.74 (m, 1H), 3.87 (s, 3H), 2.43 (s, 3H), 2.12-1.85 (m, 2H), 1.80-1.52 (m, 6H).

Step 2[IN[1067-035-P1]: 1H-NMR (400 MHz, CDCl3): δ 7.00 (s, 1H), 5.61 (s, 1H), 5.28 (s, 1H), 4.03 (s, 3H), 3.34 (s, 1H), 2.55 (s, 3H), 2.00 (d, J=40.00 Hz, 2H), 1.80-1.70 (m, 1H), 1.68-1.55 (m, 1H), 1.45-1.20 (m, 6H).

Step 2[IN11125-028-P1]: 1H-NMR (400 MHz, MeOD): δ 7.27 (s, 1H), 5.76 (s, 1H), 4.50 (s, 1H), 3.96 (s, 3H), 2.66-2.61 (m, 1H), 2.51 (s, 3H), 2.90-1.95 (m, 5H), 1.82-1.70 (m, 1H).

Step 2[IN11107-023-P1]: 1H-NMR (400 MHz, DMSO-d6): δ 7.44 (s, 1H), 7.39 (d, J=1.20 Hz, 1H), 5.74 (d, J=4.80 Hz, 1H), 3.86 (s, 3H), 3.29 (s, 2H), 2.42 (s, 3H), 1.97-1.89 (m, 2H), 1.71-1.59 (m, 5H).

Step 2[IN11107-021-P1]: 1H-NMR (400 MHz, DMSO-d6): δ 7.48-7.45 (m, 1H), 7.42 (d, J=0.80 Hz, 1H), 5.78 (s, 1H), 3.88 (s, 3H), 3.45 (s, 2H), 2.44 (s, 3H), 2.30-2.10 (m, 2H), 1.74 (t, J=44.40 Hz, 3H).

Step 2[IN11111-003-P1]: 1H-NMR (400 MHz, MeOD): δ 7.25 (d, J=0.80 Hz, 1H), 5.65 (s, 1H), 4.50 (s, 1H), 3.95 (s, 3H), 2.50 (s, 3H), 2.41 (m, 2H), 1.98-1.97 (m, 2H), 1.79 (m, 2H).

Step 2[IN11106-033-P1]: 1H-NMR (400 MHz, DMSO-d6): δ 7.40 (s, 1H), 7.32 (s, 1H), 5.76 (d, J=6.80 Hz, 1H), 3.87 (s, 3H), 2.43 (s, 3H), 1.95-1.81 (m, 2H), 1.80-1.62 (m, 2H), 1.50-1.30 (m, 3H), 1.10-0.95 (m, 2H), 0.40-0.20 (m, 4H).

Step 2[IN11106-004-P1]: 1H-NMR (400 MHz, MeOD): δ 7.26 (s, 1H), 5.76 (s, 1H), 4.10 (s, 1H), 3.98 (t, J=3.60 Hz, 1H), 3.95 (s, 4H), 3.57 (t, J=2.00 Hz, 2H), 2.50 (s, 3H), 2.00-1.96 (m, 2H), 1.58-1.53 (m, 2H).

Step 2[IN11079-072-P1]: 1H-NMR (400 MHz, DMSO-d6): δ 7.41 (s, 2H), 5.79 (s, 1H), 3.87 (s, 3H), 2.70 (s, 4H), 2.43 (s, 4H), 2.22-2.10 (m, 2H), 1.68-1.50 (m, 2H).

Step 2[IN11133-014-P1]: 1H-NMR (400 MHz, DMSO-d6): δ 7.93 (s, 1H), 7.43 (s, 1H), 5.77 (s, 1H), 4.10 (s, 1H), 3.90 (s, 3H), 3.08-2.99 (m, 2H), 2.67-2.60 (m, 2H), 2.44 (s, 3H).

Step 2[IN11055-087-P1]: 1H-NMR (400 MHz, DMSO-d6): δ 7.38 (s, 2H), 5.65 (bs, 1H), 3.86 (s, 3H), 2.42 (s, 3H), 2.22-2.17 (m, 2H), 1.70-1.65 (m, 1H), 1.48-1.43 (m, 4H), 1.22 (m, 2H), 1.11-1.08 (m, 2H).

Example-679

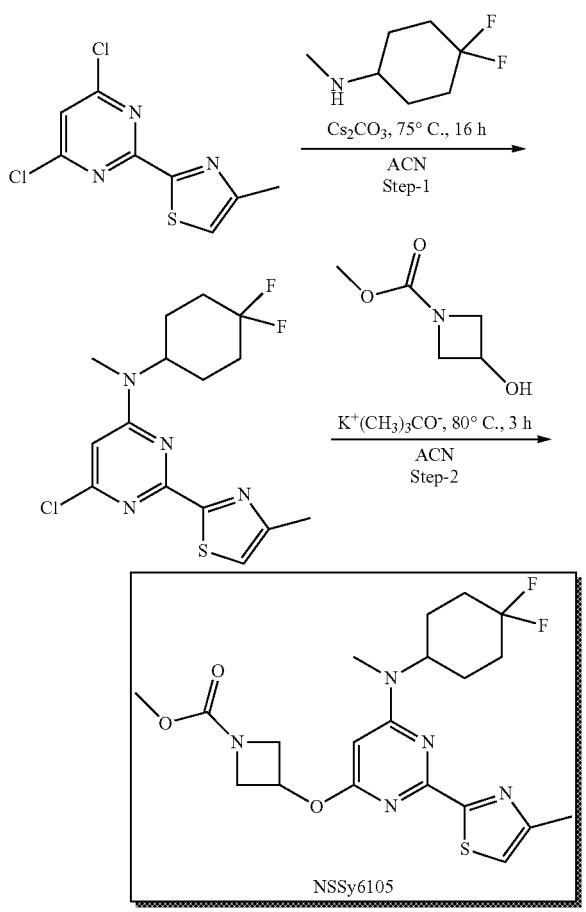

Step 1: The Procedure is similar to Step 1[B] in Example-838. 0.3 g of 2-(4,6-dichloropyrimidin-2-yl)-4-methylthiazole gave 6-chloro-N-(4,4-difluorocyclohexyl)-N-methyl-2-(4-methylthiazol-2-yl)pyrimidin-4-amine as an off-white solid (0.38 g, 86%). MS (M+1)+=359.8.

Step 2[NSSy6105]: The Procedure is similar to Step 1[B] in Example-838. 0.38 g of 6-chloro-N-(4,4-difluorocyclohexyl)-N-methyl-2-(4-methylthiazol-2-yl)pyrimidin-4-amine gave methyl 3-((6-((4,4-difluorocyclohexyl)(methyl)amino)-2-(4-methylthiazol-2-yl)pyrimidin-4-yl)oxy)azetidine-1-carboxylate as an off-white solid (0.12 g, 27%). MS (M+1)+=454.2; 1H-NMR (400 MHz, DMSO-d6): δ 7.45 (s, 2H), 6.13 (s, 1H), 5.43-5.40 (m, 1H), 4.36 (t, J=9.2 Hz, 2H), 3.92 (s, 2H), 3.58 (s, 3H), 2.95 (s, 3H), 2.45 (s, 3H), 2.20-1.85 (m, 4H), 1.85-1.66 (m, 4H).

Example-398

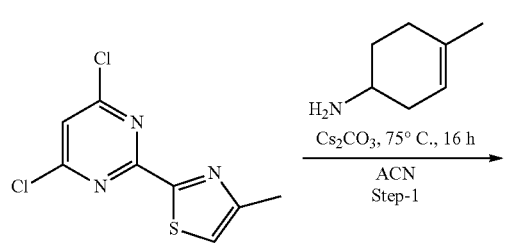

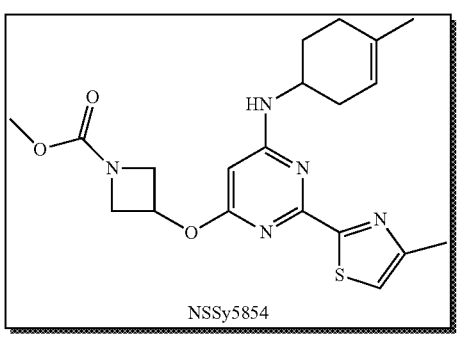

Step 1: The Procedure is similar to Step 1[B] in Example-838. 0.3 g of 2-(4,6-dichloropyrimidin-2-yl)-4-methylthiazole gave 6-chloro-N-(4-methylcyclohex-3-en-1-yl)-2-(4-methylthiazol-2-yl)pyrimidin-4-amin as a brownish gum (0.35 g, 89%). MS (M+1)+=321.0.

Step 2[NSSy5854]: The Procedure is similar to Step 1[B] in Example-838. 0.3 g of 6-chloro-N-(4-methylcyclohex-3-en-1-yl)-2-(4-methylthiazol-2-yl)pyrimidin-4-amine gave methyl 3-((6-((4-methylcyclohex-3-en-1-yl)amino)-2-(4-methylthiazol-2-yl)pyrimidin-4-yl)oxy)azetidine-1-carboxylate as an off-white solid (0.18 g, 43%). MS (M+1)+= 416.4; 1H-NMR (400 MHz, DMSO-d6): δ 7.42 (s, 2H), 6.16 (s, 1H), 5.81 (s, 1H), 5.34 (s, 2H), 4.33 (s, 1H), 3.93 (s, 2H), 3.57 (s, 3H), 2.43 (s, 3H), 2.11-1.88 (m, 5H), 1.68 (s, 3H), 1.65 (s, 1H).

Example-680

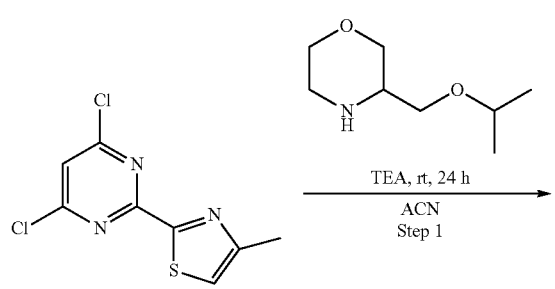

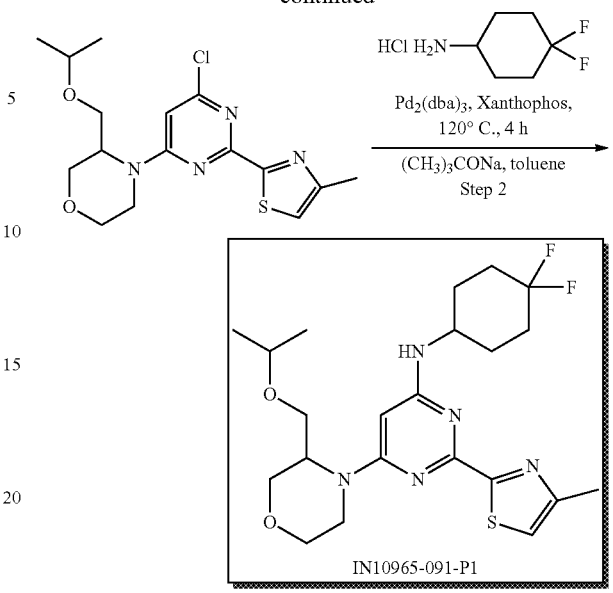

Step 1: To a stirred solution of 2-(4,6-dichloropyrimidin-2-yl)-4-methylthiazole (0.3 g, 1.22 mmol) and 3-(isopropoxymethyl)morpholine (0.21 g, 1.34 mmol) in acetonitrile (5 mL) was added trimethylamine (0.85 mL, 6.10 mmol) and stirred at rt for 24 h. The reaction mixture was diluted with ethyl acetate (100 mL), concentrated under reduced pressure to afford crude product which was purified by flash column chromatography using 35% ethyl acetate in pet-ether to afford 4-(6-chloro-2-(4-methylthiazol-2-yl)pyrimidin-4-yl)-3-(isopropoxymethyl)morpholine as an off-white solid (0.22 g, 48%). MS (M+1)+=369.1.

Step 2[IN10965-091-P1]: The Procedure is similar to Step 1[NSSy6629] in Example-839. 0.05 g of 4-(6-chloro-2-(4-methylthiazol-2-yl)pyrimidin-4-yl)-3-(isopropoxymethyl) morpholine gave N-(4,4-difluorocyclohexyl)-6-(3-(isopropoxymethyl) morpholino)-2-(4-methylthiazol-2-yl)pyrimidin-4-amine as a white solid (0.045 g, 55%). MS (M+1)+=468.2; 1H-NMR (400 MHz, DMSO-d6): δ 7.33 (s, 1H), 7.03 (d, J=7.60 Hz, 1H), 5.62 (s, 1H), 4.30 (s, 1H), 4.00-3.80 (m, 4H), 3.72-3.60 (m, 2H), 3.55-3.44 (m, 2H), 3.50-3.40 (m, 1H), 3.10-3.00 (m, 1H), 2.41 (s, 3H), 2.12-1.85 (m, 6H), 1.62-1.50 (m, 2H), 1.06 (dd, J=6.40, 13.60 Hz, 6H).

Example-681

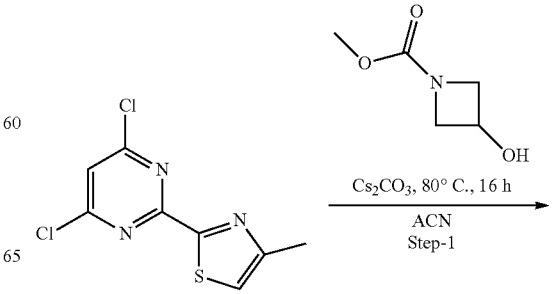

-continued

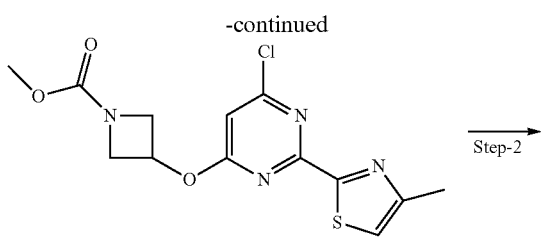

R =

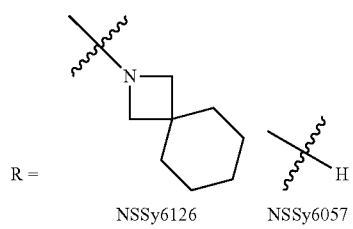
NSSy6126    NSSy6057

Step 1: The Procedure is similar to Step 1[B] in Example-838. 2.0 g of 2-(4,6-dichloropyrimidin-2-yl)-4-methylthiazole gave methyl 3-((6-chloro-2-(4-methylthiazol-2-yl)pyrimidin-4-yl)oxy) azetidine-1-carboxylate as an off-white solid (1.4 g, 52%). MS (M+1)⁺=341.2.

TABLE 40

Step 2:

| Compound No | R | Condition | Yield (%) |
|---|---|---|---|
| NSSy6126 | 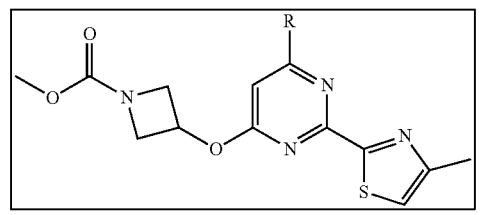 | Xanthphos, Pd₂(dba)₃, Cs₂CO₃, dioxane, 90° C., MW, 2 h | 17 |
| NSSy6057 | H | Pd/C, MeOH, rt, 16 h | 22 |

Step 2[NSSy6126]: The Procedure is similar to Step 1[NSSy6629] in Example-839. MS (M+1)⁺=430.2; ¹H-NMR (400 MHz, DMSO-d₆): δ 7.31 (s, 1H), 6.86 (s, 1H), 5.61 (s, 1H), 4.12-4.04 (m, 2H), 3.93 (d, J=9.60 Hz, 1H), 3.60-3.41 (m, 4H), 3.32-3.29 (m, 4H), 2.86 (m, 1H), 2.65 (t, J=10.40 Hz, 1H), 2.40 (s, 3H), 1.86-1.57 (m, 5H), 1.34-1.19 (m, 5H).

Step 2[NSSy6057]: The Procedure is similar to Step 2[NSSy6464] in Example-869. MS (M+1)⁺=307.0; ¹H-NMR (400 MHz, DMSO-d₆): δ 8.66 (d, J=6.00 Hz, 1H), 7.55 (s, 1H), 7.05 (d, J=5.6 Hz, 1H), 5.51-5.48 (m, 1H), 4.40 (d, J=7.2 Hz, 2H), 4.01-4.00 (m, 2H), 3.58 (s, 3H), 2.33 (s, 3H).

Example-682

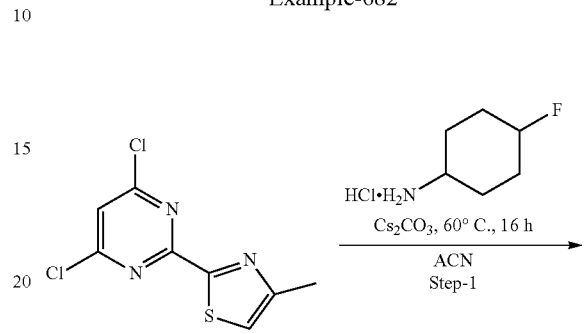

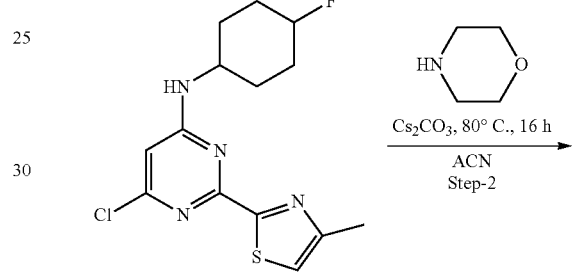

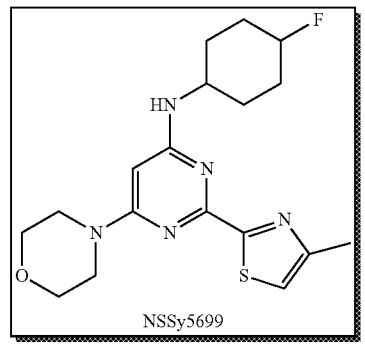

Step 1: The Procedure is similar to Step 1[B] in Example-838. 0.2 g of 2-(4,6-dichloropyrimidin-2-yl)-4-methylthiazole gave 6-chloro-N-(4-fluorocyclohexyl)-2-(4-methylthiazol-2-yl)pyrimidin-4-amine as a brownish gum (0.18 g, 67%). MS (M+1)+=327.4.

Step 2[NSSy5699]: The Procedure is similar to Step 1[B] in Example-838. 0.18 g of 6-chloro-N-(4-fluorocyclohexyl)-2-(4-methylthiazol-2-yl)pyrimidin-4-amine gave N-(4-fluorocyclohexyl)-2-(4-methylthiazol-2-yl)-6-morpholinopyrimidin-4-amine as an off-white solid (0.1 g, 48%). MS (M+1)+=378.2; 1H-NMR (400 MHz, DMSO-d6): δ 7.33 (s, 1H), 6.99-6.92 (m, 1H), 5.64 (s, 1H), 4.74 (t, J=37.20 Hz, 1H), 3.68-3.60 (m, 4H), 3.49-3.40 (m, 4H), 2.33 (s, 3H), 1.94-1.73 (m, 2H), 1.66-1.63 (m, 4H), 1.60-1.54 (m, 2H), 1.43-1.42 (m, 1H).

Example-683

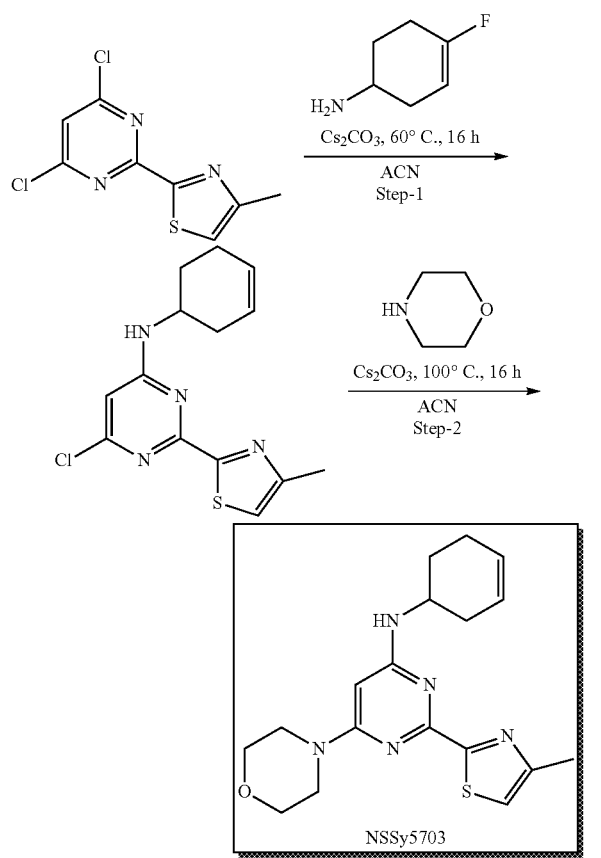

Step 1: The Procedure is similar to Step 1[B] in Example-838. 0.2 g of 2-(4,6-dichloropyrimidin-2-yl)-4-methylthiazole gave 6-chloro-N-(cyclohex-3-en-1-yl)-2-(4-methylthiazol-2-yl)pyrimidin-4-amine as an off-white solid (0.14 g, 75%). MS (M+1)+=307.4.

Step 2[NSSy5703]: The Procedure is similar to Step 1[B] in Example-838. 0.14 g of 6-chloro-N-(cyclohex-3-en-1-yl)-2-(4-methylthiazol-2-yl)pyrimidin-4-amine gave N-(cyclohex-3-en-1-yl)-2-(4-methylthiazol-2-yl)-6-morpholinopyrimidin-4-amine as an off-white solid (0.09 g, 56%). MS (M+1)+=358.2; 1H-NMR (400 MHz, DMSO-d6): δ 7.33 (s, 1H), 6.92 (d, J=7.64 Hz, 1H), 5.66 (d, J=4.36 Hz, 3H), 3.92-3.69 (m, 1H), 3.68-3.67 (m, 4H), 3.49-3.42 (m, 4H), 2.33 (s, 3H), 2.14-2.10 (m, 2H), 1.92-1.88 (m, 3H), 1.50-1.45 (m, 1H).

Example-684

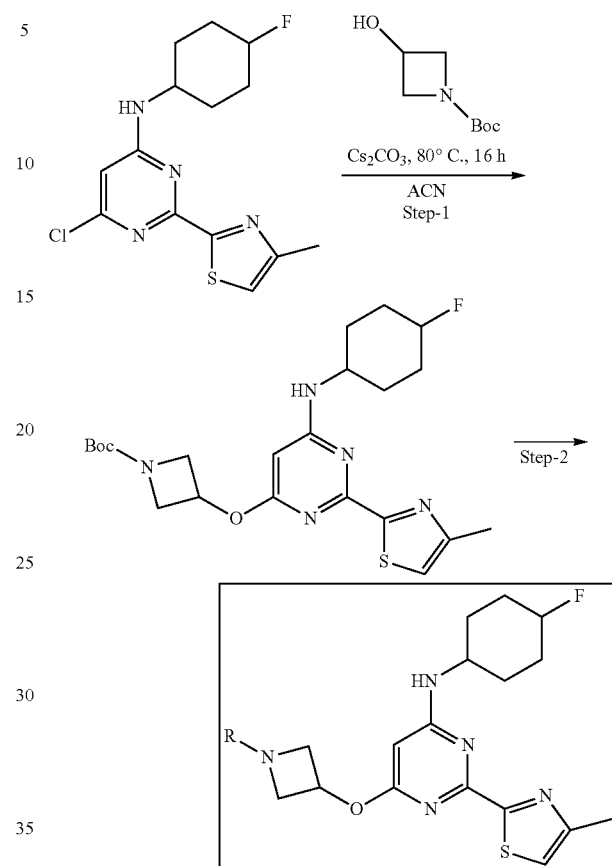

R=

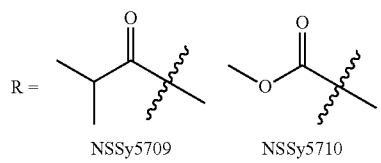

Step 1: The Procedure is similar to Step 1[B] in Example-838. 0.3 g of 6-chloro-N-(4-fluorocyclohexyl)-2-(4-methylthiazol-2-yl)pyrimidin-4-amine gave tert-butyl 3-((6-((4-fluorocyclohexyl)amino)-2-(4-methylthiazol-2-yl)pyrimidin-4-yl)oxy) azetidine-1-carboxylate as a brownish gum (0.3 g, 71%). MS (M+1)+=464.4.

TABLE 41

Step 2: The Procedure is similar to Step 2[NSSy6924] in Example-857.

| Compound No | R | Condition | Yield (%) |
|---|---|---|---|
| NSSy5709 | ![structure] | TFA, DCM, 0° C.-rt, 6 h, Isobutyryl chloride, TEA, 0° C.-rt, 1 h | 41 |

TABLE 41-continued
Step 2: The Procedure is similar to Step 2[NSSy6924] in Example-857.
| Compound No | R | Condition | Yield (%) |
|---|---|---|---|
| NSSy5710 | (methyl 2-methylpropanoate group) | TFA, DCM, 0° C.-rt, 6 h, Methyl chloroformate, TEA, 0° C.-rt, 1 h | 43 |
Step 2[NSSy5709]: MS (M+1)+=434.4; 1H-NMR (400 MHz, DMSO-d6): δ 7.42-7.41 (m, 2H), 5.83 (s, 1H), 5.36 (s, 1H), 4.80 (d, J=48.00 Hz, 1H), 4.58-4.54 (m, 1H), 4.27-4.23 (m, 1H), 4.17-4.14 (m, 1H), 3.84-3.80 (m, 1H), 2.48 (s, 3H), 1.94-1.93 (m, 2H), 1.76-1.74 (m, 4H), 1.67-1.64 (m, 4H), 0.91-0.93 (m, 6H).
Step 2[NSSy5710]: MS (M+1)+=422.1; 1H-NMR (400 MHz, DMSO-d6): δ 7.56 (s, 1H), 7.43 (d, J=0.80 Hz, 1H), 5.82 (s, 1H), 5.35 (s, 1H), 4.79 (d, J=44.80 Hz, 1H), 4.34 (s, 2H), 3.93 (s, 2H), 3.58 (s, 3H), 2.44 (s, 3H), 2.34-1.74 (m, 6H), 1.64-1.60 (m, 3H).
Example-685
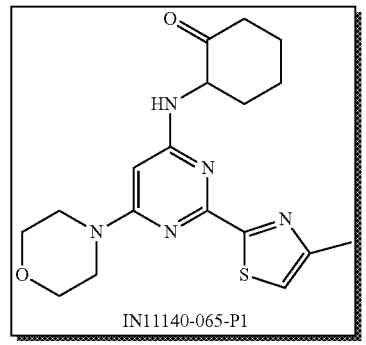
IN11140-065-P1
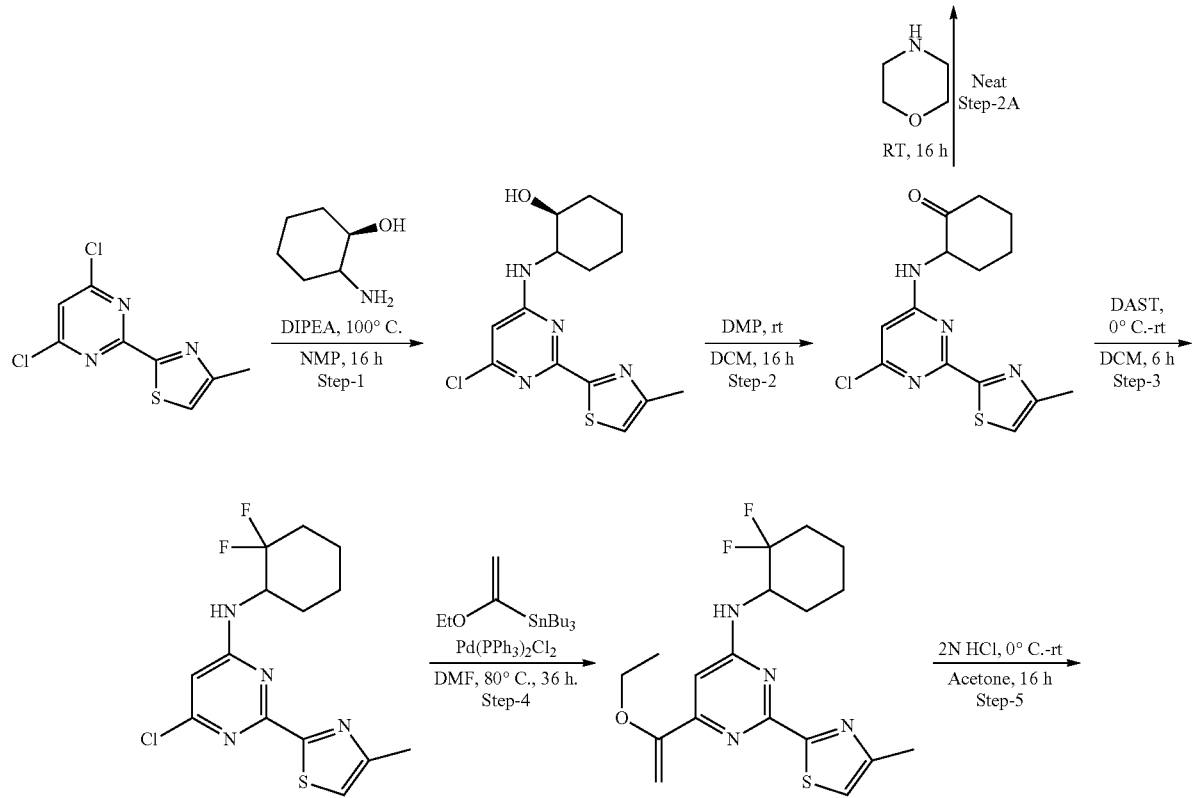

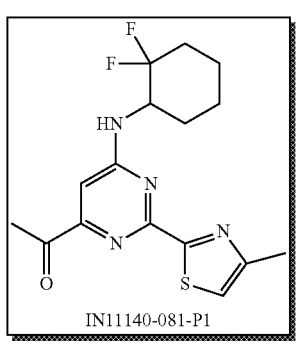 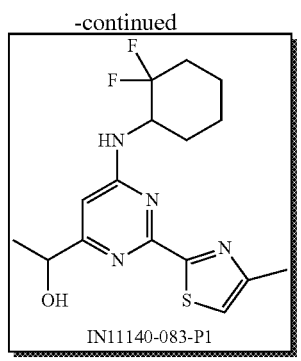 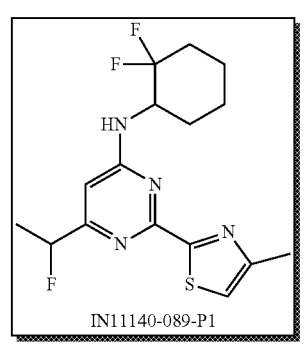

Step 1: The Procedure is similar to Step 1[B] in Example-838. 2.0 g of 2-(4,6-dichloropyrimidin-2-yl)-4-methylthiazole gave (1S)-2-((6-chloro-2-(4-methylthiazol-2-yl)pyrimidin-4-yl)amino)cyclohexan-1-ol as a brownish gum (2.0 g, 70%). MS (M+1)+=325.0.

Step 2: The Procedure is similar to Step 1[NSSy6930] in Example-867. 5.0 g of (1S)-2-((6-chloro-2-(4-methylthiazol-2-yl)pyrimidin-4-yl)amino)cyclohexan-1-ol gave 2-((6-chloro-2-(4-methylthiazol-2-yl)pyrimidin-4-yl)amino)cyclohexan-1-one as a white solid (4.4 g, 88%). MS (M+1)+=323.1.

Step 2A [IN11140-065-P1]: The Procedure is similar to Step 1[A] in Example-838. 0.05 g of 2-((6-chloro-2-(4-methylthiazol-2-yl)pyrimidin-4-yl)amino)cyclohexan-1-one gave 2-((2-(4-methylthiazol-2-yl)-6-morpholinopyrimidin-4-yl)amino)cyclohexan-1-one (0.025 g, 43%). MS (M+1)+= 374.0; 1H-NMR (400 MHz, DMSO-d6): δ 7.34 (d, J=1.2 Hz, 1H), 6.96 (s, 1H), 5.75 (s, 1H), 4.65 (bs, 1H), 3.75-3.65 (m, 5H), 3.60-3.45 (m, 5H), 2.42 (s, 4H), 2.08-2.05 (m, 1H), 1.84-1.77 (m, 2H), 1.62-1.53 (m, 3H).

Step 3: The Procedure is similar to Step 3[NSSy6917] in Example-21. 4.4 g of 2-((6-chloro-2-(4-methylthiazol-2-yl)pyrimidin-4-yl)amino)cyclohexan-1-one gave 6-chloro-N-(2,2-difluorocyclohexyl)-2-(4-methylthiazol-2-yl)pyrimidin-4-amine as a pale yellow solid (3.0 g, 64%). MS (M+1)+=345.0.

Step 4: The Procedure is similar to Step 1[NSSy6989] in Example-839. 1.0 g of 6-chloro-N-(2,2-difluorocyclohexyl)-2-(4-methylthiazol-2-yl)pyrimidin-4-amine gave N-(2,2-difluorocyclohexyl)-6-(1-ethoxyvinyl)-2-(4-methylthiazol-2-yl)pyrimidin-4-amine as a brownish gum (0.8 g, 72%). MS (M+1)+=381.2.

Step 5[IN11140-081-P1]: The Procedure is similar to Step 1[NSSy6697] in Example-873. 0.8 g of N-(2,2-difluorocyclohexyl)-6-(1-ethoxyvinyl)-2-(4-methylthiazol-2-yl)pyrimidin-4-amine gave 1-(6-((2,2-difluorocyclohexyl)amino)-2-(4-methylthiazol-2-yl)pyrimidin-4-yl) ethan-1-one as an off-white solid (0.6 g, 81%). MS (M+1)+=353.0; 1H-NMR (400 MHz, DMSO-d6): δ 8.18 (d, J=8.8 Hz, 1H), 7.48 (s, 1H), 7.10 (s, 1H), 4.70-4.55 (m, 1H), 2.67 (s, 3H), 2.47 (s, 3H), 2.14 (m, 1H), 1.99-1.94 (m, 2H), 1.75 (m, 2H), 1.49 (m, 3H).

Step 6[IN11140-083-P1]: The Procedure is similar to Step 2[NSSy6931] in Example-21. 0.1 g of 1-(6-((2,2-difluorocyclohexyl)amino)-2-(4-methylthiazol-2-yl)pyrimidin-4-yl) ethan-1-one gave 1-(6-((2,2-difluorocyclohexyl)amino)-2-(4-methylthiazol-2-yl)pyrimidin-4-yl) ethan-1-ol as an off-white solid (0.08 g, 80%). MS (M+1)+=355.2; 1H-NMR (400 MHz, DMSO-d6): δ 7.75-7.73 (m, 1H), 7.38 (s, 1H), 6.79 (s, 1H), 5.40-5.38 (m, 1H), 4.54-4.51 (m, 2H), 2.44 (s, 3H), 2.15-2.09 (m, 1H), 1.91-1.89 (m, 2H), 1.75-1.69 (m, 2H), 1.36-1.34 (m, 3H).

Step 7[IN11140-089-P1]: The Procedure is similar to Step 3[NSSy6917] in Example-21. 0.05 g of 1-(6-((2,2-difluorocyclohexyl)amino)-2-(4-methylthiazol-2-yl)pyrimidin-4-yl) ethan-1-ol gave N-(2,2-difluorocyclohexyl)-6-(1-fluoroethyl)-2-(4-methylthiazol-2-yl)pyrimidin-4-amine as an off-white solid (0.027 g, 51%). MS (M+1)+=357.2; 1H-NMR (400 MHz, DMSO-d6): δ 7.93 (s, 1H), 7.42 (s, 1H), 6.95 (s, 1H), 5.61-5.47 (m, 1H), 4.62 (s, 1H), 2.44 (s, 3H), 2.20-1.85 (m, 3H), 1.80-1.45 (m, 8H).

Example-686

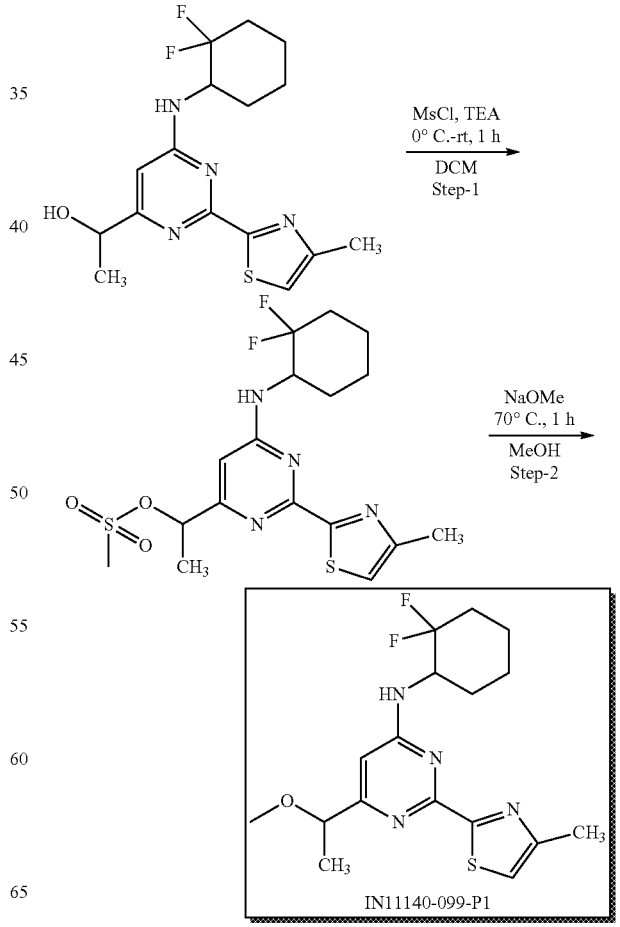

Step 1: The Procedure is similar to Step 3[IN11273-018-P1] in Example-889. 0.1 g of 1-(6-((2,2-difluorocyclohexyl)amino)-2-(4-methylthiazol-2-yl)pyrimidin-4-yl) ethan-1-ol gave 1-(6-((2,2-difluorocyclohexyl)amino)-2-(4-methylthiazol-2-yl)pyrimidin-4-yl)ethyl methanesulfonate as a brown gum (0.1 g, 83%). MS (M+1)+=433.0.

Step 2[IN11140-099-P1]: The Procedure is similar to Step 1[NSSy6519] in Example-842. 0.1 g of 1-(6-((2,2-difluorocyclohexyl)amino)-2-(4-methylthiazol-2-yl)pyrimidin-4-yl) ethyl methanesulfonate gave N-(2,2-difluorocyclohexyl)-6-(1-methoxyethyl)-2-(4-methylthiazol-2-yl)pyrimidin-4-amine as a brown solid (0.035 g, 41%). MS (M+1)+=369.2; 1H-NMR (400 MHz, DMSO-d6): δ 7.78 (d, J=8.80 Hz, 1H), 7.40 (s, 1H), 6.67 (s, 1H), 4.60 (s, 1H), 4.19 (q, J=6.40 Hz, 1H), 3.28 (s, 3H), 2.44 (s, 3H), 2.15 (s, 1H), 1.90 (m, 2H), 1.72 (s, 2H), 1.60-1.50 (m, 3H), 1.36-1.30 (m, 3H).

Example-687

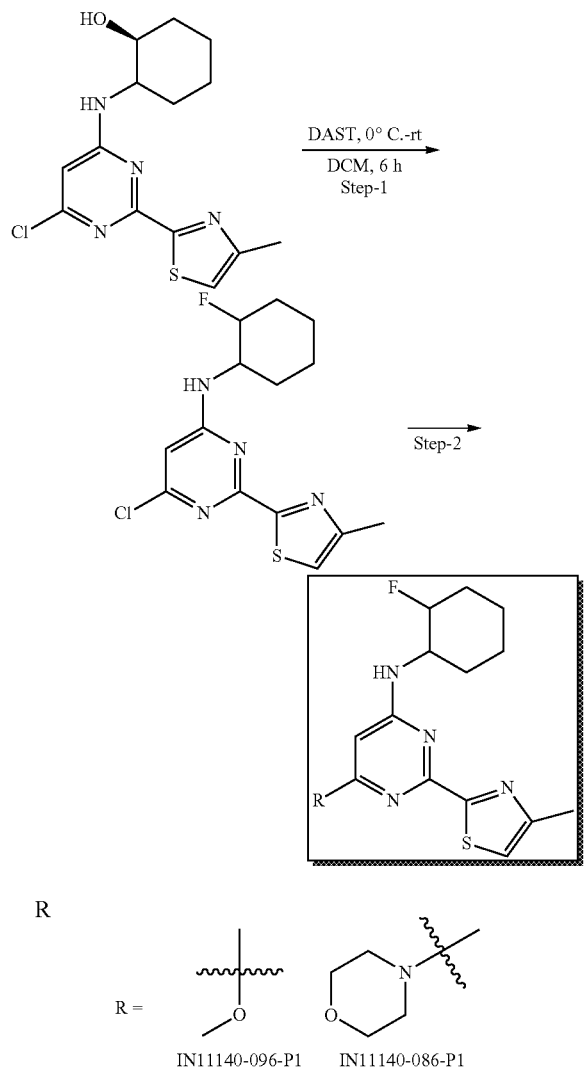

TABLE 42

| | | Step 2: | | |
|---|---|---|---|---|
| Compound No | R | Condition | Yield (%) | MS (M + 1)+ |
| IN11140-096-P1 | (methoxymethyl group) | NaOMe, 70° C., 5 h, MeOH | 23 | 323.2 |
| IN11140-086-P1 | (morpholinyl group) | Morpholine, rt, 16 h | 36 | 378.2 |

Step 2[IN11140-096-P1]: The procedure is similar to Step 1[NSSy6519] in Example-842. 1H-NMR (400 MHz, DMSO-d6): δ 7.50 (d, J=8.0 Hz, 1H), 7.41 (s, 1H), 5.83 (bs, 1H), 4.50-4.37 (m, 1H), 3.88 (s, 3H), 2.44 (s, 3H), 2.08-1.94 (m, 2H), 1.72-1.54 (m, 3H), 1.32-1.23 (m, 4H).

Step 2[IN11140-086-P1]: 1H-NMR (400 MHz, DMSO-d6): δ 7.34 (s, 1H), 7.10 (d, J=8.80 Hz, 1H), 6.14 (s, 1H), 4.50-4.35 (m, 1H), 3.69 (s, 4H), 3.50 (s, 4H), 2.42 (s, 3H), 2.08 (s, 1H), 1.92 (s, 1H), 1.75-1.45 (m, 3H), 1.35-1.25 (m, 3H).

Example-688

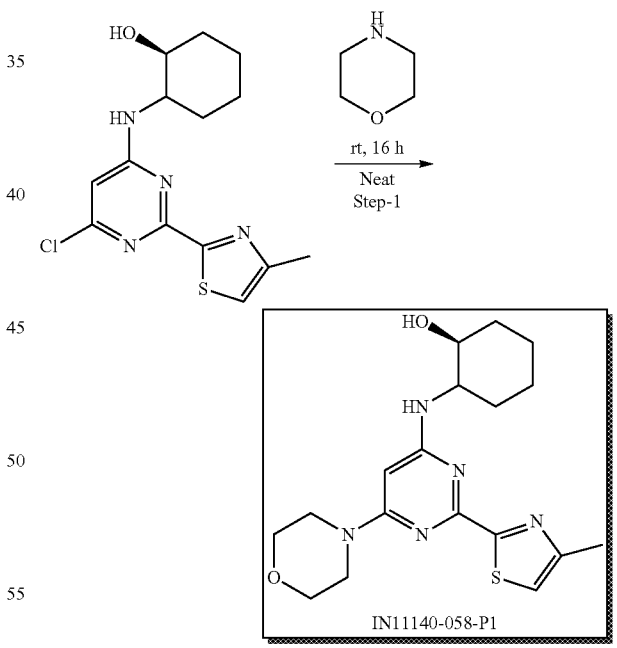

Step 1[IN11140-058-P1]: The Procedure is similar to Step 1[B] in Example-2. 0.1 g of (1S)-2-((6-chloro-2-(4-methylthiazol-2-yl)pyrimidin-4-yl)amino)cyclohexan-1-ol gave 6-chloro-N-(2-fluorocyclohexyl)-2-(4-methylthiazol-2-yl)pyrimidin-4-amine as an off-white solid (0.037 g, 32%). MS (M+1)+=376.1; 1H-NMR (400 MHz, DMSO-d6): δ 7.33 (s, 1H), 6.78 (d, J=6.80 Hz, 1H), 5.66 (s, 1H), 4.68 (d, J=4.80 Hz, 1H), 3.69 (s, 4H), 3.49 (s, 4H), 2.41 (s, 3H), 2.00-1.85 (m, 2H), 1.62-1.56 (m, 2H), 1.35-1.15 (m, 6H).

Step 1: The Procedure is similar to Step 3[NSSy6917] in Example-21. 0.5 g of (1S)-2-((6-chloro-2-(4-methylthiazol-2-yl)pyrimidin-4-yl)amino)cyclohexan-1-ol gave 6-chloro-N-(2-fluorocyclohexyl)-2-(4-methylthiazol-2-yl)pyrimidin-4-amine as a pale yellow solid (0.4 g, 80%). MS (M+1)+=225.0.

Example-689

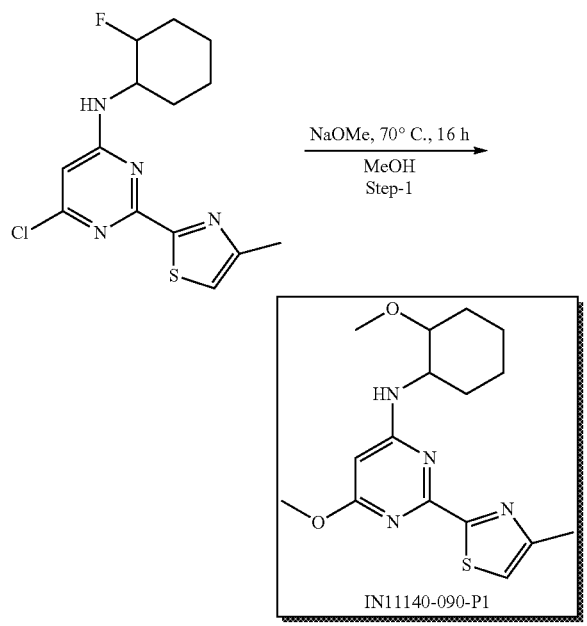

Step 1[IN11140-090-P1]: The Procedure is similar to Step 1[NSSy6519] in Example-6. 0.1 g of 6-chloro-N-(2-fluorocyclohexyl)-2-(4-methylthiazol-2-yl)pyrimidin-4-amine gave 6-methoxy-N-(2-methoxycyclohexyl)-2-(4-methylthiazol-2-yl)pyrimidin-4-amine as an off-white solid (0.04 g, 41%). MS (M+1)$^+$=335.2; $^1$H-NMR (400 MHz, DMSO-d$_6$): δ 7.39 (s, 1H), 7.31 (d, J=8.00 Hz, 1H), 5.79 (s, 1H), 3.87 (s, 3H), 3.26 (s, 3H), 3.14 (s, 1H), 2.43 (s, 3H), 2.05 (s, 1H), 1.91 (s, 1H), 1.70-1.60 (m, 2H), 1.35-1.15 (m, 5H).

Example-690

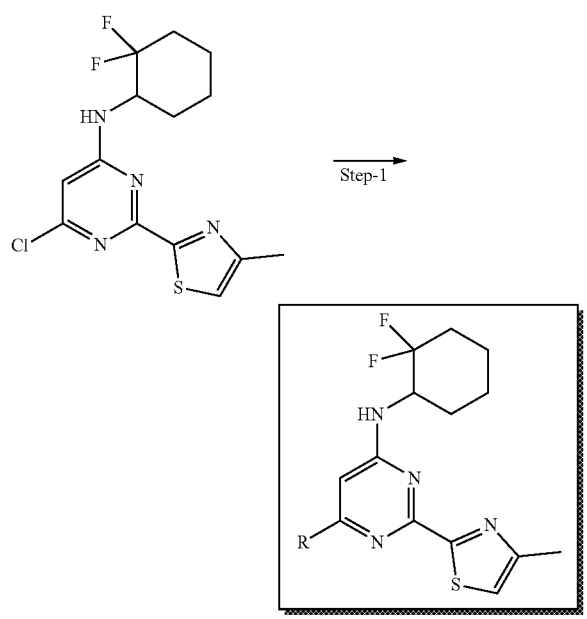

R=

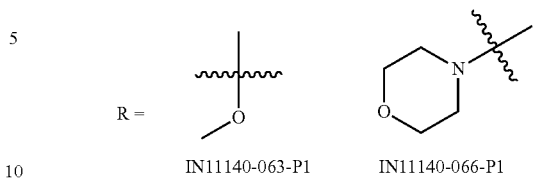

TABLE 43

| Step 1: | | | | |
|---|---|---|---|---|
| Compound No | R | Condition | Yield (%) | MS (M + 1)$^+$ |
| IN11140-063-P1 | methoxy | NaOMe, 70° C., 5 h, MeOH | 24 | 366.2 |
| IN11140-066-P1 | morpholine | Morpholine, rt, 16 h | 29 | 366.2 |

Step 1[IN11140-063-P1]: The procedure is similar to Step 1[NSSy6519] in Example-842. 1H-NMR (400 MHz, DMSO-d6): δ 8.12 (d, J=8.80 Hz, 1H), 7.50 (s, 1H), 6.68 (s, 1H), 4.59 (s, 1H), 3.53 (s, 3H), 2.45 (s, 3H), 2.15-2.05 (m, 6H), 2.00-1.70 (m, 2H).

Step 1[IN11140-066-P1]: 1H-NMR (400 MHz, DMSO-d6): δ 7.34 (d, J=1.20 Hz, 1H), 7.07 (d, J=9.20 Hz, 1H), 5.82 (s, 1H), 4.50 (s, 1H), 3.69 (t, J=4.80 Hz, 4H), 3.49 (s, 4H), 2.45 (s, 3H), 2.11-1.40 (m, 8H).

Example-691

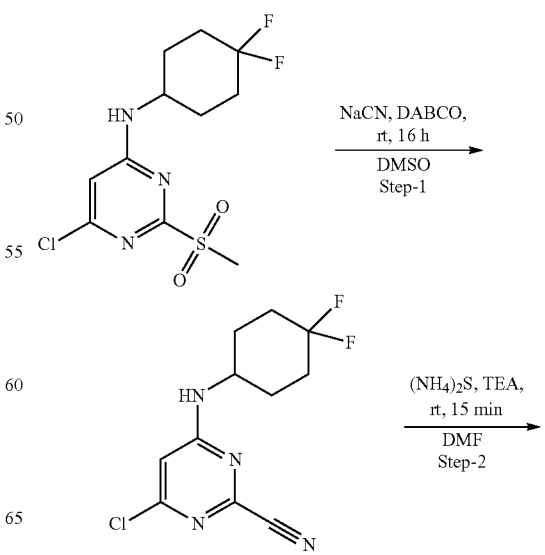

Step 2: To a stirred solution of 4-chloro-6-((4,4-difluorocyclohexyl)amino)pyrimidine-2-carbonitrile (0.9 g, 3.30 mmol) in N, N-dimethylformamide (15 mL) was added triethylamine (0.66 g, 6.60 mmol) and ammonium sulphide in water (20%) (2.24 g, 6.60 mmol) and the reaction mixture was stirred at room temperature. After 15 min, the reaction mixture was quenched with water and extracted with ethyl acetate (2×25 mL). The combined organic layer was dried over sodium sulphate and concentrated under reduced pressure to afford 4-chloro-6-((4,4-difluorocyclohexyl)amino)pyrimidine-2-carbothioamide as light brown solid (0.8 g, 80%). MS (M+1)+=307.0.

Step 3: To a stirred solution of 4-chloro-6-((4,4-difluorocyclohexyl)amino)pyrimidine-2-carbothioamide (0.8 g, 2.60 mmol) in THF (30 mL) was added Ethyl bromopyruvate (0.76 g, 3.9 mmol). The reaction mixture was stirred at room temperature. After 4 h, the reaction mixture was concentrated to afford crude product, which was dissolved in ethyl acetate and washed with 10% sodium bicarbonate solution, the organic layer was concentrated to afford ethyl 2-(4-chloro-6-((4,4-difluorocyclohexyl)amino)pyrimidin-2-yl)thiazole-4-carboxylate as an off-white solid (0.6 g, 60%). MS (M+1)+=403.0.

Step 4: The procedure is similar to Step 4[NSSy6711] in Example-854. 0.6 g of ethyl 2-(4-chloro-6-((4,4-difluorocyclohexyl)amino)pyrimidin-2-yl)thiazole-4-carboxylate gave (2-(4-chloro-6-((4,4-difluorocyclohexyl)amino)pyrimidin-2-yl)thiazol-4-yl)methanol as an off-white gum (0.4 g, 75%). MS (M+1)+=361.0.

Step 5: The procedure is similar to Step 3[NSSy6917] in Example-21. 0.4 g of (2-(4-chloro-6-((4,4-difluorocyclohexyl)amino)pyrimidin-2-yl) thiazol-4-yl) methanol gave 6-chloro-N-(4,4-difluorocyclohexyl)-2-(4-(fluoromethyl)thiazol-2-yl)pyrimidin-4-amine as a light yellow solid (0.2 g, 50%). MS (M+1)+=362.8.

Step 6[NSSy5715]: The procedure is similar to Step 1[B] in Example-838. 0.2 g of 6-chloro-N-(4,4-difluorocyclohexyl)-2-(4-(fluoromethyl)thiazol-2-yl)pyrimidin-4-amine gave N-(4,4-difluorocyclohexyl)-2-(4-(fluoromethyl) thiazol-2-yl)-6-(2-oxa-6-azaspiro[3.3]heptan-6-yl)pyrimidin-4-amine as an off-white solid (0.06 g, 26%). MS (M+1)+= 426.0; 1H-NMR (400 MHz, DMSO-d6): δ 7.92 (d, J=3.20 Hz, 1H), 7.09 (d, J=8.00 Hz, 1H), 5.56 (s, 1H), 5.44 (s, 1H), 5.32 (s, 1H), 4.73 (m, 4H), 4.16 (m, 4H), 3.95 (m, 1H), 2.08-1.91 (m, 6H), 1.58-1.55 (m, 2H).

Example-692

Step 1: The procedure is similar to Step 1[NSSy6710] in Example-854. 2.0 g of 6-chloro-N-(4,4-difluorocyclohexyl)-2-(methylsulfonyl)pyrimidin-4-amine gave 4-chloro-6-((4,4-difluorocyclohexyl)amino)pyrimidine-2-carbonitrile as an off-white gum (0.9 g, 56%). MS (M+1)+=272.7.

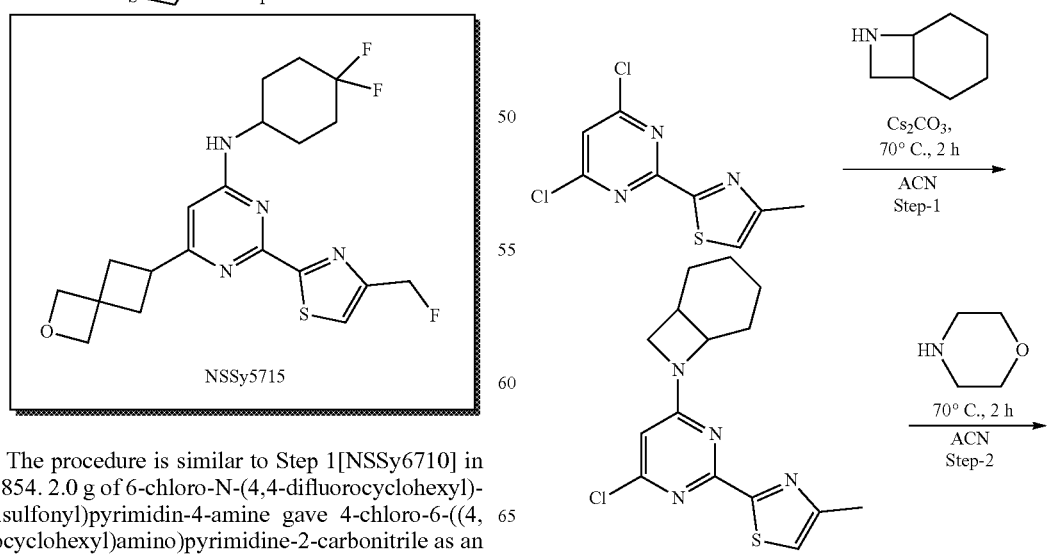

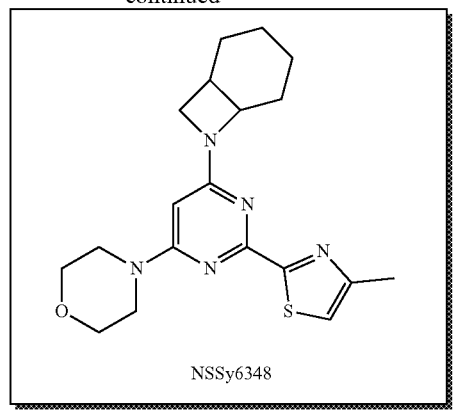

NSSy6348

Step 1: The procedure is similar to Step 1[B] in Example-838. 0.25 g of 2-(4,6-dichloropyrimidin-2-yl)-4-methylthiazole gave 2-(4-(7-azabicyclo [4.2.0] octan-7-yl)-6-chloropyrimidin-2-yl)-4-methylthiazole as a brownish gum (0.31 g, 96%). MS (M+1)+=321.1.

Step 2[NSSy6348]: The procedure is similar to Step 1[B] in Example-838. 0.2 g of 2-(4-(7-azabicyclo[4.2.0]octan-7-yl)-6-chloropyrimidin-2-yl)-4-methylthiazole gave 4-(6-(7-azabicyclo[4.2.0]octan-7-yl)-2-(4-methylthiazol-2-yl)pyrimidin-4-yl)morpholine as pale yellow solid (0.088 g, 29%). MS (M+1)+=372.1; 1H-NMR (400 MHz, DMSO-d6): δ 7.34 (s, 1H), 5.50 (s, 1H), 4.37-4.35 (m, 1H), 3.92-3.88 (m, 1H), 3.68-3.63 (m, 5H), 3.55-3.54 (m, 4H), 2.67-2.63 (m, 1H), 2.42 (s, 3H), 2.14-2.11 (m, 1H), 1.88-1.87 (m, 1H), 1.82-1.61 (m, 2H), 1.61-1.34 (m, 4H).

Example-693

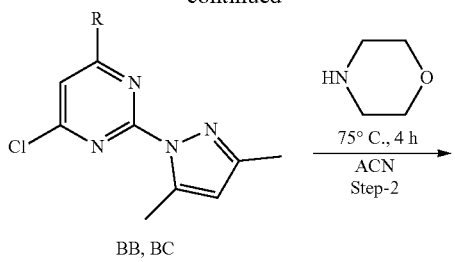

BB, BC

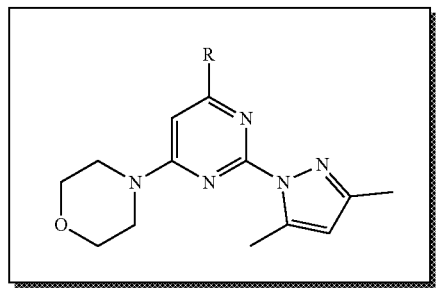

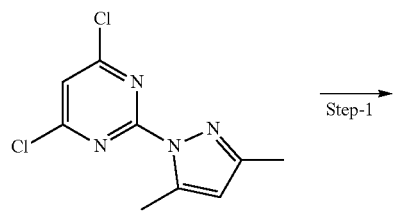

R=

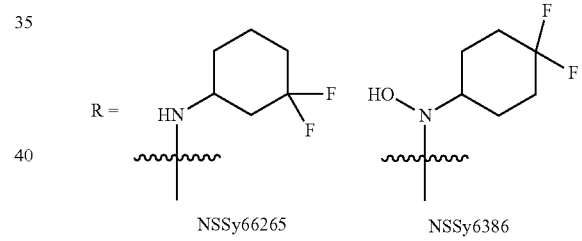

NSSy66265   NSSy6386

TABLE 44

| Step 1: The procedure is similar to Step 1[B] in Example-838. | | | | |
|---|---|---|---|---|
| Compound No | R | Condition | Yield (%) | MS (M + 1)+ |
| BB | HN—⌬(CF2) | DIPEA, ACN, 75° C., 5 h | 90 | 342.3 |
| BC | HO-N—⌬(CF2) | Cs2CO3, ACN, 75° C., 16 h | 34 | 358.5 |

TABLE 45

Step 2: The procedure is similar to Step 1[B] in Example-838.

| Compound No | R | Condition | Yield (%) | MS (M + 1)+ |
|---|---|---|---|---|
| NSSy6265 | 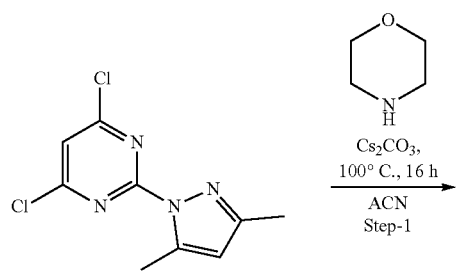 | Morpholine, ACN, 75° C., 16 h | 62 | 395.2 |
| NSSy6386 | 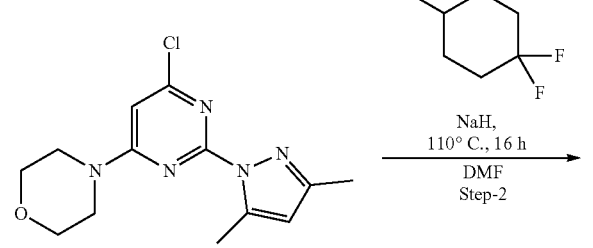 | Morpholine, ACN, 75° C., 16 h | 55 | 409.25 |

Step 2[NSSy6265]: 1H-NMR (400 MHz, DMSO-d6-80° C.): δ 7.09 (d, J=8.12 Hz, 1H), 6.01 (s, 1H), 5.54 (s, 1H), 3.96 (s, 1H), 3.68-3.66 (m, 4H), 3.45 (s, 4H), 2.49 (s, 3H), 2.33-2.30 (m, 1H), 2.15 (s, 3H), 2.00-1.90 (m, 2H), 1.82-1.67 (m, 3H), 1.49-1.45 (m, 1H), 1.30-1.24 (m, 1H).

Step 2[NSSy6386]: 1H-NMR (400 MHz, DMSO-d6): δ 9.32 (s, 1H), 6.04 (d, J=7.60 Hz, 1H), 4.48 (s, 1H), 3.67-3.54 (m, 4H), 3.53-3.42 (m, 4H), 3.32 (s, 3H), 2.16 (s, 3H), 2.09-1.83 (m, 6H), 1.69-1.52 (m, 2H).

Example-694

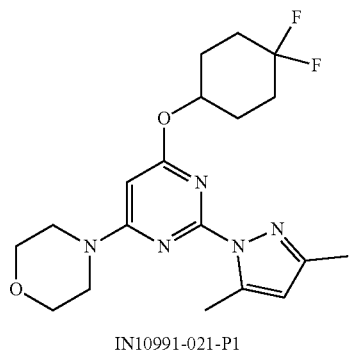

Step 1: The procedure is similar to Step 1[B] in Example-838. 0.8 g of 4,6-dichloro-2-(3,5-dimethyl-1H-pyrazol-1-yl)pyrimidine gave 4-(6-chloro-2-(3,5-dimethyl-1H-pyrazol-1-yl)pyrimidin-4-yl) morpholine as an off-white solid (0.8 g, 82%). MS (M+1)+=294.0.

Step 2[IN10991-021-P1]: To a suspension of sodium hydride (0.04 g, 1.062 mmol) in N, N-Dimethylformamide (3 mL) was added 4,4-difluorocyclohexan-1-ol (0.1 g, 0.75 mmol), stirred until effervescence ceased. 4-(6-chloro-2-(3,5-dimethyl-1H-pyrazol-1-yl)pyrimidin-4-yl) morpholine (0.2 g, 0.68 mmol) was added to the reaction mixture and heated to 110° C. for 16 h. The reaction mixture was poured into ice cold Water (10 mL) and extracted with ethyl acetate (2×10 mL). The organic layer was washed with brine solution, dried over sodium sulfate and concentrated under reduced pressure to afford crude product which was purified by flash column chromatography using 15% ethyl acetate in pet-ether to afford 4-(6-((4,4-difluorocyclohexyl)oxy)-2-(3,5-dimethyl-1H-pyrazol-1-yl)pyrimidin-4-yl)morpholine as a white solid (0.07 g, 17%). MS (M+1)+=394.1; 1H-NMR (400 MHz, DMSO-d6): δ 6.73 (s, 1H), 6.13 (s, 1H), 5.06 (s, 1H), 3.66 (s, 4H), 3.59 (s, 4H), 2.61 (s, 3H), 2.19 (s, 3H), 2.10-1.95 (m, 6H), 1.90-1.80 (m, 2H).

Example-695

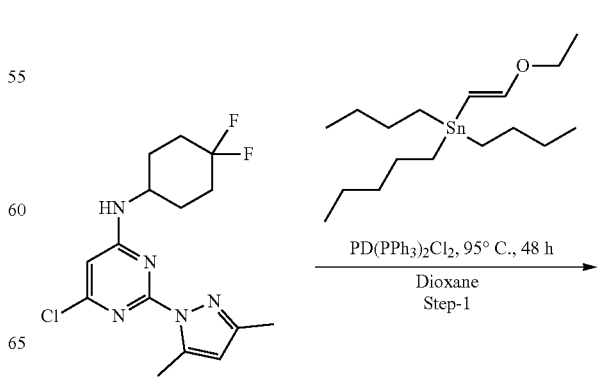

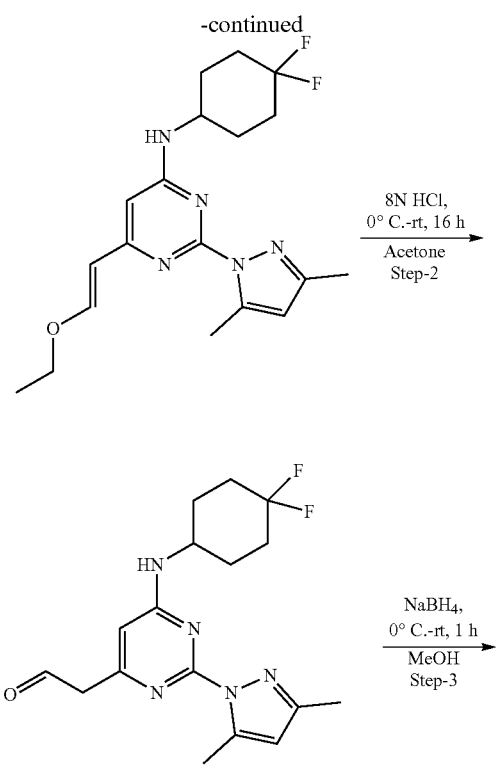

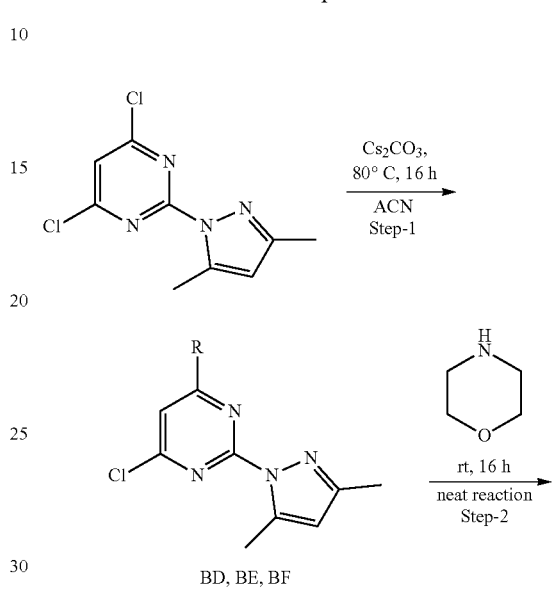

hexyl)amino)-2-(3,5-dimethyl-1H-pyrazol-1-yl)pyrimidin-4-yl) ethan-1-ol as a white solid (0.015 g, 7%). MS (M+1)+= 352.1; 1H-NMR (400 MHz, DMSO-d6): δ 7.55 (d, J=7.60 Hz, 1H), 6.27 (s, 1H), 6.03 (s, 1H), 4.67 (t, J=5.20 Hz, 1H), 4.01 (s, 1H), 3.75-3.65 (m, 2H), 2.70-2.60 (m, 4H), 2.16 (s, 3H), 2.10-1.85 (m, 7H), 1.60-1.50 (m, 2H).

Example-696

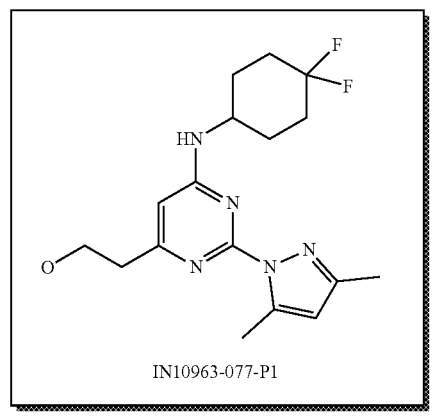

IN10963-077-P1

Step 1: The procedure is similar to Step 1[H] in Example-838. 0.5 g of 6-chloro-N-(4,4-difluorocyclohexyl)-2-(3,5-dimethyl-1H-pyrazol-1-yl)pyrimidin-4-amine gave (E)-N-(4,4-difluorocyclohexyl)-2-(3,5-dimethyl-1H-pyrazol-1-yl)-6-(2-ethoxyvinyl)pyrimidin-4-amine as a pale yellow solid (0.27 g, 49%). MS (M+1)+=378.1.

Step 2: The procedure is similar to Step 1[NSSy6697] in Example-873. 0.15 g of (E)-N-(4,4-difluorocyclohexyl)-2-(3,5-dimethyl-1H-pyrazol-1-yl)-6-(2-ethoxy vinyl)pyrimidin-4-amine gave 2-(6-((4,4-difluorocyclohexyl)amino)-2-(3,5-dimethyl-1H-pyrazol-1-yl)pyrimidin-4-yl) acetaldehyde as a brownish gum (0.14 g, 70%). MS (M+1)+=350.2.

Step 3[IN10963-077-P1]: The procedure is similar to Step 2[NSSy6931] in Example-21. 0.22 g of 2-(6-((4,4-difluorocyclohexyl)amino)-2-(3,5-dimethyl-1H-pyrazol-1-yl)pyrimidin-4-yl)acetaldehyde gave 2-(6-((4,4-difluorocyclo-

BD, BE, BF

R=

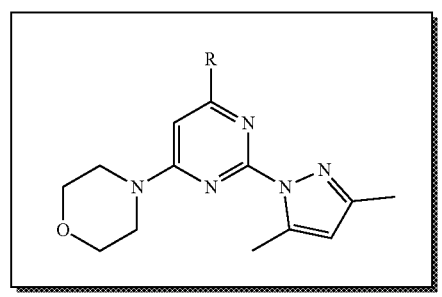

IN10963-049-P1    IN11108-019-P1

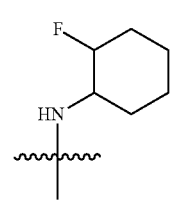 [SMILES: *NC1CCCCC1F]

IN11146-016-P1

TABLE 46

Step 1: The procedure is similar to Step 1[B] in Example-838.

| Compound No | R | Condition | Yield (%) | MS (M + 1)+ |
|---|---|---|---|---|
| BD | 4-fluorocyclohexyl-NH- | Cs₂CO₃, ACN, 80° C., 16 h | 50 | 324.0 |
| BE | 3,3-difluorocyclobutyl-NH- | Cs₂CO₃, ACN, 60° C., 16 h | 75 | 314.0 |
| BF | 2-fluorocyclohexyl-NH- | Cs₂CO₃, ACN, 80° C., 16 h | 75 | 324.0 |

TABLE 47

Step 2: The procedure is similar to Step 1[B] in Example-838.

| Compound No | R | Condition | Yield (%) | MS (M + 1)+ |
|---|---|---|---|---|
| IN10963-049-P1 | 4-fluorocyclohexyl-NH- | Morpholine, rt, 16 h | 63 | 375.1 |
| IN11108-019-P1 | 3,3-difluorocyclobutyl-NH- | Morpholine, rt, 16 h | 59 | 365.1 |
| IN11146-016-P1 | 2-fluorocyclohexyl-NH- | Morpholine, rt, 16 h | 47 | 375.1 |

Step 2[IN10963-049-P1]: 1H-NMR (400 MHz, DMSO-d6): δ 7.00 (d, J=7.60 Hz, 1H), 5.99 (s, 1H), 5.54 (s, 1H), 4.84-4.72 (m, 1H), 3.67 (s, 4H), 3.44 (s, 4H), 2.52 (s, 3H), 2.14 (s, 3H), 1.90-1.50 (m, 8H).

Step 2[IN11108-019-P1]: 1H-NMR (400 MHz, DMSO-d6): δ 7.56 (d, J=6.4 Hz, 1H), 6.01 (s, 1H), 5.51 (s, 1H), 4.11 (m, 1H), 3.68-3.65 (m, 4H), 3.50-3.43 (m, 4H), 3.31-2.96 (m, 2H), 2.67-2.59 (m, 2H), 2.55 (s, 3H), 2.14 (s, 3H).

Step 2[IN11146-016-P1]: 1H-NMR (400 MHz, DMSO-d6): δ 7.12 (s, 1H), 6.00 (s, 1H), 5.58 (s, 1H), 4.47-4.42 (m, 1H), 4.34-4.30 (m, 1H), 3.91 (s, 1H), 3.67 (s, 4H), 3.45 (s, 4H), 2.30 (s, 4H), 2.10-1.85 (m, 2H), 1.62-1.45 (m, 3H), 1.32-1.20 (m, 4H).

Example-697

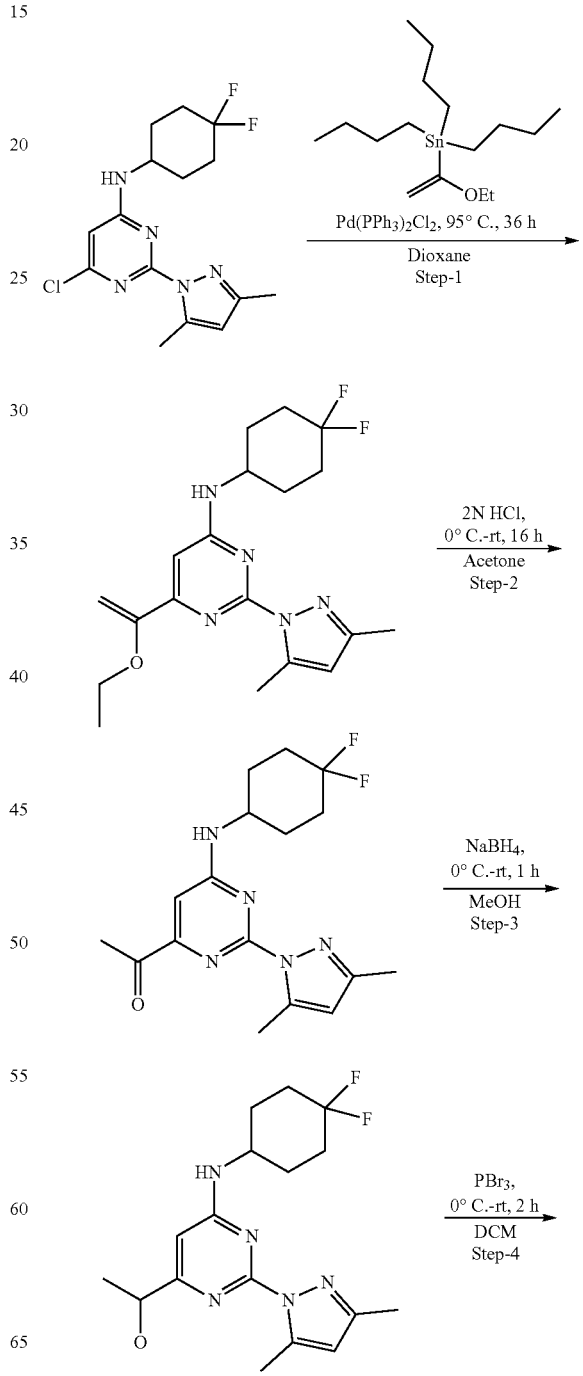

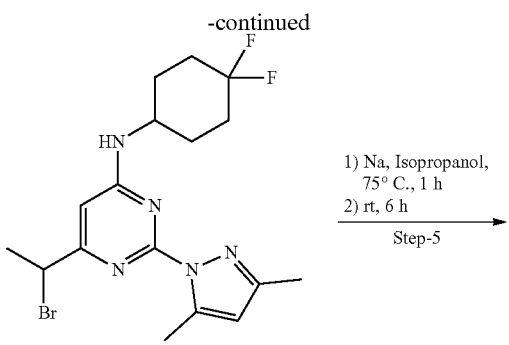

1) Na, Isopropanol, 75° C., 1 h
2) rt, 6 h
Step-5

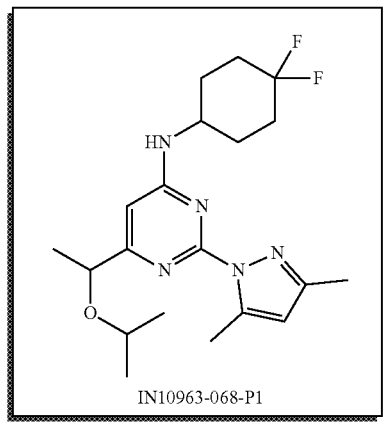

IN10963-068-P1

Step 1: The procedure is similar to Step 1[H] in Example-838. 2.0 g of 6-chloro-N-(4,4-difluorocyclohexyl)-2-(3,5-dimethyl-1H-pyrazol-1-yl)pyrimidin-4-amine gave N-(4,4-difluorocyclohexyl)-2-(3,5-dimethyl-1H-pyrazol-1-yl)-6-(1-ethoxyvinyl)pyrimidin-4-amine as a brownish gum (1.2 g, 54%). MS (M+1)+=378.1.

Step 2: The procedure is similar to Step 1[NSSy6697] in Example-873. 1.2 g of N-(4,4-difluorocyclohexyl)-2-(3,5-dimethyl-1H-pyrazol-1-yl)-6-(1-ethoxyvinyl)pyrimidin-4-amine gave 1-(6-((4,4-difluorocyclohexyl)amino)-2-(3,5-dimethyl-1H-pyrazol-1-yl)pyrimidin-4-yl)ethan-1-one as a brownish gum (1.0 g, 90%). MS (M+1)+=350.0.

Step 3: The procedure is similar to Step 2[NSSy6931] in Example-21. 0.5 g of 1-(6-((4,4-difluorocyclohexyl)amino)-2-(3,5-dimethyl-1H-pyrazol-1-yl)pyrimidin-4-yl)ethan-1-one gave 1-(6-((4,4-difluorocyclohexyl)amino)-2-(3,5-dimethyl-1H-pyrazol-1-yl)pyrimidin-4-yl)ethan-1-ol as an off-white solid (0.45 g, 89%). MS (M+1)+=352.1.

Step 4: To a stirred solution of 1-(6-((4,4-difluorocyclohexyl)amino)-2-(3,5-dimethyl-1H-pyrazol-1-yl)pyrimidin-4-yl)ethan-1-ol (0.45 g, 1.28 mmol) in dichloromethane (50 mL) was added Phosphorus tribromide (0.6 mL, 6.40 mmol) slowly portion wise at 0° C. The reaction mixture was warmed to rt and stirred for 16 h. The reaction mixture was poured in ice cold water (80 mL), extracted with DCM (3×50 mL). The combined organic layers were washed with saturated NaHCO$_3$ solution (3×20 mL) followed by brine solution (20 mL), dried over sodium sulfate, filtered and concentrated under reduced pressure to afford crude product which was purified by flash column chromatography using 30% ethyl acetate in pet-ether to afford 6-(1-bromoethyl)-N-(4,4-difluorocyclohexyl)-2-(3,5-dimethyl-1H-pyrazol-1-yl)pyrimidin-4-amine as an off-white solid (0.27 g, 51%). MS (M+1)+=414.0.

Step 5[IN10963-068-P1]: Sodium metal (0.14 g, 6.05 mmol) was added to isopropanol (20 mL) at rt, the mixture was heated at 75° C. for 1 h. The above mixture (sodium isopropoxide) was cooled to rt, then 6-(1-bromoethyl)-N-(4,4-difluorocyclohexyl)-2-(3,5-dimethyl-1H-pyrazol-1-yl)pyrimidin-4-amine (0.25 g, 0.60 mmol) was added. The reaction mixture was stirred at rt for 6 h. The reaction mixture was poured in ice cold water (40 mL), extracted with ethyl acetate (2×50 mL). The combined organic layers were washed with brine solution (20 mL), dried over sodium sulfate, filtered and concentrated under reduced pressure to afford crude product which was purified by flash column chromatography using 37% ethyl acetate in pet-ether to afford N-(4,4-difluorocyclohexyl)-2-(3,5-dimethyl-1H-pyrazol-1-yl)-6-(1-isopropoxyethyl)pyrimidin-4-amine as a white solid (0.04 g, 17%). MS (M+1)+=394.2; 1H-NMR (400 MHz, DMSO-d6): δ 7.68 (s, 1H), 6.48 (s, 1H), 6.04 (s, 1H), 4.05 (s, 1H), 3.62-3.55 (m, 1H), 2.32 (s, 3H), 2.12-1.85 (m, 6H), 1.60-1.50 (m, 2H), 1.30-1.20 (m, 6H), 1.18-1.10 (m, 7H).

Example-698

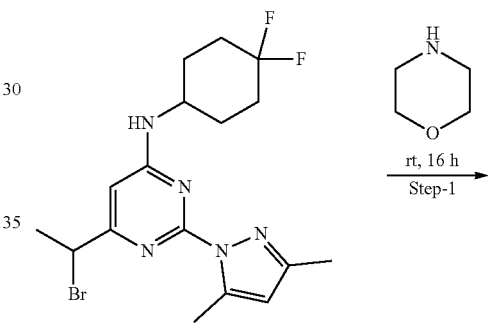

rt, 16 h
Step-1

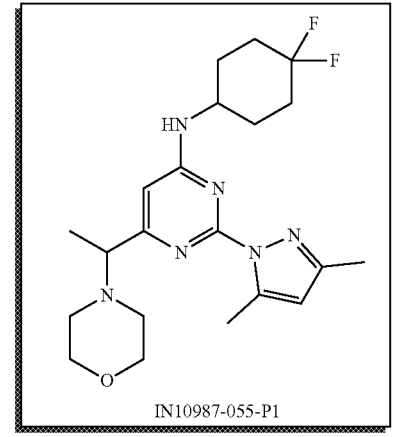

IN10987-055-P1

Step 1[IN10987-055-P1]: The procedure is similar to Step 1[B] in Example-838. 0.2 g of 6-(1-bromoethyl)-N-(4,4-difluorocyclohexyl)-2-(3,5-dimethyl-1H-pyrazol-1-yl)pyrimidin-4-amine gave N-(4,4-difluorocyclohexyl)-2-(3,5-dimethyl-1H-pyrazol-1-yl)-6-(1-morpholinoethyl)pyrimidin-4-amine as an off-white solid (0.14 g, 68%). MS (M+1)+=421.1; 1H-NMR (400 MHz, DMSO-d6): δ 7.61 (s, 1H), 6.46 (s, 1H), 6.04 (s, 1H), 4.03 (s, 1H), 3.59 (s, 3H), 2.50 (s, 5H), 2.16 (s, 4H), 2.10-1.85 (m, 8H), 1.60-1.50 (m, 2H), 1.25 (s, 4H).

Example-699

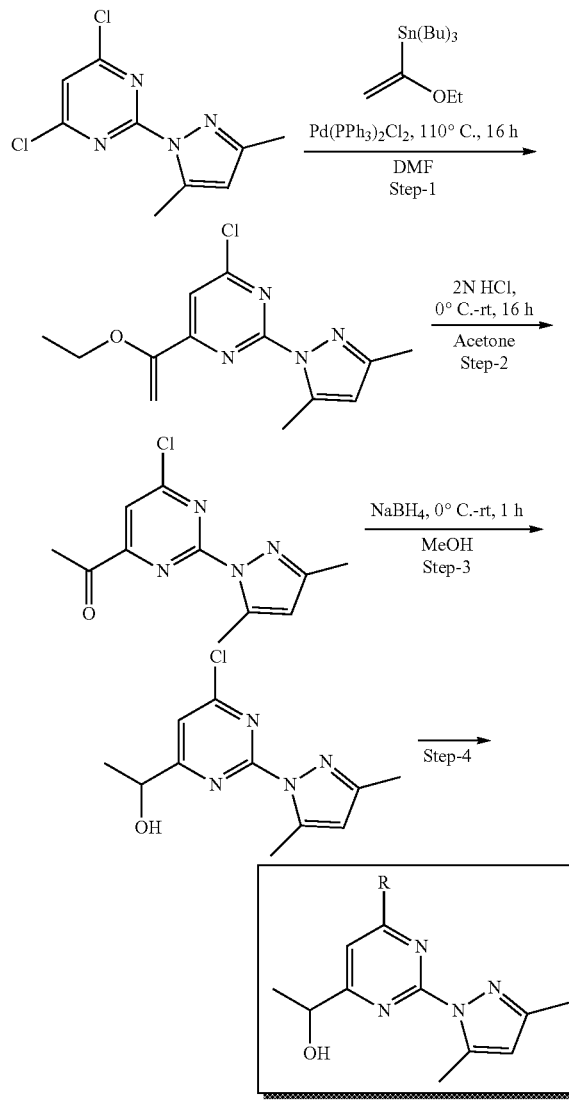

R =

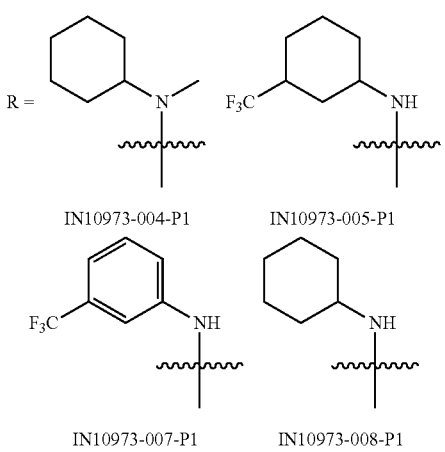

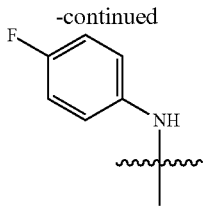

IN10973-006-P1

Step 1: The procedure is similar to Step 1[H] in Example-838. 1.8 g of 4,6-dichloro-2-(3,5-dimethyl-1H-pyrazol-1-yl)pyrimidine gave 4-chloro-2-(3,5-dimethyl-1H-pyrazol-1-yl)-6-(1-ethoxyvinyl)pyrimidine as an off-white solid (1.1 g, 53%). MS (M+1)+=279.0.

Step 2: The procedure is similar to Step 1[NSSy6697] in Example-873. 1.1 g of 4-chloro-2-(3,5-dimethyl-1H-pyrazol-1-yl)-6-(1-ethoxyvinyl)pyrimidine gave 1-(6-chloro-2-(3,5-dimethyl-1H-pyrazol-1-yl)pyrimidin-4-yl) ethan-1-one as an off-white solid (0.72 g, 72%). MS (M+1)+=251.0.

Step 3: The procedure is similar to Step 2[NSSy6931] in Example-21. 0.72 g of 1-(6-chloro-2-(3,5-dimethyl-1H-pyrazol-1-yl)pyrimidin-4-yl) ethan-1-one gave 1-(6-chloro-2-(3,5-dimethyl-1H-pyrazol-1-yl)pyrimidin-4-yl) ethan-1-ol as an off-white solid (0.65 g, 92%). MS (M+1)+=253.0.

TABLE 48

| Compound No | R | Condition | Yield (%) | MS (M + 1)+ |
|---|---|---|---|---|
| IN10973-004-P1 | cyclohexyl-N(CH3)- | rt, 16 h | 57 | 330.1 |
| IN10973-005-P1 | 3-CF3-cyclohexyl-NH- | rt, 16 h | 53 | 384.1 |
| IN10973-008-P1 | cyclohexyl-NH- | rt, 16 h | 70 | 316.1 |

Step 4[IN10973-004-P1]: 1H-NMR (400 MHz, DMSO-d6): δ 6.60 (s, 1H), 6.05 (s, 1H), 5.42 (d, J=5.20 Hz, 1H), 4.50-4.52 (m, 1H), 3.35 (s, 5H), 2.48 (s, 3H), 2.17 (s, 3H), 1.81 (d, J=12.80 Hz, 2H), 1.70-1.50 (m, 5H), 1.35 (d, J=6.80 Hz, 5H).

Step 4[IN10973-005-P1]: 1H-NMR (400 MHz, DMSO-d6): δ 7.66 (s, 1H), 6.50 (s, 1H), 6.04 (s, 1H), 5.40 (t, J=4.40 Hz, 1H), 4.46-4.32 (m, 1H), 3.89 (s, 1H), 2.43 (s, 3H), 2.16 (s, 3H), 1.90-1.59 (m, 6H), 1.38-1.26 (m, 6H).

Step 4[IN10973-008-P1]: 1H-NMR (400 MHz, DMSO-d6): δ 7.56 (d, J=7.60 Hz, 1H), 6.50 (s, 1H), 6.03 (s, 1H), 5.35 (s, 1H), 4.45 (s, 1H), 3.82 (s, 1H), 2.16 (s, 3H), 1.89 (d, J=11.20 Hz, 2H), 1.74-1.71 (m, 2H), 1.65-1.55 (m, 2H), 1.35-1.10 (m, 10H).

Example-700

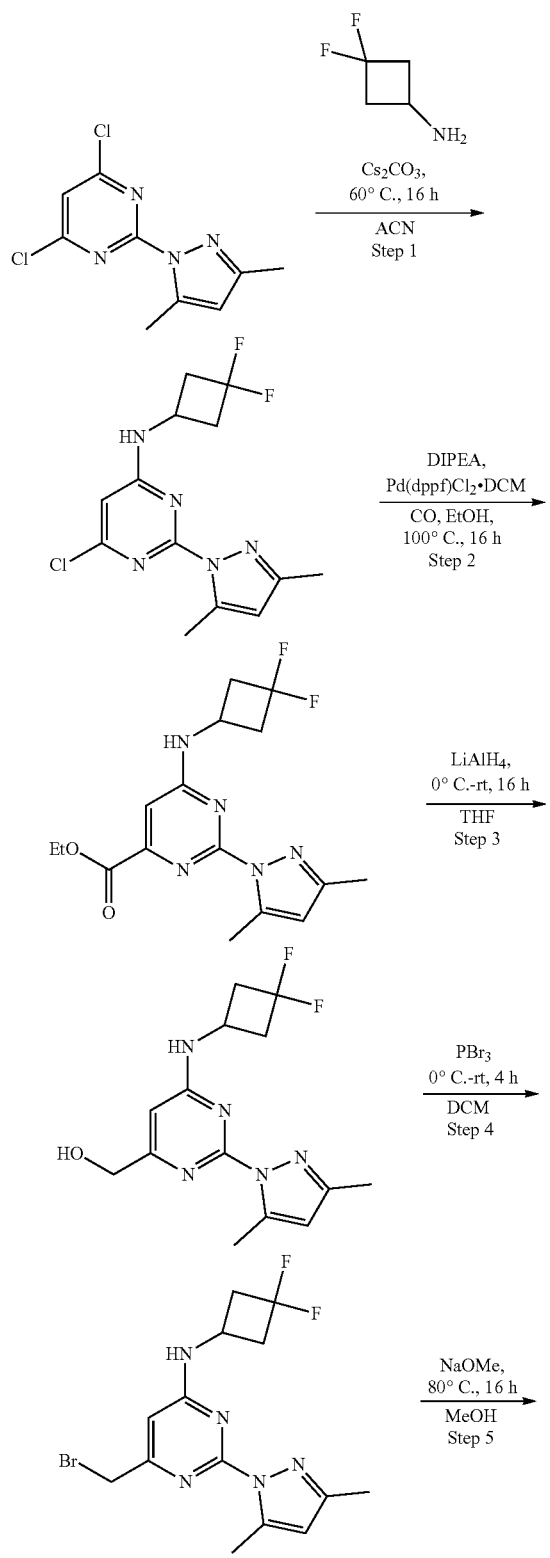

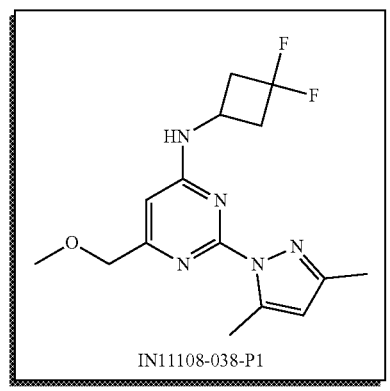

Step 1: The procedure is similar to Step 1[B] in Example-838. 0.76 g of 4,6-dichloro-2-(3,5-dimethyl-1H-pyrazol-1-yl)pyrimidine gave 6-chloro-N-(3,3-difluorocyclobutyl)-2-(3,5-dimethyl-1H-pyrazol-1-yl)pyrimidin-4-amine as an off-white solid (0.75 g, 75%). MS (M+1)+=314.0.

Step 2: To a stirred solution of 6-chloro-N-(3,3-difluorocyclobutyl)-2-(3,5-dimethyl-1H-pyrazol-1-yl)pyrimidin-4-amine (0.5 g, 1.59 mmol) in ethanol (10 mL) was added diisopropylethylamine (1.66 mL, 9.56 mmol) and [1,1'-Bis(diphenylphosphino)ferrocene]dichloropalladium(II) (1:1) DCM complex (0.065 g, 0.079 mmol). The steel bomb was sealed and filled with carbon monoxide gas up to 100 Psi pressure. Reaction mixture was heated to 100° C. for 16 h. The reaction mixture was cooled to room temperature, degassed the steel bomb and reaction mixture was concentrated under reduced pressure to obtained the crude which was purified by flash column chromatography using 3% methanol in chloroform to afford ethyl 6-((3,3-difluorocyclobutyl)amino)-2-(3,5-dimethyl-1H-pyrazol-1-yl)pyrimidine-4-carboxylate as a brown solid (0.35 g, 55%). MS (M+1)+=352.1.

Step 3: The procedure is similar to Step 4[NSSy6711] in Example-854. 0.25 g of ethyl 6-((3,3-difluorocyclobutyl)amino)-2-(3,5-dimethyl-1H-pyrazol-1-yl)pyrimidine-4-carboxylate gave (6-((3,3-difluorocyclobutyl)amino)-2-(3,5-dimethyl-1H-pyrazol-1-yl)pyrimidin-4-yl) methanol as yellowish gum (0.18 g, 82%). MS (M+1)+=310.1.

Step 4: The procedure is similar to Step 3[IN11059-090-P1] in Example-659. 0.18 g of (6-((3,3-difluorocyclobutyl)amino)-2-(3,5-dimethyl-1H-pyrazol-1-yl)pyrimidin-4-yl) methanol gave 6-(bromomethyl)-N-(3,3-difluorocyclobutyl)-2-(3,5-dimethyl-1H-pyrazol-1-yl)pyrimidin-4-amine as brownish gum (0.2 g, 95%). MS (M+1)+=374.0.

Step 5[IN11108-038-P1]: The procedure is similar to Step 1[NSSy6519] in Example-842. 0.2 g of 6-(bromomethyl)-N-(3,3-difluorocyclobutyl)-2-(3,5-dimethyl-1H-pyrazol-1-yl)pyrimidin-4-amine gave N-(3,3-difluorocyclobutyl)-2-(3,5-dimethyl-1H-pyrazol-1-yl)-6-(methoxymethyl)pyrimidin-4-amine as a brownish gum (0.023 g, 13%). MS (M+1)+=324.1; 1H-NMR (400 MHz, DMSO-d6): δ 8.17 (bs, 1H), 6.41 (bs, 1H), 6.06 (s, 1H), 4.32 (s, 3H), 3.39 (s, 3H), 3.14-3.00 (m, 2H), 2.67-2.44 (m, 6H), 2.16 (s, 3H).

Example-701

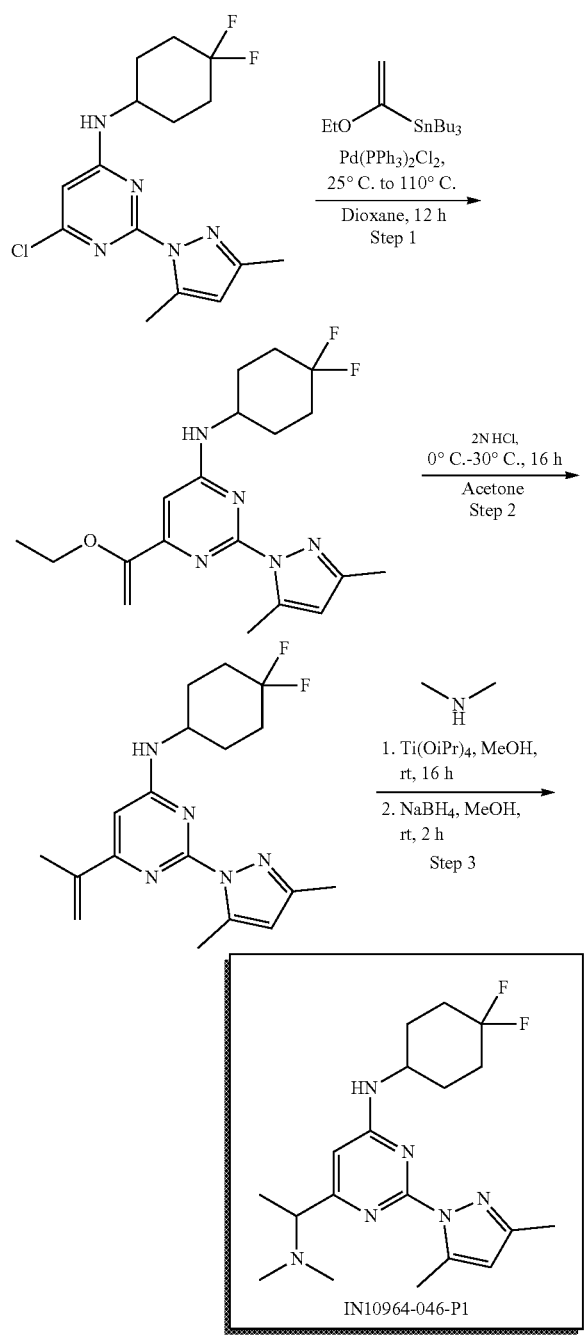

Step 1: The procedure is similar to Step 1[H] in Example-838. 0.6 g of 6-chloro-N-(4,4-difluorocyclohexyl)-2-(3,5-dimethyl-1H-pyrazol-1-yl)pyrimidin-4-amine gave N-(4,4-difluorocyclohexyl)-2-(3,5-dimethyl-1H-pyrazol-1-yl)-6-(1-ethoxyvinyl)pyrimidin-4-amine as an off-white solid (0.4 g, 60%). MS (M+1)+=378.1.

Step 2: The procedure is similar to Step 1[NSSy6697] in Example-873. 1.2 g of N-(4,4-difluorocyclohexyl)-2-(3,5-dimethyl-1H-pyrazol-1-yl)-6-(1-ethoxyvinyl)pyrimidin-4-amine gave N-(4,4-difluorocyclohexyl)-2-(3,5-dimethyl-1H-pyrazol-1-yl)-6-(prop-1-en-2-yl)pyrimidin-4-amine as a gummy solid (0.6 g, 54%). MS (M+1)+=350.1.

Step 3[IN10964-046-P1]: To a stirred solution of N-(4,4-difluorocyclohexyl)-2-(3,5-dimethyl-1H-pyrazol-1-yl)-6-(prop-1-en-2-yl)pyrimidin-4-amine (0.1 g, 0.28 mmol) and dimethylamine in MeOH (0.0037 g, 1.145 mmol) in MeOH (25 mL) was added Titanium isopropoxide (0.16 g, 0.57 mmol). The reaction mixture was stirred at rt for 16 h. The reaction mixture was diluted with MeOH, followed by NaBH4 was added. The mixture was stirred at rt for 2 h. The reaction mixture was diluted with aqueous ammonia and the precipitated solids were filtered through cellite, washed with ethyl acetate, filtrate was washed with brine solution, dried over Na2SO4, concentrated under reduced pressure to afford crude product. Which was purified by Preparative HPLC to afford N-(4,4-difluorocyclohexyl)-2-(3,5-dimethyl-1H-pyrazol-1-yl)-6-(1-(dimethylamino)ethyl)pyrimidin-4-amine as an off-white solid (0.017 g, 15%). MS (M+1)+= 379.1; 1H-NMR (400 MHz, DMSO-d6): δ 7.56 (s, 1H), 6.44 (s, 1H), 6.03 (s, 1H), 4.05 (s, 1H), 2.55 (s, 3H), 2.18 (s, 6H), 2.16 (s, 3H), 2.15-1.85 (m, 6H), 1.60-1.50 (m, 2H), 1.23 (s, 4H).

Example-702

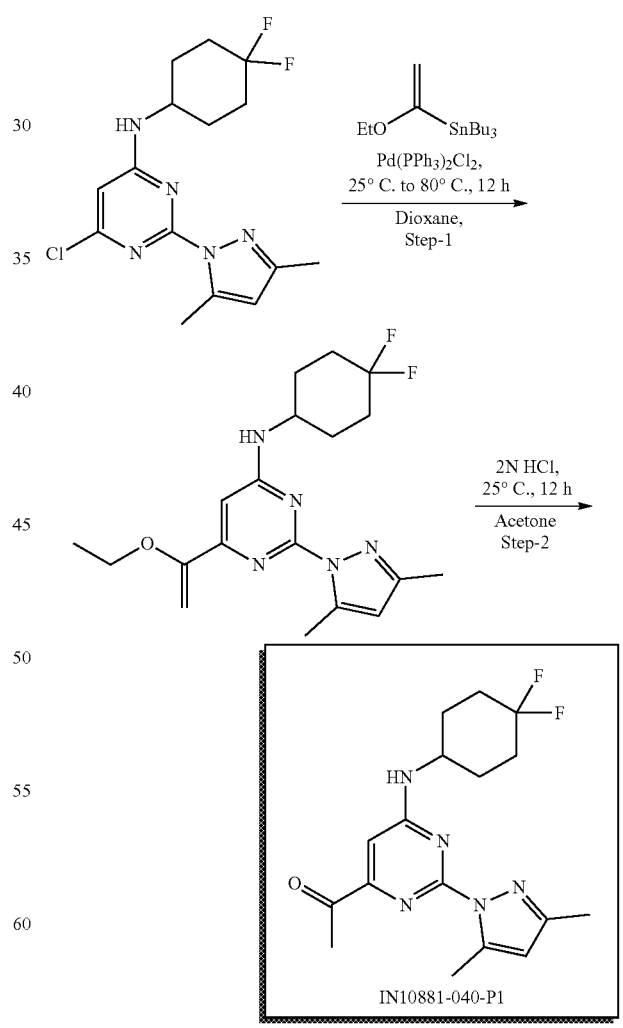

Step 1: The procedure is similar to Step 1[H] in Example-838. 0.25 g of 6-chloro-N-(4,4-difluorocyclohexyl)-2-(3,5- dimethyl-1H-pyrazol-1-yl)pyrimidin-4-amine gave N-(4,4-difluorocyclohexyl)-2-(3,5-dimethyl-1H-pyrazol-1-yl)-6-(1-ethoxyvinyl)pyrimidin-4-amine as a yellow liquid (0.23 g, 83%). MS (M+1)+=378.2.

Step 2[IN10881-040-P1]: The procedure is similar to Step 1[NSSy6697] in Example-873. 0.25 g of N-(4,4-difluorocyclohexyl)-2-(3,5-dimethyl-1H-pyrazol-1-yl)-6-(1-ethoxyvinyl)pyrimidin-4-amine gave 1-(6-((4,4-difluorocyclohexyl)amino)-2-(3,5-dimethyl-1H-pyrazol-1-yl)pyrimidin-4-yl)ethan-1-one as a yellow liquid (0.06 g, 28%). MS (M+1)+=350.1; 1H-NMR (400 MHz, DMSO-d6): δ 8.04 (d, J=6.8 Hz, 1H), 6.85 (s, 1H), 6.10 (s, 1H), 4.10 (bs, 1H), 2.58 (s, 3H), 2.54 (s, 3H), 2.16 (s, 3H), 2.09-1.96 (m, 6H), 1.60-1.55 (m, 2H).

ethyl-1H-pyrazol-1-yl)pyrimidin-4-yl) morpholine-2-carbonitrile gave 4-(6-((4,4-difluorocyclohexyl)amino)-2-(3,5-dimethyl-1H-pyrazol-1-yl) pyrimidin-4-yl) morpholine-2-carbonitrile as an off-white solid (0.04 g, 27%). MS (M+1)+=418.2; 1H-NMR (400 MHz, MeOD): δ 8.00 (s, 1H), 6.05 (s, 1H), 5.61 (s, 1H), 4.90-4.85 (m, 2H), 4.20-3.92 (m, 3H), 3.90-3.80 (m, 2H), 3.80-3.62 (m, 1H), 2.61 (s, 3H), 2.26 (s, 3H), 2.10-1.85 (m, 6H), 1.65-1.55 (m, 2H).

Example-704

Example-703

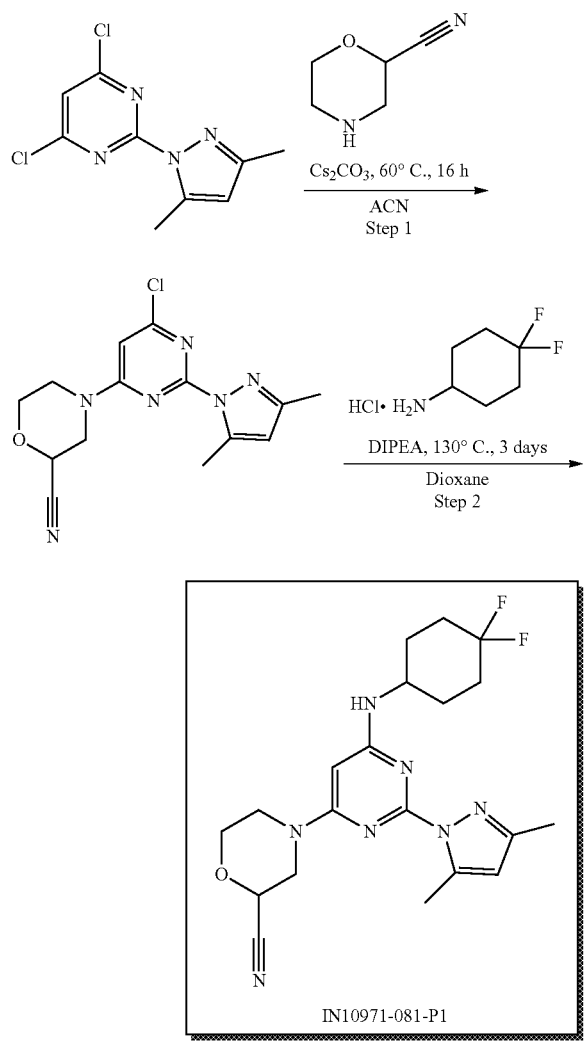

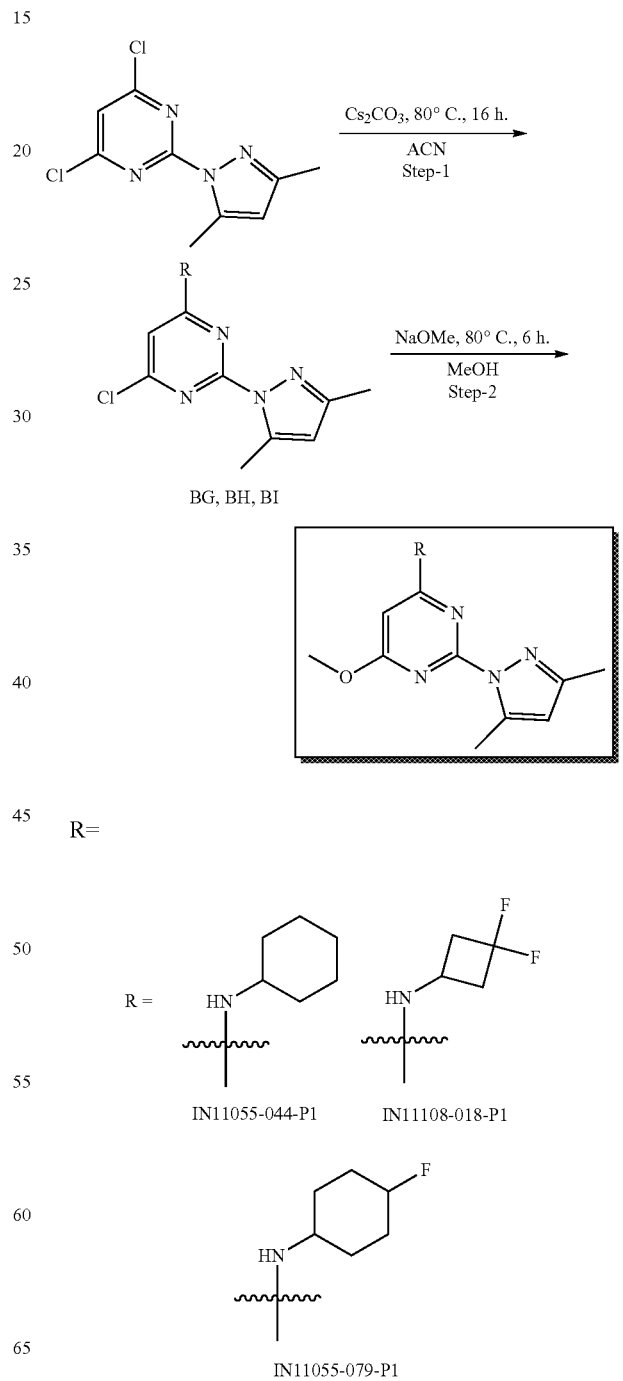

Step 1: The procedure is similar to Step 1[B] in Example-838. 0.2 g of 4,6-dichloro-2-(3,5-dimethyl-1H-pyrazol-1-yl)pyrimidine gave 4-(6-chloro-2-(3,5-dimethyl-1H-pyrazol-1-yl)pyrimidin-4-yl) morpholine-2-carbonitrile as an off-white solid (0.22 g, 84%). MS (M+1)+=319.0.

Step 2[IN10971-081-P1]: The procedure is similar to Step 1[B] in Example-838. 0.11 g of 4-(6-chloro-2-(3,5-dim-

TABLE 49

Step 1: The procedure is similar to Step 1[B] in Example-838.

| Compound No | R | Condition | Yield (%) | MS (M + 1)+ |
|---|---|---|---|---|
| BG | 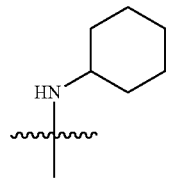 [SMILES: *NC1CCCCC1] | Cs₂CO₃, ACN, 80° C., 16 h | 59 | 306.0 |
| BH | 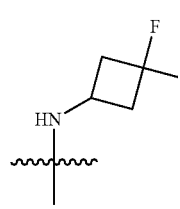 | Cs₂CO₃, ACN, 60° C., 16 h | 75 | 314.0 |
| BI | 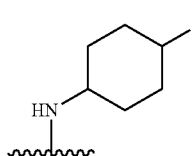 | Cs₂CO₃, ACN, 60° C., 16 h | 37 | 324 |

TABLE 50

Step 2: The procedure is similar to Step 1[NSSy6519] in Example-842.

| Compound No | R | Condition | Yield (%) | MS (M + 1)+ |
|---|---|---|---|---|
| IN11055-044-P1 | 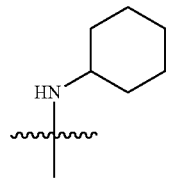 [SMILES: *NC1CCCCC1] | NaOMe, MeOH, 80° C., 6 h | 81 | 302.2 |
| IN11108-018-P1 | 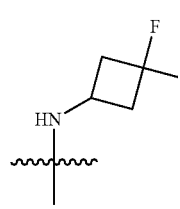 | NaOMe, MeOH, 80° C., 6 h | 43 | 310.0 |
| IN11055-079-P1 | 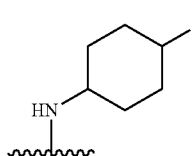 | NaOMe, MeOH, 80° C., 6 h | 71 | 320.1 |

Step 2[IN11055-044-P1]: 1H-NMR (400 MHz, DMSO-d6): δ 7.30 (d, J=8.00 Hz, 1H), 6.05 (s, 1H), 5.64 (s, 1H), 3.82 (s, 3H), 2.54 (s, 3H), 2.16 (s, 3H), 1.90-1.50 (m, 5H), 1.40-1.10 (m, 6H).

Step 2[IN11108-018-P1]: 1H-NMR (400 MHz, DMSO-d6): δ 7.94 (bs, 1H), 6.07 (s, 1H), 5.65 (s, 1H), 3.85 (s, 3H), 3.08-2.97 (m, 2H), 2.67-2.60 (m, 5H), 2.16 (s, 3H).

Step 2[IN11055-079-P1]: 1H-NMR (400 MHz, DMSO-d6): δ 7.39 (d, J=7.20 Hz, 1H), 6.05 (s, 1H), 5.67 (s, 1H), 4.85-4.70 (m, 1H), 3.83 (s, 3H), 2.54 (s, 3H), 2.16 (s, 3H), 2.00-1.88 (m, 2H), 1.75-1.50 (m, 6H).

Example-705

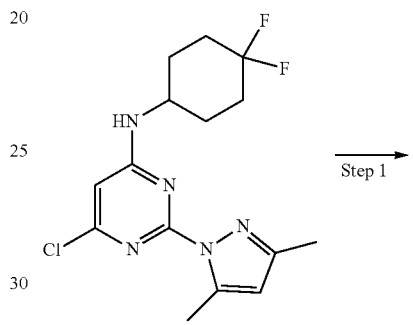

Step 1 →

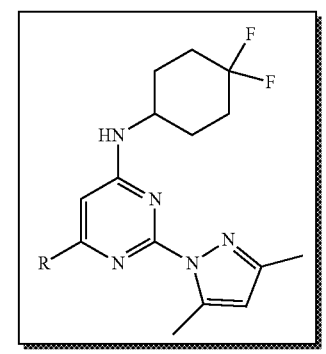

R =

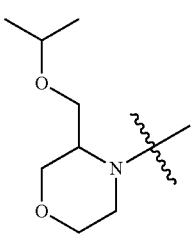 [SMILES: *N1CCOCC1COC(C)C] 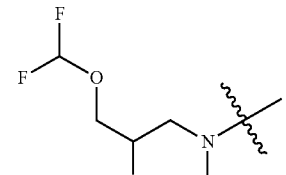

IN10965-089-P1    IN10984-022-P1

 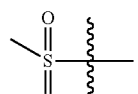

IN11067-060-P1    IN11067-61-P1

931
-continued

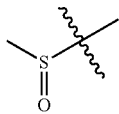 [SMILES: *S(C)=O]
IN11067-062-P1

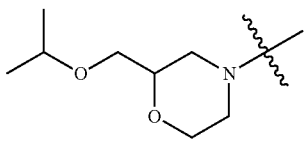 [SMILES: *N1CCOC(COC(C)C)C1]
IN10964-008-P1

932
-continued

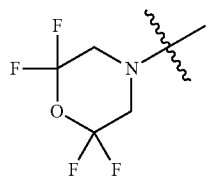
IN11030-035-P1

TABLE 51

| Step 1: | | | | |
|---|---|---|---|---|
| Compound No | R | Condition | Yield (%) | MS (M + 1)⁺ |
| IN10965-089-P1 | (isopropoxymethyl morpholine) | DIPEA, NMP, 140° C., 1 h, MW | 17 | 465.3 |
| IN10984-022-P1 | (difluoromethoxymethyl morpholine) | DIPEA, ACN, 80° C., 12 h | 19 | 473.1 |
| IN11067-060-P1 | (methylthio tert-butyl) | NaSMe, EtOH, 65° C., 3 h | 72 | 354.1 |
| IN11067-061-P1 | (methylsulfonyl tert-butyl) | m-CPBA, DCM, rt, 16 h | 8 | 386.0 |
| IN11067-062-P1 | (methylsulfinyl tert-butyl) | m-CPBA, DCM, rt, 16 h | 38 | 370.0 |
| IN10964-008-P1 | (isopropoxymethyl morpholine) | TEA, ACN, 85° C., 36 h | 26 | 465.1 |
| IN11030-035-P1 | (tetrafluoro morpholine) | Pd(OAC)₂, Xanthphos, Cs₂CO₃, Dioxane, 95° C., 16 h | 44 | 465.2 |

Step 1[IN10965-089-P1]: The procedure is similar to Step 1[NSSy6909] in Example-839. $^1$H-NMR (400 MHz, DMSO-d$_6$): δ 7.07 (d, J=8.00 Hz, 1H), 6.00 (s, 1H), 5.52 (s, 1H), 4.20 (s, 1H), 3.98-3.90 (m, 4H), 3.61-3.48 (m, 4H), 3.10-2.95 (m, 1H), 2.14 (s, 3H), 2.05-1.92 (m, 6H), 1.63-1.45 (m, 2H), 1.06 (d, J=6.00 Hz, 6H).

Step 1[IN10984-022-P1]: The procedure is similar to Step 1[B] in Example-838. 1H-NMR (400 MHz, CD3OD): δ 7.60 (d, J=1.2 Hz, 1H), 7.10 (d, J=3.2 Hz, 1H), 6.53-6.51 (m, 1H), 5.54 (s, 1H), 3.92-3.90 (m, 1H), 3.76-3.74 (m, 4H), 3.57-3.55 (m, 4H), 2.12-1.87 (m, 6H), 1.66-1.58 (m, 2H).

Step 1[IN11067-060-P1]: To a stirred solution of 6-chloro-N-(4,4-difluorocyclohexyl)-2-(3,5-dimethyl-1H-pyrazol-1-yl)pyrimidin-4-amine (0.8 g, 2.34 mmol) in Ethanol (25 mL) was added Sodium thiomethoxide (0.32 g, 4.69 mmol). And the mixture was stirred for 3 h at 65° C. The reaction mixture was cooled to rt, diluted with water, extracted with ethyl acetate (3×50 mL). The combined organic layer was washed with brine solution, dried over sodium sulfate, filtered and concentrated under reduced pressure to afford a crude product which was purified by flash column chromatography using 20% ethyl acetate in pet ether as solvent to afford N-(4,4-difluorocyclohexyl)-2-(3, 5-dimethyl-1H-pyrazol-1-yl)-6-(methylthio)pyrimidin-4-amine as an off-white solid (0.6 g, 72%). MS (M+1)+= 354.1; 1H-NMR (400 MHz, DMSO-d6): δ 7.58 (d, J=6.80 Hz, 1H), 6.22 (s, 1H), 6.05 (s, 1H), 4.10 (s, 1H), 2.53 (s, 3H), 2.48 (s, 3H), 2.16 (s, 3H), 2.12-1.83 (m, 6H), 1.61-1.48 (m, 2H).

Step 1[IN11067-061-P1]: The procedure is similar to Step 3[NSSy7062] in Example-623. 1H-NMR (400 MHz, DMSO-d6): δ 8.40 (d, J=7.20 Hz, 1H), 6.95 (s, 1H), 6.14 (s, 1H), 4.11 (s, 1H), 3.23 (s, 3H), 2.55 (s, 3H), 2.19 (s, 3H), 2.10-1.90 (m, 6H), 1.68-1.52 (m, 2H).

Step 1[IN11067-062-P1]: The procedure is similar to Step 3[NSSy7062] in Example-623. 1H-NMR (400 MHz, DMSO-d6): δ 8.22 (d, J=7.20 Hz, 1H), 6.90 (s, 1H), 6.10 (s, 1H), 4.10 (s, 1H), 3.90 (s, 3H), 2.51 (s, 3H), 3.90 (s, 3H), 2.12-1.85 (m, 6H), 1.65-1.55 (m, 2H).

Step 1[IN10964-008-P1]: The procedure is similar to Step 1[A] in Example-838. 1H-NMR (400 MHz, DMSO-d6): δ 7.11 (d, J=8.0 Hz, 1H), 6.01 (s, 1H), 5.55 (s, 1H), 4.10-3.91 (m, 4H), 3.59-3.40 (m, 5H), 2.95-2.85 (m, 1H), 2.67-2.66 (m, 2H), 2.14 (s, 3H), 2.05-1.89 (m, 7H), 1.55 (m, 3H), 1.10-1.09 (m, 6H).

Step 1[IN11030-035-P1]: The procedure is similar to Step 1[NSSy6629] in Example-839. 1H-NMR (400 MHz, DMSO-d6): δ 7.37 (d, J=7.20 Hz, 1H), 6.04 (s, 1H), 5.82 (s, 1H), 4.38 (s, 4H), 3.35 (s, 1H), 2.15 (s, 3H), 2.10-1.75 (m, 8H), 1.62-1.50 (m, 2H), 1.45-1.35 (m, 1H).

Example-706

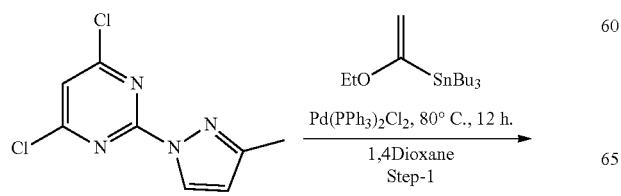

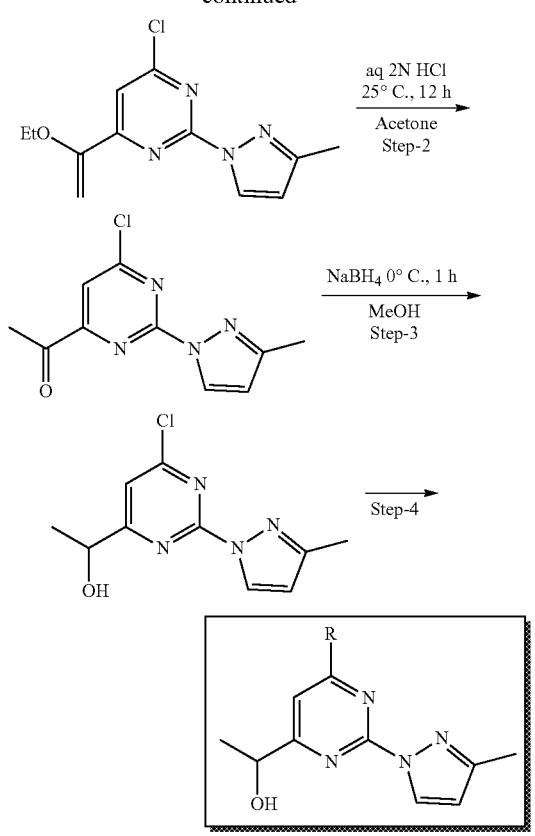

R=

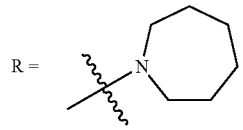 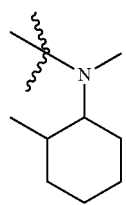

IN10881-058-P1    IN10881-059-P1

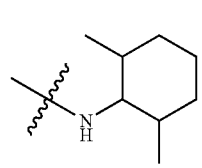 [SMILES: *NC1C(C)CCCC1C] 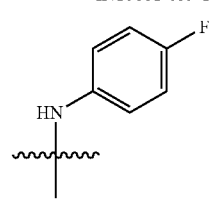

IN10881-060-P1    IN10882-054-P1

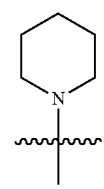 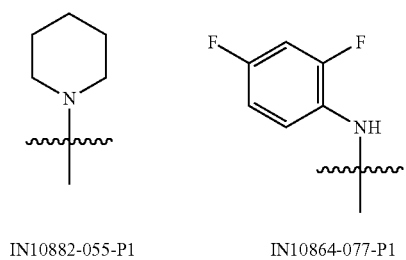

IN10882-055-P1    IN10864-077-P1

-continued

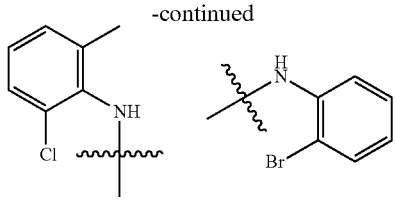

IN10864-081-P1  IN10881-057-P1

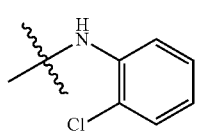

IN10881-055-P1  IN10881-054-P1

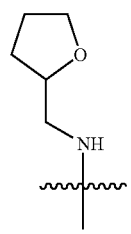

IN10880-055-P1  IN0880-056-P1

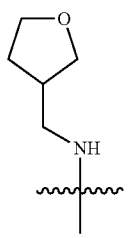

IN10880-058-P1  IN10880-059-P1

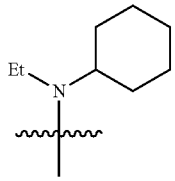

IN10881-061-P1  IN10880-062-P1

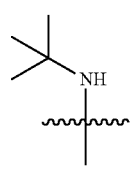

IN10880-065-P1  IN10880-064-P1

Step 1: The procedure is similar to Step 1[H] in Example-838. 3.0 g of 4,6-dichloro-2-(3-methyl-1H-pyrazol-1-yl)pyrimidine gave 4-chloro-6-(1-ethoxyvinyl)-2-(3-methyl-1H-pyrazol-1-yl)pyrimidine as an off-white solid (2.1 g, 60%). MS (M+1)+=265.0.

Step 2: The procedure is similar to Step 1[NSSy6697] in Example-873. 2.5 g of 4-chloro-6-(1-ethoxyvinyl)-2-(3-methyl-1H-pyrazol-1-yl)pyrimidine gave 1-(6-chloro-2-(3-methyl-1H-pyrazol-1-yl)pyrimidin-4-yl) ethan-1-one as a yellow solid (2.2 g, 66%). MS (M+1)+=237.0.

Step 3: The procedure is similar to Step 2[NSSy6931] in Example-21. 2.2 g of 1-(6-chloro-2-(3-methyl-1H-pyrazol-1-yl)pyrimidin-4-yl) ethan-1-one gave 1-(6-chloro-2-(3-methyl-1H-pyrazol-1-yl)pyrimidin-4-yl) ethan-1-ol as an off-white solid (1.8 g, 56%). MS (M+1)+=239.0.

TABLE 52

Step 4:

| Compound No | R | Condition | Yield (%) |
|---|---|---|---|
| IN10881-058-P1 | 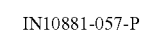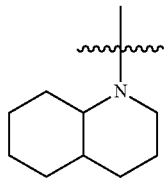 [SMILES: *N1CCCC2CCCCC21] | rt, 12 h | 42 |
| IN10881-059-P1 | 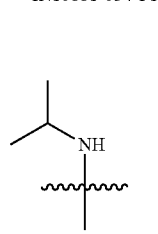 | TEA, ACN, 80° C., 24 h | 29 |
| IN10881-060-P1 | 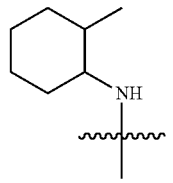 | TEA, ACN, 80° C., 24 h | 29 |
| IN10882-055-P1 | 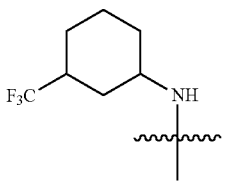 | rt, 12 h | 71 |
| IN10881-054-P1 | 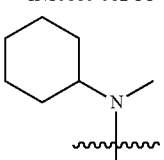 | rt, 12 h | 46 |
| IN10880-055-P1 | | rt, 12 h | 31 |
| IN10880-056-P1 | | rt, 4 h | 75 |

TABLE 52-continued

Step 4:

| Compound No | R | Condition | Yield (%) |
|---|---|---|---|
| IN10880-058-P1 | 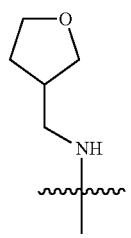 | rt, 2 h | 59 |
| IN10880-059-P1 | 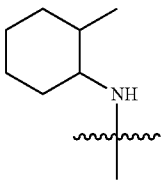 [SMILES: *NC1CCCCC1C] | rt, 2 h | 47 |
| IN10881-061-P1 | 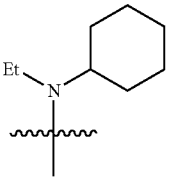 [SMILES: *N(CC)C1CCCCC1] | DMAP, ACN, 80° C., 36 h | 29 |
| IN10880-062-P1 | 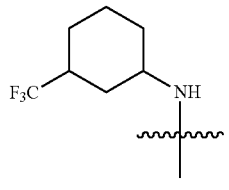 | rt, 16 h | 32 |
| IN10880-065-P1 | 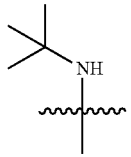 [SMILES: *NC(C)(C)C] | rt, 48 h | 27 |
| IN10880-064-P1 | 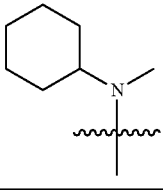 | rt, 16 h | 42 |

Step 4[IN10881-058-P1]: The procedure is similar to Step 1[A] in Example-838. MS (M+1)+=302.1; 1H-NMR (400 MHz, DMSO-d6): δ 8.44 (d, J=2.40 Hz, 1H), 6.59 (s, 1H), 6.29 (d, J=2.40 Hz, 1H), 5.38 (s, 1H), 4.51-4.49 (m, 1H), 3.81 (s, 2H), 3.55 (s, 2H), 2.26 (s, 3H), 1.75 (s, 4H), 1.50 (s, 4H), 1.36 (d, J=6.40 Hz, 3H).

Step 4[IN10881-059-P1]: The procedure is similar to Step 1[B] in Example-838. MS (M+1)+=330.1; 1H-NMR (400 MHz, DMSO-d6): δ 8.42 (s, 1H), 6.56 (d, J=13.60 Hz, 1H), 6.30 (d, J=2.00 Hz, 1H), 5.41 (s, 1H), 4.52 (t, J=5.60 Hz, 1H), 3.01 (s, 2H), 2.87 (s, 1H), 2.29 (s, 4H), 2.00-1.50 (m, 5H), 1.50-1.30 (m, 5H), 1.30-1.10 (m, 3H), 0.93 (d, J=6.80 Hz, 2H).

Step 4[IN10881-060-P1]: The procedure is similar to Step 1[B] in Example-838. MS (M+1)+=330.1; 1H-NMR (400 MHz, DMSO-d6): δ 8.42 (s, 1H), 6.56 (d, J=13.60 Hz, 1H), 6.30 (s, 1H), 5.41 (s, 1H), 4.52 (s, 1H), 3.01 (s, 2H), 2.87 (s, 1H), 2.29 (s, 4H), 1.95-1.50 (m, 5H), 1.49-1.30 (m, 6H), 1.30-1.10 (m, 3H), 0.99-0.90 (m, 2H).

Step 4[IN10882-055-P1]: The procedure is similar to Step 1[A] in Example-838. MS (M+1)+=288.1; 1H-NMR (400 MHz, DMSO-d6): δ 8.46 (d, J=2.8 Hz, 1H), 6.71 (s, 1H), 6.29 (d, J=2.4 Hz, 1H), 5.37 (d, J=5.2 Hz, 1H), 4.58-4.49 (m, 1H), 3.68 (bs, 4H), 2.26 (s, 3H), 1.72-1.56 (m, 6H), 1.37-1.32 (m, 3H).

Step 4[IN10881-054-P1]: The procedure is similar to Step 1[A] in Example-838. MS (M+1)+=342.1; 1H-NMR (400 MHz, DMSO-d6): δ 8.44 (d, J=2.0 Hz, 1H), 6.69 (d, J=2.4 Hz, 1H), 6.29 (d, J=2.4 Hz, 1H), 5.38-5.35 (m, 1H), 4.53-4.50 (m, 1H), 2.85 (bs, 1H), 2.26 (s, 3H), 1.86-1.62 (m, 7H), 1.41-1.35 (m, 9H).

Step 4[IN10880-055-P1]: The procedure is similar to Step 1[A] in Example-838. MS (M+1)+=304.0; 1H-NMR (400 MHz, DMSO-d6): δ 8.42 (s, 1H), 7.77 (s, 1H), 6.55 (s, 1H), 6.28 (d, J=2.4 Hz, 1H), 5.36 (d, J=4.00 Hz, 1H), 4.46 (d, J=5.2 Hz, 1H), 3.99 (t, J=6.4 Hz, 1H), 3.79 (d, J=7.2 Hz, 1H), 3.66-3.63 (m, 1H), 3.48 (m, 2H), 2.26 (s, 3H), 1.95-1.80 (m, 3H), 1.70-1.52 (m, 1H), 1.33 (d, J=6.0 Hz, 3H).

Step 4[IN10880-056-P1]: The procedure is similar to Step 1[A] in Example-838. MS (M+1)+=262.2; 1H-NMR (400 MHz, DMSO-d6): δ 8.40 (s, 1H), 7.56 (s, 1H), 6.45 (s, 1H), 6.28 (d, J=2.40 Hz, 1H), 5.35 (s, 1H), 4.45 (s, 1H), 4.25 (s, 1H), 2.26 (s, 3H), 1.33 (d, J=6.00 Hz, 3H), 1.18 (s, 3H), 1.17 (s, 3H).

Step 4[IN10880-058-P1]: The procedure is similar to Step 1[A] in Example-838. MS (M+1)+=304.1; 1H-NMR (400 MHz, DMSO-d6): δ 8.42 (s, 1H), 7.76 (bs, 1H), 6.50 (s, 1H), 6.28 (d, J=2.4 Hz, 1H), 5.35 (d, J=4.4 Hz, 1H), 4.47 (m, 1H), 3.79-3.70 (m, 2H), 3.66-3.60 (m, 1H), 3.49-3.46 (m, 1H), 3.38-3.36 (m, 1H), 2.26 (s, 3H), 2.02-1.94 (m, 1H), 1.65-1.57 (m, 1H), 1.34-1.33 (m, 3H).

Step 4[IN10880-059-P1]: The procedure is similar to Step 1[A] in Example-838. MS (M+1)+=316.1; 1H-NMR (400 MHz, DMSO-d6): δ 8.39 (d, J=2.40 Hz, 1H), 7.43 (s, 1H), 6.48 (s, 1H), 6.27 (d, J=2.40 Hz, 1H), 5.34-5.31 (m, 1H), 4.45 (s, 1H), 2.26 (s, 3H), 1.95-1.85 (m, 1H), 1.60-1.10 (m, 12H), 0.90-0.80 (m, 3H).

Step 4[IN10881-061-P1]: The procedure is similar to Step 1[B] in Example-838. MS (M+1)+=330.1; 1H-NMR (400 MHz, DMSO-d6): δ 8.41 (d, J=2.40 Hz, 1H), 6.57 (s, 1H), 6.30 (d, J=2.40 Hz, 1H), 5.42 (d, J=4.80 Hz, 1H), 4.70 (s, 1H), 4.55-4.50 (m, 1H), 3.50 (s, 2H), 2.27 (s, 3H), 1.75-1.55 (m, 7H), 1.48-1.30 (m, 5H), 1.35-1.10 (m, 4H).

Step 4[IN10880-062-P1]: The procedure is similar to Step 1[A] in Example-838. MS (M+1)+=370.0; 1H-NMR (400 MHz, DMSO-d6): δ 8.45-8.40 (m, 1H), 7.65 (bs, 1H), 6.47 (s, 1H), 6.30 (t, J=2.4 Hz, 1H), 5.40-5.38 (m, 1H), 4.49-4.46 (m, 1H), 4.01 (m, 1H), 2.26 (s, 3H), 1.96 (m, 1H), 1.86-1.83 (m, 2H), 1.64-1.61 (m, 1H), 1.46 (m, 1H), 1.35-1.32 (m, 3H), 1.20-1.15 (m, 3H).

Step 4[IN10880-065-P1]: The procedure is similar to Step 1[A] in Example-838. MS (M+1)+=276.1; 1H-NMR (400 MHz, DMSO-d6): δ 8.35 (d, J=3.20 Hz, 1H), 7.37 (s, 1H), 6.54 (s, 1H), 6.30 (s, 1H), 5.33 (d, J=4.40 Hz, 1H), 4.45-4.43 (m, 1H), 2.26 (s, 3H), 1.43 (s, 9H), 1.32 (d, J=6.80 Hz, 3H).

Step 4[IN10880-064-P1]: The procedure is similar to Step 1[A] in Example-838. MS (M+1)+=316.1; 1 H-NMR (400 MHz, DMSO-d6): δ 8.44 (d, J=2.40 Hz, 1H), 6.60 (s, 1H), 6.30 (d, J=2.40 Hz, 1H), 5.37 (d, J=4.80 Hz, 1H), 4.52-4.49 (m, 1H), 2.96 (s, 2H), 2.26 (s, 3H), 1.90-1.50 (m, 6H), 1.48-1.30 (m, 5H), 1.12-1.10 (m, 1H).

Example-707
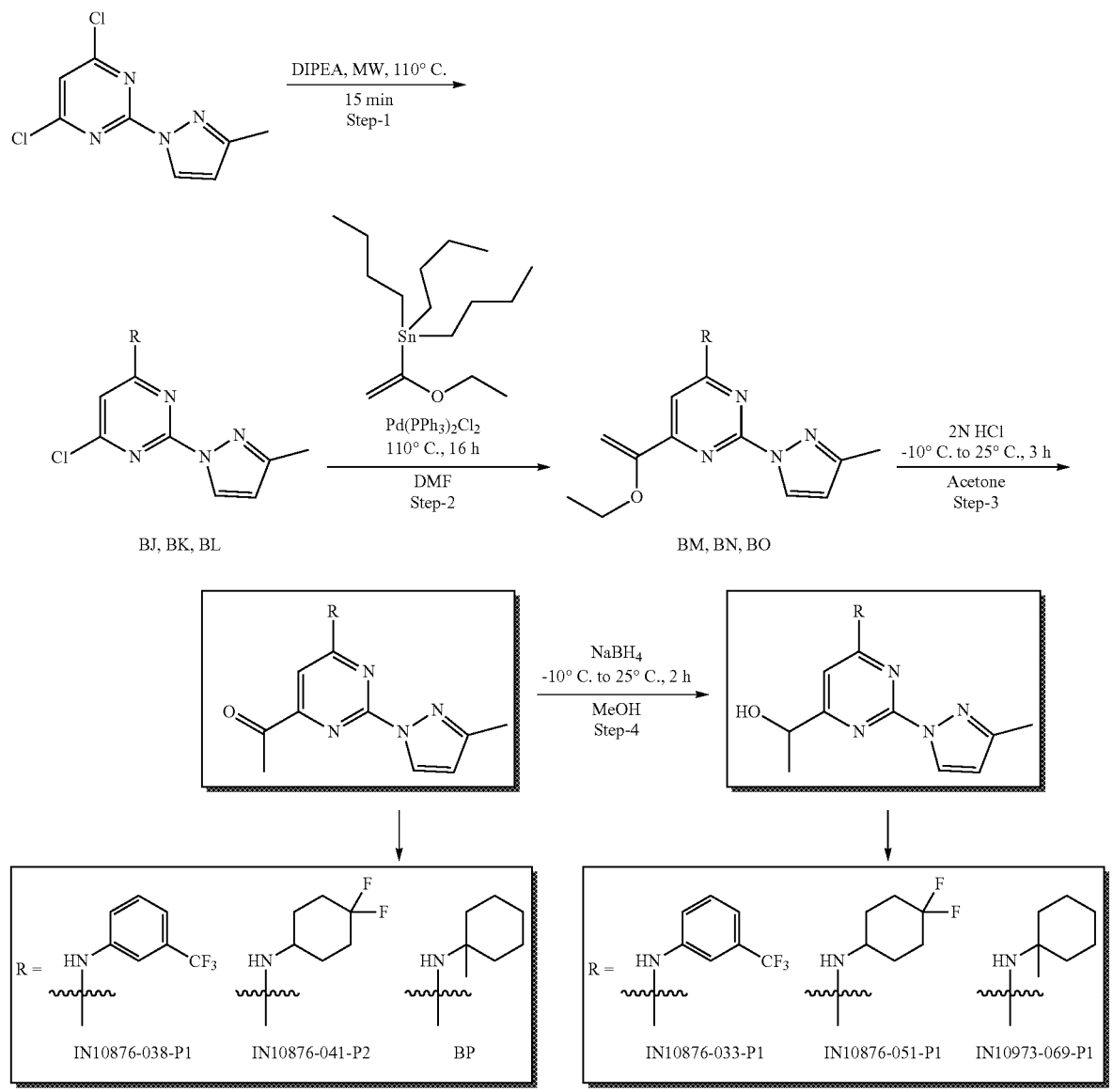
| Compound No | R | Condition | Yield (%) | MS (M + 1)+ |
|---|---|---|---|---|
| BJ | 3-CF3-phenyl-NH- | DIPEA, 110° C., 15 min | 96 | 354.1 |
| BK | 4,4-difluorocyclohexyl-NH- | Cs2CO3, ACN, 80° C., 16 h | 55 | 327.9 |
Step 1: The procedure is similar to Step 1[B] in Example-838.

TABLE 53-continued

Step 1: The procedure is similar to Step 1[B] in Example-838.

| Compound No | R | Condition | Yield (%) | MS (M + 1)+ |
|---|---|---|---|---|
| BL | (1-methylcyclohexyl)amine | Cs₂CO₃, ACN, 80° C., 16 h | 75 | 306.0 |

TABLE 54

Step 2: The procedure is similar to Step 1[H] in Example-838.

| Compound No | R | Condition | Yield (%) | MS (M + 1)+ |
|---|---|---|---|---|
| BM | 3-(trifluoromethyl)aniline | Pd(PPh₃)₂Cl₂, DMF, 110° C., 16 h | 72 | 390.2 |
| BN | 4,4-difluorocyclohexylamine | Pd(PPh₃)₂Cl₂, DMF, 110° C., 16 h | 45 | 364.0 |
| BO | 1-methylcyclohexylamine | Pd(PPh₃)₂Cl₂, DMF, 80° C., 3 days | — | 342.1 |

TABLE 55

Step 3: The procedure is similar to Step 1[NSSy6697] in Example-873.

| Compound No | R | Condition | Yield (%) | MS (M + 1)+ |
|---|---|---|---|---|
| IN10876-041-P2 | 4,4-difluorocyclohexylamine | 2N HCl, acetone, −10° C.-25° C., 3 h | 72 | 336.0 |

TABLE 55-continued

Step 3: The procedure is similar to Step 1[NSSy6697] in Example-873.

| Compound No | R | Condition | Yield (%) | MS (M + 1)+ |
|---|---|---|---|---|
| BP | 1-methylcyclohexylamine | 2N HCl, acetone, rt, 3 h | 62 | 314.1 |

Step 3[IN10876-041-P2]: 1H-NMR (400 MHz, DMSO-d6): δ 8.57 (s, 1H), 8.08 (d, J=7.60 Hz, 1H), 6.82 (s, 1H), 6.37 (d, J=2.40 Hz, 1H), 4.21 (s, 1H), 2.57 (s, 3H), 2.29 (s, 3H), 2.10-1.95 (m, 6H), 1.65-1.52 (m, 2H).

TABLE 56

Step 4: The procedure is similar to Step 2[NSSy6931] in Example-21.

| Compound No | R | Condition | Yield (%) | MS (M + 1)+ |
|---|---|---|---|---|
| IN10876-051-P1 | 4,4-difluorocyclohexylamine | NaBH₄, MeOH, −10° C.-25° C., 2 h | 49 | 338.1 |
| IN10973-69-P1 | 1-methylcyclohexylamine | NaBH₄, MeOH, −10° C.-25° C., 2 h | 33 | 316.1 |

Step 4[IN10876-051-P1]: 1H-NMR (400 MHz, DMSO-d6): δ 8.47 (s, 1H), 7.67 (s, 1H), 6.51 (s, 1H), 6.29 (d, J=2.40 Hz, 1H), 5.38 (s, 1H), 4.47 (s, 1H), 4.16 (s, 1H), 2.26 (s, 3H), 2.15-1.90 (m, 6H), 1.62-1.50 (m, 2H), 1.02 (s, 3H).

Step 4[IN10973-069-P1]: 1H-NMR (400 MHz, CD3OD): δ 8.36 (d, J=2.40 Hz, 2H), 6.48 (s, 1H), 6.31 (d, J=2.40 Hz, 1H), 4.62-4.55 (m, 1H), 2.35 (s, 3H), 2.28 (s, 2H), 1.60-1.50 (m, 7H), 1.44-1.46 (m, 7H), 0.98-0.88 (m, 1H).

Example-708

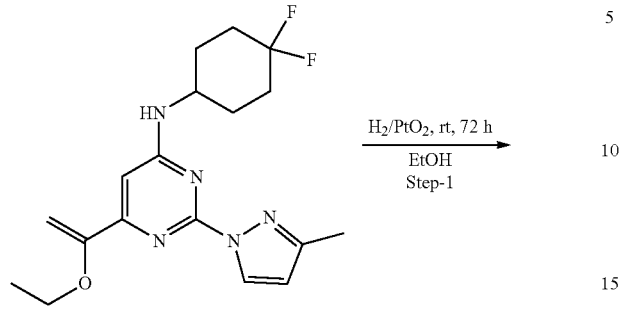

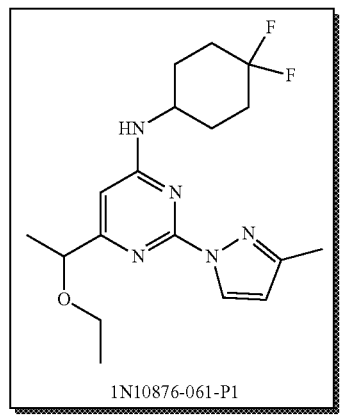

Step 1[IN10876-061-P1]: A solution of N-(4,4-difluorocyclohexyl)-6-(1-ethoxyvinyl)-2-(3-methyl-1H-pyrazol-1-yl)pyrimidin-4-amine (0.05 g, 0.13 mmol) in ethanol (2.5 mL) was added platinum oxide (0.025 g) in ethanol (2.5 mL). The reaction mixture was stirred at rt under H2 bladder for 72 h. The reaction mixture was filtered through celite, washed with ethylacetae (2×10 mL), filtrate was concentrated under reduced pressure to afford crude product. Which was purified by preparative HPLC to afford N-(4,4-difluorocyclohexyl)-6-(1-ethoxyethyl)-2-(3-methyl-1H-pyrazol-1-yl)pyrimidin-4-amine as an off-white solid (0.04 g, 20%). MS (M+1)+=366.1; 1H-NMR (400 MHz, DMSO-d6): δ 8.46 (s, 1H), 7.70 (s, 1H), 6.41 (s, 1H), 6.30 (d, J=2.40 Hz, 1H), 4.23-4.17 (m, 2H), 3.49-3.43 (m, 2H), 2.25 (s, 3H), 2.06-1.90 (m, 6H), 1.62-1.50 (m, 2H), 1.33 (d, J=6.80 Hz, 3H), 1.16 (t, J=6.80 Hz, 3H).

Example-709

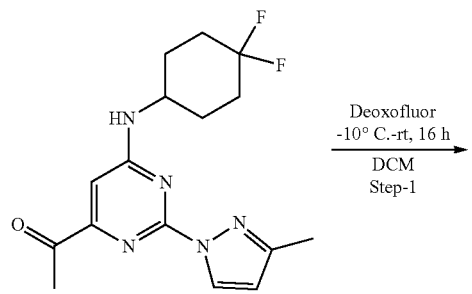

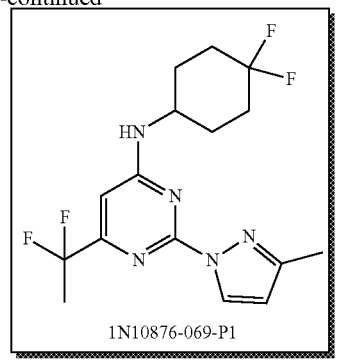

Step 1[IN10876-069-P1]: The procedure is similar to Step 3[NSSy6917] in Example-21. 0.2 g of 1-(6-((4,4-difluorocyclohexyl)amino)-2-(3-methyl-1H-pyrazol-1-yl)pyrimidin-4-yl)ethan-1-one gave N-(4,4-difluorocyclohexyl)-6-(1,1-difluoroethyl)-2-(3-methyl-1H-pyrazol-1-yl)pyrimidin-4-amine as an off-white solid (0.035 g, 16%). MS (M+1)+= 358.1; 1H-NMR (400 MHz, DMSO-d6): δ 8.53 (s, 1H), 8.06 (d, J=7.20 Hz, 1H), 6.59 (s, 1H), 6.35 (s, 1H), 4.21 (s, 1H), 2.28 (s, 3H), 2.15-1.85 (m, 9H), 1.65-1.52 (m, 2H).

Example-710

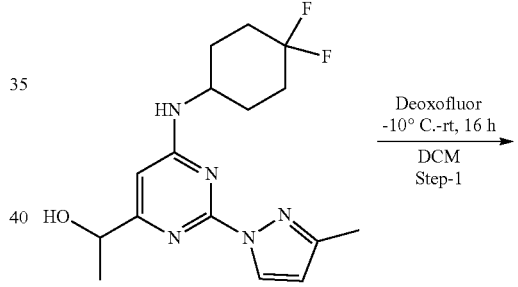

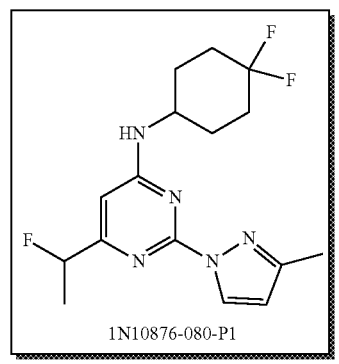

Step 1[IN10876-080-P1]: The procedure is similar to Step 3[NSSy6917] in Example-21. 0.2 g of 1-(6-((4,4-difluorocyclohexyl)amino)-2-(3-methyl-1H-pyrazol-1-yl)pyrimidin-4-yl)ethan-1-ol gave N-(4,4-difluorocyclohexyl)-6-(1-fluoroethyl)-2-(3-methyl-1H-pyrazol-1-yl)pyrimidin-4-amine as a pale yellow solid (0.06 g, 29%). MS (M+1)+= 340.1; 1H-NMR (400 MHz, DMSO-d6): δ 8.53 (s, 1H), 8.06

(d, J=7.20 Hz, 1H), 6.59 (s, 1H), 6.35 (s, 1H), 4.21 (s, 1H), 2.28 (s, 3H), 2.15-1.85 (m, 9H), 1.65-1.52 (m, 2H).

Example-711

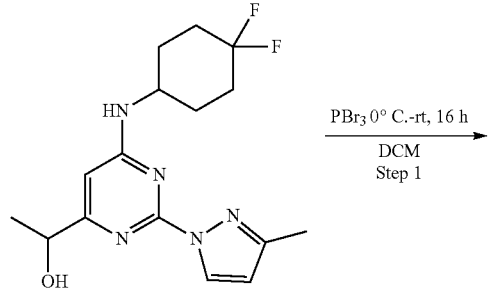

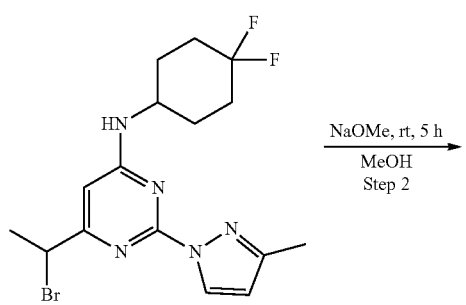

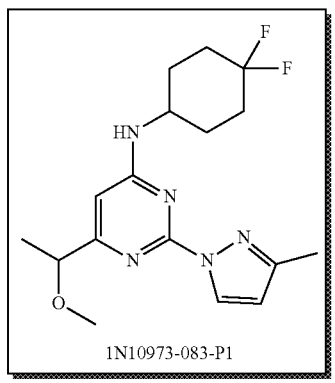

Step 1: The procedure is similar to Step 3[IN11059-090-P1] in Example-659. 0.35 g of 1-(6-((4,4-difluorocyclohexyl)amino)-2-(3-methyl-1H-pyrazol-1-yl)pyrimidin-4-yl)ethan-1-ol gave 6-(1-bromoethyl)-N-(4,4-difluorocyclohexyl)-2-(3-methyl-1H-pyrazol-1-yl)pyrimidin-4-amine as an off-white solid (0.14 g, 34%). MS (M+1)+=399.9.

Step 2[IN10973-083-P1]: The procedure is similar to Step 1[NSSy6519] in Example-842. 0.35 g of 0.14 g of 6-(1-bromoethyl)-N-(4,4-difluorocyclohexyl)-2-(3-methyl-1H-pyrazol-1-yl)pyrimidin-4-amine gave N-(4,4-difluorocyclohexyl)-6-(1-methoxyethyl)-2-(3-methyl-1H-pyrazol-1-yl)pyrimidin-4-amine as an off-white solid (0.085 g, 69%). MS (M+1)+=352.0; 1H-NMR (400 MHz, DMSO-d6): δ 8.46 (s, 1H), 7.68 (s, 1H), 6.39 (s, 1H), 6.30 (d, J=2.80 Hz, 1H), 4.13 (s, 2H), 3.25 (s, 3H), 2.26 (s, 3H), 2.10-1.90 (m, 6H), 1.65-1.52 (m, 2H), 1.31 (d, J=22.80 Hz, 3H).

Example-712

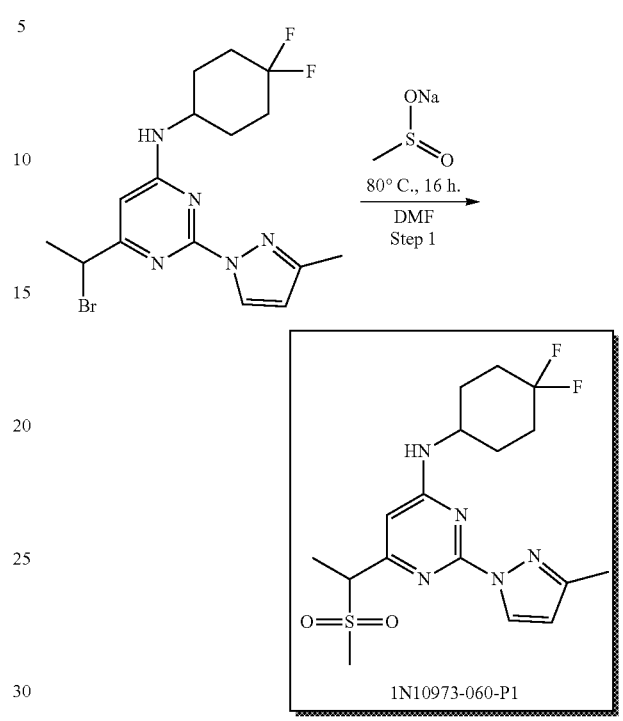

Step 1[IN10973-060-P1]: To a stirred solution of 6-(1-bromoethyl)-N-(4,4-difluorocyclohexyl)-2-(3-methyl-1H-pyrazol-1-yl)pyrimidin-4-amine (0.13 g, 0.32 mmol) in DMF (5 mL) was added methanesulfinic acid sodium salt (0.13 g, 1.302 mmol). Then heated to 80° C. for 16 h. The reaction mixture was cooled to room temperature, poured into ice cold water, extracted with ethyl acetate (3×30 mL). The combined organic layers were dried over sodium sulfate, filtered and concentrated under reduced pressure to afford crude product which was purified by flash column chromatography using 40% ethyl acetate in pet-ether to afford N-(4,4-difluorocyclohexyl)-2-(3-methyl-1H-pyrazol-1-yl)-6-(1-(methylsulfonyl)ethyl)pyrimidin-4-amine as an off-white solid (0.055 g, 42%). MS (M+1)+=400.0; 1H-NMR (400 MHz, DMSO-d6): δ 8.51 (s, 1H), 7.92 (d, J=8.00 Hz, 1H), 6.43 (s, 1H), 6.34 (d, J=2.40 Hz, 1H), 4.42 (d, J=6.40 Hz, 1H), 4.18 (s, 1H), 3.11 (s, 3H), 2.26 (s, 3H), 2.10-1.90 (m, 6H), 1.70-1.50 (m, 5H).

Example-713

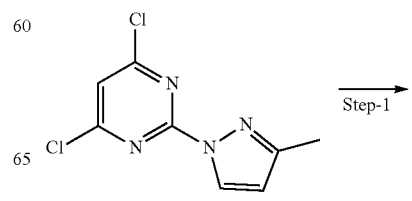

947
-continued
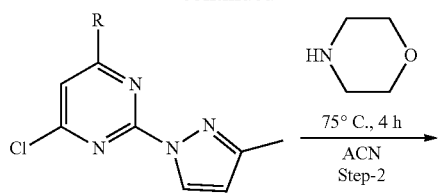
BQ, BR, BS, BT, BU, BV, BW,
BX, BY, BZ, CB, CC, CD
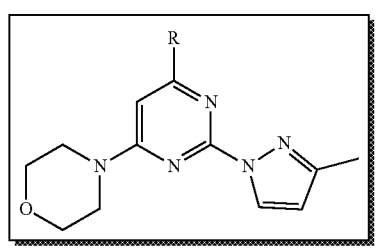
R=
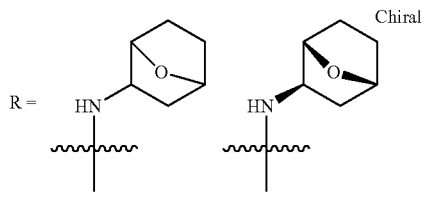
NSSy6420    NSSy6445
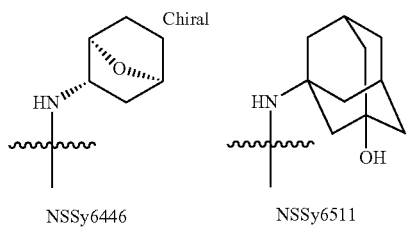
NSSy6446    NSSy6511
948
-continued
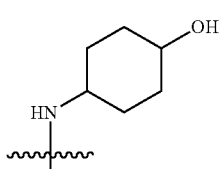
NSSy6486
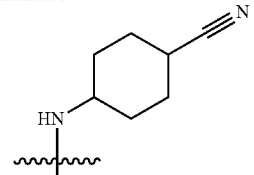
NSSy6526
IN11140-062-P1
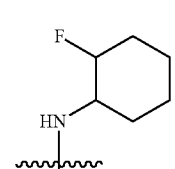
IN11133-031-P1
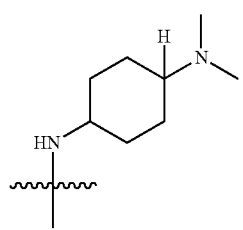 [SMILES: *NC1CCC(N(C)C)CC1]
NSSy6540
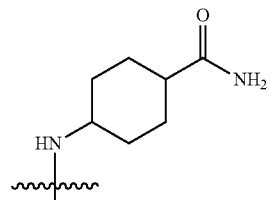
NSSy6541
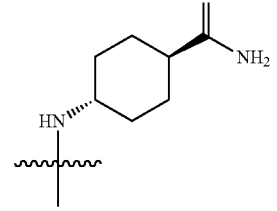
NSSy6541
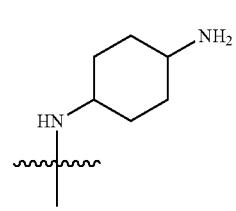 [SMILES: *NC1CCC(N)CC1]
NSSy6550
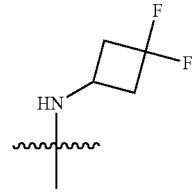 [SMILES: *NC1CC(F)(F)C1]
IN11107-020-P1
TABLE 57
| Step 1: The procedure is similar to Step 1[B] in Example-838. | | | | |
|---|---|---|---|---|
| Compound No | R | Condition | Yield (%) | MS (M + 1)+ |
| BQ | 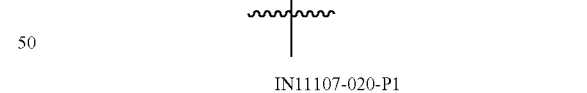 | Cs$_2$CO$_3$, ACN, 75° C., 16 h | 88 | 306.2 |

TABLE 57-continued

| Step 1: The procedure is similar to Step 1[B] in Example-838. | | | | |
|---|---|---|---|---|
| Compound No | R | Condition | Yield (%) | MS (M + 1)+ |
| BR | Chiral | Cs₂CO₃, ACN, 75° C., 16 h | — | 306.2 |
| BS | Chiral | Cs₂CO₃, ACN, 75° C., 16 h | — | 306.2 |
| BT | | Cs₂CO₃, ACN, 80° C., 16 h | 51 | 360.0 |
| BU | | DIPEA, ACN, 80° C., 16 h | 99 | 308.1 |
| BV | | Cs₂CO₃, ACN, 80° C., 16 h | 93 | 317.2 |
| BW | | DIPEA, ACN, 80° C., 16 h | 94 | 335.5 |
| BX | | Cs₂CO₃, ACN, 80° C., 16 h | 76 | 335.2 |

TABLE 57-continued

Step 1: The procedure is similar to Step 1[B] in Example-838.

| Compound No | R | Condition | Yield (%) | MS (M + 1)+ |
|---|---|---|---|---|
| BY | [trans-4-aminocarbonylcyclohexyl-NH-] | $Cs_2CO_3$, ACN, 80° C., 16 h | — | 335.2 |
| BZ | [4-aminocyclohexyl-NH-] | $Cs_2CO_3$, ACN, 80° C., 16 h | 95 | 307.0 |
| CB | [2,2-difluorocyclohexyl-NH-] | $Cs_2CO_3$, ACN, 90° C., 16 h | 28 | 328.0 |
| CC | [2-fluorocyclohexyl-NH-] | $Cs_2CO_3$, ACN, 80° C., 16 h | 66 | 310.0 |
| CD | [3,3-difluorocyclobutyl-NH-] | $Cs_2CO_3$, ACN, 60° C., 24 h | 53 | 300.0 |

TABLE 58

Step 2: The procedure is similar to Step 1[B] in Example-838.

| Compound No | R | Condition | Yield (%) | MS (M + 1)+ |
|---|---|---|---|---|
| NSSy6420 | [7-oxabicyclic-NH-] | Morpholine, ACN, 80° C., 16 h | 62 | 357.2 |

TABLE 58-continued

Step 2: The procedure is similar to Step 1[B] in Example-838.

| Compound No | R | Condition | Yield (%) | MS (M + 1)+ |
|---|---|---|---|---|
| NSSy6445 | (Chiral, oxabicyclic with HN) | Morpholine, ACN, 80° C., 16 h | — | 357.2 |
| NSSy6446 | (Chiral, oxabicyclic with HN) | Morpholine, ACN, 80° C., 16 h | — | 357.2 |
| NSSy6511 | (hydroxyadamantyl-NH) | Morpholine, ACN, 80° C., 16 h | 44 | 411.0 |
| NSSy6486 | (4-hydroxycyclohexyl-NH) | Morpholine, ACN, 80° C., 4 h | 65 | 359.0 |
| NSSy6526 | (4-cyanocyclohexyl-NH) | Morpholine, ACN, 80° C., 16 h | 86 | 368.2 |
| NSSy6540 | (4-dimethylaminocyclohexyl-NH) | Morpholine, ACN, 80° C., 16 h | 55 | 386.2 |
| NSSy6541 | (4-carbamoylcyclohexyl-NH) | Morpholine, ACN, 80° C., 16 h | 80 | 386.3 |

TABLE 58-continued

Step 2: The procedure is similar to Step 1[B] in Example-838.

| Compound No | R | Condition | Yield (%) | MS (M + 1)+ |
|---|---|---|---|---|
| NSSy6539 | *cyclohexyl with HN- and C(O)NH2* | Morpholine, ACN, 80° C., 16 h | — | 386.3 |
| NSSy6550 | *cyclohexyl with HN- and NH2* | Morpholine, ACN, 80° C., 16 h | 39 | 358.0 |
| IN11140-062-P1 | *cyclohexyl with HN- and CF2* | Morpholine, rt, 16 h | 58 | 379.0 |
| IN11133-031-P1 | *cyclohexyl with HN- and F* | Morpholine, rt, 16 h | 42 | 361.1 |
| IN11107-020-P1 | *cyclobutyl with HN- and CF2* | Morpholine, rt, 16 h | 65 | 351.1 |

Step 2[NSSy6420]: 1H-NMR (400 MHz, DMSO-d6): δ 8.39 (s, 1H), 7.02 (s 1H), 6.25 (s, 1H), 5.54 (s, 1H), 4.54 (s, 1H), 4.30 (s, 1H), 4.01 (bs, 1H), 3.67 (s, 4H), 3.47 (s, 4H), 2.23 (s, 3H), 2.0-1.95 (m, 1H), 1.41 (s, 5H).

Step 2[NSSy6445]: 1H-NMR (400 MHz, DMSO-d6): δ 8.39 (s, 1H), 7.04 (s, 1H), 6.25 (s, 1H), 5.54 (s, 1H), 4.54 (s, 1H), 4.31 (s, 1H), 4.01 (bs, 1H), 3.68 (s, 4H), 3.48 (s, 4H), 2.24 (s, 3H), 2.00-1.95 (m, 1H), 1.41 (s, 5H).

Step 2[NSSy6446]: 1H-NMR (400 MHz, DMSO-d6): δ 8.39 (s, 1H), 7.04 (s 1H), 6.26 (s, 1H), 5.49 (s, 1H), 4.54 (s, 1H), 4.31 (s, 1H), 4.01 (bs, 1H), 3.68 (s, 4H), 3.48 (s, 4H), 2.24 (s, 3H), 2.00-1.95 (m, 1H), 1.41 (s, 5H).

Step 2[NSSy6511]: 1H-NMR (400 MHz, DMSO-d6): δ 8.31 (d, J=2.40 Hz, 1H), 6.69 (s, 1H), 6.28 (d, J=2.40 Hz, 1H), 5.55 (s, 1H), 4.52 (s, 1H), 3.68-3.67 (m, 4H), 3.43-3.42 (m, 4H), 2.17 (s, 3H), 1.98 (m, 2H), 1.96 (m, 6H), 1.61-1.48 (m, 5H).

Step 2[NSSy6486]: 1H-NMR (400 MHz, DMSO-d6): δ 8.37 (s, 1H), 6.86 (s, 1H), 6.23 (s, 1H), 5.48 (s, 1H), 4.53 (s, 1H), 3.66 (s, 4H), 3.65-3.40 (m, 4H), 3.36 (s, 1H), 1.98 (s, 3H), 1.87-1.81 (m, 3H), 1.64-1.55 (m, 1H).

Step 2[NSSy6526]: 1H-NMR (400 MHz, DMSO-d6): δ 8.40 (s, 1H), 7.12 (d, J=7.92 Hz, 0.5H), 7.02 (d, J=7.92 Hz, 0.5H), 6.25 (s, 1H), 5.51 (s, 1H), 3.67 (bs, 4H), 3.49 (bs, 4H), 3.08 (bs, 0.5H), 2.69 (bs, 0.5H), 2.24 (s, 3H), 2.12-2.00 (m, 1H), 2.00-1.80 (m, 3H), 1.80-1.60 (m, 2H), 1.60-1.49 (m, 1H), 1.35-1.20 (m, 1H).

Step 2[NSSy6540]: 1H-NMR (400 MHz, DMSO-d6, 80° C.): δ 8.35 (s, 1H), 6.52 (s, 1H), 6.21 (s, 1H), 5.56 (d, J=25.20 Hz, 1H), 3.94 (s, 1H), 3.69 (s, 4H), 3.61 (s, 4H), 2.26 (s, 3H), 2.21 (s, 6H), 1.90-1.50 (m, 9H).

Step 2[NSSy6541]: 1H-NMR (400 MHz, DMSO-d6): δ 8.39 (s, 1H), 7.22 (s, 1H), 6.94 (d, J=8.32 Hz, 1H), 6.68 (s, 1H), 6.24 (s, 1H), 5.50 (s, 1H), 3.66 (bs, 4H), 3.50 (bs, 4H), 2.24 (s, 3H), 2.12-2.00 (m, 1H), 2.00-1.90 (m, 2H), 1.80-1.70 (m, 2H), 1.51-1.49 (m, 2H), 1.30-1.10 (m, 2H).

Step 2[NSSy6539]: 1H-NMR (400 MHz, DMSO-d6): δ 8.39 (s, 1H), 7.22 (s, 1H), 6.94 (d, J=8.32 Hz, 1H), 6.69 (s, 1H), 6.24 (s, 1H), 5.51 (s, 1H), 3.66 (bs, 4H), 3.50 (bs, 4H), 2.24 (s, 3H), 2.12-2.0 (m, 1H), 2.0-1.9 (m, 2H), 1.80-1.70 (m, 2H), 1.51-1.49 (m, 2H), 1.30-1.10 (m, 2H).

Step 2[NSSy6550]: 1H-NMR (400 MHz, DMSO-d6): δ 8.39 (s, 1H), 6.93 (s, 1H), 6.25 (d, J=3.20 Hz, 1H), 5.59 (s, 1H), 3.68-3.66 (m, 4H), 3.47 (m, 4H), 2.73 (m, 1H), 2.24 (s, 3H), 1.85-1.73 (m, 5H), 1.57-1.54 (m, 5H), 1.21 (m, 1H).

Step 2[IN11140-062-P1]: 1H-NMR (400 MHz, DMSO-d6): δ 8.44 (d, J=2.40 Hz, 1H), 7.11 (d, J=8.40 Hz, 1H), 6.26 (d, J=2.80 Hz, 1H), 5.69 (s, 1H), 4.50 (s, 1H), 3.72-3.65 (m, 4H), 3.52-3.42 (m, 4H), 2.25 (s, 3H), 2.15-1.65 (m, 5H), 1.60-1.40 (m, 3H).

Step 2[IN11133-031-P1]: 1H-NMR (400 MHz, DMSO-d6): δ 8.39 (d, J=2.40 Hz, 1H), 7.12 (d, J=8.80 Hz, 1H), 6.25 (d, J=2.40 Hz, 1H), 5.56 (s, 1H), 4.47-4.33 (m, 1H), 3.67 (s, 4H), 3.50 (s, 4H), 2.24 (s, 3H), 2.07 (m, 1H), 1.91 (m, 1H), 1.75-1.45 (m, 3H), 1.35-1.20 (m, 4H).

Step 2[IN11107-020-P1]: 1H-NMR (400 MHz, DMSO-d6): δ 8.40 (d, J=2.40 Hz, 1H), 7.60 (d, J=5.20 Hz, 1H), 6.26 (d, J=2.40 Hz, 1H), 5.48 (s, 1H), 4.13 (s, 1H), 3.72-3.60 (m, 4H), 3.58-3.48 (m, 4H), 3.10-2.95 (m, 2H), 2.70-2.55 (m, 2H), 2.24 (s, 3H).

Example-714

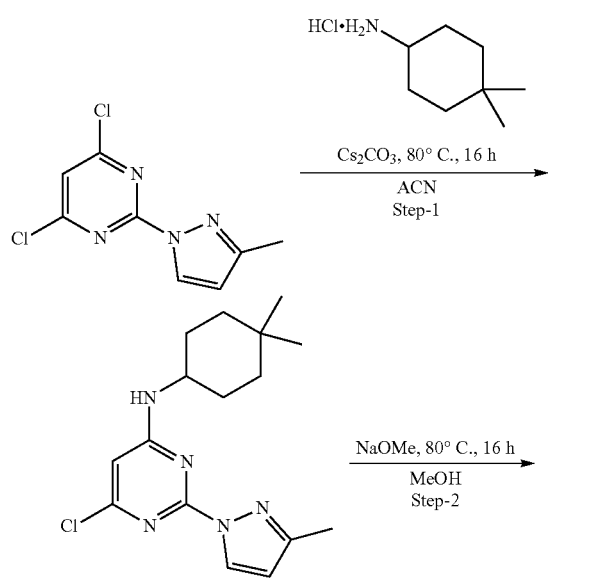

Step 1: The procedure is similar to Step 1[B] in Example-838. 0.05 g of 4,6-dichloro-2-(3-methyl-1H-pyrazol-1-yl)pyrimidine gave 6-chloro-N-(4,4-dimethylcyclohexyl)-2-(3-methyl-1H-pyrazol-1-yl)pyrimidin-4-amine as a yellow solid (0.035 g, 50%). MS (M+1)+=320.1.

Step 2[IN11055-078-P1]: The procedure is similar to Step 1[NSSY6519] in Example-842. 0.07 g of 6-chloro-N-(4,4-dimethylcyclohexyl)-2-(3-methyl-1H-pyrazol-1-yl)pyrimidin-4-amine gave N-(4,4-dimethylcyclohexyl)-6-methoxy-2-(3-methyl-1H-pyrazol-1-yl)pyrimidin-4-amine as an off-white solid (0.040 g, 57%). MS (M+1)+=316.1; 1H-NMR (400 MHz, DMSO-d6): δ 8.40 (d, J=2.40 Hz, 1H), 7.31 (d, J=7.20 Hz, 1H), 6.30 (d, J=2.40 Hz, 1H), 5.62 (s, 1H), 3.85 (s, 3H), 2.26 (s, 3H), 1.73-1.65 (m, 2H), 1.38-1.24 (m, 7H), 0.92 (s, 6H).

Example-715

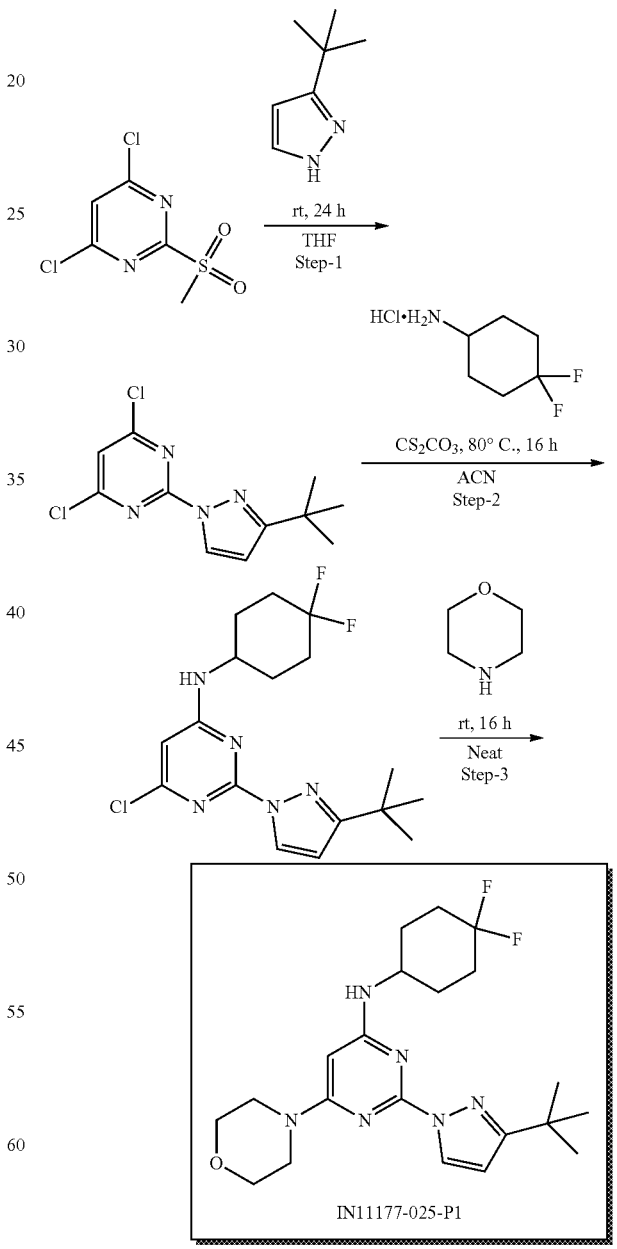

Step 1: To a stirred solution of 4,6-dichloro-2-(methylsulfonyl)pyrimidine (0.45 g, 1.98 mmol) in Tetrahydrofuran (10 mL) was added 3-(tert-butyl)-1H-pyrazole (0.2 g, 1.98 mmol). The reaction mixture stirred at rt for 24 h. The reaction mixture was diluted with ethyl acetate (100 mL) and water (80 mL) extracted and separated, organic layer was dried over anhydrous sodium sulfate, filtered and concentrated under reduced pressure to afford 2-(3-(tert-butyl)-1H-pyrazol-1-yl)-4,6-dichloropyrimidine as an off-white solid (0.1 g, 18%). MS (M+1)+=271.0.

Step 2: The procedure is similar to Step 1[B] in Example-838. 0.1 g of 2-(3-(tert-butyl)-1H-pyrazol-1-yl)-4,6-dichloropyrimidine gave 2-(3-(tert-butyl)-1H-pyrazol-1-yl)-6-chloro-N-(4,4-difluorocyclohexyl)pyrimidin-4-amine as an off-white solid (0.09 g, 66%). MS (M+1)+=371.0.

Step 3[IN11177-025-P1]: 0.08 g of 2-(3-(tert-butyl)-1H-pyrazol-1-yl)-6-chloro-N-(4,4-difluorocyclohexyl)pyrimidin-4-amine gave 2-(3-(tert-butyl)-1H-pyrazol-1-yl)-N-(4,4-difluorocyclohexyl)-6-morpholinopyrimidin-4-amine as a white solid (0.07 g, 80%). MS (M+1)+=421.0; 1H-NMR (400 MHz, DMSO-d6): δ 8.42 (d, J=2.4 Hz, 1H), 7.10 (d, J=7.6 Hz, 1H), 6.37 (d, J=2.8 Hz, 1H), 5.54 (s, 1H), 3.69 (m, 1H), 3.68-3.67 (m, 4H), 3.51 (m, 4H), 2.05-1.91 (m, 6H), 1.59-1.51 (m, 2H), 1.28 (s, 9H).

Example-716

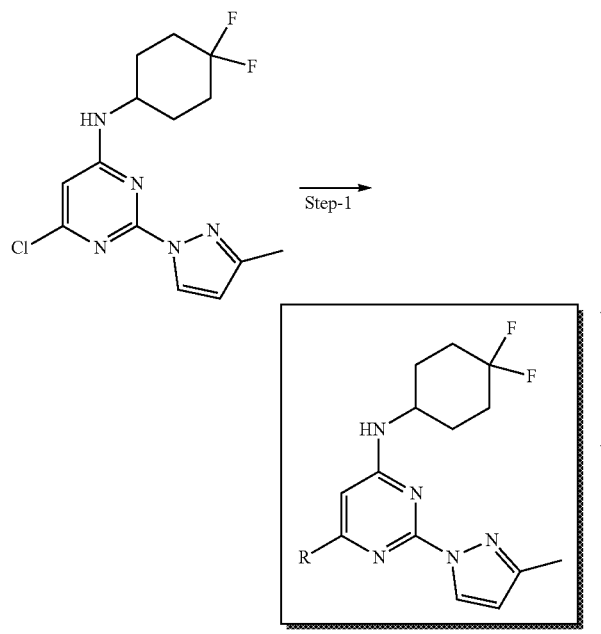

R=

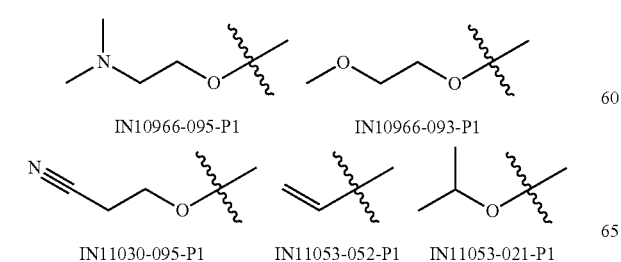

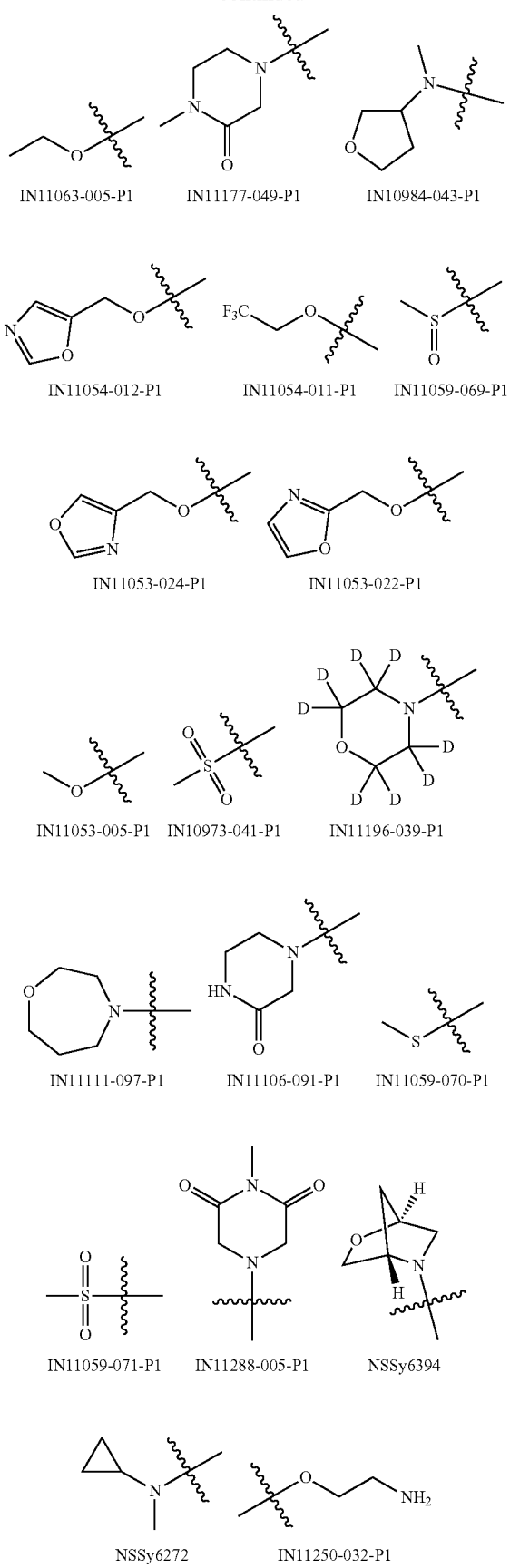

961
-continued

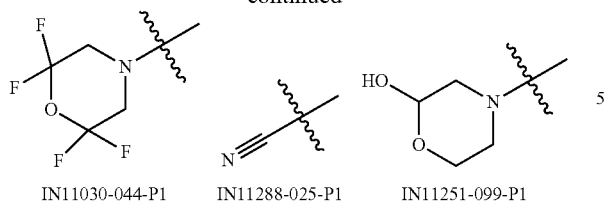

IN11030-044-P1    IN11288-025-P1    IN11251-099-P1

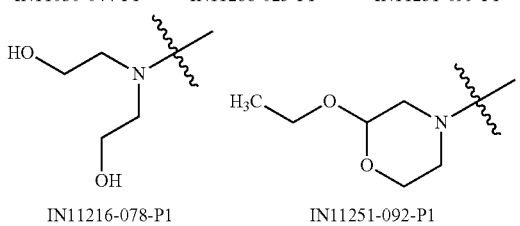

IN11216-078-P1    IN11251-092-P1

962
-continued

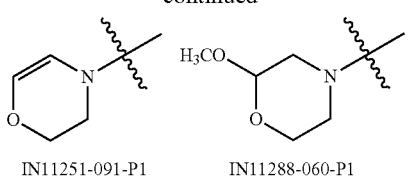

IN11251-091-P1    IN11288-060-P1

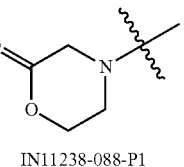

IN11238-088-P1

TABLE 59

| Step 1: | | | |
|---|---|---|---|
| Compound No | R | Condition | Yield (%) |
| NSSy6394 | 2-oxa-5-azabicyclo[2.2.1]heptane | $Cs_2CO_3$, ACN, 80° C., 16 h | 45 |
| NSSy6272 | N-cyclopropyl-N-methyl | $Cs_2CO_3$, ACN, 80° C., 16 h | 29 |
| IN10966-095-P1 | 2-(dimethylamino)ethoxy | Na, rt, 48 h | 21 |
| IN10966-093-P1 | 2-methoxyethoxy | Na, rt, 48 h | 21 |
| IN11030-095-P1 | 2-cyanoethoxy | $K_2CO_3$, 90° C., 6 h | 8 |
| IN11053-052-P1 | allyl | $Pd(PPh_3)_2Cl_2$, dioxane, 95° C., 36 h | 83 |
| IN11063-005-P1 | ethoxy | Na, EtOH, 80° C., 3 h | 43 |
| IN11177-049-P1 | 4-methyl-3-oxopiperazin-1-yl | $Cs_2CO_3$, dioxane, 150° C., 3.5 h | 27 |

TABLE 59-continued
| | Step 1: | | |
|---|---|---|---|
| Compound No | R | Condition | Yield (%) |
| IN10984-043-P1 | 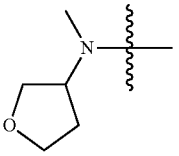 [SMILES: *N(C)C1CCOC1] | Cs₂CO₃, ACN, 100° C., 20 min, MW | 25 |
| IN11054-012-P1 | 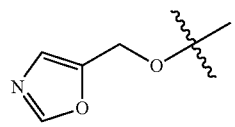 [SMILES: *OCc1cnco1] | NaH, THF, 0° C.-65° C., 1 h | 9 |
| IN11054-011-P1 | 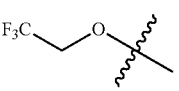 | NaH, THF, 0° C.-65° C., 1 h | 56 |
| IN11059-069-P1 | 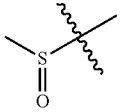 [SMILES: *S(C)=O] | m-CPBA, DCM, rt, 16 h | 43 |
| IN11053-021-P1 | 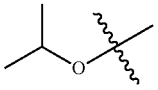 | Na, IPA, 60° C., 2 h | 10 |
| IN11053-024-P1 | 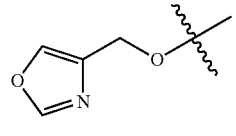 [SMILES: *OCc1cocn1] | Cs₂CO₃, ACN, 80° C., 16 h | 12 |
| IN11053-022-P1 | 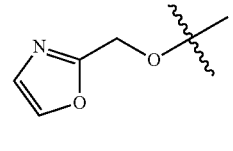 | Cs₂CO₃, ACN, 80° C., 16 h | 30 |
| IN11053-005-P1 | 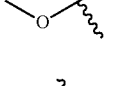 | NaOMe, MeOH, 80° C., 16 h | 34 |
| IN10973-041-P1 | 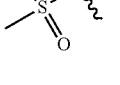 | Cs₂CO₃, ACN, 80° C., 16 h | 75 |
| IN11196-039-P1 | 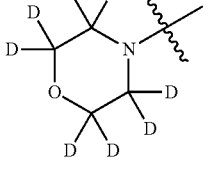 | TEA, ACN, 80° C., 48 h | 38 |
| IN11111-097-P1 | 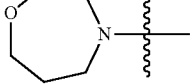 | Cs₂CO₃, ACN, 80° C., 16 h | 22 |

TABLE 59-continued
Step 1:
| Compound No | R | Condition | Yield (%) |
|---|---|---|---|
| IN11106-091-P1 | 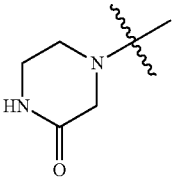 [SMILES: *N1CCNC(=O)C1] | Cs$_2$CO$_3$, dioxane, 150° C., 1 h | 19 |
| IN11059-070-P1 | 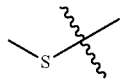 | NaSMe, EtOH, 65° C., 3 h | 35 |
| IN11059-071-P1 | 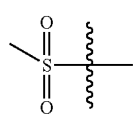 [SMILES: *S(C)(=O)=O] | m-CPBA, DCM, rt, 6 h | 28 |
| IN11288-005-P1 | 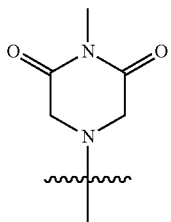 [SMILES: *N1CC(=O)N(C)C(=O)C1] | DIPEA, dioxane, 100° C., 18 h | 26 |
| IN11250-032-P1 | 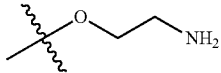 [SMILES: *OCCN] | 80° C., 16 h | 65 |
| IN11030-044-P1 | 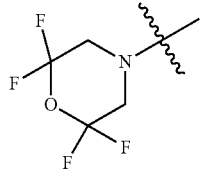 | Pd(OAc)$_2$, Xanthphos, Cs$_2$CO$_3$, 1,4-Dioxane, 95° C., 16 h | 22 |
| IN11288-025-P1 | 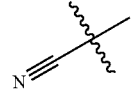 | Zn(CN)$_2$, Pd(PPh$_3$)$_4$, DMF, 150° C., 1 h, MW | 30 |
| IN11251-099-P1 | 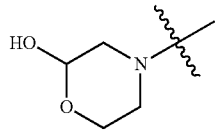 [SMILES: *N1CCOC(O)C1] | Cs$_2$CO$_3$, ACN, 80° C., 16 h | 31 |
| IN11216-078-P1 | 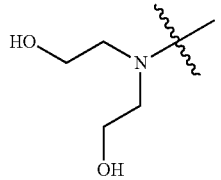 [SMILES: *N(CCO)CCO] | Cs$_2$CO$_3$, ACN, 80° C., 16 h | 41 |
| IN11251-092-P1 | 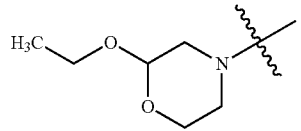 [SMILES: *N1CCOC(OCC)C1] | Cs$_2$CO$_3$, ACN, 80° C., 16 h | 73 |

TABLE 59-continued

Step 1:

| Compound No | R | Condition | Yield (%) |
|---|---|---|---|
| IN11251-091-P1 | (3,6-dihydro-2H-1,4-oxazin-4-yl, α-methyl) | Cs$_2$CO$_3$, ACN, 80° C., 16 h | 16 |
| IN11288-060-P1 | (2-methoxymorpholin-4-yl, α-methyl) | Cs$_2$CO$_3$, ACN, 80° C., 16 h | 66 |
| IN11238-088-P1 | (2-oxomorpholin-4-yl, α-methyl) | Cs$_2$CO$_3$, ACN, 80° C., 16 h | 50 |

Step 1[NSSy6394]: The procedure is similar to Step 1[B] in Example-838. MS (M+1)+=391.1; 1H-NMR (400 MHz, DMSO-d6): δ 8.42 (s, 1H), 7.02 (s, 1H), 6.25 (s, 1H), 5.26 (s, 1H), 4.97 (bs, 1H), 4.68 (s, 1H), 3.91 (s, 1H), 3.79 (s, 1H), 3.66 (s, 1H), 3.42 (s, 1H), 3.23 (s, 1H), 2.50 (s, 3H), 2.05-1.86 (m, 8H), 1.56-1.53 (m, 2H).

Step 1[NSSy6272]: The procedure is similar to Step 1[B] in Example-838. MS (M+1)+=363.2; 1H-NMR (400 MHz, DMSO-d6): δ 8.41 (s, 1H), 7.09-7.07 (d, J=8.00 Hz, 1H), 6.25 (s 1H), 5.78 (s, 1H), 3.97 (bs, 1H), 3.07 (s, 3H), 2.24 (s, 3H), 2.06-1.93 (m, 6H), 1.57-1.55 (m, 2H), 0.85 (s, 2H), 0.65 (s, 2H).

Step 1[IN10966-095-P1]: The procedure is similar to step 5[IN10963-068-P1] in Example-697. MS (M+1)+=381.0; 1H-NMR (400 MHz, DMSO-d6): δ 8.43 (s, 1H), 7.48 (s, 1H), 6.31 (d, J=2.40 Hz, 1H), 5.67 (s, 1H), 4.01 (s, 1H), 4.35 (t, J=5.20 Hz, 2H), 2.59 (t, J=5.60 Hz, 2H), 2.25 (s, 3H), 2.20 (s, 6H), 2.10-1.88 (m, 6H), 1.60-1.50 (m, 2H).

Step 1[IN10966-093-P1]: The procedure is similar to step 5[IN10963-068-P1] in Example-697. MS (M+1)+=368.0; 1H-NMR (400 MHz, DMSO-d6): δ 8.43 (s, 1H), 7.46 (s, 1H), 6.31 (s, 1H), 5.69 (s, 1H), 4.40 (s, 2H), 3.64 (t, J=5.20 Hz, 2H), 3.29 (s, 3H), 2.25 (s, 3H), 2.10-1.90 (m, 6H), 1.60-1.50 (m, 2H).

Step 1[IN11030-095-P1]: The procedure is similar to step 1[B] in Example-838. MS (M+1)+=363.1; 1H-NMR (400 MHz, DMSO-d6): δ 11.61 (s, 1H), 8.49 (d, J=2.40 Hz, 1H), 6.65 (d, J=7.60 Hz, 1H), 6.36 (s, 1H), 4.21 (s, 1H), 2.72 (t, J=7.20 Hz, 2H), 2.26 (s, 3H), 2.10-1.85 (m, 6H), 1.62-1.58 (m, 2H).

Step 1[IN11053-052-P1]: The procedure is similar to step 1[H] in Example-838. MS (M+1)+=320.0; 1H-NMR (400 MHz, DMSO-d6): δ 8.51 (s, 1H), 7.72 (s, 1H), 6.64 (q, J=6.80 Hz, 1H), 6.38 (s, 1H), 6.31 (d, J=2.40 Hz, 2H), 5.57 (d, J=10.40 Hz, 1H), 4.17 (s, 1H), 2.33 (s, 3H), 2.18-1.88 (m, 6H), 1.62-1.52 (m, 2H).

Step 1[IN11063-005-P1]: The procedure is similar to step 5[IN10963-068-P1] in Example-697. MS (M+1)+=338.2; 1H-NMR (400 MHz, DMSO-d6): δ 8.42 (bs, 1H), 7.44 (bs, 1H), 6.30 (d, J=2.4 Hz, 1H), 5.66 (bs, 1H), 4.31 (q, J=6.80 Hz, 2H), 2.25 (s, 3H), 2.04-1.91 (m, 6H), 1.31 (t, J=6.80 Hz, 3H).

Step 1[IN11177-049-P1]: The procedure is similar to step 1[NSSy6909] in Example-839. MS (M+1)+=406.1; 1H-NMR (400 MHz, CDCl3): δ 8.43 (s, 1H), 7.10 (d, J=8.00 Hz, 1H), 6.28 (s, 1H), 5.42 (s, 1H), 4.07 (s, 2H), 3.86 (s, 3H), 3.42 (t, J=5.20 Hz, 2H), 2.91 (s, 3H), 2.25 (s, 3H), 2.10-1.85 (m, 6H), 1.60-1.50 (m, 2H).

Step 1[IN10984-043-P1]: The procedure is similar to step 1[NSSy6909] in Example-839. MS (M+1)+=379.0; 1H-NMR (400 MHz, DMSO-d6): δ 8.44 (d, J=2.00 Hz, 1H), 7.03 (d, J=8.40 Hz, 1H), 6.26 (d, J=2.40 Hz, 1H), 5.40 (s, 1H), 4.00-3.95 (m, 2H), 3.69-3.35 (m, 3H), 2.86 (s, 3H), 2.21 (s, 3H), 2.10-1.80 (m, 9H), 1.60-1.50 (m, 2H).

Step 1[IN11054-012-P1]: The procedure is similar to step 2[IN10991-021-P1] in Example-694. MS (M+1)+=391.3; 1H-NMR (400 MHz, DMSO-d6): δ 8.51 (s, 1H), 8.40 (s, 1H), 7.60 (bs, 1H), 7.39 (s, 1H), 6.34 (d, J=2.4 Hz, 1H), 5.70 (bs, 1H), 5.45 (s, 2H), 2.27 (s, 4H), 2.04-1.85 (m, 6H), 1.55-1.53 (m, 2H).

Step 1[IN11054-011-P1]: The procedure is similar to step 2[IN10991-021-P1] in Example-694. MS (M+1)+=392.2; 1H-NMR (400 MHz, DMSO-d6): δ 8.53 (s, 1H), 7.65 (bs, 1H), 6.34 (d, J=2.4 Hz, 1H), 5.70 (bs, 1H), 5.09-5.02 (m, 2H), 5.07 (d, J=8.8 Hz, 2H), 3.90-3.50 (bs, 1H).

Step 1[IN11059-069-P1]: The procedure is similar to step 3[NSSy7062] in Example-623. MS (M+1)+=356.1; 1H-NMR (400 MHz, DMSO-d6): δ 8.53 (d, J=2.40 Hz, 1H), 8.22 (d, J=7.60 Hz, 1H), 6.88 (s, 1H), 6.36 (d, J=2.40 Hz, 1H), 4.24 (s, 1H), 2.82 (s, 3H), 2.27 (s, 3H), 2.15-1.95 (m, 6H), 1.65-1.55 (m, 2H).

Step 1[IN11053-021-P1]: The procedure is similar to step 5[IN10963-068-P1] in Example-697. MS (M+1)+=352.2; 1H-NMR (400 MHz, DMSO-d6): δ 8.41 (s, 1H), 7.42 (s, 1H), 6.30 (s, 1H), 5.63 (s, 1H), 5.28 (s, 1H), 4.05 (s, 1H), 2.25 (s, 3H), 2.08-1.88 (m, 6H), 1.60-1.48 (m, 2H), 1.29 (d, J=6.00 Hz, 6H).

Step 1[IN11053-024-P1]: The procedure is similar to step 1[B] in Example-838. MS (M+1)+=391.3; 1H-NMR (400 MHz, DMSO-d6): δ 8.49 (s, 1H), 8.39 (s, 1H), 8.29 (s, 1H), 7.50 (s, 1H), 6.33 (d, J=2.80 Hz, 1H), 5.70 (s, 1H), 5.28 (s, 2H), 4.00 (s, 1H), 2.33 (s, 3H), 2.12-1.85 (m, 6H), 1.60-1.50 (m, 2H).

Step 1[IN11053-022-P1]: The procedure is similar to step 1[B] in Example-838. MS (M+1)+=391.3; 1H-NMR (400 MHz, DMSO-d6): δ 8.43 (s, 1H), 8.15 (s, 1H), 7.60 (s, 1H), 7.26 (s, 1H), 6.32 (d, J=3.20 Hz, 1H), 5.75 (s, 1H), 5.49 (s, 2H), 4.10 (s, 1H), 2.25 (s, 3H), 2.80-1.85 (m, 6H), 1.56-1.48 (m, 2H).

Step 1[IN11053-005-P1]: The procedure is similar to step 1[NSSy6519] in Example-842. MS (M+1)+=324.2; 1H-NMR (400 MHz, DMSO-d6): δ 8.44 (s, 1H), 7.42 (s, 1H), 6.31 (d, J=2.80 Hz, 1H), 5.68 (s, 1H), 4.01 (s, 1H), 3.87 (s, 3H), 2.26 (s, 3H), 2.10-1.85 (m, 6H), 1.60-1.50 (m, 2H).

Step 1[IN10973-041-P1]: The procedure is similar to Step 1[B] in Example-838. MS (M+1)+=306.0; 1H-NMR (400 MHz, DMSO-d6): δ 8.58 (d, J=2.80 Hz, 1H), 8.41 (d, J=7.60 Hz, 1H), 6.95 (s, 1H), 6.39 (d, J=2.40 Hz, 1H), 4.24 (s, 1H), 3.25 (s, 3H), 2.29 (s, 3H), 2.15-1.90 (m, 6H), 1.65-1.55 (m, 2H).

Step 1[IN11196-039-P1]: The procedure is similar to Step 1[B] in Example-838. MS (M+1)+=387.3; 1H-NMR (400 MHz, DMSO-d6): δ 8.42 (s, 1H), 7.06 (s, 1H), 6.25 (s, 1H), 5.52 (s, 1H), 3.90 (s, 1H), 2.24 (s, 3H), 2.15-1.88 (m, 6H), 1.62-1.45 (m, 2H).

Step 1[IN11111-097-P1]: The procedure is similar to Step 1[B] in Example-838. MS (M+1)+=393.3; 1H-NMR (400 MHz, DMSO-d6): δ 8.40 (d, J=2.40 Hz, 1H), 6.96 (d, J=8.40 Hz, 1H), 6.24 (d, J=2.80 Hz, 1H), 5.43 (s, 1H), 3.95 (s, 1H), 3.72-3.31 (m, 8H), 2.24 (s, 3H), 2.10-1.72 (m, 8H), 1.60 (m, 2H).

Step 1[IN11106-091-P1]: The procedure is similar to step 1[NSSy6909] in Example-839. MS (M+1)+=392.2; 1H-NMR (400 MHz, DMSO-d6): δ 8.43 (s, 1H), 8.17 (s, 1H), 7.11 (d, J=8.0 Hz, 1H), 6.26 (d, J=2.4 Hz, 1H), 5.50 (s, 1H), 4.01 (s, 3H), 3.78 (s, 2H), 3.28 (s, 3H), 2.24 (s, 2H), 2.05-1.91 (m, 6H), 1.55-1.53 (m, 2H).

Step 1[IN11059-070-P1]: The procedure is similar to step 1[IN11067-060-P1] in Example-705. MS (M+1)+=340.1; 1H-NMR (400 MHz, CD3OD): δ 8.46 (d, J=2.8 Hz, 1H), 6.30 (d, J=2.4 Hz, 1H), 6.17 (s, 1H), 4.10 (m, 1H), 2.52 (s, 3H), 2.35 (s, 3H), 2.10-1.95 (m, 6H), 1.64-1.61 (m, 2H).

Step 1[IN11059-071-P1]: The procedure is similar to step 3[NSSy7062] in Example-623. MS (M+1)+=356.1; 1H-NMR (400 MHz, DMSO-d6): δ 9.12 (s, 1H), 8.82 (d, J=9.60 Hz, 1H), 7.49 (s, 1H), 6.43 (s, 1H), 4.05 (s, 1H), 3.28 (s, 3H), 2.32 (s, 3H), 2.15-1.80 (m, 8H).

Step 1[IN11288-005-P1]: The procedure is similar to Step 1[B] in Example-838. MS (M+1)+=420.2; 1H-NMR (400 MHz, DMSO-d6): δ 8.45 (s, 1H), 7.28 (d, J=8.00 Hz, 1H), 6.28 (d, J=2.40 Hz, 1H), 5.72 (s, 1H), 4.56 (s, 4H), 3.95 (s, 1H), 3.02 (s, 3H), 2.25 (s, 3H), 2.10-1.88 (m, 6H), 1.60-1.48 (m, 2H).

Step 1[IN11250-032-P1]: MS (M+1)+=353.2; 1H-NMR (400 MHz, DMSO-d6): δ 8.36 (d, J=2.40 Hz, 1H), 6.88 (d, J=8.00 Hz, 1H), 6.24 (d, J=2.40 Hz, 1H), 5.32 (s, 1H), 4.77 (t, J=5.60 Hz, 1H), 3.90 (s, 1H), 3.54-3.35 (m, 2H), 3.26 (s, 2H), 2.25 (s, 3H), 2.10-1.85 (m, 7H), 1.62-1.50 (m, 2H).

Step 1[IN11030-044-P1]: The procedure is similar to Step 1[NSSy6629] in Example-839. 1H-NMR (400 MHz, DMSO-d6): δ 8.54 (d, J=2.80 Hz, 1H), 7.40 (s, 1H), 6.29 (d, J=2.40 Hz, 1H), 5.80 (s, 1H), 4.01 (s, 1H), 4.42 (s, 4H), 2.33 (s, 3H), 2.10-1.85 (m, 6H), 1.62-1.50 (m, 2H).

Step 1[IN11288-025-P1]: The procedure is similar to Step 3[NSSy5933] in Example-808. 1H-NMR (400 MHz, DMSO-d6): δ 8.51 (s, 1H), 8.36 (d, J=6.40 Hz, 1H), 6.82 (s, 1H), 6.38 (s, 1H), 4.19 (m, 1H), 2.27 (s, 3H), 2.10-1.85 (m, 6H), 1.65-1.52 (m, 2H).

Step 1[IN11251-099-P1]: MS (M+1)+=394.9; 1H-NMR (400 MHz, DMSO-d6): δ 1.67-1.64 (m, 2H), 2.24-1.98 (m, 6H), 2.28 (s, 3H), 3.74-3.70 (m, 2H), 4.17 (t, J=5.6 Hz, 2H), 4.32 (bs, 1H), 4.97 (t, J=5.2 Hz, 1H), 6.28 (d, J=2.4 Hz, 1H), 6.60 (d, J=3.2 Hz, 1H), 7.14 (d, J=3.2 Hz, 1H), 7.57 (d, J=7.8 Hz, 1H), 8.53 (d, J=2.5 Hz, 1H).

Step 1[IN11216-078-P1]: MS (M+1)+=397.2; 1H-NMR (400 MHz, DMSO-d6): δ 1.52-1.55 (m, 2H), 1.80-1.99 (m, 6H), 2.23 (s, 3H), 3.55-3.57 (m, 8H), 3.87 (bs, 1H), 4.86 (bs, 2H), 5.42 (s, 1H), 6.26 (d, J=1.6 Hz, 1H), 6.98 (d, J=7.6 Hz, 1H), 8.39 (d, J=1.6 Hz, 1H).

Step 1[IN11251-092-P1]: MS (M+1)+=422.2; 1H-NMR (400 MHz, DMSO-d6): δ 1.14-1.11 (m, 3H), 1.57-1.50 (m, 2H), 2.05-1.87 (m, 6H), 2.22 (s, 3H), 3.59-3.39 (m, 6H), 3.69-3.60 (m, 1H), 3.92-3.70 (m, 2H), 4.71-4.69 (m, 1H), 5.50 (s, 1H), 6.23 (d, J=3 Hz, 1H), 7.03 (d, J=7.8 Hz, 1H), 8.39 (d, J=2.5 Hz, 1H).

Step 1[IN11251-091-P1]: MS (M+1)+=376.7; 1H-NMR (400 MHz, DMSO-d6): δ 1.67-1.64 (m, 2H), 2.24-1.98 (m, 6H), 2.28 (s, 3H), 3.74-3.70 (m, 2H), 4.17 (t, J=5.6 Hz, 2H), 4.32 (bs, 1H), 4.97 (t, J=5.2 Hz, 1H), 6.28 (d, J=2.4 Hz, 1H), 6.60 (d, J=3.2 Hz, 1H), 7.14 (d, J=3.2 Hz, 1H), 7.57 (d, J=7.8 Hz, 1H), 8.53 (d, J=2.5 Hz, 1H).

Step 1[IN11288-060-P1]: MS (M+1)+=408.7; 1H-NMR (400 MHz, DMSO-d6): δ 1.64-1.59 (m, 2H), 2.05-1.92 (m, 6H), 2.34 (s, 3H), 3.41 (s, 3H), 3.55-3.45 (m, 1H), 3.67-3.58 (m, 3H), 3.77-3.73 (m, 1H), 4.01-3.96 (m, 2H), 4.63-4.61 (t, J=3.6 Hz, 1H), 5.48 (s, 1H), 6.26 (d, J=2.4 Hz, 1H), 8.43-8.42 (d, J=2.4 Hz, 1H).

Step 1[IN11238-088-P1]: MS (M+1)+=393.2; 1H-NMR (400 MHz, DMSO-d6): δ 1.48-1.62 (m, 2H), 1.85-2.16 (m, 6H), 2.24 (s, 3H), 3.75 (s, 2H), 3.94 (bs, 1H), 4.41 (s, 2H), 4.53 (t, J=5.2 Hz, 2H). 5.44 (s, 1H), 6.26 (d, J=2.4 Hz, 1H), 7.16 (d, J=7.9 Hz, 1H), 8.44 (d, J=2.0 Hz, 1H).

Example-717

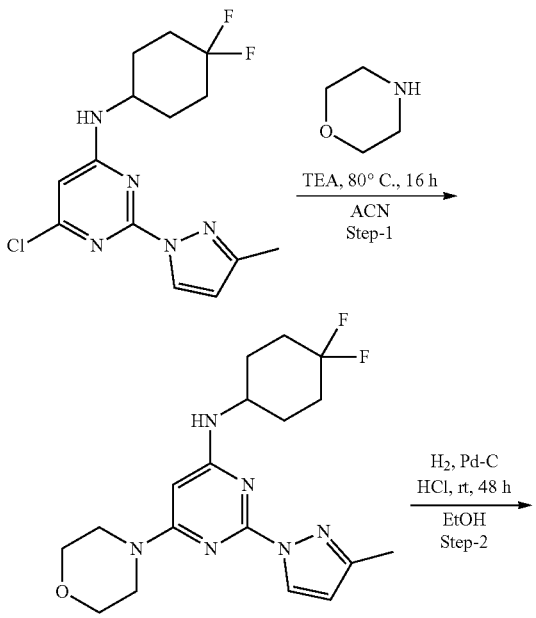

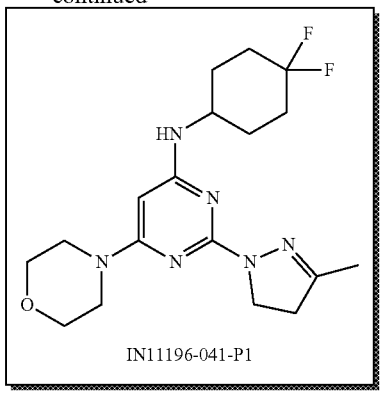

Step 1: The procedure is similar to Step 1[B] in Example-838. 14.0 g of 6-chloro-N-(4,4-difluorocyclohexyl)-2-(3-methyl-1H-pyrazol-1-yl)pyrimidin-4-amine gave N-(4,4-difluorocyclohexyl)-2-(3-methyl-1H-pyrazol-1-yl)-6-morpholinopyrimidin-4-amine as a yellow solid (10.0 g, 66%). MS (M+1)+=379.2.

Step 2[IN11196-041-P1]: The procedure is similar to Step 2[NSSy6464] in Example-869. 0.15 g of N-(4,4-difluorocyclohexyl)-2-(3-methyl-1H-pyrazol-1-yl)-6-morpholinopyrimidin-4-amine gave N-(4,4-difluorocyclohexyl)-2-(3-methyl-4,5-dihydro-1H-pyrazol-1-yl)-6-morpholinopyrimidin-4-amine as an off-white solid (0.022 g, 14%). MS (M+1)+=381.1; 1H-NMR (400 MHz, DMSO-d6): δ 6.52 (s, 1H), 5.20 (s, 1H), 3.79 (t, J=9.60 Hz, 3H), 3.69-3.60 (m, 4H), 3.50-3.45 (m, 3H), 2.80-2.60 (m, 2H), 2.10-1.80 (m, 10H), 1.60-1.45 (m, 2H).

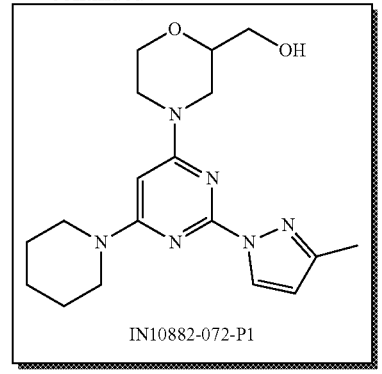

Step 1: The procedure is similar to Step 1[B] in Example-838. 0.44 g of 4,6-dichloro-2-(3-methyl-1H-pyrazol-1-yl)pyrimidine gave (4-(6-chloro-2-(3-methyl-1H-pyrazol-1-yl)pyrimidin-4-yl) morpholin-2-yl) methanol as a white solid (0.6 g, 80%). MS (M+1)+=310.0.

Step 2[IN10882-072-P1]: 0.1 g of (4-(6-chloro-2-(3-methyl-1H-pyrazol-1-yl)pyrimidin-4-yl) morpholin-2-yl) methanol gave (4-(2-(3-methyl-1H-pyrazol-1-yl)-6-(piperidin-1-yl)pyrimidin-4-yl) morpholin-2-yl) methanol as a white solid (0.06 g, 52%). MS (M+1)+=359.1; 1H-NMR (400 MHz, DMSO-d6): δ 8.43 (s, 1H), 6.26 (s, 1H), 5.77 (s, 1H), 4.82 (t, J=5.60 Hz, 1H), 4.26 (dd, J=13.20, 42.40 Hz, 2H), 3.92 (d, J=10.00 Hz, 1H), 3.62 (s, 4H), 3.55-3.44 (m, 3H), 2.88 (t, J=11.20 Hz, 1H), 2.64 (t, J=12.00 Hz, 1H), 2.25 (s, 3H), 1.63-1.53 (m, 5H).

Example-718

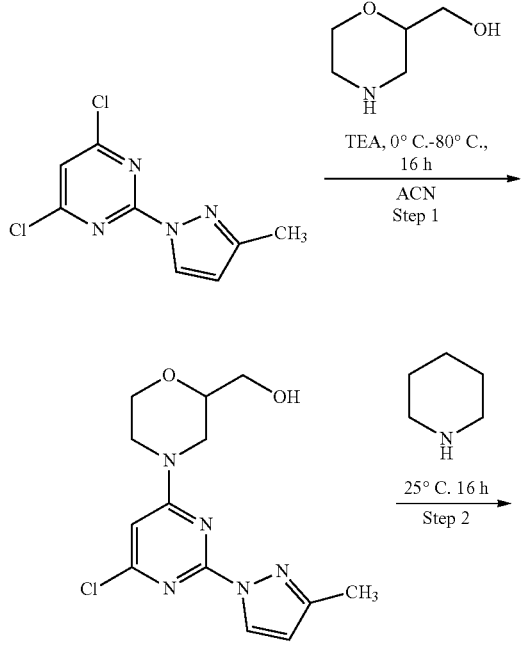

Example-719

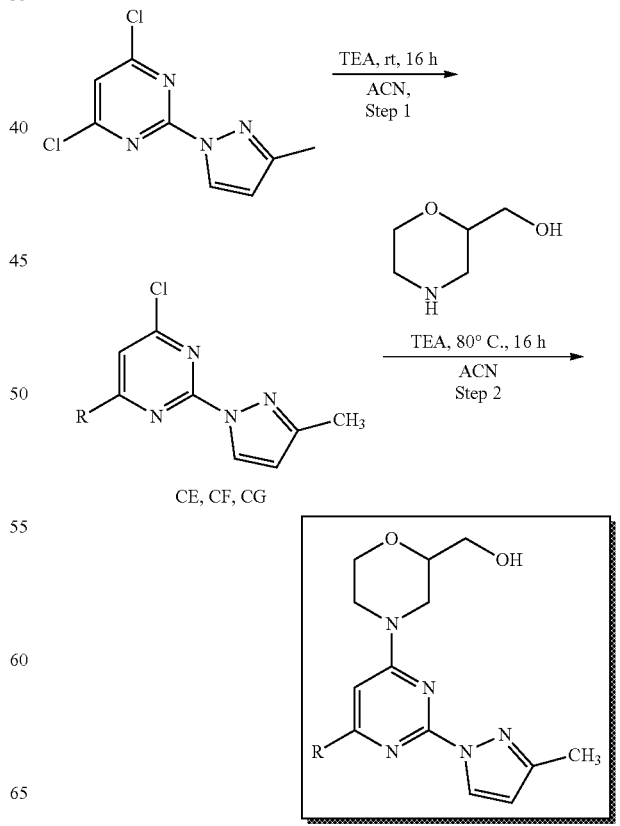

R=

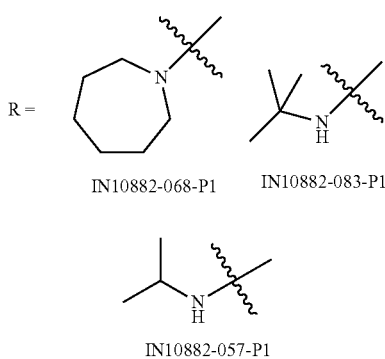

Step 2[IN10882-068-P1]: 1H-NMR (400 MHz, DMSO-d6): δ 8.41 (d, J=2.8 Hz, 1H), 6.26 (d, J=2.4 Hz, 1H), 5.59 (s, 1H), 4.85-4.80 (m, 1H), 4.35-4.15 (m, 2H), 3.95-3.91 (m, 1H), 3.64-3.39 (m, 8H), 2.91-2.84 (m, 1H), 2.67-2.60 (m, 1H), 2.25 (s, 3H), 1.72 (bs, 4H), 1.48 (bs, 4H).

Step 2[IN10882-083-P1]: 1H-NMR (400 MHz, DMSO-d6): δ 8.34 (d, J=2.40 Hz, 1H), 6.76 (s, 1H), 6.27 (d, J=2.40 Hz, 1H), 5.57 (s, 1H), 4.88-4.85 (m, 1H), 4.08-3.91 (m, 3H), 3.45-3.37 (m, 3H), 2.88-2.85 (m, 1H), 2.67-2.55 (m, 2H), 2.25 (s, 3H), 1.40 (s, 9H).

Step 2[IN10882-057-P1]: 1H-NMR (400 MHz, DMSO-d6): δ 8.38 (s, 1H), 6.89 (d, J=7.60 Hz, 1H), 6.25 (s, 1H), 5.48 (s, 1H), 4.81 (t, J=2.40 Hz, 1H), 4.18-3.91 (m, 4H), 3.55-3.40 (m, 4H), 2.90-2.84 (m, 1H), 2.66-2.63 (m, 1H), 2.33 (s, 3H), 1.15 (s, 3H), 1.13 (s, 3H).

Example-720

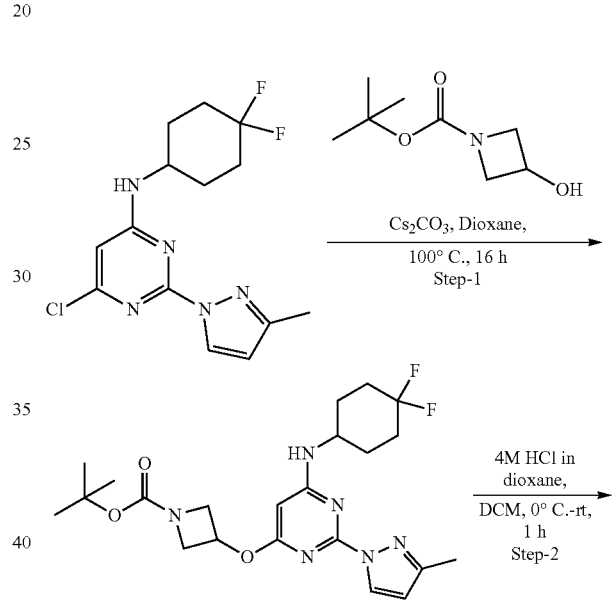

TABLE 60

Step 1: The procedure is similar to Step 1[A] in Example-838.

| Compound No | R | Condition | Yield (%) | MS (M + 1)+ |
|---|---|---|---|---|
| CE | (azepan-1-yl) | TEA, ACN, rt, 30 min | 84 | 292.0 |
| CF | (tert-butylamino) | TEA, ACN, rt, 48 h | 43 | 266.0 |
| CG | (isopropylamino) | TEA, ACN, rt, 2 h | 95 | 252.0 |

TABLE 61

Step 2: The procedure is similar to Step 1[B] in Example-838.

| Compound No | R | Condition | Yield (%) | MS (M + 1)+ |
|---|---|---|---|---|
| IN10882-068-P1 | (azepan-1-yl) | morpholin-2-ylmethanol, TEA, ACN, 0° C.-80° C., 16 h | 23 | 373.1 |
| IN10882-083-P1 | (tert-butylamino) | morpholin-2-ylmethanol, TEA, ACN, 0° C.-80° C., 16 h | 23 | 347.1 |
| IN10882-057-P1 | (isopropylamino) | morpholin-2-ylmethanol, TEA, ACN, 0° C.-80° C., 6 h | 30 | 333.1 |

-continued

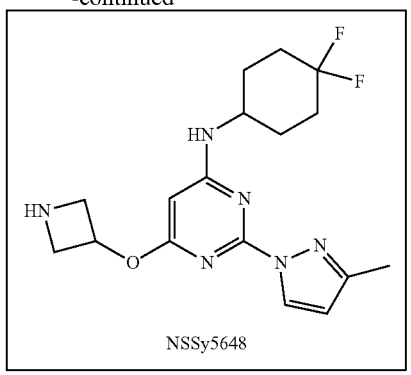

NSSy5648

Step 1: The procedure is similar to Step 1[B] in Example-838. 25 g of 6-chloro-N-(4,4-difluorocyclohexyl)-2-(3-methyl-1H-pyrazol-1-yl)pyrimidin-4-amine gave tert-butyl 3-((6-((4,4-difluorocyclohexyl)amino)-2-(3-methyl-1H-pyrazol-1-yl)pyrimidin-4-yl)oxy)azetidine-1-carboxylate as a yellow gum (32 g, 91%). MS (M+1)+=465.5.

Step 2[NSSy5648]: To a stirred solution of tert-butyl 3-((6-((4,4-difluorocyclohexyl)amino)-2-(3-methyl-1H-pyrazol-1-yl)pyrimidin-4-yl)oxy) azetidine-1-carboxylate (0.3 g, 0.64 mmol) in DCM (5 mL) was added 4 (M) HCl in dioxane (2 mL) at 0° C. and the reaction mixture was stirred at room temperature. The reaction mixture was concentrated under reduced pressure to afford crude product and which was purified by flash column chromatography using methanol in chloroform as solvent to afford 6-(azetidin-3-ylo xy)-N-(4,4-difluorocyclohexyl)-2-(3-methyl-1H-pyrazol-1-yl)pyrimidin-4-amine as a white solid (0.18 g, 60%). MS (M+1)+=365.2; 1H-NMR (400 MHz, DMSO-d6): δ 9.31 (s, 1H), 9.13 (s, 1H), 8.46 (s, 1H), 7.70 (s, 1H), 6.35 (s, 1H), 5.76 (s, 1H), 5.42 (s, 1H), 4.38 (s, 2H), 4.10-4.03 (m, 2H), 2.26 (s, 3H), 2.06-1.92 (m, 6H), 1.61-1.54 (m, 2H).

Example-721

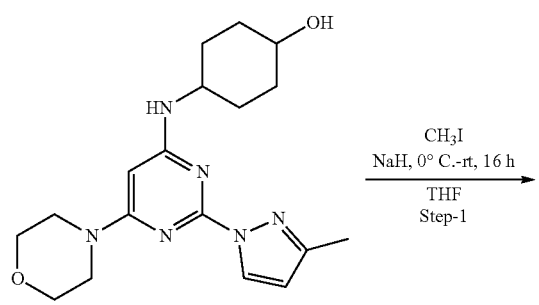

NSSy6529

Step 1[NSSy6529]: The procedure is similar to Step 5[NSSy6711] in Example-854. 0.2 g of 4-((2-(3-methyl-1H-pyrazol-1-yl)-6-morpholinopyrimidin-4-yl)amino)cyclohexan-1-ol gave N-(4-methoxycyclohexyl)-2-(3-methyl-1H-pyrazol-1-yl)-6-morpholinopyrimidin-4-amine as an off-white solid (0.035 g, 17%). MS (M+1)+=373.2; 1H-NMR (400 MHz, DMSO-d6): δ 8.38 (s, 1H), 6.91 (s, 1H), 6.25 (s, 1H), 5.51 (s, 1H), 3.68 (s, 4H), 3.47 (s, 4H), 3.24 (s, 3H), 2.24 (s, 3H), 1.99-1.79 (m, 3H), 1.61-1.53 (m, 4H), 1.23 (s, 2H).

Example-722

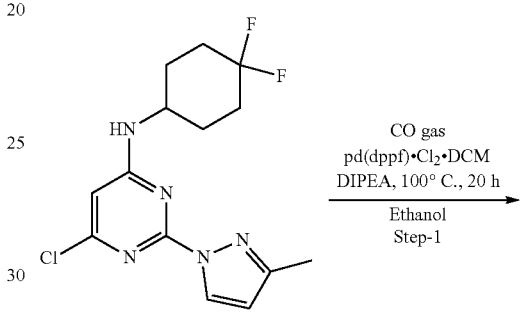

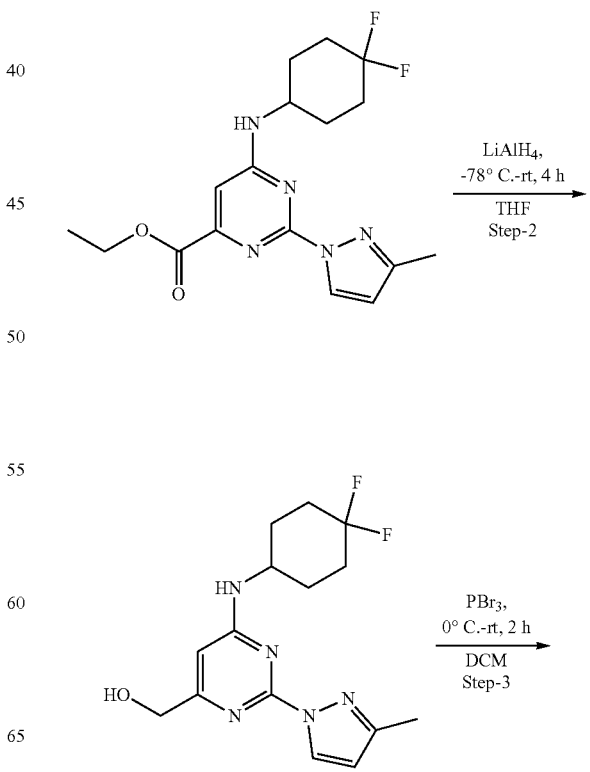

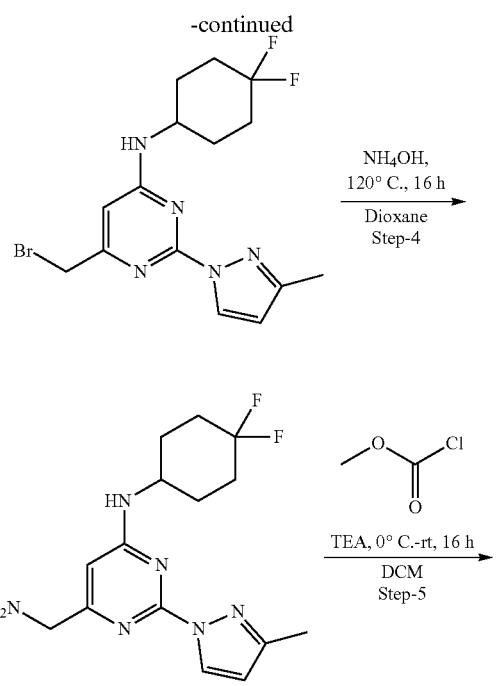

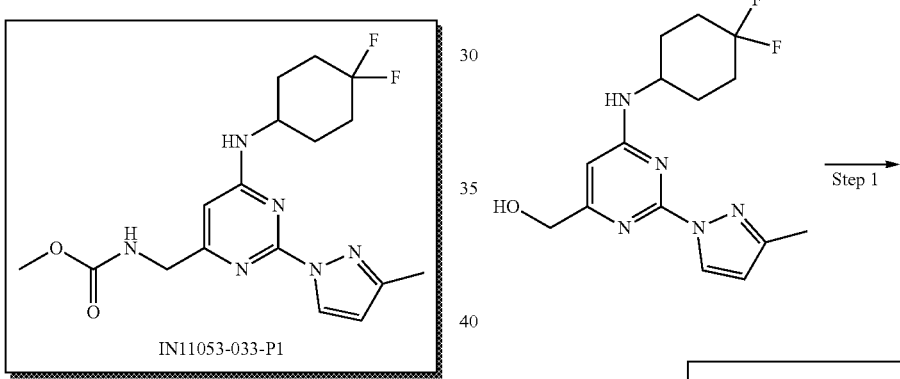

Step 1: The procedure is similar to Step 1[IN11273-018-P1] in Example-889. 2.0 g of 6-chloro-N-(4,4-difluorocyclohexyl)-2-(3-methyl-1H-pyrazol-1-yl)pyrimidin-4-amine gave ethyl 6-((4,4-difluorocyclohexyl)amino)-2-(3-methyl-1H-pyrazol-1-yl)pyrimidine-4-carboxylate as a brownish gum (1.1 g, 49%). MS (M+1)+=366.0.

Step 2: The procedure is similar to Step 4[NSSy6711] in Example-854. 1.1 g of ethyl 6-((4,4-difluorocyclohexyl) amino)-2-(3-methyl-1H-pyrazol-1-yl)pyrimidine-4-carboxylate gave (6-((4,4-difluorocyclohexyl)amino)-2-(3-methyl-1H-pyrazol-1-yl)pyrimidin-4-yl) methanol as a brown solid (0.6 g, 61%). MS (M+1)+=324.1.

Step 3: The procedure is similar to Step 3[IN11059-090-P1] in Example-659. 0.9 g of (6-((4,4-difluorocyclohexyl) amino)-2-(3-methyl-1H-pyrazol-1-yl)pyrimidin-4-yl) methanol carboxylate gave 6-(bromomethyl)-N-(4,4-difluorocyclohexyl)-2-(3-methyl-1H-pyrazol-1-yl)pyrimidin-4-amine as a brown solid (0.75 g, 71%). MS (M+1)+=386.1.

Step 4: To a stirred solution of 6-(bromomethyl)-N-(4,4-difluorocyclohexyl)-2-(3-methyl-1H-pyrazol-1-yl)pyrimidin-4-amine (0.2 g, 0.51 mmol) in Dioxane (10 mL) was added ammonium hydroxide (8 mL) at rt. The reaction mixture was heated at 120° C. for 16 h in a sealed tube vessel. The reaction was cooled to rt, diluted with ethyl acetate and dried over sodium sulfate, filtered and concentrated under reduced pressure to afford 6-(aminomethyl)-N-(4,4-difluorocyclohexyl)-2-(3-methyl-1H-pyrazol-1-yl)pyrimidin-4-amine as an off-white solid (0.17 g, 75%). MS (M+1)+=323.1.

Step 5[IN11053-033-P1]: The procedure is similar to step 1[A] in Example-838. 0.015 g of 6-(aminomethyl)-N-(4,4-difluorocyclohexyl)-2-(3-methyl-1H-pyrazol-1-yl)pyrimidin-4-amine gave of methyl ((6-((4,4-difluorocyclohexyl) amino)-2-(3-methyl-1H-pyrazol-1-yl)pyrimidin-4-yl) methyl) carbamate as a brown solid (0.04 g, 22%). MS (M+1)+=381.1; 1H-NMR (400 MHz, DMSO-d6): δ 8.46 (s, 1H), 7.72 (s, 2H), 6.30 (s, 1H), 6.26 (s, 1H), 4.15 (s, 1H), 4.04 (s, 2H), 3.58 (s, 3H), 2.26 (s, 3H), 2.10-1.90 (m, 6H), 1.60-1.52 (m, 2H).

Example-723

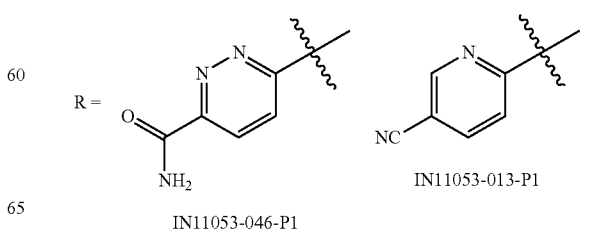

TABLE 62

Step 1: The procedure is similar to Step 1[B] in Example-838.

| Compound No | R | Condition | Yield (%) | MS (M + 1)+ |
|---|---|---|---|---|
| IN11053-046-P1 | pyridazine-3-carboxamide-6-yl | $Cs_2CO_3$, ACN, 80° C., 16 h | 42 | 445.2 |
| IN11053-013-P1 | 5-cyanopyridin-2-yl | $Cs_2CO_3$, ACN, 80° C., 16 h | 76 | 426.2 |

Step 1[IN11053-046-P1]: 1H-NMR (400 MHz, DMSO-d6): δ 8.48 (s, 1H), 8.37 (s, 1H), 8.17 (d, J=9.20 Hz, 1H), 7.80-7.70 (m, 2H), 7.52 (d, J=9.20 Hz, 1H), 6.37 (s, 1H), 6.32 (d, J=2.40 Hz, 1H), 5.49 (s, 2H), 4.15 (s, 1H), 2.27 (s, 3H), 2.10-1.90 (m, 6H), 1.60-1.50 (m, 2H).

Step 1[IN11053-013-P1]: 1H-NMR (400 MHz, CDCl3): δ 8.49 (d, J=2.00 Hz, 1H), 8.39 (d, J=2.40 Hz, 1H), 7.85-7.84 (m, 1H), 6.97 (d, J=8.80 Hz, 1H), 6.24 (s, 2H), 5.46 (s, 2H), 5.10 (s, 1H), 3.90 (s, 1H), 2.41 (s, 3H), 2.10-1.80 (m, 6H), 1.70-1.60 (m, 2H).

Example-724

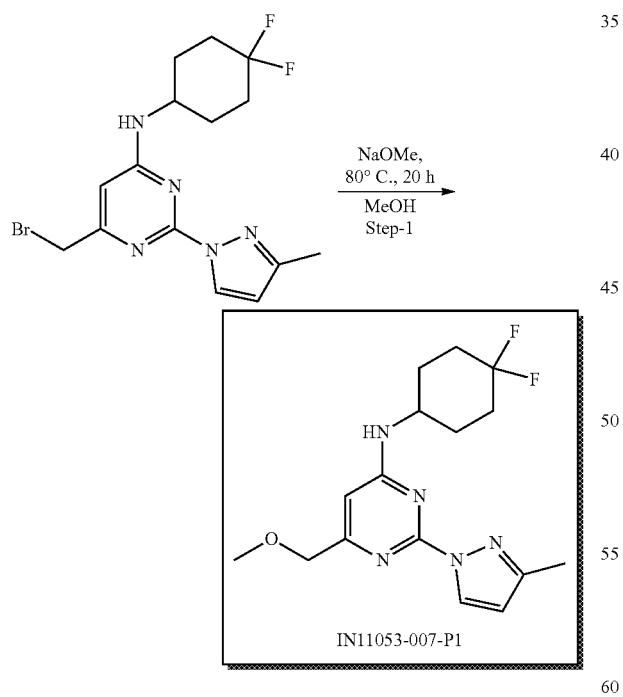

IN11053-007-P1

Step 1[IN11053-007-P1]: The procedure is similar to Step 1[NSSy6519] in Example-842. 0.2 g of 6-(bromomethyl)-N-(4,4-difluorocyclohexyl)-2-(3-methyl-1H-pyrazol-1-yl)pyrimidin-4-amine gave N-(4,4-difluorocyclohexyl)-6-(methoxymethyl)-2-(3-methyl-1H-pyrazol-1-yl)pyrimidin-4-amine as a white solid (0.09 g, 51%). MS (M+1)+=338.2; 1H-NMR (400 MHz, DMSO-d6): δ 8.45 (bs, 1H), 7.65 (bs, 1H), 6.41 (s, 1H), 6.30 (d, J=2.8 Hz, 1H), 4.30 (s, 2H), 4.15 (bs, 1H), 3.93 (s, 3H), 2.25 (s, 3H), 2.07-1.97 (m, 6H), 1.59-1.56 (m, 2H).

Example-725

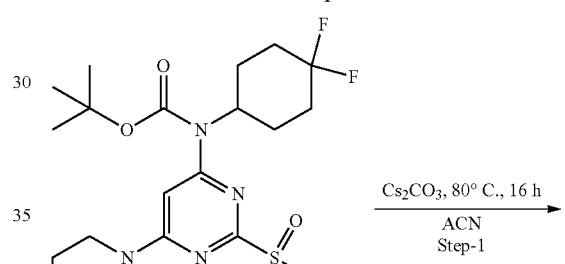

CI, CJ, CK, CL, CM

R=
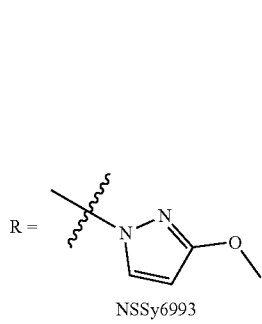
NSSy6993
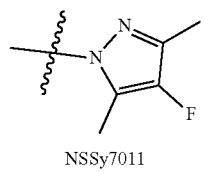
NSSy7011
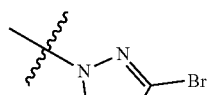
NSSy7021
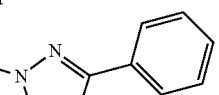
NSSy7034
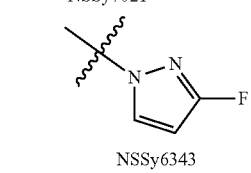
NSSy6343
IN11237-056-P1
TABLE 63
Step 1: The procedure is similar to Step 1[B] in Example-838.
| Compound No | R | Condition | Yield (%) | MS (M + 1)+ |
|---|---|---|---|---|
| CI | 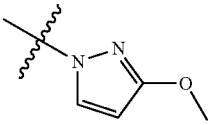 [SMILES: *n1ccc(OC)n1] | Cs₂CO₃, ACN, 80° C., 16 h | 73 | 495.0 |
| CJ | 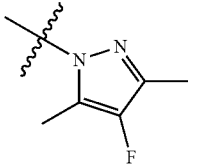 [SMILES: *n1nc(C)c(F)c1C] | Cs₂CO₃, ACN, 80° C., 16 h | 95 | 511.2 |
| CK | 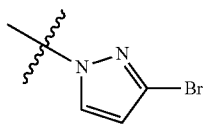 [SMILES: *n1ccc(Br)n1] | Cs₂CO₃, ACN, 80° C., 4 h | 98 | 543.1 |
| CL | 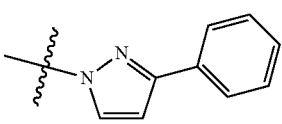 [SMILES: *n1ccc(-c2ccccc2)n1] | Cs₂CO₃, ACN, 80° C., 4 h | 92 | 541.0 |
| CM | 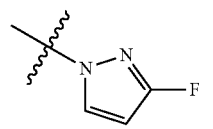 [SMILES: *n1ccc(F)n1] | Cs₂CO₃, ACN, 80° C., 16 h | 96 | 483.0 |
|  | 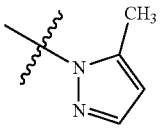 [SMILES: *n1nccc1C] | Cs₂CO₃, ACN, 80° C., 16 h | 5 | 479.2 |

TABLE 64

Step 2: The procedure is similar to Step 5[NSSy6067] in Example-628.

| Compound No | R | Condition | Yield (%) | MS (M + 1)+ |
|---|---|---|---|---|
| NSSy6993 | 3-methoxy-1H-pyrazol-1-yl | TFA, DCM, 0° C.-rt, 6 h | 62 | 395.0 |
| NSSy7011 | 4-fluoro-3,5-dimethyl-1H-pyrazol-1-yl | TFA, DCM, 0° C.-rt, 16 h | 87 | 411.2 |
| NSSy7021 | 3-bromo-1H-pyrazol-1-yl | TFA, DCM, 0° C.-rt, 6 h | 70 | 443.1 |
| NSSy7034 | 3-phenyl-1H-pyrazol-1-yl | TFA, DCM, 0° C.-rt, 6 h | 91 | 441.2 |
| NSSy6343 | 3-fluoro-1H-pyrazol-1-yl | TFA, DCM, 0° C.-rt, 16 h | 43 | 382.0 |
| IN11237-056-P1 | 5-methyl-1H-pyrazol-1-yl | TFA, DCM, 0° C.-rt, 16 h | 71 | 379.0 |

Step 2[NSSy6993]: 1H-NMR (400 MHz, DMSO-d6): δ 8.39 (d, J=2.80 Hz, 1H), 7.07 (d, J=8.00 Hz, 1H), 5.98 (d, J=2.80 Hz, 1H), 5.51 (s, 1H), 3.90 (s, 3H), 3.69-3.67 (m, 4H), 3.51 (m, 4H), 2.05-2.01 (m, 3H), 1.93-1.90 (m, 3H), 1.60-1.52 (m, 2H).

Step 2[NSSy7011]: 1H-NMR (400 MHz, DMSO-d6): δ 7.12 (s, 1H), 5.56 (s, 1H), 3.87 (s, 1H), 3.67 (s, 4H), 3.46 (s, 4H), 2.19 (s, 3H), 2.14-1.80 (m, 6H), 1.60-1.47 (m, 2H).

Step 2[NSSy7021]: 1H-NMR (400 MHz, DMSO-d6): δ 8.54 (d, J=2.00 Hz, 1H), 7.20 (d, J=8.00 Hz, 1H), 6.63 (d, J=2.40 Hz, 1H), 5.58 (s, 1H), 4.01 (s, 1H), 3.69-3.67 (m, 4H), 3.51 (s, 4H), 2.08-1.90 (m, 6H), 1.59-1.50 (m, 2H).

Step 2[NSSy7034]: 1H-NMR (400 MHz, DMSO-d6): δ 8.62 (d, J=2.60 Hz, 1H), 7.92 (d, J=7.20 Hz, 2H), 7.46 (t, J=7.68 Hz, 2H), 7.37 (t, J=7.44 Hz, 1H), 7.19 (d, J=7.96 Hz, 1H), 6.98 (d, J=2.64 Hz, 1H), 5.60 (s, 1H), 4.01 (bs, 1H), 3.72-3.70 (m, 4H), 3.56 (bs, 4H), 2.08-1.94 (m, 6H), 1.63-1.54 (m, 2H).

Step 2[NSSy6343]: 1H-NMR (400 MHz, DMSO-d6): δ 8.51 (s, 1H), 7.17 (d, J=8.16 Hz, 1H), 6.30-6.27 (m, 1H), 5.56 (s, 1H), 4.01-3.92 (m, 1H), 3.69-3.67 (m, 4H), 3.51-3.41 (m, 4H), 2.08-1.91 (m, 6H), 1.56-1.53 (m, 2H).

Step 2[IN11237-056-P1]: 1H-NMR (400 MHz, DMSO-d6): δ 7.45 (s, 1H), 7.04 (d, J=8.16 Hz, 1H), 6.20 (m, 1H), 5.56 (s, 1H), 4.01-3.92 (m, 1H), 3.69-3.67 (m, 4H), 3.51-3.41 (m, 4H), 2.08-1.91 (m, 6H), 1.56-1.53 (m, 2H).

Example-726

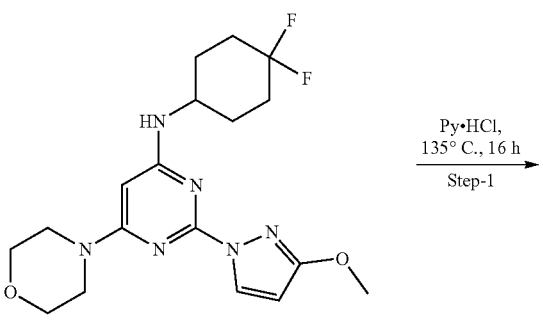

Py·HCl, 135° C., 16 h
Step-1

985

-continued

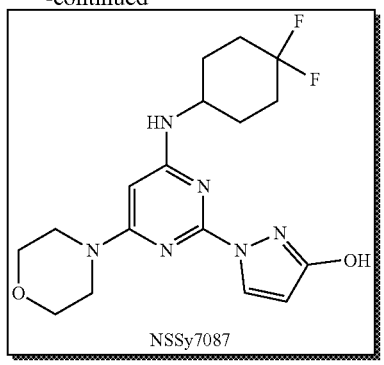

Step 1[NSSy7087]: The procedure is similar to Step 1[NSSy6972] in Example-841. 0.25 g of N-(4,4-difluorocyclohexyl)-2-(3-methoxy-1H-pyrazol-1-yl)-6-morpholinopyrimidin-4-amine gave 1-(4-((4,4-difluorocyclohexyl)amino)-6-morpholinopyrimidin-2-yl)-1H-pyrazol-3-ol as an off-white solid (0.12 g, 17%). MS (M+1)+=381.0; 1H-NMR (400 MHz, DMSO-d6): δ 10.40 (s, 1H), 6.98 (d, J=7.60 Hz, 1H), 5.79 (d, J=2.80 Hz, 1H), 5.49 (s, 1H), 3.97 (s, 1H), 3.68-3.66 (m, 4H), 3.55-3.35 (m, 4H), 2.08-2.04 (m, 3H), 2.02 (m, 3H), 1.98-1.97 (m, 2H).

Example-727

Intentionally Omitted

Example-728

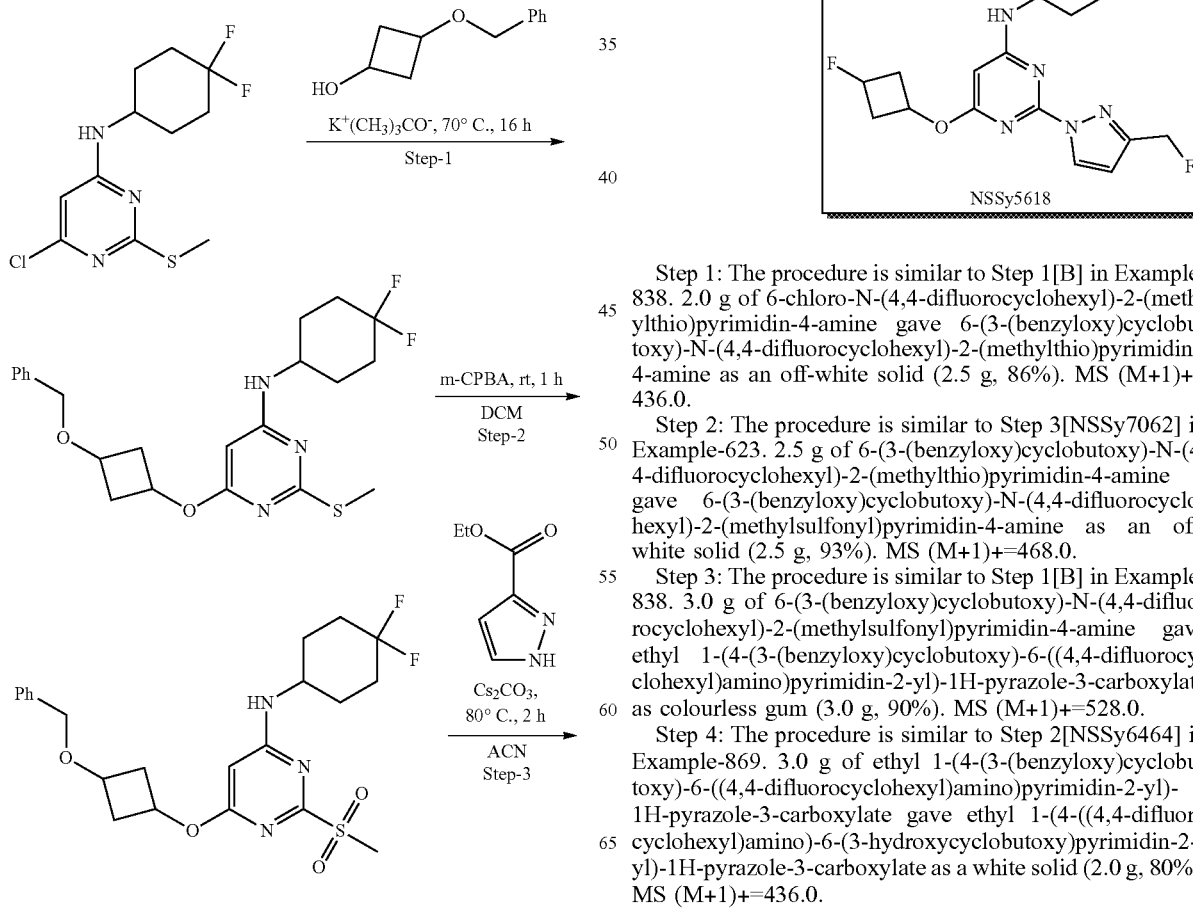

986

-continued

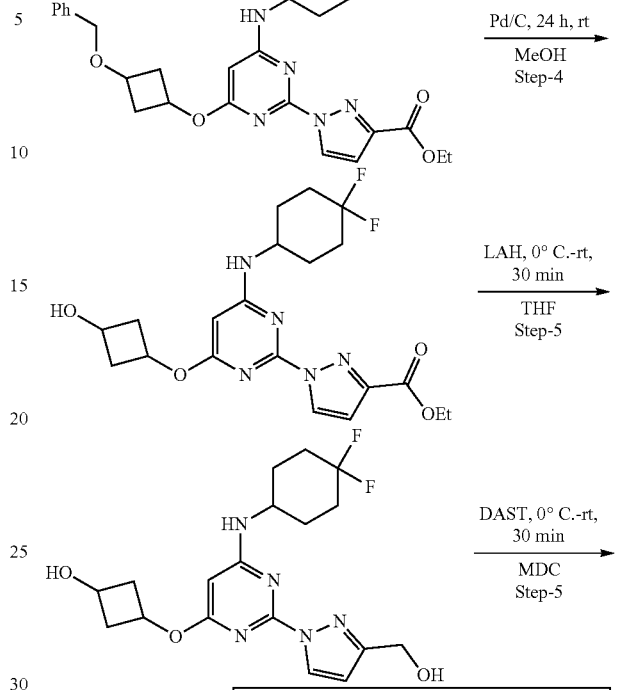

Step 1: The procedure is similar to Step 1[B] in Example-838. 2.0 g of 6-chloro-N-(4,4-difluorocyclohexyl)-2-(methylthio)pyrimidin-4-amine gave 6-(3-(benzyloxy)cyclobutoxy)-N-(4,4-difluorocyclohexyl)-2-(methylthio)pyrimidin-4-amine as an off-white solid (2.5 g, 86%). MS (M+1)+=436.0.

Step 2: The procedure is similar to Step 3[NSSy7062] in Example-623. 2.5 g of 6-(3-(benzyloxy)cyclobutoxy)-N-(4,4-difluorocyclohexyl)-2-(methylthio)pyrimidin-4-amine gave 6-(3-(benzyloxy)cyclobutoxy)-N-(4,4-difluorocyclohexyl)-2-(methylsulfonyl)pyrimidin-4-amine as an off-white solid (2.5 g, 93%). MS (M+1)+=468.0.

Step 3: The procedure is similar to Step 1[B] in Example-838. 3.0 g of 6-(3-(benzyloxy)cyclobutoxy)-N-(4,4-difluorocyclohexyl)-2-(methylsulfonyl)pyrimidin-4-amine gave ethyl 1-(4-(3-(benzyloxy)cyclobutoxy)-6-((4,4-difluorocyclohexyl)amino)pyrimidin-2-yl)-1H-pyrazole-3-carboxylate as colourless gum (3.0 g, 90%). MS (M+1)+=528.0.

Step 4: The procedure is similar to Step 2[NSSy6464] in Example-869. 3.0 g of ethyl 1-(4-(3-(benzyloxy)cyclobutoxy)-6-((4,4-difluorocyclohexyl)amino)pyrimidin-2-yl)-1H-pyrazole-3-carboxylate gave ethyl 1-(4-((4,4-difluorocyclohexyl)amino)-6-(3-hydroxycyclobutoxy)pyrimidin-2-yl)-1H-pyrazole-3-carboxylate as a white solid (2.0 g, 80%). MS (M+1)+=436.0.

Step 5: The procedure is similar to Step 4[NSSy6711] in Example-854. 0.3 g of ethyl 1-(4-((4,4-difluorocyclohexyl)amino)-6-(3-hydroxycyclobutoxy)pyrimidin-2-yl)-1H-pyrazole-3-carboxylate gave 3-((6-((4,4-difluorocyclohexyl)amino)-2-(3-(hydroxymethyl)-1H-pyrazol-1-yl)pyrimidin-4-yl)oxy)cyclobutan-1-ol as colourless gum (0.25 g, 92%). MS (M+1)+=396.0.

Step 6[NSSy5618]: The procedure is similar to Step 3[NSSy6917] in Example-21. 0.25 g of 3-((6-((4,4-difluorocyclohexyl)amino)-2-(3-(hydroxymethyl)-1H-pyrazol-1-yl)pyrimidin-4-yl)oxy)cyclobutan-1-ol gave of N-(4,4-difluorocyclohexyl)-6-(3-fluorocyclobutoxy)-2-(3-(fluoromethyl)-1H-pyrazol-1-yl)pyrimidin-4-amine as a white solid (0.1 g, 40%). MS (M+1)+=400.0; 1H-NMR (400 MHz, DMSO-d6): δ 7.60 (s, 1H), 7.55 (s, 1H), 5.80-5.69 (m, 1H), 5.50-5.40 (m, 1H), 5.38-5.23 (m, 3H), 4.20-3.71 (m, 1H), 2.68-2.67 (m, 2H), 2.56-2.54 (m, 1H), 2.34-2.33 (m, 6H), 1.95-1.60 (m, 2H).

Example-729

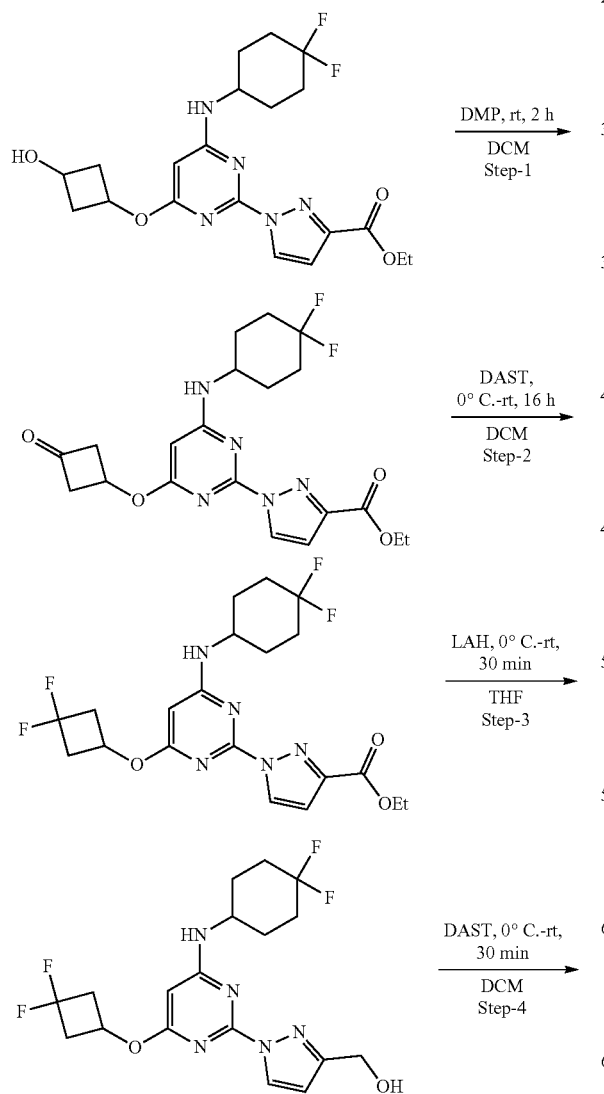

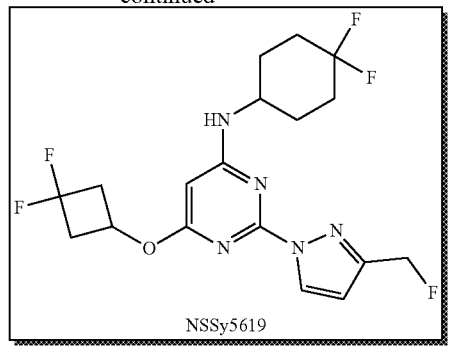

NSSy5619

Step 1: The procedure is similar to Step 1[NSSy6930] in Example-867. 1.5 g of ethyl 1-(4-((4,4-difluorocyclohexyl)amino)-6-(3-hydroxycyclobutoxy)pyrimidin-2-yl)-1H-pyrazole-3-carboxylate gave ethyl 1-(4-((4,4-difluorocyclohexyl)amino)-6-(3-oxocyclobutoxy)pyrimidin-2-yl)-1H-pyrazole-3-carboxylate as a yellow solid (1.4 g, 95%). MS (M+1)+=436.0.

Step 2: The procedure is similar to Step 3[NSSy6917] in Example-21. 0.6 g of ethyl 1-(4-((4,4-difluorocyclohexyl)amino)-6-(3-oxocyclobutoxy)pyrimidin-2-yl)-1H-pyrazole-3-carboxylate gave ethyl 1-(4-(3,3-difluorocyclobutoxy)-6-((4,4-difluorocyclohexyl)amino)pyrimidin-2-yl)-1H-pyrazole-3-carboxylate as a white solid (0.33 g, 52%). MS (M+1)+=456.0.

Step 3: The procedure is similar to Step 4[NSSy6711] in Example-854. 0.33 g of ethyl 1-(4-(3,3-difluorocyclobutoxy)-6-((4,4-difluorocyclohexyl)amino)pyrimidin-2-yl)-1H-pyrazole-3-carboxylate gave (1-(4-(3,3-difluorocyclobutoxy)-6-((4,4-difluorocyclohexyl)amino)pyrimidin-2-yl)-1H-pyrazol-3-yl) methanol as a colourless gum (0.26 g, 86%). MS (M+1)+=416.0.

Step 4[NSSy5619]: The procedure is similar to Step 3[NSSy6917] in Example-21. 0.26 g of (1-(4-(3,3-difluorocyclobutoxy)-6-((4,4-difluorocyclohexyl)amino)pyrimidin-2-yl)-1H-pyrazol-3-yl)methanol gave 6-(3,3-difluorocyclobutoxy)-N-(4,4-difluorocyclohexyl)-2-(3-(fluoromethyl)-1H-pyrazol-1-yl)pyrimidin-4-amine as a white solid (0.11 g, 39%). MS (M+1)+=418.0; 1 H-NMR (400 MHz, DMSO-d6): δ 8.59 (s, 1H), 7.77-7.62 (m, 1H), 6.65 (d, J=1.20 Hz, 1H), 5.76 (d, J=12.40 Hz, 1H), 5.49 (s, 1H), 5.37 (s, 1H), 5.15 (s, 1H), 4.15-4.05 (m, 1H), 3.19-3.01 (m, 2H), 2.81-2.69 (m, 2H), 2.04-1.94 (m, 6H), 1.56-1.53 (m, 2H).

Example-730

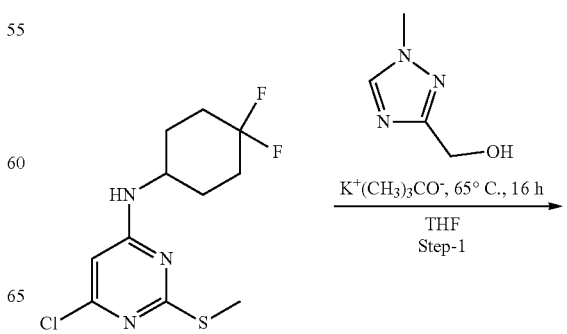

989
-continued
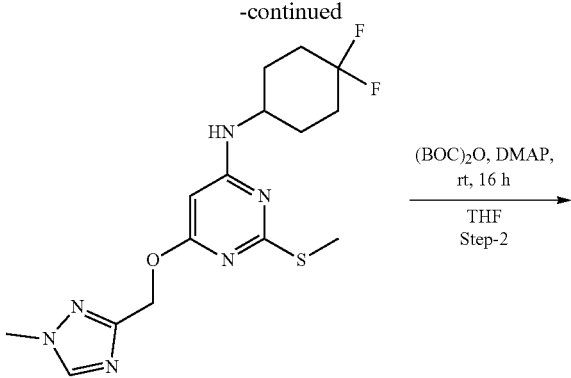
(BOC)₂O, DMAP,
rt, 16 h
———————→
THF
Step-2
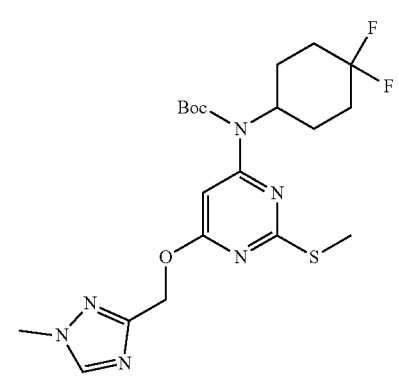
m-CPBA,
0° C.-rt, 1 h
———————→
DCM
Step-3
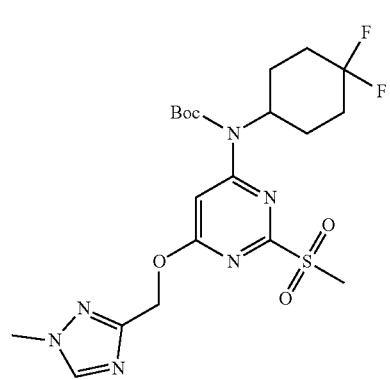
NaCN, DABCO
rt, 30 min
———————→
DMSO
Step-4
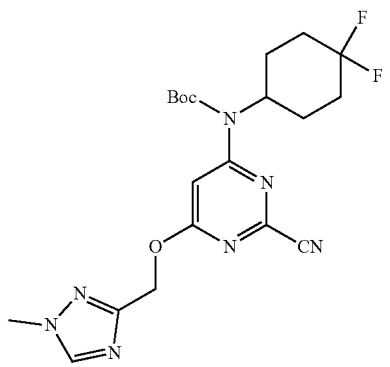
TEA, (NH₄)₂S,
0° C.-rt, 30 min
———————→
DMF
Step-5
990
-continued
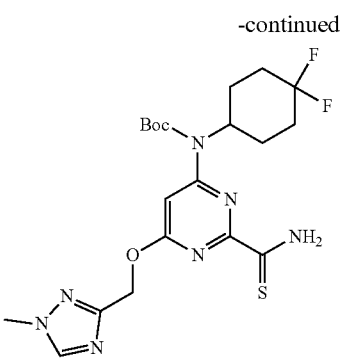
rt, 7 h
———————→
THF
Step-6
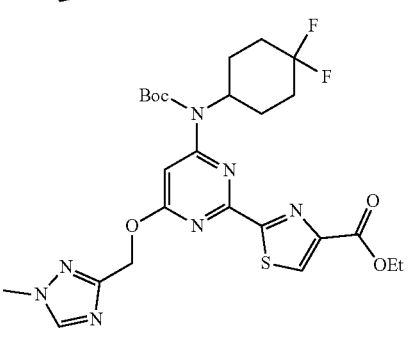
LAH, -78° C.,
30 min
———————→
THF
Step-7
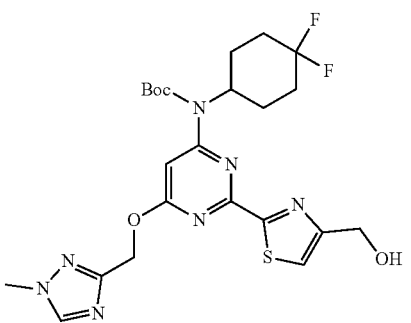
DAST,
0° C.-rt, 15 min
———————→
DCM
Step-8
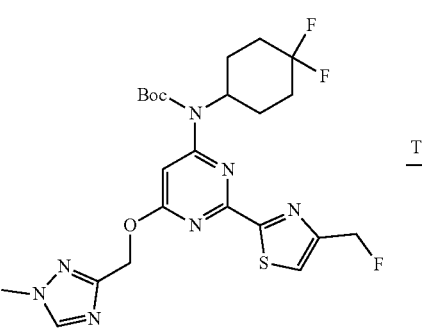
TFA, 0° C.-rt, 24 h
———————→
DCM
Step-9
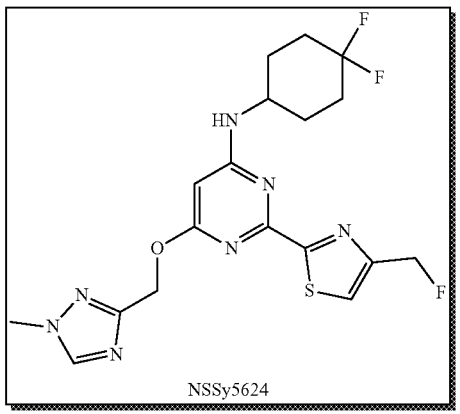
NSSy5624

Step 1: The procedure is similar to Step 1[B] in Example-838. 2.5 g of 6-chloro-N-(4,4-difluorocyclohexyl)-2-(methylthio)pyrimidin-4-amine gave N-(4,4-difluorocyclohexyl)-6-((1-methyl-1H-1,2,4-triazol-3-yl) methoxy)-2-(methylthio)pyrimidin-4-amine as a white solid (1.0 g, 32%). MS (M+1)+=371.6.

Step 2: The procedure is similar to Step 2[IN11218-026-P1] in Example-613. 3.0 g of N-(4,4-difluorocyclohexyl)-6-((1-methyl-1H-1,2,4-triazol-3-yl)methoxy)-2-(methylthio)pyrimidin-4-amine gave tert-butyl (4,4-difluorocyclohexyl)(6-((1-methyl-1H-1,2,4-triazol-3-yl)methoxy)-2-(methylthio)pyrimidin-4-yl) carbamate as a yellow solid (3.7 g, 97%). MS (M+1)+=471.2.

Step 3: The procedure is similar to Step 3[NSSy7062] in Example-623. 3.6 g of tert-butyl (4,4-difluorocyclohexyl)(6-((1-methyl-1H-1,2,4-triazol-3-yl)methoxy)-2-(methylthio)pyrimidin-4-yl)carbamate gave tert-butyl (4,4-difluorocyclohexyl) (6-((1-methyl-1H-1,2,4-triazol-3-yl)methoxy)-2-(methylsulfonyl)pyrimidin-4-yl)carbamate as a yellow solid (3.7 g, 96%). MS (M+1)+=503.8.

Step 4: The procedure is similar to Step 1[NSSY6710] in Example-854. 3.7 g of tert-butyl (4,4-difluorocyclohexyl)(6-((1-methyl-1H-1,2,4-triazol-3-yl)methoxy)-2-(methylsulfonyl)pyrimidin-4-yl)carbamate gave tert-butyl (2-cyano-6-((1-methyl-1H-1,2,4-triazol-3-yl)methoxy)pyrimidin-4-yl)(4,4-difluorocyclohexyl)carbamate as a yellow solid (3.1 g, 89%). MS (M+1)+=450.7.

Step 5: The procedure is similar to Step 5[NSSy5779] in Example-642. 3.1 g of tert-butyl (2-cyano-6-((1-methyl-1H-1,2,4-triazol-3-yl)methoxy)pyrimidin-4-yl)(4,4-difluorocyclohexyl)carbamate gave tert-butyl (2-carbamothioyl-6-((1-methyl-1H-1,2,4-triazol-3-yl)methoxy)pyrimidin-4-yl)(4,4-difluorocyclohexyl) carbamate as a yellow solid (3.2 g, 93%). MS (M+1)+=484.2.

Step 6: The procedure is similar to Step 6[NSSY5779] in Example-642. 2.0 g of tert-butyl (2-carbamothioyl-6-((1-methyl-1H-1,2,4-triazol-3-yl) methoxy)pyrimidin-4-yl)(4,4-difluorocyclohexyl)carbamate gave ethyl 2-(4-((tert-butoxycarbonyl)(4,4-difluorocyclohexyl)amino)-6-((1-methyl-1H-1,2,4-triazol-3-yl)methoxy)pyrimidin-2-yl)thiazole-4-carboxylate as an off-white solid (1.6 g, 67%). MS (M+1)+= 579.3.

Step 7: The procedure is similar to Step 4[NSSy6711] in Example-854. 1.6 g of ethyl 2-(4-((tert-butoxycarbonyl)(4,4-difluorocyclohexyl)amino)-6-((1-methyl-1H-1,2,4-triazol-3-yl)methoxy)pyrimidin-2-yl)thiazole-4-carboxylate gave tert-butyl (4,4-difluorocyclohexyl)(2-(4-(hydroxymethyl)thiazol-2-yl)-6-((l-methyl-1H-1,2,4-triazol-3-yl)methoxy)pyrimidin-4-yl)carbamate as a pale yellow solid (1.1 g, 74%). MS (M+1)+=538.5.

Step 8: The procedure is similar to Step 3[NSSy6067] in Example-628. 0.6 g of tert-butyl (4,4-difluorocyclohexyl)(2-(4-(hydroxymethyl)thiazol-2-yl)-6-((l-methyl-1H-1,2,4-triazol-3-yl)methoxy)pyrimidin-4-yl)carbamate gave tert-butyl (4,4-difluorocyclohexyl)(2-(4-(fluoromethyl)thiazol-2-yl)-6-((l-methyl-1H-1,2,4-triazol-3-yl)methoxy)pyrimidin-4-yl)carbamate as an off-white solid (0.26 g, 43%). MS (M+1)+=540.7.

Step 9[NSSy5624]: The procedure is similar to Step 5[NSSy6067] in Example-628. 0.26 g of tert-butyl (4,4-difluorocyclohexyl)(2-(4-(fluoromethyl)thiazol-2-yl)-6-((l-methyl-1H-1,2,4-triazol-3-yl)methoxy)pyrimidin-4-yl)carbamate gave N-(4,4-difluorocyclohexyl)-2-(4-(fluoromethyl)thiazol-2-yl)-6-((1-methyl-1H-1,2,4-triazol-3-yl)methoxy)pyrimidin-4-amine as a white solid (0.19 g, 92%). MS (M+1)+=440.2; 1H-NMR (400 MHz, DMSO-d6): δ 8.46 (s, 1H), 8.00 (s, 1H), 7.58 (s, 1H), 5.91 (s, 1H), 5.58 (s, 1H), 5.46 (s, 1H), 5.37 (s, 2H), 4.01 (s, 1H), 3.86 (s, 3H), 2.08-1.95 (m, 6H), 1.59-1.53 (m, 2H).

Example-731

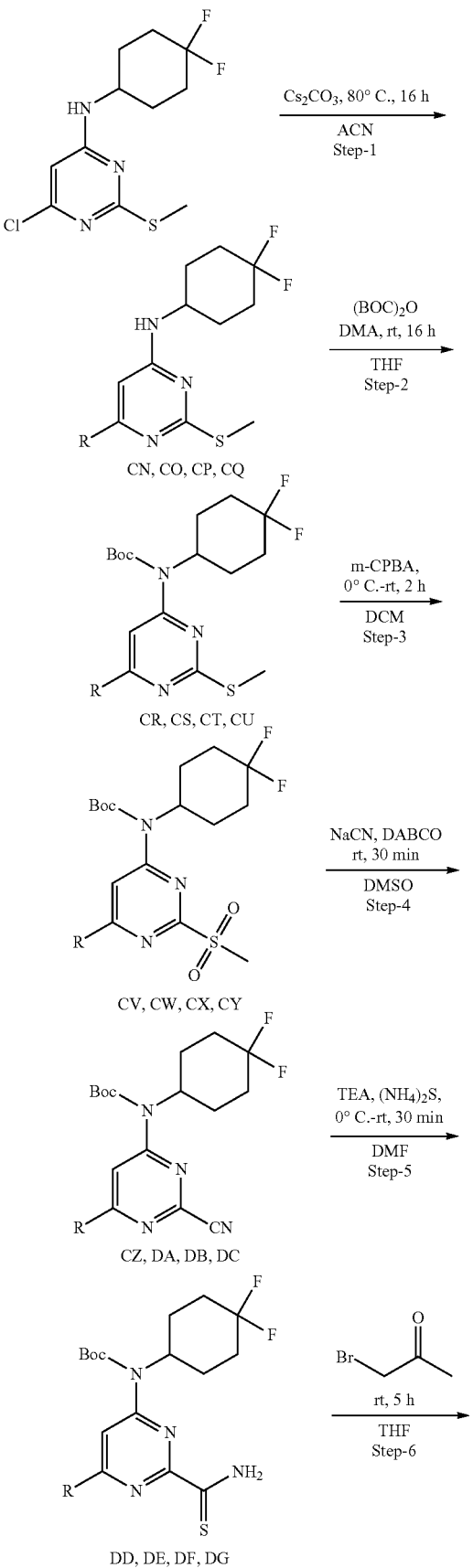

993
-continued
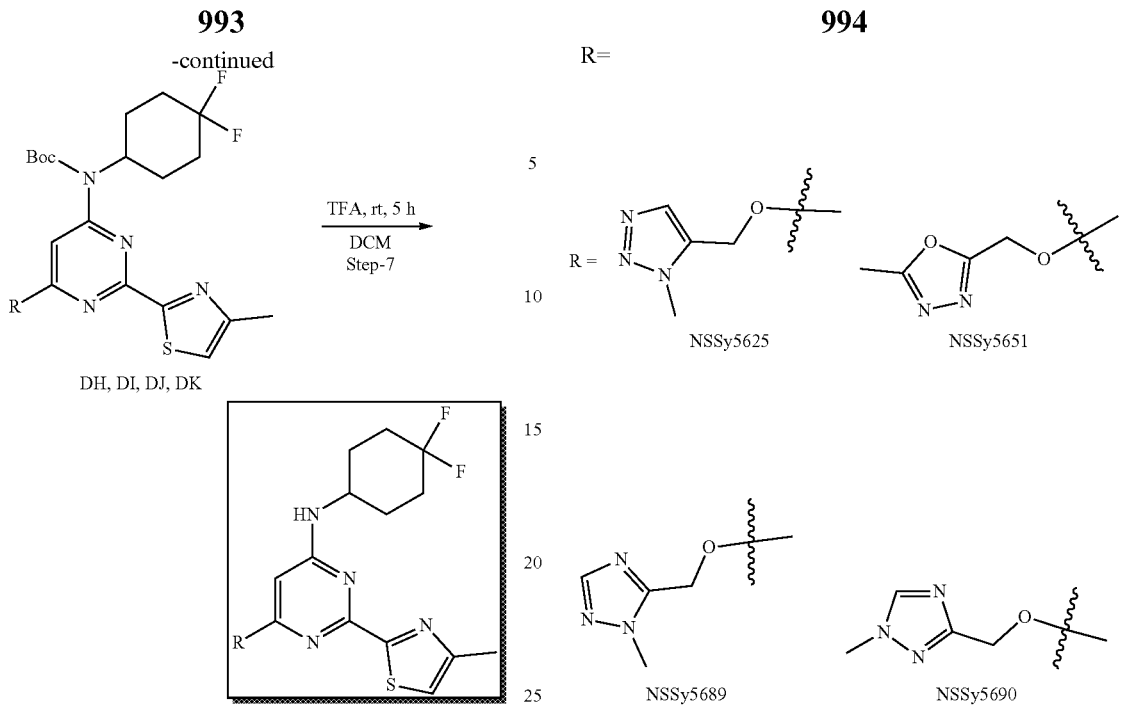
DH, DI, DJ, DK
994
R=
5
NSSy5625    NSSy5651
NSSy5689    NSSy5690
TABLE 65
Step 1: The procedure is similar to Step 1[B] in Example-838.
| Compound No | R | Condition | Yield (%) | MS (M + 1)+ |
|---|---|---|---|---|
| CN | (1-methyl-1H-1,2,3-triazol-5-yl)methoxy | Cs₂CO₃, ACN, 80° C., 16 h | 38 | 369.5 |
| CO | (5-methyl-1,3,4-oxadiazol-2-yl)methoxy | Cs₂CO₃, ACN, 80° C., 4 h | 74 | 372.0 |
| CP | (1-methyl-1H-1,2,4-triazol-5-yl)methoxy | K⁺(CH₃)₃CO⁻, THF, 65° C., 16 h | 32 | 371.6 |
| CQ | (1-methyl-1H-1,2,4-triazol-3-yl)methoxy | K⁺(CH₃)₃CO⁻, THF, 65° C., 16 h | 72 | 371.6 |

TABLE 66

Step 2: The procedure is similar to Step 2[IN11218-026-P1] in Example-613.

| Compound No | R | Condition | Yield (%) | MS (M + 1)+ |
|---|---|---|---|---|
| CR | 1-methyl-1H-1,2,3-triazol-5-yl-methoxy | (Boc)₂O, DMAP, THF, rt, 16 h | 95 | 469.4 |
| CS | 5-methyl-1,3,4-oxadiazol-2-yl-methoxy | (Boc)₂O, DMAP, THF, rt, 16 h | 84 | 472.0 |
| CT | 1-methyl-1H-1,2,4-triazol-5-yl-methoxy | (Boc)₂O, DMAP, THF, rt, 16 h | 91 | 471.2 |
| CU | 1-methyl-1H-1,2,4-triazol-3-yl-methoxy | (Boc)₂O, DMAP, THF, rt, 16 h | 97 | 471.2 |

TABLE 67

Step 3: The procedure is similar to Step 3[NSSy7062] in Example-623.

| Compound No | R | Condition | Yield (%) | MS (M + 1)+ |
|---|---|---|---|---|
| CV | 1-methyl-1H-1,2,3-triazol-5-yl-methoxy | m-CPBA, DCM, 0° C.-rt, 2 h | 78 | 503.4 |
| CW | 5-methyl-1,3,4-oxadiazol-2-yl-methoxy | m-CPBA, DCM, 0° C.-rt, 2 h | 94 | 504 |
| CX | 1-methyl-1H-1,2,4-triazol-5-yl-methoxy | m-CPBA, DCM, 0° C.-rt, 2 h | 68 | 503.8 |
| CY | 1-methyl-1H-1,2,4-triazol-3-yl-methoxy | m-CPBA, DCM, 0° C.-rt, 2 h | 97 | 503.8 |

TABLE 68

Step 4: The procedure is similar to Step 1[NSSy6710] in Example-854.

| Compound No | R | Condition | Yield (%) | MS (M + 1)+ |
|---|---|---|---|---|
| CZ | (1-methyl-1H-1,2,3-triazol-5-yl)methoxy | NaCN, DABCO, DMSO, 0° C.-rt, 15 min | 89 | 449.9 |
| DA | (5-methyl-1,3,4-oxadiazol-2-yl)methoxy | NaCN, DABCO, DMSO, 0° C.-rt, 15 min | 85 | 451.0 |
| DB | (1-methyl-1H-1,2,4-triazol-5-yl)methoxy | NaCN, DABCO, DMSO, 0° C.-rt, 15 min | 87 | 450.7 |
| DC | (1-methyl-1H-1,2,4-triazol-3-yl)methoxy | NaCN, DABCO, DMSO, 0° C.-rt, 15 min | 94 | 450.7 |

TABLE 69

Step 5: The procedure is similar to Step 5[NSSy5779] in Example-642.

| Compound No | R | Condition | Yield (%) | MS (M + 1)+ |
|---|---|---|---|---|
| DD | (1-methyl-1H-1,2,3-triazol-5-yl)methoxy | (NH4)2S, TEA, DMF, 0° C.-rt, 15 min | 91 | 483.6 |
| DE | (5-methyl-1,3,4-oxadiazol-2-yl)methoxy | (NH4)2S, TEA, DMF, 0° C.-rt, 15 min | 80 | 485.0 |
| DF | (1-methyl-1H-1,2,4-triazol-5-yl)methoxy | (NH4)2S, TEA, DMF, 0° C.-rt, 15 min | 68 | 484.2 |
| DG | (1-methyl-1H-1,2,4-triazol-3-yl)methoxy | (NH4)2S, TEA, DMF, 0° C.-rt, 15 min | 93 | 484.2 |

TABLE 70

Step 6: The procedure is similar to Step 6[NSSy5779] in Example-642.

| Compound No | R | Condition | Yield (%) | MS (M + 1)+ |
|---|---|---|---|---|
| DH | (1-methyl-1H-1,2,3-triazol-5-yl)methoxy | Bromoacetone, THF, rt, 5 h | 29 | 522.3 |
| DI | (5-methyl-1,3,4-oxadiazol-2-yl)methoxy | Bromoacetone, THF, rt, 5 h | 35 | 523.0 |
| DJ | (1-methyl-1H-1,2,4-triazol-5-yl)methoxy | Bromoacetone, THF, rt, 5 h | 16 | 522.3 |
| DK | (1-methyl-1H-1,2,4-triazol-3-yl)methoxy | Bromoacetone, THF, rt, 5 h | 40 | 522.9 |

TABLE 71

Step 7: The procedure is similar to Step 5[NSSy6067] in Example-628.

| Compound No | R | Condition | Yield (%) | MS (M + 1)+ |
|---|---|---|---|---|
| NSSy5625 | (1-methyl-1H-1,2,3-triazol-5-yl)methoxy | TFA, DCM, rt, 5 h | 85 | 422.2 |
| NSSy5651 | (5-methyl-1,3,4-oxadiazol-2-yl)methoxy | TFA, DCM, rt, 16 h | 40 | 423.0 |
| NSSy5689 | (1-methyl-1H-1,2,4-triazol-5-yl)methoxy | TFA, DCM, rt, 16 h | 14 | 422.2 |
| NSSy5690 | (1-methyl-1H-1,2,4-triazol-3-yl)methoxy | TFA, DCM, rt, 16 h | 60 | 422.8 |

Step 7[NSSy5625]: 1H-NMR (400 MHz, DMSO-d6): δ 7.86 (s, 1H), 7.54 (s, 1H), 7.46 (s, 1H), 5.88 (s, 1H), 5.53 (s, 1H), 4.14 (s, 3H), 2.46 (s, 3H), 2.08-1.92 (m, 6H), 1.58-1.55 (m, 2H).
Step 7[NSSy5651]: 1H-NMR (400 MHz, DMSO-d6): δ 7.66 (s, 1H), 7.44 (d, J=0.80 Hz, 1H), 5.91 (s, 1H), 5.59 (s, 2H), 4.13-3.92 (m, 1H), 2.43 (s, 3H), 2.32 (s, 3H), 2.07-1.94 (m, 6H), 1.60-1.55 (m, 2H).
Step 7[NSSy5689]: 1H-NMR (400 MHz, DMSO-d6): δ 7.89 (s, 1H), 7.55 (s, 1H), 7.44 (s, 1H), 5.51 (s, 2H), 4.03 (s, 3H), 2.33 (s, 3H), 2.05-1.92 (m, 6H), 1.58-1.55 (m, 2H).
Step 7[NSSy5690]: 1H-NMR (400 MHz, DMSO-d6): δ 8.64 (s, 1H), 7.50 (bs, 1H), 7.43 (s, 1H), 5.87 (bs, 1H), 5.36 (s, 2H), 4.01 (bs, 1H), 3.86 (s, 3H), 2.08 (s, 3H), 2.22-1.80 (m, 6H), 1.58-1.53 (m, 2H).
Example-732
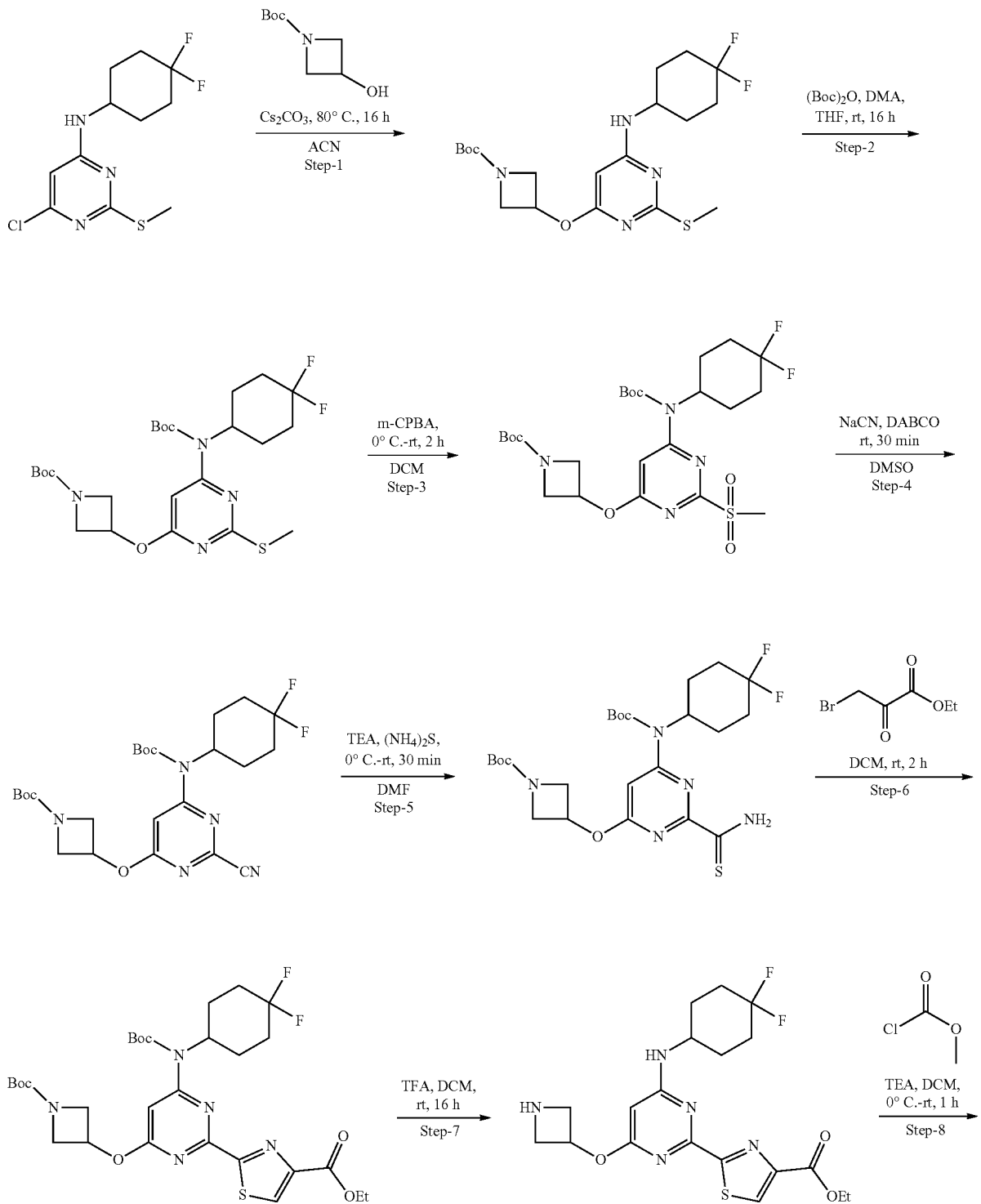

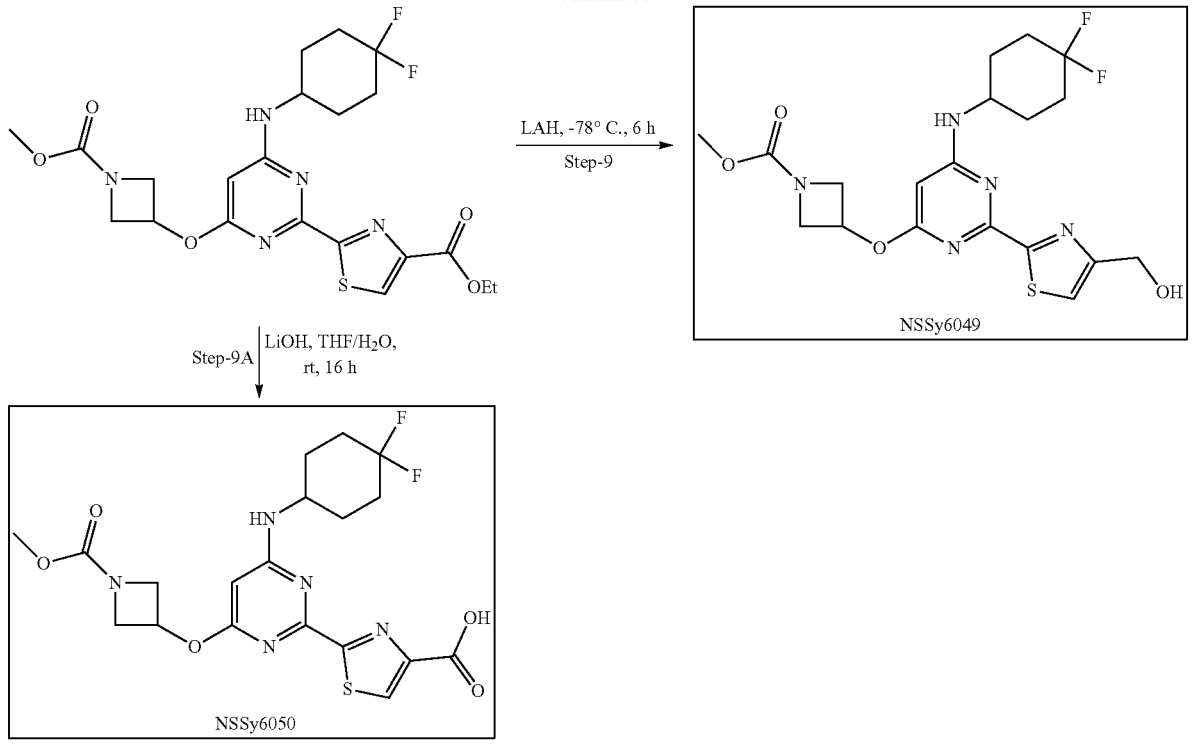

Step 1: The procedure is similar to Step 1[B] in Example-838. 500.0 g of 6-chloro-N-(4,4-difluorocyclohexyl)-2-(methylthio)pyrimidin-4-amine gave tert-butyl 3-((6-((4,4-difluorocyclohexyl)amino)-2-(methylthio)pyrimidin-4-yl)oxy) azetidine-1-carboxylate as a white solid (510.0 g, 69%). MS (M+1)+=431.2.

Step 2: The procedure is similar to Step 2[IN11218-026-P1] in Example-613. 500.0 g of tert-butyl 3-((6-((4,4-difluorocyclohexyl)amino)-2-(methylthio)pyrimidin-4-yl)oxy) azetidine-1-carboxylate gave tert-butyl 3-((6-((tert-butoxycarbonyl)(4,4-difluorocyclohexyl)amino)-2-(methylthio)pyrimidin-4-yl)oxy)azetidine-1-carboxylate as a white solid (518.0 g, 84%). MS (M+1)+=531.2.

Step 3: The procedure is similar to Step 3[NSSy7062] in Example-623. 510.0 g of tert-butyl 3-((6-((tert-butoxycarbonyl)(4,4-difluorocyclohexyl)amino)-2-(methylthio)pyrimidin-4-yl)oxy)azetidine-1-carboxylate gave tert-butyl 3-((6-((tert-butoxycarbonyl)(4,4-difluorocyclohexyl)amino)-2-(methylsulfonyl)pyrimidin-4-yl)oxy)azetidine-1-carboxylate as an off-white solid (525.0 g, 97%). MS (M+1)+=563.6.

Step 4: The procedure is similar to Step 1[NSSy6710] in Example-854. 515.0 g of tert-butyl 3-((6-((tert-butoxycarbonyl)(4,4-difluorocyclohexyl)amino)-2-(methylsulfonyl)pyrimidin-4-yl)oxy)azetidine-1-carboxylate gave tert-butyl 3-((6-((tert-butoxycarbonyl)(4,4-difluorocyclohexyl)amino)-2-cyanopyrimidin-4-yl)oxy)azetidine-1-carboxylate as an off-white solid (460.0 g, 98%). MS (M+1)+=510.2.

Step 5: The procedure is similar to Step 5[NSSy5779] in Example-642. 280.0 g of tert-butyl 3-((6-((tert-butoxycarbonyl)(4,4-difluorocyclohexyl)amino)-2-cyanopyrimidin-4-yl)oxy)azetidine-1-carboxylate gave tert-butyl 3-((6-((tert-butoxycarbonyl)(4,4-difluorocyclohexyl)amino)-2-carbamothioylpyrimidin-4-yl)oxy)azetidine-1-carboxylate as a pale yellow solid (280.0 g, 93%). MS (M+1)+=544.2.

Step 6: The procedure is similar to Step 6[NSSy5779] in Example-642. 10.0 g of tert-butyl 3-((6-((tert-butoxycarbonyl)(4,4-difluorocyclohexyl)amino)-2-carbamothioyl pyrimidin-4-yl)oxy)azetidine-1-carboxylate gave ethyl 2-(4-((tert-butoxycarbonyl)(4,4-difluorocyclohexyl)amino)-6-((1-(tert-butoxy carbonyl)azetidin-3-yl)oxy)pyrimidin-2-yl) thiazole-4-carboxylate as an off-white gummy solid (4.0 g, 36%). MS (M+1)+=639.0.

Step 7: The procedure is similar to Step 2[NSSy6924] in Example-857. 7.3 g of ethyl 2-(4-((tert-butoxycarbonyl)(4,4-difluorocyclohexyl)amino)-6-((1-(tert-butoxycarbonyl)azetidin-3-yl)oxy)pyrimidin-2-yl)thiazole-4-carboxylate gave ethyl 2-(4-(azetidin-3-yloxy)-6-((4,4-difluorocyclohexyl)amino)pyrimidin-2-yl)thiazole-4-carboxylate as an off-white gummy solid (4.8 g, 96%). MS (M+1)+=440.1.

Step 8: The procedure is similar to Step 2[NSSy6924] in Example-857. 4.8 g of ethyl 2-(4-(azetidin-3-yloxy)-6-((4,4-difluorocyclohexyl)amino)pyrimidin-2-yl)thiazole-4-carboxylate gave ethyl 2-(4-((4,4-difluorocyclohexyl)amino)-6-((1-(methoxycarbonyl)azetidin-3-yl)oxy)pyrimidin-2-yl) thiazole-4-carboxylate as an off-white solid (2.6 g, 46%). MS (M+1)+=498.0.

Step 9[NSSy6049]: The procedure is similar to Step 4[NSSy6711] in Example-854. 1.6 g of ethyl 2-(4-((4,4-difluorocyclohexyl)amino)-6-((1-(methoxycarbonyl)azetidin-3-yl)oxy)pyrimidin-2-yl)thiazole-4-carboxylate gave methyl 3-((6-((4,4-difluorocyclohexyl)amino)-2-(4-(hydroxymethyl)thiazol-2-yl)pyrimidin-4-yl)oxy)azetidine-1-carboxylate as an off-white solid (0.94 g, 64%). MS (M+1)+=456.0; 1H-NMR (400 MHz, DMSO-d6): δ 7.58 (s, 2H), 5.87 (s, 1H), 5.41-5.36 (m, 2H), 4.63 (d, J=5.20 Hz, 2H), 4.35 (s, 2H), 4.10 (s, 1H), 3.94 (s, 2H), 3.58 (s, 3H), 2.06-1.94 (m, 6H), 1.59-1.56 (m, 2H).

Step 9A [NSSy6050]: To an ice-cooled solution of ethyl 2-(4-((4,4-difluorocyclohexyl)amino)-6-((1-(methoxycarbonyl) azetidin-3-yl)oxy) pyrimidin-2-yl) thiazole-4-carboxylate (1.7 g, 3.41 mmol) in a mixture of solvent THF: Water (21:9 mL) was added Lithium hydroxide (0.16 g, 6.83 mmol) and stirred at rt for 6 h. The reaction mixture was diluted with ethyl acetate, the organic layer was separated and concentrated to afford crude product and which was dissolved in water and acidified with 1.5 N HCl, the obtained solid was filtered off and washed with hexane (100 mL), dried under high vacuum to afford 2-(4-((4,4-difluorocyclohexyl)amino)-6-((1-(methoxycarbonyl)azetidin-3-yl)oxy)pyrimidin-2-yl)thiazole-4-carboxylic acid as an off-white solid (1.2 g, 75%). MS (M+1)+=470.0; 1H-NMR (400 MHz, DMSO-d6): δ 13.08 (bs, 1H), 8.50 (bs, 1H), 7.65 (s, 1H), 5.89 (s, 1H), 5.37 (m, 1H), 4.35 (m, 2H), 3.94 (m, 2H), 3.57 (s, 3H), 2.08-1.94 (m, 6H), 1.58-1.56 (m, 2H).

Example-733

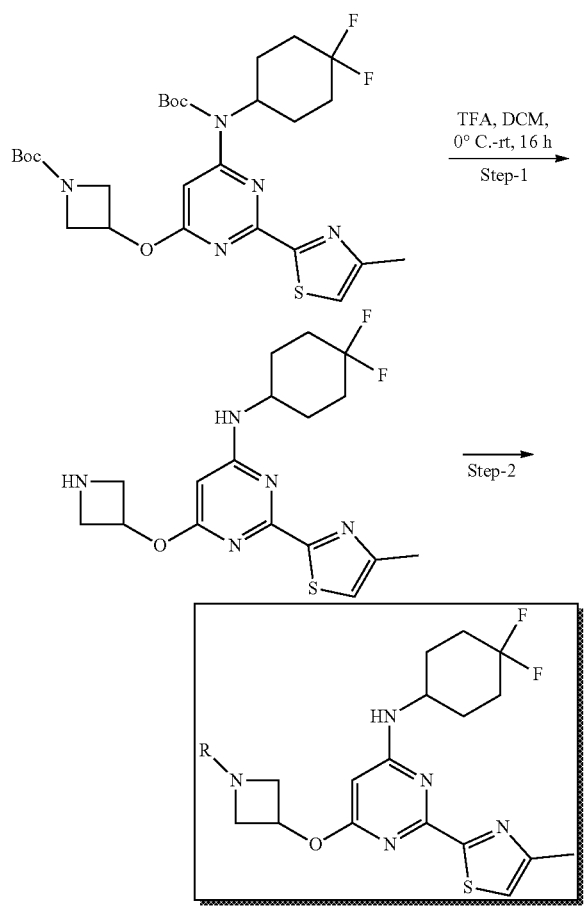

R=

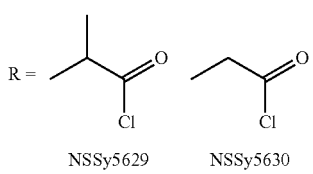

Step 1: The procedure is similar to Step 2[NSSy6924] in Example-857. 0.5 g of tert-butyl 3-((6-(((tert-butoxycarbonyl)(4,4-difluorocyclohexyl)amino)-2-(4-methyl thiazol-2-yl)pyrimidin-4-yl)oxy)azetidine-1-carboxylate gave 6-(azetidin-3-yloxy)-N-(4,4-difluorocyclohexyl)-2-(4-methylthiazol-2-yl)pyrimidin-4-amine as a pale yellow solid (0.21 g, 65%). MS (M+1)+=382.0.

TABLE 72

Step 2: The procedure is similar to Step 1[A] in Example-838

| Compound No | R | Condition | Yield (%) |
|---|---|---|---|
| NSSy5629 | | TEA, DCM, 0° C.-rt, 15 min | 45 |
| NSSy5630 | | TEA, DCM, 0° C.-rt, 15 min | 32 |

Step 2[NSSy5629]: MS (M+1)+=452.0; 1H-NMR (400 MHz, DMSO-d6): δ 7.57 (s, 1H), 7.44 (d, J=0.88 Hz, 1H), 5.87 (s, 1H), 5.38 (s, 1H), 4.57 (t, J=6.76 Hz, 1H), 4.33-4.24 (m, 1H), 4.19-4.15 (m, 1H), 3.85-3.81 (m, 1H), 2.44 (s, 3H), 2.09-1.93 (m, 6H), 1.61-1.56 (m, 2H), 0.98 (t, J=6.80 Hz, 6H).

Step 2[NSSy5630]: MS (M+1)+=438.2; 1H-NMR (400 MHz, DMSO-d6): δ 7.56 (s, 1H), 7.43 (s, 1H), 5.89 (s, 1H), 5.35 (s, 1H), 4.53 (s, 1H), 4.28-4.24 (m, 1H), 4.12 (s, 1H), 3.83 (s, 1H), 2.43 (s, 3H), 2.11-1.92 (m, 8H), 1.58-1.55 (m, 2H), 0.98-0.94 (m, 3H).

Example-734

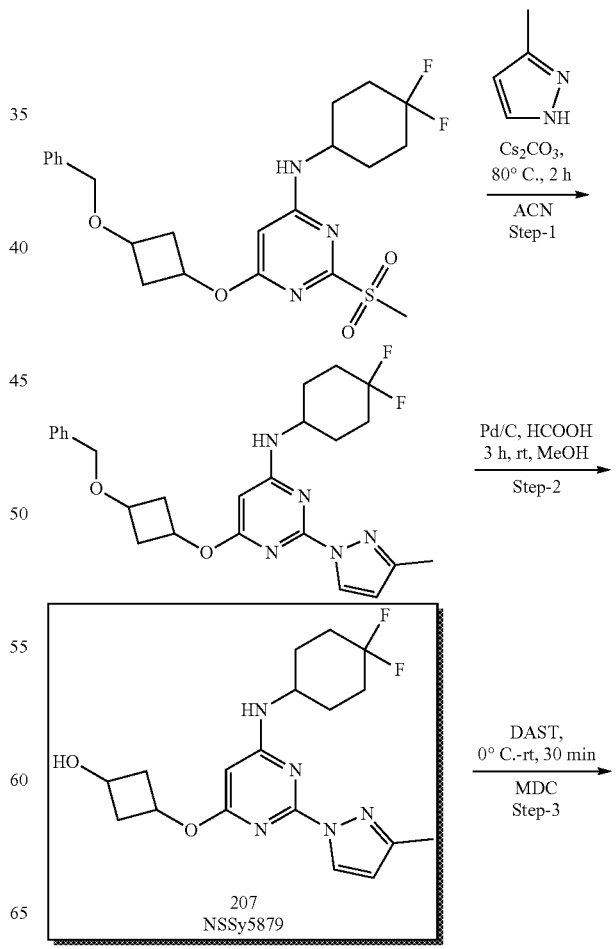

-continued

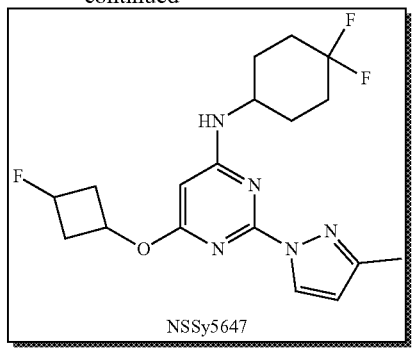

Step 1: The Procedure is similar to step 1[B] in Example-838. 2.5 g of 6-(3-(benzyloxy)cyclobutoxy)-N-(4,4-difluorocyclohexyl)-2-(methylsulfonyl)pyrimidin-4-amine gave 6-(3-(benzyloxy)cyclobutoxy)-N-(4,4-difluorocyclohexyl)-2-(3-methyl-1H-pyrazol-1-yl)pyrimidin-4-amine as an off-white solid (2.3 g, 92%). MS (M+1)+=470.2.

Step 2[NSSy5879]: The Procedure is similar to Step 2[NSSy6464] in Example-869. 1 g of 6-(3-(benzyloxy)cyclobutoxy)-N-(4,4-difluorocyclohexyl)-2-(3-methyl-1H-pyrazol-1-yl)pyrimidin-4-amine gave 3-((6-((4,4-difluorocyclohexyl)amino)-2-(3-methyl-1H-pyrazol-1-yl)pyrimidin-4-yl)oxy)cyclobutan-1-ol as an off-white solid (0.6 g, 80%). MS (M+1)+=380.2; 1H-NMR (400 MHz, DMSO-d6): δ 8.42 (s, 1H), 7.49 (s, 1H), 6.31 (d, J=2.40 Hz, 1H), 5.64 (s, 1H), 5.19 (s, 1H), 4.67 (s, 1H), 3.88-3.84 (m, 1H), 2.80-2.78 (m, 2H), 2.25 (s, 3H), 2.05-1.91 (m, 9H), 1.56-1.53 (m, 2H).

Step 3[NSSy5647]: The Procedure is similar to Step 3[NSSy6917] in Example-21. 0.2 g of 3-((6-((4,4-difluorocyclohexyl)amino)-2-(3-methyl-1H-pyrazol-1-yl)pyrimidin-4-yl)oxy)cyclobutan-1-ol gave N-(4,4-difluorocyclohexyl)-6-(3-fluorocyclobutoxy)-2-(3-methyl-1H-pyrazol-1-yl)pyrimidin-4-amine as an off-white solid (0.1 g, 50%). MS (M+1)+=382.2; $^1$H-NMR (400 MHz, DMSO-d$_6$): δ 8.36 (s, 1H), 6.25 (s, 1H), 5.50-5.49 (m, 2H), 5.40-5.26 (m, 2H), 3.55 (s, 1H), 2.83-2.77 (m, 2H), 2.64-2.59 (m, 2H), 2.41 (s, 3H), 2.15-1.88 (m, 6H), 1.72-1.62 (m, 2H).

Example-735

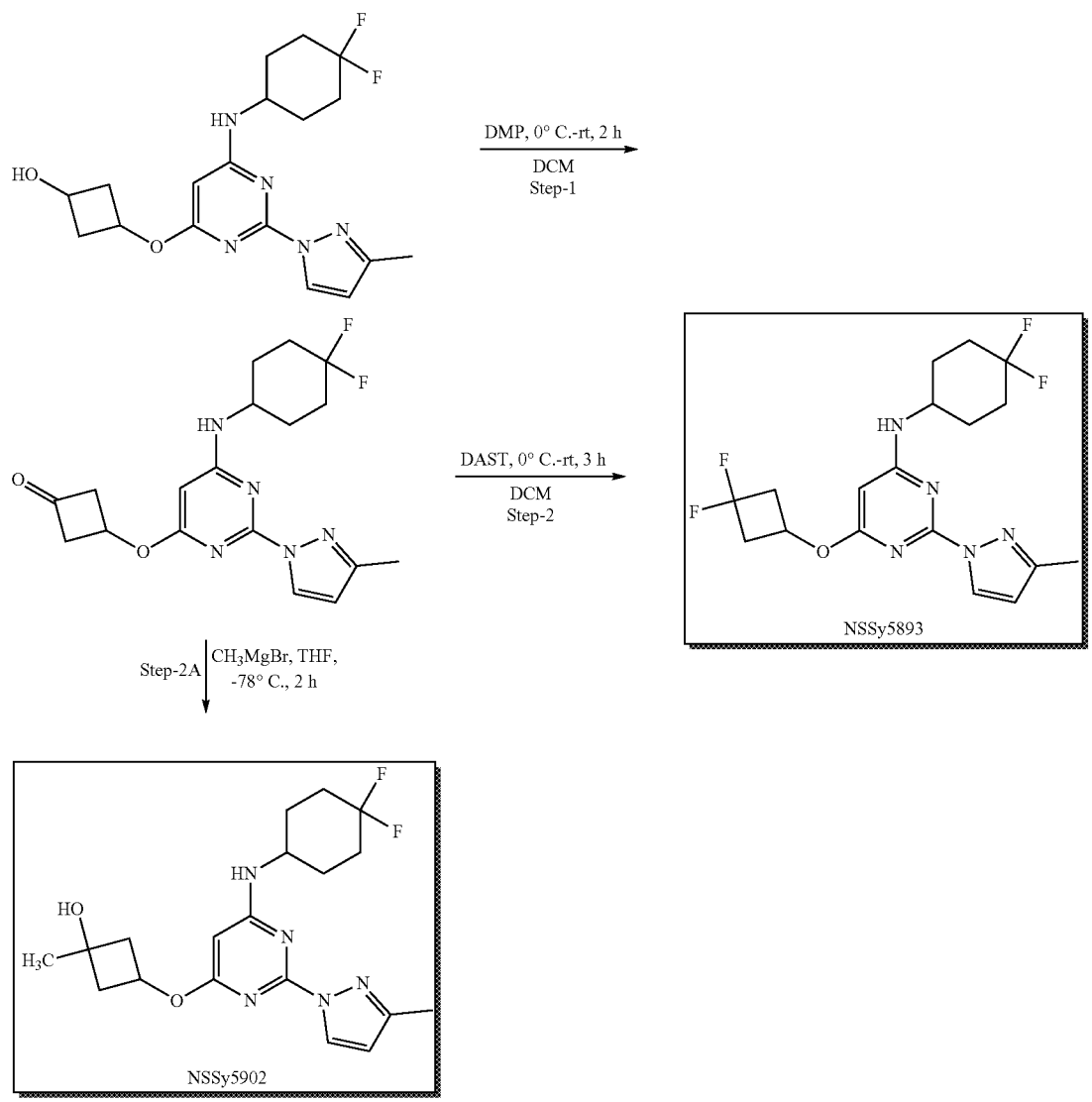

1009

Step 1: The Procedure is similar to Step 1[NSSy6930] in Example-867. 1.2 g of 3-((6-((4,4-difluorocyclohexyl) amino)-2-(3-methyl-1H-pyrazol-1-yl)pyrimidin-4-yl)oxy) cyclobutan-1-ol gave 3-((6-((4,4-difluorocyclohexyl) amino)-2-(3-methyl-1H-pyrazol-1-yl)pyrimidin-4-yl)oxy) cyclobutan-1-one as a white solid (1 g, 52%). MS (M+1)+=378.2.

Step 2[NSSy5893]: The Procedure is similar to Step 3[NSSy6917] in Example-21. 0.12 g of 3-((6-((4,4-difluorocyclohexyl)amino)-2-(3-methyl-1H-pyrazol-1-yl)pyrimidin-4-yl)oxy)cyclobutan-1-one gave 6-(3,3-difluorocyclobutoxy)-N-(4,4-difluorocyclohexyl)-2-(3-methyl-1H-pyrazol-1-yl)pyrimidin-4-amine as a pale yellow solid (0.056 g, 45%). MS (M+1)+=400.1; 1H-NMR (400 MHz, DMSO-d6): δ 8.45 (s, 1H), 7.57-7.54 (m, 1H), 6.32 (d, J=2.44 Hz, 1H), 5.70 (s, 1H), 5.14 (s, 1H), 4.16-3.90 (m, 1H), 3.34-3.18 (m, 2H), 2.77-2.68 (m, 2H), 2.33 (s, 3H), 2.26-1.94 (m, 6H), 1.60-1.54 (m, 2H).

Step 2A [NSSy5902]: The Procedure is similar to Step 4[NSSy6464] in Example-869. 1.0 g of 3-((6-((4,4-difluorocyclohexyl)amino)-2-(3-methyl-1H-pyrazol-1-yl)pyrimidin-4-yl)oxy)cyclobutan-1-one gave 3-((6-((4,4-difluorocyclohexyl)amino)-2-(3-methyl-1H-pyrazol-1-yl)pyrimidin-4-yl)oxy)-1-methylcyclobutan-1-ol as an off-white solid (0.095 g, 10%). MS (M+1)$^+$=394.2; $^1$H-NMR (400 MHz, DMSO-d$_6$): δ 8.41 (s, 1H), 7.50 (s, 1H), 6.31 (d, J=1.84 Hz, 1H), 5.64 (s, 1H), 5.16 (s, 1H), 4.72 (m, 1H), 4.10 (m, 1H), 2.51-2.48 (m, 2H), 2.25 (s, 3H), 2.15-1.91 (m, 8H), 1.56-1.53 (m, 2H), 1.28 (s, 3H).

Example-736

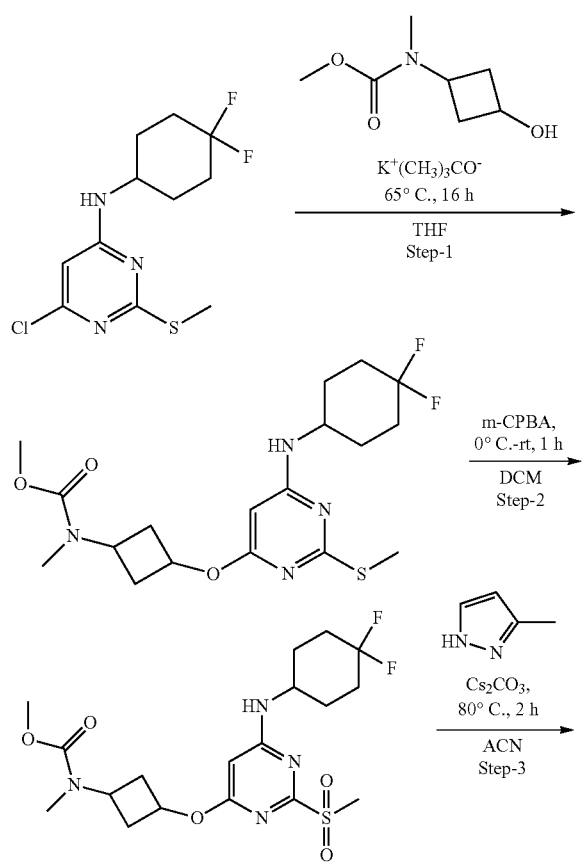

-continued

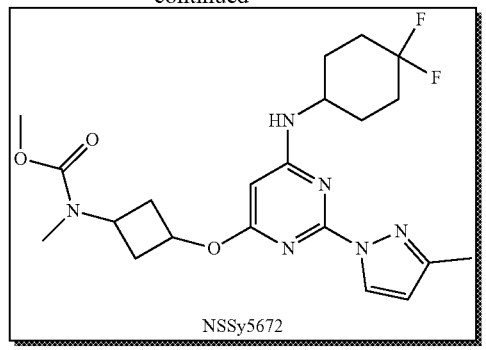

Step 1: The Procedure is similar to Step 1[B] in Example-838. 0.5 g of 6-chloro-N-(4,4-difluorocyclohexyl)-2-(methylthio)pyrimidin-4-amine gave methyl (3-((6-((4,4-difluorocyclohexyl)amino)-2-(methylthio)pyrimidin-4-yl)oxy) cyclobutyl) (methyl) carbamate as a brownish gum (0.4 g, 57%). MS (M+1)+=417.1.

Step 2: The Procedure is similar to Step 3[NSSy7062] in Example-623. 0.4 g of (3-((6-((4,4-difluorocyclohexyl) amino)-2-(methylthio)pyrimidin-4-yl)oxy)cyclobutyl) (methyl)carbamate gave methyl (3-((6-((4,4-difluorocyclohexyl)amino)-2-(methylsulfonyl)pyrimidin-4-yl)oxy)cyclobutyl) (methyl)carbamate as a white solid (0.41 g, 95%). MS (M+1)+=449.2.

Step 3[NSSy5672]: The Procedure is similar to Step 1[B] in Example-838. 0.1 g of methyl (3-((6-((4,4-difluorocyclohexyl)amino)-2-(methylsulfonyl)pyrimidin-4-yl)oxy)cyclobutyl) (methyl)carbamate gave methyl (3-((6-((4,4-difluorocyclohexyl)amino)-2-(3-methyl-1H-pyrazol-1-yl) pyrimidin-4-yl)oxy)cyclobutyl)(methyl)carbamate as an off-white solid (0.025 g, 25%). MS (M+1)+=451.0; 1H-NMR (400 MHz, DMSO-d6): δ 8.44 (s, 1H), 7.59-7.53 (m, 1H), 6.31 (s, 1H), 5.66 (s, 1H), 4.84 (s, 1H), 4.24-4.09 (m, 1H), 3.60 (s, 3H), 2.82 (s, 3H), 2.61-2.55 (m, 2H), 2.33-2.21 (m, 5H), 2.19-1.94 (m, 6H), 1.56-1.53 (m, 2H).

Example-737

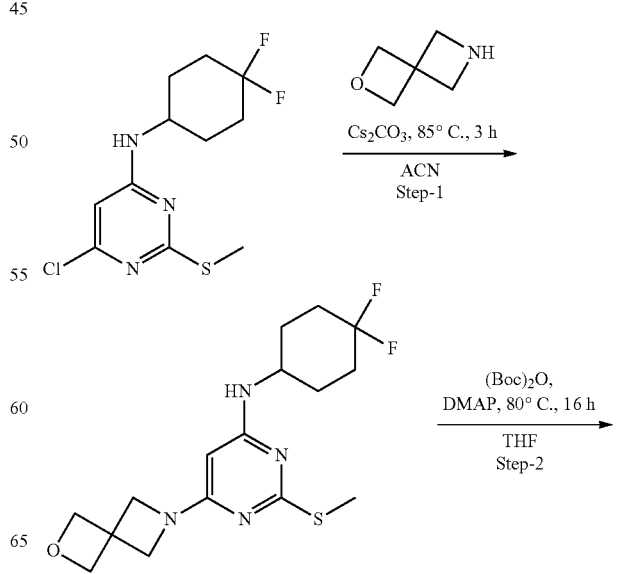

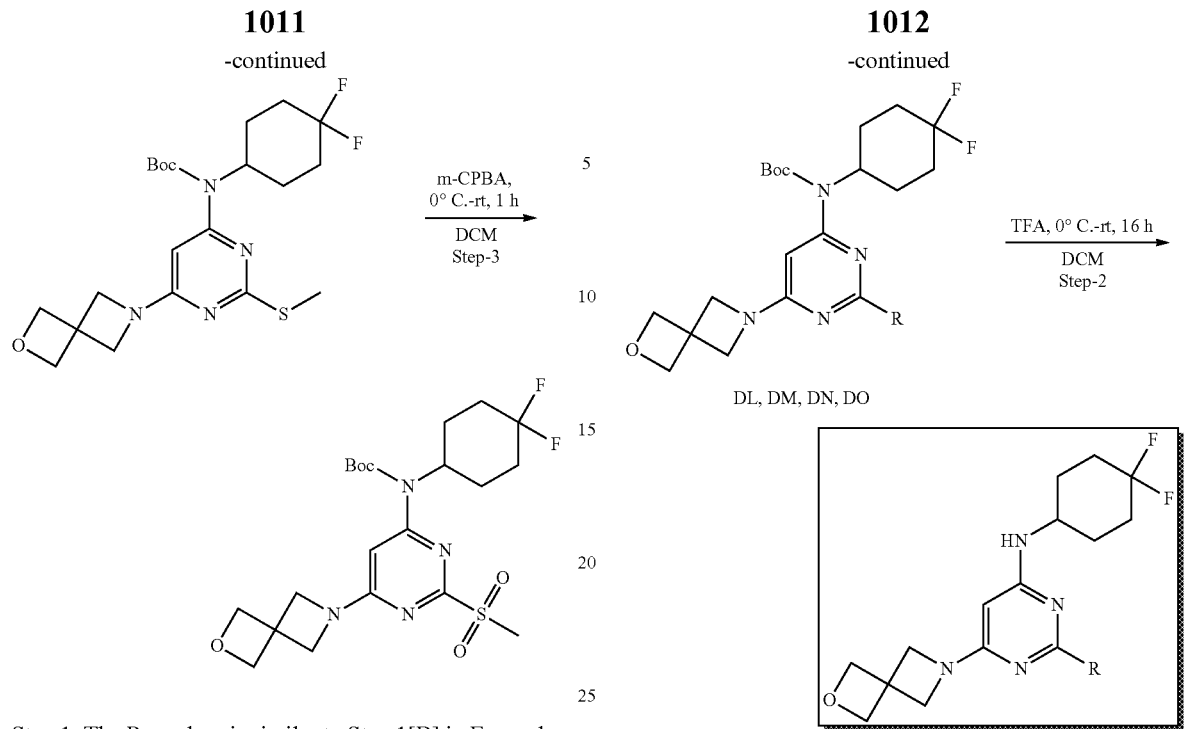

Step 1: The Procedure is similar to Step 1[B] in Example-838. 1 g of 6-chloro-N-(4,4-difluorocyclohexyl)-2-(methylthio)pyrimidin-4-amine gave N-(4,4-difluorocyclohexyl)-2-(methylthio)-6-(2-oxa-6-azaspiro [3.3] heptan-6-yl) pyrimidin-4-amine as an off-white solid (0.8 g, 66%). MS (M+1)+=357.

Step 2: The Procedure is similar to Step 2[IN11218-026-P1] in Example-613. 0.8 g of N-(4,4-difluorocyclohexyl)-2-(methylthio)-6-(2-oxa-6-azaspiro[3.3]heptan-6-yl)pyrimidin-4-amine gave tert-butyl (4,4-difluorocyclohexyl)(2-(methylthio)-6-(2-oxa-6-azaspiro[3.3]heptan-6-yl) pyrimidin-4-yl)carbamate as an off-white solid (0.91 g, 89%). MS (M+1)+=457.

Step 3: The Procedure is similar to Step 3[NSSy7062] in Example-623. 0.9 g of tert-butyl (4,4-difluorocyclohexyl)(2-(methylthio)-6-(2-oxa-6-azaspiro[3.3]heptan-6-yl)pyrimidin-4-yl)carbamate gave tert-butyl (4,4-difluorocyclohexyl)(2-(methylsulfonyl)-6-(2-oxa-6-azaspiro[3.3]heptan-6-yl)pyrimidin-4-yl)carbamate as a white solid (0.91 g, 83%). MS (M+1)+=489.

Example-738

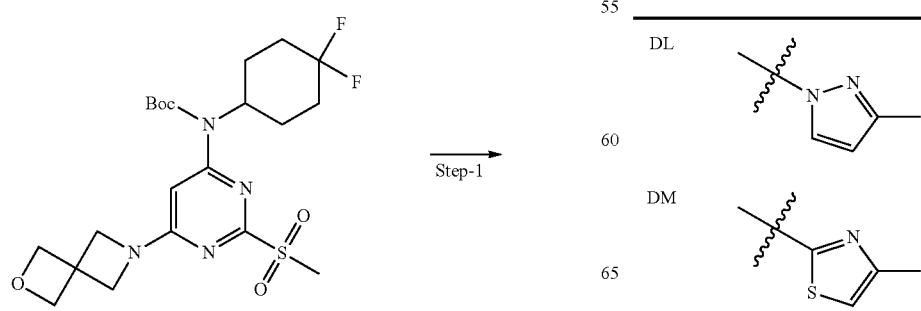

R =

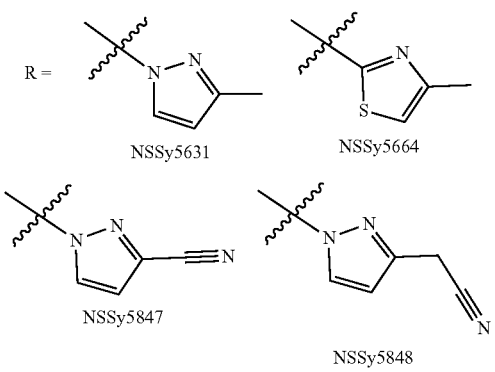

TABLE 73

| Step 1: | | | |
|---|---|---|---|
| Compound No | R | Condition | Yield (%) | MS (M + 1)+ |
| DL | ⟨pyrazole-methyl⟩ | Cs$_2$CO$_3$, ACN, 80° C., 3 h | 75 | 491.0 |
| DM | ⟨thiazole-methyl⟩ | n-BuLi, THF, −78° C., 1 h | 19 | 508.2 |

1013

TABLE 73-continued

Step 1:

| Compound No | R | Condition | Yield (%) | MS (M + 1)+ |
|---|---|---|---|---|
| DN | pyrazole-CN | Cs₂CO₃, ACN, 80° C., 3 h | 72 | 502.0 |
| DO | pyrazole-CH₂CN | Cs₂CO₃, ACN, 80° C., 3 h | 71 | 516.2 |

Step 1[DI, DK and DL]: The Procedure is similar to Step 1[B] in Example-838.
Step 1[DJ]: The Procedure is similar to Step 4[NSSy6067] in Example-628.

TABLE 74

Step 2: The Procedure is similar to Step 5[NSSy6067] in Example-628.

| Compound No | R | Condition | Yield (%) |
|---|---|---|---|
| NSSy5631 | 3-methyl-pyrazole | TFA, DCM, 0° C.-rt, 16 h | 70 |
| NSSy5664 | 4-methyl-thiazole | TFA, DCM, 0° C.-rt, 16 h | 72 |
| NSSy5847 | pyrazole-CN | TFA, DCM, 0° C.-rt, 16 h | 65 |
| NSSy5848 | pyrazole-CH₂CN | TFA, DCM, 0° C.-rt, 16 h | 62 |

Step 2[NSSy5631]: MS (M+1)+=391.2; 1H-NMR (400 MHz, DMSO-d6): δ 8.37 (s, 1H), 7.07 (d, J=7.96 Hz, 1H), 6.25 (d, J=2.48 Hz, 1H), 5.17 (s, 1H), 5.53 (s, 1H), 4.72 (s, 4H), 4.13 (s, 4H), 3.86 (s, 1H), 2.24 (s, 3H), 2.04-1.89 (m, 6H), 1.58-1.52 (m, 2H).

Step 2[NSSy5664]: MS (M+1)+=408.2; 1H-NMR (400 MHz, DMSO-d6): δ 7.34 (s, 1H), 7.03 (d, J=7.60 Hz, 1H), 5.29 (s, 1H), 4.73 (m, 4H), 4.14-4.04 (m, 4H), 3.85 (m, 1H), 2.42 (s, 3H), 2.08-1.91 (m, 6H), 1.60-1.54 (m, 2H).

Step 2[NSSy5847]: MS (M+1)+=402.4; 1H-NMR (400 MHz, DMSO-d6): δ 8.70 (s, 1H), 7.29 (d, J=8.40 Hz, 1H), 7.16 (d, J=2.80 Hz, 1H), 5.28 (s, 1H), 4.72 (m, 4H), 4.17 (m, 4H), 2.05-1.93 (m, 6H), 1.55 (m, 2H).

1014

Step 2[NSSy5848]: MS (M+1)+=416.2; 1H-NMR (400 MHz, DMSO-d6): δ 8.49 (s, 1H), 7.17 (d, J=8.40 Hz, 1H), 6.46 (d, J=2.40 Hz, 1H), 5.21 (s, 1H), 4.73 (m, 4H), 4.15 (m, 4H), 4.10 (s, 2H), 2.02-1.90 (m, 6H), 1.55-1.52 (m, 2H).

Example-739

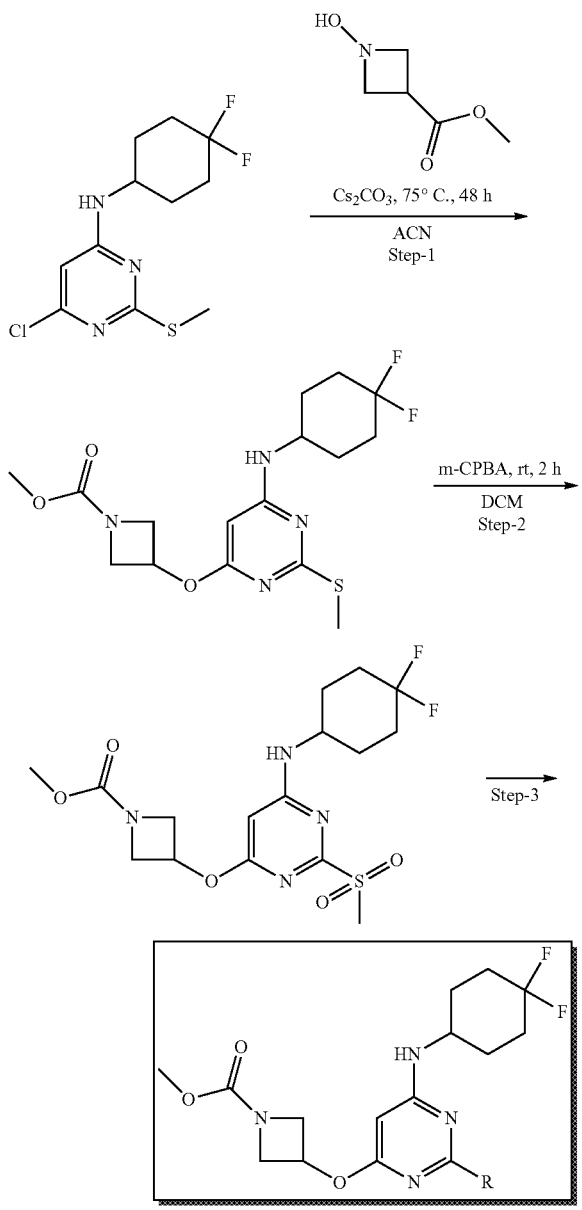

R=

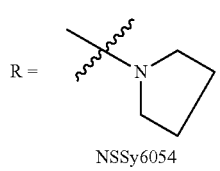
NSSy6054

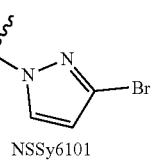
NSSy6101

-continued

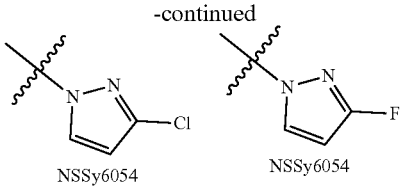

Step 1: The Procedure is similar to Step 1[B] in Example-838. 15 g of 6-chloro-N-(4,4-difluorocyclohexyl)-2-(methylthio)pyrimidin-4-amine gave methyl 3-((6-((4, 4-difluorocyclohexyl)amino)-2-(methylthio)pyrimidin-4-yl)oxy) azetidine-1-carboxylate as an off-white solid (15 g, 75%). MS (M+1)+=389.5.

Step 2: The Procedure is similar to Step 3[NSSy7062] in Example-623. 2 g of methyl 3-((6-((4,4-difluorocyclohexyl)amino)-2-(methylthio)pyrimidin-4-yl)oxy) azetidine-1-carboxylate gave methyl 3-((6-((4,4-difluorocyclohexyl)amino)-2-(methylsulfonyl)pyrimidin-4-yl)oxy) azetidine-1-carboxylate as an off-white solid (2.1 g, 97%). MS (M+1)+=421.1.

TABLE 75

Step 3: The Procedure is similar to Step 1[B] in Example-838.

| Compound No | R | Condition | Yield (%) |
|---|---|---|---|
| NSSy6054 | pyrrolidin-1-yl | Cs$_2$CO$_3$, ACN, 75° C., 16 h | 47 |
| NSSy6101 | 3-bromo-pyrazol-1-yl | Cs$_2$CO$_3$, ACN, 75° C., 3 h | 59 |
| NSSy6113 | 3-chloro-pyrazol-1-yl | Cs$_2$CO$_3$, ACN, 75° C., 3 h | 76 |
| NSSy6162 | 3-fluoro-pyrazol-1-yl | Cs$_2$CO$_3$, ACN, 75° C., 3 h | 70 |

Step 3[NSSy6054]: MS (M+1)+=412.2; 1H-NMR (400 MHz, DMSO-d6): δ 6.69 (d, J=6.96 Hz, 1H), 5.21 (s, 1H), 5.11 (s, 1H), 4.24 (bs, 2H), 3.56 (bs, 3H), 3.38 (s, 3H), 2.68 (s, 4H), 2.20-1.70 (m, 10H), 1.60-1.40 (m, 2H).

Step 3[NSSy6101]: MS (M+1)+=489.0; 1H-NMR (400 MHz, DMSO-d6-80° C.): δ 8.48 (s, 1H), 7.44 (d, J=8.00 Hz, 1H), 6.62 (s, 1H), 5.79 (s, 1H), 5.42-5.38 (m, 1H), 4.37-4.33 (m, 2H), 3.94-3.91 (m, 3H), 3.58 (s, 3H), 2.20-1.80 (m, 6H), 1.65-1.50 (m, 2H).

Step 3[NSSy6113]: MS (M+1)+=443.2; 1H-NMR (400 MHz, DMSO-d6-80° C.): δ 8.54 (s, 1H), 7.49 (d, J=6.8 Hz, 1H), 6.57 (s, 1H), 5.78 (s, 1H), 5.41-5.38 (m, 1H), 4.37-4.33 (m, 2H), 3.94-3.90 (m, 3H), 3.59 (s, 3H), 2.20-1.80 (m, 6H), 1.65-1.45 (m, 2H).

Step 3[NSSy6162]: MS (M+1)+=427.1; 1H-NMR (400 MHz, DMSO-d6-80° C.): δ 8.45 (s, 1H), 7.42 (d, J=7.6 Hz, 1H), 6.29-6.27 (m, 1H), 5.76 (s, 1H), 5.40-5.37 (m, 1H), 4.37-4.33 (m, 2H), 3.94-3.90 (m, 3H), 3.60 (s, 3H), 2.08-1.97 (m, 6H), 1.64-1.57 (m, 2H).

Example-740

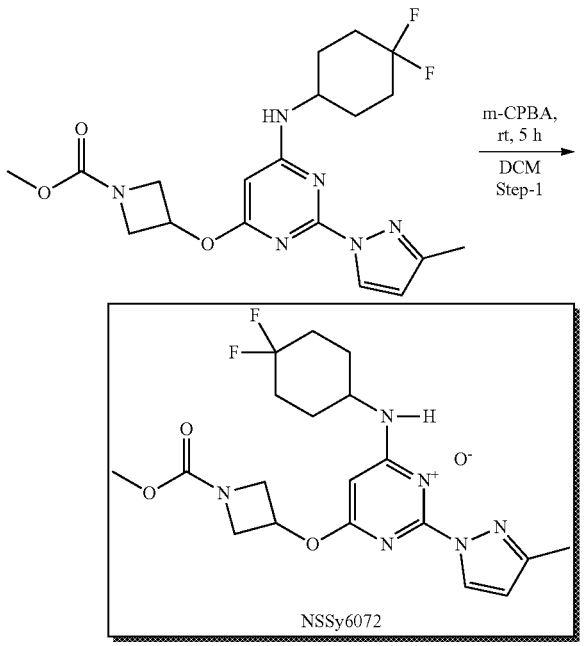

Step 1[NSSy6072]: The Procedure is similar to Step 3[NSSy7062] in Example-623: 0.3 g of methyl 3-((6-((4,4-difluorocyclohexyl)amino)-2-(3-methyl-1H-pyrazol-1-yl) pyrimidin-4-yl)oxy)azetidine-1-carboxylate gave 6-((4,4-difluorocyclohexyl)amino)-4-((1-(methoxycarbonyl)azetidin-3-yl)oxy)-2-(3-methyl-1H-pyrazol-1-yl)pyrimidine 1-oxide as an off-white solid (0.06 g, 19%). MS (M+1)+=439.2; 1H-NMR (400 MHz, DMSO-d$_6$): δ 9.29 (d, J=2.80 Hz, 1H), 8.13 (d, J=8.80 Hz, 1H), 6.41 (s, 1H), 6.36 (d, J=2.80 Hz, 1H), 5.35-5.32 (m, 1H), 4.33-4.31 (m, 1H), 3.95-3.80 (m, 2H), 3.73-3.70 (m, 1H), 3.57 (s, 1H), 2.28 (s, 3H), 2.07-1.88 (m, 7H), 1.76-1.73 (m, 2H).

Example-741

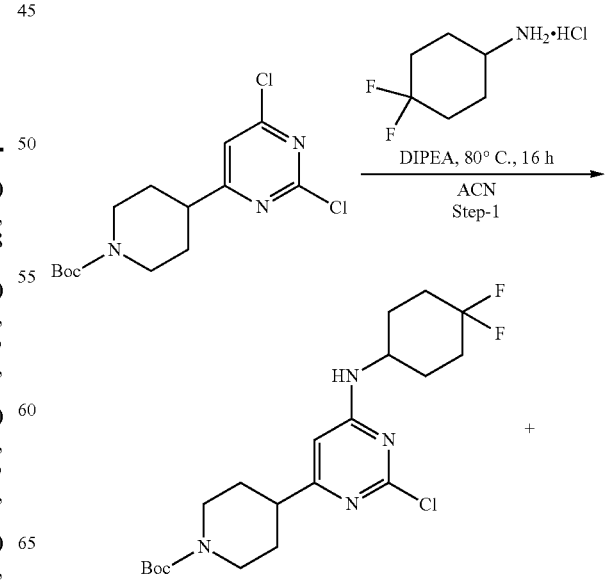

1017

-continued

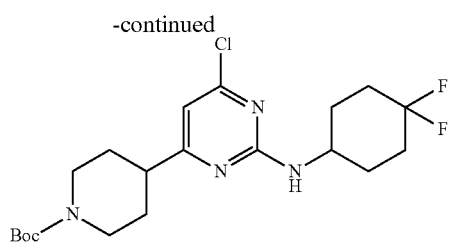

Step 1: The Procedure is similar to Step 1[B] in Example-838. 0.33 g of tert-butyl 4-(2,6-dichloropyrimidin-4-yl) piperidine-1-carboxylate gave tert-butyl 4-(2-chloro-6-((4,4-difluorocyclohexyl)amino)pyrimidin-4-yl) piperidine-1-carboxylate as an off-white solid (0.25 g, 75%). MS (M+1)+=432.2 and tert-butyl 4-(6-chloro-2-((4,4-difluorocyclohexyl)amino)pyrimidin-4-yl)piperidine-1-carboxylate as an off-white solid (0.12 g, 25%). MS (M+1)=432.2.

Example-742

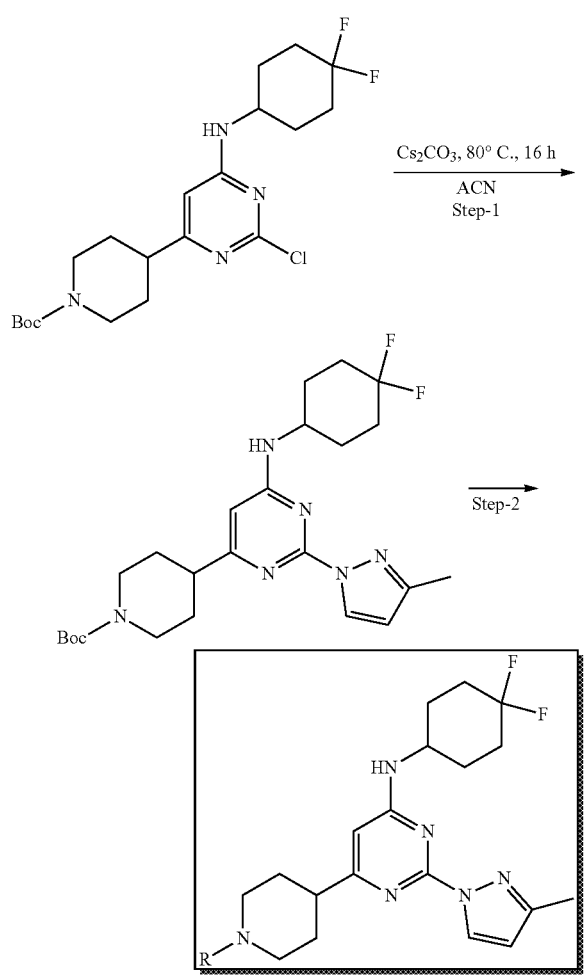

R=

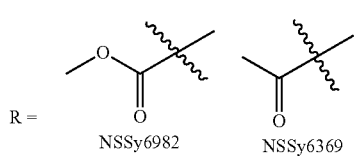

1018

Step 1: The Procedure is similar to Step 1[B] in Example-838. 0.25 g of tert-butyl 4-(2-chloro-6-((4,4-difluorocyclohexyl)amino)pyrimidin-4-yl) piperidine-1-carboxylate gave tert-butyl 4-(6-((4,4-difluorocyclohexyl)amino)-2-(3-methyl-1H-pyrazol-1-yl)pyrimidin-4-yl) piperidine-1-carboxylate as an off-white solid (0.13 g, 50%). MS (M+1)+=477.2

TABLE 76

Step 2: The Procedure is similar to Step 2[NSSy6924] in Example-857.

| Compound No | R | Condition | Yield (%) |
|---|---|---|---|
| NSSy6982 | methyl ester | a. TFA, DCM, 0° C.-rt, 16 h b. DCM, 0° C.-rt, | 40 |
| NSSy6369 | acetyl | a. TFA, DCM, 0° C.-rt, 16 h b. DCM, 0° C.-rt, | 42 |

Step 2[NSSy6982]: MS (M+1)+=434.9; 1 H-NMR (400 MHz, DMSO-d6): δ 8.51 (s, 1H), 7.34 (bs, 1H), 6.87 (s, 1H), 6.40 (d, J=4.00 Hz, 1H), 4.10 (bs, 1H), 3.61-3.60 (s, 1H), 2.69-2.60 (m, 1H), 2.57-2.54 (m, 1H) 2.26 (s, 3H), 2.08-1.85 (m, 6H), 1.61-1.55 (m, 2H), 1.24-1.22 (m, 4H).

Step 2[NSSy6369]: MS (M+1)+=419.2; 1 H-NMR (400 MHz, DMSO-d6): δ 8.45 (s, 1H), 7.59 (bs, 1H), 6.28 (s, 1H), 6.18 (bs, 1H), 4.48 (d, J=12.0 Hz, 1H), 3.14 (bs, 1H), 3.92 (d, J=12.0 Hz, 1H), 3.12 (s, 1H), 2.69-2.60 (m, 1H), 2.57-2.54 (m, 1H), 2.25 (s, 3H), 2.04-1.80 (m, 11H), 0.60 (m, 4H).

Example-743

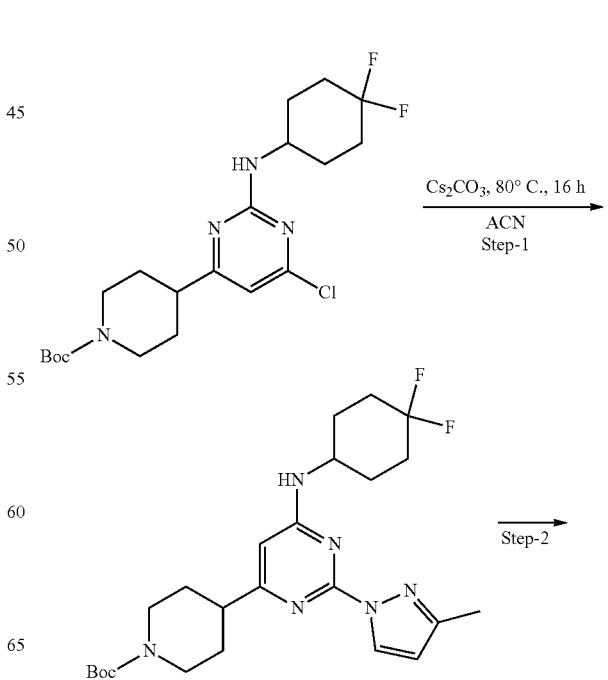

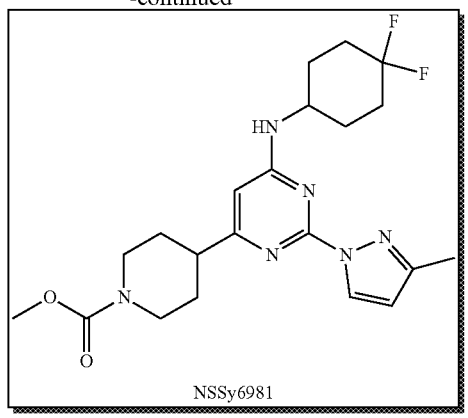

Step 1: The Procedure is similar to Step 1[B] in Example-838. 0.12 g of tert-butyl 4-(6-chloro-2-((4,4-difluorocyclohexyl)amino)pyrimidin-4-yl) piperidine-1-carboxylate gave tert-butyl 4-(2-((4,4-difluoro cyclohexyl)amino)-6-(3-methyl-1H-pyrazol-1-yl)pyrimidin-4-yl) piperidine-1-carboxylate as an off-white solid (0.062 g, 51%). MS (M+1)+=477.2.

Step 1[NSSy6981]: The Procedure is similar to Step 2[NSSy6924] in Example-857. 0.062 g of tert-butyl 4-(2-((4,4-difluoro cyclohexyl)amino)-6-(3-methyl-1H-pyrazol-1-yl)pyrimidin-4-yl)piperidine-1-carboxylate gave methyl 4-(2-((4,4-difluorocyclohexyl)amino)-6-(3-methyl-1H-pyrazol-1-yl)pyrimidin-4-yl)piperidine-1-carboxylate as an off-white solid (0.035 g, 62%). MS (M+1)+=435.2; 1H-NMR (400 MHz, DMSO-d6): δ 8.46 (s, 1H), 7.61-7.59 (m, 1H), 6.29 (s, 1H), 6.18 (s, 1H), 4.10 (s, 1H), 3.61 (s, 1H), 2.69-2.60 (m, 1H), 2.57-2.54 (m, 1H), 2.26 (s, 3H), 2.08-1.85 (m, 6H), 1.61-1.55 (m, 2H), 1.24 (m, 4H).

Example-744

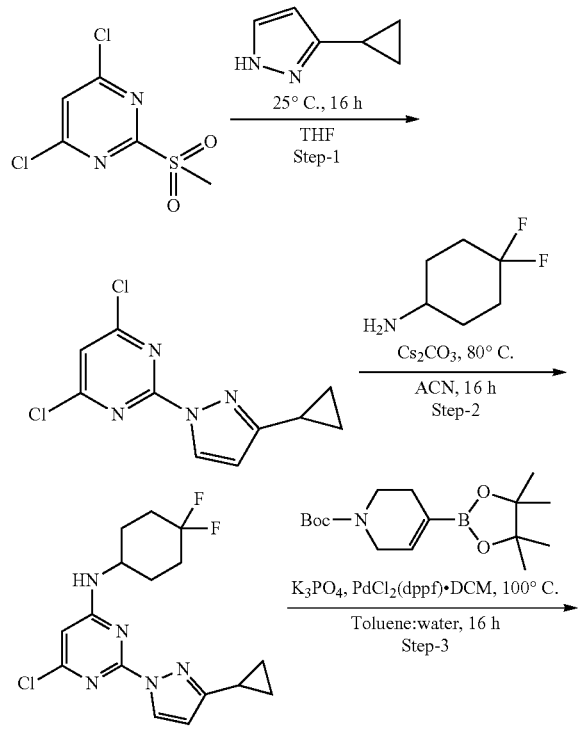

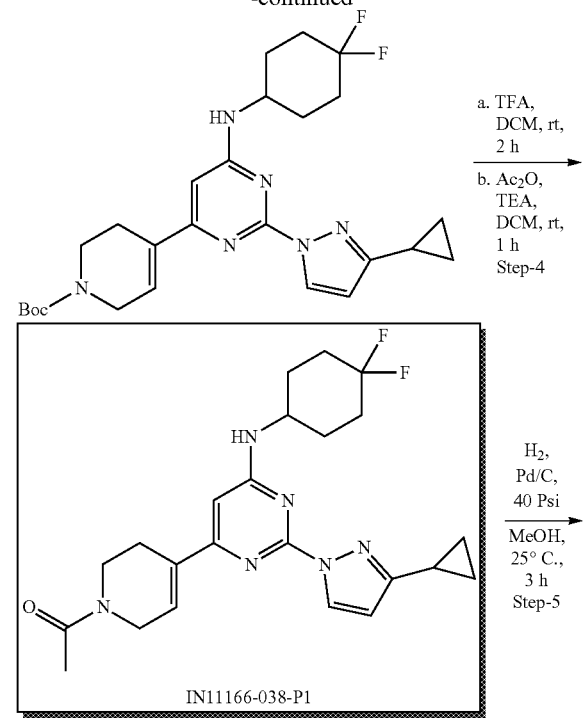

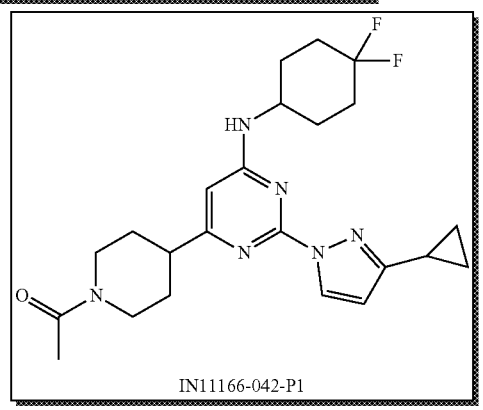

Step 1: The Procedure is similar to Step 1[IN11177-025-P1] in Example-715. 1.0 g of 4,6-dichloro-2-(methylsulfonyl)pyrimidine gave 4,6-dichloro-2-(3-cyclopropyl-1H-pyrazol-1-yl)pyrimidine as an off-white solid (1.1 g, 97%). MS (M+1)+=255.0.

Step 2: The Procedure is similar to Step 1[B] in Example-838. 1.0 g of 4,6-dichloro-2-(3-cyclopropyl-1H-pyrazol-1-yl)pyrimidine gave 6-chloro-2-(3-cyclopropyl-1H-pyrazol-1-yl)-N-(4,4-difluorocyclohexyl)pyrimidin-4-amine as an off-white solid (0.75 g, 53%). MS (M+1)+=354.0.

Step 3: The Procedure is similar to Step 2[IN11250-007-P1] in Example-620. 0.25 g of 6-chloro-2-(3-cyclopropyl-1H-pyrazol-1-yl)-N-(4,4-difluorocyclohexyl)pyrimidin-4-amine gave tert-butyl 4-(2-(3-cyclopropyl-1H-pyrazol-1-yl)-6-((4,4-difluorocyclohexyl)amino)pyrimidin-4-yl)-3,6-dihydropyridine-1(2H)-carboxylate as an off-white solid (0.25 g, 70%). MS (M+1)+=501.0.

Step 4[IN11166-038-P1]: The Procedure is similar to Step 2[NSSy6924] in Example-857. 0.25 g of tert-butyl 4-(2-(3-cyclopropyl-1H-pyrazol-1-yl)-6-((4,4-difluorocyclohexyl)amino)pyrimidin-4-yl)-3,6-dihydropyridine-1(2H)-carboxylate gave 1-(4-(2-(3-cyclopropyl-1H-pyrazol-1-yl)-6-

((4,4-difluorocyclohexyl)amino)pyrimidin-4-yl)-3,6-dihydropyridin-1(2H)-yl)ethan-1-one as an off-white solid (0.09 g, 45%). MS (M+1)+=443.3; 1H-NMR (400 MHz, DMSO-d6): δ 8.48 (s, 1H), 7.69 (s, 1H), 6.96 (s, 1H), 6.34 (s, 1H), 6.19 (s, 1H), 4.22 (s, 1H), 4.16 (s, 2H), 3.67-3.62 (m, 2H), 2.08 (s, 3H), 2.06 (s, 3H), 2.00-1.90 (m, 6H), 1.65-1.52 (m, 2H), 0.92 (d, J=4.00 Hz, 2H), 0.72 (d, J=4.40 Hz, 2H).

Step 5[IN11166-042-P1]: The Procedure is similar to Step 2[NSSy6464] in Example-869. 0.09 g of 1-(4-(2-(3-cyclopropyl-1H-pyrazol-1-yl)-6-((4,4-difluorocyclohexyl)amino)pyrimidin-4-yl)-3,6-dihydropyridin-1(2H)-yl)ethan-1-one gave 1-(4-(2-(3-cyclopropyl-1H-pyrazol-1-yl)-6-((4,4-difluorocyclohexyl)amino)pyrimidin-4-yl)piperidin-1-yl)ethan-1-one as an off-white solid (0.03 g, 33%). MS (M+1)+=445.2; 1H-NMR (400 MHz, DMSO-d6): δ 8.42 (s, 1H), 7.58 (s, 1H), 6.16 (d, J=2.40 Hz, 2H), 4.50 (d, J=12.80 Hz, 1H), 4.12 (s, 1H), 3.91 (d, J=14.00 Hz, 1H), 3.13 (t, J=10.80 Hz, 1H), 2.80-2.60 (m, 3H), 2.10-1.80 (m, 11H), 1.60-1.35 (m, 4H), 0.95-0.88 (m, 2H), 0.75-0.65 (m, 2H).

Example-745

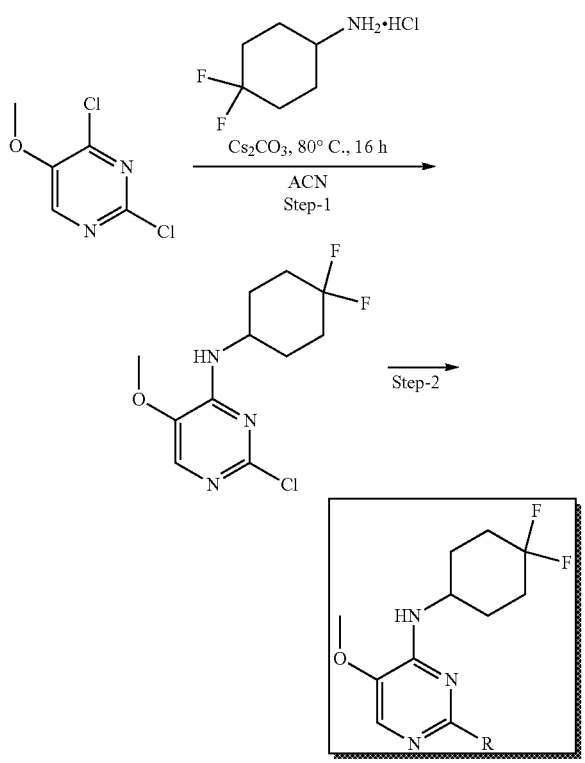

R=

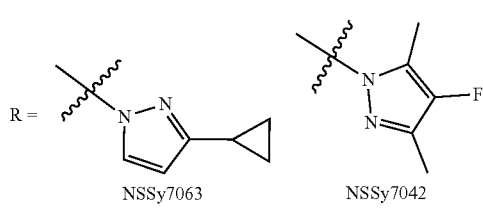

NSSy7063    NSSy7042

-continued

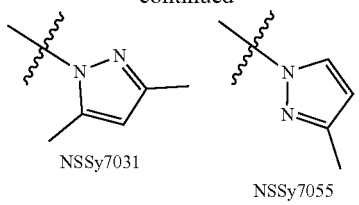

NSSy7031    NSSy7055

Step 1: The Procedure is similar to Step 1[B] in Example-838. 2 g of 2,4-Dichloro-5-Methoxypyrimidine gave 2-chloro-N-(4,4-difluoro cyclohexyl)-5-methoxypyrimidin-4-amine as an off-white solid (2.4 g, 77%). MS (M+1)+=278.4.

TABLE 77

Step 2: The Procedure is similar to Step 1[NSSy66629] in Example-839.

| Compound No | R | Condition | Yield (%) |
|---|---|---|---|
| NSSy7063 | (3-cyclopropyl-pyrazol-1-yl) | Pd2(dba)3, tBuXPhos, Cs2CO3, Dioxane, 100° C., 16 h | 58 |
| NSSy7042 | (3,5-dimethyl-4-fluoro-pyrazol-1-yl) | Pd2(dba)3, Xanthphos, Cs2CO3, Dioxane, 100° C., 16 h | 52 |
| NSSy7031 | (3,5-dimethyl-pyrazol-1-yl) | Pd2(dba)3, Xanthphos, Cs2CO3, Dioxane, 100° C., 16 h | 32 |
| NSSy7055 | (3-methyl-pyrazol-1-yl) | Pd2(dba)3, Xanthphos, Cs2CO3, Dioxane, 100° C., 16 h | 14 |

Step 2[NSSy7063]: MS (M+1)+=350.2; 1H-NMR (400 MHz, DMSO-d6): δ 8.38 (d, J=2.40 Hz, 1H), 7.74 (s, 1H), 7.22 (d, J=8.00 Hz, 1H), 6.18 (d, J=2.40 Hz, 1H), 4.19 (bs, 1H), 3.86 (s, 3H), 1.98-1.89 (m, 7H), 1.75-1.69 (m, 2H), 0.93-0.90 (m, 2H), 0.74-0.71 (m, 2H).

Step 2[NSSy7042]: MS (M+1)+=356.2; 1H-NMR (400 MHz, DMSO-d6): δ 7.81 (s, 1H), 7.27 (d, J=8.00 Hz, 1H), 4.06 (s, 1H), 3.88 (s, 3H), 2.45 (s, 3H), 2.19 (s, 3H), 2.15-1.85 (m, 6H), 1.75-1.65 (m, 2H).

Step 2[NSSy7031]: MS (M+1)+=338.2; 1H-NMR (400 MHz, DMSO-d6): δ 7.80 (s, 1H), 7.20 (d, J=8.00 Hz, 1H), 6.01 (s, 1H), 4.08 (d, J=8.40 Hz, 1H), 3.88 (s, 3H), 2.45 (s, 3H), 2.15 (s, 3H), 2.08-2.05 (m, 3H), 1.98-1.89 (m, 3H), 1.72-1.69 (m, 2H).

Step 2[NSSy7055]: MS (M+1)+=324.1; 1H-NMR (400 MHz, DMSO-d6): δ 8.40 (s, 1H), 7.74 (s, 1H), 7.21 (d, J=8.00 Hz, 1H), 6.26 (s, 1H), 4.20 (d, J=4.40 Hz, 1H), 3.86 (s, 1H), 3.86 (s, 3H), 2.06 (t, J=5.60 Hz, 4H), 1.90 (d, J=14.80 Hz, 2H), 1.75-1.68 (m, 2H).

Example-746

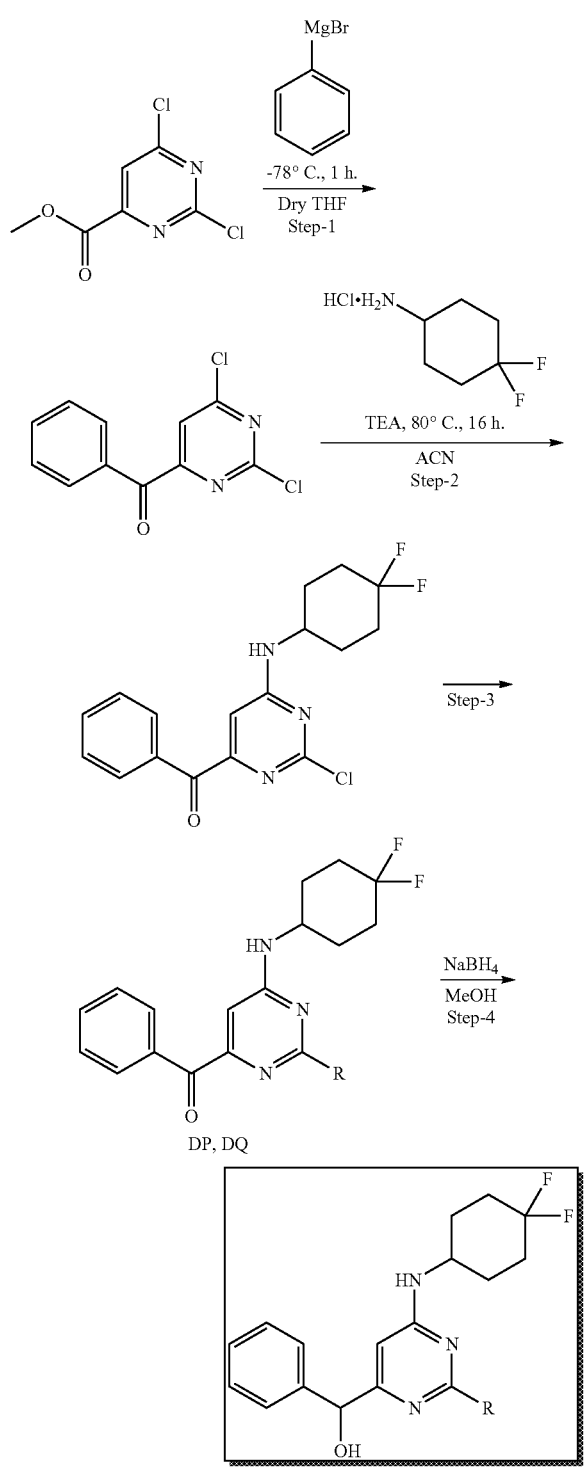

R=

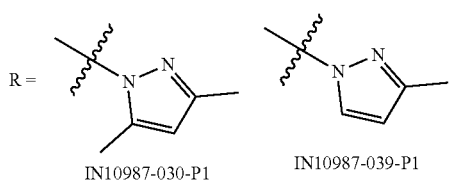

IN10987-030-P1    IN10987-039-P1

Step 1: The Procedure is similar to Step 4[NSSy6464] in Example-869. 5.0 g of methyl 2,6-dichloropyrimidine-4-carboxylate gave (2,6-dichloropyrimidin-4-yl) (phenyl) methanone as a pale yellow solid (3.1 g, 50%). MS (M+1)+= 253.0.

Step 2: The Procedure is similar to Step 1[B] in Example-838. 0.25 g of (2,6-dichloropyrimidin-4-yl) (phenyl) methanone gave (2-chloro-6-((4,4-difluorocyclohexyl)amino)pyrimidin-4-yl) (phenyl) methanone as an off-white solid (0.22 g, 64%). MS (M+1)+=352.0.

TABLE 78

Step 3: The procedure is similar to step 1[B] in Example-838.

| Compound No | R | Condition | Yield (%) | MS (M + 1)+ |
|---|---|---|---|---|
| DP | 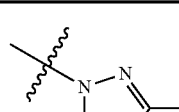 | Cs₂CO₃, 100° C., 20 min, DMF | 50 | 412.0 |
| DQ | 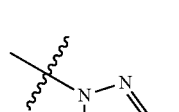 | Cs₂CO₃, 100° C., 20 min, DMF | 42 | 398.0 |

TABLE 79

Step 4: The procedure is similar to step 2[NSSy6931] in Example-21.

| Compound No | R | Condition | Yield (%) | MS (M + 1)+ |
|---|---|---|---|---|
| IN10987-030-P1 | | NaBH₄, 0° C., 30 min, MeOH | 31 | 414.0 |
| IN10987-039-P1 | | NaBH₄, 0° C., 30 min, MeOH | 45 | 400.0 |

Step 4[IN10987-030-P1]: 1H-NMR (400 MHz, DMSO-d6): δ 7.70 (s, 1H), 7.40 (d, J=7.20 Hz, 2H), 7.31 (t, J=8.00 Hz, 2H), 7.25-7.23 (m, 1H), 6.64 (s, 1H), 6.07 (s, 1H), 6.01 (s, 1H), 5.43 (s, 1H), 4.02 (s, 1H), 2.40 (s, 3H), 2.14 (s, 3H), 2.10-1.85 (m, 6H), 1.57 (m, 2H).

Step 4[IN10987-039-P1]: 1H-NMR (400 MHz, DMSO-d6): δ 8.45 (s, 1H), 7.72 (s, 1H), 7.42 (s, 1H), 7.34-7.30 (m, 2H), 7.26-7.22 (m, 2H), 6.59 (s, 1H), 6.28 (s, 1H), 6.07 (s, 1H), 5.44 (s, 1H), 4.15 (s, 1H), 2.23 (s, 3H), 2.10-1.90 (m, 6H), 1.60-1.50 (m, 2H).

1025
Example-747

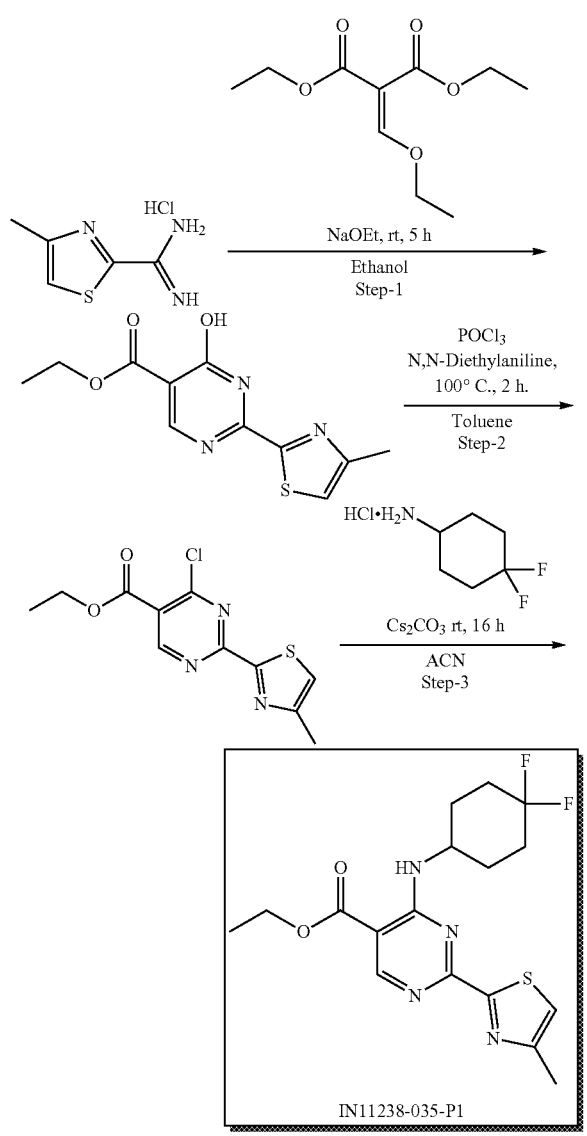

1026
Example-748

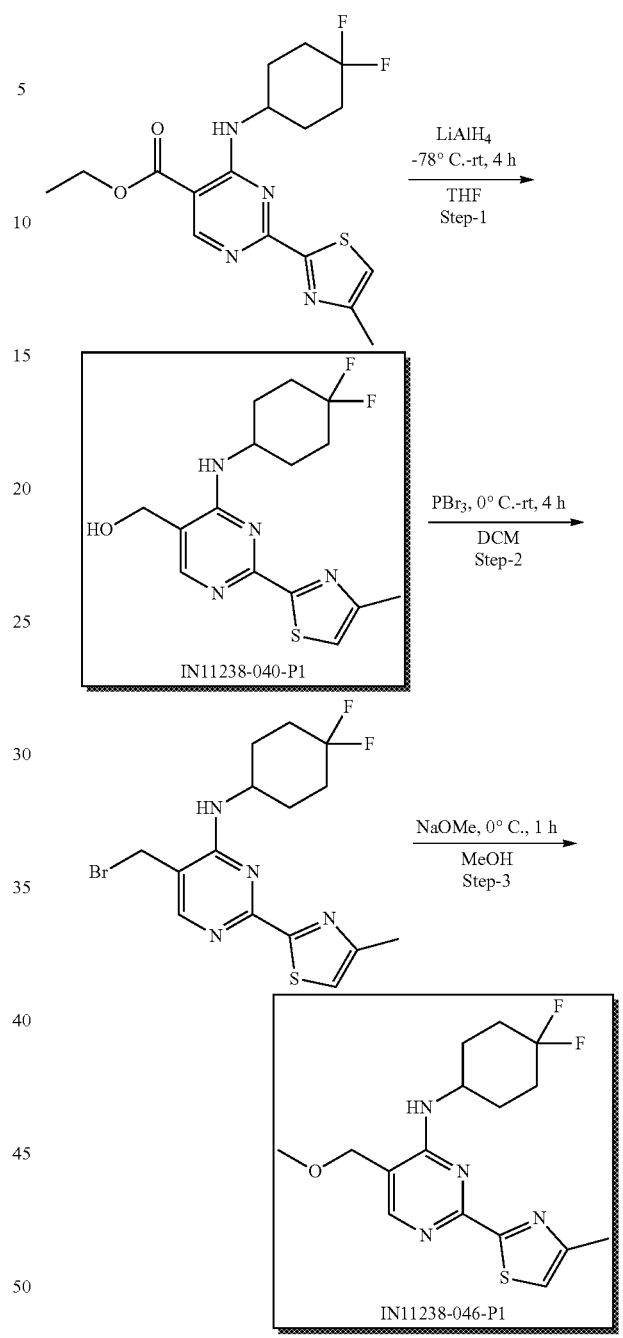

Step 1: The Procedure is similar to Step 1[IN10966-057-P2] in Example-893. 0.5 g 4-methylthiazole-2-carboximidamide gave ethyl 4-hydroxy-2-(4-methylthiazol-2-yl)pyrimidine-5-carboxylate as a yellow solid (0.18 g, 24%). MS (M+1)+=266.1.

Step 2: The Procedure is similar to Step 2[IN10966-057-P2] in Example-893. 0.15 g ethyl 4-hydroxy-2-(4-methylthiazol-2-yl)pyrimidine-5-carboxylate gave ethyl 4-chloro-2-(4-methylthiazol-2-yl)pyrimidine-5-carboxylate as a brown solid (0.15 g, 93%). MS (M+1)+=284.0.

Step 3[IN11238-035-P1]: The Procedure is similar to Step 1[B] in Example-838. 0.15 g ethyl 4-chloro-2-(4-methylthiazol-2-yl)pyrimidine-5-carboxylate gave ethyl 4-((4,4-difluorocyclohexyl)amino)-2-(4-methylthiazol-2-yl)pyrimidine-5-carboxylate as a brown solid (0.08 g, 39%). MS (M+1)+=383.1; 1H-NMR (400 MHz, DMSO-d6): δ 8.84 (s, 1H), 8.24 (d, J=7.60 Hz, 1H), 7.57 (s, 1H), 4.35-4.29 (m, 2H), 4.27 (s, 1H), 2.49 (s, 3H), 2.10-1.95 (m, 6H), 1.80-1.62 (m, 2H), 1.34 (t, J=6.80 Hz, 3H).

Step 1[IN11238-040-P1]: The Procedure is similar to Step 4[NSSy6711] in Example-854. 0.5 g of ethyl 4-((4,4-difluorocyclohexyl)amino)-2-(4-methylthiazol-2-yl)pyrimidine-5-carboxylate gave (4-((4,4-difluorocyclohexyl)amino)-2-(4-methylthiazol-2-yl)pyrimidin-5-yl) methanol as a brown solid (0.12 g, 27%). MS (M+1)+=341.1; 1H-NMR (400 MHz, DMSO-d6): δ 8.13 (s, 1H), 7.39 (s, 1H), 6.65 (d, J=7.20 Hz, 1H), 5.29 (t, J=5.20 Hz, 1H), 4.43 (d, J=5.20 Hz, 2H), 4.19 (s, 1H), 2.44 (s, 3H), 2.15-1.90 (m, 6H), 1.75-1.62 (m, 2H).

Step 2: The Procedure is similar to Step 3[IN11059-090-P1] in Example-659. 0.2 g (4-((4,4-difluorocyclohexyl)amino)-2-(4-methylthiazol-2-yl)pyrimidin-5-yl) methanol gave 5-(bromomethyl)-N-(4,4-difluorocyclohexyl)-2-(4- methylthiazol-2-yl)pyrimidin-4-amine as a brown gum (0.25 g, 95%). MS (M+1)+=403.

Step 3[IN11238-046-P1]: The Procedure is similar to Step 1[NSSy6519] in Example-842. 0.25 g 5-(bromomethyl)-N-(4,4-difluorocyclohexyl)-2-(4-methylthiazol-2-yl)pyrimidin-4-amine gave 5-(bromomethyl)-N-(4,4-difluorocyclohexyl)-2-(4-methylthiazol-2-yl)pyrimidin-4-amine as a brown solid (0.095 g, 43%). MS (M+1)+=355.2; 1H-NMR (400 MHz, DMSO-d6): δ 8.14 (s, 1H), 7.41 (s, 1H), 6.69 (d, J=7.20 Hz, 1H), 4.38 (s, 2H), 4.22 (s, 1H), 3.30 (s, 3H), 2.44 (s, 3H), 2.12-1.90 (m, 6H), 1.75-1.65 (m, 2H).

Example-749

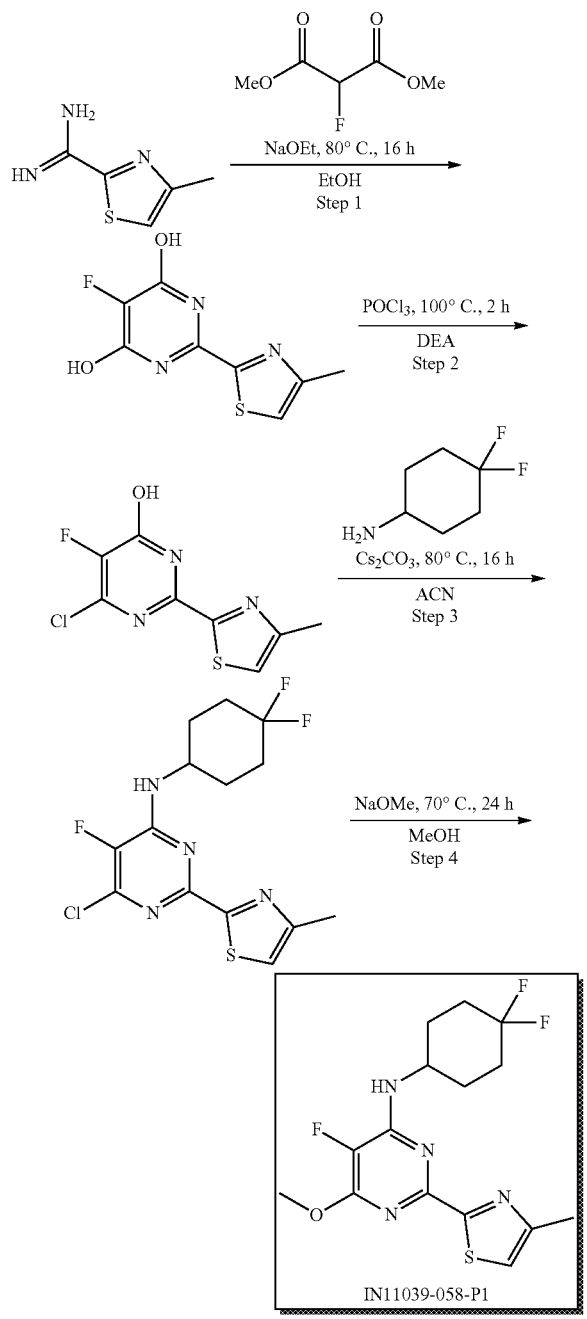

IN11039-058-P1

Step 1: The Procedure is similar to Step 1[IN10966-057-P2] in Example-893. 1.0 g of 4-methylthiazole-2-carboximidamide gave 5-fluoro-2-(4-methylthiazol-2-yl)pyrimidine-4,6-diol as a pale yellow solid (0.17 g, 13%). MS (M+1)+=228.0.

Step 2: The Procedure is similar to Step 2[IN10966-057-P2] in Example-893. 0.17 g 5-fluoro-2-(4-methylthiazol-2-yl)pyrimidine-4,6-diol gave 2-(4,6-dichloro-5-fluoropyrimidin-2-yl)-4-methylthiazole as a pale yellow solid (0.12 g, 61%). MS (M+1)+=263.9.

Step 3: The Procedure is similar to Step 1[B] in Example-838. 0.12 g 2-(4,6-dichloro-5-fluoropyrimidin-2-yl)-4-methylthiazole gave 6-chloro-N-(4,4-difluorocyclohexyl)-5-fluoro-2-(4-methylthiazol-2-yl)pyrimidin-4-amine as an off-white solid (0.06 g, 36%). MS (M+1)+=363.0.

Step 4[IN11039-058-P1]: The Procedure is similar to Step 1[NSSy6519] in Example-842. 0.06 g 6-chloro-N-(4,4-difluorocyclohexyl)-5-fluoro-2-(4-methylthiazol-2-yl)pyrimidin-4-amine gave N-(4,4-difluorocyclohexyl)-5-fluoro-6-methoxy-2-(4-methylthiazol-2-yl)pyrimidin-4-amine as an off-white solid (0.04 g, 67%). MS (M+1)+=359.0; 1H-NMR (400 MHz, CD3OD): δ 7.26 (s, 1H), 4.35-4.25 (m, 1H), 4.03 (s, 3H), 2.50 (s, 3H), 2.10-1.85 (m, 6H), 1.78-1.65 (m, 2H).

Example-750

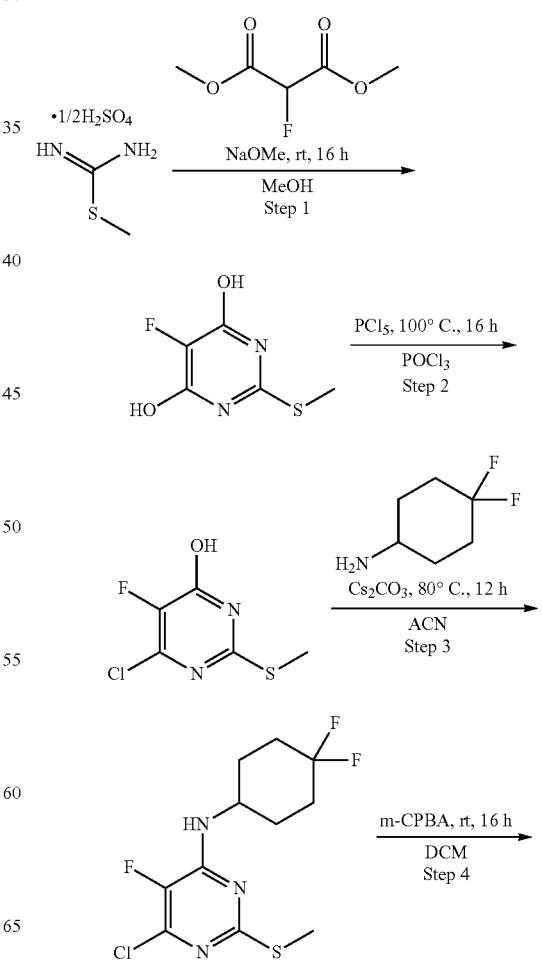

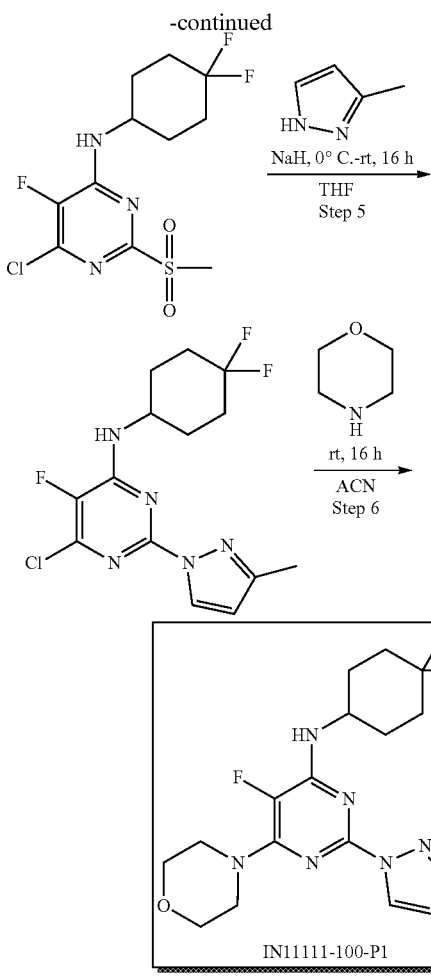

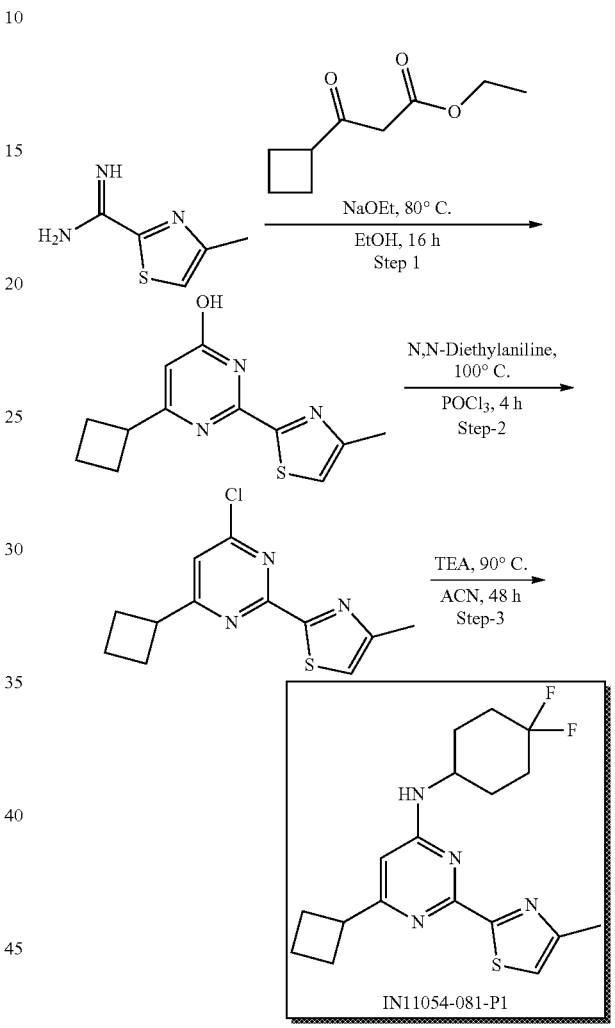

Step 1: The Procedure is similar to Step 1[IN10966-057-P2] in Example-893. 2.0 g of methyl carbamimidothioate gave 5-fluoro-2-(methylthio)pyrimidine-4,6-diol as a pale yellow solid (0.92 g, 36%). MS (M+1)+=177.0.

Step 2: The Procedure is similar to Step 3[NSSy6908] in Example-624. 0.9 g 5-fluoro-2-(methylthio)pyrimidine-4,6-diol gave 4,6-dichloro-5-fluoro-2-(methylthio)pyrimidine as a pale yellow solid (0.72 g, 66%). MS (M+1)+=212.0.

Step 3: The Procedure is similar to Step 1[B] in Example-838. 0.2 g 4,6-dichloro-5-fluoro-2-(methylthio)pyrimidine gave 6-chloro-N-(4,4-difluorocyclohexyl)-5-fluoro-2-(methylthio)pyrimidin-4-amine as a pale yellow solid (0.3 g, 95%). MS (M+1)+=310.0.

Step 4: The Procedure is similar to Step 3[NSSy7062] in Example-623. 0.3 g 6-chloro-N-(4,4-difluorocyclohexyl)-5-fluoro-2-(methylthio)pyrimidin-4-amine gave 6-chloro-N-(4,4-difluorocyclohexyl)-5-fluoro-2-(methylsulfonyl)pyrimidin-4-amine as an off-white solid (0.2 g, 60%). MS (M+1)+=342.1.

Step 5: The Procedure is similar to Step 5[NSSy6711] in Example-854. 0.2 g 6-chloro-N-(4,4-difluorocyclohexyl)-5-fluoro-2-(methylsulfonyl)pyrimidin-4-amine gave 6-chloro-N-(4,4-difluorocyclohexyl)-5-fluoro-2-(3-methyl-1H-pyrazol-1-yl)pyrimidin-4-amine as a pale yellow solid (0.1 g, 50%). MS (M+1)+=346.1.

Step 5[IN11111-100-P1]: 0.1 g 6-chloro-N-(4,4-difluorocyclohexyl)-5-fluoro-2-(3-methyl-1H-pyrazol-1-yl)pyrimidin-4-amine gave N-(4,4-difluorocyclohexyl)-5-fluoro-2-(3-methyl-1H-pyrazol-1-yl)-6-morpholinopyrimidin-4-amine as an off-white solid (0.05 g, 43%). MS (M+1)+=397.2; 1H-NMR (400 MHz, DMSO-d6): δ 8.40 (d, J=2.40 Hz, 1H), 7.08 (d, J=7.60 Hz, 1H), 6.26 (d, J=2.40 Hz, 1H), 4.14 (s, 1H), 3.69-3.60 (m, 8H), 2.24 (s, 3H), 2.80-1.85 (m, 6H), 1.72-1.60 (m, 2H).

Example-751

Step 1: The Procedure is similar to Step 1[IN10966-057-P2] in Example-893. 0.5 g of 4-methylthiazole-2-carboximidamide gave 6-cyclobutyl-2-(4-methylthiazol-2-yl)pyrimidin-4-ol as a brown liquid (0.5 g, 74%). MS (M+1)+=248.1.

Step 2: The Procedure is similar to Step 2[IN10966-057-P2] in Example-893. 0.5 g 6-cyclobutyl-2-(4-methylthiazol-2-yl)pyrimidin-4-ol gave 2-(4-chloro-6-cyclobutylpyrimidin-2-yl)-4-methylthiazole as an off-white solid (0.2 g, 40%). MS (M+1)+=266.0.

Step 3[IN11054-081-P1]: The Procedure is similar to Step 1[B] in Example-838. 0.2 g 2-(4-chloro-6-cyclobutylpyrimidin-2-yl)-4-methylthiazole gave 6-cyclobutyl-N-(4,4-difluorocyclohexyl)-2-(4-methylthiazol-2-yl)pyrimidin-4-amine as an off-white solid (0.04 g, 40%). MS (M+1)+=365.0; 1H-NMR (400 MHz, CDCl3): δ 7.00 (s, 1H), 6.14 (s, 1H), 5.09 (s, 1H), 3.79 (s, 1H), 3.61-3.52 (m, 2H), 2.30-2.25 (m, 5H), 2.20-1.85 (m, 8H), 1.70-1.60 (m, 3H).

Example-752

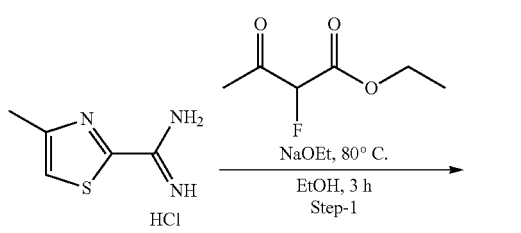

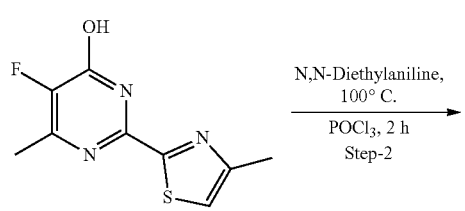

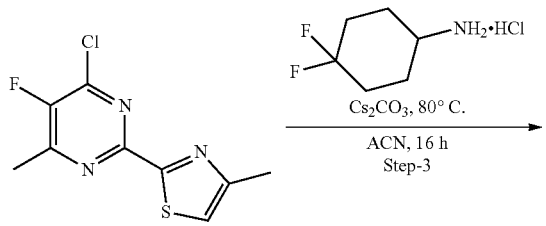

Step 1: The Procedure is similar to Step 1[IN10966-057-P2] in Example-893. 0.5 g of 4-methylthiazole-2-carboximidamide gave 5-fluoro-6-methyl-2-(4-methylthiazol-2-yl)pyrimidin-4-ol as a pale yellow solid (0.4 g, 63%). MS (M+1)+=226.1.

Step 2: The Procedure is similar to Step 2[IN10966-057-P2] in Example-893. 0.2 g 5-fluoro-6-methyl-2-(4-methylthiazol-2-yl)pyrimidin-4-ol gave 2-(4-chloro-5-fluoro-6-methylpyrimidin-2-yl)-4-methylthiazole as a pale yellow solid (0.15 g, 69%). MS (M+1)+=244.0.

Step 3[IN11106-077-P1]: The Procedure is similar to Step 1[B] in Example-838. 0.1 g 2-(4-chloro-5-fluoro-6-methyl-pyrimidin-2-yl)-4-methylthiazole gave N-(4,4-difluorocyclohexyl)-5-fluoro-6-methyl-2-(4-methylthiazol-2-yl)pyrimidin-4-amine as an off-white solid (0.06 g, 43%). MS (M+1)+=343.1; 1H-NMR (400 MHz, DMSO-d6): δ 7.59 (d, J=7.2 Hz, 1H), 7.39 (s, 1H), 4.14-4.12 (m, 1H), 2.43 (s, 3H), 2.32 (s, 3H), 2.12-1.90 (m, 6H), 1.75-1.67 (m, 2H).

Example-753

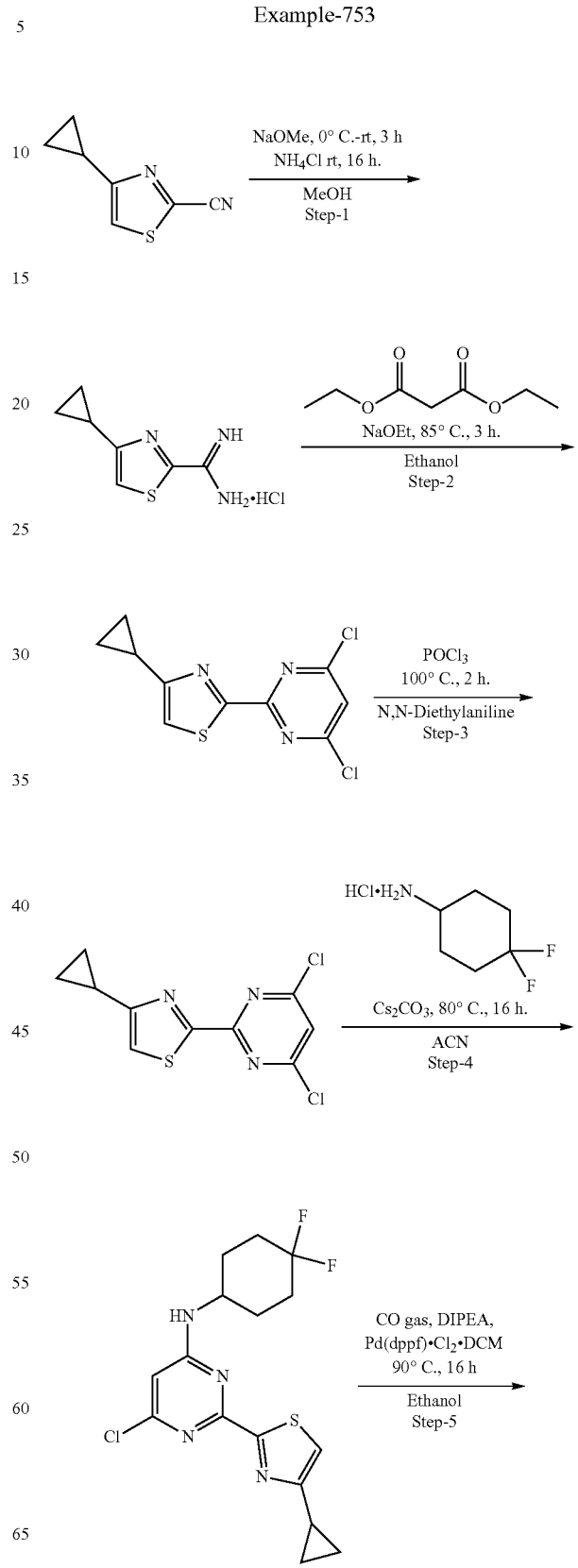

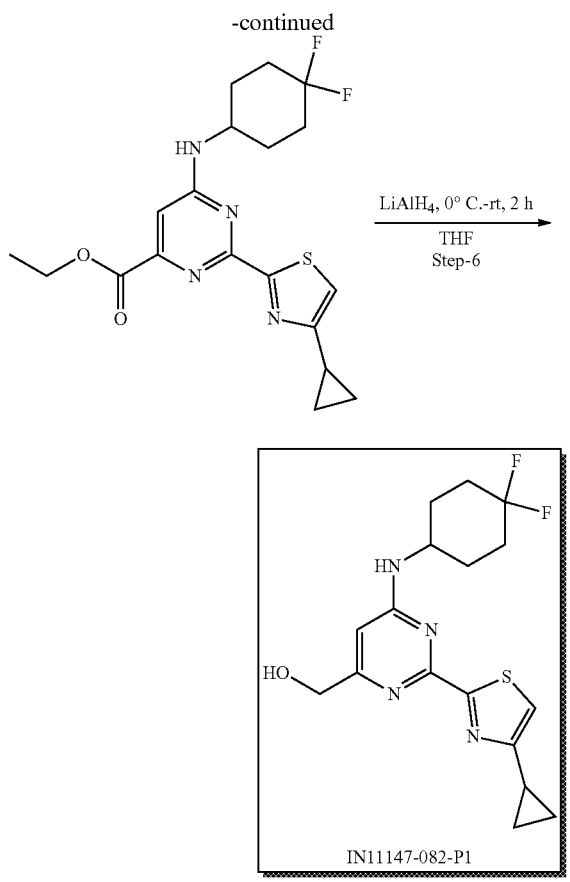

1H), 6.61 (s, 1H), 5.44 (t, J=6.00 Hz, 1H), 4.40 (d, J=5.60 Hz, 2H), 4.02 (s, 1H), 2.80-1.90 (m, 7H), 1.70-1.55 (m, 2H), 0.95-0.89 (m, 4H).

Example-754

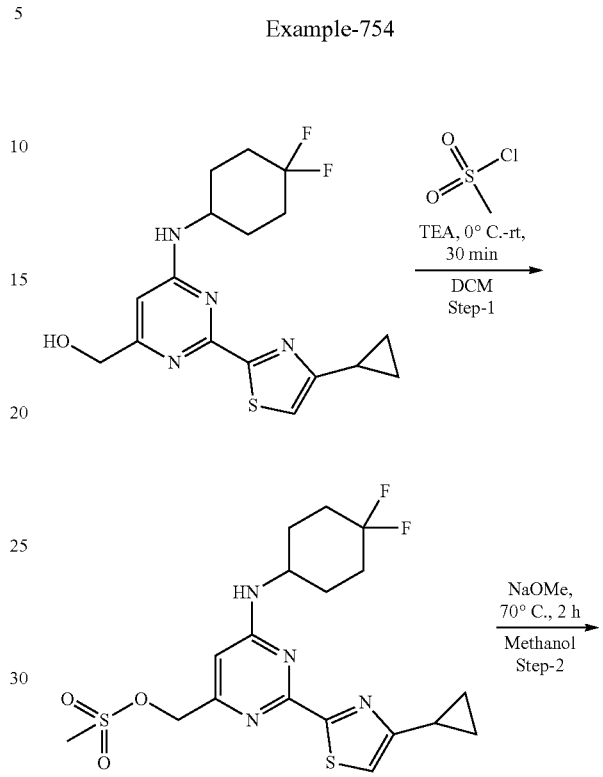

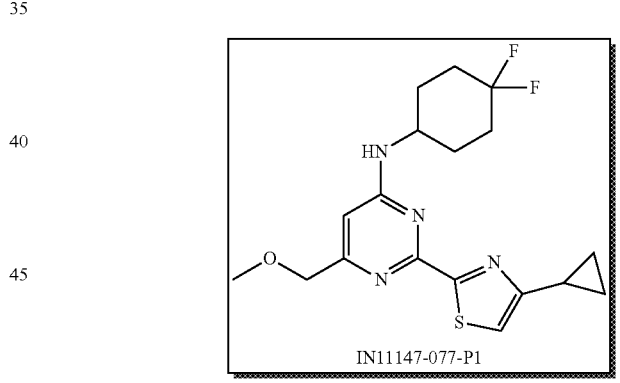

Step 1: 1.7 g of 4-cyclopropylthiazole-2-carbonitrile gave 4-cyclopropylthiazole-2-carboximidamide hydrochloride as a brown gum (2.4 g, 85%). MS (M+1)+=168.1.

Step 2: The Procedure is similar to Step 1[IN10966-057-P2] in Example-893. 1.8 g 4-cyclopropylthiazole-2-carboximidamide hydrochloride gave 2-(4-cyclopropylthiazol-2-yl)pyrimidine-4,6-diol as a pale yellow solid (1.7 g, 81%). MS (M+1)+=236.1.

Step 3: The Procedure is similar to Step 2[IN10966-057-P2] in Example-893. 1.7 g 2-(4-cyclopropylthiazol-2-yl)pyrimidine-4,6-diol gave 4-cyclopropyl-2-(4,6-dichloropyrimidin-2-yl) thiazole as a pale yellow solid (1.8 g, 91%). MS (M+1)+=274.0.

Step 4: The Procedure is similar to Step 1[B] in Example-838. 1.8 g 4-cyclopropyl-2-(4,6-dichloropyrimidin-2-yl) thiazole gave 6-chloro-2-(4-cyclopropylthiazol-2-yl)-N-(4,4-difluorocyclohexyl)pyrimidin-4-amine as a pale yellow solid (2.0 g, 81%). MS (M+1)+=371.1.

Step 5: The Procedure is similar to Step 1[IN11273-018-P1] in Example-889. 0.72 g 6-chloro-2-(4-cyclopropylthiazol-2-yl)-N-(4,4-difluorocyclohexyl)pyrimidin-4-amine gave ethyl 2-(4-cyclopropylthiazol-2-yl)-6-((4,4-difluorocyclohexyl)amino)pyrimidine-4-carboxylate as a pale yellow solid (0.39 g, 48%). MS (M+1)+=409.2.

Step 6[IN11147-082-P1]: The Procedure is similar to Step 4[NSSy6711] in Example-854. 0.3 g ethyl 2-(4-cyclopropylthiazol-2-yl)-6-((4,4-difluorocyclohexyl)amino)pyrimidine-4-carboxylate gave (2-(4-cyclopropylthiazol-2-yl)-6-((4,4-difluorocyclohexyl)amino)pyrimidin-4-yl) methanol as a pale yellow solid (0.095 g, 35%). MS (M+1)+=367.1; 1H-NMR (400 MHz, DMSO-d6): δ 7.60 (s, 1H), 7.36 (s, Step 1: The Procedure is similar to Step 3[IN11273-018-P1] in Example-889. 0.1 g (2-(4-cyclopropylthiazol-2-yl)-6-((4,4-difluorocyclohexyl)amino)pyrimidin-4-yl) methanol gave (2-(4-cyclopropylthiazol-2-yl)-6-((4,4-difluorocyclohexyl)amino)pyrimidin-4-yl)methyl methanesulfonate as a brownish gum (0.12 g, 95%). MS (M+1)+=445.1.

Step 2[IN11147-077-P1]: The Procedure is similar to Step 1[NSSy6519] in Example-842. 0.12 g (2-(4-cyclopropylthiazol-2-yl)-6-((4,4-difluorocyclohexyl)amino)pyrimidin-4-yl)methyl methanesulfonate gave 2-(4-cyclopropylthiazol-2-yl)-N-(4,4-difluorocyclohexyl)-6-(methoxymethyl)pyrimidin-4-amine as a brownish gum (0.055 g, 53%). MS (M+1)+=381.2; 1H-NMR (400 MHz, DMSO-d6): δ 7.63 (s, 1H), 7.38 (s, 1H), 6.52 (s, 1H), 4.35 (s, 2H), 4.10 (s, 1H), 3.40 (s, 3H), 2.15-1.85 (m, 7H), 1.65-1.52 (m, 2H), 0.95-0.80 (m, 4H).

Example-755

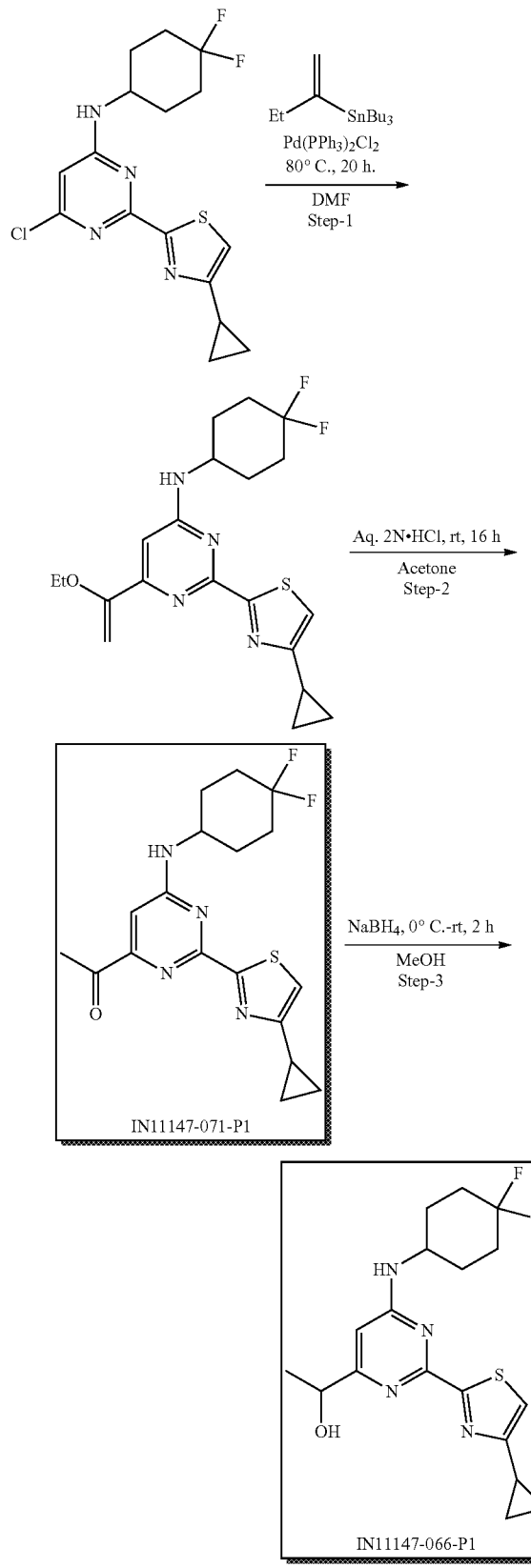

Step 1: The Procedure is similar to Step 1[H] in Example-838. 0.2 g 6-chloro-2-(4-cyclopropylthiazol-2-yl)-N-(4,4-difluorocyclohexyl)pyrimidin-4-amine gave 2-(4-cyclopropylthiazol-2-yl)-N-(4,4-difluorocyclohexyl)-6-(1-ethoxyvinyl)pyrimidin-4-amine as an off-white solid (0.2 g, 46%). MS (M+1)+=407.2.

Step 2[IN11147-071-P1]: The Procedure is similar to Step 1[NSSy6697] in Example-873. 0.2 g 2-(4-cyclopropylthiazol-2-yl)-N-(4,4-difluorocyclohexyl)-6-(1-ethoxyvinyl)pyrimidin-4-amine gave 1-(2-(4-cyclopropylthiazol-2-yl)-6-((4,4-difluorocyclohexyl)amino)pyrimidin-4-yl) ethan-1-one as a white solid (0.15 g, 80%). MS (M+1)+=379.0; 1H-NMR (400 MHz, DMSO-d6): δ 8.02 (d, J=6.80 Hz, 1H), 7.45 (s, 1H), 6.94 (s, 1H), 4.11 (s, 1H), 2.59 (s, 3H), 2.20-1.85 (m, 6H), 1.65-1.55 (m, 2H), 0.98-0.90 (m, 3H), 0.88-0.80 (m, 2H).

Step 3[IN11147-066-P1]: The Procedure is similar to Step 2[NSSy6931] in Example-21. 0.1 g 1-(2-(4-cyclopropylthiazol-2-yl)-6-((4,4-difluorocyclohexyl)amino)pyrimidin-4-yl) ethan-1-one gave 1-(2-(4-cyclopropylthiazol-2-yl)-6-((4,4-difluorocyclohexyl)amino)pyrimidin-4-yl) ethan-1-ol as a white solid (0.056 g, 56%). MS (M+1)+=381.2; 1H-NMR (400 MHz, DMSO-d6): δ 7.60 (s, 1H), 7.36 (s, 1H), 6.63 (s, 1H), 5.41 (d, J=3.6 Hz, 1H), 4.53-4.50 (m, 1H), 4.10 (m, 1H), 2.19-1.91 (m, 7H), 1.61-1.56 (m, 2H), 1.35-1.27 (m, 3H), 0.94-0.88 (m, 2H), 0.86-0.79 (m, 2H).

Example-756

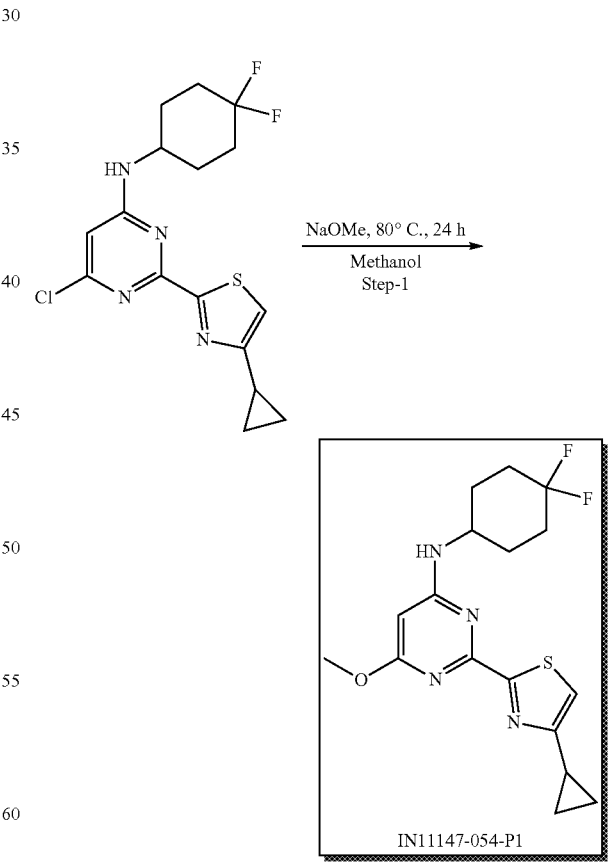

Step 1[IN11147-054-P1]: The Procedure is similar to Step 1[NSSy6519] in Example-842. 0.15 g 6-chloro-2-(4-cyclopropylthiazol-2-yl)-N-(4,4-difluorocyclohexyl)pyrimidin-4-amine gave 2-(4-cyclopropylthiazol-2-yl)-N-(4,4-difluorocyclohexyl)-6-methoxypyrimidin-4-amine as a pale yellow solid (0.045 g, 30%). MS (M+1)$^+$=367.1; $^1$H-NMR (400 MHz, DMSO-d$_6$): δ 7.46 (s, 1H), 7.39 (s, 1H), 5.82 (s, 1H), 3.87 (s, 3H), 2.15-1.85 (m, 8H), 1.62-1.50 (m, 2H), 1.00-0.80 (m, 4H).

Example-757

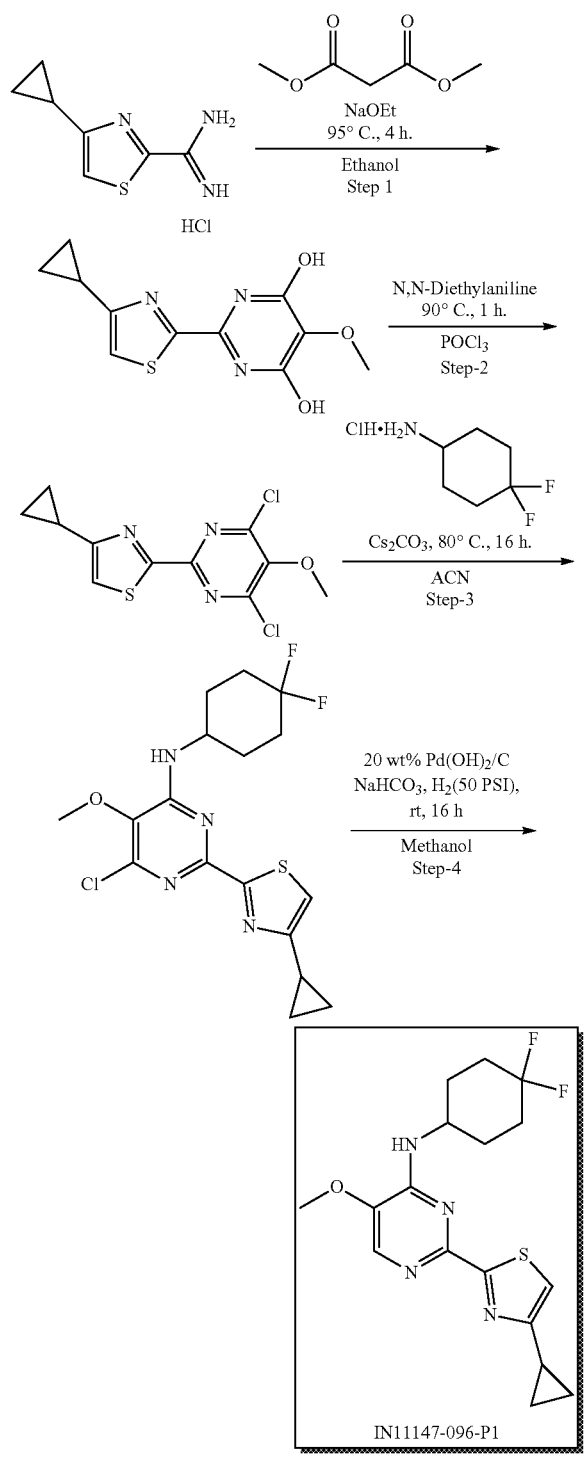

Step 1: The Procedure is similar to Step 1[IN10966-057-P2] in Example-893. 1.0 g 4-cyclopropylthiazole-2-carboxi-midamide gave 2-(4-cyclopropylthiazol-2-yl)-5-methoxy-pyrimidine-4,6-diol as a pale yellow solid (1.2 g, 92%). MS (M+1)+=266.1.

Step 2: The Procedure is similar to Step 2[IN10966-057-P2] in Example-893. 0.6 g 2-(4-cyclopropylthiazol-2-yl)-5-methoxypyrimidine-4,6-diol gave 4-cyclopropyl-2-(4,6-dichloro-5-methoxypyrimidin-2-yl) thiazole as a pale yellow solid (0.38 g, 56%). MS (M+1)+=302.0.

Step 3: The Procedure is similar to Step 1[B] in Example-838. 0.38 g 4-cyclopropyl-2-(4,6-dichloro-5-methoxypyrimidin-2-yl) thiazole gave 6-chloro-2-(4-cyclopropylthiazol-2-yl)-N-(4,4-difluorocyclohexyl)-5-methoxypyrimidin-4-amine as an off-white solid (0.27 g, 53%). MS (M+1)+=401.1.

Step 4[IN11147-096-P1]: The Procedure is similar to Step 4[NSSy6056] in Example-655. 0.15 g 6-chloro-2-(4-cyclopropylthiazol-2-yl)-N-(4,4-difluorocyclohexyl)-5-methoxypyrimidin-4-amine gave 2-(4-cyclopropylthiazol-2-yl)-N-(4,4-difluorocyclohexyl)-5-methoxypyrimidin-4-amine as a white solid (0.075 g, 55%). MS (M+1)+=367.2; 1H-NMR (400 MHz, DMSO-d6): δ 7.87 (s, 1H), 7.29 (s, 1H), 7.09 (d, J=8.00 Hz, 1H), 4.11 (s, 1H), 3.90 (s, 3H), 2.15-1.85 (m, 7H), 1.60 (s, 2H), 0.93-0.90 (m, 2H), 0.88-0.82 (m, 2H).

Example-758

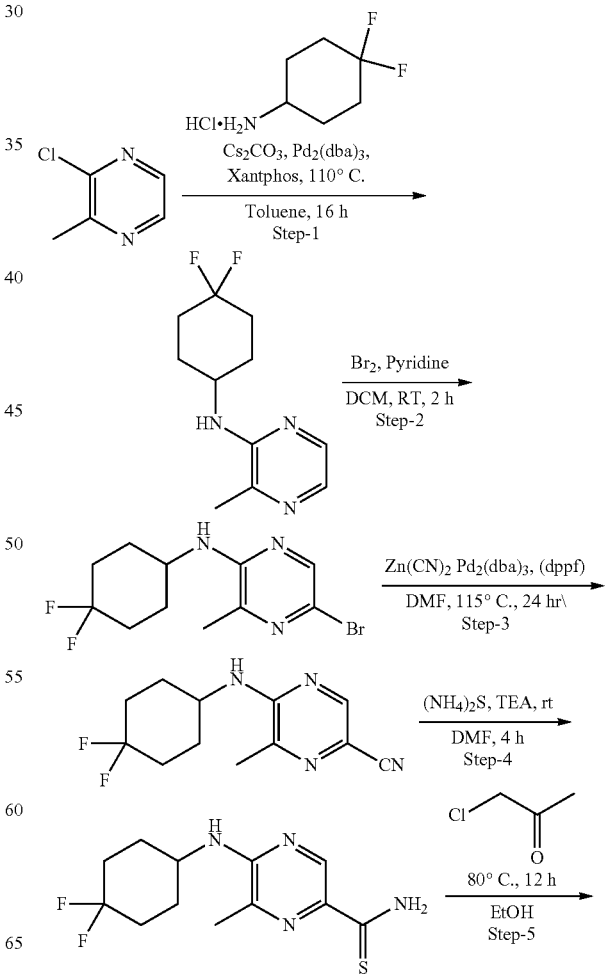

-continued

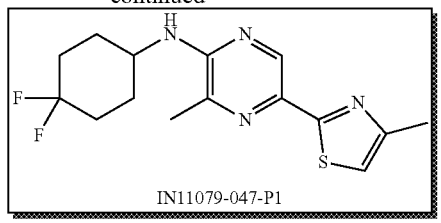

Step 1: The Procedure is similar to Step 1[NSSy6629] in Example-839. 1.0 g 2-chloro-3-methylpyrazine gave N-(4,4-difluorocyclohexyl)-3-methylpyrazin-2-amine as an off-white solid (0.9 g, 48%). MS (M+1)+=228.0.

Step 2: The Procedure is similar to Step 1[NSSy6736] in Example-26. 0.7 g N-(4,4-difluorocyclohexyl)-3-methylpyrazin-2-amine gave 5-bromo-N-(4,4-difluorocyclohexyl)-3-methylpyrazin-2-amine as an off-white solid (0.65 g, 67%). MS (M+1)+=307.0.

Step 3: The Procedure is similar to Step 3[NSSy5933] in Example-808. 0.5 g 5-bromo-N-(4,4-difluorocyclohexyl)-3-methylpyrazin-2-amine gave 5-((4,4-difluorocyclohexyl)amino)-6-methylpyrazine-2-carbonitrile as an off-white solid (0.38 g, 92%). MS (M+1)+=252.0.

Step 4: The Procedure is similar to Step 5[NSSy5779] in Example-642. 0.38 g 5-((4,4-difluorocyclohexyl)amino)-6-methylpyrazine-2-carbonitrile gave 5-((4,4-difluorocyclohexyl)amino)-6-methylpyrazine-2-carbothioamide as an off-white solid (0.2 g, 46%). MS (M+1)+=287.0.

Step 5[IN11079-047-P1]: The Procedure is similar to Step 6[NSSy5779] in Example-642: 0.2 g 5-((4,4-difluorocyclohexyl)amino)-6-methylpyrazine-2-carbothioamide gave N-(4,4-difluorocyclohexyl)-3-methyl-5-(4-methylthiazol-2-yl) pyrazin-2-amine as an off-white solid (0.08 g, 18%). MS (M+1)+=325.0; 1H-NMR (400 MHz, DMSO-d6): δ 8.52 (s, 1H), 7.19 (s, 1H), 6.63 (d, J=8.00 Hz, 1H), 4.15 (s, 1H), 2.50 (s, 3H), 2.50 (s, 3H), 2.10-1.88 (m, 6H), 1.75-1.62 (m, 2H).

Example-759

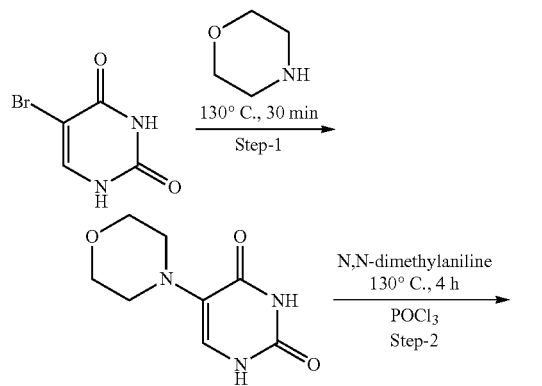

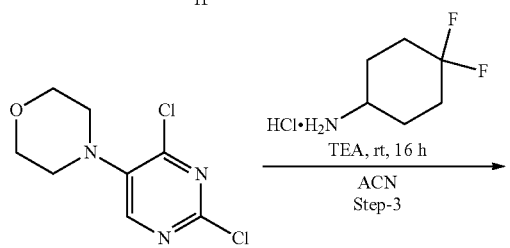

-continued

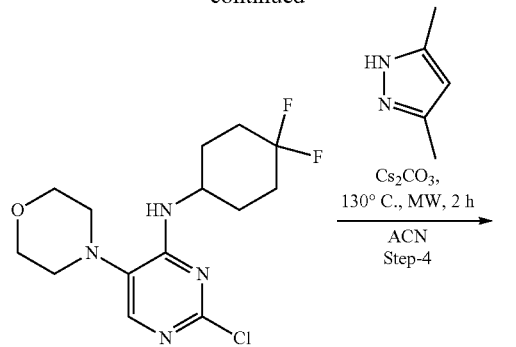

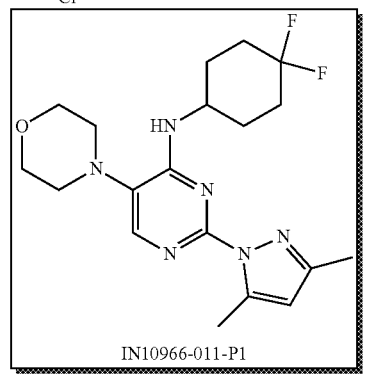

Step 1: The Procedure is similar to Step 1[B] in Example-838. 3.0 g 5-bromopyrimidine-2,4(1H,3H)-dione gave 5-morpholinopyrimidine-2,4(1H,3H)-dione as a white solid (2.7 g, 80%). MS (M+1)+=198.0.

Step 2: The Procedure is similar to Step 2[IN10966-057-P2] in Example-893. 2.7 g 5-morpholinopyrimidine-2,4(1H,3H)-dione gave 4-(2,4-dichloropyrimidin-5-yl) morpholine as an off-white solid (1.4 g, 43%). MS (M+1)+=234.0.

Step 3: The Procedure is similar to Step 1[A] in Example-838. 0.9 g 4-(2,4-dichloropyrimidin-5-yl) morpholine gave 2-chloro-N-(4,4-difluorocyclohexyl)-5-morpholinopyrimidin-4-amine as an off-white solid (0.19 g, 15%). MS (M+1)+=333.0.

Step 4[IN10966-011-P1]: The Procedure is similar to Step 1[NSSy6909] in Example-839. 0.19 g 2-chloro-N-(4,4-difluorocyclohexyl)-5-morpholinopyrimidin-4-amine gave N-(4,4-difluorocyclohexyl)-2-(3,5-dimethyl-1H-pyrazol-1-yl)-5-morpholinopyrimidin-4-amine as an off-white solid (0.033 g, 15%). MS (M+1)+=393.0; 1H-NMR (400 MHz, DMSO-d6): δ 7.93 (s, 1H), 6.60 (s, 1H), 6.03 (s, 1H), 4.10 (s, 1H), 3.78 (s, 4H), 2.84 (s, 4H), 2.52 (s, 3H), 2.15 (s, 3H), 2.10-1.85 (m, 6H), 1.84-1.76 (m, 2H).

Example-760

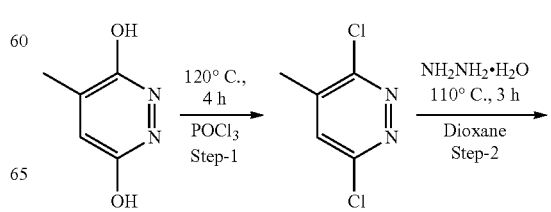

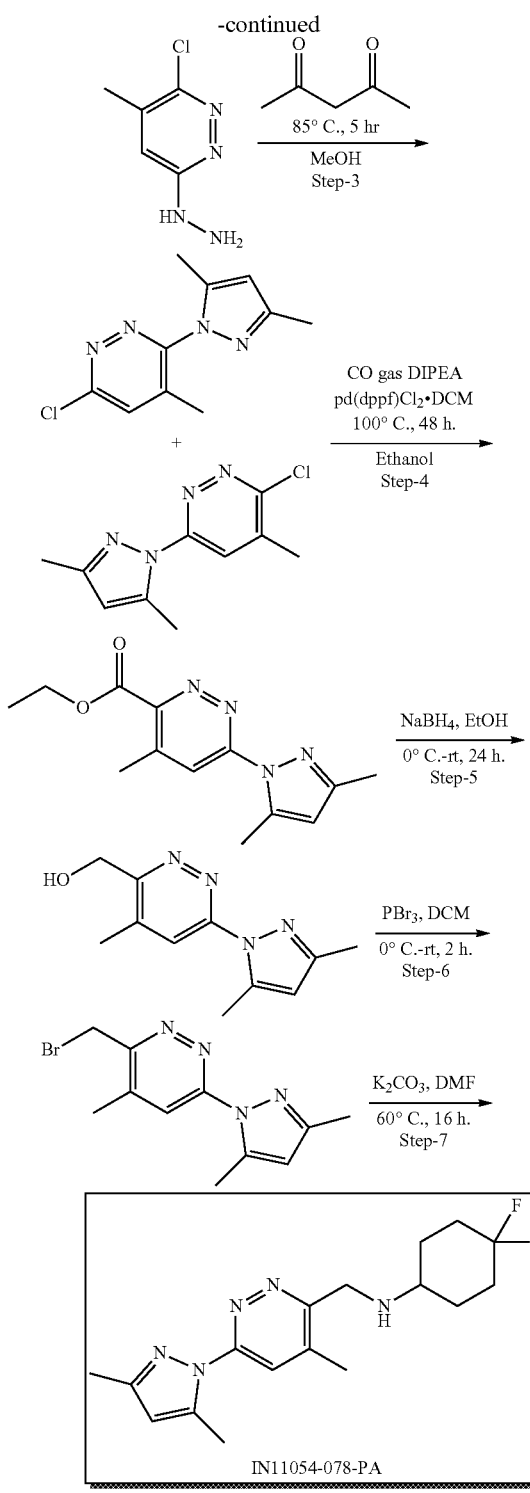

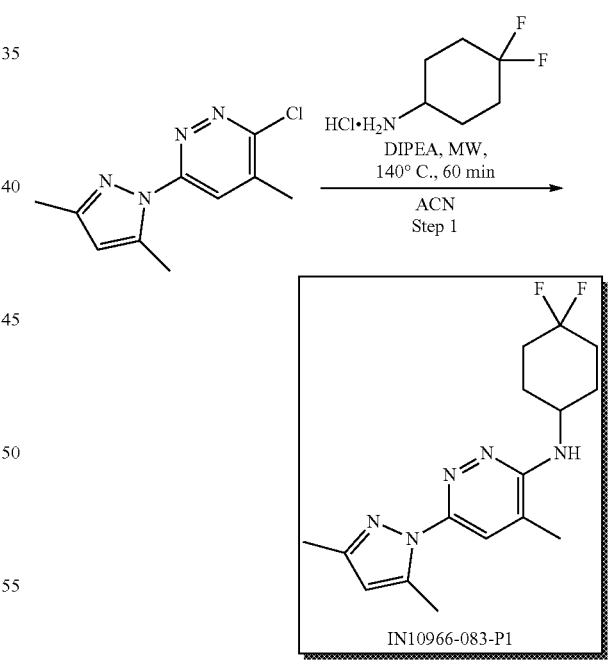

ylpyridazine gave 3-chloro-6-(3,5-dimethyl-1H-pyrazol-1-yl)-4-methylpyridazine as an off-white solid (1.0 g, 90%). MS (M+1)+=223.0.

Step 4: The Procedure is similar to Step 1[IN11273-018-P1] in Example-889. 2.0 g 3-chloro-6-(3,5-dimethyl-1H-pyrazol-1-yl)-4-methylpyridazine gave ethyl 6-(3,5-dimethyl-1H-pyrazol-1-yl)-4-methylpyridazine-3-carboxylate as a white solid (0.8 g, 34%). MS (M+1)+=260.1.

Step 5: The Procedure is similar to Step 2[NSSy6931] in Example-21. 0.5 g ethyl 6-(3,5-dimethyl-1H-pyrazol-1-yl)-4-methylpyridazine-3-carboxylate gave (6-(3,5-dimethyl-1H-pyrazol-1-yl)-4-methylpyridazin-3-yl) methanol as an off-white solid (0.3 g, 75%). MS (M+1)+=219.0.

Step 6: The Procedure is similar to Step 5[IN11059-090-P1] in Example-659. 0.5 g (6-(3,5-dimethyl-1H-pyrazol-1-yl)-4-methylpyridazin-3-yl) methanol gave 3-(bromomethyl)-6-(3,5-dimethyl-1H-pyrazol-1-yl)-4-methylpyridazine as an off-white solid (0.25 g, 39%). MS (M+1)+=282.1.

Step 7[IN11054-078-P1]: The Procedure is similar to Step 1[B] in Example-838. 0.25 g 3-(bromomethyl)-6-(3,5-dimethyl-1H-pyrazol-1-yl)-4-methylpyridazine gave N-((6-(3,5-dimethyl-1H-pyrazol-1-yl)-4-methylpyridazin-3-yl)methyl)-4,4-difluorocyclohexan-1-amine as an off-white solid (0.04 g, 13%). MS (M+1)+=336.1; 1H-NMR (400 MHz, DMSO-d6): δ 7.89 (s, 1H), 6.19 (s, 1H), 4.03 (s, 2H), 2.75-2.65 (m, 1H), 2.60 (s, 3H), 2.46 (s, 3H), 2.22 (s, 3H), 2.10-1.75 (m, 6H), 1.52-1.42 (m, 2H).

Example-761

Step 1: The Procedure is similar to Step 2[IN10966-057-P2] in Example-893. 5.0 g 4-methylpyridazine-3,6-diol gave 3,6-dichloro-4-methylpyridazine as an off-white solid (5.5 g, 85%). MS (M+1)+=163.0.

Step 2: The Procedure is similar to Step 1[IN11054-100-P1] in Example-886. 3.0 g 3,6-dichloro-4-methylpyridazine gave 3-chloro-6-hydrazineyl-4-methylpyridazine as an off-white solid (3.1 g, 80%). MS (M+1)+=159.0.

Step 3: The Procedure is similar to Step 2[IN11054-090-P1] in Example-886. 1.3 g 3-chloro-6-hydrazineyl-4-meth- Step 1[IN10966-083-P1]: The Procedure is similar to Step 1[NSSy6909] in Example-839. 0.2 g 3-chloro-6-(3,5-dimethyl-1H-pyrazol-1-yl)-4-methylpyridazine gave N-(4,4-difluorocyclohexyl)-6-(3,5-dimethyl-1H-pyrazol-1-yl)-4-methylpyridazin-3-amine as an off-white solid (0.13 g, 48%). MS (M+1)+=322.0; 1H-NMR (400 MHz, DMSO-d6): δ 7.55 (s, 1H), 6.07 (s, 2H), 4.25 (bs, 1H), 2.47 (s, 3H), 2.18 (s, 6H), 2.09-2.03 (m, 6H), 1.69-1.67 (m, 2H).

Example-762

Intentionally omitted

Example-763

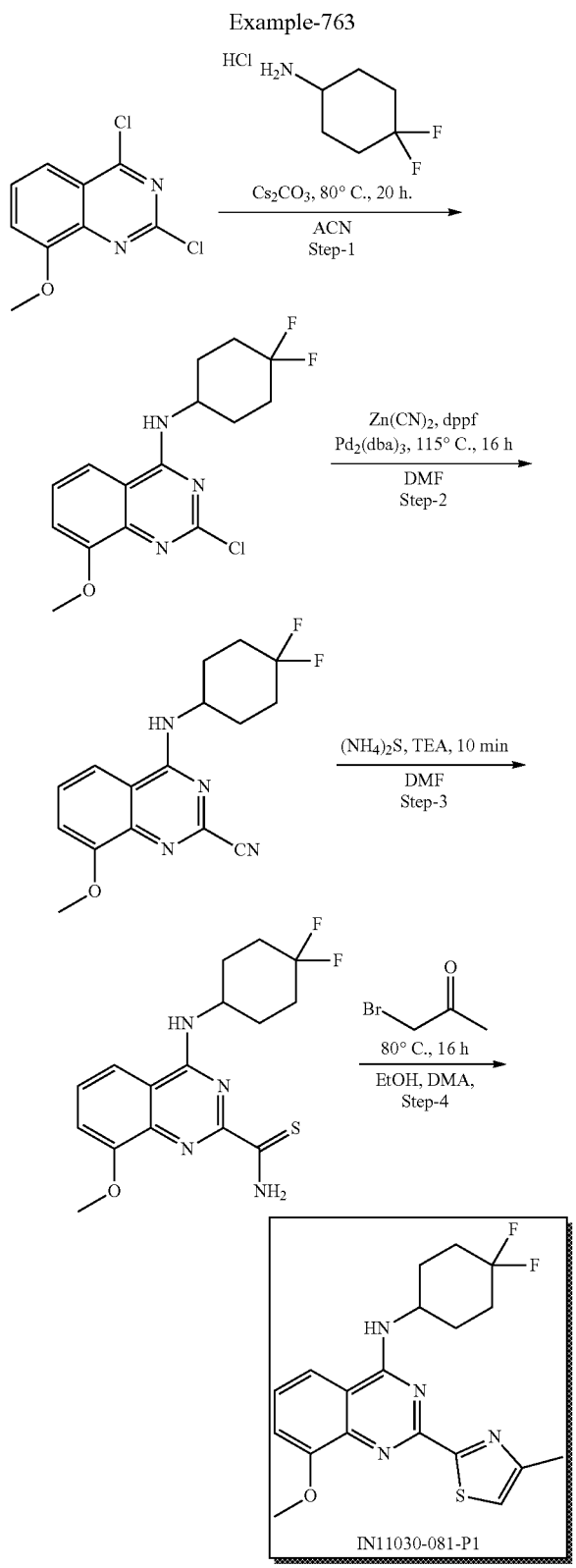

Step 1: The Procedure is similar to Step 1[B] in Example-838. 0.4 g 2,4-dichloro-8-methoxyquinazoline gave of 2-chloro-N-(4,4-difluorocyclohexyl)-8-methoxyquinazolin-4-amine as an off-white solid (0.5 g, 87%). MS (M+1)+= 328.0.

Step 2: The Procedure is similar to Step 3[IN11079-047-P1] in Example-758. 0.5 g of 2-chloro-N-(4,4-difluorocyclohexyl)-8-methoxyquinazolin-4-amine gave 4-((4,4-difluorocyclohexyl)amino)-8-methoxyquinazoline-2-carbonitrile as an off-white solid (0.35 g, 72%). MS (M+1)+=319.0.

Step 3: The Procedure is similar to Step 5[NSSy5779] in Example-642. 0.35 g of 4-((4,4-difluorocyclohexyl)amino)-8-methoxyquinazoline-2-carbonitrile gave 4-((4,4-difluorocyclohexyl)amino)-8-methoxyquinazoline-2-carbothioamide as an off-white solid (0.35 g, 90%). MS (M+1)+=353.1.

Step 4[IN11030-081-P1]: The Procedure is similar to Step 6[NSSy5779] in Example-642. 0.35 g of 4-((4,4-difluorocyclohexyl)amino)-8-methoxyquinazoline-2-carbothioamide gave N-(4,4-difluorocyclohexyl)-8-methoxy-2-(4-methylthiazol-2-yl) quinazolin-4-amine as an off-white solid (0.25 g, 64%). MS (M+1)+=391.0; 1H-NMR (400 MHz, DMSO-d6): δ 8.05 (d, J=6.80 Hz, 1H), 7.87 (d, J=8.40 Hz, 1H), 7.46 (t, J=8.40 Hz, 2H), 7.30 (d, J=7.60 Hz, 1H), 4.35 (s, 1H), 3.95 (s, 3H), 2.48 (s, 3H), 2.20-1.85 (m, 6H), 1.85-1.70 (m, 2H).

Example-764

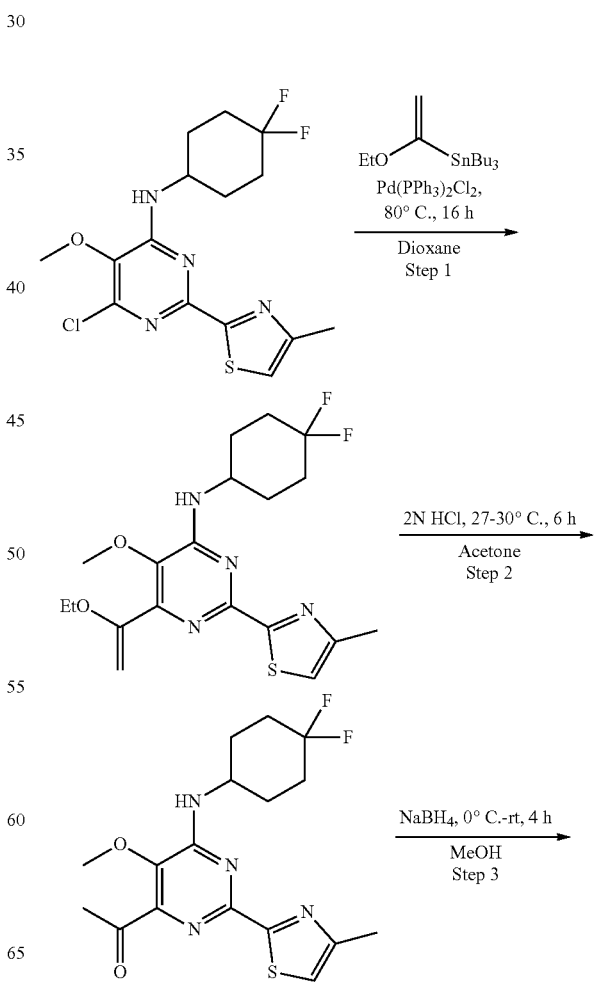

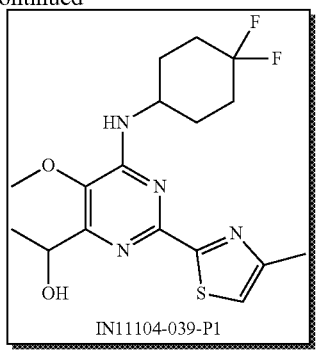

Step 1: The Procedure is similar to Step 1[H] in Example-838. 0.2 g 6-chloro-N-(4,4-difluorocyclohexyl)-5-methoxy-2-(4-methylthiazol-2-yl)pyrimidin-4-amine gave N-(4,4-difluorocyclohexyl)-6-(1-ethoxyvinyl)-5-methoxy-2-(4-methylthiazol-2-yl)pyrimidin-4-amine as an off-white solid (0.13 g, 59%). MS (M+1)+=411.0.

Step 2: The Procedure is similar to Step 1[NSSy6697] in Example-873. 0.13 g of N-(4,4-difluorocyclohexyl)-6-(1-ethoxyvinyl)-5-methoxy-2-(4-methylthiazol-2-yl)pyrimidin-4-amine gave 1-(6-((4,4-difluorocyclohexyl)amino)-5-methoxy-2-(4-methylthiazol-2-yl)pyrimidin-4-yl) ethan-1-one as an off-white solid (0.09 g, 74%). MS (M+1)+=383.0.

Step 3[IN11104-039-P1]: The Procedure is similar to Step 2[NSSy6931] in Example-21. 0.08 g of 1-(6-((4,4-difluorocyclohexyl)amino)-5-methoxy-2-(4-methylthiazol-2-yl)pyrimidin-4-yl)ethan-1-one gave 1-(6-((4,4-difluorocyclohexyl)amino)-5-methoxy-2-(4-methylthiazol-2-yl)pyrimidin-4-yl)ethan-1-ol as an off-white solid (0.07 g, 87%). MS (M+1)+=385.1; 1H-NMR (400 MHz, DMSO-d6): δ 7.36 (s, 1H), 7.18 (d, J=8.00 Hz, 1H), 5.10 (s, 1H), 4.94-4.90 (m, 1H), 3.90 (s, 1H), 3.70 (s, 3H), 3.30 (s, 3H), 2.15-1.85 (m, 6H), 1.85-1.70 (m, 2H), 1.36 (s, 3H).

Example-765

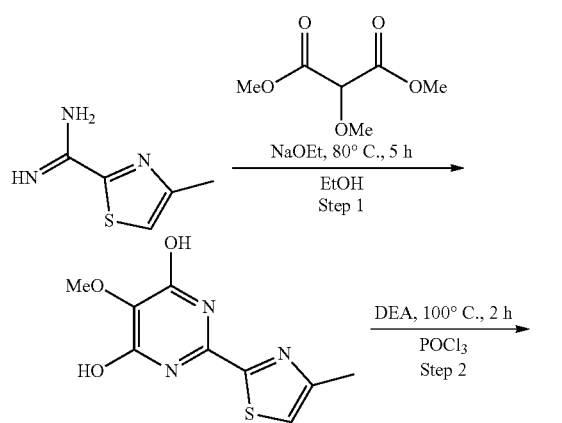

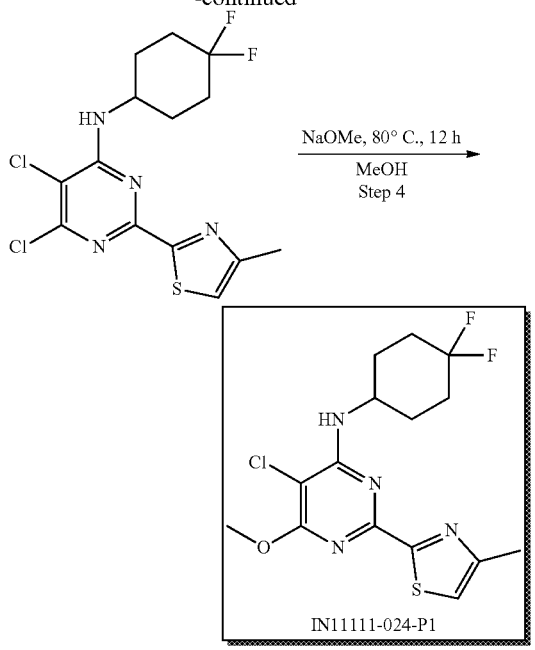

Step 1: The Procedure is similar to Step 1[IN10966-057-P2] in Example-893. 2.0 g 4-methylthiazole-2-carboximidamide gave 5-methoxy-2-(4-methylthiazol-2-yl)pyrimidine-4,6-diol as a pale yellow solid (1.8 g, 66%). MS (M+1)+=240.0.

Step 2: The Procedure is similar to Step 2[IN10966-057-P2] in Example-893. 1.8 g of 5-methoxy-2-(4-methylthiazol-2-yl)pyrimidine-4,6-diol gave 4-methyl-2-(4,5,6-trichloropyrimidin-2-yl) thiazole as a pale yellow solid (0.6 g, 28%). MS (M+1)+=282.0.

Step 3: The Procedure is similar to Step 1[B] in Example-838. 0.4 g of 4-methyl-2-(4,5,6-trichloropyrimidin-2-yl) thiazole gave 5,6-dichloro-N-(4,4-difluorocyclohexyl)-2-(4-methylthiazol-2-yl)pyrimidin-4-amine as an off-white solid (0.3 g, 55%). MS (M+1)+=378.9.

Step 4[IN11111-024-P1]: The Procedure is similar to Step 1[NSSy6519] in Example-842. 0.2 g of 5,6-dichloro-N-(4,4-difluorocyclohexyl)-2-(4-methylthiazol-2-yl)pyrimidin-4-amine gave 5-chloro-N-(4,4-difluorocyclohexyl)-6-methoxy-2-(4-methylthiazol-2-yl)pyrimidin-4-amine as an off-white solid (0.18 g, 91%). MS (M+1)+=375.0; 1H-NMR (400 MHz, DMSO-d6): δ 7.49 (s, 1H), 7.10 (d, J=7.60 Hz, 1H), 4.18 (s, 1H), 4.02 (s, 3H), 2.48 (s, 3H), 2.15-1.90 (m, 6H), 1.88-1.72 (m, 2H).

Example-766

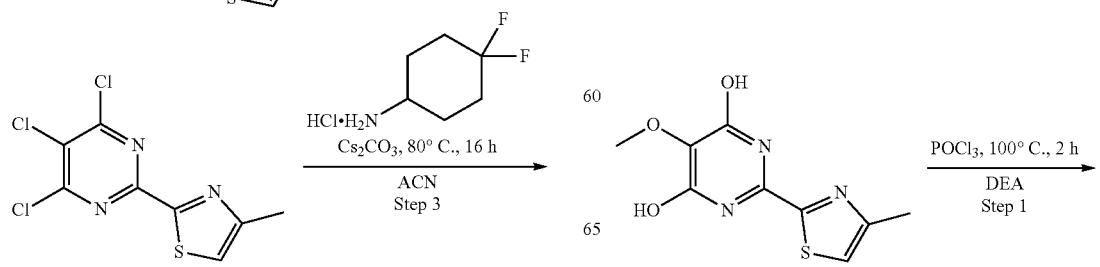

-continued

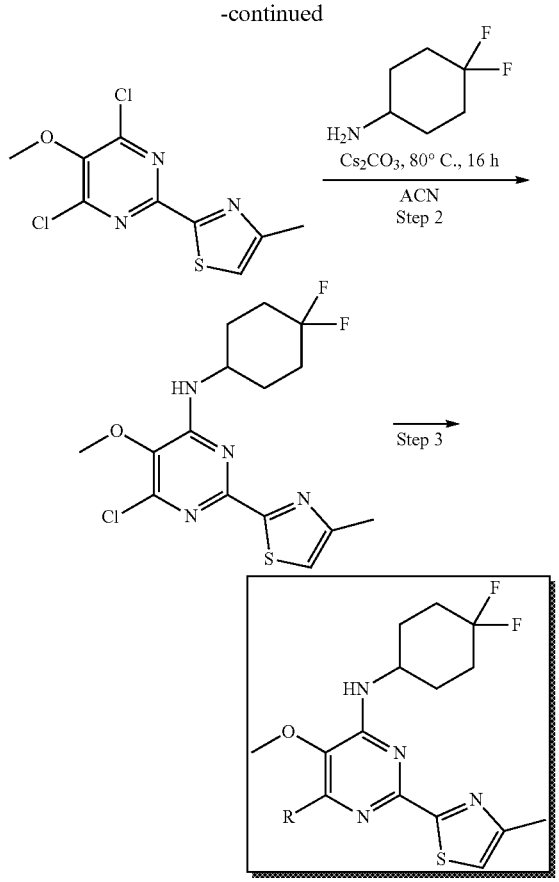

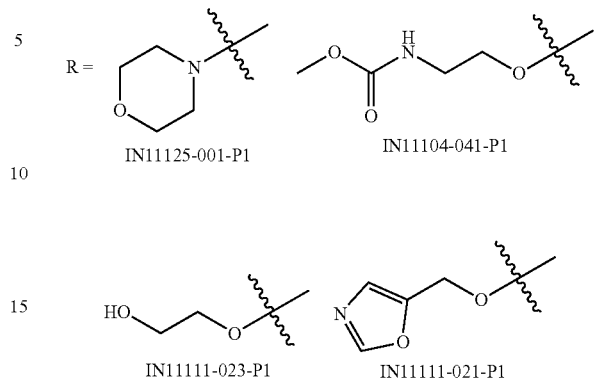

R=

IN11125-001-P1

IN11104-041-P1

IN11111-023-P1

IN11111-021-P1

Step 1: The Procedure is similar to Step 2[IN10966-057-P2] in Example-893. 1.36 g 5-methoxy-2-(4-methylthiazol-2-yl)pyrimidine-4,6-diol gave 2-(4,6-dichloro-5-methoxy-pyrimidin-2-yl)-4-methylthiazole as a pale yellow solid (0.53 g, 33%). MS (M+1)+=275.9.

Step 2: The Procedure is similar to Step 1[B] in Example-838. 0.53 g of 2-(4,6-dichloro-5-methoxypyrimidin-2-yl)-4-methylthiazole gave 6-chloro-N-(4,4-difluorocyclohexyl)-5-methoxy-2-(4-methylthiazol-2-yl)pyrimidin-4-amine as a pale yellow solid (0.53 g, 73%). MS (M+1)+=375.0.

TABLE 80

| | Step 3: | | | |
|---|---|---|---|---|
| Compound No | R | Condition | Yield (%) | MS (M + 1)+ |
| IN11125-001-P1 | *morpholine* | Cs$_2$CO$_3$, ACN, 80° C., 24 h | 29 | 426.1 |
| IN11104-041-P1 | *methyl carbamate ethoxy* | DIPEA, 0° C.-rt, DCM, 2 h | 27 | 458.1 |
| IN11111-023-P1 | *HO-ethoxy* | Step a: 2-(tert-butoxy)ethan-1-ol, NaH, THF, 70° C., 3 h Step b: 6(N) HCl, 55° C., 1 h | 90/ 45 | 457.0/ 401.0 |
| IN11111-021-P1 | *oxazol-5-ylmethoxy* | NaH, THF, 70° C., 3 h | 68 | 438.0 |

Step 3[IN11125-001-P1]: The procedure is similar to step 1[B] in Example-838. $^1$H-NMR (400 MHz, DMSO-d$_6$): δ 7.32 (d, J=1.20 Hz, 1H), 6.66 (d, J=8.00 Hz, 1H), 4.07 (s, 1H), 3.77-3.71 (m, 4H), 3.65-3.59 (m, 7H), 2.49 (s, 3H), 2.15-1.85 (m, 6H), 1.80-1.65 (m, 2H).

Step 3[IN11104-041-P1]: The procedure is similar to step 1[A] in Example-838. 1H-NMR (400 MHz, DMSO-d6): δ 7.37 (s, 1H), 7.34 (s, 1H), 6.88 (d, J=8.00 Hz, 1H), 4.37 (t, J=5.20 Hz, 2H), 4.07 (s, 1H), 3.71 (s, 3H), 3.52 (s, 3H), 3.41 (q, J=4.80 Hz, 2H), 2.43 (s, 3H), 2.15-1.85 (m, 6H), 1.80-1.65 (m, 2H).

Step 3[IN11111-023-P1]: Step a: The procedure is similar to Step 2[IN10991-021-P1] in Example-694. Step b: The procedure is similar to Step 1[NSSy6697] in Example-873. 1H-NMR (400 MHz, DMSO-d6): δ 7.37 (s, 1H), 6.88 (d, J=8.00 Hz, 1H), 4.85 (t, J=5.20 Hz, 1H), 4.40 (t, J=5.20 Hz, 1H), 4.08 (s, 1H), 3.76-3.73 (m, 5H), 3.57 (s, 1H), 2.43 (s, 3H), 2.15-1.85 (m, 6H), 1.80-1.62 (m, 2H).

Step 4[IN11111-021-P1]: The procedure is similar to Step 2[IN10991-021-P1] in Example-694. 1H-NMR (400 MHz, DMSO-d6): δ 8.41 (s, 1H), 7.41 (d, J=4.40 Hz, 2H), 7.00 (d, J=7.60 Hz, 1H), 5.52 (s, 2H), 4.08 (s, 1H), 3.66 (s, 3H), 2.45 (s, 3H), 2.15-1.85 (m, 6H), 1.75-1.65 (m, 2H).

Example-767

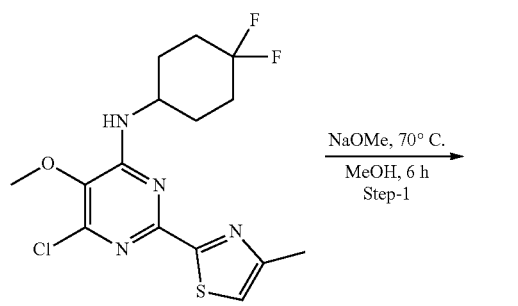

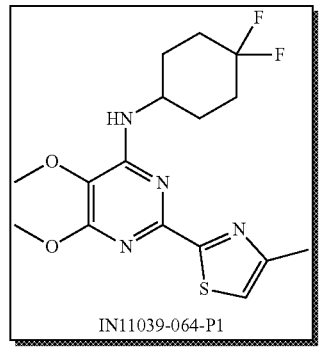

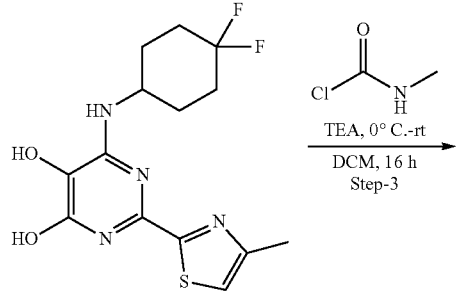

Step 1[IN11039-064-P1]: The Procedure is similar to Step 1[NSSy6519] in Example-842. 0.8 g 6-chloro-N-(4,4-difluorocyclohexyl)-5-methoxy-2-(4-methylthiazol-2-yl)pyrimidin-4-amine gave N-(4,4-difluorocyclohexyl)-5,6-dimethoxy-2-(4-methylthiazol-2-yl)pyrimidin-4-amine as an off-white solid (0.75 g, 95%). MS (M+1)+=371.1; 1H-NMR (400 MHz, CDCl3): δ 6.97 (s, 1H), 5.03 (d, J=7.60 Hz, 1H), 4.21-4.19 (m, 1H), 1.00 (s, 3H), 3.84 (s, 3H), 2.55 (s, 3H), 2.20-1.85 (m, 6H), 1.70-1.60 (m, 2H).

Step 2: To a stirred solution of N-(4,4-difluorocyclohexyl)-5,6-dimethoxy-2-(4-methylthiazol-2-yl)pyrimidin-4-amine (0.25 g, 0.13 mmol) in HBr in acetic acid (2.5 mL) was heated at 80° C. under nitrogen atmosphere for 16 h. Reaction mixture was allowed to cool down and quenched with water (5 mL), the precipitate was filtered off and solids were dissolved in ethyl acetate (50 mL) and washed with saturated bicarbonate solution, dried over sodium sulfate, filtered and concentrated under reduced pressure to afford as a dark green solid (0.22 g, 95%). MS (M+1)+=343.0

Step 3[IN11125-006-P1]: The Procedure is similar to Step 1[A] in Example-838. 0.1 g of 6-((4,4-difluorocyclohexyl)amino)-2-(4-methylthiazol-2-yl)pyrimidine-4,5-diol gave 4-((4,4-difluorocyclohexyl)amino)-6-hydroxy-2-(4-methylthiazol-2-yl)pyrimidin-5-yl methylcarbamate as a pale green solid (0.035 g, 30%). MS (M+1)+=400.0; 1H-NMR (400 MHz, DMSO-d6): δ 12.10 (s, 1H), 7.57 (s, 1H), 7.37 (s, 1H), 6.68 (s, 1H), 3.99 (s, 1H), 2.65 (d, J=4.40 Hz, 3H), 2.42 (s, 3H), 2.15-1.80 (m, 6H), 1.80-1.60 (m, 2H).

Example-768

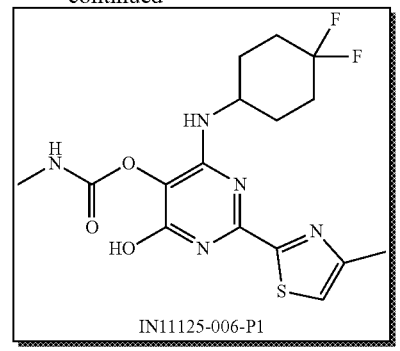

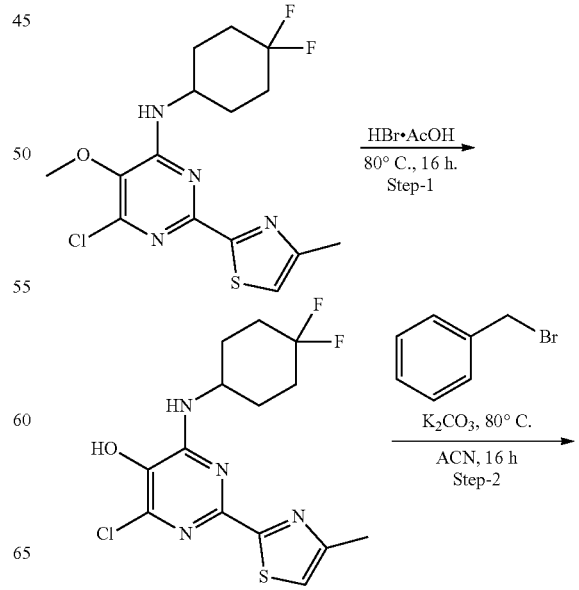

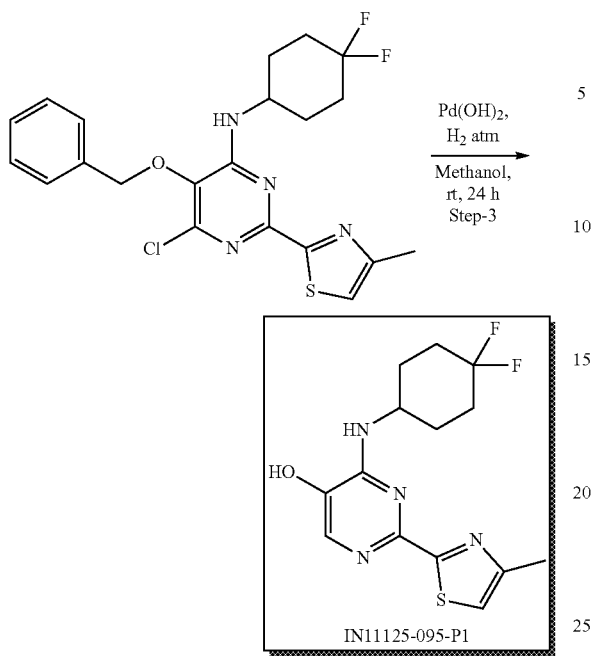

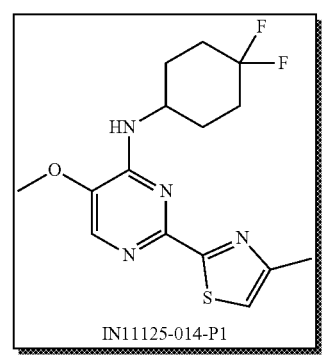

Step 1[IN11125-014-P1]: The Procedure is similar to Step 4[NSSy6056] in Example-655. 0.1 g of 6-chloro-N-(4,4-difluorocyclohexyl)-5-methoxy-2-(4-methylthiazol-2-yl)pyrimidin-4-amine gave N-(4,4-difluorocyclohexyl)-5-methoxy-2-(4-methylthiazol-2-yl)pyrimidin-4-amine as a white solid (0.045 g, 80%). MS (M+1)+=341.1; 1H-NMR (400 MHz, DMSO-d6): δ 7.88 (s, 1H), 7.31 (s, 1H), 7.07 (d, J=8.00 Hz, 1H), 4.15 (s, 1H), 3.90 (s, 3H), 2.42 (s, 3H), 2.15-1.65 (m, 8H).

Step 1: The Procedure is similar to Step 2[IN11125-006-P1] in Example-767. 2.0 g of 6-chloro-N-(4,4-difluorocyclohexyl)-5-methoxy-2-(4-methylthiazol-2-yl)pyrimidin-4-amine gave 4-chloro-6-((4,4-difluorocyclohexyl)amino)-2-(4-methylthiazol-2-yl)pyrimidin-5-ol as a pale yellow solid (2.2 g, 80%). MS (M+1)+=361.0.

Step 2: The Procedure is similar to Step 1[B] in Example-838. 0.25 g of 4-chloro-6-((4,4-difluorocyclohexyl)amino)-2-(4-methylthiazol-2-yl)pyrimidin-5-ol gave 5-(benzyloxy)-6-chloro-N-(4,4-difluorocyclohexyl)-2-(4-methylthiazol-2-yl)pyrimidin-4-amine as a white solid (0.2 g, 64%). MS (M+1)+=451.1.

Step 3[IN11125-095-P1]: The Procedure is similar to Step 4[NSSy6056] in Example-655. 0.2 g of 5-(benzyloxy)-6-chloro-N-(4,4-difluorocyclohexyl)-2-(4-methylthiazol-2-yl)pyrimidin-4-amine gave 4-((4,4-difluorocyclohexyl)amino)-2-(4-methylthiazol-2-yl)pyrimidin-5-ol as an off-white solid (0.025 g, 17%). MS (M+1)+=327.1; 1H-NMR (400 MHz, CD3OD): δ 7.56 (s, 1H), 7.22 (s, 1H), 4.32 (m, 1H), 2.49 (s, 3H), 2.11-1.93 (m, 6H), 1.77-1.71 (m, 2H).

Example-769

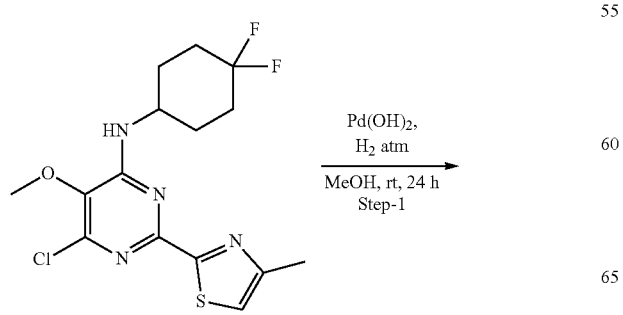

Example-770

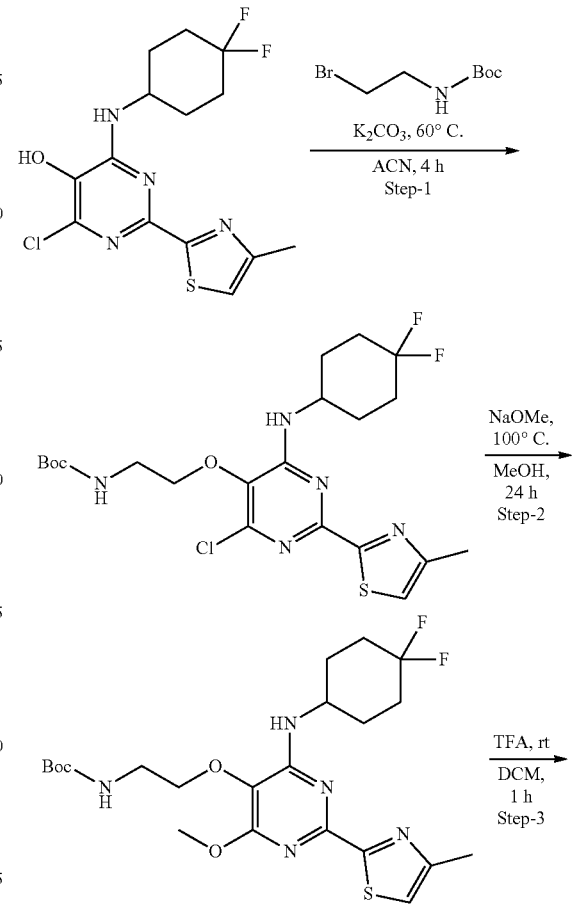

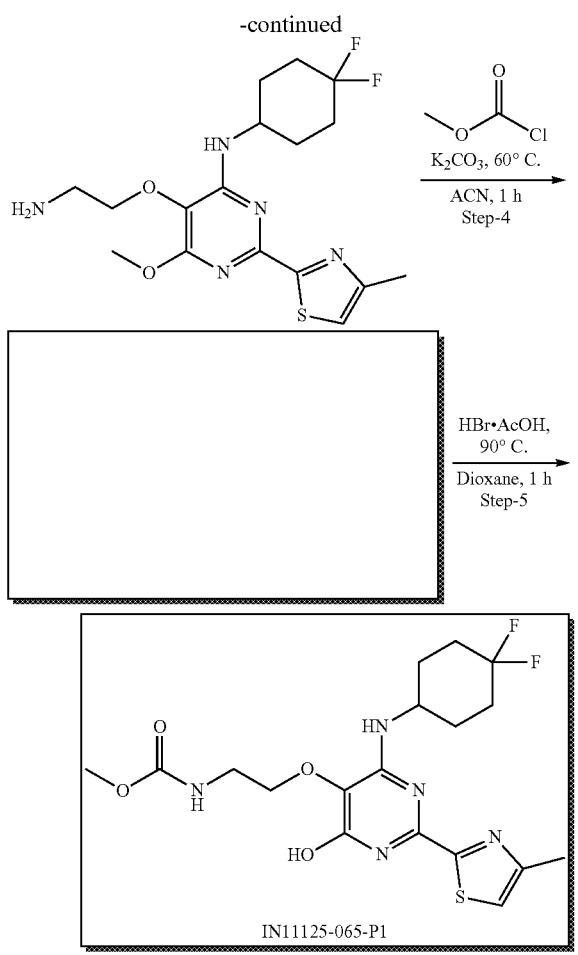

Step 5[IN11125-065-P1]: The Procedure is similar to Step 2[IN11125-006-P1] in Example-767. 0.1 g of methyl (2-((4-((4,4-difluorocyclohexyl)amino)-6-methoxy-2-(4-methylthiazol-2-yl)pyrimidin-5-yl)oxy)ethyl)carbamate gave methyl (2-((4-((4,4-difluorocyclohexyl)amino)-6-hydroxy-2-(4-methylthiazol-2-yl)pyrimidin-5-yl)oxy)ethyl)carbamate as a pale yellow solid (0.06 g, 62%). MS (M+1)+=444.0; 1H-NMR (400 MHz, CD3OD): δ 7.40 (s, 1H), 4.13-4.03 (m, 3H), 3.65 (s, 3H), 3.41-3.39 (m, 2H), 2.50 (s, 3H), 2.16-1.88 (m, 6H), 1.79-1.71 (m, 2H).

Example-771

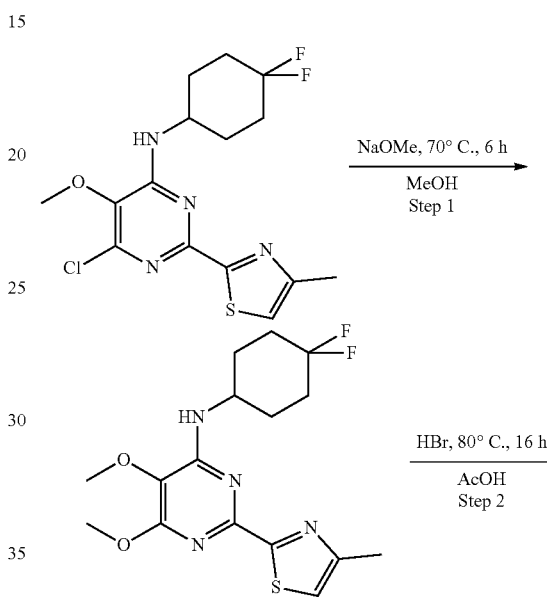

Step 1: The Procedure is similar to Step 1[B] in Example-838. 0.3 g of 4-chloro-6-((4,4-difluorocyclohexyl)amino)-2-(4-methylthiazol-2-yl)pyrimidin-5-ol gave tert-butyl (2-((4-chloro-6-((4,4-difluorocyclohexyl)amino)-2-(4-methylthiazol-2-yl)pyrimidin-5-yl)oxy)ethyl)carbamate as a pale yellow solid (0.21 g, 50%). MS (M+1)+=504.0.

Step 2: The Procedure is similar to Step 1[NSSy6519] in Example-842. 0.21 g of tert-butyl (2-((4-chloro-6-((4,4-difluorocyclohexyl)amino)-2-(4-methylthiazol-2-yl)pyrimidin-5-yl)oxy)ethyl)carbamate gave tert-butyl (2-((4-((4,4-difluorocyclohexyl)amino)-6-methoxy-2-(4-methylthiazol-2-yl)pyrimidin-5-yl)oxy)ethyl)carbamate as a pale yellow solid (0.18 g, 86%). MS (M+1)+=500.1.

Step 3: The Procedure is similar to Step 5[NSSy6067] in Example-628. 0.18 g of tert-butyl (2-((4-((4,4-difluorocyclohexyl)amino)-6-methoxy-2-(4-methylthiazol-2-yl)pyrimidin-5-yl)oxy)ethyl)carbamate gave 5-(2-aminoethoxy)-N-(4,4-difluorocyclohexyl)-6-methoxy-2-(4-methylthiazol-2-yl)pyrimidin-4-amine as a pale yellow gum (0.14 g, 96%). MS (M+1)+=400.1.

Step 4[IN11125-052-P1]: The Procedure is similar to Step 1[B] in Example-838. 0.08 g of 5-(2-aminoethoxy)-N-(4,4-difluorocyclohexyl)-6-methoxy-2-(4-methylthiazol-2-yl)pyrimidin-4-amine gave methyl (2-((4-((4,4-difluorocyclohexyl)amino)-6-methoxy-2-(4-methylthiazol-2-yl)pyrimidin-5-yl)oxy)ethyl)carbamate as a pale yellow solid (0.055 g, 60%). MS (M+1)+=458.1; 1H-NMR (400 MHz, MeOD): δ 7.23 (s, 1H), 4.20 (s, 1H), 3.80 (s, 5H), 3.55 (s, 3H), 3.40 (t, J=4.80 Hz, 2H), 2.50 (s, 3H), 2.15-1.80 (m, 6H), 1.75-1.65 (m, 2H).

Step 1: The Procedure is similar to Step 1[NSSy6519] in Example-842. 0.4 g of 6-chloro-N-(4,4-difluorocyclohexyl)-5-methoxy-2-(4-methylthiazol-2-yl)pyrimidin-4-amine gave N-(4,4-difluorocyclohexyl)-5,6-dimethoxy-2-(4-methylthiazol-2-yl)pyrimidin-4-amine as an off-white solid (0.351 g, 88%). MS (M+1)+=371.0.

Step 2[IN11039-094-P1]: The Procedure is similar to Step 2[IN11125-006-P1] in Example-767. 0.25 g of N-(4,4-difluorocyclohexyl)-5,6-dimethoxy-2-(4-methylthiazol-2-yl)pyrimidin-4-amine gave 6-((4,4-difluorocyclohexyl)amino)-2-(4-methylthiazol-2-yl) pyrimidine-4,5-diol as an off-white solid (0.22 g, 95%). MS (M+1)+=343.0; 1H-NMR (400 MHz, DMSO-d6): δ 11.95 (bs, 1H), 9.05 (bs, 1H), 7.42 (s, 1H), 6.05 (d, J=6.8 Hz, 1H), 4.06-3.95 (m, 1H), 2.42 (s, 3H), 2.12-1.86 (m, 6H), 1.73-1.64 (m, 2H).

Example-772

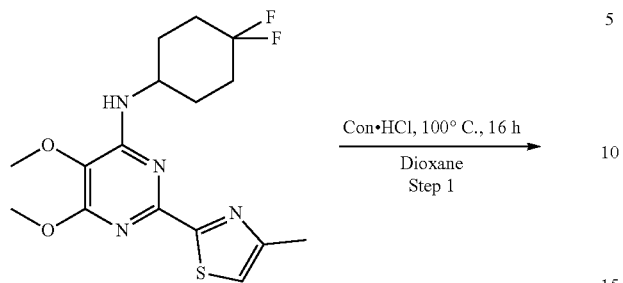

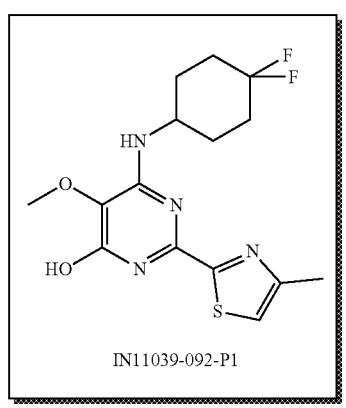

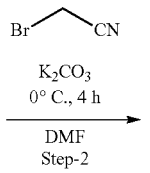

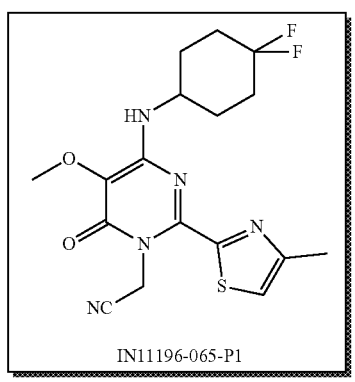

Step 1[IN11039-092-P1]: The Procedure is similar to Step 1[NSSy6972] in Example-615. 0.05 g of N-(4,4-difluorocyclohexyl)-5,6-dimethoxy-2-(4-methylthiazol-2-yl)pyrimidin-4-amine gave 4-((4,4-difluorocyclohexyl)amino)-6-methoxy-2-(4-methylthiazol-2-yl)pyrimidin-5-ol as a pale yellow solid (0.03 g, 62%). MS (M+1)+=371.0; 1H-NMR (400 MHz, DMSO-d6): δ 11.95 (bs, 1H), 7.51 (s, 1H), 6.58-6.56 (m, 1H), 4.01-3.90 (m, 1H), 3.68 (s, 3H), 2.44 (s, 3H), 2.09-1.92 (m, 6H), 1.71-1.68 (m, 2H).

Step 2[IN11196-065-P1]: The Procedure is similar to Step 1[NSSy6972] in Example-615. 0.16 g of N-(4,4-difluorocyclohexyl)-5,6-dimethoxy-2-(4-methylthiazol-2-yl)pyrimidin-4-amine gave 4-((4,4-difluorocyclohexyl)amino)-6-methoxy-2-(4-methylthiazol-2-yl)pyrimidin-5-ol as an off-white solid (0.04 g, 22%). MS (M+1)+=366.2; 1H-NMR (400 MHz, DMSO-d6): δ 7.70 (s, 1H), 6.90 (d, J=7.20 Hz, 1H), 5.64 (s, 2H), 3.96 (s, 1H), 3.71 (s, 3H), 2.30 (s, 3H), 2.15-1.85 (m, 6H), 1.75-1.65 (m, 2H).

Example-773

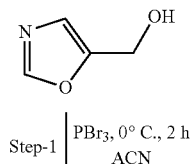

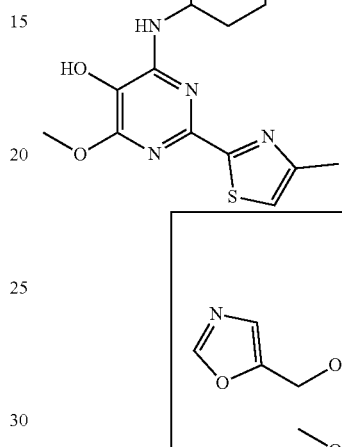

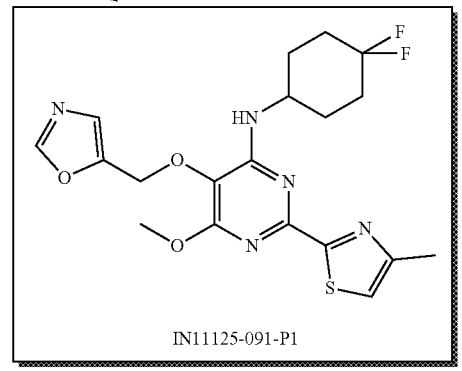

Step 1: The Procedure is similar to Step 3[IN11059-090-P1] in Example-659. 0.075 g of oxazol-5-ylmethanol gave 5-(bromomethyl) oxazole as a brown liquid (0.1 g). MS (M+1)+=163.0.

Step 2[IN11125-091-P1]: The Procedure is similar to Step [B] in Example-838. 0.090 g of 4-((4,4-difluorocyclohexyl)amino)-6-methoxy-2-(4-methylthiazol-2-yl)pyrimidin-5-ol gave N-(4,4-difluorocyclohexyl)-6-methoxy-2-(4-methylthiazol-2-yl)-5-(oxazol-5-ylmethoxy)pyrimidin-4-amine as an off-white solid (0.07 g, 63%). MS (M+1)+=438.2; 1H-NMR (400 MHz, MeOD): δ 8.20 (s, 1H), 7.24 (s, 1H), 7.13 (s, 1H), 5.13 (s, 2H), 4.24-4.21 (m, 1H), 4.06 (s, 3H), 3.90 (s, 3H), 2.20-1.90 (m, 7H), 1.65-1.55 (m, 2H).

Example-774

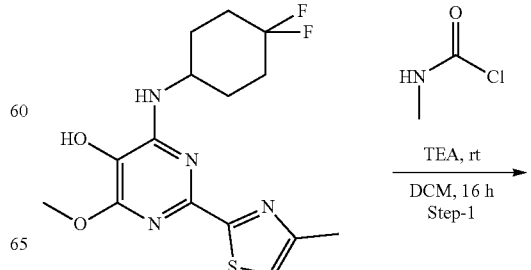

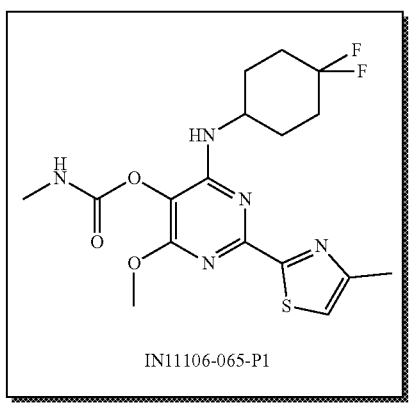

Step 1[IN11106-065-P1]: The Procedure is similar to Step 1[A] in Example-838. 0.1 g of 4-((4,4-difluorocyclohexyl)amino)-6-methoxy-2-(4-methylthiazol-2-yl)pyrimidin-5-ol gave 4-((4,4-difluorocyclohexyl)amino)-6-methoxy-2-(4-methylthiazol-2-yl)pyrimidin-5-yl methylcarbamate as an off-white solid (0.07 g, 63%). MS (M+1)+=414.0; 1H-NMR (400 MHz, DMSO-d6): δ 7.54-7.50 (m, 1H), 7.41 (d, J=0.80 Hz, 1H), 6.99 (d, J=7.20 Hz, 1H), 4.10 (s, 1H), 3.90 (s, 1H), 2.67 (d, J=4.40 Hz, 3H), 2.49 (s, 3H), 2.15-1.85 (m, 6H), 1.75-1.65 (m, 2H).

Example-775

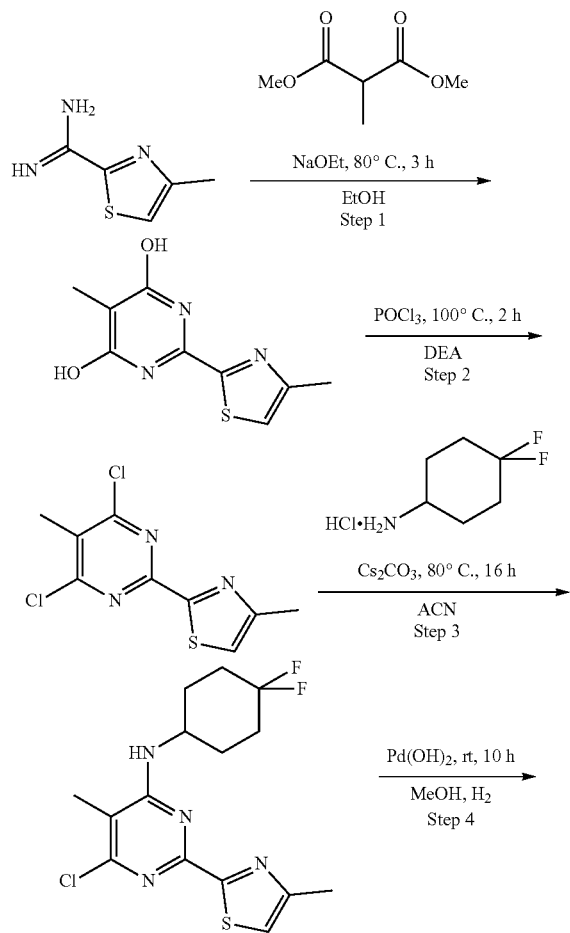

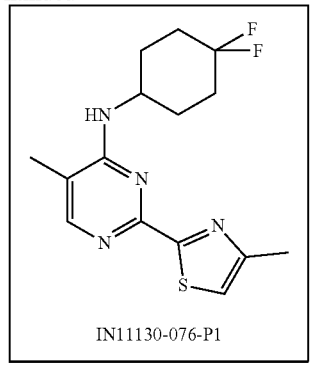

Step 1: The Procedure is similar to Step 1[IN10966-057-P2] in Example-893. 0.25 g of 4-methylthiazole-2-carboximidamide gave 5-methyl-2-(4-methylthiazol-2-yl)pyrimidine-4,6-diol as an off-white solid (0.2 g, 64%). MS (M+1)+=224.1.

Step 2: The Procedure is similar to Step 2[IN10966-057-P2] in Example-893. 0.8 g of 5-methyl-2-(4-methylthiazol-2-yl)pyrimidine-4,6-diol gave 2-(4,6-dichloro-5-methylpyrimidin-2-yl)-4-methylthiazole as a pale yellow solid (0.8 g, 68%). MS (M+1)+=260.0.

Step 3: The Procedure is similar to Step 1[B] in Example-838. 0.8 g of 2-(4,6-dichloro-5-methylpyrimidin-2-yl)-4-methylthiazole gave 6-chloro-N-(4,4-difluorocyclohexyl)-5-methyl-2-(4-methylthiazol-2-yl)pyrimidin-4-amine as an off-white solid (0.8 g, 72%). MS (M+1)+=359.1.

Step 4[IN11130-076-P1]: The Procedure is similar to Step 4[NSSy6056] in Example-655. 0.15 g of 6-chloro-N-(4,4-difluorocyclohexyl)-5-methyl-2-(4-methylthiazol-2-yl)pyrimidin-4-amine gave N-(4,4-difluorocyclohexyl)-5-methyl-2-(4-methylthiazol-2-yl)pyrimidin-4-amine as an off-white solid (0.11 g, 81%). MS (M+1)+=325.1; 1H-NMR (400 MHz, DMSO-d6): δ 8.22 (s, 1H), 8.13 (s, 1H), 7.79 (s, 1H), 4.30 (s, 1H), 2.10-1.90 (m, 11H), 1.85-1.70 (m, 3H).

Example-776

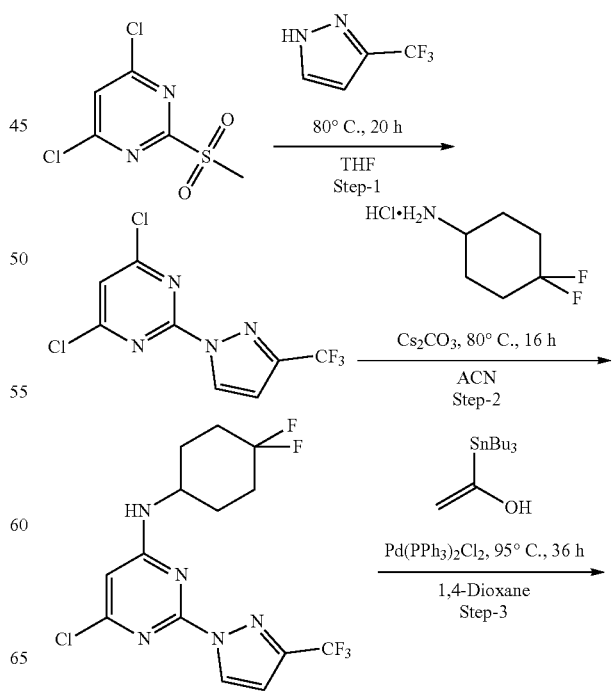

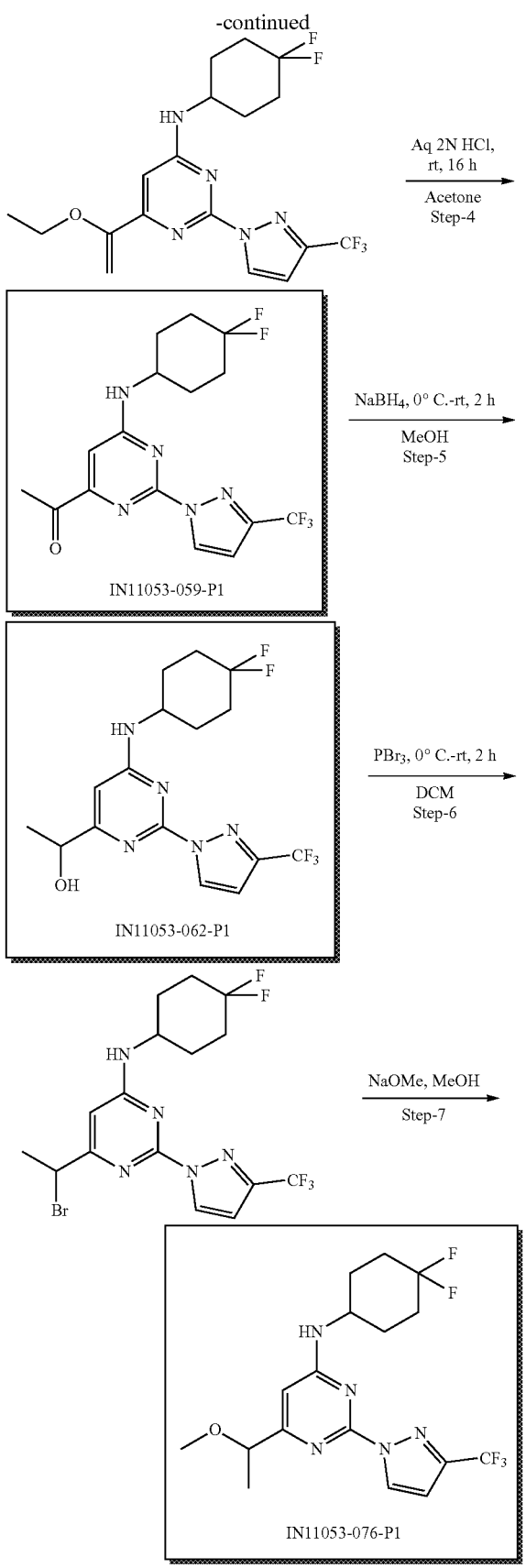

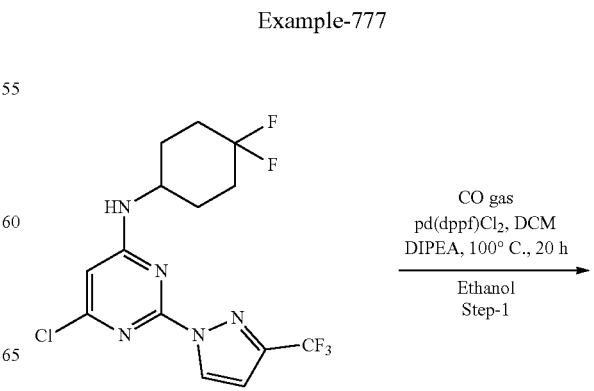

nyl)pyrimidine gave 4,6-dichloro-2-(3-(trifluoromethyl)-1H-pyrazol-1-yl)pyrimidine as a brown solid (1.2 g, 25%). MS (M+1)+=283.0.

Step 2: The Procedure is similar to Step 1[B] in Example-838. 1.2 g of 4,6-dichloro-2-(3-(trifluoromethyl)-1H-pyrazol-1-yl)pyrimidine gave 6-chloro-N-(4,4-difluorocyclohexyl)-2-(3-(trifluoromethyl)-1H-pyrazol-1-yl)pyrimidin-4-amine as a pale yellow solid (2.8 g, 70%). MS (M+1)+=382.0.

Step 3: The Procedure is similar to Step 1[H] in Example-838. 0.2 g of 6-chloro-N-(4,4-difluorocyclohexyl)-2-(3-(trifluoromethyl)-1H-pyrazol-1-yl)pyrimidin-4-amine gave N-(4,4-difluorocyclohexyl)-6-(1-ethoxyvinyl)-2-(3-(trifluoromethyl)-1H-pyrazol-1-yl)pyrimidin-4-amine as a brown gum (0.2 g, 91%). MS (M+1)+=418.1.

Step 4[IN11053-059-P1]: The Procedure is similar to Step 1[NSSy6697] in Example-873. 1.0 g of N-(4,4-difluorocyclohexyl)-6-(1-ethoxyvinyl)-2-(3-(trifluoromethyl)-1H-pyrazol-1-yl)pyrimidin-4-amine gave 1-(6-((4,4-difluorocyclohexyl)amino)-2-(3-(trifluoromethyl)-1H-pyrazol-1-yl)pyrimidin-4-yl)ethan-1-one as a white solid (0.65 g, 69%). MS (M+1)+=390.0; 1H-NMR (400 MHz, CDCl3): δ 8.81 (d, J=1.60 Hz, 1H), 6.96 (s, 1H), 6.86 (d, J=3.20 Hz, 1H), 4.36 (s, 1H), 2.65 (s, 3H), 2.15-1.90 (m, 6H), 1.75-1.60 (m, 2H).

Step 5[IN11053-062-P1]: The Procedure is similar to Step 2[NSSy6931] in Example-21. 0.36 g of 1-(6-((4,4-difluorocyclohexyl)amino)-2-(3-(trifluoromethyl)-1H-pyrazol-1-yl)pyrimidin-4-yl)ethan-1-one gave 1-(6-((4,4-difluorocyclohexyl)amino)-2-(3-(trifluoromethyl)-1H-pyrazol-1-yl)pyrimidin-4-yl)ethan-1-ol as a white solid (0.3 g, 83%). MS (M+1)+=392.1; 1H-NMR (400 MHz, DMSO-d6): δ 8.79 (bs, 1H), 7.89 (bs, 1H), 6.97 (d, J=2.8 Hz, 1H), 6.65 (s, 1H), 5.44 (d, J=3.6 Hz, 1H), 4.52 (bs, 1H), 4.20 (bs, 1H), 2.07-1.98 (m, 6H), 1.59-1.57 (m, 2H), 1.35 (d, J=5.6 Hz, 3H).

Step 6: The Procedure is similar to Step 3[IN11059-090-P1] in Example-659. 0.3 g of 1-(6-((4,4-difluorocyclohexyl)amino)-2-(3-(trifluoromethyl)-1H-pyrazol-1-yl)pyrimidin-4-yl)ethan-1-ol gave 6-(1-bromoethyl)-N-(4,4-difluorocyclohexyl)-2-(3-(trifluoromethyl)-1H-pyrazol-1-yl)pyrimidin-4-amine as an off-white solid (0.2 g, 57%). MS (M+1)+=454.0.

Step 7[IN11053-076-P1]: The Procedure is similar to Step 1[NSSy6519] in Example-842. 0.14 g of 6-(1-bromoethyl)-N-(4,4-difluorocyclohexyl)-2-(3-(trifluoromethyl)-1H-pyrazol-1-yl)pyrimidin-4-amine gave N-(4,4-difluorocyclohexyl)-6-(1-methoxyethyl)-2-(3-(trifluoromethyl)-1H-pyrazol-1-yl)pyrimidin-4-amine as a brown solid (0.03 g, 24%). MS (M+1)+=406.1; 1H-NMR (400 MHz, MeOD): δ 8.73 (s, 1H), 6.82 (d, J=2.80 Hz, 1H), 6.52 (s, 1H), 4.26-4.24 (m, 1H), 3.36 (s, 3H), 2.09-1.96 (m, 6H), 1.75-1.60 (m, 3H), 1.41-1.33 (m, 4H).

Example-777

Step 1: The Procedure is similar to Step 1[IN11177-025-P1] in Example-715. 3.8 g of 4,6-dichloro-2-(methylsulfo-

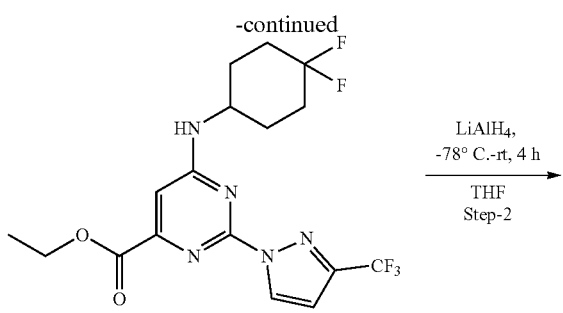

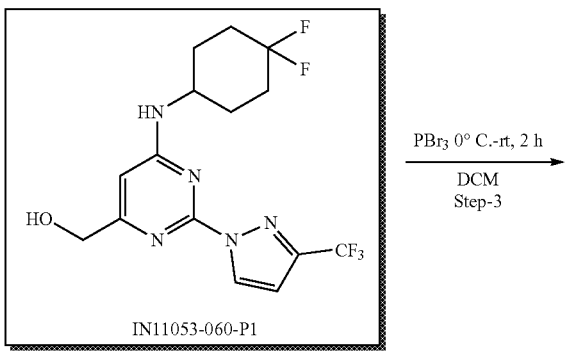

IN11053-060-P1

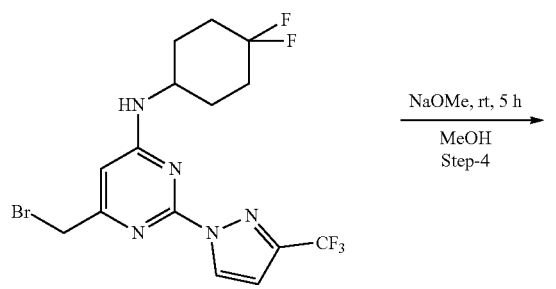

IN11053-071-P1

Step 1: The Procedure is similar to Step 1[IN11273-018-P1] in Example-889. 1.0 g of 6-chloro-N-(4,4-difluorocyclohexyl)-2-(3-(trifluoromethyl)-1H-pyrazol-1-yl)pyrimidin-4-amine gave ethyl 6-((4,4-difluorocyclohexyl)amino)-2-(3-(trifluoromethyl)-1H-pyrazol-1-yl)pyrimidine-4-carboxylate as a brownish gum (0.7 g, 45%). MS (M+1)+= 420.1.

Step 2[IN11053-060-P1]: The Procedure is similar to Step 4[NSSy6711] in Example-854. 0.6 g of ethyl 6-((4,4-difluorocyclohexyl)amino)-2-(3-(trifluoromethyl)-1H-pyrazol-1-yl)pyrimidine-4-carboxylate gave (6-((4,4-difluorocyclohexyl)amino)-2-(3-(trifluoromethyl)-1H-pyrazol-1-yl)pyrimidin-4-yl) methanol as a white solid (0.39 g, 72%). MS (M+1)+=378.0; 1H-NMR (400 MHz, DMSO-d6): δ 8.79 (s, 1H), 7.90 (s, 1H), 6.97 (d, J=2.40 Hz, 1H), 6.62 (s, 1H), 5.51 (s, 1H), 4.40 (d, J=4.40 Hz, 2H), 4.20 (s, 1H), 2.12-1.90 (m, 6H), 1.65-1.50 (m, 2H).

Step 3: The Procedure is similar to Step 3[IN11059-090-P1] in Example-659. 0.39 g of (6-((4,4-difluorocyclohexyl)amino)-2-(3-(trifluoromethyl)-1H-pyrazol-1-yl)pyrimidin-4-yl) methanol gave 6-(bromomethyl)-N-(4,4-difluorocyclohexyl)-2-(3-(trifluoromethyl)-1H-pyrazol-1-yl)pyrimidin-4-amine as a white solid (0.3 g, 66%). MS (M+1)+=440.0.

Step 4[IN11053-071-P1]: The Procedure is similar to Step 1[NSSy6519] in Example-842. 0.12 g of 6-(bromomethyl)-N-(4,4-difluorocyclohexyl)-2-(3-(trifluoromethyl)-1H-pyrazol-1-yl)pyrimidin-4-amine gave N-(4,4-difluorocyclohexyl)-6-(methoxymethyl)-2-(3-(trifluoromethyl)-1H-pyrazol-1-yl)pyrimidin-4-amine as a white solid (0.05 g, 35%). MS (M+1)+=392.0; 1H-NMR (400 MHz, DMSO-d6): δ 8.79 (s, 1H), 7.92 (s, 1H), 6.98 (s, 1H), 6.54 (s, 1H), 4.36 (s, 2H), 4.21 (s, 1H), 3.41 (s, 3H), 2.10-1.85 (m, 6H), 1.62-1.50 (m, 2H).

Example-778

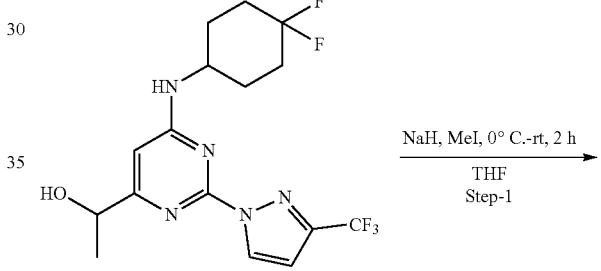

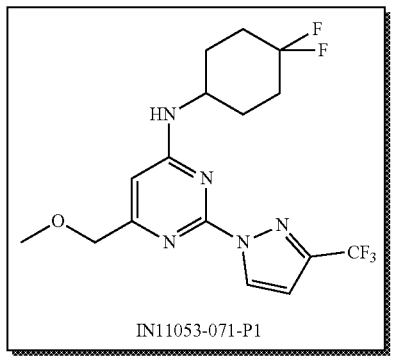

IN11053-073-P1

Step 1[IN11053-073-P1]: The Procedure is similar to Step 5[NSSy6711] in Example-854. 0.04 g of 1-(6-((4,4-difluorocyclohexyl)amino)-2-(3-(trifluoromethyl)-1H-pyrazol-1-yl)pyrimidin-4-yl)ethan-1-ol gave N-(4,4-difluorocyclohexyl)-6-(1-methoxyethyl)-N-methyl-2-(3-(trifluoromethyl)-1H-pyrazol-1-yl)pyrimidin-4-amine as an off-white solid (0.04 g, 53%). MS (M+1)+=420.1; 1H-NMR (400 MHz, DMSO-d6): δ 7.88 (s, 1H), 7.00 (d, J=2.40 Hz, 1H), 6.66 (s, 1H), 4.27 (q, J=6.40 Hz, 1H), 3.29 (s, 3H), 2.99 (s, 3H), 2.25-2.05 (m, 4H), 1.85-1.70 (m, 4H), 1.39 (d, J=6.80 Hz, 3H).

Example-779

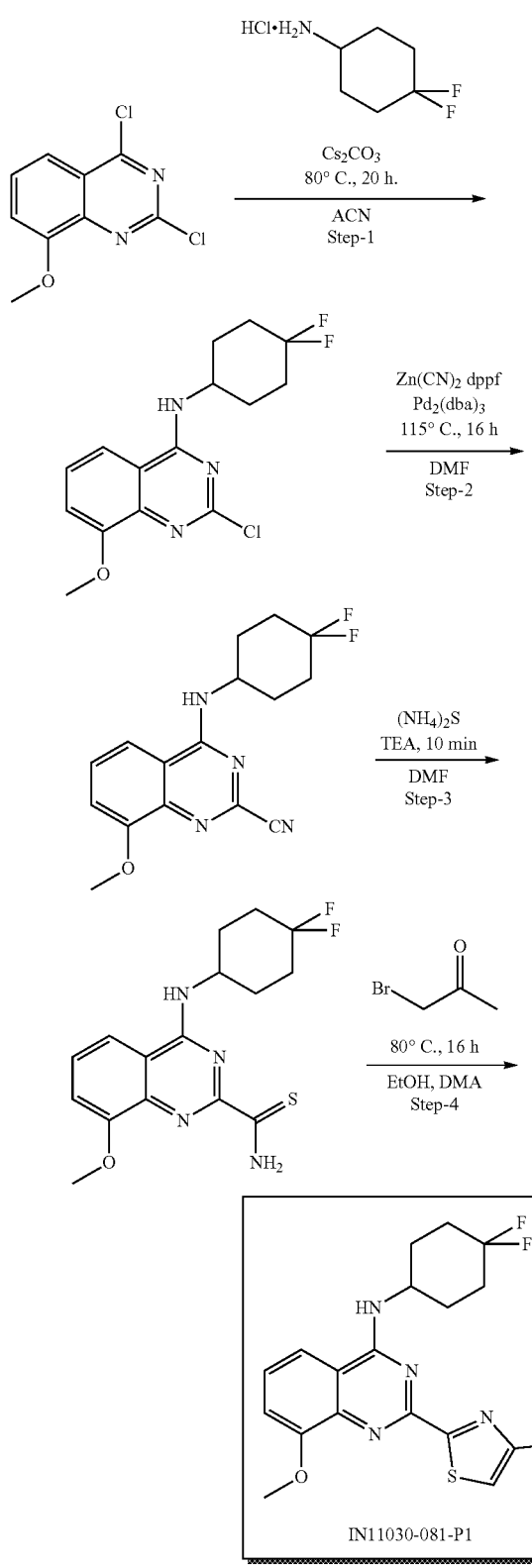

Step 1: The Procedure is similar to Step 1[B] in Example-838. 0.4 g of 2,4-dichloro-8-methoxyquinazoline gave 2-chloro-N-(4,4-difluorocyclohexyl)-8-methoxyquinazolin-4-amine (0.5 g, 87%). MS (M+1)+=328.1.

Step 2: The Procedure is similar to Step 3[IN11079-047-P1] in Example-758. 0.5 g of 2-chloro-N-(4,4-difluorocyclohexyl)-8-methoxyquinazolin-4-amine gave 4-((4,4-difluorocyclohexyl)amino)-8-methoxyquinazoline-2-carbonitrile (0.35 g, 72%). MS (M+1)+=319.

Step 3: The Procedure is similar to Step 5[NSSy5779] in Example-642. 0.35 g of 4-((4,4-difluorocyclohexyl)amino)-8-methoxyquinazoline-2-carbonitrile gave 4-((4,4-difluorocyclohexyl)amino)-8-methoxyquinazoline-2-carbothioamide (0.35 g, 90%). MS (M+1)+=353.1.

Step 4[IN11030-081-P1]: The Procedure is similar to Step 6[NSSy5779] in Example-642. 0.35 g of 4-((4,4-difluorocyclohexyl)amino)-8-methoxyquinazoline-2-carbothioamide gave N-(4,4-difluorocyclohexyl)-8-methoxy-2-(4-methylthiazol-2-yl) quinazolin-4-amine (0.25 g, 64%). MS (M+1)+=391.0; 1H-NMR (400 MHz, DMSO-d6): δ 8.05 (d, J=6.80 Hz, 1H), 7.87 (d, J=8.40 Hz, 1H), 7.46 (t, J=8.40 Hz, 2H), 7.30 (d, J=7.60 Hz, 1H), 4.35 (s, 1H), 3.95 (s, 3H), 2.48 (s, 3H), 2.20-1.85 (m, 6H), 1.85-1.70 (m, 2H).

Example-780

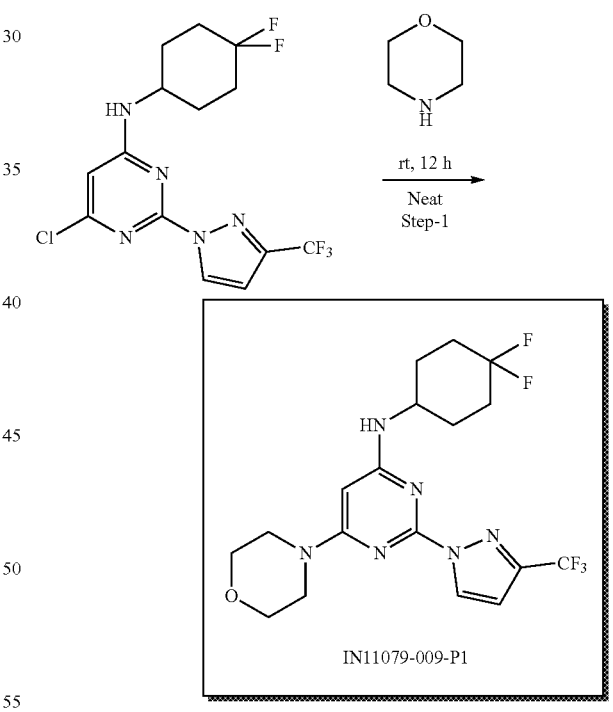

Step 1[IN11079-009-P1]: The Procedure is similar to Step 1[B] in Example-838. 0.08 g of 6-chloro-N-(4,4-difluorocyclohexyl)-2-(3-(trifluoromethyl)-1H-pyrazol-1-yl)pyrimidin-4-amine gave N-(4,4-difluorocyclohexyl)-6-morpholino-2-(3-(trifluoromethyl)-1H-pyrazol-1-yl)pyrimidin-4-amine as an off-white solid (0.148 g, 99%). MS (M+1)+=433.1; 1H-NMR (400 MHz, DMSO-d6): δ 8.74 (s, 1H), 7.30 (d, J=8.00 Hz, 1H), 6.93 (s, 1H), 5.64 (s, 1H), 3.90 (s, 1H), 3.62 (s, 4H), 3.54 (s, 4H), 2.10-1.85 (m, 6H), 1.60-1.50 (m, 2H).

Example-781

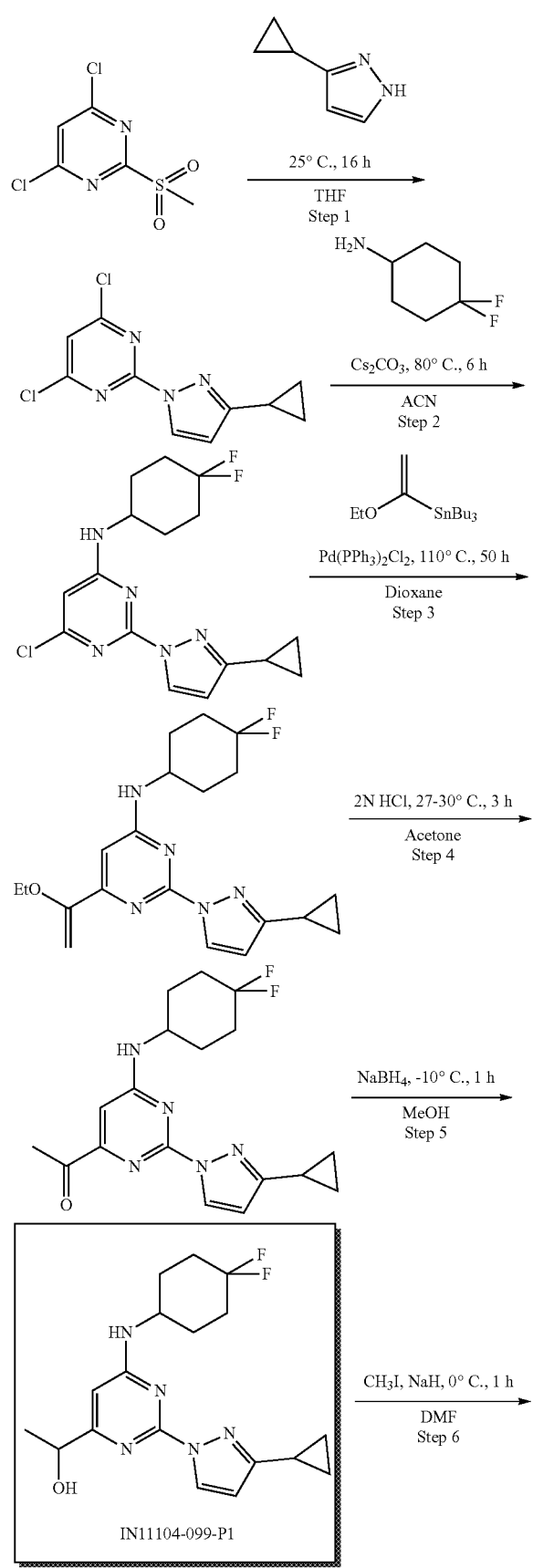

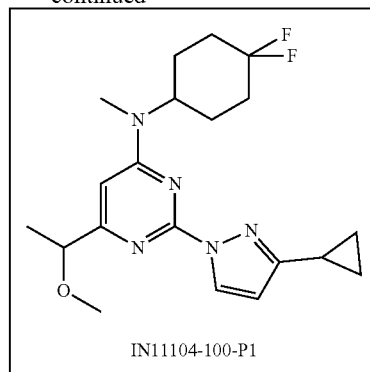

Step 1: To a solution of 4,6-dichloro-2-(methylsulfonyl) pyrimidine (1 g, 4.42 mmol) in THF was added 3-cyclopropyl-1H-pyrazole (0.48 g, 4.42 mmol) and stirred at 25° C. for 16 h. The reaction mixture was evaporated to dryness under vacuum to afford crude product, which was purified by column chromatography using ethyl acetate in pet-ether as solvent to afford 4,6-dichloro-2-(3-cyclopropyl-1H-pyrazol-1-yl)pyrimidine as an off-white solid (1.1 g, 98%). MS (M+1)+=255.0.

Step 2: The Procedure is similar to Step 1[B] in Example-838. 0.3 g of 4,6-dichloro-2-(3-cyclopropyl-1H-pyrazol-1-yl)pyrimidine gave 6-chloro-2-(3-cyclopropyl-1H-pyrazol-1-yl)-N-(4,4-difluorocyclohexyl)pyrimidin-4-amine as an off-white solid (0.29 g, 96%). MS (M+1)+=355.0.

Step 3: The Procedure is similar to Step 1[H] in Example-838. 0.3 g of 6-chloro-2-(3-cyclopropyl-1H-pyrazol-1-yl)-N-(4,4-difluorocyclohexyl)pyrimidin-4-amine gave 2-(3-cyclopropyl-1H-pyrazol-1-yl)-N-(4,4-difluorocyclohexyl)-6-(1-ethoxyvinyl)pyrimidin-4-amine as an off-white solid (0.26 g, 78%). MS (M+1)+=390.1.

Step 4: The Procedure is similar to Step 1[NSSy6697] in Example-873. 0.25 g of 2-(3-cyclopropyl-1H-pyrazol-1-yl)-N-(4,4-difluorocyclohexyl)-6-(1-ethoxyvinyl)pyrimidin-4-amine gave 1-(2-(3-cyclopropyl-1H-pyrazol-1-yl)-6-((4,4-difluorocyclohexyl)amino)pyrimidin-4-yl) ethan-1-one as an off-white solid (0.18 g, 77%). MS (M+1)+=361.9.

Step 5[IN11104-099-P1]: The Procedure is similar to Step 2[NSSy6931] in Example-21. 0.18 g of 1-(2-(3-cyclopropyl-1H-pyrazol-1-yl)-6-((4,4-difluorocyclohexyl)amino)pyrimidin-4-yl)ethan-1-one gave 1-(2-(3-cyclopropyl-1H-pyrazol-1-yl)-6-((4,4-difluorocyclohexyl)amino)pyrimidin-4-yl)ethan-1-ol as an off-white solid (0.15 g, 83%). MS (M+1)+=364.1; 1H-NMR (400 MHz, DMSO-d6): δ 8.43 (s, 1H), 7.64 (bs, 1H), 6.50 (s, 1H), 6.17 (d, J=2.4 Hz, 1H), 5.34 (d, J=4.4 Hz, 1H), 4.48-4.46 (m, 1H), 4.14 (m, 1H), 2.06-1.95 (m, 6H), 1.58-1.56 (m, 2H), 1.35-1.30 (m, 3H), 0.94-0.84 (m, 2H), 0.74-0.69 (m, 2H).

Step 6[IN11104-100-P1]: The Procedure is similar to Step 5[NSSy6711] in Example-854. 0.1 g of 1-(2-(3-cyclopropyl-1H-pyrazol-1-yl)-6-((4,4-difluorocyclohexyl)amino)pyrimidin-4-yl)ethan-1-ol gave 2-(3-cyclopropyl-1H-pyrazol-1-yl)-N-(4,4-difluorocyclohexyl)-6-(1-methoxyethyl)-N-methylpyrimidin-4-amine as a brown sticky solid (0.05 g, 46%). MS (M+1)+=392.2; 1H-NMR (400 MHz, DMSO-d6): δ 8.51 (s, 1H), 6.54 (bs, 1H), 6.20 (d, J=2.4 Hz, 1H), 4.23-4.18 (m, 1H), 3.28 (s, 3H), 3.10 (s, 3H), 2.50-1.90 (m, 5H), 1.89-1.65 (m, 4H), 1.38-1.36 (m, 3H), 0.94-0.84 (m, 2H), 0.79-0.73 (m, 2H).

Example-782

Example-783

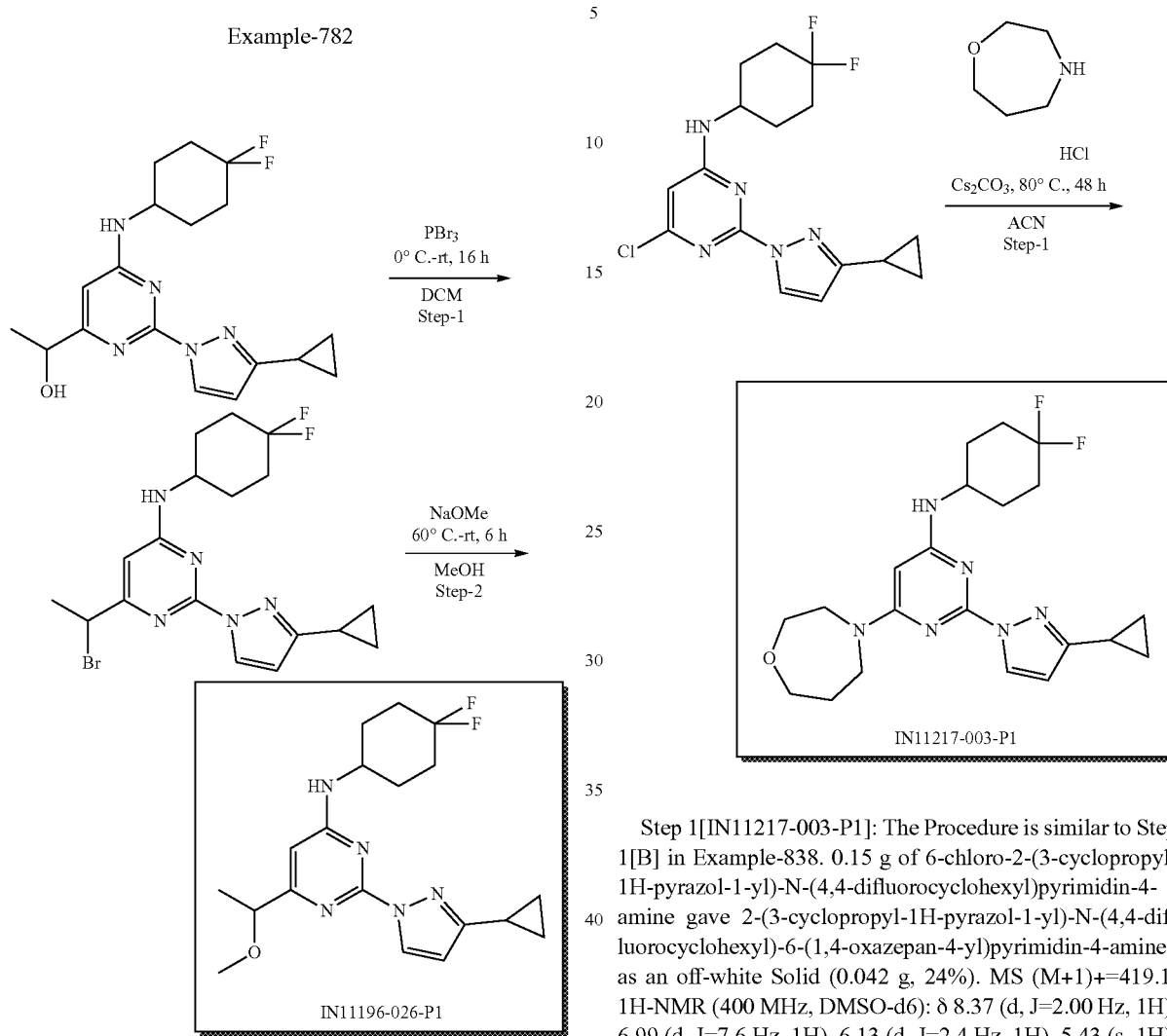

Step 1: The Procedure is similar to Step 3[IN11059-090-P1] in Example-659. 0.15 g of 1-(2-(3-cyclopropyl-1H-pyrazol-1-yl)-6-((4,4-difluorocyclohexyl)amino)pyrimidin-4-yl) ethan-1-ol gave 6-(1-bromoethyl)-2-(3-cyclopropyl-1H-pyrazol-1-yl)-N-(4,4-difluorocyclohexyl)pyrimidin-4-amine as an off-white solid (0.12 g, 80%). MS (M, M+2)+=426.1, 428.1.

Step 2[IN11196-026-P1]: The Procedure is similar to Step 1[NSSy6519] in Example-842. 0.13 g of 6-(1-bromoethyl)-2-(3-cyclopropyl-1H-pyrazol-1-yl)-N-(4,4-difluorocyclohexyl)pyrimidin-4-amine gave 2-(3-cyclopropyl-1H-pyrazol-1-yl)-N-(4,4-difluorocyclohexyl)-6-(1-methoxyethyl) pyrimidin-4-amine as an off-white Solid (0.05 g, 43%). MS (M+1)+=378.2; 1H-NMR (400 MHz, DMSO-d6): δ 8.43 (s, 1H), 7.67 (s, 1H), 6.38 (s, 1H), 6.18 (d, J=2.40 Hz, 1H), 4.10 (s, 1H), 2.33 (s, 3H), 2.10-1.85 (m, 8H), 1.65-1.50 (m, 2H), 1.33 (d, J=6.40 Hz, 3H), 0.95-0.88 (m, 2H), 0.75-0.70 (m, 2H).

Step 1[IN11217-003-P1]: The Procedure is similar to Step 1[B] in Example-838. 0.15 g of 6-chloro-2-(3-cyclopropyl-1H-pyrazol-1-yl)-N-(4,4-difluorocyclohexyl)pyrimidin-4-amine gave 2-(3-cyclopropyl-1H-pyrazol-1-yl)-N-(4,4-difluorocyclohexyl)-6-(1,4-oxazepan-4-yl)pyrimidin-4-amine as an off-white Solid (0.042 g, 24%). MS (M+1)+=419.1; 1H-NMR (400 MHz, DMSO-d6): δ 8.37 (d, J=2.00 Hz, 1H), 6.99 (d, J=7.6 Hz, 1H), 6.13 (d, J=2.4 Hz, 1H), 5.43 (s, 1H), 3.83-3.60 (m, 9H), 2.05-1.88 (m, 10H), 1.56-1.52 (m, 2H), 0.95-0.84 (m, 3H), 0.71-0.67 (m, 2H).

Example-784

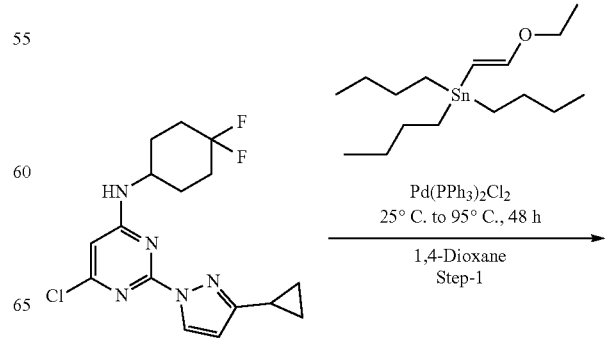

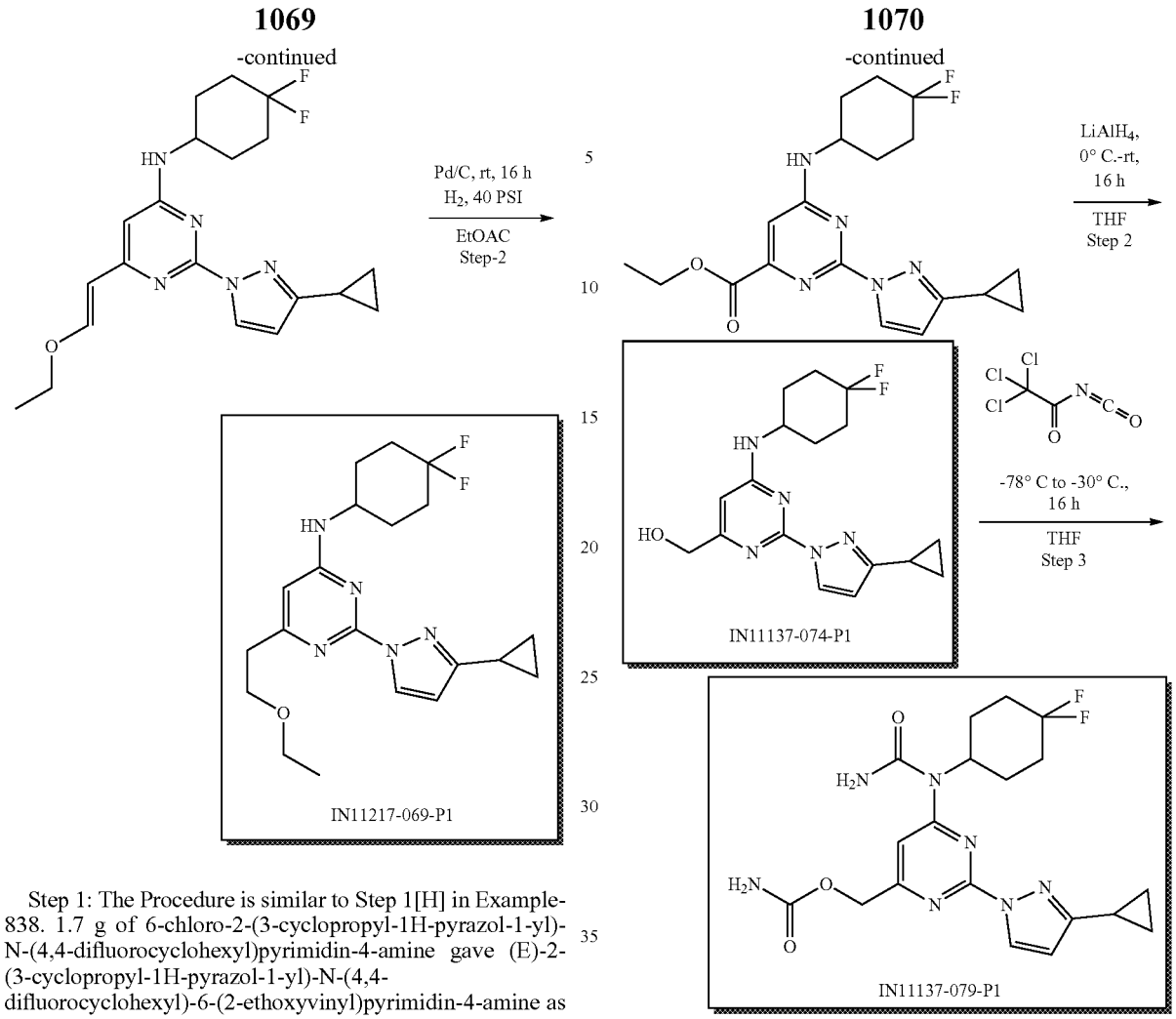

Step 1: The Procedure is similar to Step 1[H] in Example-838. 1.7 g of 6-chloro-2-(3-cyclopropyl-1H-pyrazol-1-yl)-N-(4,4-difluorocyclohexyl)pyrimidin-4-amine gave (E)-2-(3-cyclopropyl-1H-pyrazol-1-yl)-N-(4,4-difluorocyclohexyl)-6-(2-ethoxyvinyl)pyrimidin-4-amine as pale yellow solid (1.1 g, 60%). MS (M+1)+=390.2.

Step 1[IN11217-069-P1]: The Procedure is similar to Step 2[NSSy6465] in Example-869. 0.65 g of (E)-2-(3-cyclopropyl-1H-pyrazol-1-yl)-N-(4,4-difluorocyclohexyl)-6-(2-ethoxyvinyl)pyrimidin-4-amine gave 2-(3-cyclopropyl-1H-pyrazol-1-yl)-N-(4,4-difluorocyclohexyl)-6-(2-ethoxyethyl)pyrimidin-4-amine as an off-white Solid (0.48 g, 74%). MS (M+1)+=392.2; 1H-NMR (400 MHz, DMSO-d6): δ 8.42 (s, 1H), 7.65-7.57 (m, 1H), 6.24 (s, 1H), 6.18 (d, J=2.80 Hz, 1H), 4.10 (s, 1H), 3.69 (t, J=6.40 Hz, 2H), 3.44 (q, J=7.20 Hz, 2H), 2.72 (s, 2H), 2.12-1.90 (m, 6H), 1.62-1.50 (m, 2H), 1.09 (t, J=7.20 Hz, 3H), 0.97-0.90 (m, 2H), 0.76-0.70 (m, 2H).

Example-785

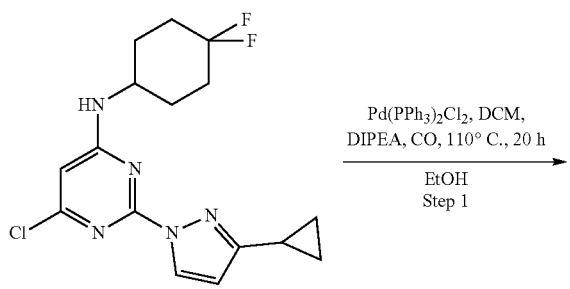

Step 1: The Procedure is similar to Step 1[IN11273-018-P1] in Example-889. 0.5 g of 6-chloro-2-(3-cyclopropyl-1H-pyrazol-1-yl)-N-(4,4-difluorocyclohexyl)pyrimidin-4-amine gave ethyl 2-(3-cyclopropyl-1H-pyrazol-1-yl)-6-((4,4-difluorocyclohexyl)amino)pyrimidine-4-carboxylate as a yellow Solid (0.45 g, 81%). MS (M+1)+=392.2.

Step 2[IN11137-074-P1]: The Procedure is similar to Step 4[NSSy6711] in Example-854. 0.45 g of ethyl 2-(3-cyclopropyl-1H-pyrazol-1-yl)-6-((4,4-difluorocyclohexyl)amino)pyrimidine-4-carboxylate gave (2-(3-cyclopropyl-1H-pyrazol-1-yl)-6-((4,4-difluorocyclohexyl)amino)pyrimidin-4-yl)methanol as an off-white solid (0.25 g, 62%). MS (M+1)+=350.2; 1H-NMR (400 MHz, DMSO-d6): δ 8.42 (s, 1H), 7.65 (s, 1H), 6.48 (s, 1H), 6.18 (d, J=2.40 Hz, 1H), 5.41 (t, J=5.20 Hz, 1H), 4.36 (d, J=5.20 Hz, 2H), 4.15 (s, 1H), 2.12-1.88 (m, 7H), 1.65-1.50 (m, 2H), 0.94-0.90 (m, 2H), 0.73-0.71 (m, 2H).

Step 3[IN11137-079-P1]: To the solution of (2-(3-cyclopropyl-1H-pyrazol-1-yl)-6-((4,4-difluorocyclohexyl)amino)pyrimidin-4-yl) methanol (0.2 g, 0.57 mmol) in THF was added 2,2,2-trichloroacetyl isocyanate (0.136 mL, 1.145 mmol) at −78° C. and allowed to stir at 30° C. for 16 h. Then the reaction mixture was quenched with 5 mL of saturated sodium bicarbonate solution and stirred for 12 h. Then extracted with ethyl acetate, dried over sodium sulfate and evaporated to dryness to afford crude product and which was purified by column chromatography using ethyl acetate in pet-ether as solvent to afford (2-(3-cyclopropyl-1H-pyrazol-1-yl)-6-(1-(4,4-difluorocyclohexyl) ureido)pyrimidin-4-yl) methyl carbamate as an off-white solid (0.05 g, 20%). MS (M+1)+=436.2; 1H-NMR (400 MHz, DMSO-d6): δ 8.45 (d, J=2.4 Hz, 1H), 6.97 (s, 1H), 6.22 (d, J=2.8 Hz, 1H), 5.10 (s, 2H), 4.62 (t, J=11.6 Hz, 1H), 2.37-2.30 (m, 2H), 2.12-1.89 (m, 8H), 1.30 (s, 1H), 1.03-0.98 (m, 2H), 0.85-0.81 (m, 2H).

Example-786

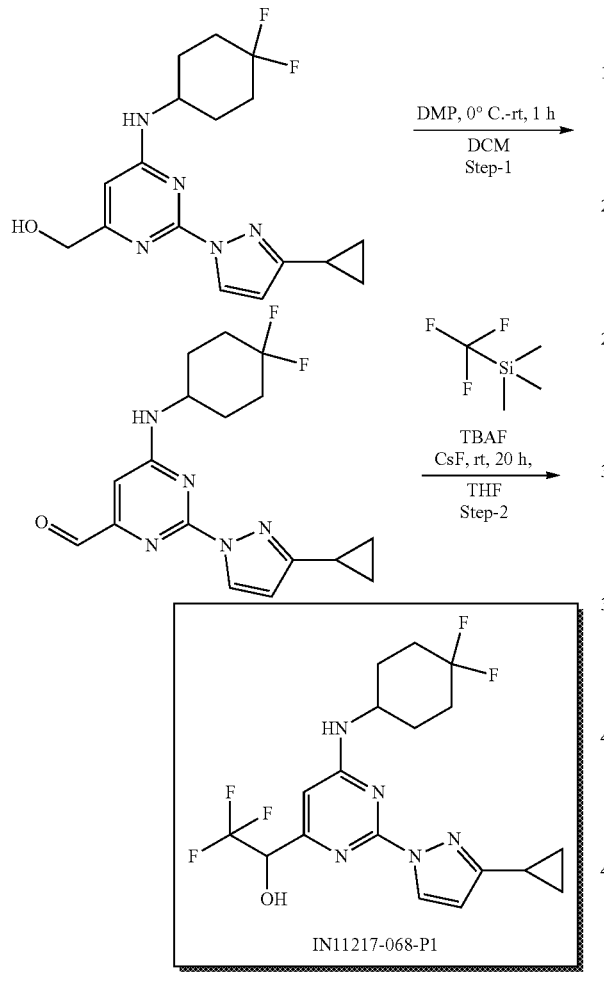

Step 1: The Procedure is similar to Step 1[NSSy6930] in Example-867. 0.27 g of (2-(3-cyclopropyl-1H-pyrazol-1-yl)-6-((4,4-difluorocyclohexyl)amino)pyrimidin-4-yl) methanol gave 2-(3-cyclopropyl-1H-pyrazol-1-yl)-6-((4,4-difluorocyclohexyl)amino)pyrimidine-4-carbaldehyde as an off-white Solid (0.17 g, crude). MS (M+1)+=348.2.

Step 2[IN11217-068-P1]: The Procedure is similar to Step 1[IN11104-100-P1] in Example-781. 0.17 g of 2-(3-cyclopropyl-1H-pyrazol-1-yl)-6-((4,4-difluorocyclohexyl)amino)pyrimidine-4-carbaldehyde gave 1-(2-(3-cyclopropyl-1H-pyrazol-1-yl)-6-((4,4-difluorocyclohexyl)amino)pyrimidin-4-yl)-2,2,2-trifluoroethan-1-ol as an off-white Solid (0.12 g, 60%). MS (M+1)+=418.2; 1H-NMR (400 MHz, DMSO-d6): δ 8.46 (s, 1H), 7.86 (s, 1H), 7.00 (d, J=6.00 Hz, 1H), 6.62 (s, 1H), 6.20 (d, J=2.00 Hz, 1H), 4.93 (t, J=6.00 Hz, 1H), 4.17-4.15 (m, 1H), 2.15-1.95 (m, 7H), 1.65-1.50 (m, 2H), 0.95-0.92 (m, 2H), 0.73-0.70 (m, 2H).

Example-787

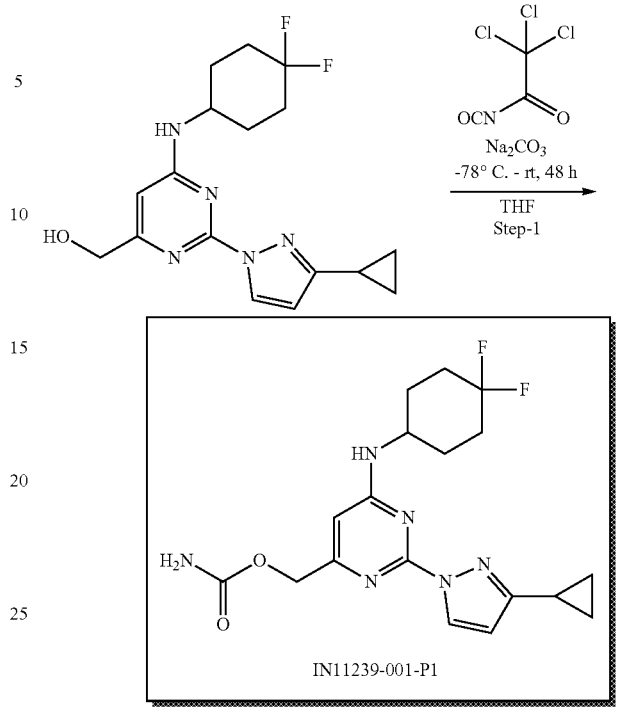

Step 1[IN11239-001-P1]: The Procedure is similar to Step 3[IN11137-079-P1] in Example-785. 0.05 g of (2-(3-cyclopropyl-1H-pyrazol-1-yl)-6-((4,4-difluorocyclohexyl)amino) pyrimidin-4-yl) methanol gave (2-(3-cyclopropyl-1H-pyrazol-1-yl)-6-((4,4-difluorocyclohexyl)amino)pyrimidin-4-yl) methyl carbamate as white solid (0.04 g, 35%). MS (M+1)+=393.2; 1H-NMR (400 MHz, DMSO-d6): δ 8.43 (s, 1H), 7.80 (s, 1H), 6.80 (m, 2H), 6.27 (s, 1H), 6.20 (d, J=2.80 Hz, 1H), 4.85 (s, 2H), 4.15 (s, 1H), 2.10-1.90 (m, 7H), 1.62-1.50 (m, 2H), 0.94-0.90 (m, 2H), 0.73-0.70 (m, 2H).

Example-788

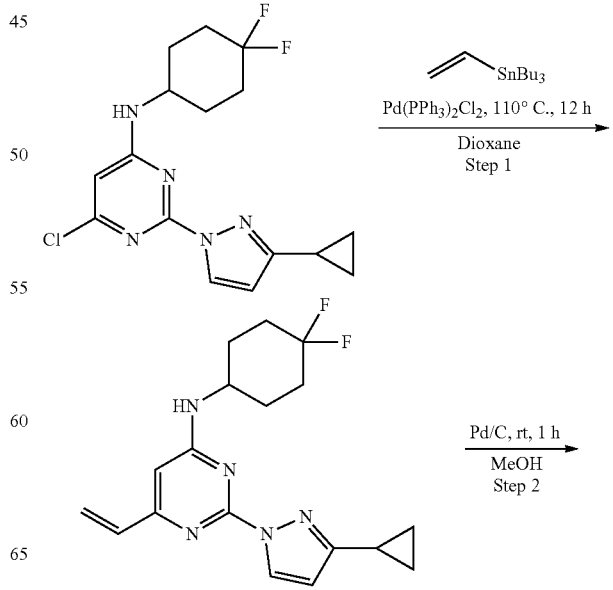

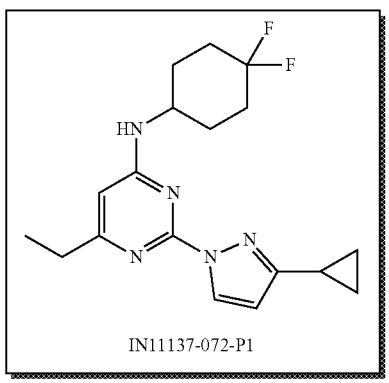

Step 1: The Procedure is similar to Step 1[H] in Example-838. 0.1 g of 6-chloro-2-(3-cyclopropyl-1H-pyrazol-1-yl)-N-(4,4-difluorocyclohexyl)pyrimidin-4-amine gave 2-(3-cyclopropyl-1H-pyrazol-1-yl)-N-(4,4-difluorocyclohexyl)-6-vinylpyrimidin-4-amine as a yellow liquid (0.05 g, 51%). MS (M+1)+=346.2.

Step 2[IN11137-072-P1]: The Procedure is similar to Step 2[NSSy6464] in Example-869. 0.15 g of 2-(3-cyclopropyl-1H-pyrazol-1-yl)-N-(4,4-difluorocyclohexyl)-6-vinylpyrimidin-4-amine gave 2-(3-cyclopropyl-1H-pyrazol-1-yl)-N-(4,4-difluorocyclohexyl)-6-ethylpyrimidin-4-amine as an off-white Solid (0.05 g, 33%). MS (M+1)+=348.2; 1H-NMR (400 MHz, DMSO-d6): δ 8.42 (s, 1H), 7.55 (s, 1H), 6.21 (s, 1H), 6.17 (s, 1H), 4.10 (m, 1H), 2.60-2.55 (m, 1H), 2.05-1.94 (m, 7H), 1.61-1.52 (m, 2H), 1.24-1.17 (m, 4H), 0.95-0.90 (m, 2H), 0.73-0.69 (m, 2H).

Example-789

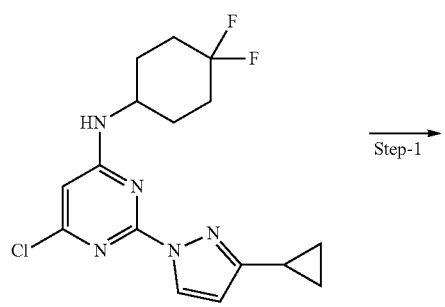

TABLE 81

| Step 1: | | | | |
|---|---|---|---|---|
| Compound No | R | Condition | Yield (%) | MS (M + 1)+ |
| IN11106-066-P1 |  | NaH, THF, 75° C., 16 h | 14 | 431.1 |
| IN11166-020-P1 | | Cs2CO3, ACN, 80° C., 16 h | 17 | 417.1 |

Step 1[IN11106-066-P1]: The Procedure is similar to Step 5[NSSy6711] in Example-854. 1H-NMR (400 MHz, DMSO-d6): δ 8.44 (s, 2H), 7.53 (s, 1H), 6.27 (s, 1H), 5.73 (s, 1H), 5.30 (s, 2H), 2.51 (s, 3H), 2.10-1.85 (m, 8H), 1.60-1.48 (m, 2H), 0.94-0.91 (m, 2H), 0.73-0.70 (m, 2H).

Step 1[IN11166-020-P1]: The Procedure is similar to Step 1[B] in Example-838. 1H-NMR (400 MHz, DMSO-d6): δ 8.48 (s, 1H), 8.40 (s, 1H), 7.60 (s, 1H), 7.41 (s, 1H), 6.24 (d, J=2.40 Hz, 1H), 5.75 (s, 1H), 5.45 (s, 2H), 2.10-1.85 (m, 8H), 1.60-1.50 (m, 2H), 0.96-0.92 (m, 2H), 0.76-0.72 (m, 2H).

Example-790

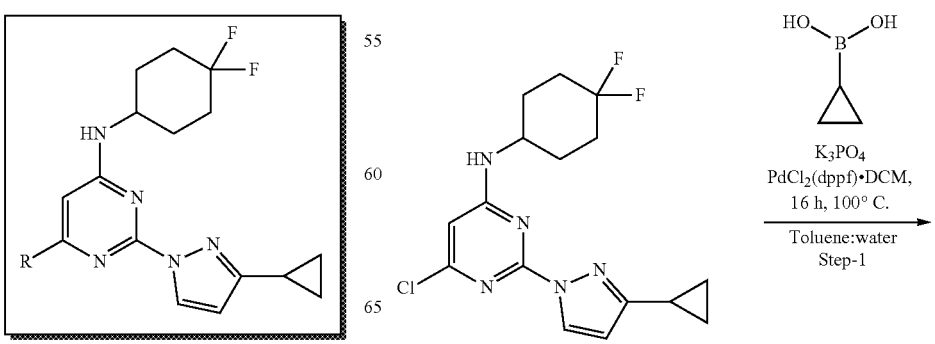

-continued

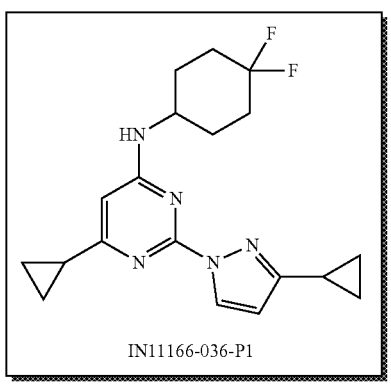

IN11166-036-P1

Step 1 IN11166-036-P1: The Procedure is similar to Step 2[IN11250-007-P1] in Example-620. 0.1 g of 6-chloro-2-(3-cyclopropyl-1H-pyrazol-1-yl)-N-(4,4-difluorocyclohexyl)pyrimidin-4-amine gave 6-cyclopropyl-2-(3-cyclopropyl-1H-pyrazol-1-yl)-N-(4,4-difluorocyclohexyl)pyrimidin-4-amine as an off-white solid (0.035 g, 35%). MS (M+1)+=360.2; 1H-NMR (400 MHz, DMSO-d6): δ 8.36 (s, 1H), 7.48 (s, 1H), 6.25 (s, 1H), 6.14 (s, 1H), 2.12-1.93 (m, 9H), 1.58-1.55 (m, 2H), 0.97-0.85 (m, 7H), 0.71-0.68 (m, 2H).

Example-791

Intentionally Omitted

Example-792

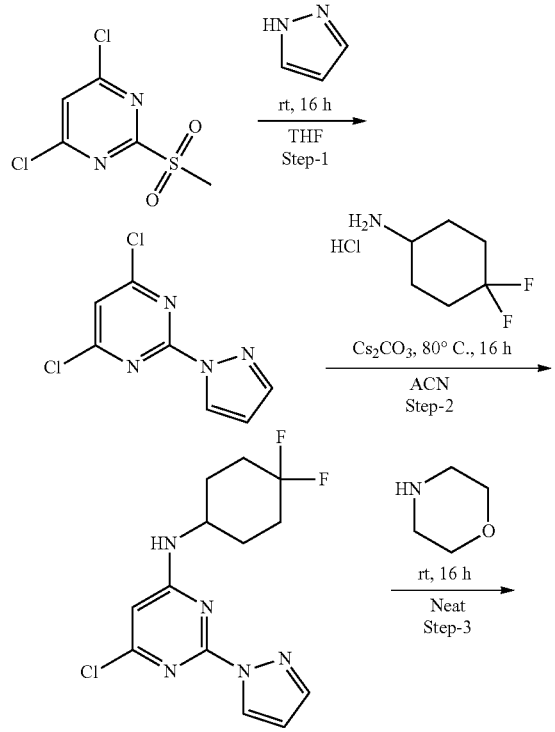

-continued

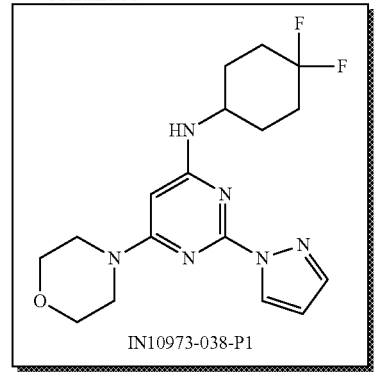

IN10973-038-P1

Step 1: The Procedure is similar to Step 1[IN11104-100-P1] in Example-781. 4 g of 4,6-dichloro-2-(methylsulfonyl)pyrimidine gave 4,6-dichloro-2-(1H-pyrazol-1-yl)pyrimidine as an off-white solid (1.9 g, 50%). MS (M+1)+=214.9.

Step 2: The Procedure is similar to Step 1[B] in Example-838. 1.05 g of 4,6-dichloro-2-(1H-pyrazol-1-yl)pyrimidine gave 6-chloro-N-(4,4-difluorocyclohexyl)-2-(1H-pyrazol-1-yl)pyrimidin-4-amine as an off-white solid (1.25 g, 81%). MS (M+1)+=314.2.

Step 3[IN10973-038-P1]: 0.1 g of 6-chloro-N-(4,4-difluorocyclohexyl)-2-(1H-pyrazol-1-yl)pyrimidin-4-amine gave N-(4,4-difluorocyclohexyl)-6-morpholino-2-(1H-pyrazol-1-yl)pyrimidin-4-amine as an off-white solid (0.1 g, 86%). MS (M+1)+=365.1; 1H-NMR (400 MHz, DMSO-d6): δ 8.53 (d, J=2.00 Hz, 1H), 7.68 (s, 1H), 7.10 (d, J=8.40 Hz, 1H), 6.45 (t, J=1.60 Hz, 1H), 5.57 (s, 1H), 3.96 (s, 1H), 3.68-3.67 (m, 4H), 3.51 (s, 4H), 2.10-1.80 (m, 6H), 1.62-1.50 (m, 2H).

Example-793

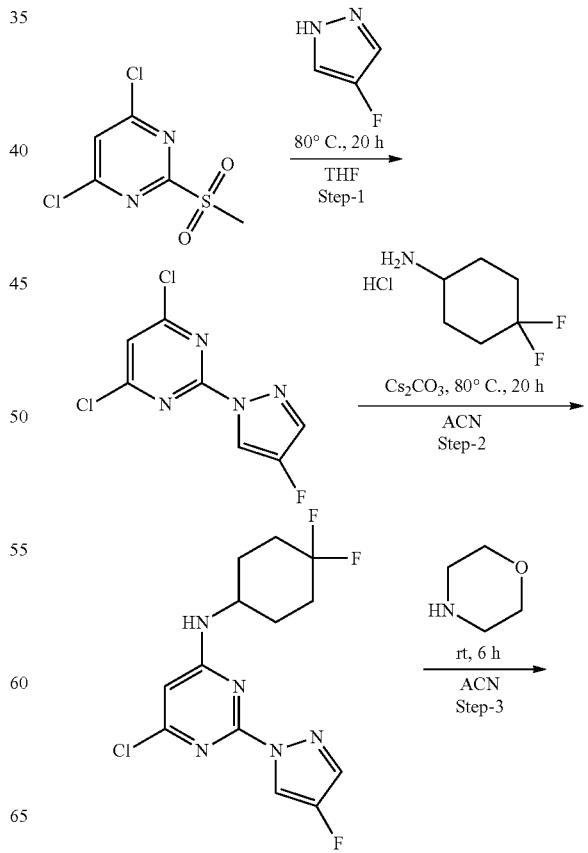

-continued

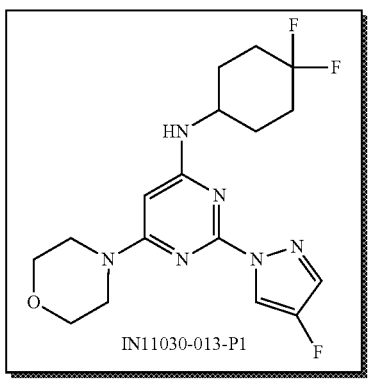

IN11030-013-P1

Step 1: The Procedure is similar to Step 1[IN11104-100-P1] in Example-781. 0.5 g of 4,6-dichloro-2-(methylsulfonyl)pyrimidine gave 4,6-dichloro-2-(4-fluoro-1H-pyrazol-1-yl)pyrimidine as an off-white solid (0.25 g, 49%). MS (M+1)+=232.9.

Step 2: The Procedure is similar to Step 1[B] in Example-838. 0.1 g of 4,6-dichloro-2-(4-fluoro-1H-pyrazol-1-yl)pyrimidine gave 6-chloro-N-(4,4-difluorocyclohexyl)-2-(4-fluoro-1H-pyrazol-1-yl)pyrimidin-4-amine as off-white solid (0.11 g, 77%). MS (M+1)+=332.0.

Step 3[IN11030-013-P1]: 0.1 g of 6-chloro-N-(4,4-difluorocyclohexyl)-2-(4-fluoro-1H-pyrazol-1-yl)pyrimidin-4-amine gave N-(4,4-difluorocyclohexyl)-2-(4-fluoro-1H-pyrazol-1-yl)-6-morpholinopyrimidin-4-amine as an off-white solid (0.09 g, 78%). MS (M+1)+=383.2; 1H-NMR (400 MHz, DMSO-d6): δ 8.59 (d, J=4.40 Hz, 1H), 7.78 (d, J=4.00 Hz, 1H), 7.13 (d, J=8.00 Hz, 1H), 5.56 (s, 1H), 4.01 (s, 1H), 3.67 (t, J=4.40 Hz, 4H), 3.50 (s, 4H), 2.04-1.93 (m, 6H), 1.55-1.52 (m, 2H).

Example-794

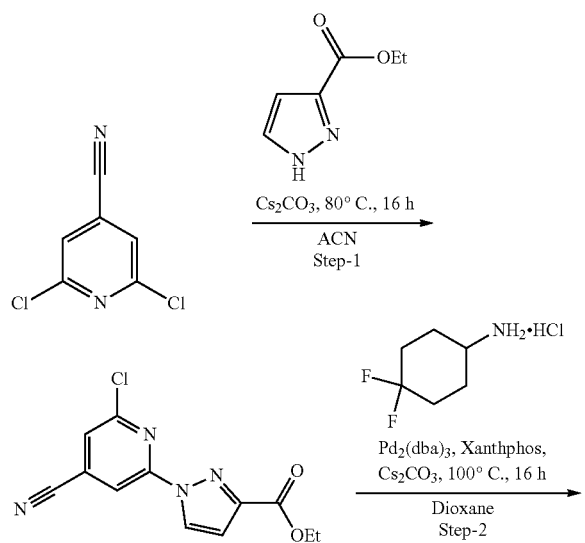

-continued

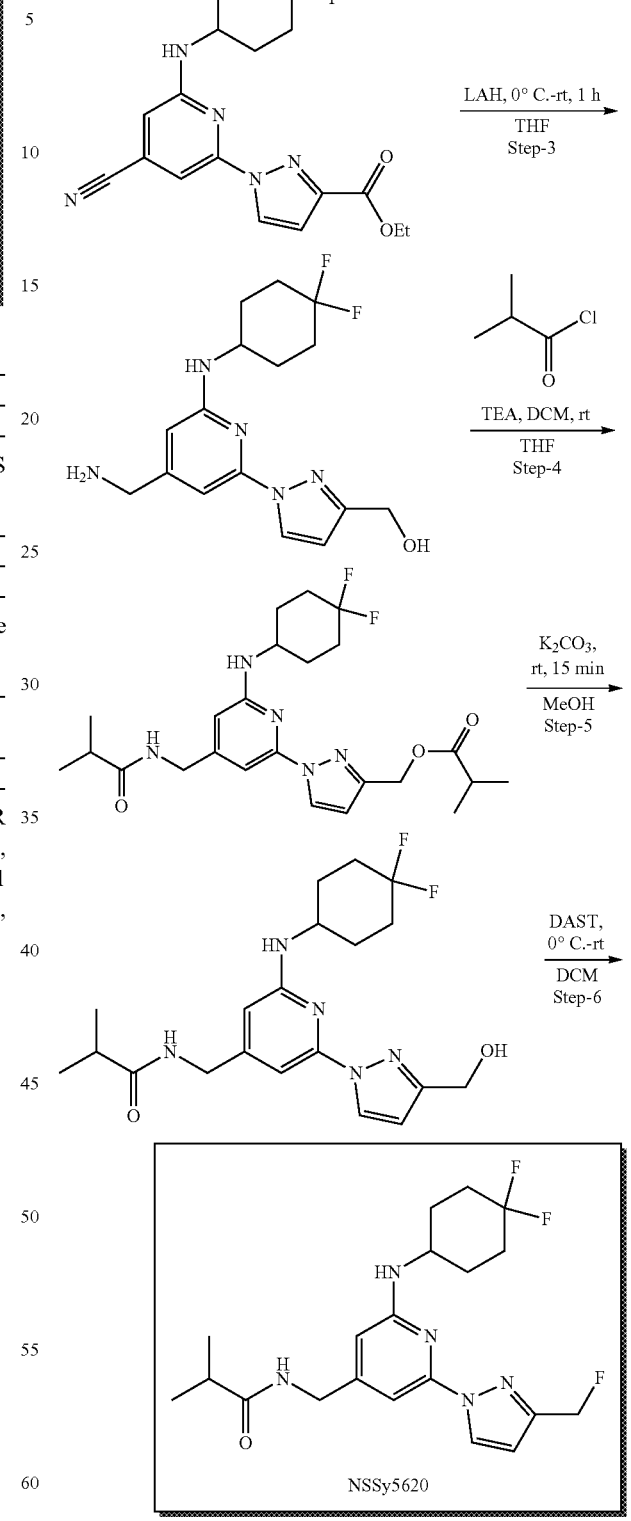

NSSy5620

Step 1: The Procedure is similar to Step 1[B] in Example-838. 6 g of 2,6-dichloroisonicotinonitrile gave ethyl 1-(6-chloro-4-cyanopyridin-2-yl)-1H-pyrazole-3-carboxylate (4.6 g, 48%). MS (M+1)+=277.

Step 2: The Procedure is similar to Step 1[NSSy6629] in Example-839. 2.5 g of ethyl 1-(6-chloro-4-cyanopyridin-2-yl)-1H-pyrazole-3-carboxylate gave ethyl 1-(4-cyano-6-((4,4-difluorocyclohexyl)amino)pyridin-2-yl)-1H-pyrazole-3-carboxylate (1.74 g, 51%). MS (M+1)+=376.4.

Step 3: The Procedure is similar to Step 4[NSSy6711] in Example-854. 1 g of ethyl 1-(4-cyano-6-((4,4-difluorocyclohexyl)amino)pyridin-2-yl)-1H-pyrazole-3-carboxylate gave (1-(4-(aminomethyl)-6-((4,4-difluorocyclohexyl)amino)pyridin-2-yl)-1H-pyrazol-3-yl)methanol (0.55 g, 61%). MS (M+1)+=338.2.

Step 4: The Procedure is similar to Step 1[A] in Example-838. 0.8 g of (1-(4-(aminomethyl)-6-((4,4-difluorocyclohexyl)amino)pyridin-2-yl)-1H-pyrazol-3-yl)methanol gave (1-(6-((4,4-difluorocyclohexyl)amino)-4-(isobutyramidomethyl)pyridin-2-yl)-1H-pyrazol-3-yl)methyl isobutyrate (0.78 g, 78%). MS (M+1)+=478.2.

Step 5: The Procedure is similar to Step 1[A] in Example-838. 0.78 g of (1-(6-((4,4-difluorocyclohexyl)amino)-4-(isobutyramidomethyl)pyridin-2-yl)-1H-pyrazol-3-yl) methyl isobutyrate gave N-((2-((4,4-difluorocyclohexyl)amino)-6-(3-(hydroxymethyl)-1H-pyrazol-1-yl)pyridin-4-yl)methyl)isobutyramide (0.67 g, 87%). MS (M+1)+=408.1.

Step 6[NSSy5620]: The Procedure is similar to Step 3[NSSy6917] in Example-21. 0.38 g of N-((2-((4,4-difluorocyclohexyl)amino)-6-(3-(hydroxymethyl)-1H-pyrazol-1-yl)pyridin-4-yl)methyl)isobutyramide gave N-((2-((4,4-difluorocyclohexyl)amino)-6-(3-(fluoromethyl)-1H-pyrazol-1-yl)pyridin-4-yl)methyl)isobutyramide, (0.038 g, 18%). MS (M+1)$^+$=410.2; $^1$H-NMR (400 MHz, DMSO-d$_6$): δ 8.56 (d, J=2.40 Hz, 1H), 8.32 (t, J=5.96 Hz, 1H), 6.91 (d, J=7.72 Hz, 2H), 6.65-6.64 (m, 1H), 6.26 (s, 1H), 5.43 (d, J=48.2 Hz, 2H), 4.19-4.04 (m, 2H), 4.02-4.01 (m, 1H), 2.41 (m, 1H), 2.07-1.97 (m, 6H), 1.58-1.54 (m, 2H), 1.06 (d, J=6.84 Hz, 6H).

Example-795

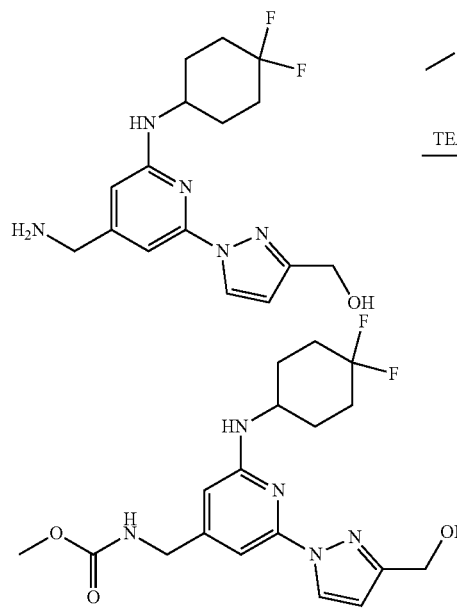

-continued

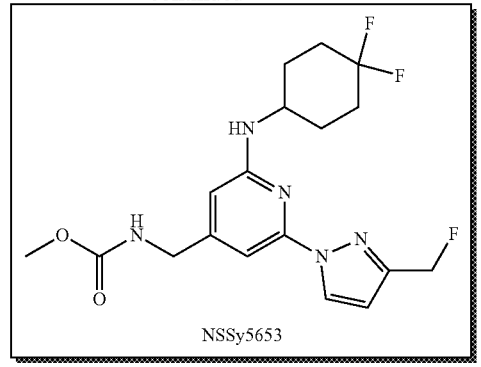

NSSy5653

Step 1: The Procedure is similar to Step 1[A] in Example-838. 0.31 g of (1-(4-(aminomethyl)-6-((4,4-difluorocyclohexyl)amino)pyridin-2-yl)-1H-pyrazol-3-yl)methanol gave methyl ((2-((4,4-difluorocyclohexyl)amino)-6-(3-(hydroxymethyl)-1H-pyrazol-1-yl)pyridin-4-yl)methyl)carbamate, (0.17 g, 50%). MS (M+1)+=396.2.

Step 2[NSSy5653]: The Procedure is similar to Step 3[NSSy6917] in Example-21. 0.17 g of methyl ((2-((4,4-difluorocyclohexyl)amino)-6-(3-(hydroxymethyl)-1H-pyrazol-1-yl)pyridin-4-yl)methyl)carbamate gave methyl ((2-((4,4-difluorocyclohexyl)amino)-6-(3-(fluoromethyl)-1H-pyrazol-1-yl)pyridin-4-yl)methyl)carbamate, (0.085 g, 50%). MS (M+1)+=398.2; 1H-NMR (400 MHz, DMSO-d6): δ 8.56 (d, J=2.00 Hz, 1H), 7.77-7.74 (m, 1H), 6.63 (s, 1H), 6.30 (s, 1H), 5.49 (s, 1H), 5.37 (s, 1H), 4.10 (d, J=6.00 Hz, 2H), 4.02 (s, 1H), 3.56 (s, 3H), 2.06-1.95 (m, 6H), 1.55-1.53 (m, 2H).

Example-796

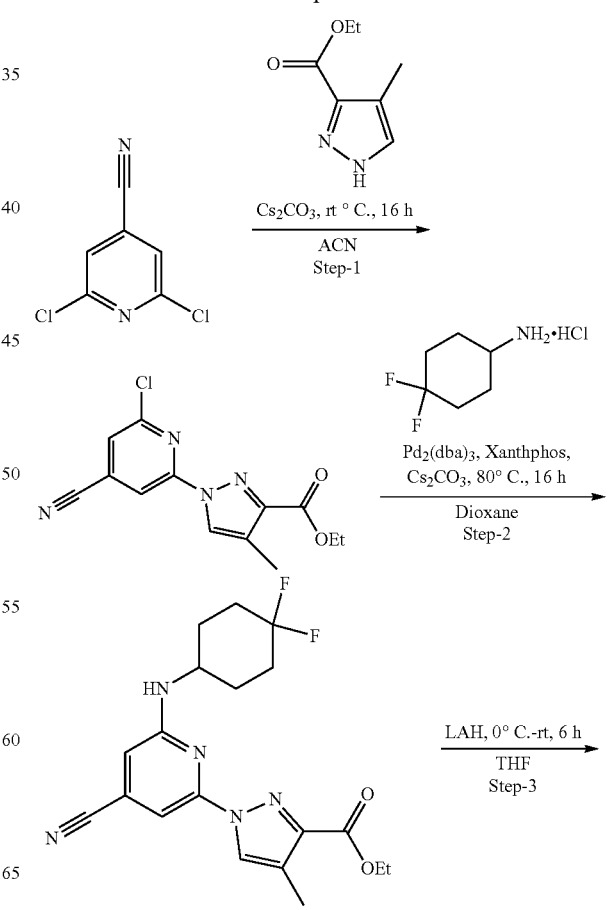

-continued

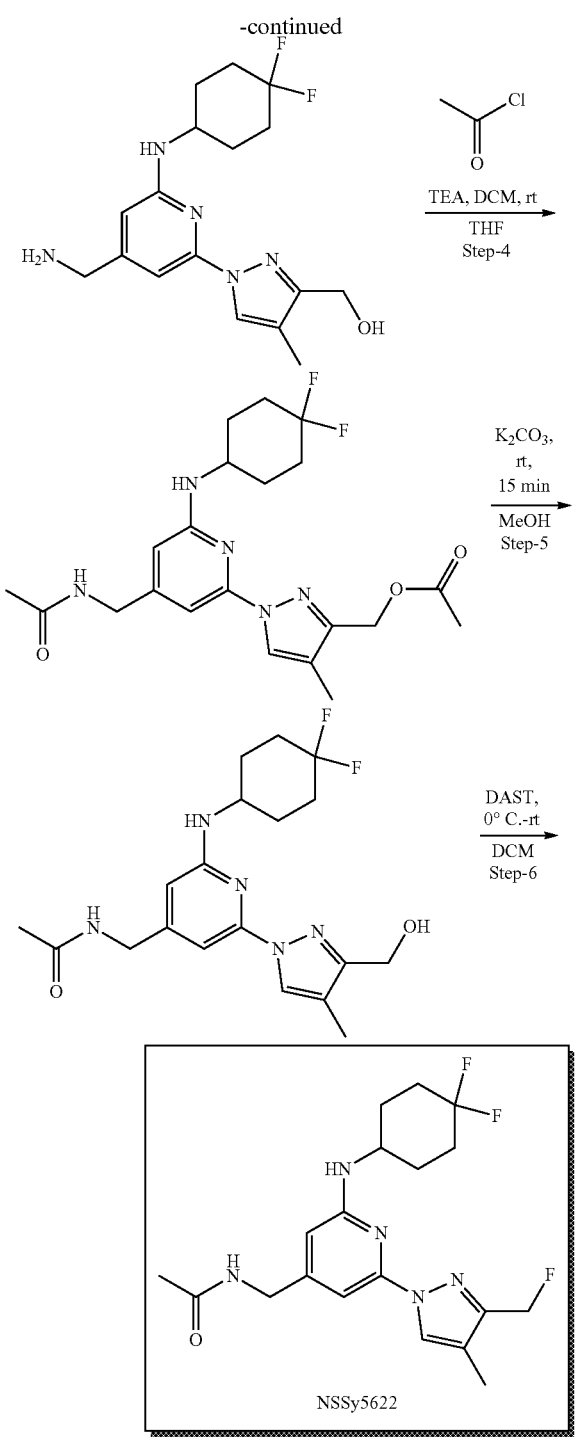

clohexyl)amino)pyridin-2-yl)-4-methyl-1H-pyrazole-3-carboxylate gave (1-(4-(aminomethyl)-6-((4,4-difluorocyclohexyl)amino)pyridine-2-yl)-4-methyl-1H-pyrazol-3-yl)methanol (0.61 g, 58%). MS (M+1)+=352.0.

Step 4: The Procedure is similar to Step 1[A] in Example-838. 0.75 g of (1-(4-(aminomethyl)-6-((4,4-difluorocyclohexyl)amino)pyridin-2-yl)-4-methyl-1H-pyrazol-3-yl)methanol gave (1-(4-(acetamidomethyl)-6-((4,4-difluorocyclohexyl)amino)pyridin-2-yl)-4-methyl-1H-pyrazol-3-yl)methyl acetate (0.61 g, 30%). MS (M+1)+=436.2.

Step 5: The Procedure is similar to Step 1[A] in Example-838. 0.7 g of (1-(4-(acetamidomethyl)-6-((4,4-difluorocyclohexyl)amino)pyridin-2-yl)-4-methyl-1H-pyrazol-3-yl)methyl acetate gave N-((2-((4,4-difluorocyclohexyl)amino)-6-(3-(hydroxymethyl)-4-methyl-1H-pyrazol-1-yl)pyridin-4-yl)methyl)acetamide (0.4 g, 64%). MS (M+1)+=394.2.

Step 6[NSSy5622]: The Procedure is similar to Step 3[NSSy6917] in Example-21. 0.15 g of N-((2-((4,4-difluorocyclohexyl)amino)-6-(3-(hydroxymethyl)-4-methyl-1H-pyrazol-1-yl)pyridin-4-yl)methyl)acetamide gave N-((2-((4,4-difluorocyclohexyl)amino)-6-(3-(fluoromethyl)-4-methyl-1H-pyrazol-1-yl)pyridin-4-yl)methyl)acetamide (0.028 g, 25%). MS (M+1)+=396.2; 1H-NMR (400 MHz, DMSO-d6): δ 8.43-8.36 (m, 2H), 6.87 (d, J=10.04 Hz, 2H), 6.26 (s, 1H), 5.49 (s, 1H), 5.37 (s, 1H), 4.16 (d, J=5.96 Hz, 2H), 4.02-4.01 (m, 1H), 3.12 (s, 1H), 2.15 (s, 3H), 2.09-1.95 (m, 7H), 1.60 (s, 3H), 1.54-1.50 (m, 2H).

Example-797

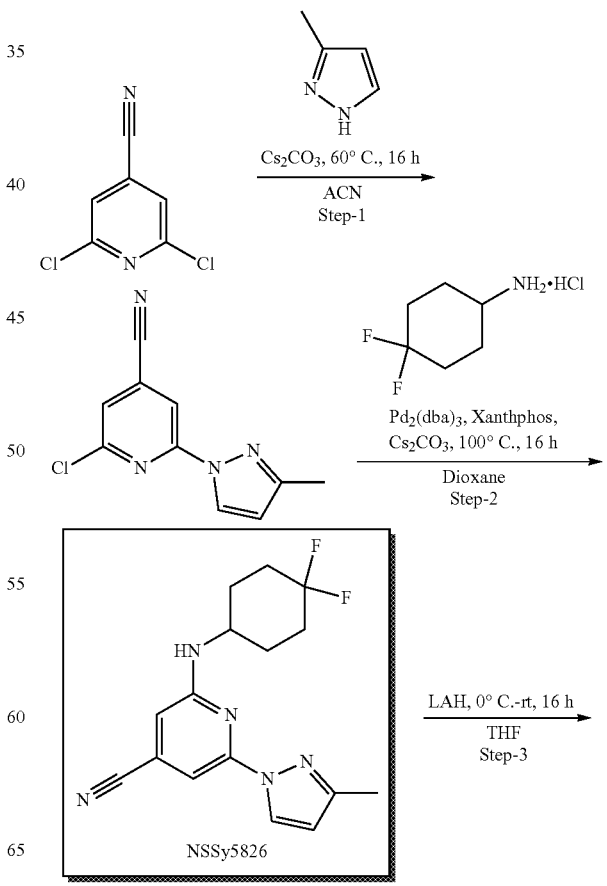

Step 1: The Procedure is similar to Step 1[B] in Example-838. 10 g of 2,6-dichloroisonicotinonitrile gave ethyl 1-(6-chloro-4-cyanopyridin-2-yl)-4-methyl-1H-pyrazole-3-carboxylate (5 g, 30%). MS (M+1)+=291.0.

Step 2: The Procedure is similar to Step 1[NSSy6629] in Example-839. 5 g of ethyl 1-(6-chloro-4-cyanopyridin-2-yl)-4-methyl-1H-pyrazole-3-carboxylate gave ethyl 1-(4-cyano-6-((4,4-difluorocyclohexyl)amino)pyridin-2-yl)-4-methyl-1H-pyrazole-3-carboxylate (1.3 g, 20%). MS (M+1)+=390.2.

Step 3: The Procedure is similar to Step 4[NSSy6711] in Example-854. 1 g of ethyl 1-(4-cyano-6-((4,4-difluorocy-

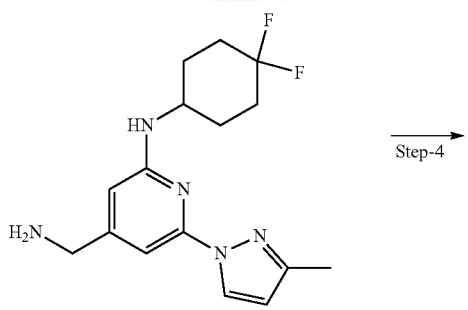

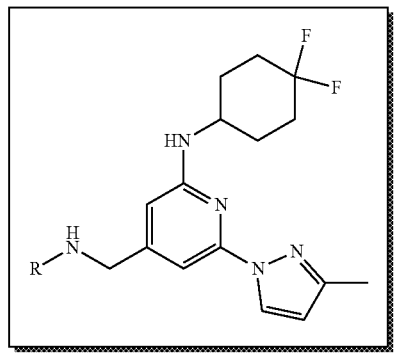

R=

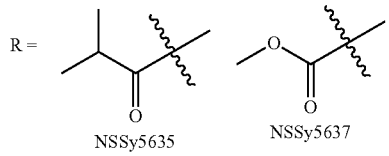

Step 1: The Procedure is similar to Step 1[B] in Example-838. 2 g of 2,6-dichloroisonicotinonitrile gave 2-chloro-6-(3-methyl-1H-pyrazol-1-yl) isonicotinonitrile (2.3 g, 92%). MS (M+1)+=219.2.

Step 2: The Procedure is similar to Step 1[NSSy6629] in Example-839. 2.2 g of 2-chloro-6-(3-methyl-1H-pyrazol-1-yl) isonicotinonitrile gave 2-((4,4-difluorocyclohexyl)amino)-6-(3-methyl-1H-pyrazol-1-yl) isonicotinonitrile (1.8 g, 54%). MS (M+1)+=318.1.

Step 3: The Procedure is similar to Step 4[NSSy6711] in Example-854. 1 g of 2-((4,4-difluorocyclohexyl)amino)-6-(3-methyl-1H-pyrazol-1-yl) isonicotinonitrile gave 4-(aminomethyl)-N-(4,4-difluorocyclohexyl)-6-(3-methyl-1H-pyrazol-1-yl)pyridin-2-amine (0.8 g, 79%). MS (M+1)+=322.

TABLE 82

| | Step 4: | | |
|---|---|---|---|
| Compound No. | R | Condition | Yield (%) |
| NSSy5635 | | Methyl chloroformate, TEA, DCM, 0° C.-rt, 20 min | 32 |

TABLE 82-continued

| | Step 4: | | |
|---|---|---|---|
| Compound No. | R | Condition | Yield (%) |
| NSSy5637 | | Iso-butyryl chloride, TEA, DCM, 0° C.-rt, 20 min | 40 |

Step 4[NSSy5635]: The Procedure is similar to Step 1[A] in Example-838. MS (M+1)+=380.2; 1H-NMR (400 MHz, DMSO-d6): δ 8.41 (d, J=2.44 Hz, 1H), 7.76-7.75 (m, 1H), 6.29 (d, J=2.48 Hz, 1H), 6.23 (s, 1H), 4.12-4.08 (m, 2H), 4.00-3.98 (m, 1H), 3.57 (s, 3H), 2.33 (s, 3H), 2.26-1.95 (m, 6H), 1.56-1.53 (m, 2H).

Step 4[NSSy5637]: The Procedure is similar to Step 1[A] in Example-838. MS (M+1)+=392.0; 1 H-NMR (400 MHz, DMSO-d6): δ 8.41 (d, J=2.32 Hz, 1H), 8.32-8.29 (m, 1H), 6.29 (d, J=2.36 Hz, 1H), 6.19 (s, 1H), 4.16 (d, J=6.00 Hz, 2H), 3.97-3.88 (m, 1H), 2.43-2.41 (m, 2H), 2.26 (s, 3H), 2.08-1.96 (m, 6H), 1.56-1.53 (m, 2H), 1.06 (d, J=6.84 Hz, 6H).

Example-798

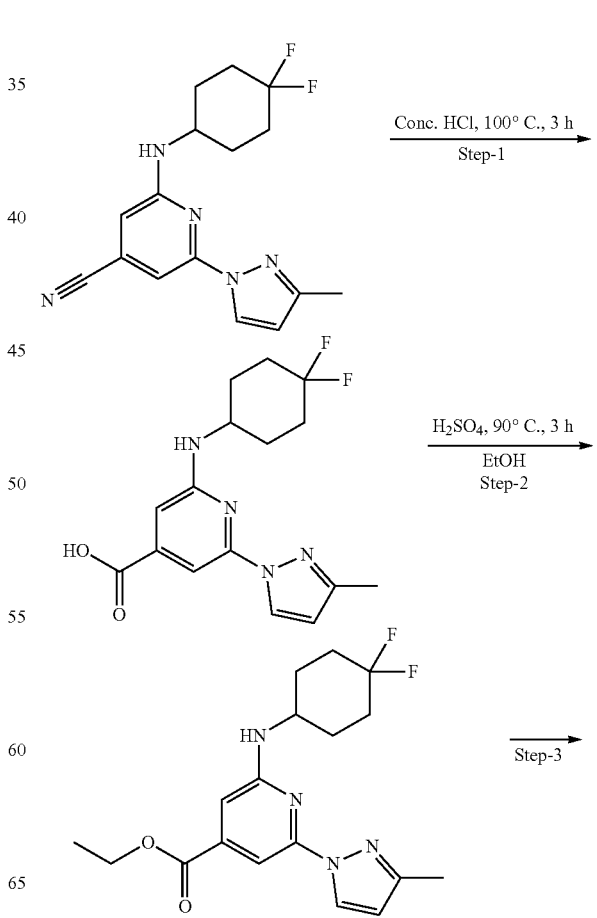

-continued

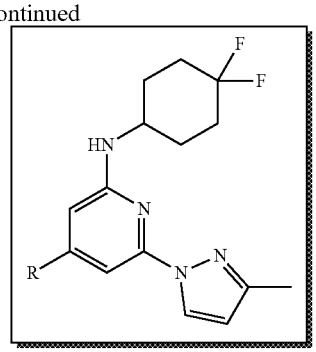

R=

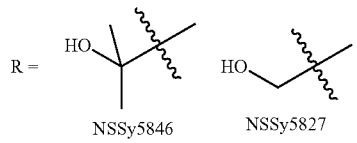

Step 1: The Procedure is similar to Step 2[NSSy6711] in Example-854. 0.85 g of 2-((4,4-difluorocyclohexyl)amino)-6-(3-methyl-1H-pyrazol-1-yl) isonicotinonitrile gave 2-((4,4-difluorocyclohexyl)amino)-6-(3-methyl-1H-pyrazol-1-yl) isonicotinic acid (0.8 g, 88%). MS (M+1)+=337.

Step 2: The Procedure is similar to Step 3[NSSy6711] in Example-854. 0.8 g of 2-((4,4-difluorocyclohexyl)amino)-6-(3-methyl-1H-pyrazol-1-yl) isonicotinic acid gave ethyl 2-((4,4-difluorocyclohexyl)amino)-6-(3-methyl-1H-pyrazol-1-yl) isonicotinate (0.75 g, 87%). MS (M+1)+=365.

TABLE 83

Step 3:

| Compound No. | R | Condition | Yield (%) |
|---|---|---|---|
| NSSy5846 | ![HO-C(CH3)2-] | CH₃MgBr, THF, 0° C.-rt, 30 min | 26 |
| NSSy5827 | ![HO-CH2-] | LAH, THF, 0° C.-rt, 3 h | 81 |

Step 3[NSSy5846]: The Procedure is similar to Step 4[NSSy6464] in Example-869. MS (M+1)+=351.2; 1H-NMR (400 MHz, DMSO-d6): δ 8.41 (d, J=2.40 Hz, 1H), 7.01 (d, J=1.20 Hz, 1H), 6.73 (d, J=7.20 Hz, 1H), 6.47 (d, J=1.20 Hz, 1H), 6.28 (d, J=2.40 Hz, 1H), 5.13 (s, 1H), 4.03-3.99 (m, 1H), 2.27 (s, 3H), 2.06-1.96 (m, 6H), 1.57-1.55 (m, 2H), 1.39 (d, J=0.80 Hz, 6H).

Step 3[NSSy5827]: The Procedure is similar to Step 4[NSSy6711] in Example-854. MS (M+1)+=323.1; 1H-NMR (400 MHz, DMSO-d6): δ 8.41 (d, J=2.40 Hz, 1H), 6.89 (s, 1H), 6.75 (d, J=7.60 Hz, 1H), 6.35 (s, 1H), 6.28 (d, J=2.40 Hz, 1H), 5.31 (t, J=6.00 Hz, 1H), 4.43 (d, J=6.00 Hz, 2H), 4.00-3.98 (m, 1H), 2.26 (s, 3H), 2.08-1.96 (m, 6H), 1.57-1.54 (m, 2H).

Example-799

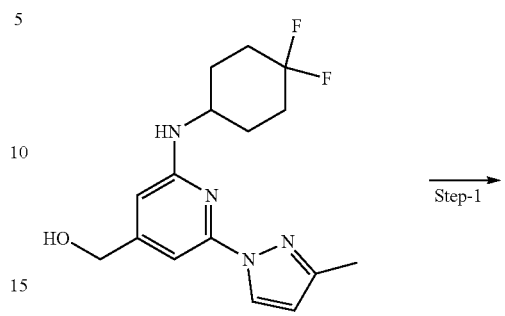

Step-1

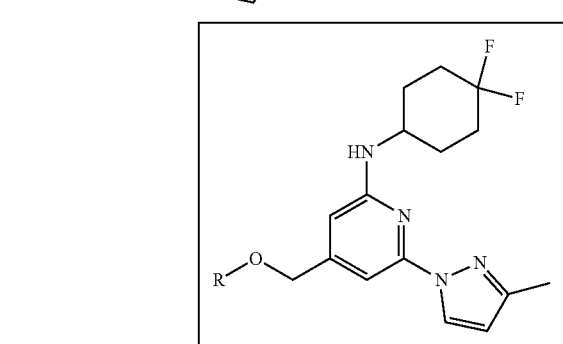

R=

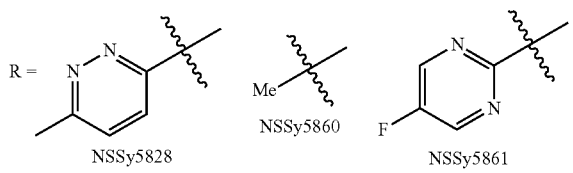

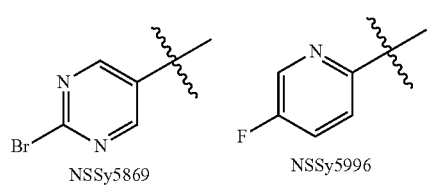

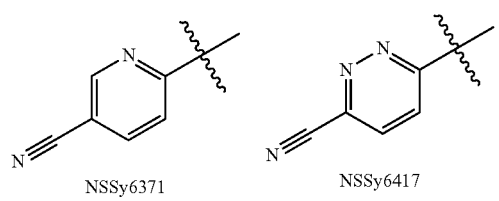

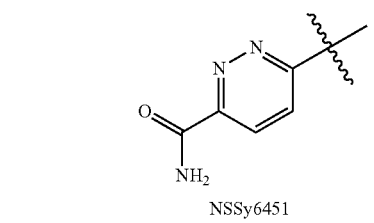

TABLE 84

Step 1:

| Compound No. | R | Condition | Yield (%) |
|---|---|---|---|
| NSSy5828 | 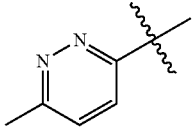 [SMILES: *c1ccc(C)nn1] | 3-bromo-6-methylpyridazine, TBAHS, 50% aq NaOH Solution, 100° C., 16 h | 36 |
| NSSy5860 | 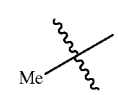 | CH$_3$I, NaH, THF, 0° C.-rt, 2 h | 55 |
| NSSy5861 | 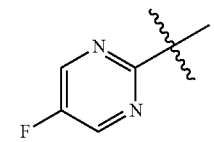 | 2-Bromo-5-fluoropyrimidine, NaH, THF, 0° C.-rt, 2 h | 49 |
| NSSy5869 | 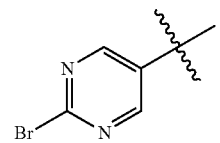 | 2-Bromo-5-fluoropyrimidine, NaH, THF, 0° C.-rt, 2 h | 08 |
| NSSy5996 | 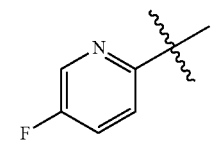 | 2,5-Difluoropyridine, TBAHS, 50% Aq NaOH Solution, 80° C., 30 min | 47 |
| NSSy6371 | 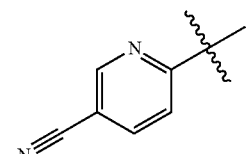 | 2-Bromo-5-Cyanopyridine, Cs$_2$CO$_3$, DMF, rt, 8 h | 20 |
| NSSy6417 | 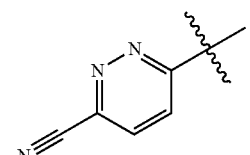 | 6-Chloro-3-Pyridazinecarbonitrile, Cs$_2$CO$_3$, DMF, rt, 16 h | 40 |
| NSSy6451 | 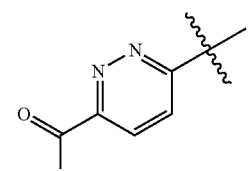 | 6-Chloropyridazine-3-Carboxamide, Cs$_2$CO$_3$, DMF, 100° C., 16 h | 40 |

Step 1[NSSy5828]: A solution of (2-((4,4-difluorocyclohexyl)amino)-6-(3-methyl-1H-pyrazol-1-yl)pyridin-4-yl)methanol (0.15 g, 0.465 mmol), 3-bromo-6-methylpyridazine (0.16 g, 0.93 mmol) and tetrabutylammonium Hydrogen sulfate (0.15 g, 0.46 mmol) in 50% aqueous sodium hydroxide solution (8 mL) was heated at 100° C. in a closed vial for 16 h. The reaction mixture was extracted with ethyl acetate (2×40 mL). The combined organic layer was dried over sodium sulphate and concentrated to afford crude which was purified by column chromatography using 55% ethyl acetate in hexane as an eluent to afford (N-(4,4-difluorocyclohexyl)-6-(3-methyl-1H-pyrazol-1-yl)-4-(((6-methylpyridazin-3-yl)oxy)methyl)pyridin-2-amine as an off-white solid (0.07 g, 36%). MS (M+1)+=415.2; 1H-NMR (400 MHz, DMSO-d6): δ 8.43 (d, J=2.40 Hz, 1H), 7.55 (d, J=8.80 Hz, 1H), 7.26 (d, J=8.80 Hz, 1H), 6.98 (s, 1H), 6.88

(d, J=7.60 Hz, 1H), 6.40 (s, 1H), 6.30 (d, J=2.40 Hz, 1H), 5.43 (s, 2H), 3.99 (m, 1H), 2.26 (s, 3H), 2.08-1.96 (m, 6H), 1.56-1.53 (m, 2H).

Step 1[NSSy5860]: The Procedure is similar to Step 5[NSSy6711] in Example-854. MS (M+1)+=337.0; 1H-NMR (400 MHz, DMSO-d6): δ 8.42 (d, J=2.36 Hz, 1H), 6.87 (s, 1H), 6.81 (d, J=7.32 Hz, 1H), 6.31-6.29 (m, 2H), 4.36 (s, 2H), 4.00-3.98 (m, 1H), 3.12 (s, 3H), 2.26 (s, 3H), 2.07-1.96 (m, 6H), 1.56-1.54 (m, 2H).

Step 1[NSSy5861]: The Procedure is similar to Step 5[NSSy6711] in Example-854. MS (M+1)+=419.2; 1H-NMR (400 MHz, DMSO-d6): δ 8.74 (s, 2H), 8.43 (d, J=2.40 Hz, 1H), 6.96 (s, 1H), 6.90 (d, J=7.28 Hz, 1H), 6.38 (s, 1H), 6.30 (d, J=2.40 Hz, 1H), 5.34 (s, 2H), 4.01-3.90 (m, 1H), 2.26 (s, 3H), 2.06-1.96 (m, 6H), 1.55-1.53 (m, 2H).

Step 1[NSSy5869]: The Procedure is similar to Step 5[NSSy6711] in Example-854. MS (M, M+2)+=479, 481; 1H-NMR (400 MHz, DMSO-d6): δ 8.75 (s, 1H), 8.58 (s, 1H), 8.44 (s, 1H), 6.98-6.94 (m, 2H), 6.41 (d, J=18.8 Hz, 1H), 6.28 (d, J=26.2 Hz, 1H), 5.26 (s, 2H), 4.00-3.80 (m, 1H), 2.27 (s, 3H), 2.06-1.96 (m, 6H), 1.56-1.53 (m, 2H).

Step 1[NSSy5996]: The Procedure is similar to Step 1[NSSy5828] in Example-799. MS (M+1)+=418.2; 1H-NMR (400 MHz, DMSO-d6): δ 8.42 (s, 1H), 8.16 (s, 1H), 7.77-7.72 (m, 1H), 7.03-7.00 (m, 1H), 6.99 (s, 1H), 6.86 (d, J=7.20 Hz, 1H), 6.36 (s, 1H), 6.29 (d, J=2.00 Hz, 1H), 5.28 (s, 2H), 4.00 (m, 1H), 2.26 (s, 3H), 2.08-1.95 (m, 6H), 1.24-1.19 (m, 2H).

Step 1[NSSy6371]: The Procedure is similar to Step 1[A] in Example-838. MS (M+1)+=425.1; 1H-NMR (400 MHz, DMSO-d6): δ 8.72 (d, J=2.40 Hz, 1H), 8.42 (d, J=2.40 Hz, 1H), 8.24-8.21 (m, 1H), 7.16 (d, J=8.80 Hz, 1H), 6.95 (s, 1H), 6.89 (d, J=7.20 Hz, 1H), 6.35 (s, 1H), 6.30 (d, J=2.40 Hz, 1H), 5.40 (s, 2H), 4.00 (s, 1H), 2.26 (s, 3H), 2.05-1.95 (m, 6H), 1.55-1.24 (m, 2H).

Step 1[NSSy6417]: The Procedure is similar to Step 1[A] in Example-838. MS (M+1)+=426.2; 1H-NMR (400 MHz, DMSO-d6): δ 8.43 (t, J=2.40 Hz, 1H), 8.31-8.27 (m, 1H), 7.66-7.62 (m, 1H), 7.01 (d, J=3.20 Hz, 1H), 6.92 (s, 1H), 6.41 (s, 1H), 6.30 (t, J=2.40 Hz, 1H), 5.58 (s, 2H), 4.01-3.98 (m, 1H), 2.27 (s, 3H), 2.06-1.99 (m, 6H), 1.56-1.50 (m, 2H).

Step 1[NSSy6451]: The Procedure is similar to Step 1[B] in Example-838. MS (M+1)+=444.2; 1H-NMR (400 MHz, DMSO-d6): δ 8.43 (d, J=2.80 Hz, 1H), 8.36 (s, 1H), 8.14 (d, J=12.00 Hz, 1H), 7.79 (s, 1H), 7.49 (d, J=12.00 Hz, 1H), 7.00 (s, 1H), 6.89 (d, J=10.00 Hz, 1H), 6.41 (s, 1H), 6.30 (d, J=3.20 Hz, 1H), 5.56 (s, 2H), 4.00 (m, 1H), 2.26 (s, 3H), 2.05-1.95 (m, 6H), 1.57 (m, 2H).

Example-800

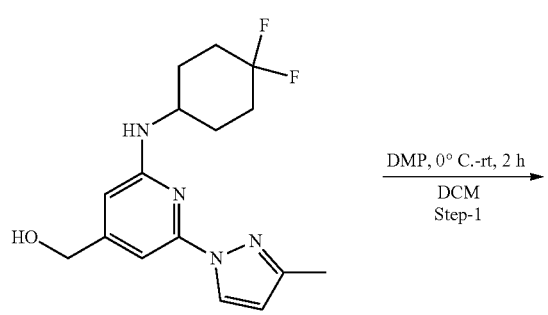

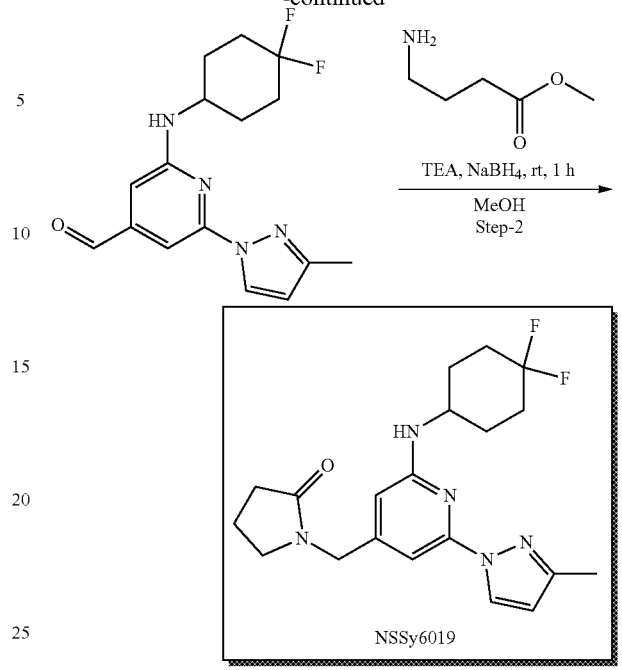

Step 1: The Procedure is similar to Step 1[NSSy6930] in Example-867. 1.5 g of (2-((4,4-difluorocyclohexyl)amino)-6-(3-methyl-1H-pyrazol-1-yl)pyridin-4-yl) methanol gave 2-((4,4-difluorocyclohexyl)amino)-6-(3-methyl-1H-pyrazol-1-yl) isonicotinaldehyde (1.2 g, 80%). MS (M+1)+=321.

Step 2[NSSy6019]: To a solution of 2-((4,4-difluorocyclohexyl)amino)-6-(3-methyl-1H-pyrazol-1-yl)isonicotinaldehyde (0.21 g, 0.655 mmol) in methanol (10 mL) was added methyl 4-aminobutanoate (0.09 g, 0.78 mmol) and triethylamine (0.086 g, 0.85 mmol), the reaction mixture was stirred at rt for 1 h. After 1 h, added Sodium borohydride (0.032 g, 0.85 mmol) to the above reaction mixture and heated at 50° C. for 16 h. The reaction mixture was concentrated and diluted with water and extracted with ethyl acetate (2×50 mL). The combined organic layer was dried over sodium sulphate and concentrated to afford crude and which was purified by column chromatography using 40% ethyl acetate in pet ether as eluent to afford 1-((2-((4,4-difluorocyclohexyl)amino)-6-(3-methyl-1H-pyrazol-1-yl)pyridin-4-yl)methyl)pyrrolidin-2-one as an off-white solid (60 mg, 23%). MS (M+1)+=390.0; 1H-NMR (400 MHz, DMSO-d6): δ 8.42 (d, J=2.40 Hz, 1H), 6.85 (d, J=7.20 Hz, 1H), 6.79 (s, 1H), 6.30 (d, J=2.40 Hz, 1H), 6.18 (s, 1H), 4.14 (m, 2H), 3.98-3.38 (m, 1H), 3.28-3.27 (m, 2H), 2.46-2.34 (m, 2H), 2.32 (s, 3H), 2.30-2.00 (m, 8H), 1.50-1.61 (m, 2H).

Example-801

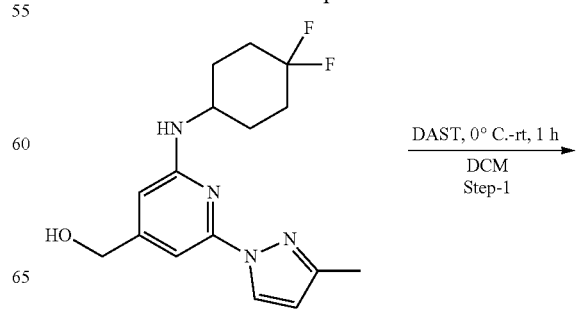

-continued

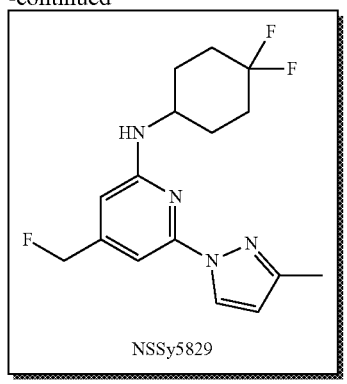

Step 1[NSSy5829]: The Procedure is similar to Step 3[NSSy6917] in Example-21. 0.12 g of (2-((4,4-difluorocyclohexyl)amino)-6-(3-methyl-1H-pyrazol-1-yl)pyridin-4-yl) methanol gave N-(4,4-difluorocyclohexyl)-4-(fluoromethyl)-6-(3-methyl-1H-pyrazol-1-yl)pyridin-2-amine (1.2 g, 15%). MS (M+1)+=325.1; 1H-NMR (400 MHz, DMSO-d6): δ 8.43 (d, J=2.40 Hz, 1H), 6.93 (d, J=7.20 Hz, 1H), 6.88 (s, 1H), 6.31 (d, J=2.40 Hz, 1H), 5.46 (s, 1H), 5.34 (s, 1H), 4.01-4.00 (m, 1H), 2.25 (s, 3H), 2.07-1.96 (m, 6H), 1.56-1.53 (m, 2H).

Example-802

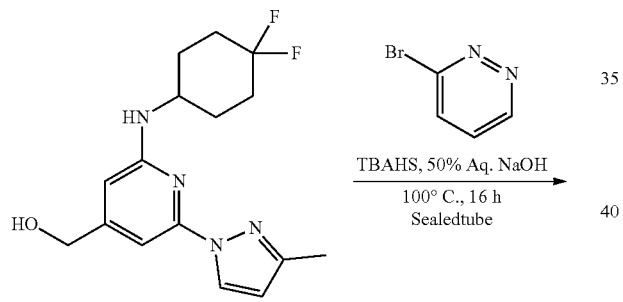

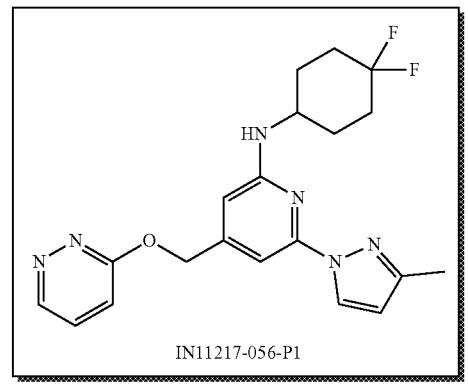

Step 1[IN11217-056-P1]: The Procedure is similar to Step 1[NSSy5828] in Example-799. 0.15 g of (2-((4,4-difluorocyclohexyl)amino)-6-(3-methyl-1H-pyrazol-1-yl)pyridin-4-yl) methanol gave N-(4,4-difluorocyclohexyl)-6-(3-methyl-1H-pyrazol-1-yl)-4-((pyridazin-3-yloxy)methyl)pyridin-2-amine as an off-white solid (0.04 g, 22%). MS (M+1)$^+$= 401.2; $^1$H-NMR (400 MHz, DMSO-d$_6$): δ 8.93-8.92 (m, 1H), 8.43 (d, J=2.4 Hz, 1H), 7.69-7.66 (m, 1H), 7.35 (dd, J=9.2, 1.6 Hz, 1H), 6.99 (s, 1H), 6.88 (d, J=7.6 Hz, 1H), 6.41 (s, 1H), 6.29 (d, J=2.0 Hz, 1H), 5.48 (s, 2H), 4.00 (m, 1H), 2.26 (s, 3H), 2.06-1.96 (m, 6H), 1.56-1.54 (m, 2H).

Example-803

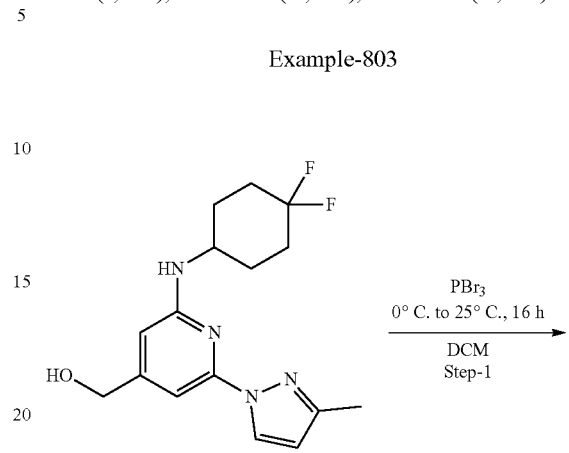

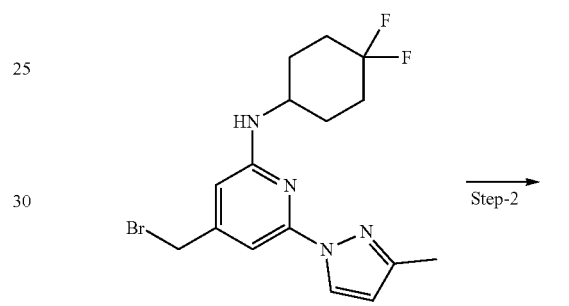

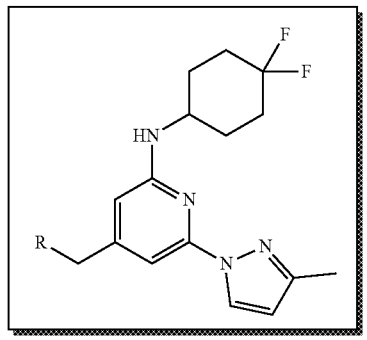

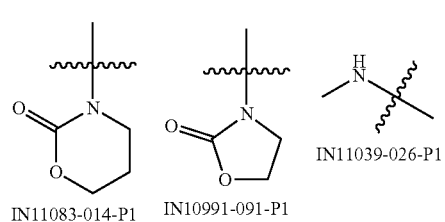

Step 1: The Procedure is similar to Step 3[IN11059-090-P1] in Example-659. 1.2 g of (2-((4,4-difluorocyclohexyl)amino)-6-(3-methyl-1H-pyrazol-1-yl)pyridin-4-yl) methanol gave 4-(bromomethyl)-N-(4,4-difluorocyclohexyl)-6-(3-methyl-1H-pyrazol-1-yl)pyridin-2-amine as an off-white solid (0.5 g, 35%). MS (M+1)$^+$=385.4.

TABLE 85

Step 2:

| Compound No | R | Condition | Yield (%) | MS (M + 1)+ |
|---|---|---|---|---|
| IN11083-014-P1 | (1,3-oxazinan-3-yl, methyl-linked) | NaH, DMF, 45° C., 48 h | 19 | 406.1 |
| IN10991-091-P1 | (oxazolidin-3-yl, methyl-linked) | NaH, DMF, 45° C., 4 h | 25 | 392.2 |
| IN11039-026-P1 | (N-methyl, dimethyl C) | CH$_3$NH$_2$ in MeOH, 70° C., 16 h | 69 | 336.2 |

[IN11083-014-P1]: The Procedure is similar to Step 2[IN10991-021-P1] in Example-694. 1H-NMR (400 MHz, DMSO-d6): δ 8.41 (d, J=2.40 Hz, 1H), 6.85-6.82 (m, 2H), 6.29 (d, J=2.40 Hz, 1H), 6.24 (s, 1H), 4.37 (s, 2H), 4.24 (t, J=5.20 Hz, 2H), 4.00 (s, 1H), 3.25-3.20 (m, 2H), 2.26 (s, 3H), 2.10-1.90 (m, 8H), 1.60-1.48 (m, 2H).

[IN10991-091-P1]: The Procedure is similar to Step 2[IN10991-021-P1] in Example-694. 1H-NMR (400 MHz, DMSO-d6): δ 8.42 (d, J=2.4 Hz, 1H), 6.88 (d, J=7.2 Hz, 1H), 6.83 (s, 1H), 6.29 (d, J=2.4 Hz, 1H), 6.26 (s, 1H), 4.33-4.26 (m, 4H), 4.08-4.00 (m, 1H), 3.50-3.46 (m, 2H), 2.26 (s, 3H), 2.09-1.96 (m, 6H), 1.56-1.54 (m, 2H).

[IN11039-026-P1]: The Procedure is similar to Step 1[A] in Example-838. 1H-NMR (400 MHz, MeOD): δ 8.37 (s, 1H), 6.94 (d, J=14.80 Hz, 1H), 6.33 (d, J=11.20 Hz, 1H), 6.25 (s, 1H), 4.11 (s, 1H), 3.95 (s, 1H), 3.64 (d, J=12.40 Hz, 2H), 2.40 (s, 3H), 2.33 (s, 3H), 2.15-1.85 (m, 6H), 1.70-1.60 (m, 2H).

Example-804

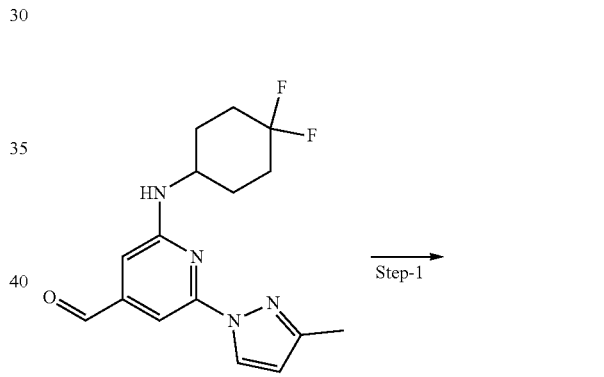

Example-805

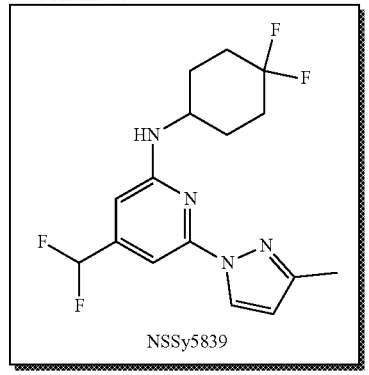

Step 1[NSSy5839]: The Procedure is similar to Step 3[NSSy6917] in Example-21. 0.12 g of 2-((4,4-difluorocyclohexyl)amino)-6-(3-methyl-1H-pyrazol-1-yl) isonicotinaldehyde gave N-(4,4-difluorocyclohexyl)-4-(difluoromethyl)-6-(3-methyl-1H-pyrazol-1-yl)pyridin-2-amine (0.1 g, 78%). MS (M+1)+=343.1; 1H-NMR (400 MHz, DMSO-d6): δ 8.47 (d, J=2.32 Hz, 1H), 7.20 (d, J=7.28 Hz, 1H), 6.95 (t, J=55.40 Hz, 1H), 6.98 (m, 1H), 6.50 (s, 1H), 6.34 (d, J=2.36 Hz, 1H), 4.05 (m, 1H), 2.27 (s, 3H), 2.09-1.99 (m, 6H), 1.60-1.57 (m, 2H).

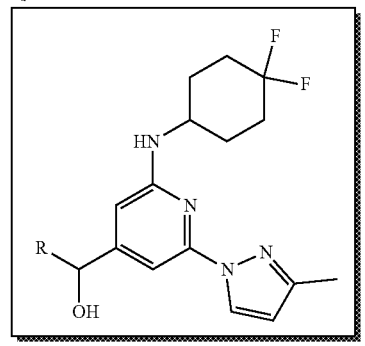

R=

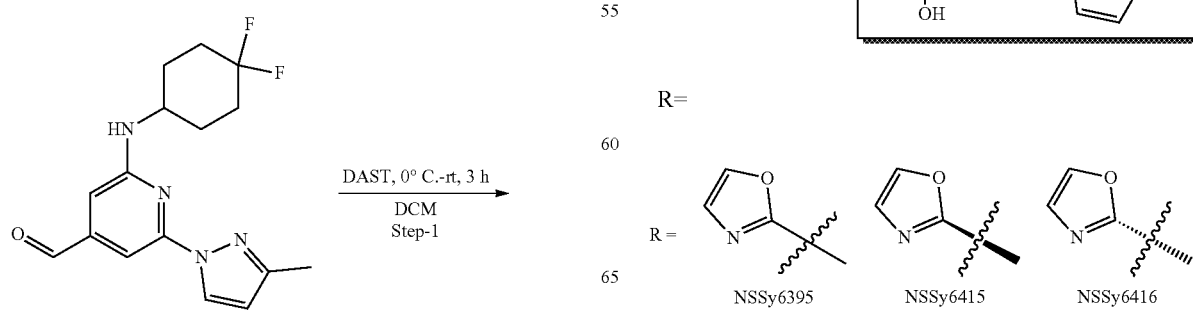

NSSy6395    NSSy6415    NSSy6416

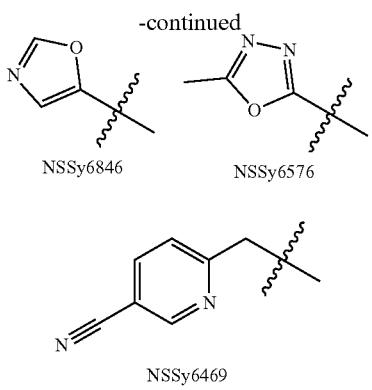

TABLE 86

| Compound No | R | Condition | Yield (%) |
|---|---|---|---|
| NSSy6395 | oxazole | Oxazole, n-BuLi, THF, −78° C., 1 h | 36 |
| NSSy6415 | oxazole | Chiral separation | — |
| NSSy6416 | oxazole | Chiral separation | — |
| NSSy6846 | oxazole | Oxazole, n-BuLi, THF, −78° C., 1 h | 02 |
| NSSy6576 | 2-methyl-1,3,4-oxadiazole | 2-methyl-1,3,4-oxadiazole, n-BuLi, THF, −78° C., 1 h | 10 |
| NSSy6469 | 5-cyanopyridin-2-yl | 6-(bromomethyl)nicotinonitrile, $^i$PrMgBr, THF, −78° C., 15 min | 36 |

Step 1[NSSy6395]: The Procedure is similar to Step 4[NSSy6067] in Example-628. MS (M+1)+=390.2; 1H-NMR (400 MHz, DMSO-d6): δ 8.40 (d, J=2.40 Hz, 1H), 8.29 (d, J=0.80 Hz, 1H), 7.99-7.98 (m, 1H), 6.95 (s, 1H), 6.82 (d, J=7.60 Hz, 1H), 6.44 (s, 1H), 6.27 (d, J=2.40 Hz, 1H), 6.04 (d, J=4.80 Hz, 1H), 5.54 (d, J=4.40 Hz, 1H), 3.98 (s, 1H), 2.25 (s, 3H), 2.06-1.95 (m, 6H), 1.56-1.54 (m, 2H).

Step 1[NSSy6415]: MS (M+1)+=390.2; 1H-NMR (400 MHz, DMSO-d6): δ 8.40 (d, J=2.40 Hz, 1H), 8.29 (d, J=0.80 Hz, 1H), 7.99-7.98 (m, 1H), 6.95 (s, 1H), 6.82 (d, J=7.60 Hz, 1H), 6.44 (s, 1H), 6.27 (d, J=2.40 Hz, 1H), 6.04 (d, J=4.80 Hz, 1H), 5.54 (d, J=4.40 Hz, 1H), 3.98 (s, 1H), 2.25 (s, 3H), 2.06-1.95 (m, 6H), 1.56-1.54 (m, 2H).

Step 1[NSSy6416]: MS (M+1)+=390.2; 1H-NMR (400 MHz, DMSO-d6): δ 8.40 (d, J=2.40 Hz, 1H), 8.29 (d, J=0.80 Hz, 1H), 7.99-7.98 (m, 1H), 6.95 (s, 1H), 6.82 (d, J=7.60 Hz, 1H), 6.44 (s, 1H), 6.27 (d, J=2.40 Hz, 1H), 6.04 (d, J=4.80 Hz, 1H), 5.54 (d, J=4.40 Hz, 1H), 3.98 (s, 1H), 2.25 (s, 3H), 2.06-1.95 (m, 6H), 1.56-1.54 (m, 2H).

Step 1[NSSy6846]: The Procedure is similar to Step 4[NSSy6067] in Example-628. MS (M+1)+=390.1; 1H-NMR (400 MHz, DMSO-d6): δ 8.30 (s, 1H), 7.99 (d, J=0.80 Hz, 1H), 7.51 (s, 1H), 6.95 (s, 1H), 6.86 (d, J=7.20 Hz, 1H), 6.50 (s, 1H), 6.23 (s, 1H), 6.06 (d, J=4.72 Hz, 1H), 5.54 (d, J=4.52 Hz, 1H), 3.90 (s, 1H), 2.61 (s, 3H), 2.09-1.89 (m, 7H), 1.56-1.53 (m, 2H).

Step 1[NSSy6576]: The Procedure is similar to Step 4[NSSy6067] in Example-628. MS (M+1)+=405.1; 1H-NMR (400 MHz, DMSO-d6): δ 8.42 (d, J=2.32 Hz, 1H), 6.95 (d, J=6.00 Hz, 2H), 6.80 (d, J=5.12 Hz, 1H), 6.46 (s, 1H), 6.30 (d, J=2.36 Hz, 1H), 5.91 (d, J=5.12 Hz, 1H), 3.99 (s, 1H), 2.48 (s, 3H), 2.25 (s, 3H), 2.10-1.85 (m, 6H), 1.60-1.50 (m, 2H).

Step 1[NSSy6469]: To a solution of 6-(bromomethyl)nicotinonitrile (0.03 g, 0.15 mmol) in tetrahydrofuran (1 mL) was added Isopropylmagnesium Bromide at −78° C. and stirred for 0.5 h. A solution of 2-((4,4-difluorocyclohexyl)amino)-6-(3-methyl-1H-pyrazol-1-yl)isonicotinaldehyde (0.05 g, 0.15 mmol) in tetrahydrofuran was added to the reaction mixture at −56° C. and stirred for 15 min at same temperature. The reaction mixture was slowly warmed to room temperature and stirred for 15 min. The reaction mixture was quenched with saturated ammonium chloride solution at 0° C. and extracted with ethyl acetate (2*20 mL). The combined organic layer was dried over sodium sulphate, filtered and concentrated under reduced pressure to afford crude and which was purified by Prep HPLC to afford 6-(2-(2-(((4,4-difluorocyclohexyl)amino)-6-(3-methyl-1H-pyrazol-1-yl)pyridin-4-yl)-2-hydroxyethyl)nicotinonitrile as an yellow solid (0.025 g, 36%). MS (M+1)+=439.1; 1H-NMR (400 MHz, DMSO-d6): δ 8.97 (s, 1H), 8.41 (s, 1H), 8.23 (m, 1H), 7.53 (d, J=8.08 Hz, 1H), 6.97 (s, 1H), 6.75 (d, J=7.32 Hz, 1H), 6.29 (d, J=14.2 Hz, 2H), 4.92 (m, 1H), 3.96 (m, 2H), 2.27 (s, 3H), 2.15-1.85 (m, 7H), 1.57-1.49 (m, 3H).

Example-806

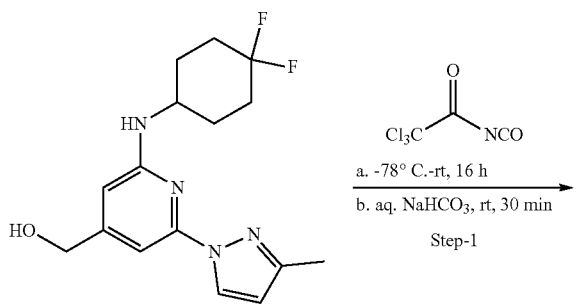

a. −78° C.-rt, 16 h
b. aq. NaHCO$_3$, rt, 30 min

Step-1

-continued

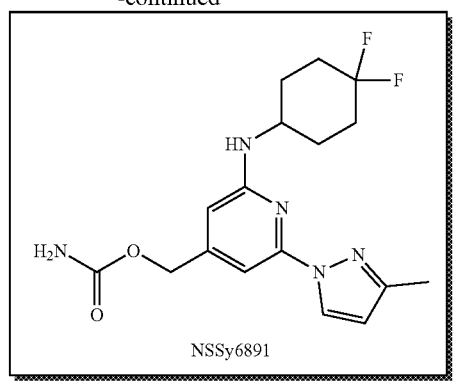

NSSy6891

Step 1[NSSy6891]: To a solution of (2-((4,4-difluorocyclohexyl)amino)-6-(3-methyl-1H-pyrazol-1-yl)pyridin-4-yl)methanol (0.1 g, 0.31 mmol) in tetrahydrofuran was added trichloroacetyl isocyanate (0.11 g, 0.62 mmol) at −78° C. and stirred at room temperature for 16 h. Added saturated sodium bicarbonate solution and stirred at room temperature for 30 min. The reaction mixture was quenched with water and extracted with ethyl acetate. The organic layer was dried over sodium sulphate, filtered and concentrated under reduced pressure to afford crude and which was purified in the Reveleris flash system instrument using 4% methanol in chloroform as eluent to afford (2-((4,4-difluorocyclohexyl)amino)-6-(3-methyl-1H-pyrazol-1-yl)pyridin-4-yl)methyl carbamate as an off-white solid (0.025 g, 23%). MS (M+1)+=366.1; 1H-NMR (400 MHz, DMSO-d6): δ 8.42 (d, J=2.40 Hz, 1H), 6.90 (s, 1H), 6.88 (s, 1H), 6.65 (s, 2H), 6.30 (d, J=2.40 Hz, 1H), 6.27 (s, 1H), 4.92 (s, 2H), 3.99 (s, 1H), 2.27 (s, 3H), 2.08-1.96 (m, 6H), 1.56-1.36 (m, 2H).

Example-807

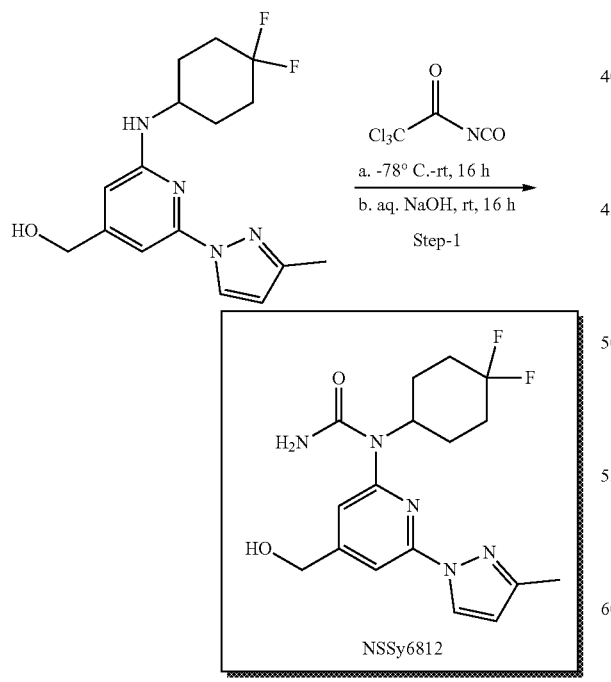

NSSy6812

Step 1[NSSy6812]: The Procedure is similar to Step 1[NSSy6891] in Example-806. 0.1 g of (2-((4,4-difluorocyclohexyl)amino)-6-(3-methyl-1H-pyrazol-1-yl)pyridin-4-yl) methanol gave 1-(4,4-difluorocyclohexyl)-1-(4-(hydroxymethyl)-6-(3-methyl-1H-pyrazol-1-yl)pyridin-2-yl) urea (0.072 g, 65%). MS (M+1)+=366.2; 1H-NMR (400 MHz, DMSO-d6): δ 8.33 (d, J=2.40 Hz, 1H), 7.71 (s, 1H), 7.02 (s, 1H), 6.39 (d, J=2.40 Hz, 1H), 6.04 (s, 2H), 5.57 (t, J=5.60 Hz, 1H), 4.61 (d, J=6.00 Hz, 2H), 4.33 (t, J=6.40 Hz, 1H), 2.30 (s, 3H), 1.89-1.70 (m, 8H).

Example-808

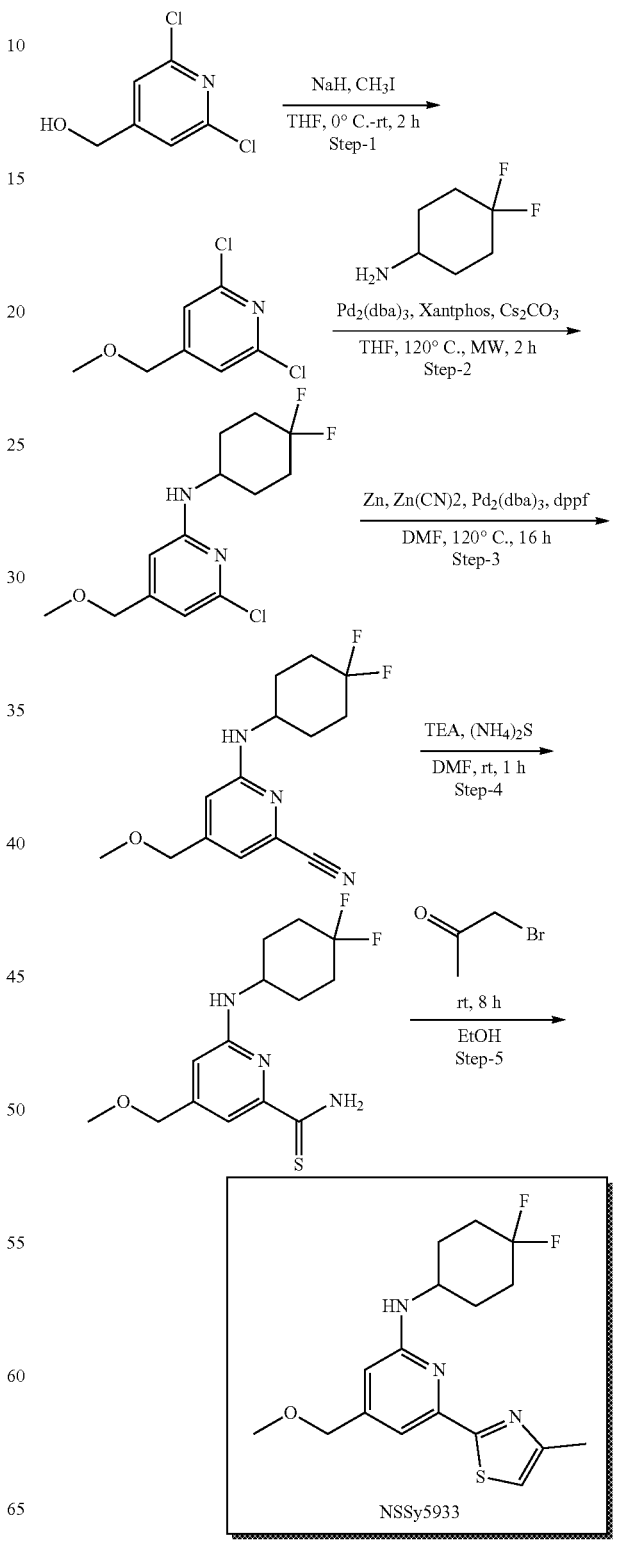

NSSy5933

Step 1: The Procedure is similar to Step 5[NSSy6711] in Example-854. 1.8 g of (2,6-dichloropyridin-4-yl) methanol gave 2,6-dichloro-4-(methoxymethyl)pyridine (1.5 g, 75%). MS (M+1)+=193.

Step 2: The Procedure is similar to Step 1[NSSy6629] in Example-839. 1.5 g of (2,6-dichloropyridin-4-yl) methanol gave 6-chloro-N-(4,4-difluorocyclohexyl)-4-(methoxymethyl)pyridin-2-amine (0.8 g, 35%). MS (M+1)+=291.

Step 3: To a stirred degassed solution of 6-chloro-N-(4, 4-difluorocyclohexyl)-4-(methoxymethyl)pyridin-2-amine (0.65 g, 2.23 mmol), 1,1'-bis(diphenylphosphino)ferrocene (0.124 g, 0.22 mmol), zinc cyanide (0.53 g, 4.47 mmol) and zinc dust (0.014 g, 0.22 mmol) in N, N-dimethylformamide (10 mL) was added tris(dibenzylideneacetone)dipalladium (0) (0.204 g, 0.22 mmol) and the mixture was heated at 120° C. for 16 h. The reaction mixture was filtered through celite bed and the filtrate was quenched with water and extracted with ethyl acetate (2×75 mL). The combined organic layer was dried over sodium sulphate and concentrated to afford 6-((4,4-difluorocyclohexyl)amino)-4-(methoxymethyl) picolinonitrile as a light brownish gum (0.65 g, 98%) and it was forwarded to the next step without any further purification. MS (M+1)+=281.

Step 4: The Procedure is similar to Step 5[NSSy5779] in Example-642. 0.6 g of 6-((4,4-difluorocyclohexyl)amino)-4-(methoxymethyl) picolino nitrile gave 6-((4,4-difluorocyclohexyl)amino)-4-(methoxymethyl)pyridine-2-carbothioamide (0.62 g, 92%). MS (M+1)+=316.

Step 5[NSSy5933]: The Procedure is similar to Step 6[NSSy5779] in Example-642. 0.6 g of 6-((4,4-difluorocyclohexyl)amino)-4-(methoxymethyl)pyridine-2-carbothioamide gave N-(4,4-difluorocyclohexyl)-4-(methoxymethyl)-6-(4-methylthiazol-2-yl)pyridin-2-amine (0.16 g, 24%). MS (M+1)+=354.0; 1H-NMR (400 MHz, DMSO-d6): δ 7.29 (d, J=0.96 Hz, 1H), 7.17 (s, 1H), 6.82 (d, J=6.92 Hz, 1H), 6.52 (s, 1H), 4.36 (d, J=16.68 Hz, 2H), 3.90-3.88 (m, 1H), 3.21 (s, 3H), 2.41 (s, 3H), 2.10-2.00 (m, 6H), 1.61-1.58 (m, 2H).

Example-809

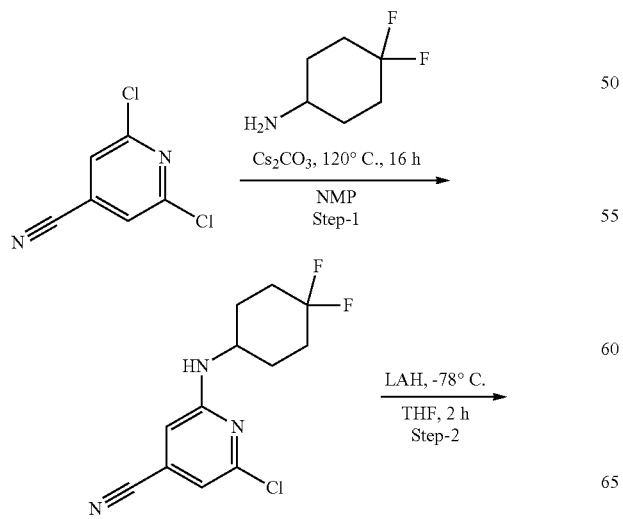

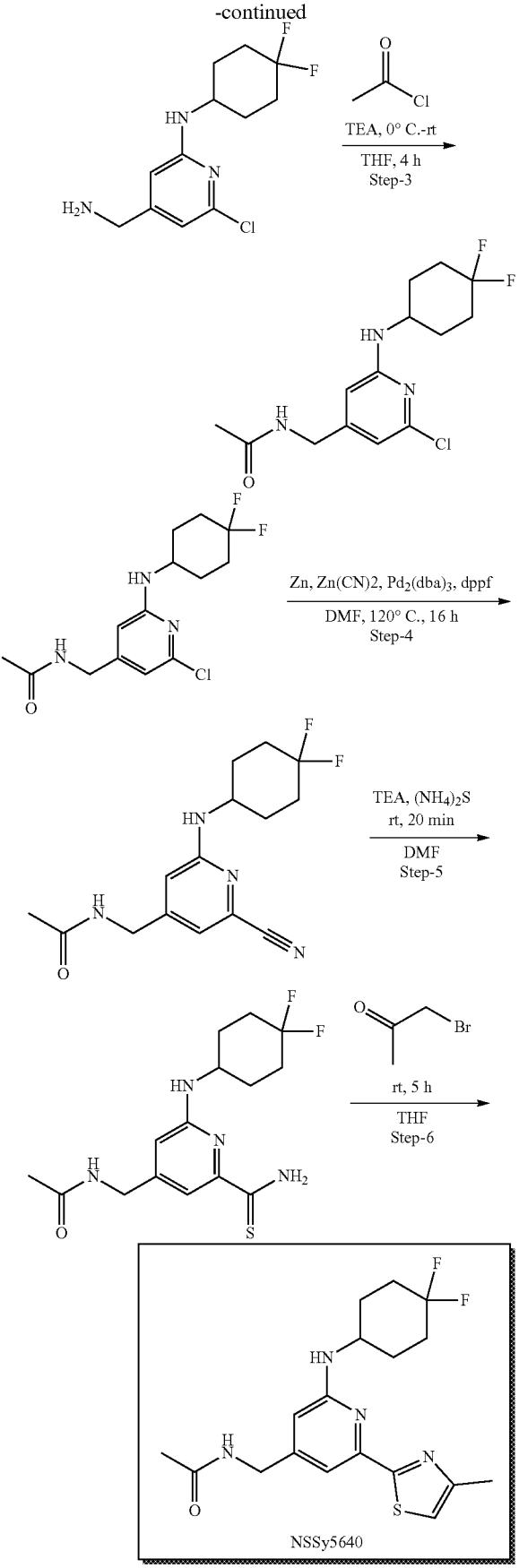

Step 1: The Procedure is similar to Step 1[B] in Example-838. 2 g of 2,6-dichloroisonicotinonitrile gave 2-chloro-6-((4,4-difluorocyclohexyl)amino) isonicotinonitrile (2 g, 63%). MS (M+1)+=272.0.

Step 2: The Procedure is similar to Step 4[NSSy6711] in Example-854. 0.1 g of 2-chloro-6-((4,4-difluorocyclohexyl) amino) isonicotinonitrile gave 4-(aminomethyl)-6-chloro-N-(4,4-difluorocyclohexyl)pyridin-2-amine (0.1 g, 99%). MS (M+1)+=276.0.

Step 3: The Procedure is similar to Step 1[A] in Example-838. 1.2 g of 4-(aminomethyl)-6-chloro-N-(4,4-difluorocyclohexyl)pyridin-2-amine gave N-((2-chloro-6-((4,4-difluorocyclohexyl)amino)pyridin-4-yl)methyl) acetamide (1 g, 72%). MS (M+1)+=318.1.

Step 4: The Procedure is similar to Step 3[NSSy5933] in Example-808. 2 g of N-((2-chloro-6-((4,4-difluorocyclohexyl)amino)pyridin-4-yl)methyl) acetamide gave N-((2-cyano-6-((4,4-difluorocyclohexyl)amino)pyridin-4-yl)methyl)acetamide (0.75 g, 38%). MS (M+1)+=309.1.

Step 5: The Procedure is similar to Step 5[NSSy5779] in Example-642. 1 g of N-((2-cyano-6-((4,4-difluorocyclohexyl)amino)pyridin-4-yl)methyl)acetamide gave N-((2-carbamothioyl-6-((4,4-difluorocyclohexyl)amino)pyridin-4-yl)methyl)acetamide (1 g, 90%). MS (M+1)+=343.1.

Step 6[NSSy5640]: The Procedure is similar to Step 6[NSSy5779] in Example-642. 0.2 g of N-((2-carbamothioyl-6-((4,4-difluorocyclohexyl)amino)pyridin-4-yl)methyl)acetamide gave N-((2-((4,4-difluorocyclohexyl)amino)-6-(4-methylthiazol-2-yl)pyridin-4-yl)methyl) acetamide (0.075 g, 34%). MS (M+1)+=381.1; 1H-NMR (400 MHz, DMSO-d6): δ 8.42 (t, J=5.72 Hz, 1H), 7.29 (d, J=0.92 Hz, 1H), 7.14 (s, 1H), 6.82 (d, J=6.76 Hz, 1H), 6.42 (s, 1H), 4.17 (d, J=5.92 Hz, 2H), 3.91-3.90 (m, 1H), 2.33 (s, 3H), 2.08-1.93 (m, 6H), 1.90 (s, 3H), 1.63-1.58 (m, 2H).

Example-810

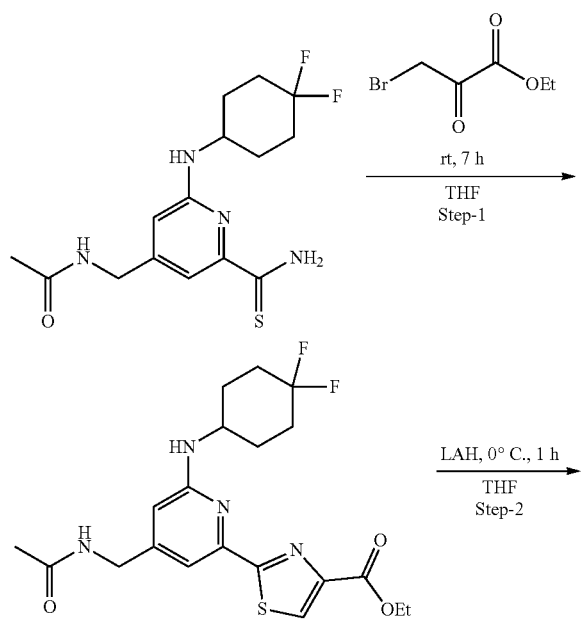

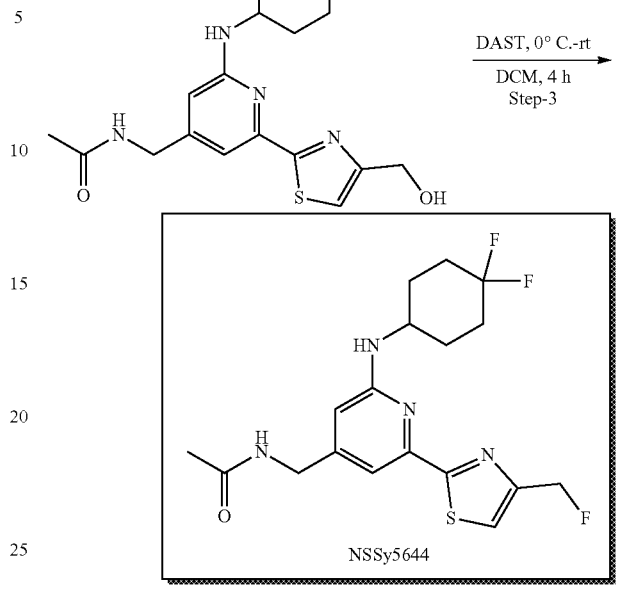

Step 1: The Procedure is similar to Step 6[NSSy5779] in Example-642. 0.8 g of N-((2-carbamothioyl-6-((4,4-difluorocyclohexyl)amino)pyridin-4-yl)methyl) acetamide gave ethyl 2-(4-(acetamidomethyl)-6-((4,4-difluorocyclohexyl)amino)pyridin-2-yl)thiazole-4-carboxylate (0.3 g, 30%). MS (M+1)+=439.2.

Step 2: The Procedure is similar to Step 4[NSSy6711] in Example-854. 0.3 g of ethyl 2-(4-(acetamidomethyl)-6-((4,4-difluorocyclohexyl)amino)pyridin-2-yl)thiazole-4-carboxylate gave N-((2-((4,4-difluorocyclohexyl)amino)-6-(4-(hydroxymethyl)thiazol-2-yl)pyridin-4-yl)methyl) acetamide (0.25 g, 92%). MS (M+1)+=397.1.

Step 3[NSSy5644]: The Procedure is similar to Step 3[NSSy6917] in Example-21. 0.25 g of N-((2-((4,4-difluorocyclohexyl)amino)-6-(4-(hydroxymethyl)thiazol-2-yl) pyridin-4-yl)methyl)acetamide gave N-((2-((4,4-difluorocyclohexyl)amino)-6-(4-(fluoromethyl)thiazol-2-yl)pyridin-4-yl)methyl) acetamide (0.08 g, 32%). MS (M+1)+=399.1; 1H-NMR (400 MHz, DMSO-d6): δ 8.44 (t, J=5.64 Hz, 1H), 7.88 (d, J=2.20 Hz, 1H), 7.19 (s, 1H), 6.89 (d, J=6.60 Hz, 1H), 6.46 (s, 1H), 5.54 (s, 1H), 5.42 (s, 1H), 4.19 (d, J=5.96 Hz, 2H), 3.91 (s, 1H), 2.09-2.01 (m, 6H), 1.95 (s, 3H), 1.59-1.56 (m, 2H).

Example-811

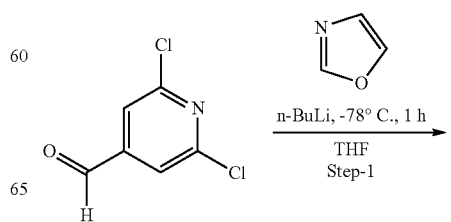

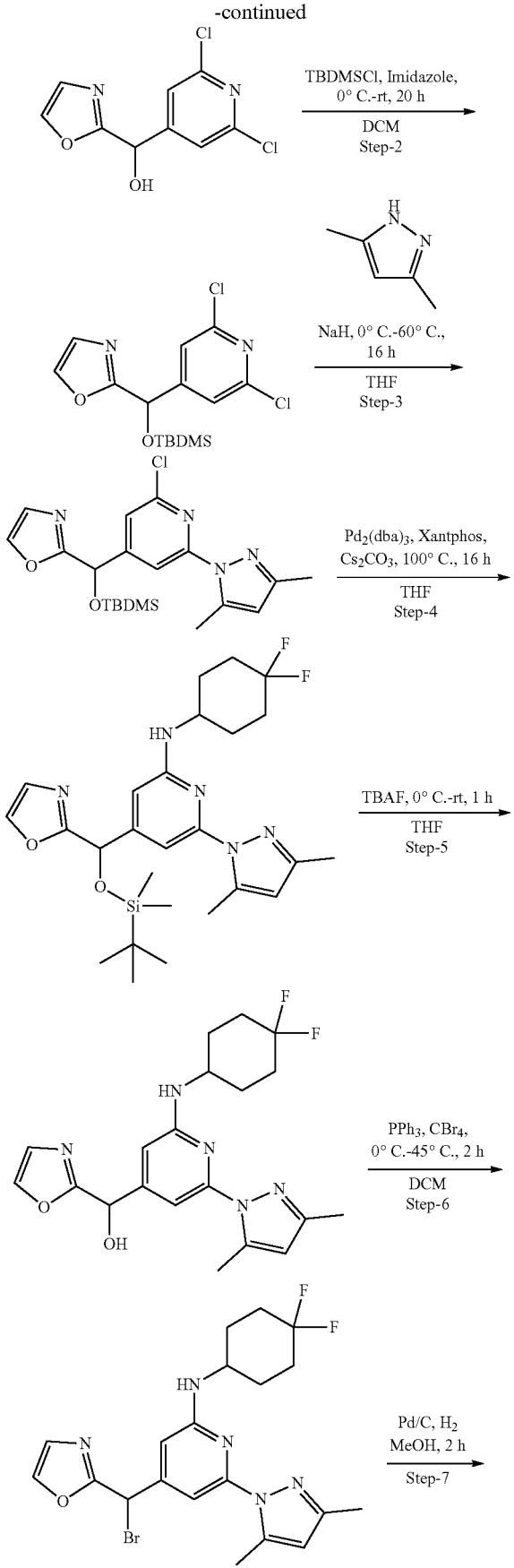

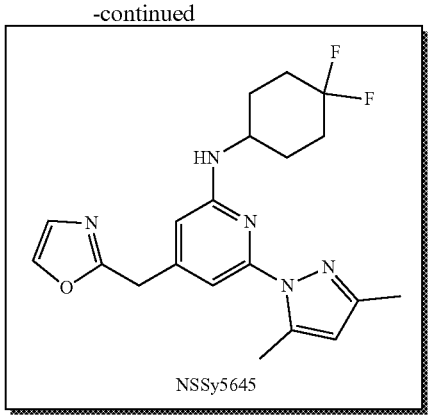

NSSy5645

Step 1: The Procedure is similar to Step 4[NSSy6067] in Example-628. 1 g of 2,6-dichloroisonicotinaldehyde gave (2,6-dichloropyridin-4-yl) (oxazol-2-yl) methanol (0.8 g, 57%). MS (M+1)+=246.

Step 2: To an ice-cooled solution of (2,6-dichloropyridin-4-yl) (oxazol-2-yl) methanol (5.7 g, 23.25 mmol) in DCM (40 mL) was added imidazole (4.12 g, 34.88 mmol) and followed by tert-butyl dimethylsilyl chloride (4.33 g, 27.91 mmol). The reaction mixture was slowly warmed to rt and stirred at rt for 20 h. The reaction mixture was quenched with water and extracted with ethyl acetate (2×75 mL). The combined organic layer was dried over sodium sulphate and concentrated to afford crude and which was purified by column chromatography using 10% ethyl acetate in hexane as eluent to afford 2-(((tert-butyldimethylsilyl)oxy)(2,6-dichloropyridin-4-yl)methyl)oxazole as an colourless liquid (6 g, 72%). MS (M+1)+=359.

Step 3: The Procedure is similar to Step 2[IN10991-021-P1] in Example-694. 2 g of 2-(((tert-butyldimethylsilyl)oxy)(2,6-dichloropyridin-4-yl)methyl)oxazole gave 2-(((tert-butyldimethylsilyl)oxy)(2-chloro-6-(3,5-dimethyl-1H-pyrazol-1-yl)pyridin-4-yl)methyl)oxazole (0.57 g, 25%). MS (M+1)+=420.2.

Step 4: The Procedure is similar to Step 1[NSSy6629] in Example-839. 0.5 g of 2-(((tert-butyldimethylsilyl)oxy)(2-chloro-6-(3,5-dimethyl-1H-pyrazol-1-yl)pyridin-4-yl) methyl)oxazole gave of 4-(((tert-butyldimethylsilyl)oxy) (oxazol-2-yl)methyl)-N-(4,4-difluorocyclohexyl)-6-(3,5-dimethyl-1H-pyrazol-1-yl)pyridin-2-amine (0.28 g, 45%). MS (M+1)+=518.2.

Step 5: To an ice cooled solution of 4-(((tert-butyldimethylsilyl)oxy) (oxazol-2-yl)methyl)-N-(4,4-difluorocyclohexyl)-6-(3,5-dimethyl-1H-pyrazol-1-yl)pyridin-2-amine (0.3 g, 0.579 mmol) in THF (4 mL) was added Tetrabutylammoniumfluoride (1M soln. in tetrahydrofuran) (0.33 mL, 1.15 mmol). The reaction mixture was slowly warmed to rt and stirred for 1 h.

The reaction was quenched with ice cold water and was extracted with ethyl acetate (2×15 mL). The combined organic layer was dried over sodium sulphate and concentrated to afford crude and which was purified by column chromatography using 50% ethyl acetate in hexane as eluent to afford (2-((4,4-difluorocyclohexyl)amino)-6-(3,5-dimethyl-1H-pyrazol-1-yl)pyridin-4-yl) (oxazol-2-yl)methanol as an yellow solid (0.19 g, 82%). MS (M+1)+=404.2.

Step 6: To an ice cooled solution of (2-((4,4-difluorocyclohexyl)amino)-6-(3,5-dimethyl-1H-pyrazol-1-yl)pyridin-4-yl) (oxazol-2-yl) methanol (0.11 g, 0.27 mmol) in DCM (10 mL) was added triphenyl phosphine (0.14 g, 0.54 mmol)

and followed by carbon tetrabromide (0.13 g, 0.40 mmol). The reaction mixture was slowly warmed to rt and heated at 45° C. for 1 h. The reaction mixture was quenched with ice-cold water and extracted with ethyl acetate (2×30 mL). The combined organic layer was dried over sodium sulphate and concentrated to afford crude and which was purified by column chromatography using 25% ethyl acetate in hexane as eluent to afford 4-(bromo(oxazol-2-yl)methyl)-N-(4,4-difluorocyclohexyl)-6-(3,5-dimethyl-1H-pyrazol-1-yl)pyridin-2-amine as an yellow solid (0.06 g, 50%). MS (M+1)+= 467.1.

Step 7[NSSy5645]: The Procedure is similar to Step 2[NSSy6464] in Example-869. 0.06 g of 4-(bromo(oxazol-2-yl)methyl)-N-(4,4-difluorocyclohexyl)-6-(3,5-dimethyl-1H-pyrazol-1-yl)pyridin-2-amine gave N-(4,4-difluorocyclohexyl)-6-(3,5-dimethyl-1H-pyrazol-1-yl)-4-(oxazol-2-ylmethyl)pyridin-2-amine (0.024 g, 50%). MS (M+1)+= 388.2; 1H-NMR (400 MHz, CDCl3): δ 7.86 (s, 1H), 7.53-7.50 (m, 1H), 7.00 (d, J=7.20 Hz, 1H), 6.20 (s, 1H), 5.99 (d, J=12.80 Hz, 1H), 3.88-3.83 (m, 3H), 3.44 (s, 1H), 2.65 (s, 3H), 2.32 (s, 3H), 2.11-1.85 (m, 8H), 1.33-1.30 (m, 3H).

Example-812

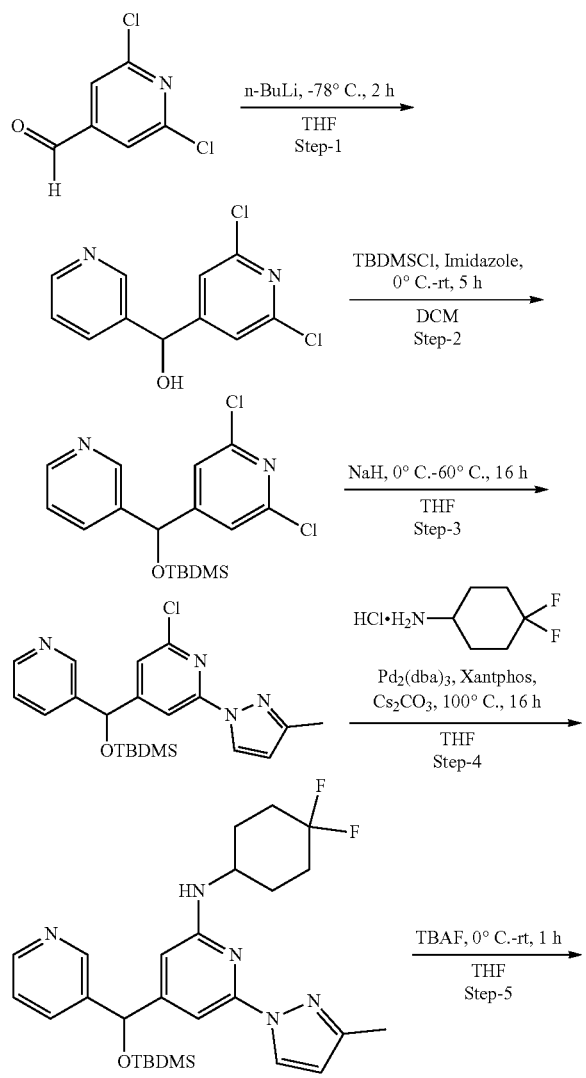

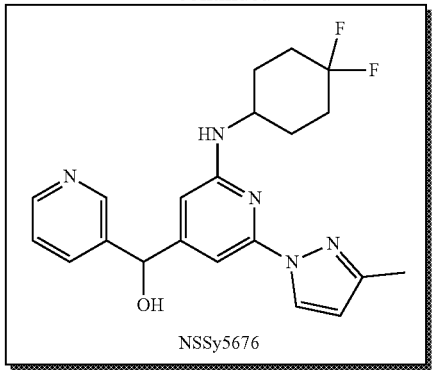

Step 1: The Procedure is similar to Step 4[NSSy6067] in Example-628. 3.6 g of 2,6-dichloroisonicotinaldehyde gave (2,6-dichloropyridin-4-yl) (pyridin-3-yl) methanol (1.4 g, 27%). MS (M+1)+=256.0.

Step 2: The Procedure is similar to Step 2[NSSy5645] in Example-811. 1 g of (2,6-dichloropyridin-4-yl) (pyridin-3-yl) methanol gave 4-(((tert-butyldimethylsilyl)oxy) (pyridin-3-yl)methyl)-2,6-dichloropyridine (0.51 g, 45%). MS (M+1)+=370.2.

Step 3: The Procedure is similar to Step 2[IN10991-021-P1] in Example-694. 0.45 g of 4-(((tert-butyldimethylsilyl)oxy)(pyridin-3-yl)methyl)-2,6-dichloropyridine gave 4-(((tert-butyldimethylsilyl)oxy)(pyridin-3-yl)methyl)-2-chloro-6-(3-methyl-1H-pyrazol-1-yl)pyridine (0.16 g, 32%). MS (M+1)+=416.0.

Step 4: The Procedure is similar to Step 1[NSSy6629] in Example-839. 0.2 g of 4-(((tert-butyldimethylsilyl)oxy) (pyridin-3-yl)methyl)-2-chloro-6-(3-methyl-1H-pyrazol-1-yl)pyridine gave 4-(((tert-butyldimethylsilyl)oxy)(pyridin-3-yl)methyl)-N-(4,4-difluorocyclohexyl)-6-(3-methyl-1H-pyrazol-1-yl)pyridin-2-amine (0.11 g, 45%). MS (M+1)+=514.2.

Step 5[NSSy5676]: The Procedure is similar to Step 5[NSSy5645] in Example-811. 0.12 g of 4-(((tert-butyldimethylsilyl)oxy)(pyridin-3-yl)methyl)-N-(4,4-difluorocyclohexyl)-6-(3-methyl-1H-pyrazol-1-yl)pyridin-2-amine gave (2-((4,4-difluorocyclohexyl)amino)-6-(3-methyl-1H-pyrazol-1-yl)pyridin-4-yl)(pyridin-3-yl)methanol (0.035 g, 37%). MS (M+1)+=401.2; 1H-NMR (400 MHz, DMSO-d6): δ 8.63 (d, J=2.04 Hz, 1H), 8.47-8.46 (m, 1H), 8.39 (d, J=2.40 Hz, 1H), 7.75-7.72 (m, 1H), 7.37-7.34 (m, 1H), 6.92 (d, J=5.08 Hz, 1H), 6.84 (d, J=7.28 Hz, 1H), 6.44 (s, 1H), 6.27 (d, J=2.40 Hz, 1H), 6.18 (t, J=4.16 Hz, 1H), 5.68 (d, J=4.16 Hz, 1H).

Example-813

Intentionally Omitted:

Example-814

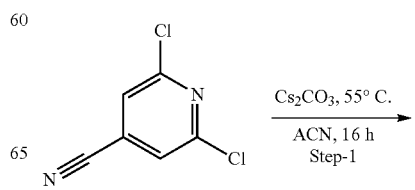

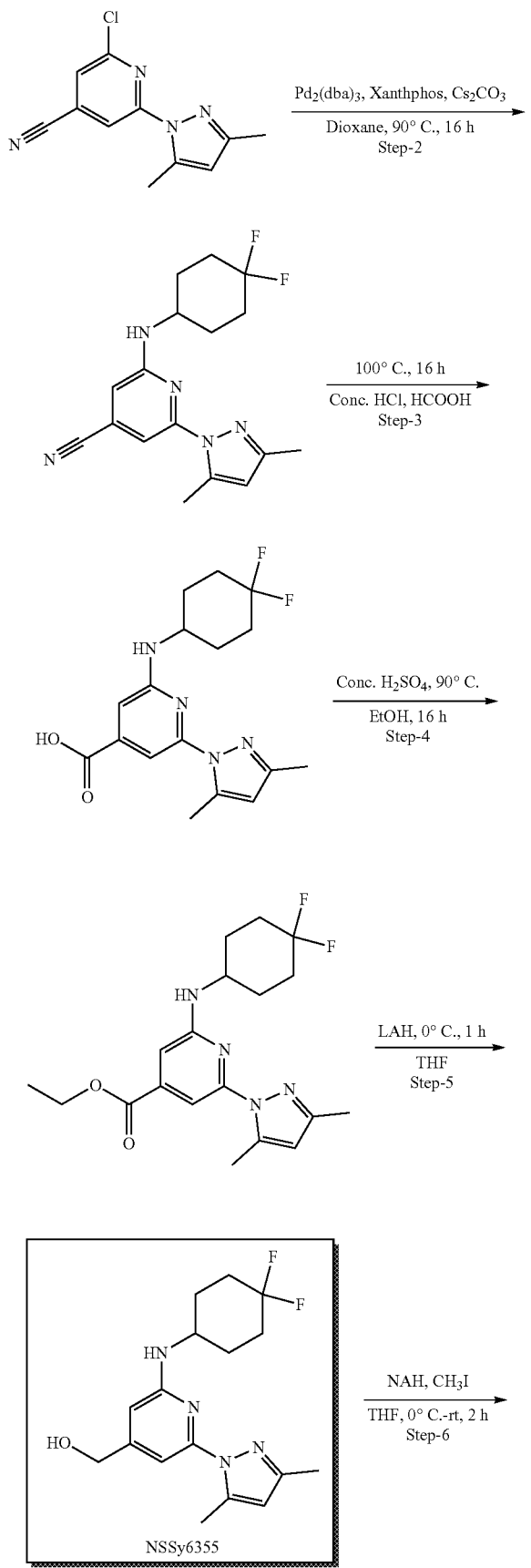

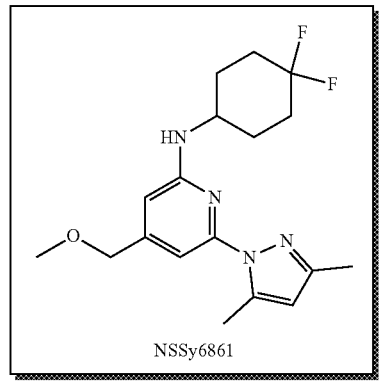

NSSy6861

Step 1: The procedure is similar to Step 1[B] in Example-838. 15 g of 2,6-dichloroisonicotinonitrile gave 2-chloro-6-(3,5-dimethyl-1H-pyrazol-1-yl) isonicotinonitrile as white solid (13.6 g, 67%). MS (M+1)+=233.1.

Step 2: The procedure is similar to Step 1[NSSy6629] in Example-839. 2-chloro-6-(3,5-dimethyl-1H-pyrazol-1-yl) isonicotinonitrile gave 2-((4,4-difluorocyclohexyl)amino)-6-(3,5-dimethyl-1H-pyrazol-1-yl) isonicotinonitrile as an off-white solid (4 g, 36%). MS (M+1)+=332.0.

Step 3: To a solution of 2-((4,4-difluorocyclohexyl)amino)-6-(3,5-dimethyl-1H-pyrazol-1-yl)isonicotinonitrile (4.7 g, 12.07 mmol) in conc.Hydrochloric acid and acetic acid ratio of (8:2) was heated at 100° C. for 16 h. The reaction mixture was concentrated under reduced pressure and the residue was quenched with ice water and stirred for 10 min, the solid formed was filtered off and washed with water and dried under vacuum to afford 2-((4,4-difluorocyclohexyl)amino)-6-(3,5-dimethyl-1H-pyrazol-1-yl)isonicotinic acid as a brown solid (4 g, 81%). MS (M+1)+=351.0.

Step 4: The procedure is similar to Step 3[NSSy6711] in Example-854. 4 g of 2-((4,4-difluorocyclohexyl)amino)-6-(3,5-dimethyl-1H-pyrazol-1-yl) isonicotinic acid gave ethyl 2-((4,4-difluorocyclohexyl)amino)-6-(3,5-dimethyl-1H-pyrazol-1-yl) isonicotinate as yellow solid (3 g, 70%). MS (M+1)+=379.2.

Step 5[NSSy6355]: The procedure is similar to Step 4[NSSy6711] in Example-854. 1.6 g of ethyl2-((4,4-difluorocyclohexyl)amino)-6-(3,5-dimethyl-1H-pyrazol-1-yl) isonicotinate gave (2-((4,4-difluorocyclohexyl)amino)-6-(3,5-dimethyl-1H-pyrazol-1-yl)pyridin-4-yl) methanol as brown solid (1.3 g, 88%). MS (M+1)+=337.1; 1H-NMR (400 MHz, DMSO-d6): δ 6.85 (s, 1H), 6.73 (d, J=7.20 Hz, 1H), 6.36 (s, 1H), 6.03 (s, 1H), 5.31-5.28 (m, 1H), 4.42 (d, J=5.60 Hz, 2H), 3.89 (d, J=5.60 Hz, 1H), 2.58 (s, 3H), 2.17 (s, 3H), 2.09-2.07 (m, 2H), 1.97-1.95 (m, 4H), 1.55-1.52 (m, 2H).

Step 6[NSSy6861]: The procedure is similar to Step 5[NSSy6711] in Example-854. 0.15 g of (2-((4,4-difluorocyclohexyl)amino)-6-(3,5-dimethyl-1H-pyrazol-1-yl)pyridin-4-yl) methanol gave N-(4,4-difluorocyclohexyl)-6-(3,5-dimethyl-1H-pyrazol-1-yl)-4-(methoxymethyl)pyridin-2-amine as white solid (0.14 g, 90%). MS (M+1)+=351.2; 1H-NMR (400 MHz, DMSO-d6): δ 6.84 (s, 1H), 6.79 (d, J=7.48 Hz, 1H), 6.32 (s, 1H), 6.04 (s, 1H), 4.35 (s, 2H), 3.90 (s, 1H), 3.34 (s, 3H), 2.59 (s, 3H), 2.17 (s, 3H), 2.10-1.80 (m, 6H), 1.60-1.50 (m, 2H).

Example-815

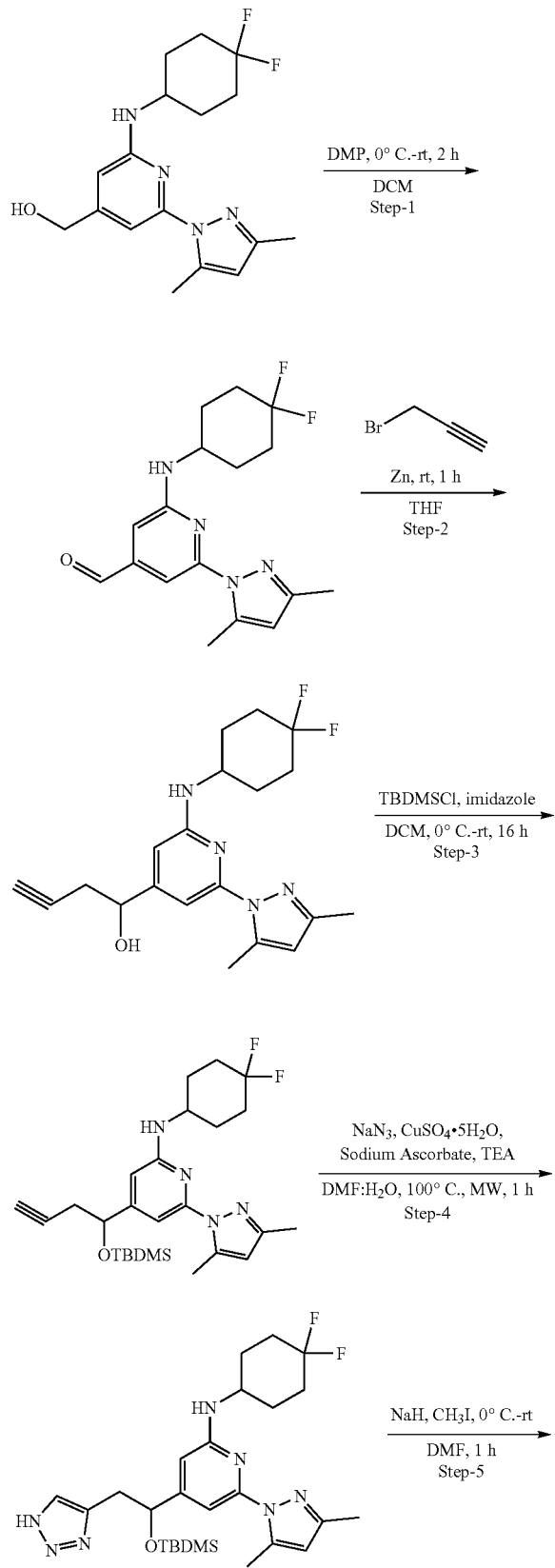

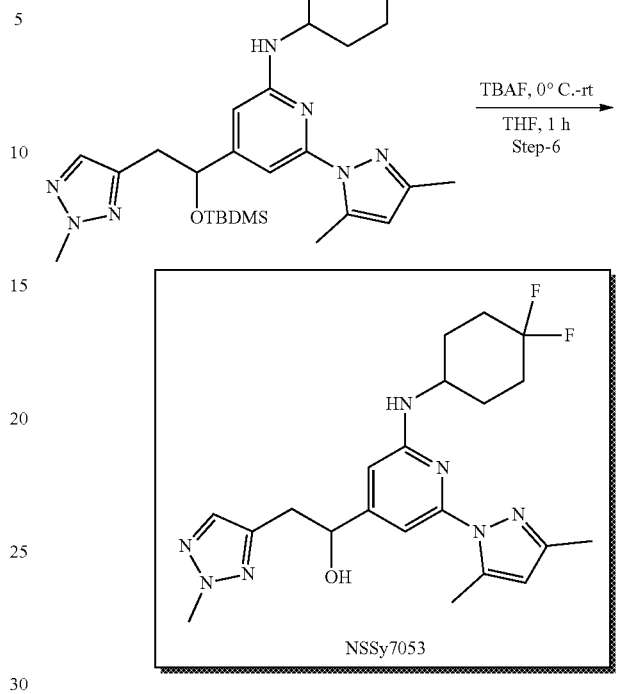

Step 1: The procedure is similar to Step 1[NSSy6930] in Example-867. 0.5 g of (2-((4,4-difluorocyclohexyl)amino)-6-(3,5-dimethyl-1H-pyrazol-1-yl)pyridin-4-yl) methanol gave 2-((4,4-difluorocyclohexyl)amino)-6-(3,5-dimethyl-1H-pyrazol-1-yl) isonicotinaldehyde as a yellow solid (0.35 g, 70%). MS (M+1)+=335.0.

Step 2: 2-((4,4-difluorocyclohexyl)amino)-6-(3,5-dimethyl-1H-pyrazol-1-yl)isonicotinaldehyde (0.35 g, 1.04 mmmol) was added to a stirred mixture of propargyl bromide (0.38 g, 2.61 mmol) and activated zinc dust (0.27 g, 4.18 mmol) in Tetrahydrofuran. The reaction was stirred at room temperature. After 1hr, the reaction was quenched with sodium bicarbonate solution and filtered through a celite bed and washed with ethyl acetate. The filtrate was extracted with ethyl acetate and washed with brine solution. The organic layer was dried over sodium sulphate, filtered and concentrated under reduced pressure to afford crude product, which was purified through column chromatography using ethyl acetate in pet-ether as solvent system to afford 1-(2-((4,4-difluorocyclohexyl)amino)-6-(3,5-dimethyl-1H-pyrazol-1-yl)pyridin-4-yl)but-3-yn-1-ol as an off-white solid (0.25 g, 63%). MS (M+1)+=375.0.

Step 3: To a solution of 1-(2-((4,4-difluorocyclohexyl) amino)-6-(3,5-dimethyl-1H-pyrazol-1-yl)pyridin-4-yl) but-3-yn-1-ol (0.280 g, 0.53 mmol) in Dichloromethane was added Imidazole (0.054 g, 0.80 mmol), Tert-butyl dimethylsilyl chloride (0.073 g, 0.47 mmol) at 0° C. and stirred at room temperature. After 5 h, the reaction was quenched with ice cold water and extracted with DCM. The combined organic extracts was washed with brine solution, dried over sodium sulphate and concentrated under reduced pressure to afford 4-(1-(((tert-butyldimethylsilyl)oxy)but-3-yn-1-yl)-N-(4,4-difluoro cyclohexyl)-6-(3,5-dimethyl-1H-pyrazol-1-yl) pyridin-2-amine as an off-white solid (0.32 g, 88%). MS (M+1)+=489.2.

Step 4: To a solution of 4-(1-((tert-butyldimethylsilyl)oxy)but-3-yn-1-yl)-N-(4,4-difluorocyclohexyl)-6-(3,5-dimethyl-1H-pyrazol-1-yl)pyridin-2-amine in N, N-Dimethylformamide and water (4:1) was added Copper (II) Sulfate Pentahydrate, Sodium ascorbate, triethylamine and the reaction mixture was irradiated under microwave at 100° C. for 1 h. The reaction mixture was filtered through celite bed, washed with ethyl acetate. The filtrate was concentrated under reduced pressure and the residue was diluted with ethyl acetate, washed with water and brine solution. The organic layer was dried over sodium sulphate, filtered and concentrated under reduced pressure to afford 4-(1-((tert-butyldimethylsilyl)oxy)-2-(1H-1,2,3-triazol-4-yl)ethyl)-N-(4,4-difluorocyclohexyl)-6-(3,5-dimethyl-1H-pyrazol-1-yl)pyridin-2-amine as a brown gum (0.25 g, 70%). MS (M+1)+=532.3.

Step 5: The procedure is similar to Step 5[NSSy6711] in Example-854. 0.25 g of 4-(1-((tert-butyldimethylsilyl)oxy)-2-(1H-1,2,3-triazol-4-yl)ethyl)-N-(4,4-difluorocyclohexyl)-6-(3,5-dimethyl-1H-pyrazol-1-yl)pyridin-2-amine gave 4-(1-((tert-butyldimethylsilyl)oxy)-2-(2-methyl-2H-1,2,3-triazol-4-yl)ethyl)-N-(4,4-difluorocyclohexyl)-6-(3,5-dimethyl-1H-pyrazol-1-yl)pyridin-2-amine as a brown oil (0.3 g, crude), MS (M+1)+=546.3.

Step 6[NSSy7053]: To a solution of 4-(1-((tert-butyldimethylsilyl)oxy)-2-(2-methyl-2H-1,2,3-triazol-4-yl)ethyl)-N-(4,4-difluorocyclohexyl)-6-(3,5-dimethyl-1H-pyrazol-1-yl)pyridin-2-amine (0.3 g, 0.54 mmol) in tetrahydrofuran was added tetrabutylammonium fluoride (0.21 g, 0.82 mmol) at 0° C. and the reaction mixture was stirred at room temperature. The reaction mixture was quenched with water and extracted with ethyl acetate. The organic layer was dried over sodium sulphate, filtered and concentrated under reduced pressure to afford crude product, which was purified by flash chromatography using ethyl acetate in pet-ether as solvent to afford 1-(2-((4,4-difluorocyclohexyl)amino)-6-(3,5-dimethyl-1H-pyrazol-1-yl)pyridin-4-yl)-2-(2-methyl-2H-1,2,3-triazol-4-yl) ethan-1-ol as an off-white solid (0.017 g, 10%). MS (M+1)+=432.2; 1 H-NMR (400 MHz, DMSO-d6): δ 7.51 (s, 1H), 6.92 (s, 1H), 6.75 (d, J=7.20 Hz, 1H), 6.35 (s, 1H), 6.04 (s, 1H), 5.54 (s, 1H), 4.71-4.70 (m, 1H), 4.07 (m, 3H), 3.89-3.88 (m, 1H), 3.19-3.15 (m, 1H), 2.96-2.85 (m, 2H), 2.59 (s, 3H), 2.18 (s, 3H), 2.09-2.07 (m, 2H), 1.97-1.85 (m, 3H), 1.61-1.50 (m, 2H).

Example-816

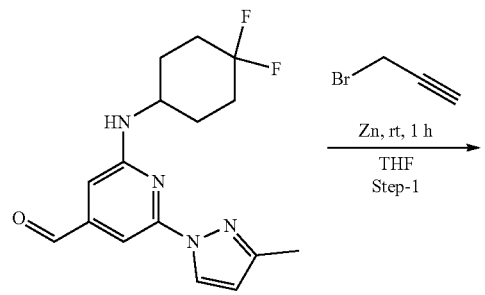

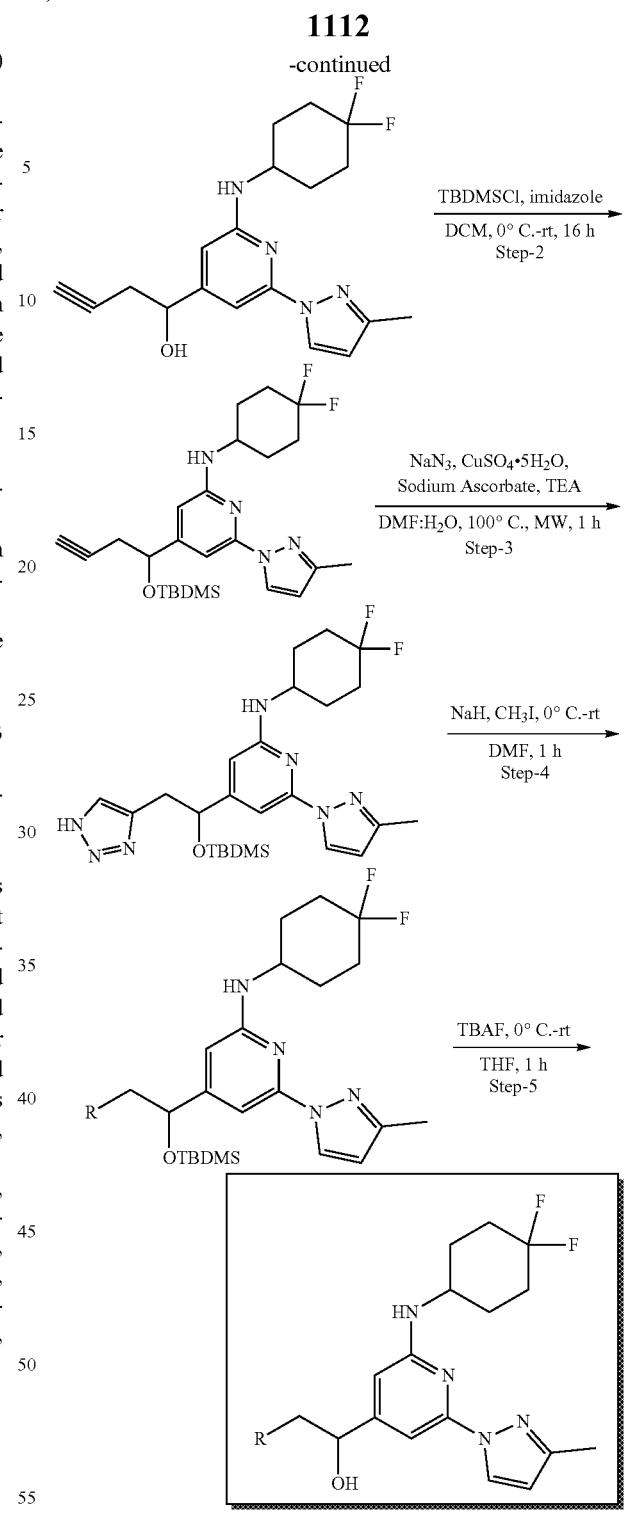

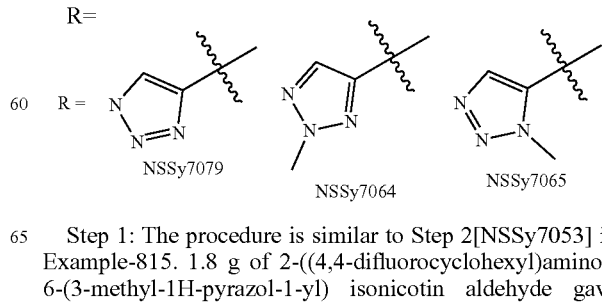

Step 1: The procedure is similar to Step 2[NSSy7053] in Example-815. 1.8 g of 2-((4,4-difluorocyclohexyl)amino)-6-(3-methyl-1H-pyrazol-1-yl) isonicotin aldehyde gave 1-(2-((4,4-difluorocyclohexyl)amino)-6-(3-methyl-1H-pyrazol-1-yl)pyridin-4-yl) but-3-yn-1-ol as a colourless oil (1.8 g, 90%). MS (M+1)+=361.0.

Step 2: The procedure is similar to Step 3[NSSy7053] in Example-815. 1.8 g 1-(2-((4,4-difluorocyclohexyl)amino)-6-(3-methyl-1H-pyrazol-1-yl)pyridin-4-yl)but-3-yn-1-ol gave 4-(1-(((tert-butyldimethylsilyl)oxy)but-3-yn-1-yl)-N-(4,4-difluorocyclohexyl)-6-(3-methyl-1H-pyrazol-1-yl) pyridin-2-amine as an off-white solid (2.2 g, 90%). MS (M+1)+=475.6.

Step 3: The procedure is similar to Step 4[NSSy7053] in Example-815. 2.2 g of 4-(1-(((tert-butyldimethylsilyl)oxy) but-3-yn-1-yl)-N-(4,4-difluorocyclohexyl)-6-(3-methyl-1H-pyrazol-1-yl)pyridin-2-amine gave 4-(1-(((tert-butyldimethylsilyl)oxy)-2-(1H-1,2,3-triazol-4-yl)ethyl)-N-(4,4-difluorocyclohexyl)-6-(3-methyl-1H-pyrazol-1-yl)pyridin-2-amine as brown gum (2 g, crude). MS (M+1)+=475.2.

Step 4: The procedure is similar to Step 5[NSSy6711] in Example-854. 2 g of 4-(1-(((tert-butyldimethylsilyl)oxy)-2-(1H-1,2,3-triazol-4-yl)ethyl)-N-(4,4-difluorocyclohexyl)-6-(3-methyl-1H-pyrazol-1-yl)pyridin-2-amine gave mixture of 4-(1-(((tert-butyldimethylsilyl)oxy)-2-(2-methyl-2H-1,2,3-triazol-4-yl)ethyl)-N-(4,4-difluorocyclohexyl)-6-(3-methyl-1H-pyrazol-1-yl)pyridin-2-amine, 4-(1-(((tert-butyldimethylsilyl)oxy)-2-(1-methyl-1H-1,2,3-triazol-5-yl) ethyl)-N-(4,4-difluorocyclohexyl)-6-(3-methyl-1H-pyrazol-1-yl)pyridin-2-amine and 4-(1-(((tert-butyldimethylsilyl) oxy)-2-(1-methyl-1H-1,2,3-triazol-4-yl)ethyl)-N-(4,4-difluorocyclohexyl)-6-(3-methyl-1H-pyrazol-1-yl)pyridin-2-amine as brown oil (1.8 g crude, 6:1:0.5 by LCMS). MS (M+1)+=532.2.

Step 5[NSSy7079, 7064, 7065]: The procedure is similar to Step 6[NSSy7053] in Example-815. 1.8 g Mixture of 4-(1-(((tert-butyldimethylsilyl)oxy)-2-(2-methyl-2H-1,2,3-triazol-4-yl)ethyl)-N-(4,4-difluorocyclohexyl)-6-(3-methyl-1H-pyrazol-1-yl)pyridin-2-amine, 4-(1-(((tert-butyldimethylsilyl)oxy)-2-(1-methyl-1H-1,2,3-triazol-5-yl)ethyl)-N-(4,4-difluorocyclohexyl)-6-(3-methyl-1H-pyrazol-1-yl) pyridin-2-amine and 4-(1-(((tert-butyldimethylsilyl)oxy)-2-(1-methyl-1H-1,2,3-triazol-4-yl)ethyl)-N-(4,4-difluorocyclohexyl)-6-(3-methyl-1H-pyrazol-1-yl)pyridin-2-amine gave 1-(2-((4,4-difluorocyclohexyl)amino)-6-(3-methyl-1H-pyrazol-1-yl)pyridin-4-yl)-2-(2-methyl-2H-1,2,3-triazol-4-yl)ethan-1-ol as white solid (0.041 g, 3%). MS (M+1)+=418.0. 1-(2-((4,4-difluorocyclohexyl)amino)-6-(3-methyl-1H-pyrazol-1-yl)pyridin-4-yl)-2-(1-methyl-1H-1,2,3-triazol-5-yl) ethan-1-ol as an off-white solid (0.14 g, 10%). MS (M+1)+=418.0; 1-(2-((4,4-difluorocyclohexyl)amino)-6-(3-methyl-1H-pyrazol-1-yl)pyridin-4-yl)-2-(1-methyl-1H-1,2,3-triazol-4-yl)ethan-1-ol as white solid (0.11 g, 10%). MS (M+1)+=418.0.

[NSSy7063]: 1H-NMR (400 MHz, DMSO-d6): δ 8.41 (s, 1H), 7.50 (s, 1H), 6.95 (s, 1H), 6.75 (d, J=7.60 Hz, 1H), 6.33 (s, 1H), 6.29 (s, 1H), 5.54 (s, 1H), 4.75-4.70 (m, 1H), 4.06 (s, 3H), 3.97 (bs, 1H), 2.97-2.68 (m, 2H), 2.26 (s, 3H), 2.07-1.95 (m, 6H), 1.56-1.51 (m, 2H).

[NSSy7065]: 1H-NMR (400 MHz, DMSO-d6): δ 8.42 (d, J=2.40 Hz, 1H), 7.49 (s, 1H), 6.99 (s, 1H), 6.79 (d, J=7.60 Hz, 1H), 6.36 (s, 1H), 6.30 (d, J=2.40 Hz, 1H), 5.69 (d, J=4.40 Hz, 1H), 4.77-4.73 (m, 1H), 4.01 (s, 1H), 3.92 (s, 3H), 3.07-3.03 (m, 1H), 2.97-2.93 (m, 1H), 2.27 (s, 3H), 2.08-1.95 (m, 6H), 1.60-1.50 (m, 2H).

[NSSy7079]: $^1$H-NMR (400 MHz, DMSO-d$_6$): δ 8.41 (d, J=2.40 Hz, 1H), 7.77 (s, 1H), 6.95 (s, 1H), 6.75 (d, J=7.60 Hz, 1H), 6.32 (s, 1H), 6.29 (d, J=2.40 Hz, 1H), 5.51 (d, J=4.80 Hz, 1H), 4.72-4.68 (m, 1H), 3.98 (s, 3H), 3.96 (s, 1H), 2.99-2.94 (m, 2H), 2.27 (s, 3H), 2.06-1.85 (m, 6H), 1.60-1.53 (m, 2H).

Example-817

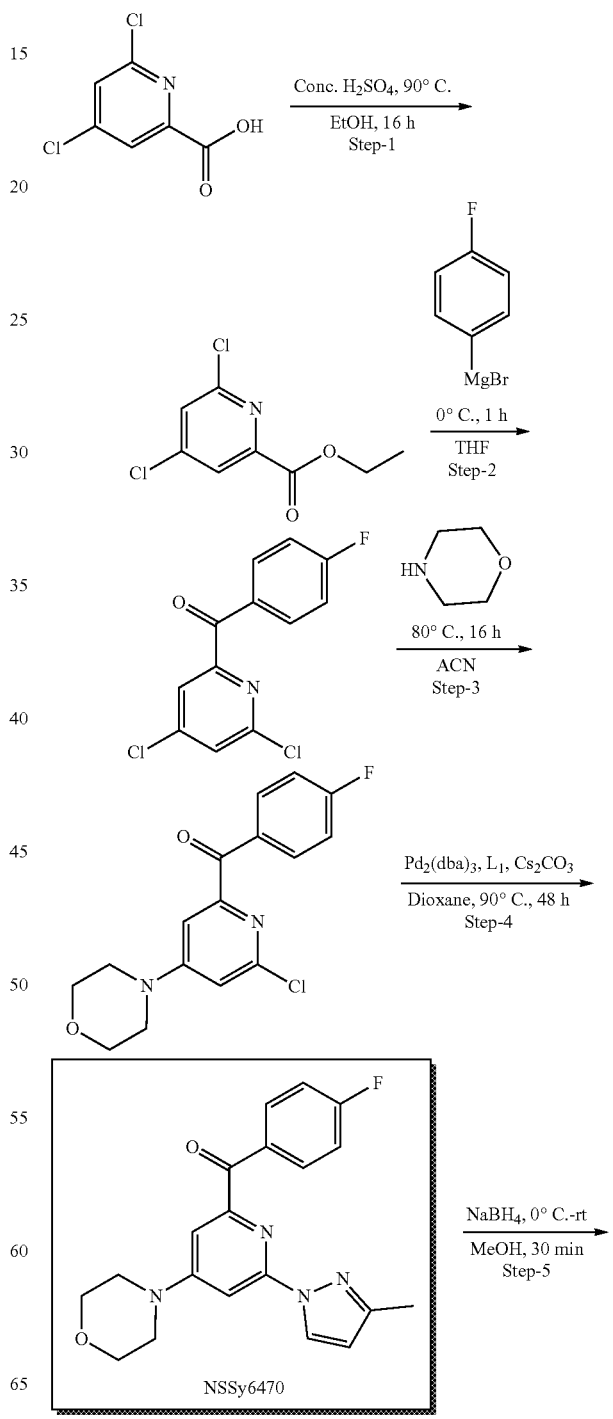

1115

-continued

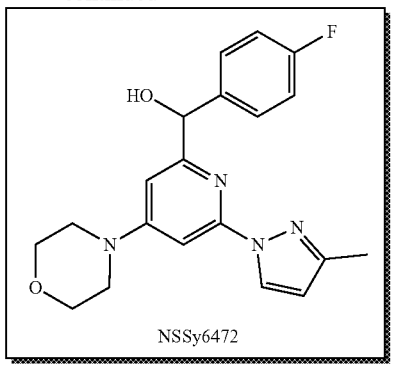

Step 1: The procedure is similar to Step 3[NSSy6711] in Example-854. 5 g of 4,6-dichloropicolinic acid gave ethyl 4,6-dichloropicolinate as colourless oil, (5 g, 87%). MS (M, M+2)+=220.0, 222.0.

Step 2: The procedure is similar to Step 4[NSSy6464] in Example-869. 0.6 g of ethyl 4,6-dichloropicolinate gave (4,6-dichloropyridin-2-yl) (4-fluorophenyl) methanone as an off-white solid (0.97 g, 97%). MS (M, M+2)+=270.0, 272.0.

Step 3: The procedure is similar to Step 1[B] in Example-2. 0.96 g of (4,6-dichloropyridin-2-yl) (4-fluorophenyl) methanone gave (6-chloro-4-morpholinopyridin-2-yl) (4-fluorophenyl) methanone as a yellow gum (0.6 g, 54%). MS (M+1)+=321.2.

Step 4[NSSy6470]: The procedure is similar to Step 1[NSSy6629] in Example-839. (L1=(r)-(−)-1-(s)-2-(dicyclohexylphosphino) ferrocenyl ethyl di-t-butylphosphine). 0.3 g of (6-chloro-4-morpholinopyridin-2-yl) (4-fluorophenyl) methanone gave (4-fluorophenyl) (6-(3-methyl-1H-pyrazol-1-yl)-4-morpholinopyridin-2-yl) methanone as a white solid (0.28 g, 82%). MS (M+1)+=367.2; 1H-NMR (400 MHz, DMSO-d6): δ 8.24 (d, J=2.0 Hz, 1H), 8.15-8.10 (m, 2H), 7.39 (t, J=17.6 Hz, 3H), 7.33 (d, J=1.6 Hz, 1H), 6.33 (d, J=2.00 Hz, 1H), 3.75-3.74 (m, 4H), 3.45-3.44 (m, 4H), 2.29 (s, 3H).

Step 5[NSSy6472]: The procedure is similar to Step 2[NSSy6931] in Example-21. 0.06 g of (4-fluorophenyl) (6-(3-methyl-1H-pyrazol-1-yl)-4-morpholinopyridin-2-yl) methanone gave (4-fluorophenyl) (6-(3-methyl-1H-pyrazol-1-yl)-4-morpholinopyridin-2-yl) methanol as white solid (0.055 g, 92%). MS (M+1)+=369.1; 1H-NMR (400 MHz, DMSO-d6): δ 8.44 (s, 1H), 8.15-8.10 (m, 2H), 7.51 (t, J=12.36 Hz, 2H), 7.07 (s, 1H), 6.95 (s, 1H), 6.30 (s, 1H), 6.06-6.05 (m, 1H), 5.59-5.58 (m, 1H), 3.73 (bs, 4H), 2.26 (s, 3H).

Example-818

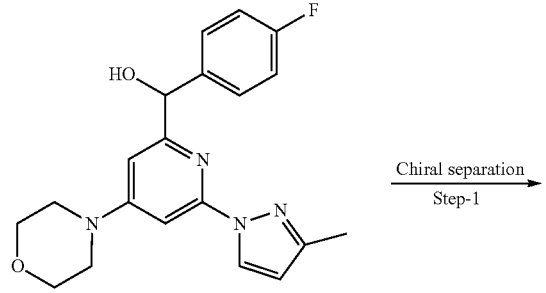

1116

-continued

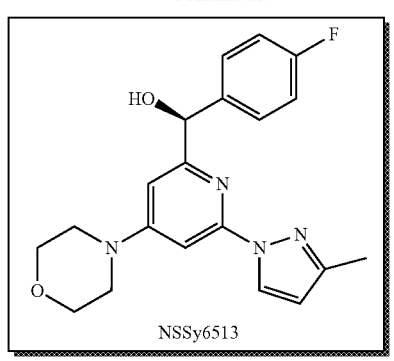

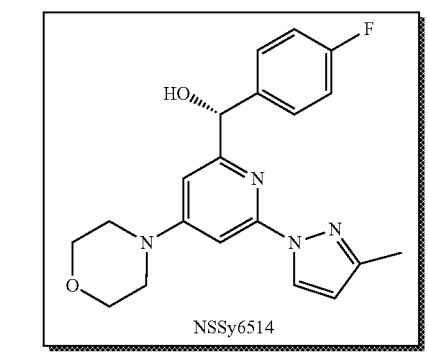

Step 1[NSSy6513, 6514]: 0.12 g of (4-fluorophenyl)(6-(3-methyl-1H-pyrazol-1-yl)-4-morpholinopyridin-2-yl) methanol gave (S)-(4-fluorophenyl)(6-(3-methyl-1H-pyrazol-1-yl)-4-morpholinopyridin-2-yl)methanol as a yellow solid (0.055 g) MS (M+1)+=369.1 and (R)-(4-fluorophenyl) (6-(3-methyl-1H-pyrazol-1-yl)-4-morpholinopyridin-2-yl) methanol as a yellow solid (0.055 g), MS (M+1)+=369.1.

[NSSy6513]: 1H-NMR (400 MHz, DMSO-d6): δ 8.44 (s, 1H), 7.52-7.48 (m, 2H), 7.14-7.06 (m, 3H), 6.95 (s, 1H), 6.30 (s, 1H), 6.06-6.05 (m, 1H), 5.59-5.58 (m, 1H), 3.73 (s, 4H), 2.26 (s, 3H).

[NSSy6514]: 1H-NMR (400 MHz, DMSO-d6): δ 8.44 (s, 1H), 7.52-7.48 (m, 2H), 7.14-7.06 (m, 3H), 6.95 (s, 1H), 6.30 (s, 1H), 6.06-6.05 (m, 1H), 5.59-5.58 (m, 1H), 3.73 (s, 4H), 2.25 (s, 3H).

Example-819

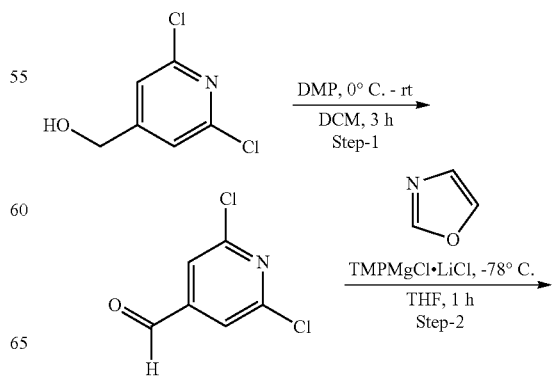

-continued

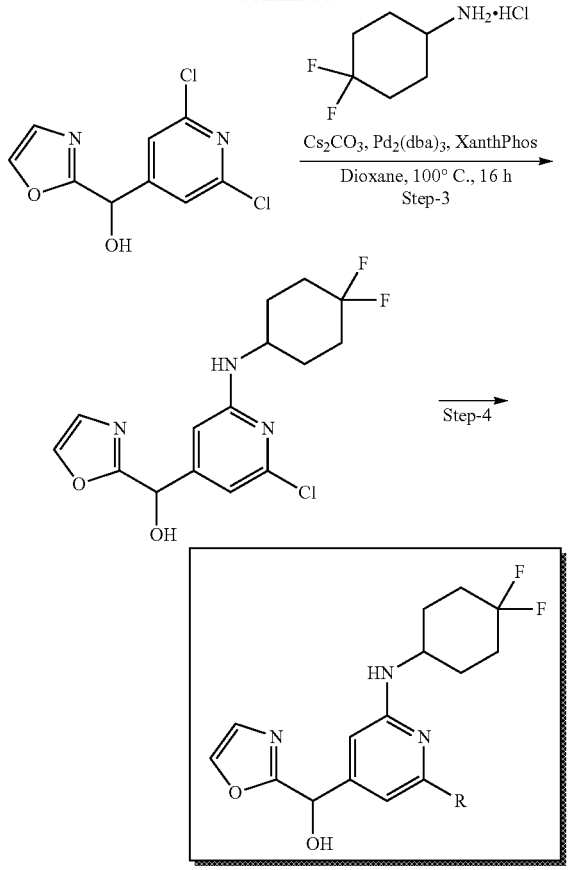

R=

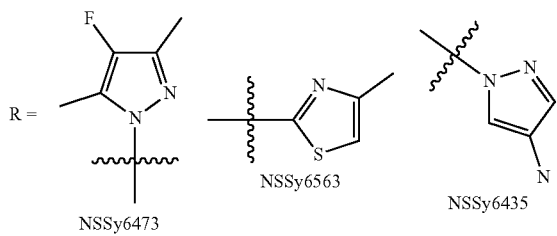

Step 1: The procedure is similar to Step 1[NSSy6930] in Example-867. 3 g of (2,6-dichloropyridin-4-yl) methanol gave 2,6-dichloroisonicotinaldehyde as an off-white solid (2.2 g, 75%). MS (M+2)+=178.0.

Step 2: To a pre-cooled (−78° C.) solution Oxazole (1.47 g, 21.30 mmol) in 2,2,6,6-tetramethylpiperidinylmagnesium chloride lithium chloride complex solution (1.0 M in THF/toluene) (2.67 g, 15.62 mmol) was added a solution of 2,6-dichloroisonicotinaldehyde (2.5 g, 14.204 mmol) in THF and stirred at same temperature. After 1 h, the reaction mixture was quenched with water and extracted with ethyl acetate. The combined organic layer was dried over sodium sulphate, filtered and concentrated to afford a crude product, which was purified by column chromatography using 30% ethyl acetate in pet ether as eluent to afford (2,6-dichloropyridin-4-yl)(oxazol-2-yl)methanol as an off-white gum (2.5 g, 73%). MS (M+1)+=246.0.

Step 3: The procedure is similar to Step 1[NSSy6629] in Example-839. 0.6 g of (2,6-dichloropyridin-4-yl) (oxazol-2-yl) methanol gave (2-chloro-6-((4,4-difluorocyclohexyl) amino)pyridin-4-yl) (oxazol-2-yl) methanol as off-white gum (0.4 g, 52%). MS (M+1)+=344.0.

TABLE 87

Step 4: The procedure is similar to Step 1[NSSy6629] in Example-839.

| Compound No | R | Condition | Yield (%) | MS (M + 1)+ |
|---|---|---|---|---|
| NSSy6473 | (4-fluoro-3,5-dimethylpyrazol-1-yl) | Pd$_2$(dba)$_3$, L$_1$, Cs$_2$CO$_3$, Dioxane, 100° C., 16 h | 16 | 422.0 |
| NSSy6563 | (4-methylthiazol-2-yl) | PdCl$_2$(PPh$_3$)$_2$, 100° C. Toluene, 16 h, sealed tube. | 14 | 407.0 |
| NSSy6435 | (4-fluoropyrazol-1-yl) | Pd$_2$(dba)$_3$, L$_1$, Cs$_2$CO$_3$, Dioxane, 100 ° C., 16 h | 5 | 394.0 |

(L$_1$ = (r)-(−)-1-(s)-2-(dicyclohexylphosphino)ferrocenyl ethyl di-t-butylphosphine)

Step 4[NSSy6473]: 1H-NMR (400 MHz, DMSO-d6): δ 8.30 (s, 1H), 7.99 (s, 1H), 6.92 (s, 1H), 6.87 (d, J=7.40 Hz, 1H), 6.47 (s, 1H), 6.05 (d, J=4.72 Hz, 1H), 5.54 (d, J=4.56 Hz, 1H), 4.03-3.89 (m, 1H), 2.50 (s, 3H), 2.09 (s, 3H), 2.07-1.86 (m, 6H), 1.58-1.52 (m, 2H).

Step 4[NSSy6563]: 1H-NMR (400 MHz, DMSO-d6): δ 8.29 (s, 1H), 8.00 (s, 1H), 7.25 (d, J=8.80 Hz, 2H), 6.83 (d, J=6.80 Hz, 1H), 6.65 (s, 1H), 6.06 (d, J=4.80 Hz, 1H), 5.56 (d, J=4.80 Hz, 1H), 3.91 (m, 1H), 2.39 (s, 3H), 2.04-1.88 (m, 6H), 1.63-1.56 (m, 2H).

Step 4[NSSy6435]: 1H-NMR (400 MHz, DMSO-d6): δ 8.60 (d, J=3.60 Hz, 1H), 8.30 (d, J=0.80 Hz, 1H), 7.99 (s, 1H), 7.80 (d, J=4.00 Hz, 1H), 6.99 (s, 1H), 6.91 (d, J=7.60 Hz, 1H), 6.49 (s, 1H), 6.08 (d, J=4.80 Hz, 1H), 5.55 (d, J=4.40 Hz, 1H), 4.07-4.05 (m, 1H), 2.10-1.95 (m, 6H), 1.58-1.54 (m, 2H).

Example-820

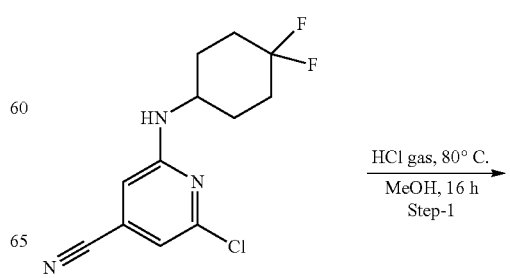

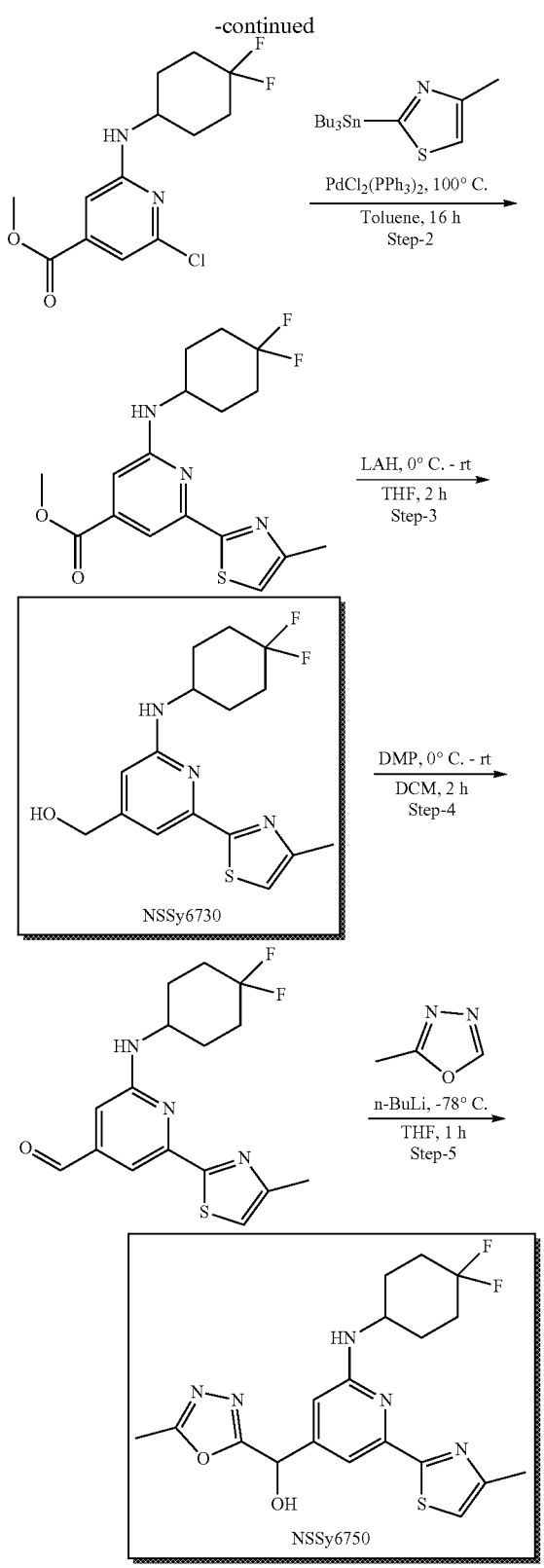

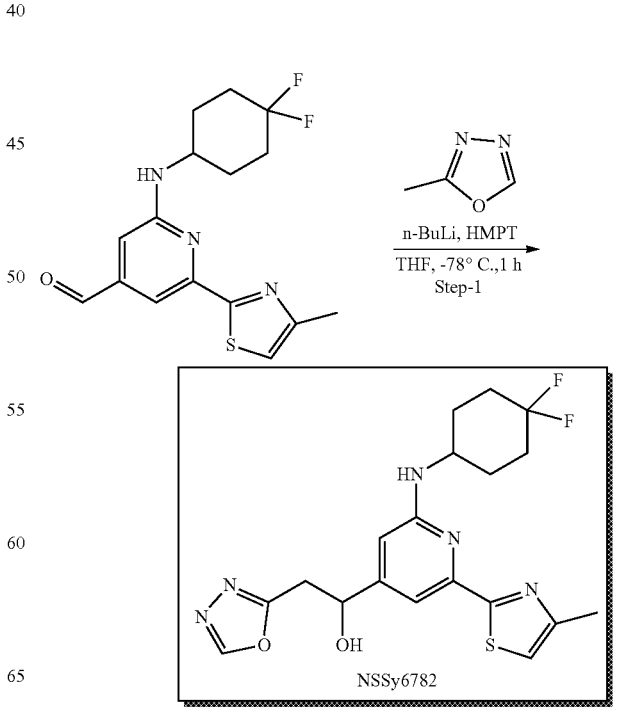

difluorocyclohexyl)amino) isonicotinate as an off-white solid (0.1 g, 90%). MS (M+1)+=305.2.

Step 2: The procedure is similar to Step 1[H] in Example-838. 0.7 g of methyl 2-chloro-6-((4,4-difluorocyclohexyl) amino) isonicotinate gave methyl 2-((4,4-difluorocyclohexyl)amino)-6-(4-methylthiazol-2-yl) isonicotinate as an off-white solid (0.52 g, 61%). MS (M+1)+=368.1.

Step 3[NSSy6730]: The procedure is similar to Step 4[NSSy6711] in Example-854. 0.5 g of methyl 2-((4,4-difluorocyclohexyl)amino)-6-(4-methylthiazol-2-yl) isonicotinate gave (2-((4,4-difluorocyclohexyl)amino)-6-(4-methylthiazol-2-yl)pyridin-4-yl) methanol as pale yellow solid (0.43 g, 93%). MS (M+1)+=340.1; 1H-NMR (400 MHz, DMSO-d6): δ 7.27 (s, 1H), 7.19 (s, 1H), 6.75 (d, J=6.80 Hz, 1H), 6.55 (s, 1H), 5.32 (t, J=5.60 Hz, 1H), 4.44 (d, J=5.60 Hz, 2H), 3.90 (s, 1H), 2.40 (s, 3H), 2.15-1.85 (m, 6H), 1.65-1.55 (m, 2H).

Step 4: The procedure is similar to Step 1[NSSy6930] in Example-867. 0.4 g of (2-((4,4-difluorocyclohexyl)amino)-6-(4-methylthiazol-2-yl)pyridin-4-yl) methanol gave 2-((4,4-difluorocyclohexyl)amino)-6-(4-methylthiazol-2-yl) isonicotinaldehyde as yellow solid (0.27 g, 70%). MS (M+1)+=338.0.

Step 5[NSSy6750]: The procedure is similar to Step 4[NSSy6067] in Example-628. 0.25 g of 2-((4,4-difluorocyclohexyl)amino)-6-(4-methylthiazol-2-yl)isonicotinaldehyde gave (2-((4,4-difluorocyclohexyl)amino)-6-(4-methylthiazol-2-yl)pyridin-4-yl)(5-methyl-1,3,4-oxadiazol-2-yl) methanol as an off-white solid (0.006 g, 15%). MS (M+1)+= 422.4; 1H-NMR (400 MHz, DMSO-d6): δ 7.30 (s, 1H), 7.25 (s, 1H), 6.97 (d, J=7.20 Hz, 1H), 6.83 (d, J=5.20 Hz, 1H), 6.68 (s, 1H), 5.95 (d, J=5.20 Hz, 1H), 3.91 (s, 1H), 2.48 (s, 3H), 2.40 (s, 3H), 2.15-1.90 (m, 6H), 1.62-1.52 (m, 2H).

Example-821

Step 1: To a solution of 2-chloro-6-((4,4-difluorocyclohexyl)amino) isonicotinonitrile (0.1 g, 0.368 mmol) in HCl in methanol (3M solution) (3 mL) is heated at 80° C. in sealed tube for 16 h. The reaction mixture was concentrated under reduced pressure to afford methyl 2-chloro-6-((4,4-

Step 1[NSSy6782]: The procedure is similar to Step 4[NSSy6067] in Example-628. 2-((4,4-difluorocyclohexyl)amino)-6-(4-methylthiazol-2-yl)isonicotinaldehyde gave 1-(2-((4,4-difluorocyclohexyl)amino)-6-(4-methylthiazol-2-yl)pyridin-4-yl)-2-(1,3,4-oxadiazol-2-yl)ethan-1-ol as an off-white (0.03 g, 20%). MS (M+1)+=422.4; 1H-NMR (400 MHz, DMSO-d6): δ 9.16 (s, 1H), 7.30 (d, J=0.80 Hz, 2H), 6.83 (d, J=6.80 Hz, 1H), 6.57 (s, 1H), 5.86 (s, 1H), 4.97-4.93 (m, 1H), 3.89 (s, 1H), 3.30-3.15 (m, 2H), 2.42 (s, 3H), 2.18-1.90 (m, 6H), 1.62-1.50 (m, 2H).

Example-822

Intentionally Omitted

Example-823

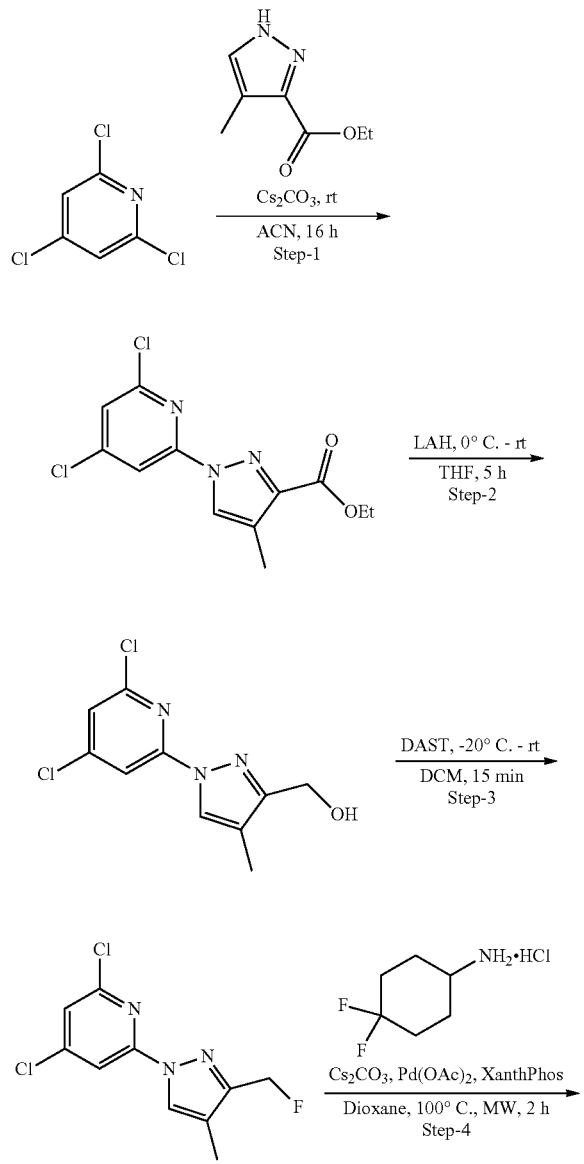

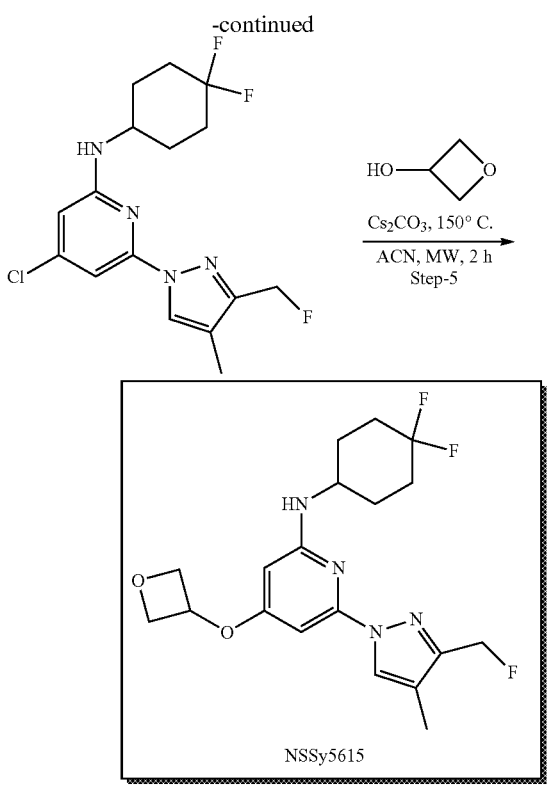

Step 1: The procedure is similar to Step 1[B] in Example-838. 15 g of 2,4,6-trichloropyridine gave ethyl 1-(4,6-dichloropyridin-2-yl)-4-methyl-1H-pyrazole-3-carboxylate as white solid (6 g, 25%). MS (M, M+2)+=300.0, 302.1.

Step 2: The procedure is similar to Step 4[NSSy6711] in Example-854. 2.25 g of ethyl 1-(4,6-dichloropyridin-2-yl)-4-methyl-1H-pyrazole-3-carboxylate gave (1-(4,6-dichloropyridin-2-yl)-4-methyl-1H-pyrazol-3-yl) methanol as off-white solid (1.12 g, 85%). MS (M, M+2)+=258.0, 260.1.

Step 3: The procedure is similar to Step 3[NSSy6917] in Example-21. 1.12 g of (1-(4,6-dichloropyridin-2-yl)-4-methyl-1H-pyrazol-3-yl) methanol gave 2,4-dichloro-6-(3-(fluoromethyl)-4-methyl-1H-pyrazol-1-yl)pyridine as white solid (0.65 g, 60%). MS (M, M+2)+=260.0, 262.1.

Step 4: The procedure is similar to Step 1[NSSy6629] in Example-839. 0.65 g of 2,4-dichloro-6-(3-(fluoromethyl)-4-methyl-1H-pyrazol-1-yl)pyridine gave 4-chloro-N-(4,4-difluorocyclohexyl)-6-(3-(fluoromethyl)-4-methyl-1H-pyrazol-1-yl)pyridin-2-amine as an off-white solid (0.22 g, 24%). MS (M+1)+=359.2.

Step 5[NSSy5615]: The procedure is similar to Step 1[NSSy6909] in Example-839. 0.2 g of 4-chloro-N-(4,4-difluorocyclohexyl)-6-(3-(fluoromethyl)-4-methyl-1H-pyrazol-1-yl)pyridin-2-amine gave N-(4,4-difluorocyclohexyl)-6-(3-(fluoromethyl)-4-methyl-1H-pyrazol-1-yl)-4-(oxetan-3-yloxy)pyridin-2-amine as an off-white solid (0.032 g, 14%). MS (M+1)+=397.2; 1H-NMR (400 MHz, DMSO-d6): δ 8.34 (s, 1H), 6.80 (d, J=7.52 Hz, 1H), 6.43 (d, J=1.72 Hz, 1H), 5.68 (s, 1H), 5.48 (s, 1H), 5.35 (s, 1H), 5.33-5.30 (m, 1H), 4.89 (t, J=6.72 Hz, 2H), 4.56 (dd, J=4.80, 7.28 Hz, 2H), 3.98 (s, 1H), 2.13 (s, 3H), 2.08-1.94 (m, 6H), 1.57-1.51 (m, 2H).

Example-824

Intentionally Omitted

Example-825

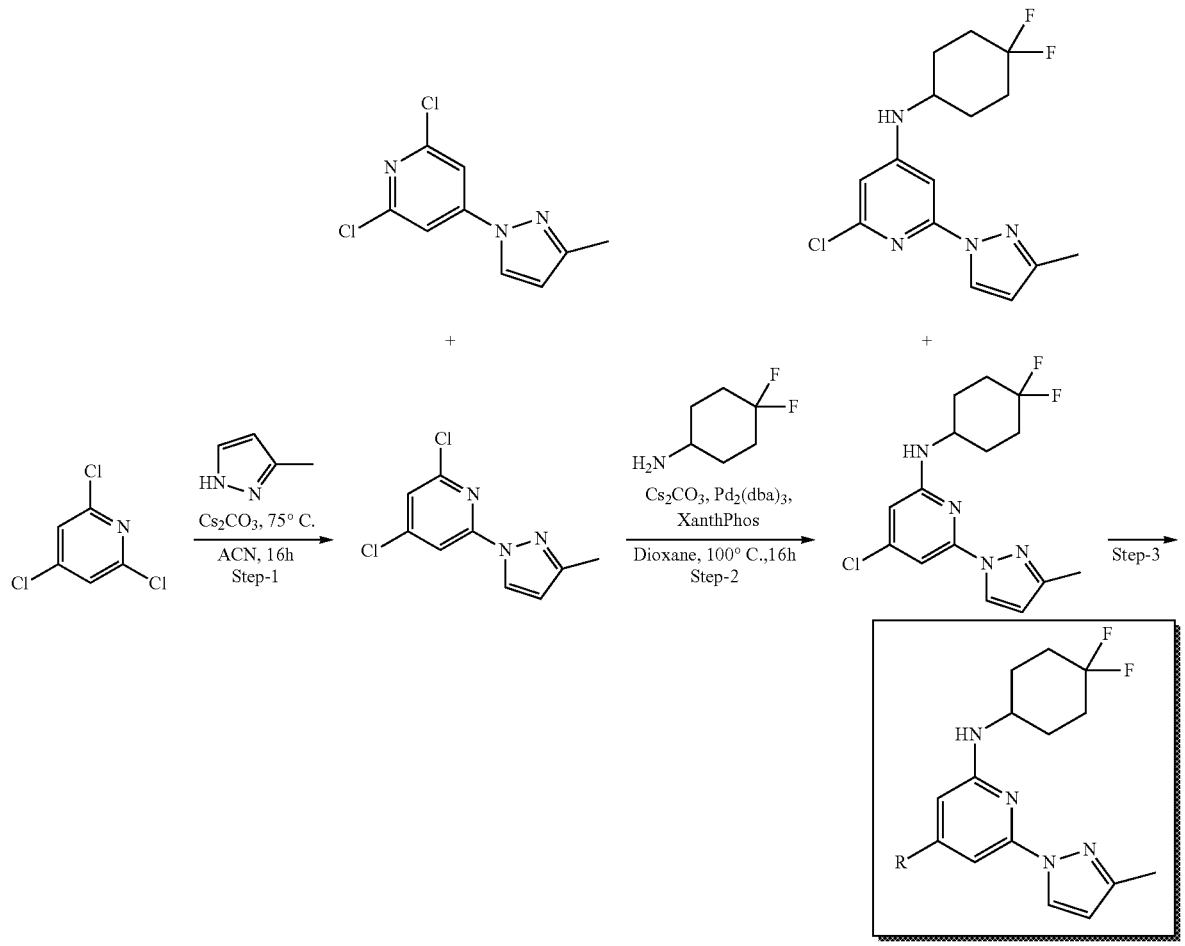

R=

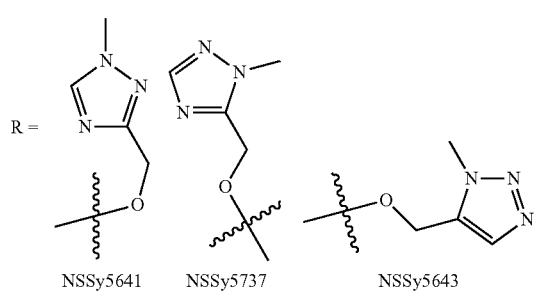

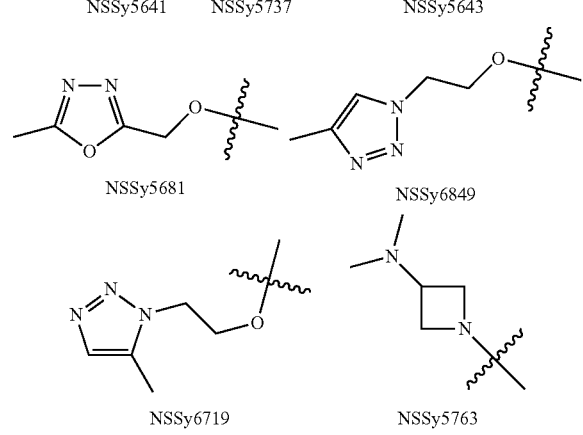

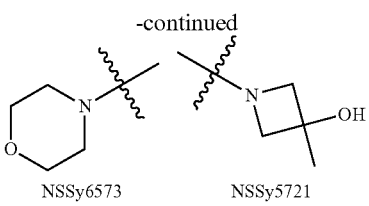

Step 1: The procedure is similar to Step 1[B] in Example-838. 10 g of 2,4,6-trichloropyridine gave 2,4-dichloro-6-(3-methyl-1H-pyrazol-1-yl)pyridine as white solid (5.8 g, 46%). MS (M, M+2)+=228.0, 230.2 and 2,6-dichloro-4-(3-methyl-1H-pyrazol-1-yl)pyridine as white solid (2.1 g, 20%). MS (M, M+2)+=228.0, 230.2.

Step 2: The procedure is similar to Step 1[NSSy6629] in Example-839. 3 g of 2,4-dichloro-6-(3-methyl-1H-pyrazol-1-yl)pyridine gave 4-chloro-N-(4,4-difluorocyclohexyl)-6-(3-methyl-1H-pyrazol-1-yl)pyridin-2-amine as colourless liquid (1.3 g, 30%). MS (M+1)+=327.2 and 2-chloro-N-(4,4-difluorocyclohexyl)-6-(3-methyl-1H-pyrazol-1-yl)pyridin-4-amine as yellow gum (0.3 g, 10%). MS (M+1)+=327.2.

TABLE 89

Step 3:

| Compound No | R | Condition | Yield (%) | MS (M + 1)+ |
|---|---|---|---|---|
| NSSy5641 | 1-methyl-1,2,4-triazol-3-yl-CH2-O- | TBAHS, 50% aq. NaOH, 95° C., 2 days. | 16 | 404.0 |
| NSSy5737 | 2-methyl-2H-1,2,4-triazol-3-yl-CH2-O- | TBAHS, 50% aq. NaOH, 95° C., 16 h. | 10 | 404.0 |
| NSSy5643 | 1-methyl-1,2,3-triazol-5-yl-CH2-O- | TBAHS, 50% aq. NaOH, 95° C., 2 days. | 64 | 404.0 |
| NSSy5681 | 5-methyl-1,3,4-oxadiazol-2-yl-CH2-O- | Cs2CO3, ACN, 130° C., MW, 2 h | 25 | 405.1 |
| NSSy6849 | 4-methyl-1,2,3-triazol-1-yl-CH2CH2-O- | Pd2(dba)3, X-Phos, K3PO4•3H2O, Dioxane, 100° C., 16 h | 20 | 418.1 |
| NSSy6719 | 5-methyl-1,2,3-triazol-1-yl-CH2CH2-O- | Pd2(dba)3, X-Phos, K3PO4•3H2O, Dioxane, 100° C., 16 h | 8 | 418.2 |
| NSSy5763 | 3-(dimethylamino)azetidin-1-yl- | Pd2(dba)3, XanthPhos, Cs2CO3, Dioxane, 100° C., 5 h | 52 | 391.1 |
| NSSy6573 | morpholin-4-yl- | Pd2(dba)3, L1, Cs2CO3, Dioxane, 100° C., 5 h (L1 = (r)-(−)-1-(s)-2-(dicyclohexylphosphino) ferrocenyl ethyl di-t-butylphosphine) | 11 | 378.2 |

TABLE 89-continued

Step 3:

| Compound No | R | Condition | Yield (%) | MS (M + 1)+ |
|---|---|---|---|---|
| NSSy5721 | (azetidine with 3-OH, 3-methyl) | Pd₂(dba)₃, XanthPhos, Cs₂CO₃, Dioxane, 120° C., MW, 3 h | 34 | 378.2 |

Step 3[NSSy5641]: The procedure is similar to Step 1[NSSy5828] in Example-799. 1H-NMR (400 MHz, DMSO-d6): δ 8.43 (s, 1H), 8.33 (d, J=2.32 Hz, 1H), 6.75 (d, J=7.28 Hz, 1H), 6.55 (s, 1H), 6.34 (t, J=2.32 Hz, 2H), 5.26 (s, 2H), 3.98 (s, 1H), 3.84 (s, 3H), 2.24 (s, 3H), 1.98-1.91 (m, 6H), 1.55-1.50 (m, 2H).

Step 3[NSSy5737]: The procedure is similar to Step 1[NSSy5828] in Example-799. 1H-NMR (400 MHz, DMSO-d6): δ 8.40 (d, J=2.40 Hz, 1H), 7.96 (s, 1H), 6.79 (d, J=7.60 Hz, 1H), 6.65 (d, J=2.00 Hz, 1H), 6.29 (d, J=2.40 Hz, 1H), 5.98 (d, J=2.00 Hz, 1H), 5.35 (s, 2H), 3.96-3.91 (m, 4H), 2.26 (s, 3H), 2.08-1.95 (m, 6H), 1.55-1.52 (m, 2H).

Step 3[NSSy5643]: The procedure is similar to Step 1[NSSy5828] in Example-799. 1H-NMR (400 MHz, DMSO-d6): δ 8.33 (s, 1H), 7.78 (s, 1H), 6.81 (d, J=7.60 Hz, 1H), 6.58 (s, 1H), 6.39 (s, 1H), 6.34 (s, 1H), 5.46 (s, 2H), 4.06 (s, 3H), 3.80-3.93 (m, 1H), 2.24 (s, 3H), 2.08-1.92 (m, 6H), 1.57-1.52 (m, 2H).

Step 3[NSSy5681]: The procedure is similar to Step 1[NSSy6909] in Example-839. 1H-NMR (400 MHz, DMSO-d6): δ 8.35 (d, J=2.40 Hz, 1H), 6.84 (d, J=7.60 Hz, 1H), 6.59 (d, J=1.60 Hz, 1H), 6.42 (d, J=1.60 Hz, 1H), 6.34 (d, J=2.80 Hz, 1H), 5.49 (s, 2H), 3.92-3.82 (m, 1H), 3.32 (s, 3H), 2.25 (s, 3H), 2.08-1.85 (m, 6H), 1.49-1.46 (m, 2H).

Step 3[NSsy6849]: The procedure is similar to Step 1[NSSy6629] in Example-839. 1H-NMR (400 MHz, DMSO-d6): δ 8.38 (d, J=2.00 Hz, 1H), 7.91 (s, 1H), 6.70 (d, J=7.60 Hz, 1H), 6.50 (dd, J=1.60, 16.60 Hz, 1H), 6.28 (d, J=2.00 Hz, 1H), 5.84 (s, 1H), 4.72-4.67 (m, 2H), 4.40 (t, J=4.80 Hz, 2H), 3.94 (s, 1H), 2.37 (s, 1H), 2.25 (s, 3H), 2.23 (s, 2H), 2.05-1.90 (m, 6H), 1.60-1.42 (m, 2H).

Step 3[NSsy6719]: The procedure is similar to Step 1[NSSy6629] in Example-839. 1H-NMR (400 MHz, DMSO-d6): δ 8.37 (s, 1H), 7.54 (s, 1H), 6.67 (s, 1H), 6.46 (s, 1H), 6.27 (s, 1H), 5.83 (s, 1H), 4.70 (s, 2H), 4.47 (s, 2H), 3.95 (s, 1H), 2.23 (d, J=5.60 Hz, 6H), 1.99 (d, J=34.40 Hz, 6H), 1.53 (s, 2H).

Step 3[NSSy5763]: The procedure is similar to Step 1[NSSy6629] in Example-839. 1H-NMR (400 MHz, DMSO-d6): δ 8.35 (d, J=2.00 Hz, 1H), 6.30 (d, J=1.64 Hz, 1H), 6.23 (d, J=2.40 Hz, 1H), 6.13 (d, J=1.60 Hz, 1H), 5.29 (d, J=1.60 Hz, 1H), 4.00-3.85 (m, 3H), 3.70-3.60 (m, 2H), 3.22-3.15 (m, 1H), 2.24 (s, 3H), 2.11 (s, 6H), 2.10-1.85 (m, 6H), 1.62-1.45 (m, 2H).

Step 3[NSSy6573]: The procedure is similar to Step 1[NSSy6629] in Example-839. 1H-NMR (400 MHz, DMSO-d6): δ 8.37 (d, J=2.40 Hz, 1H), 6.61 (d, J=1.64 Hz, 1H), 6.38 (d, J=7.64 Hz, 1H), 6.25 (d, J=2.40 Hz, 1H), 5.76 (d, J=1.72 Hz, 1H), 3.95 (s, 1H), 3.72 (t, J=4.92 Hz, 4H), 3.19 (t, J=4.68 Hz, 4H), 2.19 (s, 3H), 2.04-1.90 (m, 6H), 1.60-1.51 (m, 2H).

Step 3[NSSy5721]: The procedure is similar to Step 1[NSSy6629] in Example-839. 1H-NMR (400 MHz, DMSO-d6): δ 8.36 (d, J=2.40 Hz, 1H), 6.32 (d, J=7.60 Hz, 1H), 6.24 (d, J=2.40 Hz, 1H), 6.13 (d, J=1.60 Hz, 1H), 5.63 (s, 1H), 5.31 (d, J=2.00 Hz, 1H), 3.92 (m, 1H), 3.80-3.78 (m, 2H), 3.70-3.68 (m, 2H), 2.25 (s, 3H), 2.07-1.92 (m, 6H), 1.53-1.51 (m, 2H), 1.44 (s, 3H).

Example-826

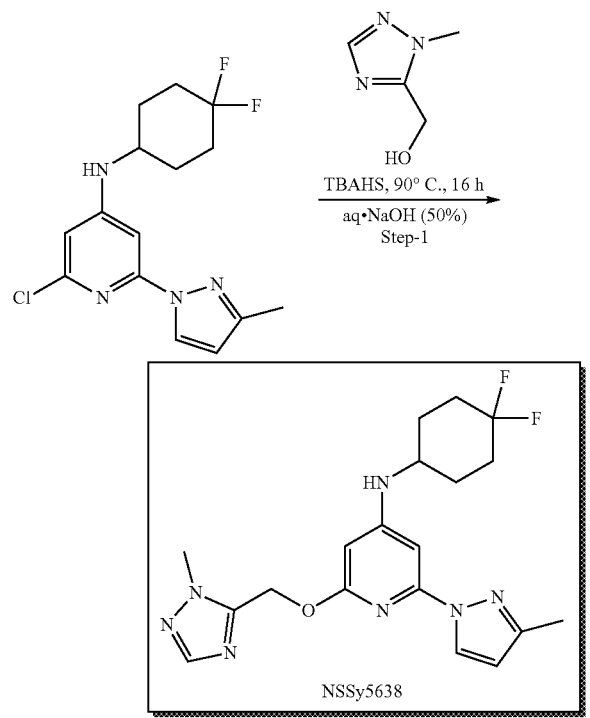

Step 1[NSSy5638]: The procedure is similar to Step 1[NSSy5828] in Example-799. 0.3 g of 2-chloro-N-(4,4-difluorocyclohexyl)-6-(3-methyl-1H-pyrazol-1-yl)pyridin-4-amine gave N-(4,4-difluorocyclohexyl)-2-((1-methyl-1H-1,2,4-triazol-5-yl)methoxy)-6-(3-methyl-1H-pyrazol-1-yl)pyridin-4-amine as an off-white solid (0.015 g, 10%). MS (M+1)+=404.0; 1H-NMR (400 MHz, DMSO-d6): δ 8.34 (d, J=2.48 Hz, 1H), 7.90 (s, 1H), 6.80 (d, J=7.52 Hz, 1H), 6.58 (d, J=1.52 Hz, 1H), 6.41 (d, J=1.52 Hz, 1H), 6.34 (d, J=2.44 Hz, 1H), 5.47 (s, 2H), 3.90 (s, 4H), 2.24 (s, 3H), 2.12-1.82 (m, 6H), 1.55-1.45 (m, 2H).

Example-827

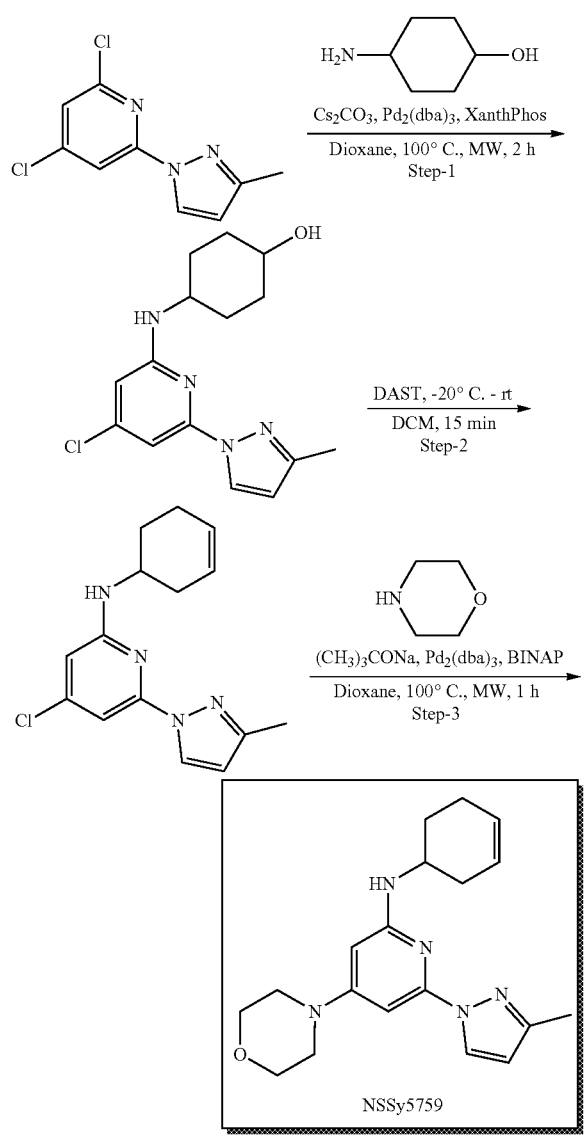

Step 1: The procedure is similar to Step 1[NSSy6629] in Example-839. 1.4 g of 2,4-dichloro-6-(3-methyl-1H-pyrazol-1-yl)pyridine gave 4-((4-chloro-6-(3-methyl-1H-pyrazol-1-yl)pyridin-2-yl)amino)cyclohexan-1-ol as an off-white solid (0.3 g, 15%). MS (M+1)+=307.1.

Step 2: The procedure is similar to Step 3[NSSy6917] in Example-21. 0.3 g of 4-((4-chloro-6-(3-methyl-1H-pyrazol-1-yl)pyridin-2-yl)amino)cyclohexan-1-ol gave 4-chloro-N-(cyclohex-3-en-1-yl)-6-(3-methyl-1H-pyrazol-1-yl)pyridin-2-amine as an off-white solid (0.11 g, 39%). MS (M+1)+= 289.0.

Step 3[NSSy5759]: The procedure is similar to Step 1[NSSy6629] in Example-839. 0.1 g of 4-chloro-N-(cyclohex-3-en-1-yl)-6-(3-methyl-1H-pyrazol-1-yl)pyridin-2-amine gave N-(cyclohex-3-en-1-yl)-6-(3-methyl-1H-pyrazol-1-yl)-4-morpholino pyridin-2-amine as a yellow solid (0.035 g, 31%). MS (M+1)+=340.0; 1H-NMR (400 MHz, DMSO-d6): δ 8.29 (d, J=2.00 Hz, 1H), 6.59 (d, J=1.60 Hz, 1H), 6.24 (t, J=3.20 Hz, 2H), 5.78 (d, J=1.60 Hz, 1H), 5.66 (s, 2H), 3.93 (s, 1H), 3.71 (t, J=4.80 Hz, 4H), 3.19 (t, J=4.80 Hz, 4H), 2.36 (d, J=10.00 Hz, 1H), 2.25 (s, 3H), 2.14 (s, 2H), 1.96-1.93 (m, 2H), 1.49-1.41 (m, 1H).

Example-828

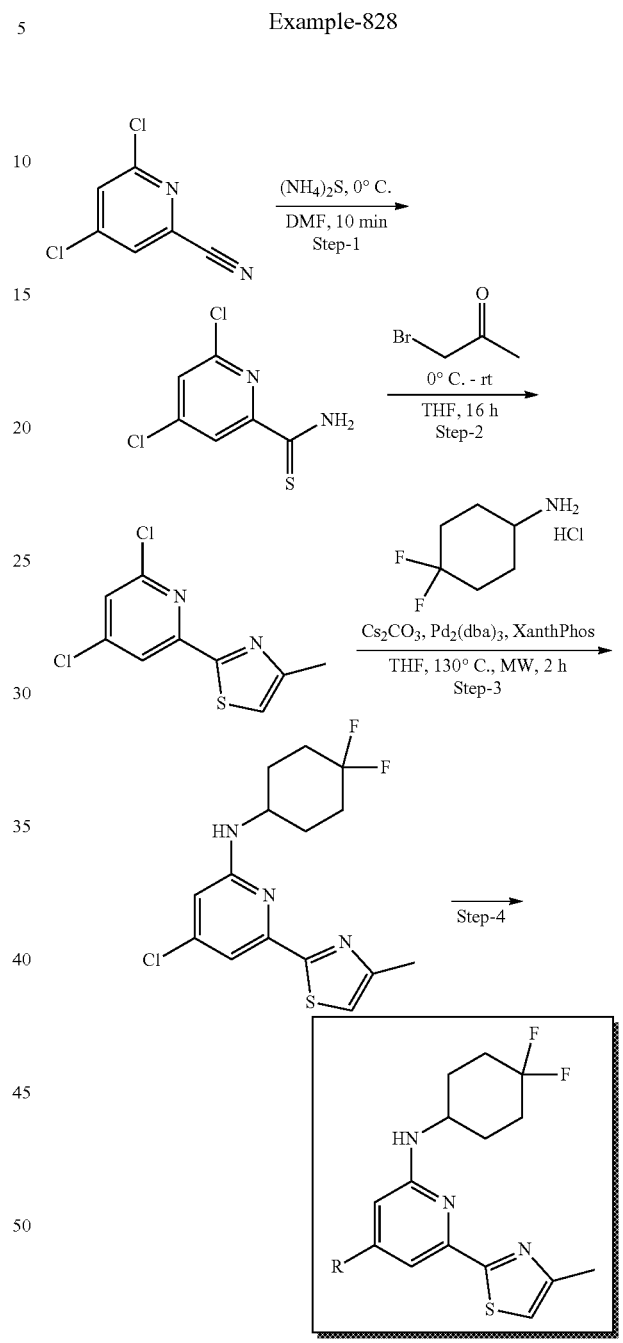

R=

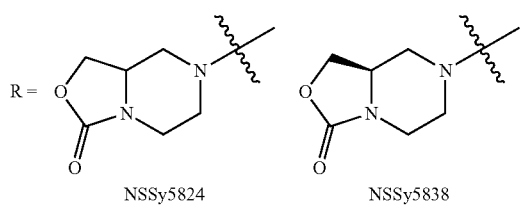

NSSy5824     NSSy5838

-continued

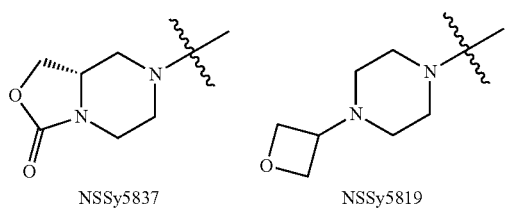

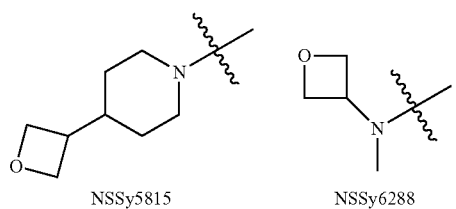

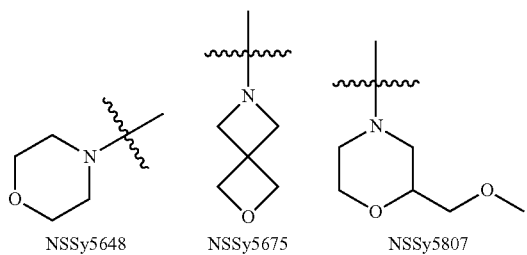

-continued

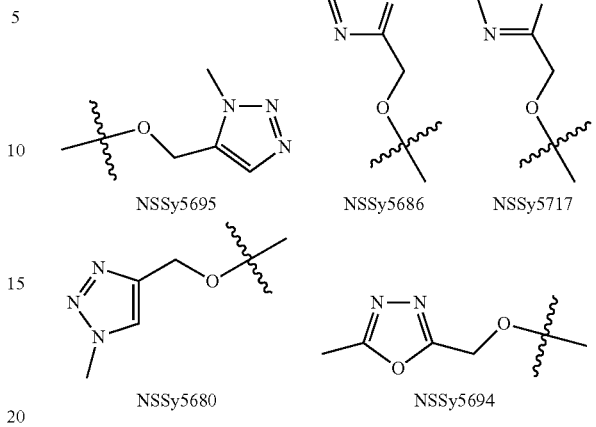

Step 1: The procedure is similar to Step 5[NSSy5779] in Example-642. 8 g gave 4,6-dichloropicolinonitrile gave 4,6-dichloropyridine-2-carbothioamide as yellow solid (6.2 g, 66%). MS (M+1)+=208.2.

Step 2: The procedure is similar to Step 6[NSSy5779] in Example-642. 6 g of 4,6-dichloropyridine-2-carbothioamide gave 2-(4,6-dichloropyridin-2-yl)-4-methylthiazole as off-white solid (6 g, 84%). MS (M, M+2)+=245.0, 247.0.

Step 3: The procedure is similar to Step 1[NSSy6629] in Example-839. 1 g of 2-(4,6-dichloropyridin-2-yl)-4-methyl-thiazole gave 4-chloro-N-(4,4-difluorocyclohexyl)-6-(4-methylthiazol-2-yl)pyridin-2-amine as yellow solid (0.55 g, 39%). MS (M+1)+=344.1.

TABLE 90

| Step 4: | | | | |
|---|---|---|---|---|
| Compound No | R | Condition | Yield (%) | MS (M + 1)+ |
| NSSy5824 | | Pd₂(dba)₃, X-Phos, Cs₂CO₃, Dioxane, 100° C., 5 h | 44 | 450.2 |
| NSSy5838 | | Pd₂(dba)₃, X-Phos, Cs₂CO₃, Dioxane, 100° C., 5 h Chiral seperation | — | 450.2 |
| NSSy5837 | | Pd₂(dba)₃, X-Phos, Cs₂CO₃, Dioxane, 100° C., 5 h Chiral Seperation | — | 450.2 |

TABLE 90-continued

Step 4:

| Compound No | R | Condition | Yield (%) | MS (M + 1)+ |
|---|---|---|---|---|
| NSSy5819 | (4-(oxetan-3-yl)piperazin-1-yl) | Pd₂(dba)₃, XanthPhos, Cs₂CO₃, Dioxane, 100° C., 16 h | 05 | 450.2 |
| NSSy5815 | (4-(oxetan-3-yl)piperidin-1-yl) | Pd₂(dba)₃, XanthPhos, Cs₂CO₃, Dioxane, 100° C., 16 h | 10 | 449.0 |
| NSSy6288 | N-methyl-N-(oxetan-3-yl)amino | Pd₂(dba)₃, X-Phos, Cs₂CO₃, THF, 65° C., 16 h | 22 | 395.0 |
| NSSy5646 | morpholin-4-yl | Pd₂(dba)₃, XanthPhos, Cs₂CO₃, Dioxane, 100° C., 2 h, MW | 20 | 395.0 |
| NSSy5675 | 2-oxa-6-azaspiro[3.3]heptan-6-yl | Pd₂(dba)₃, XanthPhos, Cs₂CO₃, THF, 130° C., 2 h, MW | 15 | 407.1 |
| NSSy5807 | 2-(methoxymethyl)morpholin-4-yl | Pd₂(dba)₃, XanthPhos, Cs₂CO₃, Dioxane, 120° C., 16 h | 20 | 439.0 |
| NSSy5695 | ((1-methyl-1H-1,2,3-triazol-5-yl)methoxy)methyl | TBAHS, 50% aq. NaOH, 95° C., 16 h | 07 | 421.0 |
| NSSy5686 | ((1-methyl-1H-1,2,4-triazol-3-yl)methoxy)methyl | TBAHS, 50% aq NaOH, 95° C., 16 h | 04 | 421.0 |

TABLE 90-continued

Step 4:

| Compound No | R | Condition | Yield (%) | MS (M + 1)+ |
|---|---|---|---|---|
| NSSy5717 | (1-methyl-1H-1,2,4-triazol-5-yl)methoxy group | TBAHS, 50% aq NaOH, 95° C., 16 h | 15 | 421.0 |
| NSSy5680 | (1-methyl-1H-1,2,3-triazol-4-yl)methoxy group | TBAHS, 50% aq NaOH, 95° C., 16 h | 21 | 421.0 |
| NSSy5694 | (5-methyl-1,3,4-oxadiazol-2-yl)methoxy group | CS$_2$CO$_3$, ACN, 150° C., MW, 3 h | 04 | 422.0 |

Step 4[NSSy5824]: The procedure is similar to Step 1[NSSy6629] in Example-839. 1H-NMR (400 MHz, DMSO-d6): δ 7.26 (s, 1H), 6.95 (s, 1H), 6.40 (d, J=6.80 Hz, 1H), 5.96 (s, 1H), 4.42 (t, J=28.00 Hz, 1H), 4.04-4.00 (m, 2H), 3.95-3.88 (m, 3H), 3.66 (dd, J=2.80, 13.00 Hz, 1H), 3.14-3.07 (m, 1H), 2.87-2.75 (m, 2H), 2.40 (s, 3H), 2.00-1.90 (m, 6H), 1.62-1.57 (m, 2H).

Step 4[NSSy5838]: The procedure is similar to Step 1[NSSy6629] in Example-839. 1H-NMR (400 MHz, DMSO-d6): δ 7.27 (d, J=0.84 Hz, 1H), 6.95 (d, J=1.92 Hz, 1H), 6.41 (d, J=7.12 Hz, 1H), 5.96 (d, J=1.92 Hz, 1H), 4.41 (t, J=8.48 Hz, 1H), 4.04-4.01 (m, 2H), 3.91-3.79 (m, 3H), 3.66 (dd, J=2.68, 13.06 Hz, 1H), 2.40 (s, 3H), 2.15-1.85 (m, 6H), 1.59-1.56 (m, 2H).

Step 4[NSSy5837]: The procedure is similar to Step 1[NSSy6629] in Example-839. 1H-NMR (400 MHz, DMSO-d6): δ 7.25 (s, 1H), 6.94 (s, 1H), 6.39 (d, J=7.20 Hz, 1H), 5.95 (s, 1H), 4.40 (t, J=8.80 Hz, 1H), 4.03-3.99 (m, 2H), 3.95-3.75 (m, 3H), 3.67-3.63 (m, 1H), 3.12-3.06 (m, 1H), 2.85-2.74 (m, 2H), 2.39 (s, 3H), 2.15-1.85 (m, 6H), 1.61-1.56 (m, 2H).

Step 4[NSSy5819]: The procedure is similar to Step 1[NSSy6629] in Example-839. 1H-NMR (400 MHz, DMSO-d6): δ 7.24 (s, 1H), 6.91 (s, 1H), 6.36 (d, J=7.2 Hz, 1H), 5.92 (s, 1H), 4.57 (t, J=6.4 Hz, 2H), 4.76 (t, J=6.0 Hz, 2H), 3.83-3.79 (bs, 1H), 3.50-3.40 (m, 1H), 3.30-3.25 (m, 4H), 2.45-2.35 (m, 7H), 2.20-1.80 (m, 6H), 1.15-1.10 (m, 2H).

Step 4[NSSy5815]: The procedure is similar to Step 1[NSSy6629] in Example-839. 1H-NMR (400 MHz, DMSO-d6): δ 7.23 (s, 1H), 6.90 (s, 1H), 6.30 (d, J=6.8 Hz, 1H), 5.92 (s, 1H), 4.60 (t, J=6.0 Hz, 2H), 4.36 (t, J=6.0 Hz, 2H), 3.83-3.79 (m, 3H), 2.82 (t, J=11.6 Hz, 2H), 2.70-2.67 (m, 1H), 2.39 (s, 3H), 2.20-1.80 (m, 7H), 1.70-1.50 (m, 4H), 1.15-1.00 (m, 2H).

Step 4[NSSy6288]: The procedure is similar to Step 1[NSSy6629] in Example-839. 1H-NMR (400 MHz, DMSO-d6): δ 7.25 (s, 1H), 6.75 (d, J=2.00 Hz, 1H), 6.35 (d, J=7.20 Hz, 1H), 5.61 (d, J=1.60 Hz, 1H), 4.88-4.83 (m, 1H), 4.79 (t, J=7.20 Hz, 2H), 4.65 (t, J=6.00 Hz, 2H), 3.87 (s, 1H), 2.96 (s, 3H), 2.41 (s, 3H), 2.15-1.85 (m, 6H), 1.62-1.50 (m, 2H).

Step 4[NSSy5646]: The procedure is similar to Step 1[NSSy6629] in Example-839. 1H-NMR (400 MHz, DMSO-d6): δ 7.25 (s, 1H), 6.92 (s, 1H), 6.38 (d, J=7.04 Hz, 1H), 5.93 (s, 1H), 3.88-3.82 (m, 4H), 3.21 (m, 4H), 2.40 (s, 3H), 2.07-1.90 (m, 6H), 1.59-1.56 (m, 2H).

Step 4[NSSy5675]: The procedure is similar to Step 1[NSSy6629] in Example-839. 1H-NMR (400 MHz, DMSO-d6): δ 7.24 (s, 1H), 6.44 (d, J=1.64 Hz, 1H), 6.35 (d, J=7.00 Hz, 1H), 5.47 (s, 1H), 4.72-4.69 (m, 4H), 4.06-3.93 (m, 4H), 3.84-3.81 (m, 1H), 2.33 (s, 3H), 2.06-1.88 (m, 6H), 1.59-1.54 (m, 2H).

Step 4[NSSy5807]: The procedure is similar to Step 1[NSSy6629] in Example-839. 1H-NMR (400 MHz, DMSO-d6): δ 7.25 (s, 1H), 6.91 (s, 1H), 6.43 (d, J=7.04 Hz, 1H), 5.94 (s, 1H), 4.13-4.09 (m, 1H), 3.94-3.93 (m, 2H), 3.62-3.39 (m, 4H), 3.46-3.42 (m, 2H), 3.30 (s, 3H), 2.91-2.85 (s, 1H), 2.67 (t, J=11.48 Hz, 1H), 2.40 (s, 3H), 2.08-1.97 (m, 6H), 1.58-1.56 (m, 2H).

Step 4[NSSy5695]: The procedure is similar to Step 1[NSSy5828] in Example-799. 1H-NMR (400 MHz, DMSO-d6): δ 7.96 (s, 1H), 7.31 (d, J=1.00 Hz, 1H), 6.96 (d, J=2.08 Hz, 1H), 6.79 (d, J=6.96 Hz, 1H), 6.17 (d, J=2.08 Hz, 1H), 5.37 (s, 2H), 3.91 (s, 3H), 3.89-3.88 (m, 1H), 2.41 (s, 3H), 2.07-1.99 (m, 6H), 1.65-1.52 (m, 2H).

Step 4[NSSy5686]: The procedure is similar to Step 1[NSSy5828] in Example-799. 1H-NMR (400 MHz, DMSO-d6): δ 8.17 (s, 1H), 7.30 (s, 1H), 6.90 (d, J=2.00 Hz, 1H), 6.71 (d, J=7.20 Hz, 1H), 6.16 (d, J=2.00 Hz, 1H), 5.20 (s, 2H), 4.05 (s, 3H), 3.85 (s, 1H), 2.32 (s, 3H), 2.02-1.99 (m, 6H), 1.59-1.56 (m, 2H).

Step 4[NSSy5717]: The procedure is similar to Step 1[NSSy5828] in Example-799. 1H-NMR (400 MHz, DMSO-d6): δ 7.85 (s, 1H), 7.31 (s, 1H), 6.91 (d, J=1.60 Hz, 1H), 6.73 (d, J=7.20 Hz, 1H), 6.15 (d, J=1.60 Hz, 1H), 5.21 (s, 2H), 4.17 (s, 3H), 3.91-3.88 (m, 1H), 2.33 (s, 3H), 2.08-1.91 (m, 6H), 1.62-1.57 (m, 2H).

Step 4[NSSy5680]: The procedure is similar to Step 1[NSSy5828] in Example-799. 1H-NMR (400 MHz, DMSO-d6): δ 8.17 (s, 1H), 7.30 (s, 1H), 6.91 (d, J=1.88 Hz, 1H), 6.71 (d, J=7.08 Hz, 1H), 6.17 (d, J=1.92 Hz, 1H), 5.20 (s, 2H), 4.06 (s, 3H), 3.86 (s, 1H), 2.33 (s, 3H), 2.07-1.91 (m, 6H), 1.62-1.57 (m, 2H).

Step 4[NSSy5694]: The procedure is similar to Step 1[NSSy6909] in Example-839. 1H-NMR (400 MHz, DMSO-d6): δ 7.33 (s, 1H), 6.95 (d, J=2.00 Hz, 1H), 6.82 (d, J=6.80 Hz, 1H), 6.16 (d, J=2.00 Hz, 1H), 5.45 (s, 2H), 4.08-3.87 (m, 1H), 2.61 (s, 3H), 2.38 (s, 3H), 2.03-2.00 (m, 6H), 1.73-1.52 (m, 2H).

Example-829

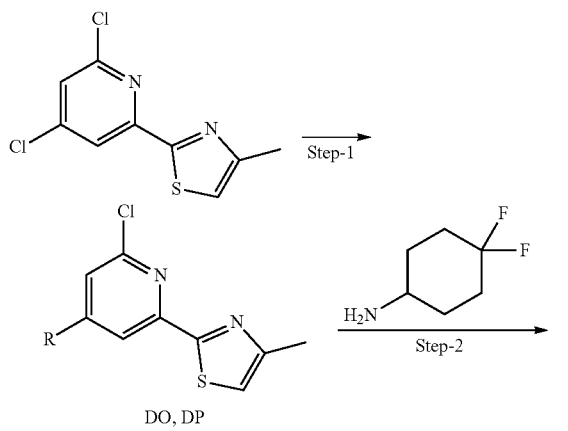

R=

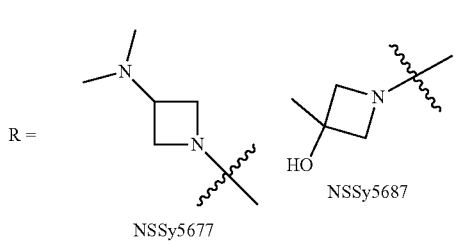

TABLE 91

Step 1: The procedure is similar to Step 1[NSSy6909] in Example-839.

| Compound No | R | Condition | Yield (%) | MS (M + 1)+ |
|---|---|---|---|---|
| DO | (dimethylamino-azetidinyl) | Cs2CO3, THF, 120° C., MW, 3 h | 21 | 309.0 |
| DP | (3-hydroxy-3-methyl-azetidinyl) | TEA, ACN, 120° C., MW, 6 h | 30 | 295.2 |

TABLE 92

Step 2: The procedure is similar to Step 1[NSSy6629] in Example-839.

| Compound No | R | Condition | Yield (%) | MS (M + 1)+ |
|---|---|---|---|---|
| NSSy5677 | (dimethylamino-azetidinyl) | Pd2(dba)3, XanthPhos, Cs2CO3, THF, 130° C., 2 h, MW | 14 | 408.0 |
| NSSy5687 | (3-hydroxy-3-methyl-azetidinyl) | Pd2(dba)3, XanthPhos, Cs2CO3, THF, 130° C., 2 h, MW | 06 | 395.2 |

Step 2[NSSy5677]: 1H-NMR (400 MHz, DMSO-d6): δ 7.24 (s, 1H), 6.46 (s, 1H), 6.32 (d, J=6.80 Hz, 1H), 5.47 (s, 1H), 3.97-3.93 (m, 2H), 3.84 (s, 1H), 3.66-3.63 (m, 2H), 3.20-3.19 (m, 1H), 2.39 (s, 3H), 2.12-1.97 (m, 12H), 1.58-1.55 (m, 2H).

Step 2[NSSy5687]: 1H-NMR (400 MHz, CDCl3): δ 9.10 (s, 1H), 6.92 (s, 1H), 6.68 (s, 1H), 6.46-6.32 (m, 1H), 5.34 (s, 1H), 4.24 (s, 1H), 3.99-3.90 (m, 4H), 2.53 (s, 3H), 2.15-1.91 (m, 6H), 1.65-1.58 (m, 2H), 1.58 (s, 3H).

Example-830

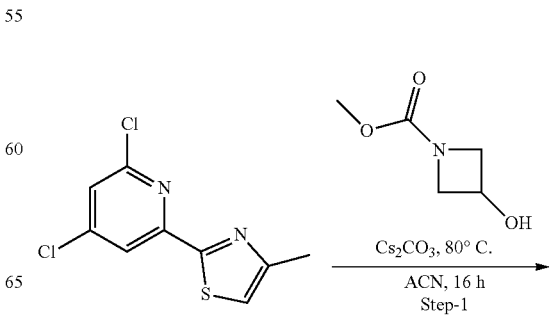

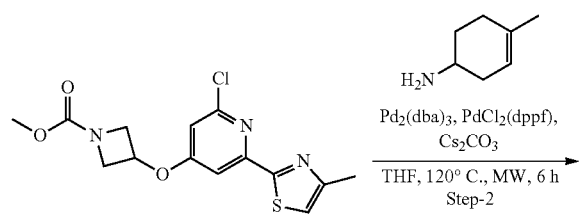

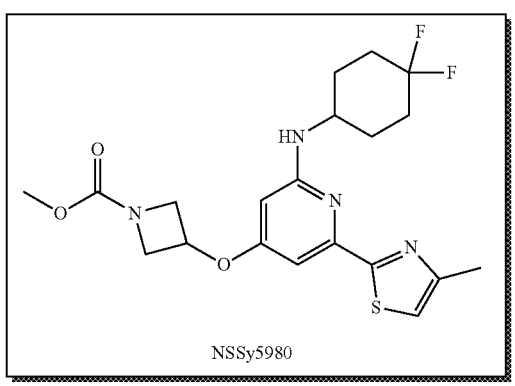

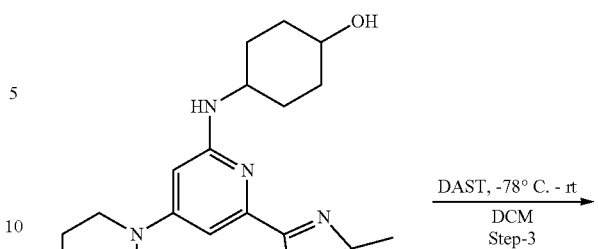

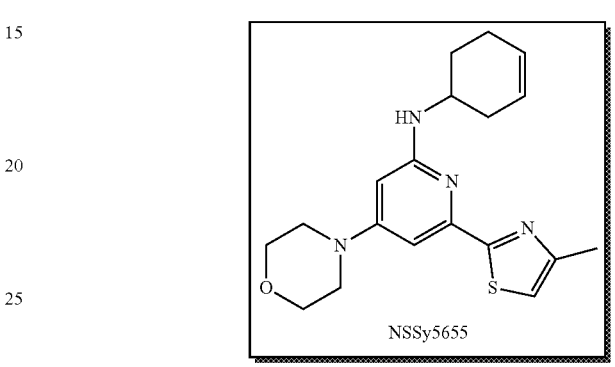

Step 1: The procedure is similar to Step 1[B] in Example-838. 0.5 g of 2-(4,6-dichloropyridin-2-yl)-4-methylthiazole gave methyl 3-((2-chloro-6-(4-methylthiazol-2-yl)pyridin-4-yl)oxy) azetidine-1-carboxylate as white solid (0.2 g, 29%). MS (M+1)+=340.2.

Step 2[NSSy5980]: The procedure is similar to Step 1[NSSy6629] in Example-839. 0.18 g of methyl 3-((2-chloro-6-(4-methylthiazol-2-yl)pyridin-4-yl)oxy)azetidine-1-carboxylate as white solid gave methyl 3-((2-((4-methylcyclohex-3-en-1-yl)amino)-6-(4-methylthiazol-2-yl) pyridin-4-yl)oxy)azetidine-1-carboxylate as white solid (0.019 g, 8%). MS (M+1)+=415.2; 1H-NMR (400 MHz, DMSO-d6): δ 7.28 (d, J=3.60 Hz, 1H), 6.70 (s, 1H), 6.57 (s, 1H), 5.89-5.85 (d, J=12.40 Hz, 1H), 5.35 (s, 1H), 5.06 (s, 1H), 4.33 (s, 2H), 3.89 (s, 2H), 3.68 (s, 1H), 3.57 (s, 3H), 2.39 (s, 3H), 2.09-1.94 (m, 4H), 1.81-1.55 (m, 5H).

Example-831

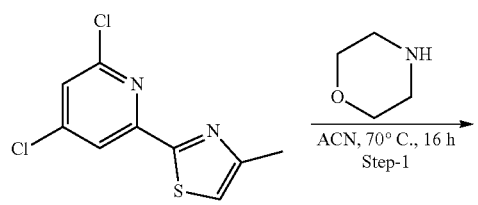

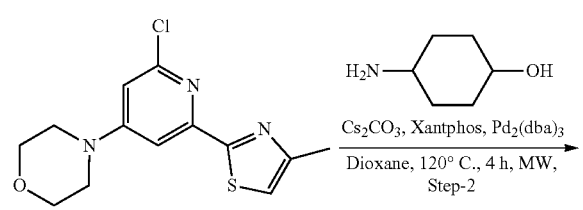

Step 1: The procedure is similar to Step 1[B] in Example-838. 1.5 g of 2-(4,6-dichloropyridin-2-yl)-4-methylthiazole gave 4-(2-chloro-6-(4-methylthiazol-2-yl)pyridin-4-yl) morpholine as a white solid (0.6 g, 62%). MS (M+1)+= 295.9.

Step 2: The procedure is similar to Step 1[NSSy6629] in Example-839. 0.15 g of 4-(2-chloro-6-(4-methylthiazol-2-yl)pyridin-4-yl) morpholine gave 4-((6-(4-methylthiazol-2-yl)-4-morpholinopyridin-2-yl)amino)cyclohexan-1-ol as a white solid (0.09 g, 47%). MS (M+1)+=374.1.

Step 3[NSSy5655]: The procedure is similar to Step 3[NSSy6917] in Example-21. 0.1 g of 4-((6-(4-methylthiazol-2-yl)-4-morpholinopyridin-2-yl)amino)cyclohexan-1-ol gave N-(cyclohex-3-en-1-yl)-6-(4-methylthiazol-2-yl)-4-morpholinopyridin-2-amine as a yellow solid (0.03 g, 32%). MS (M+1)+=357.2; 1H-NMR (400 MHz, DMSO-d6): δ 7.23 (d, J=0.88 Hz, 1H), 6.90 (d, J=1.92 Hz, 1H), 6.24 (d, J=7.28 Hz, 1H), 5.92 (d, J=1.92 Hz, 1H), 5.67-5.55 (m, 2H), 3.93-3.73 (m, 1H), 3.72-3.70 (m, 4H), 3.21-3.20 (m, 4H), 2.42 (s, 3H), 2.14-1.97 (m, 4H), 1.52-1.51 (m, 1H).

Example-832

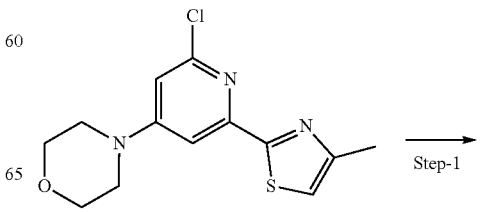

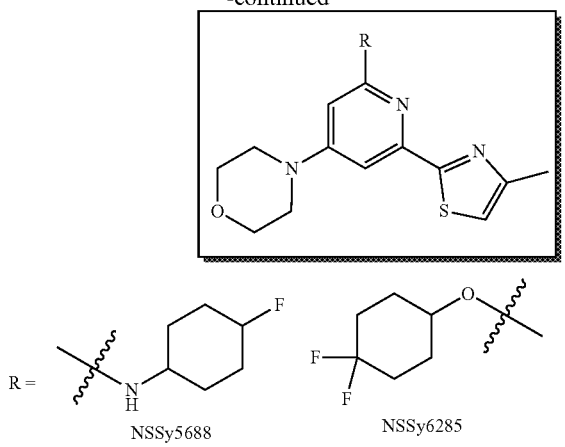

NSSy5688     NSSy6285

TABLE 93

| Compound No | R | Condition | Yield (%) |
|---|---|---|---|
| NSSy5688 | (4-fluorocyclohexyl)amino | Cs₂CO₃, Xantphos, Pd₂(dba)₃, THF, 130° C., 3 h, MW | 15 |
| NSSy6285 | (4,4-difluorocyclohexyl)oxy | TBAHS, 50% aq. sodium hydroxide, 90° C., 48 h | 10 |

Step 1[NSSy5688]: The procedure is similar to Step 1[NSSy6629] in Example-839. MS (M+1)+=377.2; 1H-NMR (400 MHz, DMSO-d6): δ 7.24-7.23 (m, 1H), 6.90 (d, J=2.00 Hz, 1H), 6.53 (s, 1H), 6.30-6.23 (m, 1H), 5.93-5.90 (m, 1H), 4.84 (s, 1H), 3.73-3.72 (m, 4H), 3.37-3.36 (m, 4H), 2.39 (s, 3H), 2.09-1.92 (m, 4H), 1.83-1.78 (m, 2H), 1.63-1.60 (m, 2H).

Step 1[NSSy6285]: The procedure is similar to Step 1[NSSy5828] in Example-799. MS (M+1)+=396.1; 1H-NMR (400 MHz, DMSO-d6-80° C.): δ 7.34 (s, 1H), 7.23 (s, 1H), 6.25 (s, 1H), 5.16 (bs, 1H), 3.72-3.32 (m, 4H), 2.68-2.67 (m, 4H), 2.42 (s, 3H), 2.20-1.97 (m, 6H), 1.96-1.85 (m, 2H).

Example-833

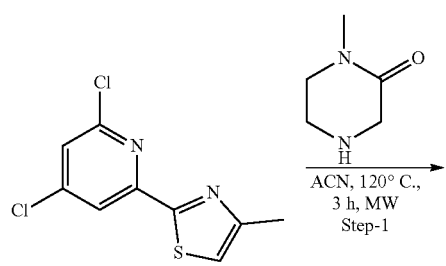

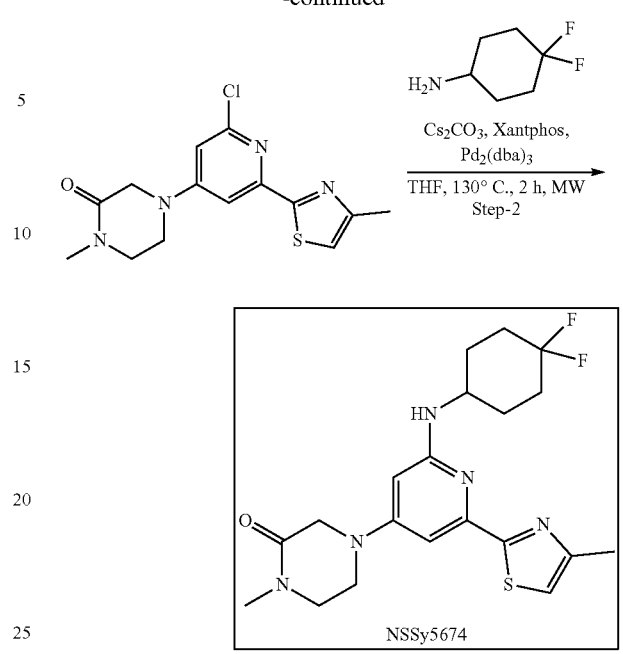

Step 1: The procedure is similar to Step 1[NSSy6909] in Example-839. 1.0 g of 2-(4,6-dichloropyridin-2-yl)-4-methylthiazole gave 4-(2-chloro-6-(4-methylthiazol-2-yl)pyridin-4-yl)-1-methylpiperazin-2-one as a pale yellow solid (0.3 g, 23%). MS (M+1)+=322.0.

Step 2[NSSy5674]: The procedure is similar to Step 1[NSSy6629] in Example-839. 0.3 g of 4-(2-chloro-6-(4-methylthiazol-2-yl)pyridin-4-yl)-1-methylpiperazin-2-one gave 4-(2-((4,4-difluorocyclohexyl)amino)-6-(4-methylthiazol-2-yl)pyridin-4-yl)-1-methylpiperazin-2-one as a pale yellow solid (0.095 g, 23%). MS (M+1)+=422.2; 1H-NMR (400 MHz, DMSO-d6): δ 7.26 (s, 1H), 6.90 (s, 1H), 6.38 (d, J=7.20 Hz, 1H), 5.88 (s, 1H), 3.87-3.85 (m, 3H), 3.60-3.58 (m, 2H), 3.45-3.43 (m, 2H), 2.86 (s, 3H), 2.34 (s, 3H), 2.07-1.91 (m, 6H), 1.61-1.56 (m, 2H).

Example-834

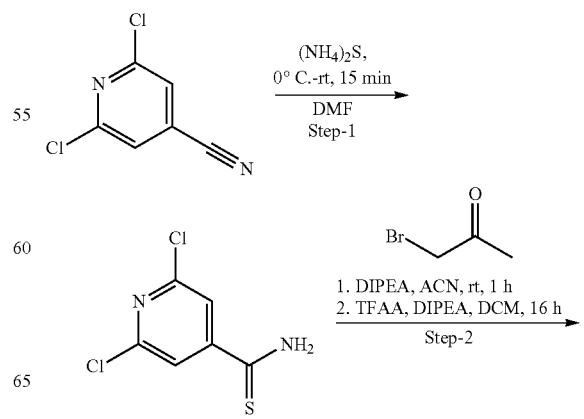

(M+1)+=396.1; 1H-NMR (400 MHz, DMSO-d6): δ 7.45 (s, 1H), 6.76 (s, 1H), 6.52 (s, 1H), 5.16 (s, 1H), 3.72 (s, 4H), 3.49 (s, 4H), 2.44 (s, 3H), 1.98-1.86 (m, 8H).

Example-835

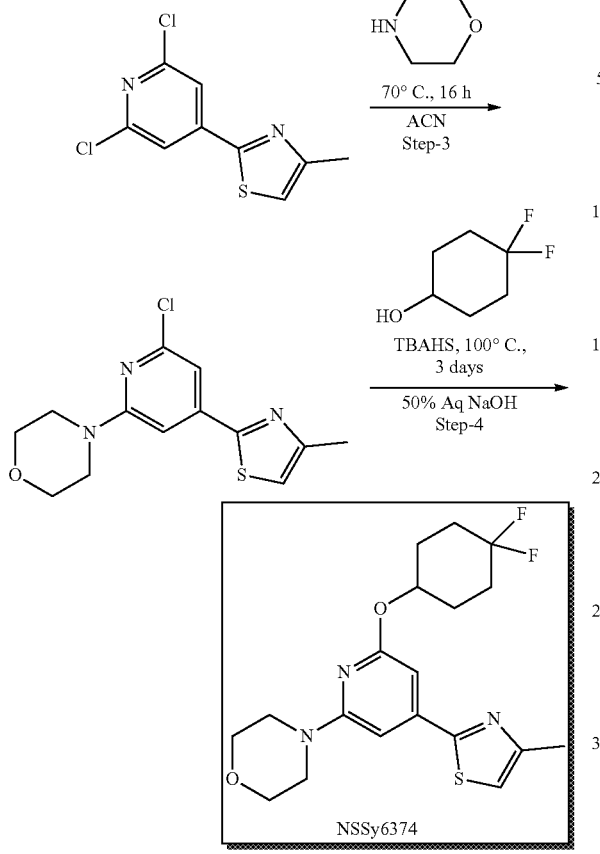

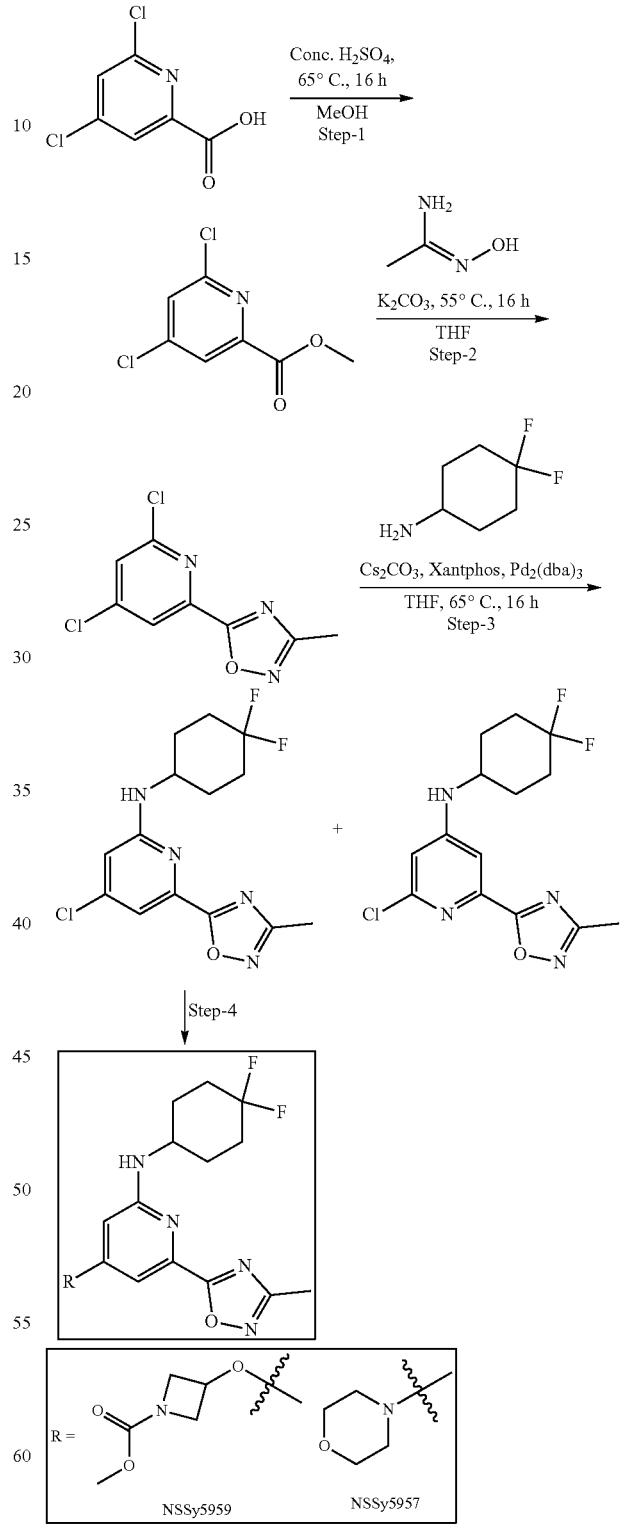

Step 1: The procedure is similar to Step 5[NSSy5779] in Example-642. 5.0 g of 2,6-dichloroisonicotinonitrile gave 2,6-dichloropyridine-4-carbothioamide as a yellow solid (4.1 g, 66%). MS (M+1)+=207.0.

Step 2: To a stirred solution of 2,6-dichloropyridine-4-carbothioamide (1 g, 4.82 mmol) in Acetonitrile (20 mL), was added Bromoacetone (0.99 g, 7.24 mmol) and N,N-Diisopropyl ethylamine (1.24 g, 9.65 mmol). The reaction mixture was stirred at room temperature for 1 h. To the above reaction mixture was added N, N-Diisopropyl ethylamine (0.93 g, 7.24 mmol) and Trifluoroacetic anhydride (2.02 g, 9.65 mmol). The reaction mixture was stirred at room temperature. The reaction mixture was extracted with ethyl acetate (100 mL), the organic layer was washed with saturated sodium bicarbonate solution (20 mL), and brine solution (20 mL), dried over sodium sulphate, filtered and concentrated under reduced pressure to afford crude product, which was purified by flash column chromatography using ethyl acetate in pet ether as solvent. The product spot was isolated with 10% ethyl acetate in pet ether to afford 2-(2,6-dichloropyridin-4-yl)-4-methylthiazole as an off-white solid (0.9 g, 76%). MS (M+1)+=245.0.

Step 3: The procedure is similar to Step 1[B] in Example-838. 0.6 g of 2-(2,6-dichloropyridin-4-yl)-4-methylthiazole gave 4-(6-chloro-4-(4-methylthiazol-2-yl)pyridin-2-yl) morpholine as an off-white solid (0.3 g, 41%). MS (M+1)+=296.0.

Step 4[NSSy6374]: The procedure is similar to Step 1[NSSy5828] in Example-799. 0.25 g of 4-(6-chloro-4-(4-methylthiazol-2-yl)pyridin-2-yl) morpholine gave 4-(6-((4, 4-difluorocyclohexyl)oxy)-4-(4-methylthiazol-2-yl)pyridin-2-yl) morpholine as a brownish gum (0.068 g, 18%). MS Step 1: The procedure is similar to Step 3[NSSy6711] in Example-854. 10.0 g of 4,6-dichloropicolinic acid gave methyl 4,6-dichloropicolinate as white solid (9 g, 85%). MS (M+1)+=208.2.

Step 2: The procedure is similar to Step 1[B] in Example-838. 5.0 g of methyl 4,6-dichloropicolinate gave 5-(4,6-dichloropyridin-2-yl)-3-methyl-1,2,4-oxadiazole as white solid (2.2 g, 40%). MS (M+1)+=231.7.

Step 3: The procedure is similar to Step 1[NSSy6629] in Example-839. 0.5 g of 5-(4,6-dichloropyridin-2-yl)-3-methyl-1,2,4-oxadiazole gave 4-chloro-N-(4,4-difluorocyclohexyl)-6-(3-methyl-1,2,4-oxadiazol-5-yl)pyridin-2-amine as colourless gum (0.24 g, 33%). MS (M+1)+=328.9.

TABLE 94

Step 4:

| Compound No | R | Condition | Yield (%) |
|---|---|---|---|
| NSSy5959 | 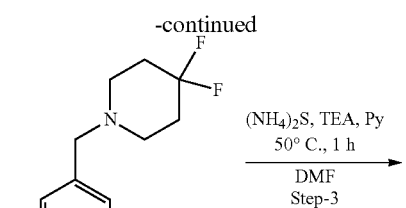 | Cs$_2$CO$_3$, ACN, 120° C., 5 h | 21 |
| NSSy5957 | 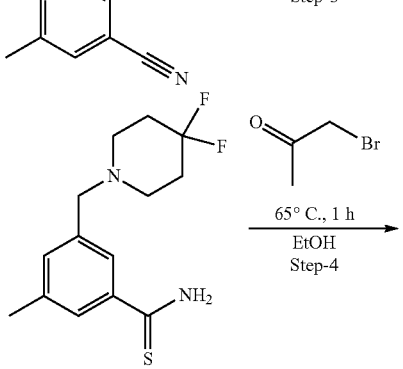 | Cs$_2$CO$_3$, X-phos, Pd$_2$(dba)$_3$, Dioxane, 90° C., 16 h, | 18 |

Step 4[NSSy5959]: The procedure is similar to Step 1[B] in Example-838. MS (M+1)+=424.2; 1H-NMR (400 MHz, DMSO-d6): δ 6.97 (d, J=7.20 Hz, 1H), 6.87 (d, J=2.00 Hz, 1H), 6.06 (d, J=2.00 Hz, 1H), 5.12-5.09 (m, 1H), 4.36 (s, 2H), 3.93 (s, 3H), 3.59 (s, 3H), 2.42 (s, 3H), 2.08-1.96 (m, 6H), 1.60-1.53 (m, 2H).

Step 1[NSSy5957]: The procedure is similar to Step 1[NSSy6629] in Example-839. MS (M+1)+=380.9; 1H-NMR (400 MHz, DMSO-d6): δ 7.03 (s, 1H), 6.57 (d, J=8.00 Hz, 1H), 6.05 (s, 1H), 3.95 (s, 1H), 3.71 (t, J=4.80 Hz, 4H), 3.22 (t, J=4.40 Hz, 4H), 2.39 (s, 3H), 2.04-1.92 (m, 6H), 1.60-1.50 (m, 2H).

Example-836

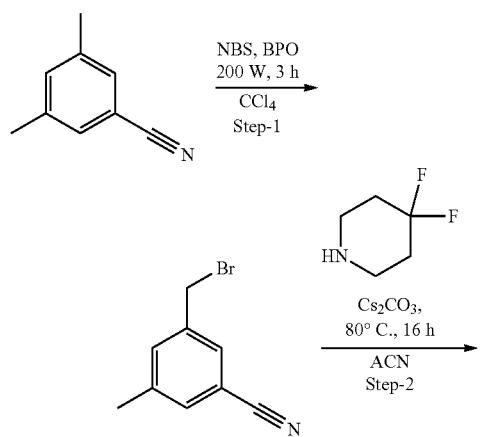

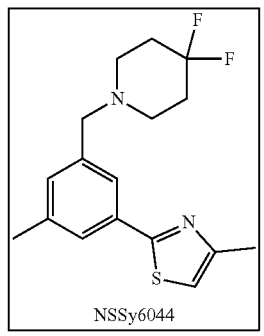

NSSy6044

Step 1: To a stirred solution of 3,5-dimethylbenzonitrile (5 g, 38.11 mmol) in carbontetrachloride (50 mL), was added N-Bromosuccinimide (6.78 g, 38.11 mmol) and benzoyl peroxide (0.46 g, 1.90 mmol). The reaction mixture was refluxed under 200 W tungsten lamp for 3 h. The reaction mixture was cooled to room temperature, filtered, concentrated under reduced pressure. The residue was crystallized from diethyl ether (10 mL) and hexane (40 mL) to afford 3-(bromomethyl)-5-methylbenzonitrile as white solid (2.5 g, 31%). MS (M+1)+=211.0.

Step 2: The procedure is similar to Step 1[B] in Example-838. 1.0 g of 3-(bromomethyl)-5-methylbenzonitrile gave 3-((4,4-difluoropiperidin-1-yl)methyl)-5-methylbenzonitrile as a pale yellow solid (0.9 g, 75%). MS (M+1)+=251.0.

Step 3: The procedure is similar to Step 5[NSSy5779] in Example-642. 0.3 g of 3-((4,4-difluoropiperidin-1-yl)methyl)-5-methylbenzonitrile gave 3-((4,4-difluoropiperidin-1-yl)methyl)-5-methylbenzothioamide as a brownish gum (0.3 g, 88%). MS (M+1)+=285.0.

Step 4[NSSy6044]: The procedure is similar to Step 6[NSSy5779] in Example-642. 0.3 g of 3-((4,4-difluoropiperidin-1-yl)methyl)-5-methylbenzothioamide gave 2-(3-((4,4-difluoropiperidin-1-yl)methyl)-5-methylphenyl)-4-methyl thiazole as a colourless gum (0.16 g, 47%). MS (M+1)+=323.0; 1H-NMR (400 MHz, DMSO-d6): δ 7.63 (d, J=15.2 Hz, 2H), 7.26 (d, J=35.6 Hz, 2H), 3.55 (s, 2H), 2.41 (s, 3H), 2.36 (s, 3H), 1.99-1.95 (m, 4H).

Example-837

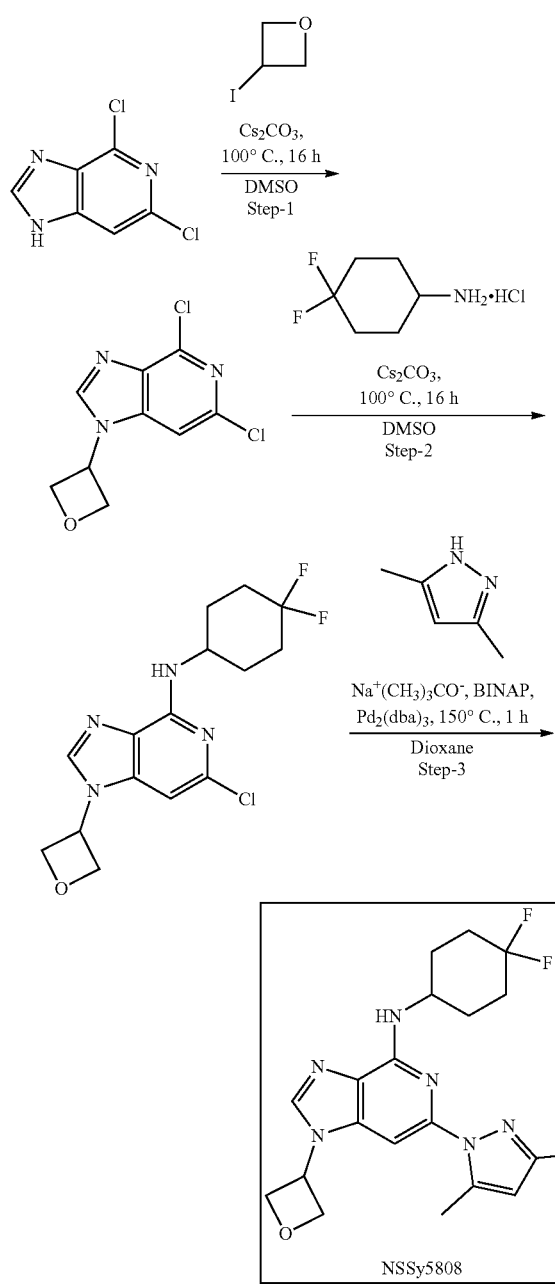

Step 1: The procedure is similar to Step 1[B] in Example-838. 3.0 g of 4,6-dichloro-1H-imidazo [4,5-c] pyridine gave 4,6-dichloro-1-(oxetan-3-yl)-1H-imidazo [4,5-c] pyridine as light brown solid (2 g, 52%). MS (M+1)+=244.0.

Step 2: The procedure is similar to Step 1[B] in Example-838. 1.0 g of 4,6-dichloro-1-(oxetan-3-yl)-1H-imidazo [4,5-c] pyridine gave 6-chloro-N-(4,4-difluorocyclohexyl)-1-(oxetan-3-yl)-1H-imidazo [4,5-c] pyridin-4-amine as an off-white solid (0.3 g, 21%). MS (M+1)+=342.0.

Step 3[NSSy5808]: The procedure is similar to Step 1[NSSy6629] in Example-839. 0.3 g of 6-chloro-N-(4,4-difluorocyclohexyl)-1-(oxetan-3-yl)-1H-imidazo[4,5-c] pyridin-4-amine gave of N-(4,4-difluorocyclohexyl)-6-(3,5-dimethyl-1H-pyrazol-1-yl)-1-(oxetan-3-yl)-1H-imidazo[4,5-c]pyridin-4-amine as an off-white solid (0.015 g, 4%). MS (M+1)+=403.2; 1H-NMR (400 MHz, DMSO-d6): δ 8.36 (s, 1H), 7.25 (s, 1H), 7.00 (d, J=8.04 Hz, 1H), 6.04 (s, 1H), 5.74-5.67 (m, 1H), 5.06 (t, J=7.4 Hz, 2H), 4.95 (t, J=6.16 Hz, 2H), 4.16 (bs, 1H), 2.67 (s, 3H), 2.19 (s, 3H), 2.22-1.80 (m, 6H), 1.58-1.53 (m, 2H).

Example-838

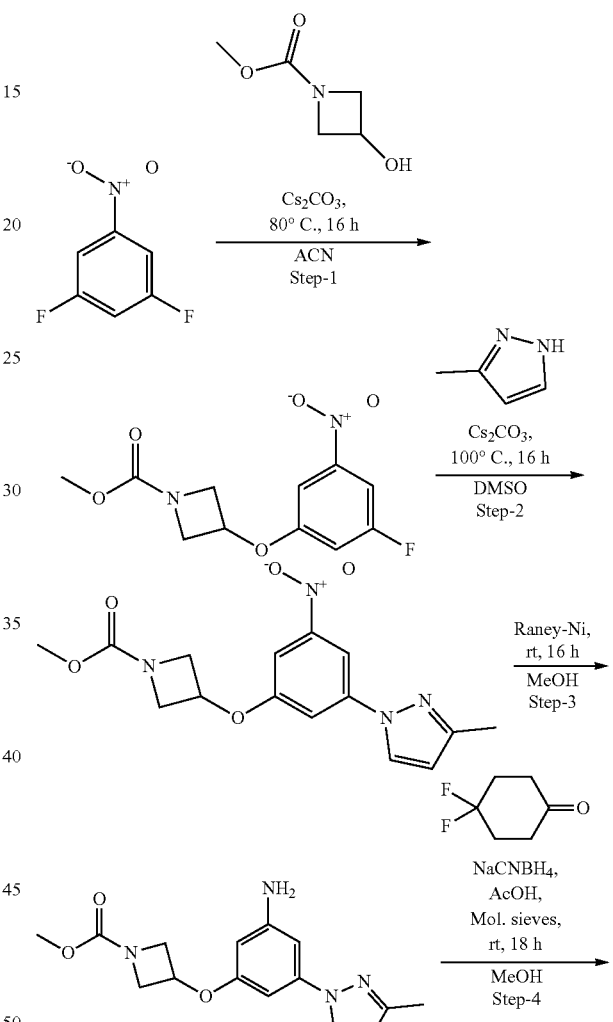

Step 1: The procedure is similar to Step 1[B] in Example-838. 0.5 g of 1,3-difluoro-5-nitrobenzene gave methyl 3-(3- fluoro-5-nitrophenoxy) azetidine-1-carboxylate as an off-white solid (0.8 g, 95%). MS (M+1)+=271.0.

Step 2: The procedure is similar to Step 1[B] in Example-838. 0.8 g of methyl 3-(3-fluoro-5-nitrophenoxy) azetidine-1-carboxylate gave methyl 3-(3-(3-methyl-1H-pyrazol-1-yl)-5-nitrophenoxy) azetidine-1-carboxylate as an off-white solid (0.25 g, 25%). MS (M+1)+=333.0.

Step 3: To a solution of methyl 3-(3-(3-methyl-1H-pyrazol-1-yl)-5-nitrophenoxy) azetidine-1-carboxylate (0.25 g, 0.75 mmol) in methanol (8 mL) was added raney-nickel (0.03 g, 0.22 mmol). The reaction mixture was stirred at room temperature under hydrogen atmosphere using bladder. After 16 h, the reaction mixture was filtered through celite, filtrate was concentrated to afford methyl 3-(3-amino-5-(3-methyl-1H-pyrazol-1-yl) phenoxy) azetidine-1-carboxylate as an off-white solid (0.21 g, 95%). MS (M+1)+=303.0.

Step 4[NSSy5934]: To a solution of methyl 3-(3-amino-5-(3-methyl-1H-pyrazol-1-yl)phenoxy)azetidine-1-carboxylate (0.23 g, 0.76 mmol) and 4,4-Difluorocyclohexanone (0.15 g, 1.14 mmol) in methanol (10 mL) was added molecular sieves powder and acetic acid and the reaction mixture was stirred at room temperature for 16 h. Sodium cyanoborohydride was added to the reaction mixture at 0° C. The reaction mixture was stirred at room temperature. The reaction mixture was quenched with water and concentrated to remove methanol, residue was extracted with ethyl acetate (2×50 mL). The combined organic layer was dried over sodium sulphate and concentrated to afford crude product, which was purified by column chromatography using 40% ethyl acetate in hexane as eluent to afford methyl 3-(3-((4,4-difluorocyclohexyl)amino)-5-(3-methyl-1H-pyrazol-1-yl)phenoxy)azetidine-1-carboxylate as an off-white solid (0.135 g, 42%). MS (M+1)+=421.0; ¹H-NMR (400 MHz, DMSO-d₆): δ 8.25 (d, J=2.40 Hz, 1H), 6.71 (d, J=1.60 Hz, 1H), 6.27 (d, J=2.40 Hz, 1H), 5.94-5.92 (m, 1H), 5.90 (s, 1H), 5.05-5.00 (m, 1H), 4.38-4.35 (m, 2H), 3.87-3.80 (m, 2H), 3.59 (s, 3H), 3.52 (d, J=8.00 Hz, 1H), 2.24 (s, 3H), 2.05-1.91 (m, 6H), 1.49-1.47 (m, 2H).

Example-839

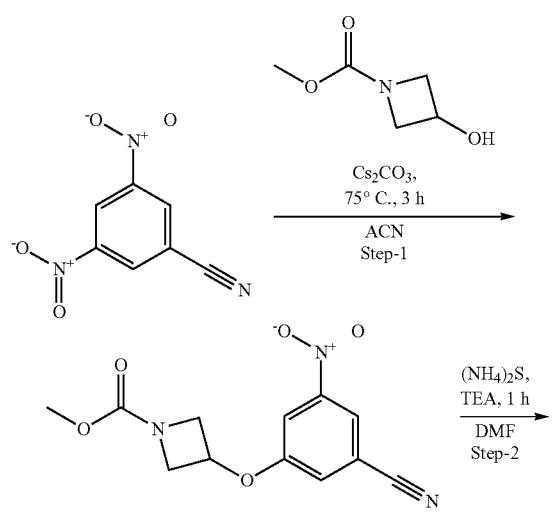

Step 1: The procedure is similar to Step 1[B] in Example-838. 0.5 g of 3,5-dinitrobenzonitrile gave methyl 3-(3-cyano-5-nitrophenoxy) azetidine-1-carboxylate as an off-white solid (0.6 g, 77%). MS (M+1)+=278.0.

Step 2: The procedure is similar to Step 5[NSSy5779] in Example-642. 1.0 g of methyl 3-(3-cyano-5-nitrophenoxy) azetidine-1-carboxylate gave methyl 3-(3-amino-5-carbamothioylphenoxy) azetidine-1-carboxylate as a brownish gum (0.8 g, 72%). MS (M+1)+=282.0.

Step 3: The procedure is similar to Step 6[NSSy5779] in Example-642. 1.1 g of methyl 3-(3-amino-5-carbamothioylphenoxy) azetidine-1-carboxylate gave methyl 3-(3-amino-5-(4-methylthiazol-2-yl) phenoxy) azetidine-1-carboxylate as an off-white solid (0.4 g, 32%). MS (M+1)+=320.0.

Step 4[NSSy5972]: The procedure is similar to Step 4[NSSy5934] in Example-838. 0.4 g of methyl 3-(3-amino-5-(4-methylthiazol-2-yl) phenoxy) azetidine-1-carboxylate gave methyl 3-(3-((4,4-difluorocyclohexyl)amino)-5-(4-methylthiazol-2-yl) phenoxy) azetidine-1-carboxylate as pale yellow solid (0.088 g, 16%). MS (M+1)+=438.0; ¹H-NMR (400 MHz, DMSO-d₆): δ 7.28 (s, 1H), 6.85 (s, 1H), 6.46 (s, 1H), 6.13 (s, 1H), 5.97 (d, J=8.40 Hz, 1H), 5.05-5.04 (m, 1H), 4.35 (m, 2H), 3.89 (m, 2H), 3.59 (s, 3H), 3.34-3.21 (m, 1H), 2.41 (s, 3H), 2.08-1.92 (m, 6H), 1.50-1.48 (m, 2H).

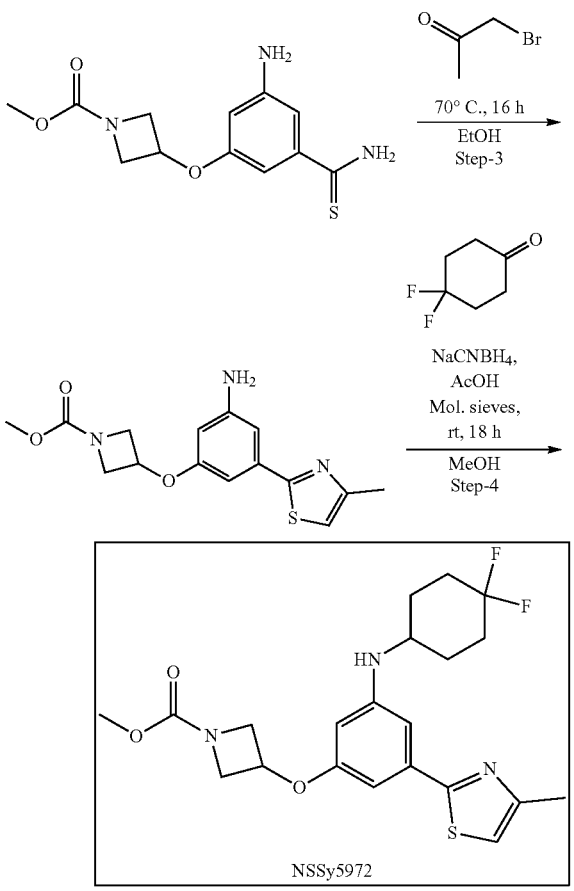

Example-840

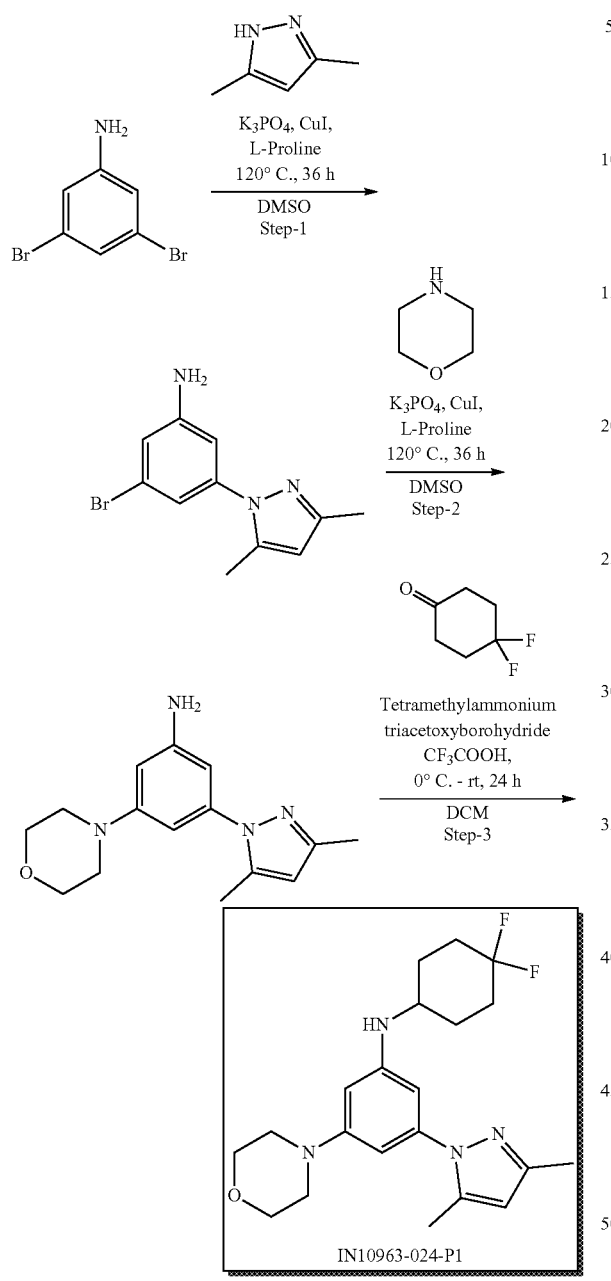

Step 1: To a solution of 3,5-Dibromoaniline (3.5 g, 13.9 mmol), 3,5-Dimethyl-1H-pyrazole (1.34 g, 13.9 mmol), Tripotassium phosphate (14.80 g, 69.7 mmol), Copper(I) iodide (1.32 g, 6.97 mmol), L-Proline (0.64 g, 5.57 mmol) in Dimethyl sulfoxide in sealed tube was heated at 120° C. for 36 h. The reaction mixture was extracted with ethyl acetate, washed with water and brine solution. The organic layer was dried over sodium sulphate, filtered and concentrated under reduced pressure to afford crude product, which was purified through column chromatography using ethyl acetate in pet-ether as solvent to afford 3-bromo-5-(3,5-dimethyl-1H-pyrazol-1-yl)aniline (0.3 g, 08%). MS (M+1)+=266.0.

Step 2: The procedure is similar to Step 1[IN10963-024-P1] in Example-840. 0.3 g of 3-bromo-5-(3,5-dimethyl-1H-pyrazol-1-yl) aniline gave 3-(3,5-dimethyl-1H-pyrazol-1-yl)-5-morpholinoaniline as a brown gum (0.15 g, 48%). MS (M+1)+=273.1.

Step 3[IN10963-024-P1]: The procedure is similar to Step 4[NSSy5934] in Example-838. 0.195 g of 3-(3,5-dimethyl-1H-pyrazol-1-yl)-5-morpholinoaniline gave N-(4,4-difluorocyclohexyl)-3-(3,5-dimethyl-1H-pyrazol-1-yl)-5-morpholinoaniline as a brown solid (0.07 g, 25%). MS (M+1)+=391.1; 1H-NMR (400 MHz, DMSO-d6): δ 6.16 (s, 3H), 5.98 (s, 1H), 5.63 (d, J=8.0 Hz, 1H), 3.73-3.70 (m, 4H), 3.50 (bs, 1H), 3.08-3.05 (m, 4H), 2.25 (s, 3H), 2.14 (s, 3H), 2.07-2.03 (m, 3H), 1.94-1.90 (m, 3H), 1.48-1.45 (m, 2H).

Example-841

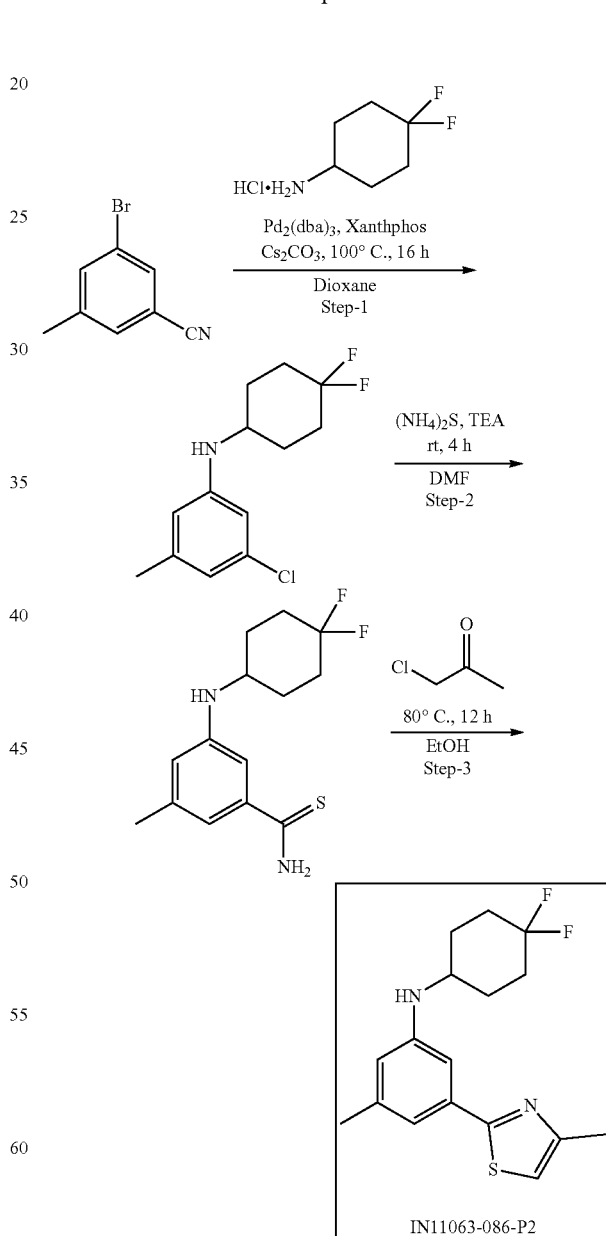

Step 1: The procedure is similar to Step 1[NSSy6629] in Example-839. 0.25 g of 3-bromo-5-methylbenzonitrile gave 3-((4,4-difluorocyclohexyl)amino)-5-methylbenzonitrile as an off-white solid (0.21 g, crude), MS (M+1)+=251.0.

Step 2: The procedure is similar to Step 5[NSSy5779] in Example-642. 0.21 g of 3-((4,4-difluorocyclohexyl)amino)-5-methylbenzonitrile gave 3-((4,4-difluorocyclohexyl) amino)-5-methylbenzothioamide as brown gum (0.25 g, crude), MS (M+1)+=285.0.

Step 3[IN11063-086-P2]: The procedure is similar to Step 6[NSSy5779] in Example-642. 0.25 g of 3-((4,4-difluorocyclohexyl)amino)-5-methylbenzothioamide gave N-(4,4-difluorocyclohexyl)-3-methyl-5-(4-methylthiazol-2-yl) aniline as brown oil (0.06 g, 60%). MS (M+1)+=323.1; 1H-NMR (400 MHz, DMSO-d6): δ7.23 (s, 1H), 7.00 (s, 1H), 6.89 (s, 1H), 6.51 (s, 1H), 5.74 (d, J=8.4 Hz, 1H), 3.51 (m, 1H), 2.39 (s, 3H), 2.25 (s, 3H), 2.10-2.00 (m, 3H), 1.95-1.92 (m, 3H), 1.54-1.49 (m, 2H).

Example-842

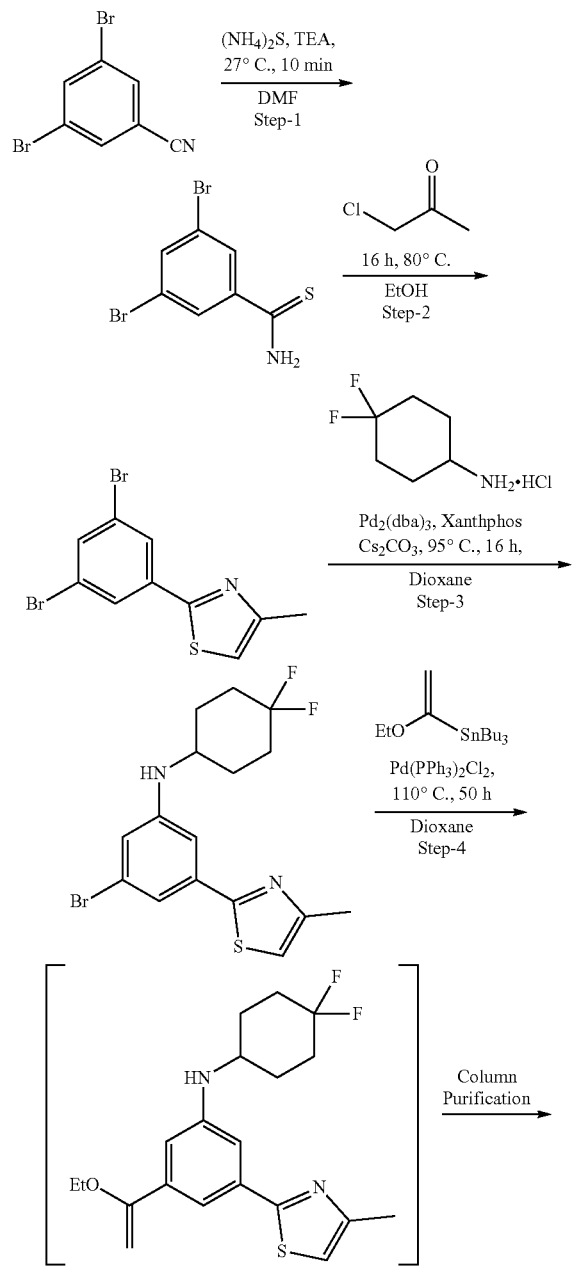

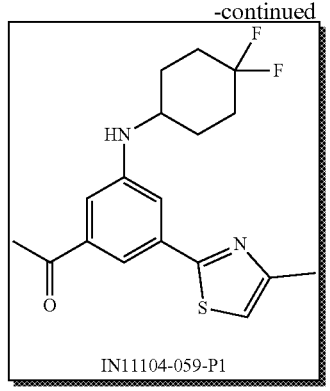

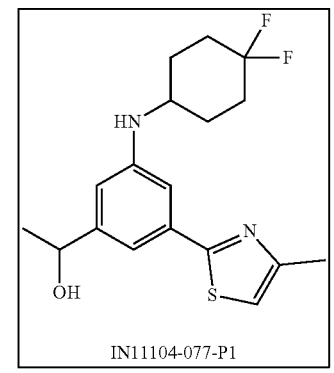 [SMILES: Cc1csc(-c2cc(NC3CCC(F)(F)CC3)cc(C(C)O)c2)n1]

Step 1: The procedure is similar to Step 5[NSSy5779] in Example-642. 2 g of 3,5-dibromobenzonitrile gave 3,5-dibromobenzothioamide as an off-white solid (2.0 g, 88%). MS (M+1)+=293.8.

Step 2: The procedure is similar to Step 6[NSSy5779] in Example-839. 2 g of 3,5-dibromobenzothioamide gave 2-(3,5-dibromophenyl)-4-methylthiazole as grey solid (0.85 g, 75%). MS (M+1)+=331.2.

Step 3: The procedure is similar to Step 1[NSSy6629] in Example-839. 1 g of 2-(3,5-dibromophenyl)-4-methylthiazole gave 3-bromo-N-(4,4-difluorocyclohexyl)-5-(4-methylthiazol-2-yl) aniline as brown gum (0.3 g, crude) MS (M+1)+=387.2.

Step 4[IN11104-059-P1]: The procedure is similar to Step 1[H] in Example-838. 0.3 g of 3-bromo-N-(4,4-difluorocyclohexyl)-5-(4-methylthiazol-2-yl) aniline gave 1-(3-((4,4-difluorocyclohexyl)amino)-5-(4-methylthiazol-2-yl)phenyl) ethan-1-one as yellow gum (0.15 g, 40%). MS (M+1)+=351.0; 1H-NMR (400 MHz, DMSO-d6): δ 7.58 (s, 1H), 7.41-7.39 (m, 1H), 7.33 (s, 1H), 7.21 (s, 1H), 6.17 (d, J=8.40 Hz, 1H), 3.55 (s, 1H), 2.60 (s, 3H), 2.43 (s, 3H), 2.10-1.90 (m, 6H), 1.60-1.48 (m, 2H).

Step 5[IN11104-077-P1]: The procedure is similar to Step 2[NSSy6931] in Example-21. 0.1 g of 1-(3-((4,4-difluorocyclohexyl)amino)-5-(4-methylthiazol-2-yl)phenyl) ethan-1-one gave 1-(3-((4,4-difluorocyclohexyl)amino)-5-(4-methylthiazol-2-yl)phenyl) ethan-1-ol as an off-white solid (0.05 g, 50%). MS (M+1)+=353.0; 1H-NMR (400 MHz, DMSO-d6): δ 7.23 (s, 1H), 7.04 (s, 1H), 7.07 (s, 1H), 6.68 (s, 1H), 5.80 (d, J=8.40 Hz, 1H), 5.11 (d, J=4.00 Hz, 1H), 4.58-4.52 (m, 1H), 3.59-3.49 (m, 1H), 2.40 (s, 3H), 2.13-1.89 (m, 6H), 1.58-1.45 (m, 2H), 1.32 (d, J=6.80 Hz, 3H).

Example-843

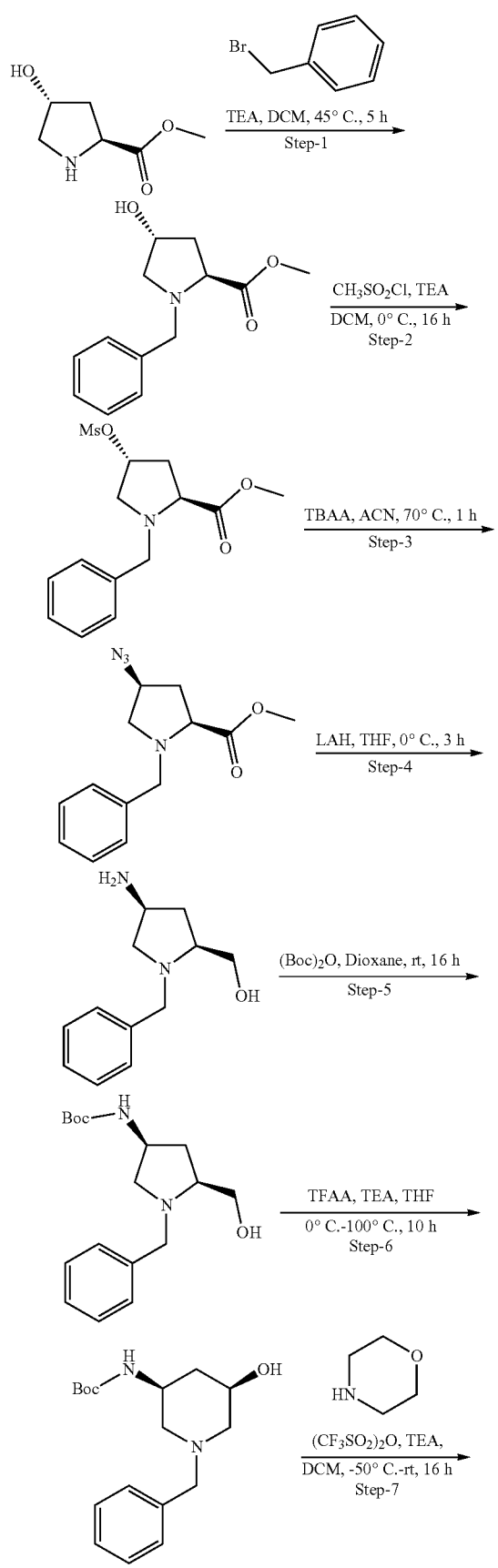

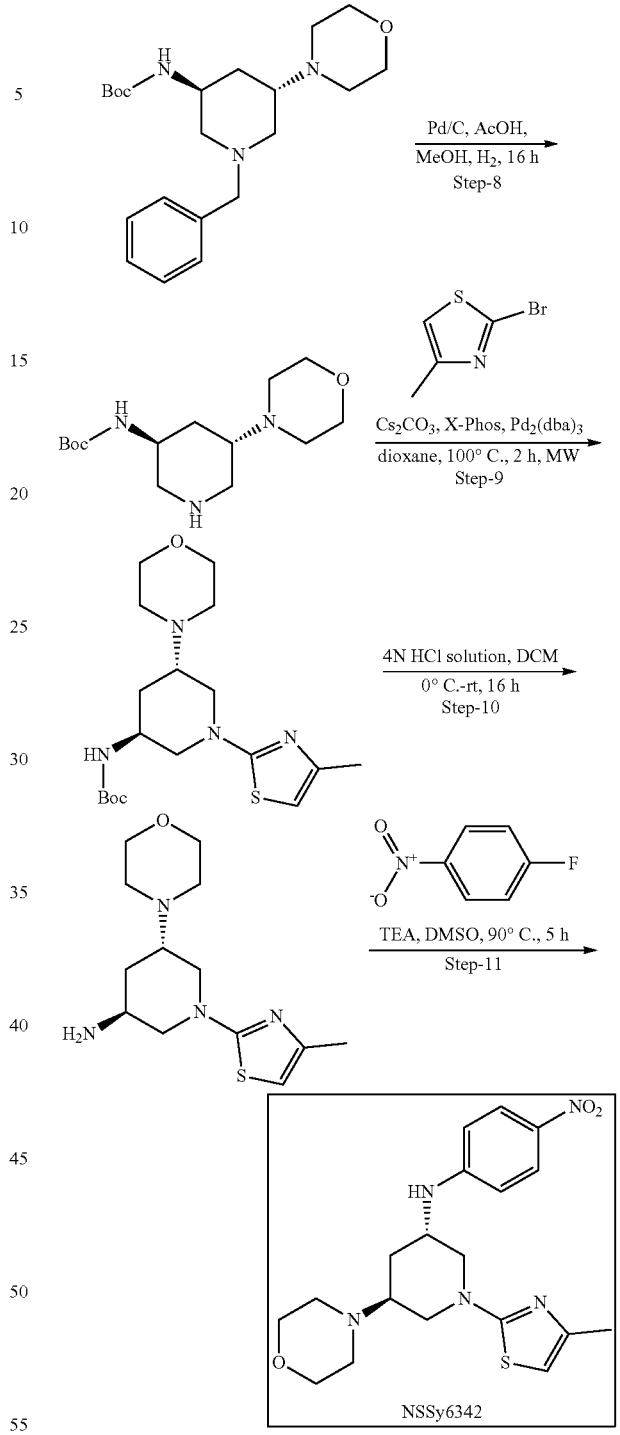

Step 1: To a stirred solution of L-4-hydroxyproline methyl ester hydrochloride (2 g, 11.01 mmol) in dichloromethane (20 mL), was added triethylamine (4.45 g, 44.04 mmol) and benzyl bromide (2.26 g, 13.21 mmol) at 0° C. The reaction mixture was heated to 45° C. for 5 h. Then the reaction mixture was partitioned between DCM (50 mL) and water (25 mL), the organic layer was dried over sodium sulphate, filtered, and concentrated under reduced pressure to afford methyl (2S,4R)-1-benzyl-4-hydroxypyrrolidine-2-carboxylate (1.8 g, 69%) as a brown colour liquid, MS (M+1)+=236.1.

Step 2: To a stirred solution of methyl (2S,4R)-1-benzyl-4-hydroxypyrrolidine-2-carboxylate (1.8 g, 7.65 mmol) in dichloromethane (20 mL) at 0° C. under argon atmosphere, was added triethylamine (4.6 mL, 33.66 mmol) followed by methanesulphonyl chloride (1.33 mL, 16.83 mmol). The reaction mixture was stirred at room temperature. The reaction mixture was diluted with DCM (25 mL), washed with water (20 mL), dried over sodium sulphate, filtered and concentrated under reduced pressure to afford methyl (2S,4R)-1-benzyl-4-((methylsulfonyl)oxy)pyrrolidine-2-carboxylate (1.8 g, 75%) as a brown colour liquid. MS (M+1)+=314.2.

Step 3: To a stirred solution of methyl (2S,4R)-1-benzyl-4-((methylsulfonyl)oxy) pyrrolidine-2-carboxylate (1.8 g, 5.744 mmol) in acetonitrile (20 mL), was added Tetra-N-Butylammonium azide (4.08 g, 14.36 mmol). The reaction mixture was heated at 70° C. for 1 h. The reaction mixture was diluted with ethyl acetate (50 mL), washed with water (25 mL), brine solution (25 mL). The organic layer was dried over sodium sulphate, filtered and concentrated under reduced pressure to afford methyl (2S,4S)-4-azido-1-benzylpyrrolidine-2-carboxylate (1.4 g, 93%) as brown liquid. MS (M+1)+=261.1.

Step 4: The procedure is similar to Step 4[NSSy6711] in Example-854. 3.3 g of methyl (2S,4S)-4-azido-1-benzylpyrrolidine-2-carboxylate gave ((2S,4S)-4-amino-1-benzylpyrrolidin-2-yl) methanol as a colourless liquid (2.5 g, 96%). MS (M+1)+=207.2.

Step 5: The procedure is similar to Step 2[IN11218-026-P1] in Example-613. 4.5 g of ((2S,4S)-4-amino-1-benzylpyrrolidin-2-yl) methanol gave tert-butyl ((3S,5S)-1-benzyl-5-(hydroxymethyl) pyrrolidin-3-yl) carbamate as a brown liquid, (4.5 g, 68%). MS (M+1)+=307.2.

Step 6: To a stirred solution of tert-butyl ((3S,5S)-1-benzyl-5-(hydroxymethyl)pyrrolidin-3-yl)carbamate (2.3 g, 7.50 mmol) in tetrahydrofuran (40 mL) was added Trifluoroacetic anhydride (1.89 g, 9.00 mmol) at 0° C. under N2 atmosphere then followed by Triethylamine (4.18 mL, 30.02 mmol). The reaction mixture was heated at 100° C. in a sealed tube for 10 h. 1 M sodium hydroxide solution (15 mL) was added to the reaction mixture and stirred for 1 h. The reaction mixture was extracted with ethyl acetate (2×50 mL), dried over sodium sulphate, filtered and concentrated under reduced pressure to afford crude product which was purified by flash column chromatography using 35% ethyl acetate in hexane as eluent to afford tert-butyl ((3S,5R)-1-benzyl-5-hydroxypiperidin-3-yl)carbamate as an off-white solid (1.5 g, 65%). MS (M+1)+=307.2.

Step 7: To a stirred solution of tert-butyl ((3S,5R)-1-benzyl-5-hydroxypiperidin-3-yl)carbamate (2.3 g, 7.50 mmol) in Dichloromethane (30 mL), was added trifluoromethanesulfonic anhydride (2.56 g, 9.00 mmol) and Triethylamine (1.21 g, 12.01 mmol) in Dichloromethane at −50° C. The resulting mixture was stirred for 1 h, then morpholine (1.30 g, 15.01 mmol) was added to the reaction and slowly warmed to room temperature. After 16 h, the reaction mixture was evaporated under reduced pressure and the residue was dissolved in ethyl acetate (150 mL), washed with saturated sodium bicarbonate and brine solution. The combined organic layer was dried over sodium sulfate, filtered and concentrated under reduced pressure to afford crude product, which was purified by flash chromatography to afford tert-butyl ((3S,5S)-1-benzyl-5-morpholinopiperidin-3-yl)carbamate as brown solid (1.6 g, 57%). MS (M+1)+=376.3.

Step 8: The procedure is similar to Step 2[NSSy6464] in Example-869. 1.6 g of afford tert-butyl ((3S,5S)-1-benzyl-5-morpholinopiperidin-3-yl) carbamate gave tert-butyl ((3S,5S)-5-morpholinopiperidin-3-yl) carbamate as a brownish gum (1.0 g, 83%). MS (M+1)+=286.0.

Step 9: The procedure is similar to Step 1[NSSy6629] in Example-839. 0.6 g of tert-butyl ((3S,5S)-5-morpholinopiperidin-3-yl) carbamate gave tert-butyl ((3S,5S)-1-(4-methylthiazol-2-yl)-5-morpholinopiperidin-3-yl) carbamate as brownish gum (0.25 g, 31%). MS (M+1)+=383.2.

Step 10: The procedure is similar to Step 4[IN11218-027-P1] in Example-613. 0.25 g of tert-butyl ((3S,5S)-1-(4-methylthiazol-2-yl)-5-morpholinopiperidin-3-yl) carbamate gave (3S,5S)-1-(4-methylthiazol-2-yl)-5-morpholinopiperidin-3-amine as a yellow solid (0.17 g, 94%). MS (M+1)+=283.2.

Step 11[NSSy6342]: To a stirred solution of (3S,5S)-1-(4-methylthiazol-2-yl)-5-morpholinopiperidin-3-amine (0.22 g, 0.77 mmol) in dimethyl sulphoxide (3 mL) was added 4-fluoronitrobenzene (0.1 g, 0.77 mmol) and triethylamine (0.23 g, 2.33 mmol). The reaction mixture was heated at 90° C. The reaction mixture was partitioned between ethyl acetate (50 mL) and water (15 mL), the organic layer was washed with brine solution (15 mL), dried over sodium sulphate, filtered and concentrated under reduced pressure to afford crude product which was purified by flash column chromatography using ethyl acetate as eluent to afford (3S,5S)-1-(4-methylthiazol-2-yl)-5-morpholino-N-(4-nitrophenyl)piperidin-3-amine as a yellow solid (0.045 g, 15%). MS (M+1)+=404.1; 1H-NMR (400 MHz, DMSO-d6): δ 8.03 (d, J=9.16 Hz, 2H), 7.37 (d, J=7.84 Hz, 1H), 6.78 (d, J=9.20 Hz, 2H), 6.41 (s, 1H), 4.06 (d, J=2.80 Hz, 1H), 3.88 (d, J=8.92 Hz, 1H), 3.64-3.58 (m, 5H), 3.05 (t, J=12.04 Hz, 1H), 2.76 (t, J=10.72 Hz, 1H), 2.57-2.51 (m, 4H), 2.29 (m, 1H), 2.16 (s, 3H), 2.09 (s, 6H), 1.53-1.44 (m, 1H).

Example-844

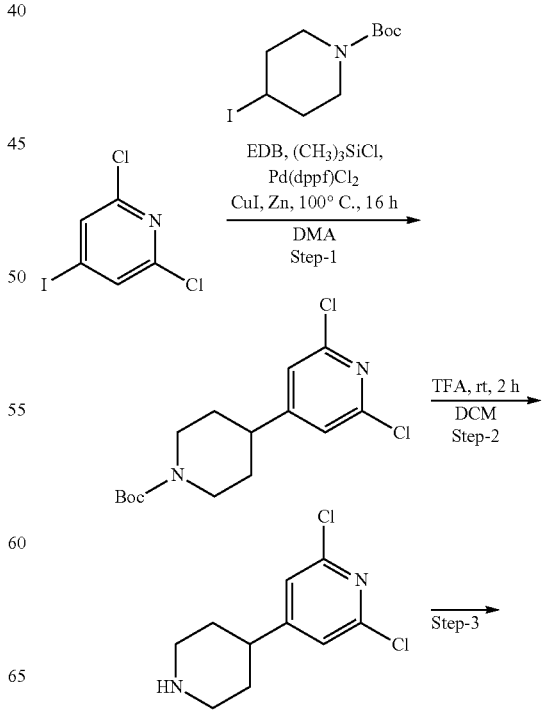

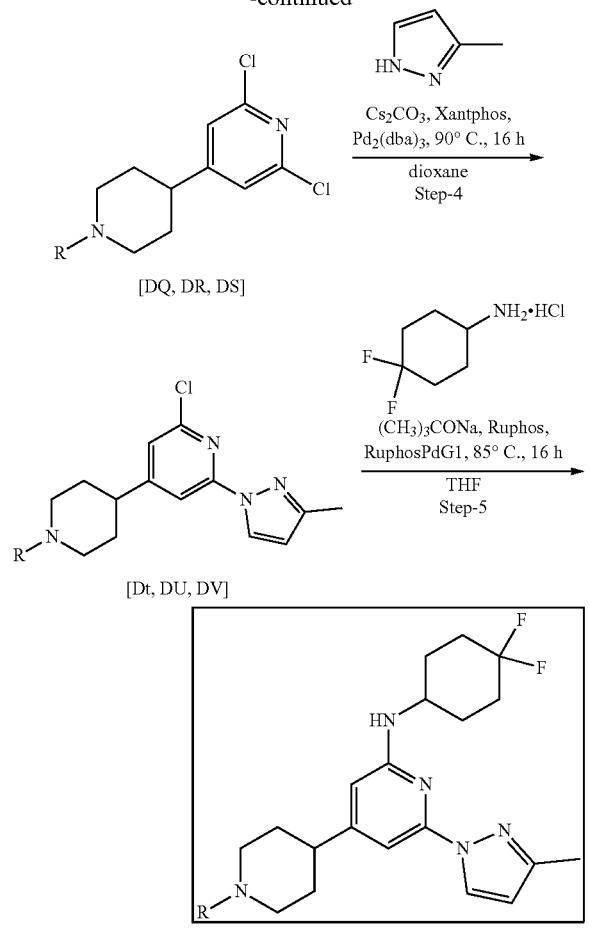

[DQ, DR, DS]

[Dt, DU, DV]

R=

R = NSSy6370, NSSy6885, NSSy6888

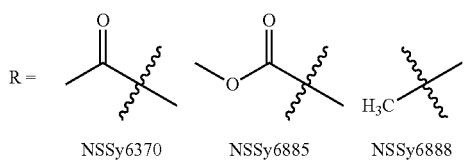

Step 1: P1: zinc dust (1.6 g, 24.83 mmol) was suspended in N, N-dimethyl acetamide (5 mL), was added chlorotrimethyl silane (0.311 g, 2.86 mmol), 1,2-dibromoethane (0.53 g, 2.86 mmol) over 5 min, the reaction mixture was stirred for 15 min, after 15 min tert-butyl 4-iodocyclohexane-1-carboxylate (6.67 g, 21.4 mmol) in N, N-dimethyl acetamide (5 mL) was added dropwise to the reaction mixture over 30 min. The addition was completed the reaction mixture was stirred for further 30 min. After 30 min the reaction mixture was passed through celite.

P2: To a stirred solution of 4-iodo-2,6-dichloro pyridine (4 g, 14.3 mmol) in N, N-dimethyl acetamide (5 mL), was added copper (I) iodide (0.275 g, 1.43 mmol) and 1,1'-bis (diphenylphosphino) ferrocene palladium dichloride (0.52 g, 0.715 mmol). The reaction mixture was purged with N2 and added to the reaction mixture of P1. The reaction mixture was heated to 100° C. for 16 h. The reaction mixture was quenched with water and extracted with ethyl acetate (2×100 mL). The combined organic layer was dried over sodium sulphate and concentrated to afford crude product which was purified by column chromatography using 20% ethyl acetate in pet-ether as eluent to afford tert-butyl 4-(2,6-dichloropyridin-4-yl) piperidine-1-carboxylate as an off-white solid (2.7 g, 57%). MS (M+1)+=332.0.

Step 2: The procedure is similar to Step 5[NSSy6067] in Example-628. 0.3 g of tert-butyl 4-(2,6-dichloropyridin-4-yl) piperidine-1-carboxylate gave 2,6-dichloro-4-(piperidin-4-yl)pyridine as a colorless gum (0.2 g, 95%). MS (M+1)+=233.1.

TABLE 95

| Compound No | R | Condition | Yield (%) | MS (M + 1)+ |
|---|---|---|---|---|
| DQ | 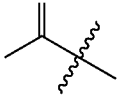 | Acetyl chloride, TEA, DCM, 0° C.-rt, 5 h | 87 | 274.0 |
| DR | 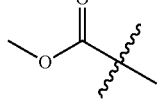 | Methylchloroformate, TEA, DCM, 0° C.-rt, 5 h | 80 | 290.1 |
| DS | 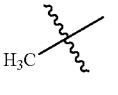 | HCHO, Pd(OH)2, MeOH, H2 atm, rt, 6 h | 95 | 247.0 |

[DQ, DR]: The procedure is similar to Step 1[A] in Example-838.

Step 3[DS]: To a stirred solution of 2,6-dichloro-4-(piperidin-4-yl)pyridine (0.45 g, 1.94 mmol) in Methanol (10 mL) was added formaldehyde, 37% solution in water (0.31 g, 3.89 mmol) and followed by Palladium Hydroxide (50 mg, 10% wt). The reaction mixture was stirred under H2 pressure for 5 h. The reaction mixture was filtered through celite, the organic layer was concentrated under reduced pressure to afford 2,6-dichloro-4-(1-methylpiperidin-4-yl) pyridine (0.45 g, 95%) as an off-white solid MS (M+1)+= 245.1.

TABLE 96

| Compound No | R | Condition | Yield (%) | MS (M + H)+ |
|---|---|---|---|---|
| DT | 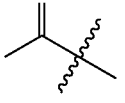 | 3-methylpyrazole, Xanthphos, Cs2CO3, Pd2(dba)3, dioxane, 90° C., 16 h | 81 | 319.0 |
| DU | 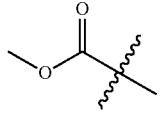 [SMILES: *C(=O)OC] | 3-methylpyrazole, t-butyl xphos, Cs2CO3, Pd2(dba)3 dioxane, 90° C., 16 h | 40 | 335.1 |

TABLE 96-continued

Step 4:

| Compound No | R | Condition | Yield (%) | MS (M + H)+ |
|---|---|---|---|---|
| DV | H₃C- | 3-methyl-pyrazole, Cs₂CO₃, NMP, 180° C., 5 min, | 30 | 291.3 |

[DT, DU]: The procedure is similar to Step 1[NSSy6629] in Example-839.

[DV]: The procedure is similar to Step 1[B] in Example-838.

TABLE 97

Step 5: The procedure is similar to Step 1[NSSy6629] in Example-839.

| Compound No | R | Condition | Yield (%) | MS (M + 1)+ |
|---|---|---|---|---|
| NSSy6370 | (ketone) | (CH₃)₃CONa, Ru-phos, Ru-phosPdG1, THF, 85° C., 16 h | 32 | 418.0 |
| NSSy6885 | (methyl ester) | (CH₃)₃CONa, Ru-phos, Ru-phosPdG1, THF, 85° C., 16 h | 40 | 434.2 |
| NSSy6888 | H₃C- | (CH₃)₃CONa, Ruphos, RuphosPdG1, THF, 85° C., 16 h | 26 | 390.0 |

Step 5[NSSy6370]: 1H-NMR (400 MHz, DMSO-d6): δ 8.39 (d, J=2.40 Hz, 1H), 6.83 (s, 1H), 6.70 (d, J=7.60 Hz, 1H), 6.27 (d, J=2.40 Hz, 1H), 6.21 (s, 1H), 4.53-4.50 (m, 1H), 3.98-3.89 (m, 2H), 3.15-3.09 (m, 1H), 2.73-2.67 (m, 1H), 2.61-2.55 (m, 1H), 2.26 (s, 3H), 2.03-1.96 (m, 9H), 1.82-1.76 (m, 2H), 1.59-1.53 (m, 3H), 1.40-1.36 (m, 1H).

Step 5[NSSy6885]: 1H-NMR (400 MHz, DMSO-d6): δ 8.39 (s, 1H), 6.83 (s, 1H), 6.70 (d, J=7.20 Hz, 1H), 6.28 (s, 1H), 6.21 (s, 1H), 4.10 (s, 2H), 4.08 (s, 1H), 3.61 (s, 3H), 2.85 (s, 2H), 2.70-2.60 (m, 1H), 2.26 (s, 3H), 2.08-1.95 (m, 6H), 1.80-1.77 (m, 2H), 1.51-1.43 (m, 4H).

Step 5[NSSy6888]: 1H-NMR (400 MHz, DMSO-d6): δ 8.39 (d, J=2.40 Hz, 1H), 6.83 (s, 1H), 6.70 (d, J=7.60 Hz, 1H), 6.28 (s, 1H), 6.22 (s, 1H), 3.97 (s, 1H), 2.85 (d, J=11.20 Hz, 2H), 2.37-2.34 (m, 1H), 2.26 (s, 3H), 2.19 (s, 3H), 2.06-1.92 (m, 8H), 1.76-1.73 (m, 2H), 1.61-1.54 (m, 4H).

Example-845

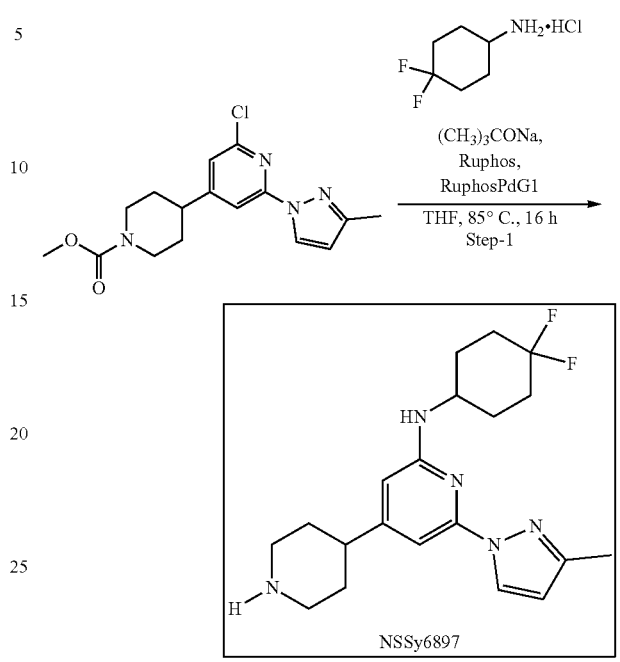

Step 1[NSSy6897]: The procedure is similar to Step 1[NSSy6629] in Example-839. 0.15 g of methyl 4-(2-chloro-6-(3-methyl-1H-pyrazol-1-yl)pyridin-4-yl) piperidine-1-carboxylate gave N-(4,4-difluorocyclohexyl)-6-(3-methyl-1H-pyrazol-1-yl)-4-(piperidin-4-yl)pyridin-2-amine as a brown solid (0.04 g, 23%). MS (M+1)+=376.0; 1H-NMR (400 MHz, DMSO-d6): δ 8.40 (d, J=2.40 Hz, 1H), 6.83 (s, 1H), 6.71 (d, J=7.60 Hz, 1H), 6.28 (d, J=2.00 Hz, 1H), 6.21 (s, 1H), 4.01 (s, 1H), 3.06 (d, J=12.00 Hz, 2H), 2.70-2.60 (m, 2H), 2.26 (s, 3H), 2.10-1.96 (m, 6H), 1.89 (s, 3H), 1.71 (d, J=12.00 Hz, 2H), 1.52-1.48 (m, 4H).

Example-846

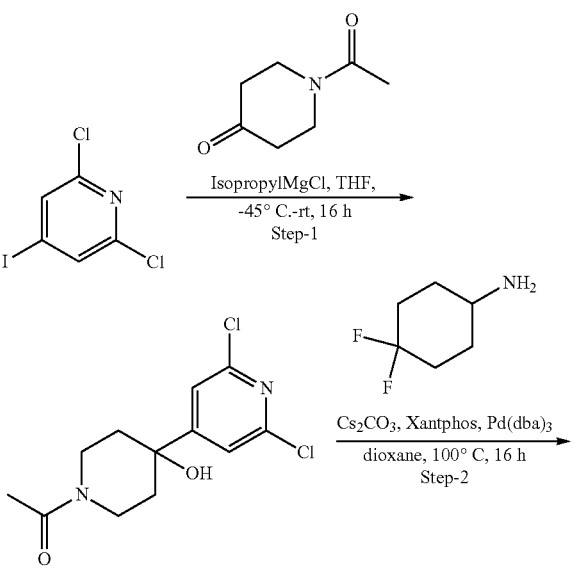

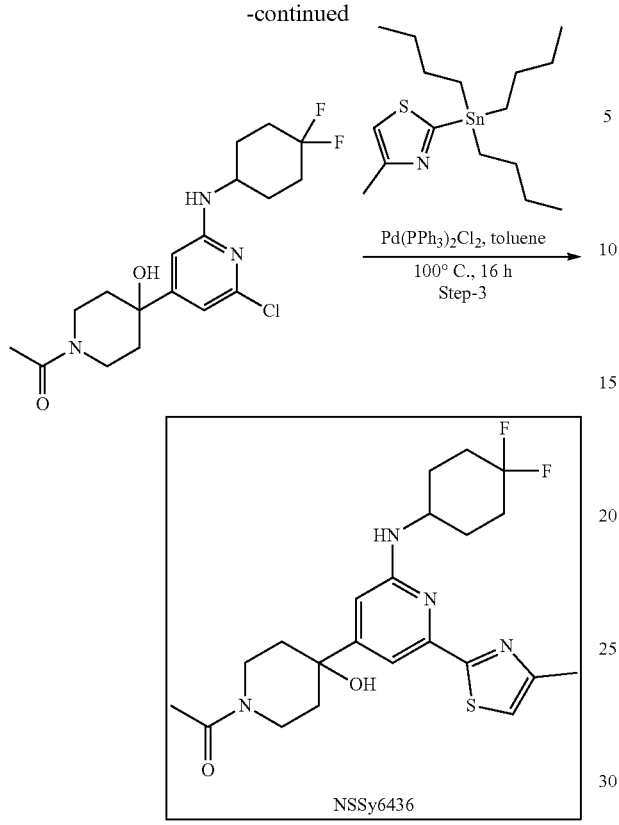

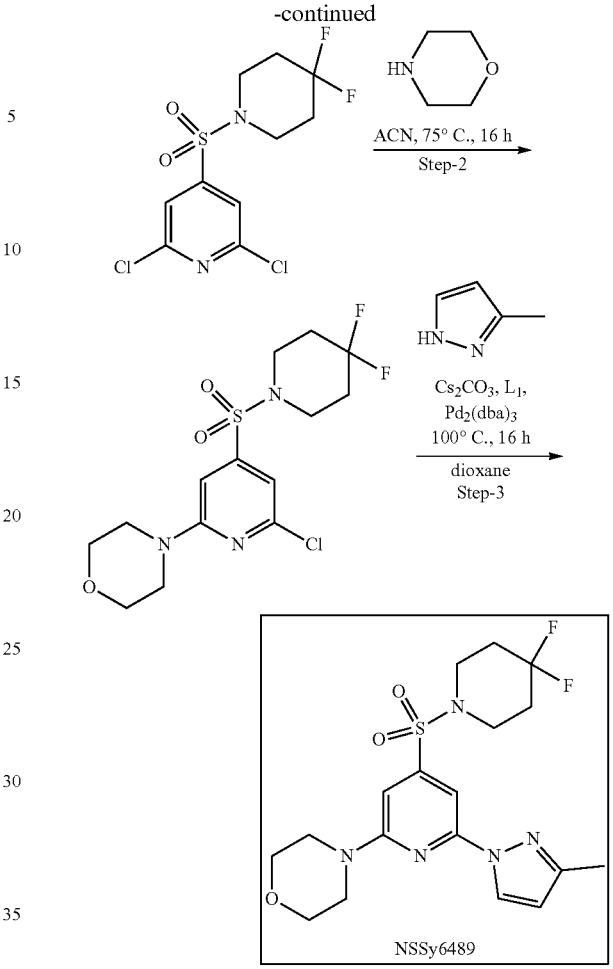

Step 1: The procedure is similar to Step 1[NSSy6469] in Example-805. 1.0 g of 2,6-dichloro-4-iodopyridine gave 1-(4-(2,6-dichloropyridin-4-yl)-4-hydroxypiperidin-1-yl) ethan-1-one as an off-white solid (0.49 g, 47%). MS (M+1)+=289.0.

Step 2: The procedure is similar to Step 1[NSSy6629] in Example-839. 0.65 g of 1-(4-(2,6-dichloropyridin-4-yl)-4-hydroxypiperidin-1-yl) ethan-1-one gave 1-(4-(2-chloro-6-((4,4-difluorocyclohexyl)amino)pyridin-4-yl)-4-hydroxypiperidin-1-yl)ethan-1-one as an off-white solid (0.35 g, 40%). MS (M+1)+=388.2.

Step 3[NSSy6436]: The procedure is similar to Step 1[H] in Example-838. 0.2 g of 1-(4-(2-chloro-6-((4,4-difluorocyclohexyl)amino)pyridin-4-yl)-4-hydroxy piperidin-1-yl) ethan-1-one gave 1-(4-(2-((4,4-difluorocyclohexyl)amino)-6-(4-methylthiazol-2-yl)pyridin-4-yl)-4-hydroxy piperidin-1-yl)ethan-1-one as an off-white solid (0.045 g, 33%). MS (M+1)+=451.1; 1H-NMR (400 MHz, DMSO-d6): δ 7.30 (d, J=14.40 Hz, 2H), 6.79 (d, J=6.80 Hz, 1H), 6.70 (s, 1H), 5.29 (s, 1H), 4.34 (d, J=11.20 Hz, 1H), 3.92 (d, J=3.60 Hz, 1H), 3.72 (d, J=11.60 Hz, 1H), 3.45-3.38 (m, 1H), 2.93-2.87 (m, 1H), 2.41 (s, 3H), 2.05 (s, 3H), 2.02-1.91 (m, 7H), 1.72-1.57 (m, 5H).

Step 1: The procedure is similar to Step 1[A] in Example-838. 0.25 g of 2,6-dichloropyridine-4-sulfonyl chloride gave 2,6-dichloro-4-((4,4-difluoropiperidin-1-yl) sulfonyl)pyridine as a yellowish gum (0.2 g, 60%). MS (M+1)+=332.1.

Step 2: The procedure is similar to Step 1[B] in Example-838. 0.05 g of 2,6-dichloro-4-((4,4-difluoropiperidin-1-yl) sulfonyl)pyridine gave 4-(6-chloro-4-((4,4-difluoropiperidin-1-yl)sulfonyl)pyridin-2-yl)morpholine as a yellowish solid (0.05 g, 87%). MS (M+1)+=382.1.

Step 3[NSSy6489]: The procedure is similar to Step 1[NSSy6629] in Example-839. 0.2 g of 4-(6-chloro-4-((4,4-difluoropiperidin-1-yl)sulfonyl)pyridin-2-yl)morpholine gave 4-(4-((4,4-difluoropiperidin-1-yl)sulfonyl)-6-(3-methyl-1H-pyrazol-1-yl)pyridin-2-yl)morpholine as a white solid (0.1 g, 45%). MS (M+1)+=428.1; 1H-NMR (400 MHz, DMSO-d6): δ 8.55 (d, J=2.40 Hz, 1H), 7.21 (d, J=0.80 Hz, 1H), 6.83 (d, J=0.80 Hz, 1H), 6.39 (d, J=2.40 Hz, 1H), 3.74-3.63 (m, 8H), 3.21 (t, J=5.20 Hz, 4H), 2.29 (s, 3H), 2.14-2.07 (m, 4H).

Example-847

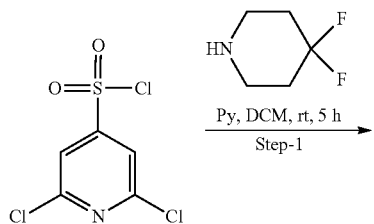

Example-848

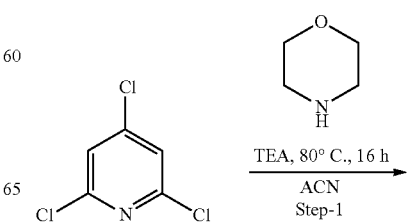

-continued

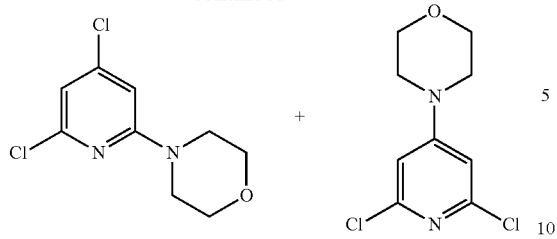

Step 1: The procedure is similar to Step 1[A] in Example-838. 5 g of 2,4,6-trichloropyridine gave 4-(4,6-dichloropyridin-2-yl) morpholine as yellow solid (1.5 g, 24%). MS (M+1)$^+$=233.0 and 4-(2,6-dichloropyridin-4-yl)morpholine as an off-white solid (2.5 g, 40%). MS (M+1)$^+$=233.0.

Example-849

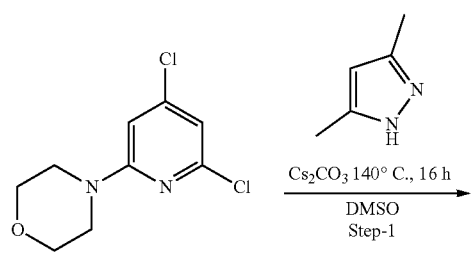

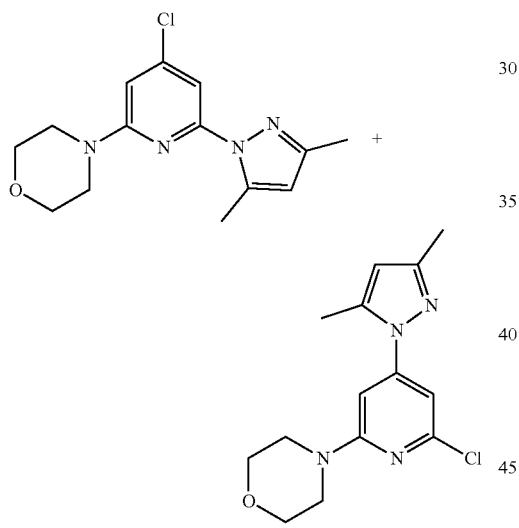

Step 1: The procedure is similar to Step 1[B] in Example-838. 1.5 g of 4-(4,6-dichloropyridin-2-yl) morpholine gave 4-(4-chloro-6-(3,5-dimethyl-1H-pyrazol-1-yl)pyridin-2-yl) morpholine as yellow solid (0.4 g, 21%). MS (M+1)+=293.1 and 4-(6-chloro-4-(3,5-dimethyl-1H-pyrazol-1-yl)pyridin-2-yl)morpholine as an off-white solid (0.5 g, 27%). MS (M+1)+=293.1.

Example-850

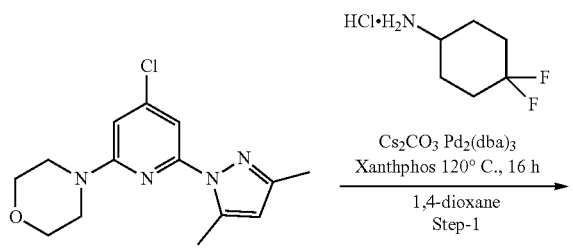

-continued

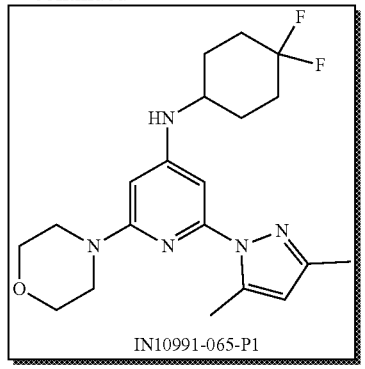

Step 1[IN10991-065-P1]: The procedure is similar to Step 1[NSSy6629] in Example-839. 0.2 g of 4-(4-chloro-6-(3,5-dimethyl-1H-pyrazol-1-yl)pyridin-2-yl) morpholine gave N-(4,4-difluorocyclohexyl)-2-(3,5-dimethyl-1H-pyrazol-1-yl)-6-morpholinopyridin-4-amine as a pale yellow solid (0.13 g, 25%). MS (M+1)+=392.3; 1H-NMR (400 MHz, DMSO-d6): δ 6.48 (s, 1H), 6.41 (d, J=7.60 Hz, 1H), 5.98 (s, 1H), 5.80 (s, 1H), 3.69 (t, J=4.80 Hz, 4H), 3.60 (s, 1H), 3.35 (t, J=4.40 Hz, 4H), 2.48 (s, 3H), 2.16 (s, 3H), 2.12-1.85 (m, 6H), 1.55-1.40 (m, 2H).

Example-851

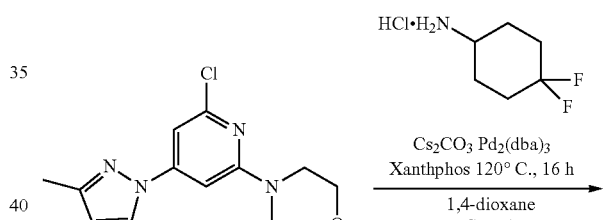

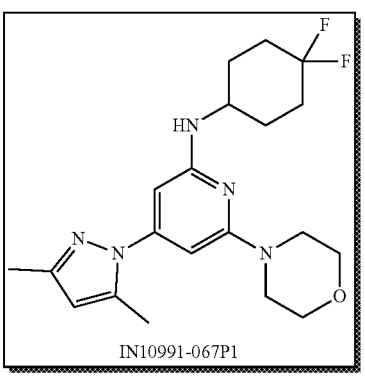

Step 1[IN10991-067-P1]: The procedure is similar to Step 1[NSSy6629] in Example-839. 0.5 g of 4-(6-chloro-4-(3,5-dimethyl-1H-pyrazol-1-yl)pyridin-2-yl) morpholine gave N-(4,4-difluorocyclohexyl)-4-(3,5-dimethyl-1H-pyrazol-1-yl)-6-morpholinopyridin-2-amine as an off-white solid (0.05 g, 8%). MS (M+1)+=392.3; 1H-NMR (400 MHz, DMSO-d6): δ 6.43 (d, J=7.20 Hz, 1H), 6.04 (s, 1H), 5.98 (d, J=5.20 Hz, 2H), 3.85 (s, 1H), 3.69-3.66 (m, 4H), 3.40-3.37 (m, 4H), 2.34 (s, 3H), 2.15 (s, 3H), 2.10-1.85 (m, 6H), 1.60-1.50 (m, 2H).

Example-852

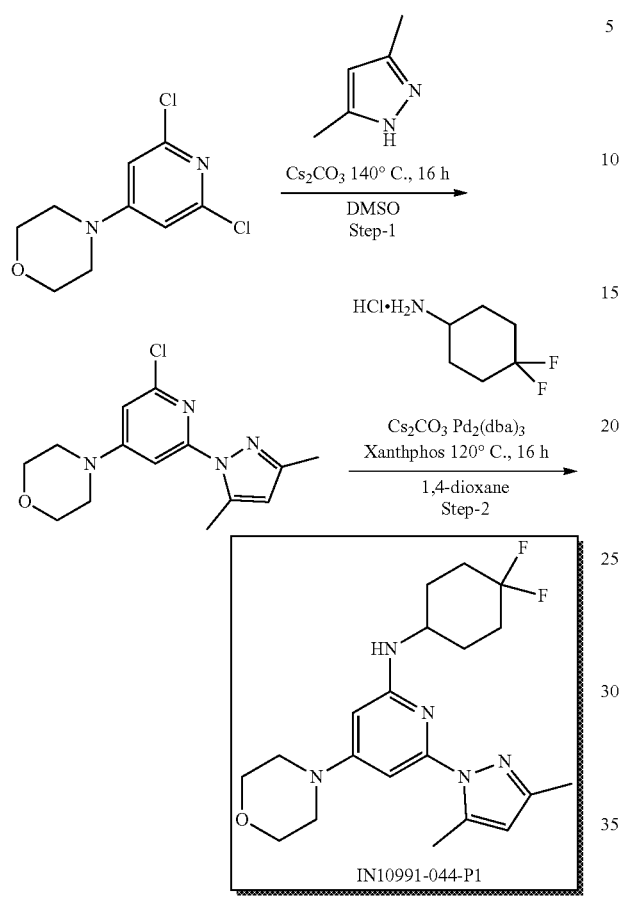

Step 1: The procedure is similar to Step 1[B] in Example-838. 0.6 g of 4-(2,6-dichloropyridin-4-yl) morpholine gave 4-(2-chloro-6-(3,5-dimethyl-1H-pyrazol-1-yl)pyridin-4-yl) morpholine as an off-white solid (0.4 g, 53%). MS (M+1)+=293.0.

Step 2[IN10991-044-P1]: The procedure is similar to Step 1[NSSy6629] in Example-839. 0.2 g of 4-(2-chloro-6-(3,5-dimethyl-1H-pyrazol-1-yl)pyridin-4-yl) morpholine gave N-(4,4-difluorocyclohexyl)-6-(3,5-dimethyl-1H-pyrazol-1-yl)-4-morpholinopyridin-2-amine as an off-white solid (0.09 g, 17%). MS (M+1)+=392.1; 1H-NMR (400 MHz, DMSO-d6): δ 6.53 (d, J=1.20 Hz, 1H), 6.36 (d, J=7.60 Hz, 1H), 5.99 (s, 1H), 5.78 (d, J=1.60 Hz, 1H), 3.85 (s, 1H), 3.72-3.69 (m, 4H), 3.15-3.18 (m, 4H), 2.54 (s, 3H), 2.15 (s, 3H), 2.10-1.80 (m, 6H), 1.60-1.48 (m, 2H).

Example-853

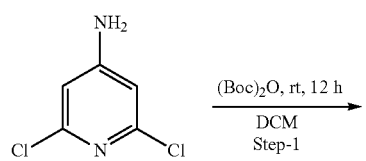

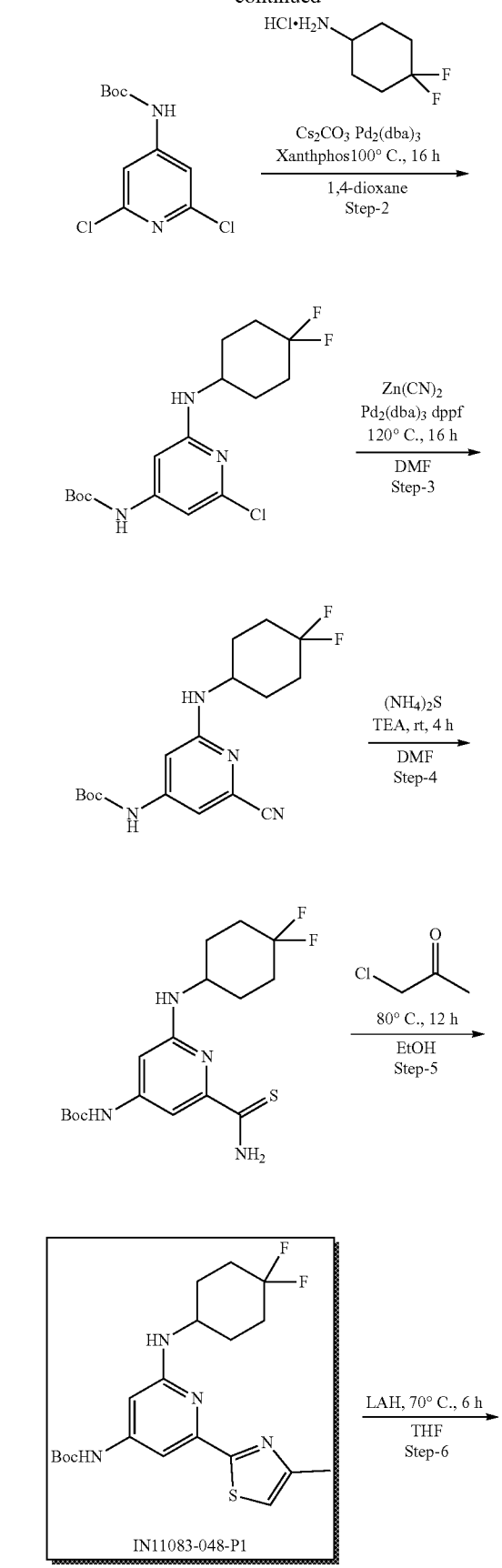

1169

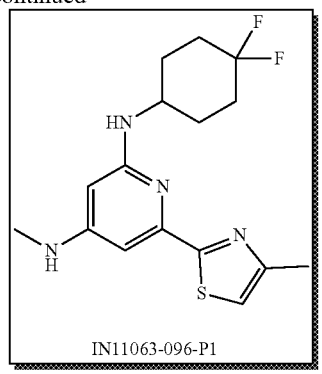

Step 1: The procedure is similar to Step 2[IN11218-026-P1] in Example-613. 4 g of 2,6-dichloropyridin-4-amine gave tert-butyl (2,6-dichloropyridin-4-yl) carbamate as white solid (6.4 g, 80%). MS (M+1)+=262.9.

Step 2: The procedure is similar to Step 1[NSSy6629] in Example-839. 2.5 g of tert-butyl (2,6-dichloropyridin-4-yl) carbamate gave tert-butyl (2-chloro-6-((4,4-difluorocyclohexyl)amino)pyridin-4-yl) carbamate as yellow solid (1.4 g, 41%). MS (M+1)+=362.9.

Step 3: The procedure is similar to Step 3[NSSy5933] in Example-808. 1.2 g of tert-butyl (2-chloro-6-((4,4-difluorocyclohexyl)amino)pyridin-4-yl)carbamate gave tert-butyl (2-cyano-6-((4,4-difluorocyclohexyl)amino)pyridin-4-yl) carbamate as an off-white solid (0.52 g, 42%). MS (M+1)+=353.1.

Step 4: The procedure is similar to Step 5[NSSy5779] in Example-642. 0.52 g of tert-butyl (2-cyano-6-((4,4-difluorocyclohexyl)amino)pyridin-4-yl)carbamate gave tert-butyl (2-carbamothioyl-6-((4,4-difluorocyclohexyl)amino)pyridin-4-yl)carbamate as brown liquid (0.7 g, crude). MS (M+1)+=387.2.

Step 5[IN11083-048-P1]: The procedure is similar to Step 6[NSSy5779] in Example-640. 0.7 g of tert-butyl (2-carbamothioyl-6-((4,4-difluorocyclohexyl)amino)pyridin-4-yl) carbamate gave tert-butyl (2-((4,4-difluorocyclohexyl)amino)-6-(4-methylthiazol-2-yl)pyridin-4-yl) carbamate as yellow solid (0.5 g, 66%). MS (M+1)+=425.1; 1H-NMR (400 MHz, DMSO-d6): δ 9.62 (s, 1H), 7.40 (d, J=1.6 Hz, 1H), 7.26 (s, 1H), 6.79 (d, J=1.6 Hz, 1H), 6.69 (d, J=6.8 Hz, 1H), 3.87 (m, 1H), 2.40 (s, 3H), 2.09-1.87 (m, 6H), 1.63-1.57 (m, 2H), 1.49 (s, 9H).

Step 6[IN11063-096-P1]: The procedure is similar to Step 4[NSSy6711] in Example-854. 0.2 g of tert-butyl (2-((4,4-difluorocyclohexyl)amino)-6-(4-methylthiazol-2-yl)pyridin-4-yl) carbamate gave N2-(4,4-difluorocyclohexyl)-N4-methyl-6-(4-methylthiazol-2-yl)pyridine-2,4-diamine as an off-white solid (0.04 g, 25%). MS (M+1)+=339.2; 1H-NMR (400 MHz, DMSO-d6): δ 7.19 (s, 1H), 6.67 (d, J=2.00 Hz, 1H), 6.29 (q, J=4.40 Hz, 1H), 6.18 (d, J=6.80 Hz, 1H), 5.58 (d, J=1.60 Hz, 1H), 3.85 (d, J=5.60 Hz, 1H), 2.52 (d, J=5.20 Hz, 3H), 2.38 (s, 3H), 2.10-1.84 (m, 6H), 1.62-1.52 (m, 2H).

1170

Example-854

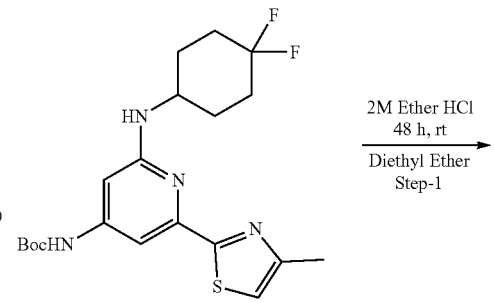

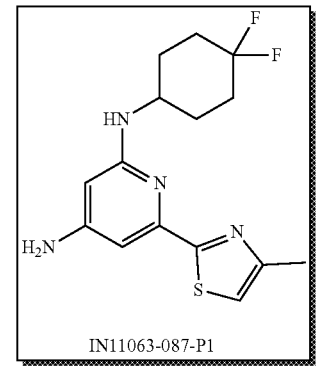

Step 1[IN11063-087-P1]: The procedure is similar to Step 4[IN11218-027-P1] in Example-613. 0.06 g of tert-butyl (2-((4,4-difluorocyclohexyl)amino)-6-(4-methylthiazol-2-yl)pyridin-4-yl) carbamate gave N2-(4,4-difluorocyclohexyl)-6-(4-methylthiazol-2-yl)pyridine-2,4-diamine as a pink solid (0.04 g, 60%). MS (M+1)+=325.2; 1H-NMR (400 MHz, DMSO-d6): δ 7.19 (s, 1H), 6.68 (s, 1H), 6.09 (d, J=6.80 Hz, 1H), 5.75 (s, 1H), 3.90 (s, 2H), 3.80 (s, 1H), 3.90 (s, 3H), 2.10-1.80 (m, 6H), 1.60-1.50 (m, 2H).

Example-855

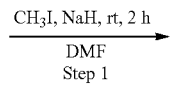

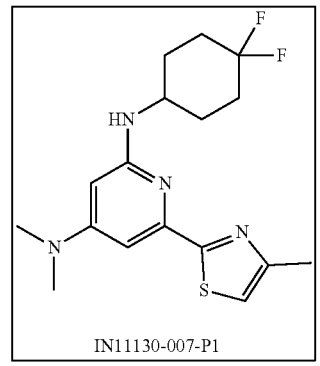

Step 1[IN11130-007-P1]: The procedure is similar to Step 5[NSSy6711] in Example-854. 0.06 g of N2-(4,4-difluorocyclohexyl)-N4-methyl-6-(4-methylthiazol-2-yl)pyridine-2,4-diamine gave N2-(4,4-difluorocyclohexyl)-N4-methyl-6-(4-methylthiazol-2-yl)pyridine-2,4-diamine as an off-white solid (0.04 g, 65%). MS (M+1)+=353.1; 1H-NMR (400 MHz, DMSO-d6): δ 7.22 (d, J=1.20 Hz, 1H), 6.76 (d, J=2.00 Hz, 1H), 6.24 (d, J=6.80 Hz, 1H), 5.71 (d, J=2.00 Hz, 1H), 3.88 (s, 1H), 2.95 (s, 6H), 2.50 (s, 3H), 2.10-1.80 (m, 6H), 1.60-1.50 (m, 2H).

Example-856

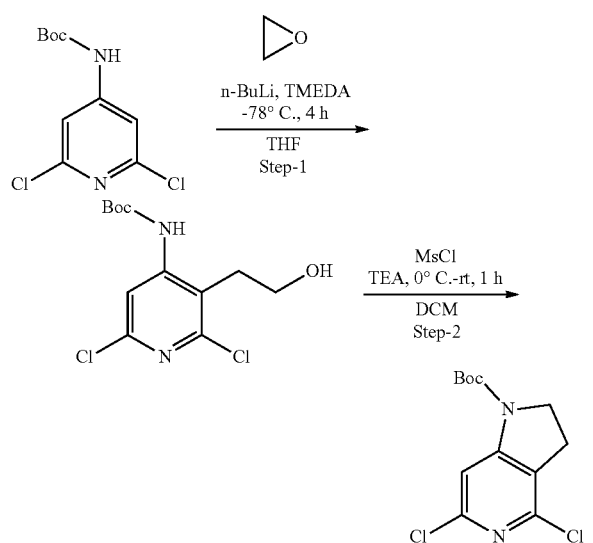

Step 1: The procedure is similar to Step 4[NSSy6067] in Example-628. 3.2 g of tert-butyl (2,6-dichloropyridin-4-yl)carbamate gave tert-butyl (2,6-dichloro-3-(2-hydroxyethyl)pyridin-4-yl) carbamate as yellow solid (2.8 g, 76%). MS (M+1)+=307.0.

Step 2: The procedure is similar to Step 3[IN11273-018-P1] in Example-889. 2.8 g of tert-butyl (2,6-dichloro-3-(2-hydroxyethyl)pyridin-4-yl) carbamate gave tert-butyl 4,6-dichloro-2,3-dihydro-1H-pyrrolo [3,2-c] pyridine-1-carboxylate as a brownish gum (3.5 g, 70%). MS (M+1)+= 289.0.

Example-857

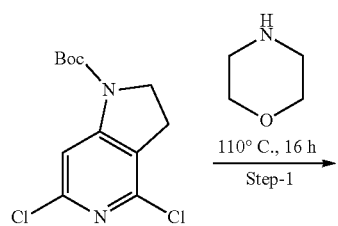

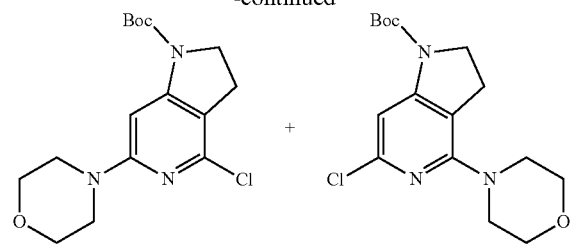

Step 1: 1 g of tert-butyl 4,6-dichloro-2,3-dihydro-1H-pyrrolo [3,2-c] pyridine-1-carboxylate gave tert-butyl 4-chloro-6-morpholino-2,3-dihydro-1H-pyrrolo [3,2-c] pyridine-1-carboxylate as an off-white solid (0.55 g, 47%). MS (M+1)+=340.1 and tert-butyl 6-chloro-4-morpholino-2,3-dihydro-1H-pyrrolo[3,2-c]pyridine-1-carboxylate as an off-white solid (0.23 g, 25%). MS (M+1)+=340.1.

Example-858

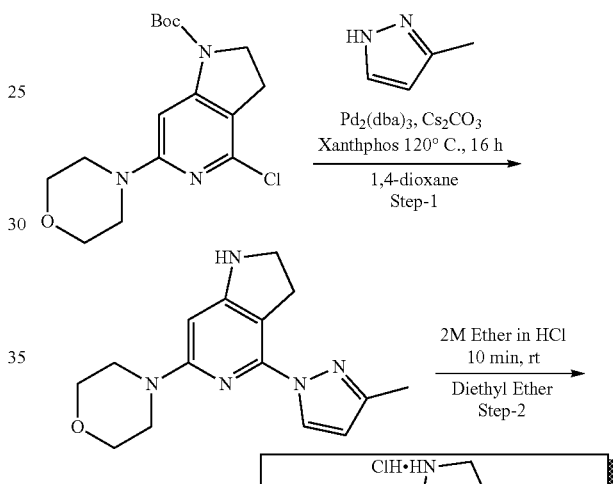

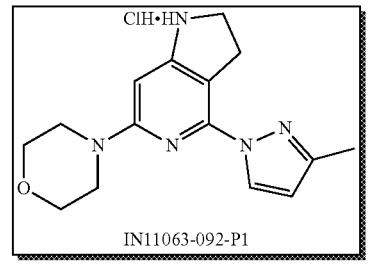

Step 1: The procedure is similar to Step 1[NSSy6629] in Example-839. 0.1 g of tert-butyl 4-chloro-6-morpholino-2,3-dihydro-1H-pyrrolo [3,2-c] pyridine-1-carboxylate gave 4-(4-(3-methyl-1H-pyrazol-1-yl)-2,3-dihydro-1H-pyrrolo [3,2-c]pyridin-6-yl)morpholine as an brownish gum (0.03 g, 28%). MS (M+1)+=286.1.

Step 2[IN11063-092-P1]: The procedure is similar to Step 4[IN11218-027-P1] in Example-613. 0.03 g of 4-(4-(3-methyl-1H-pyrazol-1-yl)-2,3-dihydro-1H-pyrrolo[3,2-c]pyridin-6-yl)morpholine gave 4-(4-(3-methyl-1H-pyrazol-1-yl)-2,3-dihydro-1H-pyrrolo[3,2-c]pyridin-6-yl)morpholine hydrochloride as an off-white solid (0.04 g, 90%). MS (M+1)+=286.1; 1H-NMR (400 MHz, DMSO-d6): δ 8.37 (d, J=2.40 Hz, 1H), 6.40 (s, 1H), 6.22 (d, J=2.40 Hz, 1H), 5.74 (s, 1H), 3.68 (t, J=4.80 Hz, 4H), 3.51 (t, J=8.40 Hz, 2H), 3.34 (t, J=5.20 Hz, 4H), 3.23 (t, J=8.80 Hz, 2H), 2.24 (s, 3H).

Example-859

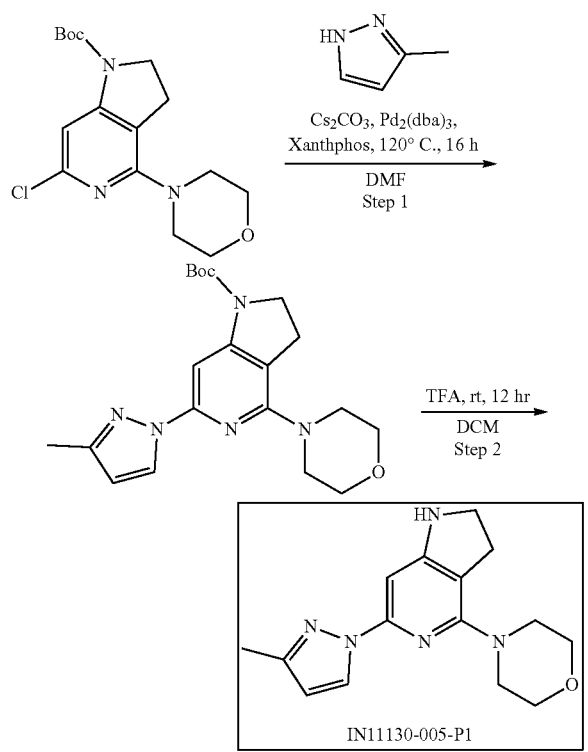

Step 1: The procedure is similar to Step 1[NSSy6629] in Example-839. 0.4 g of tert-butyl 6-chloro-4-morpholino-2,3-dihydro-1H-pyrrolo [3,2-c] pyridine-1-carboxylate gave tert-butyl 6-(3-methyl-1H-pyrazol-1-yl)-4-morpholino-2,3-dihydro-1H-pyrrolo[3,2-c]pyridine-1-carboxylate as an off-white solid (0.08 g, 18%). MS (M+1)+=386.1.

Step 2[IN11130-005-P1]: The procedure is similar to Step 5[NSSy6067] in Example-628. 0.08 g of tert-butyl 6-(3-methyl-1H-pyrazol-1-yl)-4-morpholino-2,3-dihydro-1H-pyrrolo[3,2-c]pyridine-1-carboxylate gave 4-(6-(3-methyl-1H-pyrazol-1-yl)-2,3-dihydro-1H-pyrrolo[3,2-c]pyridin-4-yl)morpholine as pale brown solid (0.05 g, 84%). MS (M+1)+=286.1; ¹H-NMR (400 MHz, DMSO-$d_6$): δ 8.32 (d, J=2.40 Hz, 1H), 6.53 (s, 1H), 6.33 (s, 1H), 6.22 (d, J=2.40 Hz, 1H), 3.69-3.63 (m, 4H), 3.52 (t, J=8.80 Hz, 2H), 3.36-3.31 (m, 4H), 2.99 (t, J=8.80 Hz, 2H), 2.24 (s, 3H).

Example-860

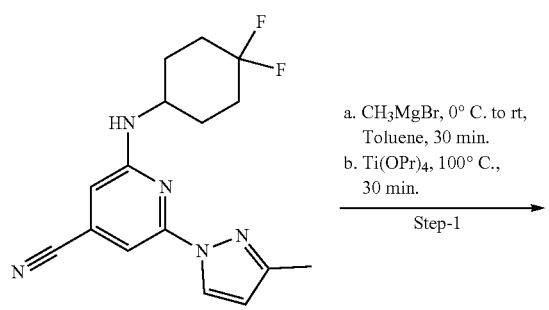

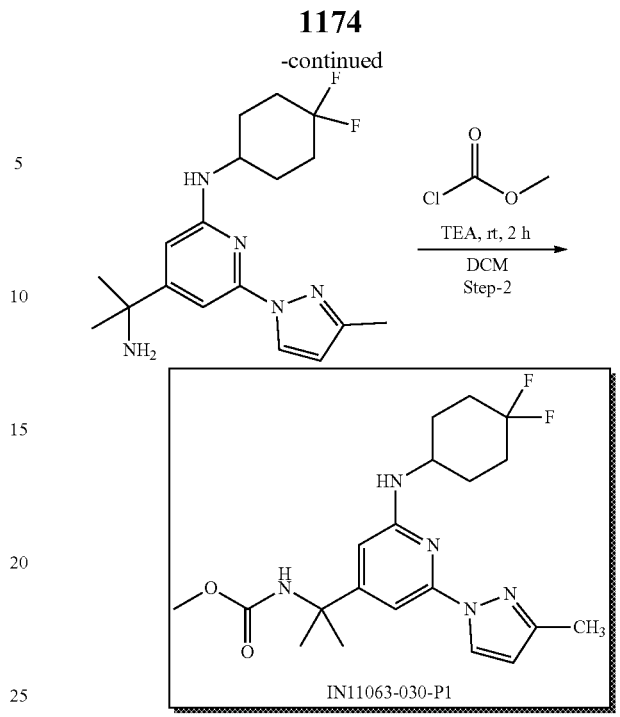

Step 1: The procedure is similar to Step 1[IN11251-001-P2] in Example-884. 0.5 g of 2-((4,4-difluorocyclohexyl)amino)-6-(3-methyl-1H-pyrazol-1-yl) isonicotinonitrile gave 4-(2-aminopropan-2-yl)-N-(4,4-difluorocyclohexyl)-6-(3-methyl-1H-pyrazol-1-yl)pyridin-2-amine as brown oil (0.65 g, crude). MS (M+1)+=350.2.

Step 2[IN11063-030-P1]: The procedure is similar to Step 1[A] in Example-838. 0.65 g of 4-(2-aminopropan-2-yl)-N-(4,4-difluorocyclohexyl)-6-(3-methyl-1H-pyrazol-1-yl) pyridin-2-amine gave methyl (2-(2-((4,4-difluorocyclohexyl)amino)-6-(3-methyl-1H-pyrazol-1-yl)pyridin-4-yl)propan-2-yl)carbamate as pale brown gum (0.06 g, 15%). MS (M+1)+=408.1; 1H-NMR (400 MHz, DMSO-d6): δ 8.37 (d, J=2.40 Hz, 1H), 6.99 (d, J=1.20 Hz, 1H), 6.38 (s, 1H), 6.24 (d, J=2.40 Hz, 1H), 3.98 (s, 1H), 3.55 (s, 3H), 2.32 (s, 3H), 2.15-1.85 (m, 7H), 1.70-1.60 (m, 3H), 1.57 (s, 6H).

Example-861

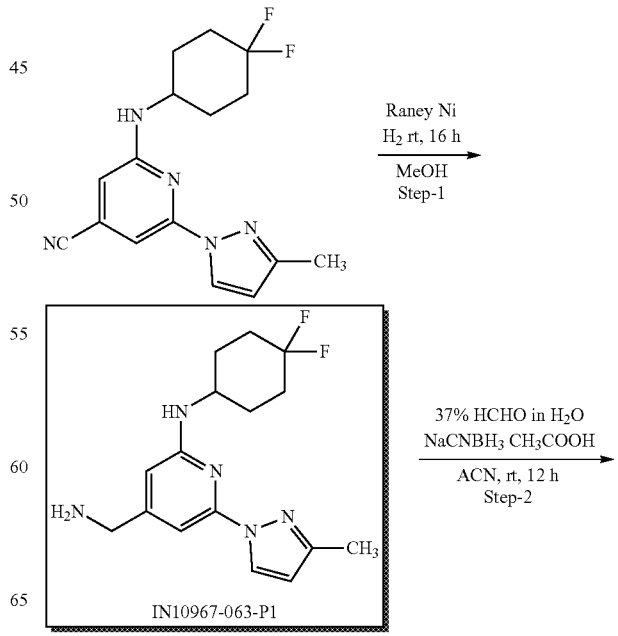

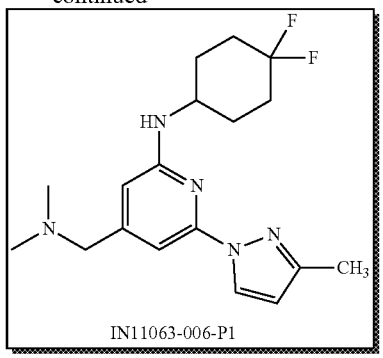

IN11063-006-P1

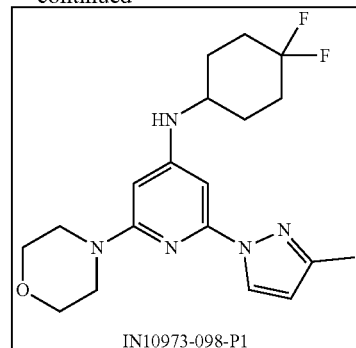

IN10973-098-P1

Step 1[IN10967-063-P1]: The procedure is similar to Step 3[NSSy5934] in Example-838. 0.25 g of 2-((4,4-difluorocyclohexyl)amino)-6-(3-methyl-1H-pyrazol-1-yl) isonicotinonitrile gave 4-(aminomethyl)-N-(4,4-difluorocyclohexyl)-6-(3-methyl-1H-pyrazol-1-yl)pyridin-2-amine as brown oil (0.21 g, 80%). MS (M+1)+=322.1; 1H-NMR (400 MHz, DMSO-d6): δ 8.40 (d, J=2.4 Hz, 1H), 6.95 (s, 1H), 6.71 (d, J=7.6 Hz, 1H), 6.34 (s, 1H), 6.27 (d, J=2.4 Hz, 1H), 4.08-4.00 (m, 1H), 3.67 (s, 2H), 3.01 (bs, 1H), 2.26 (m, 3H), 2.05-1.95 (m, 6H), 2.06-1.95 (m, 2H).

Step 2[IN11063-006-P1]: The procedure is similar to Step 4[NSSy5934] in Example-838. 0.3 g of 4-(aminomethyl)-N-(4,4-difluorocyclohexyl)-6-(3-methyl-1H-pyrazol-1-yl)pyridin-2-amine gave N-(4,4-difluorocyclohexyl)-4-((dimethylamino)methyl)-6-(3-methyl-1H-pyrazol-1-yl)pyridin-2-amine as white solid (0.125 g, 40%). MS (M+1)+=350.2; 1H-NMR (400 MHz, DMSO-d6): δ 8.40 (d, J=2.40 Hz, 1H), 6.91 (s, 1H), 6.72 (d, J=7.60 Hz, 1H), 6.31 (s, 1H), 6.28 (d, J=2.00 Hz, 1H), 4.02 (s, 1H), 3.25 (s, 2H), 2.25 (s, 3H), 2.16 (s, 6H), 2.10-1.90 (m, 6H), 1.62-1.48 (m, 2H).

Step 1: The procedure is similar to Step 1[A] in Example-838. 2 g of 2,6-dichloro-4-iodopyridine gave 4-(6-chloro-4-iodopyridin-2-yl) morpholine as an off-white solid (0.65 g, 27%). MS (M+1)+=324.8.

Step 2: The procedure is similar to Step 1[NSSy6629] in Example-839. 0.35 g of 4-(6-chloro-4-iodopyridin-2-yl) morpholine gave 2-chloro-N-(4,4-difluorocyclohexyl)-6-morpholinopyridin-4-amine as brown gummy solid (0.2 g, 55%). MS (M+1)+=332.2.

Step 3[IN10973-098-P1]: 0.1 g of 2-chloro-N-(4,4-difluorocyclohexyl)-6-morpholinopyridin-4-amine gave N-(4,4-difluorocyclohexyl)-2-(3-methyl-1H-pyrazol-1-yl)-6-morpholinopyridin-4-amine as an off-white solid (0.035 g, 30%). MS (M+1)+=378.2; 1H-NMR (400 MHz, DMSO-d6): δ 8.34 (d, J=2.40 Hz, 1H), 6.55 (s, 1H), 6.45 (d, J=8.40 Hz, 1H), 6.22 (s, 1H), 5.77 (s, 1H), 3.69 (s, 4H), 3.68 (s, 1H), 3.39 (s, 4H), 2.24 (s, 3H), 2.15-1.85 (m, 6H), 1.55-1.45 (m, 2H).

Example-862

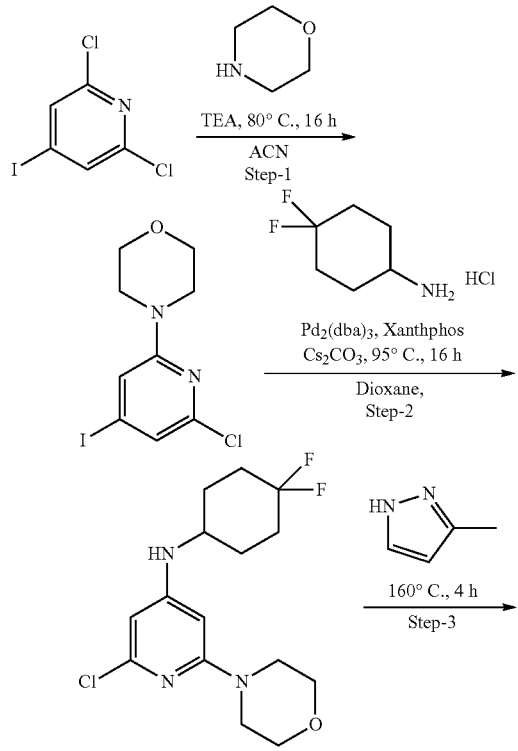

Example-863

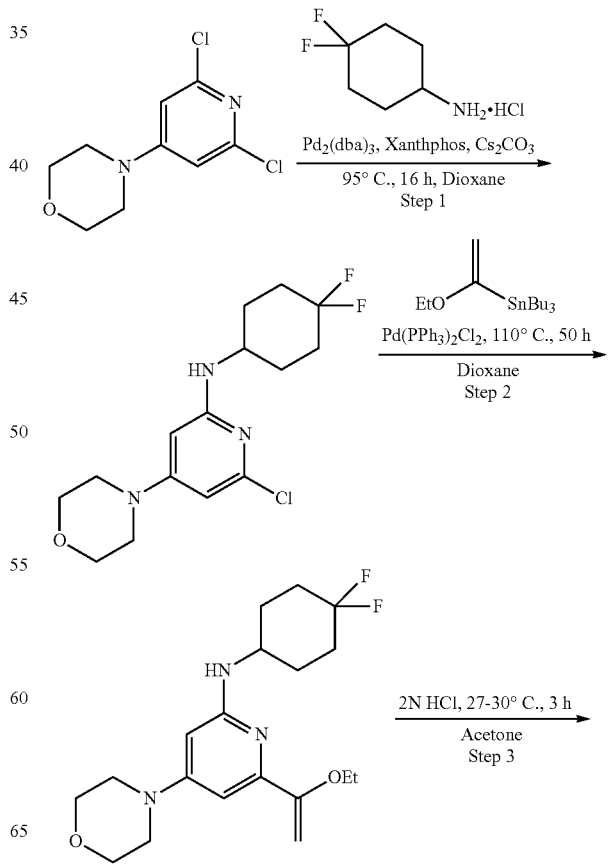

-continued

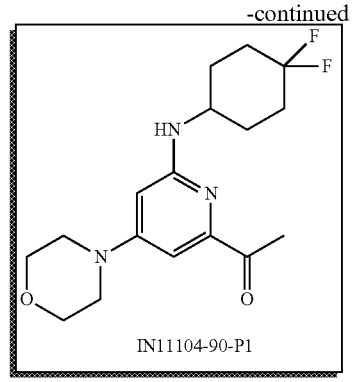

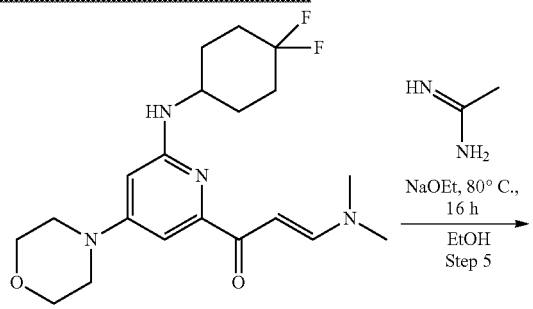

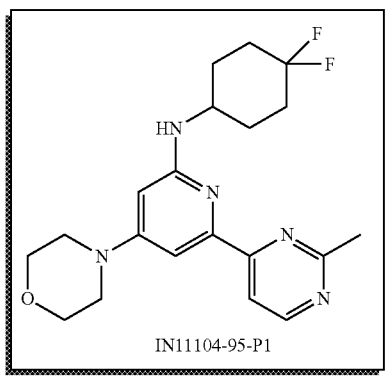

Step 1: The procedure is similar to Step 1[NSSy6629] in Example-839. 5 g of 4-(2,6-dichloropyridin-4-yl) morpholine gave 6-chloro-N-(4,4-difluorocyclohexyl)-4-morpholinopyridin-2-amine as an off-white solid (2.8 g, 39%). MS (M+1)+=332.1.

Step 2: The procedure is similar to Step 1[H] in Example-838. 2 g of 6-chloro-N-(4,4-difluorocyclohexyl)-4-morpholinopyridin-2-amine gave N-(4,4-difluorocyclohexyl)-6-(1-ethoxyvinyl)-4-morpholinopyridin-2-amine as brown gum (2.5 g, crude). MS (M+1)+=368.1.

Step 3[IN11104-090-P1]: The procedure is similar to Step 1[NSSy6697] in Example-873. 2.5 g of N-(4,4-difluorocyclohexyl)-6-(1-ethoxyvinyl)-4-morpholinopyridin-2-amine gave 1-(6-((4,4-difluorocyclohexyl)amino)-4-morpholinopyridin-2-yl) ethan-1-one as a colourless gummy solid (0.6 g, 30%). MS (M+1)+=340.1; 1H-NMR (400 MHz, DMSO-d6): δ 6.77 (d, J=1.60 Hz, 1H), 6.43 (d, J=7.20 Hz, 1H), 6.05 (d, J=1.20 Hz, 1H), 3.93 (s, 1H), 3.70 (t, J=4.40 Hz, 4H), 3.17 (t, J=4.80 Hz, 4H), 2.49 (s, 3H), 2.12-1.85 (m, 6H), 1.62-1.50 (m, 2H).

Step 4: The procedure is similar to Step 1[B] in Example-838. 0.3 g of 1-(6-((4,4-difluorocyclohexyl)amino)-4-morpholinopyridin-2-yl) ethan-1-one gave (E)-1-(6-((4,4-difluorocyclohexyl)amino)-4-morpholinopyridin-2-yl)-3-(dimethylamino) prop-2-en-1-one as a colourless gummy solid (0.3 g, 86%). MS (M+1)+=395.2.

Step 5[IN11104-095-P1]: The procedure is similar to Step 6[NSSy5779] in Example-642. 0.3 g of (E)-1-(6-((4,4-difluorocyclohexyl)amino)-4-morpholinopyridin-2-yl)-3-(dimethylamino) prop-2-en-1-one gave N-(4,4-difluorocyclohexyl)-6-(2-methylpyrimidin-4-yl)-4-morpholinopyridin-2-amine as a colourless gummy solid (0.12 g, 40%). MS (M+1)+=390.1; 1H-NMR (400 MHz, DMSO-d6): δ 8.75 (d, J=4.80 Hz, 1H), 8.06 (d, J=4.80 Hz, 1H), 7.35 (d, J=2.00 Hz, 1H), 6.38 (d, J=7.20 Hz, 1H), 6.01 (d, J=1.20 Hz, 1H), 4.03 (s, 1H), 3.74 (t, J=4.80 Hz, 3H), 3.22 (t, J=4.40 Hz, 3H), 2.67 (s, 3H), 2.12-1.90 (m, 6H), 1.62-1.50 (m, 2H), 1.23 (s, 1H), 0.89-0.84 (m, 1H).

Example-864

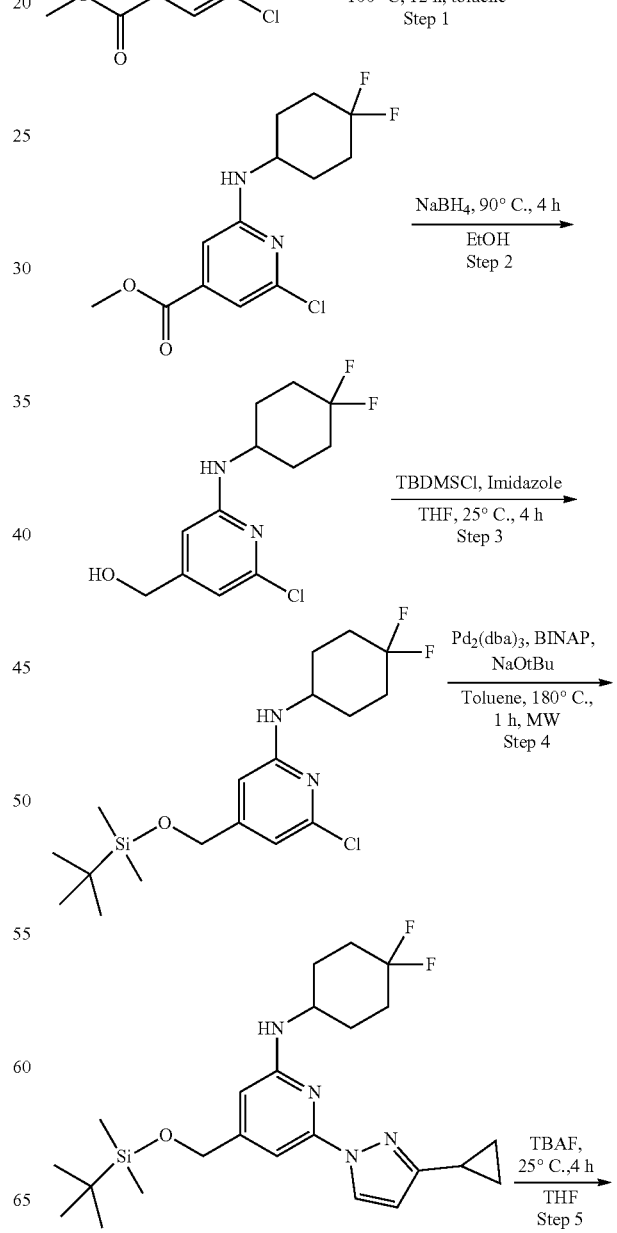

-continued

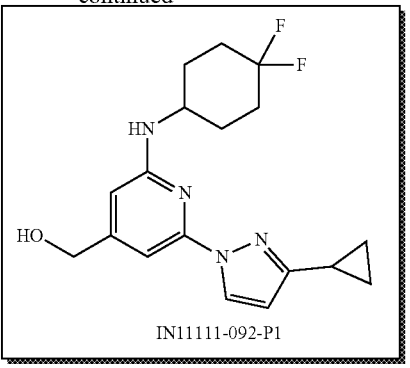

IN11111-092-P1

Step 1: The procedure is similar to Step 1[NSSy6629] in Example-839. 2 g of methyl 2,6-dichloroisonicotinate gave methyl 2-chloro-6-((4,4-difluorocyclohexyl)amino) isonicotinate as a pale yellow solid (1.4 g, 48%). MS (M+1)+=305.1.

Step 2: The procedure is similar to Step 2[NSSy6931] in Example-21. 1.4 g of methyl 2-chloro-6-((4,4-difluorocyclohexyl)amino) isonicotinate gave (2-chloro-6-((4,4-difluorocyclohexyl)amino)pyridin-4-yl) methanol as colourless gum (1.2 g, crude). MS (M+1)+=277.1.

Step 3: The procedure is similar to Step 3[NSSy7053] in Example-815. 1.2 g of (2-chloro-6-((4,4-difluorocyclohexyl)amino)pyridin-4-yl) methanol gave 4-(((tert-butyldimethylsilyl)oxy)methyl)-6-chloro-N-(4,4-difluorocyclohexyl)pyridin-2-amine as a colourless oil (1.07 g, 63%). MS (M+1)+=391.2.

Step 4: The procedure is similar to Step 1[NSSy6629] in Example-839. 0.5 g of 4-(((tert-butyldimethylsilyl)oxy)methyl)-6-chloro-N-(4,4-difluorocyclohexyl)pyridin-2-amine gave 4-(((tert-butyldimethylsilyl)oxy)methyl)-6-(3-cyclopropyl-1H-pyrazol-1-yl)-N-(4,4-difluorocyclohexyl)pyridin-2-amine as a yellow solid (0.21 g, 36%). MS (M+1)+=463.3.

Step 5[IN11111-092-P1]: The procedure is similar to Step 5[NSSy5645] in Example-811. 0.21 g of 4-(((tert-butyldimethylsilyl)oxy)methyl)-6-(3-cyclopropyl-1H-pyrazol-1-yl)-N-(4,4-difluorocyclohexyl)pyridin-2-amine gave 2-(3-cyclopropyl-1H-pyrazol-1-yl)-6-((4,4-difluorocyclohexyl)amino)pyridin-4-yl) methanol as an off-white solid (0.11 g, 70%). MS (M+1)+=349.2; 1H-NMR (400 MHz, DMSO-d6): δ 8.38 (d, J=2.40 Hz, 1H), 6.86 (s, 1H), 6.74 (d, J=7.20 Hz, 1H), 6.33 (s, 1H), 6.19 (d, J=2.40 Hz, 1H), 5.32 (t, J=5.60 Hz, 1H), 4.42 (d, J=6.00 Hz, 2H), 3.97 (s, 1H), 2.15-1.85 (m, 6H), 1.65-1.45 (m, 2H), 0.97-0.85 (m, 3H), 0.75-0.65 (m, 2H).

Example-865

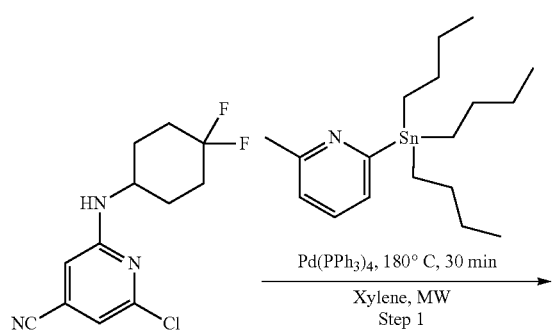

Pd(PPh3)4, 180° C, 30 min
Xylene, MW
Step 1

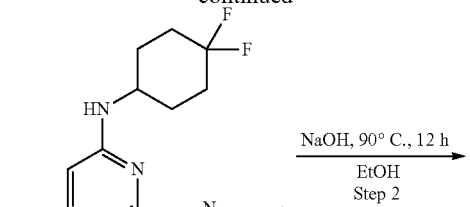

NaOH, 90° C., 12 h
EtOH
Step 2

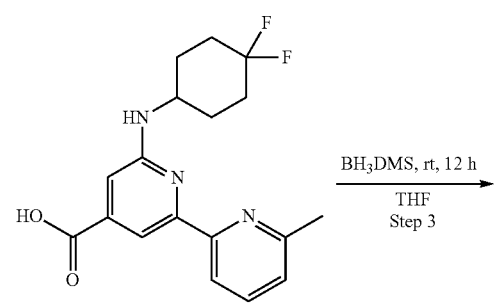

BH3DMS, rt, 12 h
THF
Step 3

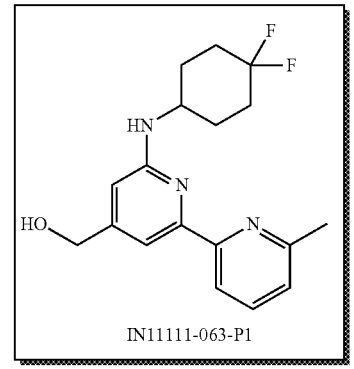

IN11111-063-P1

Step 1: The procedure is similar to Step 1[NSSy6929] in Example-839. 0.5 g of 2-chloro-6-((4,4-difluorocyclohexyl)amino) isonicotinonitrile gave 6-((4,4-difluorocyclohexyl)amino)-6'-methyl-[2,2'-bipyridine]-4-carbonitrile as a pale yellow solid (0.48 g, 80%). MS (M+1)+=329.1.

Step 2: The procedure is similar to Step 1[B] in Example-838. 0.8 g of 6-((4,4-difluorocyclohexyl)amino)-6'-methyl-[2,2'-bipyridine]-4-carbonitrile gave 6-((4,4-difluorocyclohexyl)amino)-6'-methyl-[2,2'-bipyridine]-4-carboxylic acid as a pale yellow solid (0.64 g, 75%). MS (M+1)+=346.1.

Step 3[IN11111-063-P1]: To a solution of 6-((4,4-difluorocyclohexyl)amino)-6'-methyl-[2,2'-bipyridine]-4-carboxylic acid (0.64 g, 1.84 mmol) in THF, was added BH3DMS (2M solution in THF, 4.60 mL, 9.21 mmol), at 0° C. and the reaction mixture was stirred at room temperature for 12 h. Then the reaction mixture was cooled to 0° C., quenched with methanol and heated the reaction mixture at 60° C. for 1 h, the reaction mixture was cooled to 0° C., quenched with saturated sodium bicarbonate solution and extracted with dichloromethane. The combined organic layer was washed with water and brine solution, dried over sodium sulfate, filtered and concentrated under reduced pressure to afford (6-((4,4-difluorocyclohexyl)amino)-6'-methyl-[2,2'-bipyridin]-4-yl)methanol as a yellow liquid (0.025 g, 4%). MS (M+1)+=334.1; 1H-NMR (400 MHz, DMSO-d6): δ 8.17 (d, J=7.6 Hz, 1H), 7.78-7.74 (m, 1H), 7.51 (s, 1H), 7.22 (d, J=7.6 Hz, 1H), 6.56 (d, J=6.8 Hz, 1H), 6.53 (s, 1H), 5.27 (t, J=6.00 Hz, 1H), 4.45 (d, J=8.00 Hz, 2H), 4.01 (m, 1H), 2.11-1.92 (m, 6H), 1.65-1.56 (m, 2H).

Example-866

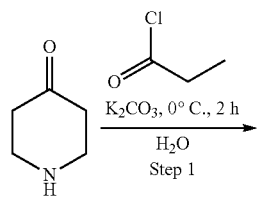

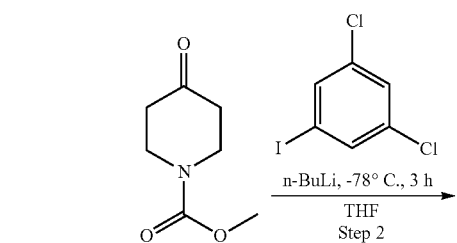

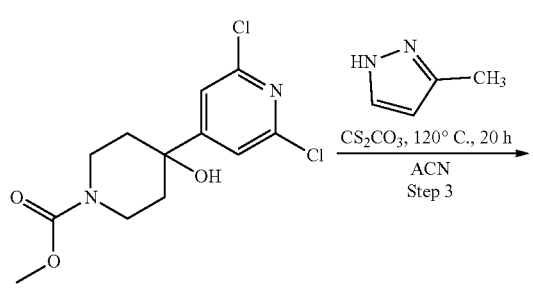

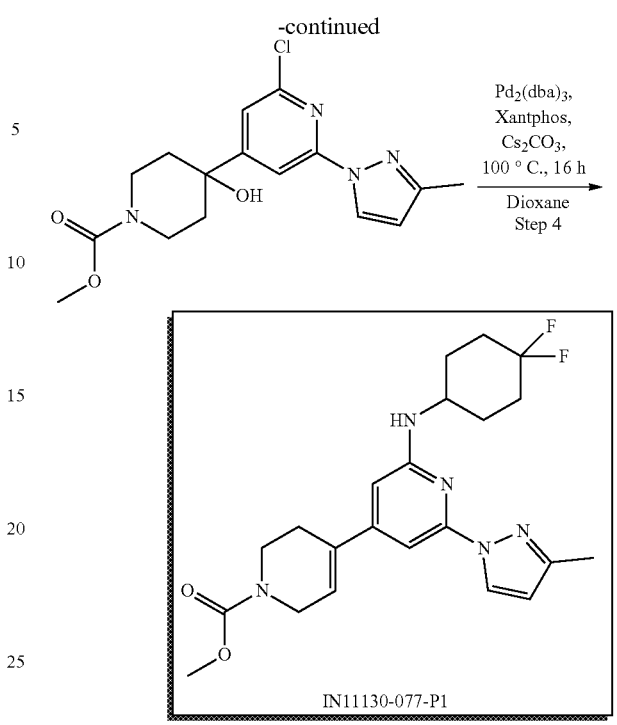

Step 1: The procedure is similar to Step 1[A] in Example-838. 2.5 g of piperidin-4-one gave methyl 4-oxopiperidine-1-carboxylate as a colourless oil (2.5 g, 98%). MS (M+1)+=158.2.

Step 2: The procedure is similar to Step 4[NSSy6067] in Example-628. 1 g of methyl 4-oxopiperidine-1-carboxylate gave methyl 4-(2,6-dichloropyridin-4-yl)-4-hydroxypiperidine-1-carboxylate as off-white solid (0.8 g, 72%). MS (M+1)+=305.1.

Step 3: The procedure is similar to Step 1[B] in Example-838. 0.6 g of methyl 4-(2,6-dichloropyridin-4-yl)-4-hydroxypiperidine-1-carboxylate gave methyl 4-(2-chloro-6-(3-methyl-1H-pyrazol-1-yl)pyridin-4-yl)-4-hydroxypiperidine-1-carboxylate as brownish gum (0.2 g, 29%). MS (M+1)+=351.1.

Step 4[IN11130-077-P1]: The procedure is similar to Step 1[NSSy6629] in Example-839. 0.15 g of methyl 4-(2-chloro-6-(3-methyl-1H-pyrazol-1-yl)pyridin-4-yl)-4-hydroxypiperidine-1-carboxylate gave methyl 2'-((4,4-difluorocyclohexyl)amino)-6'-(3-methyl-1H-pyrazol-1-yl)-3,6-dihydro-[4,4'-bipyridine]-1(2H)-carboxylate as an off-white solid (0.035 g, 18%). MS (M+1)+=432.3; 1H-NMR (400 MHz, DMSO-d6): δ 8.12 (d, J=2.40 Hz, 1H), 7.68 (d, J=8.80 Hz, 1H), 6.82 (d, J=7.20 Hz, 1H), 6.69 (s, 1H), 6.52 (d, J=8.80 Hz, 1H), 6.34 (d, J=2.40 Hz, 1H), 3.75 (s, 1H), 3.70-3.60 (m, 2H), 3.54 (s, 3H), 3.15 (s, 2H), 2.25 (s, 3H), 2.12-1.85 (m, 5H), 1.60-1.40 (m, 5H).

Example-867

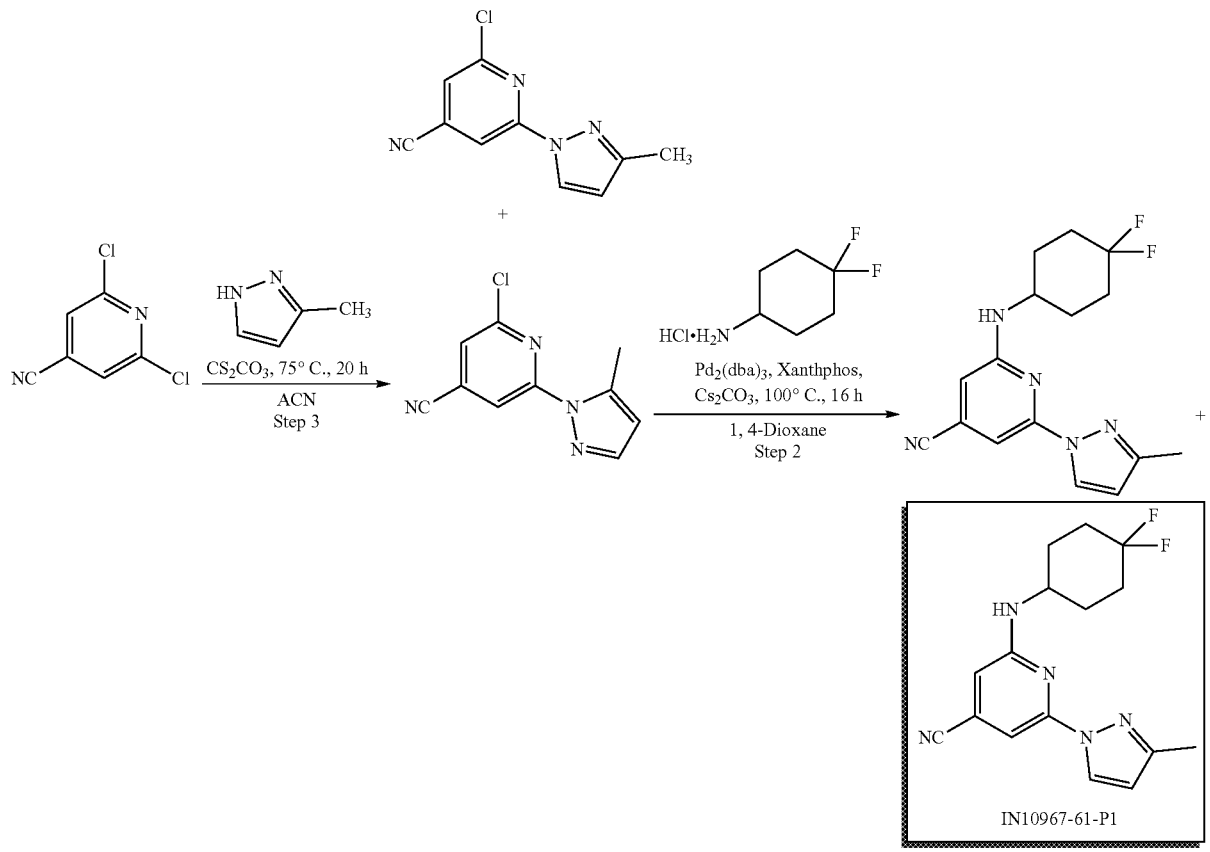

Step 1: The procedure is similar to Step 1[B] in Example-838. 2 g of 2,6-dichloroisonicotinonitrile gave mixture of 2-chloro-6-(3-methyl-1H-pyrazol-1-yl) isonicotinonitrile and 2-chloro-6-(5-methyl-1H-pyrazol-1-yl) isonicotinonitrile as a white solid (0.84 g, crude). MS (M+1)+=219.4.

Step 2[IN10967-061-P1]: The procedure is similar to Step 1[NSSy6629] in Example-839. 1.4 g of mixture of 2-chloro-6-(3-methyl-1H-pyrazol-1-yl) isonicotinonitrile and 2-chloro-6-(5-methyl-1H-pyrazol-1-yl) isonicotinonitrile gave 2-((4,4-difluorocyclohexyl)amino)-6-(3-methyl-1H-pyrazol-1-yl) isonicotinonitrile as an off-white solid (0.48 g, 24%). MS (M+1)+=318.1 and 2-((4,4-difluorocyclohexyl)amino)-6-(5-methyl-1H-pyrazol-1-yl)isonicotinonitrile as an off-white solid (0.22 g, 12%). MS (M+1)+=318.1; 1H-NMR (400 MHz, DMSO-d6): δ 7.62 (s, 1H), 7.45 (d, J=7.60 Hz, 1H), 7.15 (s, 1H), 6.72 (s, 1H), 6.30 (s, 1H), 3.90 (s, 1H), 2.67 (s, 3H), 2.11-1.85 (m, 6H), 1.60-1.50 (m, 2H).

Example-868

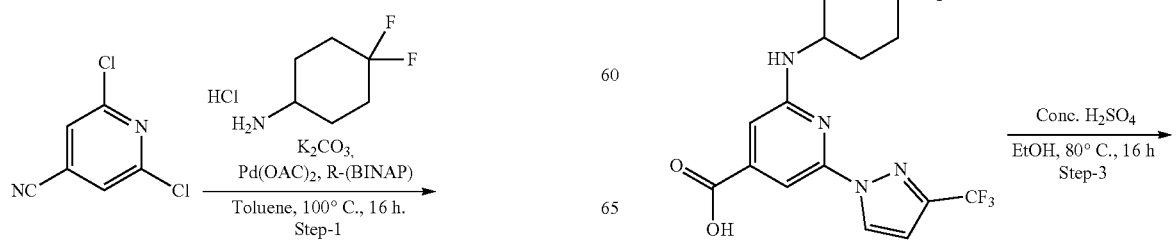

-continued

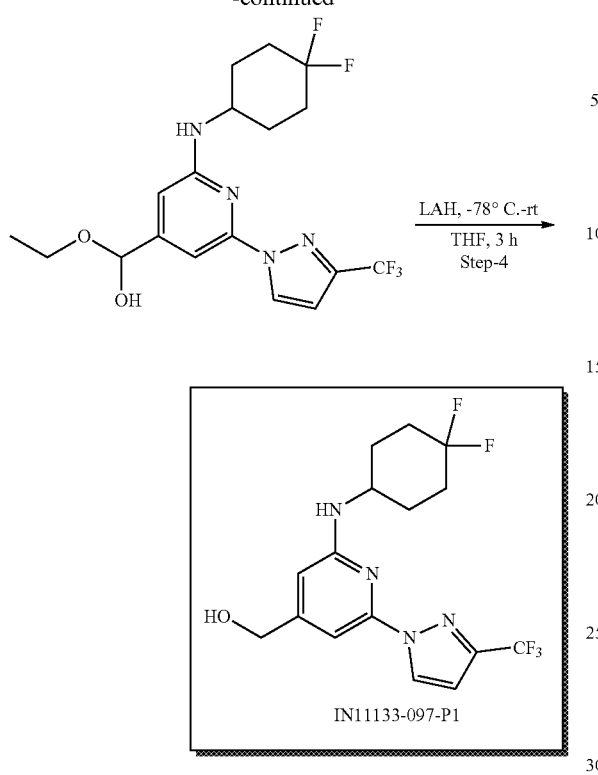

Step 1: The procedure is similar to Step 1[NSSy6629] in Example-839. 2 g of 2,6-dichloroisonicotinonitrile gave 2-chloro-6-((4,4-difluorocyclohexyl)amino) isonicotinonitrile as a brown solid (1 g, 31%). MS (M+1)+=272.2.

Step 2: The procedure is similar to Step 1[NSSy6909] in Example-839. 0.4 g of 2-chloro-6-((4,4-difluorocyclohexyl) amino) isonicotinonitrile gave mixture of 2-((4,4-difluorocyclohexyl)amino)-6-(3-(trifluoromethyl)-1H-pyrazol-1-yl) isonicotino nitrile as pale yellow solid (0.22 g, 40%). MS (M+1)+=370.2 and 2-((4,4-difluorocyclohexyl)amino)-6-(3-(trifluoromethyl)-1H-pyrazol-1-yl) isonicotinic acid as pale yellow solid (0.6 g, 90%). MS (M+1)+=391.1.

Step 3: The procedure is similar to Step 3[NSSy6711] in Example-854. 0.6 g of 2-((4,4-difluorocyclohexyl)amino)-6-(3-(trifluoromethyl)-1H-pyrazol-1-yl) isonicotinic acid gave ethyl 2-((4,4-difluorocyclohexyl)amino)-6-(3-(trifluoromethyl)-1H-pyrazol-1-yl) isonicotinate as off-white solid (0.09 g, 19%). MS (M+1)+=417.2.

Step 4[IN11133-097-P1]: The procedure is similar to Step 4[NSSy6711] in Example-854. 0.15 g of ethyl 2-((4,4-difluorocyclohexyl)amino)-6-(3-(trifluoromethyl)-1H-pyrazol-1-yl) isonicotinate gave (2-((4,4-difluorocyclohexyl) amino)-6-(3-(trifluoromethyl)-1H-pyrazol-1-yl)pyridin-4-yl) methanol as an off-white solid (0.115 g, 85%). MS (M+1)+=377.1; 1H-NMR (400 MHz, DMSO-d6): δ 8.74 (d, J=1.60 Hz, 1H), 6.99-6.97 (m, 3H), 6.49 (d, J=0.80 Hz, 1H), 5.40 (t, J=5.60 Hz, 1H), 4.47 (d, J=6.00 Hz, 2H), 4.06 (s, 1H), 2.12-1.82 (m, 6H), 1.61-1.50 (m, 2H).

Example-869

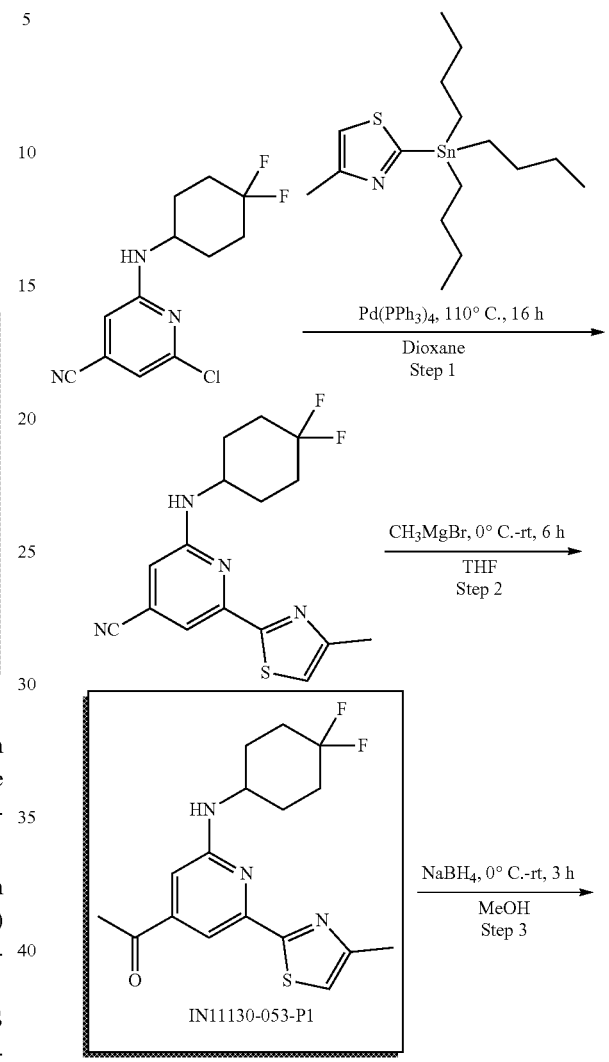

Step 1: The procedure is similar to Step 1[NSSy6989] in Example-839. 1 g of 2-chloro-6-((4,4-difluorocyclohexyl) amino) isonicotinonitrile gave 2-((4,4-difluorocyclohexyl) amino)-6-(4-methylthiazol-2-yl) isonicotinonitrile as a pale yellow solid (1 g, 81%). MS (M+1)+=335.0.

Step 2[IN11130-053-P1]: The procedure is similar to Step 4[NSSy6464] in Example-869. 0.3 g of 2-((4,4-difluorocyclohexyl)amino)-6-(4-methylthiazol-2-yl) isonicotinonitrile gave 1-(2-((4,4-difluorocyclohexyl)amino)-6-(4-methylthiazol-2-yl)pyridin-4-yl) ethan-1-one as a yellow solid (0.05 g, 16%). MS (M+1)+=350.2; 1H-NMR (400 MHz, DMSO-d6): δ 7.57 (s, 1H), 7.35 (s, 1H), 7.17 (d, J=10.40 Hz, 1H), 7.02 (s, 1H), 3.95 (s, 1H), 2.58 (s, 3H), 2.42 (s, 3H), 2.15-1.90 (m, 6H), 1.65-1.55 (m, 2H).

Step 3[IN11130-051-P1]: The procedure is similar to Step 2[NSSy6931] in Example-21. 0.35 g of 1-(2-((4,4-difluorocyclohexyl)amino)-6-(4-methylthiazol-2-yl)pyridin-4-yl) ethan-1-one gave 1-(2-((4,4-difluorocyclohexyl)amino)-6-(4-methylthiazol-2-yl)pyridin-4-yl) ethan-1-ol as a yellow solid (0.1 g, 29%). MS (M+1)+=354.0; 1H-NMR (400 MHz, DMSO-d6): δ 7.26 (s, 1H), 7.22 (s, 1H), 6.73 (d, J=6.80 Hz, 1H), 6.57 (s, 1H), 5.28 (s, 1H), 4.68-4.60 (m, 1H), 3.90 (s, 1H), 2.41 (s, 3H), 2.15-1.85 (m, 6H), 1.65-1.55 (m, 2H), 1.33 (d, J=6.80 Hz, 3H).

Example-870

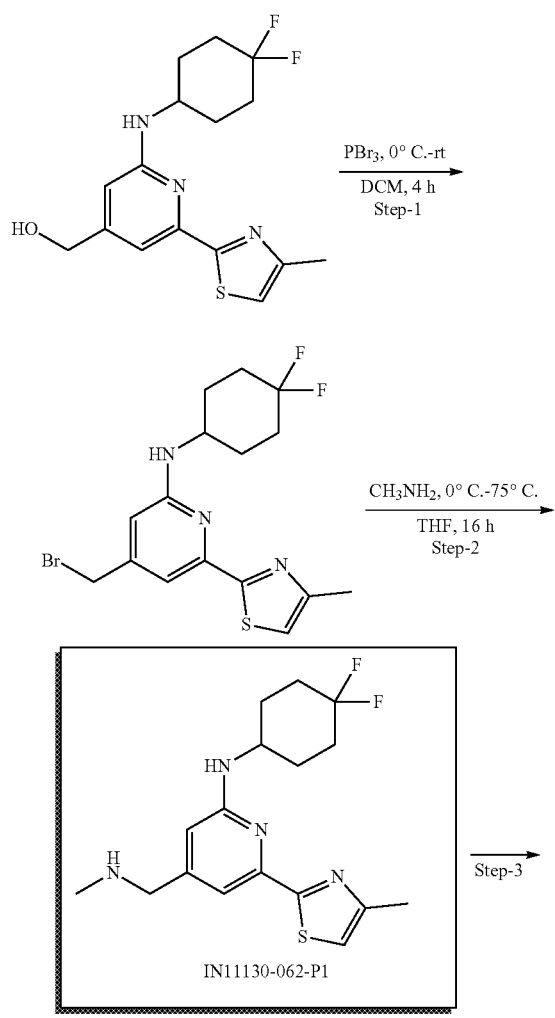

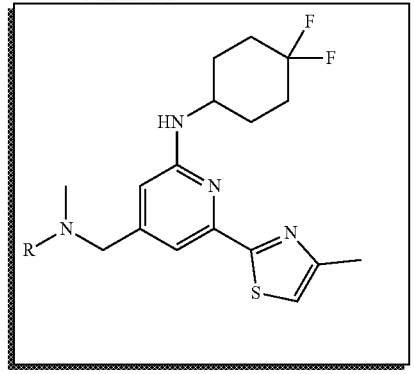

R=

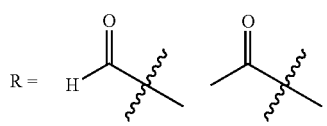

IN11133-069-P1   IN11133-068-P1

Step 1: The procedure is similar to Step 3[IN11059-090-P1] in Example-659. 0.2 g of (2-((4,4-difluorocyclohexyl)amino)-6-(4-methylthiazol-2-yl)pyridin-4-yl) methanol gave 4-(bromomethyl)-N-(4,4-difluorocyclohexyl)-6-(4-methylthiazol-2-yl)pyridin-2-amine as pale brown solid (0.2 g, 84%). MS (M, M+2)+=402.1, 404.1

Step 2[IN11133-062-P1]: The procedure is similar to Step 1[B] in Example-2. 0.1 g of 4-(bromomethyl)-N-(4,4-difluorocyclohexyl)-6-(4-methylthiazol-2-yl)pyridin-2-amine gave N-(4,4-difluorocyclohexyl)-4-((methylamino)methyl)-6-(4-methylthiazol-2-yl)pyridin-2-amine as white solid (0.035 g, 39%). MS (M+1)+=353.2; 1H-NMR (400 MHz, CD3OD): δ7.30 (s, 1H), 7.18 (d, J=1.2 Hz, 1H), 6.55 (s, 1H), 4.02 (s, 2H), 3.99 (m, 1H), 2.70 (s, 3H), 2.47 (s, 3H), 2.14-1.91 (m, 6H), 1.70-1.65 (m, 2H).

TABLE 98

| Step 3: The procedure is similar to Step 1[A] in Example-838. | | | | |
|---|---|---|---|---|
| Compound No | R | Condition | Yield (%) | M (M + 1)+ |
| IN11133-069-P1 | (aldehyde) | Ethylformate, DIPEA, THF, 70° C., 16 h | 34 | 381.2 |
| IN11133-068-P1 | (ketone) | Acetyl chloride, DIPEA DCM, 0° C.-rt, 4 h | 48 | 395.2 |

Step 3[IN11133-069-P1]: 1H-NMR (400 MHz, DMSO-d6): δ 8.24 (d, J=26.40 Hz, 1H), 7.30 (d, J=4.40 Hz, 1H), 7.09 (d, J=6.80 Hz, 1H), 6.88 (dd, J=6.80, 20.40 Hz, 1H), 6.40 (d, J=6.40 Hz, 1H), 4.42 (s, 1H), 4.37 (s, 1H), 3.90 (s, 1H), 2.89 (s, 1H), 2.69 (s, 1H), 2.41 (s, 3H), 2.10-1.88 (m, 7H), 1.65-1.50 (m, 2H).

Step 3[IN11133-068-P1]: 1H-NMR (400 MHz, DMSO-d6): δ 7.29 (d, J=5.20 Hz, 1H), 7.08 (d, J=8.40 Hz, 1H), 6.85 (dd, J=6.40, 39.00 Hz, 1H), 6.37 (s, 1H), 4.52 (s, 1H), 4.42 (s, 1H), 3.91 (s, 1H), 2.95 (s, 2H), 2.84 (s, 1H), 2.41 (s, 3H), 2.15-1.85 (m, 7H), 1.68-1.52 (m, 2H).

Example-871

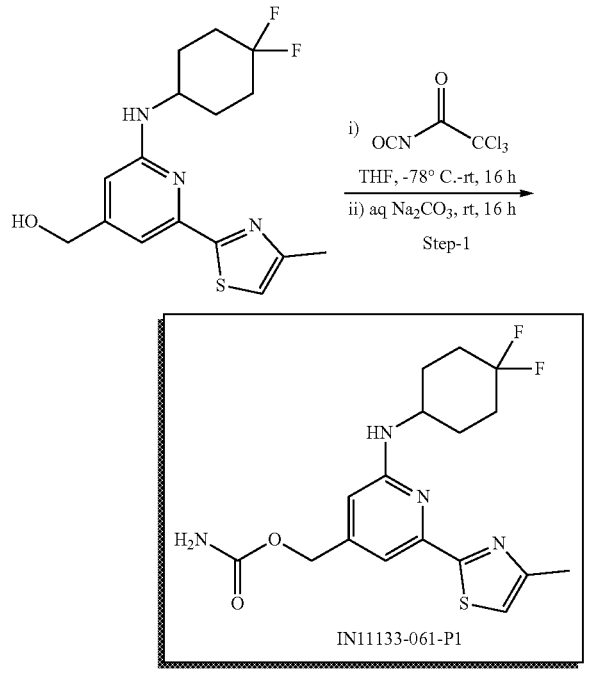

Step 1[IN11133-061-P1]: The procedure is similar to Step 3[IN11137-079-P1] in Example-785. 0.15 g of (2-((4,4-difluorocyclohexyl)amino)-6-(4-methylthiazol-2-yl)pyridin-4-yl) methanol gave (2-((4,4-difluorocyclohexyl)amino)-6-(4-methylthiazol-2-yl)pyridin-4-yl)methyl carbamate as an off-white solid (0.035 g, 15%). MS (M+1)+=383.2; 1H-NMR (400 MHz, DMSO-d6): δ 7.29 (s, 1H), 7.18 (s, 1H), 6.87 (d, J=6.80 Hz, 1H), 6.75 (s, 1H), 6.47 (s, 1H), 4.50 (s, 2H), 3.89 (s, 1H), 2.41 (s, 4H), 2.15-1.85 (m, 6H), 1.65-1.55 (m, 2H).

Example-872

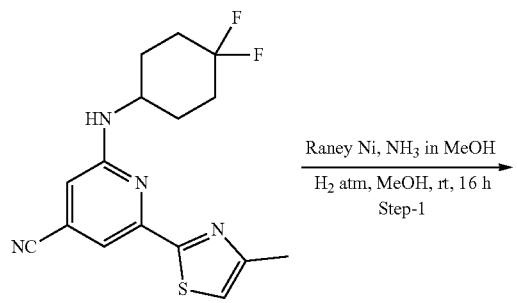

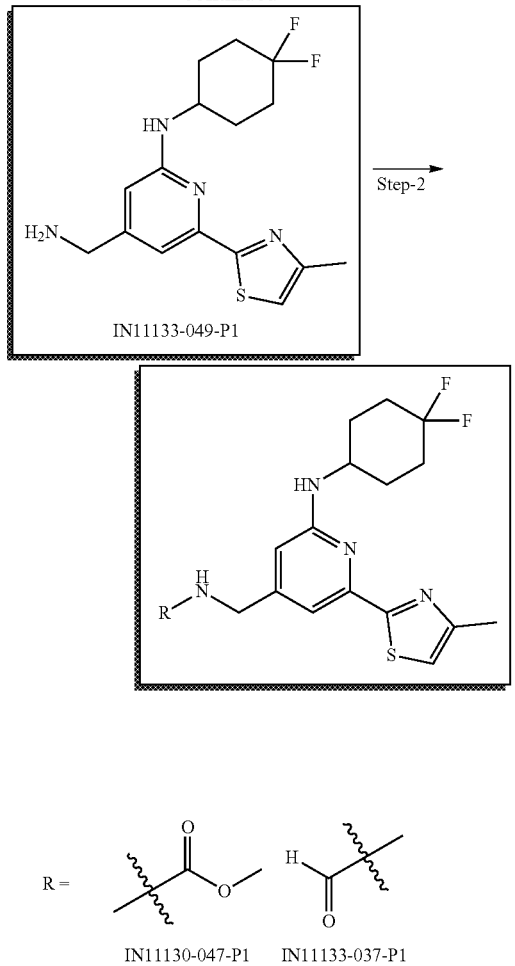

Step 1[IN11133-049-P1]: The procedure is similar to Step 3[NSSy5934] in Example-838. 0.1 g of 2-((4,4-difluorocyclohexyl)amino)-6-(4-methylthiazol-2-yl) isonicotinonitrile gave 4-(aminomethyl)-N-(4,4-difluorocyclohexyl)-6-(4-methylthiazol-2-yl)pyridin-2-amine as pale brown gum (0.04 g, 39%). MS (M+1)+=339.1; 1H-NMR (400 MHz, CDCl3): δ 7.39 (s, 1H), 6.92 (s, 1H), 6.41 (s, 1H), 4.42 (d, J=7.20 Hz, 1H), 3.90 (s, 1H), 3.84 (s, 2H), 2.50 (s, 3H), 2.20-2.10 (m, 3H), 2.15-1.85 (m, 3H), 1.70-1.60 (m, 4H).

TABLE 99

Step 2: The procedure is similar to Step 1[A] in Example-838.

| Compound No | R | Condition | Yield (%) | MS (M + 1)+ |
|---|---|---|---|---|
| IN11130-047-P1 | ![](O/methyl ester) | Methylchloroformate, TEA, DCM, 0° C.-rt, 2 h | 51 | 397.1 |
| IN11133-037-P1 | ![](H/formyl) | Ethyl formate, DIPEA THF, 70° C., 16 h | 42 | 367.0 |

[IN11130-047-P1]: 1H-NMR (400 MHz, DMSO-d6): δ 7.74 (t, J=6.00 Hz, 1H), 7.28 (s, 1H), 7.15 (s, 1H), 6.82 (d, J=6.80 Hz, 1H), 6.43 (s, 1H), 4.11 (d, J=6.00 Hz, 2H), 3.89 (s, 1H), 3.57 (s, 3H), 2.33 (s, 3H), 2.15-1.85 (m, 6H), 1.65-1.55 (m, 2H).

[IN11133-037-P1]: 1H-NMR (400 MHz, DMSO-d6): δ 8.56 (s, 1H), 8.19 (s, 1H), 7.28 (s, 1H), 7.16 (s, 1H), 3.90 (d, J=7.20 Hz, 1H), 6.43 (s, 1H), 3.90 (d, J=6.40 Hz, 2H), 3.91 (s, 1H), 2.41 (s, 3H), 2.15-1.85 (m, 6H), 1.55-1.52 (m, 2H).

Example-873

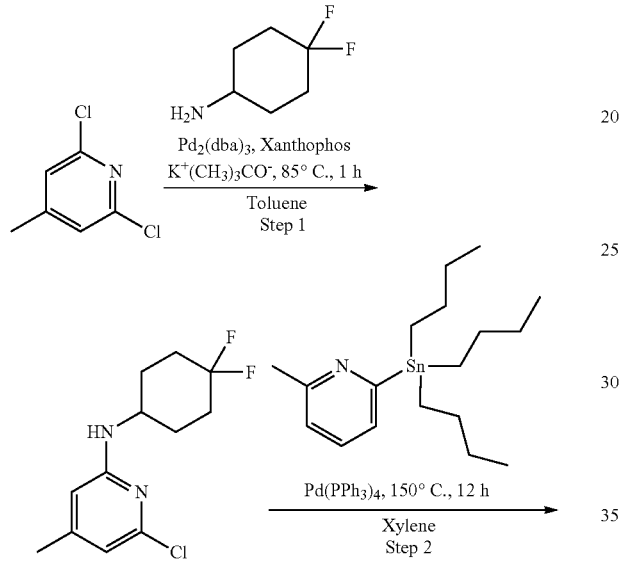

Step 1: The procedure is similar to Step 1[NSSy6629] in Example-839. 0.2 g of 2,6-dichloro-4-methylpyridine gave 6-chloro-N-(4,4-difluorocyclohexyl)-4-methylpyridin-2-amine as an off-white solid (0.14 g, 43%). MS (M+1)+=261.0.

Step 2[IN11137-041-P1]: The procedure is similar to Step 1[NSSy6989] in Example-839. 0.14 g of 6-chloro-N-(4,4-difluorocyclohexyl)-4-methylpyridin-2-amine gave N-(4,4-difluorocyclohexyl)-4,6'-dimethyl-[2,2'-bipyridin]-6-amine as an off-white solid (0.03 g, 17%). MS (M+1)+=318.1; 1H-NMR (400 MHz, DMSO-d6): δ 8.11-8.07 (m, 1H), 7.83-7.72 (m, 1H), 7.41 (bs, 1H), 7.30-7.21 (m, 1H), 6.47 (d, J=7.2 Hz, 1H), 6.35 (s, 1H), 4.10-3.80 (m, 1H), 2.55-2.45 (m, 3H), 2.23 (s, 3H), 2.10-1.92 (m, 6H), 1.64-1.55 (m, 2H).

Example-874

Intentionally Omitted

Example-875

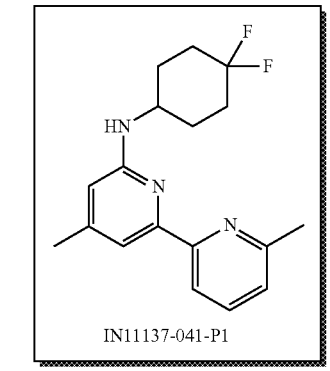

R=

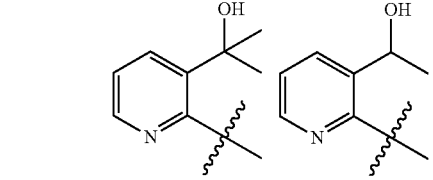

IN11039-069-P1    IN11039-066-P1

TABLE 100

Step 1: The procedure is similar to Step 2[IN10991-021-P1] in Example-694.

| Compound No | R | Condition | Yield (%) | MS (M + 1)+ |
|---|---|---|---|---|
| IN11039-069-P1 | OH (structure) | NaH, THF, 70° C., 16 h | 42 | 458.1 |

TABLE 100-continued

Step 1: The procedure is similar to Step 2[IN10991-021-P1] in Example-694.

| Compound No | R | Condition | Yield (%) | MS (M + 1)+ |
|---|---|---|---|---|
| IN11039-066-P1 | 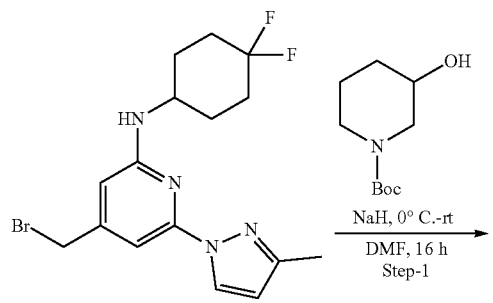 | NaH, THF, 70° C., 16 h | 16 | 444.1 |

Step 1[IN11039-069-P1]: 1H-NMR (400 MHz, DMSO-d6): δ 8.37 (d, J=2.00 Hz, 1H), 8.00 (d, J=3.60 Hz, 1H), 7.93 (d, J=7.20 Hz, 1H), 7.02 (s, 1H), 6.96 (q, J=5.60 Hz, 1H), 6.42 (s, 1H), 6.25 (d, J=2.00 Hz, 1H), 5.37 (s, 2H), 3.95 (s, 1H), 2.31 (s, 3H), 2.10-1.85 (m, 6H), 1.63 (s, 9H).

Step 1[IN11039-066-P1]: 1H-NMR (400 MHz, MeOD): δ 8.38 (d, J=2.40 Hz, 1H), 8.01 (q, J=3.60 Hz, 1H), 7.84 (q, J=2.00 Hz, 1H), 7.00-6.97 (m, 2H), 6.43 (d, J=0.80 Hz, 1H), 6.25 (d, J=2.40 Hz, 1H), 5.36 (q, J=4.40 Hz, 2H), 5.19-5.16 (m, 1H), 3.97 (s, 1H), 2.31 (s, 3H), 2.20-1.90 (m, 6H), 1.72-1.60 (m, 3H), 1.42 (d, J=4.80 Hz, 4H).

Example-876

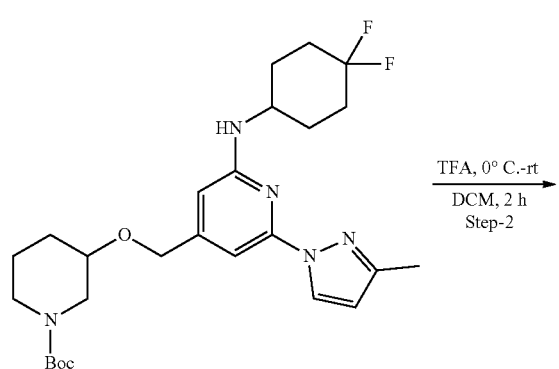

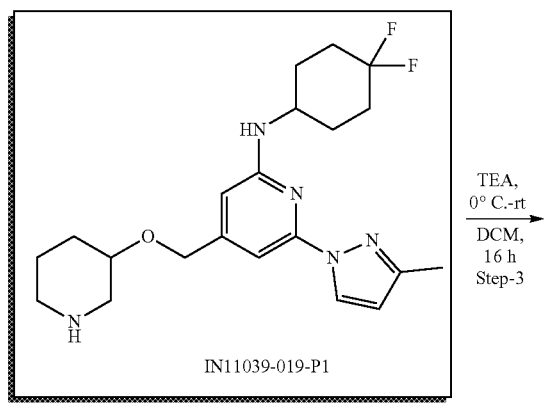

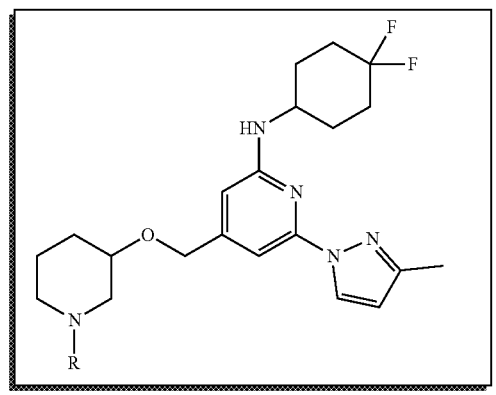

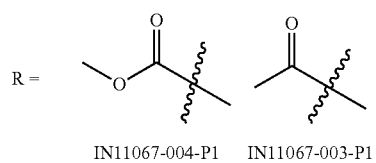

IN11067-004-P1   IN11067-003-P1

Step 1: The procedure is similar to Step 2[NSSy5701] in Example-813. 0.13 g of 4-(bromomethyl)-N-(4,4-difluorocyclohexyl)-6-(3-methyl-1H-pyrazol-1-yl)pyridin-2-amine gave tert-butyl 3-((2-((4,4-difluorocyclohexyl)amino)-6-(3-methyl-1H-pyrazol-1-yl)pyridin-4-yl)methoxy)piperidine-1-carboxylate as colourless gum (0.16 g, 93%). MS (M+1)+=506.2.

Step 2[IN11039-019-P1]: The procedure is similar to Step 5[NSSy6067] in Example-628. 0.16 g of tert-butyl 3-((2-((4,4-difluorocyclohexyl)amino)-6-(3-methyl-1H-pyrazol-1-yl)pyridin-4-yl)methoxy)piperidine-1-carboxylate gave N-(4,4-difluorocyclohexyl)-6-(3-methyl-1H-pyrazol-1-yl)-4-((piperidin-3-yloxy)methyl)pyridin-2-amine as an off-white solid (0.045 g, 35%). MS (M+1)+=406.2; 1H-NMR (400 MHz, DMSO-d6): δ 8.41 (d, J=1.60 Hz, 1H), 6.85 (s, 1H), 6.79 (d, J=7.60 Hz, 1H), 6.35 (s, 1H), 6.28 (d, J=2.40 Hz, 1H), 4.45 (s, 2H), 3.98 (s, 1H), 3.26-3.21 (m, 2H), 3.07-3.04 (m, 1H), 2.75-2.65 (m, 1H), 2.42-2.32 (m, 4H), 2.25 (s, 3H), 2.10-1.90 (m, 8H), 1.62-1.48 (m, 2H).

TABLE 101

Step 3: The procedure is similar to Step 1[A] in Example-838.

| Compound No | R | Condition | Yield (%) | MS (M + 1)+ |
|---|---|---|---|---|
| IN11067-004-P1 | (methyl ester group) | Methyl chloroformate, TEA, DCM, 0° C.-rt, 16 h | 30 | 464.2 |
| IN11067-003-P1 | (acetyl group) | Acetyl chloride, TEA, DCM, 0° C.-rt, 16 h | 51 | 448.3 |

Step 3[IN11067-004-P1]: 1H-NMR (400 MHz, DMSO-d6): δ 8.41 (d, J=2.40 Hz, 1H), 6.86 (s, 1H), 6.80 (d, J=7.60 Hz, 1H), 6.33 (s, 1H), 6.28 (d, J=2.40 Hz, 1H), 4.45 (q, J=10.80 Hz, 2H), 3.99 (s, 1H), 3.58 (s, 4H), 3.48-3.41 (m, 2H), 2.26 (s, 3H), 1.98-1.85 (m, 8H), 1.69-1.37 (m, 6H).

Step 3[IN11067-003-P1]: 1H-NMR (400 MHz, DMSO-d6): δ 8.41 (s, 1H), 6.85 (s, 1H), 6.80 (d, J=4.00 Hz, 1H), 6.33 (s, 1H), 6.28 (s, 1H), 4.50-4.40 (m, 2H), 4.00 (s, 1H), 3.85 (d, J=24.00 Hz, 1H), 3.60 (d, J=16.00 Hz, 1H), 3.50-3.35 (m, 3H), 3.25-3.20 (m, 1H), 2.26 (s, 3H), 2.15-1.85 (m, 6H), 1.70-1.50 (m, 4H), 1.50-1.30 (m, 4H).

TABLE 102

Step 1: The procedure is similar to Step 2[NSSy5701] in Example-813.

| Compound No | R | Condition | Yield (%) | MS (M + 1)+ |
|---|---|---|---|---|
| IN11039-017-P1 | (methoxyethyl-N-methyl group) | NaH, THF, 0° C.-rt, 16 h | 68 | 394.3 |
| IN11125-012-P1 | (methoxyethoxy group) | NaH, THF, 0° C.-rt, 16 h | 50 | 381.1 |

Step 1[IN11039-017-P1]: 1H-NMR (400 MHz, CD3OD): δ 8.36 (d, J=2.8 Hz, 1H), 6.95 (s, 1H), 6.36 (s, 1H), 6.25 (d, J=2.4 Hz, 1H), 3.96-3.94 (m, 1H), 3.56-3.53 (m, 2H), 3.49 (s, 2H), 3.33 (s, 4H), 2.64-2.61 (m, 2H), 2.32 (s, 3H), 2.28 (s, 3H), 2.09-1.91 (m, 6H), 1.69-1.61 (m, 2H).

Step 1[IN11125-012-P1]: 1H-NMR (400 MHz, CDCl3): δ 8.31 (d, J=2.40 Hz, 1H), 7.07 (s, 1H), 6.31 (s, 1H), 6.19 (d, J=2.40 Hz, 1H), 4.52 (s, 2H), 4.26 (d, J=114.40 Hz, 1H), 3.90-3.80 (m, 1H), 3.65-3.58 (m, 4H), 3.41 (s, 3H), 2.36 (s, 3H), 2.20-2.10 (m, 4H), 2.00-1.82 (m, 2H), 1.70-1.60 (m, 2H).

Example-877

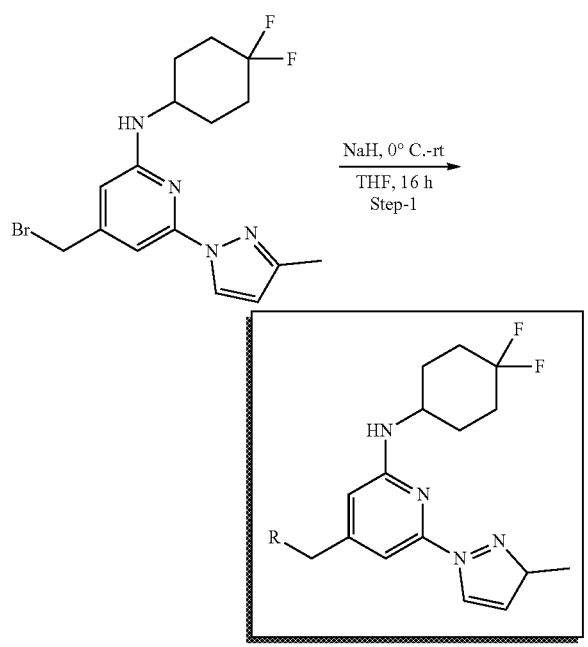

Example-878

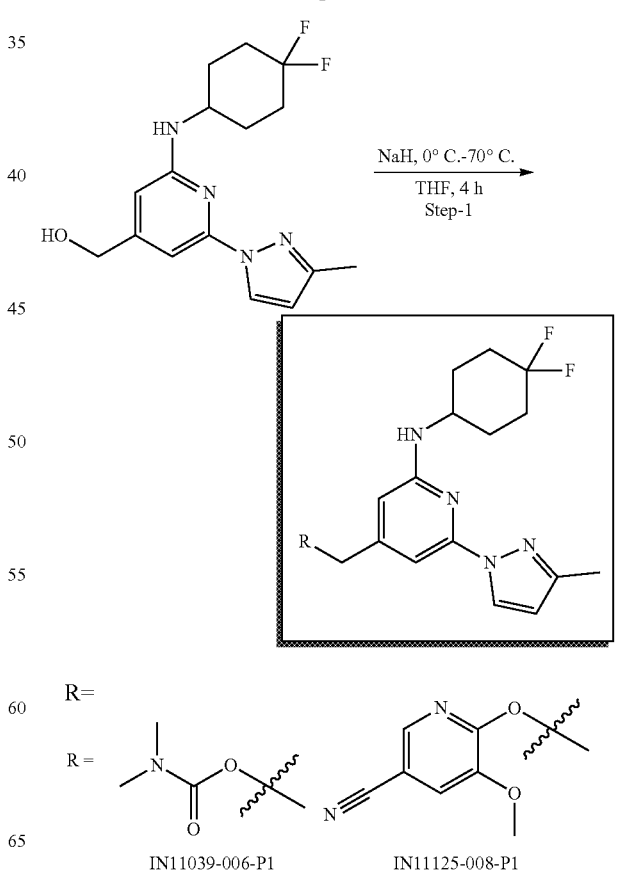

TABLE 103

Step 1: The procedure is similar to Step 2[IN10991-021-P1] in Example-694.

| Compound No | R | Condition | Yield (%) | MS (M + 1)+ |
|---|---|---|---|---|
| IN11039-006-P1 |  | NaH, THF, 0° C.-70° C., 4 h | 61 | 394.2 |
| IN11125-008-P1 | 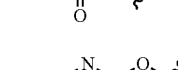 | NaH, THF, 0° C.-70° C., 4 h | 67 | 455.1 |

Step 1[IN11039-006-P1]: 1H-NMR (400 MHz, DMSO-d6): δ 8.42 (d, J=2.80 Hz, 1H), 6.90 (d, J=7.20 Hz, 1H), 6.85 (s, 1H), 6.30 (d, J=2.00 Hz, 2H), 4.99 (s, 2H), 3.99 (s, 1H), 3.00 (s, 3H), 2.86 (s, 3H), 2.26 (s, 3H), 2.10-1.90 (m, 6H), 1.62-1.50 (m, 2H).

Step 1[IN11125-008-P1]: 1H-NMR (400 MHz, DMSO-d6): δ 8.30 (d, J=2.40 Hz, 1H), 8.05 (d, J=2.00 Hz, 1H), 7.20 (d, J=2.00 Hz, 2H), 6.29 (s, 1H), 6.20 (d, J=2.40 Hz, 1H), 5.39 (s, 2H), 4.40 (d, J=7.20 Hz, 1H), 3.92 (s, 3H), 3.87 (s, 1H), 2.37 (s, 3H), 2.15-1.99 (m, 4H), 1.93-1.85 (m, 2H), 1.67-1.62 (m, 2H).

Example-879

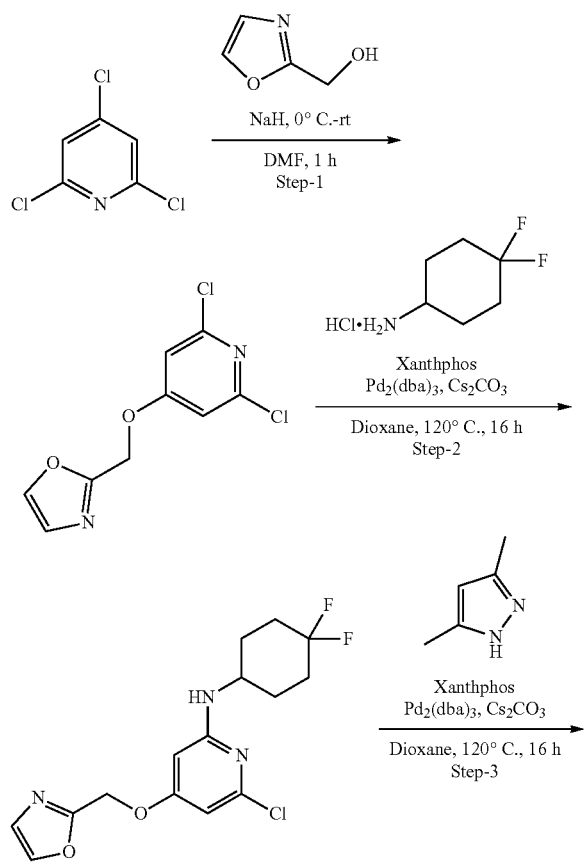

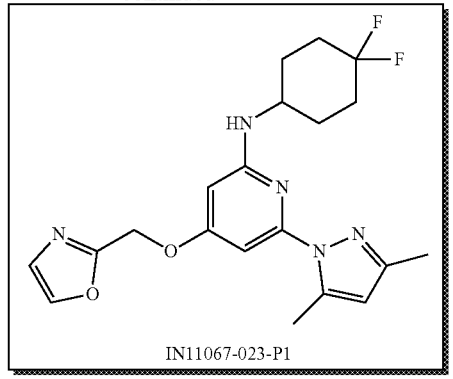

IN11067-023-P1

Step 1: The procedure is similar to Step 2[NSSy5701] in Example-813. 1 g of 2,4,6-trichloropyridine gave 2-(((2,6-dichloropyridin-4-yl)oxy)methyl) oxazole as an off-white solid (0.75 g, 60%). MS (M+1)+=245.0.

Step 2: The procedure is similar to Step 1[NSSy6629] in Example-839. 0.75 g of 2-(((2,6-dichloropyridin-4-yl)oxy) methyl) oxazole gave 6-chloro-N-(4,4-difluorocyclohexyl)-4-(oxazol-2-ylmethoxy)pyridin-2-amine as a pale green solid (0.26 g, 25%). MS (M+1)+=344.0.

Step 3[IN11067-023-P1]: The procedure is similar to Step 1[NSSy6629] in Example-839. 0.26 g of 6-chloro-N-(4,4-difluorocyclohexyl)-4-(oxazol-2-ylmethoxy)pyridin-2-amine gave N-(4,4-difluorocyclohexyl)-6-(3,5-dimethyl-1H-pyrazol-1-yl)-4-(oxazol-2-ylmethoxy)pyridin-2-amine as a white solid (0.065 g, 21%). MS (M+1)+=404.0; 1H-NMR (400 MHz, DMSO-d6): δ 8.17 (s, 1H), 7.29 (s, 1H), 6.75 (d, J=7.60 Hz, 1H), 6.61 (s, 1H), 6.03 (s, 1H), 5.97 (s, 1H), 5.24 (s, 2H), 3.87 (s, 1H), 2.57 (s, 3H), 2.19 (s, 3H), 1.90-1.85 (m, 6H), 1.55-1.45 (m, 2H).

Example-880

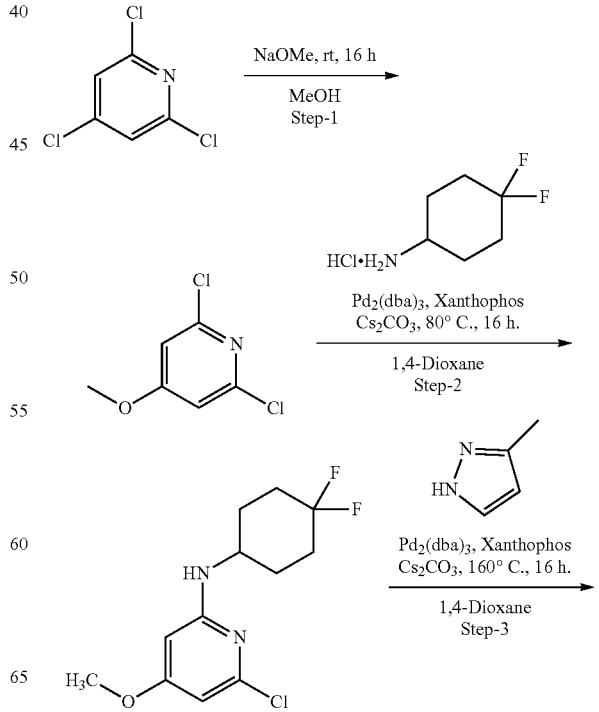

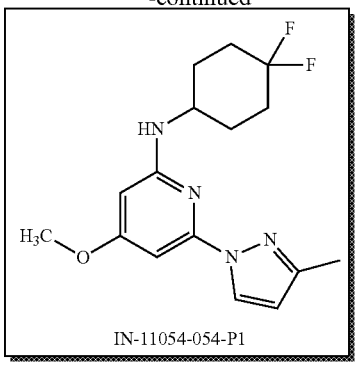

IN-11054-054-P1

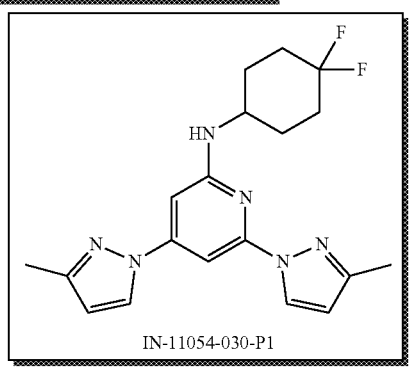

IN-11054-030-P1

Step 1: The procedure is similar to Step 1[NSSy6519] in Example-842. 3 g of 2,4,6-trichloropyridine gave 2,6-dichloro-4-methoxypyridine as a white solid (2.1 g, 72%). MS (M+1)+=177.9.

Step 2: The procedure is similar to Step 1[NSSy6629] in Example-839. 1.5 g of 2,6-dichloro-4-methoxypyridine gave 6-chloro-N-(4,4-difluorocyclohexyl)-4-methoxypyridin-2-amine as a brown solid (0.5 g, 32%). MS (M+1)+=277.3.

Step 3[IN11054-054-P1, IN11054-030-P1]: The procedure is similar to Step 1[NSSy6629] in Example-839. 0.2 g of 6-chloro-N-(4,4-difluorocyclohexyl)-4-methoxypyridin-2-amine gave N-(4,4-difluorocyclohexyl)-4-methoxy-6-(3-methyl-1H-pyrazol-1-yl)pyridin-2-amine as an off-white solid (0.018 g, 12%). MS (M+1)+=323.; 1H-NMR (400 MHz, DMSO-d6): δ 8.39 (d, J=2.40 Hz, 1H), 6.67 (d, J=7.60 Hz, 1H), 6.54 (s, 1H), 6.28 (s, 1H), 5.88 (s, 1H), 3.90 (s, 1H), 3.78 (s, 3H), 2.25 (s, 3H), 2.10-1.90 (m, 6H), 1.60-1.48 (m, 2H) and N-(4,4-difluorocyclohexyl)-4,6-bis(3-methyl-1H-pyrazol-1-yl)pyridin-2-amine as an off-white solid (0.06 g, 22%). MS (M+1)+=373.1; 1H-NMR (400 MHz, DMSO-d6): δ 8.45 (s, 1H), 8.41 (s, 1H), 7.33 (s, 1H), 6.96 (d, J=6.80 Hz, 1H), 6.75 (s, 1H), 6.38 (s, 1H), 6.33 (s, 1H), 4.02 (s, 1H), 2.29 (d, J=4.80 Hz, 6H), 2.10-1.90 (m, 6H), 1.65-1.55 (m, 2H).

Example-881

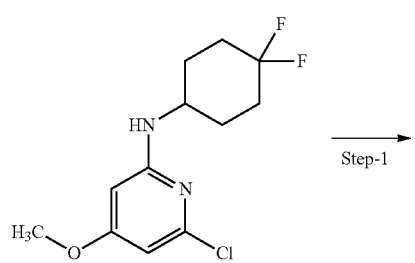

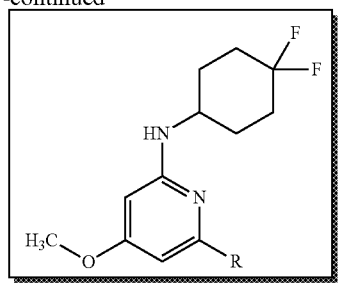

R=

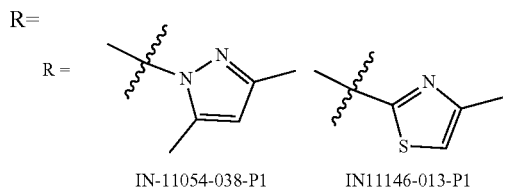

IN-11054-038-P1   IN11146-013-P1

TABLE 104

| Compound No | R | Condition | Yield (%) | MS (M + 1)+ |
|---|---|---|---|---|
| IN11054-038-P1 | pyrazole | Pd₂(dba)₃, Xanthphos, Cs₂CO₃, 1,4-Dioxane, 120° C., 16 h. | 20 | 337.2 |
| IN11146-013-P1 | thiazole | Pd(PPh₃)₄, 1,4-Dioxane, 110° C., 16 h | 55 | 340.0 |

Step 1[IN11054-038-P1]: The procedure is similar to Step 1[NSSy6629] in Example-839. 1H-NMR (400 MHz, DMSO-d6): δ 6.66 (d, J=7.20 Hz, 1H), 6.52 (s, 1H), 6.02 (s, 1H), 5.89 (s, 1H), 3.86 (s, 1H), 4.05 (s, 3H), 2.57 (s, 3H), 2.16 (s, 3H), 2.10-1.85 (m, 6H), 1.58-1.48 (m, 2H).

Step 1[IN11146-013-P1]: The procedure is similar to Step 1[NSSy6989] in Example-839. 1H-NMR (400 MHz, DMSO-d6): δ 7.29 (s, 1H), 6.84 (d, J=1.6 Hz, 1H), 6.68 (d, J=6.8 Hz, 1H), 6.07 (d, J=1.6 Hz, 1H), 3.89-3.84 (m, 1H), 3.79 (s, 3H), 2.41 (s, 3H), 2.09-1.88 (m, 6H), 1.62-1.57 (m, 2H).

Example-882

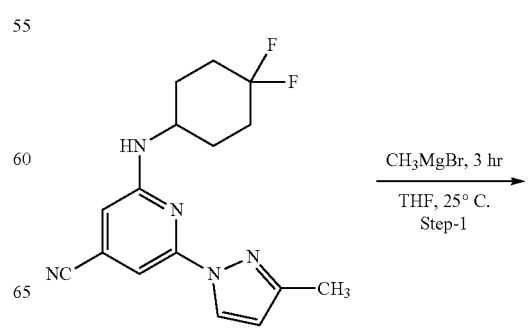

1201

-continued

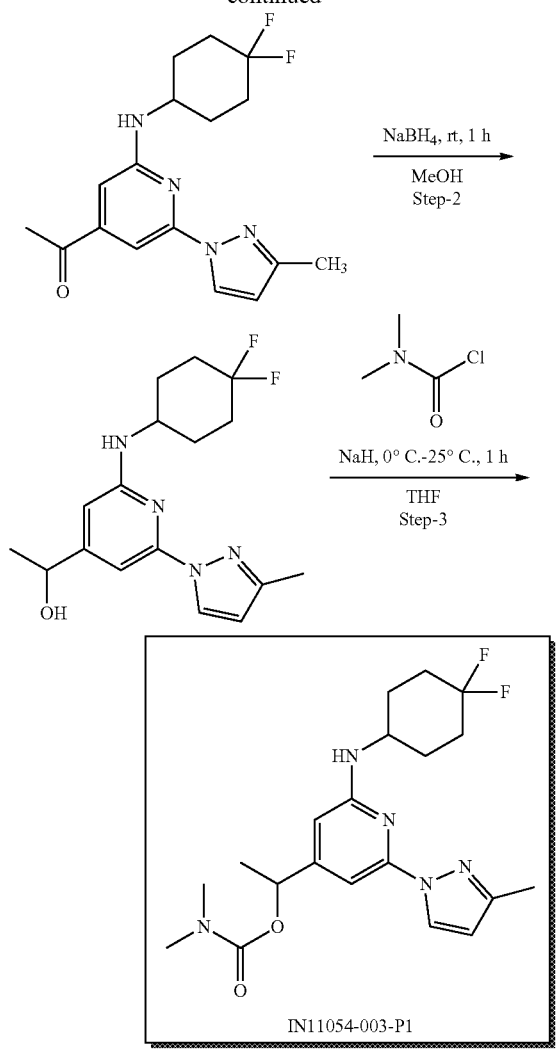

Step 1: The procedure is similar to Step 4[NSSy6464] in Example-869. 0.1 g of 2-((4,4-difluorocyclohexyl)amino)-6-(3-methyl-1H-pyrazol-1-yl) isonicotinonitrile gave 1-(2-((4,4-difluorocyclohexyl)amino)-6-(3-methyl-1H-pyrazol-1-yl)pyridin-4-yl) ethan-1-one as a yellow solid (0.1 g, 95%). MS (M+1)+=335.0.

Step 2: The procedure is similar to Step 2[NSSy6931] in Example-21. 0.2 g of 1-(2-((4,4-difluorocyclohexyl)amino)-6-(3-methyl-1H-pyrazol-1-yl)pyridin-4-yl)ethan-1-one gave 1-(2-((4,4-difluorocyclohexyl)amino)-6-(3-methyl-1H-pyrazol-1-yl)pyridin-4-yl)ethan-1-ol as a yellow solid (0.16 g, 80%). MS (M+1)+=337.2.

Step 3[IN11054-003-P1]: The procedure is similar to Step 5[NSSy6711] in Example-854. 0.1 g of 1-(2-((4,4-difluorocyclohexyl)amino)-6-(3-methyl-1H-pyrazol-1-yl)pyridin-4-yl)ethan-1-ol gave 1-(2-((4,4-difluorocyclohexyl)amino)-6-(3-methyl-1H-pyrazol-1-yl)pyridin-4-yl)ethyl dimethylcarbamate as a yellow solid (0.035 g, 29%). MS (M+1)+=408.2; 1H-NMR (400 MHz, DMSO-d6): δ 8.41 (d, J=2.40 Hz, 1H), 6.86 (t, J=3.20 Hz, 2H), 6.30-6.29 (m, 2H), 5.54 (q, J=6.40 Hz, 1H), 3.98 (s, 1H), 2.95 (s, 3H), 2.82 (s, 3H), 2.26 (s, 3H), 2.10-1.90 (m, 6H), 1.60-1.50 (m, 2H), 1.43 (d, J=6.80 Hz, 3H).

1202

Example-883

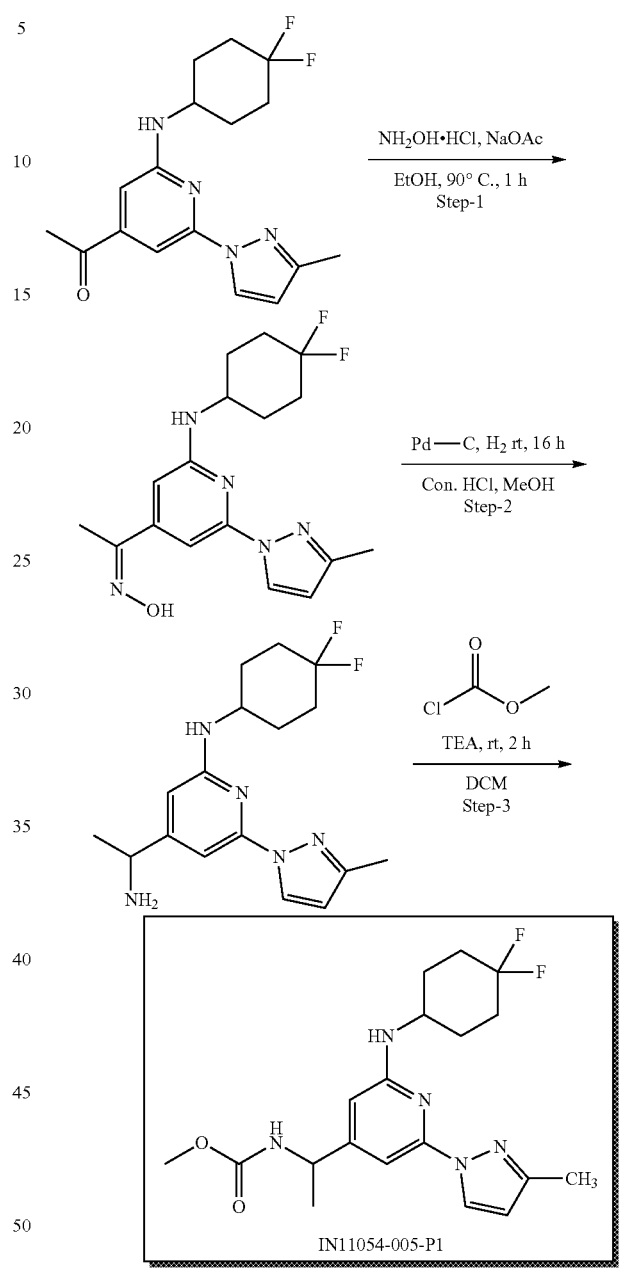

Step 1: To a solution of 1-(2-((4,4-difluorocyclohexyl)amino)-6-(3-methyl-1H-pyrazol-1-yl)pyridin-4-yl) ethan-1-one (0.2 g, 0.59 mmol) in ethanol was added hydroxylamine hydrochloride (0.082 g, 1.18 mmol) and sodium acetate (0.097 g, 1.18 mmol). The reaction mixture was heated at 90° C. for 1 h. The reaction mixture was evaporated, quenched with water, extracted with ethyl acetate. The organic layer was dried over sodium sulfate, filtered and concentrated under reduced pressure to afford (Z)-1-(2-((4,4-difluorocyclohexyl)amino)-6-(3-methyl-1H-pyrazol-1-yl)pyridin-4-yl)ethan-1-one oxime as a yellow solid (0.18 g, 89%). MS (M+1)+=350.1.

Step 2: The procedure is similar to Step 2[NSSy6464] in Example-869. 0.1 g of (Z)-1-(2-((4,4-difluorocyclohexyl)

amino)-6-(3-methyl-1H-pyrazol-1-yl)pyridine-4-yl)ethan-1-one oxime gave 4-(1-aminoethyl)-N-(4,4-difluorocyclohexyl)-6-(3-methyl-1H-pyrazol-1-yl)pyridin-2-amine as a pale brown solid (0.1 g, crude). MS (M+1)+=336.2.

Step 3[IN11054-005-P1]: The procedure is similar to Step 1[A] in Example-838. 0.1 g of 4-(1-aminoethyl)-N-(4,4-difluorocyclohexyl)-6-(3-methyl-1H-pyrazol-1-yl)pyridin-2-amine gave methyl (1-(2-((4,4-difluorocyclohexyl)amino)-6-(3-methyl-1H-pyrazol-1-yl)pyridin-4-yl)ethyl)carbamate as pale brown solid (0.025 g, 21%). MS (M+1)+= 394.2; 1H-NMR (400 MHz, DMSO-d6): δ 8.40 (d, J=2.00 Hz, 1H), 7.77 (d, J=8.00 Hz, 1H), 6.91 (s, 1H), 6.79 (d, J=7.20 Hz, 1H), 6.27 (d, J=8.00 Hz, 2H), 4.52-4.48 (m, 1H), 3.97 (s, 1H), 3.51 (s, 3H), 2.26 (s, 3H), 2.10-1.90 (m, 6H), 1.60-1.50 (m, 2H), 1.31 (d, J=7.60 Hz, 3H).

Example-884

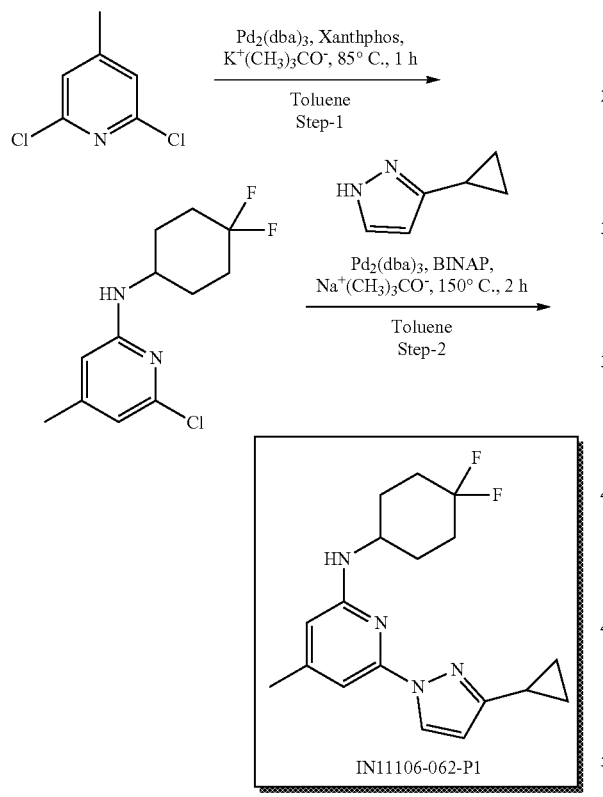

Step 1: The procedure is similar to Step 1[NSSy6629] in Example-839. 0.5 g of 2,6-dichloro-4-methylpyridine gave 6-chloro-N-(4,4-difluorocyclohexyl)-4-methylpyridin-2-amine as an off-white solid (0.35 g, 43%). MS (M+1)+= 261.0.

Step 2[IN11106-062-P1]: The procedure is similar to Step 1[NSSy6629] in Example-839. 0.5 g of 6-chloro-N-(4,4-difluorocyclohexyl)-4-methylpyridin-2-amine gave 6-(3-cyclopropyl-1H-pyrazol-1-yl)-N-(4,4-difluorocyclohexyl)-4-methylpyridin-2-amine as a white solid (0.11 g, 19%). MS (M+1)+=333.1; 1H-NMR (400 MHz, DMSO-d6): δ 8.36 (s, 1H), 6.77 (s, 1H), 6.62 (d, J=7.20 Hz, 1H), 6.18 (d, J=5.20 Hz, 2H), 3.96 (s, 1H), 2.20 (s, 3H), 2.10-1.90 (m, 7H), 1.60-1.45 (m, 2H), 0.92-0.85 (m, 2H), 0.77-0.71 (m, 2H).

Example-885

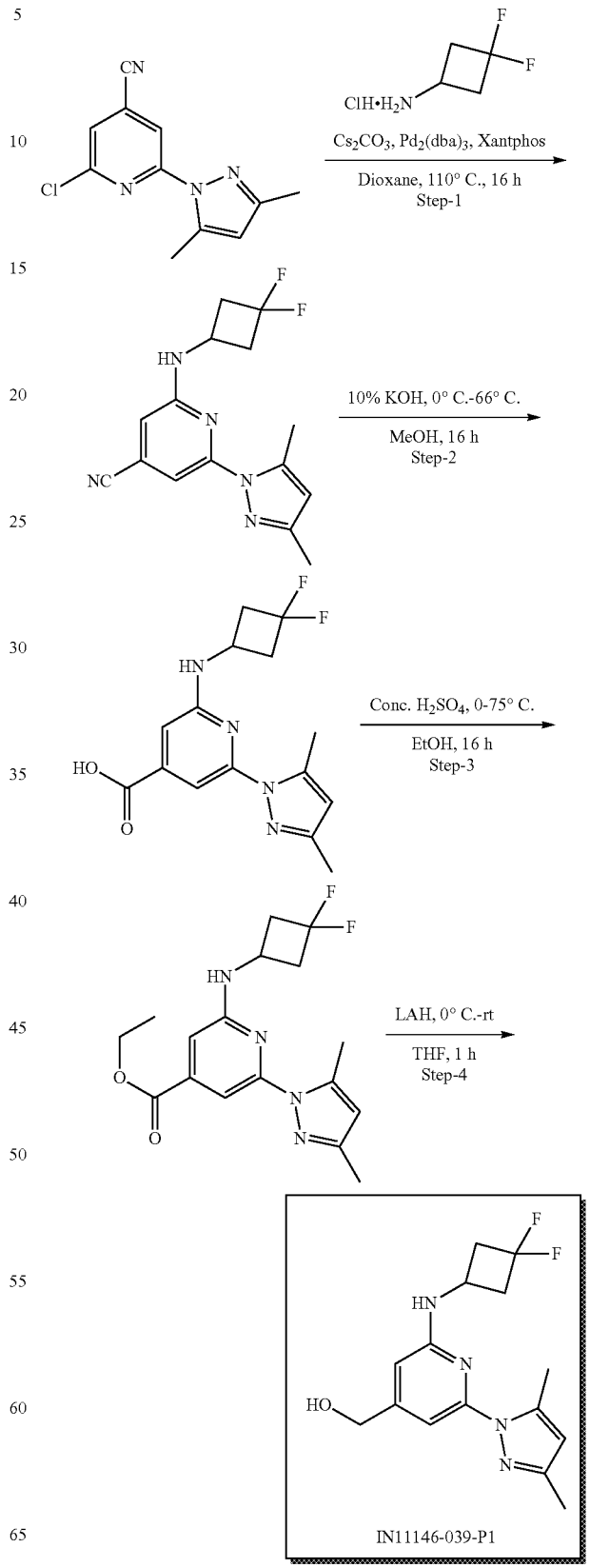

Step 1: The procedure is similar to Step 1[NSSy6629] in Example-839. 2 g of 2-chloro-6-(3,5-dimethyl-1H-pyrazol-1-yl) isonicotinonitrile gave 2-((3,3-difluorocyclobutyl)amino)-6-(3,5-dimethyl-1H-pyrazol-1-yl) isonicotinonitrile as a yellow solid (0.75 g, 29%). MS (M+1)+=304.0.

Step 2: The procedure is similar to Step 1[B] in Example-838. 0.2 g of 2-((3,3-difluorocyclobutyl)amino)-6-(3,5-dimethyl-1H-pyrazol-1-yl) isonicotinonitrile gave 2-((3,3-difluorocyclobutyl)amino)-6-(3,5-dimethyl-1H-pyrazol-1-yl) isonicotinic acid as a white solid (0.2 g, 94%). MS (M+1)+=323.0.

Step 3: The procedure is similar to Step 3[NSSy6711] in Example-854. 0.2 g of 2-((3,3-difluorocyclobutyl)amino)-6-(3,5-dimethyl-1H-pyrazol-1-yl) isonicotinic acid gave ethyl 2-((3,3-difluorocyclobutyl)amino)-6-(3,5-dimethyl-1H-pyrazol-1-yl) isonicotinate as a white solid (0.17 g, 78%). MS (M+1)+=351.0.

Step 4[IN11146-039-P1]: The procedure is similar to Step 4[NSSY6711] in Example-854. 0.17 g of ethyl 2-((3,3-difluorocyclobutyl)amino)-6-(3,5-dimethyl-1H-pyrazol-1-yl) isonicotinate gave (2-((3,3-difluorocyclobutyl)amino)-6-(3,5-dimethyl-1H-pyrazol-1-yl)pyridin-4-yl) methanol as an off-white solid (0.06 g, 40%). MS (M+1)+=309.2; 1H-NMR (400 MHz, DMSO-d6): δ 7.16 (d, J=6.00 Hz, 1H), 6.93 (s, 1H), 6.35 (s, 1H), 6.03 (s, 1H), 5.31 (t, J=5.60 Hz, 1H), 4.44 (d, J=5.60 Hz, 2H), 4.17-4.13 (m, 1H), 3.05-2.90 (m, 2H), 2.55 (s, 3H), 2.55-2.50 (m, 2H), 2.16 (s, 3H).

Example-886

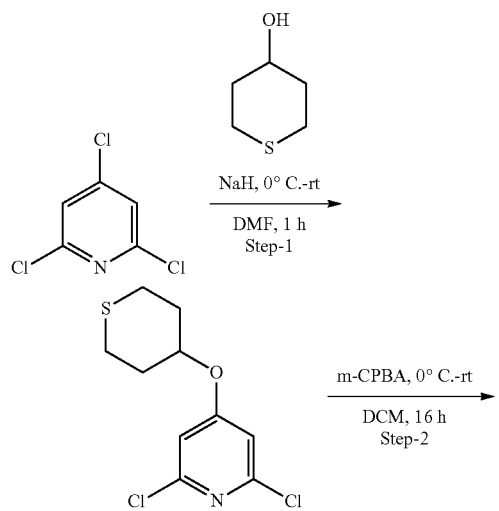

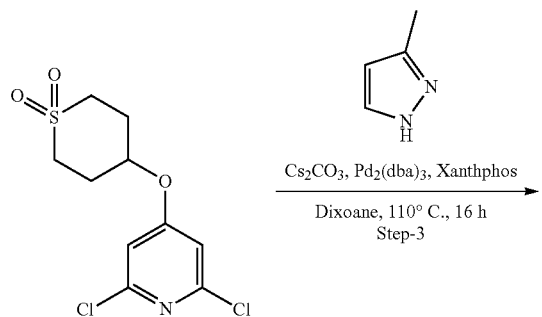

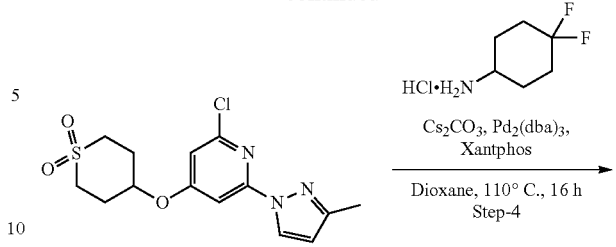

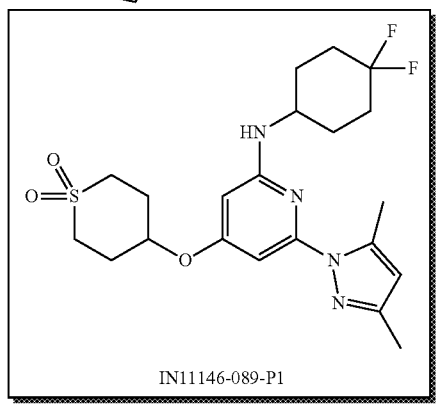

Step 1: The procedure is similar to Step 5[NSSy6711] in Example-854. 2 g of 2,4,6-trichloropyridine gave 2,6-dichloro-4-((tetrahydro-2H-thiopyran-4-yl)oxy)pyridine as a white solid (1.6 g, 55%). MS (M+1)+=264.0.

Step 2: The procedure is similar to Step 3[NSSy7062] in Example-623. 0.95 g of 2,6-dichloro-4-((tetrahydro-2H-thiopyran-4-yl)oxy)pyridine gave 4-((2,6-dichloropyridin-4-yl)oxy)tetrahydro-2H-thiopyran 1,1-dioxide as white solid (0.77 g, 68%). MS (M+1)+=298.0.

Step 3: The procedure is similar to Step 1[NSSy6629] in Example-839. 0.42 g of 4-((2,6-dichloropyridin-4-yl)oxy) tetrahydro-2H-thiopyran 1,1-dioxide gave 4-((2-chloro-6-(3-methyl-1H-pyrazol-1-yl)pyridin-4-yl)oxy)tetrahydro-2H-thiopyran 1,1-dioxide as an off-white solid (0.25 g, 51%). MS (M+1)+=342.1.

Step 4[IN11146-089-P1]: The procedure is similar to Step 1[NSSy6629] in Example-839. 0.25 g of 4-((2-chloro-6-(3-methyl-1H-pyrazol-1-yl)pyridin-4-yl)oxy)tetrahydro-2H-thiopyran 1,1-dioxide gave 4-((2-((4,4-difluorocyclohexyl)amino)-6-(3-methyl-1H-pyrazol-1-yl)pyridin-4-yl)oxy) tetrahydro-2H-thiopyran 1,1-dioxide as a white solid (0.04 g, 12%). MS (M+1)+=441.2; 1H-NMR (400 MHz, DMSO-d6): δ 8.39 (d, J=2.00 Hz, 1H), 6.70 (d, J=8.00 Hz, 1H), 6.64 (s, 1H), 6.29 (d, J=2.40 Hz, 1H), 5.92 (s, 1H), 4.70 (s, 1H), 3.94 (s, 1H), 4.12-3.15 (m, 4H), 2.33 (s, 7H), 2.10-1.90 (m, 6H), 1.60-1.48 (m, 2H).

Example-887

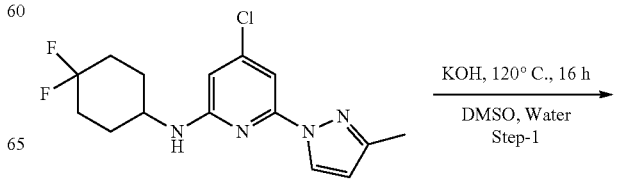

1207

-continued

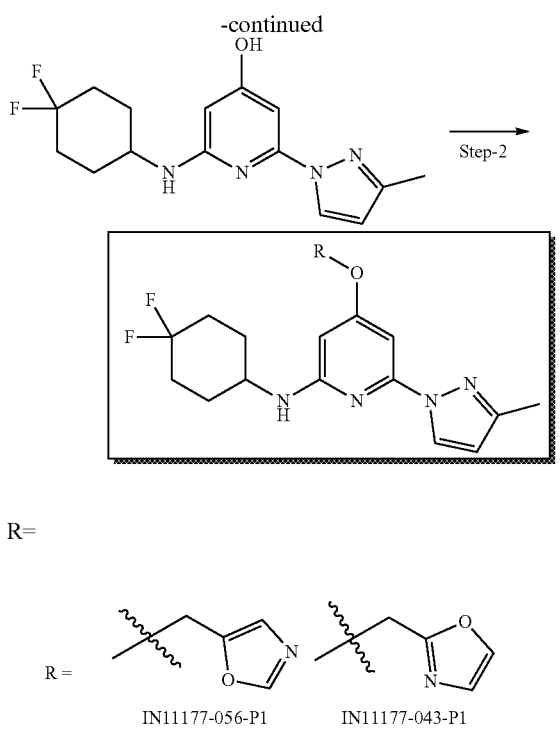

R =

IN11177-056-P1    IN11177-043-P1

Step 1: The procedure is similar to Step 1[B] in Example-838. 0.3 g of 4-chloro-N-(4,4-difluorocyclohexyl)-6-(3-methyl-1H-pyrazol-1-yl)pyridin-2-amine gave 2-((4,4-difluorocyclohexyl)amino)-6-(3-methyl-1H-pyrazol-1-yl)pyridin-4-ol as an off-white solid (0.035 g, 12%). MS (M+1)+=342.1.

TABLE 105

Step 2: The procedure is similar to Step 1[B] in Example-838.

| Compound No | R | Condition | Yield (%) | MS (M + 1)+ |
|---|---|---|---|---|
| IN11177-056-P1 | | Oxazol-5-ylmethyl methanesulfonate, K₂CO₃, DMF, 70° C., 2 h | 32 | 390.0 |
| IN11177-043-P1 | | Oxazol-2-ylmethyl methanesulfonate, K₂CO₃, DMF, 70° C., 2 h | 35 | 390.0 |

Step 2[IN11177-056-P1]: 1H-NMR (400 MHz, DMSO-d6): δ 8.44 (s, 1H), 8.39 (d, J=2.40 Hz, 1H), 7.34 (s, 1H), 6.71 (s, 1H), 6.62 (d, J=2.00 Hz, 1H), 6.29 (d, J=2.80 Hz, 1H), 5.96 (d, J=2.00 Hz, 1H), 5.23 (s, 2H), 3.95 (s, 1H), 2.26 (s, 3H), 2.10-1.90 (m, 6H), 1.60-1.48 (m, 2H).

Step 2[IN11177-043-P1]: 1H-NMR (400 MHz, DMSO-d6): δ 8.39 (s, 1H), 8.19 (s, 1H), 7.29 (s, 1H), 6.76 (d, J=7.60 Hz, 1H), 6.63 (s, 1H), 6.29 (s, 1H), 5.96 (s, 1H), 5.28 (s, 2H), 3.93 (s, 1H), 2.25 (s, 3H), 2.10-1.90 (m, 6H), 1.58-1.48 (m, 2H).

1208

Example-888

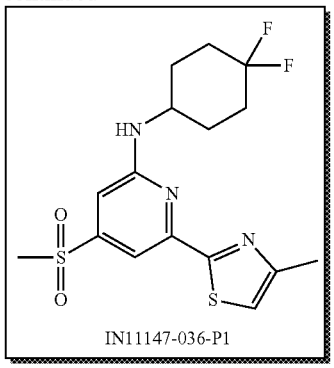

Step 1: To a solution of 2,4,6-trichloropyridine (2 g, 11.05 mmol) in methanol was added sodium thiomethoxide (1.26 g, 17.68 mmol) and stirred at room temperature for 16 h. The reaction mixture was diluted with cold water, stirred for 10 min, the solid formed was filtered and dried under vacuum to afford 2,6-dichloro-4-(methylthio)pyridine as a white solid (1.3 g, 61%). MS (M+1)+=195.8.

Step 2: The procedure is similar to Step 1[NSSy6629] in Example-839. 0.8 g of 2,6-dichloro-4-(methylthio)pyridine gave 6-chloro-N-(4,4-difluorocyclohexyl)-4-(methylthio)pyridin-2-amine as an off-white solid (0.51 g, 42%). MS (M+1)+=292.9.

Step 3[IN11147-026-P1]: The procedure is similar to Step 1[NSSy6989] in Example-839. 0.51 g of 6-chloro-N-(4,4-difluorocyclohexyl)-4-(methylthio)pyridin-2-amine gave N-(4,4-difluorocyclohexyl)-6-(4-methylthiazol-2-yl)-4-(methylthio)pyridin-2-amine as an off-white solid (0.28 g, 39%). MS (M+1)+=356.0; 1H-NMR (400 MHz, DMSO-d6): δ 7.31 (s, 1H), 7.07 (s, 1H), 6.78 (d, J=6.80 Hz, 1H), 6.38 (s, 1H), 3.90 (s, 1H), 2.48 (s, 3H), 2.44 (s, 3H), 2.12-1.88 (m, 6H), 1.62-1.52 (m, 2H).

Step 4[IN11147-031-P1 and IN11147-036-P1]: The procedure is similar to Step 3[NSSy7062] in Example-623. 0.1 g of N-(4,4-difluorocyclohexyl)-6-(4-methylthiazol-2-yl)-4-(methylthio)pyridin-2-amine gave N-(4,4-difluorocyclohexyl)-4-(methylsulfinyl)-6-(4-methylthiazol-2-yl)pyridin-2-amine as an off-white solid (0.04 g, 40%). MS (M+1)+= 372.2; 1H-NMR (400 MHz, DMSO-d6): δ 7.37 (s, 2H), 7.30 (d, J=6.80 Hz, 1H), 6.88 (s, 1H), 3.95 (s, 1H), 2.81 (s, 3H), 2.42 (s, 3H), 2.15-1.90 (m, 6H), 1.68-1.55 (m, 2H) and N-(4,4-difluorocyclohexyl)-4-(methylsulfonyl)-6-(4-methylthiazol-2-yl)pyridin-2-amine as an off-white solid (0.032 g, 30%). MS (M+1)+=388.1; 1H-NMR (400 MHz, DMSO-d6): δ 7.53-7.50 (m, 2H), 7.42 (s, 1H), 7.03 (s, 1H), 4.02 (bs, 1H), 3.28 (s, 3H), 2.44 (s, 3H), 2.10-1.85 (m, 6H), 1.65-1.55 (m, 2H).

Example-889

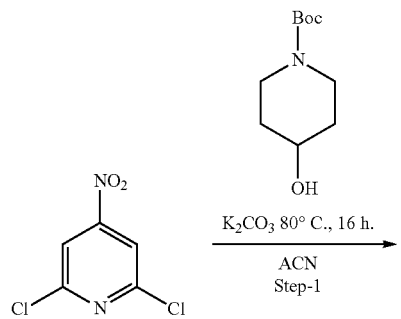

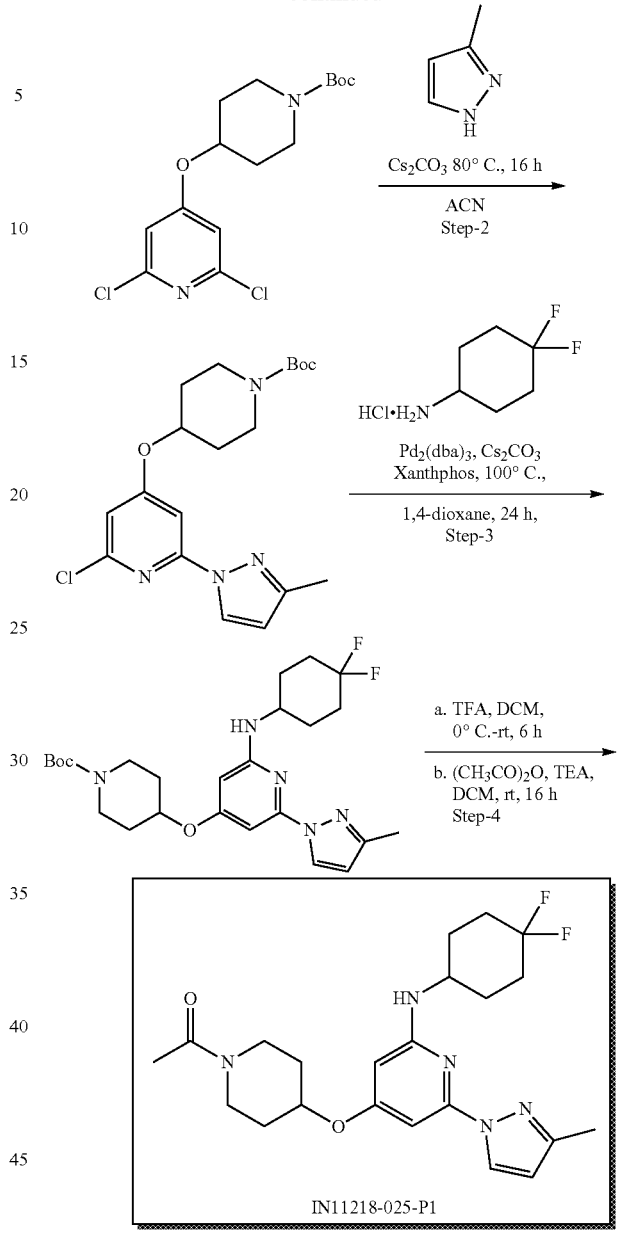

Step 1: The procedure is similar to Step 1[B] in Example-838. 0.5 g of 2,6-dichloro-4-nitropyridine gave tert-butyl 4-((2,6-dichloropyridin-4-yl)oxy) piperidine-1-carboxylate as a pale yellow solid (0.33 g, 37%). MS (M+1)+=347.1.

Step 2: The procedure is similar to Step 1[B] in Example-838. 0.33 g of tert-butyl 4-((2,6-dichloropyridin-4-yl)oxy) piperidine-1-carboxylate gave tert-butyl 4-((2-chloro-6-(3-methyl-1H-pyrazol-1-yl)pyridin-4-yl)oxy) piperidine-1-carboxylate as an off-white solid (0.11 g, 29%). MS (M+1)+= 393.2.

Step 3: The procedure is similar to Step 1[NSSy6629] in Example-839. 0.1 g of tert-butyl 4-((2-chloro-6-(3-methyl-1H-pyrazol-1-yl)pyridin-4-yl)oxy)piperidine-1-carboxylate gave tert-butyl 4-((2-((4,4-difluorocyclohexyl)amino)-6-(3-methyl-1H-pyrazol-1-yl)pyridin-4-yl)oxy)piperidine-1-carboxylate as pale yellow solid (0.06 g, 43%). MS (M+1)+= 492.3.

Step 4[IN11218-025-P1]: The procedure is similar to Step 2[NSSy6924] in Example-857. 0.06 g of tert-butyl 4-((2-((4,4-difluorocyclohexyl)amino)-6-(3-methyl-1H-pyrazol- 1-yl)pyridin-4-yl)oxy)piperidine-1-carboxylate gave 1-(4-((2-((4,4-difluorocyclohexyl)amino)-6-(3-methyl-1H-pyrazol-1-yl)pyridin-4-yl)oxy)piperidin-1-yl)ethan-1-one as an off-white solid (0.03 g, 57%). MS (M+1)+=434.3; 1H-NMR (400 MHz, DMSO-d6): δ 8.38 (d, J=2.4 Hz, 1H), 6.63 (d, J=7.2 Hz, 1H), 6.57 (d, J=2.0 Hz, 1H), 6.28 (d, J=2.4 Hz, 1H), 5.91 (d, J=2.0 Hz, 1H), 4.70-4.63 (m, 1H), 3.96-3.94 (m, 1H), 3.79-3.75 (m, 1H), 3.66-3.63 (m, 1H), 2.28 (s, 3H), 2.05-2.00 (m, 13H), 1.65-1.54 (m, 5H).

Example-890

Step 1: The procedure is similar to Step 4[NSSy6067] in Example-628. 2 g of 2,6-dichloro-4-iodopyridine gave tert-butyl 4-(2,6-dichloropyridin-4-yl)-4-hydroxypiperidine-1-carboxylate as an off-white solid (1.5 g, 30%). MS (M+1)+= 347.2.

Step 2: The procedure is similar to Step 1[B] in Example-838. 1.5 g of tert-butyl 4-(2,6-dichloropyridin-4-yl)-4-hydroxypiperidine-1-carboxylate gave tert-butyl 4-(2-chloro-6-(3-methyl-1H-pyrazol-1-yl)pyridin-4-yl)-4-hydroxypiperidine-1-carboxylate as red colour solid (0.7 g, 41%). MS (M+1)+=393.2.

Step 3: The procedure is similar to Step 1[NSSy6629] in Example-839. 0.6 g of tert-butyl 4-(2-chloro-6-(3-methyl-1H-pyrazol-1-yl)pyridin-4-yl)-4-hydroxypiperidine-1-carboxylate gave tert-butyl 4-(2-((4,4-difluorocyclohexyl)amino)-6-(3-methyl-1H-pyrazol-1-yl)pyridin-4-yl)-4-hydroxypiperidine-1-carboxylate as an off-white solid (0.4 g, crude). MS (M−H2O)+=474.3.

Step 4[IN11251-024-P1]: The procedure is similar to Step 4[NSSy6711] in Example-854. 0.35 g of tert-butyl 4-(2-((4,4-difluorocyclohexyl)amino)-6-(3-methyl-1H-pyrazol-1-yl)pyridin-4-yl)-4-hydroxypiperidine-1-carboxylate gave 4-(2-((4,4-difluorocyclohexyl)amino)-6-(3-methyl-1H-pyrazol-1-yl)pyridin-4-yl)-1-methylpiperidin-4-ol as a white solid (0.04 g, 10%). MS (M+1)+=406.3; $^1$H-NMR (400 MHz, DMSO-d$_6$): δ 8.15 (d, J=2.40 Hz, 1H), 7.63 (d, J=8.40 Hz, 1H), 6.81 (d, J=7.20 Hz, 1H), 6.73 (s, 1H), 6.50 (d, J=8.40 Hz, 1H), 6.35 (d, J=2.40 Hz, 1H), 3.85 (s, 1H), 2.48-2.22 (m, 7H), 2.10 (s, 3H), 2.05-1.80 (m, 6H), 1.60-1.40 (m, 6H).

Example-891

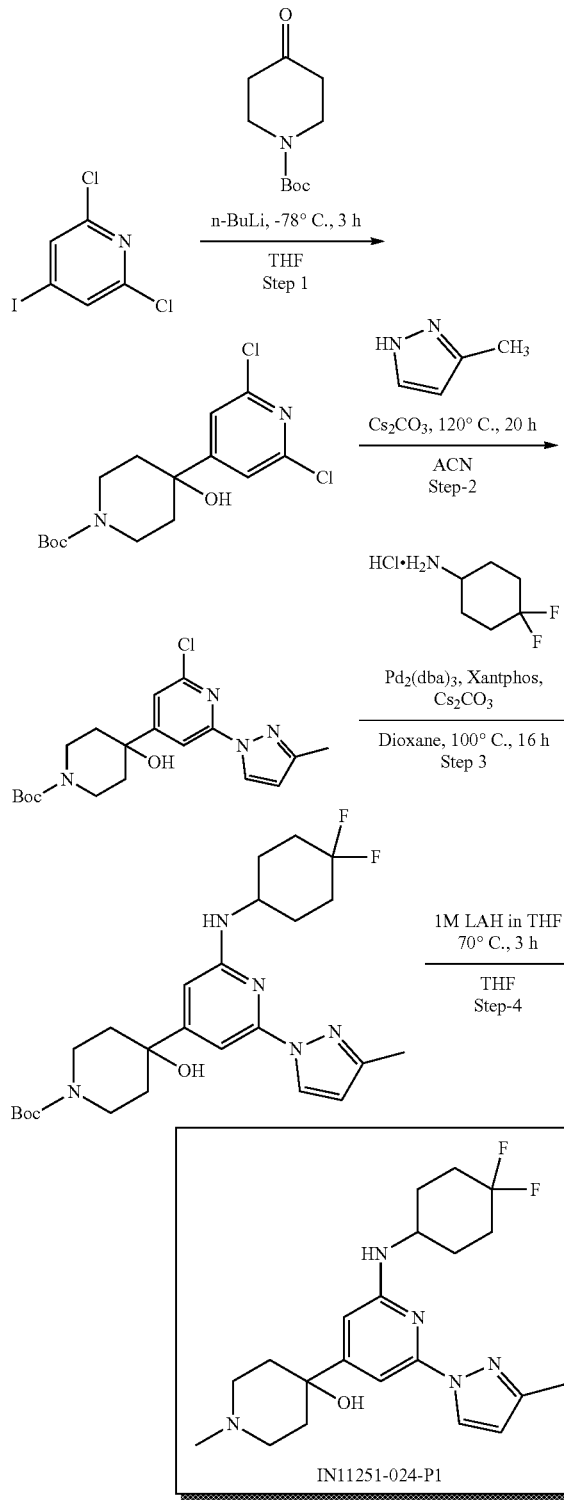

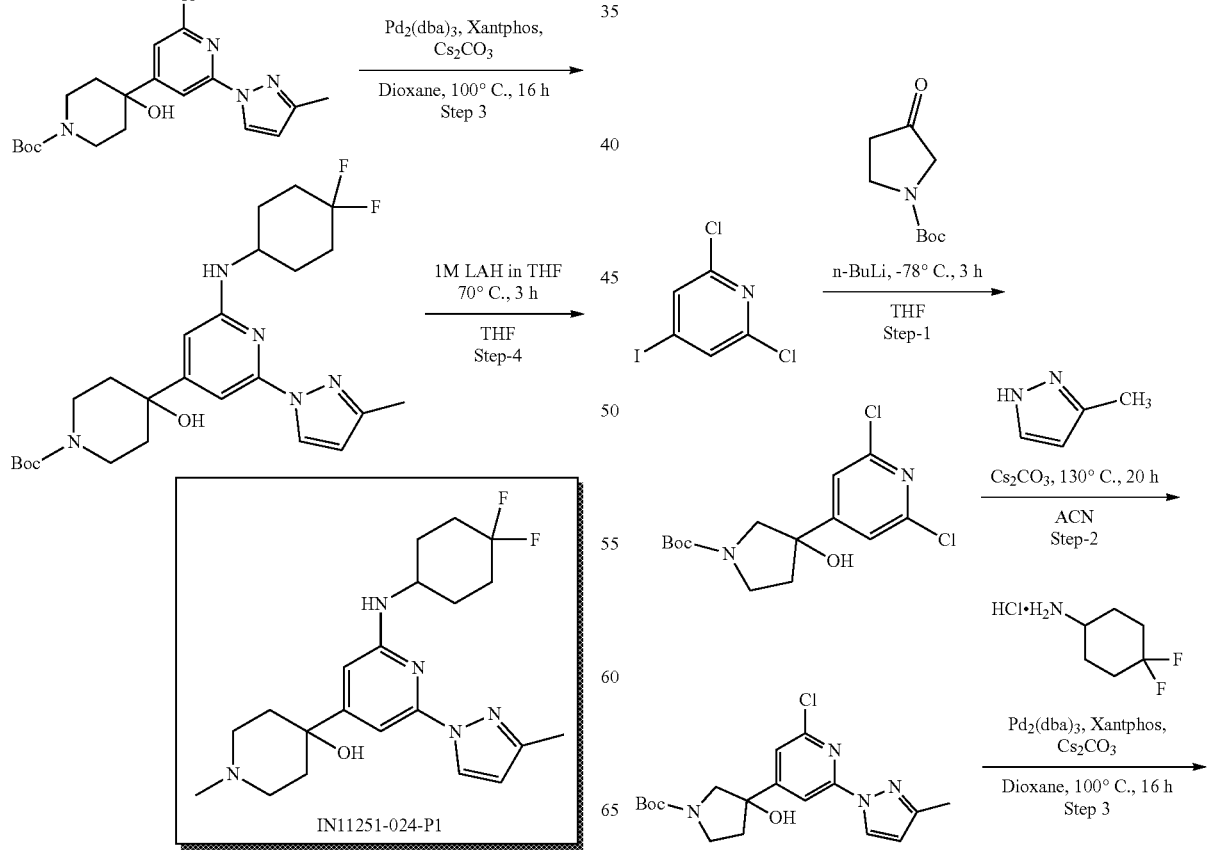

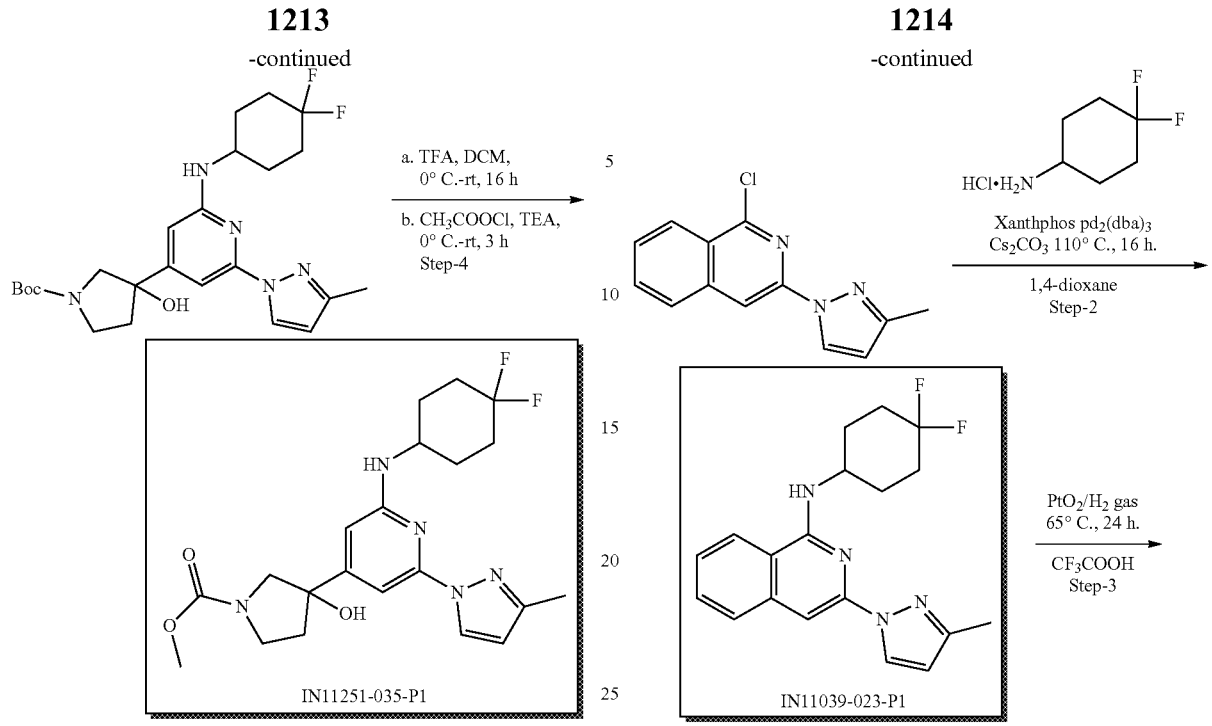

Step 1: The procedure is similar to Step 4[NSSy6067] in Example-628. 2 g of 2,6-dichloro-4-iodopyridine gave tert-butyl 3-(2,6-dichloropyridin-4-yl)-3-hydroxypyrrolidine-1-carboxylate as pale brown solid (2 g, crude).

Step 2: The procedure is similar to Step 1[B] in Example-838. 1 g of tert-butyl 3-(2,6-dichloropyridin-4-yl)-3-hydroxypyrrolidine-1-carboxylate gave tert-butyl 3-(2-chloro-6-(3-methyl-1H-pyrazol-1-yl)pyridin-4-yl)-3-hydroxypyrrolidine-1-carboxylate as an off-white solid (0.7 g, 63%). MS (M+1)+=379.2.

Step 3: The procedure is similar to Step 1[NSSy6629] in Example-839. 0.58 g of tert-butyl 3-(2-chloro-6-(3-methyl-1H-pyrazol-1-yl)pyridin-4-yl)-3-hydroxypyrrolidine-1-carboxylate gave tert-butyl 3-(2-((4,4-difluorocyclohexyl)amino)-6-(3-methyl-1H-pyrazol-1-yl)pyridin-4-yl)-3-hydroxypyrrolidine-1-carboxylate as a brown solid (0.47 g, 55%). MS (M+1)+=478.3.

Step 4[IN11251-035-P1]: The procedure is similar to Step 2[NSSy6924] in Example-857.0.47 g of tert-butyl 3-(2-((4,4-difluorocyclohexyDamino)-6-(3-methyl-1H-pyrazol-1-yl)pyridin-4-yl)-3-hydroxypyrrolidine-1-carboxylate gave methyl 3-(2-((4,4-difluorocyclohexyl)amino)-6-(3-methyl-1H-pyrazol-1-yl)pyridin-4-yl)-3-hydroxypyrrolidine-1-carboxylate as an off-white solid (0.08 g, 20%). MS (M+1)+= 436.3; $^1$H-NMR (400 MHz, DMSO-$d_6$): δ 8.41 (d, J=2.80 Hz, 1H), 7.02 (d, J=1.60 Hz, 1H), 6.81 (d, J=6.80 Hz, 1H), 6.50 (s, 1H), 6.29 (d, J=2.80 Hz, 1H), 5.57 (s, 1H), 3.99 (s, 1H), 3.65-3.40 (m, 7H), 2.26 (s, 3H), 2.20-1.90 (m, 8H), 1.62-1.50 (m, 2H).

Example-892

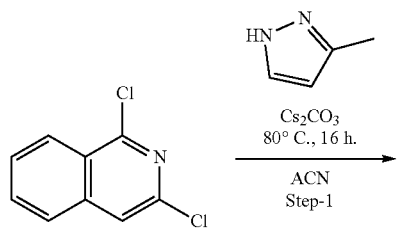

Step 1: The Procedure is similar to Step 1[B] in Example-838. 1 g of 1,3-dichloroisoquinoline gave 1-chloro-3-(3-methyl-1H-pyrazol-1-yl) isoquinoline (1.15 g, 93%). MS (M+1)+=244.1.

Step 2[IN11039-023-P1]: The Procedure is similar to Step 1[NSSy6629] in Example-839. 0.5 g of 1-chloro-3-(3-methyl-1H-pyrazol-1-yl) isoquinoline gave N-(4,4-difluorocyclohexyl)-3-(3-methyl-1H-pyrazol-1-yl)isoquinolin-1-amine (0.4 g, 57%). MS (M+1)+=343.2; 1H-NMR (400 MHz, DMSO-d6): δ 8.35 (d, J=8.80 Hz, 1H), 8.11 (d, J=2.00 Hz, 1H), 7.58 (d, J=8.40 Hz, 1H), 7.46 (t, J=7.20 Hz, 1H), 7.16 (t, J=8.00 Hz, 1H), 6.70 (s, 1H), 6.37 (d, J=2.00 Hz, 1H), 3.90-3.80 (m, 1H), 2.39 (s, 3H), 2.20-1.85 (m, 7H), 1.75-1.60 (m, 2H).

Step 3[IN11039-036-P1]: The Procedure is similar to Step 2[NSSy6464] in Example-869. 0.2 g of N-(4,4-difluorocyclohexyl)-3-(3-methyl-1H-pyrazol-1-yl) isoquinolin-1-amine gave N-(4,4-difluorocyclohexyl)-3-(3-methyl-1H-pyrazol-1-yl)-5,6,7,8-tetrahydro isoquinolin-1-amine (0.11 g, 54%). MS (M+1)+=347.1; 1H-NMR (400 MHz, CDCl3): δ 7.80 (d, J=2.40 Hz, 1H), 6.17 (d, J=2.00 Hz, 1H), 6.12 (s, 1H), 4.23 (d, J=8.00 Hz, 1H), 3.72-3.62 (m, 1H), 2.78-2.70 (m, 4H), 2.33 (s, 3H), 2.15-2.00 (m, 4H), 1.95-1.80 (m, 2H), 1.78-1.65 (m, 4H), 1.64-1.60 (m, 2H).

Example-893

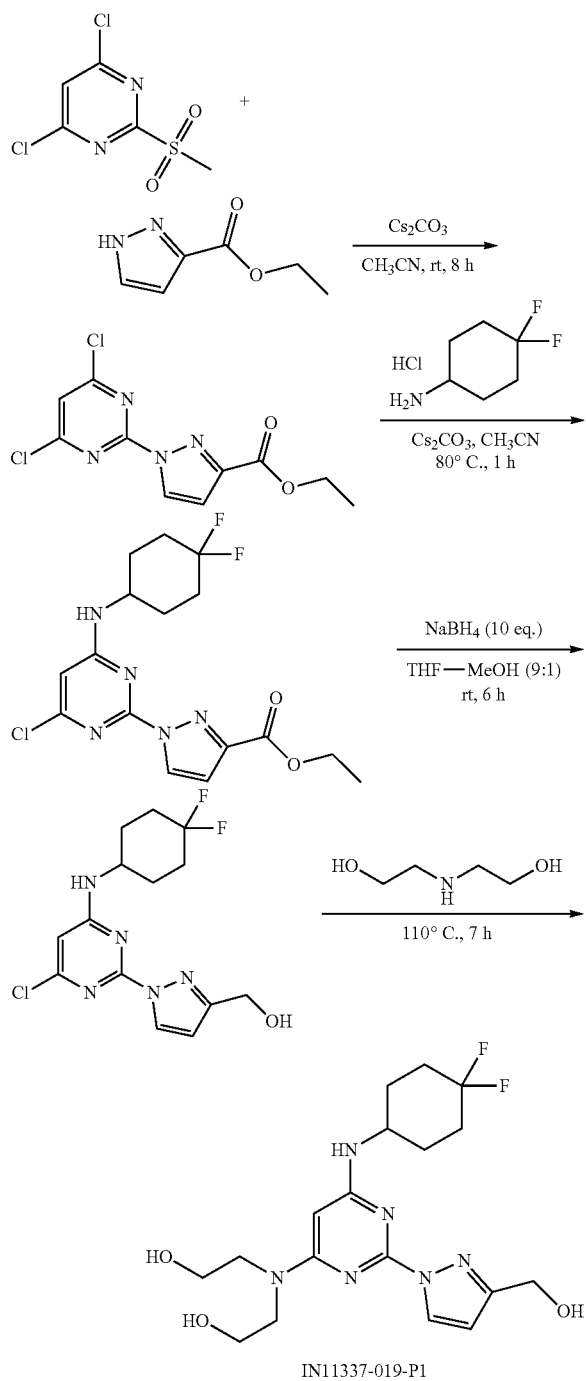

IN11337-019-P1

Step 1: A 250 mL 2-neck round-bottomed equipped with stir bar was charged with 4,6-dichloro-2-(methylsulfonyl)pyrimidine (5.0 g, 22.12 mmol, 1.0 eq.), ethyl 1H-pyrazole-3-carboxylate (3.10 g, 22.12 mmol, 1.0 eq.) and cesium carbonate (7.28 g, 22.12 mmol, 1.0 eq.) in acetonitrile (50 mL) stirred at rt for 8 h. Progress of the reaction was monitored by TLC. Reaction mass diluted with water (80 mL), extracted with ethyl acetate (2×40 mL) and the combined organic layer was washed with water (50 ml), brine (25 mL), dried over anhydrous sodium sulfate and concentrated under reduced pressure. The crude product was purified by CombiFlash by using with 15% ethyl acetate in hexane as eluent. The desired fractions were evaporated under reduced pressure to afford ethyl 1-(4,6-dichloropyrimidin-2-yl)-1H-pyrazole-3-carboxylate (off-white solid) (1.8 g, 6.26 mmol, 28%) MS (M+H): m/z=287.10.

Step 2: A 100 mL 2-neck round-bottomed equipped with stir bar was charged with ethyl 1-(4,6-dichloropyrimidin-2-yl)-1H-pyrazole-3-carboxylate (1.80 g, 6.29 mmol, 1.0 eq.), 4,4-difluorocyclohexan-1-amine hydrochloride (1.180 g, 6.92 mmol, 1.01 eq.) and cesium carbonate (4.70 g, 14.4 mmol, 2.3 eq.) in toluene (20 mL) stirred at 85° C. for 1 h. Progress of the reaction was monitored by TLC. Reaction mass cooled to rt, diluted with water (60 mL), extracted with ethyl acetate (2×50 mL). The combined organic layer was washed with water (50 mL), brine (50 mL), dried over anhydrous sodium sulfate and concentrated under reduced pressure. Crude product was triturated with diethyl ether (20.0 mL) and dried to afford ethyl 1-(4-chloro-6-((4,4-difluorocyclohexyl)amino)pyrimidin-2-yl)-1H-pyrazole-3-carboxylate (1.6 g, 6.26 mmol, 66%) MS (M+H): m/z=385.6.

Step 3: A 100 mL 2-neck round-bottomed equipped with stir bar was charged with ethyl 1-(4-chloro-6-((4,4-difluorocyclohexyl)amino)pyrimidin-2-yl)-1H-pyrazole-3-carboxylate (100.0 mg, 0.25 mmol, 1.0 eq.) added THF:Methanol (9:1 mixture) then added Sodium borohydride (98.0 mg, 2.59 mmol, 10.36 eq.) (Spectrochem) at RT, then whole reaction mixture together stirred at RT for 6 h. Progress of the reaction was monitored by TLC. Reaction mass was diluted with (water 30 mL) ethyl acetate (20 mL×2) times extracted and separated organic layer was dried over anhydrous sodium sulfate and concentrated and dried to get the crude compound. The crude product was purified by CombiFlash using 12 g column and 8% MeOH in DCM as eluents. The desired fractions were evaporated under reduced pressure to afford ethyl 1-(4-chloro-6-((4,4-difluorocyclohexyl)amino)pyrimidin-2-yl)-1H-pyrazole-3-carboxylate (40 mg, 0.116 mmol, 47%) MS (M+H): m/z=343.10.

Step 4: A 100 mL sealed tube equipped with small stir bar charged with ethyl 1-(4-chloro-6-((4,4-difluorocyclohexyl)amino)pyrimidin-2-yl)-1H-pyrazole-3-carboxylate (40.0 mg, 0.116 mmol, 1.0 eq.), Et3N (0.16 mL, 1.16 mmol, 10.0 eq.) and 2,2'-azanediylbis-ethan-1-ol (122.0 mg, 1.16 mmol, 10.0 eq.). Then sealed tube was capped tightly and heated at 110° C. for 7 h. The progress of the reaction was monitored by TLC. Reaction mass was diluted with water (10 mL) extracted with ethyl acetate (2×10 mL). The combined organic layer was washed with water (10 mL), brine (10 mL), dried over anhydrous sodium sulfate and under reduced pressure. The crude product was purified by CombiFlash using 12 g column and 10% MeOH in DCM as eluents. The desired fractions were evaporated under reduced pressure to afford 2,2'-(((6-((4,4-difluorocyclohexyl)amino)-2-(3-(hydroxymethyl)-1H-pyrazol-1-yl)pyrimidin-4-yl)azanediyl)bis-(ethan-1-ol) IN11337-019-P1 (20 mg, 0.048 mmol, 42%) MS (M+H): m/z=412.7. 1H NMR (DMSO-d6, 400 MHz) δ ppm: 1.52-1.57 (m, 2H), 1.85-2.08 (m, 6H), 3.56-3.58 (m, 8H), 4.0 (brs, 1H), 4.47 (d, J=5.6 Hz, 2H), 4.84 (t, J=5.6 Hz, 2H), 5.14 (t, J=5.6 Hz, 1H), 5.44 (s, 1H), 6.41 (d, J=2.4 Hz, 1H), 6.97 (d, J=7.6 Hz, 1H), 8.43 (d, J=3.2 Hz, 1H).

BIOLOGICAL ASSAYS

The biological activity was determined as follows. The ionic current through small-conductance $Ca^{2+}$-activated $K^+$ channels (SK channels, subtype 2) was measured using the whole-cell configuration of the patch-clamp technique in a patch-clamp set-up using HEK293 tissue culture cells expressing SK2 channels as described in Hougaard et al., British Journal of Pharmacology 151, 655-665, May 8, 2007, the entire teachings of which are incorporated herein by reference. In one aspect, a compound is defined to be an SK PAM if the compound increases current in this assay, for example, if the $SC_{100}$ value of the compound is less than or equal to 10 µM as determined by this assay. The $SC_{100}$ value is defined to be the concentration of compound that increases the basal current by 100%.

The $SC_{100}$ values are given in Table 106 and 107.

TABLE 106

| Cmpd No. | $SC_{100}$ uM |
|---|---|
| 100 | + |
| 101 | ++ |
| 102 | ++ |
| 103 | + |
| 104 | ++ |
| 105 | + |
| 106 | ++ |
| 107 | + |
| 108 | + |
| 109 | + |
| 110 | ++ |
| 111 | + |
| 112 | ++ |
| 113 | ++ |
| 114 | + |
| 115 | + |
| 116 | ++ |
| 117 | ++ |
| 118 | + |
| 119 | + |
| 120 | ++ |
| 121 | + |
| 122 | + |
| 123 | + |
| 124 | + |
| 125 | + |
| 126 | ++ |
| 127 | ++ |
| 128 | + |
| 129 | + |
| 130 | + |
| 131 | + |
| 132 | ++ |
| 133 | + |
| 134 | ++ |
| 135 | + |
| 136 | ++ |
| 137 | ++ |
| 138 | + |
| 139 | + |
| 140 | + |
| 141 | ++ |
| 142 | + |
| 143 | ++ |
| 144 | + |
| 145 | + |
| 146 | ++ |
| 147 | ++ |
| 148 | ++ |
| 149 | ++ |
| 150 | + |
| 151 | ++ |
| 152 | + |
| 153 | + |
| 154 | + |
| 155 | + |
| 156 | ++ |
| 157 | ++ |
| 158 | ++ |

TABLE 106-continued

| Cmpd No. | $SC_{100}$ uM |
|---|---|
| 159 | ++ |
| 160 | + |
| 161 | + |
| 162 | ++ |
| 163 | + |
| 164 | + |
| 165 | + |
| 166 | + |
| 167 | + |
| 168 | + |
| 169 | ++ |
| 170 | ++ |
| 171 | ++ |
| 172 | + |
| 173 | ++ |
| 174 | ++ |
| 175 | ++ |
| 176 | + |
| 177 | + |
| 178 | + |
| 179 | ++ |
| 180 | + |
| 181 | + |
| 182 | ++ |
| 183 | + |
| 184 | + |
| 185 | ++ |
| 186 | ++ |
| 187 | ++ |
| 188 | ++ |
| 189 | +++ |
| 190 | ++ |
| 191 | ++ |
| 192 | ++ |
| 193 | + |
| 194 | ++ |
| 195 | ++ |
| 196 | + |
| 197 | ++ |
| 198 | + |
| 199 | ++ |
| 200 | ++ |
| 201 | ++ |
| 202 | + |
| 203 | ++ |
| 204 | + |
| 205 | ++ |
| 206 | + |
| 207 | + |
| 208 | ++ |
| 209 | + |
| 210 | ++ |
| 211 | +++ |
| 212 | + |
| 213 | ++ |
| 214 | + |
| 215 | + |
| 216 | ++ |
| 217 | + |
| 218 | ++ |
| 219 | + |
| 220 | ++ |
| 221 | + |
| 222 | + |
| 223 | + |
| 224 | + |
| 225 | + |
| 226 | ++ |
| 227 | ++ |
| 228 | ++ |
| 229 | ++ |
| 230 | + |
| 231 | ++ |
| 232 | + |
| 233 | ++ |
| 234 | + |
| 235 | ++ |

TABLE 106-continued

| Cmpd No. | SC$_{100}$ uM |
|---|---|
| 236 | + |
| 237 | ++ |
| 238 | ++ |
| 239 | ++ |
| 240 | + |
| 241 | + |
| 242 | + |
| 243 | + |
| 244 | ++ |
| 245 | + |
| 246 | +++ |
| 247 | ++ |
| 248 | ++ |
| 249 | + |
| 250 | ++ |
| 251 | ++ |
| 252 | + |
| 253 | ++ |
| 254 | + |
| 255 | + |
| 256 | ++ |
| 257 | + |
| 258 | ++ |
| 259 | + |
| 260 | + |
| 261 | ++ |
| 262 | ++ |
| 263 | ++ |
| 264 | ++ |
| 265 | + |
| 266 | ++ |
| 267 | + |
| 268 | ++ |
| 269 | + |
| 270 | + |
| 271 | ++ |
| 272 | + |
| 273 | ++ |
| 274 | + |
| 275 | + |
| 276 | + |
| 277 | ++ |
| 278 | ++ |
| 279 | ++ |
| 280 | + |
| 281 | ++ |
| 282 | + |
| 283 | ++ |
| 284 | ++ |
| 285 | + |
| 286 | +++ |
| 287 | ++ |
| 288 | ++ |
| 289 | ++ |
| 290 | ++ |
| 291 | ++ |
| 292 | ++ |
| 293 | ++ |
| 294 | ++ |
| 295 | ++ |
| 296 | ++ |
| 297 | ++ |
| 298 | ++ |
| 299 | ++ |
| 300 | + |
| 301 | ++ |
| 302 | ++ |
| 303 | ++ |
| 304 | ++ |
| 305 | ++ |
| 306 | + |
| 307 | + |
| 308 | + |
| 309 | ++ |
| 310 | ++ |
| 311 | +++ |
| 312 | ++ |
| 313 | ++ |
| 314 | + |
| 315 | + |
| 316 | +++ |
| 317 | +++ |
| 318 | ++ |
| 319 | + |
| 320 | ++ |
| 321 | + |
| 322 | ++ |
| 323 | ++ |
| 324 | ++ |
| 325 | + |
| 326 | ++ |
| 327 | + |
| 328 | + |
| 329 | ++ |
| 330 | ++ |
| 331 | + |
| 332 | ++ |
| 333 | + |
| 334 | + |
| 335 | ++ |
| 336 | ++ |
| 337 | + |
| 338 | ++ |
| 339 | ++ |
| 340 | + |
| 341 | ++ |
| 342 | ++ |
| 343 | ++ |
| 344 | + |
| 345 | ++ |
| 346 | + |
| 347 | ++ |
| 348 | ++ |
| 349 | ++ |
| 350 | + |
| 351 | + |
| 352 | + |
| 353 | + |
| 354 | + |
| 355 | + |
| 356 | + |
| 357 | + |
| 358 | + |
| 360 | ++ |
| 361 | ++ |
| 362 | ++ |
| 363 | ++ |
| 364 | ++ |
| 365 | ++ |

+ means >1 uM;
++ means 200 nM-1000 nM;
+++ means <200 nM.

TABLE 107

| NSSy # | SC$_{100}$ (μM) |
|---|---|
| NSSy6909 | ++ |
| NSSy6957 | + |
| NSSy6629 | ++ |
| NSSy6607 | ++ |
| NSSy6598 | ++ |
| NSSy6989 | + |
| NSSy6886 | + |
| NSSy6919 | +++ |
| NSSy6936 | + |
| NSSy6972 | + |
| NSSy6389 | + |
| NSSy6564 | + |
| NSSy6519 | ++ |
| NSSy6638 | ++ |

TABLE 107-continued

| | |
|---|---|
| NSSy6639 | + |
| NSSy6644 | + |
| NSSy6654 | + |
| NSSy6391 | + |
| NSSy6558 | ++ |
| NSSy6710 | + |
| NSSy6711 | ++ |
| NSSy6499 | + |
| NSSy6524 | |
| NSSy6522 | ++ |
| NSSy6498 | |
| NSSy6585 | + |
| NSSy6608 | |
| NSSy6958 | ++ |
| NSSy6677 | + |
| NSSy6679 | ++ |
| NSSy6688 | ++ |
| NSSy6698 | + |
| NSSy6574 | + |
| NSSy6580 | + |
| NSSy6581 | + |
| NSSy6584 | + |
| NSSy6700 | + |
| NSSy6913 | ++ |
| NSSy6914 | +++ |
| NSSy6675 | + |
| NSSy6686 | ++ |
| NSSy6625 | + |
| NSSy6525 | + |
| NSSy6523 | + |
| NSSy6924 | ++ |
| NSSy6995 | NT |
| NSSy6986 | ++ |
| NSSy6722 | + |
| NSSy6684 | + |
| NSSy6704 | + |
| NSSy6800 | ++ |
| NSSy6744 | ++ |
| NSSy6783 | ++ |
| NSSy6468 | + |
| NSSy6467 | + |
| NSSy6471 | + |
| NSSy6931 | + |
| NSSy6917 | ++ |
| NSSy6930 | ++ |
| NSSy6721 | + |
| NSSy6724 | ++ |
| NSSy6464 | + |
| NSSy6590 | ++ |
| NSSy6591 | + |
| NSSy6593 | ++ |
| NSSy6736 | + |
| NSSy6678 | + |
| NSSy6604 | + |
| NSSy6697 | + |
| NSSy6729 | + |
| NSSy6612 | + |
| NSSy6613 | + |
| NSSy6651 | + |
| NSSy6614 | + |
| NSSy6650 | + |
| NSSy6674 | + |
| NSSy6941 | + |
| NSSy6945 | ++ |
| NSSy7043 | + |
| NSSy6061 | + |
| NSSy6128 | ++ |
| NSSy6935 | ++ |
| NSSy5161 | |
| NSSy7028 | + |
| NSSy7012 | + |
| NSSy6994 | ++ |
| NSSy7027 | + |
| NSSy7059 | ++ |
| NSSy6921 | + |
| NSSy7062 | ++ |
| NSSy6850 | ++ |
| NSSy6908 | ++ |
| NSSy6889 | + |
| NSSy6067 | + |

TABLE 107-continued

| | |
|---|---|
| NSSy6134 | + |
| NSSy6140 | NT |
| NSSy6133 | + |
| NSSy6165 | + |
| NSSy6132 | + |
| NSSy5662, NSSy6408 | + |
| NSSy5691 | + |
| NSSy6407 | |
| NSSy5663 | + |
| NSSy5670, NSSy6341 | ++ |
| NSSy6097 | +++ |
| NSSy6091 | ++ |
| NSSy6127 | + |
| NSSy5741 | + |
| NSSy5765 | ++ |
| NSSy5762 | ++ |
| NSSy5786 | ++ |
| NSSy5684 | + |
| NSSy5683 | + |
| NSSy6125 | ++ |
| NSSy6145 | + |
| NSSy6178 | ++ |
| NSSy6251 | ++ |
| NSSy6252 | ++ |
| NSSy6201 | + |
| NSSy5832 | + |
| NSSy5857 | ++ |
| NSSy6368 | |
| NSSy6202 | ++ |
| NSSy5835 | + |
| NSSy5830 | + |
| NSSy5887 | + |
| NSSy5779 | ++ |
| NSSy5818 | + |
| NSSy6880 | ++ |
| NSSy7001 | |
| NSSy6881 | + |
| NSSy6167 | + |
| NSSy6152 | + |
| NSSy6166 | + |
| NSSy6170 | + |
| NSSy6263 | + |
| NSSy5774 | ++ |
| NSSy5787 | ++ |
| NSSy5789 | +++ |
| NSSy5792 | ++ |
| NSSy5795 | ++ |
| NSSy6055 | +++ |
| NSSy6062 | +++ |
| NSSy6093 | ++ |
| NSSy6116 | ++ |
| NSSy6129 | ++ |
| NSSy5796 | +++ |
| NSSy6171 | ++ |
| NSSy6111 | ++ |
| NSSy5740 | ++ |
| NSSy6253 | ++ |
| NSSy5730 | ++ |
| NSSy6007 | ++ |
| NSSy6258 | ++ |
| NSSy6056 | ++ |
| NSSy6106 | + |
| NSSy5868 | +++ |
| NSSy5943 | |
| NSSy6045 | + |
| NSSy6078 | + |
| NSSy6082 | + |
| NSSy6131 | +++ |
| NSSy6100 | ++ |
| NSSy6124 | ++ |
| NSSy6115 | ++ |
| NSSy6149 | ++ |
| NSSy6099 | +++ |
| NSSy6105 | + |
| NSSy5854 | ++ |
| NSSy6126 | + |
| NSSy6057 | + |
| NSSy5699 | + |

TABLE 107-continued

| | |
|---|---|
| NSSy5703 | + |
| NSSy5709 | ++ |
| NSSy5710 | ++ |
| NSSy5715 | ++ |
| NSSy6348 | + |
| NSSy6265 | + |
| NSSy6386 | + |
| NSSy6420 | + |
| NSSy6445 | + |
| NSSy6446 | + |
| NSSy6511 | + |
| NSSy6486 | + |
| NSSy6526 | + |
| NSSy6540 | + |
| NSSy6541 | + |
| NSSy6539 | + |
| NSSy6550 | + |
| NSSy6394 | + |
| NSSy6272 | ++ |
| NSSy6529 | + |
| NSSy6993 | ++ |
| NSSy7011 | ++ |
| NSSy7021 | +++ |
| NSSy7034 | + |
| NSSy6343 | + |
| NSSy7087 | + |
| NSSy6907 | ++ |
| NSSy5618 | + |
| NSSy5619 | + |
| NSSy5624 | + |
| NSSy5625 | +++ |
| NSSy5651 | ++ |
| NSSy5689 | + |
| NSSy5690 | ++ |
| NSSy6049 | + |
| NSSy6050 | NT |
| NSSy5648 | + |
| NSSy5629 | +++ |
| NSSy5726 | ++ |
| NSSy5630 | |
| NSSy5879 | ++ |
| NSSy5647 | ++ |
| NSSy5893 | ++ |
| NSSy5902 | ++ |
| NSSy5672 | ++ |
| NSSy5631 | ++ |
| NSSy5664 | ++ |
| NSSy5847 | + |
| NSSy5848 | + |
| NSSy6054 | + |
| NSSy6101 | +++ |
| NSSy6113 | +++ |
| NSSy6162 | ++ |
| NSSy6347 | |
| NSSy6072 | + |
| NSSy6982 | +++ |
| NSSy6981 | +++ |
| NSSy6369 | ++ |
| NSSy7063 | + |
| NSSy7042 | + |
| NSSy7031 | + |
| NSSy7055 | + |
| NSSy5620 | ++ |
| NSSy5653 | ++ |
| NSSy5622 | ++ |
| NSSy5826 | ++ |
| NSSy5635 | ++ |
| NSSy5637 | ++ |
| NSSy5827, NSSy6791 | ++ |
| NSSy5828 | +++ |
| NSSy5860 | ++ |
| NSSy5861 | ++ |
| NSSy5869 | +++ |
| NSSy5996 | ++ |
| NSSy6371 | +++ |
| NSSy6417 | +++ |
| NSSy6451 | +++ |
| NSSy5846 | ++ |
| NSSy6019 | ++ |
| NSSy5829 | ++ |
| NSSy5839 | ++ |
| NSSy6395 | ++ |
| NSSy6685 | |
| NSSy6846 | + |
| NSSy6415 | ++ |
| NSSy6416 | ++ |
| NSSy6576 | ++ |
| NSSy6469 | +++ |
| NSSy6891 | ++ |
| NSSy6812 | + |
| NSSy5933 | ++ |
| NSSy5640 | ++ |
| NSSy5644 | ++ |
| NSSy5645 | ++ |
| NSSy5676 | +++ |
| NSSy5701 | +++ |
| NSSy6355 | ++ |
| NSSy6740 | |
| Nssy 6851 | |
| Nssy 5129 | |
| NSSy6861 | ++ |
| NSSy7053 | ++ |
| NSSy7079 | ++ |
| NSSy7064 | ++ |
| NSSy7065 | ++ |
| NSSy6470 | + |
| NSSy6472 | + |
| NSSy6513 | + |
| NSSy6514 | + |
| NSSy6473 | ++ |
| NSSy6563 | ++ |
| NSSy6435 | + |
| NSSy6730 | ++ |
| NSSy6750 | ++ |
| NSSy6782 | ++ |
| NSSy6773 | ++ |
| NSSy5615 | ++ |
| NSSy5713 | + |
| NSSy5632 | +++ |
| NSSy5641 | ++ |
| NSSy5722 | |
| NSSy5638 | ++ |
| NSSy5737 | ++ |
| NSSy5643, NSSy5756 | ++ |
| NSSy5681 | + |
| NSSy5753 | |
| NSSy6849 | ++ |
| NSSy6719 | +++ |
| NSSy5759 | ++ |
| NSSy5763 | ++ |
| NSSy6573 | ++ |
| NSSy5721 | ++ |
| NSSy5824 | +++ |
| NSSy5838 | +++ |
| NSSy5837 | +++ |
| NSSy5819 | ++ |
| NSSy5815 | ++ |
| NSSy6288 | ++ |
| NSSy5646 | ++ |
| NSSy5675 | +++ |
| NSSy5807 | +++ |
| NSSy5695 | ++ |
| NSSy5686 | ++ |
| NSSy5717 | +++ |
| NSSy5680 | +++ |
| NSSy5694 | +++ |
| NSSy5677 | ++ |
| NSSy5687 | ++ |
| NSSy5980 | ++ |
| NSSy5655 | ++ |
| NSSy5688 | ++ |
| NSSy6285 | + |
| NSSy5674 | +++ |
| NSSy6374 | + |
| NSSy5959 | + |
| NSSy5957 | + |
| NSSy6044 | + |
| NSSy5808 | ++ |

TABLE 107-continued

| | |
|---|---|
| NSSy5934 | + |
| NSSy5972 | + |
| NSSy6342 | + |
| NSSy6910 | +++ |
| NSSy6370 | |
| NSSy6885 | +++ |
| NSSy6897 | ++ |
| NSSy6888 | +++ |
| NSSy6436 | +++ |
| NSSy6489 | + |

| IN # | SC$_{100}$ (µM) |
|---|---|
| IN11251-020-P1 | + |
| IN11218-030-P1 | ++ |
| IN11147-096-P1 | +++ |
| IN11251-011-P2 | + |
| IN11250-007-P1 | + |
| IN11147-082-P1 | ++ |
| IN11196-080-P1 | + |
| IN11177-064-P1 | ++ |
| IN11177-049-P1 | ++ |
| IN11239-029-P1 | + |
| IN11218-026-P1 | + |
| IN11251-011-P1 | + |
| IN11250-017-P1 | + |
| IN11218-025-P1 | ++ |
| IN11177-056-P1 | +++ |
| IN11196-081-P1 | + |
| IN11196-041-P1 | + |
| IN11196-039-P1 | ++ |
| IN11239-001-P1 | ++ |
| IN11147-077-P1 | ++ |
| IN11146-089-P1 | ++ |
| IN11217-003-P1 | ++ |
| IN11147-066-P1 | ++ |
| IN11177-043-P1 | ++ |
| IN11111-097-P1 | ++ |
| IN11106-091-P1 | ++ |
| IN11125-095-P1 | + |
| IN11133-094-P1 | + |
| IN11216-001-P1 | + |
| IN11111-100-P1 | ++ |
| IN11177-029-P1 | ++ |
| IN11196-026-P1 | + |
| IN11133-097-P1 | ++ |
| IN11140-089-P1 | + |
| IN11140-096-P1 | + |
| IN11137-079-P1 | + |
| IN11130-077-P1 | + |
| IN11166-042-P1 | ++ |
| IN11147-054-P1 | ++ |
| IN11125-091-P1 | + |
| IN11140-086-P1 | + |
| IN11140-081-P1 | + |
| IN11196-007-P2 | + |
| IN11196-007-P1 | ++ |
| IN11130-076-P1 | + |
| IN11177-025-P1 | + |
| IN11111-092-P1 | ++ |
| IN11140-083-P1 | + |
| IN11147-036-P1 | +++ |
| IN11133-062-P1 | NT |
| IN11137-074-P1 | ++ |
| IN11106-077-P1 | ++ |
| IN11166-036-P1 | ++ |
| IN11133-061-P1 | +++ |
| IN11133-069-P1 | +++ |
| IN11133-068-P1 | ++ |
| IN11140-065-P1 | + |
| IN11104-059-P1 | + |
| IN11130-053-P1 | +++ |
| IN11166-038-P1 | +++ |
| IN11104-100-P1 | + |
| IN11140-066-P1 | + |
| IN11133-049-P1 | ++ |
| IN11137-072-P1 | ++ |
| IN11106-066-P1 | + |
| IN11140-063-P1 | + |
| IN11106-065-P1 | + |

TABLE 107-continued

| | |
|---|---|
| IN11147-031-P1 | ++ |
| IN11146-039-P1 | + |
| IN11104-094-P1 | ++ |
| IN11147-026-P1 | +++ |
| IN11140-058-P1 | + |
| IN11140-052-P1 | +++ |
| IN11121-042-P1 | + |
| IN11166-020-P1 | ++ |
| IN11106-062-P1 | +++ |
| IN11111-063-P1 | + |
| IN11140-062-P1 | + |
| IN11125-065-P1 | + |
| IN11108-038-P1 | + |
| IN11104-084-P2 | + |
| IN11146-033-P1 | + |
| IN11104-095-P1 | + |
| IN11130-047-P1 | +++ |
| IN11130-051-P1 | +++ |
| IN11146-016-P1 | + |
| IN11133-031-P1 | + |
| IN11137-041-P1 | + |
| IN11125-052-P1 | + |
| IN11133-037-P1 | +++ |
| IN11104-077-P1 | + |
| IN11130-031-P2 | + |
| IN11130-030-P1 | + |
| IN11146-013-P1 | ++ |
| IN11108-019-P1 | + |
| IN11108-018-P1 | + |
| IN11059-090-P1 | ++ |
| IN11059-095-P1 | ++ |
| IN11107-023-P1 | + |
| IN11107-021-P1 | + |
| IN11133-020-P1 | + |
| IN11125-028-P1 | + |
| IN11137-018-P1 | + |
| IN11106-027-P1 | + |
| IN11106-033-P1 | + |
| IN11140-007-P1 | + |
| IN11104-099-P1 | + |
| IN11079-066-P1 | + |
| IN11059-096-P1 | + |
| IN11111-024-P1 | ++ |
| IN11125-014-P1 | ++ |
| IN11104-041-P1 | ++ |
| IN11111-023-P1 | + |
| IN11107-020-P1 | + |
| IN11133-014-P1 | + |
| IN11079-072-P1 | + |
| IN11079-067-P1 | + |
| IN11054-100-P1 | NT |
| IN11130-005-P1 | + |
| IN11039-094-P1 | + |
| IN11125-012-P1 | ++ |
| IN11125-006-P1 | + |
| IN11125-001-P1 | + |
| IN11104-039-P1 | + |
| IN11111-021-P1 | ++ |
| IN11125-013-P1 | ++ |
| IN11055-087-P1 | + |
| IN11133-002-P1 | + |
| IN11130-007-P1 | ++ |
| IN11063-096-P1 | ++ |
| IN11063-092-P1 | + |
| IN11125-008-P1 | +++ |
| IN11039-092-P1 | + |
| IN11079-040-P1 | + |
| IN11059-071-P1 | + |
| IN11059-070-P1 | ++ |
| IN11067-061-P1 | + |
| IN11067-060-P1 | + |
| IN11067-062-P1 | + |
| IN11059-069-P1 | ++ |
| IN11111-003-P1 | + |
| IN11106-004-P1 | + |
| IN11063-087-P1 | ++ |
| IN11063-086-P2 | + |
| IN11054-081-P1 | ++ |
| IN11055-079-P1 | + |
| IN11067-072-P1 | + |

TABLE 107-continued

| | |
|---|---|
| IN11079-047-P1 | + |
| IN11055-069-P1 | ++ |
| IN11055-078-P1 | + |
| IN11054-078-P1 | + |
| IN11083-048-P1 | +++ |
| IN11079-033-P1 | ++ |
| IN11055-066-P1 | + |
| IN11039-069-P1 | +++ |
| IN11055-068-P1 | + |
| IN11053-076-P1 | + |
| IN11053-073-P1 | + |
| IN11053-062-P1 | + |
| IN11053-059-P1 | + |
| IN11053-060-P1 | ++ |
| IN11055-049-P1 | ++ |
| IN11125-010-P1 | ++ |
| IN11059-052-P1 | ++ |
| IN11053-071-P1 | + |
| IN11039-066-P1 | +++ |
| IN11054-054-P1 | ++ |
| IN11030-095-P1 | + |
| IN11054-046-P1 | + |
| IN11030-081-P1 | ++ |
| IN11059-047-P1 | +++ |
| IN11055-046-P1 | ++ |
| IN11055-044-P1 | + |
| IN11039-058-P1 | ++ |
| IN11053-052-P1 | ++ |
| IN11054-030-P1 | + |
| IN11067-035-P1 | ++ |
| IN11054-046-P2 | ++ |
| IN11030-083-P1 | ++ |
| IN11054-039-P1 | ++ |
| IN11079-014-P1 | + |
| IN11053-046-P1 | +++ |
| IN11054-038-P1 | + |
| IN11030-054-P1 | + |
| IN11039-036-P1 | + |
| IN11079-007-P1 | + |
| IN11079-009-P1 | ++ |
| IN11067-023-P1 | +++ |
| IN11063-030-P1 | + |
| IN11053-033-P1 | + |
| IN11083-014-P1 | + |
| IN11030-044-P1 | ++ |
| IN11039-026-P1 | ++ |
| IN10966-095-P1 | + |
| IN11053-021-P1 | + |
| IN11054-012-P1 | ++ |
| IN11053-024-P1 | + |
| IN11053-022-P1 | + |
| IN11067-004-P1 | ++ |
| IN10966-093-P1 | + |
| IN11063-005-P1 | + |
| IN11063-006-P1 | ++ |
| IN11030-035-P1 | ++ |
| IN11055-016-P1 | + |
| IN11055-015-P1 | + |
| IN10991-091-P1 | ++ |
| IN11039-023-P1 | + |
| IN11054-011-P1 | + |
| IN11053-013-P1 | ++ |
| IN11053-005-P1 | + |
| IN11067-003-P1 | ++ |
| IN11053-007-P1 | + |
| IN10966-083-P1 | + |
| IN11039-019-P1 | +++ |
| IN11039-017-P1 | ++ |
| IN11030-032-P1 | +++ |
| IN11039-009-P1 | ++ |
| IN10965-091-P1 | + |
| IN11054-005-P1 | + |
| IN11054-003-P1 | ++ |
| IN10984-079-P1 | + |
| IN11030-023-P1 | + |
| IN11039-006-P1 | +++ |
| IN10965-089-P1 | ++ |
| IN10963-077-P1 | + |
| IN10971-088-P1 | + |
| IN10991-065-P1 | + |
| IN10991-067-P1 | + |
| IN11030-013-P1 | + |
| IN10967-061-P1 | + |
| IN10966-057-P2 | ++ |
| IN10967-063-P1 | ++ |
| IN10963-068-P1 | + |
| IN10973-099-P1 | + |
| IN10973-098-P1 | + |
| IN10971-081-P1 | ++ |
| IN10971-077-P1 | + |
| IN10987-055-P1 | + |
| IN10987-056-P1 | ++ |
| IN10964-046-P1 | + |
| IN10991-044-P1 | ++ |
| IN10973-069-P1 | + |
| IN10973-083-P1 | + |
| IN10987-050-P1 | + |
| IN10973-060-P1 | + |
| IN10971-060-P1 | + |
| IN10971-059-P1 | + |
| IN10987-039-P1 | + |
| IN10984-043-P1 | + |
| IN10963-049-P1 | ++ |
| IN10964-041-P1 | ++ |
| IN10973-053-P1 | + |
| IN10966-028-P1 | ++ |
| IN10987-030-P1 | + |
| IN10973-028-P1 | + |
| IN10973-041-P1 | + |
| IN10973-038-P1 | + |
| IN10991-021-P1 | + |
| IN10984-022-P1 | ++ |
| IN10963-024-P1 | + |
| IN10971-033-P1 | + |
| IN10973-025-P1 | 1 |
| IN10966-011-P1 | + |
| IN10964-008-P1 | ++ |
| IN10964-007-P1 | +++ |
| IN10876-092-P1 | ++ |
| IN10881-099-P1 | + |
| IN10881-098-P1 | + |
| IN10881-092-P1 | +++ |
| IN10876-082-P1 | + |
| IN10876-080-P1 | + |
| IN10973-008-P1 | + |
| IN10973-004-P1 | + |
| IN10973-005-P1 | + |
| IN10880-093-P1 | ++ |
| IN10881-090-P1 | + |
| IN10882-083-P1 | + |
| IN10876-069-P1 | + |
| IN10882-072-P1 | + |
| IN10880-085-P1 | + |
| IN10880-084-P1 | + |
| IN10882-068-P1 | + |
| IN10880-065-P1 | + |
| IN10880-062-P1 | + |
| IN10876-061-P1 | + |
| IN10881-061-P1 | + |
| IN10881-060-P1 | + |
| IN10881-059-P1 | + |
| IN10881-058-P1 | + |
| IN10881-054-P1 | + |
| IN10880-059-P1 | + |
| IN10880-058-P1 | + |
| IN10880-064-P1 | + |
| IN10864-066-P1 | ++ |
| IN10882-055-P1 | + |
| IN10882-057-P1 | + |
| IN10864-060-P1 | +++ |
| IN10880-056-P1 | + |
| IN10876-041-P2 | + |
| IN10880-055-P1 | + |
| IN10882-040-P1 | + |
| IN10882-043-P1 | + |
| IN10876-051-P1 | + |
| IN10881-040-P1 | + |
| IN10880-029-P1 | + |
| IN10864-043-P1 | +++ |
| IN10881-027-P1 | ++ |

TABLE 107-continued

| Compound | Value |
|---|---|
| IN10880-033-P1 | ++ |
| IN10880-035-P1 | ++ |
| IN10881-025-P1 | ++ |
| IN10880-032-P1 | ++ |
| IN10864-034.P1 | +++ |
| IN10882-020-P1 | ++ |
| IN10881-023-P2 | ++ |
| IN10864-33.P1 | ++ |
| IN10880-018-P1 | ++ |
| IN10882-014-P1 | + |
| IN10876-013-P1 | ++ |
| IN10881-020.P1 | +++ |
| IN10881-021.P1 | ++ |
| IN10864-031-P1 | +++ |
| IN10880-014-P1 | ++ |
| IN11147-062-P1 | + |
| IN11218-034-P1 | ++ |
| IN11104-090-P1 | + |
| IN11288-025-P1 | + |
| IN11196-065-P1 | + |
| IN11216-072-P1 | + |
| IN11273-018-P1 | + |
| IN11250-031-P1 | + |
| IN11243-031-P1 | + |
| IN11216-043-P1 | + |
| IN11177-068-P1 | + |
| IN11147-071-P1 | + |
| IN11140-099-P1 | + |
| IN11140-090-P1 | + |
| IN11216-073-P1 | +++ |
| IN11217-088-P1 | + |
| IN11273-015-P2 | + |
| IN11243-050-P2 | ++ |
| IN11273-015-P1 | + |
| IN11217-069-P1 | + |
| IN11217-068-P1 | + |
| IN11273-006-P1 | + |
| IN11251-043-P1 | ++ |
| IN11216-050-P1 | ++ |
| IN11288-005-P1 | ++ |
| IN11243-042-P1 | ++ |
| IN11243-041-P1 | +++ |
| IN11250-032-P1 | ++ |
| IN11273-001-P1 | + |
| IN11238-035-P1 | + |
| IN11238-046-P1 | + |
| IN11238-040-P1 | + |
| IN11251-035-P1 | ++ |
| IN11251-024-P1 | |
| IN11217-056-P1 | ++ |
| IN11220-039-P1 | ++ |
| IN11238-088-P1 | ++ |
| IN11288-060-P1 | NT |
| IN11237-056-P1 | + |
| IN11251-091-P1 | NT |
| IN11251-092-P1 | NT |
| IN11337-019-P1 | + |

TABLE 107-continued

| Compound | Value |
|---|---|
| IN11216-078-P1 | + |
| IN11251-099-P1 | NT |

+ means >1 uM; ++ means 200 nM-1000 nM; +++ means <200 nM; NT means not tested.

Male Sprague Dawley rats were administered with either Vehicle, 10, or 30 mg/Kg Compound 359 by oral administration 30 minutes prior to harmaline injection to investigate the therapeutic effect of Compound 359 on harmaline induced tremor. Immediately following harmaline injection, animals were placed in the tremor quantification apparatus and tremor events were quantified for 60 minutes. A tremor event signal was generated when a small metal transmitter band fitted to the right forepaw of the animal moved within the electromagnetic field generated by a loop antenna within the testing apparatus. Outputs from the amplifier were digitized at a sampling rate of 1,000 Hz and the signal was processed and analyzed using LabView software (National Instruments). To minimize signal from ambulatory and grooming behavior, the signal was filtered with a 128-ms nonweigthed moving average filter, and events with amplitudes >0.5 V and lasting >300 ms in duration were counted as a tremor event. Data were analyzed in one-minute bins over the course of the test and presented as the sum of tremor events over the entire 60 minute test. As shown by FIG. 1, significant inhibition of tremors was observed at a dose of 30 mg/Kg Compound 359.

The extent to which compounds modulate SK2 channels in vivo is expressed as % SK2 $SC_{100}$, which is the ratio of the concentration of the drug free in the brain to the measured potency of the compound against the SK2 channel. It is calculated as follows: $C_{FB}=C_{MB} \times BFF$, where $C_{MB}$ is the concentration of compound measured by mass spectrometry from brains harvested immediately following tremor recording (Table 3, "Measured Brain Concentration"). $C_{FB}$ is the amount of free compound not complexed with protein and therefore free to interact with the SK2 channel (Table 3, "Calculated Brain Free Fraction"). BFF is average free fraction of compound as measured by equilibrium dialysis in separate experiments (Table 3, "Brain Free Fraction"). Free drug in brain available to interact with SK2 channels ($C_{FB}$) is arrived at by multiplying the measured total brain level ($C_{MB}$) by the average free fraction (BFF).

The amount of free compound is then expressed in terms of its potency against the SK2 channel as follows: % SK2 $SC_{100}=C_{FB}/SK2\ SC_{100} \times 100$, where SK2 $SC_{100}$ (Table 3, "SK2 $SC_{100}$") is the measured value of potency of the compound against SK2 channels and % SK2 $SC_{100}$ (Table 3, "% SK2 $SC_{100}$") is the free brain concentration ($C_{FB}$) normalized to SK2 $SC_{100}$. Thus the % SK2 $SC_{100}$ gives a measure of the degree to which each of the compounds is modulating SK2 channels regardless of differences in potency or exposure. Values are given in

TABLE 3

| Compound | Minimally Efficacious Dose (mg/Kg) | Measured Brain Concentration (μM) | Measured Brain Free Fraction | Calculated Free Brain Concentration (μM) | Measured SK2 $SC_{100}$ (μM) | Calculated % SK2 $SC_{100}$ |
|---|---|---|---|---|---|---|
| 359 | 30 | 1.3 | 0.065 | 0.08 | 0.5 | 16 |

Figure 2:
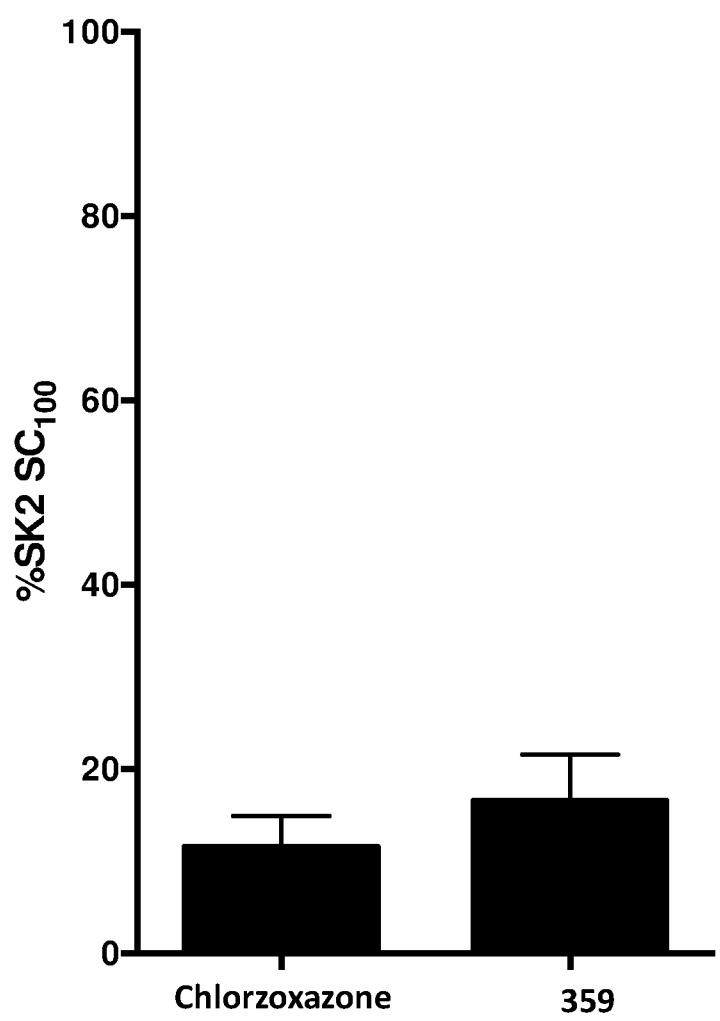
FIG. 2 is a diagram illustrating the % SK2 $SC_{100}$ of Compound 359 compared with chlorzoxazone (CHZ).

Compound 359 displayed efficacy at a dose that represented modulation of the SK2 channel, regardless of potency. See e.g., FIG. 2 showing the SK2 $SC_{100}$ Compound 1 compared to chlorzoxazone (CHZ).

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound having the structural Formula Ia:

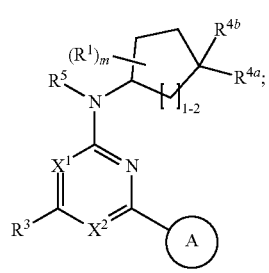

(Ia)

or a pharmaceutically acceptable salt thereof, wherein:
ring A is selected from

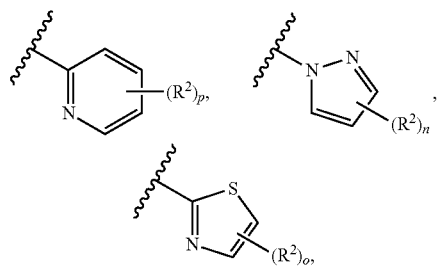

and

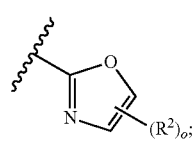

$X^1$ is selected from $C(R^a)$ and N;
$X^2$ is selected from $C(R^b)$ and N, wherein $X^1$ and $X^2$ are not simultaneously nitrogen;
each of $R^a$ and $R^b$ is independently selected from hydrogen, halo, —CN, optionally substituted $C_1$-$C_4$ alkyl, optionally substituted —O—($C_1$-$C_4$ alkyl), —OH, —NH$_2$, optionally substituted —NH($C_1$-$C_4$ alkyl), optionally substituted —N($C_1$-$C_4$ alkyl)$_2$, optionally substituted —S—($C_1$-$C_4$ alkyl), and optionally substituted —S(O)$_2$—$C_1$-$C_4$ alkyl;
each $R^2$ is independently selected from halo, —CN, optionally substituted $C_3$-$C_6$ cycloalkyl, optionally substituted —$C_1$-$C_6$ alkyl, optionally substituted —O—($C_1$-$C_4$ alkyl), optionally substituted —NH($C_1$-$C_4$ alkyl), optionally substituted —S—($C_1$-$C_4$ alkyl), optionally substituted —S(O)—($C_1$-$C_4$ alkyl), and optionally substituted —S(O)$_2$—$C_1$-$C_4$ alkyl;
$R^3$ is selected from —C(=O)NH$_2$, -heteroaryl, -heterocyclyl, -aryl, —O-carbocyclyl, —O-heterocyclyl, —O-heteroaryl, —O-aryl, —S-carbocyclyl, —S-heterocyclyl, —S-heteroaryl, —S-aryl, —S(O)-carbocyclyl, —S(O)-heterocyclyl, —S(O)-heteroaryl, —S(O)-aryl, —S(O)$_2$-carbocyclyl, —S(O)$_2$-heterocyclyl, —S(O)$_2$-heteroaryl, —S(O)$_2$-aryl, —O($C_1$-$C_4$ alkylene)carbocyclyl, —O($C_1$-$C_4$ alkylene)heterocyclyl, —O($C_1$-$C_4$ alkylene)heteroaryl, —O($C_1$-$C_4$ alkylene)aryl, —S($C_1$-$C_4$ alkylene)carbocyclyl, —S($C_1$-$C_4$ alkylene)heterocyclyl, —S($C_1$-$C_4$ alkylene)heteroaryl, —S($C_1$-$C_4$ alkylene)aryl, —S(O)($C_1$-$C_4$ alkylene)carbocyclyl, —S(O)($C_1$-$C_4$ alkylene)heterocyclyl, —S(O)($C_1$-$C_4$ alkylene)heteroaryl, —S(O)($C_1$-$C_4$ alkylene)aryl, —S(O)$_2$($C_1$-$C_4$ alkylene)carbocyclyl, —S(O)$_2$($C_1$-$C_4$ alkylene)heterocyclyl, —S(O)$_2$($C_1$-$C_4$ alkylene)heteroaryl, —S(O)$_2$($C_1$-$C_4$ alkylene)aryl, —S—($C_1$-$C_4$ alkyl), —S(O)—($C_1$-$C_4$ alkyl), and —S(O)$_2$—($C_1$-$C_4$ alkyl), wherein each of said heterocyclyl, carbocyclyl, heteroaryl, aryl, and $C_1$-$C_4$ alkylene are optionally substituted;
$R^{4a}$ is selected from fluoro and —CF$_3$;
$R^{4b}$ is selected from hydrogen and fluoro;
$R^5$ is selected from hydrogen and optionally substituted $C_1$-$C_4$ alkyl;
m is 0;
n is 1, 2 or 3;
o is 1 or 2; and
p is 1, 2, 3 or 4.

2. The compound of claim 1, wherein the compound is of the Formula II or III:

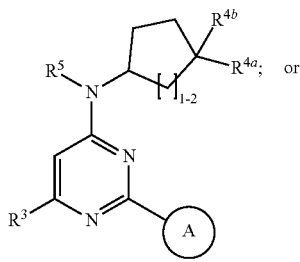

(II)

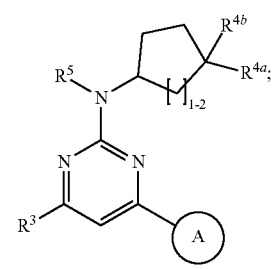

(III)

or a pharmaceutically acceptable salt thereof.

3. The compound of claim 1, or a pharmaceutically acceptable salt thereof, wherein each of said heterocyclyl, heteroaryl, carbocyclyl, aryl, and $C_1$-$C_4$ alkylene for $R^3$ are optionally substituted with 1 to 3 groups independently selected from $R^7$, where $R^7$ is halogen, CN, —OR$^c$, —NR$^d$R$^e$, —S(O)$_t$R$^c$, —NR$^c$S(O)$_2$R$^c$, —S(O)$_2$NR$^d$R$^e$, —C(=O)OR$^c$, —OC(=O)OR$^c$, —OC(=O)R$^c$, —OC (=S)OR$^c$, —C(=S)OR$^c$, —O(C=S)R$^c$, —C(=O)NR$^d$R$^e$, —NR$^c$C(=O)R$^c$, —C(=S)NR$^d$R$^e$, —NR$^c$C(=S)R$^c$, —NR$^c$(C=O)OR$^c$, —O(C=O)NR$^d$R$^e$, —NR$^c$(C=S)OR$^c$, —O(C=S)NR$^d$R$^e$, —NR$^c$(C=O)NR$^d$R$^e$, —NR$^c$(C=S) NR$^d$R$^e$, —C(=S)R$^c$, —C(=O)R$^c$, (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl or —(CH$_2$)$_{1-4}$-heteroaryl, wherein each of said (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl for R$^7$ are optionally substituted with halogen, OR$^c$, —NO$_2$, —CN, —NR$^c$C(=O)R$^c$, —NR$^d$R$^e$, —S(O)$_k$R$^c$, —C(=O)OR$^c$, —C(=O)NR$^d$R$^e$, —C(=O)R$^c$, (C$_1$-C$_3$)alkyl, halo(C$_1$-C$_3$)alkyl, (C$_1$-C$_3$) alkoxy(C$_1$-C$_3$)alkyl, (C$_1$-C$_3$)alkoxy, and halo(C$_1$-C$_3$)alkoxy; or two instances of R$^7$ are taken together on the same atom to form =O;

R$^c$ is hydrogen or (C$_1$-C$_6$)alkyl optionally substituted with 1 to 3 halogen;

R$^d$ and R$^e$ are each independently selected from hydrogen and (C$_1$-C$_6$)alkyl; and k is 0, 1 or 2.

4. The compound of claim 1, or a pharmaceutically acceptable salt thereof, wherein each of R$^a$ and R$^b$ is independently selected from hydrogen and C$_1$-C$_4$ alkyl.

5. The compound of claim 4, or a pharmaceutically acceptable salt thereof, wherein R$^a$ is selected from hydrogen, methyl, and ethyl.

6. The compound of claim 1, or a pharmaceutically acceptable salt thereof, wherein R$^5$ is selected from hydrogen, methyl and ethyl.

7. The compound of claim 1, or a pharmaceutically acceptable salt thereof, wherein R$^{4a}$ is —CF$_3$; and R$^{4b}$ is hydrogen.

8. The compound of claim 1, or a pharmaceutically acceptable salt thereof, wherein R$^5$ is hydrogen.

9. A pharmaceutical composition comprising a compound of claim 1, or a pharmaceutically acceptable salt thereof; and a pharmaceutically acceptable carrier.

10. A compound having the structural Formula II or III:

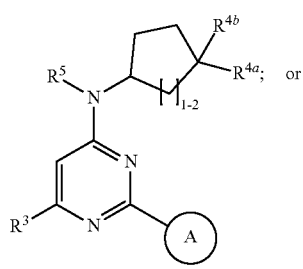

(II)

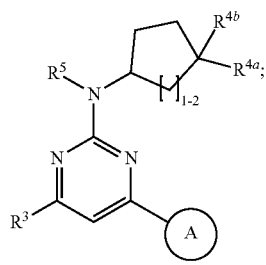

(III)

or a pharmaceutically acceptable salt thereof, wherein ring A is selected from

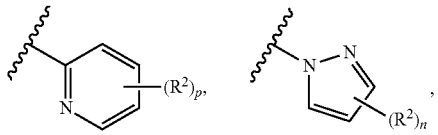

and

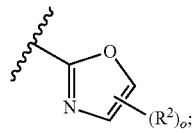

each R$^2$ is independently selected from halo, —CN, optionally substituted C$_3$-C$_6$ cycloalkyl, optionally substituted —C$_1$-C$_6$ alkyl, optionally substituted —O—(C$_1$-C$_4$ alkyl), optionally substituted —NH(C$_1$-C$_4$ alkyl), optionally substituted —S—(C$_1$-C$_4$ alkyl), optionally substituted —S(O)—(C$_1$-C$_4$ alkyl), and optionally substituted —S(O)$_2$—C$_1$-C$_4$ alkyl;

R$^3$ is selected from —C(=O)NH$_2$, -heteroaryl, -heterocyclyl, -aryl, —O-carbocyclyl, —O-heterocyclyl, —O-heteroaryl, —O-aryl, —S-carbocyclyl, —S-heterocyclyl, —S-heteroaryl, —S-aryl, —S(O)-carbocyclyl, —S(O)-heterocyclyl, —S(O)-heteroaryl, —S(O)-aryl, —S(O)$_2$-carbocyclyl, —S(O)$_2$-heterocyclyl, —S(O)$_2$-heteroaryl, —S(O)$_2$-aryl, —O(C$_1$-C$_4$ alkylene)carbocyclyl, —O(C$_1$-C$_4$ alkylene)heterocyclyl, —O(C$_1$-C$_4$ alkylene)heteroaryl, —O(C$_1$-C$_4$ alkylene)aryl, —S(C$_1$-C$_4$ alkylene)carbocyclyl, —S(C$_1$-C$_4$ alkylene)heterocyclyl, —S(C$_1$-C$_4$ alkylene)heteroaryl, —S(C$_1$-C$_4$ alkylene)aryl, —S(O)(C$_1$-C$_4$ alkylene)carbocyclyl, —S(O)(C$_1$-C$_4$ alkylene)heterocyclyl, —S(O)(C$_1$-C$_4$ alkylene)heteroaryl, —S(O)(C$_1$-C$_4$ alkylene)aryl, —S(O)$_2$(C$_1$-C$_4$ alkylene)carbocyclyl, —S(O)$_2$(C$_1$-C$_4$ alkylene)heterocyclyl, —S(O)$_2$(C$_1$-C$_4$ alkylene)heteroaryl, —S(O)$_2$(C$_1$-C$_4$ alkylene)aryl, —S—(C$_1$-C$_4$ alkyl), —S(O)—(C$_1$-C$_4$ alkyl), and —S(O)$_2$—(C$_1$-C$_4$ alkyl), wherein each of said heterocyclyl, carbocyclyl, heteroaryl, aryl, and C$_1$-C$_4$ alkylene are optionally substituted;

R$^{4a}$ is selected from fluoro and —CF$_3$;
R$^{4b}$ is selected from hydrogen and fluoro;
R$^5$ is selected from hydrogen and optionally substituted C$_1$-C$_4$ alkyl;
m is 0;
n is 1, 2 or 3;
o is 1 or 2; and
p is 1, 2, 3 or 4.

11. The compound of claim 10, or a pharmaceutically acceptable salt thereof, wherein each of said heterocyclyl, heteroaryl, carbocyclyl, aryl, and C$_1$-C$_4$ alkylene for R$^3$ are optionally substituted with 1 to 3 groups independently selected from R$^7$, where R$^7$ is halogen, CN, —OR$^c$, —NR$^d$R$^e$, —S(O)$_k$R$^c$, —NR$^c$S(O)$_2$R$^c$, —S(O)$_2$NR$^d$R$^e$, —C(=O)OR$^c$, —OC(=O)OR$^c$, —OC(=O)R$^c$, —OC(=S)OR$^c$, —C(=S)OR$^c$, —O(C=S)R$^c$, —C(=O)NR$^d$R$^e$, —NR$^c$C(=O)R$^c$, —C(=S)NR$^d$R$^e$, —NR$^c$C(=S)R$^c$, —NR$^c$(C=O)OR$^c$, —O(C=O)NR$^d$R$^e$, —NR$^c$(C=S)OR$^c$, —O(C=S)NR$^d$R$^e$, —NR$^c$(C=O)NR$^d$R$^e$, —NR$^c$(C=S)NR$^d$R$^e$, —C(=S)R$^c$, —C(=O)R$^c$, (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl or —(CH$_2$)$_{1-4}$-heteroaryl, wherein each of said (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl for R$^7$ are optionally substituted with halogen, OR$^c$, —NO$_2$, —CN, —NR$^c$C(=O)R$^c$, —NR$^d$R$^e$, —S(O)$_k$R$^c$, —C(=O)OR$^c$, —C(=O)NR$^d$R$^e$, —C(=O)R$^c$, (C$_1$-C$_3$)alkyl, halo(C$_1$-C$_3$)alkyl, (C$_1$-C$_3$)alkoxy(C$_1$-C$_3$)alkyl, (C$_1$-C$_3$)alkoxy, and halo(C$_1$-C$_3$)alkoxy; or two instances of R$^7$ are taken together on the same atom to form =O;

R$^c$ is hydrogen or (C$_1$-C$_6$)alkyl optionally substituted with 1 to 3 halogen;

R$^d$ and R$^e$ are each independently selected from hydrogen and (C$_1$-C$_6$)alkyl; and k is 0, 1 or 2.

12. The compound of claim 10, or a pharmaceutically acceptable salt thereof, wherein each of R$^a$ and R$^b$ is independently selected from hydrogen and C$_1$-C$_4$ alkyl.

13. The compound of claim 10, or a pharmaceutically acceptable salt thereof, wherein R$^a$ is selected from hydrogen, methyl, and ethyl.

14. The compound of claim 10, or a pharmaceutically acceptable salt thereof, wherein R$^5$ is selected from hydrogen, methyl and ethyl.

15. The compound of claim 10, or a pharmaceutically acceptable salt thereof, wherein R$^{4a}$ is —CF$_3$; and R$^{4b}$ is hydrogen.

16. The compound of claim 10, or a pharmaceutically acceptable salt thereof, wherein R$^5$ is hydrogen.

17. A pharmaceutical composition comprising a compound of claim 10, or a pharmaceutically acceptable salt thereof; and a pharmaceutically acceptable carrier.

* * * * *